United States Patent
Connolly et al.

(10) Patent No.: US 10,077,261 B2
(45) Date of Patent: Sep. 18, 2018

(54) IMIDAZOLIN-5-ONE DERIVATIVE USEFUL AS FASN INHIBITORS FOR THE TREATMENT OF CANCER

(71) Applicant: Janssen Pharmaceutica NV, Beerse (BE)

(72) Inventors: Peter J. Connolly, New Providence, NJ (US); Gilles C. Bignan, Bridgewater, NJ (US); Tianbao Lu, Churchville, PA (US); Michael H. Parker, Chalfont, PA (US); Donald W. Ludovici, Quakertown, PA (US); Christophe Meyer, Les Authieux sur le Port Saint Ouen (FR); Lieven Meerpoel, Beerse (BE); Karine Smans, Beerse (BE); Christian Rocaboy, Murcia (ES)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 14/851,738

(22) Filed: Sep. 11, 2015

(65) Prior Publication Data

US 2016/0002219 A1    Jan. 7, 2016

Related U.S. Application Data

(63) Continuation of application No. 14/020,122, filed on Sep. 6, 2013.

(60) Provisional application No. 61/698,125, filed on Sep. 7, 2012.

(51) Int. Cl.

| | | |
|---|---|---|
| C07D 417/14 | (2006.01) | |
| C07D 401/14 | (2006.01) | |
| C07D 405/14 | (2006.01) | |
| C07D 413/14 | (2006.01) | |
| C07D 401/06 | (2006.01) | |
| C07D 403/06 | (2006.01) | |
| C07D 403/14 | (2006.01) | |
| C07D 409/14 | (2006.01) | |
| C07D 471/04 | (2006.01) | |
| C07D 471/10 | (2006.01) | |
| C07D 487/10 | (2006.01) | |
| C07D 491/107 | (2006.01) | |
| C07D 498/04 | (2006.01) | |

(52) U.S. Cl.
CPC ......... *C07D 417/14* (2013.01); *C07D 401/06* (2013.01); *C07D 401/14* (2013.01); *C07D 403/06* (2013.01); *C07D 403/14* (2013.01); *C07D 405/14* (2013.01); *C07D 409/14* (2013.01); *C07D 413/14* (2013.01); *C07D 471/04* (2013.01); *C07D 471/10* (2013.01); *C07D 487/10* (2013.01); *C07D 491/107* (2013.01); *C07D 498/04* (2013.01)

(58) Field of Classification Search
None
See application file for complete search history.

(56) References Cited

U.S. PATENT DOCUMENTS

2013/0172384 A1* 7/2013 Adams ................ C07D 401/14
514/307

FOREIGN PATENT DOCUMENTS

| WO | WO 2004/058727 | | 6/2004 |
|---|---|---|---|
| WO | WO 2004/058727 A1 | * | 7/2004 |
| WO | WO 2012/037299 A2 | | 3/2012 |

OTHER PUBLICATIONS

Freshney, RI. Culture of Animal Cells: A Manual of Basic Technique. John Wiley and Sons. 2005, 5th Ed., p. 8.*
Dermer, GB. Another Anniversary for the War on Cancer. Bio/Technology. 1994, vol. 12, p. 320.*
Cornelison, TL. Human papillomavirus genotype 16 vaccines for cervical cancer prophylaxis and treatment. Curr. Opin. Oncol. 2000, vol. 12(5), p. 466.*
Loftus, TM. et al. Reduced Food Intake and Body Weight in Mice Treated with Fatty Acid Synthase Inhibitors. Science. 2000, vol. 288, p. 2381.*
PCT International Preliminary Report on Patentability Appln No. PCT/US2013/058416 dated Mar. 10, 2015.

(Continued)

*Primary Examiner* — Heidi Reese

(57) ABSTRACT

Disclosed are compounds, compositions and methods for treating various diseases, syndromes, conditions and disorders, including those mediated by inhibition of fatty acid synthase (FASN) enzyme, such as, cancer, obesity or related discorders, and liver related disorders. Such compounds are represented by formula (I) as follows:

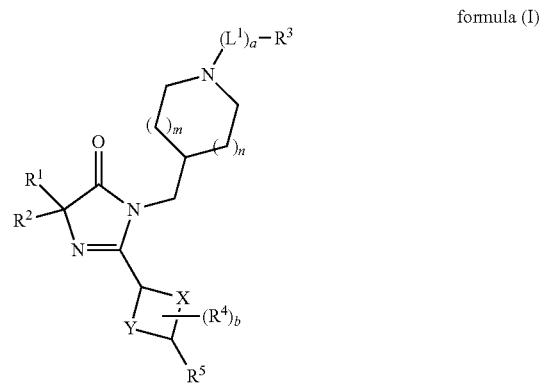

wherein $L^1$, a, b, m, n, $R^1$, $R^2$, $R^3$, $R^4$, and $R^5$ are defined herein.

16 Claims, No Drawings

(56) References Cited

OTHER PUBLICATIONS

PCT International Search Report and the Written Opinion for International Appln No. PCT/US2013/058416 dated Dec. 16, 2013.
Maier, T. et al., "Architecture of mammalian fatty acid synthase at 4.5 Å resolution", Science, 2006, pp. 1258-1262, vol. 311.
Swinnen, J.V., et al., "Stimulation of tumor-associated fatty acid synthase expression by growth factor activation of the sterol regulatory element-binding protein pathway". Oncogene, 2000, pp. 5173-5181, vol. 19.
Kuhaja, F. P., "Fatty-acid synthase and human cancer: new perspectives on its role in tumor biology", Nutrition, 2000, pp. 202-208, vol. 16.
Swinnen, J.V., et al., "Fatty acid synthase drives the synthesis of phospholipids partitioning into detergent resistant membrane microdomains", Biochem. Biophys.Res. Commun., 2000, pp 898-903, vol. 302.
Menendez, J.A., et al.,"Inhibition of fatty acid synthase (FAS) suppresses HER2/neu (erbB-2) oncogene overexpression in cancer cells", Proc. Natl Acad. Sci.USA, 2004, pp. 10715-10720, vol. 101.
Migita, et a., "Fatty Acid Synthase: A Metabolic Enzyme and Candidate Oncogene in Prostate Cancer", J Natl. Cancer Inst., 2009, pp. 519-532, vol. 101.
Bandyopadhyay, S., et al., "FAS expression inversely correlates with PTEN level in prostate cancer and a PI-3 kinase inhibitor synergizes with Fas siRNA to induce apoptosis", Oncogene, 2005, pp 5389-5395, vol. 24.
Van De Dande, T., et al., "Role of the phosphatidylinositol 3'-kinase/PTEN/Akt kinase pathway in the overexpression of fatty acid synthase in LNCaP prostate cancer cells", Cancer Res., 2002, pp. 642-646, vol. 62.
Portsmann, T., et al., "PKB/AKT induces transcription of enzymes involved in cholesterol and fatty acid biosynthesis via activation of SREBP", Oncogene, 2005, pp. 6465-6481, vol. 24.
Bays, N.W., et al., "A simplified scintillation proximity assay for fatty acid synthase activity: development and comparison with other FAS activity assays", J. Biomol. Screen., 2009, pp. 636-642, vol. 14(6).
Cha, Seung Hun, et al., "Long-term effects of a fatty acid synthase inhibitor on obese mice: food intake, hypothalamic neuropeptides, and UCP3", Elsevier, Biochemical and Biophysical Research Communications, 317 (2004) pp. 301-308.
Menendez, Javier A., et al., "Fatty Acid Synthase: Association with Insulin Resistance, Type 2 Diabetes, and Cancer", Clinical Chemistry, 55:3, (2009) pp. 425-438.
Menedez, Javier A., et al., "Fatty acid synthase and the lipogenic pheotype in cancer pathogensis", Nature Reviews Cancer, Nature Publishing Group, vol. 7, (2007) pp. 763-777.
Wu, Menendez, et al., "Antidiabetic and antiseatotic effects of the selective fatty acid synthase (FAS) inhibitor platensimycin in mouse models of diabetes", Preclinical Drug Metabolism and Pharmacokinetics, Merck Research and Laboratories, vol. 108, No. 13, (2011), pp. 5377-5383.
Zaida, Nousheen, et al., "Lipogenesis and lipolysis: The pathways exploited by the cancer cells to acquire fatty acids", Elvevier, Progress in Lipid Research 52 (2013) pp. 585-589.

* cited by examiner

IMIDAZOLIN-5-ONE DERIVATIVE USEFUL AS FASN INHIBITORS FOR THE TREATMENT OF CANCER

CROSS REFERENCE TO RELATED APPLICATIONS

The present application is a continuation application of U.S. application Ser. No. 14/020,122, filed on Sep. 6, 2013, currently pending, and claims the benefit of U.S. Provisional Application No. 61/698,125, filed Sep. 7, 2012, the entire disclosures of which are hereby incorporated in their entirety.

FIELD OF THE INVENTION

The present invention is directed to imidazolin-5-one derivatives, pharmaceutical compositions containing them, and their use as FASN inhibitors, in for example, the treatment of cancer, obesity related disorders, and liver related disorders.

BACKGROUND OF THE INVENTION

Fatty acid synthase (FASN) is a key enzyme for the synthesis of long-chain fatty acids from acetyl-coenzyme A (CoA) and malonyl-CoA that uses reduced nicotinamide adenine dinucleotidephosphate as a cofactor. The final step in the de novo synthesis of fatty acids in mammalians is carried out by FASN, a 250 kDa protein containing 7 functional domains. Through an iterative enzymatic reaction, FASN produces palmitate starting from the substrates acetylCoA and malonylCo, using NADPH (as defined below) as a cofactor (See, MAIER, T., et al., "Architecture of mammalian fatty acid synthase at 4.5 Å resolution", Science, 2006, pp 1258-1262, Vol. 311).

FASN is minimally expressed in most normal human tissues except the liver and adipose tissue, where it is expressed at high levels. Except for these lipogenic tissues (such as liver, lactating breast, fetal lung, and adipose tissue), FASN has a low expression in normal cells which use fatty acids from the diet, while tumor cells largely depend on de novo fatty acid synthesis. FASN expression is highly up-regulated in various tumors, e.g. prostate, breast, colon, and lung cancer (See, SWINNEN, J. V., et al., "Stimulation of tumor-associated fatty acid synthase expression by growth factor activation of the sterol regulatory element-binding protein pathway". Oncogene, 2000, pp 5173-5181, Vol 19; KUHAJA, F. P., "Fatty-acid synthase and human cancer: new perspectives on its role in tumor biology", Nutrition, 2000, pp 202-208, Vol. 16).

FASN overexpression leads to growth and survival advantage to the tumors achieved through multiple mechanisms. Firstly, it provides lipids for membrane synthesis. Moreover, the more saturated lipid composition of the membranes increases resistance to chemotherapy. FASN also contributes to improved growth factor receptor expression in lipid rafts (See, SWINNEN, J. V., et al., "Fatty acid synthase drives the synthesis of phospholipids partitioning into detergent resistant membrane microdomains", Biochem. Biophys. Res. Commun., 2000, pp 898-903, Vol. 302; MENENDEZ, J. A., et al., "Inhibition of fatty acid synthase (FAS) suppresses HER2/neu (erbB-2) oncogene overexpression in cancer cells", Proc. Natl Acad. Sci. USA, 2004, pp 10715-10720, Vol. 101), and improved cell signalling. Lastly, the NAPDPH consumption during palmitate synthesis in tumor cells keeps the redox balance in check.

In tumor cells, but not in normal cells, siRNA knock down or pharmacological inhibition of FASN results in apoptosis in vitro, and in a delayed tumor growth in vivo. The role of FASN as a potential oncogene has been further established in mouse models. Transgenic mouse models with FASN over expression in the prostate develop invasive prostate cancer in the presence of Androgen Receptor (See, MIGITA, et al., "Fatty Acid Synthase: A Metabolic Enzyme and Candidate Oncogene in Prostate Cancer", J Natl. Cancer Inst., 2009, pp 519-532, Vol. 101). It has been proposed that FASN exerts its oncogenic effect by inhibiting the intrinsic pathway of apoptosis. Androgens and epidermal growth factor (EGF) up-regulate FASN expression and activity. In addition, FASN is also over expressed in androgen-independent prostate cancers most likely through activation of the PI3K/Akt pathway (See, BANDYOPADHYAY, S., et al., "FAS expression inversely correlates with PTEN level in prostate cancer and a PI-3 kinase inhibitor synergizes with FAS siRNA to induce apoptosis", Oncogene, 2005, pp 5389-5395, Vol. 24; VAN DE DANDE, T., et al., "Role of the phosphatidylinositol 3'-kinase/PTEN/Akt kinase pathway in the overexpression of fatty acid synthase in LNCaP prostate cancer cells", Cancer Res., 2002, pp 642-646, Vol. 62; PORTSMANN, T., et al., "PKB/AKT induces transcription of enzymes involved in cholesterol and fatty acid biosynthesis via activation of SREBP", Oncogene, 2005, pp 6465-6481, Vol. 24). Thus, FASN is emerging as an important target for cancer therapy.

Since FASN expression is markedly increased in several human cancers compared with the corresponding normal tissue, and FASN overexpression in tumors has been associated with a poor prognosis, FASN inhibitors are viewed as potential therapeutics for the treatment of cancer. There remains a need for pharmaceutical agents for the treatment of a variety of cancers, including breast, prostate, head, neck, skin, lung, ovary, endometrium, thyroid, colon, rectum, esophagus, stomach, kidney, liver, bladder, pancreas, brain, blood, bone, and others.

FASN inhibitors have also shown promise in the treatment of other FASN-mediated diseases, disorders or conditions, such as, obesity, lack of appetite control, and inflammatory conditions. Additionally, FASN has been implicated in diabetes and/or regulation of the general wellness of the liver, and therefore has potential in the treatment of obesity, Type II diabetes mellitus, Syndrome X, and disorders of the liver; the treatment of which there remains a need for pharmaceutical agents.

SUMMARY OF THE INVENTION

The present invention is directed to compounds of formula (I)

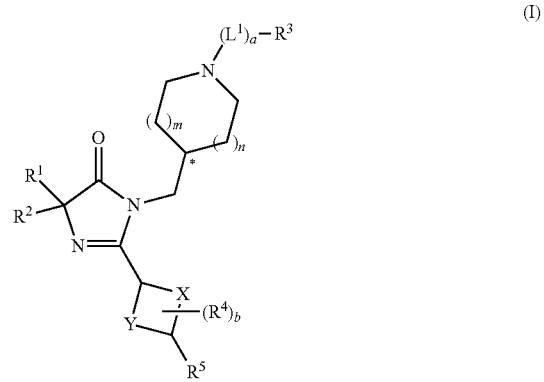

wherein

R[1] and R[2] are taken together with the carbon atom to which they are bound to form an optionally substituted ring structure selected from the group consisting of (a) $C_{3-8}$cycloalkyl; wherein the $C_{3-8}$cycloalkyl is optionally substituted with one to two R[1] groups;

(b) benzo-fused $C_{5-6}$cycloalkyl; wherein the benzo-fused $C_{5-6}$cycloalkyl is bound through a carbon atom of the $C_{5-6}$cycloalkyl portion of the ring structure; wherein the benzo-fused $C_{5-6}$cycloalkyl is optionally substituted with one to two R[11] groups;

and (c) 4 to 8-membered, saturated heterocyclyl; wherein the 4 to 8-membered, saturated heterocyclyl contains one heteroatom selected from the group consisting of O, S and N; wherein the S is optionally substituted with one to two oxo; wherein the N is substituted with R[10]; provided that the heteroatom is not present at the 2-position relative to the carbon atom of the imidazolin-5-one; and wherein the 4 to 8-membered, saturated heterocyclyl is optionally substituted with one R[11] group, and further optionally substituted with one R[12] group;

wherein R[10] is selected from the group consisting of hydrogen, $C_{1-4}$alkyl, fluorinated $C_{1-4}$alkyl, —CH$_2$-(hydroxy substituted $C_{1-4}$alkyl), —($C_{2-4}$alkyl)-O—($C_{1-5}$alkyl), —($C_{2-4}$alkenyl), —($C_{1-4}$ alkyl)-phenyl, —C(O)—NR$^A$R$^B$, —C(O)—($C_{1-3}$alkyl)-NR$^A$R$^B$, —C(O)—($C_{1-4}$alkyl), —C(O)-(fluorinated $C_{1-2}$alkyl), —C(O)—($C_{3-6}$cycloalkyl), —C(O)-phenyl, —C(O)-(5 to 6-membered heteroaryl),

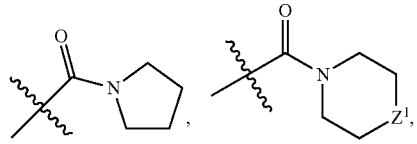

—C(O)O—($C_{1-4}$alkyl), —SO$_2$—($C_{1-4}$alkyl), —SO$_2$—NR$^A$R$^B$, phenyl and 5 to 6-membered heteroaryl;

wherein Z$^1$ is selected from the group consisting of —CH$_2$—, —O—, —N(R$^C$)—, —S—, —S(O)— and —SO$_2$—; wherein R$^A$, R$^B$ and R$^C$ are each independently selected from the group consisting of hydrogen and $C_{1-4}$alkyl;

and wherein the phenyl or 5 to 6-membered heteroaryl whether alone or as part of a substituent group, is further optionally substituted with one to two substituents independently selected from the group consisting of halogen, hydroxy, cyano, NR$^A$R$^B$, $C_{1-4}$alkyl, fluorinated $C_{1-4}$alkyl, $C_{1-4}$alkoxy and fluorinated $C_{1-4}$alkoxy;

wherein each R[11] is independently selected from the group consisting of hydroxy, oxo, halogen, $C_{1-4}$alkyl, fluorinated $C_{1-4}$alkyl, $C_{1-4}$alkoxy, fluorinated $C_{1-4}$alkoxy, hydroxy substituted $C_{1-4}$alkyl, —($C_{1-4}$alkyl)-O—($C_{1-4}$alkyl), —($C_{1-4}$alkyl)-phenyl, -cyano, —NR$^D$R$^E$, —C(O)—NR$^D$R$^E$, —C(O)—($C_{1-4}$alkyl), —C(O)-phenyl, —C(O)-(5 to 6-membered heteroaryl),

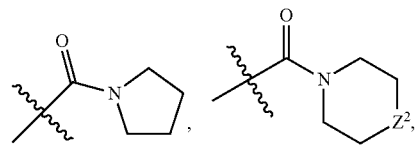

—C(O)OH, —C(O)O—($C_{1-4}$ alkyl), —SO$_2$—($C_{1-4}$alkyl), —SO$_2$—NR$^D$R$^E$, phenyl and 5 to 6-membered heteroaryl;

wherein Z$^2$ is selected from the group consisting of —CH$_2$—, —O—, —N(R$^C$)—, —S—, —S(O)— and —SO$_2$—; wherein R$^D$, R$^E$ and R$^F$ are each independently selected from the group consisting of hydrogen and $C_{1-4}$alkyl;

and wherein the phenyl or 5 to 6-membered heteroaryl, whether alone or as part of a substituent group, is further optionally substituted with one to two substituents independently selected from the group consisting of halogen, hydroxy, cyano, NR$^D$R$^E$, $C_{1-4}$alkyl, fluorinated $C_{1-4}$alkyl, $C_{1-4}$alkoxy and fluorinated $C_{1-4}$alkoxy;

and wherein R[12] is selected from the group consisting of hydroxy, oxo, halogen, $C_{1-4}$alkyl, fluorinated $C_{1-4}$ alkyl, $C_{1-4}$alkoxy, fluorinated $C_{1-4}$alkoxy and hydroxy substituted $C_{1-4}$alkyl;

m is an integer from 0 to 1; and n is an integer from 0 to 2; provided that when n is 2, then m is 1;

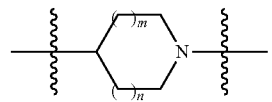

is selected from the group consisting of azetidin-3-yl, pyrrolidin-3-yl, pyrrolidin-3R-yl, pyrrolidin-3S-yl, piperidin-3-yl, piperidin-3R-yl, piperidin-2S-yl, and piperidin-4-yl;

a is an integer from 0 to 1;

L$^1$ is selected from the group consisting of —C(O)—, —C(O)O—, —C(O)—NR$^L$, —C(S)—, —SO$_2$—, —SO$_2$—NR$^L$—; wherein R$^L$ is selected from the group consisting of hydrogen and $C_{1-4}$alkyl;

R[3] is selected from the group consisting of $C_{1-4}$alkyl, fluorinated $C_{1-4}$alkyl, hydroxy substituted $C_{1-4}$alkyl, $C_{2-4}$alkenyl, $C_{3-6}$cycloalkyl, —($C_{1-4}$alkyl)-($C_{3-6}$cycloalkyl), 4 to 6-membered, saturated heterocyclyl, —($C_{1-4}$alkyl)-(4 to 6-membered, saturated heterocyclyl), —($C_{2-4}$alkenyl)-(5 to 6-membered, saturated heterocyclyl), 5 to 6-membered heteroaryl, —($C_{1-4}$alkyl)-(5 to 6-membered heteroaryl), —($C_{2-4}$alkenyl)-(5 to 6-membered heteroaryl), and NR$^V$R$^W$; wherein R$^V$ and R$^W$ are each independently selected from the group consisting of hydrogen and $C_{1-4}$alkyl;

wherein the $C_{3-6}$cycloalkyl, 4 to 6-membered saturated heterocyclyl or 5 to 6-membered heteroaryl, whether alone or as part of a substituent group, is optionally substituted with one to two substituents independently selected from the group consisting of halogen, hydroxy, cyano, $C_{1-4}$alkyl, fluorinated $C_{1-4}$alkyl, —($C_{1-4}$alkyl)-OH, $C_{1-4}$alkoxy, fluorinated $C_{1-4}$alkoxy, and NR$^G$R$^H$: wherein R$^G$ and R$^H$ are each independently selected from the group consisting of hydrogen and $C_{1-4}$alkyl;

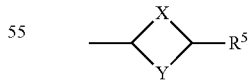

is selected from the group consisting of

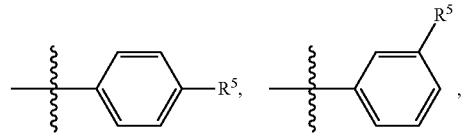

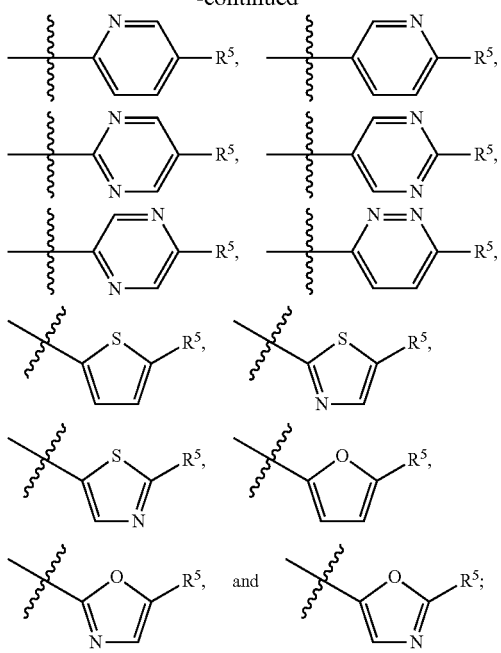

b is an integer from 0 to 2;

each R⁴ is independently selected from the group consisting of hydroxy, halogen, $C_{1-4}$alkyl, fluorinated $C_{1-4}$ alkyl, $C_{1-4}$alkoxy, fluorinated $C_{1-4}$alkoxy, cyano, and $NR^JR^K$; wherein $R^J$ and $R^K$ are each independently selected from the group consisting of hydrogen and $C_{1-4}$alkyl; provided that each R⁴ group is bound to a carbon atom;

provided that when

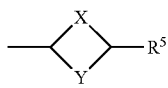

is selected from the group consisting of

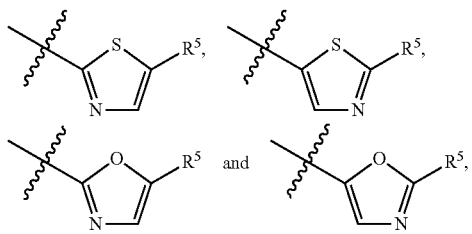

and substituted with $-(R^4)_b$, then b is an integer from 0 to 1;

R⁵ is selected from the group consisting of (a)

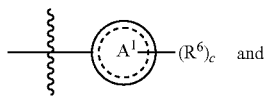 and (b)

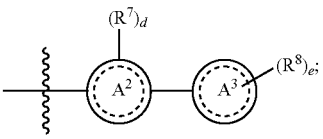

wherein

selected from the group consisting of aryl, heteroaryl and partially unsaturated heterocyclyl;

c is an integer from 0 to 2;

each R⁶ is independently selected from the group consisting of hydroxy, oxo, halogen, cyano, nitro, $C_{1-4}$alkyl, fluorinated $C_{1-4}$alkyl, hydroxy substituted $C_{1-4}$alkyl, —($C_{1-4}$alkyl)-CN, —($C_{1-4}$alkyl)-O—($C_{1-4}$alkyl), $C_{1-4}$alkoxy, fluorinated $C_{1-4}$alkoxy, —SO₂—($C_{1-4}$alkyl), —$NR^MR^N$, —($C_{1-4}$alkyl)-$NR^PR^Q$, —C(O)—($C_{1-4}$alkyl), —C(O)-(fluorinated $C_{1-2}$alkyl), —C(O)—$NR^MR^N$, —C(O)OH, —C(O)O—($C_{1-4}$alkyl), —$NR^M$—C(O)H, —$NR^M$—C(O)—($C_{1-4}$alkyl), —$NR^M$—SO₂—($C_{1-4}$ alkyl), $C_{3-6}$cycloalkyl, -cyano-($C_{3-6}$-(cycloalkyl), —($C_{1-4}$alkyl)-($C_{3-6}$cycloalkyl), —S—($C_{3-6}$cycloalkyl), —SO—($C_{3-6}$cycloalkyl), —SO₂($C_{3-6}$cycloalkyl), —NH—($C_{3-6}$cycloalkyl), —NH—SO₂—($C_{3-6}$cycloalkyl), oxetanyl, —($C_{1-2}$alkyl)-oxetanyl, tetrahydofuranyl, —($C_{1-2}$alkyl)-tetrahydro-furanyl, tetrahydro-pyranyl, and —($C_{1-2}$alkyl)-tetrahydro-pyranyl;

wherein $R^M$ and $R^N$ are each independently selected from the group consisting of hydrogen and $C_{1-4}$alkyl;

wherein $R^P$ and $R^Q$ are each independently selected from the group consisting of hydrogen and $C_{1-4}$alkyl; alternatively $R^P$ and $R^Q$ are taken together with the nitrogen atom to which they are bound to form a 5 to 6-membered saturated heterocyclyl; such 5 to 6-membered saturated heterocyclyl is optionally substituted with a substituent selected from the group consisting of halogen, $C_{1-4}$alkyl and fluorinated $C_{1-4}$alkyl;

wherein

selected from the group consisting of phenyl and 5 to 6-membered heteroaryl;

d is an integer from 0 to 1;

R⁷ is selected from the group consisting of hydroxy, halogen, cyano, nitro, $C_{1-4}$alkyl, fluorinated $C_{1-4}$alkyl, hydroxy substituted $C_{1-4}$alkyl, $C_{1-4}$alkoxy, fluorinated $C_{1-4}$alkoxy, —$NR^RR^S$, —C(O)—$NR^RR^S$, —C(O)OH and —C(O)O—($C_{1-4}$alkyl); wherein $R^R$ and $R^S$ are each independently selected from the group consisting of hydrogen and $C_{1-4}$alkyl;

wherein

is selected from the group consisting of phenyl, 5 to 6-membered saturated heterocyclyl and 5 to 6-membered heteroaryl;

e is an integer from 0 to 2;

each $R^8$ is independently selected from the group consisting of hydroxy, halogen, cyano, nitro, $C_{1-4}$alkyl, fluorinated $C_{1-4}$alkyl, hydroxy substituted $C_{1-4}$alkyl, $C_{1-4}$alkoxy, fluorinated $C_{1-4}$alkoxy, —$NR^TR^U$, —C(O)—$NR^TR^U$, —C(O)OH, —C(O)O—($C_{1-4}$alkyl), —($C_{1-4}$alkyl)-$NR^TR^U$, $C_{3-5}$cycloalkyl, —($C_{1-2}$alkyl)-($C_{3-5}$cycloalkyl), oxetanyl, —($C_{1-2}$alkyl)-oxetanyl, tetrahydofuranyl, —($C_{1-2}$alkyl)-tetrahydro-furanyl, tetrahydro-pyranyl and —($C_{1-2}$alkyl)-tetrahydro-pyranyl; wherein $R^T$ and $R^U$ are each independently selected from the group consisting of hydrogen and $C_{1-4}$alkyl;

provided that when

is a 5-membered heteroaryl, then

is bound at the 3-position, relative to the point of attachment of the

to the

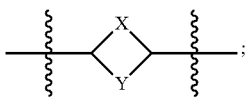

provided further than when

is phenyl or a 6-membered heteroaryl, then

is bound at the 3- or 4-position, relative to the point of attachment of the

to the

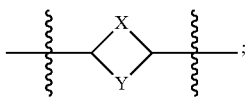

provided that when $R^1$ and $R^2$ are taken together with the carbon atom to which they are bound to form 1-(methoxycarbonyl)-azetidin-3-yl, m is 1 and n is 0 or m is 0 and n is 1;

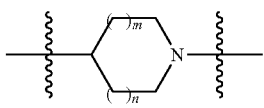

is pyrrolidin-3R-yl; -($L^1$)$_a$-$R^3$ is selected from the group consisting of —C(O)—CF, —C(O)-cyclopropyl, —C(O)-(thiazol-2-yl), —C(O)OCH$_3$ or —SO$_2$—CH$_3$,

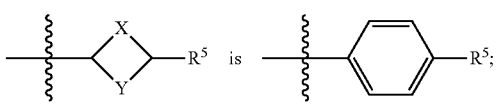

and b=0; then $R^5$ is other than quinolin-7-yl, benzofuran-5-yl, 1-methyl-indazol-5-yl, 1-methyl-pyrazol-4-yl, 4-(1-methyl-pyrazol-4-yl)-phenyl, 1,2,3,4,4a,8a-hexahydro-2-methyl-carbonyl-isoquinolin-6-yl) and 1,2,3,4-trihydro-2-methylcarbonyl-isoquinolin-2-yl;

provided further that when $R^1$ and $R^2$ are taken together with the carbon atom to which they are bound to form cyclopentyl; m is 1 and n is 0 or m is 0 and m is 1;

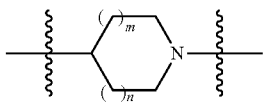

is pyrrolidin-3R-yl; -($L^1$)$_a$-$R^3$ is —C(O)-cyclopropyl;

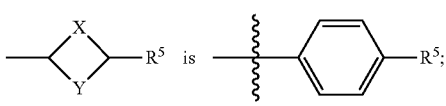

b=0 or ($R^4$)$_b$ is 2-methyl; then $R^5$ is other than 1-methyl-pyrazol-4-yl, 4-methyl-3,4-dihydro-pyrido[2,3-b]oxazon-7-yl, 2-(piperazin-1-yl)-pyridin-4-yl and 2-(4-methyl-piperazin-1-yl)-pyridin-4-yl;

provided further that when $R^1$ and $R^2$ are taken together with the carbon atom to which they are bound to form cyclopentyl; m is 1 and n is 0 or m is 0 and m is 1;

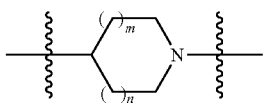

is pyrrolidin-3R-yl; -($L^1$)$_a$-$R^3$ is —SO$_2$-pyrrolidin-1-yl;

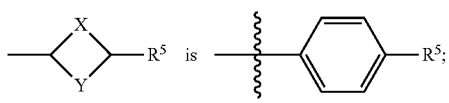

b=0 or (R⁴)$_b$ is 2-methyl; then R⁵ is other than benzofuran-5-yl;

provided further that when R¹ and R² are taken together with the carbon atom to which they are bound to form cyclopropyl; m is 0, n is 0,

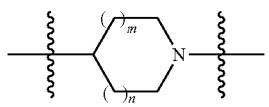

is azetidin-3-yl; -(L¹)$_a$-R³ is selected from the group consisting of —C(O)-cyclopropyl, —C(O)-(1-methyl-cyclopropyl) and —C(O)-(1-hydroxy-cyclopropyl);

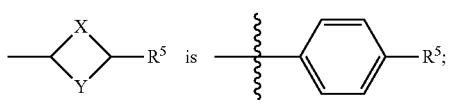

b=0 or (R⁴)$_b$ is selected from the group consisting of 2-fluoro and 2-methyl; then R⁵ is other than 1-isopropylsulfonyl-phenyl, 1-methyl-indazol-5-yl, 1-isopropyl-indazol-5-yl, 1-oxetan-3-yl, indazol-5-yl, 1-methyl-pyrazol-4-yl, 4-methyl-7-bromo-quinolin-2-yl, 5-(2-hydroxy-2-methyl-propyl)-pyridin-2-yl, 6-isopropyl-pyridin-3-yl, 6-(1-cyanomethyl)-pyridin-3-yl, 6-(2-hydroxy-2-methyl-propyl)-pyridin-3-yl, 1,5-naphthyridin-3-yl, 3-methyl-[1,2,4]triazolo[4,3-a]pyridin-6-yl, 4-(1-isobutyl-pyrazol-5-yl)-phenyl or 6-(morpholin-4-yl)-pyridin-3-yl;

provided further that when R¹ and R² are taken together with the carbon atom to which they are bound to form cyclopropyl; m is 0, n is 0,

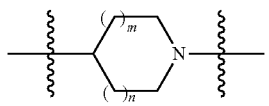

is azetidin-3-yl; -(L¹)$_a$-R³ is —C(O)-(1-hydroxy-cyclopropyl);

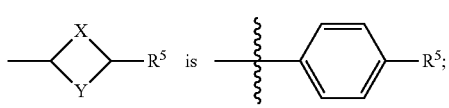

and (R⁴)$_b$ is 2-methyl; then R⁵ is other 1-methyl-indazol-5-yl;

provided further that when R¹ and R² are taken together with the carbon atom to which they are bound to form cyclopropyl; m is 0, n is 0,

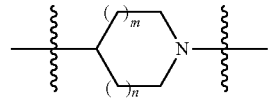

is azetidin-3-yl; -(L¹)$_a$-R³ is —C(O)-pyridin-3-yl;

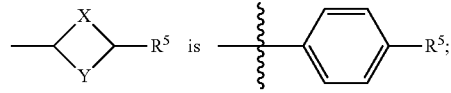

(R⁴)$_b$ is 2-methyl; then R⁵ is other than 1-methyl-indazol-5-yl;

provided further that when R¹ and R² are taken together with the carbon atom to which they are bound to form cyclopropyl; m is 0, n is 2,

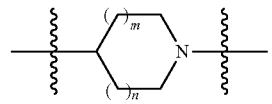

is piperidin-3R-yl or piperidin-3S-yl; -(L¹)$_a$-R³ is —C(O)-cyclopropyl;

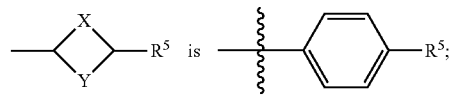

and b=0; then R⁵ is other than indazol-5-yl, benzofuran-5-yl, benzothien-5-yl, 1-methyl-indazol-5-yl, 4-(4-methylphenyl)phenyl or 4-(3-chlorophenyl)-phenyl;

provided further that when R¹ and R² are taken together with the carbon atom to which they are bound to form cyclopropyl; m is 1, n is 1,

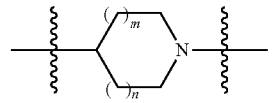

is piperidin-4-yl; -(L¹)$_a$-R³ is —C(O)-cyclopropyl;

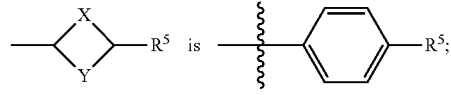

and b=0; then R⁵ is other than 4-trifluoromethyl-phenyl, 1-methyl-pyrazol-4-yl, benzoxazol-5-yl, pyridin-4-yl or 4-(1-methyl-pyrazol-4-yl)-phenyl;

provided further that when R¹ and R² are taken together with the carbon atom to which they are bound to form cyclopropyl; m is 0 and n is 1 or m is 1 and n is 0;

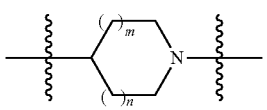

is pyrrolidin-3R-yl; -(L¹)ₐ-R³ is —C(O)-cyclopropyl;

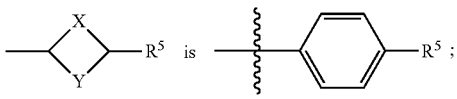

and b=0; then R⁵ is other than 5-chloro-pyridin-3-yl, 2-oxo-3,4-dihydro-quinolin-7-yl or 6-(4-methyl-piperazin-1-yl)-pyridin-3-yl;

provided further that when R¹ and R² are taken together with the carbon atom to which they are bound to form tetrahydrofuran-3,3-diyl or tetrahydropyran-4,4-diyl; m is an integer from 0 to 1 and n is 0 or m is 0 and n is an integer from 0 to 1;

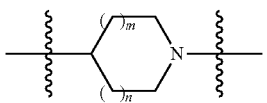

is selected from the group consisting of azetidin-3-yl, pyrrolidin-3R-yl and pyrrolidin-3-yl; -(L¹)ₐ-R³ is selected from the group consisting of —C(O)-thiazol-2-yl, —C(O)—CF₃, —C(O)OCH₃ and —SO₂—CH₃;

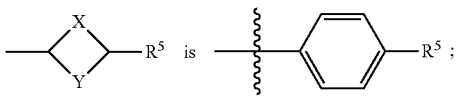

and b=0; then R⁵ is other than quinolin-7-yl, 1-methyl-indazol-5-yl, benzofuran-5-yl or 4-(1-methyl-pyrazol-4-yl)-phenyl;

and stereoisomers, tautomers, and pharmaceutically acceptable salts thereof.

The present invention is further directed to processes for the preparation of the compounds of formula (I), as described in more detail in the general synthesis schemes and examples below. The present invention is further directed to a product prepared according to any of the processes as described in the general synthesis schemes and examples below.

The present invention is further directed to intermediates in the synthesis of the compounds of formula (I), including, but not limited to, compounds of formula (XVII), compounds of formula (XXI), compounds of formula (XXIII), compounds of formula (XXV) and compounds of formula (XXVII), as described in more detail below.

Illustrative of the invention is a pharmaceutical composition comprising, consisting of and/or consisting essentially of a pharmaceutically acceptable carrier and the product prepared according to the process described herein. An illustration of the invention is a pharmaceutical composition made by mixing the product prepared according to the process described herein and a pharmaceutically acceptable carrier. Illustrating the invention is a process for making a pharmaceutical composition comprising, consisting of, and/or consisting essentially of mixing the product prepared according to the process described herein and a pharmaceutically acceptable carrier.

Exemplifying the invention are methods of treating a disorder mediated by inhibition of fatty acid synthase (FASN) enzyme (selected from the group consisting of cancer, obesity and related disorders, and liver related disorders, as defined below) comprising, consisting of, and/or consisting essentially of administering to a subject in need thereof a therapeutically effective amount of any of the compounds or pharmaceutical compositions described above.

In an embodiment, the present invention is directed to a compound of formula (I) for use as a medicament. In another embodiment, the present invention is directed to a compound of formula (I) for use in the treatment of a disorder mediated by inhibition of fatty acid synthase (FASN) enzyme (selected from the group consisting of cancer, obesity and related disorders, and liver related disorders, as defined below). In another embodiment, the present invention is directed to a composition comprising a compound of formula (I) for the treatment of a disorder mediated by inhibition of fatty acid synthase (FASN) enzyme (selected from the group consisting of cancer, obesity and related disorders and liver related disorders, as herein below).

Another example of the invention is the use of any of the compounds described herein in the preparation of a medicament for treating: (a) cancer, as defined below, (b) obesity or related disorder, (c) liver related disorder, in a subject in need thereof.

In another example, the present invention is directed to a compound as described herein for use in a methods for treating a disorder selected from the group consisting of cancer, obesity and related disorders, and liver related disorders, as herein defined, in a subject in need thereof,

DETAILED DESCRIPTION OF THE INVENTION

The present invention is directed to compounds of formula (I)

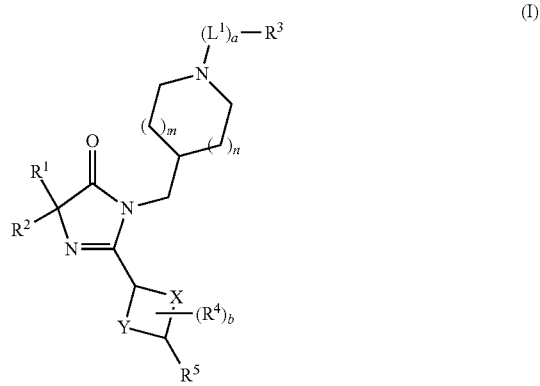

wherein R¹, R², R³, R⁴, R⁵, L¹, a, b, m, n, and

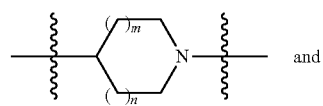

-continued

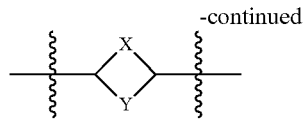

are as herein defined. The compounds of the present invention are FASN inhibitors useful in the treatment of, for example, cancer. More particularly, the compounds of formula (I) of the present invention are useful in the treatment of FASN-mediated disorders including, but not limited to, (a) cancer, as herein defined, (b) obesity and related disorders and (c) liver related disorders, as herein defined.

In a preferred embodiment, the present invention is directed to methods for the treatment of cancer comprising, consisting of, and/or consisting essentially of administering to a subjected in need thereof, a therapeutically effective amount of a compound of formula (I); wherein the cancer is selected from the group consisting of cancer of the breast, prostate, head, neck, skin, lung, ovary, endometrium, thyroid, colon, rectum, esophagus, stomach, kidney, liver, bladder, pancreas, brain, spinal cord, blood, and bone. Preferably, the cancer is selected from the group consisting of breast, prostate, colon, lung, brain, spinal cord, ovary, endometrium, thyroid, kidney, and stomach.

In another embodiment, the cancer is selected from the group consisting of glioma, glioblastoma, leukemia, Bannayan-Zonana syndrome, Cowden disease, Lhermitte-Duclos disease, breast cancer, inflammatory breast cancer, Wilm's tumor, Ewing's sarcoma, Rhabdomyosarcoma, ependymoma, medulloblastoma, sarcoma, osteosarcoma, melanoma, giant cell tumor of bone, and giant cell tumor of thyroid.

In another embodiment, the present invention is directed to methods for the treatment of obesity or a related disorder comprising, consisting of, and/or consisting essentially of administering to a subjected in need thereof, a therapeutically effective amount of a compound of formula (I); wherein the obesity or related disorder is selected from the group consisting of obesity, overweight, weight gain, Type II diabetes mellitus, Syndrome X, appetite and/or satiety modulation. Preferably, the obesity or related disorders is selected from the group consisting of obesity, Type II diabetes mellitus, Syndrome X, and appetite and/or satiety modulation, more preferably obesity or Type II diabetes mellitus.

In another embodiment, the present invention is directed to methods for the treatment of an liver related disorder comprising, consisting of, and/or consisting essentially of administering to a subjected in need thereof, a therapeutically effective amount of a compound of formula (I); wherein the liver related disorder is selected from the group consisting of dyslipidemia, elevated cholesterol levels, elevated LDL, decreased HDL, elevated triglicerides, fatty liver, non-alcoholic steatohepatitis (NASH), fatty liver, and/or non-alcoholic fatty liver disease (NAFLD). Preferably, the liver related disorder is selected from dylipidemia or elevated cholesterol levels.

In an embodiment, the present invention is directed to a pharmaceutical composition comprising, consisting of, and/or consisting essentially of a pharmaceutically acceptable carrier and a compound of formula (I). In another embodiment, the present invention is directed to a pharmaceutical composition made by mixing a compound of formula (I) and a pharmaceutically acceptable carrier. In another embodiment, the present invention is directed to a process for making a pharmaceutical composition comprising mixing a compound of formula (I) and a pharmaceutically acceptable carrier.

In an embodiment, the present invention is directed to a method of treating a disorder mediated by inhibition of fatty acid synthase (FASN) enzyme, comprising, consisting of, and/or consisting essentially of administering to a subject in need thereof a therapeutically effective amount of the compound of formula (I).

In another embodiment, the present invention is directed to a method of treating a disorder mediated by inhibition of fatty acid synthase (FASN) enzyme, wherein the disorder mediated by inhibition of fatty acid synthase (FASN) enzyme is a cancer selected from the group consisting of the breast, prostate, head, neck, skin, lung, ovary, endometrium, thyroid, colon, rectum, esophagus, stomach, kidney, liver, bladder, pancreas, brain, spinal cord, blood, and bone.

In another embodiment, the present invention is directed to a method of treating a disorder mediated by inhibition of fatty acid synthase (FASN) enzyme, wherein the disorder mediated by inhibition of fatty acid synthase (FASN) enzyme is selected from the group consisting of obesity, overweight, weight gain, Type II diabetes mellitus, Syndrome X, and appetite or satiety modulation.

In another embodiment, the present invention is directed to a method of treating a disorder mediated by inhibition of fatty acid synthase (FASN) enzyme, wherein the disorder mediated by inhibition of fatty acid synthase (FASN) enzyme is selected from the group consisting of dyslipidemia, elevated cholesterol levels, elevated LDL, decreased HDL, elevated triglicerides, fatty liver, non-alcoholic steatohepatitis (NASH), fatty liver and non-alcoholic fatty liver disease (NAFLD).

In an embodiment, the present invention is directed to a method of treating (a) cancer of the breast, prostate, head, neck, skin, lung, ovary, endometrium, thyroid, colon, rectum, esophagus, stomach, kidney, liver, bladder, pancreas, brain, spinal cord, blood or bone; (b) obesity or a related disorder selected from the group consisting of obesity, overweight, weight gain, Type II diabetes mellitus, Syndrome X, and appetite or satiety modulation; or (c) a liver related disorders selected from the group consisting of dyslipidemia, elevated cholesterol levels, elevated LDL, decreased HDL, elevated triglicerides, fatty liver, non-alcoholic steatohepatitis (NASH), fatty liver and non-alcoholic fatty liver disease (NAFLD); comprising, consisting of, and/or consisting essentially of administering to a subject in need thereof, a therapeutically effective amount of the compound of formula (I).

In another embodiment, the present invention is directed to a method of treating (a) cancer of the breast, prostate, head, neck, skin, lung, ovary, endometrium, thyroid, colon, rectum, esophagus, stomach, kidney, liver, bladder, pancreas, brain, spinal cord, blood or bone; (b) obesity or a related disorder selected from the group consisting of obesity, overweight, weight gain, Type II diabetes mellitus, Syndrome X, and appetite or satiety modulation; or (c) a liver related disorders selected from the group consisting of dyslipidemia, elevated cholesterol levels, elevated LDL, decreased HDL, elevated triglicerides, fatty liver, non-alcoholic steatohepatitis (NASH), fatty liver and non-alcoholic fatty liver disease (NAFLD); comprising, consisting of, and/or consisting essentially of administering to a subject in need thereof a therapeutically effective amount of a pharmaceutical composition comprising a compound of formula (I).

In an embodiment, the present invention is directed to the use of a compound formula (I) for the preparation of a medicament for treating: (a) cancer of the breast, prostate, head, neck, skin, lung, ovary, endometrium, thyroid, colon, rectum, esophagus, stomach, kidney, liver, bladder, pancreas, brain, spinal cord, blood or bone; (b) obesity or a related disorder selected from the group consisting of obesity, overweight, weight gain, Type II diabetes mellitus, Syndrome X, and appetite or satiety modulation; or (c) a liver related disorders selected from the group consisting of dyslipidemia, elevated cholesterol levels, elevated LDL, decreased HDL, elevated triglicerides, fatty liver, non-alcoholic steatohepatitis (NASH), fatty liver and non-alcoholic fatty liver disease (NAFLD); in a subject in need thereof.

In another embodiment, the present invention is directed to the use of a compound of formula (I), for use in a method for treating a disorder selected from the group consisting of (a) cancer of the breast, prostate, head, neck, skin, lung, ovary, endometrium, thyroid, colon, rectum, esophagus, stomach, kidney, liver, bladder, pancreas, brain, spinal cord, blood or bone; (b) obesity or a related disorder selected from the group consisting of obesity, overweight, weight gain, Type II diabetes mellitus, Syndrome X, and appetite or satiety modulation; or (c) a liver related disorders selected from the group consisting of dyslipidemia, elevated cholesterol levels, elevated LDL, decreased HDL, elevated triglicerides, fatty liver, non-alcoholic steatohepatitis (NASH), fatty liver and non-alcoholic fatty liver disease (NAFLD); in a subject in need thereof.

In another embodiment, the present invention is directed to a compound of formula (I) for use as a medicament. In another embodiment, the present invention is directed to a compound of formula (I) (as in Claim 1) for use in the treatment of a disorder mediated by inhibition of fatty acid synthase (FASN) enzyme. In another embodiment, the present invention is directed to a compound of formula (I), for use in the treatment of a disorder mediated by inhibition of fatty acid synthase (FASN) enzyme, selected from the group consisting of cancer of the breast, prostate, head, neck, skin, lung, ovary, endometrium, thyroid, colon, rectum, esophagus, stomach, kidney, liver, bladder, pancreas, brain, spinal cord, blood or bone. In another embodiment, the present invention is directed to a compound of formula (I), for use in the treatment of a disorder mediated by inhibition of fatty acid synthase (FASN) enzyme, selected from (a) obesity and related disorders or (b) liver related disorders.

In an embodiment, the present invention is directed to a composition comprising, consisting of, and/or consisting essentially of a compound of formula (I) for use in the treatment of a disorder mediated by inhibition of fatty acid synthase (FASN) enzyme.

In another embodiment, the present invention is directed to a composition comprising, consisting of, and/or consisting essentially of compound of formula (I) for use in the treatment of a disorder mediated by inhibition of fatty acid synthase (FASN) enzyme selected from the group consisting of (a) cancer of the breast, prostate, head, neck, skin, lung, ovary, endometrium, thyroid, colon, rectum, esophagus, stomach, kidney, liver, bladder, pancreas, brain, spinal cord, blood or bone; (b) obesity or a related disorder selected from the group consisting of obesity, overweight, weight gain, Type II diabetes mellitus, Syndrome X, and appetite or satiety modulation; and (c) a liver related disorders selected from the group consisting of dyslipidemia, elevated cholesterol levels, elevated LDL, decreased HDL, elevated triglicerides, fatty liver, non-alcoholic steatohepatitis (NASH), fatty liver and non-alcoholic fatty liver disease (NAFLD).

In an embodiment, the present invention is directed to compounds of formula (I)

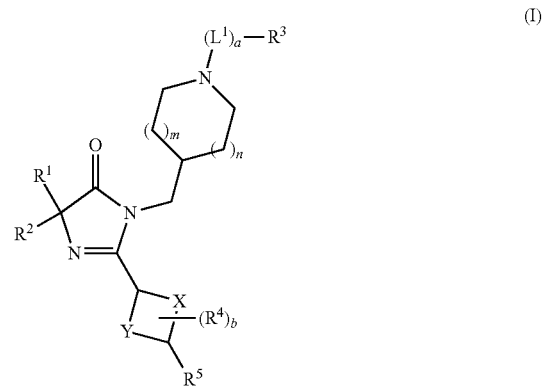

wherein
$R^1$ and $R^2$ are taken together with the carbon atom to which they are bound to form an optionally substituted ring structure selected from the group consisting of
(a) $C_{3-8}$cycloalkyl; wherein the $C_{3-8}$cycloalkyl is optionally substituted with one to two $R^{11}$ groups;
(b) benzo-fused $C_{5-6}$cycloalkyl; wherein the benzo-fused $C_{5-6}$cycloalkyl is bound through a carbon atom of the $C_{5-6}$cycloalkyl portion of the ring structure; wherein the benzo-fused $C_{5-6}$cycloalkyl is optionally substituted with one to two $R^{11}$ groups;
and (c) 4 to 8-membered, saturated heterocyclyl; wherein the 4 to 8-membered, saturated heterocyclyl contains one heteroatom selected from the group consisting of O, S and N; wherein the S is optionally substituted with one to two oxo; wherein the N is substituted with $R^{10}$; provided that the heteroatom is not present at the 2-position relative to the carbon atom of the imidazolin-5-one; and wherein the 4 to 8-membered, saturated heterocyclyl is optionally substituted with one $R^{11}$ group, and further optionally substituted with one $R^{12}$ group;
wherein $R^{10}$ is selected from the group consisting of hydrogen, $C_{1-4}$ alkyl, fluorinated $C_{1-4}$alkyl, —$CH_2$-(hydroxy substituted $C_{1-4}$alkyl), —($C_{2-4}$alkyl)-O—($C_{1-4}$alkyl), —($C_{1-4}$alkyl)-phenyl, —C(O)—$NR^AR^B$, —C(O)—($C_{1-3}$alkyl)-$NR^AR^B$, —C(O)—($C_{1-4}$alkyl), —C(O)—($C_{3-6}$cycloalkyl), —C(O)-phenyl, —C(O)-(5 to 6-membered heteroaryl),

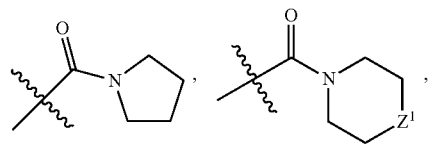

—C(O)O—($C_{1-4}$alkyl), —$SO_2$—($C_{1-4}$alkyl), —$SO_2$—$NR^AR^B$, phenyl and 5 to 6-membered heteroaryl;
wherein $Z^1$ is selected from the group consisting of —$CH_2$—, —O—, —$N(R^C)$—, —S—, —S(O)— and —$SO_2$—; wherein $R^A$, $R^B$ and $R^C$ are each independently selected from the group consisting of hydrogen and $C_{1-4}$alkyl;
and wherein the phenyl or 5 to 6-membered heteroaryl whether alone or as part of a substituent group, is further optionally substituted with one to two substituents independently selected from the group consisting of halogen, hydroxy, cyano, NR$^A$R$^B$, C$_{1-4}$alkyl, fluorinated C$_{1-4}$alkyl, C$_{1-4}$alkoxy and fluorinated C$_{1-4}$alkoxy;

wherein each R$^{11}$ is independently selected from the group consisting of hydroxy, oxo, halogen, C$_{1-4}$alkyl, fluorinated C$_{1-4}$alkyl, C$_{1-4}$alkoxy, fluorinated C$_{1-4}$alkoxy, hydroxy substituted C$_{1-4}$alkyl, —(C$_{1-4}$alkyl)-O—(C$_{1-4}$alkyl), —(C$_{1-4}$alkyl)-phenyl, -cyano, —NR$^D$R$^E$, —C(O)—NR$^D$R$^E$, —C(O)—(C$_{1-4}$alkyl), —C(O)-phenyl, —C(O)-(5 to 6-membered heteroaryl),

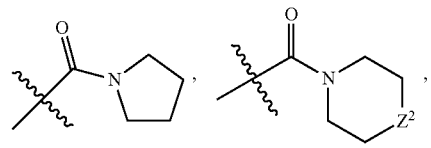

—C(O)OH, —C(O)O—(C$_{1-4}$alkyl), —SO$_2$—(C$_{1-4}$alkyl), —SO$_2$—NR$^D$R$^E$, phenyl and 5 to 6-membered heteroaryl;

wherein Z$^2$ is selected from the group consisting of —CH$_2$—, —O—, —N(R$^C$)—, S—, —S(O)— and —SO$_2$—; wherein R$^D$, R$^E$ and R$^F$ are each independently selected from the group consisting of hydrogen and C$_{1-4}$alkyl;

and wherein the phenyl or 5 to 6-membered heteroaryl whether alone or as part of a substituent group, is further optionally substituted with one to two substituents independently selected from the group consisting of halogen, hydroxy, cyano, NR$^D$R$^E$, C$_{1-4}$alkyl, fluorinated C$_{1-4}$alkyl, C$_{1-4}$alkoxy, and fluorinated C$_{1-4}$alkoxy;

and wherein R$^{12}$ is selected from the group consisting of hydroxy, oxo, halogen, C$_{1-4}$alkyl, fluorinated C$_{1-4}$ alkyl, C$_{1-4}$alkoxy, fluorinated C$_{1-4}$alkoxy, and hydroxy substituted C$_{1-4}$alkyl;

m is an integer from 0 to 1;
n is an integer from 0 to 1;

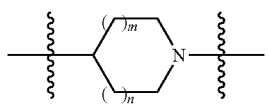

is selected from the group consisting of azetidin-3-yl, pyrrolidin-3-yl, pyrrolidin-3R-yl, pyrrolidin-3S-yl, and piperidin-4-yl;

a is an integer from 0 to 1;

L$^1$ is selected from the group consisting of —C(O)—, —C(O)—NR$^L$—, —C(S)—, —SO$_2$—, and —SO$_2$—NR$^L$—; wherein R$^L$ is selected from the group consisting of hydrogen and C$_{1-4}$alkyl;

R$^3$ is selected from the group consisting of C$_{1-4}$alkyl, fluorinated C$_{1-4}$alkyl, C$_{2-4}$alkenyl, C$_{3-8}$cycloalkyl, —(C$_{1-4}$alkyl)-(C$_{3-6}$cycloalkyl), 5 to 6-membered, saturated heterocyclyl, —(C$_{1-4}$ alkyl)-(5 to 6-membered, saturated heterocyclyl), —(C$_{2-4}$alkenyl)-(5 to 6-membered, saturated heterocyclyl), 5 to 6-membered heteroaryl, —(C$_{1-4}$alkyl)-(5 to 6-membered heteroaryl), and —(C$_{2-4}$alkenyl)-(5 to 6-membered heteroaryl);

wherein the C$_{3-6}$cycloalkyl, 5 to 6-membered, saturated heterocyclyl or 5 to 6-membered heteroaryl, whether alone or as part of a substituent group, is optionally substituted with one to two substituents independently selected from the group consisting of halogen, hydroxy, cyano, C$_{1-4}$alkyl, fluorinated C$_{1-4}$alkyl, C$_{1-4}$alkoxy, fluorinated C$_{1-4}$alkoxy, and NR$^G$R$^H$; wherein R$^G$ and R$^H$ are each independently selected from the group consisting of hydrogen and C$_{1-4}$alkyl;

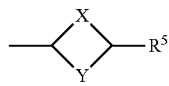

is selected from the group consisting of

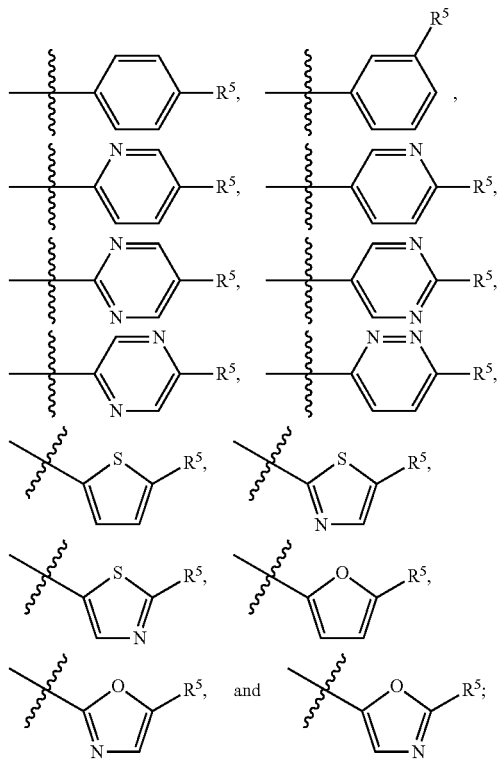

b is an integer from 0 to 2;

each R$^4$ is independently selected from the group consisting of hydroxy, halogen, C$_{1-4}$ alkyl, fluorinated C$_{1-4}$alkyl, C$_{1-4}$ alkoxy, fluorinated C$_{1-4}$alkoxy, cyano, and NR$^J$R$^K$; wherein R$^J$ and R$^K$ are each independently selected from the group consisting of hydrogen and C$_{1-4}$alkyl; provided that each R$^4$ group is bound to a carbon atom;

provided that when

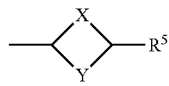

is selected from the group consisting of

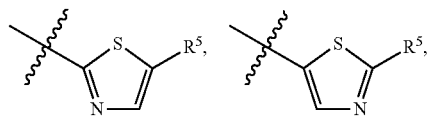

-continued

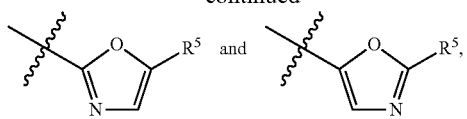

and substituted with —(R⁴)_b, then b is an integer from 0 to 1;

R⁵ is selected from

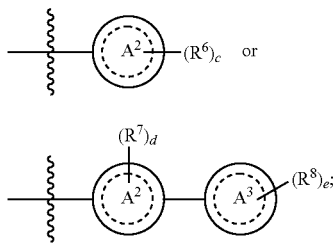

wherein

selected from the group consisting of aryl, heteroaryl, and partially unsaturated heterocyclyl;

c is an integer from 0 to 2;

each $R^6$ is independently selected from the group consisting of hydroxy, halogen, cyano, nitro, $C_{1-4}$alkyl, fluorinated $C_{1-4}$alkyl, hydroxy substituted $C_{1-4}$alkyl, $C_{1-4}$alkoxy, fluorinated $C_{1-4}$alkoxy, —NR$^M$R$^N$, —($C_{1-4}$alkyl)-NR$^P$R$^Q$, —C(O)—($C_{1-4}$alkyl), —C(O)—NR$^M$R$^N$, —C(O)OH, —C(O)O—($C_{1-4}$alkyl), —NR$^M$—C(O)H, —NR$^M$—C(O)—($C_{1-4}$alkyl), and —NR$^M$—SO$_2$—($C_{1-4}$alkyl);

wherein R$^M$ and R$^N$ are each independently selected from the group consisting of hydrogen and $C_{1-4}$alkyl;

wherein R$^P$ and R$^Q$ are each independently selected from hydrogen or $C_{1-4}$ alkyl; alternatively R$^P$ and R$^Q$ are taken together with the nitrogen atom to which they are bound to form a 5 to 6-membered saturated heterocyclyl; such 5 to 6-membered saturated heterocyclyl is optionally substituted with a substituent selected from the group consisting of halogen, $C_{1-4}$alkyl, and fluorinated $C_{1-4}$alkyl;

wherein

selected from the group consisting of phenyl and 5 to 6-membered heteroaryl;

d is an integer from 0 to 1;

R⁷ is selected from the group consisting of hydroxy, halogen, cyano, nitro, $C_{1-4}$alkyl, fluorinated $C_{1-4}$alkyl, hydroxy substituted $C_{1-4}$alkyl, $C_{1-4}$alkoxy, fluorinated $C_{1-4}$alkoxy, —NR$^R$R$^S$, —C(O)—NR$^R$R$^S$, —C(O)OH and —C(O)O—($C_{1-4}$alkyl); wherein R$^R$ and R$^S$ are each independently selected from the group consisting of hydrogen and $C_{1-4}$alkyl;

wherein

selected from the group consisting of phenyl and 5 to 6-membered heteroaryl;

e is an integer from 0 to 2;

each R⁸ is independently selected from the group consisting of hydroxy, halogen, cyano, nitro, $C_{1-4}$alkyl, fluorinated $C_{1-4}$alkyl, hydroxy substituted $C_{1-4}$alkyl, $C_{1-4}$alkoxy, fluorinated $C_{1-4}$alkoxy, —NR$^T$R$^U$, —C(O)—NR$^T$R$^U$, —C(O)OH, —C(O)O—($C_{1-4}$alkyl) and —($C_{1-4}$alkyl)-NR$^T$R$^U$;

wherein R$^T$ and R$^U$ are each independently selected from the group consisting of hydrogen and $C_{1-4}$alkyl;

provided that when

is a 5-membered heteroaryl, then

is bound at the 3-position, relative to the point of attachment of the

to the

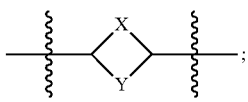

provided further than when

is phenyl or a 6-membered heteroaryl, then

is bound at the 3- or 4-position, relative to the point of attachment of the to the

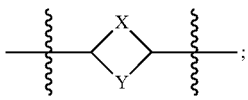

and a stereoisomer, a tautomer, and a pharmaceutically acceptable salt thereof.

In a preferred embodiment, the present invention is directed to compounds of formula (I) wherein $R^1$ and $R^2$ are taken together to form an optionally substituted ring structure selected from the group consisting of (a) $C_{3-6}$cycloalkyl; wherein the $C_{3-5}$cycloalkyl is optionally substituted with one $R^{11}$ group;

(b) benzo-fused $C_{5-6}$cycloalkyl; wherein the benzo-fused $C_{5-6}$cycloalkyl is bound through a carbon atom of the $C_{5-6}$cycloalkyl portion of the ring structure; and wherein the benzo-fused $C_{5-6}$cycloalkyl is optionally substituted with one $R^{11}$ group; and (c) 4 to 6-membered, saturated heterocyclyl; wherein the 4 to 6-membered, saturated heterocyclyl contains O or $NR^{10}$; provided that the O or $NR^{10}$ is not present at the 2-position relative to the carbon atom of the imidazolin-5-one; and wherein the 4 to 6-membered, saturated heterocyclyl containing the O or $NR^{10}$ is optionally substituted with one $R^1$ group and further optionally substituted with one $R^{12}$;

wherein $R^{10}$ is selected from the group consisting of hydrogen, $C_{1-4}$alkyl, fluorinated $C_{1-4}$alkyl, $CH_2$-(hydroxy substituted $C_{1-4}$alkyl), —($C_{2-4}$alkenyl), —($C_{1-4}$alkyl)-phenyl, —($C_2$alkyl)-O—($C_{1-4}$alkyl), —C(O)O—($C_{1-4}$alkyl), —C(O)—($C_{1-4}$alkyl), —C(O)-(fluorinated $C_{1-2}$alkyl), —C(O)—($C_{3-6}$cycloalkyl),

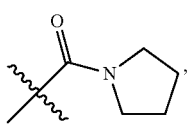 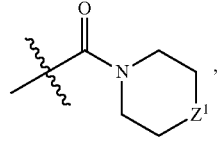

—C(O)—$NR^A R^B$, —$SO_2$—($C_{1-2}$alkyl); wherein $Z^1$ is selected from the group consisting of —$CH_2$—, —O— and —$N(R^C)$—; and wherein $R^A$, $R^B$ and $R^C$ are each independently selected from the group consisting of hydrogen and $C_{1-4}$alkyl;

wherein $R^{11}$ is independently selected from the group consisting of hydroxy, oxo, halogen, $C_{1-4}$alkyl, fluorinated $C_{1-4}$alkyl, $C_{1-4}$alkoxy, fluorinated $C_{1-4}$alkoxy, hydroxy substituted $C_{1-4}$alkyl, —($C_{1-4}$alkyl)-phenyl, -cyano, —$NR^D R^E$, —C(O)—$NR^D R^E$, —C(O)—($C_{1-4}$alkyl), —C(O)OH and —C(O)O—($C_{1-4}$alkyl);

wherein $R^{12}$ is selected from the group consisting of hydroxy, oxo, halogen, $C_{1-2}$alkyl, $CF_3$, $C_{1-2}$alkoxy, —$OCF_3$ and hydroxy substituted $C_{1-2}$alkyl;

m is an integer from 0 to 1; and n is an integer from 0 to 2; provided that when n is 2, then m is 0;

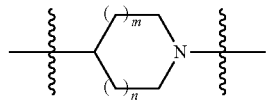

is selected from the group consisting of azetidin-3-yl, pyrrolidin-3-yl, pyrrolidin-3R-yl, pyrrolidin-3S-yl, piperidin-3-yl, piperidin-3S-yl, piperidin-3R-yl and piperidin-4-yl;

a is 1;

$L^1$ is selected from the group consisting of —C(O)—, —C(O)O—, —C(O)—$NR^L$— and —$SO_2$—; wherein $R^L$ is selected from the group consisting of hydrogen and methyl;

$R^3$ is selected from the group consisting of $C_{1-4}$alkyl, fluorinated $C_{1-2}$alkyl, hydroxy substituted $C_{1-4}$alkyl, $C_{2-4}$alkenyl, $C_{3-6}$cycloalkyl, 4 to 6-membered, saturated heterocyclyl, 5 to 6-membered heteroaryl and $NR^V R^W$; wherein $R^V$ and $R^W$ are each independently selected from the group consisting of hydrogen and $C_{1-2}$alkyl;

wherein the $C_{3-6}$cycloalkyl, 4 to 6-membered, saturated heterocyclyl or 5 to 6-membered heteroaryl, is optionally substituted with one to two substituents independently selected from the group consisting of halogen, hydroxy, cyano, $C_{1-4}$alkyl, fluorinated $C_{1-4}$alkyl, —($C_{1-2}$alkyl)-OH, $C_{1-4}$alkoxy, fluorinated $C_{1-4}$alkoxy and $NR^G R^H$; wherein $R^G$ and $R^H$ are each independently selected from the group consisting of hydrogen and $C_{1-4}$alkyl;

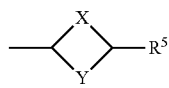

is selected from the group consisting of

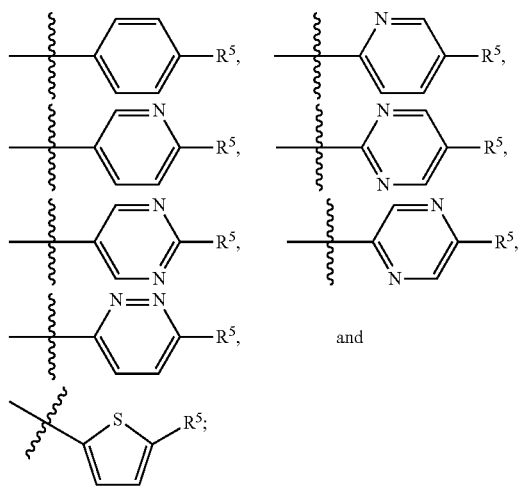

b is an integer from 0 to 1;

$R^4$ is selected from the group consisting of, halogen, $C_{1-4}$alkyl, fluorinated $C_{1-4}$alkyl, $C_{1-4}$alkoxy, fluorinated $C_{1-4}$alkoxy and $NR^J R^K$; wherein $R^J$ and $R^K$ are each independently selected from the group consisting of hydrogen and $C_{1-2}$alkyl; provided that the $R^4$ group is bound to a carbon atom;

$R^5$ is selected from the group consisting of (a)
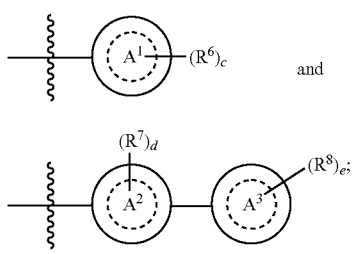
and (b)

wherein

selected from the group consisting of aryl, heteroaryl and partially unsaturated heterocyclyl;
c is an integer from 0 to 2;
each $R^6$ is independently selected from the group consisting of hydroxy, oxo, halogen, cyano, nitro, $C_{1-4}$alkyl, fluorinated $C_{1-4}$alkyl, hydroxy substituted $C_{1-4}$alkyl, cyano substituted ($C_{1-4}$alkyl), —($C_{1-2}$alkyl)-O—($C_{1-4}$alkyl), $C_{1-4}$alkoxy, fluorinated $C_{1-4}$alkoxy, —SO$_2$—($C_{1-4}$alkyl), —C(O)—($C_{1-4}$alkyl), —C(O)-(fluorinated $C_{1-2}$alkyl), —C(O)OH, —C(O)O—($C_{1-4}$alkyl), —C(O)—NR$^M$R$^N$, —NR$^M$R$^N$, —NR$^M$—C(O)H, —NR$^M$—SO$_2$—($C_{1-4}$alkyl), $C_{3-5}$cycloalkyl, 1-cyano-($C_{3-5}$cycloalkyl), —($C_{1-2}$alkyl)-($C_{3-5}$cycloalkyl), —S—($C_{3-5}$cycloalkyl), —SO$_2$—($C_{3-5}$cycloakyl), —NH—(—$C_{3-5}$cycloalkyl), —NH—SO$_2$—($C_{3-5}$cycloalkyl), oxetanyl and tetrahydro-furanyl;
wherein $R^M$ and $R^N$ are each independently selected from the group consisting of hydrogen and $C_{1-4}$alkyl; wherein

selected from the group consisting of phenyl and 5 to 6-membered heteroaryl;
d is an integer from 0 to 1;
$R^7$ is selected from the group consisting of hydroxy, halogen, cyano, $C_{1-4}$alkyl, fluorinated $C_{1-4}$alkyl, hydroxy substituted $C_{1-4}$alkyl, $C_{1-4}$alkoxy and fluorinated $C_{1-4}$alkoxy;
wherein

is selected from the group consisting of phenyl, 5 to 6-membered saturated heterocyclyl and 5 to 6-membered heteroaryl;
e is an integer from 0 to 2;
each $R^8$ is independently selected from the group consisting of hydroxy, halogen, cyano, $C_{1-4}$alkyl, fluorinated $C_{1-4}$alkyl, hydroxy substituted $C_{1-4}$alkyl, $C_{1-4}$alkoxy, fluorinated $C_{1-4}$alkoxy, —NR$^T$R$^U$, —C(O)—NR$^T$R$^U$, —C(O)OH, —C(O)O—($C_{1-4}$alkyl), —($C_{1-4}$alkyl)-NR$^T$R$^U$, $C_{3-5}$cycloalkyl, —($C_{1-2}$alkyl)-($C_{3-5}$cycloalkyl), oxetanyl, and tetrahydro-furanyl; wherein $R^T$ and $R^U$ are each independently selected from the group consisting of hydrogen and $C_{1-4}$alkyl;
provided that when

is a 5-membered heteroaryl, then

is bound at the 3-position, relative to the point of attachment of the

to the

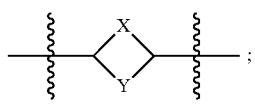
;

provided further than when

is phenyl or a 6-membered heteroaryl, then

is bound at the 3- or 4-position, relative to the point of attachment of the

to the

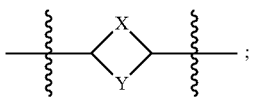

and a stereoisomer, a tautomer and a pharmaceutically acceptable salt thereof.

In another preferred embodiment, the present invention is directed to compounds of formula (I) wherein $R^1$ and $R^2$ are taken together to form an optionally substituted ring structure selected from the group consisting of (a) $C_{3-6}$cycloalkyl; wherein the $C_{3-6}$cycloalkyl is optionally substituted with one $R^{11}$ group;

(b) benzo-fused $C_{3-6}$cycloalkyl; wherein the benzo-fused $C_{5-6}$cycloalkyl is bound through a carbon atom of the $C_{5-6}$cycloalkyl portion of the ring structure; and wherein the benzo-fused $C_{5-6}$cycloalkyl is optionally substituted with one $R^{11}$ group;

and (c) 4 to 8-membered, saturated heterocyclyl; wherein the 4 to 8-membered, saturated heterocyclyl contains O or $NR^{10}$; provided that the O or $NR^{10}$ is not present at the 2-position relative to the carbon atom of the imidazolin-5-one; and wherein the 4 to 8-membered, saturated heterocyclyl containing the O or $NR^{10}$ is optionally substituted with one $R^{11}$ group and further optionally substituted with one $R^{12}$;

wherein $R^{10}$ is selected from the group consisting of hydrogen, $C_{1-4}$alkyl, fluorinated $C_{1-4}$alkyl, —$CH_2$-(hydroxy substituted $C_{1-4}$alkyl), —($C_{1-4}$alkyl)-phenyl, —C(O)—$NR^AR^B$, —C(O)—($C_{1-4}$alkyl), —C(O)—($C_{3-6}$cycloalkyl),

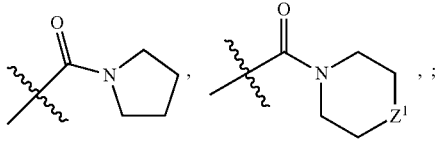

wherein $Z^1$ is selected from the group consisting of —$CH_2$—, —O— and —N($R^C$)—; and wherein $R^A$, $R^B$ and $R^C$ are each independently selected from the group consisting of hydrogen and $C_{1-4}$alkyl;

wherein $R^{11}$ is independently selected from the group consisting of hydroxy, oxo, halogen, $C_{1-4}$alkyl, fluorinated $C_{1-4}$alkyl, $C_{1-4}$alkoxy, fluorinated $C_{1-4}$alkoxy, hydroxy substituted $C_{1-4}$alkyl, —($C_{1-4}$alkyl)-phenyl, -cyano, —$NR^DR^E$, —C(O)—$NR^DR^E$, —C(O)—($C_{1-4}$alkyl), —C(O)OH and —C(O)O—($C_{1-4}$alkyl);

wherein $R^{12}$ is selected from the group consisting of hydroxy, oxo, halogen, $C_{1-2}$alkyl, $CF_3$, $C_{1-2}$alkoxy, —$OCF_3$ and hydroxy substituted $C_{1-2}$alkyl;

m is an integer from 0 to 1;
n is an integer from 0 to 1;

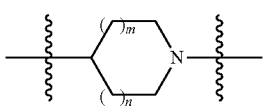

is selected from the group consisting of azetidin-3-yl, pyrrolidin-3-yl, pyrrolidin-3R-yl, pyrrolidin-3S-yl and piperidin-4-yl;

a is 1;

$L^1$ is selected from the group consisting of —C(O)—, —C(O)—$NR^L$— and —$SO_2$—; wherein $R^L$ is selected from the group consisting of hydrogen and methyl;

$R^3$ is selected from the group consisting of $C_{2-4}$alkenyl, $C_{3-6}$cycloalkyl, 5 to 6-membered, saturated heterocyclyl and 5 to 6-membered heteroaryl;

wherein the $C_{3-6}$cycloalkyl, 5 to 6-membered, saturated heterocyclyl or 5 to 6-membered heteroaryl, is optionally substituted with one to two substituents independently selected from the group consisting of halogen, hydroxy, cyano, $C_{1-4}$alkyl, fluorinated $C_{1-4}$alkyl, $C_{1-4}$alkoxy, fluorinated $C_{1-4}$alkoxy and $NR^GR^H$; wherein $R^G$ and $R^H$ are each independently selected from the group consisting of hydrogen and $C_{1-4}$alkyl;

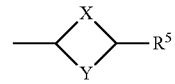

is selected from the group consisting of

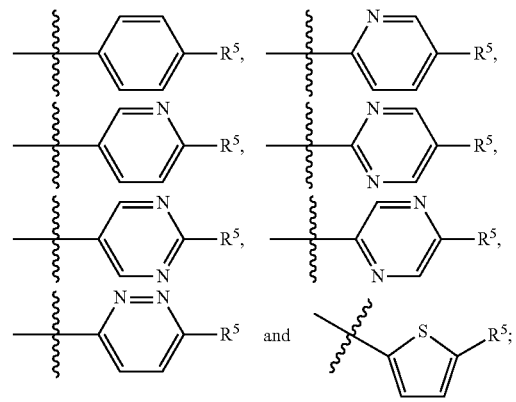

b is an integer from 0 to 1;

$R^4$ is selected from the group consisting of, halogen, $C_{1-4}$alkyl, fluorinated $C_{1-4}$alkyl, $C_{1-4}$alkoxy, fluorinated $C_{1-4}$alkoxy and $NR^JR^K$; wherein $R^J$ and $R^K$ are each independently selected from the group consisting of hydrogen and $C_{1-2}$alkyl; provided that the $R^4$ group is bound to a carbon atom;

$R^5$ is selected from the group consisting of

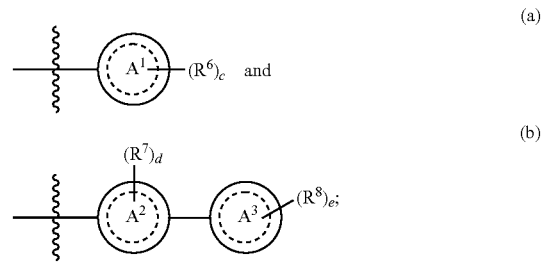

wherein

selected from the group consisting of aryl, heteroaryl and partially unsaturated heterocyclyl;

c is an integer from 0 to 2;

each $R^6$ is independently selected from the group consisting of hydroxy, halogen, cyano, nitro, $C_{1-4}$alkyl, fluorinated $C_{1-4}$alkyl, hydroxy substituted $C_{1-4}$alkyl, $C_{1-4}$alkoxy, fluorinated $C_{1-4}$alkoxy, —$NR^M R^N$, —C(O)—($C_{1-4}$alkyl), —C(O)—$NR^M R^N$, —C(O)OH, —C(O)O—($C_{1-4}$alkyl), —$NR^M$—C(O)H and —$NR^M$—$SO_2$—($C_{1-4}$alkyl);

wherein $R^M$ and $R^N$ are each independently selected from the group consisting of hydrogen and $C_{1-4}$alkyl;

wherein

selected from the group consisting of phenyl and 5 to 6-membered heteroaryl;

d is an integer from 0 to 1;

$R^7$ is selected from the group consisting of hydroxy, halogen, cyano, $C_{1-4}$alkyl, fluorinated $C_{1-4}$alkyl, hydroxy substituted $C_{1-4}$alkyl, $C_{1-4}$alkoxy and fluorinated $C_{1-4}$alkoxy;

wherein

is selected from the group consisting of phenyl and 5 to 6-membered heteroaryl;

e is an integer from 0 to 2;

each $R^8$ is independently selected from the group consisting of hydroxy, halogen, cyano, $C_{1-4}$alkyl, fluorinated $C_{1-4}$alkyl, hydroxy substituted $C_{1-4}$alkyl, $C_{1-4}$alkoxy, fluorinated $C_{1-4}$alkoxy, —$NR^T R^U$, —C(O)—$NR^T R^U$, —C(O)OH, —C(O)O—($C_{1-4}$alkyl) and —($C_{1-4}$alkyl)-$NR^T R^U$;

wherein $R^T$ and $R^U$ are each independently selected from the group consisting of hydrogen and $C_{1-4}$alkyl;

provided that when

is a 5-membered heteroaryl, then

is bound at the 3-position, relative to the point of attachment of the

to the

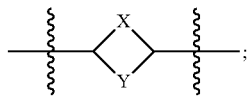

provided further than when

is phenyl or a 6-membered heteroaryl, then

is bound at the 3- or 4-position, relative to the point of attachment of the

to the

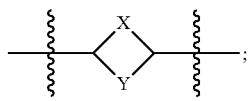

and a stereoisomer, a tautomer and a pharmaceutically acceptable salt thereof.

In another preferred embodiment, the present invention is directed to compounds of formula (I) wherein $R^1$ and $R^2$ are taken together to form an optionally substituted ring structure selected from the group consisting of (a) $C_{3-6}$cycloalkyl; and (c) 4 to 6-membered, saturated heterocyclyl; wherein the 4 to 6-membered saturated heterocyclyl contains $NR^{10}$; provided that the $NR^{10}$ is not present at the 2-position relative to the carbon atom of the imidazolidin-5-one;

wherein $R^{10}$ is selected from the group consisting of hydrogen, $C_{1-4}$alkyl, $C_{2-4}$alkenyl, —$CH_2$-(hydroxy substituted $C_{1-2}$alkyl), —$CH_2$-(phenyl), —($C_2$alkyl)-O—($C_{1-2}$alkyl), —C(O)—($C_{1-4}$alkyl), —C(O)-(fluorinated $C_{1-2}$alkyl), —C(O)-(cyclopropyl), —C(O)O—($C_{1-4}$alkyl), —C(O)—$NR^A R^B$, —$SO_2$—($C_{1-2}$alkyl), wherein $R^A$ and $R^B$ are each independently selected from the group consisting of hydrogen and methyl;

m is an integer from 0 to 1; and n is an integer from 0 to 2 provide that when n is 2, then m is 0

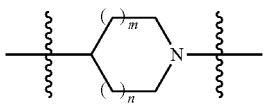

is selected from the group consisting of azetidin-3-yl, pyrrolidin-3-yl, pyrrolidin-3R-yl, pyrrolidin-3S-yl, piperidin-3-yl, piperidin-3R-yl, piperidin-3S-yl, and piperidin-4-yl;

a is 1;

$L^1$ is selected from the group consisting of —C(O)—, —C(O)O— and —SO$_2$—;

$R^3$ is selected from the group consisting of $C_{1-4}$alkyl, hydroxy substituted $C_{1-4}$alkyl, fluorinated $C_{1-2}$alkyl, $C_{2-4}$alkenyl, $C_{3-5}$cycloalkyl, 4 to 5-membered, saturated heterocyclyl, 5 to 6-membered heteroaryl and NR$^V$R$^W$; wherein the $C_{3-5}$cycloalkyl, 4 to 5-membered, saturated heterocyclyl or 5 to 6-membered heteroaryl is optionally substituted with a substituent selected from the group consisting of halogen, hydroxy, $C_{1-2}$alkyl, ($C_{1-2}$alkyl)-OH, fluorinated $C_{1-2}$alkyl, cyano and NH$_2$; and wherein R$^V$ and R$^W$ are each independently selected from the group consisting of hydrogen and methyl;

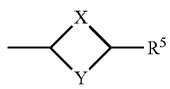

is selected from the group consisting of

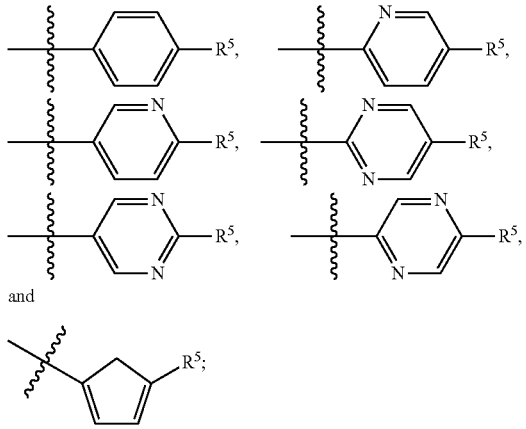

b is an integer from 0 to 1;

$R^4$ is selected from the group consisting of halogen, $C_{1-2}$alkyl and $C_{1-2}$alkoxy;

$R^5$ is selected from the group consisting of (a)

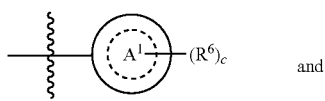 and (b)

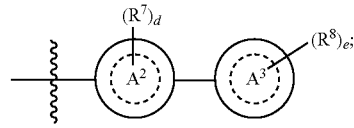

wherein

selected from the group consisting of phenyl, naphthyl, 5 to 6-membered heteroaryl, 9 to 10-membered heteroaryl and partially unsaturated 9 to 10-membered heterocyclyl;

c is an integer from 0 to 2;

each $R^6$ is independently selected from the group consisting of hydroxy, oxo, halogen, cyano, $C_{1-4}$alkyl, fluorinated $C_{1-4}$alkyl, hydroxy substituted $C_{1-4}$alkyl, cyano-substituted $C_{1-2}$alkyl, —($C_{1-2}$alkyl)-O—($C_{1-2}$alkyl), $C_{1-4}$alkoxy, fluorinated $C_{1-2}$alkoxy, —SO$_2$—($C_{1-4}$alkyl), —CO$^2$H, —C(O)O—($C_{1-2}$alkyl), —C(O)—($C_{1-2}$alkyl), —C(O)-(fluorinated $C_{1-2}$alkyl), —C(O)—NR$^M$R$^N$, —NR$^M$R$^N$, —NR$^M$—C(O)H, —R$^M$—SO$_2$—($C_{1-2}$alkyl), $C_{3-5}$ cycloalkyl, 1-cyano-cyclopropyl, —($C_{1-2}$alkyl)-($C_{3-5}$cycloalkyl), —S—($C_{3-5}$cycloalkyl), —S—($C_{3-5}$cycloalkyl), —SO$_2$alkyl)-NH—C(O)—($C_{3-5}$cycloalkyl) and —NH—SO$_2$—($C_{3-5}$cycloalkyl) and oxetan-3-yl; and wherein R$^M$ and R$^N$ are each independently selected from the group consisting of hydrogen and $C_{1-2}$alkyl;

wherein

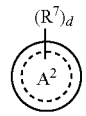

is selected from the group consisting of phenyl and 6-membered, nitrogen containing heteroaryl;

wherein

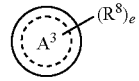

is selected from the group consisting of phenyl, 5 to 6-membered, saturated, nitrogen containing heterocyclyl and 5 to 6-membered, nitrogen containing heteroaryl;

e is an integer from 0 to 1;

$R^8$ is selected from the group consisting of halogen, $C_{1-4}$alkyl, $C_{3-5}$cycloalkyl, —($C_{1-2}$alkyl)-($C_{3-5}$cycloalkyl) and oxetanyl;

provided that the

is bound at the 3- or 4-position of the

relative to the point of attachment of the

to the

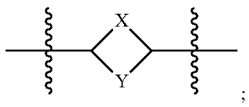
;

and a stereoisomer, a tautomer and a pharmaceutically acceptable salt thereof.

In another preferred embodiment, the present invention is directed to compounds of formula (I) wherein, $R^1$ and $R^2$ are taken together to form an optionally substituted ring structure selected from the group consisting of (a) $C_{3-6}$cycloalkyl; and (c) 4 to 6-membered, saturated heterocyclyl; wherein the 4 to 6-membered saturated heterocyclyl contains $NR^{10}$; provided that the $NR^{10}$ is not present at the 2-position relative to the carbon atom of the imidazolidin-5-one; wherein $R^{10}$ is selected from the group consisting of hydrogen, $C_{1-4}$alkyl, —CH$_2$-(hydroxy substituted $C_{1-2}$alkyl), —CH$_2$-(phenyl), —C(O)—($C_{1-4}$alkyl), —C(O)-(cyclopropyl) and —C(O)—$NR^AR^B$; wherein $R^A$ and $R^B$ are each independently selected from the group consisting of hydrogen and methyl;

m is an integer from 0 to 1;
n is an integer from 0 to 1;

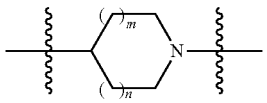

is selected from the group consisting of azetidin-3-yl, pyrrolidin-3R-yl, pyrrolidin-3S-yl and piperidin-4-yl;

a is 1;

$L^1$ is selected from the group consisting of —C(O)— and —SO$_2$—;

$R^3$ is selected from the group consisting of $C_2$alkenyl, $C_3$cycloalkyl, 5-membered, saturated heterocyclyl and 5-membered heteroaryl; wherein the $C_3$cycloalkyl, 5-membered, saturated heterocyclyl or 5-membered heteroaryl is optionally substituted with a substituent selected from the group consisting of halogen, $C_{1-2}$alkyl, fluorinated $C_{1-2}$alkyl and cyano;

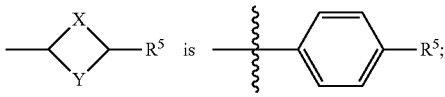

b is an integer from 0 to 1;

$R^4$ is selected from the group consisting of halogen, $C_{1-2}$alkyl and $C_{1-2}$alkoxy;

$R^5$ is selected from the group consisting of

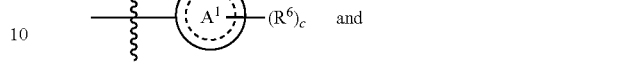

wherein

selected from the group consisting of phenyl, heteroaryl and partially unsaturated heterocyclyl;

c is an integer from 0 to 2;

each $R^6$ is independently selected from the group consisting of hydroxy, halogen, cyano, $C_{1-2}$alkyl, fluorinated $C_{1-2}$alkyl, $C_{1-2}$alkoxy, fluorinated $C_{1-2}$alkoxy, —NR$^M$R$^N$, —C(O)—($C_{1-2}$alkyl), —NR$^M$—C(O)H and —NR$^M$—SO$_2$—($C_{1-2}$alkyl); and wherein $R^M$ and $R^N$ are each independently selected from the group consisting of hydrogen and $C_{1-2}$alkyl;

wherein

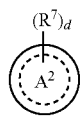

is phenyl;

wherein

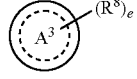

is selected from the group consisting of phenyl and 5 to 6-membered, nitrogen containing heteroaryl;

e is an integer from 0 to 1;

$R^8$ is selected from the group consisting of halogen and $C_{1-2}$alkyl;

provided than when

is phenyl, then

is bound at the 3- or 4-position, relative to the point of attachment of the

to the

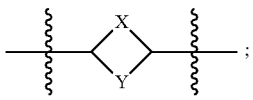

and a stereoisomer, a tautomer and a pharmaceutically acceptable salt thereof.

In another preferred embodiment, the present invention is directed to compounds of formula (I) wherein $R^1$ and $R^2$ are taken together to form a ring structure selected from the group consisting of cyclopropyl, cyclopentyl, piperidin-4,4-diyl, 1-(methyl)-piperidin-4,4-diyl, 1-(isopropyl)-piperidin-4,4-diyl, 1-(ethenyl)-piperidin-4,4-diyl, 1-(2-hydroxy-ethyl)-piperidin-4,4-diyl, 1-(methoxy-carbonyl)-piperidin-4,4-diyl, 1-(benzyl)-piperidin-4,4-diyl, 1-(methyl-carbonyl)-piperidin-4,4-diyl, 1-(isopropyl-carbonyl)-piperidin-4,4-diyl, 1-(trifluoromethyl-carbonyl)-piperidin-4,4-diyl, 1-(cyclopropyl-carbonyl)-piperidin-4,4-diyl, 1-(dimethylamino-carbonyl)-piperidin-4,4-diyl, 1-(methylsulfonyl)-piperidin-4,4-diyl, 1-(2-methoxy-ethyl)-piperidin-4,4-diyl, 1-(benzyl)-piperidin-4,4-diyl, tetrahydro-pyran-4,4-diyl, tetrahydro-furan-3,3-diyl and 1-(methoxycarbonyl)-azetidin-3,3-diyl;

m is an integer from 0 to 1; and n is an integer from 0 to 2; provided that when n is 2 then m is 1;

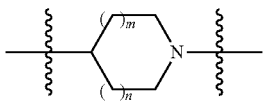

is selected from the group consisting of azetidin-3-yl, pyrrolidin-3-yl, pyrrolidin-3R-yl, pyrrolidin-3S-yl, piperidin-3R-yl, piperidin-3S-yl and piperidin-4-yl;

a is 1;

$L^1$ is selected from the group consisting of —C(O)—, —C(O)O— and —SO$_2$—;

$R^3$ is selected from the group consisting of methyl, ethyl, isopropyl, 1-hydroxyethyl, trifluoromethyl, 2,2,2-trifluoroethyl, 2-hydroxy-propan-2-yl. 3-hydroxy-2-methyl-propan-2-yl, ethenyl, cyclopropyl, 1-fluoro-cyclopropyl, 1-hydroxy-cyclopropyl, 1-hydroxymethyl-cyclopropyl, 1-methyl-cyclopropyl, 1-cyano-cyclopropyl, 1-amino-cyclopropyl, cyclobutyl, 1-methyl-cyclobutyl, amino, dimethylamino, pyrrolidin-1-yl, 1-methyl-pyrazol-3-yl, thiazol-2-yl, tetrahydro-furan-2-yl, tetrahydro-furan-2R-yl, oxetan-2-yl, oxetan-3-yl, 3-methyl-oxetan-3-yl, and pyridin-3-yl;

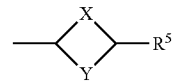

is selected from the group consisting of

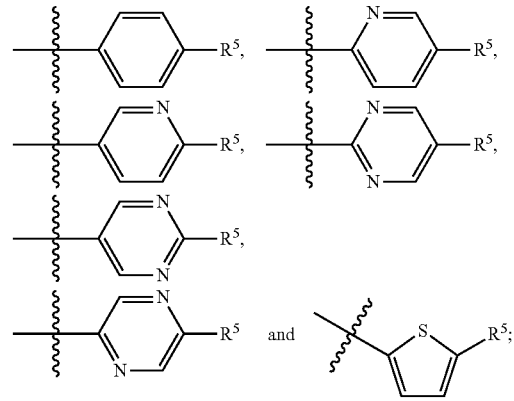

b is an integer from 0 to 1;

$R^4$ is selected from the group consisting of 2-fluoro, 3-fluoro, 2-chloro, 3-chloro, 2-methyl, 3-methyl and 2-methoxy;

$R^5$ is selected from the group consisting of

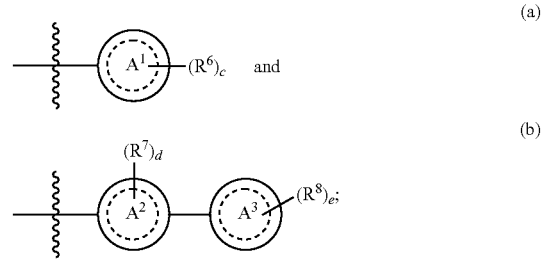

wherein

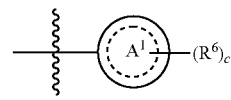

is selected from the group consisting of 3-cyano-phenyl, 4-cyano-phenyl, 3-hydroxy-phenyl, 4-hydroxy-phenyl, 3-fluoro-phenyl, 4-fluoro-phenyl, 3-chloro-phenyl, 4-chloro-phenyl, 2-fluoro-4-chloro-phenyl, 3-chloro-4-fluoro-phenyl, 2-fluoro-4-cyano-phenyl, 2-fluoro-4-(1-cyano-cuclopropyl)-phenyl, 2-fluoro-5-trifluoromethyl-phenyl, 2,4-dichloro-phenyl, 3-methyl-phenyl, 4-methyl-phenyl, 3-trifluoromethyl-phenyl, 4-trifluoromethyl-phenyl, 2-methoxy-phenyl, 3-methoxy-phenyl, 4-methoxy-phenyl, 3-trifluoromethoxy-phenyl, 4-trifluoromethoxy-phenyl, 4-(methylcarbonyl)-phenyl, 3-dimethylamino-phenyl, 4-dimethylamino-phenyl, 3-methylsulfonyl-amino-phenyl, 3-amino-4-hydroxy-phenyl, 3-formamido-4-hydroxy-phenyl 3-(cyclopropylthio)-phenyl, 3-(cyclopropylsulfonyl)-phenyl, 3-(cyclopropylcarbonyl-amino)-phenyl, 3-(cyclopropylsulfonyl-amino)-phenyl, 3-(methylsulfonyl)-phenyl, 3-(isopropylsulfonyl)-phenyl, 3-(aminocarbonyl)-phenyl, 3-carboxy-phenyl, 3-(methoxycarbonyl)-phenyl, naphth-2-yl, 6-fluoro-naphth-2-yl, 7-fluoro-naphth-2-yl, 8-fluoro-naphth-2-yl, 6-chloro-naphth-2-yl, 6-methyl-naphth-2-yl, 6-methoxy-naphth-2-yl, 8-methoxy-naphth-2-yl, 6-isopropyloxy-naphth-2-yl, 2-cyano-naphth-7-yl, 6-cyano-naphth-2-yl, 7-cyano-naphth-2-yl, 5-methoxy-naphth-2-yl, 7-methoxy-naphth-2-yl, 1,5-naphthyridin-3-yl, 1,8-naphthyridin-2-yl, 1,8-naphthyridin-3-yl, chroman-6-yl, isochroman-6-yl, isochroman-7-yl, pyridin-2-yl, pyridin-3-yl, pyridin-4-yl, 6-isopropyl-pyridin-3-yl, 6-n-propyl-pyridin-3-yl, 5-bromo-pyridin-2-yl, 5-chloro-pyridin-3-yl, 5-(2-hydroxy-2-methyl-propyl)-pyridin-2-yl, 5-(2-hydroxy-2-methyl-propyl-propyl)-pyridin-3-yl, 6-cyclopropyl-pyridin-3-yl, 6-(1-cyano-cyclopropyl)-pyridin-3-yl, 2-amino-pyrid-4-yl, 5-amino-pyridin-3-yl, 6-amino-pyridin-2-yl, 1-methyl-pyrazol-4-yl, 1-methyl-pyrazol-5-yl, indol-3-yl, indol-4-yl, indol-5-yl, indol-6-yl, 1-methyl-indol-5-yl, 1-methyl-indol-6-yl, 2-methyl-indol-5-yl, 2-hydroxymethyl-indol-5-yl, 3-(2-hydroxyethyl)-indol-5-yl, 3-cyanomethyl-indol-5-yl, 1,2-dimethyl-indol-5-yl, 1,3-dimethyl-indol-5-yl, 2,3-dimethyl-indol-5-yl, 1-methyl-3-(2-hydroxyethyl)-indol-5-yl, 1-(trifluoromethyl-carbonyl)-indol-5-yl, 2-oxo-indolin-5-yl, quinolin-2-yl, quinolin-3-yl, quinolin-5-yl, quinolin-6-yl, quinolin-7-yl, 2-chloro-quinolin-7-yl, 3-chloro-quinolin-7-yl, 4-chloro-quinolin-7-yl, 6-fluoro-quinolin-2-yl, 8-fluoro-quinolin-2-yl, 7-bromo-quinolin-2-yl, 2-hydroxy-quinolin-3-yl, 2-cyano-quinolin-6-yl, 2-cyano-quinolin-7-yl, 6-cyano-quinolin-2-yl, 2-methyl-quinolin-5-yl, 2-methyl-quinolin-6-yl, 2-methyl-quinolin-7-yl, 4-methyl-quinolin-7-yl, 2,4-dimethyl-quinolin-7-yl, 2-chloro-3-methyl-quinolin-7-yl, 2-chloro-4-methyl-quinolin-7-yl, 2-methyl-8-fluoro-quinolin-2-yl, 2-methyl-quinolin-7-yl, 2-methyl-7-bromo-quinolin-7-yl, 3-methyl-7-bromo-quinolin-7-yl, 2-methyl-4-chloro-quinolin-7-yl, 4-methyl-7-bromo-quinolin-2-yl, 2-trifluoromethyl-quinolin-7-yl, 2-oxo-quinolin-7-yl, 2-carboxy-quinolin-7-yl, 2-aminocarbonyl-quinolin-7-yl, isoquinolin-3-yl, isoquinolin-5-yl, isoquinolin-6-yl, isoquinolin-7-yl, 1-chloro-isoquinolin-6-yl, 3-chloro-isoquinolin-6-yl, 3-fluoro-isoquinolin-6-yl, 6-bromo-isoquinolin-3-yl, 1-methoxy-isoquinolin-6-yl, 3-methoxy-isoquinolin-6-yl, 1-amino-isoquinolin-6-yl, 3-amino-isoquinolin-6-yl, 1-oxo-isoquinolin-6-yl, quinazlin-7-yl, quinoxalin-6-yl, indazol-3-yl, indazol-4-yl, indazol-5-yl, indazol-6-yl, 4-chloro-indazol-5-yl, 1-methyl-indazol-3-yl, 1-methyl-indazol-4-yl, 1-methyl-indazol-5-yl, 1-methyl-indazol-6-yl, 2-methyl-indazol-4-yl, 2-methyl-indazol-5-yl, 2-methyl-indazol-6-yl, 1,3-dimethyl-indazol-5-yl, 1,4-dimethyl-indazol-5-yl, 1,7-dimethyl-indazol-5-yl, 1,8-dimethyl-indazol-5-yl, 1-ethyl-indazol-5-yl, 2-ethyl-indazol-5-yl, 1-isopropyl-indazol-5-yl, 2-isopropyl-indazol-5-yl, 1-(2-hydroxyethyl)-indazol-5-yl, 2-(2-hydroxyethyl)-indazol-5-yl, 1-(2-hydroxyethyl)-6-fluoro-indazol-5-yl, 2-(2-hydroxyethyl)-6-fluoroindazol-5-yl, 1-methyl-3-chloro-indazol-5-yl, 1-methyl-3-chloro-indazol-6-yl, 1-methyl-3-amino-indazol-6-yl, 1-methyl-3-aminocarbonyl-indazol-6-yl, 1-methyl-3-cyano-indazol-5-yl, 1-methyl-3-cyano-indazol-6-yl, 1-methyl-3-methoxy-indazol-5-yl, 1-methyl-3-methoxymethyl-indazol-5-yl, 1-methyl-3-methoxymethyl-indazol-6-yl, 1-methyl-7-methoxymethyl-indazol-4-yl, 1-methyl-3-hydroxymethyl-indazol-5-yl, 1-methyl-3-hydroxymethyl-indazol-6-yl, 1-methyl-7-hydroxymethyl-indazol-4-yl, 1-methyl-3-cyclopropyl-indazol-5-yl, 2-methyl-3-cyano-indazol-5-yl, 2-methyl-3-hydroxymethyl-indazol-5-yl, 2-methyl-3-methoxymethyl-indazol-5-yl, 1-(2-hydroxyethyl)-indazol-5-yl, 2-(2-hydroxyethyl)-indazol-5-yl), 1-(2-cyanoethyl)-indazol-5-yl, 2-(2-cyanoethyl)-indazol-5-yl, 1-oxetan-3-yl-indazol-5-yl, 1-cyclopropyl-indazol-5-yl, 1-cyclopropylmethyl-indazol-5-yl, 2-cyclopropylmethyl-indazol-5-yl, benzofuran-5-yl, benzofuran-6-yl, 2-methyl-benzofuran-5-yl, 2,3-dimethyl-benzofuran-5-yl, 2-cyano-benzofuran-5-yl, benzimidazol-2-yl, benzimidazol-5-yl, 1-methyl-benzimidazol-2-yl, 1,2-dimethyl-benzimidazol-6-yl, 1-methyl-6-fluoro-benzimidazol-2-yl, 2-oxo-benzimidazol-5-yl, benzoxazol-2-yl, benzoxazol-5-yl, 6-chloro-benzoxazol-2-yl, benzisoxazol-5-yl, benzthiazol-2-yl, benzthiazol-5-yl, 5-fluoro-benzothiazol-2-yl, 6-fluoro-benzothiazol-2-yl, 5-chloro-benzothiazol-2-yl, 6-chloro-benzothiazol-2-yl, 5,6-difluoro-benzothiazol-2-yl, 2-methyl-benzothiazol-5-yl, 2-methyl-benzothiazol-6-yl, 6-methyl-benzothiazol-2-yl, 2-methyl-benzothiazol-5-yl, 5-cyano-benzothiazol-2-yl, 6-cyano-benzothiazol-2-yl, benzothien-5-yl, 2-methyl-benzothien-5-yl, 2,3-dimethyl-benzothien-5-yl, 2,3-dihydro-benzofuran-5-yl, 2-oxo-3,4-dihydro-quinolin-7-yl, 1,2,3,4-tetrahydro-2-methylcarbonyl-isoquinolin-6-yl, 1,2,3,4,4a,8a-hexahydro-2-methyl-carbonyl-isoquinolin-6-yl, 2,3-dihydro-benzo[1,4]dioxin-6-yl, 2,3-dihydrobenzofuran-5-yl, 1,2-dimethyl-1,2-dihydro-3-oxo-indazol-5-yl, 2-oxo-3,4-dihydro-quinolin-6-yl, benzo[1,3]dioxol-5-yl, pyrrolo[2,3-b]pyridin-5-yl, 1-methyl-pyrazolo[4,3-b]pyridin-5-yl, [1,2,4]triazo[4,3-a]pyridin-6-yl, 3-methyl-[1,2,4]triazo[4,3-a]pyridin-6-yl and 4-methyl-3,4-dihydro-pyrido[3,2-b][1,4]oxazin-7-yl;

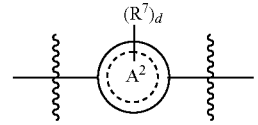

is selected from the group consisting of phenyl, pyridin-3-yl and pyridin-4-yl;

and

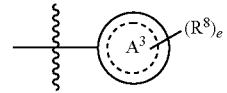

is selected from the group consisting of 4-bromo-phenyl, 3-chloro-phenyl, 4-methyl-phenyl, pyridin-3-yl, pyridin-4-yl, 1-methyl-pyrazol-3-yl, 1-methyl-pyrazol-4-yl, 1-methyl-pyrazol-5-yl, 1-isopropyl-pyrazol-4-yl, 1-isobutyl-pyrazol-5-yl, 1-(2-methylpropyl)-pyrazol-3-yl, 1-cyclopropyl-pyrazol-4-yl, 1-cyclobutyl-pyrazol-4-yl, 1-cyclopropylmethyl-pyrazol-3-yl, 1-cyclopropylmethyl-pyrazol-5-yl, 1,2,3,4-tetrazol-5-yl, pyrazol-3-yl, pyrrolidin-1-yl, morpholin-4-yl, 4-methyl-piperazin-1-yl, imidazol-1-yl, piperazin-1-yl, 4-methyl-piperazin-1-yl, and 1-(oxetan-3-yl)-pyrazol-4-yl;

provided that when

is phenyl or pyridin-3-yl, then

is bound to

at the 4-position, relative to the point of attachment of the

to the

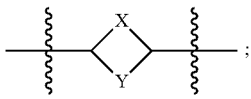

provided further that when

is pyridin-4-yl, then

is bound to

at the 3-position, relative to the point of attachment of the

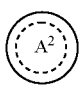

to the

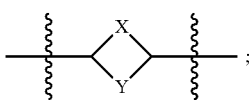

and a stereoisomer, a tautomer and a pharmaceutically acceptable salt thereof.

In another preferred embodiment, the present invention is directed to compounds of formula (I) wherein, $R^1$ and $R^2$ are taken together to form a ring structure selected from the group consisting of cyclopropyl, cyclopentyl, piperidin-4,4-diyl, 1-(methyl)-piperidin-4,4-diyl, 1-(isopropyl)-piperidin-4,4-diyl, 1-(2-hydroxy-ethyl)-piperidin-4,4-diyl, 1-(methoxy-carbonyl)-piperidin-4,4-diyl, 1-(benzyl)-piperidin-4,4-diyl, 1-(methyl-carbonyl)-piperidin-4,4-diyl, 1-(isopropyl-carbonyl)-piperidin-4,4-diyl, 1-(cyclopropyl-carbonyl)-piperidin-4,4-diyl and 1-(dimethylamino-carbonyl)-piperidin-4,4-diyl;

m is an integer from 0 to 1; n is an integer from 0 to 1;

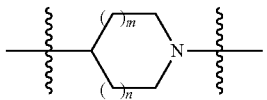

is selected from the group consisting of azetidin-3-yl, pyrrolidin-3R-yl, pyrrolidin-3S-yl and piperidin-4-yl; a is 1; $L^1$ is selected from the group consisting of —C(O)— and —SO$_2$—; $R^3$ is selected from the group consisting of 2,2,2-trifluoroethyl, ethenyl, cyclopropyl, 1-fluoro-cyclopropyl, 1-methyl-cyclopropyl, 1-cyano-cyclopropyl, pyrrolidin-1-yl, 1-methyl-pyrazol-3-yl and tetrahydro-furan-2-yl;

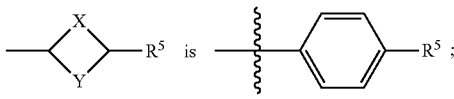

b is an integer from 0 to 1; $R^4$ is selected from the group consisting of 2-fluoro, 2-methyl, 3-methyl and 2-methoxy; $R^5$ is selected from the group consisting of (a)

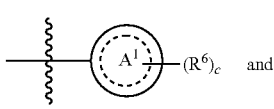 and (b)

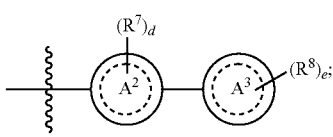

wherein

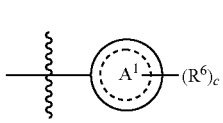

is selected from the group consisting of 4-(3-cyano-phenyl), 4-(4-cyano-phenyl), 4-(3-hydroxy-phenyl), 4-(4-hydroxy-phenyl), 4-(3-fluoro-phenyl), 4-(4-fluoro-phenyl), 4-(3-chloro-phenyl), 4-(4-chloro-phenyl), 4-(2,4-dichloro-phenyl), 4-(3-methyl-phenyl), 4-(4-methyl-phenyl), 4-(3-trifluoromethyl-phenyl), 4-(4-trifluoromethyl-phenyl), 4-(2-methoxy-phenyl), 4-(3-methoxy-phenyl), 4-(4-methoxyphenyl), 4-(3-trifluoromethoxy-phenyl), 4-(4-trifluoromethoxy-phenyl), 4-(3-dimethylamino-phenyl), 4-(4-dimethylamino-phenyl), 4-(3-methylsulfonyl-aminophenyl), 4-(3-amino-4-hydroxy-phenyl), 4-(3-formamido-4-hydroxy-phenyl), 4-(pyridin-2-yl), 4-(pyridin-3-yl), 4-(pyridin-4-yl), 4-(1-methyl-pyrazol-4-yl), 4-(1-methyl-pyrazol-5-yl), 4-(indol-4-yl), 4-(indol-5-yl), 4-(indol-6-yl), 4-(quinolin-5-yl), 4-(quinolin-6-yl), 4-(isoquinolin-5-yl), 4-(isoquinolin-6-yl), 4-(isoquinolin-7-yl), 4-(indazol-4-yl), 4-(indazol-5-yl), 4-(1-methyl-indazol-5-yl), 4-(1-methyl-indazol-6-yl), 4-(benzofuran-5-yl), 4-(2-methyl-benzofuran-5-yl), 4-(benzimidazol-5-yl), 4-(benzoxazol-2-yl), 4-(benzoxazol-5-yl), 4-(benzthiazol-5-yl), 4-(2,3-dimethyl-benzothiophen-5-yl), 4-(1,2,3,4-tetrahydro-2-methylcarbonyl-isoquinolin-6-yl) and 4-(1,2,3,4,4a,8a-hexahydro-2-methyl-carbonyl-isoquinolin-6-yl);

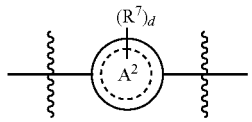

is 4-(phenyl);
and

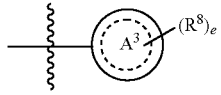

is selected from the group consisting of 4-(4-bromo-phenyl), 4-(pyridin-3-yl), 4-(pyridin-4-yl), 4-(1-methyl-pyrazol-4-yl), 4-(1-methyl-pyrazol-5-yl), 4-(tetrazol-5-yl) and 3-(pyrazol-3-yl); and a stereoisomer, a tautomer and a pharmaceutically acceptable salt thereof.

In another preferred embodiment, the present invention is directed to compounds of formula (I) wherein $R^1$ and $R^2$ are taken together to form a ring structure selected from the group consisting of cyclopropyl, cyclopentyl, piperidin-4,4-diyl, 1-(methyl)-piperidin-4,4-diyl, 1-(isopropyl)-piperidin-4,4-diyl, 1-(2-hydroxy-ethyl)-piperidin-4,4-diyl 1-(ethenylcarbony)-piperidin-4,4-diyl, 1-ethenylcarbonyl)-piperidin-4,4-diyl, 1-(trifluoromethylcarbonyl)piperidin-4,4-diyl, 1-(methoxy-carbonyl)-piperidin-4,4-diyl, 1-(2-methoxyethyl)-piperidin-4,4-diyl, 1-(benzyl)-piperidin-4,4-diyl, 1-(methyl-carbonyl)-piperidin-4,4-diyl, 1-(isopropyl-carbonyl)-piperidin-4,4-diyl, 1-(cyclopropyl-carbonyl)-piperidin-4,4-diyl, 1-(methylsulfonyl)-piperidin-4,4-diyl, 1-(dimethylamino-carbonyl)-piperidin-4,4-diyl, 1-(methoxycarbonyl)-azetidin-3,3-diyl, tetrahyrdofuran-3,3-diyl and tetrahydro-pyran-4,4-diyl;

m is an integer from 0 to 1; and n is an integer from 0 to 1;

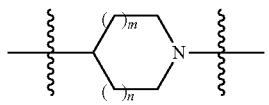

is selected from the group consisting of azetidin-3-yl, pyrrolidin-3R-yl, pyrrolidin-3S-yl and piperidin-4-yl;

a is 1;
$L^1$ is —C(O)—;
$R^3$ is selected from the group consisting of ethyl, 1-hydroxy-ethyl, isopropyl, 2-hydroxy-propan-2-yl, 3-hydroxy-2-methyl-propan-2-yl, 2,2,2-trifluoroethyl, ethenyl, cyclopropyl, 1-fluoro-cyclopropyl, 1-methyl-cyclopropyl, 1-hydroxy-cyclopropyl, 1-hydroxymethyl-cyclopropyl, 1-amino-cyclopropyl, cyclobutyl, 1-methyl-cyclobutyl, pyrrolidin-1-yl, 1-methyl-pyrazol-3-yl, oxetan-2-yl, oxetan-3-yl, 3-methyl-oxetan-3-yl, tetrahydro-furan-2-yl, tetrahydro-furan-2R-yl, tetrahydro-furan-2S-yl and dimethylamino;

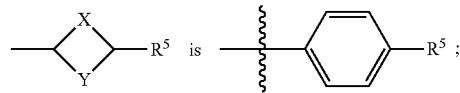

b is an integer from 0 to 1;
$R^4$ is selected from the group consisting of 2-fluoro, 2-chloro, 2-methyl, 2-methoxy, 3-fluoro and 3-methyl;
$R^5$ is

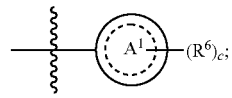

wherein

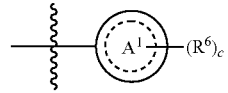

is selected from the group consisting of 4-cyano-phenyl, 3-hydroxy-phenyl, 4-hydroxy-phenyl, 3-fluoro-phenyl, 4-fluoro-phenyl, 3-chloro-phenyl, 4-chloro-phenyl, 2,4-dichloro-phenyl, 2-fluoro-4-chloro-phenyl, 3-chloro-4-fluoro-phenyl, 3-methyl-phenyl, 4-methyl-phenyl, 3-trifluoromethyl-phenyl, 3-methoxy-phenyl, 4-methoxy-phenyl, 3-aminocarbonyl-phenyl, 3-dimethylamino-phenyl, 4-dimethylamino-phenyl, 3-methylsulfonyl-amino-phenyl, 3-(cyclopropyl-sulfonylamino)-phenyl, 3-(cyclopropyl-carbonylamino)-phenyl, 3-(cyclopropyl-thio)-phenyl, 3-(cyclopropyl-sulfonyl)-phenyl, naphtha-2-yl, 6-fluoro-naphth-2-yl, 8-fluoro-naphth-2-yl, 6-chloro-naphth-2-yl, 7-fluoro-naphth-2-yl, 8-fluoro-naphth-2-yl, 6-methyl-naphth-2-yl, 5-methoxy-naphth-2-yl, 6-methoxy-naphth-2-yl, 8-methoxy-naphth-2-yl, 6-isopropoxy-naphth-2-yl, 6-cyano-naphth-2-yl, 7-methoxy-naphth-2-yl, 7-cyano-naphth-2-yl, 6-amino-pyridin-2-yl, isochroman-6-yl, isochroman-7-yl, 2-oxo-indolin-5-yl, indol-3-yl, indol-4-yl, indol-5-yl, indol-6-yl, 1-methyl-indol-5-yl, 1-methyl-indol-6-yl, 2-methyl-indol-5-yl, 1,2-dimethyl-indol-5-yl, 1,3-dimethyl-indol-5-yl, 2,3-dimethyl-indol-5-yl, 2-hydroxymethyl-indol-5-yl, 3-(2-hydroxyethyl-indol-5-yl), 3-cyanomethyl-indol-5-yl, 1-methyl-3-(2-hydroxyethyl)-indol-5-yl, quinolin-2-yl, quinolin-3-yl, quinolin-5-yl, quinolin-6-yl, quinolin-7-yl, 2-chloro-quinolin-7-yl, 4-chloro-quinolin-7-yl, 6-fluoro-quinolin-2-yl, 8-fluoro-quinolin-2-yl, 3-chloro-quinolin-7-yl, 2-methyl-quinolin-6-yl, 2-methyl-quinolin-6-yl, 4-methyl-quinolin-7-yl, 2-cyano-quinolin-6-yl, 2-chloro-3-methyl-quinolin-7-yl, isoquinolin-3-yl, isoquinolin-5-yl, isoquinolin-6-yl, isoquinolin-7-yl, 3-fluoro-isoquinolin-6-yl, 1-chloro-isoquinolin-6-yl, 3-chloro-isoquinolin-6-yl, 1-methoxy-isoquinolin-6-yl, 3-methoxy-isoquinolin-6-yl, 1-amino-isoquinolin-6-yl, 3-amino-isoquinolin-6-yl, oxo-isoquinolin-6-yl, quinazolin-7-yl, indazol-3-yl, indazol-4-yl, indazol-5-yl, indazol-6-yl, 1-methyl-indazol-5-yl, 1-methyl-indazol-6-yl, 1-methyl-indazol-3-yl, 1-methyl-indazol-4-yl, 1-methyl-indazol-5-yl, 1-methyl-indazol-6-yl, 2-methyl-indazol-4-yl, 2-methyl-indazol-5-yl, 2-methyl-indazol-6-yl, 1,3-dimethyl-indazol-5-yl, 1,4-dimethyl-indazol-5-yl, 1,8-dimethyl-indazol-5-yl, 1-ethyl-indazol-5-yl, 1-methyl-3-chloro-indazol-5-yl, 1-methyl-3-chloro-indazol-6-yl, 1-methyl-3-aminocarbonyl-indazol-6-yl, 1-methyl-3-cyano-indazol-6-yl, 1-methyl-3-amino-indazol-6-yl, 1-methyl-3-methoxy-indazol-5-yl, 1-methyl-3-methoxymethyl-indazol-5-yl, 1-methyl-3-methoxymethyl-indazol-6-yl, 1-methyl-3-hydroxymethyl-indazol-5-yl, 1-methyl-3-hydroxymethyl-indazol-6-yl, 1-methyl-3-cyclopropyl-indazol-5-yl, 1-(cyclopropylmethyl)-indazol-5-yl, benzofuran-5-yl, benzofuran-6-yl, 2-methyl-benzofuran-5-yl, 2-cyano-benzofuran-5-yl, 2,3-dimethyl-benzofuran-5-yl, benzoxazol-2-yl, benzoxazol-5-yl, 6-chloro-benzoxazol-2-yl, benzimidazol-2-yl, benzimidazol-5-yl, 1-methyl-benzimidazol-5-yl, 2-oxo-benzimidazol-5-yl, benzothiazol-2-yl, benzthiazol-5-yl, 5-chloro-benzothiazol-2-yl, 5-fluoro-benzothiazol-2-yl, 6-fluoro-benzothiazol-2-yl, 6-chloro-benzothiazol-2-yl, 5,6-difluoro-benzothiazol-2-yl, 2-methyl-benzothiazol-5-yl, 2-methyl-benzothiazol-6-yl, 5-cyano-benzothiazol-2-yl, 6-cyano-benzthiazol-2-yl, benzothien-5-yl, 2-methyl-benzothien-5-yl, 2,3-dimethyl-benzothien-5-yl, 2,3-dihydrobenzofuran-5-yl, 2-oxo-3,4-dihydro-quinolin-6-yl, benzo[1,3]dioxol-5-yl, 1,8-naphthyridin-2-yl and pyrrolo[2,3-b]pyridin-5-yl;

and a stereoisomer, a tautomer and a pharmaceutically acceptable salt thereof.

In another preferred embodiment, the present invention is directed to compounds of formula (I) wherein $R^1$ and $R^2$ are taken together to form a ring structure selected from the group consisting of cyclopropyl, cyclopentyl, piperidin-4,4-diyl, 1-(methyl)-piperidin-4,4-diyl, 1-(isopropyl)-piperidin-4,4-diyl, 1-(2-hydroxy-ethyl)-piperidin-4,4-diyl, 1-(methoxy-carbonyl)-piperidin-4,4-diyl, 1-(benzyl)-piperidin-4,4-diyl, 1-(methyl-carbonyl)-piperidin-4,4-diyl, 1-(isopropyl-carbonyl)-piperidin-4,4-diyl, 1-(cyclopropyl-carbonyl)-piperidin-4,4-diyl and 1-(dimethylamino-carbonyl)-piperidin-4,4-diyl;

m is an integer from 0 to 1; n is an integer from 0 to 1;

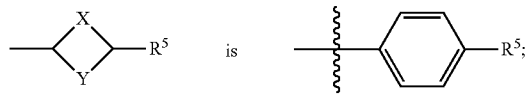

is selected from the group consisting of azetidin-3-yl, pyrrolidin-3R-yl, pyrrolidin-3S-yl and piperidin-4-yl; a is 1; $L^1$ is —C(O)—; $R^3$ is selected from the group consisting of 2,2,2-trifluoroethyl, ethenyl, cyclopropyl, 1-methyl-cyclopropyl, pyrrolidin-1-yl and 1-methyl-pyrazol-3-yl;

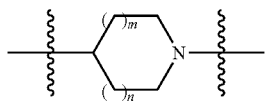

b is an integer from 0 to 1;

$R^4$ is selected from the group consisting of 2-fluoro, 2-methyl, 3-methyl and 2-methoxy; $R^5$ is

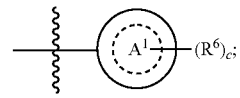

wherein

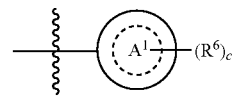

is selected from the group consisting of 4-(4-cyano-phenyl), 4-(3-hydroxy-phenyl), 4-(4-hydroxy-phenyl), 4-(3-fluoro-phenyl), 4-(4-fluoro-phenyl), 4-(3-chloro-phenyl), 4-(4-chloro-phenyl), 4-(2,4-dichloro-phenyl), 4-(3-methyl-phenyl), 4-(4-methyl-phenyl), 4-(3-trifluoromethyl-phenyl), 4-(3-methoxy-phenyl), 4-(4-methoxy-phenyl), 4-(3-dimethylamino-phenyl), 4-(4-dimethylamino-phenyl), 4-(3-methylsulfonyl-amino-phenyl), 4-(indol-4-yl), 4-(indol-5-yl), 4-(indol-6-yl), 4-(quinolin-5-yl), 4-(quinolin-6-yl), 4-(isoquinolin-5-yl), 4-(isoquinolin-6-yl), 4-(isoquinolin-7-yl), 4-(indazol-4-yl), 4-(indazol-5-yl), 4-(1-methyl-indazol-5-yl), 4-(1-methyl-indazol-6-yl), 4-(benzofuran-5-yl), 4-(2-methyl-benzofuran-5-yl), 4-(benzoxazol-2-yl), 4-(benzoxazol-5-yl), 4-(benzthiazol-5-yl) and 4-(2,3-dimethyl-benzothiophen-5-yl);

and a stereoisomer, a tautomer and a pharmaceutically acceptable salt thereof.

In another preferred embodiment, the present invention is directed to compounds of formula (I) wherein $R^1$ and $R^2$ are taken together to form a ring structure selected from the group consisting of cyclopropyl, cyclopentyl, piperidin-4,4-diyl, 1-(methyl)-piperidin-4,4-diyl, 1-(isopropyl)-piperidin-4,4-diyl, 1-(2-hydroxy-ethyl)-piperidin-4,4-diyl, 1-(methoxy-carbonyl)-piperidin-4,4-diyl, 1-(benzyl)-piperidin-4,4-diyl, 1-(methyl-carbonyl)-piperidin-4,4-diyl, 1-(isopropyl-carbonyl)-piperidin-4,4-diyl, 1-(cyclopropyl-carbonyl)-piperidin-4,4-diyl, 1-(dimethylamino-carbonyl)-piperidin-4,4-diyl, 1-(trifluoromethyl-carbonyl)-piperidin-4,4-diyl, 1-(methyl-sulfonyl)-piperidin-4,4-diyl, 1-(2-methoxyethyl)-piperidin-4,4-diyl, 1-(methoxycarbonyl)azetidin-3,3-diyl, tetrahydro-furan-3,3-diyl, tetrahydro-pyran-4,4-diyl;

m is an integer from 0 to 1; and n is an integer from 0 to 1;

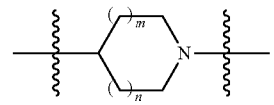

is selected from the group consisting of azetidin-3-yl, pyrrolidin-3R-yl and piperidin-4-yl;

a is 1;

$L^1$ is —C(O)—;

$R^3$ is selected from the group consisting of ethyl, cyclopropyl, 1-hydroxy-cyclopropyl, 1-fluoro-cyclopropyl, 1-methyl-cyclopropyl, 1-hydroxymethyl-cyclopropyl, cyclobutyl, tetrahydro-furan-2-yl, tetrahydro-furan-2R-yl, tetrahydro-furan-2S-yl, and oxetan-2-yl;

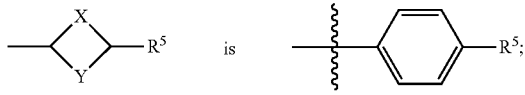 is b is an integer from 0 to 1;
R⁴ is selected from the group consisting of 2-fluoro, 2-chloro, 2-methyl, 2-methoxy, 3-fluoro and 3-methyl;
R⁵ is

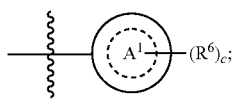

wherein

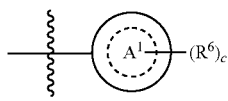

is selected from the group consisting of 4-cyano-phenyl, 3-hydroxy-phenyl, 4-fluoro-phenyl, 3-chloro-phenyl, 4-chloro-phenyl, 2-fluoro-4-chloro-phenyl, 3-chloro-4-fluoro-phenyl, 2-fluoro-4-cyano-phenyl, 2,4-dichloro-phenyl, 3-methyl-phenyl, 4-methyl-phenyl, 3-methoxy-phenyl, 4-methoxy-phenyl, 4-dimethylamino-phenyl, 3-(cyclopropyl-sulfonylamino)-phenyl, 3-(cyclopropyl-carbonylamino)-phenyl, 3-(cyclopropyl-thio)-phenyl, naphth-2-yl, 6-fluoro-naphth-2-yl, 7-fluoro-naphth-2-yl, 8-fluoro-naphth-2-yl, 6-chloro-naphth-2-yl, 6-methyl-naphth-2-yl, 6-methoxy-naphth-2-yl, 8-methoxy-naphth-2-yl, 6-cyano-naphth-2-yl, indol-3-yl, indol-4-yl, indol-5-yl, indol-6-yl, 1-methyl-indol-5-yl, 1-methyl-indol-6-yl, 2-methyl-indol-5-yl, 2,3-dimethyl-indol-5-yl, 2-(hydroxymethyl)-indol-5-yl, 3-(2-hydroxyethyl)-indol-5-yl, 3-(cyanomethyl)-indol-5-yl, 1-methyl-3-(2-hydroxyethyl)-indol-5-yl, 2-oxo-indolin-5-yl, quinolin-2-yl, quinolin-3-yl, quinolin-5-yl, quinolin-6-yl, quinolin-7-yl, 3-chloro-quinolin-7-yl, 6-fluoro-quinolin-2-yl, 8-fluoro-quinolin-2-yl, 8-fluoro-quinolin-7-yl, 4-methyl-quinolin-7-yl, 2-cyano-quinolin-6-yl, isoquinolin-5-yl, isoquinolin-6-yl, isoquinolin-7-yl, 6-fluoro-isoquinolin-6-yl, 1-aminoisoquinolin-6-yl, 3-amino-isoquinolin-6-yl, quinazolin-7-yl, indazol-3-yl, indazol-4-yl, indazol-5-yl, indazol-6-yl, 1-methyl-indazol-4-yl, 1-methyl-indazol-5-yl, 1-methyl-indazol-6-yl, 2-methyl-indazol-6-yl, 1,3-dimethyl-indazol-5-yl, 1,4-dimethyl-indazol-5-yl, 1-methyl-3-amino-indazol-6-yl, 1-methyl-3-aminocarbonyl-indazol-6-yl, 1-methyl-3-methoxymethyl-indazol-5-yl, 1-methyl-3-methoxymethyl-indazol-6-yl, 1-methyl-3-cyclopropyl-indazol-5-yl, benzofuran-5-yl, 2-methyl-benzofuran-5-yl, 2-cyano-benzofuran-5-yl, 2,3-dimethyl-benzofuran-5-yl, benzothiazol-2-yl, benzothiazol-5-yl, 6-fluoro-benzothiazol-2-yl, 6-chloro-benzothiazol-2-yl, 2-methyl-benzothiazol-5-yl, 6-methyl-benzothiazol-2-yl, 6-cyano-benzothiazol-2-yl, benzoxazol-2-yl, benzimidazol-5-yl, 1-methyl-benzimidazol-5-yl, benzothien-5-yl, 2-methyl-benzothien-5-yl, 2,3-dimethyl-benzothien-5-yl, and pyrrolo[2,3-b]pyridin-5-yl;

and a stereoisomer, a tautomer and a pharmaceutically acceptable salt thereof.

In another preferred embodiment, the present invention is directed to compounds of formula (I) wherein
R¹ and R² are taken together to form a ring structure selected from the group consisting of cyclopropyl, cyclopentyl, piperidin-4,4-diyl, 1-(methyl)-piperidin-4,4-diyl, 1-(2-hydroxy-ethyl)-piperidin-4,4-diyl, 1-(methoxy-carbonyl)-piperidin-4,4-diyl, 1-(benzyl)-piperidin-4,4-diyl, 1-(methyl-carbonyl)-piperidin-4,4-diyl, 1-(isopropyl-carbonyl)-piperidin-4,4-diyl, 1-(cyclopropyl-carbonyl)-piperidin-4,4-diyl and 1-(dimethylamino-carbonyl)-piperidin-4,4-diyl;
m is an integer from 0 to 1; n is an integer from 0 to 1;

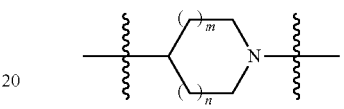

is selected from the group consisting of azetidin-3-yl, pyrrolidin-3R-yl and piperidin-4-yl; a is 1; L¹ is —C(O)—; R³ is selected from the group consisting of cyclopropyl and 1-methyl-cyclopropyl;

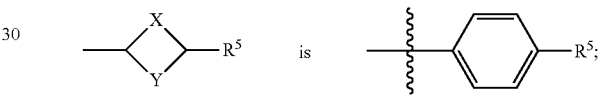

b is an integer from 0 to 1;
R⁴ is selected from the group consisting of 2-fluoro, 2-methyl, 3-methyl and 2-methoxy; R⁵ is

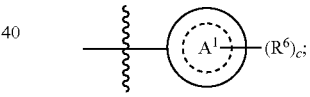

wherein

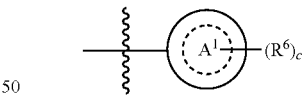

is selected from the group consisting of 4-(4-cyano-phenyl), 4-(3-hydroxy-phenyl), 4-(4-fluoro-phenyl), 4-(3-chloro-phenyl), 4-(4-chloro-phenyl), 4-(2,4-dichloro-phenyl), 4-(3-methyl-phenyl), 4-(4-methyl-phenyl), 4-(3-methoxy-phenyl), 4-(4-methoxy-phenyl), 4-(4-dimethylamino-phenyl), 4-(indol-4-yl), 4-(indol-5-yl), 4-(indol-6-yl), 4-(isoquinolin-5-yl), 4-(isoquinolin-6-yl), 4-(isoquinolin-7-yl), 4-(indazol-4-yl), 4-(indazol-5-yl), 4-(1-methyl-indazol-5-yl), 4-(1-methyl-indazol-6-yl), 4-(benzofuran-5-yl), 4-(2-methyl-benzofuran-5-yl), 4-(benzthiazol-5-yl) and 4-(2,3-dimethyl-benzothiophen-5-yl);
and a stereoisomer, a tautomer and a pharmaceutically acceptable salt thereof.

In another preferred embodiment, the present invention is directed to compounds of formula (I) wherein $R^1$ and $R^2$ are taken together to form a ring structure selected from the group consisting of cyclopropyl, cyclopentyl, 1-(methoxy-carbonyl)-piperidin-4,4-diyl, 1-(isopropyl-carbonyl)-piperidin-4,4-diyl, and 1-(dimethylamino-carbonyl)-piperidin-4,4-diyl;

m is an integer from 0 to 1; and n is 0;

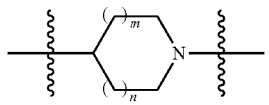

is selected from the group consisting of azetidin-3-yl and pyrrolidin-3R-yl;

a is 1;
$L^1$ is —C(O)—;
$R^3$ is selected from the group consisting of cyclopropyl, 1-fluoro-cyclopropyl, 1-hydroxy-cyclopropyl, 1-methyl-cyclopropyl, tetrahydrofuran-2S-yl and oxetan-2-yl;

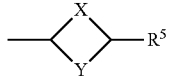 is 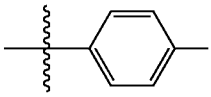

b is an integer from 0 to 1;
$R^4$ is selected from the group consisting of 2-fluoro, 2-chloro and 2-methyl;
$R^5$ is

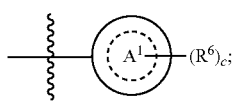

wherein

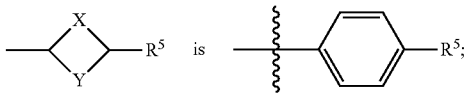

is selected from the group consisting of 3-hydroxy-phenyl, naphth-2-yl, 6-fluoro-naphth-2-yl, 7-fluoro-naphth-2-yl, 8-fluoro-naphth-2-yl, 6-chloro-naphth-2-yl, 6-methyl-naphth-2-yl, 6-methoxy-naphth-2-yl, 8-methoxy-naphth-2-yl, 6-cyano-naphth-2-yl, indol-3-yl, indol-5-yl, indol-6-yl, 1-methyl-indol-5-yl, 2-methyl-indol-5-yl, 2,3-dimethyl-indol-5-yl, 3-cyanomethyl-indol-5-yl, 2-hydroxymethyl-indol-5-yl, 3-(2-hydroxyethyl)-indol-5-yl, quinolin-3-yl, quinolin-5-yl, quinolin-7-yl, 3-chloro-quinolin-7-yl, 6-fluoro-quinolin-2-yl, 8-fluoro-quinolin-2-yl, 2-cyano-quinolin-6-yl, isoquinolin-6-yl, indazol-4-yl, indazol-5-yl, indazol-6-yl, 1-methyl-indazol-5-yl, 2-methyl-indazol-6-yl, benzofuran-5-yl, 2-methyl-benzofuran-5-yl, 2-cyano-benzofuran-5-yl, benzothiazol-2-yl, benzthiazol-5-yl, 6-chloro-benzothiazol-2-yl, 6-methyl-benzothiazol-2-yl, 6-cyano-benzothiazol-2-yl, benzoxazol-2-yl, benzimidazol-5-yl, 1-methyl-benzimidazol-5-yl, benzothien-5-yl, 2-methyl-benzothien-5-yl, and 2,3-dimethyl-benzothien-5-yl;

and a stereoisomer, a tautomer and a pharmaceutically acceptable salt thereof.

In another preferred embodiment, the present invention is directed to compounds of formula (I) wherein $R^1$ and $R^2$ are taken together to form a ring structure selected from the group consisting of cyclopropyl, cyclopentyl, 1-(methoxy-carbonyl)-piperidin-4,4-diyl, 1-(isopropyl-carbonyl)-piperidin-4,4-diyl, and 1-(dimethylamino-carbonyl)-piperidin-4,4-diyl; m is an integer from 0 to 1; n is 0;

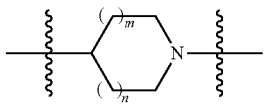

is selected from the group consisting of azetidin-3-yl and pyrrolidin-3R-yl; a is 1; $L^1$ is —C(O)—; $R^3$ is selected from the group consisting of cyclopropyl and 1-methyl-cyclopropyl;

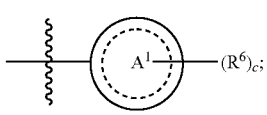 is 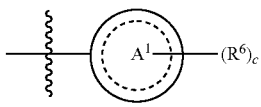

b is an integer from 0 to 1; $R^4$ is selected from the group consisting of 2-fluoro and 2-methyl; $R^5$ is

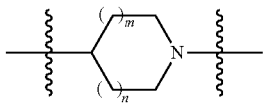

wherein

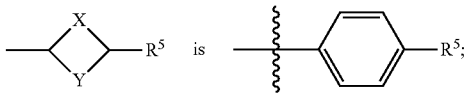

is selected from the group consisting of 4-(3-hydroxy-phenyl), 4-(indol-5-yl), 4-(indol-6-yl), 4-(isoquinolin-6-yl), 4-(indazol-4-yl), 4-(1-methyl-indazol-5-yl), and 4-(benzofuran-5-yl) and 4-(benzthiazol-5-yl);

and a stereoisomer, a tautomer and a pharmaceutically acceptable salt thereof.

In another preferred embodiment, the present invention is directed to compounds of formula (I) wherein $R^1$ and $R^2$ are taken together to form a ring structure selected from the group consisting of cyclopropyl and cyclopentyl;

m is an integer from 0 to 1; and n is 0;

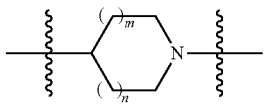

is selected from the group consisting of azetidin-3-yl and pyrrolidin-3R-yl;

a is 1;
$L^1$ is —C(O)—;

$R^3$ is selected from the group consisting of cyclopropyl, 1-hydroxy-cyclopropyl, 1-methyl-cyclopropyl and oxetan-2-yl;

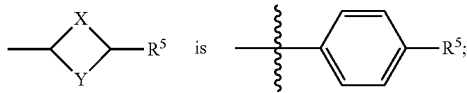

b is an integer from 0 to 1;

$R^4$ is selected from the group consisting of 2-fluoro and 2-methyl;

$R^5$ is selected from the group consisting of

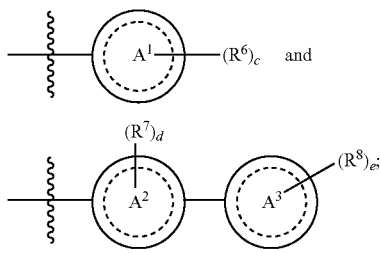

wherein

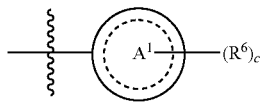

is selected from the group consisting of naphtha-2-yl, 6-chloro-naphth-2-yl, 6-fluoro-naphth-2-yl, 6-methyl-naphth-2-yl, 6-methoxy-naphth-2-yl, 6-cyano-naphth-2-yl, indol-5-yl, indol-6-yl, 1-methyl-indol-5-yl, 2-methyl-indol-5-yl, 2-hydroxymethyl-indol-5-yl, 3-(2-hydroxyethyl)-indol-5-yl, 3-cyanomethyl-indol-5-yl, indazol-5-yl, indazol-6-yl, 1-methyl-indazol-5-yl, quinolin-7-yl, 3-chloro-quinolin-7-yl, 6-fluoro-quinolin-2-yl, 8-fluoro-quinolin-2-yl, isoquinolin-6-yl, benzofuran-5-yl, 2-methyl-benzofuran-5-yl, 2-cyano-benzofuran-5-yl, benzothien-5-yl, 2-methyl-benzothien-5-yl, 2,3-dimethyl-benzothien-5-yl, benzoxazol-2-yl, benzothiazol-2-yl and 1-methyl-benzimidazol-5-yl;

wherein

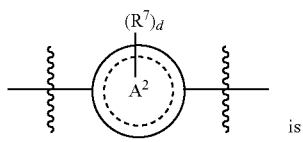

is

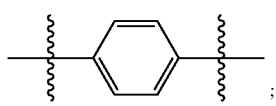

and wherein

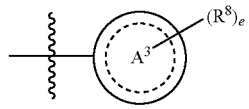

is selected from the group consisting of pyridin-4-yl and 1-methyl-pyrazol-4-yl;

and a stereoisomer, a tautomer and a pharmaceutically acceptable salt thereof.

In another preferred embodiment, the present invention is directed to compounds of formula (I) wherein $R^1$ and $R^2$ are taken together to form a ring structure selected from the group consisting of cyclopropyl, cyclopentyl, 1-(methyl)-piperidin-4,4-diyl, 1-(methoxy-carbonyl)-piperidin-4,4-diyl and 1-(benzyl)-piperidin-4,4-diyl; m is an integer from 0 to 1; n is 0;

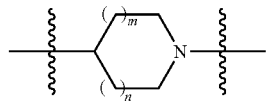

is selected from the group consisting of azetidin-3-yl and pyrrolidin-3R-yl; a is 1; $L^1$ is —C(O)—; $R^3$ is cyclopropyl;

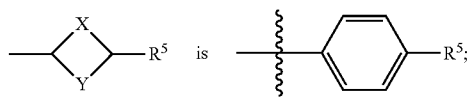

b is an integer from 0 to 1; $R^4$ is 2-methyl; $R^5$ is

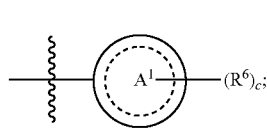

wherein

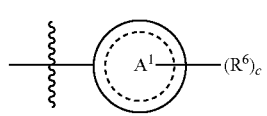

is selected from the group consisting of 4-(4-cyano-phenyl), 4-(3-hydroxy-phenyl), 4-(3-chloro-phenyl), 4-(4-chlorophenyl), 4-(4-methyl-phenyl), 4-(4-methoxy-phenyl), 4-(indol-4-yl), 4-(indol-5-yl), 4-(indol-6-yl), 4-(quinolin-5-yl), 4-(isoquinolin-6-yl), 4-(isoquinolin-7-yl), 4-(indazol-4-yl), 4-(indazol-5-yl), 4-(1-methyl-indazol-5-yl), 4-(1-methyl-indazol-6-yl), 4-(benzofuran-5-yl) and 4-(benzthiazol-5-yl);

and a stereoisomer, a tautomer and a pharmaceutically acceptable salt thereof.

In another preferred embodiment, the present invention is directed to compounds of formula (I) wherein $R^1$ and $R^2$ are taken together to form a ring structure selected from the group consisting of cyclopropyl and cyclopentyl; m is an integer from 0 to 1; n is 0;

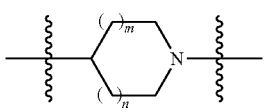

is selected from the group consisting of azetidin-3-yl and pyrrolidin-3R-yl; a is 1; $L^1$ is —C(O)—; $R^3$ is cyclopropyl;

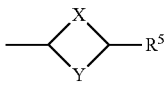

is phenyl; $R^5$ is

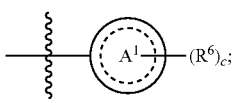

wherein

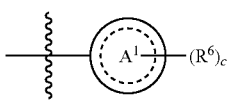

is selected from the group consisting of 4-(indol-5-yl), 4-(indol-6-yl), 4-(isoquinolin-6-yl) and 4-(benzofuran-5-yl);

and a stereoisomer, a tautomer and a pharmaceutically acceptable salt thereof.

In another preferred embodiment, the present invention is directed to compounds of formula (I) wherein $R^1$ and $R^2$ are taken together to form a ring structure selected from the group consisting of cyclopropyl, cyclopentyl and tetrahydropyran-4,4-diyl;

m is an integer from 0 to 1; and n is 0;

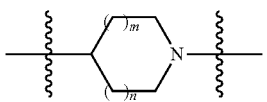

is selected from the group consisting of azetidin-3-yl and pyrrolidin-3R-yl;

a is 1;

$L^1$ is —C(O)—;

$R^3$ is selected from the group consisting of cyclopropyl, 1-fluoro-cyclopropyl, 1-hydroxy-cyclopropyl, 1-methyl-cyclopropyl, tetrahydrofuran-2-yl, tetrahydrofuran-2S-yl and oxetan-2-yl;

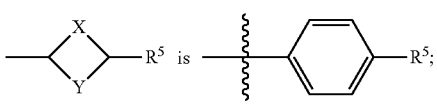

b is an integer from 0 to 1;

$R^4$ is selected from the group consisting of 2-fluoro and 2-methyl;

$R^5$ is selected from the group consisting of

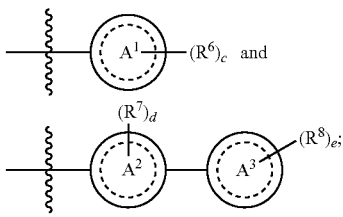

wherein

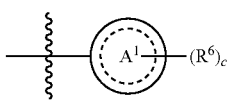

is selected from the group consisting of naphth-2-yl, 6-chloro-naphth-2-yl, 6-fluoro-naphth-2-yl, 7-fluoro-naphth-2-yl, 8-fluoro-naphth-2-yl, 6-methyl-naphth-2-yl, 6-methoxy-naphth-2-yl, 6-cyano-naphth-2-yl, indol-3-yl, indol-5-yl, indol-6-yl, 1-methyl-indol-5-yl, 2-methyl-indol-6-yl, 3-(2-hydroxyethyl)-indol-5-yl, 3-cyanomethyl-indol-5-yl, 1,3-dimethyl-indol-5-yl, 1-methyl-3-(2-hydroxyethyl)-indol-5-yl, quinolin-7-yl, 3-chloro-quinolin-7-yl, 6-fluoro-quinolin-6-yl, isoquinolin-6-yl, quinazolin-7-yl, indazol-4-yl, indazol-5-yl, indazol-6-yl, 1-methyl-indazol-5-yl, 2-methyl-indazol-6-yl, 1-methyl-3-amino-indazol-6-yl, 1-methyl-3-aminocarbonyl-indazol-6-yl, benzofuran-5-yl, 2-methyl-benzofuran-5-yl, 2-methyl-benzothien-5-yl, benzothiazol-5-yl, 6-chloro-benzothiazol-2-yl, 6-methyl-benzothiazol-2-yl, 6-cyano-benzothiazol-2-yl, benzimidazol-5-yl and 1-methyl-benzimidazol-5-yl;

wherein

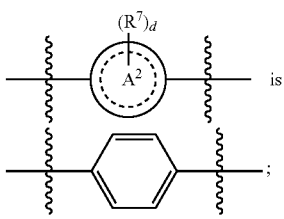

is and wherein

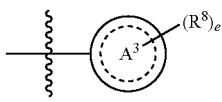

is selected from the group consisting of 1-methyl-pyrazol-4-yl, 1-isopropyl-pyrazol-4-yl, 1-cyclopropyl-pyrazol-4-yl, 1-cyclobutyl-pyrazol-4-yl, 1-methyl-pyrazol-5-yl and pyridin-4-yl;

and a stereoisomer, a tautomer and a pharmaceutically acceptable salt thereof.

In another preferred embodiment, the present invention is directed to compounds of formula (I) wherein R¹ and R² are taken together to form a ring structure selected from the group consisting of cyclopropyl and cyclopentyl;

m is an integer from 0 to 1; and n is 0;

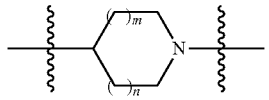

is selected from the group consisting of azetidin-3-yl and pyrrolidin-3R-yl;

a is 1;
L¹ is —C(O)—;
R³ is selected from the group consisting of cyclopropyl, 1-fluoro-cyclopropyl, 1-hydroxy-cyclopropyl, 1-methyl-cyclopropyl, 1-methyl-cyclobutyl, tetrahydrofuran-2-yl, tetrahydrofuran-2S-yl and oxetan-2-yl;

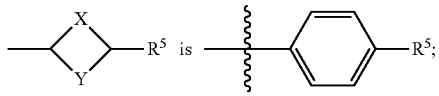

b is an integer from 0 to 1;
R⁴ is selected from the group consisting of 2-fluoro, 2-chloro and 2-methyl;
R⁵ is selected from the group consisting of

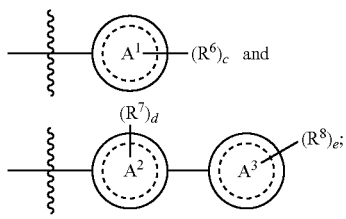

wherein

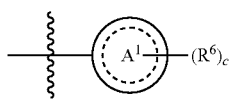

is selected from the group consisting of 3-(cyclopropylsulfonylamino)-phenyl, naphth-2-yl, 6-chloro-naphth-2-yl, 6-fluoro-naphth-2-yl, 7-fluoro-naphth-2-yl, 8-fluoro-naphth-2-yl, 6-methyl-naphth-2-yl, 6-methoxy-naphth-2-yl, 6-cyano-naphth-2-yl, indol-3-yl, indol-5-yl, indol-6-yl, 1-methyl-indol-5-yl, 2-hydroxymethyl-indol-5-yl, 2-methyl-indol-5-yl, 3-(2-hydroxyethyl)indol-5-yl, quinolin-7-yl, 3-chloro-quinolin-7-yl, 8-fluoro-quinolin-2-yl, quinazolin-7-yl, indazol-4-yl, indazol-5-yl, indazol-6-yl, 1-methyl-indazol-5-yl, 2-methyl-indazol-6-yl, 2-methyl-benzothien-5-yl, 6-chloro-benzothiazol-2-yl, 6-methyl-benzothiazol-2-yl, benzoxazol-2-yl, benzimidazol-5-yl and 1-methyl-benzimidazol-5-yl;

wherein

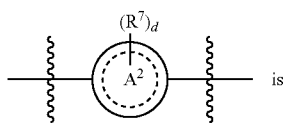

is

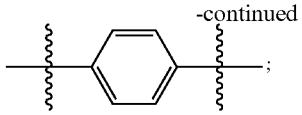

and wherein

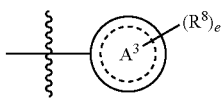

is selected from the group consisting of 1-methyl-pyrazol-4-yl, 1-isopropyl-pyrazol-4-yl, 1-cyclopropyl-pyrazol-4-yl and 1-cyclobutyl-pyrazol-4-yl;

and a stereoisomer, a tautomer and a pharmaceutically acceptable salt thereof.

In another preferred embodiment, the present invention is directed to compounds of formula (I) wherein
R¹ and R² are taken together to form cyclopropyl;
m is an integer from 0 to 1; and n is 0;

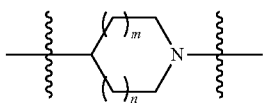

is selected from the group consisting of azetidin-3-yl and pyrrolidin-3R-yl;

a is 1;
L¹ is —C(O)—;
R³ is cyclopropyl;

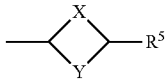

is selected from the group consisting of

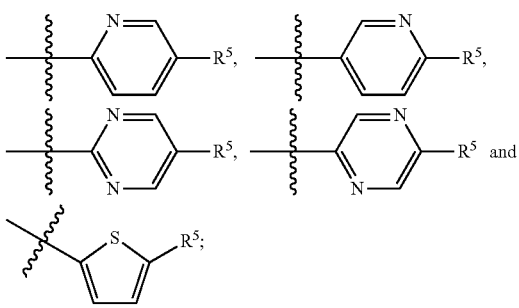

b is 0;
R⁵ is

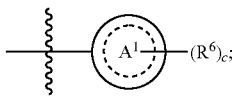

wherein

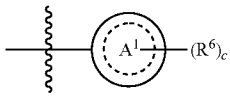

is selected from the group consisting of indol-5-yl, indol-6-yl, indazol-4-yl, indazol-5-yl, 1-methyl-indazol-5-yl, benzthiazol-5-yl, benzofuran-5-yl, benzothien-5-yl and 6-cyano-naphth-2-yl;

and a stereoisomer, a tautomer and a pharmaceutically acceptable salt thereof.

In another preferred embodiment, the present invention is directed to compounds of formula (I) wherein $R^1$ and $R^2$ are taken together to form a ring structure selected from the group consisting of cyclopropyl, cyclopentyl, tetrahydro-furan-3,3-diyl, tetrahydro-pyran-4,4-diyl, 1-(methoxycarbonyl)-azetidin-3,3-diyl, piperidin-4,4-diyl, 1-(isopropylcarbonyl)-piperidin-4,4-diyl, 1-(2-hydroxyethyl)-piperidin-4,4-diyl, 1-(dimethylamino-methylcarbonyl)-piperidin-4,4-diyl, 1-(methylsulfonyl)piperidin-4,4-diyl and 1-(cyclopropylcarbonyl)-piperidin-4,4-diyl;

m is an integer from 0 to 2; and n is an integer from 0 to 1; provided that when m is 2, then n is 0;

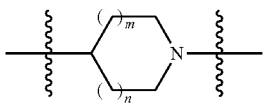

is selected from the group consisting of azetidin-3-yl, pyrrolidin-3R-yl, pyrrolidin-3R-yl, piperidin-3R-yl, and piperidin-4-yl;

a is 1;

$L^1$ is selected from the group consisting of —C(O)—, —C(O)O— and —SO$_2$—;

$R^3$ is selected from the group consisting of methyl, 1-hydroxyethyl, trifluoromethyl, cyclopropyl, 1-methyl-cyclopropyl, 1-hydroxy-cyclopropyl, tetrahydro-furan-2R-yl, pyrrolidin-1-yl and thiazol-2-yl;

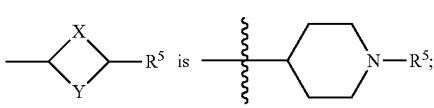

b is an integer from 0 to 1;

$R^4$ is selected from the group consisting of 2-fluoro and 2-methyl;

$R^5$ is

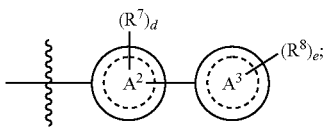

wherein

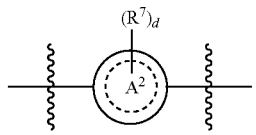

is selected from the group consisting of phenyl, pyridin-3-yl, pyridin-4-yl and pyrazol-4-yl;

and wherein

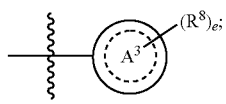

is selected from the group consisting of 4-bromo-phenyl, 3-chloro-phenyl, 4-methyl-phenyl, pyridin-3-yl, pyridin-4-yl, 1-methyl-pyrazol-3-yl, 1-(cyclopropylmethyl)-pyrazol-3-yl, 1-(2-methylpropyl)-pyrazol-3-yl, 1-methyl-pyrazol-4-yl, 1-isopropyl-pyrazol-4-yl, 1-cyclopropyl-pyrazol-4-yl, 1-cyclobutyl-pyrazol-4-yl, 1-methyl-pyrazol-5-yl, 1-isobutyl-pyrazol-5-yl, 1-(cyclopropylmethyl)-pyrazol-5-yl, tetrazol-5-yl, 5-methyl-oxazdiazol-2-yl, piperazin-1-yl, 4-methyl-piperazin-1-yl, pyrrolidin-1-yl, morpholin-14-yl, imidazol-1-yl and oxetan-3-yl;

provided that when

is phenyl or pyridin-3-yl, then

is bound to

at the 4-position, relative to the binding position of the

to the

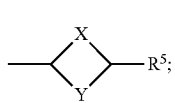

provided further that when

is pyridin-4-yl or pyrazol-4-yl, then

is bound to

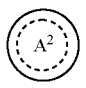

at the 3-position, relative to the binding position of the

to the

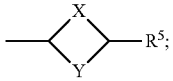

and a stereoisomer, a tautomer and a pharmaceutically acceptable salt thereof.

In another preferred embodiment, the present invention is directed to compounds of formula (I) wherein $R^1$ and $R^2$ are taken together to form a ring structure selected from the group consisting of cyclopropyl and cyclopentyl; n is an integer from 0 to 1; m is an integer from 0 to 1;

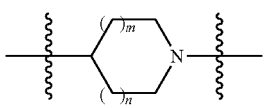

is selected from the group consisting of azetidin-3-yl, pyrrolidin-3R-yl and piperidin-4-yl; a is 1; $L^1$ is —C(O)—; $R^3$ is cyclopropyl;

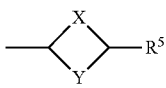

is phenyl; $R^5$ is

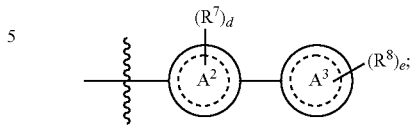

wherein

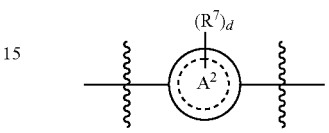

is 4-(phenyl); and wherein

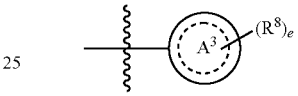

is selected from the group consisting of 4-(4-bromo-phenyl), 4-(pyridin-3-yl), 4-(pyridin-4-yl), 4-(1-methyl-pyrazol-4-yl), 4-(1-methyl-pyrazol-5-yl), 4-(tetrazol-5-yl), and 3-(pyrazol-3-yl);

and a stereoisomer, a tautomer and a pharmaceutically acceptable salt thereof.

In another preferred embodiment, the present invention is directed to compounds of formula (I) wherein $R^1$ and $R^2$ are taken together to form a ring structure selected from the group consisting of cyclopropyl and cyclopentyl;

m is an integer from 0 to 1; and n is 0;

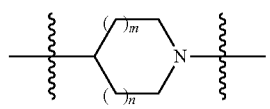

is selected from the group consisting of azetidin-3-yl and pyrrolidin-3R-yl;

a is 1;

$L^1$ is —C(O)—;

$R^3$ is selected from the group consisting of cyclopropyl, 1-hydroxy-cyclopropyl and 1-methyl-cyclopropyl;

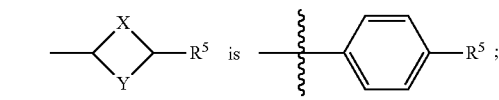

b is an integer from 0 to 1;

$R^4$ is selected from the group consisting of 2-fluoro and 2-methyl;

$R^5$ is

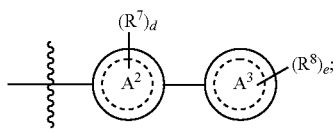

wherein

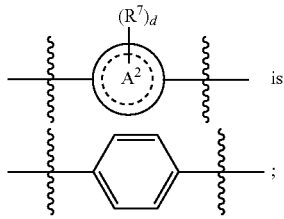 is

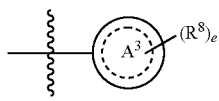 ;

and wherein

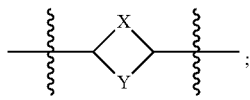

is selected from the group consisting of 4-(pyridin-3-yl), 4-(pyridin-4-yl), 4-(1-methyl-pyrazol-4-yl), 4-(1-isopropyl-pyrazol-4-yl), 4-(1-cyclopropyl-pyrazol-4-yl), 4-(1-cyclobutyl-pyrazol-4-yl), 4-(1-methyl-pyrazol-5-yl, and 4-(5-methyl-oxadiazol-2-yl);
wherein

is bound to the

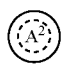

phenyl at the 4-position, relative to the point of attachment of the

phenyl to the

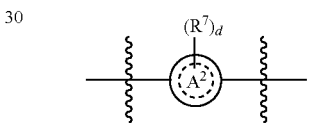 ;

and a stereoisomer, a tautomer and a pharmaceutically acceptable salt thereof.

In another preferred embodiment, the present invention is directed to compounds of formula (I) wherein $R^1$ and $R^2$ are taken together to form cyclopropyl; m is an integer from 0 to 1; n is 0;

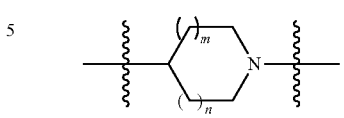

is selected from the group consisting of azetidin-3-yl and pyrrolidin-3R-yl; a is 1; $L^1$ is —C(O)—; $R^3$ is cyclopropyl;

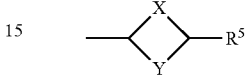

is phenyl; $R^5$ is

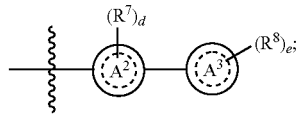

wherein

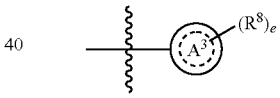

is 4-(phenyl); and wherein

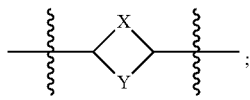

is selected from the group consisting of 4-(pyridin-3-yl) and 4-(1-methyl-pyrazol-4-yl);
and a stereoisomer, a tautomer and a pharmaceutically acceptable salt thereof.

In a preferred embodiment, the present invention is directed to compounds of formula (I) wherein $R^1$ and $R^2$ are taken together to form an optionally substituted ring structure selected from the group consisting of (a) $C_{3-6}$cycloalkyl; wherein the $C_{3-8}$cycloalkyl is optionally substituted with one $R^{11}$ group; (b) benzo-fused $C_{5-6}$cycloalkyl; wherein the benzo-fused $C_{5-6}$cycloalkyl is bound through a carbon atom of the $C_{5-6}$cycloalkyl portion of the ring structure; and wherein the benzo-fused $C_{5-6}$cycloalkyl is optionally substituted with one $R^{11}$ group; and (c) 4 to 8-membered, saturated heterocyclyl; wherein the 4 to 8-membered, saturated heterocyclyl contains O or $NR^{10}$; provided that the O or $NR^{10}$ is not present at the 2-position relative to the carbon atom of the imidazolin-5-one; and wherein the 4 to 8-membered, saturated heterocyclyl containing the O or $NR^{10}$ is optionally substituted with one $R^{11}$ group and further optionally substituted with one $R^{12}$ group.

In another preferred embodiment, the present invention is directed to compounds of formula (I) wherein $R^1$ and $R^2$ are taken together to form an optionally substituted ring structure selected from the group consisting of (a) $C_{3-6}$cycloalkyl; and (c) 4 to 6-membered, saturated heterocyclyl;

wherein the 4 to 6-membered saturated heterocyclyl contains $NR^{10}$; provided that the $NR^{10}$ is not present at the 2-position relative to the carbon atom of the imidazolidin-5-one.

In another preferred embodiment, the present invention is directed to compounds of formula (I) wherein $R^1$ and $R^2$ are taken together to form an optionally substituted ring structure selected from the group consisting of (a) $C_{3-6}$cycloalkyl; wherein the $C_{3-8}$cycloalkyl is optionally substituted with one $R^{11}$ group; (b) benzo-fused $C_{5-6}$cycloalkyl; wherein the benzo-fused $C_{5-6}$cycloalkyl is bound through a carbon atom of the $C_{5-6}$cycloalkyl portion of the ring structure; and wherein the benzo-fused $C_{5-6}$cycloalkyl is optionally substituted with one $R^{11}$ group; and (c) 4 to 6-membered, saturated heterocyclyl; wherein the 4 to 6-membered, saturated heterocyclyl contains O or $NR^{10}$; provided that the O or $NR^{10}$ is not present at the 2-position relative to the carbon atom of the imidazolin-5-one; and wherein the 4 to 6-membered, saturated heterocyclyl containing the O or $NR^{10}$ is optionally substituted with one $R^{11}$ group and further optionally substituted with one $R^{12}$.

In another preferred embodiment, the present invention is directed to compounds of formula (I) wherein $R^1$ and $R^2$ are taken together to form an optionally substituted ring structure selected from the group consisting of (a) $C_{3-6}$cycloalkyl; and (c) 4 to 6-membered, saturated heterocyclyl; wherein the 4 to 6-membered saturated heterocyclyl contains $NR^{10}$; provided that the $NR^{10}$ is not present at the 2-position relative to the carbon atom of the imidazolidin-5-one.

In another preferred embodiment, the present invention is directed to compounds of formula (I) wherein $R^1$ and $R^2$ are taken together to form a ring structure selected from the group consisting of cyclopropyl, cyclopentyl, piperidin-4,4-diyl, 1-(methyl)-piperidin-4,4-diyl, 1-(isopropyl)-piperidin-4,4-diyl, 1-(ethenyl)-piperidin-4,4-diyl, 1-(2-hydroxy-ethyl)-piperidin-4,4-diyl, 1-(methoxy-carbonyl)-piperidin-4,4-diyl, 1-(benzyl)-piperidin-4,4-diyl, 1-(methyl-carbonyl)-piperidin-4,4-diyl, 1-(isopropyl-carbonyl)-piperidin-4,4-diyl, 1-(trifluoromethyl-carbonyl)-piperidin-4,4-diyl, 1-(cyclopropyl-carbonyl)-piperidin-4,4-diyl, 1-(dimethylamino-carbonyl)-piperidin-4,4-diyl, 1-(methyl-sulfonyl)-piperidin-4,4-diyl, 1-(2-methoxy-ethyl)-piperidin-4,4-diyl, 1-(benzyl)-piperidin-4,4-diyl, tetrahydro-pyran-4,4-diyl, tetrahydro-furan-3,3-diyl, and 1-(methoxycarbonyl)-azetidin-3,3-diyl.

In another preferred embodiment, the present invention is directed to compounds of formula (I) wherein $R^1$ and $R^2$ are taken together to form a ring structure selected from the group consisting of cyclopropyl, cyclopentyl, piperidin-4,4-diyl, 1-(methyl)-piperidin-4,4-diyl, 1-(isopropyl)-piperidin-4,4-diyl, 1-(2-hydroxy-ethyl)-piperidin-4,4-diyl, 1-(ethenyl-carbonyl)-piperidin-4,4-diyl, 1-(trifluoromethyl-carbonyl)piperidin-4,4-diyl, 1-(methoxy-carbonyl)-piperidin-4,4-diyl, 1-(2-methoxyethyl)-piperidin-4,4-diyl, 1-(benzyl)-piperidin-4,4-diyl, 1-(methyl-carbonyl)-piperidin-4,4-diyl, 1-(isopropyl-carbonyl)-piperidin-4,4-diyl, 1-(cyclopropyl-carbonyl)-piperidin-4,4-diyl, 1-(methylsulfonyl)-piperidin-4,4-diyl, 1-(dimethylamino-carbonyl)-piperidin-4,4-diyl, 1-(methoxycarbonyl)-azetidin-3,3-diyl, tetrahyrdofuran-3,3-diyl, and tetrahydro-pyran-4,4-diyl.

In another preferred embodiment, the present invention is directed to compounds of formula (I) wherein $R^1$ and $R^2$ are taken together to form a ring structure selected from the group consisting of cyclopropyl, cyclopentyl, piperidin-4,4-diyl, 1-(methyl)-piperidin-4,4-diyl, 1-(isopropyl)-piperidin-4,4-diyl, 1-(2-hydroxy-ethyl)-piperidin-4,4-diyl, 1-(methoxy-carbonyl)-piperidin-4,4-diyl, 1-(benzyl)-piperidin-4,4-diyl, 1-(methyl-carbonyl)-piperidin-4,4-diyl, 1-(isopropyl-carbonyl)-piperidin-4,4-diyl, 1-(cyclopropyl-carbonyl)-piperidin-4,4-diyl, 1-(dimethylamino-carbonyl)-piperidin-4,4-diyl, 1-(trifluoromethyl-carbonyl)-piperidin-4,4-diyl, 1-(methyl-sulfonyl)-piperidin-4,4-diyl, 1-(2-methoxyethyl)-piperidin-4,4-diyl, 1-(methoxycarbonyl) azetidin-3,3-diyl, tetrahydro-furan-3,3-diyl, and tetrahydro-pyran-4,4-diyl.

In another preferred embodiment, the present invention is directed to compounds of formula (I) wherein $R^1$ and $R^2$ are taken together to form a ring structure selected from the group consisting of cyclopropyl, cyclopentyl, tetrahydro-furan-3,3-diyl, tetrahydro-pyran-4,4-diyl, 1-(methoxycarbonyl)-azetidin-3,3-diyl, piperidin-4,4-diyl, 1-(isopropylcarbonyl)-piperidin-4,4-diyl, 1-(2-hydroxyethyl)-piperidin-4,4-diyl, 1-(dimethylamino-methylcarbonyl)-piperidin-4,4-diyl, 1-(methylsulfonyl)piperidin-4,4-diyl, and 1-(cyclopropyl-carbonyl)-piperidin-4,4-diyl.

In another preferred embodiment, the present invention is directed to compounds of formula (I) wherein $R^1$ and $R^2$ are taken together to form a ring structure selected from the group consisting of cyclopropyl, cyclopentyl, piperidin-4,4-diyl, 1-(methyl)-piperidin-4,4-diyl, 1-(isopropyl)-piperidin-4,4-diyl, 1-(2-hydroxy-ethyl)-piperidin-4,4-diyl, 1-(methoxy-carbonyl)-piperidin-4,4-diyl, 1-(benzyl)-piperidin-4,4-diyl, 1-(methyl-carbonyl)-piperidin-4,4-diyl, 1-(isopropyl-carbonyl)-piperidin-4,4-diyl, 1-cyclopropylcarbonyl)-piperidin-4,4-diyl, and 1-(dimethylamino-carbonyl)-piperidin-4,4-diyl.

In another preferred embodiment, the present invention is directed to compounds of formula (I) wherein $R^1$ and $R^2$ are taken together to form a ring structure selected from the group consisting of cyclopropyl, cyclopentyl, piperidin-4,4-diyl, 1-(methyl)-piperidin-4,4-diyl, 1-(2-hydroxy-ethyl)-piperidin-4,4-diyl, 1-(methoxy-carbonyl)-piperidin-4,4-diyl, 1-(benzyl)-piperidin-4,4-diyl, 1-(methyl-carbonyl)-piperidin-4,4-diyl, 1-(isopropyl-carbonyl)-piperidin-4,4-diyl, 1-(cyclopropyl-carbonyl)-piperidin-4,4-diyl, and 1-(dimethylamino-carbonyl)-piperidin-4,4-diyl.

In another preferred embodiment, the present invention is directed to compounds of formula (I) wherein $R^1$ and $R^2$ are taken together to form a ring structure selected from the group consisting of cyclopropyl, cyclopentyl, 1-(methoxy-carbonyl)-piperidin-4,4-diyl, 1-(isopropyl-carbonyl)-piperidin-4,4-diyl, and 1-(dimethylamino-carbonyl)-piperidin-4,4-diyl.

In another preferred embodiment, the present invention is directed to compounds of formula (I) wherein $R^1$ and $R^2$ are taken together to form a ring structure selected from the group consisting of cyclopropyl, cyclopentyl, 1-(methyl)-piperidin-4,4-diyl, 1-(methoxy-carbonyl)-piperidin-4,4-diyl, and 1-(benzyl)-piperidin-4,4-diyl.

In another preferred embodiment, the present invention is directed to compounds of formula (I) wherein $R^1$ and $R^2$ are taken together to form a ring structure selected from the group consisting of cyclopropyl, cyclopentyl, and tetrahydropyran-4,4-diyl.

In another preferred embodiment, the present invention is directed to compounds of formula (I) wherein $R^1$ and $R^2$ are taken together to form a ring structure selected from the group consisting of cyclopropyl and cyclopentyl. In another preferred embodiment, the present invention is directed to compounds of formula (I) wherein $R^1$ and $R^2$ are taken together to form cyclopropyl.

In a preferred embodiment, the present invention is directed to compounds of formula (I) wherein $R^{10}$ is selected from the group consisting of hydrogen, C$_{1-4}$alkyl, fluorinated C$_{1-4}$alkyl, —CH$_2$-(hydroxy substituted C$_{1-4}$alkyl), —(C$_{1-4}$alkyl)-phenyl, —C(O)—NR$^A$R$^B$, —C(O)—(C$_{1-4}$alkyl), —C(O)—(C$_{3-6}$cycloalkyl),

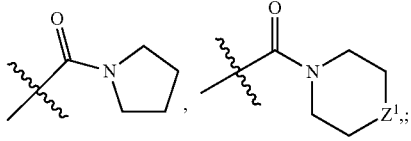

wherein Z$^1$ is selected from the group consisting of —CH$_2$—, —O— and —N(R$^C$)—; and wherein R$^A$, R$^B$ and R$^C$ are each independently selected from the group consisting of hydrogen and C$_{1-4}$alkyl.

In another preferred embodiment, the present invention is directed to compounds of formula (I) wherein R$^{10}$ is selected from the group consisting of hydrogen, C$_{1-4}$alkyl, —CH$_2$-(hydroxy substituted C$_{1-2}$alkyl), —CH$_2$-(phenyl), —C(O)—(C$_{1-4}$alkyl), —C(O)-(cyclopropyl) and —C(O)—NR$^A$R$^B$; wherein R$^A$ and R$^B$ are each independently selected from the group consisting of hydrogen and methyl.

In another preferred embodiment, the present invention is directed to compounds of formula (I) wherein R$^{10}$ is selected from the group consisting of hydrogen, C$_{1-4}$alkyl, fluorinated C$_{1-4}$alkyl, —CH$_2$-(hydroxy substituted C$_{1-4}$alkyl), —(C$_{2-4}$alkenyl), —(C$_{1-4}$alkyl)-phenyl, —(C$_2$alkyl)-O—(C$_{1-4}$alkyl), —C(O)O—(C$_{1-4}$alkyl), —C(O)—(C$_{1-4}$alkyl), —C(O)-(fluorinated C$_{1-2}$alkyl), —C(O)—(C$_{3-6}$cycloalkyl),

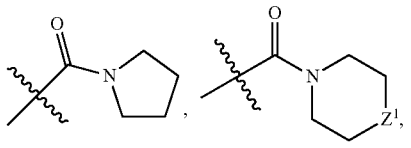

—C(O)—NR$^A$R$^B$, —SO$_2$(C$_{1-2}$alkyl); wherein Z$^1$ is selected from the group consisting of —CH$_2$—, —O— and —N(R$^C$)—; and wherein R$^A$, R$^B$ and R$^C$ are each independently selected from the group consisting of hydrogen and C$_{1-4}$alkyl.

In another preferred embodiment, the present invention is directed to compounds of formula (I) wherein R$^{10}$ is selected from the group consisting of hydrogen, C$_{1-4}$alkyl, C$_{2-4}$alkenyl, —CH$_2$-(hydroxy substituted C$_{1-2}$alkyl), —CH$_2$-(phenyl), —(C$_2$alkyl)-O—(C$_{1-2}$alkyl), —C(O)—(C$_{1-4}$alkyl), —C(O)-(fluorinated C$_{1-2}$alkyl), —C(O)-(cyclopropyl), —C(O)O—(C$_{1-4}$alkyl), —C(O)—NR$^A$R$^B$, —SO$_2$—(C$_{1-2}$alkyl), wherein R$^A$ and R$^B$ are each independently selected from the group consisting of hydrogen and methyl.

In a preferred embodiment, the present invention is directed to compounds of formula (I) wherein R$^{11}$ is independently selected from the group consisting of hydroxy, oxo, halogen, C$_{1-4}$alkyl, fluorinated C$_{1-4}$alkyl, C$_{1-4}$alkoxy, fluorinated C$_{1-4}$alkoxy, hydroxy substituted C$_{1-4}$alkyl, —(C$_{1-4}$ alkyl)-phenyl, -cyano, —NR$^D$R$^E$, —C(O)—NR$^D$R$^E$, —C(O)—(C$_{1-4}$alkyl), —C(O)OH and —C(O)O—(C$_{1-4}$ alkyl); wherein R$^{12}$ is selected from the group consisting of hydroxy, oxo, halogen, C$_{1-2}$alkyl, CF$_3$, C$_{1-2}$alkoxy, —OCF$_3$ and hydroxy substituted C$_{1-2}$alkyl.

In another preferred embodiment, the present invention is directed to compounds of formula (I) wherein R$^{12}$ is independently selected from the group consisting of hydroxy, oxo, halogen, C$_{1-4}$alkyl, fluorinated C$_{1-4}$alkyl, C$_{1-4}$alkoxy, fluorinated C$_{1-4}$alkoxy, hydroxy substituted C$_{1-4}$ alkyl, —(C$_{1-4}$alkyl)-phenyl, -cyano, —NR$^D$R$^E$, —C(O)—NR$^D$R$^E$, —C(O)—(C$_{1-4}$alkyl), —C(O)OH and —C(O)O—(C$_{1-4}$ alkyl).

In a preferred embodiment, the present invention is directed to compounds of formula (I) wherein R$^{12}$ is selected from the group consisting of hydroxy, oxo, halogen, C$_{1-2}$alkyl, CF$_3$, C$_{1-2}$alkoxy, —OCF$_3$ and hydroxy substituted CO$_{1-2}$alkyl. In another preferred embodiment, the present invention is directed to compounds of formula (I) wherein R$^{12}$ is selected from the group consisting of —OH, oxo, —Cl, —F, —CH$_3$, CF$_3$, —OCH$_3$, —OCF$_3$, —CH$_2$—OH and —CH$_2$CH$_2$—OH.

In a preferred embodiment, the present invention is directed to compounds of formula (I) wherein m is an integer from 0 to 1; and n is an integer from 0 to 2; provided that when n is 2, then m is 0.

In another preferred embodiment, the present invention is directed to compounds of formula (I) wherein m is 0. In another preferred embodiment, the present invention is directed to compounds of formula (I) wherein m is 1.

In another preferred embodiment, the present invention is directed to compounds of formula (I) wherein n is 0. In another preferred embodiment, the present invention is directed to compounds of formula (I) wherein n is 1. In another preferred embodiment, the present invention is directed to compounds of formula (I) wherein n is 2.

In a preferred embodiment, the present invention is directed to compounds of formula (I) wherein m is 0 and n is 0. In a preferred embodiment, the present invention is directed to compounds of formula (I) wherein m is 1 and n is 1. In another preferred embodiment, the present invention is directed to compounds of formula (I) wherein m is 1 and n is 0 or alternatively, m is 0 and n is 1. In another preferred embodiment, the present invention is directed to compounds of formula (I) wherein m is 0 and n is 2.

In a preferred embodiment, the present invention is directed to compounds of formula (I) wherein

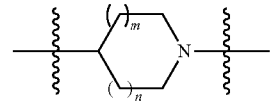

is selected from the group consisting of azetidin-3-yl, pyrrolidin-3-yl, pyrrolidin-3R-yl, pyrrolidin-3S-yl, piperidin-3-yl, piperidin-3S-yl, piperidin-3R-yl and piperidin-4-yl.

In another preferred embodiment, the present invention is directed to compounds of formula (I) wherein

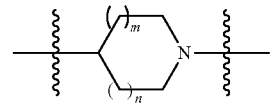

is selected from the group consisting of azetidin-3-yl, pyrrolidin-3-yl, pyrrolidin-3R-yl, pyrrolidin-3S-yl and piperidin-4-yl. In another preferred embodiment, the present invention is directed to compounds of formula (I) wherein

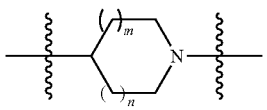

is selected from the group consisting of azetidin-3-yl, pyrrolidin-3R-yl, pyrrolidin-3S-yl and piperidin-4-yl. In another preferred embodiment the present invention is directed to compounds of formula (I) wherein

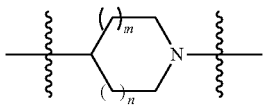

is selected from the group consisting of azetidin-3-yl, pyrrolidin-3R-yl and piperidin-4-yl. In another preferred embodiment, the present invention is directed to compounds of formula (I) wherein

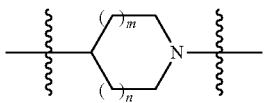

is selected from the group consisting of azetidin-3-yl and pyrrolidin-3R-yl.

In a preferred embodiment, the present invention is directed to compounds of formula (I) wherein a is 1. In another preferred embodiment, the present invention is directed to compounds of formula (I) wherein a is 0.

In a preferred embodiment, the present invention is directed to compounds of formula (I) wherein $L^1$ is selected from the group consisting of —C(O)—, —C(O)O—, —C(O)—NR$^L$— and —SO$_2$—; wherein R$^L$ is selected from the group consisting of hydrogen and methyl. In another preferred embodiment, the present invention is directed to compounds of formula (I) wherein $L^1$ is selected from the group consisting of —C(O)—, —C(O)O— and —SO$_2$—.

In another preferred embodiment, the present invention is directed to compounds of formula (I) wherein L is selected from the group consisting of —C(O)—, —C(O)—NR$^L$— and —SO$_2$—; wherein R$^L$ is selected from the group consisting of hydrogen and methyl. In another preferred embodiment, the present invention is directed to compounds of formula (I) wherein $L^1$ is selected from the group consisting of —C(O)— and —SO$_2$—. In another preferred embodiment, the present invention is directed to compounds of formula (I) wherein $L^1$ is —C(O)—.

In a preferred embodiment, the present invention is directed to compounds of formula (I) wherein $R^3$ is selected from the group consisting of $C_{1-4}$alkyl, fluorinated $C_{1-2}$alkyl, hydroxy substituted $C_{1-4}$alkyl, $C_{2-4}$alkenyl, $C_{3-6}$cycloalkyl, 4 to 6-membered, saturated heterocyclyl, 5 to 6-membered heteroaryl and NR$^V$R$^W$; wherein R$^V$ and R$^W$ are each independently selected from the group consisting of hydrogen and $C_{1-2}$alkyl; wherein the $C_{3-6}$cycloalkyl, 4 to 6-membered, saturated heterocyclyl or 5 to 6-membered heteroaryl, is optionally substituted with one to two substituents independently selected from the group consisting of halogen, hydroxy, cyano, $C_{1-4}$alkyl, fluorinated $C_{1-4}$alkyl, —($C_{1-2}$alkyl)-OH, $C_{1-4}$alkoxy, fluorinated $C_{1-4}$alkoxy, and NR$^G$R$^H$; wherein R$^G$ and R$^H$ are each independently selected from the group consisting of hydrogen and $C_{1-4}$alkyl.

In another preferred embodiment, the present invention is directed to compounds of formula (I) wherein $R^3$ is selected from the group consisting of $C_{1-4}$ alkyl, hydroxy substituted $C_{1-4}$alkyl, fluorinated $C_{1-2}$alkyl, $C_{2-4}$alkenyl, $C_{3-5}$cycloalkyl, 4 to 5-membered, saturated heterocyclyl, 5 to 6-membered heteroaryl and NR$^V$R$^W$; wherein the $C_{3-5}$cycloalkyl, 4 to 5-membered, saturated heterocyclyl or 5 to 6-membered heteroaryl is optionally substituted with a substituent selected from the group consisting of halogen, hydroxy, $C_{1-2}$alkyl, ($C_{1-2}$alkyl)-OH, fluorinated $C_{1-2}$alkyl, cyano and NH$_2$; and wherein R$^V$ and R$^W$ are each independently selected from the group consisting of hydrogen and methyl.

In another preferred embodiment, the present invention is directed to compounds of formula (I) wherein $R^3$ is selected from the group consisting of $C_{2-4}$alkenyl, $C_{3-6}$cycloalkyl, 5 to 6-membered, saturated heterocyclyl and 5 to 6-membered heteroaryl; wherein the $C_{3-6}$cycloalkyl, 5 to 6-membered, saturated heterocyclyl or 5 to 6-membered heteroaryl, is optionally substituted with one to two substituents independently selected from the group consisting of halogen, hydroxy, cyano, $C_{1-4}$alkyl, fluorinated $C_{1-4}$alkyl, $C_{1-4}$alkoxy, fluorinated $C_{1-4}$alkoxy and NR$^G$R$^H$; wherein R$^G$ and R$^H$ are each independently selected from the group consisting of hydrogen and $C_{1-4}$alkyl. In another preferred embodiment, the present invention is directed to compounds of formula (I) wherein $R^3$ is selected from the group consisting of $C_2$alkenyl, $C_3$cycloalkyl, 5-membered, saturated heterocyclyl and 5-membered heteroaryl; wherein the $C_3$cycloalkyl, 5-membered, saturated heterocyclyl or 5-membered heteroaryl is optionally substituted with a substituent selected from the group consisting of halogen, $C_{1-2}$alkyl, fluorinated $C_{1-2}$alkyl and cyano.

In another preferred embodiment, the present invention is directed to compounds of formula (I) wherein $R^3$ is selected from the group consisting of methyl, ethyl, isopropyl, 1-hydroxyethyl, trifluoromethyl, 2,2,2-trifluoroethyl, 2-hydroxy-propan-2-yl. 3-hydroxy-2-methyl-propan-2-yl, ethenyl, cyclopropyl, 1-fluoro-cyclopropyl, 1-hydroxy-cyclopropyl, 1-hydroxymethyl-cyclopropyl, 1-methyl-cyclopropyl, 1-cyano-cyclopropyl, 1-amino-cyclopropyl, cyclobutyl, 1-methyl-cyclobutyl, amino, dimethylamino, pyrrolidin-1-yl, 1-methyl-pyrazol-3-yl, thiazol-2-yl, tetrahydro-furan-2-yl, tetrahydro-furan-2R-yl, oxetan-2-yl, oxetan-3-yl, 3-methyl-oxetan-3-yl, and pyridin-3-yl.

In another preferred embodiment, the present invention is directed to compounds of formula (I) wherein $R^3$ is selected from the group consisting of ethyl, 1-hydroxy-ethyl, isopropyl, 2-hydroxy-propan-2-yl, 3-hydroxy-2-methyl-propan-2-yl, 2,2,2-trifluoroethyl, ethenyl, cyclopropyl, 1-fluoro-cyclopropyl, 1-methyl-cyclopropyl, 1-hydroxy-cyclopropyl, 1-hydroxymethyl-cyclopropyl, 1-amino-cyclopropyl, cyclobutyl, 1-methyl-cyclobutyl, pyrrolidin-1-yl, 1-methyl-pyrazol-3-yl, oxetan-2-yl, oxetan-3-yl, 3-methyl-oxetan-3-yl, tetrahydro-furan-2-yl, tetrahydro-furan-2R-yl, tetrahydro-furan-2S-yl and dimethylamino.

In another preferred embodiment, the present invention is directed to compounds of formula (I) wherein $R^3$ is selected from the group consisting of 2,2,2-trifluoroethyl, ethenyl, cyclopropyl, 1-fluoro-cyclopropyl, 1-methyl-cyclopropyl, 1-cyano-cyclopropyl, pyrrolidin-1-yl, 1-methyl-pyrazol-3-yl and tetrahydro-furan-2-yl. In another preferred embodiment, the present invention is directed to compounds of formula (I) wherein $R^3$ is selected from the group consisting of 2,2,2-trifluoroethyl, ethenyl, cyclopropyl, 1-methyl-cyclopropyl, pyrrolidin-1-yl and 1-methyl-pyrazol-3-yl.

In another preferred embodiment, the present invention is directed to compounds of formula (I) wherein $R^3$ is selected from the group consisting of ethyl, cyclopropyl, 1-hydroxy-cyclopropyl, 1-fluoro-cyclopropyl, 1-methyl-cyclopropyl, 1-hydroxymethyl-cyclopropyl, cyclobutyl, tetrahydro-furan-2-yl, tetrahydro-furan-2R-yl, tetrahydro-furan-2S-yl, and oxetan-2-yl. In another preferred embodiment, the present invention is directed to compounds of formula (I) wherein $R^3$ is selected from the group consisting of cyclopropyl, 1-fluoro-cyclopropyl, 1-hydroxy-cyclopropyl, 1-methyl-cyclopropyl, tetrahydrofuran-2S-yl and oxetan-2-yl. In another preferred embodiment, the present invention is directed to compounds of formula (I) wherein $R^3$ is selected from the group consisting of cyclopropyl, 1-fluoro-cyclopropyl, 1-hydroxy-cyclopropyl, 1-methyl-cyclopropyl, tetrahydrofuran-2-yl, tetrahydrofuran-2S-yl and oxetan-2-yl. In another preferred embodiment, the present invention is directed to compounds of formula (I) wherein $R^3$ is selected from the group consisting of methyl, 1-hydroxyethyl, trifluoromethyl, cyclopropyl, 1-methyl-cyclopropyl, 1-hydroxy-cyclopropyl, tetrahydro-furan-2R-yl, pyrrolidin-1-yl and thiazol-2-yl.

In another preferred embodiment, the present invention is directed to compounds of formula (I) wherein $R^3$ is selected from the group consisting of cyclopropyl, 1-hydroxy-cyclopropyl, 1-methyl-cyclopropyl and oxetan-2-yl. In another preferred embodiment, the present invention is directed to compounds of formula (I) wherein $R^3$ is selected from the group consisting of cyclopropyl, 1-hydroxy-cyclopropyl and 1-methyl-cyclopropyl. In another preferred embodiment, the present invention is directed to compounds of formula (I) wherein $R^3$ is selected from the group consisting of cyclopropyl and 1-methyl-cyclopropyl. In another preferred embodiment, the present invention is directed to compounds of formula (I) wherein $R^3$ is cyclopropyl.

In a preferred embodiment, the present invention is directed to compounds of formula (I) wherein

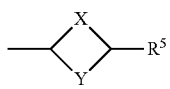

is selected from the group consisting of

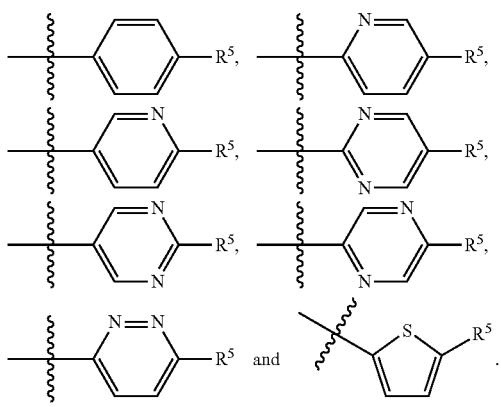

In another preferred embodiment, the present invention is directed to compounds of formula (I) wherein

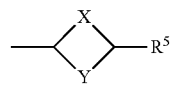

is selected from the group consisting of

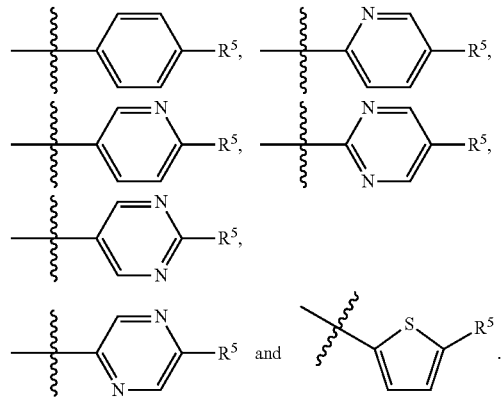

In another preferred embodiment, the present invention is directed to compounds of formula (I) wherein

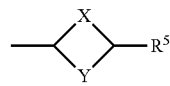

is selected from the group consisting of

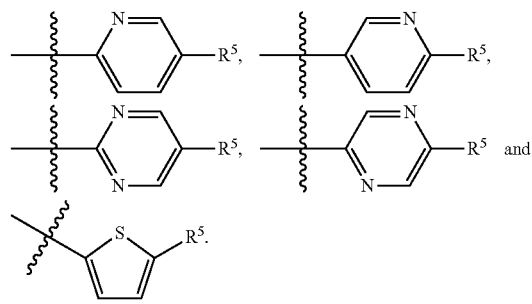

In another preferred embodiment, the present invention is directed to compounds of formula (I) wherein

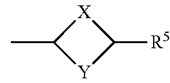

is selected from the group consisting of

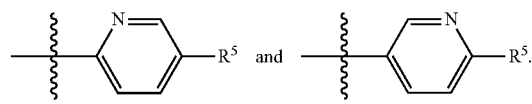

In another preferred embodiment, the present invention is directed to compounds of formula (I) wherein

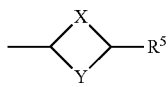

is selected from the group consisting of

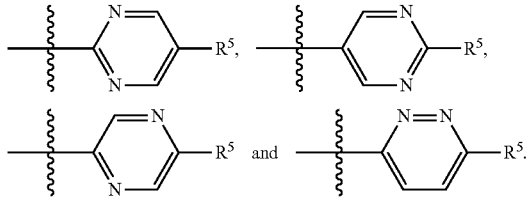

In another preferred embodiment, the present invention is directed to compounds of formula (I) wherein

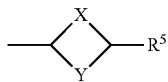

is selected from the group consisting of

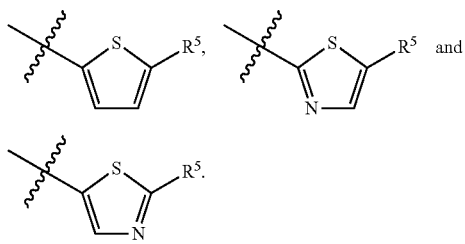

In another preferred embodiment, the present invention is directed to compounds of formula (I) wherein

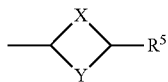

is selected from the group consisting of

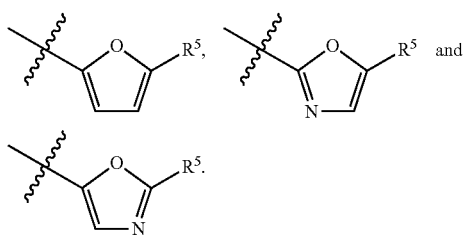

In another preferred embodiment, the present invention is directed to compounds of formula (I) wherein

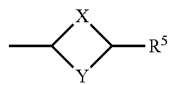

is selected from the group consisting of

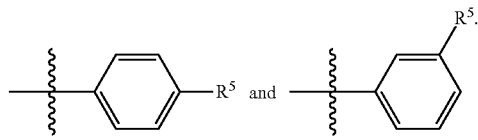

In another preferred embodiment, the present invention is directed to compounds of formula (I) wherein

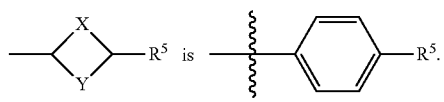

One skilled in the art will recognize that in the embodiments of the present invention, as described herein, the

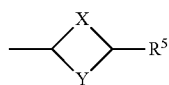

substituent group is further substituted with —(R⁴)$_b$, as herein defined.

In a preferred embodiment, the present invention is directed to compounds of formula (I) wherein b is an integer from 0 to 1. In another preferred embodiment, the present invention is directed to compounds of formula (I) wherein b is 1. In another preferred embodiment, the present invention is directed to compounds of formula (I) wherein b is 1

In a preferred embodiment, the present invention is directed to compounds of formula (I) wherein R⁴ is selected from the group consisting of, halogen, $C_{1-4}$alkyl, fluorinated $C_{1-4}$alkyl, $C_{1-4}$alkoxy, fluorinated $C_{1-4}$alkoxy and NR$^J$R$^K$; wherein R$^J$ and R$^K$ are each independently selected from the group consisting of hydrogen and $C_{1-2}$alkyl; provided that the R⁴ group is bound to a carbon atom. In another preferred embodiment, the present invention is directed to compounds of formula (I) wherein R⁴ is selected from the group consisting of halogen, $C_{1-2}$alkyl and $C_{1-2}$alkoxy.

In another preferred embodiment, the present invention is directed to compounds of formula (I) wherein R⁴ is selected from the group consisting of halogen, $C_{1-2}$alkyl and $C_{1-2}$alkoxy.

In another preferred embodiment, the present invention is directed to compounds of formula (I) wherein R⁴ is selected from the group consisting of 2-fluoro, 3-fluoro, 2-chloro, 3-chloro, 2-methyl, 3-methyl and 2-methoxy. In another preferred embodiment, the present invention is directed to compounds of formula (I) wherein R⁴ is selected from the group consisting of 2-fluoro, 2-chloro, 2-methyl, 2-methoxy, 3-fluoro and 3-methyl. In another preferred embodiment, the present invention is directed to compounds of formula (I) wherein R⁴ is selected from the group consisting of 2-fluoro, 2-chloro, and 2-methyl.

In another preferred embodiment, the present invention is directed to compounds of formula (I) wherein $R^4$ is selected from the group consisting of 2-fluoro, 2-methyl, 3-methyl and 2-methoxy. In another preferred embodiment, the present invention is directed to compounds of formula (I) wherein $R^4$ is selected from the group consisting of 2-fluoro and 2-methyl. In another preferred embodiment, the present invention is directed to compounds of formula (I) wherein $R^4$ is 2-methyl.

In a preferred embodiment, the present invention is directed to compounds of formula (I) wherein $R^5$ is

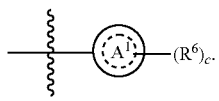

In another preferred embodiment, the present invention is directed to compounds of formula (I) wherein $R^5$ is

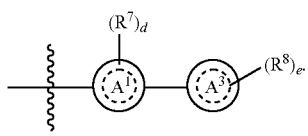

In a preferred embodiment, the present invention is directed to compounds of formula (I) wherein $R^5$ is

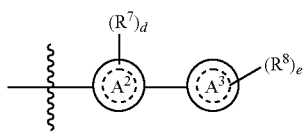

and where

is a 5-membered heteroaryl, and

is bound at the 3-position, relative to the point of attachment of the

to the

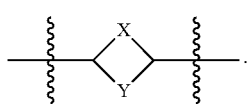

In another preferred embodiment, the present invention is directed to compounds of formula (I) wherein $R^5$ is

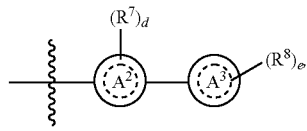

wherein

is phenyl or a 6-membered heteroaryl, and

is bound at the 3- or 4-position, relative to the point of attachment of the

to the

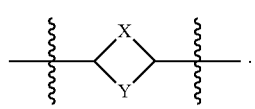

In another preferred embodiment, the present invention is directed to compounds of formula (I) wherein $R^5$ is

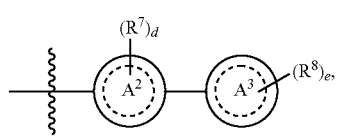

wherein

is phenyl or a 6-membered heteroaryl, and

is bound at the 4-position, relative to the point of attachment of the

to the

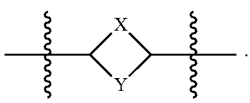

In a preferred embodiment, the present invention is directed to compounds of formula (I) wherein

selected from the group consisting of aryl, heteroaryl and partially unsaturated heterocyclyl. In another preferred embodiment, the present invention is directed to compounds of formula (I) wherein

selected from the group consisting of phenyl, heteroaryl and partially unsaturated heterocyclyl.

In another preferred embodiment, the present invention is directed to compounds of formula (I) wherein

selected from the group consisting of phenyl, naphthyl, 5 to 6-membered heteroaryl, 9 to 10-membered heteroaryl and partially unsaturated 9 to 10-membered heterocyclyl.

In another preferred embodiment, the present invention is directed to compounds of formula (I) wherein

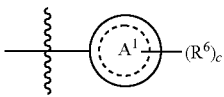

is selected from the group consisting of 3-cyano-phenyl, 4-cyano-phenyl, 3-hydroxy-phenyl, 4-hydroxy-phenyl, 3-fluoro-phenyl, 4-fluoro-phenyl, 3-chloro-phenyl, 4-chloro-phenyl, 2-fluoro-4-chloro-phenyl, 3-chloro-4-fluoro-phenyl, 2-fluoro-4-cyano-phenyl, 2-fluoro-4-(1-cyano-cuclopropyl)-phenyl, 2-fluoro-5-trifluoromethyl-phenyl, 2,4-dichloro-phenyl, 3-methyl-phenyl, 4-methyl-phenyl, 3-trifluoromethyl-phenyl, 4-trifluoromethyl-phenyl, 2-methoxy-phenyl, 3-methoxy-phenyl, 4-methoxy-phenyl, 3-trifluoromethoxy-phenyl, 4-trifluoromethoxy-phenyl, 4-(methylcarbonyl)-phenyl, 3-dimethylamino-phenyl, 4-dimethylamino-phenyl, 3-methylsulfonyl-amino-phenyl, 3-amino-4-hydroxy-phenyl, 3-formamido-4-hydroxy-phenyl 3-(cyclopropylthio)-phenyl, 3-(cyclopropylsulfonyl)-phenyl, 3-(cyclopropylcarbonyl-amino)-phenyl, 3-(cyclopropylsulfonyl-amino)-phenyl, 3-(methylsulfonyl)-phenyl, 3-(isopropylsulfonyl)-phenyl, 3-(aminocarbonyl)-phenyl, 3-carboxy-phenyl, 3-(methoxycarbonyl)-phenyl, naphth-2-yl, 6-fluoro-naphth-2-yl, 7-fluoro-naphth-2-yl, 8-fluoro-naphth-2-yl, 6-chloro-naphth-2-yl, 6-chloro-naphth-2-methyl-naphth-2-yl, 6-methoxy-naphth-2-yl, 8-methoxy-naphth-2-yl, 6-isopropyloxy-naphth-2-yl, 2-cyano-naphth-7-yl, 6-cyano-naphth-2-yl, 7-cyano-naphth-2-yl, 5-methoxy-naphth-2-yl, 7-methoxy-naphth-2-yl, 1,5-naphthyridin-3-yl, 1,8-naphthyridin-2-yl, 1,8-naphthyridin-3-yl, chroman-6-yl, isochroman-6-yl, isochroman-7-yl, pyridin-2-yl, pyridin-3-yl, pyridin-4-yl, 6-isopropyl-pyridin-3-yl, 6-n-propyl-pyridin-3-yl, 5-bromo-pyridin-2-yl, 5-chloro-pyridin-3-yl, 5-(2-hydroxy-2-methyl-propyl)-pyridin-2-yl, 5-(2-hydroxy-2-methyl-propyl)-pyridin-3-yl, 6-cyclopropyl-pyridin-3-yl, 6-(1-cyano-cyclopropyl)-pyridin-3-yl, 2-amino-pyrid-4-yl, 5-amino-pyridin-3-yl, 6-amino-pyridin-2-yl, 1-methyl-pyrazol-4-yl, 1-methyl-pyrazol-5-yl, indol-3-yl, indol-4-yl, indol-5-yl, indol-6-yl, 1-methyl-indol-5-yl, 1-methyl-indol-6-yl, 2-methyl-indol-5-yl, 2-hydroxymethyl-indol-5-yl, 3-(2-hydroxyethyl)-indol-5-yl, 3-cyanomethyl-indol-5-yl, 1,2-dimethyl-indol-5-yl, 1,3-dimethyl-indol-5-yl, 2,3-dimethyl-indol-5-yl, 1-methyl-3-(2-hydroxyethyl)-indol-5-yl, 1-(trifluoromethyl-carbonyl)-indol-5-yl, 2-oxo-indolin-5-yl, quinolin-2-yl, quinolin-3-yl, quinolin-5-yl, quinolin-6-yl, quinolin-7-yl, 2-chloro-quinolin-7-yl, 3-chloro-quinolin-7-yl, 4-chloro-quinolin-7-yl, 6-fluoro-quinolin-2-yl, 8-fluoro-quinolin-2-yl, 7-bromo-quinolin-2-yl, 2-hydroxy-quinolin-3-yl, 2-cyano-quinolin-6-yl, 2-cyano-quinolin-7-yl, 6-cyano-quinolin-2-yl, 2-methyl-quinolin-5-yl, 2-methyl-quinolin-6-yl, 2-methyl-quinolin-7-yl, 4-methyl-quinolin-7-yl, 2,4-dimethyl-quinolin-7-yl, 2-chloro-3-methyl-quinolin-7-yl, 2-chloro-4-methyl-quinolin-7-yl, 2-methyl-8-fluoro-quinolin-2-yl, 2-methyl-quinolin-7-yl, 2-methyl-7-bromo-quinolin-7-yl, 3-methyl-7-bromo-quinolin-7-yl, 2-methyl-4-chloro-quinolin-7-yl, 4-methyl-7-bromo-quinolin-2-yl, 2-trifluoromethyl-quinolin-7-yl, 2-oxo-quinolin-7-yl, 2-carboxy-quinolin-7-yl, 2-aminocarbonyl-quinolin-7-yl, isoquinolin-3-yl, isoquinolin-5-yl, isoquinolin-6-yl, isoquinolin-7-yl, 1-chloro-isoquinolin-6-yl, 3-chloro-isoquinolin-6-yl, 3-fluoro-isoquinolin-6-yl, 6-bromo-isoquinolin-3-yl, 1-methoxy-isoquinolin-6-yl, 3-methoxy-isoquinolin-6-yl, 1-amino-isoquinolin-6-yl, 3-amino-isoquinolin-6-yl, 1-oxo-isoquinolin-6-yl, quinazlin-7-yl, quinoxalin-6-yl, indazol-3-yl, indazol-4-yl, indazol-5-yl, indazol-6-yl, 4-chloro-indazol-5-yl, 1-methyl-indazol-3-yl, 1-methyl-indazol-4-yl, 1-methyl-indazol-5-yl, 1-methyl-indazol-6-yl, 2-methyl-indazol-4-yl, 2-methyl-indazol-5-yl, 2-methyl-indazol-6-yl, 1,3-dimethyl-indazol-5-yl, 1,4-dimethyl-indazol-5-yl, 1,7-dimethyl-indazol-5-yl, 1,8-dimethyl-indazol-5-yl, 1-ethyl-indazol-5-yl, 2-ethyl-indazol-5-yl, 1-isopropyl-indazol-5-yl, 2-isopropyl-indazol-5-yl, 1-(2-hydroxyethyl)-indazol-5-yl, 2-(2-hydroxyethyl)-indazol-5-yl, 1-(2-hydroxyethyl)-6-fluoro-indazol-5-yl, 2-(2-hydroxyethyl)-6-fluoro-indazol-5-yl, 1-methyl-3-chloro-indazol-5-yl, 1-methyl-3-chloro-indazol-6-yl, 1-methyl-3-amino-indazol-6-yl, 1-methyl-3-aminocarbonyl-indazol-6-yl, 1-methyl-3-cyano-indazol-5-yl, 1-methyl-3-cyano-indazol-6-yl, 1-methyl-3-methoxy-indazol-5-yl, 1-methyl-3-methoxymethyl-indazol-5-yl, 1-methyl-3-methoxymethyl-indazol-6-yl, 1-methyl-7-methoxymethyl-indazol-4-yl, 1-methyl-3-hydroxymethyl-indazol-5-yl, 1-methyl-3-hydroxymethyl-indazol-6-yl, 1-methyl-7-hydroxymethyl-indazol-4-yl, 1-methyl-3-cyclopropyl-indazol- 5-yl, 2-methyl-3-cyano-indazol-5-yl, 2-methyl-3-hydroxymethyl-indazol-5-yl, 2-methyl-3-methoxymethyl-indazol-5-yl, 1-(2-hydroxyethyl)-indazol-5-yl, 2-(2-hydroxyethyl)-indazol-5-yl), 1-(2-cyanoethyl)-indazol-5-yl, 2-(2-cyanoethyl)-indazol-5-yl, 1-oxetan-3-yl-indazol-5-yl, 1-cyclopropyl-indazol-5-yl, 1-cyclopropylmethyl-indazol-5-yl, 2-cyclopropylmethyl-indazol-5-yl, benzofuran-5-yl, benzofuran-6-yl, 2-methyl-benzofuran-5-yl, 2,3-dimethyl-benzofuran-5-yl, 2-cyano-benzofuran-5-yl, benzimidazol-2-yl, benzimidazol-5-yl, 1-methyl-benzimidazol-2-yl, 1,2-dimethyl-benzimidazol-6-yl, 1-methyl-6-fluoro-benzimidazol-2-yl, 2-oxo-benzimidazol-5-yl, benzoxazol-2-yl, benzoxazol-5-yl, 6-chloro-benzoxazol-2-yl, benzisoxazol-5-yl, benzthiazol-2-yl, benzthiazol-5-yl, 5-fluoro-benzothiazol-2-yl, 6-fluoro-benzothiazol-2-yl, 5-chloro-benzothiazol-2-yl, 6-chloro-benzothiazol-2-yl, 5,6-difluoro-benzothiazol-2-yl, 2-methyl-benzothiazol-5-yl, 2-methyl-benzothiazol-6-yl, 6-methyl-benzothiazol-2-yl, 2-methyl-benzothiazol-5-yl, 5-cyano-benzothiazol-2-yl, 6-cyano-benzothiazol-2-yl, benzothien-5-yl, 2-methyl-benzothien-5-yl, 2,3-dimethyl-benzothien-5-yl, 2,3-dihydro-benzofuran-5-yl, 2-oxo-3,4-dihydro-quinolin-7-yl, 1,2,3,4-tetrahydro-2-methylcarbonyl-isoquinolin-6-yl, 1,2,3,4,4a,8a-hexahydro-2-methyl-carbonyl-isoquinolin-6-yl, 2,3-dihydro-benzo[1,4]dioxin-6-yl, 2,3-dihydrobenzofuran-5-yl, 1,2-dimethyl-1,2-dihydro-3-oxo-indazol-5-yl, 2-oxo-3,4-dihydro-quinolin-6-yl, benzo[1,3]dioxol-5-yl, pyrrolo[2,3-b]pyridin-5-yl, 1-methyl-pyrazolo[4,3-b]pyridin-5-yl, [1,2,4]triazo[4,3-a]pyridin-6-yl, 3-methyl-[1,2,4]triazo[4,3-a]pyridin-6-yl, and 4-methyl-3,4-dihydro-pyrido[3,2-b][1,4]oxazin-7-yl.

In another preferred embodiment, the present invention is directed to compounds of formula (I) wherein

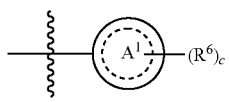

is selected from the group consisting of 4-cyano-phenyl, 3-hydroxy-phenyl, 4-hydroxy-phenyl, 3-fluoro-phenyl, 4-fluoro-phenyl, 3-chloro-phenyl, 4-chloro-phenyl, 2,4-dichloro-phenyl, 2-fluoro-4-chloro-phenyl, 3-chloro-4-fluoro-phenyl, 3-methyl-phenyl, 4-methyl-phenyl, 3-trifluoromethyl-phenyl, 3-methoxy-phenyl, 4-methoxy-phenyl, 3-aminocarbonyl-phenyl, 3-dimethylamino-phenyl, 4-dimethylamino-phenyl, 3-methylsulfonyl-amino-phenyl, 3-(cyclopropyl-sulfonylamino)-phenyl, 3-(cyclopropyl-carbonylamino)-phenyl, 3-(cyclopropyl-thio)-phenyl, 3-(cyclopropyl-sulfonyl)-phenyl, naphtha-2-yl, 6-fluoro-naphth-2-yl, 8-fluoro-naphth-2-yl, 6-chloro-naphth-2-yl, 7-fluoro-naphth-2-yl, 8-fluoro-naphth-2-yl, 6-methyl-naphth-2-yl, 5-methoxy-naphth-2-yl, 6-methoxy-naphth-2-yl, 8-methoxy-naphth-2-yl, 6-isopropoxy-naphth-2-yl, 6-cyano-naphth-2-yl, 7-methoxy-naphth-2-yl, 7-cyano-naphth-2-yl, 6-amino-pyridin-2-yl, isochroman-6-yl, isochroman-7-yl, 2-oxo-indolin-5-yl, indol-3-yl, indol-4-yl, indol-5-yl, indol-6-yl, 1-methyl-indol-5-yl, 1-methyl-indol-6-yl, 2-methyl-indol-5-yl, 1,2-dimethyl-indol-5-yl, 1,3-dimethyl-indol-5-yl, 2,3-dimethyl-indol-5-yl, 2-hydroxymethyl-indol-5-yl, 3-(2-hydroxyethyl-indol-5-yl), 3-cyanomethyl-indol-5-yl, 1-methyl-3-(2-hydroxyethyl)-indol-5-yl, quinolin-2-yl, quinolin-3-yl, quinolin-5-yl, quinolin-6-yl, quinolin-7-yl, 2-chloro-quinolin-7-yl, 4-chloro-quinolin-7-yl, 6-fluoro-quinolin-2-yl, 8-fluoro-quinolin-2-yl, 3-chloro-quinolin-7-yl, 2-methyl-quinolin-6-yl, 2-methyl-quinolin-6-yl, 4-methyl-quinolin-7-yl, 2-cyano-quinolin-6-yl, 2-chloro-3-methyl-quinolin-7-yl, isoquinolin-3-yl, isoquinolin-5-yl, isoquinolin-6-yl, isoquinolin-7-yl, 3-fluoro-isoquinolin-6-yl, 1-chloro-isoquinolin-6-yl, 3-chloro-isoquinolin-6-yl, 1-methoxy-isoquinolin-6-yl, 3-methoxy-isoquinolin-6-yl, 1-amino-isoquinolin-6-yl, 3-amino-isoquinolin-6-yl, oxo-isoquinolin-6-yl, quinazolin-7-yl, indazol-3-yl, indazol-4-yl, indazol-5-yl, indazol-6-yl, 1-methyl-indazol-5-yl, 1-methyl-indazol-6-yl, 1-methyl-indazol-3-yl, 1-methyl-indazol-4-yl, 1-methyl-indazol-5-yl, 1-methyl-indazol-6-yl, 2-methyl-indazol-4-yl, 2-methyl-indazol-5-yl, 2-methyl-indazol-6-yl, 1,3-dimethyl-indazol-5-yl, 1,4-dimethyl-indazol-5-yl, 1,8-dimethyl-indazol-5-yl, 1-ethyl-indazol-5-yl, 1-methyl-3-chloro-indazol-5-yl, 1-methyl-3-chloro-indazol-6-yl, 1-methyl-3-aminocarbonyl-indazol-6-yl, 1-methyl-3-cyano-indazol-6-yl, 1-methyl-3-amino-indazol-6-yl, 1-methyl-3-methoxy-indazol-5-yl, 1-methyl-3-methoxymethyl-indazol-5-yl, 1-methyl-3-methoxymethyl-indazol-6-yl, 1-methyl-3-hydroxymethyl-indazol-5-yl, 1-methyl-3-hydroxymethyl-indazol-6-yl, 1-methyl-3-cyclopropyl-indazol-5-yl, 1-(cyclopropylmethyl)-indazol-5-yl, benzofuran-5-yl, benzofuran-6-yl, 2-methyl-benzofuran-5-yl, 2-cyano-benzofuran-5-yl, 2,3-dimethyl-benzofuran-5-yl, benzoxazol-2-yl, benzoxazol-5-yl, 6-chloro-benzoxazol-2-yl, benzimidazol-2-yl, benzimidazol-5-yl, 1-methyl-benzimidazol-5-yl, 2-oxo-benzimidazol-5-yl, benzothiazol-2-yl, benzthiazol-5-yl, 5-chloro-benzothiazol-2-yl, 5-fluoro-benzothiazol-2-yl, 6-fluoro-benzothiazol-2-yl, 6-chloro-benzothiazol-2-yl, 5,6-difluoro-benzothiazol-2-yl, 2-methyl-benzothiazol-5-yl, 2-methyl-benzothiazol-6-yl, 5-cyano-benzothiazol-2-yl, 6-cyano-benzthiazol-2-yl, benzothien-5-yl, 2-methyl-benzothien-5-yl, 2,3-dimethyl-benzothien-5-yl, 2,3-dihydrobenzofuran-5-yl, 2-oxo-3,4-dihydro-quinolin-6-yl, benzo[1,3]dioxol-5-yl, 1,8-naphthyridin-2-yl, and pyrrolo[2,3-b]pyridin-5-yl.

In another preferred embodiment, the present invention is directed to compounds of formula (I) wherein

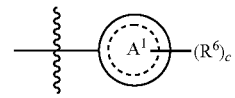

is selected from the group consisting of 4-cyano-phenyl, 3-hydroxy-phenyl, 4-fluoro-phenyl, 3-chloro-phenyl, 4-chloro-phenyl, 2-fluoro-4-chloro-phenyl, 3-chloro-4-fluoro-phenyl, 2-fluoro-4-cyano-phenyl, 2,4-dichloro-phenyl, 3-methyl-phenyl, 4-methyl-phenyl, 3-methoxy-phenyl, 4-methoxy-phenyl, 4-dimethylamino-phenyl, 3-(cyclopropyl-sulfonylamino)-phenyl, 3-(cyclopropyl-carbonylamino)-phenyl, 3-(cyclopropyl-thio)-phenyl, naphth-2-yl, 6-fluoro-naphth-2-yl, 7-fluoro-naphth-2-yl, 8-fluoro-naphth-2-yl, 6-chloro-naphth-2-yl, 6-methyl-naphth-2-yl, 6-methoxy-naphth-2-yl, 8-methoxy-naphth-2-yl, 6-cyano-naphth-2-yl, indol-3-yl, indol-4-yl, indol-5-yl, indol-6-yl, 1-methyl-indol-5-yl, 1-methyl-indol-6-yl, 2-methyl-indol-5-yl, 2,3-dimethyl-indol-5-yl, 2-(hydroxymethyl)-indol-5-yl, 3-(2-hydroxyethyl)-indol-5-yl, 3-(cyanomethyl)-indol-5-yl, 1-methyl-3-(2-hydroxyethyl)-indol-5-yl, 2-oxo-indolin-5-yl, quinolin-2-yl, quinolin-3-yl, quinolin-5-yl, quinolin-6-yl, quinolin-7-yl, 3-chloro-quinolin-7-yl, 6-fluoro-quinolin-2-yl, 8-fluoro-quinolin-2-yl, 8-fluoro-quinolin-7-yl, 4-methyl-quinolin-7-yl, 2-cyano-quinolin-6-yl, isoquinolin-5-yl, isoquinolin-6-yl, isoquinolin-7-yl, 6-fluoro-isoquinolin-6-yl, 1-amino-isoquinolin-6-yl, 3-amino-isoquinolin-6-yl, quinazolin-7-yl, indazol-3-yl, indazol-4-yl, indazol-5-yl, indazol-6-yl, 1-methyl-indazol-4-yl, 1-methyl-indazol-5-yl, 1-methyl-indazol-6-yl, 2-methyl-indazol-6-yl, 1,3-dimethyl-indazol-5-yl, 1,4-dimethyl-indazol-5-yl, 1-methyl-3-amino-indazol-6-yl, 1-methyl-3-aminocarbonyl-indazol-6-yl, 1-methyl-3-methoxymethyl-indazol-5-yl, 1-methyl-3-methoxymethyl-indazol-6-yl, 1-methyl-3-cyclopropyl-indazol-5-yl, benzofuran-5-yl, 2-methyl-benzofuran-5-yl, 2-cyano-benzofuran-5-yl, 2,3-dimethyl-benzofuran-5-yl, benzothiazol-2-yl, benzothiazol-5-yl, 6-fluoro-benzothiazol-2-yl, 6-chloro-benzothiazol-2-yl, 2-methyl-benzothiazol-5-yl, 6-methyl-benzothiazol-2-yl, 6-cyano-benzothiazol-2-yl, benzoxazol-2-yl, benzimidazol-5-yl, 1-methyl-benzimidazol-5-yl, benzothien-5-yl, 2-methyl-benzothien-5-yl, 2,3-dimethyl-benzothien-5-yl, and pyrrolo[2,3-b]pyridin-5-yl.

In another preferred embodiment, the present invention is directed to compounds of formula (I) wherein

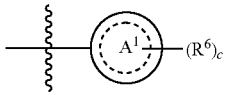

is selected from the group consisting of 3-cyano-phenyl, 4-cyano-phenyl, 3-hydroxy-phenyl, 4-hydroxy-phenyl, 3-fluoro-phenyl, 4-fluoro-phenyl, 3-chloro-phenyl, 4-chloro-phenyl, 2,4-dichloro-phenyl, 3-methyl-phenyl, 4-methyl-phenyl, 3-trifluoromethyl-phenyl, 4-trifluoromethyl-phenyl, 2-methoxy-phenyl, 3-methoxy-phenyl, 4-methoxy-phenyl, 3-trifluoromethoxy-phenyl, 4-trifluoromethoxy-phenyl, 3-dimethylamino-phenyl, 4-dimethylamino-phenyl, 3-methylsulfonyl-amino-phenyl, 3-amino-4-hydroxy-phenyl, 3-formamido-4-hydroxy-phenyl, pyridin-2-yl, pyridin-3-yl, pyridin-4-yl, 1-methyl-pyrazol-4-yl, 1-methyl-pyrazol-5-yl, indol-4-yl, indol-5-yl, indol-6-yl, quinolin-5-yl, quinolin-6-yl, isoquinolin-5-yl, isoquinolin-6-yl, isoquinolin-7-yl, indazol-4-yl, indazol-5-yl, 1-methyl-indazol-5-yl, 1-methyl-indazol-6-yl, benzofuran-5-yl, 2-methyl-benzofuran-5-yl, benzimidazol-5-yl, benzoxazol-2-yl, benzoxazol-5-yl, benzthiazol-5-yl, 2,3-dimethyl-benzothiophen-5-yl, 1,2,3,4-tetrahydro-2-methylcarbonyl-isoquinolin-6-yl, and 1,2,3,4,4a,8a-hexahydro-2-methylcarbonyl-isoquinolin-6-yl.

In another preferred embodiment, the present invention is directed to compounds of formula (I) wherein

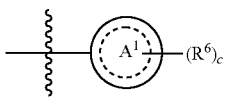

is selected from the group consisting of 3-hydroxy-phenyl, naphth-2-yl, 6-fluoro-naphth-2-yl, 7-fluoro-naphth-2-yl, 8-fluoro-naphth-2-yl, 6-chloro-naphth-2-yl, 6-methyl-naphth-2-yl, 6-methoxy-naphth-2-yl, 8-methoxy-naphth-2-yl, 6-cyano-naphth-2-yl, indol-3-yl, indol-5-yl, indol-6-yl, 1-methyl-indol-5-yl, 2-methyl-indol-5-yl, 2,3-dimethyl-indol-5-yl, 3-cyanomethyl-indol-5-yl, 2-hydroxymethyl-indol-5-yl, 3-(2-hydroxyethyl)-indol-5-yl, quinolin-3-yl, quinolin-5-yl, quinolin-7-yl, 3-chloro-quinolin-7-yl, 6-fluoro-quinolin-2-yl, 8-fluoro-quinolin-2-yl, 2-cyano-quinolin-6-yl, isoquinolin-6-yl, indazol-4-yl, indazol-5-yl, indazol-6-yl, 1-methyl-indazol-5-yl, 2-methyl-indazol-6-yl, benzofuran-5-yl, 2-methyl-benzofuran-5-yl, 2-cyano-benzofuran-5-yl, benzothiazol-2-yl, benzthiazol-5-yl, 6-chloro-benzothiazol-2-yl, 6-methyl-benzothiazol-2-yl, 6-cyano-benzothiazol-2-yl, benzoxazol-2-yl, benzimidazol-5-yl, 1-methyl-benzimidazol-5-yl, benzothien-5-yl, 2-methyl-benzothien-5-yl, and 2,3-dimethyl-benzothien-5-yl.

In another preferred embodiment, the present invention is directed to compounds of formula (I) wherein

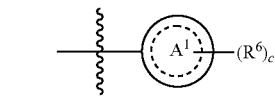

is selected from the group consisting of 4-cyano-phenyl, 3-hydroxy-phenyl, 4-hydroxy-phenyl, 3-fluoro-phenyl, 4-fluoro-phenyl, 3-chloro-phenyl, 4-chloro-phenyl, 2,4-dichloro-phenyl, 3-methyl-phenyl, 4-methyl-phenyl, 3-trifluoromethyl-phenyl, 3-methoxy-phenyl, 4-methoxy-phenyl, 3-dimethylamino-phenyl, 4-dimethylamino-phenyl, 3-methylsulfonyl-amino-phenyl, indol-4-yl, indol-5-yl, indol-6-yl, quinolin-5-yl, quinolin-6-yl, isoquinolin-5-yl, isoquinolin-6-yl, isoquinolin-7-yl, indazol-4-yl, indazol-5-yl, 1-methyl-indazol-5-yl, 1-methyl-indazol-6-yl, benzofuran-5-yl, 2-methyl-benzofuran-5-yl, benzoxazol-2-yl, benzoxazol-5-yl, benzthiazol-5-yl, and 2,3-dimethyl-benzothiophen-5-yl.

In another preferred embodiment, the present invention is directed to compounds of formula (I) wherein

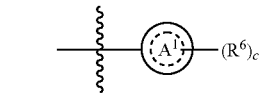

is selected from the group consisting of naphtha-2-yl, 6-chloro-naphth-2-yl, 6-fluoro-naphth-2-yl, 6-methyl-naphth-2-yl, 6-methoxy-naphth-2-yl, 6-cyano-naphth-2-yl, indol-5-yl, indol-6-yl, 1-methyl-indol-5-yl, 2-methyl-indol-5-yl, 2-hydroxymethyl-indol-5-yl, 3-(2-hydroxyethyl)-indol-5-yl, 3-cyanomethyl-indol-5-yl, indazol-5-yl, indazol-6-yl, 1-methyl-indazol-5-yl, quinolin-7-yl, 3-chloro-quinolin-7-yl, 6-fluoro-quinolin-2-yl, 8-fluoro-quinolin-2-yl, isoquinolin-6-yl, benzofuran-5-yl, 2-methyl-benzofuran-5-yl, 2-cyano-benzofuran-5-yl, benzothien-5-yl, 2-methyl-benzothien-5-yl, 2,3-dimethyl-benzothien-5-yl, benzoxazol-2-yl, benzothiazol-2-yl, and 1-methy-benzimidazol-5-yl.

In another preferred embodiment, the present invention is directed to compounds of formula (I) wherein

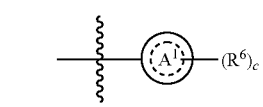

is selected from the group consisting of naphth-2-yl, 6-chloro-naphth-2-yl, 6-fluoro-naphth-2-yl, 7-fluoro-naphth-2-yl, 8-fluoro-naphth-2-yl, 6-methyl-naphth-2-yl, 6-methoxy-naphth-2-yl, 6-cyano-naphth-2-yl, indol-3-yl, indol-5-yl, indol-6-yl, 1-methyl-indol-5-yl, 2-methyl-indol-6-yl, 3-(2-hydroxyethyl)-indol-5-yl, 3-cyanomethyl-indol-5-yl, 1,3-dimethyl-indol-5-yl, 1-methyl-3-(2-hydroxyethyl)-indol-5-yl, quinolin-7-yl, 3-chloro-quinolin-7-yl, 6-fluoro-quinolin-6-yl, isoquinolin-6-yl, quinazolin-7-yl, indazol-4-yl, indazol-5-yl, indazol-6-yl, 1-methyl-indazol-5-yl, 2-methyl-indazol-6-yl, 1-methyl-3-amino-indazol-6-yl, 1-methyl-3-aminocarbonyl-indazol-6-yl, benzofuran-5-yl, 2-methyl-benzofuran-5-yl, 2-methyl-benzothien-5-yl, benzothiazol-5-yl, 6-chloro-benzothiazol-2-yl, 6-methyl-benzothiazol-2-yl, 6-cyano-benzothiazol-2-yl, benzimidazol-5-yl, and 1-methyl-benzimidazol-5-yl.

In another preferred embodiment, the present invention is directed to compounds of formula (I) wherein

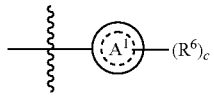

is selected from the group consisting of 4-cyano-phenyl, 3-hydroxy-phenyl, 4-fluoro-phenyl, 3-chloro-phenyl, 4-chloro-phenyl, 2,4-dichloro-phenyl, 3-methyl-phenyl, 4-methyl-phenyl, 3-methoxy-phenyl, 4-methoxy-phenyl, 4-dimethylamino-phenyl, indol-4-yl, indol-5-yl, indol-6-yl, isoquinolin-5-yl, isoquinolin-6-yl, isoquinolin-7-yl, indazol-4-yl, indazol-5-yl, 1-methyl-indazol-5-yl, 1-methyl-indazol-6-yl, benzofuran-5-yl, 2-methyl-benzofuran-5-yl, benzthiazol-5-yl, and 2,3-dimethyl-benzothiophen-5-yl.

In another preferred embodiment, the present invention is directed to compounds of formula (I) wherein

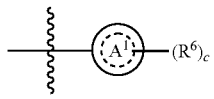

is selected from the group consisting of indol-5-yl, indol-6-yl, indazol-4-yl, indazol-5-yl, 1-methyl-indazol-5-yl, benzthiazol-5-yl, benzofuran-5-yl, benzothien-5-yl, and 6-cyano-naphth-2-yl.

In another preferred embodiment, the present invention is directed to compounds of formula (I) wherein

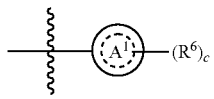

is selected from the group consisting of 3-hydroxy-phenyl, indol-5-yl, indol-6-yl, isoquinolin-6-yl, indazol-4-yl, 1-methyl-indazol-5-yl, benzofuran-5-yl, and benzthiazol-5-yl.

In another preferred embodiment, the present invention is directed to compounds of formula (I) wherein

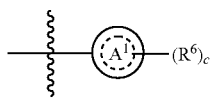

is selected from the group consisting of 4-cyano-phenyl, 3-hydroxy-phenyl, 3-chloro-phenyl, 4-chloro-phenyl, 4-methyl-phenyl, 4-methoxy-phenyl, indol-4-yl, indol-5-yl, indol-6-yl, quinolin-5-yl, isoquinolin-6-yl, isoquinolin-7-yl, indazol-4-yl, indazol-5-yl, 1-methyl-indazol-5-yl, 1-methyl-indazol-6-yl, benzofuran-5-yl, and benzthiazol-5-yl.

In another preferred embodiment, the present invention is directed to compounds of formula (I wherein

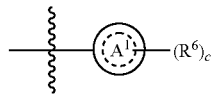

is selected from the group consisting of indol-5-yl, indol-6-yl, isoquinolin-6-yl, and benzofuran-5-yl.

In a preferred embodiment, the present invention is directed to compounds of formula (I) wherein c is an integer from 0 to 2.

In a preferred embodiment, the present invention is directed to compounds of formula (I) wherein each $R^6$ is independently selected from the group consisting of hydroxy, oxo, halogen, cyano, nitro, $C_{1-4}$alkyl, fluorinated $C_{1-4}$alkyl, hydroxy substituted $C_{1-4}$alkyl, cyano substituted ($C_{1-4}$alkyl), —($C_{1-2}$alkyl)-O—($C_{1-4}$alkyl), $C_{1-4}$alkoxy, fluorinated $C_{1-4}$alkoxy, —SO$_2$—($C_{1-4}$alkyl), —C(O)—($C_{1-4}$alkyl), —C(O)-(fluorinated $C_{1-2}$alkyl), —C(O)OH, —C(O)O—($C_{1-4}$alkyl), —C(O)—NR$^M$R$^N$, —NR$^M$R$^N$, —NR$^M$—C(O)H, —NR$^M$—SO$_2$—($C_{1-4}$alkyl), $C_{3-5}$cycloalkyl, 1-cyano-($C_{3-5}$cycloalkyl), —($C_{1-2}$alkyl)-($C_{3-5}$cycloalkyl), —S—($C_{3-5}$cycloalkyl), —SO$_2$—($C_{3-5}$cycloalkyl), —NH—($C_{3-5}$cycloalkyl), —NH—SO$_2$—($C_{3-5}$cycloalkyl), oxetanyl, and tetrahydro-furanyl; wherein $R^M$ and $R^N$ are each independently selected from the group consisting of hydrogen and $C_{1-4}$alkyl; wherein

selected from the group consisting of phenyl and 5 to 6-membered heteroaryl.

In another preferred embodiment, the present invention is directed to compounds of formula (I) wherein each $R^6$ is independently selected from the group consisting of hydroxy, oxo, halogen, cyano, $C_{1-4}$alkyl, fluorinated $C_{1-2}$alkyl, hydroxy substituted $C_{1-4}$alkyl, cyano-substituted $C_{1-2}$alkyl, —($C_{1-2}$alkyl)-O—($C_{1-2}$alkyl), $C_{1-4}$alkoxy, fluorinated $C_{1-2}$alkoxy, —SO$_2$—($C_{1-4}$alkyl), —CO$^2$H, —C(O)O—($C_{1-2}$alkyl), —C(O)—($C_{1-2}$alkyl), —C(O)-(fluorinated $C_{1-2}$alkyl), —C(O)—NR$^M$R$^N$, —NR$^M$R$^N$, —NR$^M$—C(O)H, —NR$^M$—SO$_2$—($C_{1-2}$alkyl), $C_{3-5}$cycloalkyl, 1-cyano-cyclopropyl, —($C_{1-2}$alkyl)-($C_{3-5}$cycloalkyl), —S—($C_{3-5}$cycloalkyl), —SO$_2$—($C_{3-6}$cycloalkyl), —NH—C(O)—($C_{3-5}$cycloalkyl) and —NH—SO$_2$—($C_{3-5}$cycloalkyl), and oxetan-3-yl; and wherein $R^M$ and $R^N$ are each independently selected from the group consisting of hydrogen and $C_{1-2}$alkyl.

In another preferred embodiment, the present invention is directed to compounds of formula (I) wherein each $R^6$ is independently selected from the group consisting of hydroxy, halogen, cyano, nitro, $C_{1-4}$alkyl, fluorinated $C_{1-4}$alkyl, hydroxy substituted $C_{1-4}$alkyl, $C_{1-4}$alkoxy, fluorinated $C_{1-4}$alkoxy, —NR$^M$R$^N$, —C(O)—($C_{1-4}$alkyl), —C(O)—NR$^M$R$^N$, —C(O)OH, —C(O)O—($C_{1-4}$alkyl), —NR$^M$—C(O)H, and —NR$^M$—SO$_2$—($C_{1-4}$alkyl); wherein $R^M$ and $R^N$ are each independently selected from the group consisting of hydrogen and $C_{1-4}$alkyl. In another preferred embodiment, the present invention is directed to compounds of formula (I) wherein each $R^6$ is independently selected from the group consisting of hydroxy, halogen, cyano, $C_{1-2}$alkyl, fluorinated $C_{1-2}$alkyl, $C_{1-2}$alkoxy, fluorinated $C_{1-2}$alkoxy, —NR$^M$R$^N$, —C(O)—($C_{1-2}$alkyl), —NR$^M$—C(O)H and —NR$^M$—SO$_2$—($C_{1-2}$alkyl); and wherein $R^M$ and $R^N$ are each independently selected from the group consisting of hydrogen and $C_{1-2}$alkyl.

In a preferred embodiment, the present invention is directed to compounds of formula (I) wherein

selected from the group consisting of phenyl and 5 to 6-membered heteroaryl. In another preferred embodiment, the present invention is directed to compounds of formula (I) wherein

is selected from the group consisting of phenyl and 6-membered, nitrogen containing heteroaryl.

In another preferred embodiment, the present invention is directed to compounds of formula (I) wherein

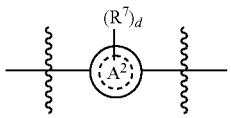

is selected from the group consisting of phenyl, pyridin-3-yl, pyridin-4-yl, and pyrazol-4-yl. In another preferred embodiment, the present invention is directed to compounds of formula (I) wherein

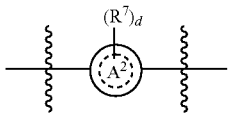

is selected from the group consisting of phenyl, pyridin-3-yl and pyridin-4-yl.

another preferred embodiment In another preferred embodiment, the present invention is directed to compounds of formula (I) wherein

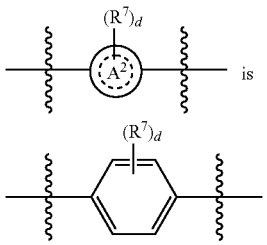

In another preferred embodiment, the present invention is directed to compounds of formula (I) wherein

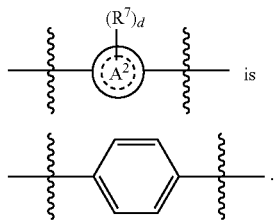 is

In a preferred embodiment, the present invention is directed to compounds of formula (I) wherein d is an integer from 0 to 1.

In a preferred embodiment, the present invention is directed to compounds of formula (I) wherein $R^7$ is selected from the group consisting of hydroxy, halogen, cyano, $C_{1-4}$alkyl, fluorinated $C_{1-4}$alkyl, hydroxy substituted $C_{1-4}$alkyl, $C_{1-4}$alkoxy and fluorinated $C_{1-4}$alkoxy.

In a preferred embodiment, the present invention is directed to compounds of formula (I) wherein

is selected from the group consisting of phenyl, 5 to 6-membered saturated heterocyclyl and 5 to 6-membered heteroaryl. In another preferred embodiment, the present invention is directed to compounds of formula (I) wherein

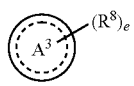

is selected from the group consisting of phenyl, 5 to 6-membered, saturated, nitrogen containing heterocyclyl and 5 to 6-membered, nitrogen containing heteroaryl.

In another preferred embodiment, the present invention is directed to compounds of formula (I) wherein

is selected from the group consisting of phenyl and 5 to 6-membered heteroaryl. In another preferred embodiment, the present invention is directed to compounds of formula (I) wherein

is selected from the group consisting of phenyl and 5 to 6-membered, nitrogen containing heteroaryl.

In another preferred embodiment, the present invention is directed to compounds of formula (I) wherein

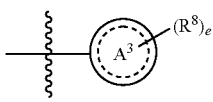

is selected from the group consisting of 4-bromo-phenyl, 3-chloro-phenyl, 4-methyl-phenyl, pyridin-3-yl, pyridin-4-yl, 1-methyl-pyrazol-3-yl, 1-methyl-pyrazol-4-yl, 1-methyl-pyrazol-5-yl, 1-isopropyl-pyrazol-4-yl, 1-isobutyl-pyrazol-5-yl, 1-(2-methylpropyl)-pyrazol-3-yl, 1-cyclopropyl-pyrazol-4-yl, 1-cyclobutyl-pyrazol-4-yl, 1-cyclopropyl methyl-pyrazol-3-yl, 1-cyclopropylmethyl-pyrazol-5-yl, 1,2,3,4-tetrazol-5-yl, pyrazol-3-yl, pyrrolidin-1-yl, morpholin-4-yl, 4-methyl-piperazin-1-yl, imidazol-1-yl, piperazin-1-yl, 4-methyl-piperazin-1-yl, and 1-(oxetan-3-yl)-pyrazol-4-yl.

In another preferred embodiment, the present invention is directed to compounds of formula (I) wherein and wherein

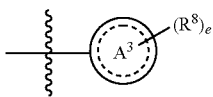

is selected from the group consisting of 4-bromo-phenyl, 3-chloro-phenyl, 4-methyl-phenyl, pyridin-3-yl, pyridin-4-yl, 1-methyl-pyrazol-3-yl, 1-(cyclopropylmethyl)-pyrazol-3-yl, 1-(2-methylpropyl)-pyrazol-3-yl, 1-methyl-pyrazol-4-yl, 1-isopropyl-pyrazol-4-yl, 1-cyclopropyl-pyrazol-4-yl, 1-cyclobutyl-pyrazol-4-yl, 1-methyl-pyrazol-5-yl, 1-isobutyl-pyrazol-5-yl, 1-(cyclopropylmethyl)-pyrazol-5-yl, tetrazol-5-yl, 5-methyl-oxazdiazol-2-yl, piperazin-1-yl, 4-methyl-piperazin-1-yl, pyrrolidin-1-yl, morpholin-14-yl, imidazol-1-yl, and oxetan-3-yl.

In another preferred embodiment, the present invention is directed to compounds of formula (I) wherein

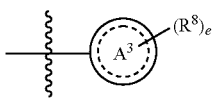

is selected from the group consisting of pyridin-3-yl, pyridin-4-yl, 1-methyl-pyrazol-4-yl, 1-isopropyl-pyrazol-4-yl, 1-cyclopropyl-pyrazol-4-yl, 1-cyclobutyl-pyrazol-4-yl, 1-methyl-pyrazol-5-yl, and 5-methyl-oxadiazol-2-yl.

In another preferred embodiment, the present invention is directed to compounds of formula (I) wherein

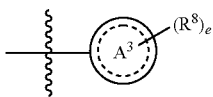

is selected from the group consisting of 4-bromo-phenyl, pyridin-3-yl, pyridin-4-yl, 1-methyl-pyrazol-4-yl, 1-methyl-pyrazol-5-yl, tetrazol-5-yl, and pyrazol-3-yl. In another preferred embodiment, the present invention is directed to compounds of formula (I) wherein

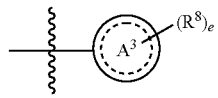

is selected from the group consisting of 4-bromo-phenyl, pyridin-3-yl, pyridin-4-yl, 1-methyl-pyrazol-4-yl, 1-methyl-pyrazol-5-yl, tetrazol-5-yl, and pyrazol-3-yl. In another preferred embodiment, the present invention is directed to compounds of formula (I) wherein

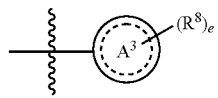

is selected from the group consisting of 1-methyl-pyrazol-4-yl, 1-isopropyl-pyrazol-4-yl, 1-cyclopropyl-pyrazol-4-yl, 1-cyclobutyl-pyrazol-4-yl, 1-methyl-pyrazol-5-yl, and pyridin-4-yl. In another preferred embodiment, the present invention is directed to compounds of formula (I) wherein

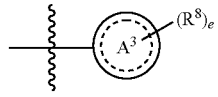

is selected from the group consisting of pyridin-3-yl and 1-methyl-pyrazol-4-yl.

In a preferred embodiment, the present invention is directed to compounds of formula (I) wherein e is an integer from 0 to 2. In another preferred embodiment, the present invention is directed to compounds of formula (I) wherein e is an integer from 0 to 1.

In a preferred embodiment, the present invention is directed to compounds of formula (I) wherein each $R^8$ is independently selected from the group consisting of hydroxy, halogen, cyano, $C_{1-4}$alkyl, fluorinated $C_{1-4}$alkyl, hydroxy substituted $C_{1-4}$alkyl, $C_{1-4}$alkoxy, fluorinated $C_{1-4}$alkoxy, $-NR^TR^U$, $-C(O)-NR^TR^U$, $-C(O)OH$, $-C(O)O-(C_{1-4}$alkyl$)$, $-(C_{1-4}$alkyl$)-NR^TR^U$, $C_{3-5}$cycloalkyl, $-(C_{1-2}$alkyl$)-(C_{3-5}$cycloalkyl$)$, oxetanyl, and tetrahydro-furanyl; wherein $R^T$ and $R^U$ are each independently selected from the group consisting of hydrogen and $C_{1-4}$alkyl. In another preferred embodiment, the present invention is directed to compounds of formula (I) wherein $R^8$ is selected from the group consisting of halogen, $C_{1-4}$alkyl, $C_{3-5}$cycloalkyl, $-(C_{1-2}$alkyl$)-(C_{3-5}$cycloalkyl$)$, and oxetanyl.

In a preferred embodiment, the present invention is directed to compounds of formula (I) wherein each $R^8$ is independently selected from the group consisting of hydroxy, halogen, cyano, $C_{1-4}$ alkyl, fluorinated $C_{1-4}$alkyl, hydroxy substituted $C_{1-4}$alkyl, $C_{1-4}$alkoxy, fluorinated $C_{1-4}$alkoxy, $-NR^TR^U$, $-C(O)-NR^TR^U$, $-C(O)OH$, $-C(O)O-(C_{1-4}$ alkyl$)$ and $-(C_{1-4}$alkyl$)-NR^TR^U$; wherein $R^T$ and $R^U$ are each independently selected from the group consisting of hydrogen and $C_{1-4}$alkyl. In another preferred embodiment, the present invention is directed to compounds of formula (I) wherein $R^8$ is selected from the group consisting of halogen and $C_{1-2}$alkyl.

In a preferred embodiment, the present invention is directed to compounds of formula (I) selected from the group consisting of 5-[4-(1-Benzofuran-5-yl)phenyl]-6-{[1-(cyclopropylcarbonyl)azetidin-3-yl]methyl}-4,6-diazaspiro[2.4]hept-4-en-7-one; 6-{[1-(Cyclopropylcarbonyl)azetidin-3-yl]methyl}-5-[4'-(1-methyl-1H-pyrazol-4-yl)biphenyl-4-yl]-4,6-diazaspiro[2.4]hept-4-en-7-one; (R)-6-((1-(Cyclopropanecarbonyl)pyrrolidin-3-yl)methyl)-5-(4'-(1-methyl-1H-pyrazol-4-yl)-[1,1'-biphenyl]-4-yl)-4,6-diazaspiro[2.4]hept-4-en-7-one; (R)-6-((1-

(cyclopropanecarbonyl)pyrrolidin-3-yl)methyl)-5-(4-(2-methyl-1H-indol-5-yl)phenyl)-4,6-diazaspiro[2.4]hept-4-en-7-one; 6-(4-(6-((1-(cyclopropanecarbonyl)azetidin-3-yl)methyl)-7-oxo-4,6-diazaspiro[2.4]hept-4-en-5-yl)-3-fluorophenyl)-2-naphthonitrile; (R)-6-((1-(cyclopropanecarbonyl)pyrrolidin-3-yl)methyl)-5-(2-methyl-4-(1-methyl-1H-indazol-5-yl)phenyl)-4,6-diazaspiro[2.4]hept-4-en-7-one; 6-((1-(cyclopropanecarbonyl)azetidin-3-yl)methyl)-5-(2-methyl-4-(1-methyl-1H-indazol-5-yl)phenyl)-4,6-diazaspiro[2.4]hept-4-en-7-one; 6-((1-(cyclopropanecarbonyl)azetidin-3-yl)methyl)-5-(2-fluoro-4-(1-methyl-1H-indazol-5-yl)phenyl)-4,6-diazaspiro[2.4]hept-4-en-7-one; 5-(4-(benzo[d]thiazol-2-yl)-2-fluorophenyl)-6-((1-(cyclopropanecarbonyl)azetidin-3-yl)methyl)-4,6-diazaspiro[2.4]hept-4-en-7-one; 6-((1-(cyclopropanecarbonyl)azetidin-3-yl)methyl)-5-(2-fluoro-4-(2-methyl-1H-indol-5-yl)phenyl)-4,6-diazaspiro[2.4]hept-4-en-7-one; 6-((1-(cyclopropanecarbonyl)azetidin-3-yl)methyl)-5-(2-fluoro-4-(1-methyl-1H-indol-5-yl)phenyl)-4,6-diazaspiro[2.4]hept-4-en-7-one; (R)-6-((1-(cyclopropanecarbonyl)pyrrolidin-3-yl)methyl)-5-(2-fluoro-4-(1-methyl-1H-indazol-5-yl)phenyl)-4,6-diazaspiro[2.4]hept-4-en-7-one, and stereoisomers, tautomers, and pharmaceutically acceptable salts thereof.

In another preferred embodiment, the present invention is directed to compounds of formula (I) selected from the group consisting of 6-{[1-(Cyclopropylcarbonyl)azetidin-3-yl]methyl}-5-[4'-(1-methyl-1H-pyrazol-4-yl)biphenyl-4-yl]-4,6-diazaspiro[2.4]hept-4-en-7-one; (R)-6-((1-(Cyclopropanecarbonyl)pyrrolidin-3-yl)methyl)-5-(4'-(1-methyl-1H-pyrazol-4-yl)-[1,1'-biphenyl]-4-yl)-4,6-diazaspiro[2.4]hept-4-en-7-one; (R)-6-((1-(cyclopropanecarbonyl)pyrrolidin-3-yl)methyl)-5-(2-fluoro-4-(1-methyl-1H-indazol-5-yl)phenyl)-4,6-diazaspiro[2.4]hept-4-en-7-one; and stereoisomers, tautomers and pharmaceutically acceptable salts thereof.

In an embodiment, the present invention is directed to compounds of formula (I) wherein $R^1$ and $R^2$ are taken together with the carbon atom to which they are bound to form a ring structure other than tetrahydrofuran-3,3-diyl or tetrahydropyran-4,4-diyl.

In an embodiment, the present invention is directed to compounds of formula (I) wherein $(L^1)_a$ is other than —SO$_2$-pyrrolidin-1-yl or —SO$_2$-pyridin-3-yl. In another embodiment, the present invention is directed to compounds of formula (I) wherein $(L^1)_a$ is other than C(O)-thiazol-2-yl, —C(O)—CF$_3$, —C(O)OCH$_3$ or —SO$_2$—CH$_3$.

In an embodiment, the present invention is directed to compounds of formula (I) wherein $R^5$ is other than 1,2,3,4,4a,8a-hexahydro-2-methyl-carbonyl-isoquinolin-6-yl), 1,2,3,4-trihydro-2-methylcarbonyisoquinolin-2-yl, 4-methyl-3,4-dihydro-pyrido[2,3-b]oxazon-7-yl, 2-oxo-3,4-dihydro-quinolin-7-yl, 5-chloro-pyridin-3-yl, 5-(2-hydroxy-2-methyl-propyl)-pyridin-2-yl, 6-isopropyl-pyridin-3-yl, 6-(1-cyanomethyl)-pyridin-3-yl, 6-(2-hydroxy-2-methyl-propyl)-pyridin-3-yl, 2-(piperazin-1-yl)-pyridin-4-yl, 2-(4-methyl-piperazin-1-yl)-pyridin-4-yl, 6-(morpholin-4-yl)-pyridin-3-yl, 1,5-naphthyridin-3-yl, 3-methyl-[1,2,4]triazolo[4,3-a]pyridin-6-yl, or 6-(4-methyl-piperazin-1-yl)-pyridin-3-yl.

In an embodiment, the present invention is directed to compounds of formula (I) as herein described, provided that when $R^1$ and $R^2$ are taken together with the carbon atom to which they are bound to form 1-(methoxycarbonyl)-azetidin-3-yl, m is 1 and n is 0 or m is 0 and n is 1;

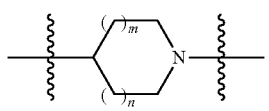

is pyrrolidin-3R-yl; $-(L^1)_a$-$R^3$ is selected from the group consisting of —C(O)—CF$_3$, —C(O)-cyclopropyl, —C(O)-(thiazol-2-yl), —C(O)OCH$_3$, and —SO$_2$—CH$_3$,

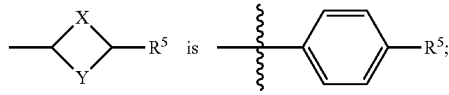

and b=0; then $R^5$ is other than quinolin-7-yl, benzofuran-5-yl, 1-methyl-indazol-5-yl, 1-methyl-pyrazol-4-yl, 4-(1-methyl-pyrazol-4-yl)-phenyl, 1,2,3,4,4a,8a-hexahydro-2-methyl-carbonyl-isoquinolin-6-yl), or 1,2,3,4-trihydro-2-methylcarbonyl-isoquinolin-2-yl In another embodiment, the present invention is directed to compounds of formula (I) as herein described, provided that when $R^1$ and $R^2$ are taken together with the carbon atom to which they are bound to form cyclopentyl; m is 1 and n is 0 or m is 0 and m is 1;

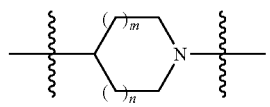

is pyrrolidin-3R-yl; $-(L^1)_a$-$R^3$ is —C(O)-cyclopropyl;

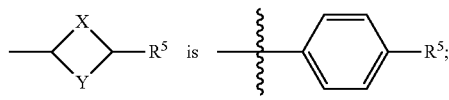

b=0 or $(R^4)_b$ is 2-methyl; then $R^5$ is other than 1-methyl-pyrazol-4-yl, 4-methyl-3,4-dihydro-pyrido[2,3-b]oxazon-7-yl, 2-(piperazin-1-yl)-pyridin-4-yl or 2-(4-methyl-piperazin-1-yl)-pyridin-4-yl.

In another embodiment, the present invention is directed to compounds of formula (I) as herein described, provided that when $R^1$ and $R^2$ are taken together with the carbon atom to which they are bound to form cyclopentyl; m is 1 and n is 0 or m is 0 and m is 1;

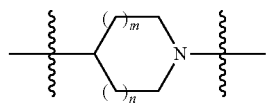

is pyrrolidin-3R-yl; $-(L^1)_a$-$R^3$ is —SO$_2$-pyrrolidin-1-yl;

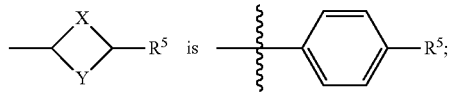

b=0 or $(R^4)_b$ is 2-methyl; then $R^5$ is other than benzofuran-5-yl.

In another embodiment, the present invention is directed to compounds of formula (I) as herein described, provided that when $R^1$ and $R^2$ are taken together with the carbon atom to which they are bound to form cyclopropyl; m is 0, n is 0,

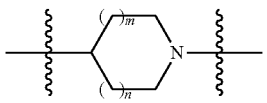

is azetidin-3-yl; -(L¹)ₐ-R³ is selected from the group consisting of —C(O)-cyclopropyl, —C(O)-(1-methyl-cyclopropyl) and —C(O)-(1-hydroxy-cyclopropyl);

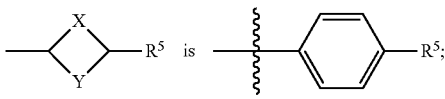

b=0 or (R⁴)ᵦ is selected from the group consisting of 2-fluoro and 2-methyl; then R⁵ is other than 1-isopropylsulfonyl-phenyl, 1-methyl-indazol-5-yl, 1-isopropyl-indazol-5-yl, 1-oxetan-3-yl, indazol-5-yl, 1-methyl-pyrazol-4-yl, 4-methyl-7-bromo-quinolin-2-yl, 5-(2-hydroxy-2-methyl-propyl)-pyridin-2-yl, 6-isopropyl-pyridin-3-yl, 6-(1-cyanomethyl)-pyridin-3-yl, 6-(2-hydroxy-2-methyl-propyl)-pyridin-3-yl, 1,5-naphthyridin-3-yl, 3-methyl-[1,2,4]triazolo[4,3-a]pyridin-6-yl, 4-(1-isobutyl-pyrazol-5-yl)-phenyl, or 6-(morpholin-4-yl)-pyridin-3-yl.

In another embodiment, the present invention is directed to compounds of formula (I) as herein described, provided that when R¹ and R² are taken together with the carbon atom to which they are bound to form cyclopropyl; m is 0, n is 0,

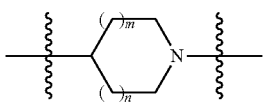

is azetidin-3-yl; -(L¹)ₐ-R³ is —C(O)-(1-hydroxy-cyclopropyl);

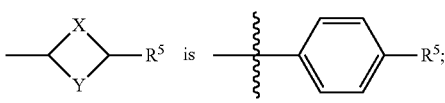

and (R⁴)) is 2-methyl; then R⁵ is other 1-methyl-indazol-5-yl.

In another embodiment, the present invention is directed to compounds of formula (I) as herein described, provided that when R¹ and R² are taken together with the carbon atom to which they are bound to form cyclopropyl; m is 0, n is 0,

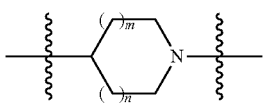

is azetidin-3-yl; -(L¹)-R³ is —C(O)-pyridin-3-yl;

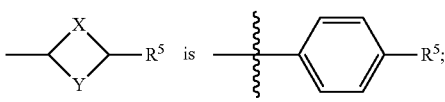

(R⁴)ᵦ is 2-methyl; then R⁵ is other than 1-methyl-indazol-5-yl.

In another embodiment, the present invention is directed to compounds of formula (I) as herein described, provided that when R¹ and R² are taken together with the carbon atom to which they are bound to form cyclopropyl; m is 0, n is 2,

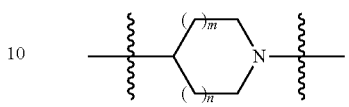

is piperidin-3R-yl or piperidin-3S-yl; -(L¹)ₐ-R³ is —C(O)-cyclopropyl;

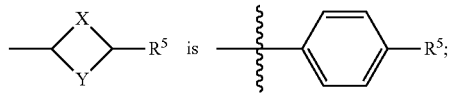

and b=0; then R⁵ is other than indazol-5-yl, benzofuran-5-yl, benzothien-5-yl, 1-methyl-indazol-5-yl, 4-(4-methylphenyl)phenyl, or 4-(3-chlorophenyl)-phenyl.

In another embodiment, the present invention is directed to compounds of formula (I) as herein described, provided that when R¹ and R² are taken together with the carbon atom to which they are bound to form cyclopropyl; m is 1, n is 1,

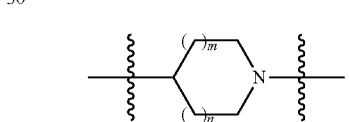

is piperidin-4-yl; -(L¹)ₐ-R³ is —C(O)-cyclopropyl;

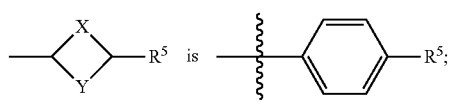

and b=0; then R⁵ is other 4-trifluoromethylphenyl, 1-methyl-pyrazol-4-yl, benzoxazol-5-yl, pyridin-4-yl, or 4-(1-methyl-pyrazol-4-yl)-phenyl.

In another embodiment, the present invention is directed to compounds of formula (I) as herein described, provided that when R¹ and R² are taken together with the carbon atom to which they are bound to form cyclopropyl; m is 0 and n is 1 or m is 1 and n is 0;

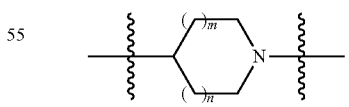

is pyrrolidin-3R-yl; -(L¹)ₐ-R³ is —C(O)-cyclopropyl;

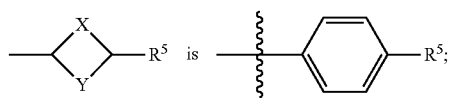

and b=0; then $R^5$ is other than 5-chloro-pyridin-3-yl, 2-oxo-3,4-dihydro-quinolin-7-yl, or 6-(4-methyl-piperazin-1-yl)pyridin-3-yl.

In another embodiment, the present invention is directed to compounds of formula (I) as herein described, provided that when $R^1$ and $R^2$ are taken together with the carbon atom to which they are bound to form tetrahydrofuran-3,3-diyl or tetrahydropyran-4,4-diyl; m is an integer from 0 to 1 and n is 0 or m is 0 and n is an integer from 0 to 1;

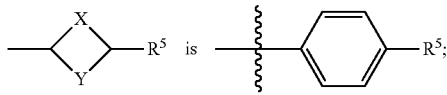

is selected from the group consisting of azetidin-3-yl, pyrrolidin-3R-yl and pyrrolidin-3-yl; $(L^1)_a$-$R^3$ is selected from the group consisting of —C(O)-thiazol-2-yl, —C(O)—CF$_3$, —C(O)OCH$_3$ and —SO$_2$—CH$_3$;

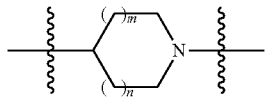

and b=0; then $R^5$ is other than quinolin-7-yl, 1-methyl-indazol-5-yl, benzofuran-5-yl, or 4-(1-methyl-pyrazol-4-yl)-phenyl.

In another embodiment, the present invention is directed to compounds of formula (I) as herein described, provided that when $R^1$ and $R^2$ are taken together with the carbon atom to which they are bound to form 1-(methoxycarbonyl)-azetidin-3-yl; m is 1 and n is 0 or m is 0 and m is 1;

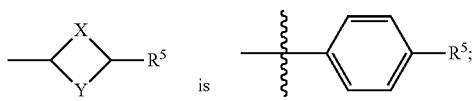

is pyrrolidin-3R-yl; -$(L^1)$-$R^3$ is —C(O)-cyclopropyl;

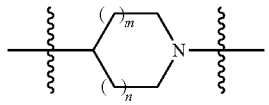

and b=0; then $R^5$ is other than quinolin-7-yl, benzofuran-5-yl, or 1-methyl-indazol-5 yl.

In another embodiment, the present invention is directed to compounds of formula (I) as herein described, provided that when $R^1$ and $R^2$ are taken together with the carbon atom to which they are bound to form cyclopropyl; m is 0, n is 0,

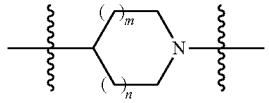

is azetidin-3-yl; -$(L^1)_a$-$R^3$ is selected from the group consisting of —C(O)-cyclopropyl, —C(O)-(1-methyl-cyclopropyl) and —C(O)-(1-hydroxy-cyclopropyl);

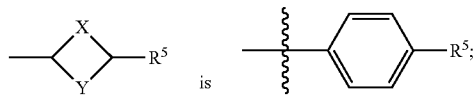

b=0 or ($R^4$)), is selected from the group consisting of 2-fluoro and 2-methyl; then $R^5$ is other than 1-methyl-indazol-5-yl or indazol-5-yl.

In another embodiment, the present invention is directed to compounds of formula (I) as herein described, provided that when $R^1$ and $R^2$ are taken together with the carbon atom to which they are bound to form cyclopropyl; m is 1, n is 1,

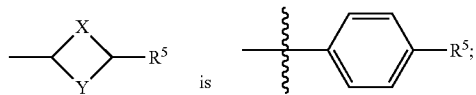

is piperidin-4-yl; -$(L^1)_a$-$R^3$ is —C(O)-cyclopropyl;

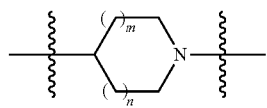

and b=0; then R is other than benzoxazol-5-yl.

In another embodiment, the present invention is directed to compounds of formula (I) as herein described, provided that when $R^1$ and $R^2$ are taken together with the carbon atom to which they are bound to form cyclopropyl; m is 0 and n is 1 or m is 1 and n is 0;

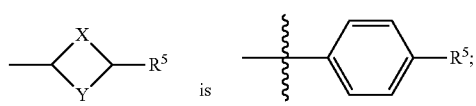

is pyrrolidin-3R-yl; -$(L^1)_a$-$R^3$ is —C(O)-cyclopropyl;

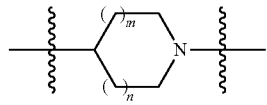

and b=0; then R is other than 2-oxo-3,4-dihydro-quinolin-7-yl.

In another embodiment, the present invention is directed to compounds of formula (I) as herein described, provided that when $R^1$ and $R^2$ are taken together with the carbon atom to which they are bound to form 1-(methoxycarbonyl)-azetidin-3-yl; m is 1 and n is 0 or m is 0 and m is 1;

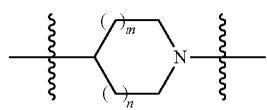

is pyrrolidin-3R-yl; -$(L^1)$-$R^3$ is selected from the group consisting of —C(O)—CF$_3$, —C(O)-cyclopropyl, —C(O)-(thiazol-2-yl), —C(O)OCH$_3$, and —SO$_2$—CH$_3$;

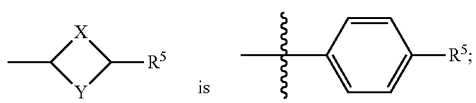 is 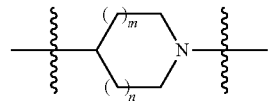

and b=0: then R⁵ is other than 4-(1-methyl-pyrazol-4-yl)-phenyl.

In another embodiment, the present invention is directed to compounds of formula (I) as herein described, provided that when R¹ and R² are taken together with the carbon atom to which they are bound to form cyclopentyl; m is 1 and n is 0 or m is 0 and m is 1;

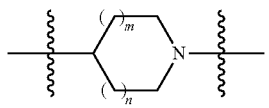

is pyrrolidin-3R-yl; -(L¹)$_a$-R³ is —C(O)-cyclopropyl;

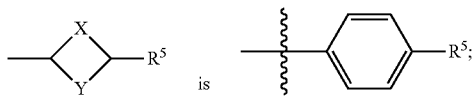 is 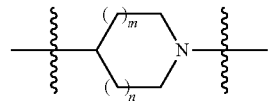

b=0 or (R⁴)$_b$ is 2-methyl; then R⁵ is other than 2-(piperazin-1-yl)-pyridin-4-yl or 2-(4-methyl-piperazin-1-yl)-pyridin-4-yl.

In another embodiment, the present invention is directed to compounds of formula (I) as herein described, provided that when R¹ and R² are taken together with the carbon atom to which they are bound to form cyclopropyl; m is 0, n is 0, and

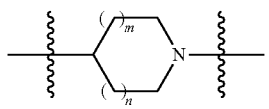

is azetidin-3-yl; -(L¹)$_a$-R³ is selected from the group consisting of —C(O)-cyclopropyl, —C(O)-(1-methyl-cyclopropyl) and —C(O)-(1-hydroxy-cyclopropyl);

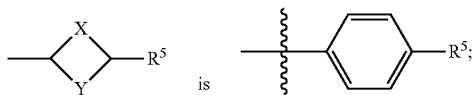 is 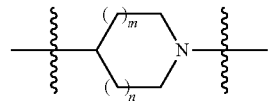

b=0 or (R⁴)$_b$ is selected from the group consisting of 2-fluoro and 2-methyl; then R⁵ is other than 4-(1-isobutyl-pyrazol-5-yl)-phenyl.

In another embodiment, the present invention is directed to compounds of formula (I) as herein described, provided that when R¹ and R² are taken together with the carbon atom to which they are bound to form cyclopropyl; m is 0, n is 2, is piperidin-3R-yl; -(L¹)$_a$-R³ is —C(O)-cyclopropyl;

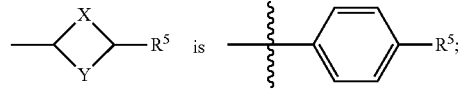

and b=0; then R⁵ is other than 4-(4-methylphenyl)phenyl or 4-(3-chlorophenyl)-phenyl.

In another embodiment, the present invention is directed to compounds of formula (I) as herein described, provided that when R¹ and R² are taken together with the carbon atom to which they are bound to form cyclopropyl; m is 1, n is 1, and

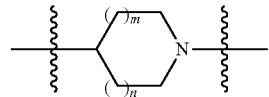

is piperidin-4-yl; -(L¹)$_a$-R is —C(O)-cyclopropyl;

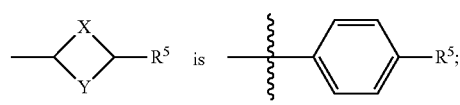

and b=0; then R⁵ is other than 4-(1-methyl-pyrazol-4-yl)-phenyl.

In another embodiment, the present invention is directed to compounds of formula (I) as herein described, provided that when R¹ and R² are taken together with the carbon atom to which they are bound to form cyclopropyl; m is 0 and n is 1 or m is 1 and n is 0;

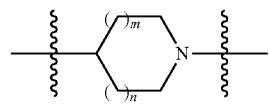

is pyrrolidin-3R-yl; -(L¹)$_a$-R³ is —C(O)-cyclopropyl;

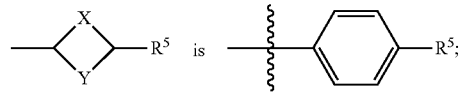

and b=0; then R⁵ is other than 6-(4-methyl-piperazin-1-yl)-pyridin-3-yl.

In another embodiment, the present invention is directed to compounds of formula (I) as herein described, provided that when R¹ and R² are taken together with the carbon atom to which they are bound to form tetrahydrofuran-3,3-diyl or tetrahydropyran-4,4-diyl; m is an integer from 0 to 1 and n is 0 or m is 0 and n is an integer from 0 to 1;

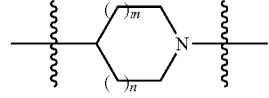

is selected from the group consisting of azetidin-3-yl, pyrrolidin-3R-yl, and pyrrolidin-3-yl; -(L$^1$)$_a$-R$^3$ is selected from the group consisting of —C(O)—CF$_3$, —C(O)OCH$_3$, and —SO$_2$—CH$_3$;

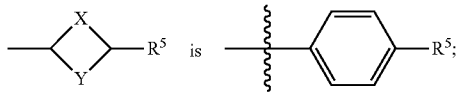

and b=0; then R$^5$ is other than 4-(1-methyl-pyrazol-4-yl)-phenyl.

Additional embodiments of the present invention, include those wherein the substituents selected for one or more of the variables defined herein (e.g. R$^1$, R$^2$, R$^3$, R$^4$, R$^5$, L$^1$, a, b, m, n,

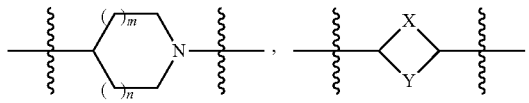

etc.) are independently selected to be any individual substituent or any subset of substituents selected from the complete list as defined herein.

In additional embodiments, the present invention is directed to any single compound or subset of compounds, selected from the representative compounds listed in Tables 1-4, below.

Representative compounds of formula (I) of the present invention are listed in Table 1 to 4, below. Unless otherwise noted, where a stereogenic center is present in the listed compound, the compound was prepared as a mixture of stereo-configurations. Where a stereogenic center is present, the S- and R-designations are intended to indicate that the exact stereo-configuration of the center has been determined.

As used herein, for example, as in the Tables below, the "R$^1$ & R$^2$ taken together" substituent group is named independent of the imidazolid-5-one core with which it forms a spiro-ring system, with the two of the spiro-bond positions denoted in the name. For example, wherein R$^1$ and R$^2$ are taken together with the carbon atom to which they are bound to form a spiro-ring of the following structure:

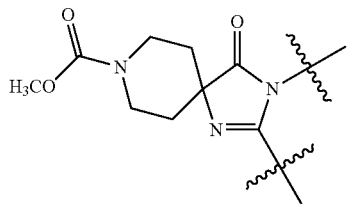 [SMILES: *C1=NC2(CCN(C(=O)OC)CC2)C(=O)N1*]

the substituent group "R$^1$ & R$^2$ taken together" is named/denoted as 1-(methoxy-carbonyl)-piperidin-4,4-diyl; wherein the "4,4-diyl" nomenclature indicating that the two bonds creating the spiro linkage are made through the 4-position on the piperidine portion of the spiro-ring structure.

TABLE 1

Representative Compounds of Formula (I)

| ID No. | R$^1$ & R$^2$ taken together | (L$^1$)$_a$ | R$^3$ | (R$^4$)$_b$ | 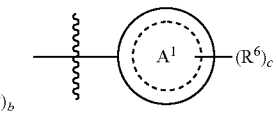 |
|---|---|---|---|---|---|
| 1 | cyclopentyl | pyrrolidin-3R-yl | C(O) | cyclopropyl | b = 0 | 4-cyano-phenyl |
| 2 | cyclopentyl | pyrrolidin-3R-yl | C(O) | cyclopropyl | b = 0 | benzofuran-5-yl |

TABLE 1-continued

Representative Compounds of Formula (I)

| ID No. | R¹ & R² taken together | (L¹)ₐ | R³ | (R⁴)ᵦ | A¹(R⁶)c |
|---|---|---|---|---|---|
| 3 | cyclopentyl | pyrrolidin-3R-yl | C(O) | cyclopropyl | b = 0 | pyridin-4-yl |
| 4 | cyclopentyl | pyrrolidin-3R-yl | C(O) | cyclopropyl | b = 0 | indol-5-yl |
| 5 | cyclopentyl | pyrrolidin-3R-yl | C(O) | cyclopropyl | b = 0 | pyridin-3-yl |
| 6 | cyclopropyl | piperidin-4-yl | C(O) | cyclopropyl | b = 0 | pyridin-3-yl |
| 7 | cyclopropyl | piperidin-4-yl | C(O) | cyclopropyl | b = 0 | 4-cyano-phenyl |
| 8 | cyclopropyl | piperidin-4-yl | C(O) | cyclopropyl | b = 0 | 1-methyl-pyrazol-5-yl |
| 9 | cyclopropyl | piperidin-4-yl | C(O) | cyclopropyl | b = 0 | 1-methyl-pyrazol-4-yl |
| 10 | cyclopropyl | piperidin-4-yl | C(O) | cyclopropyl | b = 0 | indol-5-yl |
| 11 | cyclopentyl | pyrrolidin-3R-yl | C(O) | cyclopropyl | b = 0 | quinolin-6-yl |
| 12 | cyclopentyl | pyrrolidin-3R-yl | C(O) | cyclopropyl | b = 0 | isoquinolin-6-yl |
| 13 | cyclopentyl | pyrrolidin-3R-yl | C(O) | cyclopropyl | b = 0 | 1-methyl-pyrazol-4-yl |
| 14 | 1-(methoxy-carbonyl)-piperidin-4,4-diyl | pyrrolidin-3R-yl | C(O) | cyclopropyl | b = 0 | benzofuran-5-yl |
| 15 | 1-(methoxy-carbonyl)-piperidin-4,4-diyl | pyrrolidin-3R-yl | C(O) | cyclopropyl | b = 0 | indol-5-yl |
| 16 | 1-(methoxy-carbonyl)-piperidin-4,4-diyl | azetidin-3-yl | C(O) | cyclopropyl | b = 0 | benzofuran-5-yl |
| 17 | 1-(methoxy-carbonyl)-piperidin-4,4-diyl | azetidin-3-yl | C(O) | cyclopropyl | b = 0 | indol-5-yl |
| 18 | cyclopentyl | pyrrolidin-3R-yl | C(O) | cyclopropyl | b = 0 | pyridin-2-yl |
| 19 | cyclopropyl | piperidin-4-yl | C(O) | cyclopropyl | b = 0 | 1-methyl-indazol-5-yl |

TABLE 1-continued

Representative Compounds of Formula (I)

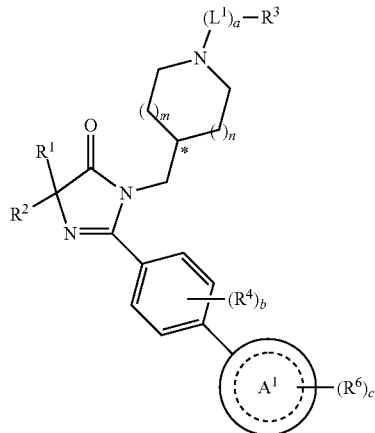

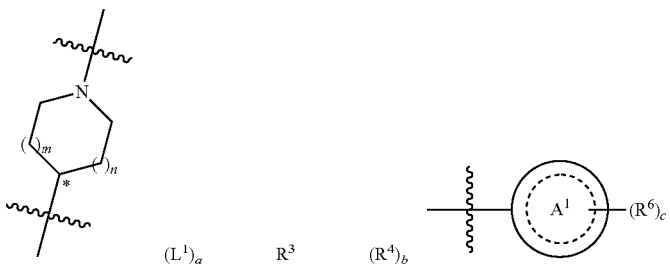

| ID No. | R¹ & R² taken together | | (L¹)ₐ | R³ | (R⁴)_b | |
|---|---|---|---|---|---|---|
| 20 | cyclopropyl | piperidin-4-yl | C(O) | cyclopropyl | b = 0 | isoquinolin-6-yl |
| 22 | cyclopentyl | pyrrolidin-3R-yl | C(O) | cyclopropyl | b = 0 | quinolin-4-yl |
| 24 | cyclopropyl | piperidin-4-yl | C(O) | cyclopropyl | b = 0 | 1-methyl-indazol-6-yl |
| 25 | cyclopropyl | piperidin-4-yl | C(O) | cyclopropyl | b = 0 | isoquinolin-7-yl |
| 26 | cyclopropyl | piperidin-4-yl | C(O) | cyclopropyl | b = 0 | benzimidazol-5-yl |
| 27 | cyclopropyl | pyrrolidin-3R-yl | C(O) | cyclopropyl | b = 0 | 1-methyl-indazol-6-yl |
| 28 | cyclopropyl | pyrrolidin-3R-yl | C(O) | cyclopropyl | b = 0 | 1-methyl-indazol-5-yl |
| 29 | cyclopropyl | piperidin-4-yl | C(O) | cyclopropyl | b = 0 | indazol-5-yl |
| 30 | cyclopropyl | pyrrolidin-3R-yl | C(O) | cyclopropyl | b = 0 | isoquinolin-7-yl |
| 31 | cyclopropyl | pyrrolidin-3R-yl | C(O) | cyclopropyl | b = 0 | indol-5-yl |
| 32 | cyclopropyl | piperidin-4-yl | C(O) | cyclopropyl | b = 0 | pyridin-4-yl |
| 33 | cyclopentyl | pyrrolidin-3R-yl | C(O) | cyclopropyl | b = 0 | indol-6-yl |
| 34 | cyclopentyl | pyrrolidin-3R-yl | C(O) | cyclopropyl | b = 0 | 1-methyl-indazol-6-yl |
| 35 | cyclopentyl | pyrrolidin-3R-yl | C(O) | cyclopropyl | b = 0 | 1-methyl-indazozl-5-yl |
| 36 | cyclopentyl | pyrrolidin-3R-yl | C(O) | cyclopropyl | b = 0 | benzoxazol-2-yl |
| 37 | cyclopropyl | piperidin-4-yl | C(O) | cyclopropyl | b = 0 | benzoxazol-5-yl |
| 38 | cyclopropyl | azetidin-3-yl | C(O) | cyclopropyl | b = 0 | 1-methyl-indazol-6-yl |
| 39 | cyclopropyl | azetidin-3-yl | C(O) | cyclopropyl | b = 0 | 1-methyl-indazol-5-yl |
| 40 | cyclopropyl | azetidin-3-yl | C(O) | cyclopropyl | b = 0 | indol-5-yl |
| 41 | cyclopropyl | azetidin-3-yl | C(O) | cyclopropyl | b = 0 | 4-cyano-phenyl |
| 42 | cyclopropyl | azetidin-3-yl | C(O) | cyclopropyl | b = 0 | 1-methyl-pyrazol-4-yl |

TABLE 1-continued

Representative Compounds of Formula (I)

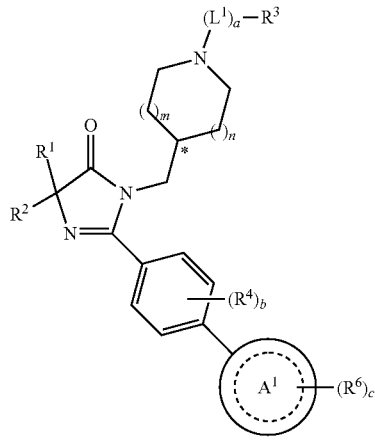

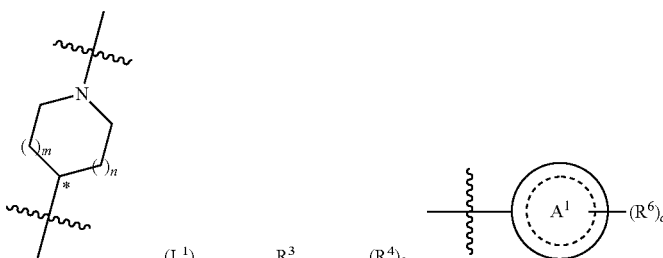

| ID No. | R¹ & R² taken together | | (L¹)ₐ | R³ | (R⁴)ᵦ | |
|---|---|---|---|---|---|---|
| 43 | cyclopropyl | azetidin-3-yl | C(O) | cyclopropyl | b = 0 | 1-methyl-pyreazol-5-yl |
| 47 | cyclopropyl | pyrrolidin-3R-yl | C(O) | cyclopropyl | b = 0 | isoquinolin-6-yl |
| 48 | cyclopropyl | pyrrolidin-3R-yl | C(O) | cyclopropyl | b = 0 | 4-cyano-phenyl |
| 49 | cyclopropyl | azetidin-3-yl | C(O) | cyclopropyl | b = 0 | benzofuran-5-yl |
| 50 | cyclopropyl | azetidin-3-yl | C(O) | cyclopropyl | b = 0 | 4-hydroxy-phenyl |
| 51 | cyclopropyl | azetidin-3-yl | C(O) | cyclopropyl | b = 0 | indazol-5-yl |
| 52 | cyclopropyl | azetidin-3-yl | C(O) | cyclopropyl | b = 0 | benzoxazol-5-yl |
| 53 | cyclopropyl | azetidin-3-yl | C(O) | cyclopropyl | b = 0 | 3-amino-4-hydroxy-phenyl |
| 54 | cyclopropyl | azetidin-3-yl | C(O) | cyclopropyl | b = 0 | 3-form-amido-4-hydroxy-phenyl |
| 55 | cyclopropyl | piperidin-4-yl | C(O) | cyclopropyl | b = 0 | 4-hydroxy-phenyl |
| 57 | cyclopropyl | piperidin-4-yl | C(O) | cyclopropyl | b = 0 | benzothiazol-5-yl |
| 58 | cyclopropyl | pyrrolidin-3R-yl | C(O) | cyclopropyl | b = 0 | benzofuran-5-yl |
| 63 | 1-(benzyl)-piperidin-4,4-diyl | pyrrolidin-3R-yl | C(O) | cyclopropyl | b = 0 | indol-5-yl |
| 64 | cyclopropyl | pyrrolidin-3R-yl | C(O) | cyclopropyl | b = 0 | 4-hydroxy-phenyl |
| 66 | cyclopentyl | pyrrolidin-3R-yl | C(O) | cyclopropyl | b = 0 | quinolin-5-yl |
| 67 | cyclopentyl | pyrrolidin-3R-yl | C(O) | cyclopropyl | b = 0 | isoquinolin-5-yl |
| 68 | cyclopentyl | pyrrolidin-3R-yl | C(O) | cyclopropyl | b = 0 | indol-4-yl |
| 69 | cyclopentyl | pyrrolidin-3R-yl | C(O) | cyclopropyl | b = 0 | isoquinolin-7-yl |
| 71 | cyclopropyl | pyrrolidin-3R-yl | C(O) | cyclopropyl | b = 0 | benzothiazol-5-yl |
| 72 | cyclopentyl | pyrrolidin-3R-yl | C(O) | cyclopropyl | 2-methyl | benzofuran-5-yl |
| 73 | cyclopentyl | pyrrolidin-3R-yl | C(O) | cyclopropyl | 2-methyl | indol-5-yl |

TABLE 1-continued

Representative Compounds of Formula (I)

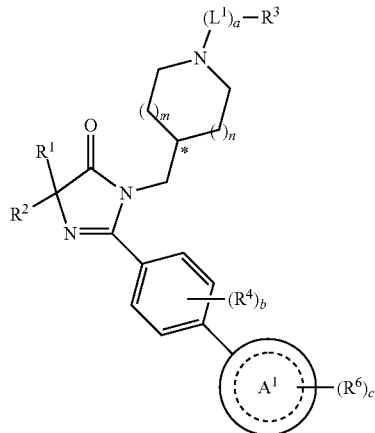

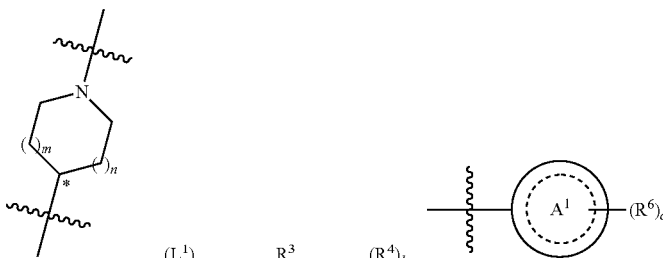

| ID No. | R¹ & R² taken together | (L¹)ₐ | R³ | (R⁴)_b | |
|---|---|---|---|---|---|
| 74 | cyclopentyl | pyrrolidin-3R-yl | C(O) | cyclopropyl | 2-methyl | isoquinolin-6-yl |
| 75 | cyclopentyl | piperidin-4-yl | C(O) | cyclopropyl | b = 0 | benzofuran-5-yl |
| 76 | cyclopentyl | piperidin-4-yl | C(O) | cyclopropyl | b = 0 | indol-5-yl |
| 77 | cyclopentyl | piperidin-4-yl | C(O) | cyclopropyl | b = 0 | isoquinolin-6-yl |
| 78 | cyclopentyl | azetidin-3-yl | C(O) | cyclopropyl | b = 0 | indol-5-yl |
| 79 | cyclopentyl | azetidin-3-yl | C(O) | cyclopropyl | b = 0 | isoquinolin-6-yl |
| 80 | cyclopentyl | azetidin-3-yl | C(O) | cyclopropyl | b = 0 | benzofuran-5-yl |
| 81 | 1-methyl-piperidin-4,4-diyl | pyrrolidin-3R-yl | C(O) | cyclopropyl | b = 0 | indol-5-yl |
| 82 | cyclopentyl | pyrrolidin-3R-yl | C(O) | cyclopropyl | b = 0 | 4-chloro-phenyl |
| 83 | cyclopentyl | pyrrolidin-3R-yl | C(O) | cyclopropyl | b = 0 | 3-cyano-phenyl |
| 84 | cyclopentyl | pyrrolidin-3R-yl | C(O) | cyclopropyl | b = 0 | 3-methyl-sulfonyl-amino-phenyl |
| 85 | cyclopentyl | pyrrolidin-3R-yl | C(O) | cyclopropyl | b = 0 | 4-methoxy-phenyl |
| 90 | 1-(benzyl)-piperidin-4,4-diyl) | pyrrolidin-3R-yl | C(O) | ethenyl | b = 0 | benzofuran-5-yl |
| 92 | cyclopentyl | pyrrolidin-3R-yl | C(O) | cyclopropyl | b = 0 | indazol-4-yl |
| 93 | cyclopentyl | pyrrolidin-3R-yl | C(O) | cyclopropyl | 2-methyl | 4-chloro-phenyl |
| 94 | cyclopentyl | pyrrolidin-3R-yl | C(O) | cyclopropyl | 2-methyl | 2,4-dichloro-phenyl |
| 95 | 1-(benzyl)-piperidin-4,4-diyl) | pyrrolidin-3R-yl | C(O) | NH₂ | b = 0 | benzofuran-3-yl |
| 96 | 1-(benzyl)-piperidin-4,4-diyl) | pyrrolidin-3R-yl | C(O) | cyclopropyl | b = 0 | benzofuran-5-yl |
| 97 | cyclopropyl | piperidin-4-yl | C(O) | cyclopropyl | b = 0 | 4-methyl-phenyl |

TABLE 1-continued

Representative Compounds of Formula (I)

| ID No. | R¹ & R² taken together | | (L¹)ₐ | R³ | (R⁴)_b | |
|---|---|---|---|---|---|---|
| 98 | cyclopropyl | piperidin-4-yl | C(O) | cyclopropyl | b = 0 | 2-methoxy-phenyl |
| 99 | cyclopropyl | piperidin-4-yl | C(O) | cyclopropyl | b = 0 | 4-methoxy-phenyl |
| 100 | cyclopropyl | pyrrolidin-3R-yl | C(O) | cyclopropyl | b = 0 | 4-methyl-phenyl |
| 101 | cyclopropyl | pyrrolidin-3R-yl | C(O) | cyclopropyl | b = 0 | 3-methyl-phenyl |
| 102 | cyclopropyl | pyrrolidin-3R-yl | C(O) | cyclopropyl | b = 0 | 3-fluoro-phenyl) |
| 103 | cyclopropyl | pyrrolidin-3R-yl | C(O) | cyclopropyl | b = 0 | 4-methoxy-phenyl |
| 104 | cyclopropyl | pyrrolidin-3R-yl | C(O) | cyclopropyl | b = 0 | 4-trifluoro-methyl-phenyl |
| 105 | cyclopropyl | pyrrolidin-3R-yl | C(O) | cyclopropyl | b = 0 | 4-fluoro-phenyl) |
| 106 | piperidin-4,4-yl | pyrrolidin-3R-yl | C(O) | cyclopropyl | b = 0 | isoquinolin-6-yl |
| 107 | cyclopropyl | piperidin-4-yl | C(O) | cyclopropyl | b = 0 | 4-trifluoro-methyl-phenyl |
| 108 | cyclopropyl | piperidin-4-yl | C(O) | cyclopropyl | b = 0 | 3-hydroxy-phenyl |
| 109 | cyclopropyl | piperidin-4-yl | C(O) | cyclopropyl | b = 0 | 4-chloro-phenyl |
| 110 | cyclopropyl | piperidin-4-yl | C(O) | cyclopropyl | b = 0 | 4-fluoro-phenyl |
| 111 | cyclopropyl | piperidin-4-yl | C(O) | cyclopropyl | b = 0 | 3-methyl-phenyl |
| 112 | cyclopropyl | pyrrolidin-3R-yl | C(O) | cyclopropyl | b = 0 | 3-chloro-phenyl |
| 113 | cyclopropyl | pyrrolidin-3R-yl | C(O) | cyclopropyl | b = 0 | 3-methoxy-phenyl |
| 114 | cyclopropyl | pyrrolidin-3R-yl | C(O) | cyclopropyl | b = 0 | 4-chloro-phenyl |
| 115 | cyclopropyl | pyrrolidin-3R-yl | C(O) | cyclopropyl | b = 0 | 3-hydroxy-phenyl |
| 116 | cyclopentyl | pyrrolidin-3R-yl | C(O) | 1-methyl-cycloprop-1-yl | b = 0 | benzofuran-5-yl |
| 117 | cyclopentyl | pyrrolidin-3S-yl | C(O) | pyrrolidin-1-yl | b = 0 | benzofuran-5-yl |
| 118 | cyclopentyl | pyrrolidin-3R-yl | C(O) | 1-methyl-pyrazol-3-yl | b = 0 | benzofuran-5-yl |

TABLE 1-continued

Representative Compounds of Formula (I)

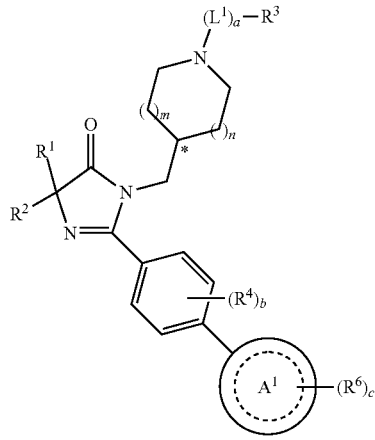

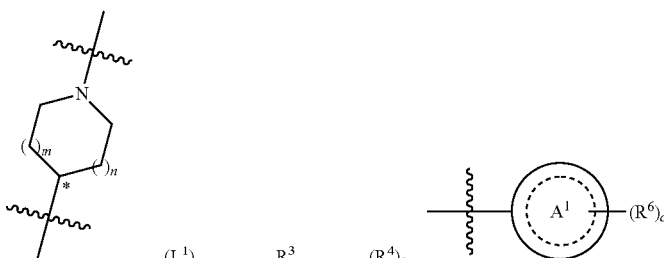

| ID No. | R¹ & R² taken together | $(L^1)_a$ | R³ | $(R^4)_b$ | |
|---|---|---|---|---|---|
| 119 | cyclopentyl | pyrrolidin-3R-yl | C(O) | 2,2,2-trifluoro-ethyl | b = 0 | benzofuran-5-yl |
| 120 | cyclopentyl | pyrrolidin-3R-yl | C(O) | cyclopropyl | 2-fluoro | benzofuran-5-yl |
| 121 | cyclopentyl | pyrrolidin-3R-yl | C(O) | cyclopropyl | 2-fluoro | 4-chloro-phenyl |
| 123 | cyclopropyl | pyrrolidin-3R-yl | C(O) | cyclopropyl | b = 0 | 3-cyano-phenyl |
| 124 | cyclopropyl | pyrrolidin-3R-yl | C(O) | cyclopropyl | b = 0 | 4-dimethyl-amino-phenyl |
| 125 | cyclopropyl | pyrrolidin-3R-yl | C(O) | cyclopropyl | b = 0 | 4-trifluoro-methoxy-phenyl |
| 126 | cyclopropyl | pyrrolidin-3R-yl | C(O) | cyclopropyl | b = 0 | 3-trifluoro-methyl-phenyl |
| 127 | 1-(2-hydroxy-ethyl)-piperidin-4,4-diyl | pyrrolidin-3R-yl | C(O) | cyclopropyl | b = 0 | 1-methyl-indazol-5-yl |
| 128 | piperidin-4,4-diyl | pyrrolidin-3R-yl | C(O) | cyclopropyl | b = 0 | 1-methyl-indazol-5-yl |
| 129 | 1-(isopropyl-carbonyl)-piperidin-4,4-yl | azetidin-3-yl | C(O) | cyclopropyl | b = 0 | benzofuran-5-yl |
| 130 | piperidin-4,4-diyl | azetidin-3-yl | C(O) | cyclopropyl | b = 0 | benzofuran-5-yl |
| 131 | piperidin-4,4-diyl | azetidin-3-yl | C(O) | cyclopropyl | b = 0 | 1-methyl-indazol-5-yl |
| 132 | piperidin-4,4-diyl | azetidin-3-yl | C(O) | cyclopropyl | b = 0 | isoquinolin-6-yl |
| 133 | piperidin-4,4-diyl | pyrrolidin-3R-yl | C(O) | cyclopropyl | b = 0 | benzofuran-5-yl |
| 134 | 1-(cyclopropyl-carbonyl)-piperidin-4,4-diyl | azetidin-3-yl | C(O) | cyclopropyl | b = 0 | benzofuran-5-yl |

TABLE 1-continued

Representative Compounds of Formula (I)

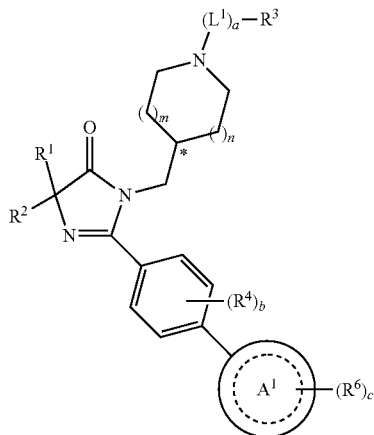

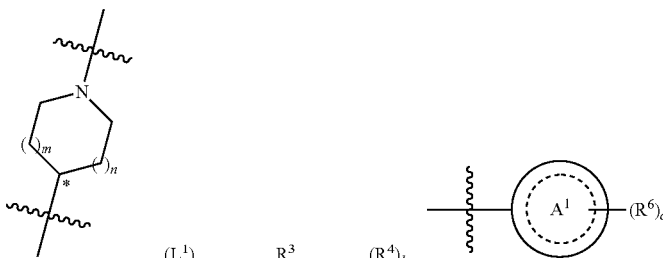

| ID No. | R¹ & R² taken together | (L¹)ₐ | R³ | (R⁴)ᵦ | A¹-(R⁶)c |
|---|---|---|---|---|---|
| 135 | 1-(isopropyl-carbonyl)-piperidin-4,4-diyl | azetidin-3-yl | C(O) | cyclopropyl | b = 0 | 1-methyl-indazol-5-yl |
| 136 | 1-(dimethyl-amino-methyl-carbonyl)-piepridin-4,4-diyl | azetidin-3-yl | C(O) | cyclopropyl | b = 0 | 1-methyl-indazol-5-yl |
| 137 | 1-(isopropyl-carbonyl)-piperidin-4,4-diyl | azetidin-3-yl | C(O) | cyclopropyl | b = 0 | isoquinolin-6-yl |
| 138 | 1-(methyl-carbonyl)-piperidin-4,4-yl | pyrrolidin-3R-yl | C(O) | cyclopropyl | b = 0 | 1-methyl-indazol-5-yl |
| 139 | 1-(isopropyl-carbonyl)-piperidin-4,4-diyl | pyrrolidin-3R-yl | C(O) | cyclopropyl | b = 0 | 1-methyl-indazol-5-yl |
| 140 | 1-(cyclopropyl-carbonyl)-piperidin-4,4-yl | pyrrolidin-3R-yl | C(O) | cyclopropyl | b = 0 | 1-methyk-indazol-5-yl |
| 141 | 1-(dimethyl-amino-methyl-carbonyl)-piperidin-4,4-diyl | pyrrolidin-3R-yl | C(O) | cyclopropyl | b = 0 | 1-methyl-indazol-5-yl |
| 142 | 1-(dimethyl-amino-methyl-carbonyl)-piperidin-4,4-diyl | pyrrolidin-3R-yl | C(O) | cyclopropyl | b = 0 | isoquinolin-6-yl |

TABLE 1-continued

Representative Compounds of Formula (I)

| ID No. | R¹ & R² taken together | (L¹)ₐ | R³ | (R⁴)ᵦ | A¹–(R⁶)_c |
|---|---|---|---|---|---|
| 143 | 1-(isopropyl-carbonyl)-piperidin-4,4-diyl | pyrrolidin-3R-yl | C(O) | cyclopropyl | b = 0 | isoquinolin-6-yl |
| 144 | 1-(methyl-carbonyl)-piperidin-4,4-diyl | pyrrolidin-3R-yl | C(O) | cyclopropyl | b = 0 | isoquinolin-6-yl |
| 145 | cyclopropyl | pyrrolidin-3R-yl | C(O) | cyclopropyl | b = 0 | 3-dimethyl-amino-phenyl |
| 146 | cyclopropyl | pyrrolidin-3R-yl | C(O) | cyclopropyl | b = 0 | 3-trifluoro-methoxy-phenyl |
| 147 | 1-(methyl-carbonyl)-piperidin-4,4-diyl | pyrrolidin-3R-yl | C(O) | cyclopropyl | b = 0 | indol-5-yl |
| 148 | 1-(methyl-carbonyl)-piperidin-4,4-diyl | pyrrolidin-3R-yl | C(O) | cyclopropyl | b = 0 | indazol-5-yl |
| 149 | 1-(dimethyl-amino-methyl-carbonyl)-piperidin-4,4-diyl | azetidin-3-yl | C(O) | cyclopropyl | b = 0 | benzofuran-5-yl |
| 150 | 1-(methyl-carbonyl)-piperidin-4,4-diyl | pyrrolidin-3R-yl | C(O) | cyclopropyl | b = 0 | benzofuran-5-yl |
| 151 | 1-(isopropyl-carbonyl)-piperidin-4,4-diyl | pyrrolidin-3R-yl | C(O) | cyclopropyl | b = 0 | benzofuran-5-yl |
| 152 | 1-(cyclopropyl-carbonyl)-piperidin-4,4-diyl | pyrrolidin-3R-yl | C(O) | cyclopropyl | b = 0 | benzofuran-5-yl |

TABLE 1-continued

Representative Compounds of Formula (I)

| ID No. | R¹ & R² taken together | (L¹)ₐ | R³ | (R⁴)_b | A¹ (R⁶)_c |
|---|---|---|---|---|---|
| 153 | 1-(dimethyl-amino-methyl-carbonyl)-piperidin-4,4-diyl | pyrrolidin-3R-yl | C(O) | cyclopropyl | b = 0 | benzofuran-5-yl |
| 154 | 1-(dimethyl-amino-methyl-carbonyl)-piperidin-4,4-diyl | azetidin-3-yl | C(O) | cyclopropyl | b = 0 | isoquinolin-6-yl |
| 155 | piperidin-4,4-diyl | pyrrolidin-3R-yl | C(O) | cyclopropyl | b = 0 | 2-methyl-benzofuran-5-yl |
| 156 | cyclopentyl | pyrrolidin-3R-yl | C(O) | cyclopropyl | 2-methoxy | benzofuran-5-yl |
| 157 | cyclopentyl | pyrrolidin-3R-yl | C(O) | cyclopropyl | 2-methoxy | indol-5-yl |
| 158 | cyclopropyl | piperidin-4-yl | C(O) | cyclopropyl | b = 0 | 3-fluoro-phenyl |
| 159 | 1-(2-hydroxy-ethyl)-piperidin-4,4-diyl | pyrrolidin-3R-yl | C(O) | cyclopropyl | b = 0 | isoquinolin-6-yl |
| 160 | 1-(methyl-carbonyl)-piperidin-4,4-diyl | pyrrolidin-3R-yl | C(O) | cyclopropyl | b = 0 | 1,2,3,4-trihydro-2-methyl-carbonyl-isoquinolin-6-yl |
| 161 | 1-(methyl-carbonyl)-piperidin-4,4-diyl | pyrrolidin-3R-yl | C(O) | cyclopropyl | b = 0 | 1,2,3,4,4a,8a-hexahydro-2-methyl-carbonyl-isoquinolin-6-yl |
| 162 | 1-(isopropyl)-piperidin-4,4-diyl | pyrrolidin-3R-yl | C(O) | cyclopropyl | b = 0 | 1-methyl-indazol-5-yl |

TABLE 1-continued

Representative Compounds of Formula (I)

| ID No. | R¹ & R² taken together | (L¹)ₐ | R³ | (R⁴)ᵦ | A¹ (R⁶)c |
|---|---|---|---|---|---|
| 163 | 1-(isopropyl)-piperidin-4,4-diyl | pyrrolidin-3R-yl | C(O) | cyclopropyl | b = 0 | isoquinolin-6-yl |
| 164 | 1-(dimethyl-amino-methyl-carbonyl)-piperidin-4,4-diyl | pyrrolidin-3R-yl | C(O) | cyclopropyl | b = 0 | indol-5-yl |
| 165 | 1-(dimethyl-amino-methyl-carbonyl)-piperidin-4,4-diyl | pyrrolidin-3R-yl | C(O) | cyclopropyl | b = 0 | indazol-5-yl |
| 166 | 1-(isopropyl)-piperidin-4,4-diyl | azetidin-3-yl | C(O) | cyclopropyl | b = 0 | benzofuran-5-yl |
| 167 | 1-(isopropyl)-piperidin-4,4-diyl | pyrrolidin-3R-yl | C(O) | cyclopropyl | b = 0 | benzofuran-5-yl |
| 168 | 1-(2-hydroxy-ethyl)-piperidin-4,4-diyl | pyrrolidin-3R-yl | C(O) | cyclopropyl | b = 0 | benzofuran-5-yl |
| 169 | 1-(isopropyl)-piperidin-4,4-diyl | azetidin-3-yl | C(O) | cyclopropyl | b = 0 | 1-methyl-indazol-5-yl |
| 170 | 1-(2-hydroxy-ethyl)-piperidin-4,4-diyl | azetidin-3-yl | C(O) | cyclopropyl | b = 0 | 1-methyl-indazol-5-yl |
| 171 | 1-(cyclopropyl-carbonyl)-piperidin-4,4-diyl | pyrrolidin-3R-yl | C(O) | cyclopropyl | b = 0 | 2-methyl-benzofuran-5-yl |

TABLE 1-continued

Representative Compounds of Formula (I)

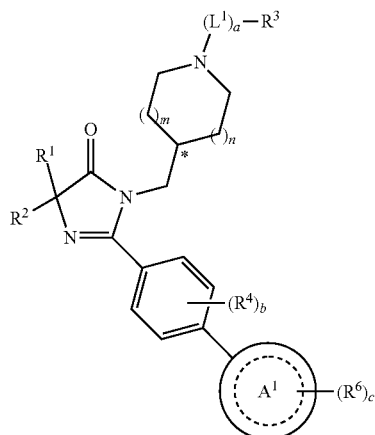

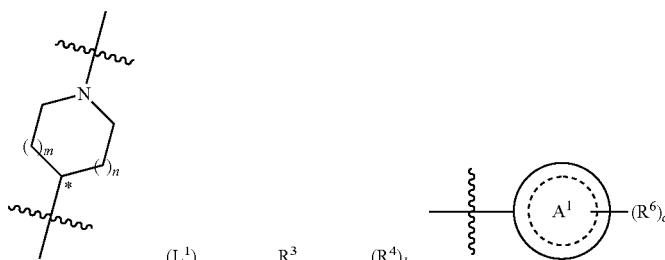

| ID No. | R¹ & R² taken together | | (L¹)ₐ | R³ | (R⁴)ᵦ | |
|---|---|---|---|---|---|---|
| 172 | 1-(isopropyl-carbonyl)-piperidin-4,4-diyl | | pyrrolidin-3R-yl | C(O) | cyclopropyl | b = 0 | 2-methyl-benzofuran-5-yl |
| 173 | 1-(2-hydroxy-ethyl)-piperidin-4,4-diyl | | pyrrolidin-3R-yl | C(O) | cyclopropyl | b = 0 | 2-methyl-benzofuran-5-yl |
| 174 | 1-(dimethyl-amino-methyl-carbonyl)-piperidin-4,4-diyl | | pyrrolidin-3R-yl | C(O) | cyclopropyl | b = 0 | 2-methyl-benzofuran-5-yl |
| 178 | cyclopropyl | | azetidin-3-yl | C(O) | cyclopropyl | b = 0 | 2-methyl-benzofuran-5-yl |
| 179 | cyclopropyl | | azetidin-3-yl | C(O) | cyclopropyl | 2-methyl | 2-methyl-benzofuran-5-yl |
| 180 | cyclopropyl | | pyrrolidin-3R-yl | C(O) | cyclopropyl | 3-methyl | benzofuran-5-yl |
| 181 | 1-(methyl-carbonyl)-piperidin-4,4-diyl | | pyrrolidin-3R-yl | C(O) | cyclopropyl | b = 0 | 2,3-dimethyl-benzothien-5-yl |
| 182 | 1-(dimethyl-amino-methyl-carbonyl)-piperidin-4,4-diyl | | pyrrolidin-3R-yl | C(O) | cyclopropyl | b = 0 | 2,3-dimethyl-benzothien-5-yl |
| 183 | 1-(isopropyl-carbonyl)-piperidin-4,4-diyl | | pyrrolidin-3R-yl | C(O) | cyclopropyl | b = 0 | 2,3-dimethyl-benzothien-5-yl |
| 184 | 1-(isopropyl)-piperidin-4,4-diyl | | pyrrolidin-3R-yl | C(O) | cyclopropyl | b = 0 | 2,3-dimethyl-benzothien-5-yl |

TABLE 1-continued

Representative Compounds of Formula (I)

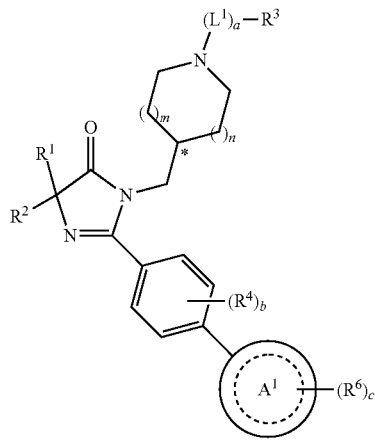

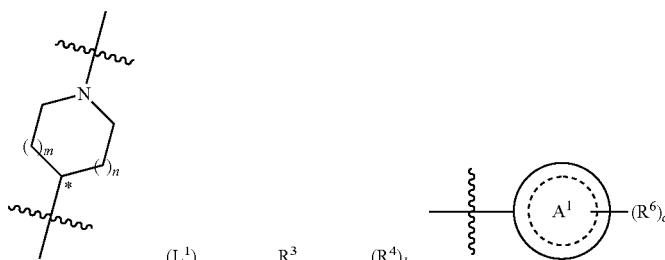

| ID No. | R¹ & R² taken together | (L¹)ₐ | R³ | (R⁴)ᵦ | |
|---|---|---|---|---|---|
| 185 | 1-(2-hydroxy-ethyl)-piperidin-4,4-diyl | azetidin-3-yl | C(O) | cyclopropyl | b = 0 | benzofuran-5-yl |
| 186 | 1-(isopropyl)-piperidin-4,4-diyl | pyrrolidin-3R-yl | C(O) | cyclopropyl | b = 0 | 2-methyl-benzofuran-5-yl |
| 187 | 1-(isopropyl)-piperidin-4,4-diyl | azetidin-3-yl | C(O) | cyclopropyl | b = 0 | indol-5-yl |
| 188 | 1-(isopropyl)-piperidin-4,4-diyl | azetidin-3-yl | C(O) | cyclopropyl | b = 0 | indazol-5-yl |
| 189 | cyclopentyl | pyrrolidin-3S-yl | SO₂ | pyrrolidin-1-yl | b = 0 | benzofuran-5-yl |
| 190 | cyclopentyl | pyrrolidin-3R-yl | C(O) | tetrahydro-furan-2S-yl | b = 0 | benzofuran-5-yl |
| 191 | cyclopentyl | pyrrolidin-3R-yl | C(O) | tetrahydro-furan-2R-yl | b = 0 | benzofuran-5-yl |
| 192 | cyclopentyl | pyrrolidin-3R-yl | C(O) | 1-cyano-cyclopropyl | b = 0 | benzofuran-5-yl |
| 193 | 1-(benzyl)-piperidin-4,4-diyl) | pyrrolidin-3R-yl | C(O) | cyclopropyl | b = 0 | isoquinolin-6-yl |
| 200 | cyclopropyl | pyrrolidin-3R-yl | C(O) | 1-hydroxy-cyclopropyl | b = 0 | 1-methyl-indazol-5-yl |
| 201 | cyclopropyl | pyrrolidin-3R-yl | C(O) | 1-methyl-cyclopropyl | b = 0 | 1-methyl-indazol-5-yl |
| 202 | cyclopropyl | pyrrolidin-3R-yl | C(O) | 1-hydroxy-cyclopropyl | b = 0 | 2-fluoro-4-chloro-phenyl |
| 203 | cyclopropyl | pyrrolidin-3R-yl | C(O) | 1-hydroxy-cyclopropyl | b = 0 | 6-methoxy-naphth-2-yl |
| 204 | cyclopropyl | pyrrolidin-3R-yl | C(O) | oxetan-2-yl | b = 0 | 1-methyl-indazol-5-yl |
| 205 | cyclopropyl | azetidin-3-yl | C(O) | tetrahydro-furan-2-yl | 2-methyl | 1-methyl-indazol-5-yl |
| 206 | cyclopropyl | azetidin-3-yl | C(O) | tetrahydro-furan-2S-yl | 2-methyl | 1-methyl-indazol-5-yl |

TABLE 1-continued

Representative Compounds of Formula (I)

| ID No. | R¹ & R² taken together | (L¹)ₐ | R³ | (R⁴)ᵦ | |
|---|---|---|---|---|---|
| 207 | cyclopropyl | azetidin-3-yl | C(O) | 1-methyl-cyclopropyl | 2-methyl | 1-methyl-indazol-5-yl |
| 208 | cyclopropyl | azetidin-3-yl | C(O) | 1-methyl-cyclobutyl | 2-methyl | 1-methyl-indazol-5-yl |
| 209 | cyclopropyl | pyrrolidin-3R-yl | C(O) | cyclopropyl | b = 0 | 3-chloro-4-fluoro-phenyl |
| 210 | cyclopropyl | pyrrolidin-3S-yl | C(O) | cyclopropyl | b = 0 | indol-5-yl |
| 211 | cyclopropyl | pyrrolidin-3S-yl | C(O) | cyclopropyl | b = 0 | benzothien-5-yl |
| 212 | cyclopropyl | pyrrolidin-3R-yl | C(O) | cyclopropyl | b = 0 | 3-cyanomethyl-indol-5-yl |
| 213 | cyclopropyl | pyrrolidin-3R-yl | C(O) | cyclopropyl | b = 0 | 2,3-dimethyl-indol-5-yl |
| 214 | cyclopropyl | pyrrolidin-3R-yl | C(O) | cyclopropyl | b = 0 | 2-methyl-indol-5-yl |
| 215 | cyclopropyl | pyrrolidin-3R-yl | C(O) | cyclopropyl | b = 0 | 1-methyl-indol-5-yl |
| 216 | cyclopropyl | pyrrolidin-3R-yl | C(O) | cyclopropyl | b = 0 | 2-hydroxy-methyl-indol-5-yl |
| 217 | cyclopropyl | pyrrolidin-3R-yl | C(O) | cyclopropyl | b = 0 | 3-(2-hydroxyethyl)-indol-5-yl |
| 218 | cyclopropyl | pyrrolidin-3R-yl | C(O) | cyclopropyl | b = 0 | 1,3-dimethyl-indazol-5-yl |
| 219 | cyclopropyl | pyrrolidin-3R-yl | C(O) | cyclopropyl | b = 0 | 3-amino-isoquinolin-6-yl |
| 220 | cyclopropyl | pyrrolidin-3R-yl | C(O) | cyclopropyl | b = 0 | 3-fluoro-isoquinolin-6-yl |
| 221 | cyclopropyl | pyrrolidin-3R-yl | C(O) | cyclopropyl | b = 0 | 1-methyl-3-aminocarbonyl-indazol-6-yl |
| 222 | cyclopropyl | azetidin-3-yl | C(O) | cyclopropyl | 2-fluoro | 6-cyano-naphth-2-yl |
| 223 | cyclopropyl | azetidin-3-yl | C(O) | oxetan-2-yl | 2-methyl | 6-fluoro-naphth-2-yl |
| 224 | cyclopropyl | azetidin-3-yl | C(O) | oxetan-2-yl | 2-methyl | 6-cyano-naphth-2-yl |
| 225 | cyclopropyl | azetidin-3-yl | C(O) | 1-fluoro-cyclopropyl | 2-fluoro | 6-cyano-naphth-2-yl |
| 226 | cyclopropyl | azetidin-3-yl | C(O) | oxetan-2-yl | 2-fluoro | 6-cyano-naphth-2-yl |

TABLE 1-continued

Representative Compounds of Formula (I)

| ID No. | R¹ & R² taken together | (L¹)ₐ | R³ | (R⁴)ᵦ | |
|---|---|---|---|---|---|
| 227 | cyclopropyl | azetidin-3-yl | C(O) | cyclopropyl | 2-fluoro | 2-methyl-indazol-6-yl |
| 228 | cyclopropyl | azetidin-3-yl | C(O) | cyclopropyl | 2-fluoro | 6-fluoro-quinolin-2-yl |
| 229 | cyclopropyl | pyrrolidin-3R-yl | C(O) | cyclopropyl | 2-fluoro | 2-cyano-quinolin-6-yl |
| 230 | cyclopropyl | pyrrolidin-3R-yl | C(O) | cyclopropyl | 2-methyl | benzothien-5-yl |
| 231 | cyclopropyl | pyrrolidin-3R-yl | C(O) | cyclopropyl | 2-methyl | 2,3-dimethyl-benzothien-5-yl |
| 232 | cyclopropyl | pyrrolidin-3R-yl | C(O) | cyclopropyl | 2-fluoro | benzofuran-5-yl |
| 233 | cyclopropyl | pyrrolidin-3R-yl | C(O) | cyclopropyl | 2-fluoro | benzothien-5-yl |
| 234 | cyclopropyl | pyrrolidin-3R-yl | C(O) | cyclopropyl | 2-fluoro | indol-5-yl |
| 236 | cyclopropyl | pyrrolidin-3R-yl | C(O) | cyclopropyl | 2-fluoro | indol-6-yl |
| 237 | cyclopropyl | pyrrolidin-3R-yl | C(O) | cyclopropyl | 2-fluoro | indazol-4-yl |
| 238 | cyclopropyl | pyrrolidin-3R-yl | C(O) | cyclopropyl | 2-fluoro | indol-5-yl |
| 239 | cyclopropyl | pyrrolidin-3R-yl | C(O) | cyclopropyl | 2-methyl | indol-6-yl |
| 240 | cyclopropyl | pyrrolidin-3R-yl | C(O) | cyclopropyl | 2-fluoro | benzofuran-5-yl |
| 241 | cyclopropyl | pyrrolidin-3R-yl | C(O) | cyclopropyl | 2-fluoro | benzothien-5-yl |
| 242 | cyclopropyl | pyrrolidin-3R-yl | C(O) | cyclopropyl | 2-fluoro | 2-methyl-benzofuran-5-yl |
| 243 | cyclopropyl | pyrrolidin-3R-yl | C(O) | cyclopropyl | 2-fluoro | 2-methyl-benzothien-5-yl |
| 244 | cyclopropyl | pyrrolidin-3R-yl | C(O) | cyclopropyl | 2-fluoro | 2,3-dimethyl-benzofuran-5-yl |
| 245 | cyclopropyl | pyrrolidin-3R-yl | C(O) | cyclopropyl | 2-fluoro | 2,3-dimethyl-benzothien-5-yl |
| 246 | cyclopropyl | pyrrolidin-3R-yl | C(O) | cyclopropyl | 2-fluoro | indol-5-yl |
| 247 | cyclopropyl | pyrrolidin-3R-yl | C(O) | cyclopropyl | 2-fluoro | indol-6-yl |
| 248 | cyclopropyl | pyrrolidin-3R-yl | C(O) | cyclopropyl | 2-fluoro | quinolin-6-yl |

TABLE 1-continued

Representative Compounds of Formula (I)

| ID No. | R¹ & R² taken together | (L¹)ₐ | R³ | (R⁴)ᵦ | A¹(R⁶)c |
|---|---|---|---|---|---|
| 249 | cyclopropyl | pyrrolidin-3R-yl | C(O) | cyclopropyl | 2-fluoro | quinolin-7-yl |
| 250 | cyclopropyl | pyrrolidin-3R-yl | C(O) | cyclopropyl | 2-fluoro | quinolin-5-yl |
| 251 | cyclopropyl | pyrrolidin-3R-yl | C(O) | cyclopropyl | 2-fluoro | benzoxazol-2-yl |
| 252 | cyclopropyl | pyrrolidin-3R-yl | C(O) | cyclopropyl | 2-fluoro | benzthiazol-2-yl |
| 253 | cyclopropyl | pyrrolidin-3R-yl | C(O) | cyclopropyl | 2-fluoro | indazol-5-yl |
| 254 | cyclopropyl | pyrrolidin-3R-yl | C(O) | cyclopropyl | 2-fluoro | 2-cyano-benzofuran-5-yl |
| 255 | cyclopropyl | pyrrolidin-3R-yl | C(O) | cyclopropyl | 2-methyl | 2-cyano-benzofuran-5-yl |
| 256 | cyclopropyl | pyrrolidin-3R-yl | C(O) | cyclopropyl | b = 0 | 2-cyano-benzofuran-5-yl |
| 257 | cyclopropyl | pyrrolidin-3R-yl | C(O) | cyclopropyl | 2-fluoro | quinolin-3-yl |
| 258 | cyclopropyl | pyrrolidin-3R-yl | C(O) | cyclopropyl | 2-fluoro | quinazolin-7-yl |
| 259 | cyclopropyl | pyrrolidin-3R-yl | C(O) | cyclopropyl | 2-fluoro | 6-fluoro-quinolin-2-yl |
| 260 | cyclopropyl | pyrrolidin-3R-yl | C(O) | cyclopropyl | 2-fluoro | 8-fluoro-quinolin-2-yl |
| 261 | cyclopropyl | pyrrolidin-3R-yl | C(O) | cyclopropyl | 2-fluoro | indol-3-yl |
| 262 | cyclopropyl | pyrrolidin-3R-yl | C(O) | cyclopropyl | 2-methyl | 1-mehtyl-indazol-5-yl |
| 263 | cyclopropyl | azetidin-3-yl | C(O) | cyclopropyl | 2-methyl | 2-methyl-indol-5-yl |
| 264 | cyclopropyl | azetidin-3-yl | C(O) | 1-hydroxy-cyclopropyl | 2-chloro | 1-methyl-indazol-5-yl |
| 265 | cyclopropyl | pyrrolidin-3R-yl | C(O) | 1-methyl-cyclopropyl | 2-methyl | 1-methyl-indazol-5-yl |
| 266 | cyclopropyl | pyrrolidin-3R-yl | C(O) | 1-methyl-cycloprropyl | 2-methyl | 6-fluoro-naphth-2-yl |
| 268 | cyclopropyl | azetidin-3-yl | C(O) | cyclopropyl | 2-fluoro | 6-cyano-benzthiazol-2-yl |
| 269 | cyclopropyl | azetidin-3-yl | C(O) | 1-methyl-cyclopropyl | 2-methyl | 6-cyano-naphth-2-yl |
| 270 | cyclopropyl | azetidin-3-yl | C(O) | cyclopropyl | 2-fluoro | 6-methyl-benzthiazol-2-yl |

TABLE 1-continued

Representative Compounds of Formula (I)

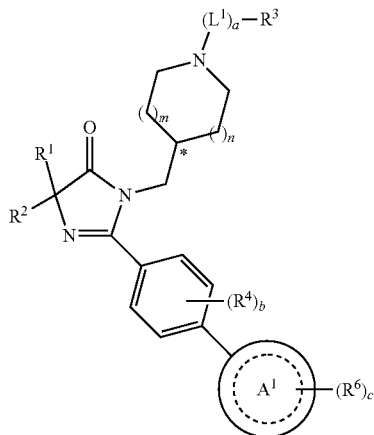

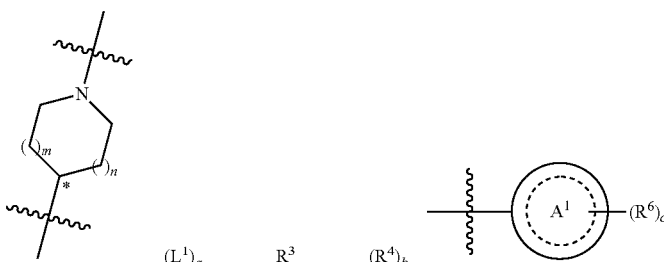

| ID No. | R¹ & R² taken together | (L¹)ₐ | R³ | (R⁴)ᵦ | |
|---|---|---|---|---|---|
| 271 | cyclopropyl | azetidin-3-yl | C(O) | cyclopropyl | 2-fluoro | 6-fluoro-benzthiazol-2-yl |
| 272 | cyclopropyl | azetidin-3-yl | C(O) | 1-hydroxy-cyclopropyl | 2-methyl | 6-cyano-naphth-2-yl |
| 273 | cyclopropyl | azetidin-3-yl | C(O) | 1-fluoro-cyclopropyl | 2-methyl | 6-cyano-naphth-2-yl |
| 274 | cyclopropyl | azetidin-3-yl | C(O) | cyclopropyl | 2-fluoro | 6-chloro-benzthiazol-2-yl |
| 275 | cyclopropyl | azetidin-3-yl | C(O) | cyclopropyl | b = 0 | 6-fluoro-quinolin-2-yl |
| 276 | cyclopropyl | azetidin-3-yl | C(O) | cyclopropyl | b = 0 | 2-cyano-quinolin-6-yl |
| 277 | cyclopropyl | azetidin-3-yl | C(O) | cyclopropyl | b = 0 | 6-cyano-quinolin-2-yl |
| 278 | cyclopropyl | pyrrolidin-3R-yl | C(O) | cyclopropyl | 2-methyl | benzofuran-5-yl |
| 279 | cyclopropyl | pyrrolidin-3R-yl | C(O) | cyclopropyl | 2-methyl | benzothien-5-yl |
| 280 | cyclopropyl | pyrrolidin-3R-yl | C(O) | cyclopropyl | 2-methyl | 2-methyl-benzofuran-5-yl |
| 281 | cyclopropyl | pyrrolidin-3R-yl | C(O) | cyclopropyl | 2-methyl | 2-methyl-benzothien-5-yl |
| 282 | cyclopropyl | pyrrolidin-3R-yl | C(O) | cyclopropyl | 2-methyl | 2,3-dimethyl-benzofuran-5-yl |
| 283 | cyclopropyl | pyrrolidin-3R-yl | C(O) | cyclopropyl | 2-methyl | 2,3-dimethyl-benzothien-5-yl |
| 284 | cyclopropyl | pyrrolidin-3R-yl | C(O) | cyclopropyl | 2-methyl | indol-5-yl |
| 286 | cyclopropyl | pyrrolidin-3R-yl | C(O) | cyclopropyl | 2-methyl | indazol-5-yl |
| 287 | cyclopropyl | azetidin-3-yl | C(O) | cyclopropyl | 2-methyl | benzofuran-5-yl |
| 288 | cyclopropyl | azetidin-3-yl | C(O) | cyclopropyl | 2-methyl | benzothien-5-yl |
| 289 | cyclopropyl | azetidin-3-yl | C(O) | cyclopropyl | 2-methyl | 2-methyl-benzofuran-5-yl |
| 290 | cyclopropyl | azetidin-3-yl | C(O) | cyclopropyl | 2-methyl | 2,3-dimethyl-benzothien-5-yl |
| 291 | cyclopropyl | azetidin-3-yl | C(O) | cyclopropyl | 2-methyl | indol-5-yl |
| 292 | cyclopropyl | azetidin-3-yl | C(O) | cyclopropyl | 2-methyl | 1-methyl-indazol-5-yl |

TABLE 1-continued

Representative Compounds of Formula (I)

| ID No. | R¹ & R² taken together | (L¹)ₐ | R³ | (R⁴)ᵦ | |
|---|---|---|---|---|---|
| 293 | cyclopropyl | azetidin-3-yl | C(O) | cyclopropyl | 2-methyl | indazol-5-yl |
| 294 | cyclopropyl | pyrrolidin-3R-yl | C(O) | cyclopropyl | b = 0 | 2-methyl-benzofuran-5-yl |
| 295 | cyclopropyl | pyrrolidin-3R-yl | C(O) | cyclopropyl | b = 0 | 2-methyl-benzothien-5-yl |
| 296 | cyclopropyl | pyrrolidin-3R-yl | C(O) | cyclopropyl | b = 0 | 2,3-dimethyl-benzothien-5-yl |
| 297 | cyclopropyl | pyrrolidin-3R-yl | C(O) | cyclopropyl | b = 0 | indazol-5-yl |
| 298 | cyclopropyl | pyrrolidin-3R-yl | C(O) | cyclopropyl | b = 0 | benothien-5-yl |
| 299 | cyclopropyl | azetidin-3-yl | C(O) | cyclopropyl | b = 0 | indol-6-yl |
| 300 | cyclopropyl | azetidin-3-yl | C(O) | cyclopropyl | b = 0 | indazol-4-yl |
| 301 | cyclopropyl | pyrrolidin-3R-yl | C(O) | cyclopropyl | b = 0 | indol-6-yl |
| 302 | cyclopropyl | pyrrolidin-3R-yl | C(O) | cyclopropyl | b = 0 | indazol-4-yl |
| 303 | cyclopropyl | azetidin-3-yl | C(O) | cyclopropyl | 2-methyl | indol-6-yl |
| 304 | cyclopropyl | azetidin-3-yl | C(O) | cyclopropyl | 2-methyl | indazol-4-yl |
| 305 | cyclopropyl | pyrrolidin-3R-yl | C(O) | cyclopropyl | 2-methyl | indol-6-yl |
| 306 | cyclopropyl | pyrrolidin-3R-yl | C(O) | cyclopropyl | 2-methyl | indazol-4-yl |
| 307 | cyclopropyl | pyrrolidin-3R-yl | C(O) | cyclopropyl | b = 0 | benzoxazol-2-yl |
| 308 | cyclopropyl | pyrrolidin-3R-yl | C(O) | cyclopropyl | b = 0 | benzthiazol-2-yl |
| 309 | cyclopropyl | pyrrolidin-3R-yl | C(O) | cyclopropyl | b = 0 | quinolin-7-yl |
| 310 | cyclopropyl | pyrrolidin-3R-yl | C(O) | cyclopropyl | b = 0 | quinolin-5-yl |
| 311 | cyclopropyl | pyrrolidin-3R-yl | C(O) | cyclopropyl | b = 0 | 6-fluoro-naphth-2-yl |
| 312 | cyclopropyl | pyrrolidin-3R-yl | C(O) | cyclopropyl | b = 0 | quinazolin-7-yl |

TABLE 1-continued

Representative Compounds of Formula (I)

| ID No. | R¹ & R² taken together | (L¹)ₐ | R³ | (R⁴)ᵦ | |
|---|---|---|---|---|---|
| 313 | cyclopropyl | pyrrolidin-3R-yl | C(O) | cyclopropyl | b = 0 | 8-fluoro-naphth-2-yl |
| 314 | cyclopropyl | pyrrolidin-3R-yl | C(O) | cyclopropyl | b = 0 | indol-3-yl |
| 315 | cyclopropyl | azetidin-3-yl | C(O) | cyclopropyl | b = 0 | 8-fluoro-quinolin-7-yl |
| 317 | cyclopropyl | pyrrolidin-3R-yl | C(O) | cyclopropyl | 2-methyl | 2-methyl-indol-5-yl |
| 318 | cyclopropyl | pyrrolidin-3R-yl | C(O) | cyclopropyl | 2-fluoro | 3-(cyclopropyl-sulfonyl-amino)-phenyl |
| 319 | cyclopropyl | pyrrolidin-3R-yl | C(O) | cyclopropyl | 2-fluoro | 2-methyl-indol-5-yl |
| 320 | cyclopropyl | azetidin-3-yl | C(O) | cyclopropyl | 2-fluoro | 6-chloro-naphth-2-yl |
| 321 | cyclopropyl | azetidin-3-yl | C(O) | 1-methyl-cyclopropyl | 2-methyl | 6-chloro-naphth-2-yl |
| 324 | cyclopropyl | azetidin-3-yl | C(O) | cyclopropyl | 2-fluoro | 7-fluoro-naphth-2-yl |
| 332 | cyclopropyl | azetidin-3-yl | C(O) | 1-methyl-cyclopropyl | 2-methyl | 6-methoxy-naphth-2-yl |
| 334 | cyclopropyl | azetidin-3-yl | C(O) | 1-methyl-cyclopropyl | 2-methyl | 6-methyl-naphth-2-yl |
| 335 | cyclopropyl | azetidin-3-yl | C(O) | 1-methyl-cyclopropyl | 2-methyl | 1-methyl-indazol-6-yl |
| 336 | cyclopropyl | azetidin-3-yl | C(O) | 1-methyl-cyclopropyl | 2-methyl | 2-methyl-indazol-6-yl |
| 339 | cyclopropyl | azetidin-3-yl | C(O) | cyclopropyl | b = 0 | 3-chloro-quinolin-7-yl |
| 340 | cyclopropyl | azetidin-3-yl | C(O) | 1-methyl-cyclopropyl | 2-methyl | 3-chloro-quinolin-7-yl |
| 343 | cyclopropyl | azetidin-3-yl | C(O) | cyclopropyl | b = 0 | 1-methyl-benzimidazol-5-yl |
| 344 | cyclopropyl | azetidin-3-yl | C(O) | cyclopropyl | b = 0 | 1-methyl-indol-5-yl |
| 345 | cyclopropyl | azetidin-3-yl | C(O) | cyclopropyl | b = 0 | quinolin-2-yl |
| 346 | cyclopropyl | azetidin-3-yl | C(O) | cyclopropyl | 2-fluoro | quinolin-7-yl |
| 347 | cyclopropyl | azetidin-3-yl | C(O) | cyclopropyl | 2-fluoro | 1-methyl-indazol-5-yl |

TABLE 1-continued

Representative Compounds of Formula (I)

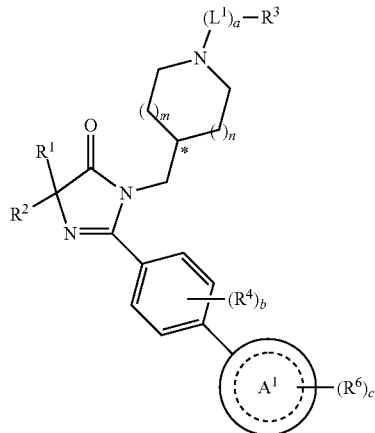

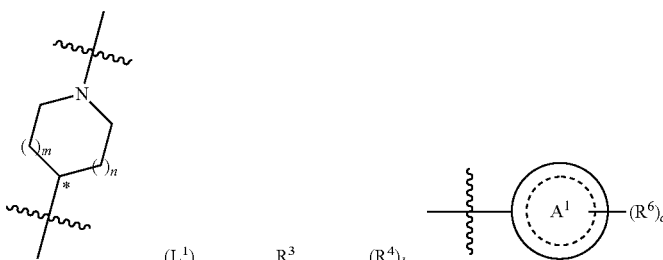

| ID No. | R¹ & R² taken together | (L¹)ₐ | R³ | (R⁴)ᵦ | |
|---|---|---|---|---|---|
| 348 | cyclopropyl | azetidin-3-yl | C(O) | cyclopropyl | 2-fluoro | 1-methyl-benzimidazol-5-yl |
| 349 | cyclopropyl | azetidin-3-yl | C(O) | cyclopropyl | 2-fluoro | 6-fluoro-naphth-2-yl |
| 350 | cyclopropyl | azetidin-3-yl | C(O) | cyclopropyl | 2-fluoro | 8-fluoro-naphth-2-yl |
| 351 | cyclopropyl | azetidin-3-yl | C(O) | cyclopropyl | 2-fluoro | 6-methoxy-naphth-2-yl |
| 352 | cyclopropyl | azetidin-3-yl | C(O) | 1-methyl-cyclopropyl | 2-fluoro | 2-methyl-benzothien-5-yl |
| 353 | cyclopropyl | azetidin-3-yl | C(O) | cyclopropyl | 2-fluoro | 2-methyl-benzofuran-5-yl |
| 354 | cyclopropyl | pyrrolidin-3R-yl | C(O) | 1-hydroxy-cyclopropyl | 2-fluoro | 2-methyl-benzothien-5-yl |
| 355 | cyclopropyl | pyrrolidin-3R-yl | C(O) | 1-hydroxy-cyclopropyl | 2-fluoro | 2-methyl-benzofuran-5-yl |
| 356 | cyclopropyl | azetidin-3-yl | C(O) | cyclopropyl | 2-fluoro | 2-methyl-benzothiazol-5-yl |
| 357 | cyclopropyl | azetidin-3-yl | C(O) | 1-methyl-cyclopropyl | 2-fluoro | 1-methyl-indazol-5-yl |
| 359 | cyclopropyl | azetidin-3-yl | C(O) | 1-methyl-cyclopropyl | 2-fluoro | 6-fluoro-naphth-2-yl |
| 361 | cyclopropyl | pyrrolidin-3R-yl | C(O) | 1-methyl-cyclopropyl | 2-fluoro | 1-methyl-indazol-5-yl |
| 363 | cyclopropyl | pyrrolidin-3R-yl | C(O) | 1-methyl-cyclopropyl | 2-fluoro | 6-fluoro-naphth-2-yl |
| 365 | cyclopropyl | azetidin-3-yl | C(O) | 1-hydroxy-cyclopropyl | 2-fluoro | 6-fluoro-naphth-2-yl |
| 366 | cyclopropyl | azetidin-3-yl | C(O) | 1-hydroxy-cyclopropyl | 2-fluoro | 6-methoxy-naphth-2-yl |
| 368 | cyclopropyl | azetidin-3-yl | C(O) | cyclopropyl | 2-fluoro | naphth-2-yl |
| 369 | cyclopropyl | azetidin-3-yl | C(O) | oxetan-2-yl | 2-fluoro | 6-fluoro-naphth-2-yl |
| 370 | cyclopropyl | pyrrolidin-3R-yl | C(O) | 1-hydroxy-cyclopropyl | 2-fluoro | 1-methyl-indazol-5-yl |
| 372 | cyclopropyl | azetidin-3-yl | C(O) | 1-hydroxy-cyclopropyl | 2-fluoro | naphth-2-yl |
| 373 | cyclopropyl | azetidin-3-yl | C(O) | 1-hydroxy-cyclopropyl | 2-fluoro | 6-cyano-naphth-2-yl |

TABLE 1-continued

Representative Compounds of Formula (I)

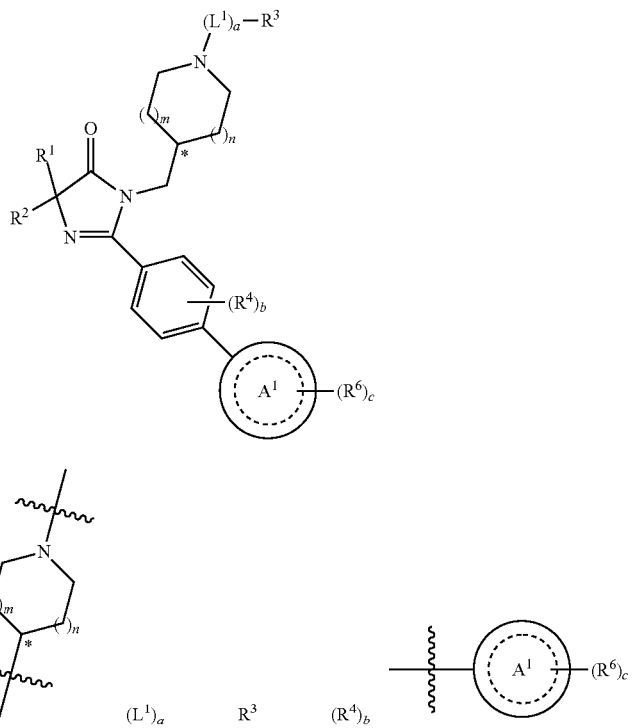

| ID No. | R¹ & R² taken together | (L¹)ₐ | R³ | (R⁴)ᵦ | A¹ |
|---|---|---|---|---|---|
| 374 | cyclopropyl | azetidin-3-yl | C(O) | 1-hydroxy-cyclopropyl | 2-fluoro | 8-fluoro-naphth-2-yl |
| 375 | cyclopropyl | azetidin-3-yl | C(O) | 1-hydroxy-cyclopropyl | 2-fluoro | 8-methoxy-naphth-2-yl |
| 377 | cyclopropyl | azetidin-3-yl | C(O) | 1-hydroxy-cyclopropyl | 2-fluoro | 1-methyl-benzimidazol-5-yl |
| 378 | cyclopropyl | azetidin-3-yl | C(O) | 1-methyl-cyclopropyl | 2-fluoro | 1-methyl-benzimidazol-5-yl |
| 380 | cyclopropyl | azetidin-3-yl | C(O) | cyclopropyl | 2-fluoro | 8-methoxy-naphth-2-yl |
| 381 | cyclopropyl | pyrrolidin-3R-yl | C(O) | 1-hydroxy-cyclopropyl | 2-fluoro | 6-fluoro-naphth-2-yl |
| 383 | cyclopropyl | azetidin-3-yl | C(O) | 1-hydroxy-cyclopropyl | 2-fluoro | 6-chloro-naphth-2-yl |
| 384 | cyclopropyl | azetidin-3-yl | C(O) | 1-hydroxy-cyclopropyl | 2-fluoro | 7-fluoro-naphth-2-yl |
| 385 | cyclopropyl | azetidin-3-yl | C(O) | 1-hydroxy-cyclopropyl | 2-fluoro | 6-cyano-naphth-2-yl |
| 387 | cyclopropyl | pyrrolidin-3R-yl | C(O) | cyclopropyl | 3-fluoro | 2-methyl-benzofuran-5-yl |
| 388 | cyclopropyl | pyrrolidin-3R-yl | C(O) | cyclopropyl | 3-methyl | 2-methyl-benzofuran-5-yl |
| 389 | cyclopropyl | piperidin-3R-yl | C(O) | cyclopropyl | b = 0 | indazol-5-yl |
| 391 | cyclopropyl | azetidin-3-yl | C(O) | cyclopropyl | 2-methyl | 2-methyl-benzothien-5-yl |
| 392 | cyclopropyl | azetidin-3-yl | C(O) | cyclopropyl | 3-methyl | benzothien-5-yl |
| 393 | cyclopropyl | azetidin-3-yl | C(O) | cyclopropyl | 3-methyl | benzofuran-5-yl |
| 394 | cyclopropyl | piperidin-3R-yl | C(O) | cyclopropyl | b = 0 | benzothien-5-yl |
| 395 | cyclopropyl | piperidin-3R-yl | C(O) | cyclopropyl | b = 0 | benzofuran-5-yl |
| 396 | cyclopropyl | piperidin-3R-yl | C(O) | cyclopropyl | b = 0 | 1-methyl-indazol-5-yl |
| 398 | cyclopropyl | azetidin-3-yl | C(O) | cyclopropyl | 2-methyl | 2,3-dimethyl-benzofuran-5-yl |

TABLE 1-continued

Representative Compounds of Formula (I)

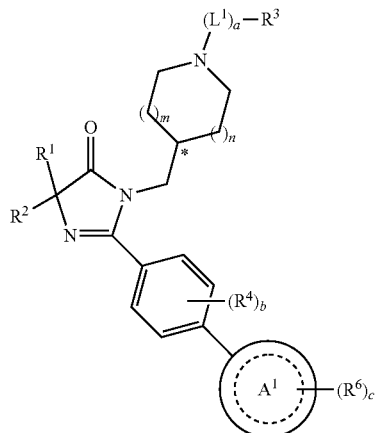

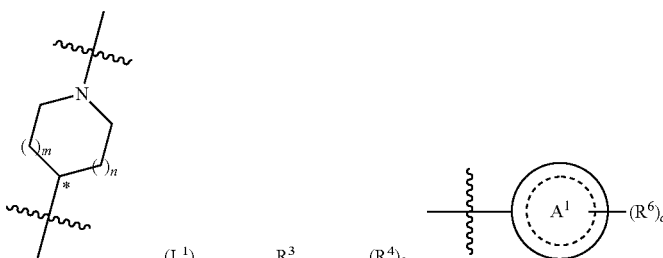

| ID No. | R¹ & R² taken together | (L¹)ₐ | R³ | (R⁴)ᵦ | |
|---|---|---|---|---|---|
| 399 | cyclopropyl | pyrrolidin-3R-yl | C(O) | cyclopropyl | 3-fluoro | 2,3-dimethyl-benzofuran-5-yl |
| 400 | cyclopropyl | pyrrolidin-3R-yl | C(O) | cyclopropyl | b = 0 | 6-amino-pyridin-2-yl |
| 401 | cyclopropyl | pyrrolidin-3R-yl | C(O) | cyclopropyl | b = 0 | 3-methoxy-carbonyl-phenyl |
| 404 | cyclopropyl | azetidin-3-yl | C(O) | cyclopropyl | 3-fluoro | benzothien-5-yl |
| 405 | cyclopropyl | pyrrolidin-3R-yl | C(O) | cyclopropyl | 3-fluoro | 1-methyl-indazol-5-yl |
| 406 | cyclopropyl | pyrrolidin-3R-yl | C(O) | cyclopropyl | 3-fluoro | 2,3-dimethyl-benzothien-5-yl |
| 408 | cyclopropyl | pyrrolidin-3S-yl | C(O) | cyclopropyl | b = 0 | 4-hydroxy-phenyl |
| 409 | cyclopropyl | pyrrolidin-3S-yl | C(O) | cyclopropyl | b = 0 | benzofuran-5-yl |
| 410 | cyclopropyl | pyrrolidin-3S-yl | C(O) | cyclopropyl | b = 0 | 1-methyl-indazol-5-yl |
| 414 | cyclopropyl | pyrrolidin-3R-yl | C(O) | cyclopropyl | 3-fluoro | indazol-5-yl |
| 415 | cyclopropyl | azetidin-3-yl | C(O) | cyclopropyl | 3-fluoro | benzofuran-5-yl |
| 416 | cyclopropyl | azetidin-3-yl | C(O) | cyclopropyl | 3-fluoro | 2-methyl-benzofuran-5-yl |
| 417 | cyclopropyl | azetidin-3-yl | C(O) | cyclopropyl | 3-fluoro | 2,3-dimethyl-benzofuran-5-yl |
| 418 | cyclopropyl | azetidin-3-yl | C(O) | cyclopropyl | b = 0 | 2,3-dimethyl-benzothien-5-yl |
| 431 | cyclopropyl | pyrrolidin-3S-yl | C(O) | cyclopropyl | b = 0 | indazol-5-yl |
| 432 | cyclopropyl | azetidin-3-yl | C(O) | cyclopropyl | b = 0 | 2-methyl-benzothien-5-yl |
| 433 | cyclopropyl | azetidin-3-yl | C(O) | cyclopropyl | 3-fluoro | 2-methyl-benzothien-5-yl |
| 434 | cyclopropyl | azetidin-3-yl | C(O) | cyclopropyl | 3-fluoro | 2,3-dimethyl-benzothien-5-yl |
| 435 | cyclopropyl | azetidin-3-yl | C(O) | cyclopropyl | 3-methyl | indol-5-yl |
| 436 | cyclopropyl | azetidin-3-yl | C(O) | cyclopropyl | 3-methyl | 1-methyl-indazol-5-yl |
| 440 | cyclopropyl | azetidin-3-yl | C(O) | cyclopropyl | 3-fluoro | indol-5-yl |

TABLE 1-continued

Representative Compounds of Formula (I)

| ID No. | R¹ & R² taken together | (L¹)ₐ | R³ | (R⁴)ᵦ | |
|---|---|---|---|---|---|
| 441 | cyclopropyl | azetidin-3-yl | C(O) | cyclopropyl | 3-fluoro | 1-methyl-indazol-5-yl |
| 442 | cyclopropyl | azetidin-3-yl | C(O) | cyclopropyl | 3-fluoro | indol-6-yl |
| 443 | cyclopropyl | azetidin-3-yl | C(O) | cyclopropyl | 3-fluoro | indazol-4-yl |
| 444 | cyclopropyl | pyrrolidin-3R-yl | C(O) | cyclopropyl | 3-methyl | indazol-5-yl |
| 445 | cyclopropyl | pyrrolidin-3R-yl | C(O) | cyclopropyl | 3-methyl | indazol-4-yl |
| 446 | cyclopropyl | azetidin-3-yl | C(O) | cyclopropyl | 3-methyl | 2-methyl-benzothien-5-yl |
| 447 | cyclopropyl | azetidin-3-yl | C(O) | cyclopropyl | 3-methyl | 2,3-dimethyl-benzothien-5-yl |
| 448 | cyclopropyl | azetidin-3-yl | C(O) | cyclopropyl | 3-methyl | indazol-5-yl |
| 449 | cyclopropyl | azetidin-3-yl | C(O) | cyclopropyl | 3-methyl | indol-5-yl |
| 450 | cyclopropyl | pyrrolidin-3R-yl | C(O) | cyclopropyl | 3-methyl | 1-methyl-indazol-5-yl |
| 451 | cyclopropyl | azetidin-3-yl | C(O) | cyclopropyl | 3-fluoro | indazol-5-yl |
| 452 | cyclopropyl | pyrrolidin-3R-yl | C(O) | cyclopropyl | b = 0 | 2-amino-pyridin-4-yl |
| 453 | cyclopropyl | pyrrolidin-3R-yl | C(O) | cyclopropyl | b = 0 | isochroman-7-yl |
| 454 | cyclopropyl | pyrrolidin-3R-yl | C(O) | cyclopropyl | b = 0 | 1-isopropyl-indazol-5-yl |
| 455 | cyclopropyl | pyrrolidin-3R-yl | C(O) | cyclopropyl | b = 0 | quinolin-6-yl |
| 456 | cyclopropyl | pyrrolidin-3R-yl | C(O) | cyclopropyl | b = 0 | 2,3-dihydro-benzo[1,4]dioxin-6-yl |
| 457 | cyclopropyl | pyrrolidin-3R-yl | C(O) | cyclopropyl | b = 0 | 2-oxo-indolin-5-yl |
| 460 | cyclopropyl | azetidin-3-yl | C(O) | cyclopropyl | 3-methyl | 2-cyano-benzofuran-5-yl |
| 461 | cyclopropyl | pyrrolidin-3R-yl | C(O) | cyclopropyl | b = 0 | 2-oxo-indolin-5-yl |
| 462 | cyclopropyl | pyrrolidin-3R-yl | C(O) | cyclopropyl | b = 0 | 2,3-dihydro-benzofuran-5-yl |
| 463 | cyclopropyl | pyrrolidin-3R-yl | C(O) | cyclopropyl | 3-fluoro | 2-cyano-benzofuran-5-yl |

TABLE 1-continued

Representative Compounds of Formula (I)

| ID No. | R¹ & R² taken together | $(L^1)_a$ | R³ | $(R^4)_b$ | |
|---|---|---|---|---|---|
| 464 | cyclopropyl | pyrrolidin-3R-yl | C(O) | cyclopropyl | b = 0 | chroman-6-yl |
| 465 | cyclopropyl | pyrrolidin-3R-yl | C(O) | cyclopropyl | b = 0 | 1-methyl-3-cyclopropyl-indazol-5-yl |
| 466 | cyclopropyl | pyrrolidin-3R-yl | C(O) | cyclopropyl | b = 0 | 3-chloro-isoquinolin-6-yl |
| 467 | cyclopropyl | pyrrolidin-3R-yl | C(O) | cyclopropyl | b = 0 | 1-oxo-isoquinolin-6-yl |
| 468 | cyclopropyl | pyrrolidin-3R-yl | C(O) | cyclopropyl | b = 0 | 1-methoxy-isoquinolin-6-yl |
| 469 | cyclopropyl | pyrrolidin-3R-yl | C(O) | cyclopropyl | b = 0 | 1-amino-isoquinolin-6-yl |
| 470 | cyclopropyl | pyrrolidin-3R-yl | C(O) | cyclopropyl | b = 0 | 3-methoxy-isoquinolin-6-yl |
| 471 | cyclopropyl | pyrrolidin-3R-yl | C(O) | cyclopropyl | b = 0 | isochroman-6-yl |
| 472 | cyclopropyl | azetidin-3-yl | C(O) | ethyl | 2-methyl | 1-methyl-indazol-5-yl |
| 473 | cyclopropyl | azetidin-3-yl | C(O) | isopropyl | 2-methyl | 1-methyl-indazol-5-yl |
| 474 | cyclopropyl | pyrrolidin-3R-yl | C(O) | cyclopropyl | b = 0 | quinolin-3-yl |
| 475 | cyclopropyl | azetidin-3-yl | C(O) | cyclopropyl | b = 0 | 2-cyano-benzofuran-5-yl |
| 476 | cyclopropyl | pyrrolidin-3R-yl | C(O) | cyclopropyl | 3-methyl | 2-cyano-benzofuran-5-yl |
| 477 | cyclopropyl | azetidin-3-yl | C(O) | cyclopropyl | 3-fluoro | 2-cyano-benzofuran-5-yl |
| 478 | cyclopropyl | pyrrolidin-3R-yl | C(O) | cyclopropyl | b = 0 | 6-bromo-isoquinolin-3-yl |
| 479 | cyclopropyl | pyrrolidin-3R-yl | C(O) | cyclopropyl | b = 0 | 1-chloro-isoquinolin-6-yl |
| 480 | cyclopropyl | azetidin-3-yl | C(O) | 1-hydroxy-methyl-cyclopropyl | 2-methyl | 1-methyl-indazol-5-yl |
| 481 | cyclopropyl | azetidin-3-yl | C(O) | cyclopropyl | b = 0 | quinoxalin-6-yl |
| 483 | cyclopropyl | pyrrolidin-3R-yl | C(O) | cyclopropyl | b = 0 | 1-methyl-3-amino-indazol-6-yl |

TABLE 1-continued

Representative Compounds of Formula (I)

| ID No. | R¹ & R² taken together | $(L^1)_a$ | R³ | $(R^4)_b$ | |
|---|---|---|---|---|---|
| 484 | cyclopropyl | pyrrolidin-3R-yl | C(O) | cyclopropyl | b = 0 | 1-methyl-3-methoxymethyl-indazol-6-yl |
| 485 | cyclopropyl | pyrrolidin-3R-yl | C(O) | cyclopropyl | b = 0 | 1-methyl-3-hydroxymethyl-indazol-6-yl |
| 486 | cyclopropyl | pyrrolidin-3R-yl | C(O) | cyclopropyl | b = 0 | 1-methyl-7-methoxymethyl-indazol-4-yl |
| 487 | cyclopropyl | pyrrolidin-3R-yl | C(O) | cyclopropyl | b = 0 | 1-methyl-7-hydroxymethyl-indazol-5-yl |
| 488 | cyclopropyl | azetidin-3-yl | C(O) | dimethylamino | 2-methyl | 1-methyl-indazol-5-yl |
| 489 | cyclopropyl | azetidin-3-yl | C(O) | cyclobutyl | 2-methyl | 1-methyl-indazol-5-yl |
| 490 | cyclopropyl | pyrrolidin-3R-yl | C(O) | oxetan-3-yl | b = 0 | 1-methyl-indazol-5-yl |
| 491 | cyclopropyl | azetidin-3-yl | C(O) | cyclopropyl | b = 0 | 1,4-dimethyl-indazol-5-yl |
| 492 | cyclopropyl | azetidin-3-yl | C(O) | cyclopropyl | b = 0 | 1,7-dimethyl-indazol-5-yl |
| 493 | cyclopropyl | pyrrolidin-3R-yl | C(O) | cyclopropyl | b = 0 | 1-methyl-3-cyano-indazol-6-yl |
| 494 | cyclopropyl | pyrrolidin-3R-yl | C(O) | cyclopropyl | b = 0 | 3-amino-carbonyl-phenyl |
| 495 | cyclopropyl | azetidin-3-yl | C(O) | 2-hydroxy-propan-2-yl | 2-methyl | 1-methyl-indazol-5-yl |
| 496 | cyclopropyl | azetidin-3-yl | C(O) | 3-methyl-oxetan-3-yl | 2-methyl | 1-methyl-indazol-5-yl |
| 497 | cyclopropyl | pyrrolidin-3R-yl | C(O) | cyclopropyl | b = 0 | benzimidazol-2-yl |
| 498 | cyclopropyl | azetidin-3-yl | C(O) | 1-hydroxy-cyclopropyl | 2-methyl | 1-methyl-indazol-5-yl |
| 499 | cyclopropyl | azetidin-3-yl | C(O) | cyclopropyl | 2-methyl | 1-methyl-indazol-5-yl |
| 500 | cyclopropyl | pyrrolidin-3R-yl | C(O) | cyclopropyl | b = 0 | 1,2-dimethyl-1,2-dihydro-3-oxo-indazol-5-yl |
| 501 | cyclopropyl | azetidin-3-yl | C(O) | cyclopropyl | b = 0 | 2-cyclopropyl-methyl-indazol-5-yl |

TABLE 1-continued

Representative Compounds of Formula (I)

| ID No. | R¹ & R² taken together | (L¹)ₐ | R³ | (R⁴)_b | (A¹-(R⁶)_c) |
|---|---|---|---|---|---|
| 502 | cyclopropyl | azetidin-3-yl | C(O) | cyclopropyl | b = 0 | 3-fluoro-isoquinolin-6-yl |
| 503 | cyclopropyl | azetidin-3-yl | C(O) | cyclopropyl | b = 0 | 1-mehtyl-pyrazolo[3,4-b]pyridin-5-yl |
| 504 | cyclopropyl | azetidin-3-yl | C(O) | cyclopropyl | b = 0 | benzoisoxazol-5-yl |
| 505 | cyclopropyl | azetidin-3-yl | C(O) | cyclopropyl | b = 0 | 1-ethyl-indazol-5-yl |
| 506 | cyclopropyl | azetidin-3-yl | C(O) | cyclopropyl | b = 0 | 2-ethyl-indazol-5-yl |
| 507 | cyclopropyl | azetidin-3-yl | C(O) | cyclopropyl | b = 0 | 2-methyl-indazol-5-yl |
| 508 | cyclopropyl | azetidin-3-yl | C(O) | cyclopropyl | b = 0 | 1-isopropyl-indol-5-yl |
| 510 | cyclopropyl | azetidin-3-yl | C(O) | cyclopropyl | b = 0 | 2-methyl-quinolin-6-yl |
| 511 | cyclopropyl | azetidin-3-yl | C(O) | cyclopropyl | b = 0 | 1,8-naphthyridin-2-yl |
| 512 | cyclopropyl | pyrrolidin-3R-yl | C(O) | cyclopropyl | b = 0 | 2-oxo-3,4-dihydro-quinolin-6-yl |
| 513 | cyclopropyl | azetidin-3-yl | C(O) | cyclopropyl | b = 0 | 2-methyl-quinolin-7-yl |
| 515 | cyclopropyl | azetidin-3-yl | C(O) | cyclopropyl | b = 0 | 1-methyl-indazol-4-yl |
| 518 | cyclopropyl | azetidin-3-yl | C(O) | thiazol-2-yl | 2-methyl | 1-methyl-indazol-5-yl |
| 519 | cyclopropyl | azetidin-3-yl | C(O) | cyclopropyl | b = 0 | quinolin-3-yl |
| 520 | cyclopropyl | azetidin-3-yl | C(O) | cyclopropyl | 2-fluoro | 1,8-dimethyl-indazol-5-yl |
| 521 | cyclopropyl | azetidin-3-yl | C(O) | cyclopropyl | 2-fluoro | 1-ethyl-indazol-5-yl |
| 522 | cyclopropyl | azetidin-3-yl | C(O) | cyclopropyl | 2-fluoro | 1-cyclopropyl-indazol-5-yl |
| 523 | cyclopropyl | azetidin-3-yl | C(O) | cyclopropyl | 2-fluoro | 1-cyclopropyl-methyl-indazol-5-yl |
| 524 | cyclopropyl | azetidin-3-yl | C(O) | cyclopropyl | 2-fluoro | 2-cyclopropyl-methyl-indazol-5-yl |

TABLE 1-continued

Representative Compounds of Formula (I)

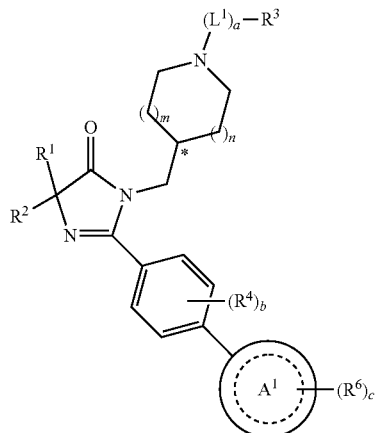

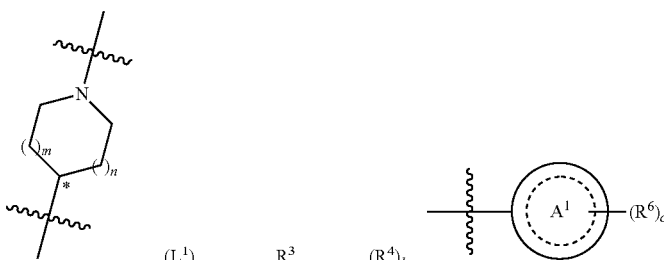

| ID No. | R¹ & R² taken together | (L¹)ₐ | R³ | (R⁴)ᵦ | |
|---|---|---|---|---|---|
| 525 | cyclopropyl | azetidin-3-yl | C(O) | cyclopropyl | 2-fluoro | 1-isopropyl-indazol-5-yl |
| 527 | cyclopropyl | azetidin-3-yl | C(O) | cyclopropyl | 2-fluoro | 1-(2-hydroxyethyl)-indazol-5-yl |
| 528 | cyclopropyl | pyrrolidin-3R-yl | C(O) | cyclopropyl | b = 0 | indazol-3-yl |
| 529 | cyclopropyl | pyrrolidin-3R-yl | C(O) | cyclopropyl | 2-fluoro | indazol-3-yl |
| 530 | cyclopropyl | azetidin-3-yl | C(O) | cyclopropyl | b = 0 | 1-methyl-3-hydroxymethyl-indazol-5-yl |
| 531 | cyclopropyl | azetidin-3-yl | C(O) | cyclopropyl | b = 0 | isoquinolin-3-yl |
| 532 | cyclopropyl | azetidin-3-yl | C(O) | cyclopropyl | b = 0 | 2-hydroxy-quinolin-3-yl |
| 533 | cyclopropyl | azetidin-3-yl | C(O) | cyclopropyl | b = 0 | 1-(2-cyanoethyl)-indazol-5-yl |
| 535 | cyclopropyl | azetidin-3-yl | C(O) | cyclopropyl | b = 0 | 2-methyl-4-chloro-quinolin-7-yl |
| 536 | cyclopropyl | azetidin-3-yl | C(O) | cyclopropyl | 2-fluoro | 2-(2-hydroxyethyl)-indazol-5-yl |
| 537 | cyclopropyl | azetidin-3-yl | C(O) | cyclopropyl | 2-fluoro | 2-fluoro-4-chloro-phenyl |
| 538 | cyclopropyl | pyrrolidin-3R-yl | C(O) | cyclopropyl | 2-fluoro | benzimidazol-2-yl |
| 539 | cyclopropyl | azetidin-3-yl | C(O) | cyclopropyl | b = 0 | 1,2,4-triazolo[4,3-1]pyridin-6-yl |
| 540 | cyclopropyl | azetidin-3-yl | C(O) | cyclopropyl | b = 0 | 2-chloro-quinolin-7-yl |
| 541 | cyclopropyl | azetidin-3-yl | C(O) | cyclopropyl | b = 0 | 1-methyl-indol-6-yl |
| 543 | cyclopropyl | azetidin-3-yl | C(O) | cyclopropyl | b = 0 | quinazolin-7-yl |
| 545 | cyclopropyl | azetidin-3-yl | C(O) | oxetan-2-yl | 2-methyl | 1-methyl-indazol-5-yl |
| 546 | cyclopropyl | azetidin-3-yl | C(O) | 3-hydroxy-2-methyl-propan-2-yl | 2-methyl | 1-methyl-indazol-5-yl |

TABLE 1-continued

Representative Compounds of Formula (I)

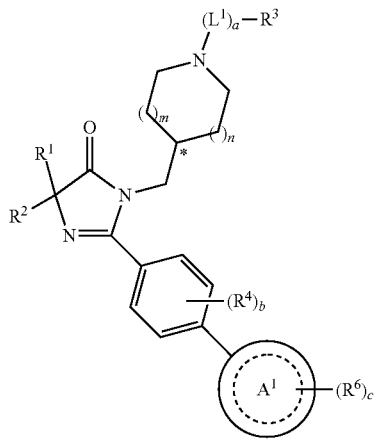

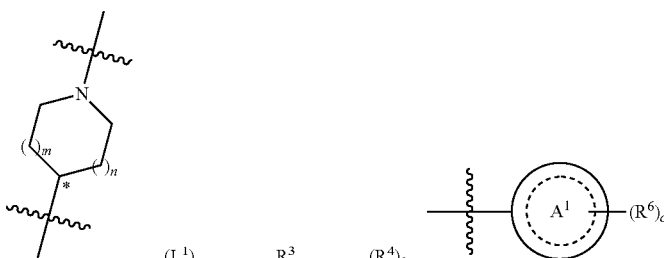

| ID No. | R¹ & R² taken together | | (L¹)ₐ | R³ | (R⁴)ᵦ | |
|---|---|---|---|---|---|---|
| 548 | cyclopropyl | azetidin-3-yl | C(O) | cyclopropyl | 2-fluoro | 2-methyl-benzothien-5-yl |
| 549 | cyclopropyl | azetidin-3-yl | C(O) | cyclopropyl | b = 0 | 2-(2-hydroxyethyl)-indazol-5-yl |
| 550 | cyclopropyl | azetidin-3-yl | C(O) | cyclopropyl | b = 0 | 1-isopropyl-indazol-5-yl |
| 551 | cyclopropyl | azetidin-3-yl | C(O) | cyclopropyl | b = 0 | 2-isopropyl-indazol-5-yl |
| 552 | cyclopropyl | azetidin-3-yl | C(O) | cyclopropyl | b = 0 | 1-(2-hydroxyethyl)-6-fluoro-indazol-5-yl |
| 553 | cyclopropyl | azetidin-3-yl | C(O) | cyclopropyl | b = 0 | 2-(2-hydroxyethyl)-6-fluoro-indazol-5-yl |
| 554 | cyclopropyl | azetidin-3-yl | C(O) | cyclopropyl | b = 0 | 4-methyl-quinolin-7-yl |
| 555 | cyclopropyl | azetidin-3-yl | C(O) | cyclopropyl | b = 0 | 2-chloro-3-methyl-quinolin-7-yl |
| 556 | cyclopropyl | azetidin-3-yl | C(O) | cyclopropyl | b = 0 | 1-(2-hydroxyethyl)-indazol-5-yl |
| 557 | cyclopropyl | pyrrolidin-3R-yl | C(O) | cyclopropyl | b = 0 | 1-methyl-3-methoxy-indazol-5-yl |
| 558 | cyclopropyl | azetidin-3-yl | C(O) | cyclopropyl | 2-fluoro | 2-methyl-benzothiazol-6-yl |
| 559 | cyclopropyl | azetidin-3-yl | C(O) | cyclopropyl | b = 0 | 2-chloro-4-methyl-quinolin-7-yl |
| 560 | cyclopropyl | azetidin-3-yl | C(O) | cyclopropyl | b = 0 | 8-fluoro-quinolin-2-yl |
| 561 | cyclopropyl | azetidin-3-yl | C(O) | cyclopropyl | b = 0 | 2-methyl-8-fluoro-quinolin-7-yl |
| 562 | cyclopropyl | azetidin-3-yl | C(O) | cyclopropyl | b = 0 | 2-methyl-benzothiazol-5-yl |

TABLE 1-continued

Representative Compounds of Formula (I)

| ID No. | R¹ & R² taken together | | (L¹)ₐ | R³ | (R⁴)ᵦ | |
|---|---|---|---|---|---|---|
| 563 | cyclopropyl | azetidin-3-yl | C(O) | cyclopropyl | | 4-chloro-quinolin-7-yl |
| 564 | cyclopropyl | azetidin-3-yl | C(O) | 1-amino-cyclopropyl | 2-methyl | 1-methyl-indazol-5-yl |
| 568 | cyclopropyl | azetidin-3-yl | C(O) | cyclopropyl | 2-fluoro | 1-methyl-3-(2-hydroxyethyl)-indol-5-yl |
| 569 | cyclopropyl | azetidin-3-yl | C(O) | cyclopropyl | 2-fluoro | 1,2-dimethyl-indol-5-yl |
| 570 | cyclopropyl | azetidin-3-yl | C(O) | cyclopropyl | b = 0 | 2,4-dimethyl-quinolin-7-yl |
| 571 | cyclopropyl | azetidin-3-yl | C(O) | cyclopropyl | 2-methyl | 3-(cyclopropyl-carbonyl-amino)-phenyl |
| 572 | cyclopropyl | azetidin-3-yl | C(O) | 1-hydroxy-cyclopropyl | 2-fluoro | 1-methyl-indazol-5-yl |
| 573 | cyclopropyl | azetidin-3-yl | C(O) | cyclopropyl | 2-fluoro | 1,3-dimethyl-indol-5-yl |
| 574 | cyclopropyl | azetidin-3-yl | C(O) | cyclopropyl | 2-fluoro | 2-methyl-quinolin-7-yl |
| 575 | cyclopropyl | azetidin-3-yl | C(O) | cyclopropyl | 2-fluoro | 2-methyl-quinolin-5-yl |
| 576 | cyclopropyl | azetidin-3-yl | C(O) | 1-methyl-cyclopropyl | 2-methyl | 2-methyl-quinolin-7-yl |
| 578 | cyclopropyl | azetidin-3-yl | C(O) | cyclopropyl | 2-methyl | 2-(cyclopropyl-sulfonyl-amino)-phenyl |
| 579 | cyclopropyl | azetidin-3-yl | C(O) | 1-methyl-cyclopropyl | 2-methyl | 2-aminocarbonyl-quinolin-7-yl |
| 580 | cyclopropyl | azetidin-3-yl | C(O) | 1-methyl-cyclopropyl | 2-methyl | 2-fluoro-4-cyano-phenyl |
| 581 | cyclopropyl | azetidin-3-yl | C(O) | 1-methyl-cyclopropyl | 2-methyl | 6-isopropyloxy-naphthyl-2-yl |
| 582 | cyclopropyl | azetidin-3-yl | C(O) | cyclopropyl | 2-methyl | 1,2-dimethyl-indol-5-yl |
| 583 | cyclopropyl | azetidin-3-yl | C(O) | cyclopropyl | b = 0 | 2-carboxy-quinolin-7-yl |
| 584 | cyclopropyl | azetidin-3-yl | C(O) | cyclopropyl | 2-chloro | 1-methyl-indazol-5-yl |
| 585 | cyclopropyl | pyrrolidin-3R-yl | C(O) | cyclopropyl | 2-fluoro | 3-(cyclopropyl-carbonyl-amino)-phenyl |

TABLE 1-continued

Representative Compounds of Formula (I)

| ID No. | R¹ & R² taken together | (L¹)ₐ | R³ | (R⁴)ᵦ | |
|---|---|---|---|---|---|
| 586 | cyclopropyl | azetidin-3-yl | C(O) | cyclopropyl | 2-methyl | 1-methyl-3-hydroxymethyl-indazol-5-yl |
| 587 | cyclopropyl | azetidin-3-yl | C(O) | cyclopropyl | 2-methyl | 2-methyl-3-hydroxymethyl-indazol-5-yl |
| 588 | cyclopropyl | azetidin-3-yl | C(O) | cyclopropyl | 2-methyl | 1-methyl-3-methoxymethyl-indazol-5-yl |
| 589 | cyclopropyl | azetidin-3-yl | C(O) | cyclopropyl | 2-methyl | 2-methyl-3-methoxymethyl-indazol-5-yl |
| 590 | cyclopropyl | azetidin-3-yl | C(O) | cyclopropyl | 2-methyl | 1-methyl-3-chloro-indazol-6-yl |
| 591 | cyclopropyl | azetidin-3-yl | C(O) | cyclopropyl | 2-methyl | 1-methyl-3-chloro-indazol-5-yl |
| 592 | cyclopropyl | azetidin-3-yl | C(O) | cyclopropyl | 2-fluoro | 4-chloro-indazol-5-yl |
| 593 | cyclopropyl | azetidin-3-yl | C(O) | 1-methyl-cyclopropyl | 2-methyl | 2-fluoro-4-(1-cyano-cyclopropyl)-phenyl |
| 594 | cyclopropyl | azetidin-3-yl | C(O) | 1-methyl-cyclopropyl | 2-methyl | 2-chloro-quinolin-7-yl |
| 595 | cyclopropyl | azetidin-3-yl | C(O) | 1-methyl-cyclopropyl | 2-methyl | 7-bromo-quinolin-2-yl |
| 596 | cyclopropyl | azetidin-3-yl | C(O) | 1-methyl-cyclopropyl | 2-methyl | 2-chloro-3-methyl-quinolin-7-yl |
| 597 | cyclopropyl | azetidin-3-yl | C(O) | 1-methyl-cyclopropyl | 2-methyl | 2-methyl-4-chloro-quinolin-7-yl |
| 598 | cyclopropyl | azetidin-3-yl | C(O) | 1-methyl-cyclopropyl | 2-methyl | 2-methyl-indazol-4-yl |
| 599 | cyclopropyl | azetidin-3-yl | C(O) | 1-methyl-cyclopropyl | 2-methyl | 1-methyl-indazol-4-yl |
| 600 | cyclopropyl | azetidin-3-yl | C(O) | 1-methyl-cyclopropyl | 2-methyl | 1-methyl-indazol-3-yl |
| 603 | cyclopropyl | azetidin-3-yl | C(O) | 1-methyl-cyclopropyl | 2-methyl | 2-methyl-quinolin-5-yl |

TABLE 1-continued

Representative Compounds of Formula (I)

| ID No. | R¹ & R² taken together | (L¹)ₐ | R³ | (R⁴)ᵦ | |
|---|---|---|---|---|---|
| 604 | cyclopropyl | azetidin-3-yl | C(O) | 1-methyl-cyclopropyl | 2-methyl | 2-cyano-quinolin-7-yl |
| 605 | cyclopropyl | azetidin-3-yl | C(O) | 1-methyl-cyclopropyl | 2-methyl | 4-methyl-7-beomo-quinolin-2-yl |
| 606 | cyclopropyl | azetidin-3-yl | C(O) | cyclopropyl | 2-fluoro | 1-methyl-3-chloro-indazol-6-yl |
| 607 | cyclopropyl | azetidin-3-yl | C(O) | cyclopropyl | 2-fluoro | 1-methyl-3-choro-indazol-5-yl |
| 608 | cyclopropyl | azetidin-3-yl | C(O) | cyclopropyl | 2-fluoro | 1-methyl-3-methoxymethyl-indazol-5-yl |
| 609 | cyclopropyl | azetidin-3-yl | C(O) | cyclopropyl | 2-fluoro | 1-methyl-3-hydroxymethyl-indazol-5-yl |
| 610 | cyclopropyl | azetidin-3-yl | C(O) | cyclopropyl | 2-methyl | 2-methyl-3-cyano-indazol-5-yl |
| 611 | cyclopropyl | azetidin-3-yl | C(O) | cyclopropyl | b = 0 | 2-cyano-quinolin-7-yl |
| 612 | cyclopropyl | azetidin-3-yl | C(O) | cyclopropyl | 3-chloro | 1-methyl-indazol-5-yl |
| 613 | cyclopropyl | pyrrolidin-3R-yl | C(O) | cyclopropyl | 2-methyl | 3-(cyclopropyl-sulfonyl-amino)-phenyl |
| 614 | cyclopropyl | pyrrolidin-3R-yl | C(O) | cyclopropyl | 2-methyl | 3-(cyclopropyl-carbonyl-amino)-phenyl |
| 615 | cyclopropyl | azetidin-3-yl | C(O) | cyclopropyl | 2-fluoro | 3-(cyclopropyl-carbonyl-amino)-phenyl |
| 616 | cyclopropyl | azetidin-3-yl | C(O) | cyclopropyl | 2-fluoro | 7-cyano-methyl-2-yl |
| 617 | cyclopropyl | azetidin-3-yl | C(O) | 1-hydroxy-cyclopropyl | 2-fluoro | 7-methoxy-naphth-2-yl |
| 618 | cyclopropyl | azetidin-3-yl | C(O) | cyclopropyl | 2-fluoro | 7-methoxy-naphth-2-yl |
| 619 | cyclopropyl | azetidin-3-yl | C(O) | cyclopropyl | 2-fluoro | 3-(cyclopropyl-carbonyl-amino)-phenyl |

TABLE 1-continued

Representative Compounds of Formula (I)

| ID No. | R¹ & R² taken together | (L¹)ₐ | R³ | (R⁴)ᵦ | |
|---|---|---|---|---|---|
| 620 | cyclopropyl | azetidin-3-yl | C(O) | 1-methyl-cyclopropyl | 2-methyl | 2-trifluoromethyl-quinolin-7-yl |
| 621 | cyclopropyl | azetidin-3-yl | C(O) | 1-hydroxy-cyclopropyl | 2-fluoro | 7-cyano-naphth-2-yl |
| 622 | cyclopropyl | azetidin-3-yl | C(O) | 1-hydroxy-cyclopropyl | 3-chloro | 1-mehtyl-indazol-5-yl |
| 624 | cyclopropyl | azetidin-3-yl | C(O) | 1-methyl-cyclopropyl | 2-methyl | 2-chloro-4-methyl-quinolin-7-yl |
| 627 | cyclopropyl | azetidin-3-yl | C(O) | 1-methyl-cyclopropyl | 2-methyl | 1-methyl-indazol-5-yl |
| 628 | cyclopropyl | azetidin-3-yl | C(O) | 1-hydroxy-cyclopropyl | 2-methyl | 1-methyl-indazol-5-yl |
| 629 | cyclopropyl | azetidin-3-yl | C(O) | cyclopropyl | 2-methyl | 4-chloro-indazol-6-yl |
| 630 | cyclopropyl | azetidin-3-yl | C(O) | cyclopropyl | 2-fluoro | 2-fluoro-5-trifluoromethyl-phenyl |
| 631 | cyclopropyl | azetidin-3-yl | C(O) | cyclopropyl | 2-fluoro | 3-(isopropyl-sulfonyl)-phenyl |
| 632 | cyclopropyl | pyrrolidin-3R-yl | C(O) | cyclopropyl | 2-fluoro | 3-(isopropyl-sulfonyl)-phenyl |
| 633 | cyclopropyl | pyrrolidin-3R-yl | C(O) | cyclopropyl | 2-methyl | 3-(methyl-sulfonyl)-phenyl |
| 634 | cyclopropyl | pyrrolidin-3R-yl | C(O) | cyclopropyl | 2-fluoro | 3-(methyl-sulfonyl)-phenyl |
| 635 | cyclopropyl | azetidin-3-yl | C(O) | cyclopropyl | 2-fluoro | 5-methoxy-naphth-2-yl |
| 636 | cyclopropyl | pyrrolidin-3R-yl | C(O) | cyclopropyl | 2-methyl | 3-(isopropyl-sulfonyl)-phenyl |
| 637 | cyclopropyl | azetidin-3-yl | C(O) | 1-fluoro-cyclopropyl | 2-fluoro | 1-methyl-indazol-5-yl |
| 638 | cyclopropyl | azetidin-3-yl | C(O) | cyclopropyl | 2-fluoro | 5-fluoro-benzothiazol-2-yl |
| 639 | cyclopropyl | azetidin-3-yl | C(O) | cyclopropyl | 2-fluoro | 5,6-difluoro-benzothiazol-2-yl |
| 640 | cyclopropyl | azetidin-3-yl | C(O) | cyclopropyl | 2-methyl | 3-(cyclopropyl-sulfonyl)-phenyl |
| 641 | cyclopropyl | pyrrolidin-3R-yl | C(O) | cyclopropyl | 2-fluoro | 3-(cyclopropyl-thio)-phenyl |

TABLE 1-continued

Representative Compounds of Formula (I)

| ID No. | R¹ & R² taken together | (L¹)ₐ | R³ | (R⁴)ᵦ | |
|---|---|---|---|---|---|
| 642 | cyclopropyl | pyrrolidin-3R-yl | C(O) | cyclopropyl | 2-methyl | 3-(cyclopropyl-thio)-phenyl |
| 643 | cyclopropyl | azetidin-3-yl | C(O) | cyclopropyl | 2-fluoro | 5-chloro-benzothiazol-2-yl |
| 644 | cyclopropyl | azetidin-3-yl | C(O) | cyclopropyl | 2-fluoro | 2-methyl-indazol-5-yl |
| 645 | cyclopropyl | azetidin-3-yl | C(O) | cyclopropyl | 2-fluoro | 3-(cyclopropyl-thio)-phenyl |
| 646 | cyclopropyl | pyrrolidin-3R-yl | C(O) | cyclopropyl | 2-methyl | 3-(cyclopropyl-sulfonyl)-phenyl |
| 647 | cyclopropyl | pyrrolidin-3R-yl | C(O) | cyclopropyl | 2-fluoro | 3-(cyclopropyl-sulfonyl)-phenyl |
| 648 | cyclopropyl | azetidin-3-yl | C(O) | cyclopropyl | 2-fluoro | 1-methyl-benzimidazol-2-yl |
| 649 | cyclopropyl | azetidin-3-yl | C(O) | cyclopropyl | 2-fluoro | 6-chloro-benzoxazol-2-yl |
| 650 | cyclopropyl | azetidin-3-yl | C(O) | cyclopropyl | 2-methyl | 3-(cyclopropyl-sulfonyl)-phenyl |
| 651 | cyclopropyl | azetidin-3-yl | C(O) | cyclopropyl | 2-fluoro | 3-(cyclopropyl-sulfonyl)-phenyl |
| 652 | cyclopropyl | azetidin-3-yl | C(O) | cyclopropyl | 2-fluoro | 5-cy7ano-benzothiazol-2-yl |
| 653 | cyclopropyl | azetidin-3-yl | C(O) | cyclopropyl | 2-fluoro | 1-methyl-6-fluoro-benzimidazol-2-yl |
| 654 | cyclopropyl | azetidin-3-yl | C(O) | cyclopropyl | 2-fluoro | 1,2-dimethyl-benzimidazol-6-yl |
| 661 | tetrahydro-pyran-4,4-diyl | pyrrolidin-3R-yl | C(O) | cyclopropyl | b = 0 | quinolin-7-yl |
| 662 | tetrahydro-pyran-4,4-diyl | pyrrolidin-3R-yl | C(O) | 1-hydroxy-ethyl | b = 0 | quinolin-7-yl |
| 663 | tetrahydro-pyran-4,4-diyl | pyrrolidin-3R-yl | C(O) | tetrahydro-furan-2R-yl | b = 0 | quinolin-7-yl |

TABLE 1-continued

Representative Compounds of Formula (I)

| ID No. | R¹ & R² taken together | | (L¹)ₐ | R³ | (R⁴)ᵦ | |
|---|---|---|---|---|---|---|
| 664 | tetrahydro-pyran-4,4-diyl | pyrrolidin-3R-yl | C(O)O | methyl | b = 0 | quinolin-7-yl |
| 665 | tetrahydro-pyran-4,4-diyl | pyrrolidin-3R-yl | C(O) | pyrrolidin-1-yl | b = 0 | quinolin-7-yl |
| 666 | tetrahydro-pyran-4,4-diyl | pyrrolidin-3R-yl | C(O) | thiazol-2-yl | b = 0 | quinolin-7-yl |
| 667 | tetrahydro-pyran-4,4-diyl | pyrrolidin-3R-yl | C(O) | cyclopropyl | b = 0 | benzofuran-5-yl |
| 668 | tetrahydro-pyran-4,4-diyl | pyrrolidin-3R-yl | C(O) | 1-hydroxy-ethyl | b = 0 | benzofuran-5-yl |
| 669 | tetrahydro-pyran-4,4-diyl | pyrrolidin-3R-yl | C(O) | tetrahydro-furan-2R-yl | b = 0 | benzofuran-5-yl |
| 670 | tetrahydro-pyran-4,4-diyl | pyrrolidin-3R-yl | C(O) | trifluoromethyl | b = 0 | benzofuran-5-yl |
| 671 | tetrahydro-pyran-4,4-diyl | pyrrolidin-3S-yl | C(O) | pyrrolidin-1-yl | b = 0 | benzofuran-5-yl |
| 672 | tetrahydro-pyran-4,4-diyl | pyrrolidin-3R-yl | C(O) | cyclopropyl | b = 0 | 1-methyl-indazol-5-yl |
| 673 | tetrahydro-pyran-4,4-diyl | pyrrolidin-3R-yl | C(O) | 1-hydroxy-ethyl | b = 0 | 1-methyl-indazol-5-yl |
| 674 | tetrahydro-pyran-4,4-diyl | pyrrolidin-3R-yl | C(O) | tetrahydro-furan-2R-yl | b = 0 | 1-methyl-indazol-5-yl |
| 675 | tetrahydro-pyran-4,4-diyl | pyrrolidin-3S-yl | C(O) | pyrrolidin-1-yl | b = 0 | 1-methyl-indazol-5-yl |
| 680 | tetrahydro-furan-3,3-diyl | pyrrolidin-3R-yl | C(O) | cyclopropyl | b = 0 | quinolin-7-yl |
| 681 | tetrahydro-furan-3,3-diyl | pyrrolidin-3R-yl | C(O) | 1-hydroxy-ethyl | b = 0 | quinolin-7-yl |

TABLE 1-continued

Representative Compounds of Formula (I)

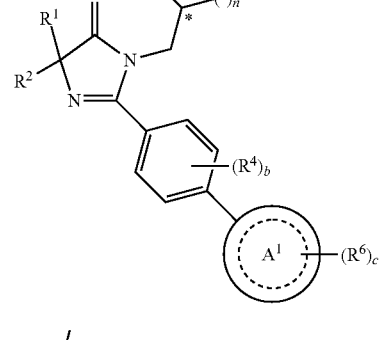

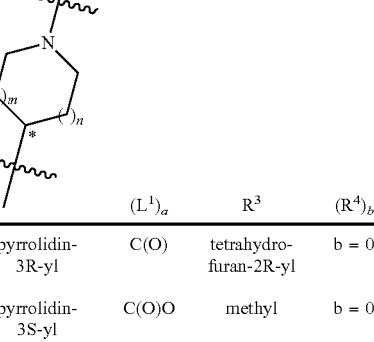

| ID No. | R¹ & R² taken together | (L¹)ₐ | R³ | (R⁴)_b | A¹(R⁶)_c |
|---|---|---|---|---|---|
| 682 | tetrahydro-furan-3,3-diyl | pyrrolidin-3R-yl | C(O) | tetrahydro-furan-2R-yl | b = 0 | quinolin-7-yl |
| 683 | tetrahydro-furan-3,3-diyl | pyrrolidin-3S-yl | C(O)O | methyl | b = 0 | quinolin-7-yl |
| 684 | tetrahydro-furan-3,3-diyl | pyrrolidin-3R-yl | C(O) | trifluoromethyl | b = 0 | quinolin-7-yl |
| 685 | tetrahydro-furan-3,3-diyl | pyrrolidin-3S-yl | C(O) | pyrrolidin-1-yl | b = 0 | quinolin-7-yl |
| 686 | tetrahydro-furan-3,3-diyl | pyrrolidin-3R-yl | C(O) | cyclopropyl | b = 0 | benzofuran-5-yl |
| 687 | tetrahydro-furan-3,3-diyl | pyrrolidin-3R-yl | C(O) | 1-hydroxy-ethyl | b = 0 | benzofuran-5-yl |
| 688 | tetrahydro-furan-3,3-diyl | pyrrolidin-3R-yl | C(O) | tetrahydro-furan-2R-yl | b = 0 | benzofuran-5-yl |
| 689 | tetrahydro-furan-3,3-diyl | pyrrolidin-3S-yl | C(O) | pyrrolidin-1-yl | b = 0 | benzofuran-5-yl |
| 690 | tetrahydro-furan-3,3-diyl | pyrrolidin-3R-yl | C(O) | cyclopropyl | b = 0 | 1-methyl-indazol-5-yl |
| 691 | tetrahydro-furan-3,3-diyl | pyrrolidin-3R-yl | C(O) | 1-hydroxy-ethyl- | b = 0 | 1-methyl-indazol-5-yl |
| 692 | tetrahydro-furan-3,3-diyl | pyrrolidin-3R-yl | C(O) | tetrahydro-furan-2R-yl | b = 0 | 1-methyl-indazol-5-yl |
| 693 | tetrahydro-furan-3,3-diyl | pyrrolidin-3S-yl | C(O) | pyrrolidin-1-yl | b = 0 | 1-methyl-indazol-5-yl |
| 698 | tetrahydro-pyran-4,4-diyl | azetidin-3-yl | C(O) | cyclopropyl | b = 0 | quinolin-7-yl |
| 699 | tetrahydro-pyran-4,4-diyl | azetidin-3-yl | C(O) | 1-hydroxy-ethyl | b = 0 | quinolin-7-yl |

TABLE 1-continued

Representative Compounds of Formula (I)

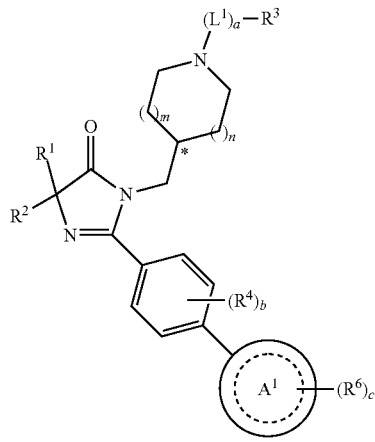

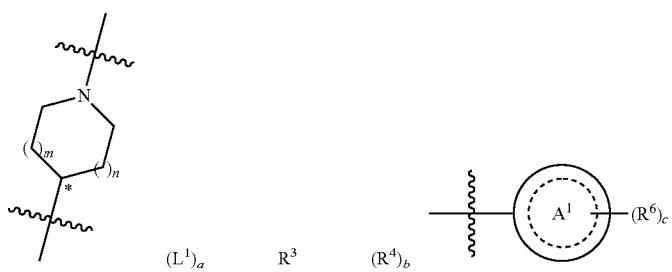

| ID No. | R¹ & R² taken together | $(L^1)_a$ | R³ | $(R^4)_b$ | |
|---|---|---|---|---|---|
| 700 | tetrahydro-pyran-4,4-diyl | azetidin-3-yl | C(O) | tetrahydro-furan-2R-yl | b = 0 | quinolin-7-yl |
| 701 | tetrahydro-pyran-4,4-diyl | azetidin-3-yl | C(O) | pyrrolidin-1-yl | b = 0 | quinolin-7-yl |
| 702 | tetrahydro-pyran-4,4-diyl | azetidin-3-yl | C(O) | cyclopropyl | b = 0 | benzofuran-5-yl |
| 703 | tetrahydro-pyran-4,4-diyl | azetidin-3-yl | C(O) | 1-hydroxy-ethyl | b = 0 | benzofuran-5-yl |
| 704 | tetrahydro-pyran-4,4-diyl | azetidin-3-yl | C(O) | tetrahydro-furan-2R-yl | b = 0 | benzofuran-5-yl |
| 705 | tetrahydro-pyran-4,4-diyl | azetidin-3-yl | C(O) | pyrrolidin-1-yl | b = 0 | benzofuran-5-yl |
| 706 | tetrahydro-pyran-4,4-diyl | azetidin-3-yl | C(O) | cyclopropyl | b = 0 | 1-methyl-indazol-5-yl |
| 707 | tetrahydro-pyran-4,4-diyl | azetidin-3-yl | C(O) | 1-hydroxy-ethyl | b = 0 | 1-methyl-indazol-5-yl |
| 708 | tetrahydro-pyran-4,4-diyl | azetidin-3-yl | C(O) | tetrahydro-furan-2R-yl | b = 0 | 1-methyl-indazol-5-yl |
| 709 | tetrahydro-pyran-4,4-diyl | azetidin-3-yl | C(O) | pyrrolidin-1-yl | b = 0 | 1-methyl-indazol-5-yl |
| 714 | tetrahydro-furan-3,3-diyl | azetidin-3-yl | C(O) | cyclopropyl | b = 0 | quinolin-7-yl |
| 715 | tetrahydro-furan-3,3-diyl | azetidin-3-yl | C(O) | 1-hydroxy-ethyl | b = 0 | quinolin-7-yl |
| 716 | tetrahydro-furan-3,3-diyl | azetidin-3-yl | C(O) | tetrahydro-furan-2R-yl | b = 0 | quinolin-7-yl |

TABLE 1-continued

Representative Compounds of Formula (I)

| ID No. | R¹ & R² taken together | (L¹)ₐ | R³ | (R⁴)ᵦ | A¹ |
|---|---|---|---|---|---|
| 717 | tetrahydro-furan-3,3-diyl | azetidin-3-yl | C(O) | pyrrolidin-1-yl | b = 0 | quinolin-7-yl |
| 718 | tetrahydro-furan-3,3-diyl | azetidin-3-yl | C(O) | cyclopropyl | b = 0 | benzofuran-5-yl |
| 719 | tetrahydro-furan-3,3-diyl | azetidin-3-yl | C(O) | 1-hydroxy-ethyl | b = 0 | benzofuran-5-yl |
| 720 | tetrahydro-furan-3,3-diyl | azetidin-3-yl | C(O) | tetrahydro-furan-2R-yl | b = 0 | benzofuran-5-yl |
| 721 | tetrahydro-furan-3,3-diyl | azetidin-3-yl | C(O) | pyrrolidin-1-yl | b = 0 | benzofuran-5-yl |
| 722 | tetrahydro-furan-3,3-diyl | azetidin-3-yl | C(O) | cyclopropyl | b = 0 | 1-methyl-indazol-5-yl |
| 723 | tetrahydro-furan-3,3-diyl | azetidin-3-yl | C(O) | 1-hydroxy-ethyl | b = 0 | 1-methyl-indazol-5-yl |
| 724 | tetrahydro-furan-3,3-diyl | azetidin-3-yl | C(O) | tetrahydro-furan-2R-yl | b = 0 | 1-methyl-indazol-5-yl |
| 728 | 1-(methoxy-carbonyl)-azetidin-3,3-diyl | pyrrolidin-3R-yl | C(O) | cyclopropyl | b = 0 | quinolin-7-yl |
| 729 | 1-(methoxy-carbonyl)-azetidin-3,3-diyl | pyrrolidin-3R-yl | C(O) | 1-hydroxy-ethyl | b = 0 | quinolin-7-yl |
| 730 | 1-(methoxy-carbonyl)-azetidin-3,3-diyl | pyrrolidin-3R-yl | C(O) | tetrahydro-furan-2R-yl | b = 0 | quinolin-7-yl |
| 731 | 1-(methoxy-carbonyl)-azetidin-3,3-diyl | pyrrolidin-3R-yl | C(O) | trifluoromethyl | b = 0 | quinolin-7-yl |

TABLE 1-continued

Representative Compounds of Formula (I)

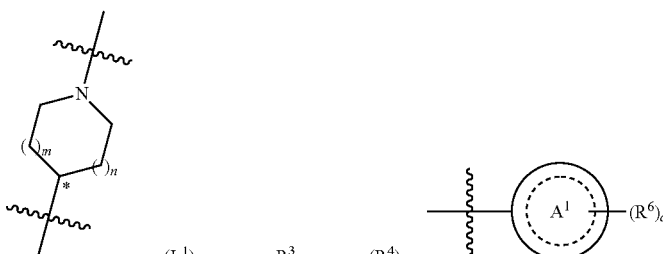

| ID No. | R¹ & R² taken together | $(L^1)_a$ | R³ | $(R^4)_b$ | |
|---|---|---|---|---|---|
| 732 | 1-(methoxy-carbonyl)-azetidin-3,3-diyl | pyrrolidin-3R-yl | C(O) | pyrrolidin-1-yl | b = 0 | quinolin-7-yl |
| 733 | 1-(methoxy-carbonyl)-azetidin-3,3-diyl | pyrrolidin-3R-yl | C(O) | cyclopropyl | b = 0 | benzofuran-5-yl |
| 734 | 1-(methoxy-carbonyl)-azetidin-3,3-diyl | pyrrolidin-3R-yl | C(O) | 1-hydroxy-ethyl | b = 0 | benzofuran-5-yl |
| 735 | 1-(methoxy-carbonyl)-azetidin-3,3-diyl | pyrrolidin-3R-yl | C(O) | tetrahydro-furan-2R-yl | b = 0 | benzofuran-5-yl |
| 736 | 1-(methoxy-carbonyl)-azetidin-3,3-diyl | pyrrolidin-3S-yl | C(O) | pyrrolidin-1-yl | b = 0 | benzofuran-5-yl |
| 737 | 1-(methoxy-carbonyl)-azetidin-3,3-diyl | pyrrolidin-3R-yl | C(O) | cyclopropyl | b = 0 | 1-methyl-indazol-5-yl |
| 738 | 1-(methoxy-carbonyl)-azetidin-3,3-diyl | pyrrolidin-3R-yl | C(O) | 1-hydroxy-ethyl | b = 0 | 1-methyl-indazol-5-yl |
| 739 | 1-(methoxy-carbonyl)-azetidin-3,3-diyl | pyrrolidin-3R-yl | C(O) | tetrahydro-furan-2R-yl | b = 0 | 1-methyl-indazol-5-yl |
| 740 | 1-(methoxy-carbonyl)-azetidin-3,3-diyl | pyrrolidin-3S-yl | C(O) | pyrrolidin-1-yl | b = 0 | 1-methyl-indazol-5-yl |
| 741 | 1-(ethenyl-carbonyl)-piperidin-4,4-diyl | pyrrolidin-3R-yl | C(O) | cyclopropyl | b = 0 | benzofuran-6-yl |

TABLE 1-continued

Representative Compounds of Formula (I)

| ID No. | R¹ & R² taken together | (L¹)ₐ | R³ | (R⁴)ᵦ | |
|---|---|---|---|---|---|
| 742 | 1-(2-hydroxy-ethyl)-piperidin-4,4-diyl | pyrrolidin-3R-yl | C(O) | cyclopropyl | b = 0 | 2,3-dimethyl-benzothien-5-yl |
| 743 | 1-(isopropyl)-piperidin-4,4-yl | pyrrolidin-3R-yl | C(O) | cyclopropyl | b = 0 | indazol-5-yl |
| 744 | 1-(isopropyl)-piperidin-4,4-diyl | pyrrolidin-3R-yl | C(O) | cyclopropyl | b = 0 | indazol-5-yl |
| 745 | 1-(methyl-sulfonyl)-piperidin-4,4-diyl | pyrrolidin-3R-yl | C(O) | cyclopropyl | b = 0 | indazol-5-yl |
| 746 | 1-(methyl-sulfonyl)-piperidin-4,4-diyl | pyrrolidin-3R-yl | C(O) | cyclopropyl | b = 0 | benzofuran-5-yl |
| 747 | 1-(2-(methoxy)ethyl)-piperidin-4,4-diyl | pyrrolidin-3R-yl | C(O) | cyclopropyl | b = 0 | indol-5-yl |
| 748 | 1-(2-(methoxy)ethyl)-piperidin-4,4-diyl | pyrrolidin-3R-yl | C(O) | cyclopropyl | b = 0 | indazol-5-yl |
| 749 | 1-(2-(methoxy)ethyl)-piperidin-4,4-diyl | pyrrolidin-3R-yl | C(O) | cyclopropyl | b = 0 | benzofuran-5-yl |
| 750 | 1-(2-(methoxy)ethyl)-piperidin-4,4-diyl | pyrrolidin-3R-yl | C(O) | cyclopropyl | b = 0 | 1-methyl-indazol-5-yl |

TABLE 1-continued

Representative Compounds of Formula (I)

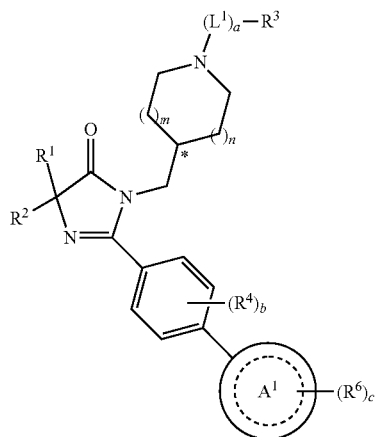

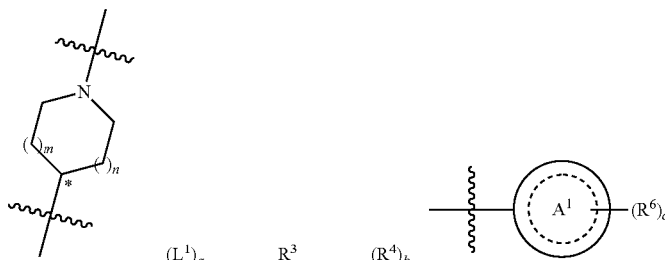

| ID No. | R¹ & R² taken together | | (L¹)ₐ | R³ | (R⁴)ᵦ | |
|---|---|---|---|---|---|---|
| 751 | 1-(trifluoro-methyl)-carbonyl)-piperidin-4,4-diyl | | pyrrolidin-3R-yl | C(O) | cyclopropyl | b = 0 | indol-5-yl |
| 752 | 1-(trifluoro-methyl)-carbonyl)-piperidin-4,4-diyl | | pyrrolidin-3R-yl | C(O) | cyclopropyl | b = 0 | 1-methyl-indazol-5-yl |
| 753 | 1-(isopropyl-carbonyl)-piperidin-4,4-diyl | | azetidin-3-yl | C(O) | cyclopropyl | b = 0 | indol-5-yl |
| 754 | 1-(isopropyl-carbonyl)-piperidin-4,4-diyl | | azetidin-3-yl | C(O) | cyclopropyl | b = 0 | indazol-5-yl |
| 755 | 1-(2-(methoxy)ethyl)-piperidin-4,4-diyl | | azetidin-3-yl | C(O) | cyclopropyl | b = 0 | indol-5-yl |
| 756 | 1-(2-(methoxy-ethyl)-piperidin-4,4-diyl | | azetidin-3-yl | C(O) | cyclopropyl | b = 0 | indazol-5-yl |
| 757 | 1-(2-hydroxy-ethyl)-piperidin-4,4-diyl | | azetidin-3-yl | C(O) | cyclopropyl | b = 0 | indol-5-yl |
| 758 | 1-(2-hydroxy-ethyl)-piperidin-4,4-diyl | | azetidin-3-yl | C(O) | cyclopropyl | b = 0 | indazol-5-yl |

TABLE 1-continued

Representative Compounds of Formula (I)

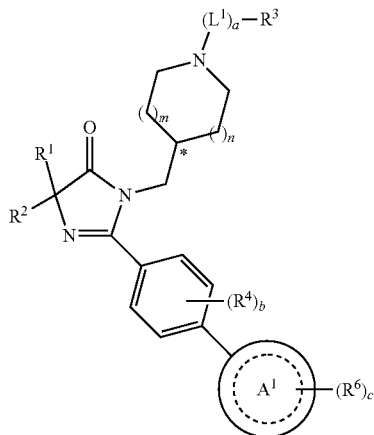

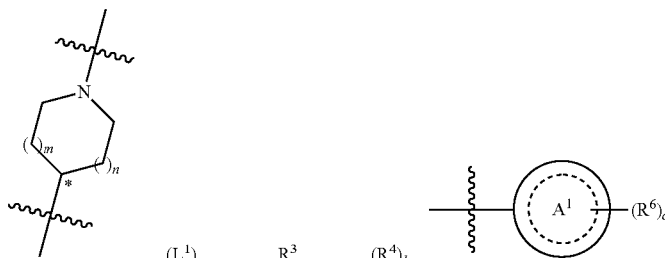

| ID No. | R¹ & R² taken together | (L¹)ₐ | R³ | (R⁴)ᵦ | |
|---|---|---|---|---|---|
| 760 | 1-(methyl-sulfonyl)-piperidin-4,4-diyl | azetidin-3-yl | C(O) | cyclopropyl | b = 0 | benzofuran-5-yl |
| 761 | 1-(methyl-sulfonyl)-piperidin-4,4-diyl | azetidin-3-yl | C(O) | cyclopropyl | b = 0 | 1-methyl-indazol-5-yl |
| 762 | 1-(methyl-sulfonyl)-piperidin-4,4-diyl | azetidin-3-yl | C(O) | cyclopropyl | b = 0 | indol-5-yl |
| 763 | 1-(methyl-sulfonyl)-piperidin-4,4-diyl | azetidin-3-yl | C(O) | cyclopropyl | b = 0 | indazol-5-yl |
| 764 | 1-(trifluoro-methyl-carbonyl)-piperidin-4,4-diyl | azetidin-3-yl | C(O) | cyclopropyl | b = 0 | benzofuran-5-yl |
| 765 | 1-(trifluoro-methyl-carbonyl)-piperidin-4,4-diyl | azetidin-3-yl | C(O) | cyclopropyl | | indol-5-yl |
| 766 | 1-(trifluoro-methyl-carbonyl)-piperidin-4,4-diyl | azetidin-3-yl | C(O) | cyclopropyl | b = 0 | indazol-5-yl |
| 775 | cyclopropyl | azetidin-3-yl | C(O) | cyclopropyl | 2-methyl | 3-methylsulfonyl-phenyl |
| 776 | cyclopropyl | azetidin-3-yl | C(O) | cyclopropyl | 2-methyl | 3-isopropylsulfonyl-phenyl |
| 777 | cyclopropyl | azetidin-3-yl | C(O) | cyclopropyl | 2-fluoro | 3-methylsulfonyl-phenyl |

TABLE 1-continued

Representative Compounds of Formula (I)

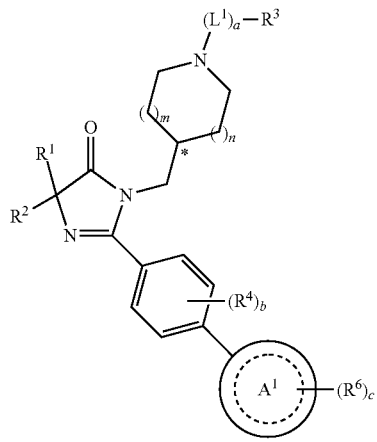

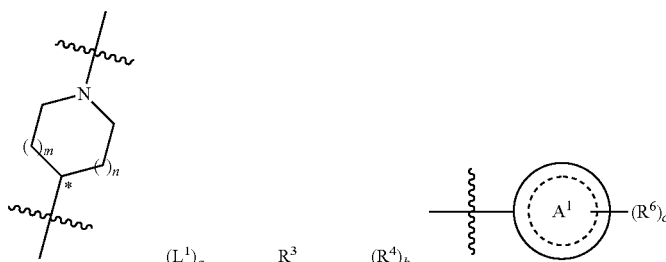

| ID No. | R¹ & R² taken together | (L¹)ₐ | R³ | (R⁴)ᵦ | |
|---|---|---|---|---|---|
| 784 | cyclopropyl | azetidin-3-yl | C(O) | cyclopropyl | b = 0 | 6-isopropyl-pyridin-3-yl |
| 787 | cyclopropyl | azetidin-3-yl | C(O) | 1-methyl-cyclopropyl | 2-methyl | 3-methyl-7-bromo-quinolin-2-yl |
| 788 | cyclopropyl | azetidin-3-yl | C(O) | cyclopropyl | b = 0 | 1-oxetan-3-yl-indazol-5-yl |
| 789 | cyclopropyl | azetidin-3-yl | C(O) | cyclopropyl | 2-fluoro | 1-oxetan-3-yl-indazol-5-yl |
| 790 | cyclopropyl | azetidin-3-yl | C(O) | cyclopropyl | b = 0 | 2-methyl-quinolin-5-yl |
| 791 | cyclopropyl | azetidin-3-yl | C(O) | cyclopropyl | b = 0 | 4-methyl-7-bromo-quinolin-2-yl |
| 792 | cyclopropyl | azetidin-3-yl | C(O) | cyclopropyl | b = 0 | 1-methyl-1H-pyrazolo[4,3-b]pyridin-5-yl |
| 793 | cyclopropyl | azetidin-3-yl | C(O) | cyclopropyl | b = 0 | 3-methyl-[1,2,4]triazolo[4,3-a]pyridin-6-yl |
| 794 | cyclopropyl | azetidin-3-yl | C(O) | cyclopropyl | b = 0 | 5-(2-hydroxy-2-methyl-propyl)-pyrid-2-yl |
| 795 | cyclopropyl | azetidin-3-yl | C(O) | cyclopropyl | b = 0 | 6-n-propyl-pyridin-3-yl |
| 796 | cyclopropyl | azetidin-3-yl | C(O) | 1-hydroxy-cyclopropyl | 2-methyl | 1-methyl-indazol-5-yl |
| 797 | cyclopropyl | azetidin-3-yl | C(O) | cyclopropyl | b = 0 | 6-(2-hydroxy-2-methyl-propyl)-pyridin-3-yl |
| 798 | cyclopropyl | azetidin-3-yl | C(O) | cyclopropyl | b = 0 | 6-chyclopropyl-pyridin-3-yl |
| 799 | cyclopropyl | azetidin-3-yl | C(O) | cyclopropyl | b = 0 | 1,,8-naphthyridin-3-yl |
| 800 | cyclopropyl | azetidin-3-yl | C(O) | cyclopropyl | b = 0 | 6-(1-cyano-cyclopropyl)-pyrid-3-yl |
| 801 | cyclopropyl | azetidin-3-yl | C(O) | cyclopropyl | b = 0 | 1,5-naphthyridin-3-yl |
| 802 | cyclopropyl | pyrrolidin-3R-yl | C(O) | cyclopropyl | b = 0 | 5-chloro-pyridin-3-yl |

TABLE 1-continued

Representative Compounds of Formula (I)

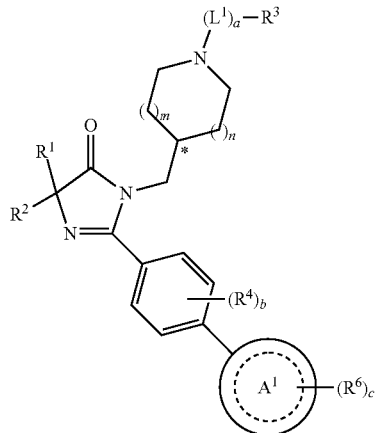

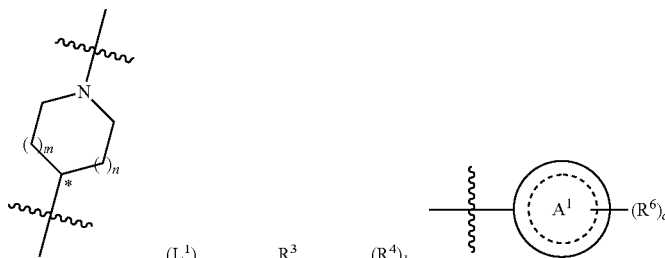

| ID No. | R¹ & R² taken together | (L¹)ₐ | R³ | (R⁴)ᵦ | |
|---|---|---|---|---|---|
| 803 | cyclopropyl | azetidin-3-yl | C(O) | cyclopropyl | b = 0 | 1-cyclopropyl-indazol-5-yl |
| 804 | cyclopropyl | azetidin-3-yl | C(O) | cyclopropyl | b = 0 | 1-cycloprropyl-methyl-indazol-3-yl |
| 805 | cyclopropyl | azetidin-3-yl | C(O) | pyridin-3-yl | 2-methyl | 1-methyl-indazol-5-yl |
| 807 | cyclopropyl | azetidin-3-yl | C(O) | cyclopropyl | b = 0 | 1-isopropyl-indazol-5-yl |
| 808 | cyclopropyl | azetidin-3-yl | C(O) | cyclopropyl | b = 0 | 2-isopropyl-indazol-5-yl |
| 809 | cyclopropyl | pyrrolidin-3R-yl | C(O) | cyclopropyl | b = 0 | 2-oxo-3,4-dihydro-quinolin-7-yl |
| 811 | cyclopropyl | pyrrolidin-3R-yl | C(O) | cyclopropyl | b = 0 | 2-isopropyl-indazol-5-yl |
| 814 | cyclopropyl | azetidin-3-yl | C(O) | cyclopropyl | 3-methyl | 2,3-dimethyl-benzofu-5-yl |
| 816 | cyclopropyl | piperidin-3S-yl | C(O) | cyclopropyl | b = 0 | indazol-5-yl |
| 817 | cyclopropyl | piperidin-3S-yl | C(O) | cyclopropyl | b = 0 | benzothien-5-yl |
| 818 | cyclopropyl | piperidin-3S-yl | C(O) | cyclopropyl | b = 0 | benzofuran-5-yl |
| 819 | cyclopropyl | piperidin-3S-yl | C(O) | cyclopropyl | b = 0 | 1-methyl-indazol-5-yl |
| 822 | cyclopentyl | pyrrolidin-3R-yl | C(O) | cyclopropyl | 2-methyl | 4-methyl-3,4-dihydro-2H-pyrido[3,2-b][1,4]oxazin-7-yl |
| 834 | cyclopropyl | azetidin-3-yl | C(O) | cyclopropyl | 2-fluoro | 1-methyl-3-cyano-indazol-5-yl |
| 836 | cyclopropyl | azetidin-3-yl | C(O) | cyclopropyl | 2-methyl | 1-methyl-3-cyano-indazol-5-yl |
| 837 | cyclopropyl | azetidin-3-yl | C(O) | 1-hydroxy-cyclopropyl | 2-fluoro | 1-(2-hydroxyethyl)-indazol-5-yl |
| 839 | cyclopropyl | azetidin-3-yl | C(O) | cyclopropyl | b = 0 | 2-methyl-7-bromo-quinolin-2-yl |

TABLE 1-continued

Representative Compounds of Formula (I)

| ID No. | R¹ & R² taken together | (L¹)ₐ | R³ | (R⁴)_b | |
|---|---|---|---|---|---|
| 840 | cyclopropyl | azetidin-3-yl | C(O) | cyclopropyl | b = 0 | 2-oxo-quinolin-7-yl |
| 841 | cyclopropyl | azetidin-3-yl | C(O) | cyclopropyl | b = 0 | 7-bromo-quinolin-2-yl |
| 842 | cyclopropyl | azetidin-3-yl | C(O) | cyclopropyl | b = 0 | 2-(2-cyanoethyl)-indazol-5-yl |
| 843 | cyclopropyl | piperidin-3S-yl | C(O) | cyclopropyl | b = 0 | indol-5-yl |
| 844 | cyclopropyl | pyrrolidin-3R-yl | C(O) | cyclopropyl | b = 0 | 1-methyl-indazol-5-yl |
| 845 | cyclopropyl | pyrrolidin-3R-yl | C(O) | cyclopropyl | 2-fluoro | indol-5-yl |
| 846 | cyclopropyl | azetidin-3-yl | C(O) | cyclopropyl | b = 0 | 2,3-dimethyl-benzofuran-5-yl |
| 847 | cyclopropyl | pyrrolidin-3R-yl | C(O) | cyclopropyl | b = 0 | 2,3-dimethyl-benzofuran-5-yl |
| 848 | cyclopropyl | pyrrolidin-3R-yl | C(O) | cyclopropyl | b = 0 | 3-carboxyphenyl |
| 849 | cyclopropyl | pyrrolidin-3R-yl | C(O) | cyclopropyl | 3-methyl | 2-methyl-benzothien-5-yl |
| 850 | cyclopropyl | pyrrolidin-3R-yl | C(O) | cyclopropyl | 3-fluoro | 2-methyl-benzothien-5-yl |
| 851 | cyclopropyl | pyrrolidin-3R-yl | C(O) | cyclopropyl | b = 0 | indol-5-yl |
| 855 | cyclopentyl | pyrrolidin-3R-yl | C(O) | cyclopropyl | 2-methyl | 5-chloro-pyridin-3-yl |
| 859 | cyclopropyl | piperidin-4-yl | C(O) | cyclopropyl | b = 0 | 4-trifluoromethyl-phenyl |
| 867 | cyclopropyl | pyrrolidin-3R-yl | C(O) | cyclopropyl | b = 0 | 5-amino-pyridin-3-yl |
| 868 | cyclopropyl | azetidin-3-yl | C(O) | cyclopropyl | 2-fluoro | benzothiazol-2-yl |
| 869 | cyclopropyl | azetidin-3-yl | C(O) | cyclopropyl | 2-fluoro | 2-methyl-indol-5-yl |
| 870 | cyclopropyl | azetidin-3-yl | C(O) | cyclopropyl | 2-fluoro | 1-methyl-indol-5-yl |
| 871 | cyclopropyl | pyrrolidin-3R-yl | C(O) | cyclopropyl | 2-fluoro | 1-methyl-indazol-5-yl |
| 872 | cyclopropyl | azetidin-3-yl | C(O) | 1-hydroxy-cyclopropyl | 2-fluoro | 6-cyano-methyl-2-yl |

TABLE 1-continued

Representative Compounds of Formula (I)

| ID No. | R¹ & R² taken together | (L¹)ₐ | R³ | (R⁴)ᵦ | A¹-(R⁶)c |
|---|---|---|---|---|---|
| 873 | cyclopentyl | pyrrolidin-3R-yl | C(O) | cyclopropyl | 2-methyl | indol-6-yl |
| 874 | cyclopentyl | pyrrolidin-3R-yl | C(O) | cyclopropyl | 2-fluoro | indol-6-yl |
| 875 | cyclopentyl | pyrrolidin-3R-yl | C(O) | cyclopropyl | 2-fluoro | quinolin-7-yl |
| 876 | cyclopentyl | pyrrolidin-3R-yl | C(O) | cyclopropyl | 2-fluoro | benzothien-7-yl |
| 877 | cyclopentyl | pyrrolidin-3R-yl | C(O) | cyclopropyl | 2-fluoro | benzimidazol-5-yl |
| 878 | cyclopentyl | pyrrolidin-3R-yl | C(O) | 1-hydroxy-cyclopropyl | b = 0 | benzofuran-5-yl |
| 879 | cyclopentyl | pyrrolidin-3R-yl | C(O) | cyclopropyl | 2-fluoro | indazol-6-yl |
| 880 | cyclopentyl | pyrrolidin-3R-yl | C(O) | cyclopropyl | 2-fluoro | 1-methyl-indazol-5-yl |
| 881 | cyclopentyl | pyrrolidin-3R-yl | C(O) | cyclopropyl | 2-fluoro | pyrrolo[2,3-b]pyridin-5-yl |
| 883 | cyclopentyl | pyrrolidin-3R-yl | C(O) | cyclopropyl | 2-methyl | benzo[1,3]dioxol-5-yl |
| 884 | cyclopentyl | pyrrolidin-3R-yl | C(O) | cyclopropyl | 2-methyl | 2,3-dihydrobenzofuran-5-yl |
| 885 | cyclopentyl | pyrrolidin-3R-yl | C(O) | cyclopropyl | 2-fluoro | 2-oxo-benzimidazol-5-yl |
| 886 | cyclopentyl | pyrrolidin-3R-yl | C(O) | cyclopropyl | 2-fluoro | 4-(methylcarbonyl)-phenyl |
| 887 | cyclopropyl | azetidin-3-yl | C(O) | cyclopropyl | b = 0 | 5-bromo-pyridin-2-yl |
| 888 | tetrahydro-pyran-4,4-diyl | azetidin-3-yl | SO₂ | methyl | b = 0 | benzofuran-5-yl |
| 889 | tetrahydro-pyran-4,4-diyl | pyrrolidin-3S-yl | C(O)O | methyl | b = 0 | benzofuran-5-yl |
| 890 | tetrahydro-pyran-4,4-diyl | pyrrolidin-3R-yl | C(O) | trifluoromethyl | b = 0 | 1-methyl-indazol-5-yl |
| 892 | tetrahydro-furan-3,3-diyl | pyrrolidin-3R-yl | C(O) | thiazol-2-yl | b = 0 | 1-methyl-indazol-5-yl |

TABLE 1-continued

Representative Compounds of Formula (I)

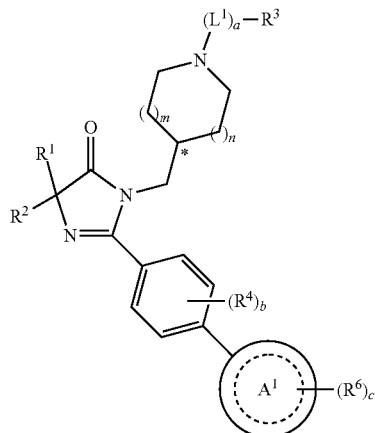

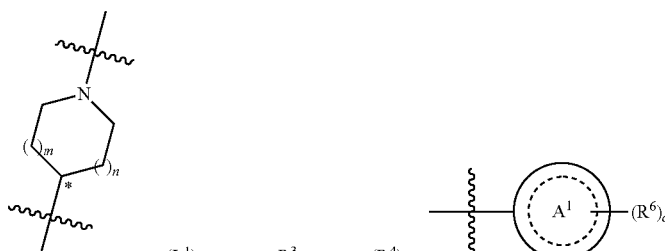

| ID No. | R¹ & R² taken together | | (L¹)$_a$ | R³ | (R⁴)$_b$ | |
|---|---|---|---|---|---|---|
| 895 | tetrahydro-furan-3,3-diyl | azetidin-3-yl | C(O) | trifluoromethyl | b = 0 | quinolin-7-yl |
| 896 | tetrahydro-furan-3,3-diyl | pyrrolidin-3-yl | SO$_2$ | methyl | b = 0 | quinolin-7-yl |
| 897 | tetrahydro-furan-3,3-diyl | azetidin-3-yl | C(O) | trifluoromethyl | b = 0 | benzofuran-5-yl |
| 898 | tetrahydro-furan-3,3-diyl | azetidin-3-yl | SO$_2$ | methyl | b = 0 | benzofuran-5-yl |
| 900 | 1-methoxycarbonyl)-azetidin-3,3-diyl | pyrrolidin-3S-yl | SO$_2$ | methyl | b = 0 | quinolin-7-yl |
| 902 | tetrahydro-pyran-4,4-diyl | azetidin-3-yl | SO$_2$ | methyl | b = 0 | 1-methyl-indazol-5-yl |
| 903 | tetrahydro-furan-3,3-diyl | azetidin-3-yl | C(O)O | methyl | b = 0 | quinolin-7-yl |
| 904 | tetrahydro-furan-3,3-diyl | azetidin-3-yl | C(O)O | methyl | b = 0 | benzofuran-5-yl |
| 905 | tetrahydro-furan-3,3-diyl | azetidin-3-yl | C(O)O | methyl | b = 0 | 1-methyl-indazol-5-yl |
| 907 | 1-methoxycarbonyl)-azetidin-3,3-diyl | pyrrolidin-3R-yl | C(O) | trifluoromethyl | b = 0 | 1-methyl-indazol-5-yl |
| 908 | tetrahydro-pyran-4,4-diyl | azetidin-3-yl | C(O) | thiazol-2-yl | b = 0 | 1-methyl-indazol-5-yl |
| 909 | tetrahydro-furan-3,3-diyl | azetidin-3-yl | C(O) | thiazol-2-yl | b = 0 | 1-methyl-indazol-5-yl |
| 910 | tetrahydro-pyran-4,4-diyl | azetidin-3-yl | C(O) | trifluoromethyl | b = 0 | quinolin-7-yl |

TABLE 1-continued

Representative Compounds of Formula (I)

| ID No. | R¹ & R² taken together | $(L^1)_a$ | R³ | $(R^4)_b$ | |
|---|---|---|---|---|---|
| 912 | tetrahydro-pyran-4,4-diyl | azetidin-3-yl | SO₂ | methyl | b = 0 | quinolin-7-yl |
| 913 | tetrahydro-pyran-4,4-diyl | pyrrolidin-3S-yl | SO₂ | methyl | b = 0 | benzofuran-5-yl |
| 914 | tetrahydro-furan-3,3-diyl | pyrrolidin-3S-yl | SO₂ | methyl | b = 0 | benzofuran-5-yl |
| 915 | tetrahydro-furan-3,3-diyl | pyrrolidin-3S-yl | C(O)O | methyl | b = 0 | 1-methyl-indazol-5-yl |
| 916 | 1-methoxycarbonyl)-azetidin-3,3-diyl | pyrrolidin-3S-yl | C(O)O | methyl | b = 0 | 1-methyl-indazol-5-yl |
| 917 | 1-methoxycarbonyl)-azetidin-3,3-diyl | pyrrolidin-3S-yl | SO₂ | methyl | b = 0 | 1-methyl-indazol-5-yl |
| 920 | tetrahydro-furan-3,3-diyl | pyrrolidin-3R-yl | C(O) | thiazol-2-yl | b = 0 | quinolin-7-yl |
| 922 | tetrahydro-pyran-4,4-diyl | azetidin-3-yl | C(O)O | methyl | b = 0 | quinolin-7-yl |
| 923 | 1-methoxycarbonyl)-azetidin-3,3-diyl | pyrrolidin-3R-yl | C(O) | thiazol-2-yl | b = 0 | 1-methyl-indazol-5-yl |
| 925 | cyclopropyl | piperidin-3R-yl | C(O) | cyclopropyl | b = 0 | 4-hydroxy-phenyl |
| 926 | tetrahydro-pyran-4,4-diyl | pyrrolidin-3S-yl | SO₂ | methyl | b = 0 | 1-methyl-indazol-5-yl |
| 928 | tetrahydro-pyran-4,4-diyl | azetidin-3-yl | C(O)O | methyl | b = 0 | benzofuran-5-yl |

TABLE 1-continued

Representative Compounds of Formula (I)

| ID No. | R¹ & R² taken together | (L¹)ₐ | R³ | (R⁴)ᵦ | A¹-(R⁶)c |
|---|---|---|---|---|---|
| 930 | tetrahydro-furan-3,3-diyl | azetidin-3-yl | C(O) | thiazol-2-yl | b = 0 | quinolin-7-yl |
| 931 | 1-methoxycar-bonyl)-azetidin-3,3-diyl | pyrrolidin-3S-yl | C(O) | methyl | b = 0 | benzofuran-5-yl |
| 932 | tetrahydro-furan-3,3-diyl | azetidin-3-yl | C(O) | thiazol-2-yl | b = 0 | benzofuran-5-yl |
| 933 | tetrahydro-furan-3,3-diyl | pyrrolidin-3S-yl | SO₂ | methyl | b = 0 | 1-methyl-indazol-5-yl |
| 934 | tetrahydro-furan-3,3-diyl | pyrrolidin-3-yl | C(O) | thiazol-2-yl | b = 0 | benzofuran-5-yl |
| 935 | tetrahydro-pyran-4,4-diyl | azetidin-3-yl | C(O) | trifluoromethyl | b = 0 | 1-methyl-indazol-5-yl |
| 937 | tetrahydro-furan-3,3-diyl | azetidin-3-yl | C(O) | trifluoromethyl | b = 0 | 1-methyl-indazol-5-yl |
| 938 | tetrahydro-furan-3,3-diyl | pyrrolidin-3-yl | C(O) | trifluoromethyl | b = 0 | benzofuran-5-yl |
| 941 | tetrahydro-pyran-4,4-diyl | azetidin-3-yl | C(O)O | methyl | b = 0 | 1-methyl-indazol-5-yl |
| 942 | tetrahydro-furan-3,3-diyl | azetidin-3-yl | SO₂ | methyl | b = 0 | quinolin-7-yl |
| 944 | tetrahydro-furan-3,3-diyl | azetidin-3-yl | SO₂ | methyl | b = 0 | 1-methyl-indazol-5-yl |
| 945 | tetrahydro-furan-3,3-diyl | azetidin-3-yl | C(O) | pyrrolidin-1-yl | b = 0 | 1-methyl-indazol-5-yl |
| 946 | 1-(methoxycar-bonyl)-azetidin-3,3-diyl | pyrrolidin-3R-yl | C(O) | trifluoromethyl | b = 0 | benzofuran-5-yl |

TABLE 1-continued

Representative Compounds of Formula (I)

| ID No. | R¹ & R² taken together | (L¹)ₐ | R³ | (R⁴)ᵦ | A¹-(R⁶)꜀ |
|---|---|---|---|---|---|
| 947 | tetrahydro-pyran-4,4-diyl | azetidin-3-yl | C(O) | thiazol-2-yl | b = 0 | quinolin-7-yl |
| 949 | tetrahydro-pyran-4,4-diyl | azetidin-3-yl | C(O) | thiazol-2-yl | b = 0 | benzofuran-5-yl |
| 951 | 1-isopropyl-piperidin-4,4-diyl | azetidin-3-yl | C(O) | cyclopropyl | b = 0 | isoquinolin-6-yl |
| 952 | 1-(trifluoro-methyl-carbonyl)-piperidin-4,4-diyl | azetidin-3-yl | C(O) | cyclopropyl | b = 0 | 1-(trifluoromethyl-carbonyl)-indol-5-yl |
| 953 | tetrahydro-pyran-4,4-diyl | pyrrolidin-3S-yl | C(O)O | methyl | b = 0 | 1-methyl-indazol-5-yl |
| 954 | tetrahydro-furan-3,3-diyl | pyrrolidin-3S-yl | C(O)O | methyl | b = 0 | benzofuran-5-yl |
| 955 | tetrahydro-furan-3,3-diyl | pyrrolidin-3R-yl | C(O)O | trifluoromethyl | b = 0 | 1-methyl-indazol-5-yl |
| 956 | 1-(methoxycar-bonyl)-azetidin-3,3-diyl | pyrrolidin-3S-yl | SO₂ | methyl | b = 0 | benzofuran-5-yl |
| 957 | 1-(methoxycar-bonyl)-azetidin-3,3-diyl | pyrrolidin-3R-yl | C(O) | thiazol-2-yl | b = 0 | benzofuran-5-yl |
| 958 | tetrahydro-pyran-4,4-diyl | pyrrolidin-3R-yl | C(O) | thiazol-2-yl | b = 0 | benzofuran-5-yl |
| 959 | tetrahydro-pyran-4,4-diyl | pyrrolidin-3R-yl | C(O) | thiazol-2-yl | b = 0 | 1-methyl-indazol-5-yl |
| 960 | tetrahydro-pyran-4,4-diyl | pyrrolidin-3S-yl | SO₂ | methyl | b = 0 | quinolin-7-yl |

TABLE 1-continued

Representative Compounds of Formula (I)

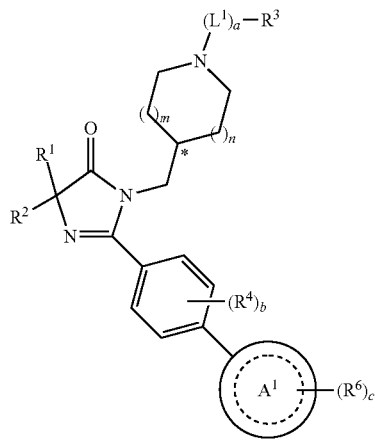

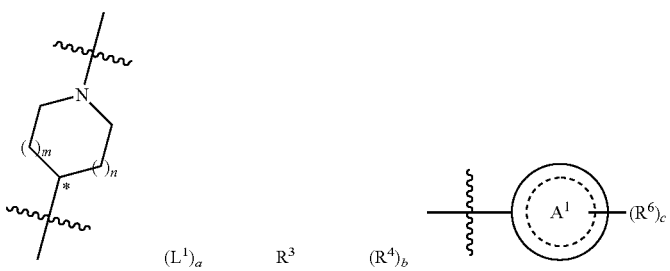

| ID No. | R¹ & R² taken together | (L¹)ₐ | R³ | (R⁴)ᵦ | A¹–(R⁶)𝒸 |
|---|---|---|---|---|---|
| 961 | tetrahydro-pyran-4,4-diyl | azetidin-3-yl | C(O) | trifluoromethyl | b = 0 | benzofuran-5-yl |
| 962 | 1-(methoxycar-bonyl)-azetidin-3,3-diyl | pyrrolidin-3R-yl | C(O) | thiazol-2-yl | b = 0 | quinolin-7-yl |
| 963 | 1-(methoxycar-bonyl)-azetidin-3,3-diyl | pyrrolidin-3S-yl | C(O) | methyl | b = 0 | quinolin-7-yl |
| 964 | 1-(trifluoro-methyl-carbonyl)-piperidin-4,4-diyl | azetidin-3-yl | C(O) | cyclopropyl | b = 0 | 1-methyl-indazol-5-yl |
| 965 | tetrahydro-pyran-4,4-diyl | pyrrolidin-3R-yl | C(O) | trifluoromethyl | b = 0 | quinolin-7-yl |
| 966 | 1-(2-hydroxy-ethyl)-piperidin-4,4-diyl | pyrrolidin-3R-yl | C(O) | cyclopropyl | b = 0 | indazol-5-yl |
| 967 | 1-(2-hydroxy-ethyl)-piperidin-4,4-diyl | pyrrolidin-3R-yl | C(O) | cyclopropyl | b = 0 | indol-5-yl |
| 968 | 1-(trifluoro-methyl-carbonyl)-piperidin-4,4-diyl | pyrrolidin-3R-yl | C(O) | cyclopropyl | b = 0 | benzofuran-5-yl |

TABLE 1-continued

Representative Compounds of Formula (I)

| ID No. | R¹ & R² taken together | (L¹)ₐ | R³ | (R⁴)_b | |
|---|---|---|---|---|---|
| 969 | cyclopropyl | pyrrolidin-3S-yl | C(O) | cyclopropyl | b = 0 | 4-hydroxy-phenyl |
| 970 | 1-(methyl-sulfonyl)-piperidin-4,4-diyl | pyrrolidin-3R-yl | C(O) | cyclopropyl | b = 0 | 1-methyl-indazol-5-yl |

In Table 2 below, the 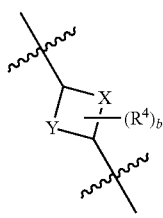 portion of the compound of formula (I) is incorporated into the compound of formula (I) (as drawn at the beginning of Table 2) and in the orientation as drawn in the Table.

TABLE 2
Representative Compounds of Formula (I)
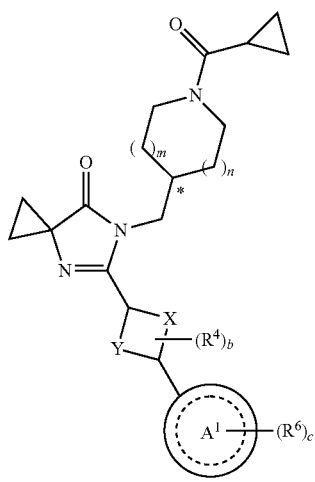
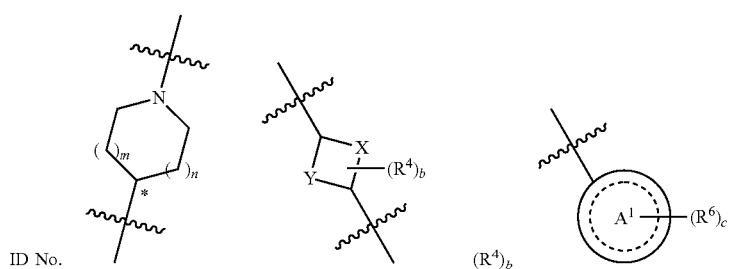
| ID No. | | | $(R^4)_b$ | |
|---|---|---|---|---|
| 341 | pyrrolidin-3R-yl | 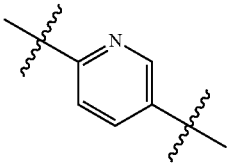 [SMILES: *c1ccc(*)nc1] | b = 0 | indol-5-yl |
| 342 | pyrrolidin-3R-yl | 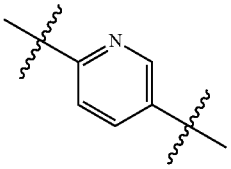 [SMILES: *c1ccc(*)nc1] | b = 0 | benzthiazol-5-yl |
| 390 | pyrrolidin-3R-yl | 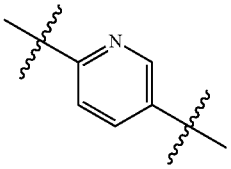 [SMILES: *c1ccc(*)nc1] | b = 0 | benzofuran-5-yl |
| 397 | pyrrolidin-3R-yl | 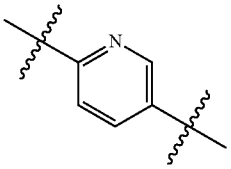 [SMILES: *c1ccc(*)nc1] | b = 0 | 1-methyl-indazol-5-yl |

TABLE 2-continued
Representative Compounds of Formula (I)
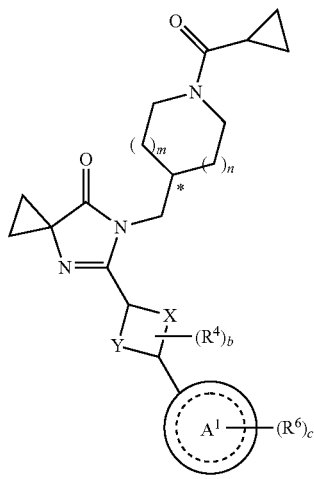
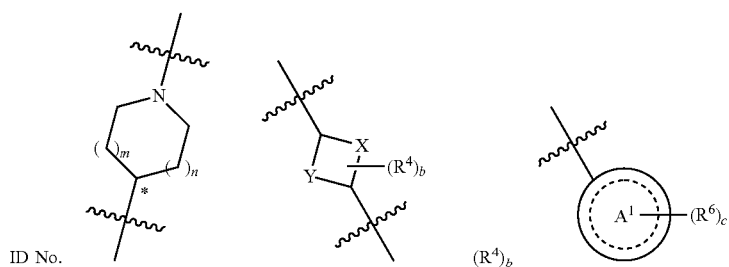
| ID No. | | (R⁴)_b | |
|---|---|---|---|
| 402 | pyrrolidin-3R-yl | 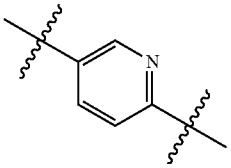 [SMILES: *c1ccc(*)nc1] b = 0 | indol-5-yl |
| 419 | pyrrolidin-3R-yl | 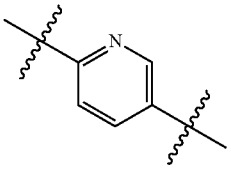 [SMILES: *c1ccc(*)nc1] b = 0 | indazol-5-yl |
| 420 | pyrrolidin-3R-yl | 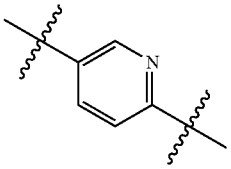 [SMILES: *c1ccc(*)nc1] b = 0 | benzofuran-5-yl |
| 421 | pyrrolidin-3R-yl | 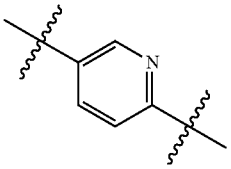 [SMILES: *c1ccc(*)nc1] b = 0 | 1-methyl-indazol-5-yl |

TABLE 2-continued

Representative Compounds of Formula (I)

| ID No. | | (R⁴)_b | |
|---|---|---|---|
| 422 | pyrrolidin-3R-yl | (thiophene linker) | b = 0 | benzofuran-5-yl |
| 423 | pyrrolidin-3R-yl | (thiophene linker) | b = 0 | indol-5-yl |
| 424 | pyrrolidin-3R-yl | (thiophene linker) | b = 0 | indazol-5-yl |
| 425 | pyrrolidin-3R-yl | (thiophene linker) | b = 0 | benzothien-5-yl |
| 426 | pyrrolidin-3R-yl | (thiophene linker) | b = 0 | indol-6-yl |

TABLE 2-continued
Representative Compounds of Formula (I)
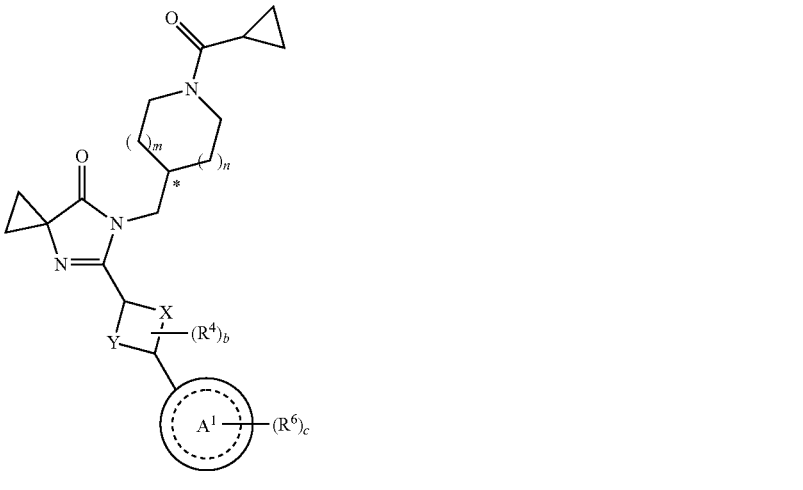
| ID No. | | (R⁴)_b | | |
|---|---|---|---|---|
| 427 | pyrrolidin-3R-yl |  | b = 0 | indazol-4-yl |
| 428 | pyrrolidin-3R-yl |  | b = 0 | indol-6-yl |
| 429 | pyrrolidin-3R-yl |  | b = 0 | indazol-4-yl |
| 430 | pyrrolidin-3R-yl |  | b = 0 | 1-methyl-indazol-5-yl |

TABLE 2-continued
Representative Compounds of Formula (I)
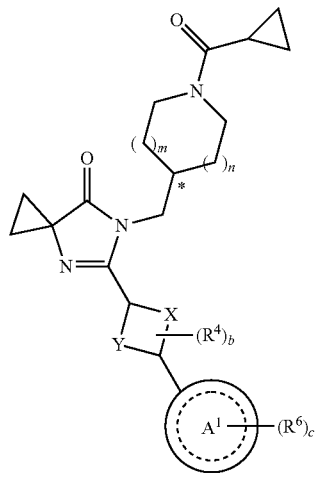
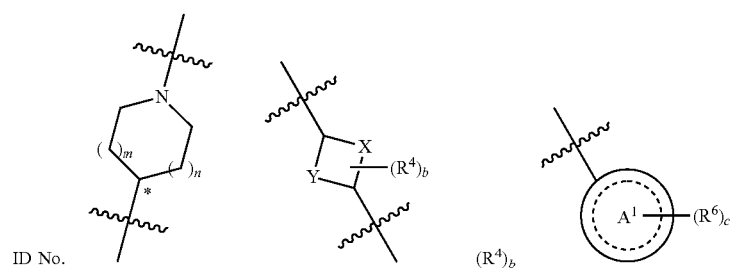
| ID No. | | (R⁴)ᵦ | | |
|---|---|---|---|---|
| 437 | pyrrolidin-3R-yl | 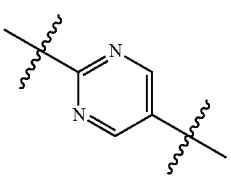 [SMILES: *c1cnc(*)nc1] | b = 0 | benzofuran-5-yl |
| 438 | pyrrolidin-3R-yl | 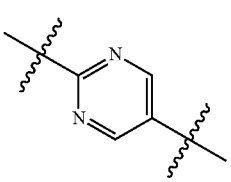 [SMILES: *c1cnc(*)nc1] | b = 0 | 1-methyl-indazol-5-yl |
| 439 | pyrrolidin-3R-yl | 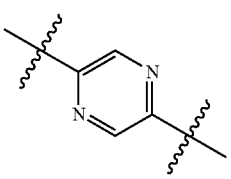 [SMILES: *c1cnc(*)cn1] | b = 0 | benzofuran-5-yl |

TABLE 2-continued
Representative Compounds of Formula (I)
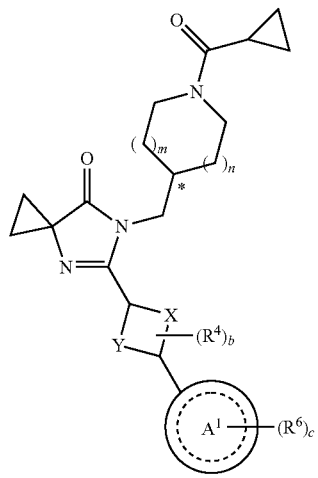
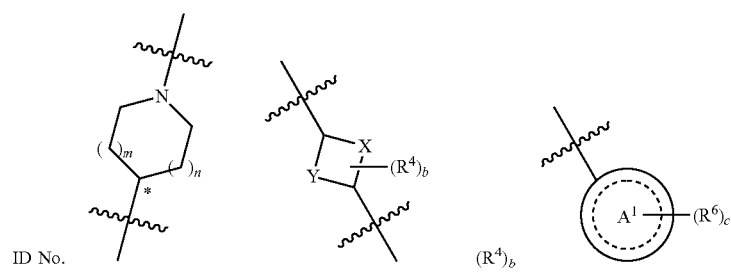
| ID No. | | (R⁴)_b | | |
|---|---|---|---|---|
| 458 | pyrrolidin-3R-yl | 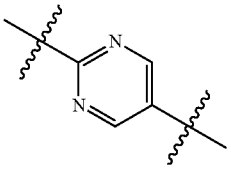 [SMILES: *c1cnc(*)nc1] | b = 0 | benzofuran-5-yl |
| 459 | pyrrolidin-3R-yl | 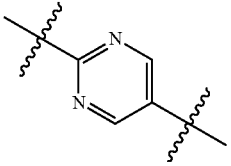 [SMILES: *c1cnc(*)nc1] | b = 0 | 1-methyl-indazol-5-yl |
| 971 | azetidin-3-yl | 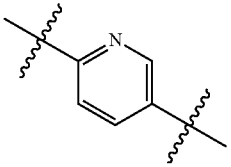 [SMILES: *c1ccc(*)nc1] | b = 0 | 6-cyano-naphth-2-yl |

TABLE 3

Representative Compounds of Formula (I)

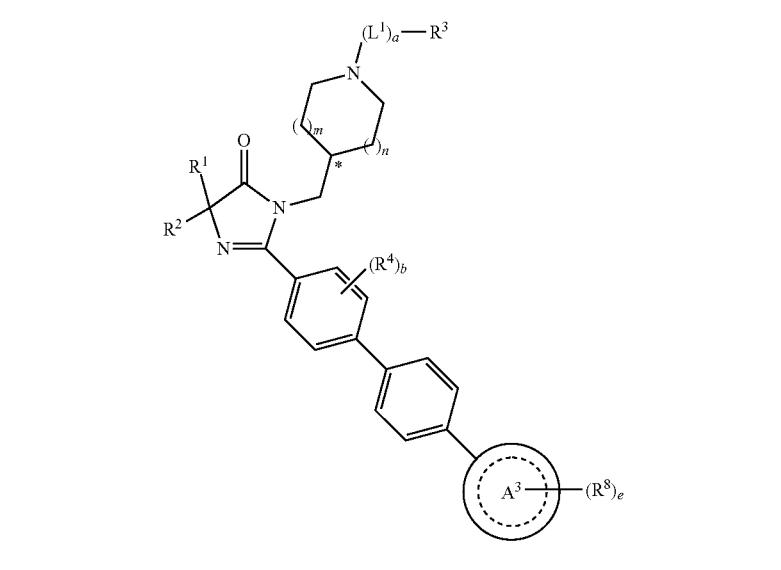

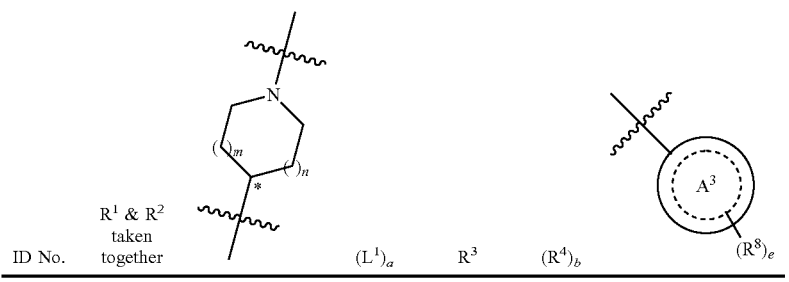

| ID No. | R¹ & R² taken together | (L¹)ₐ | R³ | (R⁴)ᵦ | (R⁸)ₑ |
|---|---|---|---|---|---|
| 21 | cyclopropyl | piperidin-4-yl | C(O) | cyclopropyl | b = 0 | 4-bromo-phenyl |
| 23 | cyclopropyl | piperidin-4-yl | C(O) | cyclopropyl | b = 0 | pyridin-3-yl |
| 56 | cyclopropyl | piperidin-4-yl | C(O) | cyclopropyl | b = 0 | 1-methyl-pyrazol-4-yl |
| 59 | cyclopropyl | azetidin-3-yl | C(O) | cyclopropyl | b = 0 | 1-methyl-pyrazol-4-yl |
| 60 | cyclopropyl | azetidin-3-yl | C(O) | cyclopropyl | b = 0 | pyridin-3-yl |
| 61 | cyclopropyl | piperidin-4-yl | C(O) | cyclopropyl | b = 0 | pyridin-4-yl |
| 62 | cyclopropyl | piperidin-4-yl | C(O) | cyclopropyl | b = 0 | 1-methyl-pyrazol-5-yl |
| 65 | cyclopropyl | pyrrolidin-3R-yl | C(O) | cyclopropyl | b = 0 | 1-methyl-pyrazol-4-yl |
| 70 | cyclopentyl | pyrrolidin-3R-yl | C(O) | cyclopropyl | b = 0 | 3-(pyrazol-3-yl) |
| 91 | cyclopentyl | pyrrolidin-3R-yl | C(O) | cyclopropyl | b = 0 | tetrazol-5-yl |
| 122 | cyclopropyl | pyrrolidin-3R-yl | C(O) | cyclopropyl | b = 0 | pyridin-3-yl |
| 235 | cyclopropyl | pyrrolidin-3R-yl | C(O) | cyclopropyl | b = 0 | pyridin-4-yl |
| 267 | cyclopropyl | pyrrolidin-3R-yl | C(O) | 1-methyl-cyclopropyl | 2-methyl | 1-methyl-pyrazol-4-yl |
| 316 | cyclopropyl | pyrrolidin-3R-yl | C(O) | cyclopropyl | 2-methyl | 1-methyl-pyrazol-4-yl |
| 322 | cyclopropyl | azetidin-3-yl | C(O) | cyclopropyl | 2-fluoro | 1-methyl-pyrazol-4-yl |
| 323 | cyclopropyl | pyrrolidin-3R-yl | C(O) | cyclopropyl | 2-fluoro | 1-methyl-pyrazol-4-yl |
| 325 | cyclopropyl | azetidin-3-yl | C(O) | cyclopropyl | 2-methyl | 1-isopropyl-pyrazol-4-yl |
| 326 | cyclopropyl | azetidin-3-yl | C(O) | cyclopropyl | 2-methyl | 1-cyclopropyl-pyrazol-4-yl |
| 327 | cyclopropyl | azetidin-3-yl | C(O) | cyclopropyl | 2-fluoro | 1-isopropyl-pyrazol-4-yl |

TABLE 3-continued

Representative Compounds of Formula (I)

| ID No. | R¹ & R² taken together | | (L¹)ₐ | R³ | (R⁴)ᵦ | (R⁸)ₑ |
|---|---|---|---|---|---|---|
| 328 | cyclopropyl | azetidin-3-yl | C(O) | cyclopropyl | 2-fluoro | 1-cyclopropyl-pyrazol-4-yl |
| 329 | cyclopropyl | azetidin-3-yl | C(O) | cyclopropyl | 2-fluoro | 1-cyclobutyl-pyrazol-4-yl |
| 330 | cyclopropyl | azetidin-3-yl | C(O) | cyclopropyl | 2-methyl | 1-cyclobutyl-pyrazol-4-yl |
| 331 | cyclopropyl | azetidin-3-yl | C(O) | cyclopropyl | b = 0 | 1-isopropyl-pyrazol-4-yl |
| 333 | cyclopropyl | azetidin-3-yl | C(O) | cyclopropyl | 2-methyl | 1-methyl-pyrazol-4-yl |
| 337 | cyclopropyl | azetidin-3-yl | C(O) | 1-methyl-cyclopropyl | 2-methyl | 1-cyclopropyl-pyrazol-4-yl |
| 338 | cyclopropyl | azetidin-3-yl | C(O) | 1-methyl-cyclopropyl | 2-methyl | 1-cyclobutyl-pyrazol-4-yl |
| 358 | cyclopropyl | azetidin-3-yl | C(O) | 1-methyl-cyclopropyl | 2-fluoro | 1-methyl-pyrazol-4-yl |
| 362 | cyclopropyl | pyrrolidin-3R-yl | C(O) | 1-methyl-cyclopropyl | 2-fluoro | 1-methyl-pyrazol-5-yl |
| 364 | cyclopropyl | pyrrolidin-3R-yl | C(O) | 1-methyl-cyclopropyl | 2-fluoro | 1-methyl-pyrazol-4-yl |
| 371 | cyclopropyl | pyrrolidin-3R-yl | C(O) | 1-hydroxy-cyclopropyl | 2-fluoro | 1-methyl-pyrazol-5-yl |
| 379 | cyclopropyl | pyrrolidin-3R-yl | C(O) | 1-hydroxy-cyclopropyl | 2-fluoro | 1-methyl-pyrazol-4-yl |
| 382 | cyclopropyl | azetidin-3-yl | C(O) | 1-hydroxy-cyclopropyl | 2-fluoro | 1-methyl-pyrazol-4-yl |
| 407 | cyclopropyl | pyrrolidin-3R-yl | C(O) | cyclopropyl | b = 0 | 1-methyl-pyrazol-5-yl |
| 411 | cyclopropyl | pyrrolidin-3S-yl | C(O) | cyclopropyl | b = 0 | 1-methyl-pyrazol-4-yl |
| 412 | cyclopropyl | pyrrolidin-3S-yl | C(O) | cyclopropyl | b = 0 | 3-chlorophenyl |
| 413 | cyclopropyl | pyrrolidin-3S-yl | C(O) | cyclopropyl | b = 0 | 4-methylphenyl |
| 514 | cyclopropyl | azetidin-3-yl | C(O) | cyclopropyl | b = 0 | 1-methyl-pyrazol-5-yl |
| 516 | cyclopropyl | azetidin-3-yl | C(O) | cyclopropyl | b = 0 | 1-isopropyl-pyrazol-4-yl |

TABLE 3-continued

Representative Compounds of Formula (I)

| ID No. | R¹ & R² taken together | (L¹)ₐ | R³ | (R⁴)ᵦ | (R⁸)ₑ |
|---|---|---|---|---|---|
| 517 | cyclopropyl | azetidin-3-yl | C(O) | cyclopropyl | b = 0 | 1-methyl-pyrazol-4-yl |
| 534 | cyclopropyl | azetidin-3-yl | C(O) | cyclopropyl | b = 0 | 1-methyl-pyrazol-4-yl |
| 542 | cyclopropyl | azetidin-3-yl | C(O) | cyclopropyl | b = 0 | 1-methyl-pyrazol-3-yl |
| 544 | cyclopropyl | azetidin-3-yl | C(O) | cyclopropyl | b = 0 | 1-isobutyl-pyrazol-4-yl |
| 547 | cyclopropyl | azetidin-3-yl | C(O) | cyclopropyl | 2-fluoro | 1-methyl-pyrazol-3-yl |
| 566 | cyclopropyl | azetidin-3-yl | C(O) | 1-methyl-cyclopropyl | 2-fluoro | 1-methyl-pyrazol-5-yl |
| 577 | cyclopropyl | azetidin-3-yl | C(O) | 1-hydroxy-cyclopropyl | 2-fluoro | 1-methyl-pyrazol-5-yl |
| 601 | cyclopropyl | azetidin-3-yl | C(O) | 1-methyl-cyclopropyl | 2-methyl | 1-cyclopropylmethyl-pyrazol-3-yl |
| 602 | cyclopropyl | azetidin-3-yl | C(O) | 1-methyl-cyclopropyl | 2-methyl | 1-(2-methylpropyl)-pyrazol-3-yl |
| 623 | cyclopropyl | pyrrolidin-3R-yl | C(O) | 1-methyl-cyclopropyl | 2-methyl | 1-methyl-pyrazol-5-yl |
| 655 | tetrahydro-pyran-4,4-diyl | pyrrolidin-3R-yl | C(O) | cyclopropyl | b = 0 | 1-methyl-pyrazol-4-yl |
| 656 | tetrahydro-pyran-4,4-diyl | pyrrolidin-3R-yl | C(O) | 1-hydroxy-ethyl | b = 0 | 1-methyl-pyrazol-4-yl |
| 657 | tetrahydro-pyran-4,4-diyl | pyrrolidin-3R-yl | C(O) | tetrahydro-furan-2R-yl | b = 0 | 1-methyl-pyrazol-4-yl |
| 658 | tetrahydro-pyran-4,4-diyl | pyrrolidin-3S-yl | C(O) | methyl | b = 0 | 1-methyl-pyrazol-4-yl |
| 659 | tetrahydro-pyran-4,4-diyl | pyrrolidin-3R-yl | C(O) | trifluoro-methyl | b = 0 | 1-methyl-pyrazol-4-yl |

TABLE 3-continued

Representative Compounds of Formula (I)

| ID No. | R¹ & R² taken together | (L¹)ₐ | R³ | (R⁴)ᵦ | (R⁸)ₑ |
|---|---|---|---|---|---|
| 660 | tetrahydro-pyran-4,4-diyl | pyrrolidin-3R-yl | C(O) | pyrrolidin-1-yl | b = 0 | 1-methyl-pyrazol-4-yl |
| 676 | tetrahydro-furan-3,3-diyl | pyrrolidin-3R-yl | C(O) | cyclopropyl | b = 0 | 1-methyl-pyrazol-4-yl |
| 677 | tetrahydro-furan-3,3-diyl | pyrrolidin-3R-yl | C(O) | 1-hydroxy-ethyl | b = 0 | 1-methyl-pyrazol-4-yl |
| 678 | tetrahydro-furan-3,3-diyl | pyrrolidin-3R-yl | C(O) | tetrahydro-furan-2R-yl | b = 0 | 1-methyl-pyrazol-4-yl |
| 679 | tetrahydro-furan-3,3-diyl | pyrrolidin-3S-yl | C(O) | pyrrolidin-1-yl | b = 0 | 1-methyl-pyrazol-4-yl |
| 694 | tetrahydro-pyran-4,4-diyl | azetidin-3-yl | C(O) | cyclopropyl | b = 0 | 1-methyl-pyrazol-4-yl |
| 695 | tetrahydro-pyran-4,4-diyl | azetidin-3-yl | C(O) | 1-hydroxy-ethyl | b = 0 | 1-methyl-pyrazol-4-yl |
| 696 | tetrahydro-pyran-4,4-diyl | azetidin-3-yl | C(O) | tetrahydro-furan-2R-yl | b = 0 | 1-methyl-pyrazol-4-yl |
| 697 | tetrahydro-pyran-4,4-diyl | azetidin-3-yl | C(O) | pyrrolidin-1-yl | b = 0 | 1-methyl-pyrazol-4-yl |
| 710 | tetrahydro-furan-3,3-diyl | azetidin-3-yl | C(O) | cyclopropyl | b = 0 | 1-methyl-pyrazol-4-yl |
| 711 | tetrahydro-furan-3,3-diyl | azetidin-3-yl | C(O) | 1-hydroxy-ethyl | b = 0 | 1-methyl-pyrazol-4-yl |
| 712 | tetrahydro-furan-3,3-diyl | azetidin-3-yl | C(O) | tetrahydro-furan-2R-yl | b = 0 | 1-methyl-pyrazol-4-yl |
| 713 | tetrahydro-furan-3,3-diyl | azetidin-3-yl | C(O) | pyrrolidin-1-yl | b = 0 | 1-methyl-pyrazol-4-yl |

TABLE 3-continued

Representative Compounds of Formula (I)

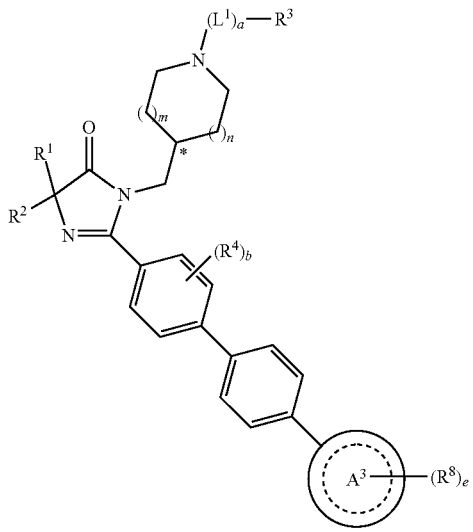

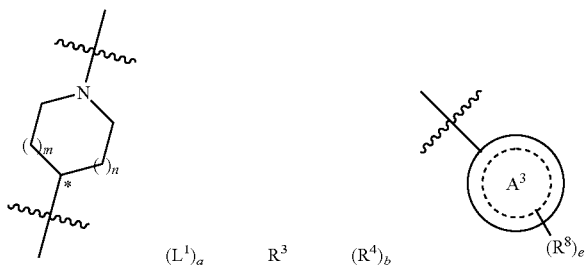

| ID No. | R¹ & R² taken together | $(L^1)_a$ | R³ | $(R^4)_b$ | $(R^8)_e$ |
|---|---|---|---|---|---|
| 725 | 1-(methoxy-carbonyl)-azetidin-3,3-diyl | pyrrolidin-3R-yl | C(O) | cyclopropyl | b = 0 | 1-methyl-pyrazol-4-yl |
| 726 | 1-(methoxy-carbonyl)-azetidin-3,3-diyl | pyrrolidin-3R-yl | C(O) | 1-hydroxy-ethyl | b = 0 | 1-methyl-pyrazol-4-yl |
| 727 | 1-(methoxy-carbonyl)-azetidin-3,3-diyl | pyrrolidin-3R-yl | C(O) | tetrahydro-furan-2R-yl | b = 0 | 1-methyl-pyrazol-4-yl |
| 759 | piperidin-4,4-diyl | azetidin-3-yl | C(O) | cyclopropyl | b = 0 | 1-methyl-pyrazol-4-yl |
| 767 | 1-(isopropyl-carbonyl)-piperidin-4,4-diyl | azetidin-3-yl | C(O) | cyclopropyl | b = 0 | 1-methyl-pyrazol-4-yl |
| 768 | 1-(dimethyl-amino-methyl-carbonyl)-piperidin-4,4-diyl | azetidin-3-yl | C(O) | cyclopropyl | b = 0 | 1-methyl-pyrazol-4-yl |
| 769 | 1-(methyl-sulfonyl)-piperidin-4,4-diyl | azetidin-3-yl | C(O) | cyclopropyl | b = 0 | 1-methyl-pyrazol-4-yl |
| 770 | 1-(cyclopropyl-carbonyl)-piperidin-4,4-diyl | azetidin-3-yl | C(O) | cyclopropyl | b = 0 | 1-methyl-pyrazol-4-yl |
| 771 | 1-(isopropyl)-piperidin-4,4-diyl | azetidin-3-yl | C(O) | cyclopropyl | b = 0 | 1-methyl-pyrazol-4-yl |

TABLE 3-continued

Representative Compounds of Formula (I)

| ID No. | R¹ & R² taken together | (L¹)ₐ | R³ | (R⁴)ᵦ | A³ (R⁸)ₑ |
|---|---|---|---|---|---|
| 772 | 1-(2-hydroxy-ethyl)-piperidin-4,4-diyl | azetidin-3-yl | C(O) | cyclopropyl | b = 0 | 1-methyl-pyrazol-4-yl |
| 785 | cyclopropyl | azetidin-3-yl | C(O) | 1-methyl-cyclopropyl | 2-methyl | 1-isobutyl-pyrazol-5-yl |
| 786 | cyclopropyl | azetidin-3-yl | C(O) | 1-methyl-cyclopropyl | 2-methyl | 1-cyclopropylmethyl-pyrazol-5-yl |
| 812 | cyclopropyl | piperidin-3S-yl | C(O) | cyclopropyl | b = 0 | 4-methyl-phenyl |
| 813 | cyclopropyl | piperidin-3S-yl | C(O) | cyclopropyl | b = 0 | 3-chlorophenyl |
| 815 | cyclopropyl | piperidin-3S-yl | C(O) | cyclopropyl | b = 0 | 1-methyl-pyrazol-4-yl |
| 820 | cyclopropyl | piperidin-3R-yl | C(O) | cyclopropyl | b = 0 | 3-chloro-phenyl |
| 821 | cyclopropyl | piperidin-3R-yl | C(O) | cyclopropyl | b = 0 | 4-methyl-phenyl |
| 823 | cyclopropyl | piperidin-3R-yl | C(O) | cyclopropyl | b = 0 | 1-methyl-pyrazol-4-yl |
| 882 | cyclopentyl | pyrrolidin-3R-yl | C(O) | cyclopropyl | 2-methyl | 5-methyl-oxadiazol-2-yl |
| 891 | 1-methoxy-carbonyl)-azetidin-3,3-diyl | pyrrolidin-3S-yl | SO₂ | methyl | b = 0 | 1-methyl-pyrazol-4-yl |
| 893 | tetrahydro-pyran-4,4-diyl | azetidin-3-yl | C(O) | trifluoro-methyl | b = 0 | 1-methyl-pyrazol-4-yl |
| 894 | tetrahydro-furan-3,3-diyl | pyrrolidin-3S-yl | C(O)O | methyl | b = 0 | 1-methyl-pyrazol-4-yl |
| 899 | tetrahydro-furan-3,3-diyl | azetidin-3-yl | C(O) | trifluoro-methyl | b = 0 | 1-methyl-pyrazol-4-yl |

TABLE 3-continued

Representative Compounds of Formula (I)

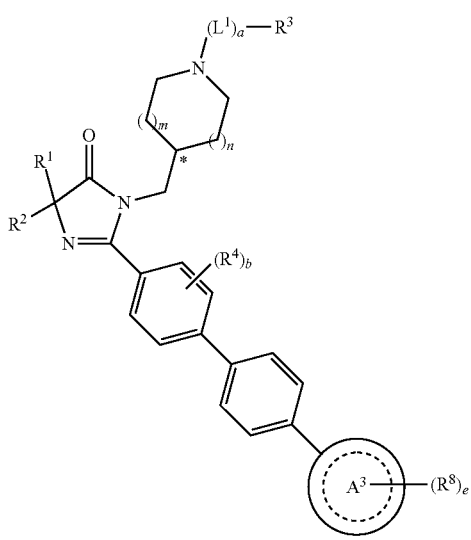

| ID No. | R¹ & R² taken together | (L¹)ₐ | R³ | (R⁴)ᵦ | (R⁸)ₑ |
|---|---|---|---|---|---|
| 901 | tetrahydro-furan-3,3-diyl | azetidin-3-yl | C(O) | thiazol-2-yl | b = 0 | 1-methyl-pyrazol-4-yl |
| 906 | 1-methoxy-carbonyl)-azetidin-3,3-diyl | pyrrolidin-3S-yl | C(O)O | methyl | b = 0 | 1-methyl-pyrazol-4-yl |
| 911 | tetrahydro-pyran-4,4-diyl | azetidin-3-yl | C(O) | thiazol-2-yl | b = 0 | 1-methyl-pyrazol-4-yl |
| 918 | tetrahydro-pyran-4,4-diyl | pyrrolidin-3S-yl | SO₂ | methyl | b = 0 | 1-methyl-pyrazol-4-yl |
| 919 | 1-methoxy-carbonyl)-azetidin-3,3-diyl | pyrrolidin-3R-yl | C(O) | trifluoro-methyl | b = 0 | 1-methyl-pyrazol-4-yl |
| 921 | tetrahydro-pyran-4,4-diyl | azetidin-3-yl | SO₂ | methyl | b = 0 | 1-methyl-pyrazol-4-yl |
| 924 | 1-methoxy-carbonyl)-azetidin-3,3-diyl | pyrrolidin-3S-yl | C(O) | pyrrolidin-1-yl | b = 0 | 1-methyl-pyrazol-4-yl |
| 927 | tetrahydro-furan-3,3-diyl | azetidin-3-yl | C(O)O | methyl | b = 0 | 1-methyl-pyrazol-4-yl |
| 929 | 1-methoxy-carbonyl)-azetidin-3,3-diyl | pyrrolidin-3R-yl | C(O) | thiazol-2-yl | b = 0 | 1-methyl-pyrazol-4-yl |

TABLE 3-continued

Representative Compounds of Formula (I)

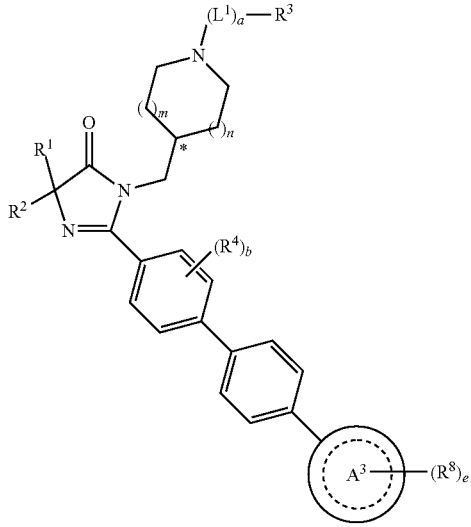

| ID No. | R¹ & R² taken together | (L¹)ₐ | R³ | (R⁴)ᵦ | (R⁸)ₑ |
|---|---|---|---|---|---|
| 936 | tetrahydro-pyran-4,4-diyl | azetidin-3-yl | C(O)O | methyl | b = 0 | 1-methyl-pyrazol-4-yl |
| 939 | tetrahydro-furan-3,3-diyl | pyrrolidin-3-yl | SO₂ | methyl | b = 0 | 1-methyl-pyrazol-4-yl |
| 940 | tetrahydro-furan-3,3-diyl | pyrrolidin-3-yl | C(O) | trifluoro-methyl | b = 0 | 1-methyl-pyrazol-4-yl |
| 943 | tetrahydro-furan-3,3-diyl | pyrrolidin-3-yl | C(O) | thiazol-2-yl | b = 0 | 1-methyl-pyrazol-4-yl |
| 948 | tetrahydro-pyran-4,4-diyl | pyrrolidin-3R-yl | C(O) | thiazol-2-yl | b = 0 | 1-methyl-pyrazol-4-yl |
| 950 | tetrahydro-furan-3,3-diyl | azetidin-3-yl | SO₂ | methyl | b = 0 | 1-methyl-pyrazol-4-yl |

TABLE 4

Representative Compounds of Formula (I)

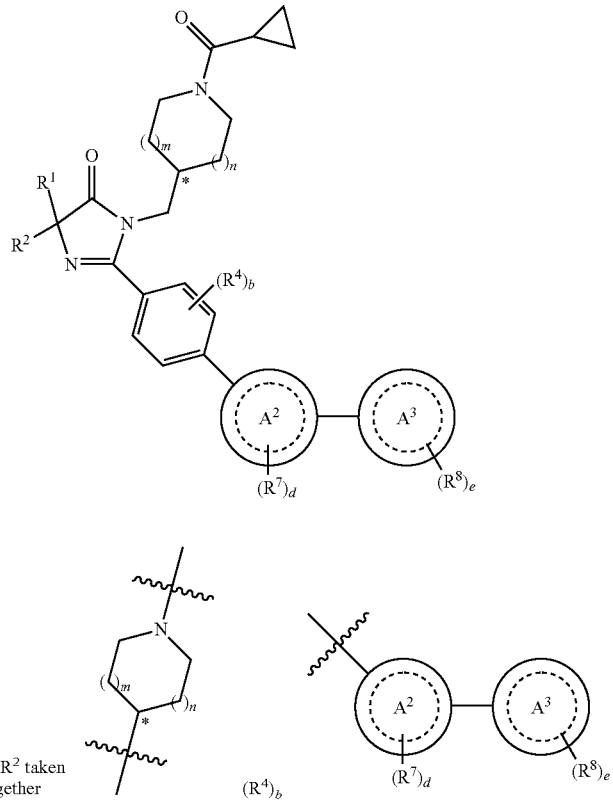

| ID No. | R¹ & R² taken together | (R⁴)_b | (R⁷)_d | (R⁸)_e |
|---|---|---|---|---|
| 44 | cyclopentyl | pyrrolidin-3R-yl | b = 0 | 6-(4-methyl-piperazin-1-yl)-piperidin-3-yl |
| 482 | cyclopropyl | azetidin-3-yl | b = 0 | 6-(pyrrolidin-1-yl)-pyridin-3-yl) |
| 509 | cyclopropyl | azetidin-3-yl | b = 0 | 6-(imidazol-1-yl)-pyridin-3-yl) |
| 526 | cyclopropyl | azetidin-3-yl | 2-fluoro | 6-(imidazol-1-yl)-pyridin-3-yl) |
| 806 | cyclopropyl | azetidin-3-yl | b = 0 | 6-(morpholin-4-yl)-pyridin-3-yl) |
| 828 | cyclopentyl | pyrrolidin-3R-yl | b = 0 | 2-(piperazin-1-yl)-pyridin-4-yl) |
| 829 | cyclopentyl | pyrrolidin-3R-yl | b = 0 | 2-(4-methylpiperazin-1-yl)-piperidin-4-yl |
| 838 | cyclopropyl | azetidin-3-yl | b = 0 | 1-(oxetan-3-yl)-pyrazol-4-yl |

In an embodiment, the present invention is directed to compounds of formula (I) as herein described provided that the compound of formula (I) is other than one or more of compounds independently selected from the group as listed in Table 5, below.

TABLE 5

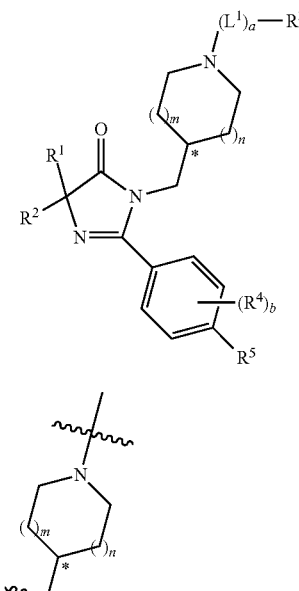

| ID No. | R¹ & R² taken together | | $(L^1)_a$ | R³ | $(R^4)_b$ | R⁵ |
|---|---|---|---|---|---|---|
| 8 | cyclopropyl | | piperidin-4-yl | C(O) | cyclopropyl | b = 0 | 4-(1-methyl-pyrazol-5-yl) |
| 9 | cyclopropyl | | piperidin-4-yl | C(O) | cyclopropyl | b = 0 | 4-(1-methyl-pyrazol-4-yl) |
| 13 | cyclopentyl | | pyrrolidin-3R-yl | C(O) | cyclopropyl | b = 0 | 4-(1-methyl-pyrazol-4-yl) |
| 32 | cyclopropyl | | piperidin-4-yl | C(O) | cyclopropyl | b = 0 | 4-(pyridin-4-yl) |
| 37 | cyclopropyl | | piperidin-4-yl | C(O) | cyclopropyl | b = 0 | 4-(benzoxazol-5-yl) |
| 42 | cyclopropyl | | azetidin-3-yl | C(O) | cyclopropyl | b = 0 | 4-(1-methyl-pyrazol-4-yl) |
| 44 | cyclopropyl | | pyrrolidin-3R-yl | C(O) | cyclopropyl | b = 0 | 6-(4-methyl-piperazin-1-yl)-pyridin-3-yl |
| 62 | cyclopropyl | | piperidin-4-yl | C(O) | cyclopropyl | b = 0 | 4-(1-methyl-pyrazol-5-yl)-phenyl |
| 91 | cyclopentyl | | pyrrolidin-3R-yl | C(O) | cyclopropyl | b = 0 | 4-(tetrazol-5-yl)-phenyl |
| 107 | cyclopropyl | | piperidin-4-yl | C(O) | cyclopropyl | b = 0 | 4-(4-trifluoro-methyl-phenyl) |
| 160 | 1-(methyl-carbonyl)-piperidin-4,4-diyl | | pyrrolidin-3R-yl | C(O) | cyclopropyl | b = 0 | 4-(1,2,3,4-trihydro-2-methyl-carbonyl-isoquinolin-6-yl) |
| 161 | 1-(methyl-carbonyl)-piperidin-4,4-diyl | | pyrrolidin-3R-yl | C(O) | cyclopropyl | b = 0 | 4-(1,2,3,4-4a,8a-hexahydro-2-methyl-carbonyl-isoquinolin-6-yl) |
| 189 | cyclopentyl | | pyrrolidin-3S-yl | SO₂ | pyrrolidin-1-yl | b = 0 | 4-(benzofuran-5-yl) |
| 776 | cyclopropyl | | azetidin-3-yl | C(O) | cyclopropyl | 2-methyl | 3-isopropylsulfonyl-phenyl |
| 784 | cyclopropyl | | azetidin-3-yl | C(O) | cyclopropyl | b = 0 | 6-isopropyl-pyridin-3-yl |
| 785 | cyclopropyl | | azetidin-3-yl | C(O) | 1-methyl-cyclopropyl | 2-methyl | 4-(1-isobutyl-pyrazol-5-yl)-phenyl |
| 788 | cyclopropyl | | azetidin-3-yl | C(O) | cyclopropyl | b = 0 | 1-oxetan-3-yl-indazol-5-yl |
| 789 | cyclopropyl | | azetidin-3-yl | C(O) | cyclopropyl | 2-fluoro | 1-oxetan-3-yl-indazol-5-yl |
| 791 | cyclopropyl | | azetidin-3-yl | C(O) | cyclopropyl | b = 0 | 4-methyl-7-beomo-quinolin-2-yl |

TABLE 5-continued

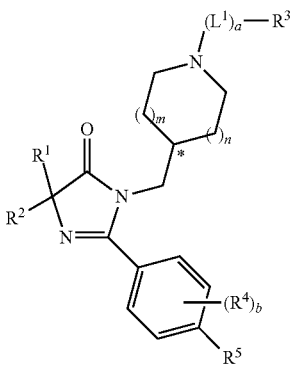

| ID No. | R¹ & R² taken together | (L¹)ₐ | R³ | (R⁴)ᵦ | R⁵ |
|---|---|---|---|---|---|
| 793 | cyclopropyl | azetidin-3-yl | C(O) | cyclopropyl | b = 0 | 3-methyl-[1,2,4]triazolo[4,3-a]pyridin-6-yl |
| 794 | cyclopropyl | azetidin-3-yl | C(O) | cyclopropyl | b = 0 | 5-(2-hydroxy-2-methyl-propyl)-pyrid-2-yl |
| 796 | cyclopropyl | azetidin-3-yl | C(O) | 1-hydroxy-cyclopropyl | 2-methyl | 1-methyl-indazol-5-yl |
| 797 | cyclopropyl | azetidin-3-yl | C(O) | cyclopropyl | b = 0 | 6-(2-hydroxy-2-methyl-propyl)-pyridin-3-yl |
| 800 | cyclopropyl | azetidin-3-yl | C(O) | cyclopropyl | b = 0 | 6-(1-cyano-cyclopropyl)-pyrid-3-yl |
| 801 | cyclopropyl | azetidin-3-yl | C(O) | cyclopropyl | b = 0 | 1,5-naphthyridin-3=yl |
| 802 | cyclopropyl | pyrrolidin-3R-yl | C(O) | cyclopropyl | b = 0 | 5-chloro-pyridin-3-yl |
| 805 | cyclopropyl | azetidin-3-yl | C(O) | pyridin-3-yl | 2-methyl | 1-methyl-indazol-5-yl |
| 806 | cyclopropyl | azetidin-3-yl | C(O) | cyclopropyl | b = 0 | 6-(morpholin-4-yl)pyridin-3-yl |
| 807 | cyclopropyl | azetidin-3-yl | C(O) | cyclopropyl | b = 0 | 1-isopropyl-indazol-5-yl |
| 809 | cyclopropyl | pyrrolidin-3R-yl | C(O) | cyclopropyl | b = 0 | 2-oxo-3,4-dihydro-quinolin-7-yl |
| 812 | cyclopropyl | piperidin-3S-yl | C(O) | cyclopropyl | b = 0 | 4-(4-methyl-phenyl)-phenyl |
| 813 | cyclopropyl | piperidin-3S-yl | C(O) | cyclopropyl | b = 0 | 4-(3-chloro-phenyl)-phenyl |
| 815 | cyclopropyl | piperidin-3S-yl | C(O) | cyclopropyl | b = 0 | 4-(1-methyl-pyrazol-4-yl)-phenyl |
| 816 | cyclopropyl | piperidin-3S-yl | C(O) | cyclopropyl | b = 0 | indazol-5-yl |
| 817 | cyclopropyl | piperidin-3S-yl | C(O) | cyclopropyl | b = 0 | benzothien-5-yl |
| 818 | cyclopropyl | piperidin-3S-yl | C(O) | cyclopropyl | b = 0 | benzofuran-5-yl |
| 819 | cyclopropyl | piperidin-3S-yl | C(O) | cyclopropyl | b = 0 | 1-methyl-indazol-5-yl |
| 821 | cyclopropyl | piperidin-3R-yl | C(O) | cyclopropyl | b = 0 | 4-(4-methyl-phenyl)-phenyl |
| 822 | cyclopentyl | pyrrolidin-3R-yl | C(O) | cyclopropyl | 2-methyl | 4-methyl-3,4-dihydro-2H-pyrido[3,2-b][1,4]oxazin-7-yl |

TABLE 5-continued

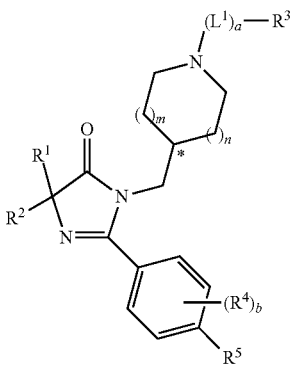

| ID No. | R¹ & R² taken together | $(L^1)_a$ | R³ | $(R^4)_b$ | R⁵ |
|---|---|---|---|---|---|
| 828 | cyclopentyl | pyrrolidin-3R-yl | C(O) | cyclopropyl | b = 0 | 2-(piperazin-1-yl)piperidin-4-yl |
| 829 | cyclopentyl | pyrrolidin-3R-yl | C(O) | cyclopropyl | b = 0 | 2-(4-methylpiperazin-1-yl)-pyridin-4-yl |
| 859 | cyclopropyl | piperidin-4-yl | C(O) | cyclopropyl | b = 0 | 4-trifluoromethyl-phenyl |
| 888 | tetrahydro-pyran-4,4-diyl | azetidin-3-yl | SO2 | methyl | b = 0 | benzofuran-5-yl |
| 891 | 1-methoxy-carbonyl)-azetidin-3,3-diyl | pyrrolidin-3S-yl | SO2 | methyl | b = 0 | 4-(1-methyl-pyrazol-4-yl)-phenyl |
| 892 | tetrahydro-furan-3,3-diyl | pyrrolidin-3R-yl | C(O) | thiazol-2-yl | b = 0 | 1-methyl-indazol-5-yl |
| 893 | tetrahydro-pyran-4,4-diyl | azetidin-3-yl | C(O) | trifluoro-methyl | b = 0 | 4-(1-methyl-pyrazol-4-yl)-phenyl |
| 894 | tetrahydro-furan-3,3-diyl | pyrrolidin-3S-yl | C(O)O | methyl | b = 0 | 4-(1-methyl-pyrazol-4-yl)-phenyl |
| 895 | tetrahydro-furan-3,3-diyl | azetidin-3-yl | C(O) | trifluoro-methyl | b = 0 | quinolin-7-yl |
| 896 | tetrahydro-furan-3,3-diyl | pyrrolidin-3-yl | SO2 | methyl | b = 0 | quinolin-7-yl |
| 897 | tetrahydro-furan-3,3-diyl | azetidin-3-yl | C(O) | trifluoro-methyl | b = 0 | benzofuran-5-yl |
| 898 | tetrahydro-furan-3,3-diyl | azetidin-3-yl | SO2 | methyl | b = 0 | benzofuran-5-yl |
| 899 | tetrahydro-furan-3,3-diyl | azetidin-3-yl | C(O) | trifluoro-methyl | b = 0 | 4-(1-methyl-pyrazol-4-yl)-phenyl |
| 900 | 1-methoxycarbonyl)-azetidin-3,3-diyl | pyrrolidin-3S-yl | SO2 | methyl | b = 0 | quinolin-7-yl |
| 901 | tetrahydro-furan-3,3-diyl | azetidin-3-yl | C(O) | thiazol-2-yl | b = 0 | 4-(1-methyl-pyrazol-4-yl)-phenyl |
| 902 | tetrahydro-pyran-3,3-diyl | azetidin-3-yl | SO2 | methyl | b = 0 | 1-methyl-indazol-5-yl |

TABLE 5-continued

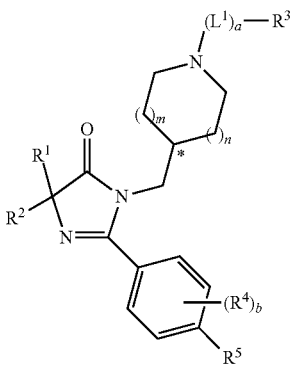

| ID No. | R¹ & R² taken together | $(L^1)_a$ | R³ | $(R^4)_b$ | R⁵ |
|---|---|---|---|---|---|
| 903 | tetrahydro-furan-3,3-diyl | azetidin-3-yl | C(O)O | methyl | b = 0 | quinolin-7-yl |
| 904 | tetrahydro-furan-3,3-diyl | azetidin-3-yl | C(O)O | methyl | b = 0 | benzofuran-5-yl |
| 905 | tetrahydro-furan-3,3-diyl | azetidin-3-yl | C(O)O | methyl | b = 0 | 1-methyl-indazol-5-yl |
| 906 | 1-methoxy-carbonyl)-azetidin-3,3-diyl | pyrrolidin-3S-yl | C(O)O | methyl | b = 0 | 4-(1-methyl-pyrazol-4-yl)-phenyl |
| 907 | 1-methoxy-carbonyl)-azetidin-3,3-diyl | pyrrolidin-3R-yl | C(O) | trifluoro-methyl | b = 0 | 1-methyl-indazol-5-yl |
| 908 | tetrahydro-pyran-4,4-diyl | azetidin-3-yl | C(O) | thiazol-2-yl | b = 0 | 1-methyl-indazol-5-yl |
| 909 | tetrahydro-furan-3,3-diyl | azetidin-3-yl | C(O) | thiazol-2-yl | b = 0 | 1-methyl-indazol-5-yl |
| 910 | tetrahydro-pyran-4,4-diyl | azetidin-3-yl | C(O) | trifluoro-methyl | b = 0 | quinolin-7-yl |
| 911 | tetrahydro-pyran-4,4-diyl | azetidin-3-yl | C(O) | thiazol-2-yl | b = 0 | 4-(1-methyl-pyrazol-4-yl)-phenyl |
| 912 | tetrahydro-pyran-4,4-diyl | azetidin-3-yl | SO2 | methyl | b = 0 | quinolin-7-yl |
| 913 | tetrahydro-pyran-4,4-diyl | pyrrolidin-3S-yl | SO2 | methyl | b = 0 | benzofuran-5-yl |
| 914 | tetrahydro-furan-3,3-diyl | pyrrolidin-3S-yl | SO2 | methyl | b = 0 | benzofuran-5-yl |
| 915 | tetrahydro-furan-3,3-diyl | pyrrolidin-3S-yl | C(O)O | methyl | b = 0 | 1-methyl-indazol-5-yl |
| 916 | 1-methoxy-carbonyl)-azetidin-3,3-diyl | pyrrolidin-3S-yl | C(O)O | methyl | b = 0 | 1-methyl-indazol-5-yl |
| 917 | 1-methoxy-carbonyl)-azetidin-3,3-diyl | pyrrolidin-3S-yl | SO2 | methyl | b = 0 | 1-methyl-indazol-5-yl |

TABLE 5-continued

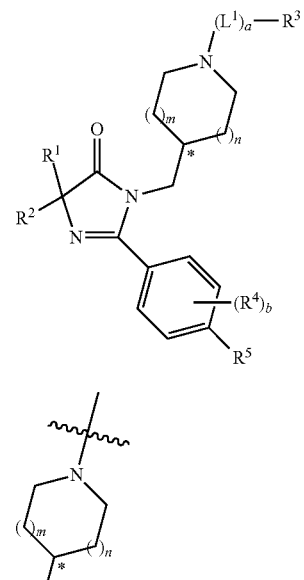

| ID No. | R¹ & R² taken together | | $(L^1)_a$ | $R^3$ | $(R^4)_b$ | $R^5$ |
|---|---|---|---|---|---|---|
| 918 | tetrahydro-pyran-4,4-diyl | pyrrolidin-3S-yl | SO2 | methyl | b = 0 | 4-(1-methyl-pyrazol-4-yl)-phenyl |
| 919 | 1-methoxy-carbonyl)-azetidin-3,3-diyl | pyrrolidin-3R-yl | C(O) | trifluoro-methyl | b = 0 | 4-(1-methyl-pyrazol-4-yl)-phenyl |
| 921 | tetrahydro-pyran-4,4-diyl | azetidin-3-yl | SO2 | methyl | b = 0 | 4-(1-methyl-pyrazol-4-yl)-phenyl |
| 923 | 1-methoxy-carbonyl)-azetidin-3,3-diyl | pyrrolidin-3R-yl | C(O) | thiazol-2-yl | b = 0 | 1-methyl-indazol-5-yl |
| 925 | cyclopropyl | piperidin-3R-yl | C(O) | cyclopropyl | b = 0 | 4-hydroxy-phenyl |
| 926 | tetrahydro-pyran-4,4-diyl | pyrrolidin-3S-yl | SO2 | methyl | b = 0 | 1-methyl-indazol-5-yl |
| 927 | tetrahydro-furan-3,3-diyl | azetidin-3-yl | C(O)O | methyl | b = 0 | 4-(1-methyl-pyrazol-4-yl)-phenyl |
| 928 | tetrahydro-pyran-4,4-diyl | azetidin-3-yl | C(O)O | methyl | b = 0 | benzofuran-5-yl |
| 929 | 1-methoxy-carbonyl)-azetidin-3,3-diyl | pyrrolidin-3R-yl | C(O) | thiazol-2-yl | b = 0 | 4-(1-methyl-pyrazol-4-yl)-phenyl |
| 930 | tetrahydro-furan-3,3-diyl | azetidin-3-yl | C(O) | thiazol-2-yl | b = 0 | quinolin-7-yl |
| 932 | tetrahydro-furan-3,3-diyl | azetidin-3-yl | C(O) | thiazol-2-yl | b = 0 | benzofuran-5-yl |
| 933 | tetrahydro-furan-3,3-diyl | pyrrolidin-3S-yl | SO2 | methyl | b = 0 | 1-methyl-indazol-5-yl |
| 934 | tetrahydro-furan-3,3-diyl | pyrrolidin-3-yl | C(O) | thiazol-2-yl | b = 0 | benzofuran-5-yl |
| 935 | tetrahydro-pyran-4,4-diyl | azetidin-3-yl | C(O) | trifluoro-methyl | b = 0 | 1-methyl-indazol-5-yl |
| 936 | tetrahydro-pyran-4,4-diyl | azetidin-3-yl | C(O)O | methyl | b = 0 | 4-(1-methyl-pyrazol-4-yl)-phenyl |

TABLE 5-continued

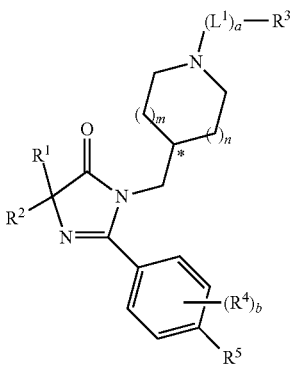

| ID No. | R¹ & R² taken together | $(L^1)_a$ | R³ | $(R^4)_b$ | R⁵ |
|---|---|---|---|---|---|
| 937 | tetrahydro-furan-3,3-diyl | azetidin-3-yl | C(O) | trifluoro-methyl | b = 0 | 1-methyl-indazol-5-yl |
| 939 | tetrahydro-furan-3,3-diyl | pyrrolidin-3-yl | SO2 | methyl | b = 0 | 4-(1-methyl-pyrazol-4-yl)-phenyl |
| 941 | tetrahydro-pyran-4,4-diyl | azetidin-3-yl | C(O)O | methyl | b = 0 | 1-methyl-indazol-5-yl |
| 942 | tetrahydro-furan-3,3-diyl | azetidin-3-yl | SO2 | methyl | b = 0 | quinolin-7-yl |
| 943 | tetrahydro-furan-3,3-diyl | pyrrolidin-3-yl | C(O) | thiazol-2-yl | b = 0 | 4-(1-methyl-pyrazol-4-yl)-phenyl |
| 944 | tetrahydro-furan-3,3-diyl | azetidin-3-yl | SO2 | methyl | b = 0 | 1-methyl-indazol-5-yl |
| 947 | tetrahydro-pyran-4,4-diyl | azetidin-3-yl | C(O) | thiazol-2-yl | b = 0 | quinolin-7-yl |
| 948 | tetrahydro-pyran-4,4-diyl | pyrrolidin-3R-yl | C(O) | thiazol-2-yl | b = 0 | 4-(1-methyl-pyrazol-4-yl)-phenyl |
| 949 | tetrahydro-pyran-4,4-diyl | azetidin-3-yl | C(O) | thiazol-2-yl | b = 0 | benzofuran-5-yl |
| 950 | tetrahydro-furan-3,3-diyl | azetidin-3-yl | SO2 | methyl | b = 0 | 4-(1-methyl-pyrazol-4-yl)-phenyl |
| 954 | tetrahydro-furan-3,3-diyl | pyrrolidin-3S-yl | C(O)O | methyl | b = 0 | benzofuran-5-yl |
| 956 | 1-(methoxy-carbonyl)-azetidin-3,3-diyl | pyrrolidin-3S-yl | SO2 | methyl | b = 0 | benzofuran-5-yl |
| 957 | 1-(methoxy-carbonyl)-azetidin-3,3-diyl | pyrrolidin-3R-yl | C(O) | thiazol-2-yl | b = 0 | benzofuran-5-yl |
| 958 | tetrahydro-pyran-4,4-diyl | pyrrolidin-3R-yl | C(O) | thiazol-2-yl | b = 0 | benzofuran-5-yl |
| 959 | tetrahydro-pyran-4,4-diyl | pyrrolidin-3R-yl | C(O) | thiazol-2-yl | b = 0 | 1-methyl-indazol-5-yl |

TABLE 5-continued

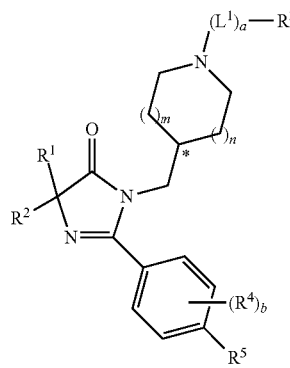

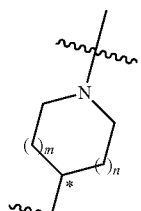

| ID No. | R¹ & R² taken together | (L¹)ₐ | R³ | (R⁴)_b | R⁵ |
|---|---|---|---|---|---|
| 960 | tetrahydro-pyran-4,4-diyl | pyrrolidin-3S-yl | SO2 | methyl | b = 0 | quinolin-7-yl |
| 961 | tetrahydro-pyran-4,4-diyl | azetidin-3-yl | C(O) | trifluoro-methyl | b = 0 | benzofuran-5-yl |

The present invention is further directed to intermediates in the synthesis of the compounds of formula (I), as described in more detail herein. In a preferred embodiment, the present invention is directed to compounds of formula (XVIII)

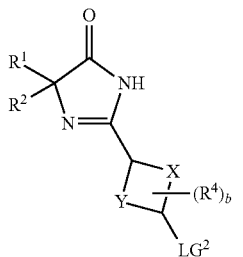

(XVIII)

wherein R¹, R², R⁴, b,

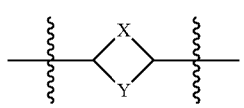

and LG² are as herein defined. In another preferred embodiment, the present invention is directed to compounds of formula (XXI)

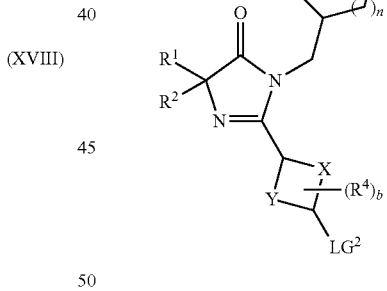

(XXI)

wherein R¹, R², R⁴, b, m, n,

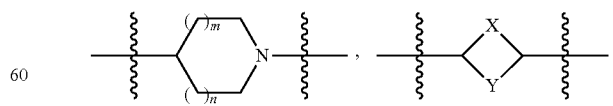

and LG² are as herein defined. In another preferred embodiment, the present invention is directed to compounds of formula (XXIII)

(XXIII)

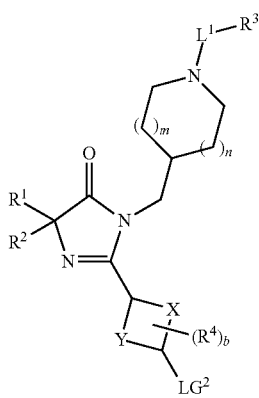

wherein $R^1$, $R^2$, $R^3$, $R^4$, $L^1$, b, m, n,

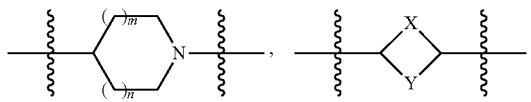

and $LG^2$ are as herein defined. In another preferred embodiment, the present invention is directed to compounds of formula (XXV)

(XXV)

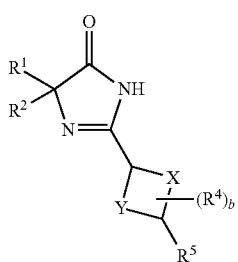

wherein $R^1$, $R^2$, $R^4$, $R^5$, b and

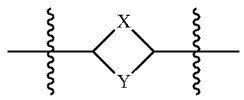

are as herein defined. In another preferred embodiment, the present invention is directed to compounds of formula (XXVII)

(XXVII)

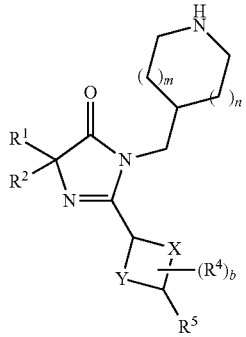

wherein $R^1$, $R^2$, $R^4$, $R^5$, b, m, n,

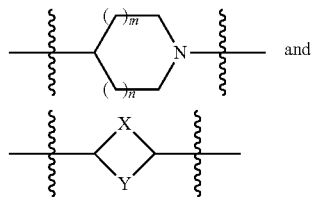

are as herein defined.

Definitions

As used herein, unless otherwise noted, the term "halogen" means chloro, bromo, fluoro, and iodo. Preferably, the halogen is bromo, chloro or fluoro.

As used herein, unless otherwise noted, the term "oxo" when used to define a substituent group means an oxygen atom which is bound to a chain or ring carbon atom through a double bond (i.e. =O).

As used herein, the term "$C_{X-Y}$alkyl" whether used alone or as part of a substituent group, means any straight and branched carbon chain composition of between X and Y carbon atoms. For example, "$C_{1-6}$alkyl" means any straight or branched carbon chain composition of between 1 and 6 carbon atoms, including, but not limited to, methyl, ethyl, propyl, isopropyl, butyl, isobutyl, sec-butyl, t-butyl, n-pentyl, n-hexyl, and the like.

One skilled in the art will recognize that the term "—($C_{X-Y}$alkyl)-" denotes any $C_{X-Y}$alkyl carbon chain as herein defined, wherein said $C_{X-Y}$alkyl chain is divalent and is bound through two points of attachment, preferably through two terminal carbon atoms. For example, "—($C_{1-4}$alkyl)-" includes, but is not limited to —$CH_2$—, —$CH_2CH_2$—, —$CH(CH_3)$—, —$CH_2CH_2CH_2$—, —$CH_2CH(CH_3)$—, —$CH_2CH_2CH_2CH_2$—, $CH_2CH(CH_3)CH_2$—, and the like.

As used herein, unless otherwise noted, the term "halogenated $C_{X-Y}$alkyl" means any $C_{X-Y}$alkyl group as defined above substituted with at least one halogen atom, preferably at least one fluoro atom. For example, "halogenated $C_{1-4}$alkyl" includes, but is not limited to, —$CF_3$, —$CCl_3$, —$CH_2I$, —$CH_2Br$, —$CH_2$—$CF_3$, —$CH_2$—$CCl_3$, —$CF_2$—$CF_2$—$CF_2$—$CF_3$, and the like. Similarly, as used herein, unless otherwise noted, the term "fluorinated $C_{X-Y}$alkyl" means any $C_{X-Y}$alkyl group as defined above substituted with at least one fluoro atom. For example, the term "fluorinated $C_{1-4}$alkyl" includes, but is not limited to —$CF_3$, —$CH_2$—$CF_3$, —$CF_2$—$CF_2$—$CF_2$—$CF_3$, and the like.

As used herein, unless otherwise noted, the term "hydroxy substituted $C_{X-Y}$alkyl" means $C_{X-Y}$alkyl group as defined above substituted with at least one hydroxy group. Preferably, the $C_{X-Y}$alkyl group is substituted with one hydroxy group. Preferably, the $C_{X-Y}$alkyl group is substituted with a hydroxy group at the terminal carbon. For example, the term "hydroxy substituted $C_{1-4}$alkyl" includes, but is not limited to, —CH$_2$(OH), —CH$_2$—CH$_2$(OH), —CH$_2$—CH(OH)—CH$_2$, and the like.

As used herein, the term "$C_{X-Y}$alkenyl" whether used alone or as part of a substituent group, means any straight and branched carbon chain composition of between X and Y carbon atoms comprising at least one unsaturated double bond. For example, "$C_{2-4}$alkyl" means any straight or branched carbon chain composition of between 2 and 4 carbon atoms, comprising at least one double bond. Suitably examples include, but are not limited to, —CH=CH$_2$, —CH$_2$—CH=CH$_2$, —CH=CH$_2$—CH$_3$, —CH$_2$—CH$_2$—CH=CH$_2$, —CH$_2$—CH=CH—CH$_3$, and the like.

As used herein, unless otherwise noted, "$C_{X-Y}$alkoxy" wherein X and Y are integers, denotes an oxygen ether radical of the above described straight or branched chain $C_{X-Y}$alkyl groups. For example, the term "$C_{1-4}$alkoxy" includes, but is not limited to methoxy, ethoxy, n-propoxy, sec-butoxy, t-butoxy, n-hexyloxy and the like.

As used herein, unless otherwise noted, the term "halogenated $C_{X-Y}$alkoxy" wherein X and Y are integers means any oxygen ether radical as defined above substituted with at least one halogen atom, preferably at least one fluoro atom. For example, the term "halogenated $C_{1-4}$alkoxy" includes, but is not limited to, —OCF$_3$, —OCCl$_3$, —OCH$_2$I, —OCH$_2$Br, —OCH$_2$—CF$_3$, —OCH$_2$—CCl$_3$, OF$_2$—CF$_2$—CF$_2$—CF$_3$, and the like. Similarly, as used herein, unless otherwise noted, the term "fluorinated $C_{X-Y}$alkoxy" means any oxygen ether radical as defined above substituted with at least one fluoro atom. For example, the term "fluorinated $C_{1-4}$alkoxy" includes, but is not limited to —OCF$_3$, —OCH$_2$—CF$_3$, —OCF$_2$—CF$_2$—CF$_2$—CF$_3$, and the like.

As used herein, unless otherwise noted, the term "$C_{X-Y}$cycloalkyl" wherein X and Y are integers means any stable saturated ring system comprising between X and Y carbon ring atoms. For example, the term "$C_{1-8}$cycloalkyl" means any stable 3 to 8-membered saturated ring structure, including cyclopropyl, cyclobutyl, cyclopentyl, cyclohexyl, cycloheptyl and cyclooctyl.

As used herein, unless otherwise noted, the term "benzo-fused $C_{X-Y}$cycloalkyl" wherein X and Y are integers, means any stable monocyclic, saturated ring structure comprising between X and Y carbon ring atoms, which saturated ring structure is benzo-fused. Suitable examples include 2,3-dihydro-1H-indenyl and 1,2,3,4-tetrahydro-naphthyl.

As used herein, unless otherwise noted, "aryl" means any carbocylic aromatic ring structure as phenyl, naphthyl, and the like. Preferably, the aryl is phenyl or naphthyl, more preferably phenyl.

As used herein, unless otherwise noted, "heteroaryl" denotes any five or six-membered monocyclic aromatic ring structure containing at least one heteroatom selected from the group consisting of O, N and S, optionally containing one to three additional heteroatoms independently selected from the group consisting of O, N and S; or any nine or ten-membered bicyclic aromatic ring structure containing at least one heteroatom selected from the group consisting of O, N and S, optionally containing one to four additional heteroatoms independently selected from the group consisting of O, N and S; and wherein the heteroaryl contains one of more S heteroatom(s), said S heteroatom(s) are each independently optionally substituted with one to two oxo groups. The heteroaryl group may be attached at any heteroatom or carbon atom of the ring such that the result is a stable structure.

Examples of suitable heteroaryl groups include, but are not limited to, pyrrolyl, furyl, thienyl, oxazolyl, imidazolyl, purazolyl, isoxazolyl, isothiazolyl, triazolyl, thiadiazolyl, tetrazolyl, pyridinyl, pyridazinyl, pyrimidinyl, pyrazinyl, pyranyl, furazanyl, indolizinyl, indolyl, isoindolinyl, indazolyl, benzofuranyl, benzothienyl, benzimidazolyl, benzthiazolyl, benzoxazolyl, purinyl, quinolizinyl, quinolinyl, isoquinolinyl, isothiazolyl, cinnolinyl, phthalazinyl, quinazolinyl, quinoxalinyl, naphthyridinyl, pteridinyl, pyrrolo[2,3-b]pyridinyl, pyrazolo[4,3-b]pyridinyl, [1,2,4]triazo[4,3-a]pyridinyl, and the like.

As used herein, unless otherwise noted, the term "5 to 6-membered heteroaryl" denotes any five or six membered monocyclic aromatic ring structure containing at least one heteroatom selected from the group consisting of O, N and S, optionally containing one to three additional heteroatoms independently selected from the group consisting of O, N and S; wherein the 5 to 6-membered heteroaryl contains one of more S heteroatom(s), said S heteroatom(s) are each independently optionally substituted with one to two oxo groups. The 5 to 6-membered heteroaryl may be attached at any heteroatom or carbon atom of the ring such that the result is a stable structure. Suitable examples include, but are not limited to, pyrrolyl, furyl, thienyl, oxazolyl, thiazolyl, imidazolyl, purazolyl, isoxazolyl, isothiazolyl, triazolyl, thiadiazolyl, tetrazolyl, pyridinyl, pyridazinyl, pyrimidinyl, pyrazinyl, pyranyl, furazanyl, and the like. Preferred 5 to 6-membered heteroaryl include one or more selected from the group consisting of pyrrolyl, furanyl, thienyl, oxazolyl, thiazolyl, imidazolyl, pyrazoly, triazolyl, tetrazolyl, pyridinyl, pyrimidinyl, pyrazonyl, and pyranyl.

As used herein, unless otherwise noted, the term "6-membered, nitrogen containing heteroaryl" denotes any six-membered monocyclic aromatic ring structure containing at least one N heteroatom, optionally containing one to three additional heteroatoms independently selected from the group consisting of O and N. The 6-membered heteroaryl may be attached at any heteroatom or carbon atom of the ring such that the result is a stable structure. Suitable examples include, but are not limited to, pyridinyl, pyridazinyl, pyrimidinyl, pyrazinyl, pyranyl, furazanyl, and the like.

As used herein, unless otherwise noted, the term "9 to 10-membered heteroaryl" denotes any nine or ten-membered bicyclic aromatic ring structure containing at least one heteroatom selected from the group consisting of O, N and S, optionally containing one to four additional heteroatoms independently selected from the group consisting of O, N and S; wherein the 9 to 10-membered heteroaryl contains one of more S heteroatom(s), said S heteroatom(s) are each independently optionally substituted with one to two oxo groups. The 9 to 10-membered heteroaryl may be attached at any heteroatom or carbon atom of the ring such that the result is a stable structure. Suitable examples include, but are not limited to, indolizinyl, indolyl, isoindolinyl, indazolyl, benzofuranyl, benzothienyl, benzimidazolyl, benzthiazolyl, benzoxazolyl, purinyl, quinolizinyl, quinolinyl, isoquinolinyl, isothiazolyl, cinnolinyl, phthalazinyl, quinazolinyl, quinoxalinyl, naphthyridinyl, pteridinyl, pyrrolo[2,3-b]pyridinyl, pyrazolo[4,3-b]pyridinyl, [1,2,4]triazo[4,3-a]pyridinyl, and the like.

As used herein, the term "heterocycyl" denotes any four to eight-membered monocyclic, saturated or partially unsaturated ring structure containing at least one heteroatom selected from the group consisting of O, N and S, optionally containing one to three additional heteroatoms independently selected from the group consisting of O, N and S; or a nine to ten-membered saturated, partially unsaturated or partially aromatic (e.g. benzo-fused) bicyclic ring system containing at least one heteroatom selected from the group consisting of 0, N and S, optionally containing one to four additional heteroatoms independently selected from the group consisting of O, N and S; and wherein the heterocyclcyl contains one of more S heteroatom(s), said S heteroatom(s) are each independently optionally substituted with one to two oxo groups. The heterocyclyl group may be attached at any heteroatom or carbon atom of the ring such that the result is a stable structure.

Suitably examples include, but are not limited to, pyrrolinyl, pyrrolidinyl, dioxalanyl, imidazolinyl, imidazolidinyl, pyrazolinyl, pyrazolidinyl, piperidinyl, 1,4-dioxanyl, morpholinyl, 1,4-dithianyl, thiomorpholinyl, piperazinyl, trithianyl, azepanyl, 1,4-diazepanyl, 1,4-oxazepanyl, indolinyl, isoindolinyl, chromenyl, 3,4-methylenedioxyphenyl, 2,3-dihydrobenzofuranyl, tetrahydro-furanyl, and the like. Preferred heterocycloalkyl groups include one or more selected from the group consisting of pyrrolidinyl, dioxalkanyl, imidazolidinyl, pyrazolinyl, pyrazolidinyl, piperidinyl, morpholinyl, piperazinyl, azepanyl, 1,4-diazepanyl, 1,4-oxazepanyl, indolinyl, 2,3-dihydro-furanyl and tetrahydrofuranyl.

As used herein, unless otherwise noted, the term "5 to 6-membered saturated heterocyclyl" denotes any 5 to 6-membered monocyclic, saturated ring structure containing at least one heteroatom selected from the group consisting of O, S and N, optionally containing one to three additional heteroatoms independently selected from the group consisting of O, S and N; and wherein the 5 to 6-membered saturated heterocyclyl contains one or more S heteroatom(s), said S heteroatom(s) are each independently, optionally substituted with one to two oxo groups. The 5 to 6-membered saturated heterocyclyl group may be attached at any heteroatom or carbon atom of the ring such that the result is a stable structure. Suitable examples include, but are not limited to Suitably examples include, but are not limited to, pyrrolidinyl, dioxolanyl, imidazolidinyl, pyrazolidinyl, piperidinyl, 1,4-dioxanyl, morpholinyl, 1,4-dithianyl, thiomorpholinyl, piperazinyl, azepanyl, 1,4-diazepanyl, 1,4-oxazapanyl, and the like. Preferably, the 5 to 6-membered saturated heterocyclyl include one or more selected from the group consisting of pyrrolidinyl, dioxolanyl, piperidinyl, 1,4-dioxanyl, morpholinyl, piperazinyl, azepanyl, 1,4-diazepanyl and 1,4-oxazapanyl.

As used herein, unless otherwise noted, the term "partially unsaturated heteroaryl" denotes any five to seven-membered monocyclic partially unsaturated ring structure containing at least one unsaturated (e.g. double) bond and further containing at least one heteroatom selected from the group consisting of O, N and S, optionally containing one to three additional heteroatoms independently selected from the group consisting of O, N and S; or a nine to elevenmembered partially unsaturated or partially aromatic (e.g. benzo-fused) bicyclic ring system containing at least one unsaturated (e.g. double) bond and further containing at least one heteroatom selected from the group consisting of O, N and S, optionally containing one to four additional heteroatoms independently selected from the group consisting of O, N and S; and wherein the partially unsaturated heterocyclyl contains one of more S heteroatom(s), said S heteroatom(s) are each independently optionally substituted with one to two oxo groups. The partially unsaturated heterocyclyl may be attached at any heteroatom or carbon atom of the ring such that the result is a stable structure. Suitably examples include, but are not limited to, indolinyl, isoindolinyl, 2,3-dihydrobenzofuranyl, 1,3-dihydroisobenzofuranyl, 2,3-dihydrobenzo[b]thienyl, 1,3-dihydrobenzo[c]thienyl, chromanyl, isochromanyl, 3,4-dihydro-quinolinyl, 1,2,3,4-tetrahydroquinolinyl, 1,2,3,4-tetrahydro-isoquinolinyl, 1,2,3,4,4a,8a-hexahydro-isoquinolinyl, 1,2-dihydro-indazolyl, 2,3-dihydro-benzo[1,4]dioxin-6-yl, 3,4-dihydro-pyrido[3,2-b][1,4]oxazin-7-yl, and the like.

When a particular group is "substituted" (e.g., $C_{X\text{-}Y}$alkyl, $C_{X\text{-}Y}$cycloalkyl, aryl, heteroaryl, heterocyclyl, etc.) that group may have one or more substituents, preferably from one to five substituents, more preferably from one to three substituents, most preferably from one to two substituents, independently selected from the list of substituents.

With reference to substituents, the term "independently" means that when more than one of such substituents is possible, such substituents may be the same or different from each other.

As used herein, the notation "*" denotes the presence of a stereogenic center.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Preferably, when the compound is present as an enantiomer, the enantiomer is present at an enantiomeric excess of greater than or equal to about 80%, more preferably, at an enantiomeric excess of greater than or equal to about 90%, more preferably still, at an enantiomeric excess of greater than or equal to about 95%, more preferably still, at an enantiomeric excess of greater than or equal to about 98%, most preferably, at an enantiomeric excess of greater than or equal to about 99%. Similarly, when the compound is present as a diastereomer, the diastereomer is present at an diastereomeric excess of greater than or equal to about 80%, more preferably, at an diastereomeric excess of greater than or equal to about 90%, more preferably still, at an diastereomeric excess of greater than or equal to about 95%, more preferably still, at an diastereomeric excess of greater than or equal to about 98%, most preferably, at an diastereomeric excess of greater than or equal to about 99%.

Furthermore, some of the crystalline forms for the compounds of the present invention may exist as polymorphs and as such are intended to be included in the present invention. In addition, some of the compounds of the present invention may form solvates with water (i.e., hydrates) or common organic solvents, and such solvates are also intended to be encompassed within the scope of this invention.

Furthermore, it is intended that within the scope of the present invention, any element, in particular when mentioned in relation to a compound of formula (I), shall comprise all isotopes and isotopic mixtures of said element, either naturally occurring or synthetically produced, either with natural abundance or in an isotopically enriched form. For example, a reference to hydrogen includes within its scope $^1$H, $^2$H (D), and $^3$H (T). Similarly, references to carbon and oxygen include within their scope respectively $^{12}$C, $^{13}$C and $^{14}$C and $^{16}$O and $^{18}$O. The isotopes may be radioactive or non-radioactive. Radiolabelled compounds of formula (I) may comprise a radioactive isotope selected from the group of $^3H$, $^{11}C$, $^{18}F$, $^{122}I$, $^{123}I$, $^{125}I$, $^{131}I$, $^{75}Br$, $^{77}Br$ and $^{82}Br$. Preferably, the radioactive isotope is selected from the group of $^3H$, IC and $^{18}F$.

Unless otherwise denoted through use of a "-" symbol, under standard nomenclature used throughout this disclosure, the terminal portion of the designated side chain is described first, followed by the adjacent functionality toward the point of attachment. Thus, for example, a "phenyl$C_1$-$C_6$alkylaminocarbonyl$C_1$-$C_6$alkyl" substituent refers to a group of the formula

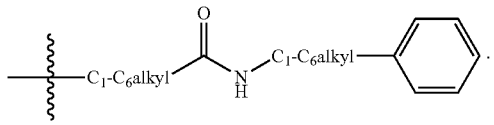

Abbreviations used in the specification, particularly the Schemes and Examples, are as follows:
AcOH or HOAc=Acetic acid
Boc or BOC=tert-Butoxycarbonyl
BSA=Bovine Serum Albumin
Cbz=Carboxybenzyl
CDI=Carbonyldiimidazole
CoA=Acetyl coenzyme-A
$Cu(OAc)_2$=Copper Acetate
DCE=Dichloroethane
DCM=Dichloromethane
DIPEA or DIEA=Diisopropylethylamine
DMAP=4-N,N-Dimethylaminopyridine
DME=Dimethyl Ether
DMF=N,N-Dimethylformamide
DMP or Dess-Martin=1,1,1-Triacetoxy-1,1-dihydro-1,2-benziodoxol-Periodinane 3(1H)-one
DMSO=Dimethylsulfoxide
DTT=Dithiothreiito
EDAC or EDCI=1-Ethyl-3-(3-dimethylaminopropyl) carbodiimide
EDTA=Ethylenediaminetetraacetic acid
$Et_3N$ or TEA=Triethylamine
$Et_2O$=Diethyl ether
EtOAc=Ethyl acetate
FASN=Fatty Acid Synthase
FBS Fetal Bovine Serum
HATU=o-(7-Azabenzotriazol-1-yl)-N,N,N',N'-tetramethyluronium hexafluorophosphate
HBTU=2-(1H-Benzotriazole-1-yl)-1,1,3,3-Tetramethyluronium hexafluorophosphate
hFASN=Human fatty Acid Synthase
HOBT or HOBt=1-Hydroxybenzotriazole
HPLC=High Performance Liquid Chromatography
LHMDS=Lithium Bis(trimethylsilyl)amide
MeCN=Acetonitrile
MeOH=Methanol
MEM=Eagle's minimum essential medium
Mesylate=Methanesulfonate
Mesyl=Methanesulfonyl
MOM=Methoxymethyl
MS-Cl=Mesyl Chloride
MTBE=Methyl tert-Butyl Ether
MTT=Methyl Thiazolyl Tetrazolium
NADPH Nicotinaride adenine dinucleotide phosphate
NMP=1-Methyl-2-pyrrolidinone
PBS=Phosphate-buffered Saline
Pd/C=Palladium on Carbon Catalyst
$Pd_2(OAc)_2$=Palladium(II)acetate
$Pd_2(dba)_2$=Bis(dibenzylidene acetone)dipalladium(0)
Pd(dppf)=Palladium diphenyiphosphinoferrocene
$Pd(PPh_3)_4$=Tetrakistriphenylphosphine palladium (0)
$PPh_3$=Triphenylphosphine
RT or rt=Room temperature
t-BOC or Boc=Tert-Butoxycarbonyl
t-BuOK=Potassium tert-Butoxide
TEA=Triethylamine
TFA=Trifluoroacetic Acid
THF=Tetrahydro-furan
THP Tetrahydro-pyranyl
TMOF=Trimethylorthoformate
TMS=Trimethylsilyl
TMS-Cl=Trimethylsilyl chloride
Tosylate=p-Toluenesulfonate
Tosyl=p-Toluenesulfonyl
Triflate or OTf=Trifluoromethanesulfonate
Triflyl=Trifluoromethanesulfonyl As used herein, unless otherwise noted, the term "isolated form" means that the compound is present in a form which is separate from any solid mixture with another compound(s), solvent system, or biological environment. In an embodiment of the present invention, the compound of formula (I) is present in an isolated form.

As used herein, unless otherwise noted, the term "substantially pure form" means that the mole percent of impurities in the isolated compound is less than about 5 mole percent, preferably less than about 2 mole percent, more preferably, less than about 0.5 mole percent, most preferably, less than about 0.1 mole percent. In an embodiment of the present invention, the compound of formula (I) is present as a substantially pure form.

As used herein, unless otherwise noted, the term "substantially free of a corresponding salt form(s)" when used to described the compound of formula (I) means that mole percent of the corresponding salt form(s) in the isolated base of formula (I) is less than about 5 mole percent, preferably less than about 2 mole percent, more preferably, less than about 0.5 mole percent, most preferably less than about 0.1 mole percent. In an embodiment of the present invention, the compound of formula (I) is present in a form which is substantially free of corresponding salt form(s).

As used herein, unless otherwise noted, the terms "treating", "treatment" and the like, include the management and care of a subject or patient (preferably mammal, more preferably human) for the purpose of combating a disease, condition, or disorder and includes the administration of a compound of the present invention to prevent the onset of the symptoms or complications, alleviate the symptoms or complications, or eliminate the disease, condition, or disorder.

As used herein, unless otherwise noted, the term "prevention" includes (a) reduction in the frequency of one or more symptoms; (b) reduction in the severity of one or more symptoms; (c) the delay or avoidance of the development of additional symptoms; (d) delay or avoidance of the development of the disorder or condition; and/or (f) the delay or avoidance of the progression of the disorder or condition.

One skilled in the art will recognize that when the present invention is directed to methods of prevention, a subject in need of thereof (i.e. a subject in need of prevention) includes any subject or patient (preferably a mammal, more preferably a human) who has experienced or exhibited at least one symptom of the disorder, disease, or condition to be prevented. Further, a subject in need thereof may additionally be a subject (preferably a mammal, more preferably a human) who has not exhibited any symptoms of the disorder, disease, or condition to be prevented, but who has been deemed by a physician, clinician, or other medical profession to be at risk of developing such disorder, disease, or condition. For example, the subject may be deemed at risk of developing a disorder, disease, or condition (and therefore in need of prevention or preventive treatment) as a consequence of the subject's medical history, including, but not limited to, family history, pre-disposition, co-existing (co-morbid) disorders or conditions, genetic testing, and the like.

The term "subject" as used herein, refers to an animal, preferably a mammal, most preferably a human, who has been the object of treatment, observation or experiment. Preferably, the subject has experienced and/or exhibited at least one symptom of the disease or disorder to be treated and/or prevented.

The term "therapeutically effective amount" as used herein, means an amount of active compound or pharmaceutical agent that elicits the biological or medicinal response in a tissue system, animal, or human that is being sought by a researcher, veterinarian, medical doctor, or other clinician, which response includes alleviation of the symptoms of the disease or disorder being treated.

As used herein, the term "composition" is encompasses a product comprising, consisting of and/or consisting essentially of the specified ingredients in the specified amounts, as well as any product that results, directly or indirectly, from combinations of the specified ingredients in the specified amounts.

As more extensively provided in this written description, terms such as "reacting" and "reacted" are used herein in reference to a chemical entity that is any one of: (a) the actually recited form of such chemical entity and (b) any of the forms of such chemical entity in the medium in which the compound is being considered when named.

One skilled in the art will recognize that, where not otherwise specified, the reaction step(s) is performed under suitable conditions, according to known methods, to provide the desired product. One skilled in the art will further recognize that, in the specification and claims as presented herein, when a reagent or reagent class/type (e.g., base, solvent, etc.) is recited in more than one step of a process, the individual reagents are independently selected for each reaction step and may be the same of different from each other. For example when two steps of a process recite an organic or inorganic base as a reagent, the organic or inorganic base selected for the first step may be the same or different than the organic or inorganic base of the second step. Further, one skilled in the art will recognize that when a reaction step of the present invention may be carried out in a variety of solvents or solvent systems, said reaction step may also be carried out in a mixture of the suitable solvents or solvent systems.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

To provide a more concise description, some of the quantitative expressions herein are recited as a range from about amount X to about amount Y. It is understood that when a range is recited, the range is not limited to the recited upper and lower bounds, but rather includes the full range from about amount X through about amount Y, or any amount or range therein.

Examples of suitable solvents, bases, reaction temperatures, and other reaction parameters and components are provided in the detailed descriptions which follow herein.

One skilled in the art will recognize that the listing of said examples is not intended, and should not be construed, as limiting in any way the invention set forth in the claims which follow thereafter. One skilled in the art will further recognize that when a reaction step of the present invention may be carried out in a variety of solvents or solvent systems, such reaction step may also be carried out in a mixture of the suitable solvents or solvent systems.

As used herein, unless otherwise noted, the term "aprotic solvent" means any solvent that does not yield a proton. Suitable examples include, but are not limited to DMF, 1,4-dioxane, THF, acetonitrile, pyridine, dichloroethane, dichloromethane, MTBE, toluene, acetone, and the like.

As used herein, unless otherwise noted, the term "leaving group" means a charged or uncharged atom or group which departs during a substitution or displacement reaction. Suitable examples include, but are not limited to, Br, Cl, I, mesylate, tosylate, triflate, and the like.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

As used herein, unless otherwise noted, the term "nitrogen protecting group" means a group which may be attached to a nitrogen atom to protect said nitrogen atom from participating in a reaction and which may be readily removed following the reaction. Suitable nitrogen protecting groups include, but are not limited to carbamates—groups of the formula —C(O)O—R wherein R is for example methyl, ethyl, t-butyl, benzyl, phenylethyl, $CH_2$=CH—$CH_2$—, and the like; amides—groups of the formula —C(O)—R' wherein R' is for example methyl, phenyl, trifluoromethyl, and the like; N-sulfonyl derivatives—groups of the formula —$SO_2$—R" wherein R" is for example tolyl, phenyl, trifluoromethyl, 2,2,5,7,8-pentamethylchroman-6-yl-, 2,3,6-trimethyl-4-methoxybenzene, and the like. Other suitable nitrogen protecting groups may be found in texts such as T. W. Greene & P. G. M. Wuts, *Protective Groups in Organic Synthesis*, John Wiley & Sons, 1991.

As used herein, unless otherwise noted, the term "oxygen protecting group" means a group which may be attached to an oxygen atom to protect such oxygen atom from participating in a reaction and which may be readily removed following the reaction. Suitable oxygen protecting groups include, but are not limited to, acetyl, benzoyl, t-butyl-dimethylsilyl, trimethylsilyl (TMS), methoxymethyl (MOM), tetrahydro-pyranyl (THP), and the like. Other suitable oxygen protecting groups may be found in texts such as T. W. Greene & P. G. M. Wuts, *Protective Groups in Organic Synthesis*, John Wiley & Sons, 1991.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as, (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

Additionally, chiral HPLC against a standard may be used to determine percent enantiomeric excess (% ee). The enantiomeric excess may be calculated as follows

[(Rmoles−Smoles)/(Rmoles+Smoles)]×100% where Rmoles and Smoles are the R and S mole fractions in the mixture such that Rmoles+Smoles=1. The enantiomeric excess may alternatively be calculated from the specific rotations of the desired enantiomer and the prepared mixture as follows:

ee=([α−obs]/[α−max])×100.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" encompasses the treatment of the various disorders described with the compound specifically disclosed or with a compound that may not be specifically disclosed, but converts to the specified compound in vivo after administration to the patient. Conventional procedures for the selection and preparation of suitable prodrug derivatives are described, for example, in *Design of Prodrugs*, ed. H. Bundgaard, Elsevier, 1985.

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts that may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid, or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include, but are not limited to, the following: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide, and valerate.

Representative acids that may be used in the preparation of pharmaceutically acceptable salts include, but are not limited to, the following: acids including acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hipuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinc acid, nitric acid, oleic acid, orotic acid, oxalic acid, palmitic acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid, and undecylenic acid.

Representative bases which may be used in the preparation of pharmaceutically acceptable salts include, but are not limited to, the following: bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine, and zinc hydroxide.

General Synthetic Schemes

Compounds of formula (I) may be prepared according to the process outlined in Scheme 1, below.

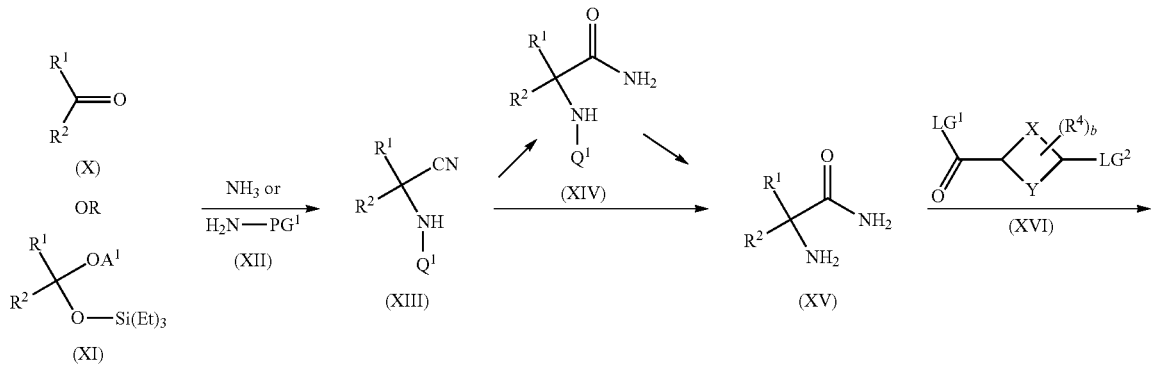

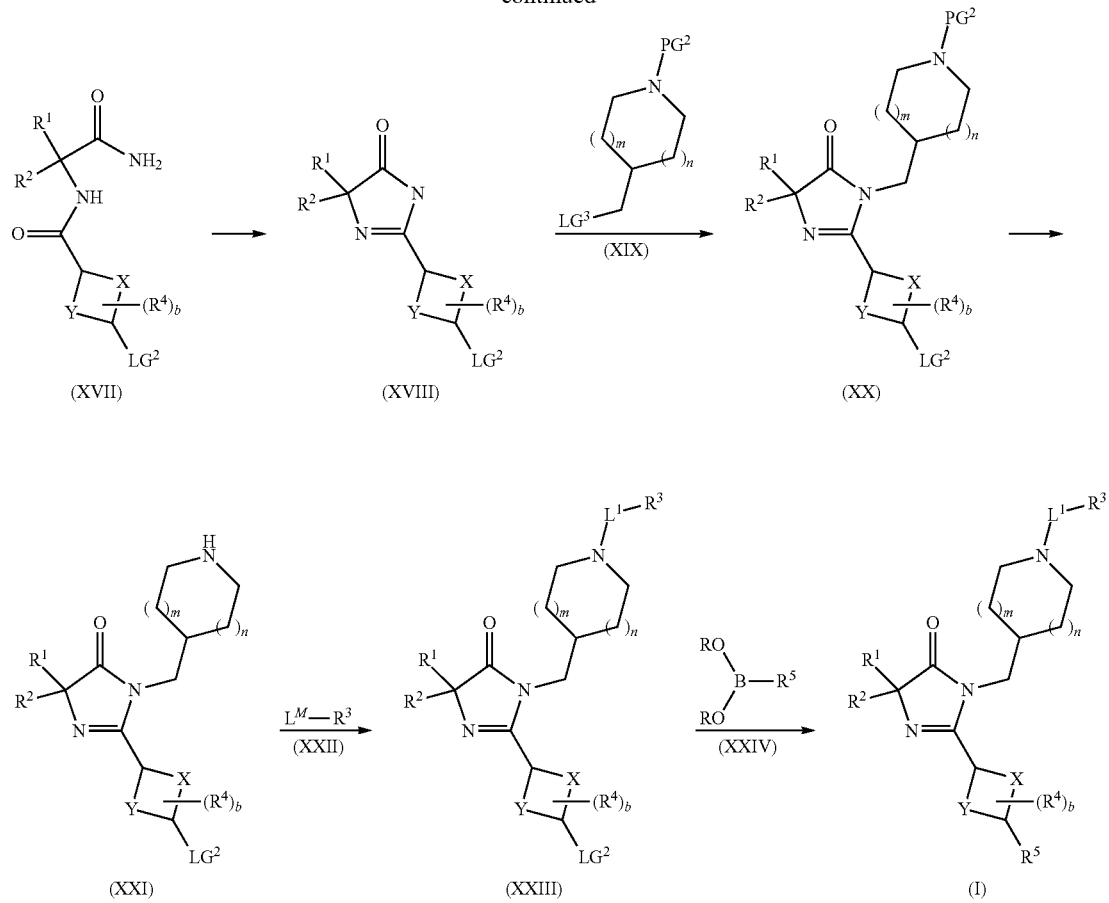

Accordingly, a suitably substituted compound of formula (X), a known compound or compound prepared by known methods, is reacted with NH₃ or with a suitably substituted compound of formula (XII), wherein PG¹ is a suitably selected nitrogen protecting group such as Boc, Cbz, benzyl, 1-phenethyl, and the like; in the presence of a suitably selected source of cyanide, such as KCN, NaCN, TMS-CN, and the like; in a suitably selected solvent or mixture of solvents such as methanol, ethanol, water, and the like; to yield the corresponding compound of formula (XIII), wherein Q¹ is hydrogen or PG¹, respectively.

Alternatively, a suitably substituted compound of formula (XI), wherein A¹ is $C_{1-2}$alkyl, a known compound or compound prepared by known methods, is reacted with NH₃ or a suitably substituted compound of formula (XII), wherein PG¹ is a suitably selected nitrogen protecting group such as Boc, Cbz, benzyl, 1-phenylethyl, and the like; in the presence of a suitably selected source of cyanide, such as TMS-CN, and the like; in a suitably selected solvent or mixture of solvents such as glacial HOAc, and the like; to yield the corresponding compound of formula (XIII), wherein Q¹ is hydrogen or PG¹, respectively.

The compound of formula (XII) is reacted to yield the corresponding compound of formula (XV), through a one-step or two step reaction.

Where the compound of formula (XIII) Q¹ is hydrogen, the compound of formula (XIII) is reacted with hydrogen peroxide, in the presence of a suitably selected inorganic base, such as K₂CO₃, Na₂CO₃, and the like; in a suitably selected solvent, such as, DMSO, DMF, NMP, and the like; to yield the corresponding compound of formula (XV). Alternatively, the compound of formula (XII) when Q¹ is hydrogen is reacted with a suitably selected acid, such as, conc. aq. H₂SO₄, and the like; in a suitably selected solvent such as DCM, and the like; to yield the corresponding compound of formula (XV).

Where the compound of formula (XIII) having Q¹ is PG¹, the compound of formula (XII) is reacted with is reacted with hydrogen peroxide in the presence of a suitably selected inorganic base, such as, K₂CO₃, Na₂CO₃, and the like; in a suitably selected solvent, such as, DMSO, DMF, NMP, and the like; to yield the corresponding compound of formula (XIV), where Q¹ is PG¹. Alternatively, when the compound of formula (XIII) where Q¹ is PG¹ is reacted with a suitably selected acid, such as, conc. aq. H₂SO₄, and the like; in a suitably selected solvent, such as DCM, and the like; to yield the corresponding compound of formula (XIV) where Q¹ is PG¹. The compound of formula (XIV) is then de-protected according to known methods to remove the PG¹ group and yield the corresponding compound of formula (XV). For example, wherein PG¹ is benzyl, the compound of formula (XIV) is de-protected by reacting with hydrogen in the presence of a suitable selected catalyst such as Pd/C, and the like.

The compound of formula (XV) is reacted with a suitably substituted compound of formula (XVI), wherein LG¹ is a suitably selected leaving group such as Cl, Br, OH, and the like, and wherein LG² is a suitably selected leaving group such as Cl, Br, OH, triflate, B(OH)₂, B(OC$_{1-2}$alkyl)₂,

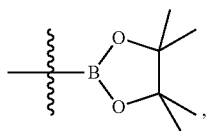 [SMILES: *B1OC(C)(C)C(C)(C)O1]

and the like, a known compound or compound prepared by known methods; to yield the corresponding compound of formula (XVII).

More particularly, wherein $LG^1$ is Cl, Br, and the like, the compound of formula (XV) is reacted with the compound of formula (XVI), in the presence of a suitably selected organic base such as pyridine, TEA, DIPEA, and the like; optionally in the presence of DMAP, and the like; in a suitably selected solvent such as DCM, DCE, THF, and the like; to yield the corresponding compound of formula (XVII). Alternatively, wherein $LG^1$ is OH, and the like, the compound of formula (XV) is reacted with the compound of formula (XVI), in the presence of a suitably selected coupling reagent such as HATU, HBTU, CDI, EDAC, and the like, in the presence of a suitably selected organic base such as pyridine, TEA, DIPEA, and the like; in a suitably selected organic solvent such as NMP, DMF, DCM, DCE, and the like, to yield the corresponding compound of formula (XVII).

The compound of formula (XVII) is reacted (to effect ring closure) with a suitably selected base such as t-BuOK, NaOH, $NaOCH_3$, LHMDS, and the like; in a suitably selected organic solvent or mixture of solvents such as methanol, ethanol, water, 1,4-dioxane, and the like, and wherein the base in LHMDS, in a suitably selected organic solvent such as THF, and the like; to yield the corresponding compound of formula (XVIII).

The compound of formula (XVIII) is reacted with a suitably substituted compound of formula (XIX), wherein $PG^2$ is a suitably selected nitrogen protecting group such as Boc, benzyl, Cbz, benzoyl, and the like, and wherein $LG^3$ is a suitably selected leaving group such as Br, I, Cl, mesylate, tosylate, triflate, and the like, a known compound or compound prepared by known methods; in the presence of a suitably selected base such as $K_2CO_3$, $Na_2CO_3$, NaH, and the like; in a suitably selected solvent such as DMF, DMP, THF, 1,4-doxane, and the like; to yield the corresponding compound of formula (XX).

The compound of formula (XX) is then de-protected according to known methods to yield the corresponding compound of formula (XXI). For example, wherein $PG^2$ is Boc, the compound of formula (XXI) is de-protected by reacting with a suitably selected acid, in a suitably selected organic solvent, for example reacting with HCl in 1,4-dioxane, or reacting with TFA in DCM.

The compound of formula (XXI) is reacted with a suitably substituted compound of formula (XXII), a known compound or compound prepared by known methods, to yield the corresponding compound of formula (XXIII). More particularly, the compound of formula (XXI) is reacted with (a) a compound of formula (XXII), wherein $L^M$ is selected from the group consisting of O=C=N($R^L$)— and S=C=N($R^L$)—; in a suitably selected organic solvent such as DCM, DCE, THF, and the like, to yield the corresponding compound of formula (XXIII) wherein $L^1$ is —C(O)—N($R^L$)— or —C(S)—N($R^L$)—, respectively;

or (b) a compound of formula (XXII), wherein $L^M$ is selected from the group consisting of Cl—C(O)—N($R^L$)— and Cl—C(S)—N($R^L$)—; in the presence of a suitably selected organic base such as pyridine, TEA, DIPEA, and the like; optionally in the presence of DMAP, and the like; in a suitably selected solvent such as DCM, DCE, THF, and the like;

or (c) a compound of formula (XXII), wherein $L^M$ is selected from the group consisting of $LG^4$-C(O)—, $LG^4$-C(S)—, $LG^4$-$SO_2$— and $LG^4$-$SO_2$—N($R^L$)—, wherein $LG^4$ is a suitably selected leaving group such as Cl, Br, and the like; in the presence of a suitably selected organic base such as pyridine, TEA, DIPEA, and the like; optionally in the presence of DMAP, and the like; in a suitably selected solvent such as DCM, DCE, THF, and the like;

or (d) a compound of formula (XXII), wherein $L^M$ is selected from the group consisting of $LG^4$-C(O)—, $LG^4$-C(S)—, $LG^4$-$SO_2$— and $LG^4$-$SO_2$—N($R^L$)—, wherein $LG^4$ is a suitably selected leaving group such as OH, and the like, in the presence of a suitably selected coupling reagent such as HATU, HBTU, CDI, EDAC, and the like, in the presence of a suitably selected organic base such as pyridine, TEA, DIPEA, and the like; in a suitably selected organic solvent such as NMP, DMF, DCM, DCE, and the like;

to yield the corresponding compound of formula (XXIII).

The compound of formula (XXIII) is reacted with a suitably substituted compound of formula (XXIV), wherein the two R groups are each H, are each the same $C_{1-2}$alkyl or are taken together as —C($CH_3$)$_2$—C($CH_3$)$_2$— to form a ring (i.e. to form the

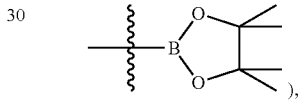

a known compound or compound prepared by known methods, under Suzuki coupling conditions, more particularly, in the presence of a suitably selected catalysts or catalyst system, such as Pd(PPh$_3$)$_4$, Pd$_2$(dba)$_3$, Pd(dppf), a mixture of Pd(OAc)$_2$ and PPh$_3$, and the like; in the presence of a suitably selected inorganic base such as $K_2CO_3$, $Cs_2CO_3$, $Na_2CO_3$, and the like; in a suitably selected solvent such as DME, 1,4-dioxane, and the like, preferably mixed with water; to yield the corresponding compound of formula (I).

Alternatively, wherein on the compound of formula (XXIII), $LG^2$ is OH, the compound of formula (XXIII) may be reacted with triflic anhydride, in the presence of a suitably selected base such as TEA, pyridine, and the like, in a suitably selected solvent such as DCM, DCE, and the like; to convert the $LG^2$ leaving group from OH to triflate; and then reacting the resulting compound with a suitably substituted compound of formula (XXIV), as described above; to yield the corresponding compound of formula (I).

One skilled in the art will recognize that the $R^5$ substituent group may alternatively be incorporated into the desired compound of formula (I) by reacting a compound of formula (XXIII), wherein the LG$^2$ group is replaced with a group of the formula —B(OR)$_2$ (wherein the two R groups are each H, are each the same $C_{1-2}$alkyl or are taken together as —C(CH$_3$)$_2$—C(CH$_3$)$_2$— to form a ring (i.e., to form the

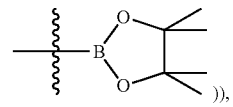

with a suitably substituted compound of formula (XXIV), wherein the —B(OR)$_2$ substitutent is replaced with a suitably selected leaving group, such as Cl, Br, triflate, and the like, under Suzuki coupling conditions, more particularly, in the presence of a suitably selected catalysts or catalyst system, such as Pd(PPh$_3$)$_4$, Pd$_2$(dba)$_3$, Pd(dppf), a mixture of Pd(OAc)$_2$ and PPh$_3$, and the like; in the presence of a suitably selected inorganic base, such as K$_2$CO$_3$, Cs$_2$CO$_3$, Na$_2$CO$_3$, and the like; in a suitably selected solvent, such as DME, 1,4-dioxane, and the like, preferably mixed with water.

Compounds of formula (I) may alternatively be prepared according to the process as outlined in Scheme 2, below.

Scheme 2

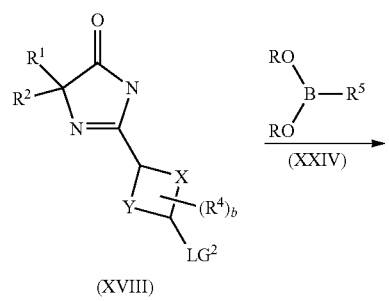

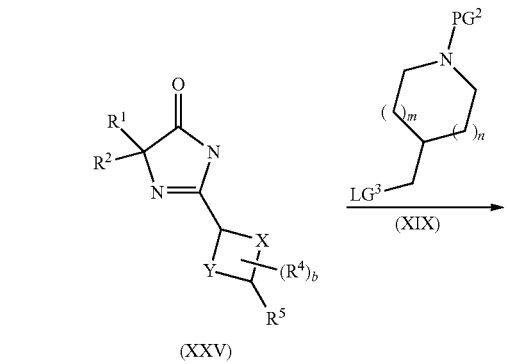

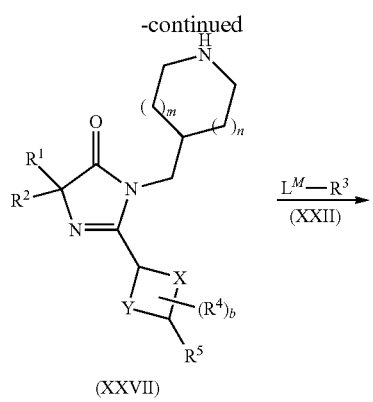

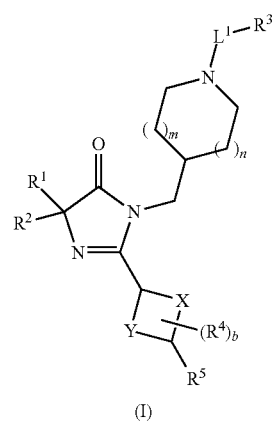

Accordingly, a suitably substituted compound of formula (XVII), prepared for example as outlined in Scheme 1 above, is reacted with a suitably substituted compound of formula (XXIV), wherein the two R groups are each H, are each the same C$_{1-2}$alkyl or are taken together as —C(CH$_3$)$_2$—C(CH$_3$)$_2$— to form a ring (i.e. to form the

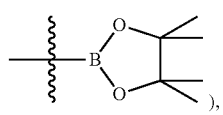

a known compound or compound prepared by known methods, under Suzuki coupling conditions, more particularly, in the presence of a suitably selected catalysts or catalyst system, such as Pd(PPh$_3$)$_4$, Pd$_2$(dba)$_3$, Pd(dppf), a mixture of Pd(OAc)$_2$ and PPh$_3$, and the like; in the presence of a suitably selected inorganic base, such as K$_2$CO$_3$, Cs$_2$CO$_3$, Na$_2$CO$_3$, and the like; in a suitably selected solvent, such as DME, 1,4-dioxane, and the like, preferably mixed with water; to yield the corresponding compound of formula (XV).

The compound of formula (XV) is reacted with a suitably substituted compound of formula (XIX), wherein PG$^2$ is a suitably selected nitrogen protecting group, such as Boc, benzyl, Cbz, benzoyl, and the like, and wherein $LG^3$ is a suitably selected leaving group such as Br, I, Cl, mesylate, tosylate, triflate, and the like, a known compound or compound prepared by known methods; in the presence of a suitably selected base, such as $K_2CO_3$, $Na_2CO_3$, NaH, and the like; in a suitably selected solvent, such as DMF, DMP, THF, 1,4-doxane, and the like; to yield the corresponding compound of formula (XXVI).

The compound of formula (XXVI) is de-protected according to known methods to yield the corresponding compound of formula (XVII). For example, wherein $PG^2$ is Boc, the compound of formula (XVI) is de-protected by reacting with a suitably selected acid, in a suitably selected organic solvent, for example reacting with HCl in 1,4-dioxane, or reacting with TFA in DCM.

The compound of formula (XVII) is then further reacted with a suitably substituted compound of formula (XXII), a known compound or compound prepared by known methods, as outlined in more detail in Scheme 1 above; to yield the corresponding compound of formula (I).

Compounds of formula (I) may alternatively be prepared according to the process as outlined in Scheme 3, below.

Scheme 3

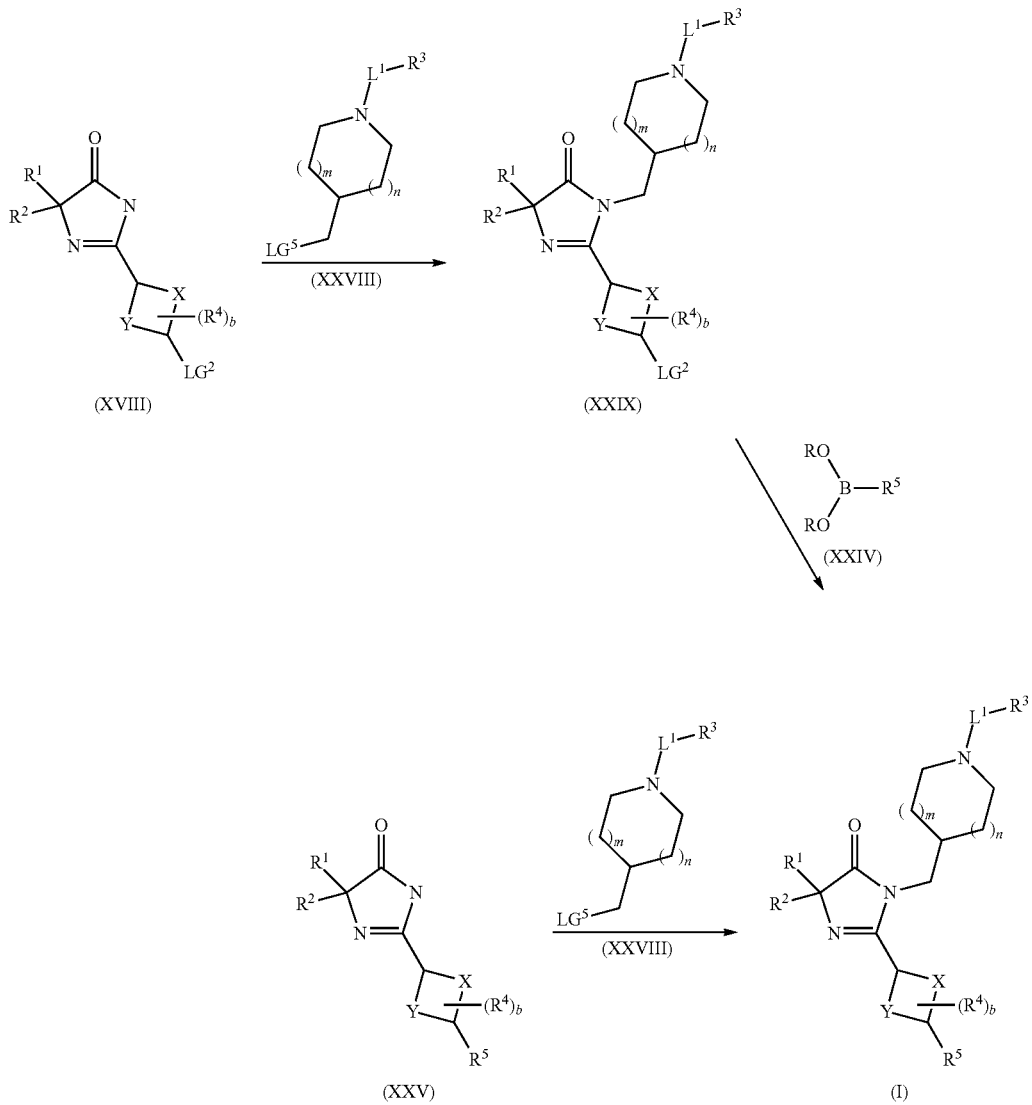

Accordingly, a suitably substituted compound of formula (XVIII), prepared for example as outlined in Scheme 1 above, is reacted with a suitably substituted compound of formula (XXVIII), wherein $LG^5$ is a suitably selected leaving group, such as Cl, Br, I, mesylate, tosylate triflate, and the like, a known compound or compound prepared as described herein; in the presence of a suitably selected base, such as $K_2CO_3$, $Na_2CO_3$, NaH, and the like; in a suitably selected solvent, such as DMF, DMP, THF, 1,4-doxane, and the like; to yield the corresponding compound of formula (XXIX).

The compound of formula (XXIX) is reacted with a suitably substituted compound of formula (XXIV), wherein the two R groups are each H, are each the same $C_{1-2}$alkyl or are taken together as $—C(CH_3)_2—C(CH_3)_2—$ to form a ring (i.e. to form the

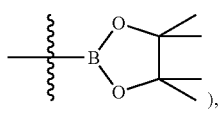

a known compound or compound prepared by known methods, under Suzuki coupling conditions, more particularly, in the presence of a suitably selected catalysts or catalyst system, such as Pd(PPh$_3$)$_4$, Pd$_2$(dba)$_3$, Pd(dppf), a mixture of Pd(OAc)$_2$ and PPh$_3$, and the like; in the presence of a suitably selected inorganic base, such as K$_2$CO$_3$, Cs$_2$CO$_3$, Na$_2$CO$_3$, and the like; in a suitably selected solvent, such as DME, 1,4-dioxane, and the like, preferably mixed with water; to yield the corresponding compound of formula (I).

Alternatively, a suitably substituted compound of formula (XXV), prepared for example, as described in Scheme 2 above, is reacted with a suitably substituted compound of formula (XVIII), prepared for example as outlined in Scheme 1 above, is reacted with a suitably substituted compound of formula (XXVIII), wherein LG$^5$ is a suitably selected leaving group, such as Cl, Br, I, mesylate, tosylate, triflate, and the like, a known compound or compound prepared as described herein; in the presence of a suitably selected base, such as K$_2$CO$_3$, Na$_2$CO$_3$, NaH, and the like; in a suitably selected solvent, such as DMF, DMP, THF, 1,4-doxane, and the like; to yield the corresponding compound of formula (I).

The compound of formula (XXVIII) is a known compound or a compound that may be prepared, for example, according to the process outlined in Scheme 4, below.

Scheme 4

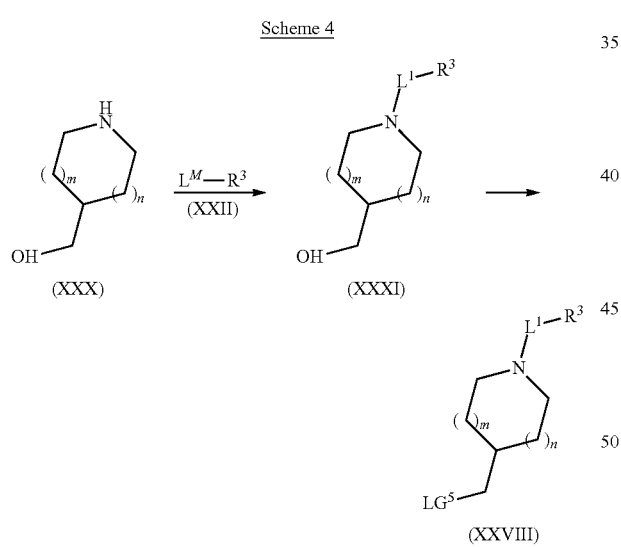

Accordingly, a suitably substituted compound of formula (XXX), a known compound or compound prepared by known methods (for example, by de-protecting the corresponding known, nitrogen-protected compound), is reacted with a suitably substituted compound of formula (XXII), a known compound or compound prepared by known methods, to yield the corresponding compound of formula (XXIII), according to the process as outlined in Scheme 1 above; to yield the corresponding compound of formula (XXXI).

The compound of formula (XXXI) is reacted with a suitably selected source of chlorine, such as POCl$_3$, SOCl$_2$, and the like; or suitably selected source of bromine, such as PBr$_3$, POBr$_3$, CBr$_4$ in combination with PPh$_3$, and the like; or suitably selected source of iodine, such as I$_2$ in the presence of PPh$_3$; or suitably selected source of mesylate, such as MsCl, and the like; or other suitable selected source of any other suitable LG$^5$ leaving group; according to known methods; to yield the corresponding compound of formula (XXVIII).

Compounds of formula (XXV) may be prepared, for example, according to the process outlined in Scheme 5, below.

Scheme 5

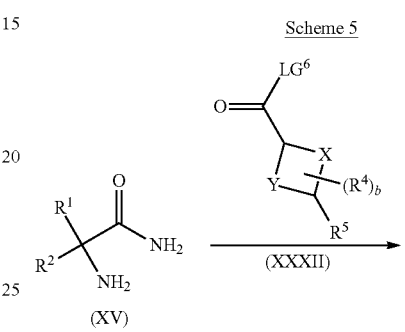

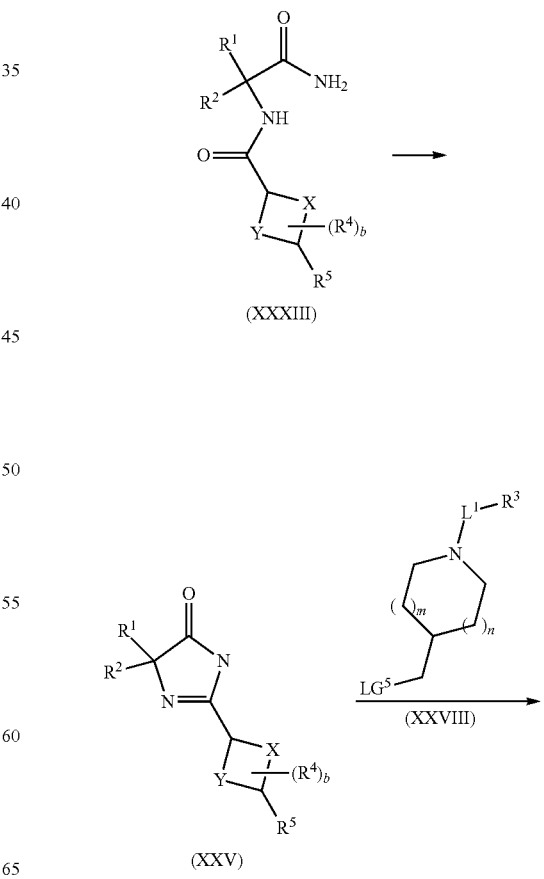

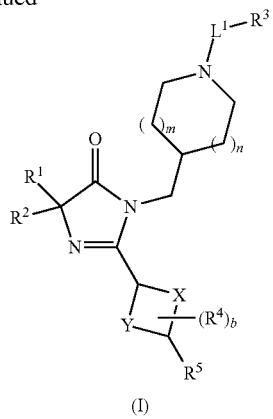

(I)

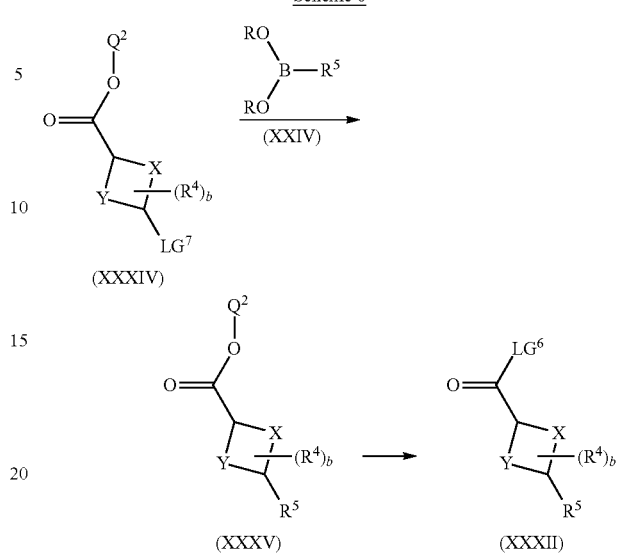

Scheme 6

Accordingly, a suitably substituted compound of formula (XV), prepared for example as described in Scheme 1 above, is reacted with a suitably substituted compound of formula (XXXII), wherein LG$^6$ wherein LG$^1$ is a suitably selected leaving group, such as Cl, Br, OH, and the like, to yield the corresponding compound of formula (XXXIII).

More particularly, wherein LG$^6$ is Cl, Br, and the like, the compound of formula (XV) is reacted with the compound of formula (XXXII), in the presence of a suitably selected organic base, such as pyridine, TEA, DIPEA, and the like; optionally in the presence of DMAP, and the like; in a suitably selected solvent such as DCM, DCE, THF, and the like. Alternatively, wherein LG$^6$ is OH, and the like, the compound of formula (XV) is reacted with the compound of formula (XXXII), in the presence of a suitably selected coupling reagent, such as HATU, HBTU, CDI, EDAC, and the like, in the presence of a suitably selected organic base, such as pyridine, TEA, DIPEA, and the like; in a suitably selected organic solvent, such as NMP, DMF, DCM, DCE, and the like.

The compound of formula (XXXIII) is reacted (to effect ring closure) with a suitably selected base, such as t-BuOK, NaOH, NaOCH$_3$, LHMDS, and the like; in a suitably selected organic solvent or mixture of solvents, such as methanol, ethanol, water, 1,4-dioxane, and the like, and wherein the base in LHMDS, in a suitably selected organic solvent, such as THF, and the like; to yield the corresponding compound of formula (XXV).

The compound of formula (XXV) is reacted with a suitably substituted compound of formula (XXVIII), wherein LG$^5$ is a suitably selected leaving group, such as Cl, Br, I, mesylate, tosylate, triflate, and the like, a known compound or compound prepared as described herein; in the presence of a suitably selected base, such as K$_2$CO$_3$, Na$_2$CO$_3$, NaH, and the like; in a suitably selected solvent, such as DMF, DMP, THF, 1,4-doxane, and the like; to yield the corresponding compound of formula (I).

One skilled in the art will recognize that the compound of formula (XXV) may alternatively be reacted with a suitably substituted compound of formula (XIX), the product de-protected and then further reacted with a suitably substituted compound of formula (XXII), to yield the corresponding compound of formula (I); as described in for, Scheme 1 or Scheme 2, above; to yield the corresponding compound of formula (I).

The compound of formula (XXIV) is a known compound or compound prepared for example, as described in Scheme 6, below.

Accordingly, a suitable substituted compound of formula (XXXIV), wherein Q$^2$ is hydrogen or a suitably selected oxygen protecting group, such as benzyl, C$_{1-4}$alkyl (preferably methyl, ethyl, or t-butyl), and the like, and wherein LG$^7$ is a suitably selected leaving group, such as Cl, Br, I, triflate, and the like, a known compound or compound prepared by known methods, is reacted with a suitably substituted compound of formula (XXIV), wherein the two R groups are each H, are each the same C$_{1-2}$alkyl or are taken together as —C(CH$_3$)$_2$—C(CH$_3$)$_2$— to form a ring (i.e., to form the

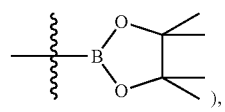 [SMILES: *B1OC(C)(C)C(C)(C)O1]

a known compound or compound prepared by known methods, under Suzuki coupling conditions, more particularly, in the presence of a suitably selected catalysts or catalyst system, such as Pd(PPh$_3$)$_4$, Pd$_2$(dba)$_3$, Pd(dppf), a mixture of Pd(OAc)$_2$ and PPh$_3$, and the like; in the presence of a suitably selected inorganic base, such as K$_2$CO$_3$, Cs$_2$CO$_3$, Na$_2$CO$_3$, and the like; in a suitably selected solvent, such as DME, 1,4-dioxane, and the like, preferably mixed with water; to yield the corresponding compound of formula (XXXV).

The compound of formula (XXXV) is reacted to yield the corresponding compound of formula (XXXII). More particularly, wherein Q$^2$ is hydrogen, the compound of formula (XXXV) is reacted with a suitably selected source of chlorine, such as POCl$_3$, SOCl$_2$, and the like; or suitably selected source of bromine, such as PBr$_3$, and the like; or suitably selected source of iodine, such as I$_2$ in the presence of PPh$_3$; according to known methods; to yield the corresponding compound of formula (XXXII) wherein LG$^6$ is chloro, bromo or iodo, respectively. Alternatively, wherein Q$^2$ is a suitably selected oxygen protecting group, for example, benzyl, the compound of formula (XXXV) is de-protected by hydrogenolysis (reacting with hydrogen in the presence of a Pd/C catalyst), according to known methods; according to known methods, to yield the corresponding compound of formula (XXXII) wherein LG$^6$ is OH. Alternatively still, wherein Q$^2$ is a suitably selected oxygen protecting group such as t-butyl, the compound of formula (XXXV) is de-protected by with a suitably selected acid, in a suitably selected organic solvent, according to known methods (e.g., with HCl in 1,4-dioxane or with TFA in DCM), to yield the corresponding compound of formula (XXXII) wherein LG$^6$ is OH. Alternatively still, wherein Q$^2$ is a suitably selected oxygen protecting group, such as C$_{1-4}$alkyl, and the like, for example methyl or ethyl, the compound of formula (XXXV) is de-protected by reacting with a suitably selected base, in a suitably selected mixture of water and an organic solvent, according to known methods (for example reacting with NaOH or KOH in a mixture of water, THF and methanol), to yield the corresponding compound of formula (XXXII), wherein LG$^6$ is OH.

Compounds of formula (I) may alternatively be prepared according to the process outlined in Scheme 7, below.

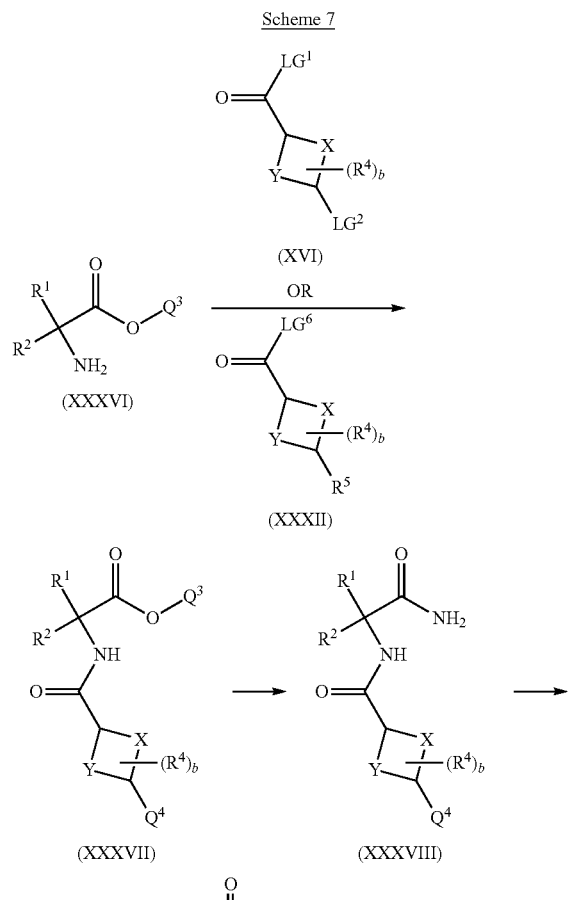

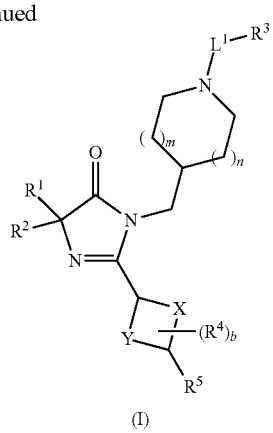

Accordingly, a suitably substituted compound of formula (XXXVI), wherein Q$^3$ is hydrogen or a suitably selected oxygen protecting group, such as benzyl, C$_{1-4}$alkyl (preferably methyl, ethyl or t-butyl), and the like, a known compound or compound prepared by known methods, is reacted with a suitably substituted compound of formula (XVI), wherein LG$^1$ is a suitably selected leaving group, such as Cl, Br, OH, and the like, and wherein LG$^2$ is a suitably selected leaving group, such as Cl, Br, OH, triflate, B(OH)$_2$, B(OC$_{1-2}$alkyl)$_2$,

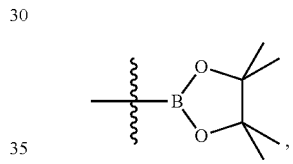

and the like, a known compound or compound prepared by known methods; according to known methods, for example, according to the process as outlined in Scheme 1 above; to yield the corresponding compound of formula (XXXVII), wherein Q$^4$ is the corresponding LG$^2$ group.

Alternatively, a suitably substituted compound of formula (XXXVI), wherein Q$^3$ is hydrogen or a suitably selected oxygen protecting group such as benzyl, C$_{1-4}$alkyl (preferably methyl, ethyl or t-butyl), and the like, a known compound or compound prepared by known methods; is reacted with a suitably substituted compound of formula (XXXII), wherein LG$^6$ is a suitably selected leaving group, such as Cl, Br, OH, and the like, a known compound or compound prepared by known methods; according to known methods, for example, according to the process as outlined in Scheme 5 above; to yield the corresponding compound of formula (XXXVII) wherein Q$^4$ is R$^5$.

The compound of formula (XXXVII) is then reacted to yield the corresponding compound of formula (XXXVIII). More particularly, wherein (a) Q$^3$ is hydrogen, the compound of formula (XXXVII) is reacted with ammonia or a suitably selected source of ammonia such as NH$_4$Cl, NH$_4$OH, gaseous NH$_3$, and the like; in the presence of a suitably selected coupling reagent, such as HATU, HBTU, CDI, EDAC, and the like, in the presence of a suitably selected organic base, such as pyridine, TEA, DIPEA, and the like; in a suitably selected organic solvent, such as NMP, DMF, DCM, DCE, and the like; to yield the corresponding compound of formula (XXXVII);

(b) $Q^3$ is a suitably selected oxygen protecting group, such as methyl, ethyl and the like, the compound of formula (XXXVII) is reacted with ammonia or a suitably selected source of ammonia, such as concentrated $NH_4OH$, $NH_4Cl$, gaseous $NH_3$, and the like, according to known methods (for example as described in (a) above), to yield the corresponding compound of formula (XXXVIII);

or (c) wherein $Q^3$ is a suitably selected oxygen protecting group, such as benzyl, t-butyl, and the like, the compound of formula (XXXVII) is de-protected according to known methods (e.g., wherein $Q^2$ is benzyl, t-butyl and the like, by hydrogenolysis, reacting with hydrogen in the presence of a catalyst such as Pd/C), or by reacting with a suitably selected acid, in a suitably selected organic solvent (e.g., reacting with HCl, in 1,4-dioxane or reacting with TFA in DCM) to yield the corresponding compound of formula (XXXVII) wherein $Q^3$ is hydrogen; such compound is then reacted with ammonia or a suitably selected source of ammonia as described in (a) above, to yield the corresponding compound of formula (XXXVIII).

The compound of formula (XXXVIII) is reacted (to effect ring closure) with a suitably selected base, such as t-BuOK, NaOH, $NaOCH_3$, LHMDS, and the like; in a suitably selected organic solvent or mixture of solvents, such as methanol, ethanol, water, 1,4-dioxane, and the like, and wherein the base in LHMDS, in a suitably selected organic solvent, such as THF, and the like; to yield the corresponding compound of formula (XXXIX).

The compound of formula (XXXIX) is reacted, according to the procedures as described herein, to yield the desired compound of formula (I). For example, the compound of formula (XXXIX), wherein $Q^4$ is a suitably elected leaving group, may be substituted for the compound of formula (XVIII) in Scheme 1 reacted according to the procedure as described in Scheme 1, to yield the desired compound of formula (I). Alternatively, the compound of formula (XXXIX), wherein $Q^4$ is $R^5$, may be substituted for the compound of formula (XV) in Scheme 2 or the compound of formula (XXV) in Scheme 3, and reacted as described therein, respectively, to yield the corresponding compound of formula (I).

Compounds of formula (I), wherein $R^1$ and $R^2$ are taken together with the carbon atom to which they are bound to form an optionally substituted 4 to 8-membered, saturated heterocyclyl of the formula

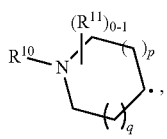

wherein p and q are each independently selected to be an integer from 0 to 2, and wherein the "•" denotes the carbon atom of the spiro attachment to the imidazolidin-5-one core, may alternatively prepared as described in Scheme 8, below.

Scheme 8

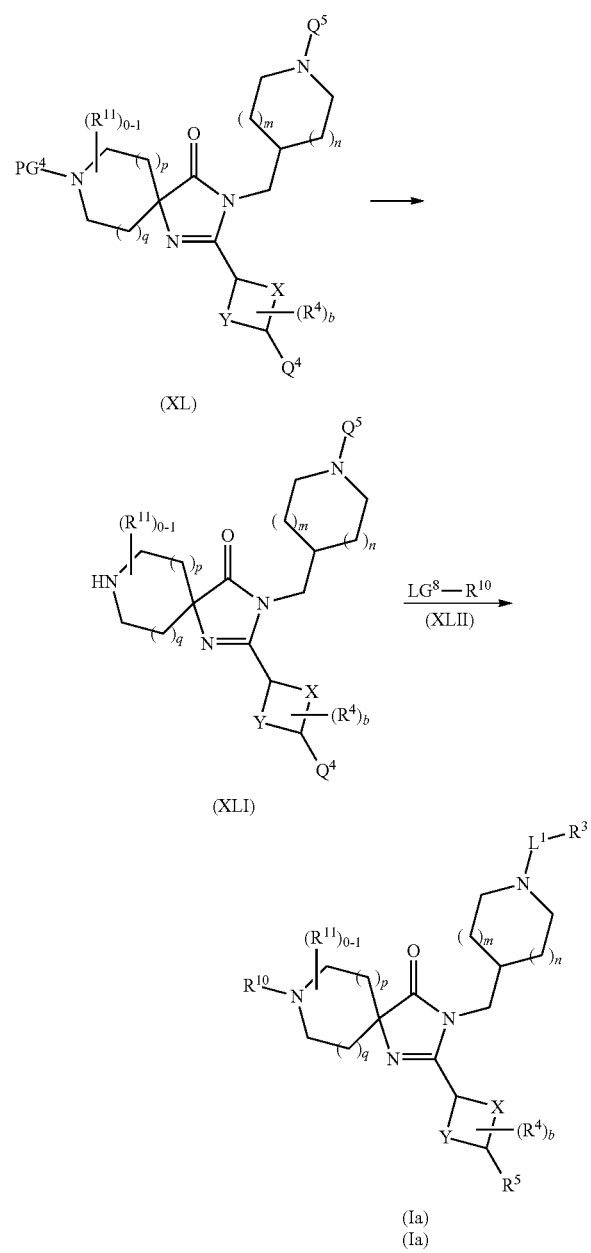

Accordingly, a suitably substituted compound of formula (XL) wherein $PG^4$ is a suitably selected nitrogen protecting group, such as Boc, Cbz, benzyl, and the like, wherein $Q^4$ is $—R^5$ or a suitably selected leaving group, such as Cl, Br, I, OH, and the like, and wherein $Q^5$ is $-L^1-R^3$ or a suitably selected nitrogen protecting group such as Boc, benzyl, Cbz, and the like; and wherein $Q^5$ is a nitrogen protecting group, then preferably, $PG^4$ and the $Q^5$ nitrogen protecting group are selected such that the two nitrogen protecting groups are removed under different conditions (i.e., the two nitrogen protecting groups are different and are selected such that each may be selectively removed without removing the other), a known compound or compound prepared by known methods, for example, as described in Scheme 1 above, is de-protected to remove the $PG^4$ group, according to known methods, to yield the corresponding compound of formula (XLI). For example, wherein PG$^4$ is Boc, the compound of formula (XL) may be de-protected by reacting with a suitably selected acid, such as HCl, and the like, in a suitably selected organic solvent, such as 1,4-dioxane, and the like.

The compound of formula (XLI) is then reacted to yield the corresponding compound of formula (I). Wherein the compound of formula (XLI) Q$^4$ is —R$^5$ and Q$^5$ is -L$^1$-R$^3$, then the compound of formula (XLI) is reacted with a suitably selected compound of formula (XLII), wherein LG$^8$ is OH or a suitably selected leaving group, such as Cl, Br, mesylate, tosylate, and the like, a known compound or compound prepared by known methods, according to known methods readily recognized by those skilled in the art, e.g., alkylation, peptide coupling, and the like, to yield the corresponding compound of formula (I). Alternatively, the compound of formula (XLI) may be reacted with a suitably selected compound of formula (XLII) wherein LG$^5$ includes an aldehyde or ketone carbonyl group, as would be readily recognized by one skilled in the art, under reductive amination conditions as known in the art, (for example, reacting with sodium triacetoxyborohydride and acetic acid, in a suitably selected solvent, such as DCM, DCE, THF, and the like; or reacting with cyanoborohydride in a suitably selected solvent, such as methanol, and the like), to yield the corresponding compound of formula (I).

Wherein the compound of formula (XLI) Q$^4$ is a suitably selected leaving group and/or Q$^5$ is a suitably selected nitrogen protecting group, then the compound of formula (XLI) may alternatively be reacted to: (a) attach the R$^5$ group by reacting with, for example, a suitably substituted compound of formula (XXIV), as described in, for example, Scheme 1, above; (b) remove of the Q$^5$ nitrogen protecting group and then attach the -L$^1$-R$^3$ group by reacting with, for example, a suitably substituted compound of formula (XXII), as described in, for example, Scheme 1 above; and (c) attach the —R$^{10}$ group, as described above; in any order or sequence; to yield the corresponding compound of formula (I).

One skilled in the art will further recognize that the compounds of formula (I) of the present invention may be prepared according to the methods as described herein, or alternatively by attaching substituent groups, such as

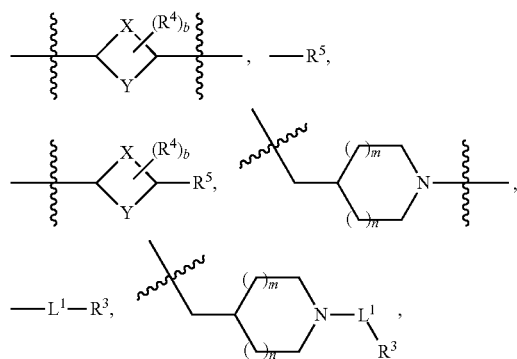

R$^{10}$, etc., and effecting ring closure to form the imidazolidin-4-one ring core, in any order or sequence, protecting and de-protecting reactive groups, as necessary or desirable, according to methods as described herein or known to those skilled in the art. One skilled in the art will further recognize that some such sequences may result in reaction steps with better reactivity profiles, yields and/or selectivity, and thus may be more efficient or desirable than other routes.

One skilled in the art will further recognize that when any of the coupling steps described above a reactant is substituted with a suitably selected leaving group, such as OH, triflate, and the like, such coupling may alternatively be effected by converting the leaving group to a group of the formula —B(OR)$_2$, wherein the two R groups are each H, are each the same C$_{1-2}$alkyl or are taken together as —C(CH$_3$)$_2$—C(CH$_3$)$_2$— to form a ring (i.e., to form the

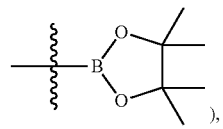

), and then completing the coupling under Suzuki coupling conditions, as herein described and known to those skilled in the art.

The present invention further comprises pharmaceutical compositions containing one or more compounds of formula (I) with a pharmaceutically acceptable carrier. Pharmaceutical compositions containing one or more of the compounds of the invention described herein as an active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus, for liquid oral preparations, such as suspensions, elixirs and solutions, suitable carriers and additives include water, glycols, oils, alcohols, flavoring agents, preservatives, stabilizers, coloring agents and the like; for solid oral preparations, such as powders, capsules, and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually include sterile water and other ingredients may be added to increase solubility or preservation. Injectable suspensions or solutions may also be prepared utilizing aqueous carriers along with appropriate additives.

To prepare the pharmaceutical compositions of this invention, one or more compounds of the present invention as an active ingredient is intimately admixed with a pharmaceutical carrier according to conventional pharmaceutical compounding techniques, such carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as, for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually include sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.01 mg to about 1000 mg or any amount or range therein, and may be given at a dosage of from about 0.01 mg/kg/day to about 300 mg/kg/day, or any amount or range therein, preferably from about 0.1 mg/kg/day to about 100 mg/kg/day, or any amount or range therein, preferably from about 0.50 mg/kg/day to about 50 mg/kg/day, or any amount or range therein, preferably from about 0.75 mg/kg/day to about 15 mg/kgiday, or any amount or range therein, preferably from about 1.0 mg/kg/day to about 7.5 mg/kg/day, or any amount or range therein, preferably from about 1.5 mg/kg/day to about 5.0 mg/kg/day, or any amount or range therein. The dosages, however, may be varied depending upon the requirement of the patients, the severity of the condition being treated and the compound being employed. The use of either daily administration or post-periodic dosing may be employed.

Preferably these compositions are in unit dosage forms, such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions, such as tablets, the principal active ingredient(s) is mixed with a pharmaceutical carrier, e.g., conventional tableting ingredients, such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from about 0.01 mg to about 1,000 mg, or any amount or range therein, of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials include a number of polymeric acids with materials, such as shellac, cetyl alcohol and cellulose acetate.

The liquid forms in which the compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums, such as tragacanth, acacia, alginate, dextran, sodium carboxymethylcellulose, methylcellulose, polyvinyl-pyrrolidone or gelatin.

The method of treating disorders described in the present invention may also be carried out using a pharmaceutical composition including any of the compounds as defined herein and a pharmaceutically acceptable carrier. The pharmaceutical composition may contain between about 0.01 mg and about 1000 mg of the compound, or any amount or range therein; preferably from about 1.0 mg to about 500 mg of the compound, or any amount or range therein, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixers, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, pharmaceutically acceptable inert carrier, such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars, such as glucose or beta-lactose, corn sweeteners, natural and synthetic gums, such as acacia, tragacanth or sodium oleate, sodium stearate, magnesium stearate, sodium benzoate, sodium acetate, sodium chloride, and the like. Disintegrators include, without limitation, starch, methyl cellulose, agar, bentonite, xanthan gum and the like.

The liquid forms in suitably flavored suspending or dispersing agents such as the synthetic and natural gums, e.g., tragacanth, acacia, methyl-cellulose and the like. For parenteral administration, sterile suspensions and solutions are desired. Isotonic preparations that generally contain suitable preservatives are employed when intravenous administration is desired.

To prepare a pharmaceutical composition of the present invention, a compound of formula (I) as the active ingredient is intimately admixed with a pharmaceutical carrier according to conventional pharmaceutical compounding techniques, which carrier may take a wide variety of forms depending of the form of preparation desired for administration (e.g., oral or parenteral). Suitable pharmaceutically acceptable carriers are well known in the art. Descriptions of some of these pharmaceutically acceptable carriers may be found in *The Handbook of Pharmaceutical Excipients*, published by the American Pharmaceutical Association and the Pharmaceutical Society of Great Britain.

Methods of formulating pharmaceutical compositions have been described in numerous publications such as *Pharmaceutical Dosage Forms: Tablets, Second Edition, Revised and Expanded*, Volumes 1-3, edited by Lieberman et al; *Pharmaceutical Dosage Forms: Parenteral Medications*, Volumes 1-2, edited by Avis et al; and *Pharmaceutical Dosage Forms: Disperse Systems*, Volumes 1-2, edited by Lieberman et al; published by Marcel Dekker, Inc.

Compounds of this invention may be administered in any of the foregoing compositions and according to dosage regimens established in the art whenever treatment of disorders mediated by inhibition of fatty acid synthase (FASN) enzyme, as described herein, is required.

The daily dosage of the products may be varied over a wide range from about 0.01 mg to about 1,000 mg per adult human per day, or any amount or range therein. For oral administration, the compositions are preferably provided in the form of tablets containing about 0.01, 0.05, 0.1, 0.5, 1.0, 2.5, 5.0, 10.0, 15.0, 25.0, 50.0, 100, 150, 200, 250, 500 and 1000 milligrams of the active ingredient each for the symptomatic adjustment of the dosage to the patient to be treated. An effective amount of the drug is ordinarily supplied at a dosage level of from about 0.01 mg/kg to about 300 mg/kg of body weight per day, or any amount or range therein. Preferably, the range is from about 0.5 to about 50.0 mg/kg of body weight per day, or any amount or range therein. More preferably, from about 0.75 to about 15.0 mg/kg of body weight per day, or any amount or range therein. More preferably, from about 1.0 to about 7.5 mg/kg of body weight per day, or any amount or range therein. The compounds may be administered on a regimen of 1 to 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

One skilled in the art will recognize that, both in vivo and in vitro trials using suitable, known and generally accepted cell and/or animal models are predictive of the ability of a test compound to treat or prevent a given disorder.

One skilled in the art will further recognize that human clinical trails including first-in-human, dose ranging and efficacy trials, in healthy patients and/or those suffering from a given disorder, may be completed according to methods well known in the clinical and medical arts.

The following Examples are set forth to aid in the understanding of the invention, and are not intended and should not be construed to limit in any way the invention set forth in the claims that follow thereafter.

SYNTHESIS EXAMPLES

In the following Examples, some synthesis products are listed as having been isolated as a residue. It will be understood by one of ordinary skill in the art that the term "residue" does not limit the physical state in which the product was isolated and may include, for example, a solid, an oil, a foam, a gum, a syrup, and the like.

Example 1

2-[4-(1-Benzofuran-5-yl)phenyl]-3-{[(3R)-1-(cyclopropylcarbonyl)pyrrolidin-3-yl]methyl-}3-diazaspiro [4.4]non-1-en-4-one (Compound #2)

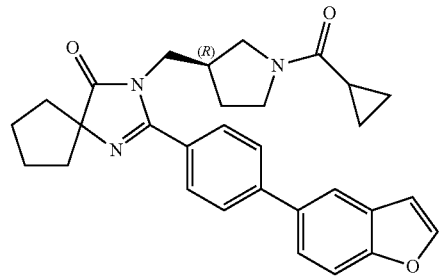

STEP A:
4-Bromo-N-(1-carbamoylcyclopentyl)benzamide

A mixture 1-aminocyclopentanecarboxamide (0.5 g, 3.9 mmol), 4-bromobenzoic acid (0.784 g, 3.9 mmol), EDCI (0.747 g, 3.9 mmol), HOBt (0.527 g, 3.9 mmol) and DIEA (0.67 mL, 3.9 mmol) in DMF (10 mL) was stirred at room temperature for 1 day. The reaction mixture was partitioned between EtOAc and aqueous saturated NaHCO$_3$. The organic phase was washed with brine, dried over Na$_2$SO$_4$, filtered and concentrated in vacuo to yield 4-bromo-N-(1-carbamoylcyclopentyl)benzamide (1.2 g, 99%).

$^1$H NMR (400 MHz, DMSO-d$_6$) δ ppm 1.54-1.82 (m, 3H), 1.89-2.04 (m, 2H), 2.04-2.23 (m, 2H), 6.76 (br. s., 1H), 7.09 (br. s., 1H), 7.66 (d, J=8.6 Hz, 2H), 7.83 (d, J=8.6 Hz, 2H), 8.36 (s, 1H); MS m/z 313.0 (M+H)$^+$.

STEP B: 2-(4-Bromophenyl)-1,3-diazaspiro[4.4] non-1-en-4-one

A mixture of 4-bromo-N-(1-carbamoylcyclopentyl)benzamide (1.0 g, 3.21 mmol) and NaOH (0.64 g, 16.06 mmol) in H$_2$O (3.25 mL) and MeOH (50 mL) was stirred at 65° C. for 1 day. The reaction mixture was partitioned between water (300 mL) and EtOAc (300 mL). The organic phase was washed with brine, dried over Na$_2$SO$_4$, filtered and concentrated in vacuo to yield 2-(4-bromophenyl)-1,3-diazaspiro[4.4]non-1-en-4-one (0.9 g, 95%).

$^1$H NMR (400 MHz, DMSO-d$_6$) δ ppm 1.69-1.79 (m, 2H), 1.80-1.92 (m, 6H), 5.76 (s, 1H), 7.74 (d, J=8.3 Hz, 2H), 7.90 (d. J=7.6 Hz, 2H); MS m/z 295.0 (M+H)$^+$.

STEP C: (S)-ter-Butyl 3-((2-(4-bromophenyl)-4-oxo-1,3-diazaspiro[4.4]non-1-en-3-yl)methyl)pyrrolidine-1-carboxylate To a stirring solution of 2-(4-bromophenyl)-1,3-diazaspiro[4.4]non-1-en-4-one (50 mg, 0.17 mmol) and (R)-tert-butyl 3-(bromomethyl)pyrrolidine-1-carboxylate (90.1 mg, 0.34 mmol) in DMF (3 mL) was added Cs$_2$CO$_3$ (139 mg, 0.42 mmol). After stirring at room temperature for 1 h and 65° C. for 17 h, the reaction mixture was partitioned between aqueous NaHCO₃ and EtOAc. The organic phase was washed with brine, dried over Na₂SO₄, filtered and concentrated in vacuo to yield a residue. The residue was purified by flash chromatography (silica gel, 40% EtOAc/heptane) to yield (S)-ter-butyl 3-((2-(4-bromophenyl)-4-oxo-1,3-diazaspiro[4.4]non-1-en-3-yl)methyl)pyrrolidine-1-carboxylate (62 mg, 76%).

¹H NMR (400 MHz, CDCl₃) δ ppm 1.42 (s, 9H), 1.74-1.82 (m, 1H), 1.82-1.91 (m, 2H), 1.91-2.10 (m, 7H), 2.24 (dt, J=14.7, 7.4 Hz, 1H), 2.73-2.89 (m, 1H), 3.11-3.40 (m, 3H), 3.49-3.68 (m, 2H), 7.45 (d, J=8.6 Hz, 2H), 7.64 (d, J=8.1 Hz, 2H); MS m/z 476.1 (M+H)⁺.

STEP D: (R)-2-(4-Bromophenyl)-3-(pyrrolidin-3-ylmethyl)-1,3-diazaspiro[4.4]non-1-en-4-one To a stirring solution of (S)-tert-butyl 3-((2-(4-bromophenyl)-4-oxo-1,3-diazaspiro[4.4]non-1-en-3-yl)methyl)pyrrolidine-1-carboxylate (270 mg, 0.56 mmol) in 1,4-dioxane was added 4M HCl in 1,4-dioxane (17 mL). After stirring overnight at room temperature the reaction mixture was concentrated to yield (R)-2-(4-bromophenyl)-3-(pyrrolidin-3-ylmethyl)-1,3-diazaspiro[4.4]non-1-en-4-one, as its corresponding HCl salt, as a solid, which was directly used into the next step; MS m/z 376 (M+H)⁺.

STEP E: (R)-2-(4-Bromophenyl)-3-((1-(cyclopropanecarbonyl)pyrrolidin-3-yl)methyl)-1,3-diazaspiro[4.4]non-1-en-4-one To a stirring solution of (R)-2-(4-bromophenyl)-3-(pyrrolidin-3-ylmethyl)-1,3-diazaspiro[4.4]non-1-en-4-one HOC salt (234 mg, 0.56 mmol) in DCM (15 mL) and DIPEA (0.21 mL, 1.25 mmol) was added cyclopropanecarbonyl chloride (0.053 mL, 0.56 mmol). After stirring at room temperature for 3 h, the reaction mixture was partitioned between aqueous NaHCO₃ and DCM. The organic phase was washed with brine, dried over Na₂SO₄, filtered and concentrated in vacuo to yield (R)-2-(4-bromophenyl)-3-((1-(cyclopropanecarbonyl)pyrrolidin-3-yl)methyl)-1,3-diazaspiro[4.4]non-1-en-4-one (250 mg, 99%).

¹H NMR (400 MHz, DMSO-d₆) δ ppm 0.58-0.74 (m, 4H), 1.40-1.64 (m, 1H), 1.68 (td, J=12.0, 6.8 Hz, 1H), 1.73-1.83 (m, 3H), 1.88 (br. s., 6H), 2.04-2.14 (m, 1H), 2.80 (dd, J=11.6, 7.1 Hz, 1H), 3.03-3.14 (m, 1H), 3.17-3.28 (m, 1H), 3.38-3.55 (m, 2H), 3.58 (t, J=8.1 Hz, 2H), 7.60-7.68 (m, 2H), 7.71-7.78 (m, 2H); MS m/z 444.1 (M+H)⁺.

STEP F: (R)-2-(4-(Benzofuran-5-ylphenyl)-3-((1-(cyclopropanecarbonyl)pyrrolidin-3-yl)methyl)-1,3-diazaspiro[4.4]non-1-en-4-one, Compound #2

To a solution of (R)-2-(4-bromophenyl)-3-((1-(cyclopropanecarbonyl)pyrrolidin-3-yl)methyl)-1,3-diazaspiro[4.4]non-1-en-4-one (150 mg, 0.338 mmol) and benzofuran-5-ylboronic acid (86.32 mg, 0.506 mol) in DME (3 mL) was added under argon aqueous 2M Na₂CO₃ (0.35 mL, 0.709 mmol) and Pd(PPh₃)₄ (15 mg, 0.013 mmol). The reaction mixture was refluxed for 16 h, filtered and concentrated in vacuo and the resulting residue was purified by preparative reverse-phase chromatography to yield (R)-2-(4-(benzofuran-5-yl)phenyl)-3-((1-(cyclopropanecarbonyl)pyrrolidin-3-yl)methyl)-1,3-diazaspiro[4.4]non-1-en-4-one (80 mg, 49%).

¹H NMR (400 MHz, CDCl₃) δ ppm 0.66-0.77 (m, 2H), 0.86-1.01 (m, 2H), 1.23-1.75 (m, 3H), 1.78-2.17 (m, 9H), 2.28-2.56 (m, 1H), 2.99-3.25 (m, 1H), 3.26-3.57 (m, 2H), 3.57-3.82 (m, 3H), 6.85 (s, 1H), 7.56 (d, 1H), 7.61 (d, 1H), 7.64-7.71 (m, 3H), 7.73-7.80 (m, 2H), 7.84 (s, 1H); MS m/z 482.3 (M+H)⁺.

Following the procedure described in Example 1, above, selecting and substituting the appropriate reagents, starting materials, and purification methods, and adjusting reaction temperatures, times and other variables or parameters, as needed or desirable, as would be readily recognized by those skilled in the art, the following intermediate compounds were prepared:

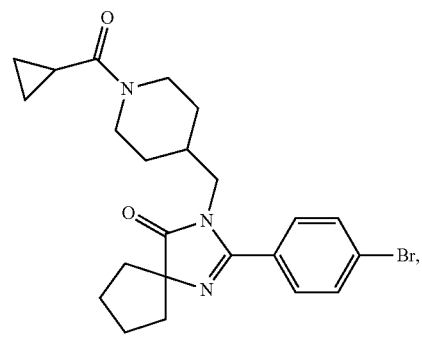

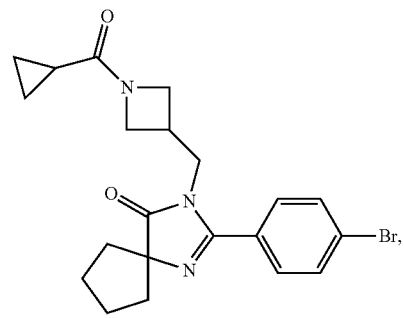

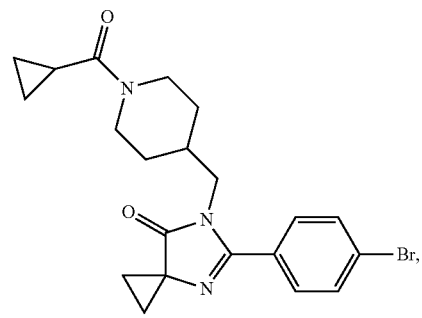

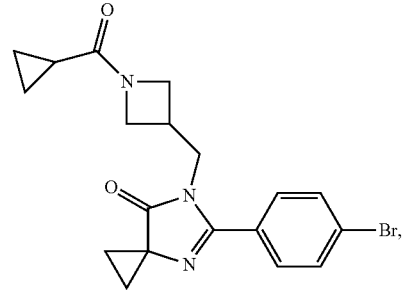

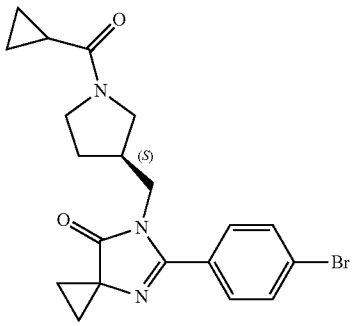

and

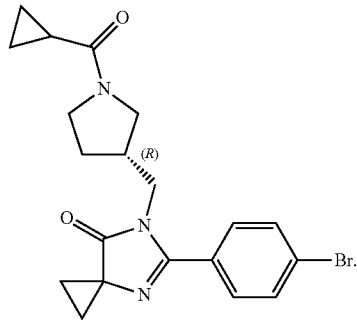

Following the procedure described in Example 1, above, selecting and substituting the appropriate reagents, starting materials, and purification methods, and adjusting reaction temperatures, times and other variables or parameters, as needed or desirable, as would be readily recognized by those skilled in the art, the following compounds of formula (I) of the invention were prepared.

| ID No. | Structure | Compound Name & Physical Data |
|---|---|---|
| 75 | 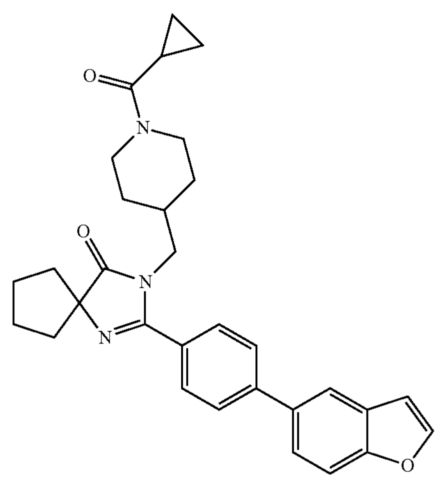 [SMILES: O=C(C1CC1)N1CCC(CN2C(=O)C3(CCCC3)N=C2c2ccc(-c3ccc4occc4c3)cc2)CC1] | 1-[4-(1-Benzofuran-5-yl)phenyl]-3-{[1-(cyclopropylcarbonyl)piperidin-4-yl]methyl}-1,3-diazaspiro[4.4]non-1-en-4-one<br>$^1$H NMR (400 MHz, CDCl$_3$) δ ppm 0.70 (dd, J = 7.8, 3.2 Hz, 2 H), 0.87-0.95 (m, 2 H), 0.95-1.02 (m, 1 H), 1.02-1.17 (m, 1 H), 1.40-1.62 (m, 2 H), 1.63-1.72 (m, 1 H), 1.73-1.84 (m, 2 H), 1.85-2.15 (m, 8 H), 2.47 (t, J = 11.7 Hz, 1 H), 2.97 (t, J = 12.5 Hz, 1 H), 3.57 (dd, J = 15.7, 7.1 Hz, 2 H), 4.07-4.22 (m, 1 H), 4.51 (d, J = 12.2 Hz, 1 H), 6.85 (d, J = 2.0 Hz, 1 H), 7.52-7.60 (m, 2 H), 7.62-7.66 (m, 2 H), 7.69 (d, J = 2.2 Hz, 1 H), 7.75 (d, J = 8.3 Hz, 2 H), 7.85 (s, 1 H);<br>MS m/z 496.2 (M + H)$^+$. |
| 76 | 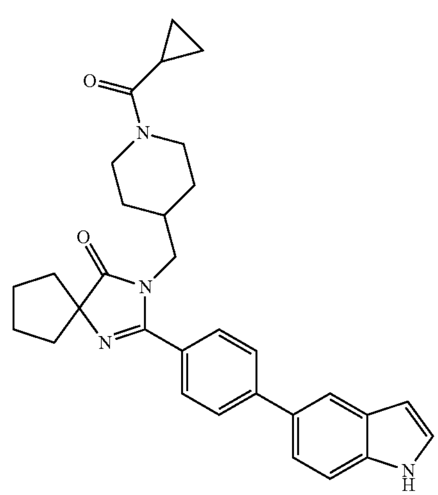 [SMILES: O=C(C1CC1)N1CCC(CN2C(=O)C3(CCCC3)N=C2c2ccc(-c3ccc4[nH]ccc4c3)cc2)CC1] | 3-{[1-(Cyclopropylcarbonyl)piperidin-4-yl]methyl}-2-[4-(1H-indol-5-yl)phenyl]-1,3-diazaspiro[4.4]non-1-en-4-one<br>$^1$H NMR (400 MHz, CDCl$_3$) δ ppm 0.71 (dd, J = 7.8, 3.2 Hz, 2 H), 0.83-0.96 (m, 2 H), 0.96-1.03 (m, 1 H), 1.03-1.19 (m, 1 H), 1.47 (br. s., 1 H), 1.56 (br. s., 1 H), 1.62-1.72 (m, 1 H), 1.72-1.86 (m, 2 H), 1.87-2.16 (m, 9 H), 2.46 (t, J =12.2 Hz, 1 H), 2.96 (t, J = 12.0 Hz, 1 H), 3.58 (dd, J = 9.8, 8.1 Hz, 2 H), 4.50 (br. s., 1 H), 6.63 (br. s., 1 H), 7.26 (br. s., 1 H), 7.43-7.52 (m, 2 H), 7.62 (d, J = 8.3 Hz, 2 H), 7.78 (d, J = 8.1 Hz, 2 H), 7.92 (s, 1 H), 8.61 (br. s., 1 H);<br>MS m/z 495.3 (M + H)$^+$ |

| ID No. | Structure | Compound Name & Physical Data |
|---|---|---|
| 77 | 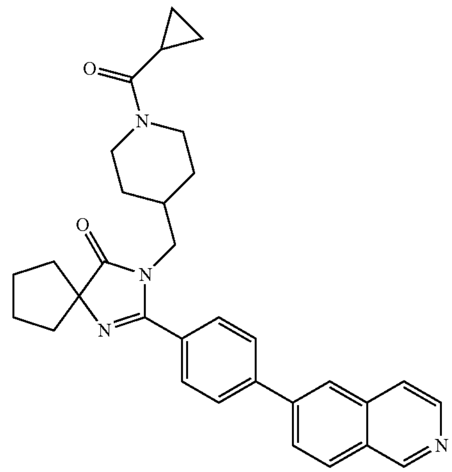 [SMILES: O=C(C1CC1)N1CCC(CN2C(=O)C3(CCCC3)N=C2c2ccc(-c3ccc4cnccc4c3)cc2)CC1] | 3-{[1-(Cyclopropylcarbonyl)piperidin-4-yl]methyl}-2-(4-isoquinolin-6-ylphenyl)-1,3-diazaspiro[4.4]non-1-en-4-one<br>$^1$H NMR (400 MHz, CDCl$_3$) δ ppm 0.62-0.77 (m, 2 H), 0.85-1.03 (m, 3 H), 1.03-1.16 (m, 1 H), 1.41-1.63 (m, 2 H), 1.63-1.71 (m, 1 H), 1.81 (m, J = 11.3, 7.5, 3.8, 3.8 Hz, 1 H), 1.88-2.17 (m, 8 H), 2.46 (t, J = 11.5 Hz, 1 H), 2.97 (t, J = 12.5 Hz, 1 H), 3.50-3.70 (m, 2 H), 4.04-4.23 (m, 1 H), 4.50 (d, J = 12.0 Hz, 1 H), 7.63-7.77 (m, 3 H), 7.81-7.95 (m, 3 H), 8.03-8.15 (m, 2 H), 8.59 (d, J = 5.6 Hz, 1 H), 9.32 (s, 1 H); MS m/z 507.3 (M + H)$^+$ |
| 78 | 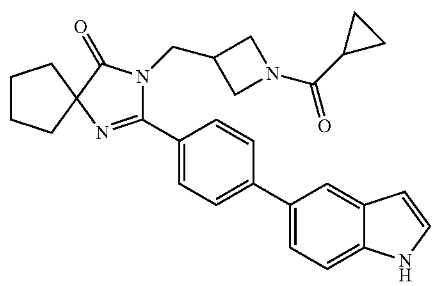 [SMILES: O=C(C1CC1)N1CC(CN2C(=O)C3(CCCC3)N=C2c2ccc(-c3ccc4[nH]ccc4c3)cc2)C1] | 3-{[1-(Cyclopropylcarbonyl)azetidin-3-yl]methyl}-2-[4-(1H-indol-5-yl)phenyl]-1,3-diazaspiro[4.4]non-1-en-4-one<br>$^1$H NMR (400 MHz, CDCl$_3$) δ ppm 0.77 (dd, J 7.6, 3.5 Hz, 2 H), 0.92-1.03 (m, 2 H), 1.24-1.38 (m, 1 H), 1.96-2.25 (m, 6 H), 2.25-2.39 (m, 2 H), 2.80-2.98 (m, 1 H), 3.70 (br. s., 1 H), 3.85-4.41 (m, 5 H), 6.65 (br. s., 1 H), 7.30 (br. s., 1 H), 7.45 (d, 1 H), 7.50 (d, J = 8.1 Hz, 1 H), 7.77 (d, J = 8.1 Hz, 2 H), 7.88 (d, J = 8.1 Hz, 2 H), 7.93 (s, 1 H), 8.52 (br. s., 2 H); MS m/z 467.0 (M + H)$^+$ |
| 79 | 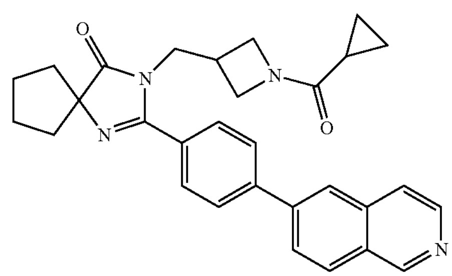 [SMILES: O=C(C1CC1)N1CC(CN2C(=O)C3(CCCC3)N=C2c2ccc(-c3ccc4cnccc4c3)cc2)C1] | 3-{[1-(Cyclopropylcarbonyl)azetidin-3-yl]methyl}-2-(4-isoquinolin-6-ylphenyl)-1,3-diazaspiro[4.4]non-1-en-4-one<br>$^1$H NMR (400 MHz, CDCl$_3$) δ ppm 0.70 (dd, J 7.3, 3.8 Hz, 2 H), 0.84-0.96 (m, 2 H), 1.23-1.34 (m, 1 H), 1.71-2.16 (m, 10 H), 2.70-2.84 (m, 1 H), 3.57 (dd, J = 9.9, 5.8 Hz, 1 H), 3.82-4.05 (m, 4 H), 7.72 (d, J = 8.1 Hz, 2 H), 7.75 (d, J = 6.1 Hz, 1 H), 7.88 (d, J = 8.1 Hz, 2 H), 7.91 (d, 1 H), 8.07 (s, 1 H), 8.12 (d, J = 8.6 Hz, 1 H), 8.60 (d, J = 5.6 Hz, 1 H), 9.33 (s, 1 H); MS m/z 478.9 (M + H)$^+$ |
| 80 | 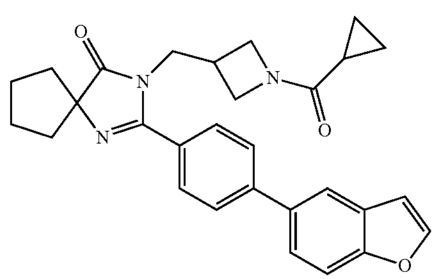 [SMILES: O=C(C1CC1)N1CC(CN2C(=O)C3(CCCC3)N=C2c2ccc(-c3ccc4occc4c3)cc2)C1] | 2-[4-(1-Benzofuran-5-yl)phenyl]-3-{[1-(cyclopropylcarbonyl)azetidin-3-yl]methyl}-1,3-diazaspiro[4.4]non-1-en-4-one<br>$^1$H NMR (400 MHz, CDCl$_3$) δ ppm 0.77 (dd, J = 7.3, 3.3 Hz, 2 H), 0.88-1.03 (m, 2 H), 1.21-1.38 (m, 1 H), 1.99-2.29 (m, 8 H), 2.79-2.98 (m, 1 H), 3.68 (br. s., 1 H), 3.90-4.23 (m, 4 H), 4.24-4.41 (m, 1 H), 6.87 (s, 1 H), 7.57 (d, J = 8.6 Hz, 1 H), 7.63 (d, J = 8.6 Hz, 1 H), 7.71 (d, J = 2.5 Hz, 1 H), 7.75-7.83 (m, 2 H), 7.84-7.92 (m, 3 H); MS m/z 468.0 (M + H)$^+$ |

-continued

| ID No. | Structure | Compound Name & Physical Data |
|---|---|---|
| 74 | 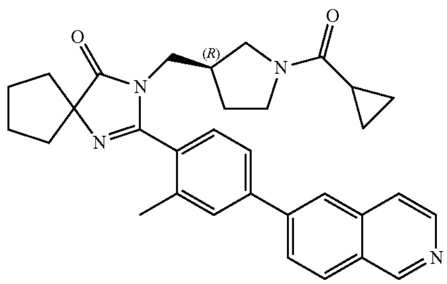 | 3-{[(3R)-1-(cyclopropylcarbonyl)pyrrolidin-3-yl]methyl}-2-(4-isoquinolin-6-yl-2-methylphenyl)-1,3-diazaspiro[4.4]non-1-en-4-one<br>¹H NMR (400 MHz, DMSO-d₆) δ ppm 0.56-0.68 (m, 4 H), 1.27-1.66 (m, 2 H), 1.69-1.98 (m, 9 H), 2.10-2.34 (m, 1 H), 2.39 (s, 3 H), 2.74-3.32 (m, 3 H), 3.36-3.59 (m, 3 H), 7.62 (dd, J = 18.4, 7.8 Hz, 1 H), 7.81-7.88 (m, 1 H), 7.91 (d, J = 5.6 Hz, 2 H), 8.10 (d, J = 8.6 Hz, 1 H), 8.25 (d, J = 8.6 Hz, 1 H),<br>8.38 (s, 1 H), 8.55 (d, J = 5.6 Hz, 1 H), 9.37 (s, 1 H);<br>MS m/z 506.9 (M + H)⁺ |
| 1 | 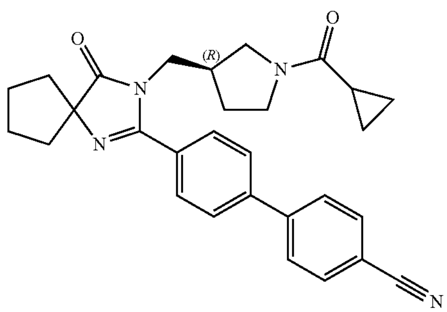 | 4'-(3-{[(3R)-1-(Cyclopropylcarbonyl)pyrrolidin-3-yl]methyl}-4-oxo-1,3-diazaspiro[4.4]non-1-en-2-yl)biphenyl-4-carbonitrile<br>¹H NMR (400 MHz, CDCl₃) δ ppm 0.64-0.78 (m, 2 H), 0.86-1.01 (m, 2 H), 1.39-1.88 (m, 3 H), 1.88-2.15 (m, 8 H), 2.25-2.54 (m, 1 H), 2.92-3.27 (m, m1 H), 3.27-3.58 (m, 2 H), 3.58-3.83 (m, 3 H), 7.69-7.82 (m, 8 H);<br>MS m/z 467.3 (M + H)⁺ |
| 66 | 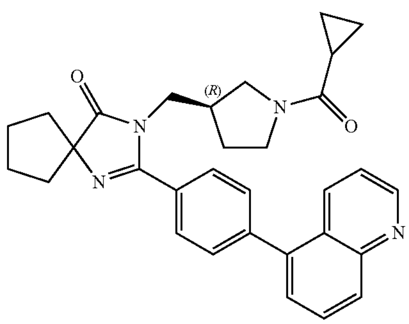 | 3-{[(3R)-1-(Cyclopropylcarbonyl)pyrrolidin-3-yl]methyl}-2-(4-quinolin-5-ylphenyl)-1,3-diazaspiro[4.4]non-1-en-4-one<br>¹H NMR (400 MHz, CDCl₃) δ ppm 0.68-0.78 (m, 2 H), 0.88-1.03 (m, 2 H), 1.42-2.01 (m, 6 H), 2.02-2.16 (m, 4 H), 2.34-2.61 (m, 1 H), 2.99-3.61 (m, 3 H), 3.62-3.84 (m, 3 H), 7.36-7.44 (m, 1 H), 7.55 (d, J = 7.1 Hz, 1 H), 7.59-7.67 (m, 2 H), 7.70-7.77 (m, 2 H), 7.80 (t, J = 7.8 Hz, 1 H), 8.19 (dt, J = 8.5, 4.6 Hz, 2 H), 8.97 (d, J = 4.0 Hz,<br>1 H);<br>MS m/z 493.2 (M + H)⁺ |
| 67 | 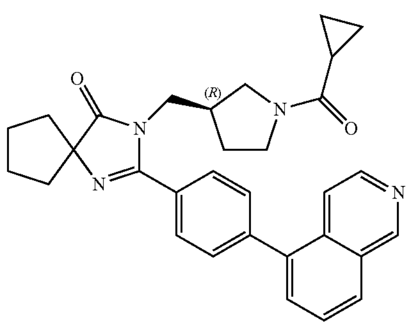 | 3-{[(3R)-1-(Cyclopropylcarbonyl)pyrrolidin-3-yl]methyl}-2-(4-isoquinolin-5-ylphenyl)-1,3-diazaspiro[4.4]non-1-en-4-one<br>¹H NMR (400 MHz, CDCl₃) δ ppm 0.73 (dd, J = 7.8, 3.3 Hz, 2 H), 0.88-1.03 (m, 2 H), 1.44-1.76 (m, 2 H), 1.76-2.18 (m, 9 H), 2.34-2.62 (m, 1 H), 2.99-3.31 (m, 1 H), 3.31-3.62 (m, 2 H), 3.62-3.85 (m, 3 H), 7.61-7.78 (m, 7 H), 8.02-8.10 (m, 1 H), 8.53 (dd, J = 5.8, 2.8 Hz, 1 H), 9.35 (s, 1 H);<br>MS m/z 493.2 (M + H)⁺ |
| 68 | 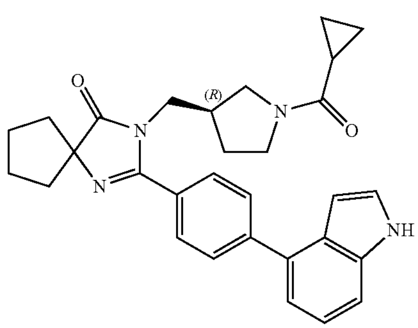 | 3-{[(3R)-1-(Cyclopropylcarbonyl)pyrrolidin-3-yl]methyl}-2-[4-(1H-indol-4-yl)phenyl]-1,3-diazaspiro[4.4]non-1-en-4-one<br>¹H NMR (400 MHz, CDCl₃) δ ppm 0.76 (dd, J = 7.8, 2.8 Hz, 2 H), 0.98 (d, J = 4.5 Hz,<br>2 H), 1.41-1.75 (m, 2 H), 1.88-2.38 (m, 9 H), 2.41-2.66 (m, 1 H), 3.10-3.33 (m, ,1 H), 3.60 (d, 3 H), 3.86-4.00 (m, 2 H), 6.68 (br. s., 1 H), 7.23 (d, 1 H), 7.30 (d, 1 H), 7.32 (d, J = 3.0 Hz, 1 H), 7.48 (d, J = 8.1 Hz,<br>1 H), 7.83 (d, J = 8.6 Hz, 2 H), 7.94 (d, J = 8.1 Hz, 2 H), 8.53 (br. s., 1 H);<br>MS m/z 481.2 (M + H)⁺ |

| ID No. | Structure | Compound Name & Physical Data |
|---|---|---|
| 69 | 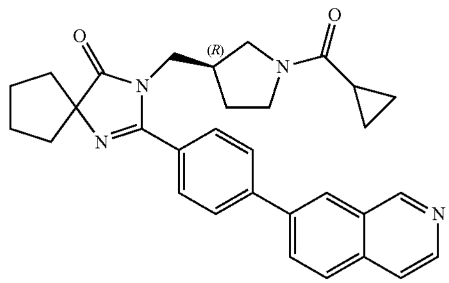 | 3-{[(3R)-1-(Cyclopropylcarbonyl)pyrrolidin-3-yl]methyl}-2-(4-isoquinolin-7-ylphenyl)-1,3-diazaspiro[4.4]non-1-en-4-one<br>¹H NMR (400 MHz, CDCl₃) δ ppm 0.65-0.80 (m, 2 H), 0.86-1.03 (m, 2 H), 1.43-2.17 (m, 11 H), 2.28-2.55 (m, 1 H), 2.96-3.58 (m, 3 H), 3.59-3.83 (m, 3 H), 7.70-7.78 (m, 3 H),k 7.82-7.91 (m, 2 H), 7.93-8.04 (m, 2 H), 8.23 (s, 1 H), 8.58 (d, J = 6.1 Hz, 1 H), 9.37 (s, 1 H);<br>MS m/z 493.2 (M + H)⁺ |
| 70 | 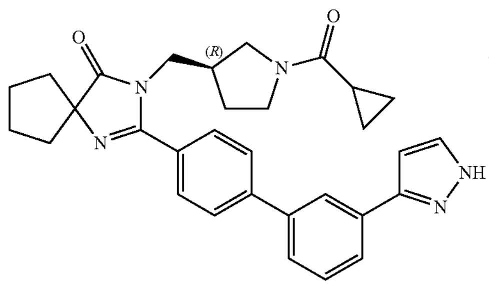 | 3-{[(3R)-1-(Cyclopropylcarbonyl)pyrrrolidin-3-yl]methyl}-2-[3'-(1H-pyrazol-3-yl)biphenyl-4-yl]-1,3-diazaspiro[4.4]non-1-en-4-one<br>¹H NMR (400 MHz, CDCl₃) δ ppm 0.77 (d, J = 6.6 Hz, 2 H), 0.90-1.04 (m, 2 H), 1.41-1.76 (m, 2 H), 1.86-2.17 (m, 5 H), 2.17-2.36 (m, 4 H), 2.38-2.70 (m, 1 H), 2.98-3.64 (m, 3 H), 3.64-4.00 (m, 3 H), 6.83 (d, J = 2.5 Hz, 1 H), 7.59 (t, J = 7.8 Hz, 1 H), 7.68 (d, J = 7.6 Hz, 1 H), 7.77 (d, J = 7.6 Hz,<br>1 H), 7.81-7.91 (m, 5 H), 7.96-8.05 (m, 1 H);<br>MS m/z 508.3 (M + H)⁺ |
| 11 | 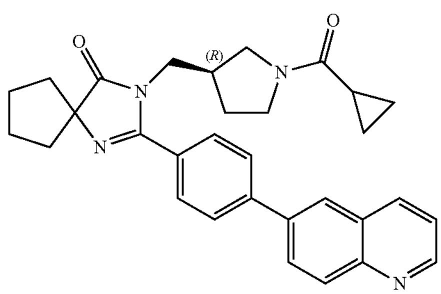 | 3-{[(3R)-1-(Cyclopropylcarbonyl)pyrrolidin-3-yl]methyl}-2-(4-quinolin-6-ylphenyl)-1,3-diazaspiro[4.4]non-1-en-4-one<br>¹H NMR (400 MHz, DMSO-d₆) δ ppm 0.57-0.70 (m, 4 H), 1.35-1.70 (m, 2 H), 1.71-2.14 (m, 26 H), 2.21-2.45 (m, 1 H), 2.83-3.52 (m, 3 H), 3.52-3.67 (m, 1 H), 3.77 (t, J = 8.8 Hz, 2 H), 7.92 (dd, J = 8.1, 4.5 Hz, 1 H), 8.01 (t, J = 7.3 Hz, 2 H), 8.18 (dd, J = 7.8,<br>4.3 Hz, 2 H), 8.33-8.40 (m, 1 H), 8.41-8.48 (m, 1 H), 8.69 (s, 1 H), 8.91 (d, J = 8.1 Hz, 1 H), 9.18 (d, J = 3.5 Hz, 1 H);<br>MS m/z 493.3 (M + H)⁺ |
| 12 | 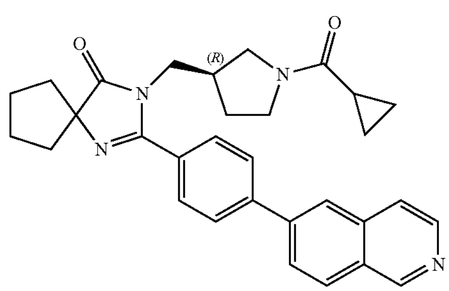 | 3-{[(3R)-1-(Cyclopropylcarbonyl)pyrrolidin-3-yl]methyl}-2-(4-isoquinolin-6-ylphenyl)-1,3-diazaspiro[4.4]non-1-en-4-one<br>¹H NMR (400 MHz, DMSO-d₆) δ ppm 0.64 (d, J = 5.1 Hz, 4 H), 1.31-1.74 (m, 2 H), 1.74-2.16 (m, 9 H), 2.19-2.45 (m, 1 H), 2.82-3.51 (m, 3 H), 3.52-3.67 (m, 1 H), 3.69-3.83 (m, 2 H), 8.05 (t, J = 8.1 Hz, 2 H), 8.24 (dd, J = 8.1, 5.1 Hz, 2 H), 8.47 (d, J = 8.6 Hz, 1 H), 8.53 (d, J = 6.6 Hz, 1 H), 8.67 (d, J = 9.1 Hz, 1 H), 8.73 (d, J = 6.6 Hz,<br>1 H), 8.80 (s, 1 H), 9.94 (s, 1 H);<br>MS m/z 493.3 (M + H)⁺ |
| 13 | 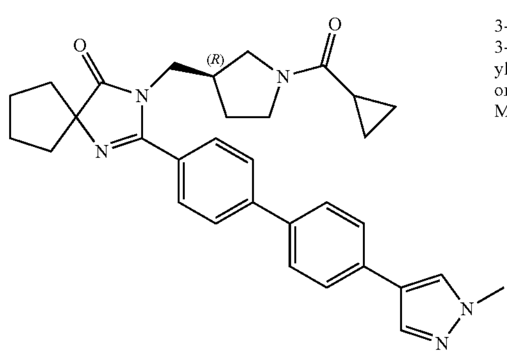 | 3-{[(3R)-1-(Cyclopropylcarbonyl)pyrrolidin-3-yl]methyl}-2-[4-(1-methyl-1H-pyrazol-4-yl)phenyl]-1,3-diazaspiro[4.4]non-1-en-4-one<br>MS m/z 446.3 (M + H)⁺ |

-continued

| ID No. | Structure | Compound Name & Physical Data |
|---|---|---|
| 72 | 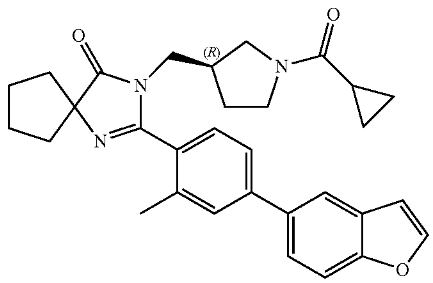 | 2-[4-(1-Benzofuran-5-yl)-2-methylphenyl]-3-{[(3R)-1-(cyclopropylcarbonyl)pyrrolidin-3-yl]methyl}-1,3-diazaspiro[4.4]non-1-en-4-one<br>$^1$H NMR (400 MHz, CDCl$_3$) δ ppm 0.72-0.85 (m, 2 H), 0.93-1.07 (m, 2 H), 1.42-1.70 (m, 2 H), 1.84-2.35 (m, 9 H), 2.38-2.61 (m, 1 H), 2.43 (s, 3 H), 2.98-3.26 (m, 1 H), 3.31-3.75 (m, 5 H), 6.86 (s, 1 H), 7.41-8.08 (m, 11 H);<br>MS m/z 495.9 (M + H)$^+$ |
| 73 | 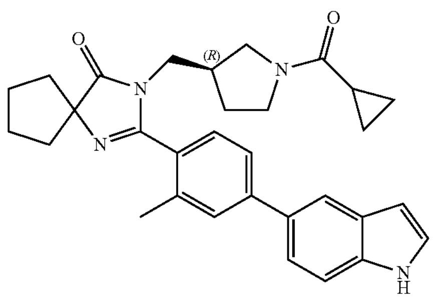 | 3-{[(3R)-1-(Cyclopropylcarbonyl)pyrrolidin-3-yl]methyl}-2-[4-(1H-indol-5-yl)-2-methylphenyl]-1,3-diazaspiro[4.4]non-1-en-4-one<br>$^1$H NMR (400 MHz, CDCl$_3$) δ ppm 0.77 (d, J = 7.6 Hz, 2 H), 0.92-1.07 (m, 2 H), 1.42-1.68 (m, 2 H), 1.83-2.17 (m, 5 H), 2.18-2.38 (m, 4 H), 2.42 (s, 3 H), 2.44-2.61 (m, 1 H), 3.00-3.25 (m, 1 H), 3.30-3.75 (m, 5 H), 6.63 (br. s., 1 H), 7.29 (br. s., 1 H), 7.39-7.52 (m, 3 H), 7.61-7.70 (m, 2 H), 7.90 (s, 1 H), 8.45 (br. s., 1 H);<br>MS m/z 495.0 (M + H)$^+$ |
| 93 | 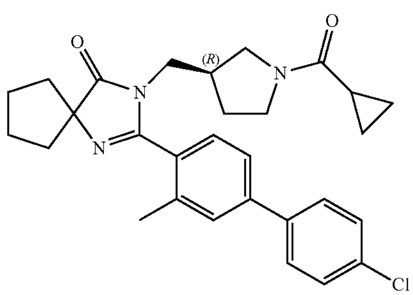 | 2-(4'-Chloro-3-methylbiphenyl-4-yl)-3-{[(3R)-1-(cyclopropylcarbonyl)pyrrolidin-3-yl]methyl}-1,3-diazaspiro[4.4]non-1-en-4-one<br>$^1$H NMR (400 MHz, CDCl$_3$) δ ppm 0.71-0.85 (m, 2 H), 0.92-1.07 (m, 2 H), 1.39-1.71 (m, 2 H), 1.82-2.31 (m, 8 H), 2.33-2.59 (m, 1 H), 2.42 (s, 3 H), 2.95-3.27 (m, 1 H), 3.30-3.74 (m, 5 H), 7.43-7.52 (m, 3 H), 7.56 (d, J = 9.1 Hz, 4 H);<br>MS m/z 489.9 (M + H)$^+$ |
| 3 | 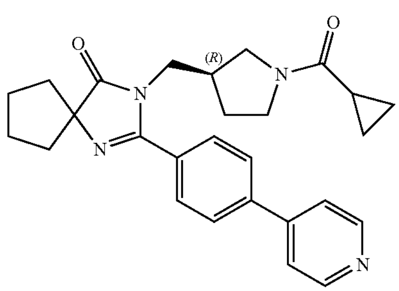 | 3-{[(3R)-1-(Cyclopropylcarbonyl)pyrrolidin-3-yl]methyl}-2-(4-pyridin-4-ylphenyl)-1,3-diazaspiro[4.4]non-1-en-4-one<br>MS m/z 443.2 (M + H)$^+$ |
| 4 | 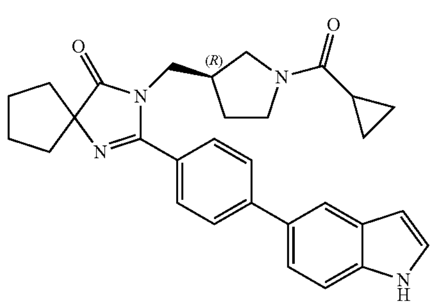 | 3-{[(3R)-1-(Cyclopropylcarbonyl)pyrrolidin-3-yl]methyl}-2-[4-(1H-indol-5-yl)phenyl]-1,3-diazaspiro[4.4]non-1-en-4-one<br>$^1$H NMR (400 MHz, CDCl$_3$) δ ppm 0.78 (dd, J 7.6, 3.0 Hz, 2 H), 0.90-1.06 (m, 2 H), 1.39-1.76 (m, 2 H), 1.84-2.67 (m, 10 H), 3.06-3.78 (m, 4 H), 3.84-4.02 (m, 2 H), 6.64 (br. s., 1 H), 7.29 (br. s., 1 H), 7.41-7.52 (m, 2 H), 7.76-7.82 (m, 2 H), 7.83-7.90 (m, 2 H), 7.93 (s, 1 H), 8.51-8.62 (m, 1 H);<br>MS m/z 481.3 (M + H)$^+$ |

-continued

| ID No. | Structure | Compound Name & Physical Data |
|---|---|---|
| 5 | 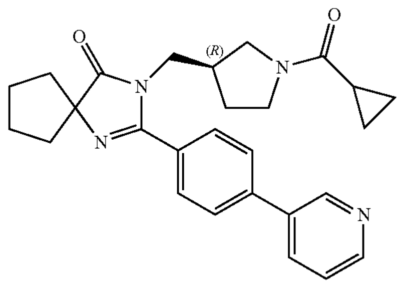 | 3-{[(3R)-1-(Cyclopropylcarbonyl)pyrrolidin-3-yl]methyl}-2-(4-pyridin-3-ylphenyl)-1,3-diazaspiro[4.4]non-1-en-4-one<br>MS m/z 443.2 (M + H)⁺ |
| 22 | 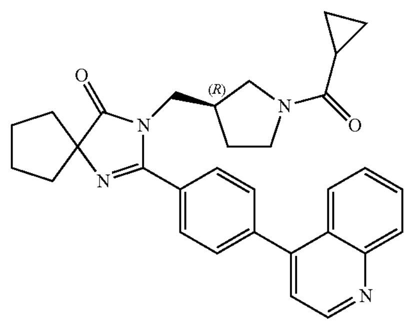 | 3-{[(3R)-1-(Cyclopropylcarbonyl)pyrrolidin-0 3-yl]methyl}-2-(4-quyinolin-4-ylphenyl)-1,3-diazaspiro[4.4]non-1-en-4-one<br>MS m/z 493.3 (M + H)⁺ |
| 82 | 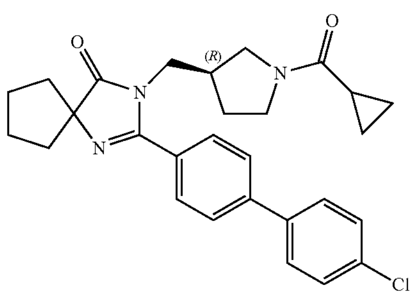 | 2-(4'-Chlorobiphenyl-4-yl)-3-{[(3R)-1-(cyclopropylcarbonyl)pyrrolidin-3-yl]phenyl}-3-diazaspiro[4.4]non-1-en-4-one<br>$^1$H NMR (400 MHz, CDCl$_3$) δ ppm 0.70-0.86 (m, 2 H), 0.98 (br. s., 2 H), 1.41-2.33 (m, 10 H), 2.35-2.64 (m, 1 H), 3.03-3.32 (m, 1 H), 3.32-3.63 (m, 2 H), 3.63-3.76 (m, 1 H), 3.77-3.94 (m, 2 H), 7.48 (d, 2 H), 7.58 (d, J = 8.6 Hz, 2 H), 7.80 (s, 4 H);<br>MS m/z 476.1 (M + H)⁺ |
| 83 | 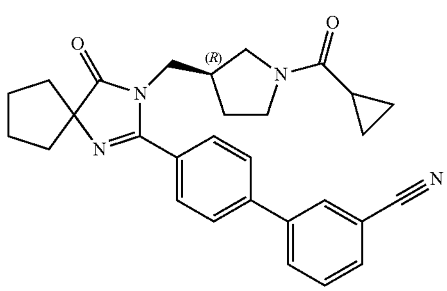 | 4'-(3-{[(3R)-1-(Cyclopropylcarbonyl)pyrrolidin-3-yl]methyl}-4-oxo-1,3-diazaspiro[4.4]non-1-en-2-yl)biphenyl-3-carbonitrile<br>MS m/z 467.3 (M + H)⁺ |
| 84 | 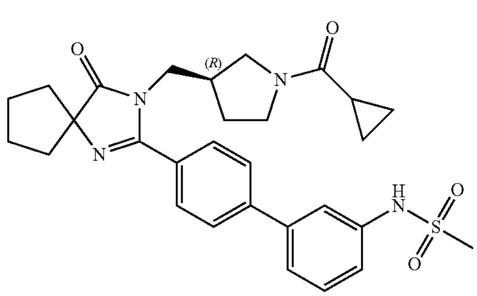 | N-[4'-(3-{(3R)-1-(Cyclopropylcarbonyl)pyrrolidin-3-yl]methyl}-4-oxo-1,3-diazaspiro[4.4non-1-en-2-yl)biphenyl-3-yl]methanesulfonamide<br>$^1$H NMR (400 MHz, CDCl$_3$) δ ppm 0.71-0.85 (m, 2 H), 0.91-1.06 (m, 2 H), 1.45-1.81 (m, 2 H), 1.92-2.18 (m, 5 H), 2.19-2.46 (m, 4 H), 2.47-2.78 (m, 1 H), 3.01 (s, 3 H), 3.04-4.00 (m, 6 H), 7.16-7.24 (m, 2 H), 7.25-7.31 (m, 1 H), 7.32-7.42 (m, 1 H), 7.55-7.65 (m, 2 H), 7.78-7.89 (m, 2 H), 8.06 (br. s., 1 H);<br>MS m/z 535.2 (M + H)⁺ |

-continued

| ID No. | Structure | Compound Name & Physical Data |
|---|---|---|
| 85 | 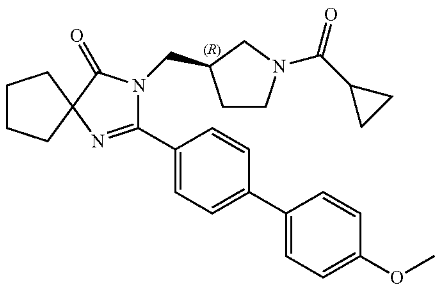 | 3-{[(3R)-1-(Cyclopropylcarbonyl)pyrrolidin-3-yl]methyl}-2-(4'-methoxybiphenyl-4-yl)-1,3-diazaspiro[4.4]non-1-en-4-one<br>$^1$H NMR (400 MHz, CDCl$_3$) δ ppm 0.68-0.83 (m, 2 H), 0.92-1.03 (m, 2 H), 1.38-1.72 (m, 2 H), 1.84-2.34 (m, 8 H), 2.35-2.63 (m, 1 H), 3.05-3.31 (m, 1 H), 3.31-3.75 (m, 3 H), 3.80-3.96 (m, 4 H), 7.03 (d, J = 8.6 Hz, 2 H), 7.60 (d, J = 8.6 Hz, 2 H), 7.78 (s, 4 H);<br>MS m/z 472.2 (M + H)$^+$ |
| 18 | 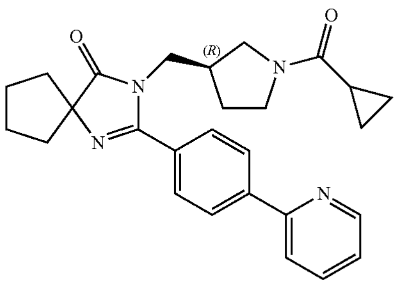 | 3-{[(3R)-1-(Cyclopropylcarbonyl)pyrrolidin-3-yl]methyl}-2-(4-pyridin-2-ylphenyl)-1,3-diazaspiro[4.4]non-1-en-4-one<br>MS m/z 443.3 (M + H)$^+$ |
| INT-E | 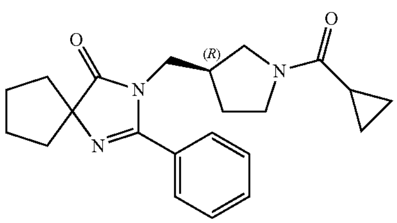 | 3-{[(3R)-1-(Cyclopropylcarbonyl)pyrrolidin-3-yl]methyl}-2-phenyl-1,3-diazaspiro[4.4]non-1-en-4-one<br>MS m/z 366.3 (M + H)$^+$ |
| 33 | 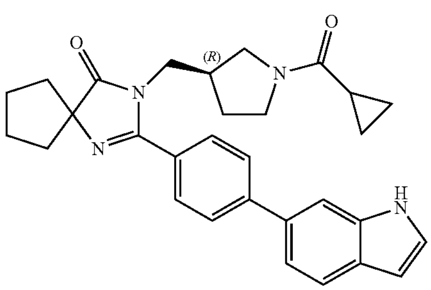 | 3-{[(3R)-1-(Cyclopropylcarbonyl)pyrrolidin-3-yl]methyl}-2-[4-(1H-indol-6-yl)phenyl]-1,3-diazaspiro[4.4]non-1-en-4-one<br>$^1$H NMR (400 MHz, CDCl$_3$) δ ppm 0.77 (dd, J = 7.6, 2.5 Hz, 2 H), 0.91-1.03 (m, 2 H), 1.41-1.72 (m, 2 H), 1.88-2.36 (m, 9 H), 2.39-2.63 (m, 1 H), 3.28 (dd, J = 10.1, 7.6 Hz, 1 H), 3.32-3.75 (m, 3 H), 3.83-3.96 (m, 2 H), 6.61 (br. s., 1 H), 7.32 (t, J = 2.8 Hz, 1 H), 7.39 (d, J = 9.1 Hz, 1 H), 7.65 (s, 1 H), 7.74 (d, J = 8.6 Hz, 1 H), 7.76-7.81 (m, 2 H), 7.82-7.88 (m, 2 H), 8.60-8.70 (m, 1 H);<br>MS m/z 481.2 (M + H)$^+$ |
| 34 | 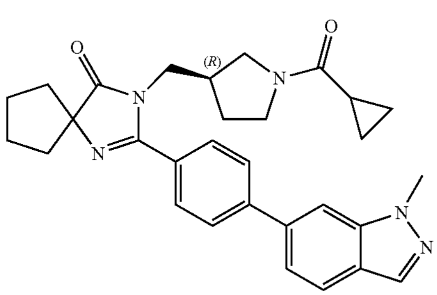 | 3-{[(3R)-1-(Cyclopropylcarbonyl)pyrrolidin-3-yl]methyl}-2-[4-(1-methyl-1H-indazol-6-yl)phenyl]-1,3-diazaspiro[4.4]non-1-en-4-one<br>$^1$H NMR (400 MHz, CDCl$_3$) δ ppm 0.72-0.84 (m, 2 H), 0.94-1.04 (m, 2 H), 1.41-1.76 (m, 2 H), 1.86-2.36 (m, 9 H), 2.38-2.67 (m, 1 H), 3.06-3.34 (m, 1 H), 3.34-3.65 (m, 2 H), 3.65-3.77 (m, 1 H), 3.80-4.01 (m, 2 H), 4.18 (s, 3 H), 7.44 (d, J = 8.1 Hz, 1 H), 7.64 (s, 1 H), 7.82-7.88 (m, 3 H), 7.89-7.95 (m, 2 H), 8.07 (s, 1 H);<br>MS m/z 496.4 (M + H)$^+$ |

-continued

| ID No. | Structure | Compound Name & Physical Data |
|---|---|---|
| 35 | 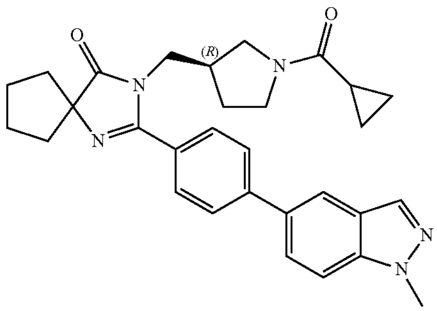 | 3-{[(3R)-1-(Cyclopropylcarbonyl)pyrrolidin-3-yl]methyl}-2-[4-(1-methyl-1H-indazol-5-yl)phenyl]-1,3-diazaspiro[4.4]non-1-en-4-one<br>¹H NMR (400 MHz, CDCl₃) δ ppm 0.70-0.83 (m, 2 H), 0.93-1.04 (m, 2 H), 1.40-1.75 (m, 2 H), 1.87-2.36 (m, 9 H), 2.38-2.67 (m, 1 H), 3.06-3.33 (m, 1 H), 3.33-3.76 (m, 3 H), 3.81-3.98 (m, 2 H), 4.13 (s, 3 H), 7.53 (d, J = 9.1 Hz, 1 H), 7.70 (d, J = 9.1 Hz, 1 H), 7.83 (d, 2 H), 7.88 (d, 2 H),<br>8.01 (s, 1 H), 8.10 (s, 1 H);<br>MS m/z 496.4 (M + H)⁺ |
| 91 | 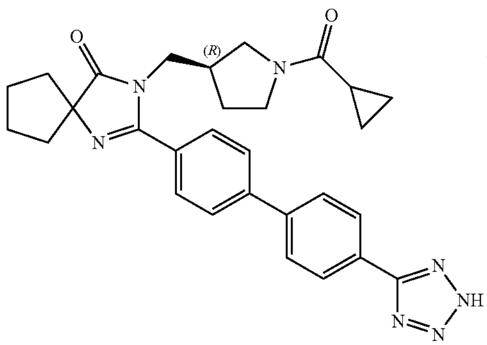 | 3-{[(3R)-1-(Cycloprropylcarbonyl)pyrrolidin-3-yl]methyl}-2-[4'-(2H-tetrazol-5-yl)biphenyl-4-yl]-1,3-diazaspiro[4.4]non-1-en-4-one<br>MS m/z 509.9 (M + H)⁺ |
| 92 | 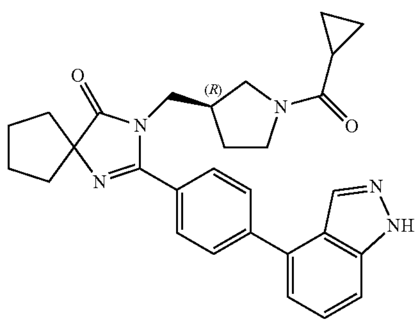 | 3-{[(3R)-1-(Cyclopropylcarbonyl)pyrrolidin-3-yl]methyl}-2-[4-(1H-indazol-4-yl)phenyl]-1,3-diazaspiro[4.4]non-1-en-4-one<br>¹H NMR (400 MHz, CDCl₃) δ ppm 0.65-0.79 (m, 2 H), 0.87-1.03 (m, 2 H), 1.43-1.73 (m, 2 H), 1.81-2.01 (m, 4 H), 2.02-2.20 (m, 5 H), 2.34-2.59 (m, 1 H), 3.02-3.30 (m, 1 H), 3.30-3.85 (m, 5 H), 7.27-7.32 (m, 1 H), 7.43-7.52 (m, 1 H), 7.52-7.59 (m, 1 H), 7.69-7.79 (m, 2 H), 7.79-7.89 (m, 2 H), 8.19 (br. s., 1 H);<br>MS m/z 482.0 (M + H)⁺ |
| 94 | 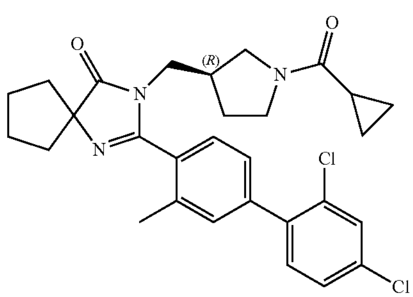 | 3-{[(3R)-1-(Cyclopropylcarbonyl)pyrrolidin-3-yl]methyl}-2-(2',4'-dichloro-3-methylbiphenyl-4-yl)-1,3-diazaspiro[4.4]non-1-en-4-one<br>¹H NMR (400 MHz, CDCl₃) δ ppm 0.63-0.83 (m, 2 H), 0.85-1.05 (m, 2 H), 1.38-1.71 (m, 2 H), 1.74-2.19 (m, 9 H), 2.37 (s, 3 H), 2.39-2.52 (m, 1 H), 2.95-3.24 (m, 1 H), 3.25-3.41 (m, 1 H), 3.43-3.71 (m, 4 H), 7.27-7.31 (m, 1 H), 7.31-7.43 (m, 4 H), 7.52 (s, 1 H);<br>MS m/z 523.8 (M + H)⁺ |
| 39 | 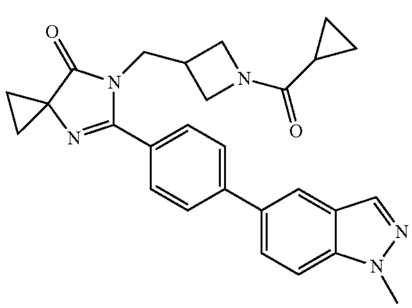 [SMILES: Cn1ncc2cc(-c3ccc(C4=NC5(CC5)C(=O)N4CC4CN(C(=O)C5CC5)C4)cc3)ccc21] | 6-{[1-(Cyclopropylcarbonyl)azetidin-3-yl]methyl}-5-[4-(1-methyl-1H-indazol-5-yl)phenyl]-4,6-diazaspiro[2.4]hept-4-en-7-one<br>1H NMR (300 MHz, CDCl₃) δ ppm 0.63-0.76 (m, 2 H), 0.84-0.96 (m, 2 H), 1.19-1.37 (m, 2 H), 1.73-1.83 (m, 2 H), 1.83-1.93 (m, 2 H), 2.77-2.94 (m, 1 H), 3.61 (dd, J = 9.8, 5.6 Hz, 1 H), 3.91-4.04 (m, 2 H), 4.04-4.11 (m, 1 H), 4.14 (s, 3 H), 4.24 (t, J = 8.2 Hz, 1 H), 7.51 (d, J = 8.7 Hz, 1 H),<br>7.63-7.74 (m, 3 H), 7.79 (d, J = 8.2 Hz, 2 H), 7.99 (s, 1 H), 8.07 (s, 1 H);<br>MS m/z 454 (M + H)⁺ |

| ID No. | Structure | Compound Name & Physical Data |
|---|---|---|
| 38 | 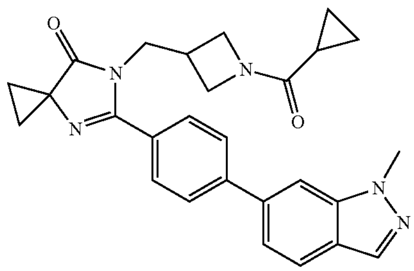 [SMILES: Cn1ncc2ccc(-c3ccc(C4=NC5(CC5)C(=O)N4CC4CN(C(=O)C5CC5)C4)cc3)cc21] | m.p. 191.8° C.<br>6-{[1-(Cyclopropylcarbonyl)azetidin-3-yl]methyl}-5-[4-(1-methyl-1H-indazol-6-yl)phenyl]-4,6-diazaspiro[2.4]hept-4-en-7-one<br>1H NMR (300 MHz, CDCl$_3$) δ ppm 0.64-0.74 (m, 2 H), 0.87-0.94 (m, 2 H), 1.23-1.36 (m, 2 H), k 1.75-1.84 (m, 2 H), 1.84-1.93 (m, 2 H), 2.79-2.94 (m, 1 H), 3.61 (dd, J = 9.8, 5.6 Hz, 1 H), 3.90-4.04 (m, 2 H), 4.04-4.14 (m, 1 H), 4.16 (s, 3 H), 4.25 (t, J = 8.3 Hz, 1 H), 7.44 (dd, J = 8.5, 1.2 Hz,<br>1 H), 7.62 (s, 1 H), 7.70 (d, J = 8.2 Hz, 2 H), 7.80-7.88 (m, 3 H), 8.04 (s, 1 H);<br>MS m/z 454 (M + H)$^+$<br>m.p. 174.6° C. |
| 51 | 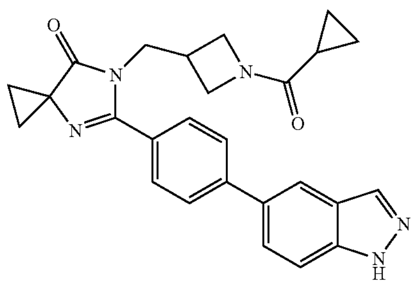 [SMILES: O=C(C1CC1)N1CC(CN2C(=O)C3(CC3)N=C2c2ccc(-c3ccc4[nH]ncc4c3)cc2)C1] | 6-{[1-(Cyclopropylcarbonyl)azetidin-3-yl]methyl}-5-[4-(1H-indazol-5-yl)phenyl]-4,6-diazaspiro[2.4]hept-4-en-7-one<br>1H NMR (300 MHz, CDCl$_3$) δ ppm 0.63-0.75 (m, 2 H), 0.87-0.97 (m, 2 H), 1.23-1.37 (m, 1 H), 1.74-1.84 (m, 2 H), 1.84-1.93 (m, 2 H), 2.76-2.96 (m, 1 H), 3.62 (dd, J = 9.8, 5.6 Hz, 1 H), 3.90-4.16 (m, 4 H), 4.25 (t, J = 89.3 Hz, 1 H), 7.59 (d, J = 8.7<br>Hz, 1 H), 7.64-7.72 (m, 3 H), 7.79 (d, J = 8.4 Hz, 2 H), 8.02 (s, 1 H), 8.16 (s, 1 H), 10.39 (br. s., 1 H);<br>MS m/z 440 (M + H)$^+$<br>m.p. >300° C. |
| 40 | 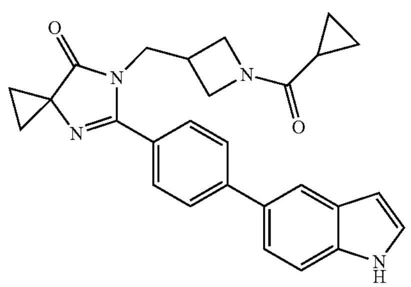 [SMILES: O=C(C1CC1)N1CC(CN2C(=O)C3(CC3)N=C2c2ccc(-c3ccc4[nH]ccc4c3)cc2)C1] | 6-{[1-(Cyclopropylcarbonyl)azetidin-3-yl]methyl}-5-[4-(1H-indol-5-yl)phenyl]-4,6-diazaspiro[2.4]hept-4-en-7-one<br>1H NMR (300 MHz, CDCl$_3$) δ ppm 0.62-0.77 (m, 2 H), 0.83-1.01 (m, 2 H), 1.22-1.37 (m, 1 H), 1.73-1.83 (m, 2 H), 1.83-1.92 (m, 2 H), 2.73-2.97 (m, 1 H), 3.63 (dd, J = 9.9, 5.6 Hz, 1 H), 3.88-4.16 (m, 4 H), 4.23 (t, J = 8.2 Hz, 1 H), 6.58-6.69 (m, 1 H), 7.29 (d, J = 2.9 Hz, 1 H), 7.44-7.52 (m, 2 H), 7.64 (d, J = 8.2 Hz, 2 H), 7.80 (d, J = 8.2 Hz, 2 H), 7.92 (s, 1 H), 8.43 (br. s., 1 H);<br>MS m/z 439 (M + H)$^+$<br>m.p. 190.8° C. |
| 43 | 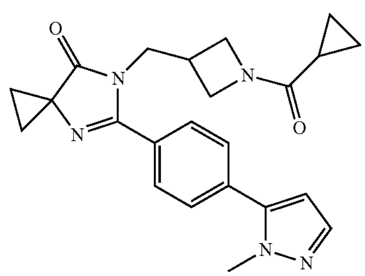 [SMILES: Cn1nccc1-c1ccc(C2=NC3(CC3)C(=O)N2CC2CN(C(=O)C3CC3)C2)cc1] | 6-{[1-(Cyclopropylcarbonyl)azetidin-3-yl]methyl}-5-[4-(1-methyl-1H-pyrazol-5-yl)phenyl]-4,6-diazaspiro[2.4]hept-4-en-7-one<br>MS m/z 404 (M + H)$^+$<br>m.p. 164.9° C. |
| 42 | 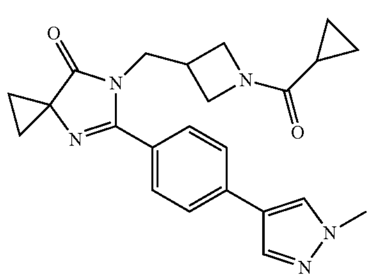 [SMILES: Cn1cc(-c2ccc(C3=NC4(CC4)C(=O)N3CC3CN(C(=O)C4CC4)C3)cc2)cn1] | 6-{[1-(Cyclopropylcarbonyl)azetidin-3-yl]methyl}-5-[4-(1-methyl-1H-pyrazol-4-yl)phenyl]-4,6-diazaspiro[2.4]hept-4-en-7-one<br>MS m/z 404 (M + H)$^+$<br>m.p. 164.7° C. |

-continued

| ID No. | Structure | Compound Name & Physical Data |
|---|---|---|
| 41 | 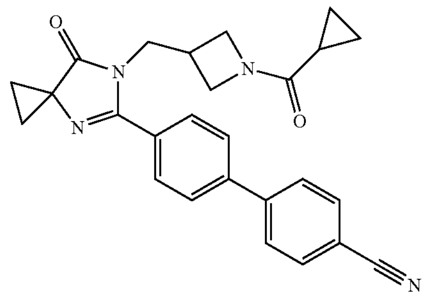 [SMILES: N#Cc1ccc(-c2ccc(C3=NC4(CC4)C(=O)N3CC3CN(C(=O)C4CC4)C3)cc2)cc1] | 4'-(6-{[1-(Cyclopropylcarbonyl)azetidin-3-yl]methyl}-7-oxo-4,6-diazaspiro[2.4]hept-4-en-5-yl)biphenyl-4-carbonitrile<br>1H NMR (300 MHz, CDCl$_3$) δ ppm 0.63-0.76 (m, 2 H), 0.85-0.96 (m, 2 H), 1.23-1.36 (m, 1 H), 1.74-1.83 (m, 2 H), 1.83-1.94 (m, 2 H), 2.70-2.95 (m, 1 H), 3.57 (dd, J = 9.9, 5.6 Hz, 1 H), 3.87-4.02 (m, 3 H), 4.02-4.16 (m, 1 H), 4.24 (t, J = 8.3 Hz, 1 H), 7.65-7.85 (m, 8 H);<br>MS m/z 425 (M + H)$^+$.<br>m.p. 182.8° C. |
| 52 | 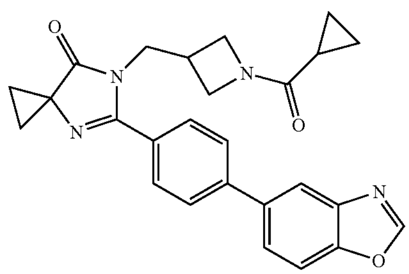 [SMILES: O=C(C1CC1)N1CC(CN2C(=O)C3(CC3)N=C2c2ccc(-c3ccc4ocnc4c3)cc2)C1] | 5-[4-(1,3-Benzoxazol-5-yl)phenyl]-6-{[1-(cyclopropylcarbonyl)azetidin-3-yl]methyl}-4,6-diazaspiro[2.4]hept-4-en-7-one<br>1H NMR (300 MHz, CDCl$_3$) δ ppm 0.65-0.78 (m, 2 H), 0.91 (t, J = 3.7 Hz, 2 H), 1.23-1.35 (m, 1 H), 1.75-1.84 (m, 2 H), 1.88 (quin, J = 3.5 Hz, 2 H), 2.77-2.95 (m, 1 H), 3.62 (dd, J = 9.9, 5.6 Hz, 1 H), 3.88-4.16 (m, 4 H), 4.25 (t, J = 8.2 Hz, 1 H), 7.64-7.75 (m, 4 H), 7.79 (d, J = 8.4 Hz, 2 H), 8.05 (s, 1 H), 8.17 (s, 1 H);<br>MS m/z 441 (M + H)$^+$ |
| 53 | 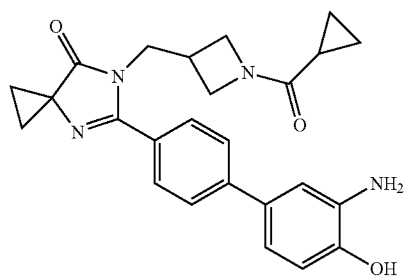 [SMILES: Nc1cc(-c2ccc(C3=NC4(CC4)C(=O)N3CC3CN(C(=O)C4CC4)C3)cc2)ccc1O] | 5-(3'-Amino-4'-hydroxybiphenyl-4-yl)-6-{[1-(cyclopropylcarbonyl)azetidin-3-yl]methyl}-4,6-diazaspiro[2.4]hept-4-en-7-one<br>MS m/z 459 (M + H)$^+$ |
| 54 | 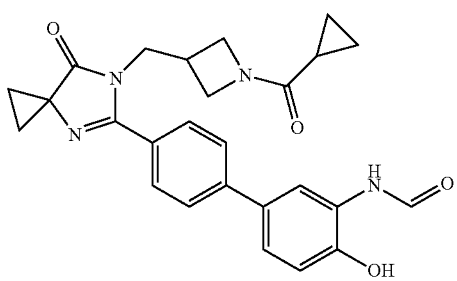 [SMILES: O=CNc1cc(-c2ccc(C3=NC4(CC4)C(=O)N3CC3CN(C(=O)C4CC4)C3)cc2)ccc1O] | N-[4'-(6-{[-(Cyclopropylcarbonyl)azetidin-3-yl]methyl}-7-oxo-4,6-diazaspiro[2.4]hept-4-en-5-yl)-4-hydroxybiphenyl-3-yl]formamide<br>MS m/z 431 (M + H)$^+$ |
| 50 | 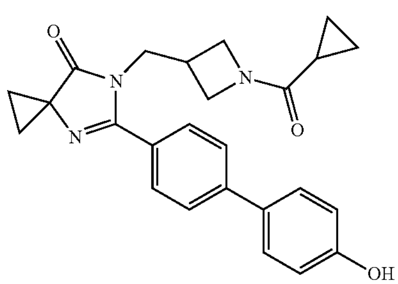 [SMILES: O=C(C1CC1)N1CC(CN2C(=O)C3(CC3)N=C2c2ccc(-c3ccc(O)cc3)cc2)C1] | 6-{[1-(Cyclopropylcarbonyl)azetidin-3-yl]methyl}-5-(4'-hydroxybiphenyl-4-yl)-4,6-diazaspiro[2.4]hept-4-en-7-one<br>1H NMR (300 MHz, CDCl$_3$) δ ppm 0.65-0.80 (m, 2 H), 0.89-1.01 (m, 2 H), 1.23-1.38 (m, 1 H), 1.73-1.84 (m, 2 H), 1.84-1.95 (m, 2 H), 2.75-2.96 (m, 1 H), 3.61 (dd, J = 10.0, 5.7 Hz, 1 H), 3.84-4.15 (m, 4 H), 4.27 (t, J = 8.5 Hz, 1 H), 6.82 (d, J = 8.5 Hz, 2 H), 7.41 (d, J = 8.5 Hz, 2 H), 7.52-7.65 (m, 4 H), 7.67 (s, 1 H);<br>MS m/z 416 (M + H)$^+$ |

| ID No. | Structure | Compound Name & Physical Data |
|---|---|---|
| 120 | 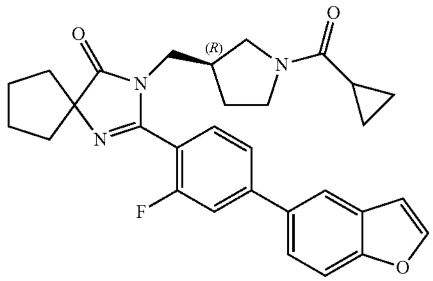 | 2-[4-(1-Benzofuran-5-yl)-2-fluorophenyl]-3-{[(3R)-1-(cyclopropylcarbonyl)pyrrolidin-3-yl]methyl}-1,3-diazaspiro[4.4]non-1-en-4-one<br>¹H NMR (400 MHz, CDCl₃) δ ppm 0.76 (d, J = 8.1 Hz, 2 H), 0.90-1.07 (m, 2 H), 1.41-1.73 (m, 2 H), 1.81-2.26 (m, 9 H), 2.35-2.63 (m, 1 H), 2.97-3.28 (m, 1 H), 3.28-3.79 (m, 5 H), 6.87 (s, 1 H), 7.49-7.59 (m, 2 H), 7.63 (d, J = 8.6 Hz, 2 H), 7.68-7.80 (m, 2 H), 7.86 (s, 1 H);<br>MS m/z 499.9 (M + H)⁺ |
| 121 | 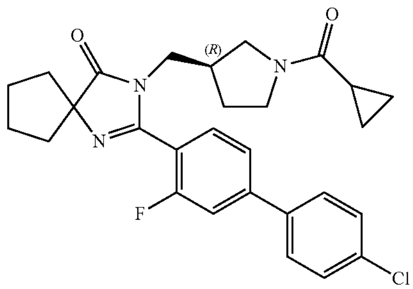 | 2-(4'-Chloro-3-fluorobiphenyl-4-yl)-3-{[(3R)-1-(cyclopropylcarbonyl)pyrrolidin-3-yl]methyl}-1,3-diazaspiro[4.4]non-1-en-4-one<br>¹H NMR (400 MHz, CDCl₃) δ ppm 0.70-0.89 (m, 2 H), 0.90-1.11 (m, 2 H), 1.39-1.72 (m, 2 H), 1.81-2.28 (m, 9 H), 2.34-2.62 (m, 1 H), 2.95-3.28 (m, 1 H), 3.29-3.77 (m, 5 H), 7.42-7.52 (m, 3 H), 7.56 (d, J = 8.6 Hz, 3 H), 7.73 (t, J = 7.6 Hz, 1 H);<br>MS m/z 493.9 (M + H)⁺ |
| 156 | 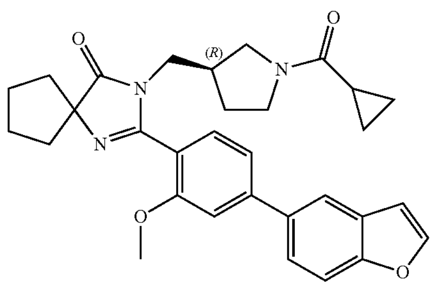 | 2-[4-(1-Benzofuran-5-yl)-2-methoxyphenyl]-3-{[(3R)-1-(cyclopropylcarbonyl)pyrrolidin-3-yl]methyl}-1,3-diazaspiro[4.4]non-1-en-4-one<br>¹H NMR (400 MHz, CDCl₃) δ ppm 0.67-0.84 (m, 2 H), 0.90-1.02 (m, 2 H), 1.38-1.66 (m, 2 H), 1.81-2.64 (m, 10 H), 2.98-3.22 (m, 1 H), 3.28-3.78 (m, 5 H), 4.00 (s, 3 H), 6.86 (d, 1 H), 7.24-7.30 (m, 1 H), 7.40 (d, J = 7.6 Hz, 1 H), 7.51-7.58 (m, 1 H), 7.62 (d, 1 H), 7.65-7.76 (m, 2 H), 7.85 (s, 1 H);<br>MS m/z 511.9 (M + H)⁺ |
| 157 | 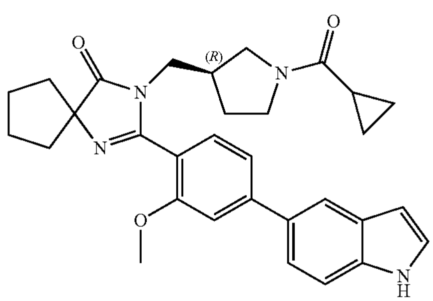 | 3-{[(3R)-1-(Cyclopropylcarbonyl)pyrrolidin-3-yl]methyl}-2-[4-(1H-indol-5-yl)-2-methoxyphenyl]-1,3-diazaspiro[4.4]non-1-en-4-one<br>¹H NMR (400 MHz, CDCl₃) δ ppm 0.67-0.82 (m, 2 H), 0.89-1.03 (m, 2 H), 1.38-1.64 (m, 2 H), 1.82-2.63 (m, 10 H), 2.99-3.20 (m, 1 H), 3.26-3.85 (m, 5 H), 3.93-4.04 (m, 3 H), 6.64 (br. s., 1 H), 7.29 (d, J = 7.1 Hz, 2 H), 7.34-7.44 (m, 2 H), 7.44-7.51 (m, 1 H), 7.61-7.71 (m, 1 H), 7.89 (s, 1 H), 8.48-8.64 (m, 1 H);<br>MS m/z 511.0 (M + H)⁺ |
| 178 | 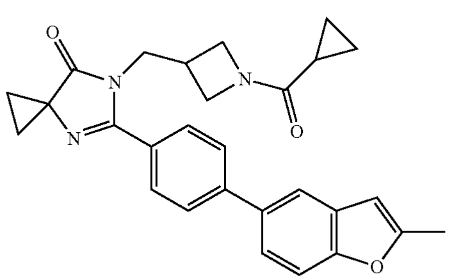 [SMILES: Cc1cc2cc(-c3ccc(C4=NC5(CC5)C(=O)N4CC4CN(C(=O)C5CC5)C4)cc3)ccc2o1] | 6-{[1-(Cyclopropylcarbonyl)azetidin-3-yl]methyl}-5-[4-(2-methyl-1-benzofuran-5-yl)phenyl]-4,6-diazaspiro[2.4]hept-4-en-7-one<br>¹H NMR (300 MHz, CDCl₃) δ ppm 0.62-0.73 (m, 2 H), 0.80-0.99 (m, 2 H), 1.24-1.38 (m, 2 H), 1.74-1.82 (m, 2 H), 1.82-1.93 (m, 2 H), 2.50 (s, 3 H), 2.73-2.94 (m, 1 H), 3.62 (dd, J = 9.6, 5.6 Hz, 1 H), 3.85-4.15 (m, 3 H), 4.23 (t, J = 8.2 Hz, 1 H), 6.44 (s, 1 H), 7.40-7.55 (m, 2 H), 7.65 (d, J = 8.1 Hz, 2 H), 7.72 (s, 1 H), 7.77 (d, J = 8.2 Hz, 2 H);<br>MS m/z 454 (M + H)⁺<br>m.p. 166.3° C. |

| ID No. | Structure | Compound Name & Physical Data |
|---|---|---|
| 179 | 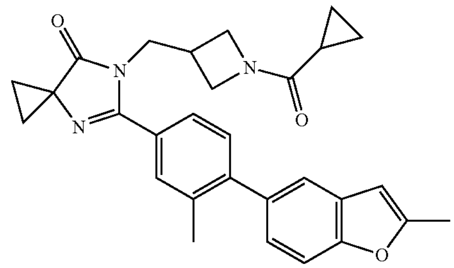 [SMILES: Cc1cc2cc(-c3ccc(C4=NC5(CC5)C(=O)N4CC4CN(C(=O)C5CC5)C4)cc3C)ccc2o1] | 6-{[1-(Cyclopropylcarbonyl)azetidin-3-yl]methyl}-5-[3-methyl-4-(2-methyl-1-benzofuran-5-yl)phenyl]-4,6-diazaspiro[2.4]hept-4-en-7-one<br>$^1$H NMR (300 MHz, CDCl$_3$) δ ppm 0.66-0.78 (m, 2 H), 0.85-1.01 (m, 2 H), 1.27-1.40 (m, 1 H), 1.70-1.82 (m, 2 H), 1.82-1.95 (m, 2 H), 2.34 (s, 3 H), 2.50 (s, 3 H), 2.75-3.02 (m, 1 H), 3.63 (dd, J = 8.6, 5.6 Hz, 1 H), 3.86-4.16 (m, 4 H), 4.25 (t, H = 7.9 Hz, 1 H), 6.41 (s, 1 H), 7.15 (d, J = 8.1 Hz, 1 H), 7.44-7.64 (m, 5 H); MS m/z 468 (M + H)$^+$<br>m.p. 170.1° C. |
| 180 | 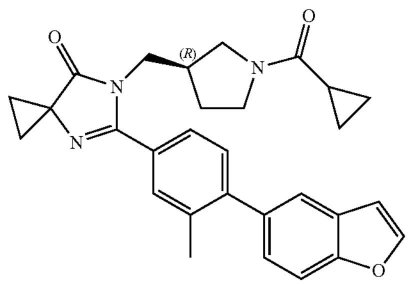 | 5-[4-(1-Benzofuran-5-yl)-3-methylphenyl]-6-{[(3R)-1-(cyclopropylcarbonyl)pyrrolidin-3-yl]methyl}-4,6-diazaspiro[2.4]hept-4-en-7-one<br>$^1$H NMR (300 MHz, CDCl$_3$) δ ppm 0.66-0.78 (m, 2 H), 0.92-1.02 (m, 2 H), 1.40-2.11 (m, 7 H), 2.34 (s, m3 H), 2.39-2.71 (m, 1 H), 2.96-3.98 (m, 6 H), 6.82 (s, 1 H), 7.18-7.31 (m, 1 H), 7.35-7.48 (m, 2 H), 7.49-7.61 (m, 3 H), 7.69 (s, 1 H); MS m/z 468 (M + H)$^+$<br>m.p. 71.9° C. |

Example 2

(R)-5-(4-(Benzofuran-5-yl)phenyl)-6-((1-(cyclopropanecarbonyl)pyrrolidin-3-yl)methyl)-4,6-diazaspiro[2.4]hept-4-en-7-one (Compound #58)

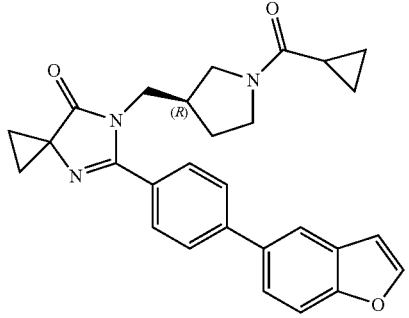

STEP A: (R)-Cyclopropyl-(3-(hydroxymethyl)pyrrolidin-1-yl)methanone

To a solution of (R)-pyrrolidin-3-ylmethanol (3.45 g, 25.07 mmol) and DIPEA (8.50 mL, 50 mmol) in DCM (100 mL) was added at 0° C. cyclopropanecarbonyl chloride (2.27 mL, 25.1 mmol). After stirring for 5 h at room temperature, the reaction mixture was partitioned between DCM and aqueous 1.0M NaOH (100 mL) and water (50 mL). The organic phase was washed with brine, dried over MgSO$_4$, filtered and concentrated in vacuo to yield a residue. The residue was purified by flash chromatography (silica gel, 0 to 10% MeOH/DCM) to yield (R)-cyclopropyl (3-(hydroxymethyl)pyrrolidin-1-yl)methanone (2.53 g, 60%).

$^1$H NMR (300 MHz, CDCl$_3$) δ ppm 0.64-0.84 (m, 2H), 0.89-1.09 (m, 2H), 1.42-2.69 (m, 5H), 3.24 (dd, J=12.1, 7.1 Hz, 0.5H), 3.34-3.52 (m, 1H), 3.52-3.89 (m, 4.5H); MS n/z 170 (M+H)$^+$.

STEP B: (R)-(1-(Cyclopropanecarbonyl)pyrrolidin-3-yl)methyl methanesulfonate

To a solution of (R)-cyclopropyl(3-(hydroxymethyl)pyrrolidin-1-yl)methanone (2.53 g, 14.95 mmol) and triethylamine (4.17 mL, 29.9 mmol) in DCM (70 mL) was added at 0° C. methanesulfonyl chloride (1.39 mL, 17.9 mmol). After stirring overnight at room temperature, the reaction mixture was partitioned between DCM (100 mL) and water (50 mL). The organic phase was washed with brine, dried over MgSO$_4$, filtered and concentrated in vacuo to yield a residue. The residue was purified by flash chromatography (silica gel, 0 to 10% MeOH/DCM) to yield (R)-(1-(cyclopropanecarbonyl)pyrrolidin-3-yl)methyl methanesulfonate (3.41 g, 92%).

$^1$H NMR (300 MHz, CDCl$_3$) δ ppm 0.64-0.88 (m, 2H), 0.87-1.11 (m, 2H), 1.50-2.31 (m, 3H), 2.53-2.88 (m, 1H), 3.03 (s, 1.5H), 3.05 (s, 1.5H), 3.20-3.37 (m, 0.5H), 3.38-3.56 (m, 1H), 3.57-3.96 (m, 2.5H), 4.05-4.39 (m, 2H); MS m/z 248 (M+H)$^+$.

STEP C: ((R)-5-(4-Bromophenyl)-6-((1-(cyclopropanecarbonyl)pyrrolidin-3-yl)methyl)-4,6-diazaspiro[2.4]hept-4-en-7-one To a stirring solution of 5-(4-bromophenyl)-4,6-diazaspiro[2.4]hept-4-en-7-one (1.53 g, 5.77 mmol) and (R)-(1-(cyclopropanecarbonyl) pyrrolidin-3-yl)methyl methanesulfonate (1.43 g, 5.77 mmol) in DMF (25 mL) was added Cs$_2$CO$_3$ (3.76 g, 11.5 mmol). After stirring at room temperature for 6 h at 65° C., the reaction mixture was filtered through a pad of diatomaceous earth and further washed with EtOAc (3×20 ml). The filtrate was concentrated and the residue was partitioned between EtOAc and water. The organic phase was washed with brine, dried over Na$_2$SO$_4$, filtered and concentrated in vacuo to yield a residue. The residue was purified by flash chromatography (silica gel, 100% EtOAc and then 0-10% MeOH/DCM) to yield (R)-5-(4-bromophenyl)-6-((1-(cyclopropanecarbonyl) pyrrolidin-3-yl)methyl)-4,6-diazaspiro[2.4]hept-4-en-7-one (1 g, 40%).

$^1$H NMR (300 MHz, CDCl$_3$) δ ppm 0.63-0.82 (m, 2H), 0.86-1.05 (m, 2H), 1.38-2.07 (m, 7H), 2.27-2.57 (m, 1H), 2.93-3.08 (m, 0.5H), 3.16-3.39 (m, 1H), 3.44-3.84 (m, 4.5H), 7.41-7.54 (m, 2H), 7.62-7.73 (m, 2H); MS m/z 416 (M+H)$^+$.

STEP D: (R)-5-(4-(Benzofuran-5-yl)phenyl)-6-((1-(cyclopropanecarbonyl)pyrrolidin-3-yl)methyl)-4,6-diazaspiro[2.4]hept-4-en-7-one To a solution of (R)-5-(4-bromophenyl)-6-((1-(cyclopropanecarbonyl)pyrrolidin-3-yl)methyl)-4,6-diazaspiro[2.4]hept-4-en-7-one (104 mg, 0.25 mmol) in acetonitrile (2 mL) was added 2-(benzofuran-5-yl)-4,4,5,5-tetramethyl-1,3,2-dioxaborolane (73.23 mg, 0.3 mmol), aqueous 1.0M Na$_2$CO$_3$ (0.5 mL, 0.5 mmol) and Bis(triphenylphosphine) palladium(II) chloride (9.12 mg, 0.013 mmol). The reaction mixture was bubbled with nitrogen for 5 min and heated to 85° C. for 2 h under nitrogen atmosphere. The resulting mixture was diluted with DCM and the organic layer was filtered and concentrated to yield a residue which was purified by flash chromatography (silica gel, 0-10% MeOH/DCM) and re-purified by reverse phase prep-HPLC to yield (R)-5-(4-(benzofuran-5-yl)phenyl)-6-((1-(cyclopropanecarbonyl)pyrrolidin-3-yl)methyl)-4,6-diazaspiro[2.4]hept-4-en-7-one (20 mg, 17%).

$^1$H NMR (300 MHz, CDCl$_3$) δ ppm 0.62-0.79 (m, 2H), 0.88-1.01 (m, 2H), 1.39-2.08 (m, 8H), 2.33-2.68 (m, 1H), 2.97-3.17 (m, 0.5H), 3.18-3.43 (m, 1H), 3.45-3.94 (m, 4.5H), 6.85 (d, J=1.8 Hz, 1H), 7.51-7.64 (m, 2H), 7.64-7.73 (m, 3H), 7.73-7.81 (m, 2H), 7.85 (s, 1H); MS m/z 454.0 (M+H)$^+$.

Following the procedure described in Example 2, above, selecting and substituting the appropriate reagents, starting materials, and purification methods, and adjusting reaction temperatures, times and other variables or parameters, as needed or desirable, as would be readily recognized by those skilled in the art, the following compounds of formula (I) of the invention were prepared.

| ID No. | Structure | Compound Name & Physical Data |
|---|---|---|
| 10 | 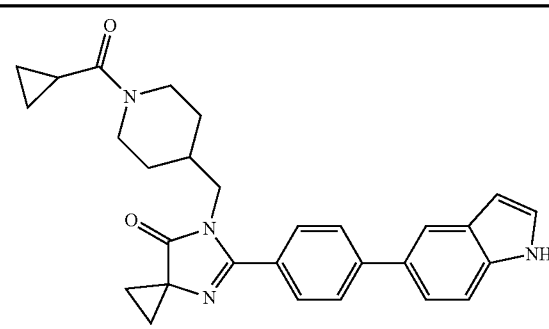 | 6-{[1-(Cyclopropylcarbonyl)piperidin-4-yl]methyl}-5-[4-(1H-indol-5-yl)phenyl]-4,6-diazaspiro[2.4]hept-4-en-7-one<br>$^1$H NMR (300 MHz, CDCl$_3$) δ ppm 0.59-0.82 (m, 2 H), 0.87-0.97 (m, 2 H), 0.97-1.17 (m, 2 H), 1.52-1.92 (m, 9 H), 2.34-2.65 (m, 1 H), 2.82-3.11 (m, 1 H), 3.60-3.76 (m, 1 H), 4.15 (d, J = 12.1 Hz, 1 H), 4.53 (d, J = 11.4 Hz, 1 H), 6.63 (t, J = 2.3 Hz, 1 H), 7.26 (d, J = 2.9 Hz, 1 H), 7.41-7.55 (m, 2 H), 7.64 (d, J = 8.4 Hz, 2 H), 7.79 (d, J = 8.4 Hz, 2 H), 7.93 (s, 1 H), 8.63 (br. s., 1 H);<br>MS m/z 467 (M + H)$^+$<br>m.p. 129.4° C. |
| 9 | 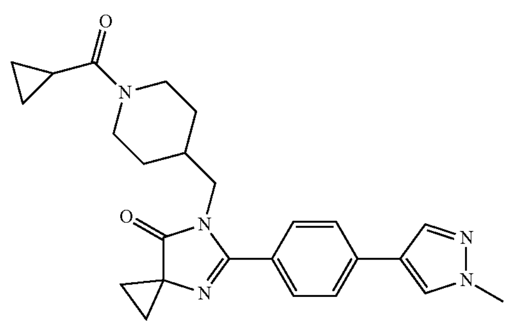 [SMILES: Cn1cc(-c2ccc(C3=NC4(CC4)C(=O)N3CC3CCN(C(=O)C4CC4)CC3)cc2)cn1] | 6-{[1-(Cyclopropylcarbonyl)piperidin-4-yl]methyl}-5-[4-(1-methyl-1H-pyrazol-4-yl)phenyl]-4,6-diazaspiro[2.4]hept-4-en-7-one<br>MS m/z 432 (M + H)$^+$<br>m.p. 144.5° C. |
| 8 | 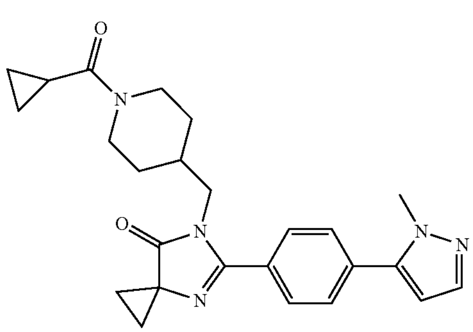 [SMILES: Cn1nccc1-c1ccc(C2=NC3(CC3)C(=O)N2CC2CCN(C(=O)C3CC3)CC2)cc1] | 6-{[1-(Cyclopropylcarbonyl)piperidin-4-yl]methyl}-5-[4-(1-methyl-1H-pyrazol-5-yl)phenyl]-4,6-diazaspiro[2.4]hept-4-en-7-one<br>MS m/z (M + H)$^+$<br>m.p. 75.9° C. |

| ID No. | Structure | Compound Name & Physical Data |
|---|---|---|
| 7 | 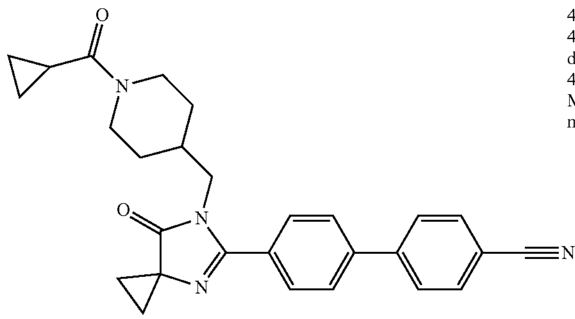 [SMILES: N#Cc1ccc(-c2ccc(C3=NC4(CC4)C(=O)N3CC3CCN(C(=O)C4CC4)CC3)cc2)cc1] | 4'-(6-{[1-(Cyclopropylcarbonyl)piperidin-4-yl]methyl}-7-oxo-4,6-diazaspiro[2.4]hept-4-en-5-yl)biphenyl-4-carbonitrile<br>MS m/z 453 (M + H)+<br>m.p. 154.5° C. |
| 6 | 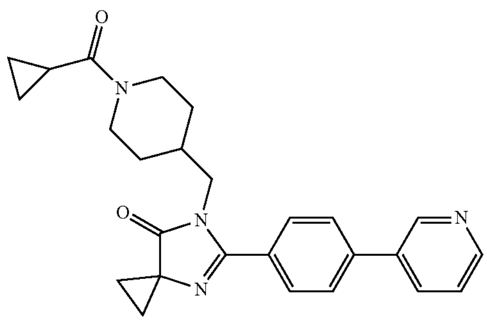 [SMILES: O=C(C1CC1)N1CCC(CN2C(=O)C3(CC3)N=C2c2ccc(-c3cccnc3)cc2)CC1] | 6-{[1-(Cyclopropylcarbonyl)piperidin-4-yl]methyl}-5-(4-pyridin-3-ylphenyl)-4,6-diazaspiro[2.4]hept-4-en-7-one<br>MS m/z 429 (M + H)+<br>m.p. 132.0° C. |
| 20 | 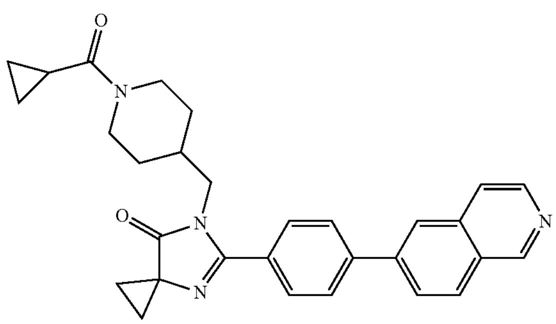 [SMILES: O=C(C1CC1)N1CCC(CN2C(=O)C3(CC3)N=C2c2ccc(-c3ccc4cnccc4c3)cc2)CC1] | 6-{[1-(Cyclopropylcarbonyl)piperidin-4-yl]methyl}-5-(4-isoquinolin-6-ylphenyl)-4,6-diazaspiro[2.4]hept-4-en-7-one<br>$^1$H NMR (300 MHz, CDCl$_3$) δ ppm 0.65-0.76 (m, 2 H), 0.88-0.95 (m, 2 H), 0.95-1.23 (m, 2 H), 1.48-1.75 (m, 4 H), 1.75-1.83 (m, 2 H), 1.83-1.99 (m, 3 H), 2.48 (t, J = 11.5 Hz, 1 H), 2.99 (t, J = 12.1 Hz, 1 H), 3.69 (dd, J = 14.2, 6.9 Hz, 2 H), 4.16 (d, J = 11.8 Hz, 1 H), 4.53 (d, J = 12.1 Hz, 1 H), 7.68-7.79 (m, 3 H), 7.87 (d, J = 8.4 Hz, 2 H), 7.91 (dd, J = 8.6, 1.7 Hz, 1 H), 8.04-8.16 (m, 2 H), 8.60 (d, J = 5.8 Hz, 1 H), 9.32 (s, 1 H);<br>MS m/z 479 (M + H)+<br>m.p. 97.9° C. |
| 19 | 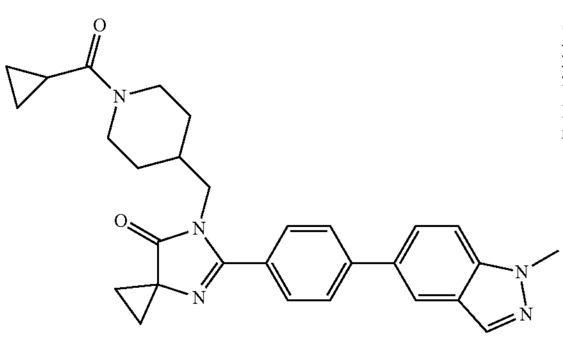 [SMILES: Cn1ncc2cc(-c3ccc(C4=NC5(CC5)C(=O)N4CC4CCN(C(=O)C5CC5)CC4)cc3)ccc21] | 6-{[1-(Cyclopropylcarbonyl)piperidin-4-yl]methyl}-5-[4-(1-methyl-1H-indazol-5-yl)phenyl]-4,6-diazaspiro[2.4]hept-4-en-7-one<br>MS m/z 482 (M + H)+<br>m.p. 107.7° C. |

| ID No. | Structure | Compound Name & Physical Data |
|---|---|---|
| 24 | 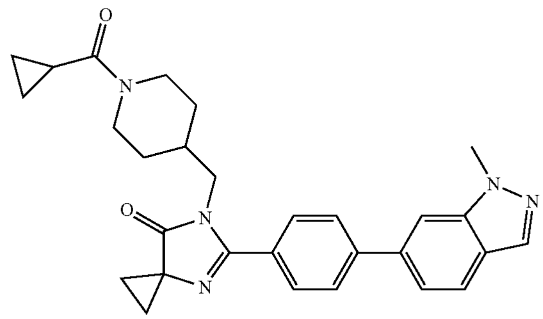 [SMILES: Cn1ncc2ccc(-c3ccc(C4=NC5(CC5)C(=O)N4CC4CCN(C(=O)C5CC5)CC4)cc3)cc21] | 6-{[1-(Cyclopropylcarbonyl)piperidin-4-yl]methyl}-5-[4-(1-methyl-1H-indazol-6-yl)phenyl]-4,6-diazaspiro[2.4]hept-4-en-7-one<br>MS m/z 482 (M + H)$^+$<br>m.p. 104.0° C. |
| 29 | 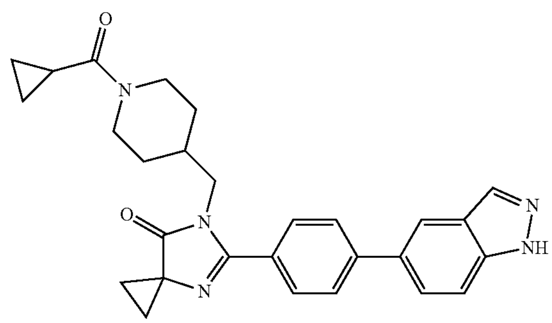 [SMILES: O=C(C1CC1)N1CCC(CN2C(=O)C3(CC3)N=C2c2ccc(-c3ccc4[nH]ncc4c3)cc2)CC1] | 6-{[1-(Cyclopropylcarbonyl)piperidin-4-yl]methyl}-5-[4-(1H-indazol-5-yl)phenyl]-4,6-diazaspiro[2.4]hept-4-en-7-one<br>$^1$H NMR (300 MHz, CDCl$_3$) δ ppm 0.62-0.77 (m, 2 H), 0.89-0.97 (m, 2 H), 1.06 (d, J = 19.0 hz, 2 H), 1.51-1.73 (m, 3 H), 1.75-1.94 (m, 6 H), 2.49 (t, J = 11.3 Hz, 1 H), 2.99 (t, J = 11.8 Hz, 1 H), 3.55-3.82 (m, 2 H), 4.16 (d, J = 12.5 Hz, 1 H), 4.54 (d, J = 11.7 Hz, 1 H), 7.58 (m, J = 8.7 Hz, 1 H), 7.63-7.73 (m, 3 H), 7.77 (m, J = 8.2 Hz, 2 H), 8.02 (s, 1 H), 8.16 (br. s., 1 H);<br>MS m/z 468 (M + H)$^+$<br>m.p. 179.9° C. |
| 25 | 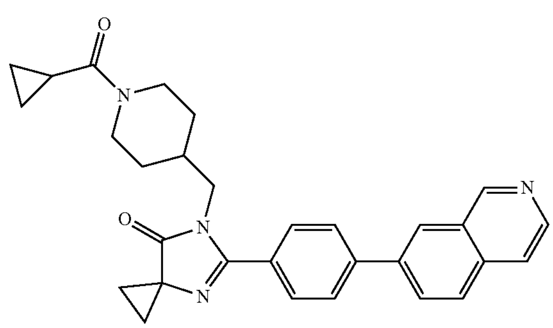 [SMILES: O=C(C1CC1)N1CCC(CN2C(=O)C3(CC3)N=C2c2ccc(-c3ccc4ccncc4c3)cc2)CC1] | 6-{[1-(Cyclopropylcarbonyl)piperidin-4-yl]methyl}-5-(4-isoquinolin-7-ylphenyl)-4,6-diazaspiro[2.4]hept-4-en-7-one<br>MS m/z 479 (M + H)$^+$<br>m.p. 151.1° C. |
| 30 | 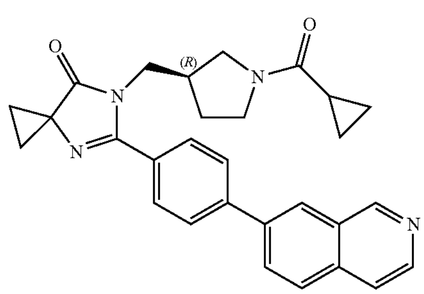 | 6-{[(3R)-1-(Cyclopropylcarbonyl)pyrrolidin-3-yl]methyl}-5-(4-isoquinolin-7-ylphenyl)-4,6-diazaspiro[2.4]hept-4-en-7-one<br>$^1$H NMR (300 MHz, CDCl$_3$) δ ppm 0.60-0.78 (m, 2 H), 0.87-1.03 (m, 2 H), 1.42-2.08 (m, 7.5 H), 2.33-2.50 (m, 0.5 H), 2.51-2.68 (m, 0.5 H), 3.05 (dd, J = 12.0, 7.2 Hz, 0.5 H), 3.17-3.44 (m, 1 H), 3.49-3.89 (m, 4 H), 7.66-7.80 (m, 3 H), 7.83-7.92 (m, 2 H), 7.92-8.05 (m, 2 H), 8.23 (s, 1 H), 8.59 (br. s., 1 H), 9.37 (br. s., 1 H);<br>MS m/z 465 (M + H)$^+$<br>m.p. 92.3° C. |

-continued

| ID No. | Structure | Compound Name & Physical Data |
|---|---|---|
| 28 | 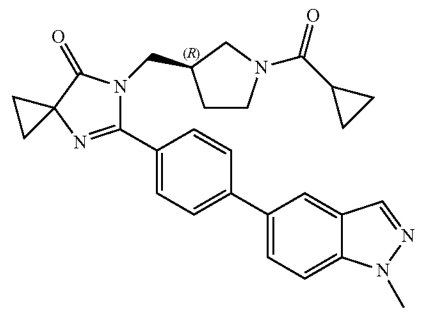 | 6-{[(3R)-1-(Cyclopropylcarbonyl)pyrrolidin-3-yl]methyl}-5-[4-(1-methyl-1H-indazol-5-yl)phenyl]-4,6-diazaspiro[2.4]hept-4-en-7-one<br>$^1$H NMR (300 MHz, CDCl$_3$) δ ppm 0.61-0.79 (m, 2 H), 0.84-1.05 (m, 2 H), 1.38-2.09 (m, 8 H), 2.37-2.51 (m, 0.5 H), 2.52-2.67 (m, 0.5 H), 3.06 (dd, J = 12.0, 7.1 Hz, 0.5 H), 3.22-3.39 (m, 1 H), 3.47-3.92 (m, 4.5 H), 4.13 (s, 3 H), 7.50 (d, J = 8.7 Hz, 1 H), 7.63-7.73 (m, 3 H), 77.3-7.83 (m, 2 H), 7.98 (s, 1 H), 8.06 (s, 1 H);<br>MS m/z 468 (M + H)$^+$<br>m.p. 169.6° C. |
| 27 | 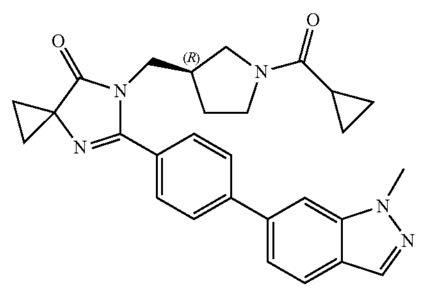 | 6-{[(3R)-1-(Cyclopropylcarbonyl)pyrrolidin-3-yl]methyl}-5-[4-(1-methyl-1H-indazol-6-yl)phenyl]-4,6-diazaspiro[2.4]hept-4-en-7-one<br>$^1$H NMR (300 MHz, CDCl$_3$) δ ppm 0.57-0.81 (m, 2 H), 0.83-1.05 (m, 2 H), 1.38-2.12 (m, 8 H), 2.34-2.50 (m, 0.5 H), 2.51-2.69 (m, 0.5 H), 2.97-3.14 (m, 0.5 H), 3.18-3.43 (m, 1 H), 3.43-3.97 (m, 4.5 H), 4.15 (s, 3 H), 7.43 (d, J = 8.0 Hz, 1 H), 7.61 (br. s., 1 H), 7.65-7.77 (m, 2 H), 7.77-7.93 (m, 3 H), 8.03 (br. s., 1 H);<br>MS m/z 468 (M + H)$^+$<br>m.p. 138.2° C. |
| 31 | 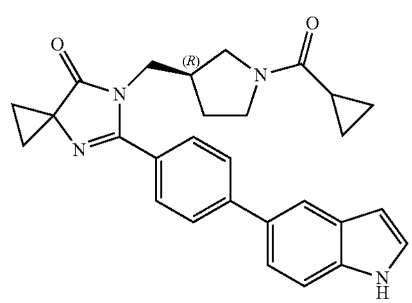 | 6-{[(3R)-1-(Cyclopropylcarbonyl)pyrrolidin-3-yl]methyl}-5-[4-(1H-indol-5-yl)phenyl]-4,6-diazaspiro[2.4]hept-4-en-7-one<br>$^1$H NMR (300 MHz, CDCl$_3$) δ ppm 0.62-0.83 (m, 2 H), 0.83-1.07 (m, 2 H), 1.39-2.09 (m, 8 H), 2.32-2.65 (m, 1 H), 3.09 (dd, J = 12.0, 6.8 Hz, 0.5 H), 3.19-3.41 (m, 1 H), 3.42-3.97 (m, 4.5 H), 6.62 (br. s., 1 H), 7.27 (s, 1 H), 7.46 (d, J = 3.0 Hz, 2 H), 7.65 (dd, J = 8.0, 4.2 Hz, 2 H), 77.3-7.84 (m, 2 H), 7.91 (s, 1 H), 8.65 (br. s., 1 H);<br>MS m/z 453 (M + H)$^+$<br>m.p. 178.2° C. |
| 47 | 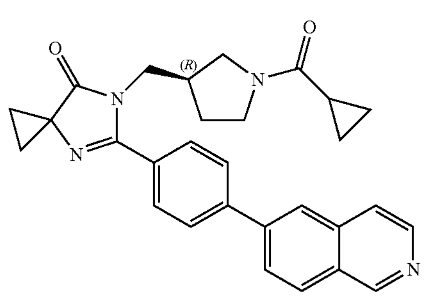 | 6-{[(3R)-1-(Cyclopropylcarbonyl)pyrrolidin-3-yl]methyl}-5-(4-isoquinolin-6-ylphenyl)-4,6-diazaspiro[2.4]hept-4-en-7-one<br>$^1$H NMR (300 MHz, CDCl$_3$) δ ppm 0.63-0.78 (m, 2 H), 0.87-1.01 (m, 2 H), 1.41-1.58 (m, 1.5 H), 1.65-2.10 (m, 5.5 H), 2.35-2.69 (m, 1 H), 3.05 (dd, J = 12.0 Hz, 7.2 Hz, 1 H), 3.23-3.41 (m, 0.5 H), 3.49-3.89 (m, 4.5 H), 7.70-7.80 (m, 3 H), 7.84-7.94 (m, 3 H), 8.07 (s, 1 H), 8.11 (d, J = 8.5 Hz, 1 H), 8.60 (d, J = 5.6 Hz, 1 H), 9.32 (s, 1 H);<br>MS m/z 465 (M + H)$^+$<br>m.p. 162.3° C. |

-continued

| ID No. | Structure | Compound Name & Physical Data |
|---|---|---|
| 64 | 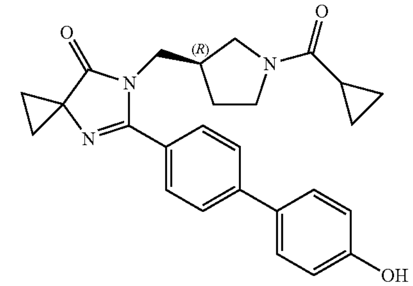 | 6-{[(3R)-1-(Cyclopropylcarbonyl)pyrrolidin-3-yl]methyl}-5-(4'-hydroxybiphenyl-4-yl)-4,6-diazaspiro[2.4]hept-4-en-7-one<br>$^1$H NMR (300 MHz, CDCl$_3$) δ ppm 0.68-0.83 (m, 2 H), 0.92-1.07 (m, 2 H), 1.38-2.16 (m, 7 H), 2.34-2.72 (m, 1 H), 3.05 (dd, J = 12.0, 7.2 Hz, 0.5 H), 3.17-3.99 (m, 5.5 H), 6.72-6.93 (m, 23 H), 7.32-7.50 (m, 2 H), 7.54-7.74 (m, 4 H), 7.80-8.25 (m, 1 H);<br>MS m/z 430 (M + H)$^+$ |
| 48 | 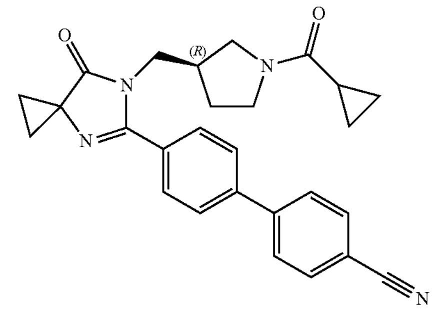 | 4'-(6-{[(3R)-1-(Cyclopropylcarbonyl)pyrrolidin-3-yl]methyl}-7-oxo-4,6-diazaspiro[2.4]hept-4-en-5-yl)biphenyl-4-carbonitrile<br>$^1$H NMR (300 MHz, CDCl$_3$) δ ppm 0.66-0.77 (m, 2 H), 0.89-1.00 (m, m2 H), 1.42-1.56 (m, 1.5 H), 1.64-2.11 (m, 5.5 H), 2.31-2.67 (m, 1 H), 3.02 (dd, J = 12.1, 7.3 Hz, 0.5 H), 3.22-3.39 (m, ,1 H), 3.44-3.92 (m, 4.5 H), 7.67-7.89 (m, 8 H);<br>MS m/z 439 (M + H)$^+$<br>m.p. 90.7° C. |
| 32 | 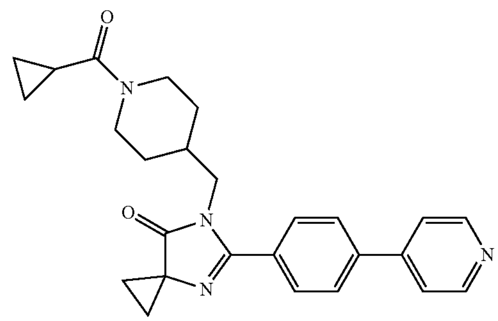 [SMILES: O=C(C1CC1)N1CCC(CN2C(=O)C3(CC3)N=C2c2ccc(-c3ccncc3)cc2)CC1] | 6-{[1-(Cyclopropylcarbonyl)piperidin-4-yl]methyl}-5-(4-pyridin-4-ylphenyl)-4,6-diazaspiro[2.4]hept-4-en-7-one<br>MS m/z 429 (M + H)$^+$<br>m.p. >300° C. |
| 26 | 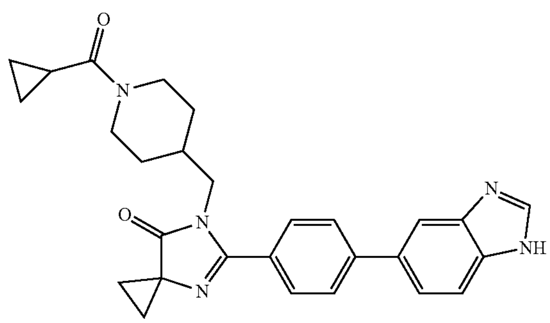 [SMILES: O=C(C1CC1)N1CCC(CN2C(=O)C3(CC3)N=C2c2ccc(-c3ccc4[nH]cnc4c3)cc2)CC1] | 5-[4-(1H-Benzimidazol-5-yl)phenyl]-6-{[1-(cyclopropylcarbonyl)piperidin-4-yl]methyl}-4,6-diazaspiro[2.4]hept-4-en-7-one<br>$^1$H NMR (300 MHz, CDCl$_3$) δ ppm 0.56-1.40 (m, 8 H), 1.45-2.01 (m, 6 H), 2.39-2.62 (m, 1 H), 2.84-3.13 (m, 1 H), 3.55-3.82 (m, 3 H), 4.05-4.27 (m, 1 H), 4.41-4.62 (m, 1 H), 7.42-7.94 (m, 8 H), 8.13 (br. s., 1 H);<br>MS m/z 468 (M + H)$^+$<br>m.p. 144° C. |
| 37 | 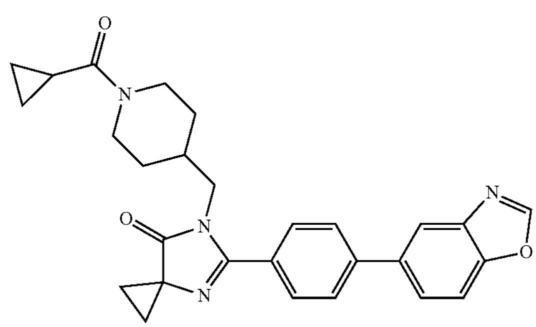 [SMILES: O=C(C1CC1)N1CCC(CN2C(=O)C3(CC3)N=C2c2ccc(-c3ccc4ocnc4c3)cc2)CC1] | 5-[4-(1,3-Benzoxazol-5-yl)phenyl]-6-{[1-(cyclopropylcarbonyl)piperidin-4-yl]methyl}-4,6-diazaspiro[2.4]hept-4-en-7-one<br>MS m/z 469 (M + H)$^+$ |

| ID No. | Structure | Compound Name & Physical Data |
|---|---|---|
| 55 | 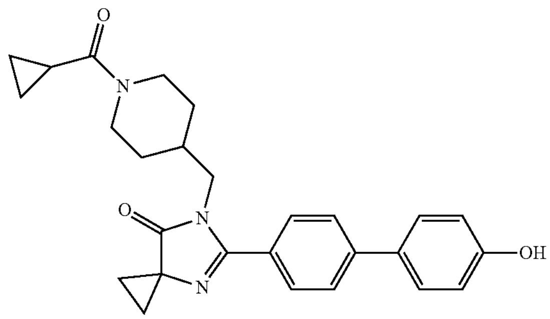 [SMILES: O=C(C1CC1)N1CCC(CN2C(=O)C3(CC3)N=C2c2ccc(-c3ccc(O)cc3)cc2)CC1] | 6-{[1-(Cyclopropylcarbonyl)piperidin-4-yl]methyl}-5-(4'-hydroxybiphenyl-4-yl)-4,6-diazaspiro[2.4]hept-4-en-7-one<br>MS m/z 444 (M + H)<sup>+</sup><br>m.p. 161.7° C. |
| 57 | 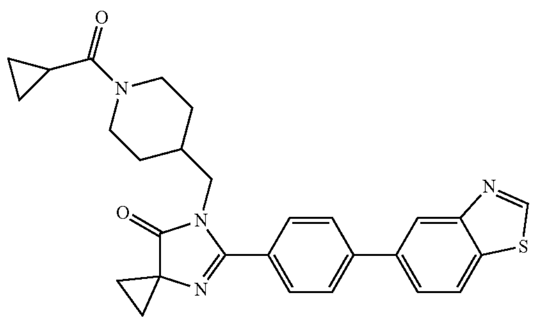 [SMILES: O=C(C1CC1)N1CCC(CN2C(=O)C3(CC3)N=C2c2ccc(-c3ccc4scnc4c3)cc2)CC1] | 5-[4-(1,3-Benzothiazol-5-yl)phenyl]-6-{[1-(cyclopropylcarbonyl)piperidin-4-yl]methyl}-4,6-diazaspiro[2.4]hept-4-en-7-one<br>$^1$H NMR (300 MHz, CDCl$_3$) δ ppm 0.41-0.73 (m, 2 H), 0.79-0.89 (m, 1 H), 1.39-1.90 (m, 9 H), 2.23-2.53 (m, 1 H), 2.76-3.06 (m, 1 H), 3.22-3.49 (m, 2 H), 3.49-3.80 (m, 3 H), 3.93-4.24 (m, 1 H), 4.24-4.60 (m, 1 H), 7.53-7.85 (m, 5 H), 8.00 (d, J = 8.0 Hz, 1 H), 8.34 (br. s., 1 H), 9.00 (br. s., 1 H);<br>MS m/z 485 (M + H)<sup>+</sup><br>m.p. 152.6° C. |
| 71 | 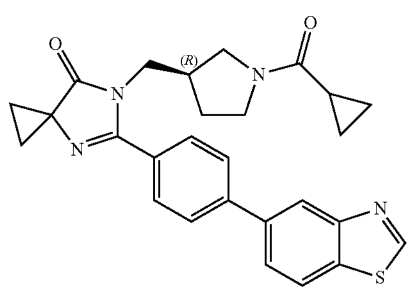 | 5-[4-(1,3-Benzothiazol-5-yl)phenyl]-6-{[(3R)-1-(cyclopropylcarbonyl)pyrrolidin-3-yl]methyl}-4,6-diazaspiro[2.4]hept-4-en-7-one<br>$^1$H NMR (300 MHz, DMSO-d6) δ ppm 0.47-0.76 (m, 4 H), 1.29-1.67 (m, 4.5 H), 1.67-1.82 (m, 2 H), 1.82-1.97 (m, 1 H), 2.18-2.45 (m, 1 H), 2.90 (dd, J = 11.5, 6.8 Hz, 0.5 H), 3.05-3.28 (m, 2 H), 3.40-3.63 (m, 2 H), 3.68-3.85 (m, 2 H), 7.78-7.86 (m, 1 H), 7.90 (d, J = 8.2 Hz, 1 H), 7.99 (d, J = 7.1 Hz, 2 H), 8.30 (d, J = 8.2 Hz, 1 H), 8.46 (br. s., 1 H), 9.47 (s, 1 H)<br>MS m/z 471 (M + H)<sup>+</sup><br>m.p. 82.7° C. |
| 105 | 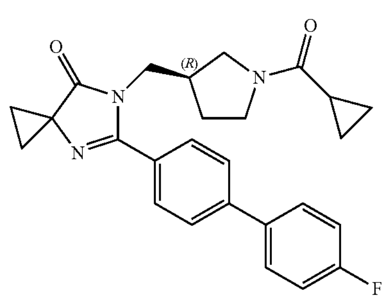 | 6-{[(3R)-1-(Cyclopropylcarbonyl)pyrrolidin-3-yl]methyl}-5-(4'-fluorobiphenyl-4-yl)-4,6-diazaspiro[2.4]hept-4-en-7-one<br>$^1$H NMR (300 MHz, CDCl$_3$) δ ppm 0.66-0.75 (m, 2 H), 0.90-0.98 (m, 2 H), 1.41-1.59 (m, 2 H), 1.65-2.08 (m, 5 H), 2.31-2.67 (m, 1 H), 3.04 (dd, J = 12.0, 7.1 Hz, 0.5 H), 3.21-3.38 (m, 1 H), 3.50-3.90 (m, 4.5 H), 7.18 (t, J = 8.7 Hz, 2 H), 7.56-7.64 (m, 2 H), 7.64-7.75 (m, 4 H);<br>MS m/z 432 (M + H)<sup>+</sup><br>m.p. 153.7° C. |

| ID No. | Structure | Compound Name & Physical Data |
|---|---|---|
| 104 | 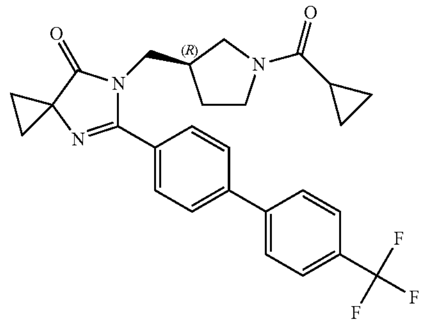 | 6-{[(3R)-1-(Cyclopropylcarbonyl)pyrrolidin-3-yl]methyl}-5-[4'-(trifluoromethyl)biphenyl-4-yl]-4,6-diazaspiro[2.4]hept-4-en-7-one<br>MS m/z 482 (M + H)$^+$<br>m.p. 253.8° C. |
| 115 | 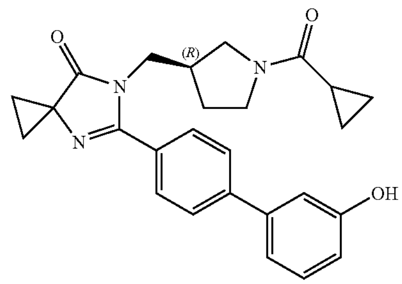 | 6-{[(3R)-1-(Cyclopropylcarbonyl)pyrrolidin-3-yl]methyl}-5-(3'-hydroxybiphenyl-4-yl)-4,6-diazaspiro[2.4]hept-4-en-7-one<br>$^1$H NMR (300 MHz, CDCl$_3$) δ ppm 0.61-0.88 (m, 2 H), 0.89-1.13 (m, 2 H), 1.39-2.18 (m, 7 H), 2.34-2.71 (m, 1 H), 2.92-4.20 (m, 6 H), 6.64-6.98 (m, 2 H), 6.97-7.18 (m, 1 H), 7.18-7.41 (m, 1 H), 7.45-7.87 (m, 4 H), 8.07-8.57 (m, 1 H);<br>MS m/z 430 (M + H)$^+$<br>m.p. >300° C. |
| 103 | 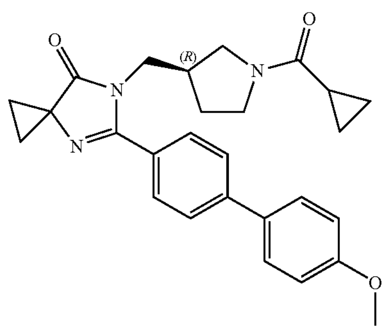 | 6-{[(3R)-1-(Cyclopropylcarbonyl)pyrrolidin-3-yl]methyl}-5-(4'-methoxybiphenyl-4-yl)-4,6-diazaspiro[2.4]hept-4-en-7-one<br>$^1$H NMR (300 MHz, CDCl$_3$) δ ppm 0.62-0.75 (m, 2 H), 0.88-0.98 (m, 2 H), 1.41-1.57 (m, 2 H), 1.62-2.01 (m, 6 H), 2.32-2.63 (m, 0.5 H), 3.18-3.37 (m, 1 H), 3.49-3.86 (m, 4.5 H), 3.87 (s, 3 H), 7.01 (d, J = 8.7 Hz, 2 H), 7.57 (d, J = 8.7 Hz, 2 H), 7.64 (dd, J = 8.4, 1.9 Hz, 2 H), 7.69 (dd, J = 8.4, 3.8 Hz, 2 H);<br>MS m/z 444 (M + H)$^+$<br>m.p. 76.6° C. |
| 102 | 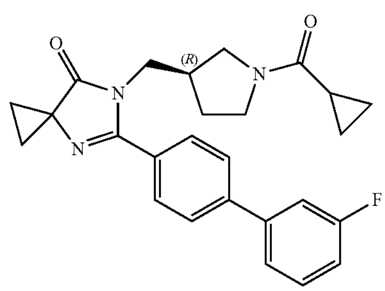 | 6-{[(3R)-1-(Cyclopropylcarbonyl)pyrrolidin-3-yl]methyl}-5-(3'-fluorobiphenyl-4-yl)-4,6-diazaspiro[2.4]hept-4-en-7-one<br>$^1$H NMR (300 MHz, CDCl$_3$) δ ppm 0.62-0.78 (m, 2 H), 0.86-1.02 (m, 2 H), 1.41-2.08 (m, 7 H), 2.33-2.65 (m, 1 H), 3.04 (dd, J = 12.1, 7.1 Hz, 0.5 H), 3.20-3.39 (m, 1 H), 3.50-3.90 (m, 4.5 H), 7.05-7.16 (m, 1 H), 7.30-7.38 (m, 1 H), 7.38-7.51 (m, 2 H), 7.65-7.78 (m, 4 H);<br>MS m/z 432 (M + H)$^+$<br>m.p. 131.1° C. |
| 101 | 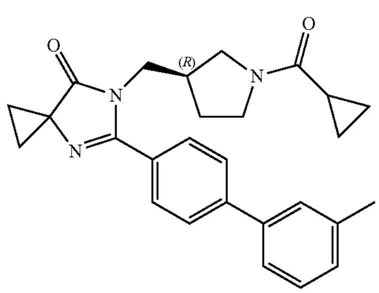 | 6-{[(3R)-1-(Cyclopropylcarbonyl)pyrrolidin-3-yl]methyl}-5-(3'-methylbiphenyl-4-yl)-4,6-diazaspiro[2.4]hept-4-en-7-one<br>$^1$H NMR (300 MHz, CDCl$_3$) δ ppm 0.71 (dd, J = 7.7, 3.0 Hz, 2 H), 0.87-1.02 (m, 2 H), 1.42-2.08 (m, 7 H), 2.35-2.62 (m, 1 H), 2.45 (s, 3 H), 3.06 (dd, J = 12.0, 7.0 Hz, 0.5 H), 3.20-3.39 (m, 1 H), 3.43-3.90 (m, 4.55 H), 7.23 (d, J = 7.0 Hz, 1 H), 7.33-7.51 (m, 3 H), 7.63-7.70 (m, 2 H), 7.70-7.79 (m, 2 H);<br>MS m/z 428 (M + H)$^+$<br>m.p. >300° C. |

| ID No. | Structure | Compound Name & Physical Data |
|---|---|---|
| 100 | 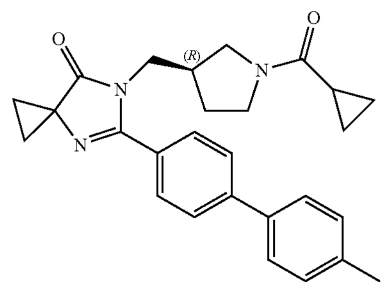 | 6-{[(3R)-1-(Cyclopropylcarbonyl)pyrrolidin-3-yl]methyl}-5-(4'-methylbiphenyl-4-yl)-4,6-diazaspiro[2.4]hept-4-en-7-one<br>$^1$H NMR (300 MHz, CDCl$_3$) δ ppm 0.62-0.78 (m, 2 H), 0.90-1.00 (m, 2 H), 1.38-2.10 (m, 7 H), 2.35-2.69 (m, 1 H), 2.41-2.44 (m, 3 H), 3.06 (dd, J = 12.0, 6.9 Hz, 0.5 H), 3.14-3.41 (m, 1 H), 3.40-3.93 (m, 4.5 H), 7.29 (d, J = 8.1 Hz, 2 H), 7.54 (d, J = 8.1 Hz, 2 H), 7.61-7.69 (m, 2 H), 7.69-7.78 (m, 2 H);<br>MS m/z 428 (M + H)$^+$<br>m.p. 123.3° C. |
| 114 | 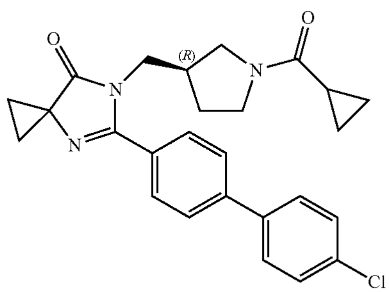 | 5-(4'-Chlorobiphenyl-4-yl)-6-{[(3R)-1-(cyclopropylcarbonyl)pyrrolidin-3-yl]methyl}-4,6-diazaspiro[2.4]hept-4-en-7-one<br>$^1$H NMR (300 MHz, CDCl$_3$) δ ppm 0.62-0.81 (m, 2 H), 0.86-1.04 (m, 2 H), 1.38-2.10 (m, 7 H), 2.30-2.66 (m, 1 H), 3.04 (dd, J = 12.0, 7.1 Hz, 0.5 H), 3.18-3.41 (m, 1 H), 3.42-3.93 (m, 4.5 H), 7.45 (d, J = 8.1 Hz, 2 H), 7.57 (d, J = 8.5 Hz, 2 H), 7.63-7.80 (m, 4 H);<br>MS m/z 448 (M + H)$^+$ |
| 113 | 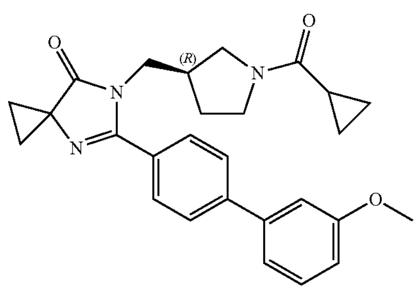 | 6-{[(3R)-1-(Cyclopropylcarbonyl)pyrrolidin-3-yl]methyl}-5-(3'-methoxybiphenyl-4-yl)-4,6-diazaspiro[2.4]hept-4-en-7-one<br>$^1$H NMR (300 MHz, CDCl$_3$) δ ppm 0.60-0.81 (m, 2 H), 0.83-1.04 (m, 2 H), 1.37-2.10 (m, 7 H), 2.26-2.67 (m, 1 H), 2.91-3.87 (m, 6 H), 3.89 (s, 3 H), 6.95 (d, J = 8.0 Hz, 1 H), 7.11-7.26 (m, 2 H), 7.40 (t, J = 7.8 Hz, 1 H), 7.56-7.86 (m, 4 H);<br>MS m/z 444 (M + H)$^+$ |
| 112 | 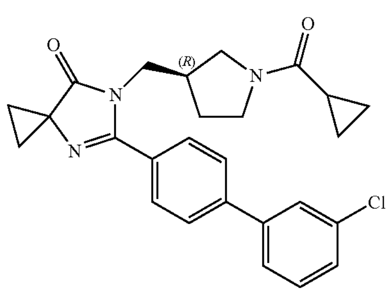 | 5-(3'-Chlorobiphenyl-4-yl)-6-{[(3R)-1-(cyclopropylcarbonyl)pyrrolidin-3-yl]methyl}-4,6-diazaspiro[2.4]hept-4-en-7-one<br>$^1$H NMR (300 MHz, CDCl$_3$) δ ppm 0.63-0.78 (m, 2 H), 0.86-1.04 (m, 2 H), 1.38-2.09 (m, 7 H), 2.31-2.66 (m, 1 H), 3.04 (dd, J = 12.0, 7.0 Hz, 0.5 H), 3.17-3.40 (m, 1 H), 3.50-3.91 (m, 4.5 H), 7.34-7.47 (m, 2 H), 7.47-7.56 (m, 1 H), 7.62 (s, 1 H), 7.65-7.78 (m, 4 H);<br>MS m/z 448 (M + H)$^+$<br>m.p. 129.4° C. |
| 123 | 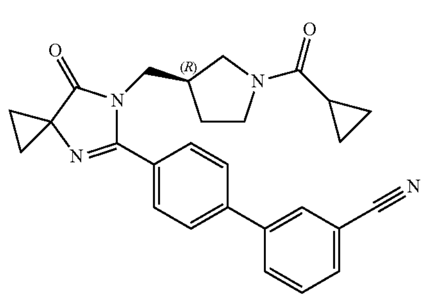 | 4'-(6-{[(3R)-1-(Cyclopropylcarbonyl)pyrrolidin-3-yl]methyl}-7-oxo-4,6-diazaspiro[2.4]hept-4-en-5-yl)biphenyl-3-carbonitrile<br>MS m/z 439 (M + H)$^+$<br>m.p. 171.4° C. |

| ID No. | Structure | Compound Name & Physical Data |
|---|---|---|
| 145 | 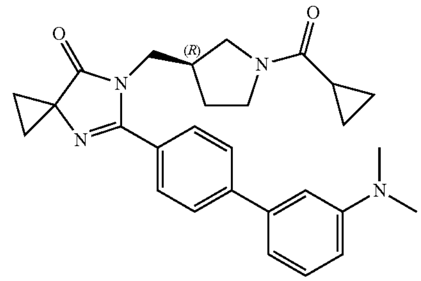 | 6-{[(3R)-1-(Cyclopropylcarbonyl)pyrrolidin-3-yl]methyl}-5-[3'-(dimethylamino)biphenyl-4-yl]-4,6-diazaspiro[2.4]hept-4-en-7-one<br>$^1$H NMR (300 MHz, DMSO-d6) δ ppm 0.56-0.70 (m, 4 H), 1.31-1.67 (m, 4 H), 1.67-1.94 (m, 3 H), 2.16-2.45 (m, 1 H), 2.89 (dd, J = 11.8, 6.9 Hz, 0.5 H), 2.97 (s, 6 H), 3.06-3.30 (m, 1.5 H), 3.37-3.65 (m, 2 H), 3.74 (t, J = 7.1 Hz, 2 H), 6.78 (dd, J = 8.1, 1.8 Hz, 1 H), 6.95-7.04 (m, 2 H), 7.30 (m, J = 8.1, 8.1 Hz, 1 H), 7.71-7.79 (m, 2 H), 7.79-7.88 (m, 2 H);<br>MS m/z 457 (M + H)$^+$<br>m.p. 74.0° C. |
| 124 | 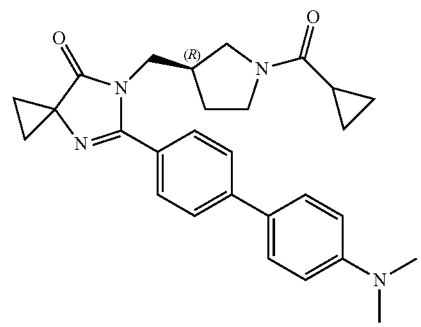 | 6-{[(3R)-1-(Cyclopropylcarbonyl)pyrrolidin-3-yl]methyl}-5-[4'-(dimethylamino)biphenyl-4-yl]-4,6-diazaspiro[2.4]hept-4-en-7-one<br>$^1$H NMR (300 MHz, DMSO-d6) δ ppm 0.63 (d, J = 5.2 Hz, 4 H), 1.47-1.66 (m, 4 H), 1.67-1.94 (m, 3 H), 2.16-2.44 (m, 1 H), 2.89 (dd, J = 11.8, 6.9 Hz, 0.5 H), 2.96 (s, 6 H), 3.06-3.30 (m, 2 H), 3.36-3.60 (m, 1.5 H), 3.74 (t, J = 76.7 Hz, 2 H), 6.82 (d, J = 8.7 Hz, 2 H), 7.62 (d, J = 8.4 Hz, 2 H), 7.66-7.80 (m, 4 H);<br>MS m/z 457 (M + H)$^+$<br>m.p. 274.9° C. |
| 125 | 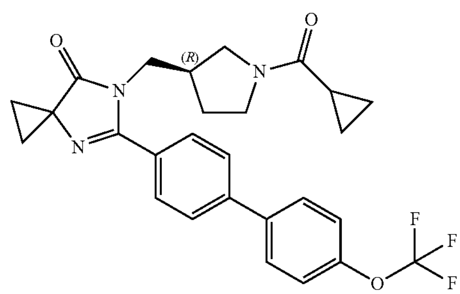 | 6-{[(3R)-1-(Cyclopropylcarbonyl)pyrrolidin-3-yl]methyl}-5-[4'-(trifluoromethoxy)biphenyl-4-yl]-4,6-diazaspiro[2.4]hept-4-en-7-one<br>MS m/z 498 (M + H)$^+$<br>m.p. 146.2° C. |
| 126 | 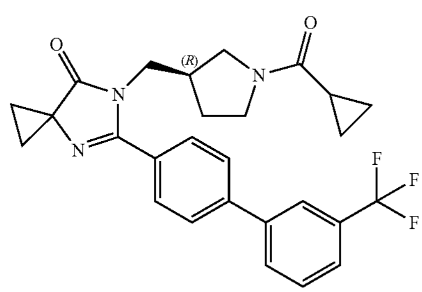 | 6-{[(3R)-1-(Cyclopropylcarbonyl)pyrrolidin-3-yl]methyl}-5-[3'-(trifluoromethyl)biphenyl-4-yl]-4,6-diazaspiro[2.4]hept-4-en-7-one<br>$^1$H NMR (300 MHz, CDCl$_3$) δ ppm 0.62-0.80 (m, 2 H), 0.88-1.04 (m, 2 H), 1.39-1.60 (m, 2 H), 1.73-2.12 (m, 5 H), 2.31-2.67 (m, 1 H), 3.04 (dd, J = 11.8, 7.1 Hz, 0.5 H), 3.19-3.40 (m, 1 H), 3.40-3.94 (m, 4.5 H), 7.55-7.95 (m, 8 H);<br>MS m/z 482 (M + H)$^+$<br>m.p. 120.5° C. |
| 146 | 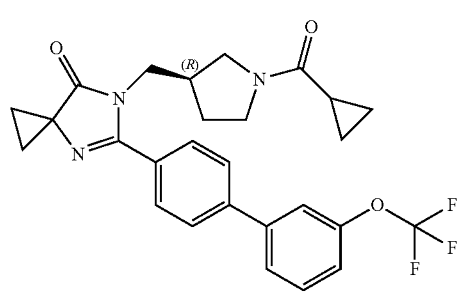 | 6-{[(3R)-1-(Cyclopropylcarbonyl)pyrrolidin-3-yl]methyl}-5-[3'-(trifluoromethoxy)biphenyl-4-yl]-4,6-diazaspiro[2.4]hept-4-en-7-one<br>MS m/z 498 (M + H)$^+$<br>m.p. 76.3° C. |

-continued

| ID No. | Structure | Compound Name & Physical Data |
|---|---|---|
| 111 | 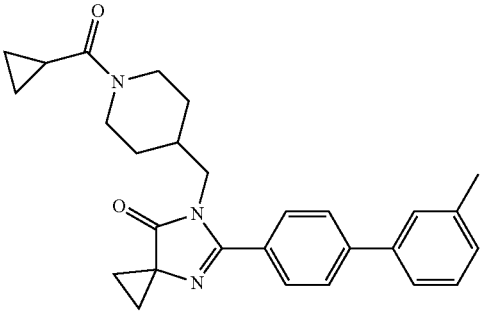 [SMILES: Cc1cccc(-c2ccc(C3=NC4(CC4)C(=O)N3CC3CCN(C(=O)C4CC4)CC3)cc2)c1] | 6-{[1-(Cyclopropylcarbonyl)piperidin-4-yl]methyl}-5-(3'-methylbiphenyl-4-yl)-4,6-diazaspiro[2.4]hept-4-en-7-one<br>MS m/z 442 (M + H)+<br>m.p. 101.9° C. |
| 97 | 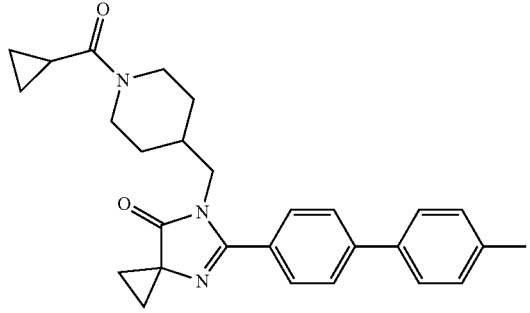 [SMILES: Cc1ccc(-c2ccc(C3=NC4(CC4)C(=O)N3CC3CCN(C(=O)C4CC4)CC3)cc2)cc1] | 6-{[1-(Cyclopropylcarbonyl)piperidin-4-yl]methyl}-5-(4'-methylbiphenyl-4-yl)-4,6-diazaspiro[2.4]hept-4-en-7-one<br>MS m/z 442 (M + H)+<br>m.p. 167.1° C. |
| 99 | 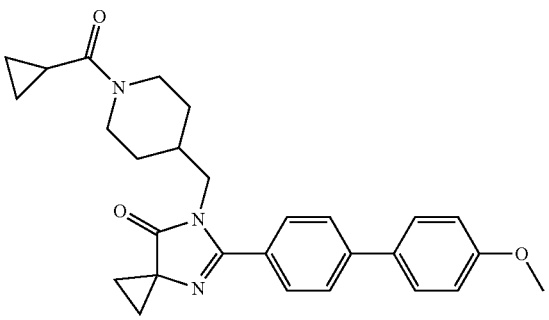 [SMILES: COc1ccc(-c2ccc(C3=NC4(CC4)C(=O)N3CC3CCN(C(=O)C4CC4)CC3)cc2)cc1] | 6-{[1-(Cyclopropylcarbonyl)piperidin-4-yl]methyl}-5-(4'-methylbiphenyl-4-yl)-4,6-diazaspiro[2.4]hept-4-en-7-one<br>MS m/z 458 (M + H)+<br>m.p. >300° C. |
| 98 | 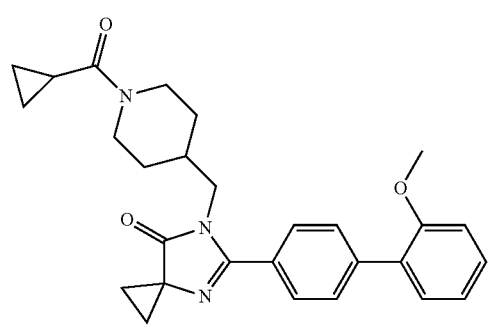 [SMILES: COc1ccccc1-c1ccc(C2=NC3(CC3)C(=O)N2CC2CCN(C(=O)C3CC3)CC2)cc1] | 6-{[1-(Cyclopropylcarbonyl)piperidin-4-yl]methyl}-5-(2'-methoxybiphenyl-4-yl)-4,6-diazaspiro[2.4]hept-4-en-7-one<br>MS m/z 458 (M + H)+<br>m.p. >300° C. |
| 110 | 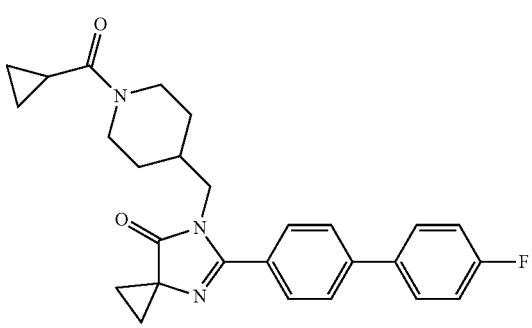 [SMILES: O=C(C1CC1)N1CCC(CN2C(=O)C3(CC3)N=C2c2ccc(-c3ccc(F)cc3)cc2)CC1] | 6-{[1-(Cyclopropylcarbonyl)piperidin-4-yl]methyl}-5-(4'-fluorobiphenyl-4-yl)-diazaspiro[2.4]hept-4-en-7-one<br>MS m/z 446 (M + H)+<br>m.p. 169.9° C. |

| ID No. | Structure | Compound Name & Physical Data |
|---|---|---|
| 109 | 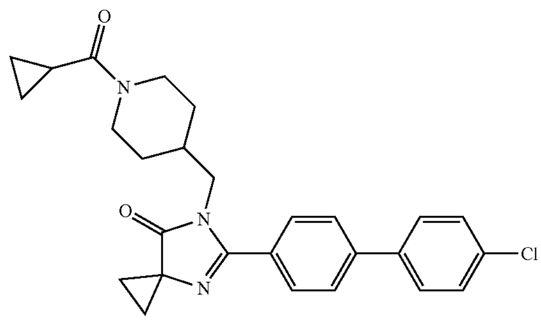 [SMILES: O=C(C1CC1)N1CCC(CN2C(=O)C3(CC3)N=C2c2ccc(-c3ccc(Cl)cc3)cc2)CC1] | 5-(4'-Chlorobiphenyl-4-yl)-6-{[1-(cyclopropylcarbonyl)piperidin-4-yl]methyl}-4,6-diazaspiro[2.4]hept-4-en-7-one<br>MS m/z 462 (M + H)$^+$<br>m.p. 196.8° C. |
| 55 | 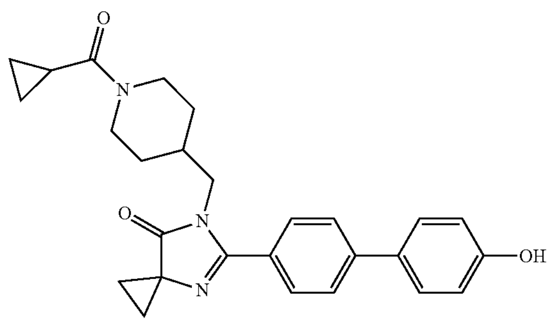 [SMILES: O=C(C1CC1)N1CCC(CN2C(=O)C3(CC3)N=C2c2ccc(-c3ccc(O)cc3)cc2)CC1] | 6-{[1-(Cyclopropylcarbonyl)piperidin-4-yl]methyl}-5-(4'-hydroxybiphenyl-4-yl)-4,6-diazaspiro[2.4]hept-4-en-7-one<br>MS m/z 444 (M + H)$^+$<br>m.p. 153.1° C. |
| 108 | 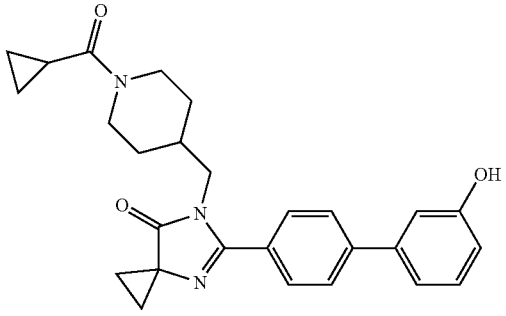 [SMILES: O=C(C1CC1)N1CCC(CN2C(=O)C3(CC3)N=C2c2ccc(-c3cccc(O)c3)cc2)CC1] | 6-{[1-(Cyclopropylcarbonyl)piperidin-4-yl]methyl}-5-(3'-hydroxybiphenyl-4-yl)-4,6-diazaspiro[2.4]hept-4-en-7-one<br>MS m/z 444 (M + H)$^+$<br>m.p. >300° C. |
| 107 | 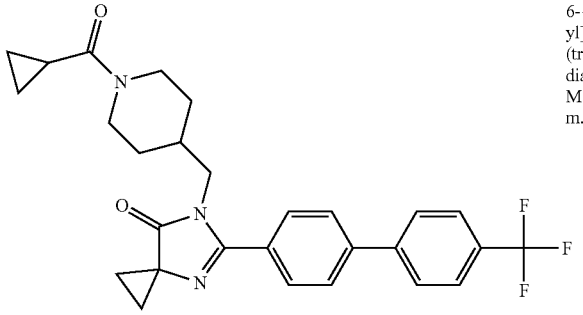 | 6-{[1-(Cyclopropylcarbonyl)piperidin-4-yl]methyl}-5-[4'-(trifluoromethyl)biphenyl-4-yl]-4,6-diazaspiro[2.4]hept-4-en-7-one<br>MS m/z 496 (M + H)$^+$<br>m.p. 187.7° C. |

| ID No. | Structure | Compound Name & Physical Data |
|---|---|---|
| 158 | 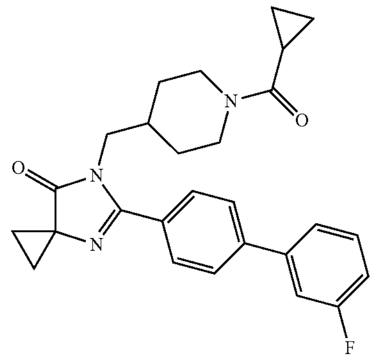 [SMILES: O=C(C1CC1)N1CCC(CN2C(=O)C3(CC3)N=C2c2ccc(-c3cccc(F)c3)cc2)CC1] | 6-{[1-(Cyclopropylcarbonyl)piperidin-4-yl]methyl}-5-(3'-fluorobiphenyl-4-yl)-4,6-diazaspiro[2.4]hept-4-en-7-one<br>MS m/z 446 (M + H)+ |

Example 3

(R)-6-((1-(Cyclopropanecarbonyl)pyrrolidin-3-yl)methyl)-5-(4'-(methyl-1H-pyrazol-4-yl)-[1,1'-biphenyl]-4-yl)-4,6-diazaspiro[2.4]hept-4-en-7-one (Compound #65)

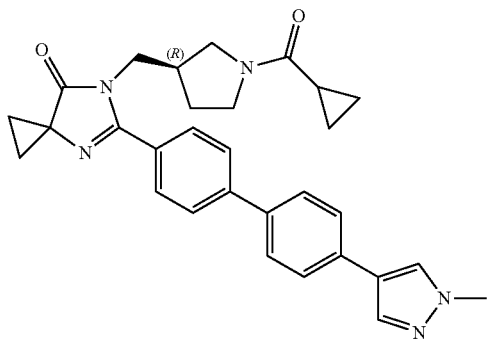

STEP A: (R)-6-((1-(cyclopropanecarbonyl)pyrrolidin-3-yl)methyl)-5-(4'-hydroxy-[1,1'-biphenyl]-4-yl)-4,6-diazaspiro[2.4]hept-4-en-7-one (Compound #64)

(R)-5-(4-Bromophenyl)-6-((1-(cyclopropanecarbonyl)pyrrolidin-3-yl)methyl)-4,6-diazaspiro[2.4]hept-4-en-7-one (0.465 g, 1.117 mmol), (4-hydroxyphenyl)boronic acid (0.2 g, 1.45 mmol), tetrakis(triphenylphosphine) palladium (0.063 g, 0.055 mmol), aqueous 1.0M sodium carbonate (2.23 mL, 2.23 mmol) and 1,4-dioxane (5 mL) were combined and bubbled with nitrogen for 5 min. The resulting mixture was heated to reflux under nitrogen for 3 h. The resulting mixture was diluted with DCM (30 mL), dried over MgSO$_4$, filtered and concentrated in vacuo to yield a residue which was purified by flash chromatography (silica gel 0-10% MeOH in DCM) to yield (R)-6-((1-(cyclopropanecarbonyl)pyrrolidin-3-yl)methyl)-5-(4'-hydroxy-[1,1'-biphenyl]-4-yl)-4,6-diazaspiro[2.4]hept-4-en-7-one (175 mg, 36%).

$^1$H NMR (300 MHz, CDCl$_3$) δ ppm 0.68-0.83 (m, 2H), 0.92-1.07 (m, 2H), 1.38-2.16 (m, 7H), 2.34-2.72 (m, 1H), 3.05 (dd, J=12.0, 7.2 Hz, 0.5H), 3.17-3.99 (m, 5.5H), 6.72-6.93 (m, 2H), 7.32-7.50 (m, 2H), 7.54-7.74 (m, 4H), 7.80-8.25 (m, 1H); MS m/z 430.0 (M+H)+.

STEP B: (R)-4'-(6-((1-(Cyclopropanecarbonyl)pyrrolidin-3-yl)methyl)-7-oxo-4,6-diazaspiro[2.4]hept-4-en-5-yl)-[1,1'-biphenyl]-4-yl trifluoromethanesulfonate To a solution of (R)-6-((1-(cyclopropanecarbonyl)pyrrolidin-3-yl)methyl)-5-(4'-hydroxy-[1,1'-biphenyl]-4-yl)-4,6-diazaspiro[2.4]hept-4-en-7-one (175 mg, 0.407 mmol) in DCM (5 mL) and pyridine (1 mL) was added at 0° C. trifluoromethanesulfonic anhydride (0.082 mL, 0.488 mmol). After stirring for 2 h at room temperature, the reaction mixture was quenched with water and partitioned between 1.0M aqueous solution of Na$_2$CO$_3$ and DCM. The organic phase was dried over MgSO$_4$, filtered and concentrated in vacuo to yield residue which was purified by flash chromatography (silica gel, 0 to 5% MeOH in DCM) to yield (R)-4'-(6-((1-(cyclopropanecarbonyl)pyrrolidin-3-yl)methyl)-7-oxo-4,6-diazaspiro[2.4]hept-4-en-5-yl)[1,1'-biphenyl]-4-yl trifluoromethanesulfonate (81 mg, 35%).

$^1$H NMR (300 MHz, CDCl$_3$) δ ppm 0.64-0.78 (m, 2H), 0.88-0.99 (m, 2H), 1.39-1.58 (m, 2H), 1.63-1.93 (m, 5H), 1.95-2.06 (m, 1H), 2.31-2.67 (m, 1H), 3.02 (dd, J=12.0, 7.2 Hz, 0.5H), 3.21-3.40 (m, 1H), 3.47-3.86 (m, 4.5H), 7.40 (d, J=8.7 Hz, 2H), 7.64-7.76 (m, 6H); MS m/z 562.0 (M+H)+.

STEP C: (R)-6-((1-(Cyclopropanecarbonyl)pyrrolidin-3-yl)ethyl)-5-(4'-(1-methyl-1H-pyrazol-4-yl)-[1,1'-biphenyl]-4-yl)-4,6-diazaspiro[2.4]hept-4-en-7-one To a solution of (R)-4'-(6-((1-(cyclopropanecarbonyl)pyrrolidin-3-yl)methyl)-7-oxo-4,6-diazaspiro[2.4]hept-4-en-5-yl)-[1,1'-biphenyl]-4-yl trifluoromethanesulfonate (75 mg, 0.134 mmol) in acetonitrile (2 mL) was added 1-methyl-4-(4,4,5,5-tetramethyl-1,3,2-dioxaborolan-2-yl)-1H-pyrazole (33.5 mg, 0.161 mmol), aqueous 1.0M Na$_2$CO$_3$ (0.27 mL, 0.27 mmol) and bis(triphenylphosphine) palladium (II) chloride (4.91 mg, 0.007 mmol). The resulting mixture was bubbled with nitrogen for 5 min and heated to 85° C. for 2 h. The resulting mixture was diluted with DCM (30 mL), dried over MgSO$_4$, filtered and concentrated in vacuo to yield a residue which was purified by flash chromatography (silica gel, 0 to 5% MeOH in DCM) to yield a residue which was re-crystallized from MeCN to yield (R)-6-((1-(cyclopropanecarbonyl)pyrrolidin-3-yl)methyl)-5-(4'-(1-methyl-1H-pyrazol-4-yl)-[1,1'-biphenyl]-4-yl)-4,6-diazaspiro[2.4]hept-4-en-7-one (41 mg, 60%).

$^1$H NMR (300 MHz, CDCl$_3$) δ ppm 0.64-0.77 (m, 2H), 0.90-1.00 (m, 2H), 1.42-1.73 (m, 2H), 1.73-1.84 (m, 2H), 1.84-1.92 (m, 2H), 1.92-2.10 (m, 1H), 2.36-2.66 (m, 1H), 3.06 (dd, J=12.0, 7.1 Hz, 0.5H), 3.20-3.40 (m, 1H), 3.50-3.89 (m, 4.5H), 3.98 (s, 3H), 7.59 (m, J=8.2 Hz, 2H), 7.62-7.72 (m, 5H), 7.73-7.80 (m, 2H), 7.83 (s, 1H); MS m/z 494.0 (M+H)$^+$.

Following the procedure described in Example 3, above, selecting and substituting the appropriate reagents, starting materials, and purification methods, and adjusting reaction temperatures, times and other variables or parameters, as needed or desirable, as would be readily recognized by those skilled in the art, the following compounds of formula (I) of the invention were prepared.

| ID No. | Structure | Compound Name & Physical Data |
|---|---|---|
| 21 | 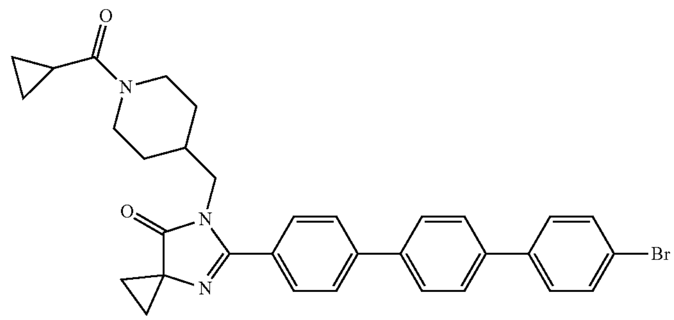 [SMILES: O=C(C1CC1)N1CCC(CN2C(=O)C3(CC3)N=C2c2ccc(-c3ccc(-c4ccc(Br)cc4)cc3)cc2)CC1] | 5-(4''-Bromo-1,1':4',1''-terphenyl-4-yl)-6-{[1-(cyclopropylcarbonyl)piperidin-4-yl]methyl}-4,6-diazaspiro[2.4]hept-4-en-7-one<br>$^1$H NMR (300 MHz, CDCl$_3$) δ ppm 0.66-0.76 (m, 2 H), 0.87-0.96 (m, 2 H), 0.96-1.21 (m, 2 H), 1.49-1.56 (m, 1 H), 1.61-1.73 (m, 2 H), 1.73-1.83 (m, 2 H), 1.83-1.93 (m, 3 H), 2.48 (t, J = 12.2 Hz, 1 H), 2.99 (t, J = 11.8 Hz, 1 H), 3.69 (t, J = 8.2 Hz, 2 H),k 4.16 (d, J = 11.8 Hz, 1 H), 4.53 (d, J = 10.9 Hz, 1 H), 7.53 (d, J = 8.5 Hz, 2 H), 7.61 (d, J = 8.5 Hz, 2 H), 7.65-7.85 (m, 8 H); MS m/z 582 (M + H)$^+$<br>m.p. 241.1° C. |
| 23 | 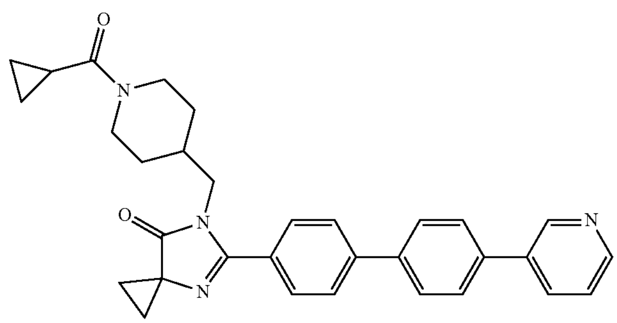 [SMILES: O=C(C1CC1)N1CCC(CN2C(=O)C3(CC3)N=C2c2ccc(-c3ccc(-c4cccnc4)cc3)cc2)CC1] | 6-{[1-(Cyclopropylcarbonyl)piperidin-4-yl]methyl}-5-(4'-pyridin-3-ylbiphenyl-4-yl)-4,6-diazaspiro[2.4]hept-4-en-7-one<br>$^1$H NMR (300 MHz, CDCl$_3$) δ ppm 0.71 (dd, J = 7.8, 3.1 Hz, 2 H), 0.89-0.97 (m, 2 H), 0.97-1.11 (m, 2 H), 1.47-1.73 (m, 3 H), 1.73-1.83 (m, 2 H), 1.83-1.96 (m, 3 H), 2.49 (t, J = 12.3 Hz, 1 H), 2.99 (t, J = 12.8 Hz, 1 H), 3.69 (t, J = 8.1 Hz, 2 H), 4.03-4.32 (m, 1 H), 4.53 (d, J = 10.3 Hz, 1 H), 7.42 (dd, J = 7.6, 4.9 Hz, 1 H), 7.71 (t, J = 8.7 Hz, 4 H), 7.79 (dd, J = 8.3, 2.3 Hz, 4 H), 7.95 (d, J = 8.0 Hz, 1 H), 8.64 (d, J = 3.6 Hz, 1 H), 8.93 (br. s., 1 H); MS m/z 505 (M + H)$^+$<br>m.p. 155.1° C. |
| 56 | 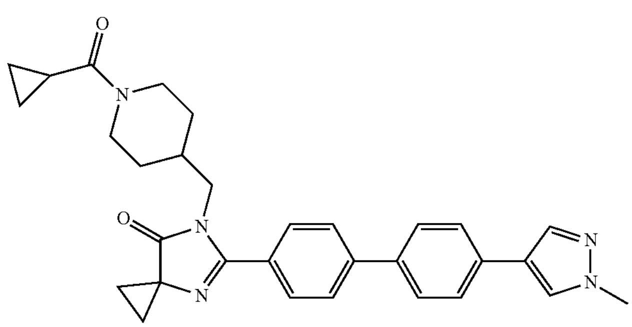 [SMILES: Cn1cc(-c2ccc(-c3ccc(C4=NC5(CC5)C(=O)N4CC4CCN(C(=O)C5CC5)CC4)cc3)cc2)cn1] | 6-{[1-(Cyclopropylcarbonyl)piperidin-4-yl]methyl}-5-[4'-(1-methyl-1H-p;yrazol-4-yl)biphenyl-4-yl]-4,6-diazaspiro[2.4]hept-4-en-7-one<br>$^1$H NMR (300 MHz, CDCl$_3$) δ ppm 0.71 (dd, J = 7.8, 3.1 Hz, 2 H), 0.88-0.96 (m, 2 H), 0.97-1.33 (m, 3 H), 1.67 (td, J = 8.2, 4.3 Hz, 2 H), 1.73-1.81 (m, 2 H), 1.82-1.94 (m, 3 H), 2.33-2.63 (m, 1 H), 2.85-3.09 (m, 1 H), 3.60-3.75 (m, 2 H), 3.98 (s, 3 H), 4.06-4.27 (m, 1 H), 4.40-4.65 (m, 1 H), 7.55-7.62 (m, 2 H), 7.62-7.72 (m, 5 H), 7.72-7.80 (m, 2 H), 7.83 (s, 1 H); MS m/z 508 (M + H)$^+$<br>m.p. 186.8° C. |

-continued

| ID No. | Structure | Compound Name & Physical Data |
|---|---|---|
| 61 | 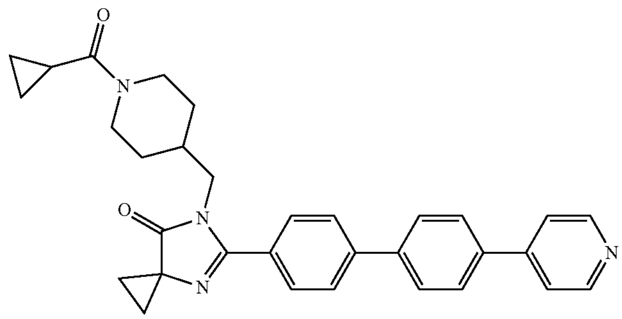 [SMILES: O=C(C1CC1)N1CCC(CN2C(=O)C3(CC3)N=C2c2ccc(-c3ccc(-c4ccncc4)cc3)cc2)CC1] | 6-{[1-(Cyclopropylcarbonyl)piperidin-4-yl]methyl}-5-(4'-pyridin-4-ylbiphenyl-4-yl)-4,6-diazaspiro[2.4]hept-4-en-7-one<br>MS m/z 505 (M + H)+<br>m.p. 162.1° C. |
| 62 | 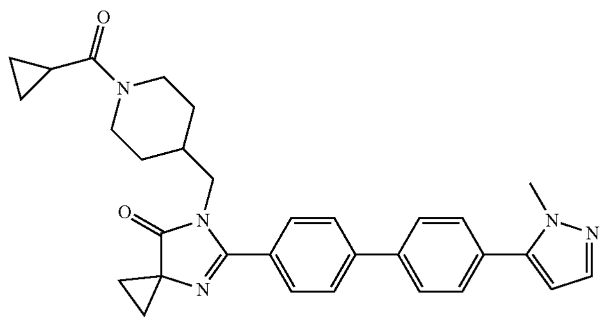 [SMILES: Cn1nccc1-c1ccc(-c2ccc(C3=NC4(CC4)C(=O)N3CC3CCN(C(=O)C4CC4)CC3)cc2)cc1] | 6-{[1-(Cyclopropylcarbonyl)piperidin-4-yl]methyl}-5-[4'-(1-methyl-1H-pyrazol-5-yl)biphenyl-4-yl]-4,6-diazaspiro[2.4]hept-4-en-7-one<br>MS m/z 508 (M + H)+<br>m.p. 119.2° C. |
| 122 | 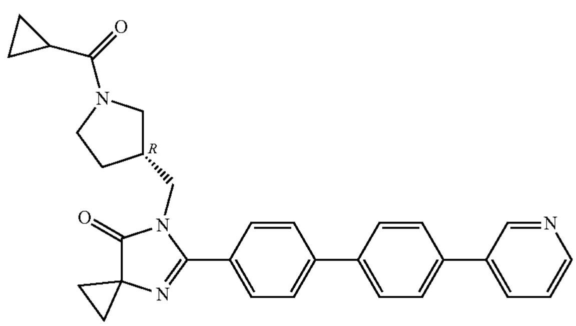 | 6-{[(3R)-1-(Cyclopropylcarbonyl)pyrrolidin-3-yl]methyl}-5-(4'-pyridin-3-ylbiphenyl-4-yl)-4,6-diazaspiro[2.4]hept-4-en-7-one<br>$^1$H NMR (300 MHz, CDCl$_3$) δ ppm 0.61-0.83 (m, 2 H), 0.84-1.06 (m, 2 H), 1.36-2.13 (m, 6 H), 2.28-2.71 (m, 1 H), 3.06 (dd, J = 12.0, 7.1 Hz, 0.5 H), 3.21-3.41 (m, 1 H), 3.41-4.03 (m, 4.5 H), 7.43 (d, J = 4.7 Hz, 1 H), 7.60-7.89 (m, 8 H), 7.95 (d, J = 7.7 Hz, 1 H), 8.64 (br. s., 1 H), 8.93 (br. s., 1 H);<br>MS m/z 491 (M + H)+<br>m.p. 149.7° C. |
| 59 | 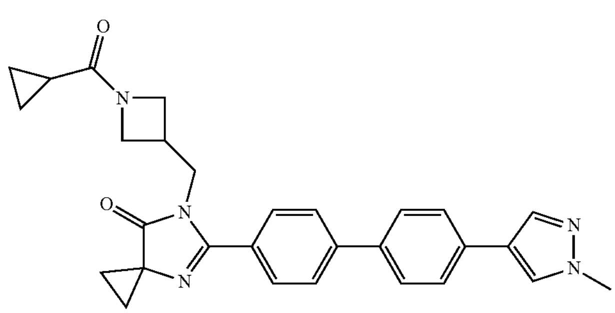 [SMILES: Cn1cc(-c2ccc(-c3ccc(C4=NC5(CC5)C(=O)N4CC4CN(C(=O)C5CC5)C4)cc3)cc2)cn1] | 6-{[1-(Cyclopropylcarbonyl)azetidin-3-yl]methyl}-5-[4'-(1-methyl-1H-pyrazol-4-yl)biphenyl-4-yl]-4,6-diazaspiro[2.4]hept-4-en-7-one<br>1H NMR (300 MHz, CDCl$_3$) δ ppm 0.63-0.84 (m, 2 H), 0.84-1.06 (m, 2 H), 1.23-1.38 (m, 1 H), 1.72-1.84 (m, 2 H), 1.84-1.99 (m, 2 H), 2.75-3.00 (m, 1 H), 3.61 (dd, J = 9.8, 5.6 Hz, 1 H), 3.90-4.15 (m, 4 H), 4.00 (s, 3 H), 4.23 (t, J = 8.2 Hz, 1 H), 7.54-7.72 (m, 6 H), 7.72-7.96 (m, 4 H);<br>MS m/z 480 (M + H)+<br>m.p. 203.4° C. |

| ID No. | Structure | Compound Name & Physical Data |
|---|---|---|
| 60 | 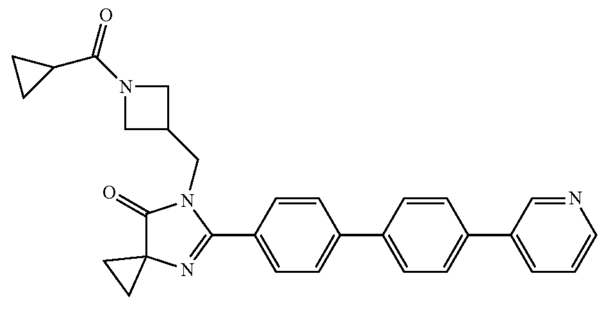 [SMILES: O=C(C1CC1)N1CC(CN2C(=O)C3(CC3)N=C2c2ccc(-c3ccc(-c4cccnc4)cc3)cc2)C1] | 6-{[1-(Cyclopropylcarbonyl)azetidin-3-yl]methyl}-5-(4'-pyridin-3-ylbiphenyl-4-yl)-4,6-diazaspiro[2.4]hept-4-en-7-one<br>1H NMR (300 MHz, CDCl₃) δ ppm 0.65-<br>0.77 (m, 2 H), 0.91 (t, J = 3.9 Hz, 2 H), 1.25-1.36 (m, 1 H), 1.75-1.84 (m, 2 H), 1.84-1.94 (m, 2 H), 2.77-2.96 (m, 1 H), 3.61 (dd, J = 9.9, 5.8 Hz, 1 H), 3.89-4.16 (m, 4 H), 4.25 (t, J = 8.3 Hz, 1 H), 7.42 (dd, J = 7.9, 4.9 Hz, 1 H), 7.66-7.89 (m, 8 H), 7.95 (dt, J = 7.9, 1.9 Hz, 1 H), 8.64 (dd, J = 4.8, 1.5 Hz, 1<br>H), 8.93 (d, J = 2.2 Hz, 1 H);<br>MS m/z 477 (M + H)⁺ |

Example 4

2-[4-(1,3-Benzoxazol-2-yl)phenyl]-3-{[(3R)-1-(cyclopropylcarbonyl)pyrrolidin-3-yl]methyl}-1,3-diazaspiro[4.4]non-1-en-4-one (Compound #36)

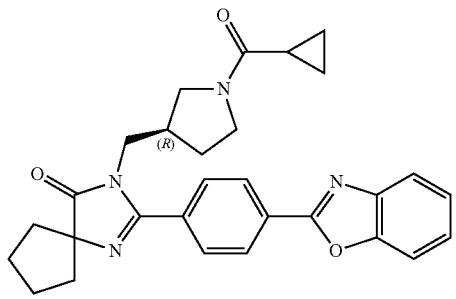

To a flask under argon was added (R)-2-(4-bromophenyl)-3-((1-(cyclopropanecarbonyl)pyrrolidin-3-yl)methyl)-1,3-diazaspiro[4.4]non-1-en-4-one (122 mg, 0.275 mmol), benzo[d]oxazole (40 mg, 0.329 mmol), K₂CO₃ (76 mg, 0.549 mmol), Pd(OAc)₂ (1.3 mg, 0.0055 mmol), Cu(OAc)₂ (10.7 mg, 0.0549 mmol), PPh₃ (36 mg, 0.137 mmol) and 1 mL of toluene. The reaction mixture was heated at 110° C. for 6 hrs, the solvent evaporated, and the residue purified by preparative reverse-phase chromatography to yield 2-[4-(1,3-benzoxazol-2-yl)phenyl]-3-{[(3R)-1-(cyclopropylcarbonyl)pyrrolidin-3-yl]methyl}-1,3-diazaspiro[4.4]non-1-en-4-one (65.3 mg, 47%).

¹H NMR (400 MHz, CDCl₃) δ ppm 0.79 (d, J=5.1 Hz, 2H), 0.92-1.07 (m, 2H), 1.40-1.76 (m, 2H), 1.83-2.31 (m, 9H), 2.33-2.58 (m, 1H), 3.03-3.32 (m, 1H), 3.32-3.91 (m, 5H), 7.39-7.49 (m, 2H), 7.65 (d, J=6.6 Hz, 1H), 7.86 (t, J=7.3 Hz, 3H), 8.49 (d, J=6.6 Hz, 2H). MS m/z 483.3 (M+H)⁺.

Example 5

(R)-Methyl 2-(4-(benzofuran-5-yl)phenyl)-3-((1-(cyclopropanecarbonyl)pyrrolidin-3-yl)methyl)-4-oxo-1,3,8-triazaspiro[4.5]dec-1-ene-8-carboxylate (Compound #14)

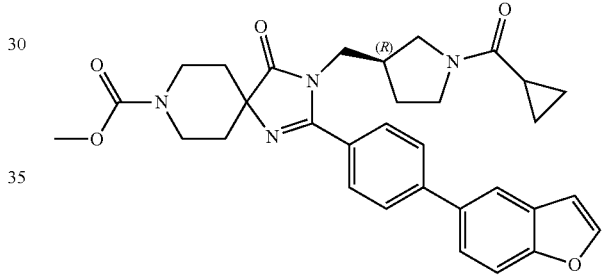

STEP A: 4-tert-Butyl 4-(4-bromobenzamido)-4-carbamoylpiperidine-1-carboxylate A mixture tert-butyl 4-amino-4-carbamoylpiperidine-1-carboxylate (0.848 g, 3.41 mmol), 4-bromobenzoic acid (0.687 g, 3.41 mmol), EDCI (0.655 g, 3.41 mmol), HOBt (0.462 g, 3.41 mmol) and DIPEA (0.59 mL, 3.41 mmol) in DMF (16 mL) was stirred at room temperature for 1 day. The reaction mixture was partitioned between EtOAc and aqueous saturated NaHCO₃. The organic phase was washed with brine, dried over Na₂SO₄, filtered and concentrated in vacuo to yield 4-tert-butyl 4-(4-bromobenzamido)-4-carbamoylpiperidine-1-carboxylate (1.21 g, 83%).

¹H NMR (400 MHz, DMSO-d₆) δ ppm 1.40 (s, 9H), 1.76-1.93 (m, 2H), 2.01-2.19 (m, 2H), 3.09 (br. s., 2H), 3.57-3.80 (m, 2H), 6.93 (br. s., 1H), 7.16 (br. s., 1H), 7.68 (d, J=8.6 Hz, 2H), 7.84 (d, J=8.6 Hz, 2H), 8.21 (s, 1H); MS m/z 450.1 (M+Na)⁺).

STEP B: tert-Butyl 2-(4-bromophenyl)-4-oxo-1,3,8-triazaspiro[4.5]dec-1-ene-8-carboxylate A mixture of 4-tert-butyl 4-(4-bromobenzamido)-4-carbamoylpiperidine-1-carboxylate (1.6 g, 3.75 mmol) and NaOH (0.75 g, 18.76 mmol) in H₂O (3.80 mL) and MeOH (65 mL) was stirred at 65° C. for 1 day. The reaction mixture was partitioned between water (400 mL) and EtOAc (2×350 mL). The organic phase was washed with brine, dried over $Na_2SO_4$, filtered and concentrated in vacuo to yield 2-(4-bromophenyl)-1,3-diazaspiro[4.4]non-1-en-4-one (1.53 g, 100%).

$^1$H NMR (400 MHz, DMSO-$d_6$) δ ppm 1.35-1.53 (m, 11H), 1.61-1.74 (m, 2H), 3.28 (br. s., 3H), 3.80-3.98 (m, 2H), 7.77 (d, J=8.3 Hz, 2H), 7.94 (d, J=8.1 Hz, 2H); MS m/z 410.0 (M+H)$^+$.

STEP C: 2-(4-Bromophenyl)-1,3,8-triazaspiro[4.5]dec-1-en-4-one

To a stirring solution of (tert-butyl 2-(4-bromophenyl)-4-oxo-1,3,8-triazaspiro[4.5]dec-1-ene-8-carboxylate (400 mg, 0.98 mmol) in 1,4-dioxane (7 mL) was added 4M HCl in 1,4-dioxane (8 mL). After stirring at room temperature for 5 h, the reaction mixture was concentrated to yield 2-(4-bromophenyl)-1,3,8-triazaspiro[4.5]dec-1-en-4-one as its corresponding HCl salt, as a solid; which was directly used in the next step.

MS m/z 310.0 (M+H)$^+$.

STEP D: Methyl 2-(4-bromophenyl-4-oxo-1,3,8-triazaspiro[4.5]dec-1-ene-8-carboxylate To a stirring solution of 2-(4-bromophenyl)-1,3,8-triazaspiro[4.5]dec-1-en-4-one HCl salt (172 mg, 0.5 mmol) in DCM (15 mL) and DIPEA (0.43 mL, 2.5 mmol) was added methyl chloroformate (49.6 mg, 0.52 mmol) at 0° C. After stirring at room temperature overnight, the reaction mixture was partitioned between aqueous $NaHCO_3$ and DCM. The organic phase was washed with brine, dried over $Na_2SO_4$, filtered and concentrated in vacuo to yield methyl 2-(4-bromophenyl)-4-oxo-1,3,8-triazaspiro[4.5]dec-1-ene-8-carboxylate (183 mg, 100%).

$^1$H NMR (400 MHz, CDCl$_3$) δ ppm 1.52-1.64 (m, 2H), 1.89-2.07 (m, 2H), 3.45-3.59 (m, 2H), 3.76 (s, 3H), 3.98-4.25 (m, 2H), 7.64-7.71 (m, 2H), 7.77-7.84 (m, 2H); MS n/z 368.0 (M+H)$^+$.

STEP E: (S)-Methyl 2-(4-bromophenyl)-3-((1-(tert-butoxycarbonyl)pyrrolidin-3-yl)methyl)-4-oxo-1,3,8-triazaspiro[4.5]dec-1-ene-8-carboxylate To a stirring solution of methyl 2-(4-bromophenyl)-4-oxo-1,3,8-triazaspiro[4.5]dec-1-ene-8-carboxylate (100 mg, 0.27 mmol) and (R)-tert-butyl 3-(bromomethyl)pyrrolidine-1-carboxylate (144 mg, 0.54 mmol) in DMF (4.5 mL) was added Cs$_2$CO$_3$ (222 mg, 0.68 mmol). After stirring at room temperature for 5 min and 65° C. for 17 h, the reaction mixture was partitioned between aqueous NaHCO$_3$ and EtOAc. The organic phase was washed with brine, dried over Na$_2$SO$_4$, filtered and concentrated in vacuo to yield a residue. The residue was purified by flash chromatography (silica gel, 40% EtOAc/heptane) to yield (S)-methyl 2-(4-bromophenyl)-3-((1-(tert-butoxycarbonyl)pyrrolidin-3-yl)methyl)-4-oxo-1,3,8-triazaspiro[4.5]dec-1-ene-8-carboxylate (122 mg, 81%).

$^1$H NMR (400 MHz, CDCl$_3$) δ ppm 1.17 (br. s., 1H), 1.41 (s, 9H), 1.46-1.56 (m, 2H), 1.67-1.82 (m, 2H), 1.87-2.02 (m, 2H), 2.23 (d, J=6.8 Hz, 1H), 2.71-2.87 (m, 1H), 3.09-3.39 (m, 2H), 3.47 (s, 3H), 3.53-3.68 (m, 2H), 3.72 (s, 2H), 3.94-4.20 (m, 2H), 7.45 (d, J=8.3 Hz, 2H), 7.66 (d, J=8.1 Hz, 2H); MS n/z 540.0 (M+H)$^+$.

STEP F: (R)-Methyl 2-(4-bromophenyl)-4-oxo-3-(pyrrolidin-3-ylmethyl)-1,3,8-triazaspiro[4.5]dec-1-ene-8-carboxylate To a stirring solution of (S)-methyl 2-(4-bromophenyl)-3-((1-(tert-butoxycarbonyl)pyrrolidin-3-yl)methyl)-4-oxo-1,3,8-triazaspiro[4.5]dec-1-ene-8-carboxylate (162 mg, 0.295 mmol) in 1,4-dioxane (3 mL) was added 4M HCl in 1,4-dioxane (5 mL). After stirring overnight at room temperature the reaction mixture was concentrated to yield (R)-methyl 2-(4-bromophenyl)-4-oxo-3-(pyrrolidin-3-ylmethyl)-1,3,8-triazaspiro[4.5]dec-1-ene-8-carboxylate as its corresponding HCl salt, as a solid; which was directly used into the next step.

MS m/z 451.0 (M+H)$^+$.

STEP G: (R)-Methyl 2-(4-bromophenyl)-3-((1-(cyclopropanecarbonyl)pyrrolidin-3-yl)methyl)-4-oxo-1,3,8-triazaspiro[4.5]dec-1-ene-8-carboxylate To a stirring solution of (R)-methyl 2-(4-bromophenyl)-4-oxo-3-(pyrrolidin-3-ylmethyl)-1,3,8-triazaspiro[4.5]dec-1-ene-8-carboxylate (150 mg, 0.334 mmol) in DCM (10 mL) and DIPEA (0.28 mL, 1.67 mmol) was added cyclopropanecarbonyl chloride (0.038 mL, 0.40 mmol). After stirring at room temperature for 3 h, the reaction mixture was partitioned between aqueous NaHCO$_3$ and DCM. The organic phase was washed with brine, dried over Na$_2$SO$_4$, filtered and concentrated in vacuo to yield (R)-methyl 2-(4-bromophenyl)-3-((1-(cyclopropanecarbonyl)pyrrolidin-3-yl)methyl)-4-oxo-1,3,8-triazaspiro[4.5]dec-1-ene-8-carboxylate (130 mg, 75%).

$^1$H NMR (400 MHz, CDCl$_3$) δ ppm 0.68-0.80 (m, 2H), 0.90-0.99 (m, 2H), 1.38-1.64 (m, 5H), 1.72-1.84 (m, 1H), 1.87-2.04 (m, 3H), 2.18-2.44 (m, 1H), 2.95 (dd. J=12.0, 7.1 Hz, 1H), 3.13-3.34 (m, 1H), 3.41-3.71 (m, 7H), 3.73 (s, 3H), 3.96-4.23 (m, 2H), 7.46 (dd, J=8.3, 5.9 Hz, 2H), 7.62-7.73 (m, 2H); MS m/z 517.0 (M+H)$^+$.

STEP H: (R)-Methyl 2-(4-(benzofuran-5-yl)phenyl)-3-((1-(cyclopropanecarbonyl)pyrrolidin-3-yl)methyl)-4-oxo-1,3,8-triazaspiro[4.5]dec-1-ene-8-carboxylate (Compound #14)

To a solution of (R)-methyl 2-(4-bromophenyl)-3-((1-(cyclopropanecarbonyl)pyrrolidin-3-yl)methyl)-4-oxo-1,3,8-triazaspiro[4.5]dec-1-ene-8-carboxylate (50 mg, 0.097 mmol) and benzofuran-5-ylboronic acid (24.0 mg, 0.145 mol) in DME (2 mL) was added under argon aqueous 2M Na$_2$CO$_3$ (0.1 mL, 0.20 mmol) and Pd(PPh$_3$)$_4$ (3.4 mg, 0.003 mmol). The reaction mixture was refluxed for 16 h, filtered, concentrated in vacuo and the resulting residue was purified by flash chromatography (silica gel, 2.5% MeOH/DCM) to yield (R)-methyl 2-(4-(benzofuran-5-yl)phenyl)-3-((1-(cyclopropanecarbonyl)pyrrolidin-3-yl)methyl)-4-oxo-1,3,8-triazaspiro[4.5]dec-1-ene-8-carboxylate (45 mg, 84%).

$^1$H NMR (400 MHz, CDCl$_3$) δ ppm 0.71 (dd, J=7.6, 2.9 Hz, 2H), 0.89-0.96 (m, 2H), 1.38-1.68 (m, 4H), 1.82 (dd, J=11.5, 5.1 Hz, 1H), 1.89-2.09 (m, 3H), 2.38-2.54 (m, 1H), 3.00 (dd, J=12.0, 7.1 Hz, 1H), 3.15-3.35 (m, 1H), 3.42-3.70 (m, 5H), 3.71-3.78 (m, 4H), 4.15 (br. s., 2H), 6.85 (d, J=2.0 Hz, 1H), 7.53-7.58 (m, 1H), 7.61 (d, J=8.6 Hz, 1H), 7.63-7.72 (m, 3H), 7.73-7.81 (m, 2H), 7.84 (s, 1H); MS m/z 555.0 (M+H)$^+$.

Following the procedure described in Example 5, above, selecting and substituting the appropriate reagents, starting materials, and purification methods, and adjusting reaction temperatures, times and other variables or parameters, as needed or desirable, as would be readily recognized by those skilled in the art, the following compounds of formula (I) of the invention were prepared.

| ID No. | Structure | Compound Name & Physical Data |
|---|---|---|
| 15 | 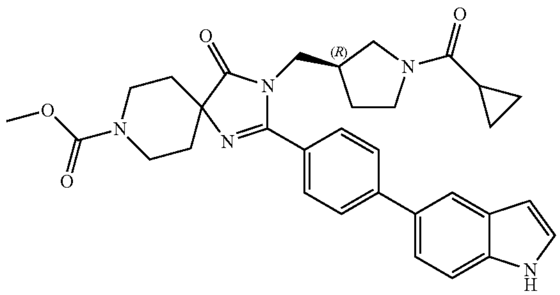 | Methyl 3-{[(3R)-1-(cyclopropylcarbonyl)pyrrolidin-3-yl]methyl}-2-[4-(1H-indol-5-yl)phenyl]-4-oxo-1,3,8-triazaspiro[4.5]dec-1-ene-8-carboxylate<br>$^1$H NMR (400 MHz, CDCl$_3$) δ ppm 0.64-0.77 (m, 2 H), 0.88-0.99 (m, 2 H), 1.42-1.64 (m, 4 H), 1.77-2.09 (m, 3 H), 2.23-2.53 (m, 1 H), 2.94-3.34 (m, 1 H), 3.46-3.72 (m, 5 H), 3.72-3.79 (m, 4 H), 3.96-4.26 (m, 2 H), 6.62 (br. s., 1 H), 7.28 (br. s., 1 H), 7.43-7.49 (m, 2 H), 7.63 (t, J = 7.8 Hz, 2 H), 7.74-7.83 (m, 2 H), 7.90 (s, 1 H), 8.62 (br. s., 1 H);<br>MS m/z 554.2 (M + H)$^+$ |
| 16 | 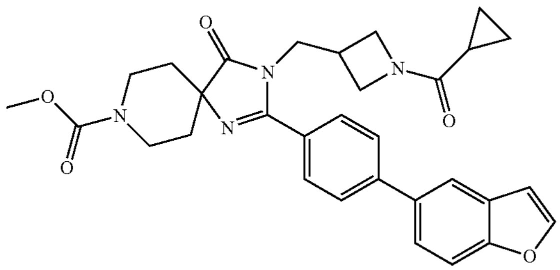 [SMILES: COC(=O)N1CCC2(CC1)N=C(c1ccc(-c3ccc4occc4c3)cc1)N(CC1CN(C(=O)C3CC3)C1)C2=O] | Methyl 2-[4-(1-benzofuran-5-yl)phenyl]-3-{[1-(cyclopropylcarbonyl)azetidin-3-yl]methyl}-4-oxo-1,3,8-triazaspiro[4.5]dec-1-ene-8-carboxylate<br>$^1$H NMR (400 MHz, CDCl$_3$) δ ppm 0.70 (dd, J = 7.8, 3.4 Hz, 2 H), 0.85-0.94 (m, 2 H), 1.22-1.33 (m, 1 H), 1.54 (d, J = 13.2 Hz, 2 H), 1.92-2.06 (m, 2 H), 2.75 (br. s., 1 H), 3.44-3.61 (m, 3 H), 3.75 (s, 3 H), 3.84-4.08 (m, 5 H), 4.08-4.24 (m, 2 H), 6.86 (d, J = 2.0 Hz, 1 H), 7.56 (dd, J = 8.6, 1.7 Hz, 1 H), 7.62 (d, J = 8.6 Hz, 1 H), 7.65 (d, J = 8.3 Hz, 2 H), 7.70 (d, J = 2.0 Hz, 1 H), 7.78 (d, J = 8.3 Hz, 2 H), 7.84 (d, J = 1.5 Hz, 1 H);<br>MS m/z 541.0 (M + H)$^+$ |
| 17 | 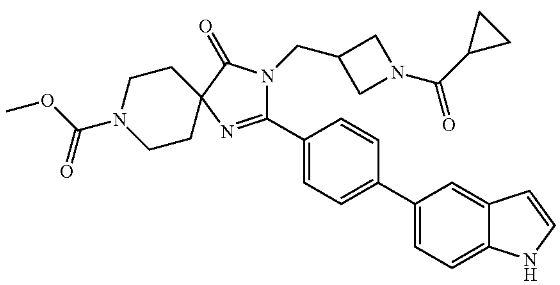 [SMILES: COC(=O)N1CCC2(CC1)N=C(c1ccc(-c3ccc4[nH]ccc4c3)cc1)N(CC1CN(C(=O)C3CC3)C1)C2=O] | Methyl 3-{[1-(cyclopropylcarbonyl)azetidin-3-yl]methyl}-2-[4-(1H-indol-5-yl)phenyl]-4-oxo-1,3,8-triazaspiro[4.5]dec-1-ene-8-carboxylate<br>$^1$H NMR (400 MHz, CDCl$_3$) δ ppm 0.70 (dd, J = 7.8, 3.2 Hz, 2 H), 0.91 (br. s., 2 H), 1.21-1.34 (m, 1 H), 1.54 (d, J = 12.7 Hz, 2 H), 1.90-2.06 (m, 2 H), 2.75 (br. s., 1 H), 3.45-3.63 (m, 3 H), 3.75 (s, 3 H), 3.82-4.07 (m, 4 H), 4.07-4.25 (m, 2 H), 6.64 (br. s., 1 H), 7.29 (t, J = 2.7 Hz, 1 H), 7.42-7.51 (m, 2 H), 7.62 (m, J = 8.3 Hz, 2 H), 7.80 (m, J = 8.1 Hz, 2 H), 7.91 (s, 1 H), 8.56 (br. s., 1 H);<br>MS m/z 540.3 (M + H)$^+$ |

Example 6

(R)-2-(4-(1H-Indol-5-yl)phenyl)-8-benzyl-3-((1-(cyclopropanecarbonyl)pyrrolidin-3-ylmethyl)-1,3,8-triazaspiro[4.5]dec-1-en-4-one (Compound #63)

and (R)-2-(4-(1H-indol-5-yl)phenyl)-3-((1-(cyclopropanecarbonyl)pyrrolidin-3-yl)methyl-8-methyl-1,3,8-triazaspiro[4.5]dec-1-en-4-one (Compound #81)

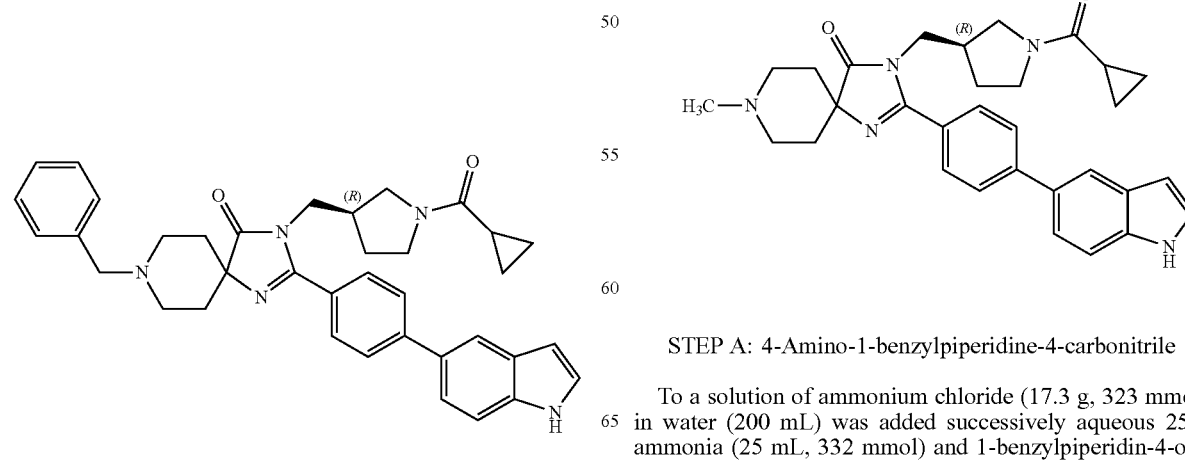

STEP A: 4-Amino-1-benzylpiperidine-4-carbonitrile

To a solution of ammonium chloride (17.3 g, 323 mmol) in water (200 mL) was added successively aqueous 25% ammonia (25 mL, 332 mmol) and 1-benzylpiperidin-4-one (11.43 g, 60 mmol). The resulting mixture was stirred at room temperature for 20 min and sodium cyanide (14.7 g, 300 mmol) was added in portions over 15 min. After stirring for 1 day, the reaction mixture was partitioned between water (200 mL) and DCM (2×200 mL). The organic phase was dried over MgSO$_4$, filtered and concentrated in vacuo to yield a residue. The residue was purified by flash chromatography (silica gel, 50% EtOAc/heptanes to 100% EtOAc) to yield 4-amino-1-benzylpiperidine-4-carbonitrile (6.15 g, 47%).

$^1$H NMR (300 MHz, CDCl$_3$) δ ppm 1.69-1.86 (m, 4H), 2.00 (dt, J=13.1, 2.1 Hz, 2H), 2.27-2.45 (m, 2H), 2.83 (dt, J=12.4, 3.6 Hz, 2H), 3.55 (s, 2H), 7.21-7.39 (m, 5H); MS m/z 216 (M+H)$^+$.

STEP B: 4-Amino-1-benzylpiperidine-4-carboxamide

To a solution of 4-amino-1-benzylpiperidine-4-carbonitrile (6.15 g, 28.6 mmol) in DCM (70 mL) at −5° C. was added 95-97% sulfuric acid (50 mL). The reaction mixture was stirred at 0 to 5° C. overnight and the organic layer was discarded. The resulting mixture was poured onto crushed ice (1000 mL) and the pH adjusted to pH 9 with aqueous 5N NaOH, keeping the temperature below 10° C. The resulting mixture was partitioned between water and EtOAc (3×500 mL). The organic phase was dried over MgSO$_4$, filtered and concentrated in vacuo to yield a residue. The residue was purified by flash chromatography (silica gel, 5% MeOH in DCM) to yield 2-(4-bromophenyl)-1,3-diazaspiro[4.4]non-1-en-4-one (5.06 g, 76%).

$^1$H NMR (300 MHz, CDCl$_3$) δ ppm 1.29-1.57 (m, 4H), 2.14-2.39 (m, 4H), 2.71-2.84 (m, 2H), 3.55 (s, 2H), 5.41 (br. s., 1H), 7.20-7.38 (m, 5H), 7.45 (br. s., 1H); MS m/z 234 (M+H)$^+$.

STEP C: 1-Benzyl-4-(4-bromobenzamido)piperidine-4-carboxamide

A mixture 4-amino-1-benzylpiperidine-4-carboxamide (2 g, 8.31 mmol), 4-bromobenzoic acid (1.67 g, 8.31 mmol), EDCI (1.59 g, 8.31 mmol), HOBt (1.12 g, 8.31 mmol) and DIPEA (1.43 mL, 8.31 mmol) in DMF (45 mL) was stirred at room temperature for 1 day. The reaction mixture was partitioned between EtOAc and aqueous saturated NaHCO$_3$. The organic phase was washed with brine, dried over Na$_2$SO$_4$, filtered and concentrated in vacuo to yield 1-benzyl-4-(4-bromobenzamido)piperidine-4-carboxamide (3.4 g, 99%).

$^1$H NMR (400 MHz, DMSO-d$_6$) δ ppm 1.74-1.87 (m, 2H), 1.97-2.14 (m, 4H), 2.45 (d, J=11.5 Hz, 2H), 3.21 (s, 2H), 3.29 (s, 2H), 6.73 (s, 1H), 6.94 (s, 1H), 7.04-7.23 (m, 5H), 7.54 (d, J=8.3 Hz, 2H), 7.67 (d, J=8.6 Hz, 2H), 7.91 (s, 1H); MS m/z 418.0 (M+H)$^+$.

STEP D: 8-Benzyl-2-(4-bromophenyl)-1,3,8-triazaspiro[4.5]dec-1-en-4-one

A mixture of 1-benzyl-4-(4-bromobenzamido)piperidine-4-carboxamide (2 g, 4.8 mmol) and NaOH (0.96 g, 24.0 mmol) in H$_2$O (4.81 mL) and MeOH (80 mL) was stirred at 65° C. for 1 day. The reaction mixture was partitioned between water (300 mL) and EtOAc (2×300 mL). The organic phase was washed with brine, dried over Na$_2$SO$_4$, filtered and concentrated in vacuo to yield 8-benzyl-2-(4-bromophenyl)-1,3,8-triazaspiro[4.5]dec-1-en-4-one (1.56 g, 82%).

$^1$H NMR (400 MHz, DMSO-d$_6$) δ ppm 1.36-1.54 (m, 2H), 1.76-1.90 (m, 2H), 2.42-2.45 (m, 2H), 2.70-2.82 (m, 2H), 3.56 (s, 2H), 7.21-7.28 (m, 1H), 7.30-7.37 (m, 4H), 7.75 (d, J=7.8 Hz, 2H), 7.90 (br. s., 2H); MS m/z 400.0 (M+H)$^+$.

STEP E: (S)-tert-Butyl 3-((8-benzyl-2-(4-bromophenyl)-4-oxo-1,3,8-triazaspiro[4.5]dec-1-en-3-yl)methyl)pyrrolidine-1-carboxylate To a stirring solution of 8-benzyl-2-(4-bromophenyl)-1,3,8-triazaspiro[4.5]dec-1-en-4-one (0.95 g, 2.38 mmol) and (R)-tert-butyl 3-(iodomethyl)pyrrolidine-1-carboxylate (1.33 g, 4.77 mmol) in DMF (10 mL) was added K$_2$CO$_3$ (0.66 g, 4.77 mmol). After stirring at 65° C. for 48 h, the reaction mixture was partitioned between water and EtOAc. The organic phase was washed with brine, dried over MgSO$_4$, filtered and concentrated in vacuo to yield a residue. The residue was purified by flash chromatography (silica gel, 2-5% MeOH/DCM) to yield (S)-tert-butyl 3-((8-benzyl-2-(4-bromophenyl)-4-oxo-1,3,8-triazaspiro[4.5]dec-1-en-3-yl)methyl)pyrrolidine-1-carboxylate (0.75 g, 57%).

$^1$H NMR (400 MHz, CDCl$_3$) δ ppm 1.17 (br. s., 1H), 1.41 (s, 9H), 1.46-1.56 (m, 2H), 1.67-1.82 (m, 2H), 1.87-2.02 (m, 2H), 2.23 (d, J=6.8 Hz, 1H), 2.71-2.87 (m, 1H), 3.09-3.39 (m, 2H), 3.47 (s, 3H), 3.53-3.68 (m, 2H), 3.72 (s, 3H), 3.94-4.20 (m, 2H), 7.45 (d, J=8.3 Hz, 2H), 7.66 (d, J=8.1 Hz, 2H); MS n/z 540.0 (M+H)$^+$.

STEP F: (R)-8-Benzyl-2-(4-bromophenyl)-3-(pyrrolidin-3-ylmethyl)-1,3,8-triazaspiro[4.5]dec-1-en-4-one To a stirring solution of (S)-tert-butyl 3-((8-benzyl-2-(4-bromophenyl)-4-oxo-1,3,8-triazaspiro[4.5]dec-1-en-3-yl)methyl)pyrrolidine-1-carboxylate (5.05 g, 8.68 mmol) in 1,4-dioxane (20 mL) was added 4M HCl in 1,4-dioxane (20 mL). After stirring for 4 h at room temperature the reaction mixture was diluted with diethyl ether; the precipitate was filtered off, washed with diethyl ether and dried to yield (R)-8-benzyl-2-(4-bromophenyl)-3-(pyrrolidin-3-ylmethyl)-1,3,8-triazaspiro[4.5]dec-1-en-4-one, as its corresponding bis-HCl salt (5.06 g, 95%).

MS m/z 481.0 (M+H)$^+$.

STEP G: (R)-8-Benzyl-2-(4-bromophenyl)-3-((1-(cyclopropanecarbonyl)pyrrolidin-3-yl)methyl)-1,3,8-triazaspiro[4.5]dec-1-en-4-one To a stirring solution of (R)-8-benzyl-2-(4-bromophenyl)-3-(pyrrolidin-3-ylmethyl)-1,3,8-triazaspiro[4.5]dec-1-en-4-one (5.05 g, 8.66 mmol) in DCM (100 mL) and triethylamine (6.04 mL, 43.3 mmol) was added at 0° C. cyclopropanecarbonyl chloride (0.87 mL, 9.53 mmol). After stirring at room temperature for 1 h, MeOH (5 mL) was added to the solution and the reaction mixture was partitioned between aqueous 1M NaOH and DCM. The organic phase was dried over MgSO$_4$, filtered and concentrated in vacuo to yield ((R)-8-benzyl-2-(4-bromophenyl)-3-((1-(cyclopropanecarbonyl)pyrrolidin-3-yl)methyl)-1,3,8-triazaspiro[4.5]dec-1-en-4-one (4.94 g, 99%).

$^1$H NMR (400 MHz, CDCl$_3$) δ ppm 0.68-0.80 (m, 2H), 0.90-0.99 (m, 2H), 1.38-1.64 (m, 5H), 1.72-1.84 (m, 1H), 1.87-2.04 (m, 3H), 2.18-2.44 (m, 1H), 2.95 (dd, J=12.0, 7.1 Hz, 1H), 3.13-3.34 (m, 1H), 3.41-3.71 (m, 7H), 3.73 (s, 3H), 3.96-4.23 (m, 2H), 7.46 (dd, J=8.3, 5.9 Hz, 2H), 7.62-7.73 (m, 2H); MS m/z 549.0 (M+H)+.

STEP H: (R)-2-(4-(1H-Indol-5-yl)phenyl)-8-benzyl-3-((1-(cyclopropanecarbonyl)pyrrolidin-3-yl)methyl)-1,3,8-triazaspiro[4.5]dec-1-en-4-one (Compound #63)

((R)-8-benzyl-2-(4-bromophenyl)-3-((1-(cyclopropanecarbonyl)pyrrolidin-3-yl)methyl)-1,3,8-triazaspiro[4.5]dec-1-en-4-one (0.382 g, 0.695 mmol), 1H-indol-5-yl-5-boronic acid (0.134 g, 0.834 mmol), tetrakis(triphenylphosphine) palladium (0.040 g, 0.035 mmol), potassium carbonate (0.192 g, 0.241 mmol), dioxane (25 mL) and water (2 mL) were combined and the resulting mixture was heated at reflux for 16 h. The mixture was diluted with water and extracted with ethyl acetate. The extracts were concentrated to a dark oil, which was purified by flash chromatography (silica gel, 0 to 5% methanol in dichloromethane) to yield (R)-2-(4-(1H-indol-5-yl)phenyl)-8-benzyl-3-((1-(cyclopropanecarbonyl) pyrrolidin-3-yl) methyl)-1,3,8-triazaspiro[4.5]dec-1-en-4-one as a slightly pink solid (0.183 g)

$^1$H NMR (400 MHz, CDCl$_3$) δ ppm 0.67-0.73 (m, 2H), 0.89-0.97 (m, 2H), 1.39-1.66 (m, 3H), 1.75-2.02 (m, 2H), 2.08-2.21 (m, 2H), 2.28-2.51 (m, 1H), 2.68 (t, J=11.1 Hz, 2H), 2.83-2.95 (m, 1H), 3.02 (dd, J=12.1, 7.1 Hz, 1H), 3.13-3.34 (m, 1H), 3.43-3.76 (m, 7H), 6.61 (br. s., 1H), 7.22-7.29 (m, 2H), 7.30-7.39 (m, 4H), 7.44 (d, J=8.6 Hz, 2H), 7.61 (t, J=8.1 Hz, 2H), 7.77 (dd, J=10.1, 8.1 Hz, 2H), 7.89 (s, 1H), 8.73 (d, J=7.1 Hz, 1H) MS m/z 586.3 (M+H)+.

STEP I: (R)-2-(4-(1H-Indol-5-yl)phenyl)-3-((1-(cyclopropanecarbonyl)pyrrolidin-3-yl)methyl)-8-methy-1,3,8-triazaspiro[4.5]dec-1-en-4-one (Compound #81)

(R)-2-(4-(1H-indol-5-yl)phenyl)-8-benzyl-3-((1-(cyclopropanecarbonyl) pyrrolidin-3-yl)methyl)-1,3,8-triazaspiro[4.5]dec-1-en-4-one (0.050 g, 0.085 mmol) was dissolved in a mixture of formic acid (0.5 mL) in methanol (5 mL). 10% palladium on carbon (0.005 g) was added. The resulting mixture was heated at reflux for 16 h. The mixture was then diluted with brine and extracted 3 times with ethyl acetate. The combined ethyl acetate extracts were washed with saturated aqueous sodium bicarbonate, filtered through diatomaceous earth, and concentrated under vacuum. The resulting oil was purified by flash chromatography (silica gel, 0 to 5% methanol in dichloromethane) to yield (R)-2-(4-(1H-Indol-5-yl)phenyl)-3-((1-(cyclopropanecarbonyl)pyrrolidin-3-yl)methyl)-8-methyl-1,3,8-triazaspiro[4.5]dec-1-en-4-one as a white solid (0.003 g).

$^1$H NMR (400 MHz, CDCl$_3$) δ ppm 0.60-0.78 (m, 2H), 0.84-0.97 (m, 2H), 1.15-1.33 (m, 1H), 1.37-1.56 (m, 2H), 1.75-1.99 (m, 1H), 2.05-2.21 (m, 2H), 2.27-2.52 (m, 4H), 2.64 (t, J=10.8 Hz, 2H), 2.74-2.90 (m, 2H), 3.02 (dd, J=12.0, 6.8 Hz, 1H), 3.13-3.33 (m, 1H), 3.61 (m, J=13.4 Hz, 5H), 6.64 (t, J=2.2 Hz, 0H), 7.19-7.34 (m, 1H), 7.41-7.55 (m, 2H), 7.60-7.66 (m, 2H), 7.79 (dd, J=8.3, 6.4 Hz, 2H), 7.90 (s, 1H), 8.34 (br. s., 1H) MS m/z 510.0 (M+H)+.

Following the procedure described in Example 6, above, selecting and substituting the appropriate reagents, starting materials, and purification methods, and adjusting reaction temperatures, times and other variables or parameters, as needed or desirable, as would be readily recognized by those skilled in the art, the following compound of formula (I) of the invention was prepared.

| ID No. | Structure | Compound Name & Physical Data |
|---|---|---|
| 193 | 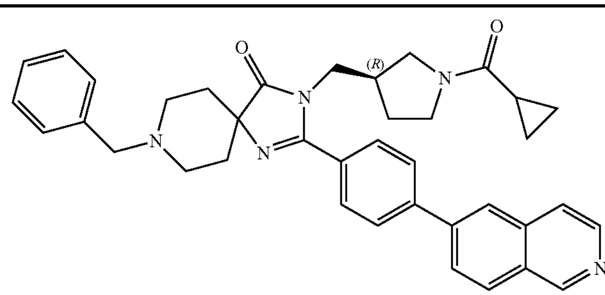 | 8-Benzyl-3-{[(3R)-1-(cyclopropylcarbonyl)pyrrrolidin-3-yl]methyl}-2-(4-isoquinolin-6-ylphenyl)-1,3,8-triazaspiro[4.5]dec-1-en-4-one<br>$^1$H NMR (300 MHz, CDCl$_3$) δ ppm 0.63-0.76 (m, 2 H), 0.84-1.01 (m, 2 H), 1.36-1.71 (m, 3 H), 1.71-2.00 (m, 2 H), 2.07-2.26 (m, 2 H), 2.26-2.56 (m, 1 H), 2.68 (t, J = 10.7 Hz, 2 H), 2.78-3.06 (m, 3 H), 3.12-3.40 (m, 1 H), 3.41-3.84 (m, 6 H), 7.20-7.43 (m, 5 H), 7.67-7.77 (m, 3 H), 7.80-7.95 (m, 3 H), 8.01-8.16 (m, 2 H), 8.60 (d, J = 5.8 Hz, 1 H), 9.32 (s, 1 H); MS m/z 554.2 (M + H)+ |

Example 7

(R)-3-((1-(Cyclopropanecarbonyl)pyrrolidin-3-yl)methyl)-2-(4-(1-methyl-1H-indazol-5-yl)phenol)-1,3,8-triazaspiro[4.5]dec-1-en-4-one (Compound #128)

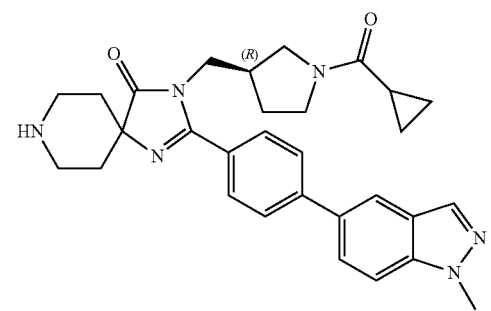

and (R)-3-((1-(cyclopropanecarbonyl)pyrrolidin-3-yl)methyl)-8-isobutyryl-2-(4-(1-methyl-1H-indazol-5-yl)phenyl)-1,3,8-triazaspiro[4.5]dec-1-en-4-one (Compound #139)

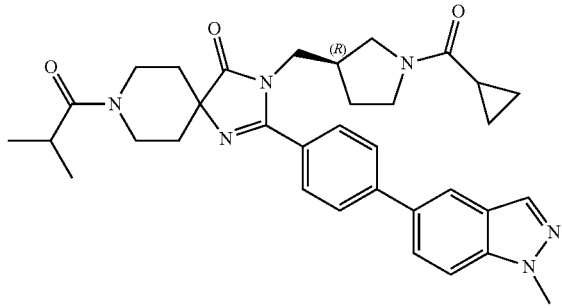

STEP A: (R)-2-(4-Bromophenyl-3-((1-(cyclopropanecarbonyl)pyrrolidin-3-yl)methyl)-1,3,8-triazaspiro[4.5]dec-1-en-4-one To a stirring suspension of (R)-8-benzyl-2-(4-bromophenyl)-3-((1-(cyclopropanecarbonyl)pyrrolidin-3-yl)methyl)-1,3,8-triazaspiro[4.5]dec-1-en-4-one (4.94 g, 8.54 mmol) and potassium bicarbonate (10.26 g, 102.5 mmol) in DCM (100 mL) was added 1-chloroethyl chloroformate (2.65 mL, 24.6 mmol). After refluxing for 1.5 h the reaction mixture was filtered and the filtrate concentrated in vacuo. The residue was dissolved in MeOH (100 mL) and the solution was refluxed for 1 h, cooled down to room temperature and concentrated in vacuo. The residue was triturated with diethyl ether and the solid was filtered and dried to yield (R)-2-(4-bromophenyl)-3-((1-(cyclopropanecarbonyl)pyrrolidin-3-yl)methyl)-1,3,8-triazaspiro[4.5]dec-1-en-4-one (4.5 g, 99%).
MS m/z 459.0 (M+H)$^+$.

STEP B: (R)-3-((1-(Cyclopropanecarbonyl)pyrrolidin-3-yl)methyl)-2-(4-(1-methyl-1H-indazol-5-phenyl)-1,3,8-triazaspiro[4.5]dec-1-en-4-one (Compound #128)

(R)-2-(4-Bromophenyl)-3-((1-(cyclopropanecarbonyl)pyrrolidin-3-yl)methyl)-1,3,8-triazaspiro[4.5]dec-1-en-4-one (1 g, 1.9 mmol), 1-methyl-5-(4,4,5,5-tetramethyl-1,3,2-dioxaborolan-2-yl)-1H-indazole (0.652 g, 2.28 mmol), aqueous 1.0M Na$_2$CO$_3$ (4 mL, 4 mmol) and acetonitrile (20 mL) were combined and bubbled with nitrogen for 15 min. Bis(triphenylphosphine)palladium (II) chloride (0.067 g, 0.095 mmol) was added and the mixture was heated at 85° C. for 1.5 h. The resulting mixture was diluted with water and extracted with DCM.

The extracts were concentrated to yield a residue which was purified by flash chromatography (silica gel, DCM/MeOH/NH$_4$OH 910.910.1) to yield (R)-3-((1-(cyclopropanecarbonyl)pyrrolidin-3-yl)methyl)-2-(4-(1-methyl-1H-indazol-5-yl)phenyl)-1,3,8-triazaspiro[4.5]dec-1-en-4-one (0.573 g, 54%).
$^1$H NMR (300 MHz, DMSO-d6) δ ppm 0.56-0.71 (m, 4H), 1.26-2.04 (m, 7H), 2.05-2.39 (m, 1H), 2.74-3.60 (m, 9H), 3.65 (t, J=6.9 Hz, 2H), 4.09 (s, 3H), 7.71-7.85 (m, 4H), 7.86-7.95 (m, 2H), 8.08-8.19 (m, 2H); MS m/z 511.0 (M+H)$^+$.

STEP C: (R)-3-((1-(Cyclopropanecarbonyl)pyrrolidin-3-yl)methyl)-8-isobutyryl-2-(4-(1-methyl-1H-indazol-5-yl)phenyl)-1,3,8-triazaspiro[4.5]dec-1-en-4-one (Compound #139)

To a stirring solution of (R)-3-((1-(cyclopropanecarbonyl)pyrrolidin-3-yl)methyl)-2-(4-(1-methyl-1H-indazol-5-yl)phenyl)-1,3,8-triazaspiro[4.5]dec-1-en-4-one (80 mg, 0.147 mmol) in DCM (5 mL) and Et$_3$N (0.20 mL, 1.43 mmol) was added isobutyryl chloride (0.019 mL, 0.176 mmol). After stirring at room temperature for 1 h, the reaction mixture was quenched with MeOH (0.5 mL) and partitioned between aqueous 1.0 M NaOH and DCM. The organic phase was dried over MgSO$_4$, filtered and concentrated in vacuo to yield a residue which was purified by flash chromatography (silica gel, 0 to 7.5% MeOH in DCM) and re-purified by reverse phase prep-HPLC to yield (R)-3-((1-(cyclopropanecarbonyl)pyrrolidin-3-yl)methyl)-8-isobutyryl-2-(4-(1-methyl-1H-indazol-5-yl)phenyl)-1,3,8-triazaspiro[4.5]dec-1-en-4-one (74 mg, 86%).
$^1$H NMR (300 MHz, CDCl$_3$) δ ppm 0.71 (d, J=4.7 Hz, 2H), 0.79-1.05 (m, 2H), 1.14-1.25 (m, 6H), 1.27-2.14 (m, 8H), 2.14-2.61 (m, 1H), 2.71-3.10 (m, 2H), 3.10-3.84 (m, 6H), 3.86-4.08 (m, 1H), 4.06-4.21 (m, 3H), 4.52 (br. s., 1H), 7.51 (d, J=8.8 Hz, 1H), 7.61-7.75 (m, 3H), 7.75-7.85 (m, 2H), 7.97 (s, 1H), 8.07 (s, 1H); MS nm/z 581.0 (M+H)$^+$; m.p. 104.2° C.

Following the procedure described in Example 7, above, selecting and substituting the appropriate reagents, starting materials, and purification methods, and adjusting reaction temperatures, times and other variables or parameters, as needed or desirable, as would be readily recognized by those skilled in the art, the following compounds of formula (I) of the invention were prepared.

| ID No. | Structure | Compound Name & Physical Data |
|---|---|---|
| 106 | 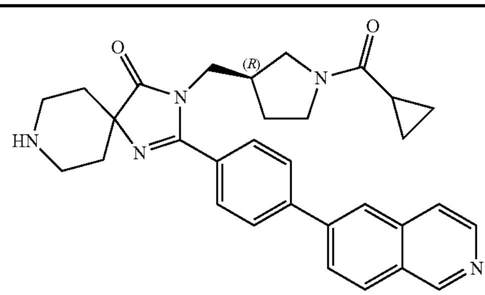 | 3-{[(3R)-1-(Cyclopropylcarbonyl)pyrrolidin-3-yl]methyl}-2-(4-isoquinolin-6-ylphenyl)-1,3,8-triazaspiro[4.5]dec-1-en-4-one<br>$^1$H NMR (300 MHz, DMSO-d6) δ ppm 0.63 (d, J = 5.2 Hz, 4 H), 1.25-2.00 (m, 7 H), 2.01-2.40 (m, 1 H), 2.76-3.76 (m, 11 H), 7.87 (dd, J = 8.1, 4.9 Hz, 2 H), 7.93 (d, J = 5.8 Hz, 1 H), 7.97-8.17 (m, 3 H), 8.26 (d, J = 8.7 Hz, 1 H), 8.39 (s, 1 H), 8.56 (d, J = 5.8 Hz, 1 H), 9.37 (s, 1 H); MS m/z 508 (M + H)$^+$ |

| ID No. | Structure | Compound Name & Physical Data |
|---|---|---|
| 130 | 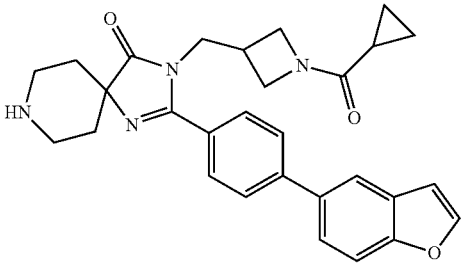 [SMILES: O=C(C1CC1)N1CC(CN2C(=O)C3(CCNCC3)N=C2c2ccc(-c3ccc4occc4c3)cc2)C1] | 2-[4-(1-Benzofuran-5-yl)phenyl]-3-{[1-(cyclopropylcarbonyl)azetidin-3-yl]methyl}-1,3,8-triazaspiro[4.5]dec-1-en-4-one<br>MS m/z 483 (M + H)$^+$ |
| 131 | 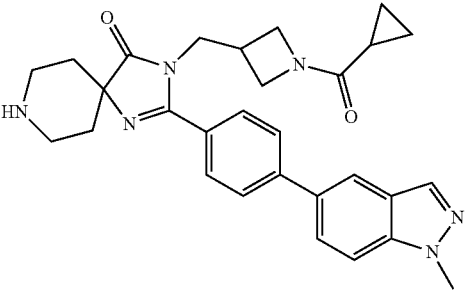 [SMILES: Cn1ncc2cc(-c3ccc(C4=NC5(CCNCC5)C(=O)N4CC4CN(C(=O)C5CC5)C4)cc3)ccc21] | 3-{[1-(Cyclopropylcarbonyl)azetidin-3-yl]methyl}-2-[4-(1-methyl-1H-indazol-5-yl)phenyl]-1,3,8-triazaspiro[4.5]dec-1-en-4-one<br>MS m/z 497 (M + H)$^+$ |
| 132 | 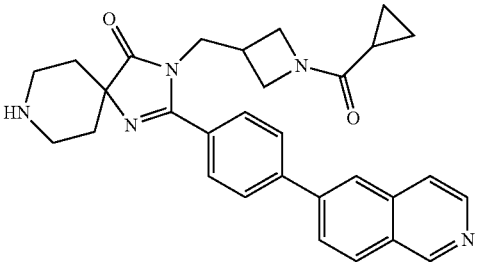 [SMILES: O=C(C1CC1)N1CC(CN2C(=O)C3(CCNCC3)N=C2c2ccc(-c3ccc4cnccc4c3)cc2)C1] | 3-{[1-(Cyclopropylcarbonyl)azetidin-3-yl]methyl}-2-(4-isoquinolin-6-ylphenyl)-1,3,8-triazaspiro[4.5]dec-1-en-4-one<br>MS m/z 494 (M + H)$^+$ |
| 133 | 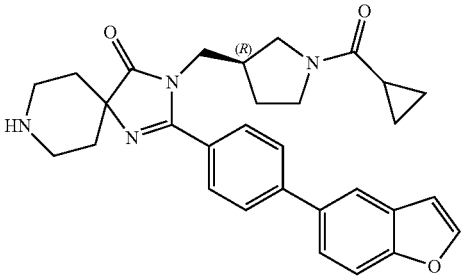 | 2-[4-(1-Benzofuran-5-yl)phenyl]-3-{[(3R)-1-(cyclopropylcarbonyl)pyrrolidin-3-yl]methyl}-1,3,8-triazaspiro[4.5]dec-1-en-4-one<br>$^1$H NMR (300 MHz, DMSO-d6) δ ppm 0.53-0.72 (m, 4 H), 1.25-1.93 (m, 5 H), 2.08-2.40 (m, 1 H), 2.74-3.59 (m, 10 H), 3.65 (t, J = 6.9 Hz, 2 H), 4.08 (br. s., 1 H), 6.98-7.08 (m, 1 H), 7.62-7.83 (m, 4 H), 7.83-7.93 (m, 2 H), 7.99-8.09 (m, 2 H);<br>MS m/z 497 (M + H)$^+$ |
| 155 | 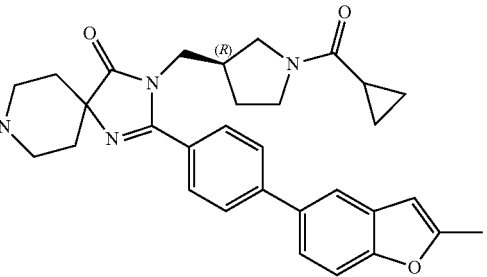 | 3-{[(3R_=1=(Cyclopropylcarbonyl)pyrrolidin-3-yl]methyl}-2-[4-(2-methyl-1-benzofuran-5-yl)phenyl]-1,3,8-triazaspiro[4.5]dec-1-en-4-one<br>$^1$H NMR (300 MHz, DMSO-d6) δ ppm 0.53-0.70 (m, 4 H), 1.22-1.95 (m, 6 H), 2.03-2.39 (m, 1 H), 2.48 (s, 3 H), 2.76-3.27 (m, 7 H), 3.36-3.59 (m, 3 H), 3.58-3.72 (m, 2 H), 6.66 (s, 1 H), 7.60 (s, 2 H), 7.70-7.82 (m, 2 H), 7.82-7.92 (m, 3 H);<br>MS m/z 511 (M + H)$^+$<br>m.p. 95.5° C. |

| ID No. | Structure | Compound Name & Physical Data |
|---|---|---|
| 138 | 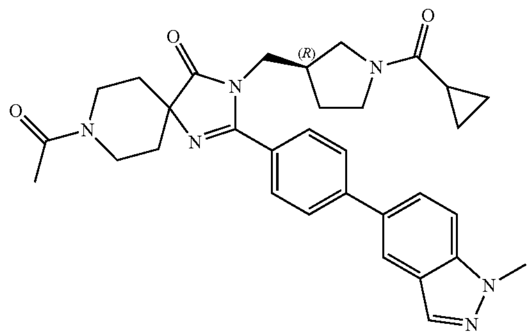 | 8-Acetyl-3-{[(3R)-1-(cyclopropylcarbonyl)pyrrolidin-3-yl]methyl}-2-[4-(1-methyl-1H-indazol-5-yl)phenyl]-1,3,8-triazaspiro[4.5]dec-1-en-4-one<br>$^1$H NMR (300 MHz, CDCl$_3$) δ ppm 0.72 (dd, J = 7.5, 3.2 Hz, 2 H), 0.94 (br. s., 2 H), 1.32-1.68 (m, 4 H), 1.74-2.12 (m, 3 H), 2.16 (s, 3 H), 2.34-2.58 (m, 1 H), 2.80-3.99 (m, 9 H), 4.13 (s, 3 H), 4.37-4.59 (m, 1 H), 7.51 (d, J = 8.7 Hz, 1 H), 7.80 (dd, J = 8.2, 3.9 Hz, 2 H), 7.97 (s, 1 H), 8.07 (s, 1 H);<br>MS m/z 553 (M + H)$^+$<br>m.p. 111.2° C. |
| 140 | 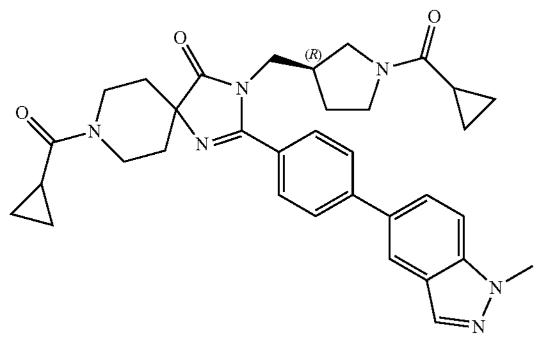 | 8-(Cyclopropylcarbonyl)-3-{[(3R)-1-(cyclopropylcarbonyl)pyrrolidin-3-yl]methyl}-2-[4-(1-methyl-1H-indazol-5-yl)phenyl]-1,3,8-triazaspiro[4.5]dec-1-en-4-one<br>$^1$H NMR (300 MHz, CDCl$_3$) δ ppm 0.63-0.76 (m, 2 H), 0.76-0.88 (m, 2 H), 0.88-0.99 (m, 2 H), 1.04 (br. s., 2 H), 1.36-1.56 (m, 2 H), 1.71-2.63 (m, 6 H), 2.85-3.95 (m, 9 H), 4.14 (s, 3 H), 4.17-4.33 (m, 1 H), 4.37-4.59 (m, 1 H), 7.51 (d, J = 8.7 Hz, 1 H), 7.69 (d, J = 8.8 Hz, 3 H), 7.75-7.86 (m, 2 H), 7.98 (s, 1 H), 8.07 (s, 1 H);<br>MS m/z 579 (M + H)$^+$<br>m.p. 114.8° C. |
| 141 | 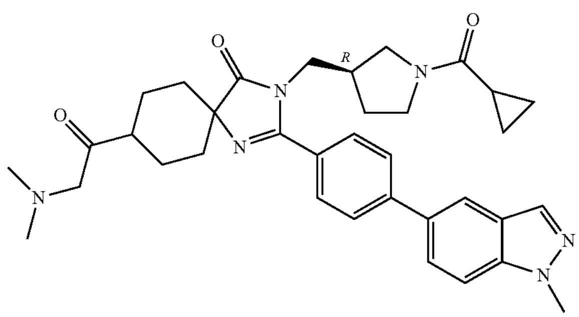 | 3-{[(3R)-1-(Cyclopropylcarbonyl)pyrrolidin-3-yl]methyl}-8-(N,N-dimethylglycyl)-2-[4-(1-methyl-1H-indazol-5-yl)phenyl]-1,3,8-triazaspiro[4.5]dec-1-en-4-one<br>$^1$H NMR (300 MHz, CDCl$_3$) δ ppm 0.71 (d, J = 4.4 Hz, 2 H), 0.93 (br. s., 2 H), 1.35-1.76 (m, 4 H), 1.74-2.13 (m, 4 H), 2.31 (s, 6 H), 2.35-2.59 (m, 1 H), 2.85-3.86 (m, 9 H), 4.04-4.18 (m, 1 H), 4.13 (s, 3 H), 4.31-4.55 (m, 1 H), 7.50 (d, J = 8.7 Hz, 1 H), 7.61-7.74 (m, 3 H), 7.74-7.86 (m, 2 H), 7.97 (s, 1 H), 8.06 (s, 1 H);<br>MS m/z 596 (M + H)$^+$<br>m.p. 127.5° C. |
| 142 | 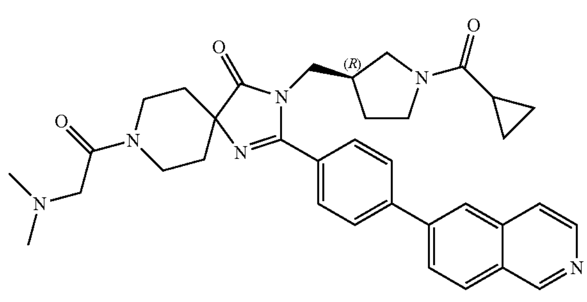 | 3-{[(3R)-1-(Cyclopropylcarbonyl)pyrrolidin-3-yl]methyl}-8-(N,N-dimethylglycyl)-2-(4-isoquinolin-6-ylphenyl)-1,3,8-triazaspiro[4.5]dec-1-en-4-one<br>$^1$H NMR (300 MHz, CDCl$_3$) δ ppm 0.72 (dt, J = 4.9, 2.4 Hz, 2 H), 0.84-1.03 (m, 2 H), 1.33-2.14 (m, 9 H), 2.33 (s, 6 H), 2.36-2.63 (m, 1 H), 2.85-3.99 (m, 8 H), 4.03-4.32 (m, 1 H), 4.30-4.60 (m, 1 H), 7.64-7.83 (m, 3 H), 7.89 (dd, J = 8.7, 2.1 Hz, 3 H), 7.99-8.19 (m, 2 H), 8.60 (d, J = 5.6 Hz, 1 H), 9.32 (s, 1 H);<br>MS m/z 593 (M + H)$^+$<br>m.p. 94.2° C. |

| ID No. | Structure | Compound Name & Physical Data |
|---|---|---|
| 143 | 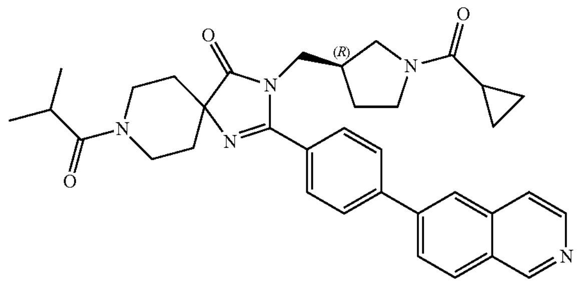 | 3-{[(3R)-1-(Cyclopropylcarbonyl)pyrrolidin-3-yl]methyl}-2-(4-isoquinolin-6-ylphenyl)-8-(2-methylpropanoyl)-1,3,8-triazaspiro[4.5]dec-1-en-4-one<br>¹H NMR (300 MHz, CDCl₃) δ ppm 0.61-0.80 (m, 2 H), 0.83-1.02 (m, 2 H), 1.13-1.27 (m, 6 H), 1.35-1.71 (m, 4 H), 1.86-2.14 (m, 3 H), 2.18-2.62 (m, 1 H), 2.87 (dt, J = 13.5, 6.7 Hz, 1 H), 2.92-3.89 (m, 9 H), 3.98 (d, J = 12.0 Hz, 1 H), 4.50 (d, J = 12.4 Hz, 1 H), 7.75 (d, J = 7.8 Hz, 3 H), 7.89 (dd, J = 8.6, 2.0 Hz, 2 H), 7.97-8.20 (m, 2 H), 8.61 (br. s., 1 H), 9.34 (br. s., 1 H);<br>MS m/z 578 (M + H)⁺<br>m.p. 129.9° C. |
| 144 | 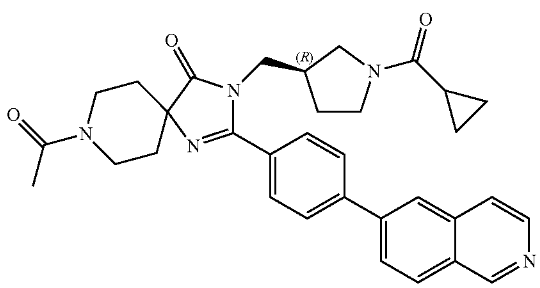 | 8-Acetyl-3-{[(3R)-1-(cyclopropylcarbonyl)pyrrolidin-3-yl]methyl}-2-(4-isoquinolin-6-ylphenyl)-1,3,8-triazaspiro[4.5]dec-1-en-4-one<br>¹H NMR (300 MHz, CDCl₃) δ ppm 0.65-0.80 (m, 2 H), 0.83-1.02 (m, 2 H), 1.36-1.69 (m, 4 H), 1.88-2.13 (m, 3 H), 2.17 (s, 3 H), 2.20-2.61 (m, 1 H), 2.79-4.01 (m, 9 H), 4.38-4.56 (m, 1 H), 7.68-7.82 (m, 3 H), 7.84-7.96 (m, 3 H), 8.01-8.16 (m, 2 H), 8.60 (d, J = 5.5 Hz, 1 H), 9.33 (br. s., 1 H);<br>MS m/z 550 (M + H)⁺<br>m.p. 123.1° C. |
| 134 | 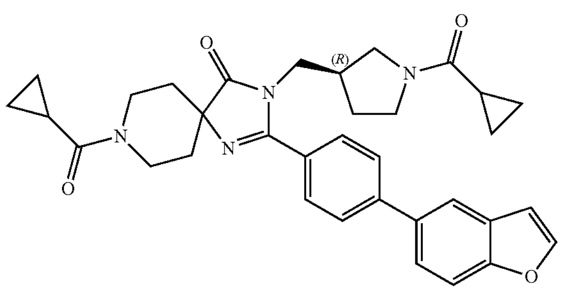 | 2-[4-(1-Benzofuran-5-yl)phenyl]-8-(cyclopropylcarbonyl)-3-{[1-(cyclopropylcarbonyl)azetidin-3-yl]methyl}-1,3,8-triazaspiro[4.5]dec-1-en-4-one<br>¹H NMR (300 MHz, DMSO-d6) δ ppm 0.52-0.70 (m, 4 H), 1.25-1.93 (m, 7 H), 2.08-2.39 (m, 1 H), 2.75-3.03 (m, 4 H), 3.03-3.59 (m, 6 H), 3.65 (t, J = 6.9 Hz, 2 H), 4.08 (br. s., 1 H), 7.04 (d, J = 1.6 Hz, 1 H), 7.61-7.83 (m, 4 H), 7.82-7.93 (m, 2 H), 8.00-8.11 (m, 2 H);<br>MS m/z 551 (M + H)⁺<br>m.p. 93.6° C. |
| 149 | 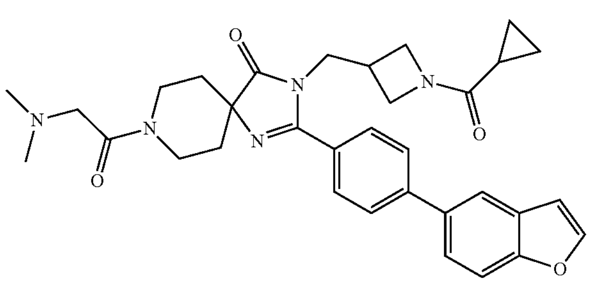 [SMILES: CN(C)CC(=O)N1CCC2(CC1)N=C(c1ccc(-c3ccc4occc4c3)cc1)N(CC1CN(C(=O)C3CC3)C1)C2=O] | 2-[4-(1-Benzofuran-5-yl)phenyl]-3-{[1-(cyclopropylcarbonyl)azetidin-3-yl]methyl}-8-(N,N-dimethylglycyl)-1,3,8-triazaspiro[4.5]dec-1-en-4-one<br>¹H NMR (300 MHz, DMSO-d6) δ ppm 0.56-0.68 (m, 4 H), 1.14-1.30 (m, 3 H), 1.30-1.43 (m, 1 H), 1.44-1.60 (m, 2 H), 1.62-1.79 (m, 1 H), 1.79-1.99 (m, 1 H), 2.35 (s, 6 H), 2.55-2.71 (m, 1 H), 3.13-3.27 (m, 2 H), 3.67-3.81 (m, 2 H), 3.88 (d, J = 7.3 Hz, 2 H), 3.96 (d, J = 13.3 Hz, 1 H), 4.13 (t, J = 8.2 Hz, 1 H), 4.28 (d, J = 12.9 Hz, 1 H), 7.04 (d, J = 1.9 Hz, 1 H), 7.65-7.76 (m, 2 H), 7.79 (d, J = 8.2 Hz, 2 H), 7.90 (m, J = 8.2 Hz, 2 H), 7.96-8.12 (m, 2 H);<br>MS m/z 568 (M + H)⁺<br>m.p. 130.1° C. |

| ID No. | Structure | Compound Name & Physical Data |
|---|---|---|
| 150 | 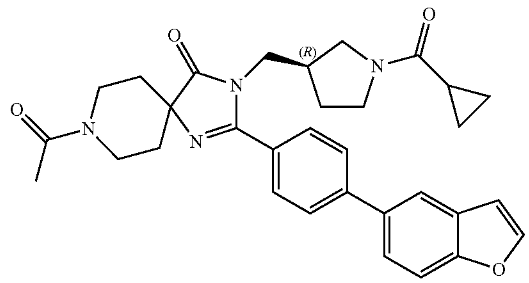 | 8-Acetyl-2-[4-(1-benzofuran-5-yl)phenyl]-3-{[(3R)-1-(cyclopropylcarbonyl)pyrrolidin-3-yl]methyl}-1,3,8-triazaspiro[4.5]dec-1-en-4-one<br>$^1$H NMR (300 MHz, DMSO-d6) δ ppm 0.63 (d, J = 5.6 Hz, 4 H), 1.41-1.95 (m, 6 H), 2.07 (s, 3 H), 2.1-2.3 (m, 1 H), 2.77-2.92 (m, 0.5 H), 2.96-3.30 (m, 3.5 H), 3.36-3.60 (m, 3 H), 3.66 (t, J = 7.1 Hz, 2 H), 3.86 (d, J = 13.7 Hz, 1 H), 4.29 (d, J = 12.9 Hz, 1 H), 7.04 (d, J = 1.8 Hz, 1 H), 7.65-7.76 (m, 2 H), 7.76-7.85 (m, 2 H), 7.85-7.92 (m, 2 H), 7.97-8.10 (m, 2 H);<br>MS m/z 539 (M + H)$^+$<br>m.p. 96.6° C. |
| 151 | 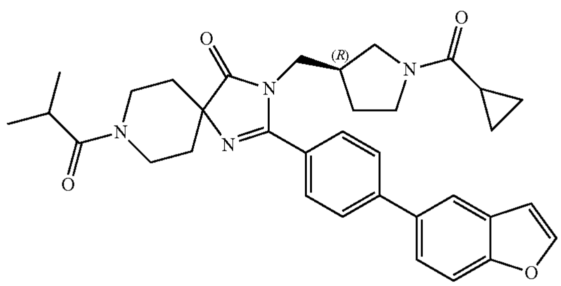 | 2-[4-(1-Benzofuran-5-yl)phenyl]-3-{[(3R)-1-(cyclopropylcarbonyl)pyrrolidin-3-yl]methyl}-8-(2-methylpropanoyl)-1,3,8-triazaspiro[4.5]dec-1-en-4-one<br>$^1$H NMR (300 MHz, DMSO-d6) δ ppm 0.63 (d, J = 5.5 Hz, 4 H), 0.94-1.11 (m, 6 H), 1.42-1.94 (m, 6 H), 2.10-2.41 (m, 1 H), 2.74-3.29 (m, 5 H), 3.37-3.62 (m, 3 H), 3.61-3.72 (m, 2 H), 3.98 (d, J = 13.5 Hz, 1 H), 4.32 (d, J = 11.7 Hz, 1 H), 7.04 (d, J = 1.8 Hz, 1 H), 7.63-7.76 (m, 2 H), 7.76-7.85 (m, 2 H), 7.85-7.95 (m, 2 H), 7.99-8.11 (m, 2 H);<br>MS m/z 567 (M + H)$^+$<br>m.p. 105.5° C. |
| 152 | 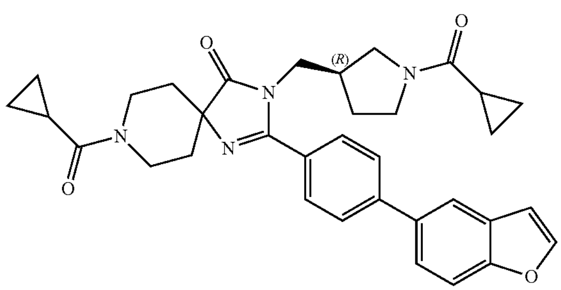 | 2-[4-(1-Benzofuran-5-yl)phenyl]-8-(cyclopropylcarbonyl)-3-{[(3R)-1-(cyclopropylcarbonyl)pyrrolidin-3-yl]methyl}-1,3,8-triazaspiro[4.5]dec-1-en-4-one<br>$^1$H NMR (300 MHz, DMSO-d6) δ ppm 0.51-0.68 (m, 4 H), 0.68-0.89 (m, 4 H), 1.38-1.94 (m, 7 H), 1.95-2.11 (m, 1 H), 2.11-2.40 (m, 1 H), 2.77-2.95 (m, 0.5 H), 3.11 (m, 2.5 H), 3.39-3.77 (m, 5 H), 4.15-4.39 (m, 2 H), 7.04 (s, 1 H), 7.65-7.77 (m, 2 H), 7.77-7.85 (m, 2 H), 7.85-7.98 (m, 2 H), 7.98-8.14 (m, 2 H);<br>MS m/z 565 (M + H)$^+$<br>m.p. 115.1° C. |
| 153 | 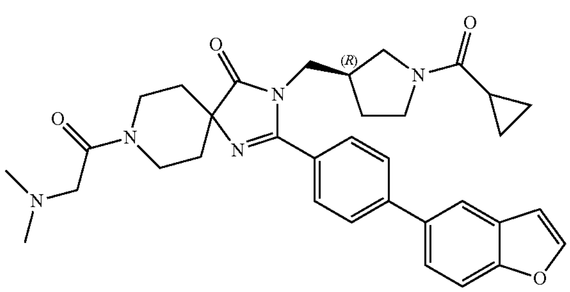 | 2-[4-(1-Benzofuran-5-yl)phenyl]-3-{[(3R)-1-(cyclopropylcarbonyl)pyrrolidin-3-yl]methyl}-8-(N,N-dimethylglycyl)-1,3,8-triazaspiro[4.5]dec-1-en-4-one<br>$^1$H NMR (300 MHz, DMSO-d6) δ ppm 0.55-0.72 (m, 4 H), 1.42-1.97 (m, 6 H), 2.22 (s, 6 H), 2.24-2.41 (m, 1 H), 2.86 (dd, J = 12.0, 7.4 Hz, 0.5 H), 2.97-3.29 (m, 5.5 H), 3.37-3.62 (m, 3 H), 3.62-3.73 (m, 2 H), 4.07 (d, J = 13.1 Hz, 1 H), 4.29 (d, J = 12.8 Hz, 1 H), 7.05 (d, J = 1.6 Hz, 1 H), 7.66-7.77 (m, 2 H), 7.77-7.85 (m, 2 H), 7.85-7.96 (m, 2 H), 8.00-8.12 (m, 2 H);<br>MS m/z 582 (M + H)$^+$<br>m.p. 92° C. |

| ID No. | Structure | Compound Name & Physical Data |
|---|---|---|
| 135 | 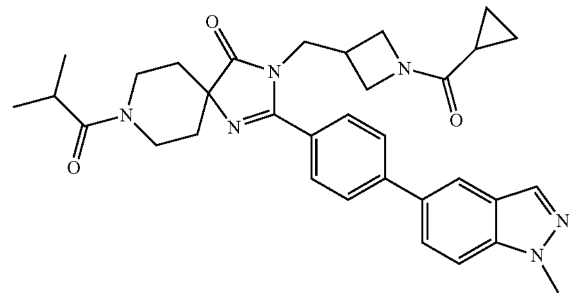 [SMILES: CC(C)C(=O)N1CCC2(CC1)N=C(c1ccc(-c3ccc4c(cnn4C)c3)cc1)N(CC1CN(C(=O)C3CC3)C1)C2=O] | 3-{[1-(Cyclopropylcarbonyl)azetidin-3-yl]methyl}-2-[4-(1-methyl-1H-indazol-5-yl)phenyl]-8-(2-methylpropanoyl)-1,3,8-triazaspiro[4.5]dec-1-en-4-one<br>MS m/z 567 (M + H)+<br>m.p. 160.8° C. |
| 136 | 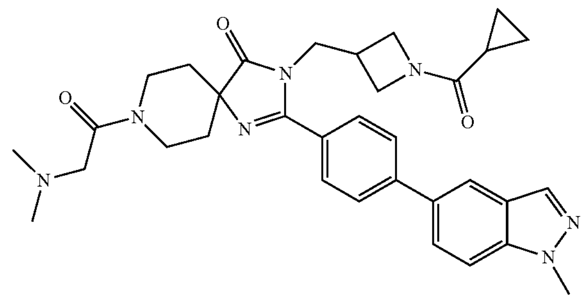 [SMILES: CN(C)CC(=O)N1CCC2(CC1)N=C(c1ccc(-c3ccc4c(cnn4C)c3)cc1)N(CC1CN(C(=O)C3CC3)C1)C2=O] | 3-{[1-(Cyclopropylcarbonyl)azetidin-3-yl]methyl}-8-(N,N-dimethylglycyl)-2-[4-(1-methyl-1H-indazol-5-yl)phenyl]-1,3,8-triazaspiro[4.5]dec-1-en-4-one<br>MS m/z 582 (M + H)+<br>m.p. 102.3° C. |
| 137 | 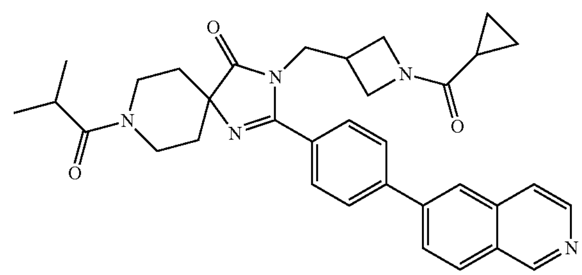 [SMILES: CC(C)C(=O)N1CCC2(CC1)N=C(c1ccc(-c3ccc4cnccc4c3)cc1)N(CC1CN(C(=O)C3CC3)C1)C2=O] | 3-{[1-(Cyclopropylcarbonyl)azetidin-3-yl]methyl}-2-(4-isoquinolin-6-ylphenyl)-8-(2-methylpropanoyl)-1,3,8-triazaspiro[4.5]dec-1-en-4-one<br>¹H NMR (300 MHz, DMSO-d6) δ ppm 0.50-0.72 (m, 4 H), 0.91-1.16 (m, 6 H), 1.31-1.44 (m, 1 H), 1.44-1.91 (m, 4 H), 2.54-2.71 (m, 1 H), 2.85-3.02 (m, 1 H), 3.08-3.27 (m, 1 H), 3.34-3.42 (m, 1 H), 3.46-3.66 (m, 1 H), 3.66-3.81 (m, 2 H), 3.88 (d, J = 7.4 Hz, 2 H), 3.98 (d, J = 12.6 Hz, 1 H), 4.09-4.22 (m, 1 H), 4.32 (d, J = 13.2 Hz, 1 H), 7.83-7.97 (m, 3 H), 8.01-8.18 (m, 3 H), 8.27 (d, J = 8.7 Hz, 1 H), 8.39 (s, 1 H), 8.56 (d, J = 5.8 Hz, 1 H), 9.38 (s, 1 H);<br>MS m/z 564 (M + H)+<br>m.p. 157.5° C. |
| 154 | 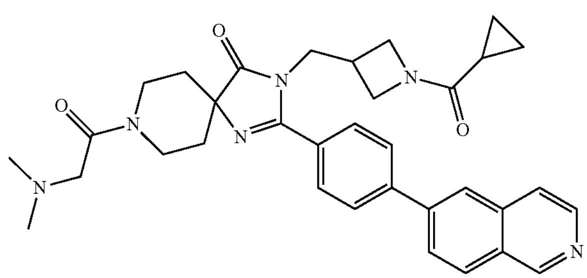 [SMILES: CN(C)CC(=O)N1CCC2(CC1)N=C(c1ccc(-c3ccc4cnccc4c3)cc1)N(CC1CN(C(=O)C3CC3)C1)C2=O] | 3-{[1-(Cyclopropylcarbonyl)azetidin-3-yl]methyl}-8-(N,N-dimethylglycyl)-2-(4-isoquinolin-6-ylphenyl)-1,3,8-triazaspiro[4.5]dec-1-en-4-one<br>¹H NMR (300 MHz, DMSO-d6) δ ppm 0.52-0.71 (m, 4 H), 1.29-1.43 (m, 1 H), 1.43-1.62 (m, 2 H), 1.62-1.78 (m, 1 H), 1.87 (t, J = 9.8 Hz, 1 H), 2.21 (s, 6 H), 2.55-2.71 (m, 1 H), 2.96-3.27 (m, 3 H), 3.43-3.62 (m, 2 H), 3.65-3.82 (m, 2 H), 3.88 (d, J = 7.3 Hz, 2 H), 4.06 (d, J = 13.5 Hz, 1 H), 4.15 (t, J = 8.2 Hz, 1 H), 4.27 (d, J = 12.8 Hz, 1 H), 7.82-7.99 (m, 3 H), 7.99-8.16 (m, 3 H), 8.27 (d, J = 8.7 Hz, 1 H), 8.39 (s, 1 H), 8.56 (d, J = 5.8 Hz, 1 H), 9.38 (s, 1 H);<br>MS m/z 579 (M + H)+<br>m.p. 233.0° C. |

| ID No. | Structure | Compound Name & Physical Data |
|---|---|---|
| 171 | 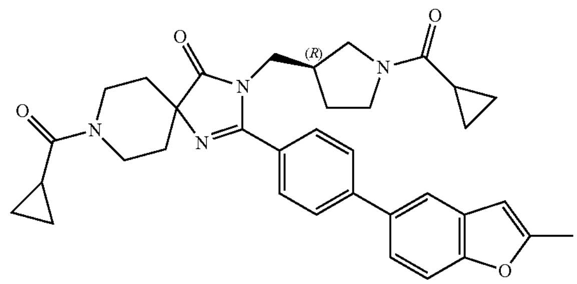 | 8-(Cyclopropylcarbonyl)-3-{[(3R)-1-(cyclopropylcarbonyl)pyrrolidin-3-yl]methyl}-2-[4-(2-methyl-1-benzofuran-5-yl)phenyl]-1,3,8-triazaspiro[4.5]dec-1-en-4-one<br>$^1$H NMR (300 MHz, CDCl$_3$) δ ppm 0.61-0.76 (m, 2 H), 0.76-0.85 (m, 2 H), 0.86-0.99 (m, 2 H), 0.99-1.09 (m, 2 H), 1.36-2.17 (m, 9 H), 2.50 (s, 3 H), 2.89-3.99 (m, 8 H), 4.09-4.34 (m, 1 H), 4.34-4.61 (m, 1 H), 6.45 (s, 1 H), 7.36-7.58 (m, 2 H), 7.59-7.74 (m, 3 H), 7.73-7.88 (m, 2 H);<br>MS m/z 579 (M + H)$^+$<br>m.p. 137.1° C. |
| 172 | 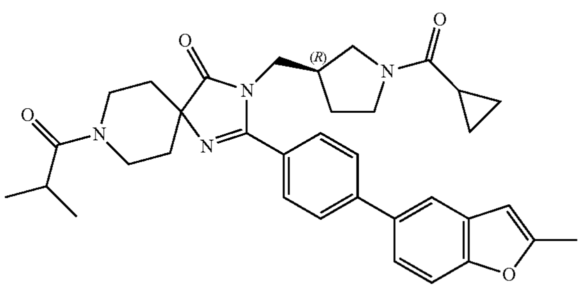 | 3-{[(3R)-1-(Cyclopropylcarbonyl)pyrrolidin-3-yl]methyl}-2-[4-(2-methyl-1-benzofuran-5-yl)phenyl]-8-(2-methylpropanoyl)-1,3,8-triazaspiro[4.5]dec-1-en-4-one<br>$^1$H NMR (300 MHz, CDCl$_3$) δ ppm ppm 0.64-0.80 (m, 2 H), 0.85-1.01 (m, 2 H), 1.03-1.25 (m, 10 H), 1.35-2.12 (m, 6 H), 2.50 (s, 3 H), 2.72-3.86 (m, 7 H), 3.86-4.06 (m, 1 H), 4.37-4.62 (m, 1 H), 6.44 (s, 1 H), 7.38-7.56 (m, 2 H), 7.58-7.73 (m, 3 H), 77.3-7.84 (m, 2 H);<br>MS m/z 581 (M + H)$^+$<br>m.p. 115.5° C. |
| 174 | 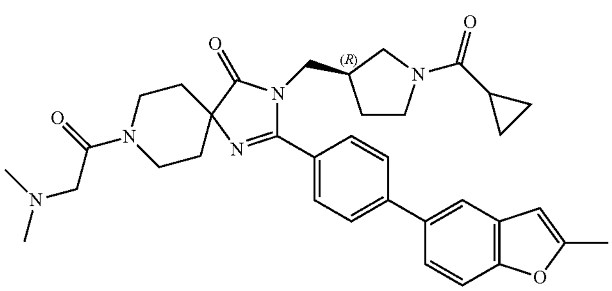 | 3-{[(3R)-1-(Cyclopropylcarbonyl)pyrrolidin-3-yl]methyl}-8-(N,N-dimethylglycyl)-2-[4-(2-methyl-1-benzofuran-5-yl)phenyl]-1,3,8-triazaspiro[4.5]dec-1-en-4-one<br>$^1$H NMR (300 MHz, CDCl$_3$) δ ppm 0.55-0.78 (m, 2 H), 0.82-1.03 (m, 2 H), 1.35-1.73 (m, 4 H), 1.72-2.13 (m, 3 H), 2.31 (s, 6 H), 2.49 (s, 3 H), 2.89-3.87 (m, 11 H), 4.05-4.21 (m, 1 H), 4.30-4.55 (m, 1 H), 6.44 (s, 1 H), 7.38-7.56 (m, 2 H), 7.58-7.72 (m, 3 H), 7.72-7.83 (m, 2 H);<br>MS m/z 596 (M + H)$^+$<br>m.p. 90.3° C. |
| 181 | 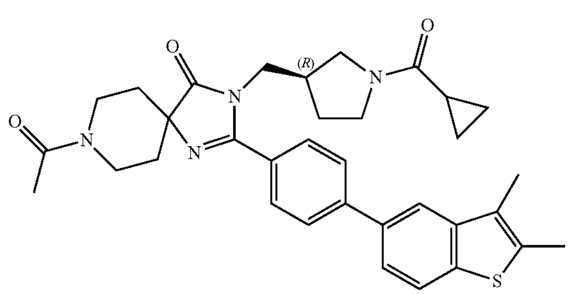 | 8-Acetyl-3-{[(3R)-1-(cyclopropylcarbonyl)pyrrolidin-3-yl]methyl}-2-[4-(2,3-dimethyl-1-benzothiophen-5-yl)phenyl]-1,3,8-triazaspiro[4.5]dec-1-en-4-one<br>$^1$H NMR (300 MHz, DMSO-d$_6$) δ ppm 0.64 (d, J = 5.4 Hz, 4 H), 1.31-1.94 (m, 6 H), 2.07 (s, 3 H), 2.37 (s, 3 H), 2.50 (s, 3 H), 2.78-3.30 (m, 4 H), 3.32-3.60 (m, 4 H), 3.60-3.74 (m, 2 H), 3.77-3.93 (m, 1 H), 4.18-4.38 (m, 1 H), 7.68 (d, J = 8.7 Hz, 1 H), 7.75-7.89 (m, 2 H), 7.90-8.07 (m, 4 H);<br>MS m/z 583 (M + H)$^+$<br>m.p. 117.7° C. |

| ID No. | Structure | Compound Name & Physical Data |
|---|---|---|
| 182 | 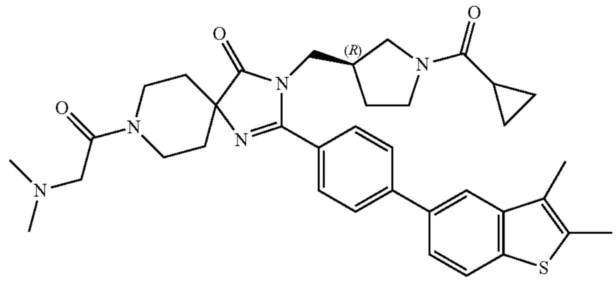 | 3-{[(3R)-1-(Cyclopropylcarbonyl)pyrrolidin-3-yl]methyl}-2-[4-(2,3-dimethyl-1-benzothiophen-5-yl)phenyl]-8-(N,N-dimethylglycyl)-1,3,8-triazaspiro[4.5]dec-1-en-4-one<br>$^1$H NMR (300 MHz, DMSO-$d_6$) δ ppm 0.64 (d, J = 5.4 Hz, 4 H), 1.28-1.97 (m, 7 H), 2.21 (s, 6 H), 2.37 (s, 3 H), 2.50 (s, 3 H), 2.76-3.28 (m, 6 H), 3.34-3.61 (m, 3 H), 3.60-3.75 (m, 2 H), 3.95-4.14 (m, 1 H), 4.18-4.37 (m, 1 H), 7.68 (d, J = 7.8 Hz, 1 H), 7.75-7.90 (m, 2 H), 7.97 (d, J = 8.9 Hz, 4 H);<br>MS m/z 626 (M + H)$^+$<br>m.p. 107.9° C. |
| 183 | 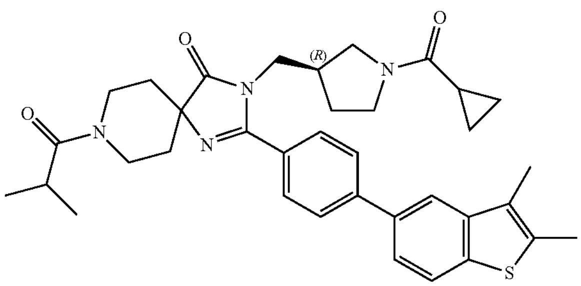 | 3-{[(3R)-1-(Cyclopropylcarbonyl)pyrrolidin-3-yl]methyl}-2-[4-(2,3-dimethyl-1-benzothiophen-5-yl)phenyl]-8-(2-methylpropanoyl)-1,3,8-triazaspiro[4.5]dec-1-en-4-one<br>$^1$H NMR (300 MHz, DMSO-$d_6$) δ ppm 0.51-0.71 (m, 4 H), 0.94-1.13 (m, 6 H), 1.28-1.99 (m, 6 H), 2.12-2.35 (m, 1 H), 2.37 (s, 3 H), 2.50 (s, 3 H), 2.76-3.30 (m, 5 H), 3.33-3.78 (m, 5 H), 3.84-4.12 (m, 1 H), 4.19-4.43 (m, 1 H), 7.68 (d, J = 8.9 Hz, 1 H), 7.82 (dd, J = 8.0, 5.4 Hz, 2 H), 7.97 (d, J = 8.7 Hz, 4 H);<br>MS m/z 611 (M + H)$^+$<br>m.p. 136.4° C. |

Example 8

(R)-3-((1-(Cyclopropanecarbonyl)pyrrolidin-3-yl)methyl)-8-(2-hydroxyethyl)-2-(4-(1-methyl-1H-indazol-5-yl)phenyl)-1,3,8-triazaspiro[4.5]dec-1-en-4-one (Compound #127)

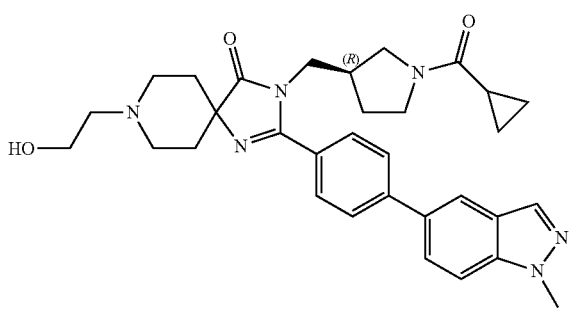

A mixture of (R)-3-((1-(cyclopropanecarbonyl)pyrrolidin-3-yl)methyl)-2-(4-(1-methyl-1H-indazol-5-yl)phenyl)-1,3,8-triazaspiro[4.5]dec-1-en-4-one (0.080 g, 0.157 mmol), 2-bromoethanol (0.056 mL, 0.785 mmol), and potassium carbonate (0.044 g, 0.314 mmol) in acetonitrile (5 mL) was heated at 65° C. overnight. The resulting mixture was allowed to cool to room temperature and was diluted with DCM (20 mL). The inorganic solids were filtered and the filtrate was concentrated yield a residue. The residue was purified by flash chromatography (silica gel, 0 to 100% of DCM:MeOH: 25% NH$_4$OH 9:0.9:0.1 in DCM). The fractions containing the desired product were concentrated to a sticky oil that was triturated with Et$_2$O to yield 3-{[(3R)-1-(Cyclopropylcarbonyl)pyrrolidin-3-yl]methyl}-8-(2-hydroxyethyl)-2-[4-(1-methyl-1H-indazol-5-yl)phenyl]-1,3,8-triazaspiro[4.5]dec-1-en-4-one, as an off-white solid (0.042 g, 48%).

$^1$H NMR (300 MHz, CDCl$_3$) δ ppm 0.60-0.82 (m, 2H), 0.82-1.03 (m, 2H), 1.33-2.61 (m, 10H), 2.61-3.11 (m, 6H), 3.09-3.85 (m, 7H), 4.13 (s, 3H), 7.50 (d, J=8.7 Hz, 1H), 7.58-7.72 (m, 3H), 7.72-7.85 (m, 2H), 7.97 (s, 1H), 8.06 (s, 1H); MS m/z 555 (M+H)$^+$; m.p. 99.6° C.;

Following the procedure described in Example 8, above, selecting and substituting the appropriate reagents, starting materials, and purification methods, and adjusting reaction temperatures, times and other variables or parameters, as needed or desirable, as would be readily recognized by those skilled in the art, the following compounds of formula (I) of the invention were prepared.

| ID No. | Structure | Compound Name & Physical Data |
|---|---|---|
| 159 | 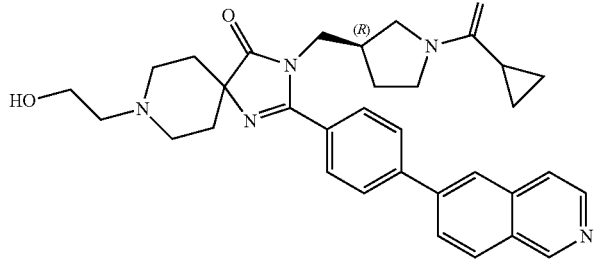 | 3-{[(3R)-1-(Cyclopropylcarbonyl)pyrrolidin-3-yl]methyl}-8-(2-hydroxyethyl)-2-(4-isoquinolin-6-ylphenyl)-1,3,8-triazaspiro[4.5]dec-1-en-4-one<br>$^1$H NMR (300 MHz, CDCl$_3$) δ ppm 0.64-0.76 (m, 2 H), 0.89-1.00 (m, 2 H), 1.37-1.71 (m, 4 H), 1.73-2.23 (m, 6 H), 2.23-2.58 (m, 1 H), 2.69 (t, J = 5.2 Hz, 2 H), 2.79 (t, J = 11.1 Hz, 2 H), 2.86-3.07 (m, 3 H), 3.14-3.39 (m, 1 H), 3.57-3.85 (m, 5 H), 7.67-7.80 (m, 3 H), 7.88 (dd, J = 8.2, 3.8 Hz, 3 H), 7.99-8.17 (m, 2 H), 8.60 (d, J = 5.5 Hz, 1 H), 9.32 (br. s., 1 H); MS m/z 552 (M + H)$^+$ |
| 168 | 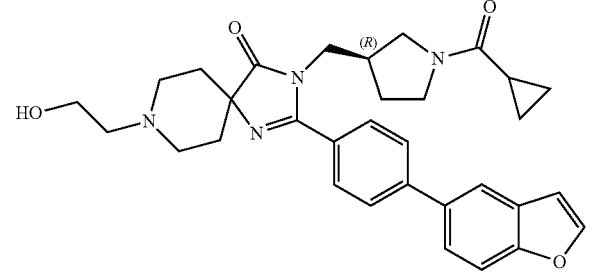 | 2-[4-(1-Benzofuran-5-yl)phenyl]-3-{[(3R)-1-(cyclopropylcarbonyl)pyrrolidin-3-yl]methyl}-8-(2-hydroxyethyl)-1,3,8-triazaspiro[4.5]dec-1-en-4-one<br>$^1$H NMR (300 MHz, DMSO-d$_6$) δ ppm 0.54-0.72 (m, 4 H), 1.41-2.00 (m, 7 H), 2.09-2.38 (m, 1 H), 2.52-2.64 (m, 2 H), 2.74-2.93 (m, 3 H), 3.02-3.28 (m, 3 H), 3.39-3.72 (m, 7 H), 4.41 (br. s., 1 H), 7.04 (d, J = 1.8 Hz, 1 H), 7.63-7.82 (m, 4 H), 7.83-7.92 (m, 2 H), 8.03 (s, 1 H), 8.06 (d, J = 1.9 Hz, 1 H); MS m/z 541 (M + H)$^+$<br>m.p. 105.7° C. |
| 170 | 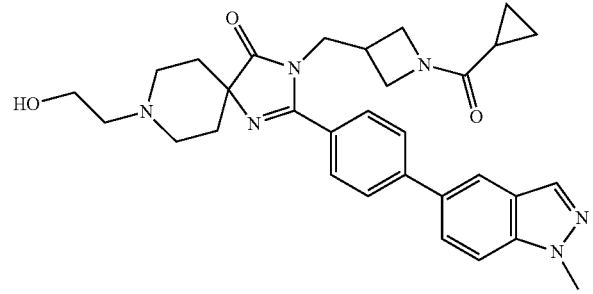 [SMILES: Cn1ncc2cc(-c3ccc(C4=NC5(CCN(CCO)CC5)C(=O)N4CC4CN(C(=O)C5CC5)C4)cc3)ccc21] | 3-{[1-(Cyclopropylcarbonyl)azetidin-3-yl]methyl}-8-(2-hydroxyethyl)-2-[4-(1-methyl-1H-indazol-5-yl)phenyl]-1,3,8-triazaspiro[4.5]dec-1-en-4-one<br>MS m/z 541 (M + H)$^+$<br>m.p. >300° C. |
| 173 | 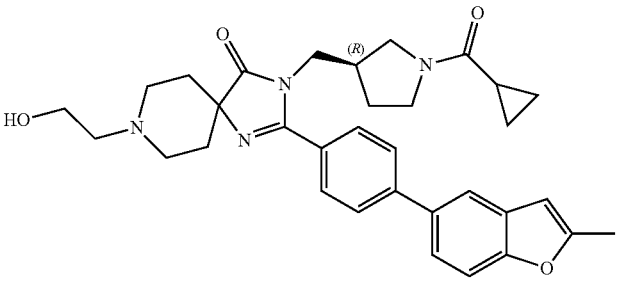 | 3-{[(3R)-1-(Cyclopropylcarbonyl)pyrrolidin-3-yl]methyl}-8-(2-hydroxyethyl)-2-[4-(2-methyl-1-benzofuran-5-yl)phenyl]-1,3,8-triazaspiro[4.5]dec-1-en-4-one<br>$^1$H NMR (300 MHz, CDCl$_3$) δ ppm 0.63-0.78 (m, 2 H), 0.94 (br. s., 2 H), 1.34-1.56 (m, 2 H), 1.70-2.46 (m, 7 H), 2.50 (s, 3 H), 2.58-3.10 (m, 6 H), 3.10-3.39 (m, 1 H), 3.38-3.91 (m, 8 H), 6.44 (s, 1 H), 7.37-7.56 (m, 2 H), 7.56-7.86 (m, 5 H); MS m/z 555 (M + H)$^+$<br>m.p. 130.3° C. |
| 185 | 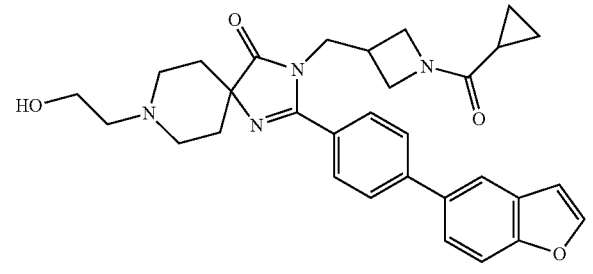 [SMILES: O=C(C1CC1)N1CC(CN2C(=O)C3(CCN(CCO)CC3)N=C2c2ccc(-c3ccc4occc4c3)cc2)C1] | 2-[4-(1-Benzofuran-5-yl)phenyl]-3-{[1-(cyclopropylcarbonyl)azetidin-3-yl]methyl}-8-(2-hydroxyethyl)-1,3,8-triazaspiro[4.5]dec-1-en-4-one<br>$^1$H NMR (300 MHz, DMSO-d$_6$) δ ppm 0.52-0.72 (m, 4 H), 1.38 (br. s., 1 H), 1.81 (br. s., 2 H), 2.18-2.45 (m, 2 H), 2.57-2.72 (m, 1 H), 3.18-3.96 (m, 14 H), 4.11-4.21 (m, 1 H), 7.04 (d, J = 1.5 Hz, 1 H), 7.66-7.76 (m, 2 H), 7.76-7.86 (m, 2 H), 7.87-7.98 (m, 2 H), 8.00-8.11 (m, 2 H), 10.40 (br. s., 1 H); MS m/z 527 (M + H)$^+$<br>m.p. 253.4° C. |

Example 9

(R)-2-(4-(1H-Indol-5-yl)phenyl)-8-acetyl-3-((1-(cyclopropanecarbonyl)pyrrolidin-3-yl)methyl)-1,3,8-triazaspiro[4.5]dec-1-en-4-one (Compound #147)

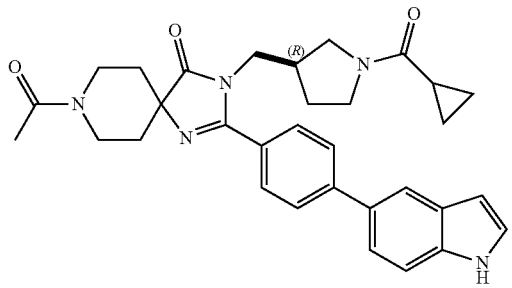

STEP A: (R)-8-Acetyl-2-(4-bromophenyl)-3-((1-(cyclopropanecarbonyl)pyrrolidin-3-yl)methyl)-1,3,8-triazaspiro[4.5]dec-1-en-4-one To a stirring solution of (R)-2-(4-bromophenyl)-3-((1-(cyclopropanecarbonyl)pyrrolidin-3-yl)methyl)-1,3,8-triazaspiro[4.5]dec-1-en-4-one (0.300 mg, 0.605 mmol) and Et$_3$N (0.252 mL, 1.82 mmol) in DCM (10 mL) was added acetyl chloride (0.065 mL, 0.908 mmol). After 1 h at room temperature, the resulting mixture was diluted with DCM (50 mL) and was washed with 0.5 M aqueous Na$_2$CO$_3$. The aqueous layer was extracted with additional DCM (10 mL) and the combined organic layers were dried over MgSO$_4$, filtered, and concentrated to yield a residue which was purified by flash chromatography on Silica gel using 0 to 4.7% MeOH/DCM. The resulting residue was triturated with di-isopropyl ether to yield (R)-8-acetyl-2-(4-bromophenyl)-3-((1-(cyclopropanecarbonyl)pyrrolidin-3-yl)methyl)-1,3,8-triazaspiro[4.5]dec-1-en-4-one as a white solid (0.165 g, 53%).

MS m/z 501 (M+H)$^+$.

STEP B: 8-Acetyl-3-{[(3R)-1-(cyclopropylcarbonyl)pyrrolidin-3-yl]methyl}-2-[4-(1H-indol-5-yl)phenyl]-1,3,8-triazaspiro[4.5]dec-1-en-4-one (Compound #147)

(R)-8-Acetyl-2-(4-bromophenyl)-3-((1-(cyclopropanecarbonyl)pyrrolidin-3-yl)methyl)-1,3,8-triazaspiro[4.5]dec-1-en-4-one (0.075 g, 0.150 mmol), 5-indolylboronic acid (0.029 g, 0.180 mmol), 1.0 M aqueous Na$_2$CO$_3$ (0.30 mL, 0.30 mmol) and 1,4-dioxane (2 mL) were combined and bubbled with nitrogen for 15 min. Bis(triphenylphosphine)palladium(II) chloride (0.006 g, 0.008 mmol) was added and the resulting mixture was heated to 85° C. for 2 h. The resulting mixture was cooled to room temperature, diluted with DCM (50 mL), and washed successively with water (15 mL) and saturated aqueous NaCl. The organic layer was dried over MgSO$_4$, filtered, and concentrated to yield a residue which was purified by flash chromatography (silica gel, 0 to 10% MeOH/DCM). The resulting residue was triturated with di-isopropyl ether to yield 8-acetyl-3-{[(3R)-1-(cyclopropylcarbonyl)pyrrolidin-3-yl]methyl}-2-[4-(1H-indol-5-yl)phenyl]-1,3,8-triazaspiro[4.5]dec-1-en-4-one, as a white solid, (0.040 g, 47%).

$^1$H NMR (300 MHz, DMSO-d6) δ ppm 0.52-0.72 (m, 4H), 1.28-1.95 (m, 6H), 2.07 (s, 3H), 2.13-2.39 (m, 1H), 2.86 (dd, J=11.7, 7.0 Hz, 0.5H), 3.01-3.30 (m, 3.5H), 3.37-3.62 (m, 3H), 3.62-3.75 (m, 2H), 3.75-3.93 (m, 1H), 4.15-4.40 (m, 1H), 6.52 (br. s., 1H), 7.40 (t, J=2.7 Hz, 1H), 7.44-7.56 (m, 2H), 7.71-7.81 (nm, 2H), 7.82-7.90 (m, 2H), 7.93 (s, 1H), 11.21 (br. s., 1H); MS m/z 538 (M+H)$^+$; m.p. 291.7° C.

Following the procedure described in Example 9, above, selecting and substituting the appropriate reagents, starting materials, and purification methods, and adjusting reaction temperatures, times and other variables or parameters, as needed or desirable, as would be readily recognized by those skilled in the art, the following compounds of formula (I) of the invention were prepared.

| ID No. | Structure | Compound Name & Physical Data |
|---|---|---|
| 148 | 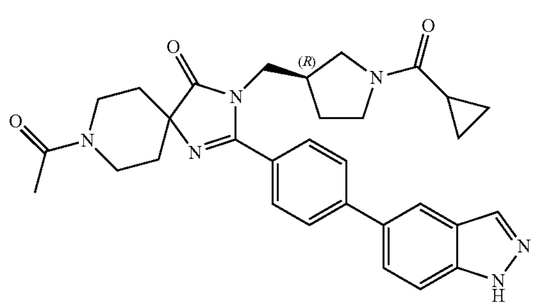 | 8-Acetyl-3-{[(3R)-1-(cyclopropylcarbonyl)pyrrolidin-3-yl]methyl}-2-[4-(1H-indazol-5-yl)phenyl]-1,3,8-triazaspiro[4.5]dec-1-en-4-one<br>$^1$H NMR (300 MHz, DMSO-d6) δ ppm 0.54-0.74 (m, 4 H), 1.31-1.96 (m, 6 H), 2.07 (s, 3 H), 2.12-2.41 (m, 1 H), 2.78-2.96 (m, 0.5 H), 2.96-3.61 (m, 6.5 H), 3.67 (t, J = 6.9 Hz, 2 H), 3.76-3.94 (m, 1 H), 4.30 (d, J = 13.6 Hz, 1 H), 7.61-7.72 (m, 1 H), 7.71-7.86 (m, 3 H), 7.86-7.98 (m, 2 H), 8.03-8.33 (m, 2 H), 13.18 (s, 1 H)<br>MS m/z 539 (M + H)$^+$<br>m.p. 187.3° C. |

| ID No. | Structure | Compound Name & Physical Data |
|---|---|---|
| 129 | 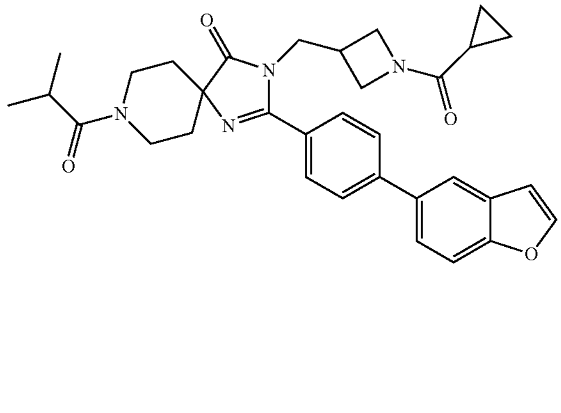 [SMILES: CC(C)C(=O)N1CCC2(CC1)N=C(c1ccc(-c3ccc4occc4c3)cc1)N(CC1CN(C(=O)C3CC3)C1)C2=O] | 2-[4-(1-Benzofuran-5-yl)phenyl]-3-{[1-(cyclopropylcarbonyl)azetidin-3-yl]methyl}-8-(2-methylpropanoyl)-1,3,8-triazaspiro[4.5]dec-1-en-4-one<br>$^1$H NMR (300 MHz, DMSO-$d_6$) δ ppm 0.51-0.68 (m, 4 H), 0.92-1.10 (m, 6 H), 1.27-1.90 (m, 5 H), 2.54-2.71 (m, 1 H), 2.84-3.01 (m, 1 H), 3.17 (t, J = 11.1 Hz, 1 H), 3.32-3.80 (m, 4 H), 3.88 (d, J = 7.3 Hz, 2 H), 3.98 (d, J = 13.3 Hz, 1 H), 4.15 (t, J = 8.2 Hz, 1 H), 4.32 (d, J = 12.4 Hz, 1 H), 6.92-7.15 (m, 1 H), 7.65-7.76 (m, 2 H), 7.79 (d, J = 8.2 Hz, 2 H), 7.90 (d, J = 8.2 Hz, 2 H), 7.99-8.14 (m, 2 H); MS m/z 553 (M + H)$^+$ m.p. 237.2° C. |
| 164 | 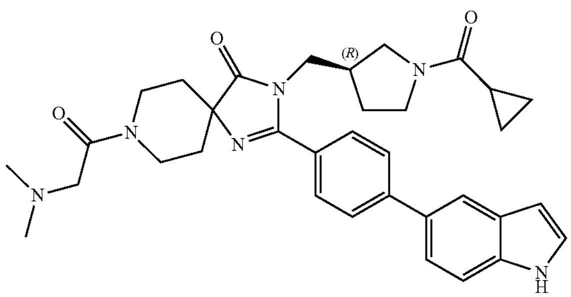 | 3-{[(3R)-1-(Cyclopropylcarbonyl)pyrrolidin-3-yl]methyl}-8-(N,N-dimethylflycyl)-2-[4-(1H-indol-5-yl)phenyl]-1,3,8-triazaspiro[4.5]dec-1-en-4-one<br>$^1$H NMR (300 MHz, DMSO-$d_6$) δ ppm 0.52-0.73 (m, 4 H), 1.27-1.96 (m, 7 H), 2.21 (s, 6 H), 2.23-2.40 (m, 1 H), 2.86 (dd, J = 11.5, 6.9 Hz, 0.5 H), 2.97-3.29 (m, 5 H), 3.41-3.61 (m, 2.5 H), 3.67 (t, J = 7.0 Hz, 2 H), 4.06 (d, J = 13.5 Hz, 1 H), 4.27 (d, J = 12.6 Hz, 1 H), 6.52 (br. s., 1 H), 7.37-7.45 (m, 1 H), 7.45-7.56 (m, 2 H), 7.70-7.82 (m, 2 H), 7.82-7.91 (m, 2 H), 7.93 (s, 1 H), 11.21 (br. s., 1 H); MS m/z 581 (M + H)$^+$ m.p. 129.1° C. |
| 165 | 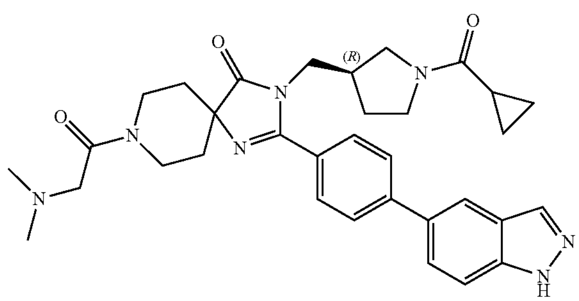 | 3-{[(3R)-1-(Cyclopropylcarbonyl)pyrrolidin-3-yl]methyl}-8-(N,N-dimethylglycyl)-2-[4-(1H-indazol-5-yl)phenyl]-1,3,8-triazaspiro[4.5]dec-1-en-4-one<br>$^1$H NMR (300 MHz, DMSO-$d_6$) δ ppm 0.64 (br. s., 4 H), 1.24-2.02 (m, 7 H), 2.20 (br. s., 6 H), 2.24-2.39 (m, 1 H), 2.70-3.27 (m, 5 H), 3.39-3.60 (m, 4 H), 3.60-3.79 (m, 2 H), 4.06 (d, J = 12.6 Hz, 1 H), 4.28 (d, J = 12.6 Hz, 1 H), 7.57-7.71 (m, 1 H), 7.71-7.85 (m, 2 H), 7.85-8.00 (m, 2 H), 8.07-8.26 (m, 2 H), 13.03 (br. s., 1 H); MS m/z 582 (M + H)$^+$ m.p. 176.4° C. |

Example 10

(R)-2-(4-(Benzofuran-5-yl)phenyl)-3-((1-(1-methylcyclopropanecarbonyl)pyrrolidin-3-yl)methyl)-1,3-diazaspiro[4.4]non-1-en-4-one (Compound #116)

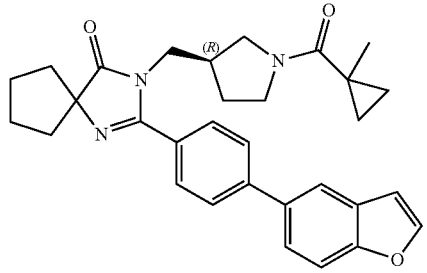

STEP A: (S)-tert-Butyl 3-((2-(4-(benzofuran-5-yl)phenyl)-4-oxo-1,3-diazaspiro[4.4]non-1-en-3-yl)ethyl)pyrrolidine-1-carboxylate (S)-ter-Butyl 3-((2-(4-bromophenyl)-4-oxo-1,3-diazaspiro[4.4]non-1-en-3-yl)methyl)pyrrolidine-1-carboxylate (1.0 g, 2.1 mmol), benzofuran-5-ylboronic acid (0.52 g, 3.15 mmol), tetrakis(triphenylphosphine) palladium (0.073 g, 0.063 mmol), potassium carbonate (0.466 g, 4.4 mmol), DME (27 mL) and water (2.2 mL) were combined and the resulting mixture was heated to reflux for 16 h under argon atmosphere. The resulting mixture was concentrated concentrated in vacuo and the residue was purified by flash chromatography (silica gel, 10% to 60% EtOAc in heptane) to yield (S)-tert-butyl 3-((2-(4-(benzofuran-5-yl)phenyl)-4-oxo-1,3-diazaspiro[4.4]non-1-en-3-yl)methyl) pyrrolidine-1-carboxylate (1.05 g, 98%).

¹H NMR (400 MHz, CDCl₃) δ ppm 1.41 (s, 9H), 1.74-1.85 (m, 1H), 1.88-1.99 (m, 3H), 1.99-2.13 (m, 6H), 2.26-2.40 (m, 1H), 2.81-2.95 (m, 1H), 3.13-3.24 (m, 1H), 3.24-3.32 (m, 1H), 3.33-3.43 (m, 1H), 3.61-3.77 (m, 2H), 6.85 (s, 1H), 7.54-7.63 (m, 2H), 7.65 (d, J=7.8 Hz, 2H), 7.69 (s, 1H), 7.75 (d, J=8.1 Hz, 2H), 7.85 (s, 1H); MS m/z 514.3 (M+H)⁺.

STEP B: (R)-2-(4-(Benzofuran-5-yl)phenyl)-3-(pyrrolidin-3-ylmethyl)-1,3-diazaspiro[4.4]non-1-en-4-one To a stirring solution of (S)-tert-butyl 3-((2-(4-(benzofuran-5-yl)phenyl)-4-oxo-1,3-diazaspiro[4.4]non-1-en-3-yl)methyl)pyrrolidine-1-carboxylate (0.9 g, 1.75 mmol) in DCM (36 mL) was added TFA (9 mL). After stirring 2.5 h at room temperature under nitrogen the reaction mixture was concentrated to yield (R)-2-(4-(benzofuran-5-yl)phenyl)-3-(pyrrolidin-3-ylmethyl)-1,3-diazaspiro[4.4]non-1-en-4-one, as its corresponding TFA salt, as an oil, which was directly used directly into the next step.
MS m/z 414.1 (M+H)⁺.

STEP C: (R)-2-(4-(Benzofuran-5-yl)phenyl)-3-((1-(1-methylcyclopropanecarbonyl)pyrrolidin-3-yl)methyl)-1,3-diazaspiro[4.4]non-1-en-4-one (Compound #116)

To a stirring solution of (R)-2-(4-(benzofuran-5-yl)phenyl)-3-(pyrrolidin-3-ylmethyl)-1,3-diazaspiro[4.4]non-1-en-4-one TFA salt (41.3 mg, 0.1 mmol) in DCM (2.5 mL) and DIPEA (0.086 mL, 0.5 mmol) was added 1-methylcyclopropanecarbonyl chloride (0.014 mg, 0.12 mmol). After stirring at room temperature overnight, the reaction mixture was concentrated in vacuo and the resulting residue was purified by flash chromatography (silica gel, 25% to 65% EtOAc in heptane) to yield (R)-2-(4-(benzofuran-5-yl)phenyl)-3-((1-(1-methylcyclopropanecarbonyl)pyrrolidin-3-yl)methyl)-1,3-diazaspiro[4.4]non-1-en-4-one (36.5 mg, 74%).

¹H NMR (400 MHz, CDCl₃) δ ppm 0.44-0.55 (m, 2H), 0.78-1.01 (m, 2H), 1.19-1.24 (m, 3H), 1.38-1.64 (m, 2H), 1.78-2.02 (m, 4H), 2.02-2.13 (m, 4H), 2.30-2.44 (m, 1H), 3.08 (br. s., 1H), 3.26-3.54 (m, 2H), 3.53-3.84 (m, 2H), 6.85 (br. s., 1H), 7.53-7.63 (m, 2H), 7.66 (d, J=8.1 Hz, 2H), 7.69 (d, J=2.0 Hz, 1H), 7.76 (d, J=8.1 Hz, 2H), 7.84 (s, 1H); MS m/z 496.2 (M+H)⁺.

Following the procedure described in Example 10, above, selecting and substituting the appropriate reagents, starting materials, and purification methods, and adjusting reaction temperatures, times and other variables or parameters, as needed or desirable, as would be readily recognized by those skilled in the art, the following compounds of formula (I) of the invention were prepared.

| ID No. | Structure | Compound Name & Physical Data |
|---|---|---|
| 119 | 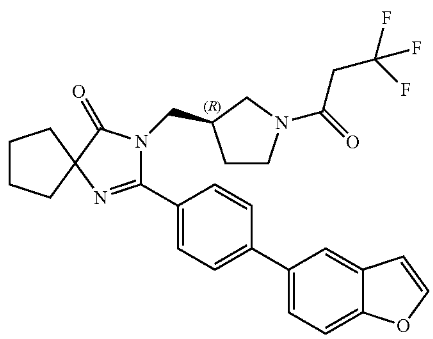 | 2-[4-(1-Benzofuran-5-yl)phenyl]-3-{[(3R)-1-(3,3,3-trifluoropropanoyl)pyrrolidin-3-yl]methyl}-1,3-diazaspiro[4.4]non-1-en-4-one<br>¹H NMR (400 MHz, CDCl₃) δ ppm 1.45-1.68 (m, 1 H), 1.83-2.13 (m, 9 H), 2.31-2.51 (m, 1 H), 3.00-3.16 (m, 3 H), 3.30-3.49 (m, 2 H), 3.50-3.62 (m, 1 H), 3.62-3.77 (m, 2 H), 6.85 (s, 1 H), 7.56 (d, J = 8.6 Hz, 1 H), 7.61 (d, J = 8.6 Hz, 1 H), 7.65 (d, J = 7.3 Hz, 2 H), 7.69 (s, 1 H), 7.73-7.80 (m, 2 H), 7.84 (s, 1 H); MS m/z 524.1 (M + H)⁺ |
| 118 | 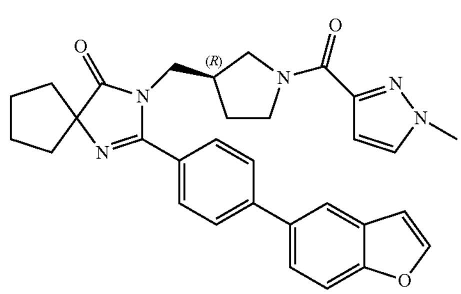 | 2-[4-(1-Benzofuran-5-yl)phenyl]-3-({(3R)-1-[(1-methyl-1H-pyrazol-3-yl)carbonyl]pyrrolidin-3-yl}methyl)-1,3-diazaspiro[4.4]non-1-en-4-one<br>¹H NMR (400 MHz, CDCl₃) δ ppm 1.42-1.65 (m, 1 H), 1.79 (s, 2 H), 1.83-2.12 (m, 9 H), 2.34-2.39 (m, 1 H), 3.43-3.55 (m, 1 H), 3.61-3.81 (m, 3 H), 3.82 (s, 1 H), 3.90 (s, 2 H), 4.00 (dd, J 11.7, 7.1 Hz, 1 H), 6.72 (dd, J = 8.6, 2.0 Hz, 1 H), 6.84 (s, 1 H), 7.30 (d, J = 2.0 Hz, 1 H), 7.50-7.62 (m, 2 H), 7.62-7.70 (m, 3 H), 7.70-7.76 (m, 2 H), 7.82 (d, J = 10.5 Hz, 1 H); MS m/z 522.2 (M + H)⁺ |

| ID No. | Structure | Compound Name & Physical Data |
|---|---|---|
| 117 | 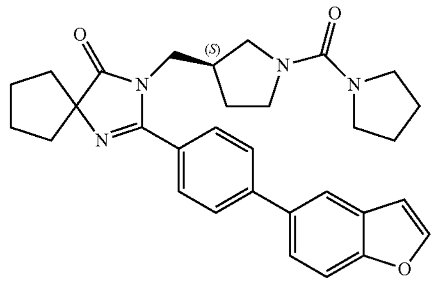 | 2-[4-(1-Benzofuran-5-yl)phenyl]-3-{[(3S)-1-(pyrrolidin-1-ylcarbonyl)pyrrolidin-3-yl]methyl}-1,3-diazaspiro[4.4]non-1-en-4-one<br>$^1$H NMR (400 MHz, CDCl$_3$) δ ppm 1.39-1.51 (m, 1 H), 1.67-1.84 (m, 6 H), 1.88-2.02 (m, 4 H), 2.02-2.12 (m, 4 H), 2.26-2.39 (m, 1 H), 2.99 (dd, J = 10.4, 7.2 Hz, 1 H), 3.20-3.37 (m, 6 H), 3.63-3.78 (m, 2 H), 6.85 (s, 1 H), 7.53-7.63 (m, 2 H), 7.63-7.68 (m, 2 H), 7.69 (d, J = 2.0 Hz, 1 H), 7.75 (d, J = 8.3 Hz, 2 H), 7.84 (s, 1 H); MS m/z 511.2 (M + H)$^+$ |
| 189 | 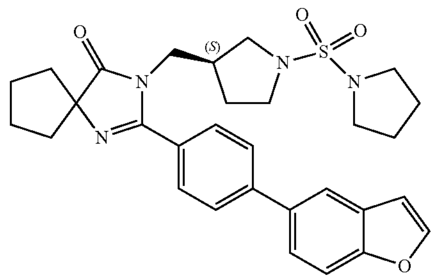 | 2-[4-(1-Benzofuran-5-yl)phenyl]-3-{[(3S)-1-(pyrrolidin-1-ylsulfonyl)pyrrolidin-3-yl]methyl}-1,3-diazaspiro[4.4]non-1-en-4-one<br>$^1$H NMR (400 MHz, CHLOROFORM-d) δ ppm 1.51-1.63 (m, 1 H), 1.84-1.90 (m, 4 H), 1.90-2.01 (m, 1 H), 2.01-2.16 (m, 4 H), 2.17-2.27 (m, 2 H), 2.28-2.38 (m, 2 H), 2.55 (dt, J = 14.0, 7.1 Hz, 1 H), 3.00 (dd, J = 10.0, 6.4 Hz, 1 H), 3.18-3.31 (m, 6 H), 3.35 (dd, J = 10.1, 7.0 Hz, 1 H), 3.93 (d, J = 7.3 Hz, 2 H), 6.87 (d, J = 1.2 Hz, 1 H), 7.58 (dd, J = 8.6, 1.7 Hz, 1 H), 7.63 (d, J = 8.6 Hz, 1 H), 7.71 (d, J = 2.2 Hz, 1 H), 7.84 (d, J = 8.6 Hz, m2 H), 7.86-7.91 (m, 3 H)<br>MS m/z 547.2 (M + H)$^+$ |
| 90 | 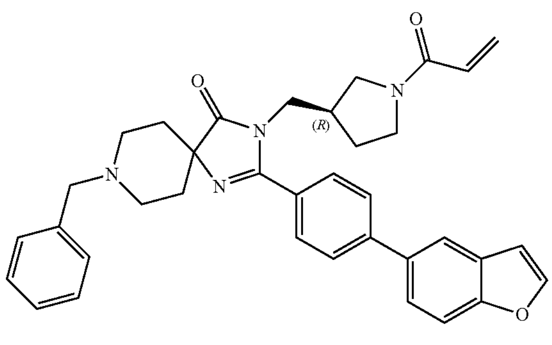 | 3-{[(3R)-1-Acryloylpyrrolidin-3-yl]methyl}-2-[4-(1-benzofuran-5-yl)phenyl]-8-benzyl-1,3,8-triazaspiro[4.5]dec-1-en-4-one<br>$^1$H NMR (400 MHz, CDCl$_3$) δ ppm 1.40-1.67 (m, 2 H), 1.76-2.02 (m, 2 H), 2.08-2.24 (m, 2 H), 2.27-2.53 (m, 1 H), 2.62-2.74 (m, 2 H), 2.84-2.94 (m, 2 H), 3.03-3.16 (m, 1 H), 3.27-3.45 (m, 1 H), 3.45-3.59 (m, 2 H), 3.59-3.77 (m, 4 H), 5.56-5.70 (m, 1 H), 6.19-6.39 (m, 2 H), 6.79-6.90 (m, 1 H), 7.23-7.30 (m, 1 H), 7.34 (t, J = 7.1 Hz, 2 H), 7.37-7.41 (m, 2 H), 7.55 (d, J = 8.6 Hz, 1 H), 7.61 (d, J = 8.6 Hz, 1 H), 7.63-7.67 (m, 2 H), 7.69 (d, J = 2.0 Hz, 1 H), 7.76 (dd, J = 8.1, 5.1 Hz, 2 H), 7.84 (s, 1 H); MS m/z 573.0 (M + H)$^+$ |

Example 11

2-(4-(Benzofuran-5-yl)phenyl)-3-(((R)-1-((S)-tetrahydro-furan-2-carbonyl)pyrrolidin-3-yl)methyl)-1,3-diazaspiro[4.4]non-1-en-4-one (Compound #190)

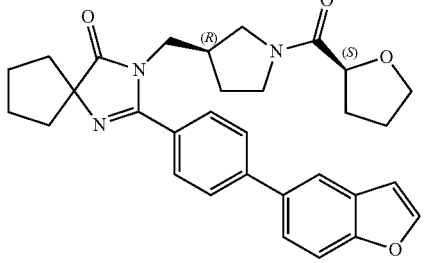

To a stirring solution of (R)-2-(4-(benzofuran-5-yl)phenyl)-3-(pyrrolidin-3-ylmethyl)-1,3-diazaspiro[4.4]non-1-en-4-one (44 mg, 0.109 mmol) and tetrahydro-furan-2-carboxylic acid (12.9 mg, 0.109 mmol) in DCM (2.5 mL) and Et$_3$N (0.22 mL, 1.63 mmol) was added HATU (53.8 mg, 0.14 mmol). After stirring at room temperature overnight, the reaction mixture was concentrated in vacuo and the resulting residue was purified by flash chromatography (silica gel, 25% to 65% EtOAc in heptane) to yield 2-[4-(1-benzofuran-5-yl)phenyl]-3-({(3R)-1-[(2S)-tetrahydrofuran-2-ylcarbonyl]pyrrolidin-3-yl}methyl)-1,3-diazaspiro[4.4]non-1-en-4-one (36.7 mg, 66%).

$^1$H NMR (400 MHz, CHLOROFORM-d) δ ppm 1.43-1.70 (m, 1H), 1.81-2.11 (m, 9H), 2.11-2.32 (m, 4H), 2.38-2.62 (m, 1H), 3.11 (dd, J=12.2, 7.3 Hz, 1H), 3.28-3.44 (m, 1H), 3.49-3.65 (m, 2H), 3.77-3.96 (m, 4H), 4.37-4.47 (m, 1H), 6.86 (d, J=2.2 Hz, 1H), 7.56 (dd, J=8.8, 2.0 Hz, 1H), 7.62 (d, J=8.6 Hz, 1H), 7.71 (d, J=2.2 Hz, 1H), 7.80-7.90 (m, 5H);

MS m/z 512.3 (M+H)$^+$.

Following the procedure described in Example 11, above, selecting and substituting the appropriate reagents, starting materials, and purification methods, and adjusting reaction temperatures, times and other variables or parameters, as needed or desirable, as would be readily recognized by those skilled in the art, the following compounds of formula (I) of the invention were prepared.

| ID No. | Structure | Compound Name & Physical Data |
|---|---|---|
| 191 | 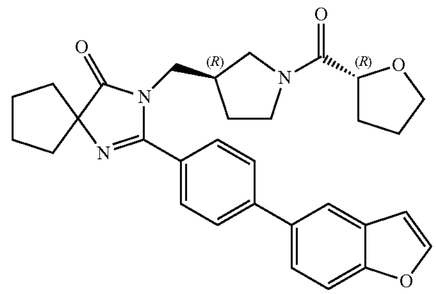 | 2-[4-(1-Benzofuran-5-yl)phenyl]-3-({(3R)-1-[(2R)-tetrahydro-furan-2-ylcarbonyl]pyrrolidin-3-yl}methyl)-1,3-diazaspiro[4.4]non-1-en-4-one<br>$^1$H NMR (400 MHz, CHLOROFORM-d) δ ppm 1.46-1.71 (m, 1 H), 1.84-2.14 (m, 9 H), 2.15-2.32 (m, 4 H), 2.51 (dt, J = 14.7, 7.1 Hz, 1 H), 3.09-3.21 (m, 1 H), 3.42 (dt, J = 11.1, 7.6 Hz, 1 H), 3.52-3.63 (m, 1 H), 3.63-3.77 (m, 1 H), 3.79-3.86 (m, 1 H), 3.86-3.97 (m, 3 H), 4.34-4.47 (m, 1 H), 6.86 (d, J = 1.2 Hz, 1 H), 7.56 (d, J = 8.6 Hz, 1 H), 7.59-7.64 (m, 1 H), 7.68-7.73 (m, 1 H), 7.81-7.91 (m, 5 H);<br>MS m/z 512.3 (M + H)$^+$ |
| 192 | 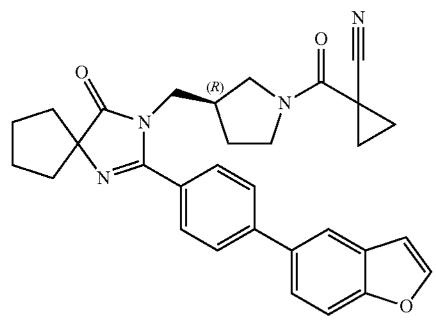 | 1-{[(3R)-3-({2-[4-(1-Benzofuran-5-yl)phenyl]-4-oxo-1,3-diazaspiro[4.4]non-1-en-3-yl}methyl)pyrrolidin-1-yl]carbonyl}cyclopropancarbonitrile<br>$^1$H NMR (400 MHz, CHLOROFORM-d) δ ppm 1.42-1.63 (m, 3 H), 1.63-1.81 (m, 2 H), 1.99-2.16 (m, 5 H), 2.18-2.29 (m, 2 H), 2.29-2.41 (m, 2 H), 2.47-2.68 (m, 1 H), 3.16 (dd, J = 12.3, 7.2 Hz, 1 H), 3.39-3.67 (m, 2 H), 3.82 (dt, J = 10.6, 7.5 Hz, 1 H), 3.89-4.06 (m, 3 H), 6.87 (d, J = 1.7 Hz, 1 H), 7.58 (dd, J = 8.6, 1.7 Hz, 1 H), 7.64 (d, J = 8.6 Hz, 1 H), 7.71 (d, J = 2.2 Hz, 1 H), 7.81-7.94 (m, 5 H);<br>MS m/z 507.1 (M + H)$^+$ |

Example 12

8-Acetyl-2-[4-(2-acetyl-1,2,3,4-tetrahydroisoquinolin-6-yl)phenyl]-3-{[3R)-1-(cyclopropylcarbonyl)pyrrolidin-3-yl]methyl}-1,3,8-triazaspiro[4.5]dec-1-en-4-one (Compound #160)

and 8-Acetyl-2-[4-(2-acetyl-1,2,3,4,4a,8a-hexahydroisoquinolin-6-yl)phenyl]-3-{[(3R)-1-(cyclopropylcarbonyl)pyrrolidin-3-yl]methyl}-1,3,8-triazaspiro[4.5]dec-1-en-4-one (Compound #161)

STEP A: (R)-3-((1-(cyclopropanecarbonyl)pyrrolidin-3-yl)methyl-2-(4-(1,2,3,4-tetrahydroisoquinolin-6-yl)phenyl)-1,3,8-triazaspiro[4.5]dec-1-en-4-one, and (R)-3-((1-(cyclopropanecarbonyl)pyrrolidin-3-yl)methyl)-2-(4-(1,2,3,4,4a,8a-hexahydroisoquinolin-6-yl)phenyl)-1,3,8-triazaspiro[4.5]dec-1-en-4-one 10% Palladium on carbon (0.10 g) was added to a solution of 8-benzyl-3-{[(3R)-1-(cyclopropylcarbonyl)pyrrolidin-3- yl]methyl}-2-(4-isoquinolin-6-ylphenyl)-1,3,8-triazaspiro[4.5]dec-1-en-4-one (0.635 g, 1.06 mmol) in MeOH (15 mL) under a nitrogen atmosphere. The reaction vessel was connected to a balloon filled with hydrogen and the vessel was evacuated and filled with hydrogen three times. After stirring under hydrogen overnight, HOAc (1 mL, 15.8 mmol) was added and the reaction again placed under hydrogen atmosphere and stirred for several days. The suspension was filtered through a pad of diatomaceous earth and the solids were washed three times with MeOH (20 mL). The combined filtrates were concentrated to dryness, then dissolved in DCM (30 mL) and washed with 1M aqueous NaOH (20 mL). The organic layer was dried over MgSO₄, filtered, and concentrated to yield a mixture of (R)-3-((1-(cyclopropanecarbonyl)pyrrolidin-3-yl)methyl)-2-(4-(1,2,3,4-tetrahydroisoquinolin-6-yl)phenyl)-1,3,8-triazaspiro[4.5]dec-1-en-4-one and (R)-3-((1-(cyclopropanecarbonyl)pyrrolidin-3-yl)methyl)-2-(4-(1,2,3,4,4a,8a-hexahydroisoquinolin-6-yl)phenyl)-1,3,8-triazaspiro[4.5]dec-1-en-4-one (0.506 g).
MS n/z 512 and 514 (M+H)$^+$.

STEP B: 8-Acetyl-2-[4-(2-acetyl-1,2,3,4-tetrahydroisoquinolin-6-yl)phenyl]-3-{[(3R)-1-(cyclopropylcarbonyl)pyrrolidin-3-yl]methyl}-1,3,8-triazaspiro[4.5]dec-1-en-4-one (Compound #160), and 8-Acetyl-2-[4-(2-acetyl-1,2,3,4,4a,8a-hexahydroisoquinolin-6-yl)phenyl]-3-{[(3R)-1-(cyclopropylcarbonyl)pyrrolidin-3-yl]methyl}-1,3,8-triazaspiro[4.5]dec-1-en-4-one (Compound #161)

Acetyl chloride (0.283 mL, 3.98 mmol) was added to the mixture of (R)-3-((1-(cyclopropanecarbonyl)pyrrolidin-3-yl)methyl)-2-(4-(1,2,3,4-tetrahydroisoquinolin-6-yl)phenyl)-1,3,8-triazaspiro[4.5]dec-1-en-4-one, and (R)-3-((1-(cyclopropanecarbonyl)pyrrolidin-3-yl)methyl)-2-(4-(1,2,3,4,4a,8a-hexahydroisoquinolin-6-yl)phenyl)-1,3,8-triazaspiro[4.5]dec-1-en-4-one, prepared as described in Step A above, (0.406 g, 0.793 mmol) and Et₃N (1.12 mL, 8.00 mmol) in DCM (20 mL) at 0° C. The resulting mixture was allowed to warm to room temperature and MeOH (2 mL) was added after 30 min. DCM (20 mL) was added and the organic solution was washed once with 1M aq. NaOH. The organic layer was dried over MgSO₄, filtered, and concentrated; the resulting residue was filtered through a short pad of silica gel and eluted with 10% MeOH/DCM. Fractions containing the desired products were concentrated to yield a mixture that was further purified by reverse-phase HPLC using 10-46% CH₃CN/0.1% aq. TFA. Fractions containing a mixture of the desired products were combined, diluted with DCM (50 mL), and washed with 1 M aq. NaOH. The organic layer was dried over MgSO₄, filtered, and concentrated. The resulting material was re-purified by flash chromatography (silica gel, 0-10% MeOH/DCM) to yield (a) 8-Acetyl-2-[4-(2-acetyl-1,2,3,4-tetrahydroisoquinolin-6-yl)phenyl]-3-{[(3R)-1-(cyclopropylcarbonyl)pyrrolidin-3-yl]methyl}-1,3,8-triazaspiro[4.5]dec-1-en-4-one (0.030 g).
$^1$H NMR (300 MHz, CDCl₃) δ ppm 0.62-0.81 (m, 2H), 0.85-1.01 (m, 2H), 1.35-1.73 (m, 3H), 1.72-2.10 (m, 4H), 2.13-2.17 (m, 3H), 2.20 (d, J=2.2 Hz, 3H), 2.23-2.56 (m, 2H), 2.82-4.01 (m, 12H), 4.35-4.60 (m, 1H), 4.68 (s, 1H), 4.79 (s, 1H), 7.19-7.35 (m, 1H), 7.35-7.57 (nm, 2H), 7.56-7.84 (m, 4H); MS m/z 596, m.p. 104.5° C.

(b) 8-Acetyl-2-[4-(2-acetyl-1,2,3,4,4a,8a-hexahydroisoquinolin-6-yl)phenyl]-3-{[(3R)-1-(cyclopropylcarbonyl)pyrrolidin-3-yl]methyl}-1,3,8-triazaspiro[4.5]dec-1-en-4-one (0.010 g).

$^1$H NMR (300 MHz, CDCl₃) δ ppm 0.67-0.80 (m, 2H), 0.96 (d, J=3.8 Hz, 2H), 1.37-1.68 (m, 4H), 1.78-2.08 (m, 3H), 2.12 (s, 3H), 2.21 (d, J=2.1 Hz, 3H), 2.23-2.75 (m, 2H), 2.76-3.11 (m, 4H), 3.11-3.94 (m, 9H), 4.21-4.55 (m, 1H), 4.68 (s, 1H), 4.79 (s, 1H), 5.36-5.56 (m, 1H), 7.16-7.28 (m, 1H), 7.34-7.49 (m, 4H), 7.66 (d, J=6.7 Hz, 2H); MS m/z 598.

and (c) a mixture of the compound of (a) and the compound of (b); (0.120 g).

Example 13

3-{[(3R)-1-(Cyclopropylcarbonyl)pyrrolidin-3-yl]methyl}-2-(4-isoquinolin-6-ylphenyl)-8-(1-methylethy)-1,3,8-triazaspiro[4.5]dec-1-en-4-one (Compound #163)

A mixture of 3-{[(3R)-1-(cyclopropylcarbonyl)pyrrolidin-3-yl]methyl}-2-(4-isoquinolin-6-ylphenyl)-1,3,8-triazaspiro[4.5]dec-1-en-4-one (0.080 g, 0.158 mmol), acetone (0.0464 mL, 0.632 mmol), sodium triacetoxyborohydride (0.0403 g, 0.190 mmol), and AcOH (0.010 mL, 0.158 mmol) in THF (5 mL) was stirred at room temperature for 24 h. 1M aq. NaOH (5 mL) was added and the reaction mixture was extracted with DCM (2×10 mL). The combined organic layers were dried over MgSO₄, filtered, and concentrated. The resulting residue was purified by flash chromatography (silica gel, 0-10% of MeOH in DCM). Fractions containing desired product were concentrated and re-purified by reverse-phase HPLC using 30-73% 1:1 CH₃CN/MeOH in aq. 25 mM NH₄CO₃. Fractions containing desired product were concentrated, dissolved in MeOH (2 mL), and treated with 4N HCl in 1,4-dioxane (0.100 mL). The resulting solution was concentrated and the residue triturated with Et₂O, filtered, and dried under high vacuum to yield 3-{[(3R)-1-(cyclopropylcarbonyl)pyrrolidin-3-yl]methyl}-2-(4-isoquinolin-6-ylphenyl)-8-(1-methylethyl)-1,3,8-triazaspiro[4.5]dec-1-en-4-one, dihydrochloride, as a white solid, (0.069 g, 70%).

$^1$H NMR (300 MHz, DMSO-d₆) δ ppm 0.64 (d, J=3.6 Hz, 4H), 1.27-1.40 (m, 7H), 1.47-2.04 (m, 5H), 2.14-2.43 (m, 1H), 2.86 (dd, J=11.7, 7.3 Hz, 0.5H), 3.03-3.20 (m, 1H), 3.20-3.34 (m, 2.5H), 3.43-3.63 (m, 7H), 3.69 (t, J=7.3 Hz, 2H), 7.99 (dd, J=7.9, 5.2 Hz, 2H), 8.20 (dd, J=8.0, 3.8 Hz, 2H), 8.47 (d, J=8.8 Hz, 1H), 8.55 (d, J=6.5 Hz, 1H), 8.68 (d, J=8.7 Hz, 1H), 8.73 (d, J=6.6 Hz, 1H), 8.79 (s, 1H), 9.95 (s, 1H), 10.74-11.18 (m, 1H); MS m/z 550; m.p.>300° C.

Following the procedure described in Example 13, above, selecting and substituting the appropriate reagents, starting materials, and purification methods, and adjusting reaction temperatures, times and other variables or parameters, as needed or desirable, as would be readily recognized by those skilled in the art, the following compounds of formula (I) of the invention were prepared.

| ID No. | Structure | Compound Name & Physical Data |
|---|---|---|
| 162 | 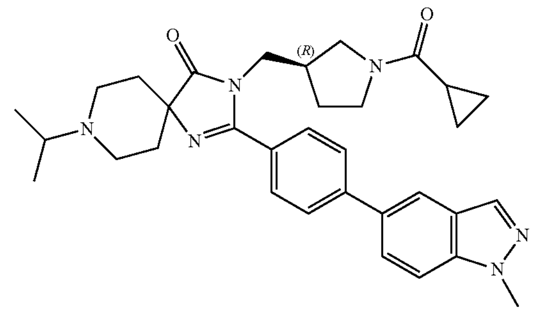 | 3-{[(3R)-1-(Cyclopropylcarbonyl)pyrrolidin-3-yl]methyl}-8-(1-methylethyl)-2-[4-(1-methyl-1H-indazol-5-yl)phenyl]-1,3,8-triazaspiro[4.5]dec-1-en-4-one dihydrochloride<br>MS m/z 553 (M + H)⁺ |
| 166 | 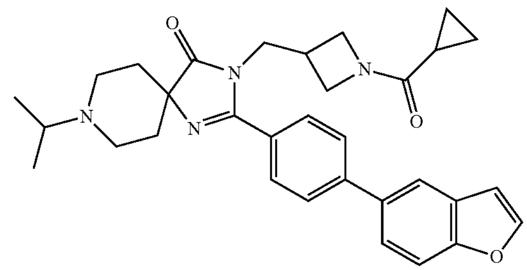 [SMILES: CC(C)N1CCC2(CC1)N=C(c1ccc(-c3ccc4occc4c3)cc1)N(CC1CN(C(=O)C3CC3)C1)C2=O] | 2-[4-(1-Benzofuran-5-yl)phenyl]-3-{[1-(cyclopropylcarbonyl)azetidin-3-yl]methyl}-8-(1-methylethyl)-1,3,8-triazaspiro[4.5]dec-1-en-4-one<br>MS m/z 525 (M + H)⁺ |
| 167 | 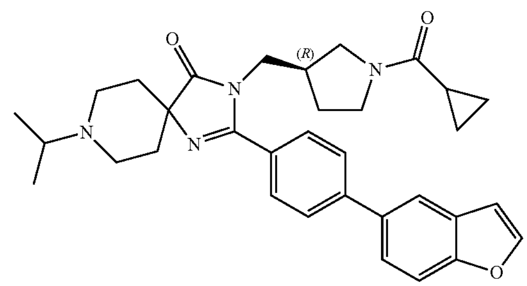 | 2-[4-(1-Benzofuran-5-yl)phenyl]-3-{[(3R)-1-(cyclopropylcarbonyl)pyrrolidin-3-yl]methyl}-8-(1-methylethyl)-1,3,8-triazaspiro[4.5]dec-1-en-4-one<br>¹H NMR (300 MHz, CDCl₃) δ ppm 0.63-0.76 (m, 2 H), 0.88-0.97 (m, 2 H), 1.14 (d, J = 6.5 Hz, 6 H), 1.36-1.74 (m, 4 H), 1.74-2.09 (m, 2 H), 2.06-2.56 (m, 4 H), 2.75-3.08 (m, 5 H), 3.12-3.36 (m, 1 H), 3.48-3.80 (m, 3 H), 6.85 (d, J = 1.8 Hz, 1 H), 7.51-7.57 (m, 1 H), 7.58-7.71 (m, 4 H), 7.71-7.80 (m, 2 H), 7.80-7.88 (m, 1 H);<br>MS m/z 539 (M + H)⁺ |
| 169 | 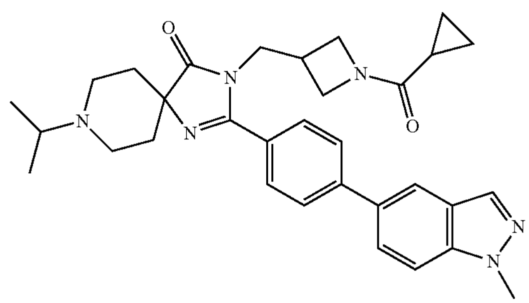 [SMILES: CC(C)N1CCC2(CC1)N=C(c1ccc(-c3ccc4c(cnn4C)c3)cc1)N(CC1CN(C(=O)C3CC3)C1)C2=O] | 3-{[1-(Cyclopropylcarbonyl)azetidin-3-yl]methyl}-8-(1-methylethyl)-2-[4-(1-methyl-1H-indazol-5-yl)phenyl]-1,3,8-triazaspiro[4.5]dec-1-en-4-one<br>MS m/z 539 (M + H)⁺<br>m.p. 93.1° C. |
| 184 | 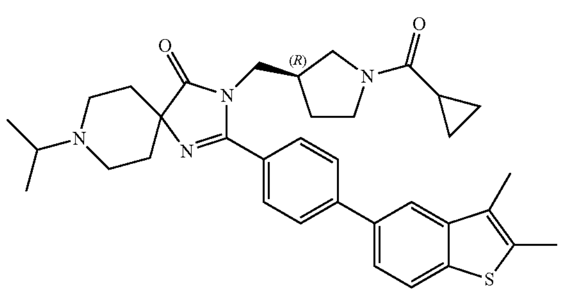 | 3-{[(3R)-1-(Cyclopropylcarbonyl)pyrrolidin-3-yl]methyl}-2-[4-(2,3-dimethyl-1-benzothiophen-5-yl)phenyl]-8-(1-methylethyl)-1,3,8-triazaspiro[4.5]dec-1-en-4-one<br>¹H NMR (300 MHz, DMSO-d₆) δ ppm 0.56-0.69 (m, 4 H), 0.96-1.09 (m, 6 H), 1.41-1.94 (m, 6 H), 2.09-2.34 (m, 1 H), 2.34-2.39 (m, 3 H), 2.37 (s, 3 H), 2.50 (s, 3 H), 2.56-2.70 (m, 2 H), 2.70-2.91 (m, 2 H), 3.04-3.17 (m, 1 H), 3.26 (d, J = 4.9 Hz, 1 H), 3.33-3.59 (m, 1 H), 3.65 (t, J = 7.5 Hz, 2 H), 7.67 (dd, J = 9.2 Hz, 1 H), 7.78 (dd, J = 7.8, 5.6 Hz, 2 H), 7.91-8.03 (m, 4 H);<br>MS m/z 583 (M + H)⁺<br>m.p. 118.4° C. |

-continued

| ID No. | Structure | Compound Name & Physical Data |
|---|---|---|
| 186 | 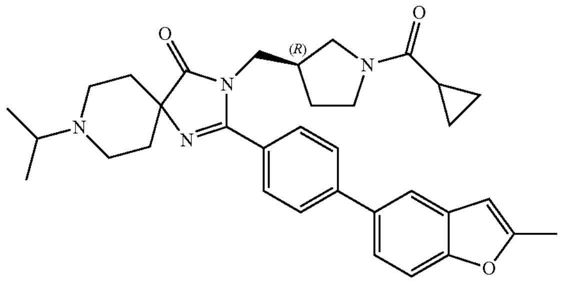 | 3-{[(3R)-1-(Cyclopropylcarbonyl)pyrrolidin-3-yl]methyl}-2-[4-(2-methyl-1-benzofuran-5-yl)phenyl]-8-(1-methylethyl)-1,3,8-triazaspiro[4.5]dec-1-en-4-one<br>$^1$H NMR (300 MHz, DMSO-$d_6$) δ ppm 0.64 (d, J = 4.5 Hz, 4 H), 1.16-2.06 (m, 13 H), 2.07-2.45 (m, 4 H), 2.76-3.27 (m, 4 H), 3.40-3.76 (m, 7 H), 6.66 (s, 1 H), 7.60 (s, 2 H), 7.72-7.84 (m, 2 H), 7.84-7.97 (m, 3 H);<br>MS m/z 553 (M + H)$^+$<br>m.p. 143.1° C. |
| 187 | 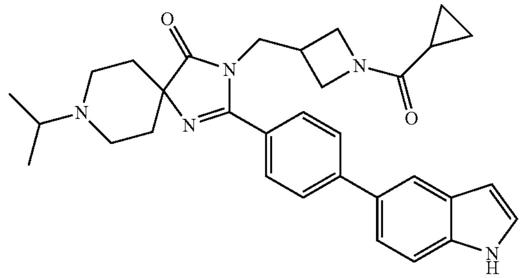 [SMILES: CC(C)N1CCC2(CC1)N=C(c1ccc(-c3ccc4[nH]ccc4c3)cc1)N(CC1CN(C(=O)C3CC3)C1)C2=O] | 3-{[1-(Cyclopropylcarbonyl)azetidin-3-yl]methyl}-2-[4-(1H-indol-5-yl)phenyl]-8-(1-methylethyl)-1,3,8-triazaspiro[4.5]dec-1-en-4-one<br>$^1$H NMR (300 MHz, CDCl$_3$) δ ppm 0.69 (dd, J = 7.8, 3.2 Hz, 2 H), 0.84-0.94 (m, 2 H), 1.14 (d, J = 6.6 Hz, 6 H), 1.20-1.36 (m, 2 H), 1.64 (d, J = 12.8 Hz, 2 H), 1.98-2.26 (m, 3 H), 2.63-3.05 (m, 5 H), 3.49-3.63 (m, 1 H), 3.77-4.02 (m, 3 H), 4.09-4.24 (m, 1 H), 6.63 (br. s., 1 H), 7.27-7.33 (m, 1 H), 7.42-7.52 (m, 2 H), 7.61 (d, J = 8.2 Hz, 2 H), 7.79 (d, J = 8.2 Hz, 2 H), 7.90 (s, 1 H), 8.55 (br. s., 1 H);<br>MS m/z 524 (M + H)$^+$ |
| 188 | 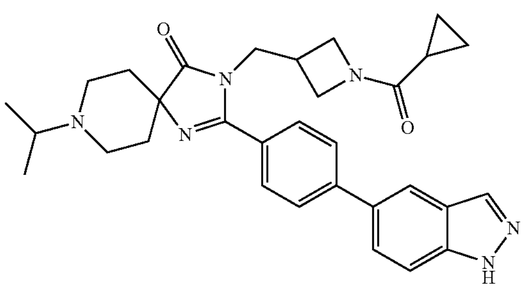 [SMILES: CC(C)N1CCC2(CC1)N=C(c1ccc(-c3ccc4[nH]ncc4c3)cc1)N(CC1CN(C(=O)C3CC3)C1)C2=O] | 3-{[1-(Cyclopropylcarbonyl)azetidin-3-yl]methyl}-2-[4-(1H-indazol-5-yl)phenyl]-8-(1-methylethyl)-1,3,8-triazaspiro[4.5]dec-1-en-4-one<br>$^1$H NMR (300 MHz, DMSO-$d_6$) δ ppm 0.55-0.67 (m, 4 H), 1.02 (d, J = 6.3 Hz, 6 H), 1.23 (br. s., 1 H), 1.31-1.57 (m, 3 H), 1.85 (t, J = 9.9 Hz, 2 H), 2.54-2.70 (m, 3 H), 2.70-2.89 (m, 3 H), 3.65-3.81 (m, 2 H), 3.86 (d, J = 7.1 Hz, 2 H), 4.14 (t, J = 7.9 Hz, 1 H), 7.58-7.70 (m, 1 H), 7.75 (d, J = 8.0 Hz, 3 H), 7.90 (d, J = 8.0 Hz, 2 H), 8.16 (d, J = 4.7 Hz, 2 H), 13.17 (br. s., 1 H);<br>MS m/z 525 (M + H)$^+$<br>m.p. 162.6° C. |

Example 14

5-[4-(1-Benzofuran-5-yl)phenyl]-6-{[1-(cyclopropylcarbonyl)azetidin-3-yl]methyl}-4,6-diazaspiro[2.4]hept-4-en-7-one (Compound #49)

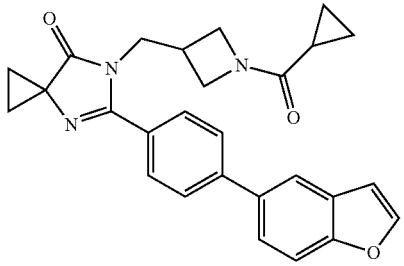 [SMILES: O=C(C1CC1)N1CC(CN2C(=O)C3(CC3)N=C2c2ccc(-c3ccc4occc4c3)cc2)C1]

STEP A: tert-Butyl 3-((5-(4-bromophenyl)-7-oxo-4,6-diazaspiro[2.4]hept-4-en-6-yl)methyl)azetidine-1-carboxylate To a stirring solution of 5-(4-bromophenyl)-4,6-diazaspiro[2.4]hept-4-en-7-one (9.9 g, 33.6 mmol) and tert-butyl 3-(bromomethyl)azetidine-1-carboxylate (12.6 g, 50.4 mmol) in DMF (180 mL) was added Cs$_2$CO$_3$ (36.5 g, 67.1 mmol). After stirring for 3 h at 830° C. under nitrogen, the reaction mixture was cooled and filtered through a pad of diatomaceous earth. The filtrate was concentrated and the residue was partitioned between EtOAc (250 mL) and water (150 mL). The organic phase was washed with brine, dried over MgSO$_4$, filtered, and concentrated in vacuo. The residue was purified by flash chromatography (silica gel, 0-75% EtOAc in heptane) to yield tert-butyl 3-((5-(4-bromophenyl)-7-oxo-4,6-diazaspiro[2.4]hept-4-en-6-yl)methyl)azetidine-1-carboxylate (10.7 g, 73%); MS m/z 434 (M+H)$^+$.

STEP B: 6-(Azetidin-3-ylmethyl)-5-(4-bromophenyl)-4,6-diazaspiro[2.4]hept-4-en-7-one TFA (50 mL) was added to an ice-cold solution of tert-butyl 3-((5-(4-bromophenyl)-7-oxo-4,6-diazaspiro[2.4]hept-4-en-6-yl)methyl)azetidine-1-carboxylate (10.7 g, 24.6 mmol) in DCM (100 mL). The solution was allowed to warm to room temperature and was stirred 1 h. The solution was concentrated in vacuo and the residue was co-evaporated twice with toluene (100 mL). The residue was pumped at high vacuum to yield 6-(azetidin-3-ylmethyl)-5-(4-bromophenyl)-4,6-diazaspiro[2.4]hept-4-en-7-one TFA salt (20.3 g), which was used in the next step without purification; MS m/z 334 (M+H)$^+$.

STEP C: 5-(4-Bromophenyl)-6-((1-(cyclopropanecarbonyl)azetidin-3-yl)methyl-4,6-diazaspiro[2.4]hept-4-en-7-one Cyclopropanecarbonyl chloride (2.46 mL, 27.1 mmol) was added dropwise to an ice cold solution of 5-(4-bromophenyl)-6-((1-(cyclopropanecarbonyl)azetidin-3-yl)methyl)-4,6-diazaspiro[2.4]hept-4-en-7-one (13.9 g, 24.6 mmol) and TEA (7.0 mL, 50.2 mmol) in DCM (100 mL). The resulting mixture was stirred 1 h and MeOH (2 mL) was added. The reaction mixture was diluted with DCM (150 mL) and washed successively with water (150 mL) and 1M aqueous $Na_2CO_3$ (150 mL). The organic layer was dried over $MgSO_4$ and concentrated in vacuo to yield a residue, which was purified by flash chromatography (silica gel, 0-5% MeOH in DCM) to give 5-(4-bromophenyl)-6-((1-(cyclopropanecarbonyl)azetidin-3-yl)methyl)-4,6-diazaspiro[2.4]hept-4-en-7-one as an amorphous solid (7.66 g, 77%); MS m/z 402 (M+H)+.

STEP D: 5-[4-(1-Benzofuran-5-yl)phenyl]-6-{[1-(cyclopropylcarbonyl)azetidin-3-yl]methyl}-4,6-diazaspiro[2.4]hept-4-en-7-one (Compound #49)

To a solution of 5-(4-bromophenyl)-6-((1-(cyclopropanecarbonyl)azetidin-3-yl)methyl)-4,6-diazaspiro[2.4]hept-4-en-7-one (7.66 g, 19.0 mmol) in acetonitrile (100 mL) was added 2-(benzofuran-5-yl)-4,4,5,5-tetramethyl-1,3,2-dioxaborolane (5.58 g, 22.9 mmol), aqueous 1.0M $Na_2CO_3$ (40 mL, 40 mmol) and bis(triphenylphosphine)palladium(II) chloride (0.33 g, 0.48 mmol). The reaction mixture was bubbled with nitrogen for 5 min and heated at 85° C. for 2 h under nitrogen atmosphere. The resulting mixture was cooled to room temperature and partitioned between EtOAc (200 mL) and brine (50 mL). The aqueous layer was extracted with EtOAc (50 mL) and the combined organic layers were dried over $MgSO_4$ and concentrated in vacuo to yield a reddish oil. The reddish oil was purified by flash chromatography (silica gel, 0-5% MeOH in DCM) to yield a beige foam after concentration and pumping at high vacuum. The foam was crystallized from acetonitrile (30 mL) and washed with acetonitrile (3×10 mL) to yield 5-[4-(1-benzofuran-5-yl)phenyl]-6-{[1-(cyclopropylcarbonyl)azetidin-3-yl]methyl}-4,6-diazaspiro[2.4]hept-4-en-7-one as a light beige solid (5.70 g, 68%).

1H NMR (300 MHz, CDCl3) δ ppm 0.64-0.76 (m, 2H), 0.86-0.97 (m, 2H), 1.22-1.36 (m, 1H), 1.74-1.83 (m, 2H), 1.83-1.94 (m, 2H), 2.77-2.95 (m, 1H), 3.62 (dd, J=9.7, 5.6 Hz, 1H), 3.90-4.16 (m, 4H), 4.23 (t, J=8.2 Hz, 1H), 6.85 (d, J=2.1 Hz, 1H), 7.53-7.74 (m, 5H), 7.78 (d, J=8.4 Hz, 2H), 7.84-7.89 (m, 1H); MS m/z 440 (M+H)+; m.p. 181.3° C.

An additional batch of the compound of Example 14 was prepared, with measured physical properties as listed below.

| ID No. | Structure | Compound Name & Physical Data |
|---|---|---|
| 49 | 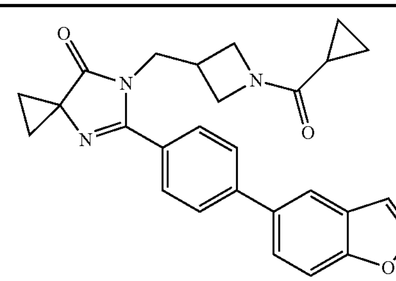 | 5-[4-(1-Benzofuran-5-yl)phenyl]-6-{[1-(cyclopropylcarbonyl)azetidin-3-yl]methyly-4,6-diazaspiro[2.4]hept-4-en-7-one<br>1H NMR (300 MHz, CDCl3) δ ppm 0.64-0.76 (m, 2 H), 0.86-0.97 (m, 2 H), 1.22-1.36 (m, 1 H), 1.74-1.83 (m, 2 H), 1.83-1.94 (m, 2 H), 2.77-2.95 (m, 1 H), 3.62 (dd, J = 9.7, 5.6 Hz, 1 H), 6.85 (d, J = 2.1 Hz, 1 H), 7.53-7.74 (m, 5 H), 7.78 (d, J = 8.4 Hz, 2 H), 7.84-7.89 (m, 1 H); MS m/z 440 (M + H)+<br>m.p. 182.0° C. |

Additional representative compounds of formula (I) of the present invention were prepared according to the procedures as described in the general synthesis schemes and examples detailed herein, selecting and substituting the appropriate reagents, starting materials, and purification methods, and adjusting reaction temperatures, times and other variables or parameters, as needed or desirable, as would be readily recognized by those skilled in the art. Measured physical properties for said compounds were as listed below.

| ID No. | Structure | Compound Name & Physical Data |
|---|---|---|
| 44 | 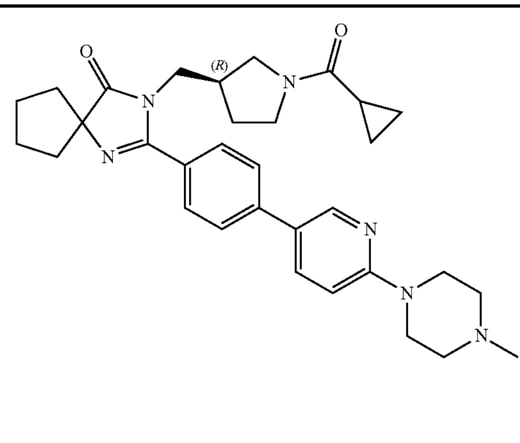 | 3-{[(3R)-1-(Cyclopropylcarbonyl)pyrrolidin-3-yl]methyl}-2-{4-[6-(4-methylpiperazin-1-yl)pyridin-3-yl]phenyl}-1,3-diazaspiro[4.4]non-1-en-4-one<br>MS m/z 541.3 (M + H)+ |

| ID No. | Structure | Compound Name & Physical Data |
|---|---|---|
| 95 | 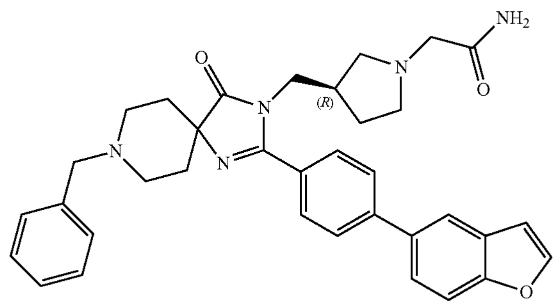 | 2-[(3R)-3-({2-[4-(1-Benzofuran-5-yl)phenyl]-8-benzyl-4-oxo-1,3,8-triazaspiro[4.5]dec-1-en-3-yl}methyl)pyrrolidin-1-yl]acetamide<br>MS m/z 576.0 (M + H)+ |
| 96 | 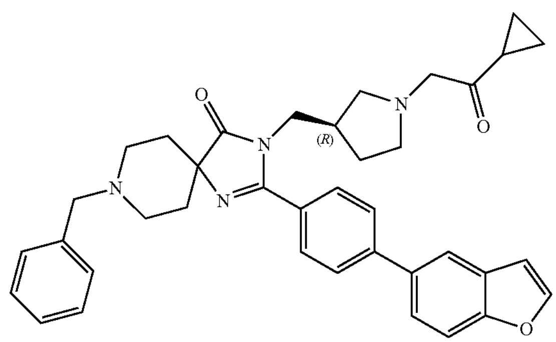 | 2-[4-(1-Benzofuran-5-yl)phenyl]-8-benzyl-3-{[(3R)-1-(2-cyclopropyl-2-oxoethyl)pyrrolidin-3-yl]methyl}-1,3,8-triazaspiro[4.5]dec-1-en-4-one<br>MS m/z 600.9 (M + H)+ |
| 200 | 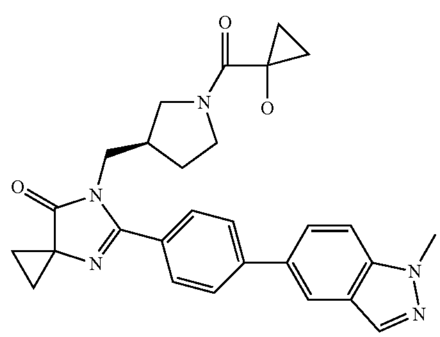 [SMILES: Cn1ncc2cc(-c3ccc(C4=NC5(CC5)C(=O)N4C[C@@H]4CCN(C(=O)C5(O)CC5)C4)cc3)ccc21] | (R)-6-hydroxycyclopropanecarbonyl)pyrrolidin-3-yl)methyl)-5-(4-(1-methyl-1H-indazol-5-yl)phenyl)-4,6-diazaspiro[2.4]hept-4-en-7-one<br>$^1$H NMR (400 MHz, CHLOROFORM-d) δ ppm 0.84-0.94 (m, 2 H), 1.09 (d, J = 9.6 Hz, 1 H), 1.22 (br. s., 1 H), 1.49 (d, J = 11.1 Hz, 1 H), 1.75-1.80 (m, 2 H), 1.84-1.98 (m, 3 H), 2.45 (dt, J = 14.1, 7.1 Hz, 1 H), 2.87 (br. s., 0.5 H), 3.09 (br. s., 1 H), 3.38 (br. s., 0.5 H), 3.52 (br. s., 1.5 H), 3.64 (br. s., 0.5 H), 3.80 (d, J = 6.6 Hz, 3 H), 4.09-4.15 (m, 3 H), 7.50 (d, H = 9.1 Hz, 1 H), 7.68 (d, J = 7.6 Hz, 3 H), 7.78 (d, J = 8.6 Hz, 2 H), 7.98 (s, 1 H), 8.06 (s, 1 H), MS m/z 484.1 (M + H)+ |
| 201 | 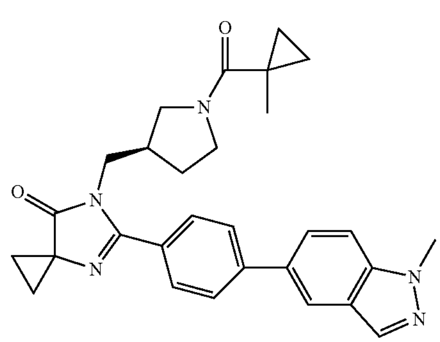 [SMILES: Cn1ncc2cc(-c3ccc(C4=NC5(CC5)C(=O)N4C[C@@H]4CCN(C(=O)C5(C)CC5)C4)cc3)ccc21] | (R)-5-(4-(1-methyl-1H-indazol-5-yl)phenyl)-6-((1-(1-methylcyclopropanecarbonyl)pyrrolidin-3-yl)methyl)-4,6-diazaspiro[2.4]hept-4-en-7-one<br>$^1$H NMR (400 MHz, CHLOROFORM-d) δ ppm 0.44-0.55 (m, 2 H), 0.78-0.86 (m, 1 H), 0.91 (d, J = 9.1 Hz, 1 H), 1.22 (s, 3 H), 1.60 (br. s., 1 H), 1.68 (br. s., 1 H), 1.74-1.81 (m, 2 H), 1.84-1.98 (m, 3 H), 2.46 (dt, J = 14.4, 7.5 Hz, 1 H), 3.09 (br. s., 1 H), 3.34 (br. s., 0.5 H), 3.48 (br. s., 1.5 H), 3.65 (br. s., 1 H), 3.82 (br. s., 2 H), 4.13 (s, 3 H), 7.50 (d, J = 8.6 Hz, 1 H), 7.68 (d, J = 7.6 Hz, 3 H), 7.75-7.81 (m, 2 H), 7.97 (s, 1 H), 8.06 (s, 1 H). MS m/z 482.2 (M + H)+ |

| ID No. | Structure | Compound Name & Physical Data |
|---|---|---|
| 202 | 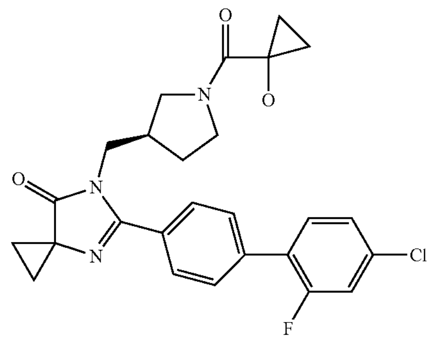 [SMILES: O=C(N1CC[C@@H](CN2C(=O)C3(CC3)N=C2c2ccc(-c3ccc(Cl)cc3F)cc2)C1)C1(O)CC1] | (R)-5-(4'-chloro-2'-fluoro[1,1'-biphenyl]-4-yl)-6-((1-(1-hydroxycyclopropanecarbonyl)pyrrolidin-3-yl)methyl)-4,6-diazaspiro[2.4]hept-4-en-7-one<br>$^1$H NMR (400 MHz, CHLOROFORM-d) δ ppm 0.92 (br. s., 2 H), 1.12 (br. s., 2 H), 1.73-1.81 (m, 2 H), 1.83-1.98 (m, m3 H), 2.44 (dt, J = 14.1, 7.1 Hz, 1 H), 2.60 (d, J = 18.2 Hz, 1 H), 2.69 (br s, 1 H), 2.74 (br. s., 1 H), 2.99 (d, J = 13.1 Hz, 1 H), 3.10 (d, J = 14.7 Hz, 1 H), 3.39 (br. s., 1 H), 3.52 (br. s., 1 H), 3.65 (br. s., 1 H), 3.79 (d, J = 7.1 Hz, 3 H), 7.19-7.26 (m, 3 H), 7.41 (q, J = 8.6 Hz, 2 H), 7.61 (d, J = 7.1 Hz, 1 H), 7.89 (d, J = 8.6 Hz, 1 H). MS m/z 482.2 (M + H)+ |
| 203 | 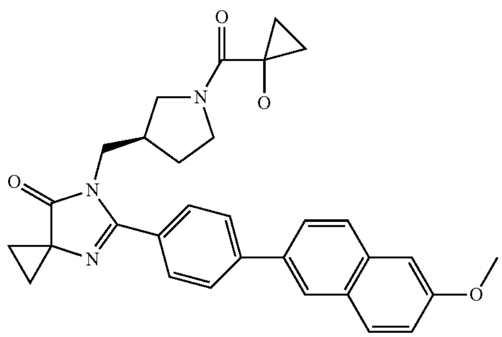 [SMILES: COc1ccc2cc(-c3ccc(C4=NC5(CC5)C(=O)N4C[C@@H]4CCN(C(=O)C5(O)CC5)C4)cc3)ccc2c1] | (R)-6-((1-(1-hydroxycyclopropanecarbonyl)pyrrolidin-3-yl)methyl)-5-(4-(6-methoxynaphthalen-2-yl)phenyl)-4,6-diazaspiro[2.4]hept-4-en-7-one<br>$^1$H NMR (400 MHz, CHLOROFORM-d) δ ppm 0.88 (br. s., 2 H), 1.07 (br. s., 2 H), 1.49 (br. s., 1 H), 1.74-1.80 (m, 2 H), 1.84-1.97 (m, 3 H), 2.44 (dt, J = 14.0, 6.9 Hz, 1 H), 3.10 (br. s., 1 H), 3.32 (br. s., 1 H), 3.51 (br. s., 1.5 H), 3.59-3.72 (m, 1 H), 3.80 (d, J = 6.6 Hz, 2.5 H), 3.95 (s, 3 H), 7.15-7.23 (m, 2 H), 7.69 (d, J = 8.6 Hz, 2 H), 7.74 (d, J = 8.6 Hz, 1 H), 7.79-7.87 (m, 4 H), 8.03 (s, 1 H). MS m/z 510.4 (M + H)+ |
| 204 | 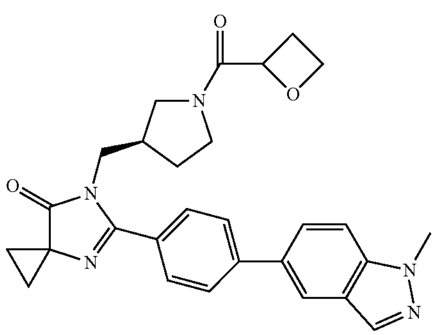 | 5-(4-(1-methyl-1H-indazol-5-yl)phenyl)-6-(((3R)-1-(oxetane-2-carbonyl)pyrrolidin-3-yl)methyl)-4,6-diazaspiro[2.4]hept-4-en-7-one<br>$^1$H NMR (400 MHz, CHLOROFORM-d) δ ppm 1.44-1.57 (m, 1 H), 1.73-1.81 (m, 2 H), 1.87 (d, J = 3.0 Hz, 2 H), 1.90-1.99 (m, 1 H), 2.46 (dt, J = 13.6, 6.8 Hz, 1 H), 2.68-2.84 (m, 1 H), 2.86-3.04 (m, 1 H), 3.05-3.23 (m, 1 H), 3.24-3.33 (m, 0.5 H), 3.33-3.45 (m, 1 H), 3.46-3.66 (m, 1.5 H), 3.74-3.87 (m, 2 H), 4.13 (s, 3 H), 4.48-4.59 (m, 1 H), 4.59-4.70 (m, 1 H), 5.04-5.21 (m, 1 H), 7.50 (d, J = 8.6 Hz, 1 H), 7.64-7.72 (m, 3 H), 7.77 (d, J = 8.6 Hz, 2 H), 7.98 (s, 1 H), 8.06 (s, 1 H). MS m/z 494.4 (M + H)+ |
| 205 | 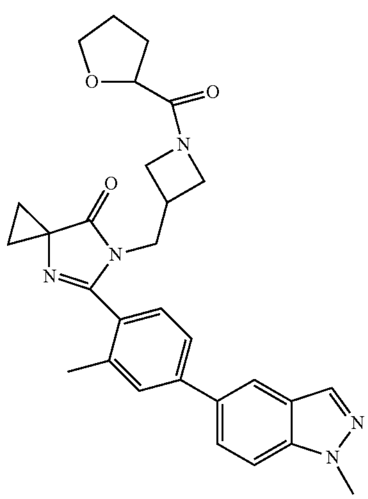 [SMILES: Cc1cc(-c2ccc3c(cnn3C)c2)ccc1C1=NC2(CC2)C(=O)N1CC1CN(C(=O)C2CCCO2)C1] | 5-(2-methyl-4-(1-methyl-1H-indazol-5-yl)phenyl)-6-((1-(tetrahytdro-furan-2-carbonyl)azetidin-3-yl)methyl)-4,6-diazaspiro[2.4]hept-4-en-7-one<br>$^1$H NMR (300 MHz, DMSO-$d_6$) δ ppm 1.55-1.64 (m, 2 H), 1.64-1.83 (m, 5 H), 1.86-1.99 (m, 1 H), 2.36 (s, 3 H), 2.56-2.66 (m, 1 H), 3.36-3.44 (m, 1 H), 3.59-3.74 (m, 5 H), 3.74-3.84 (m, 1 H), 4.10 (s, 3 H), 4.11-4.23 (m, 2 H), 7.55 (d, J = 8.0 Hz, 1 H), 7.67-7.87 (m, 4 H), 8.13 (d, J = 2.9 Hz, 2 H). MS m/z 498.3 (M + H)+ |

| ID No. | Structure | Compound Name & Physical Data |
|---|---|---|
| 206 | 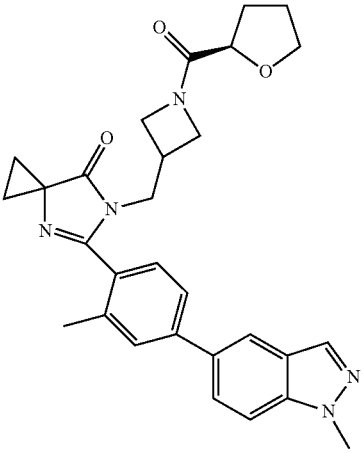 [SMILES: Cc1cc(-c2ccc3c(cnn3C)c2)ccc1C1=NC2(CC2)C(=O)N1CC1CN(C(=O)[C@H]2CCCO2)C1] | (S)-5-(2-methyl-4-(1-methyl-1H-indazol-5-yl)phenyl)-6-((1-(tetrahydro-furan-2-carbonyl)azetidin-3-yl)methyl)-4,6-diazaspiro[2.4]hept-4-en-7-one<br>$^1$H NMR (300 MHz, DMSO-d$_6$) δ ppm 1.56-1.64 (m, 2 H), 1.64-1.85 (m, 5 H), 1.86-1.99 (m, 1 H), 2.36 (s, 3 H), 2.61 (d, J = 4.9 Hz, 1 H), 3.35-3.44 (m, 1 H), 3.59-3.74 (m, 5 H), 3.74-3.85 (m, 1 H), 4.10 (s, 3 H), 4.12-4.23 (m, 2 H), 7.55 (d, J = 8.0 Hz, 1 H), 87.68-7.85 (m, 4 H), 8.11-8.17 (m, 2 H). MS m/z 498.2 (M + H)+ |
| 207 | 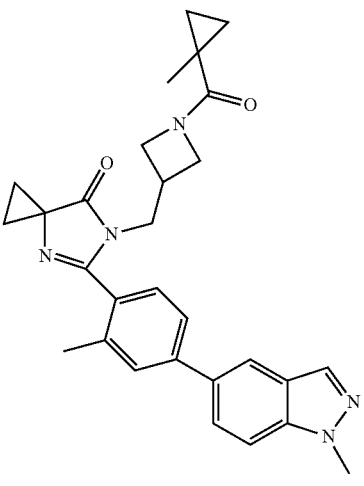 [SMILES: Cc1cc(-c2ccc3c(cnn3C)c2)ccc1C1=NC2(CC2)C(=O)N1CC1CN(C(=O)C2(C)CC2)C1] | 5-(2-methyl-4-(1-methyl-1H-indazol-5-yl)phenyl)-6-((1-(1-methylcyclopropanecarbonyl)azetidin-3-yl)methyl)-4,6-diazaspiro[2.4]hept-4-en-7-one<br>$^1$H NMR (300 MHz, DMSO-d$_6$) δ ppm 0.11 (d, J = 2.2 Hz, 2 H), 0.51 (s, 2 H), 0.83 (s, 3 H), 1.29-1.40 (m, 2 H), 1.48-1.58 (m, 2 H), 2.12 (s, 3 H), 2.29-2.42 (m, 1 H), 3.13-3.39 (m, 2 H), 3.39-3.50 (m, 2 H), 3.55-3.75 (m, 2 H), 3.85 (s, 3 H), 7.31 (d, J = 8.0 Hz, 1 H), 7.43-7.62 (m, 4 H), 7.88 (s, 2 H). MS m/z 482.3 (M + H)+ |
| 208 | 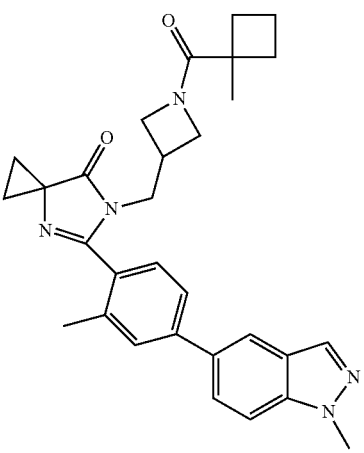 [SMILES: Cc1cc(-c2ccc3c(cnn3C)c2)ccc1C1=NC2(CC2)C(=O)N1CC1CN(C(=O)C2(C)CCC2)C1] | 5-(2-methyl-4-(1-methyl-1H-indazol-5-yl)phenyl)-6-((1-(1-methylcyclobutanecarbonyl)azetidin-3-yl)methyl)-4,6-diazaspiro[2.4]hept-4-en-7-one<br>$^1$H NMR (300 MHz, DMSO-d$_6$) δ ppm 1.14 (s, 3 H), 1.45-1.63 (m, 5 H), 1.71-1.89 (m, 3 H), 2.02-2.29 (m, 2 H), 2.36 (s, 3 H), 2.58 (br. s., 1 H), 3.34-3.47 (m, 2 H), 3.53-3.67 (m, 1 H), 3.75 (d, J = 15.1 Hz, 2 H), 4.00 (t, J = 8.4 Hz, 1 H), 4.10 (s, 3 H), 7.55 (d, J = 8.0 Hz, 1 H), 7.67-7.84 (m, 4 H), 8.13 (s, 2 H). MS m/z 496.3 (M + H)+ |

| ID No. | Structure | Compound Name & Physical Data |
|---|---|---|
| 209 | 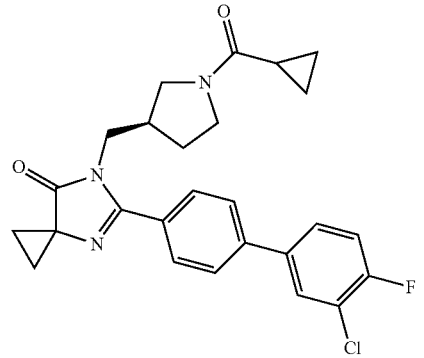 [SMILES: O=C(C1CC1)N1CC[C@@H](CN2C(=O)C3(CC3)N=C2c2ccc(-c3ccc(F)c(Cl)c3)cc2)C1] | (R)-5-(3-chloro-4-fluoro-[1,1-biphenyl]-4-yl)-6-((1-(cyclopropanecarbonyl)pyrrolidin-3-yl)methyl)-4,6-diazaspiro[2.4]hept-4-en-7-one<br>$^1$H NMR (300 MHz, DMSO-$d_6$) δ ppm 0.65 (d, J = 6.7 Hz, 4 H), 1.33-1.66 (m, 4 H), 1.69-1.93 (m, 3 H), 2.25 (d, J = 7.0 Hz, 1 H), 2.88 (dd, J = 11.8, 6.9 Hz, 1 H), 3.09-3.19 (m, 1 H), 3.19-3.30 (m, 1 H), 3.40-3.62 (m, 1 H), 3.75 (t, J = 6.4 Hz, 2 H), 7.56 (t, J = 8.9 Hz, 1 H), 7.81 (dd, J = 8.3, 4.2 Hz, 3 H), 7.90 (dd, J = 8.4, 2.2 Hz, 2 H), 8.01 (d, J = 7.0 Hz, 1 H). MS m/z 466 (M + H)+ |
| 210 | 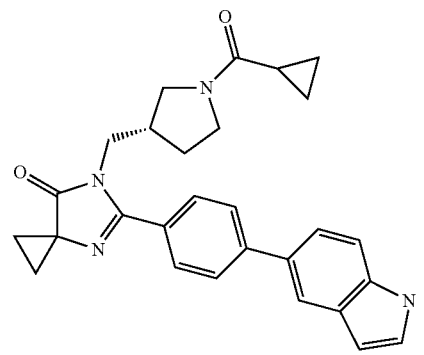 [SMILES: O=C(C1CC1)N1CC[C@H](CN2C(=O)C3(CC3)N=C2c2ccc(-c3ccc4[nH]ccc4c3)cc2)C1] | (S)-5-(4-(1H-indol-5-yl)phenyl)-6-((1-(cy7clopropanecarbonyl)pyrrolidin-3-yl)methyl)-4,6-diazaspiro[2.4]hept-4-en-7-one<br>$^1$H NMR (300 MHz, DMSO-$d_6$) δ ppm 0.55-0.75 (m, 4 H), 1.35-1.69 (m, 4 H), 1.69-1.97 (m, 3 H), 2.20-2.35 (m, 1 H), 2.92 (dd, J = 11.8, 6.9 Hz, 0.5 H), 3.06-3.21 (m, 1 H), 3.21-3.31 (m, 1 H), 3.42-3.66 (m, 1.5 H), 3.77 (t, J = 6.7 Hz, 2 H), 6.52 (d, J = 2.9 Hz, 1 H), 7.41 (d, J = 3.0 Hz, 1 H), 7.44-7.55 (m, 2 H), 7.77 (dd, J = 8.2, 3.7 Hz, 2 H), 7.86 (d, J = 89.1 Hz, 2 H), 7.94 (s, 1 H), 11.09 (br. s., 1 H). MS m/z 453 (M + H)+ |
| 211 | 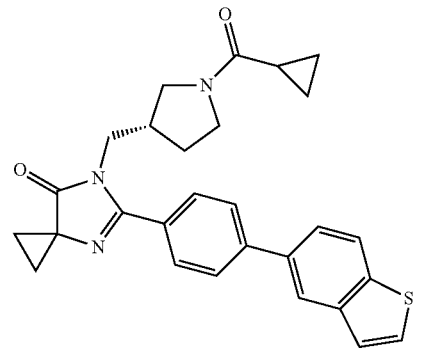 [SMILES: O=C(C1CC1)N1CC[C@H](CN2C(=O)C3(CC3)N=C2c2ccc(-c3ccc4sccc4c3)cc2)C1] | (S)-5-(4-(benzo[b]thiophen-5-yl)phenyl)-6-((1-(cyclopropanecarbonyl)pyrrolidin-3-yl)methyl)-4,6-diazaspiro[2.4]hept-4-en-7-one<br>$^1$H NMR (300 MHz, DMSO-$d_6$) δ ppm 0.32-0.50 (m, 4 H), 1.11-1.44 (m, 4 H), 1.46-1.72 (m, 3 H), 1.97-2.12 (m, 1 H), 2.67 (dd, J = 11.8, 6.9 Hz, 10.5 H), 2.84-2.98 (m, 1 H), 2.98-3.07 (m, 1 H), 3.18-3.40 (m, 1.5 H), 3.54 (t, mJ = 6.5 Hz, 2 H), 7.32 (d, J = 5.5 Hz, 1 H), 7.47-7.65 (m, 4 H), 7.65-7.76 (m, 2 H), 7.90 (d, J = 8.5 Hz, 1 H), 8.05 (s, 1 H). MS m/z 470 (M + H)+ |
| 212 | 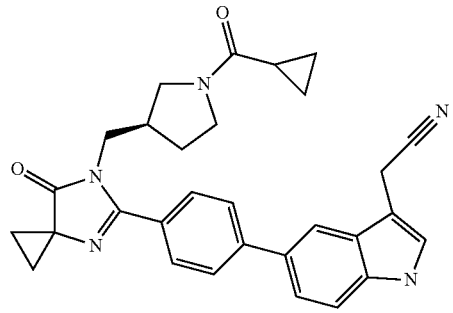 [SMILES: N#CCc1c[nH]c2ccc(-c3ccc(C4=NC5(CC5)C(=O)N4C[C@@H]4CCN(C(=O)C5CC5)C4)cc3)cc12] | (R)-2-(5-(4-(6-((1-(cyclopropanecarbonyl)pyrrolidin-3-yl)methyl)-7-oxo-4,6-diazaspiro[2.4]hept-4-en-5-yl)phenyl)-1H-indole-3-yl)acetonitrile<br>$^1$H NMR (300 MHz, DMSO-$d_6$) δ ppm 0.65 (d, J = 6.7 Hz, 4 H), 1.52-1.69 (m, 4 H), 1.70-1.97 (m, 3 H), 2.29 (br. s., 0.5 H), 2.38 (br. s., 0.5 H), 2.84-3.00 (m, 0.5 H), 3.19 (br. s., 1 H), 3.41 (br. s., 0.5 H), 3.45-3.66 (m, 2 H), 3.78 (t, J = 7.1 Hz, 2 H), 4.13 (s, 2 H), 7.43 (s, 1 H), 7.47-7.61 (m, 2 H), 7.73-7.85 (m, 2 H), 7.85-7.95 (m, 2 H), 8.02 (s, 1 H), 11.26 (br. s., 1 H). MS m/z 492 (M + H)+ |

| ID No. | Structure | Compound Name & Physical Data |
|---|---|---|
| 213 | 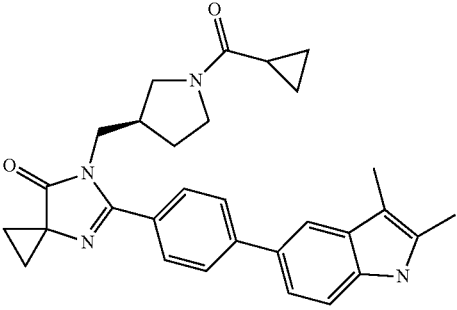 [SMILES: Cc1[nH]c2ccc(-c3ccc(C4=NC5(CC5)C(=O)N4C[C@@H]4CCN(C(=O)C5CC5)C4)cc3)cc2c1C] | (R)-6-((1-(cyclopropanecarbonyl)pyrrolidin-3-yl)methyl)-5-(4-(2,3-dimethyl-1H-indol-5-yl)phenyl)-4,6-diazaspiro[2.4]hept-4-en-7-one<br>$^1$H NMR (300 MHz, DMSO-d$_6$) δ ppm 0.66 (br. s., 4 H), 1.60 (br. s., 4 H), 1.79 (br. s., 3 H), 2.23 (s, 3 H), 2.35 (br. s., 3 H), 2.37-2.47 (m, 1 H), 2.93 (br. s., 0.5 H), 3.16 (br. s., 1 H), 3.28 (br. s., 1 H), 3.50 (br. s., 1.5 H), 3.78 (br. s., 2 H), 7.28-7.47 (m, 2 H), 7.75 (br. s., 3 H), 7.87 (d, J = 7.3 Hz, 2 H), 10.79 (br. s., 1 H). MS m/z 481 (M + H)+ |
| 214 | 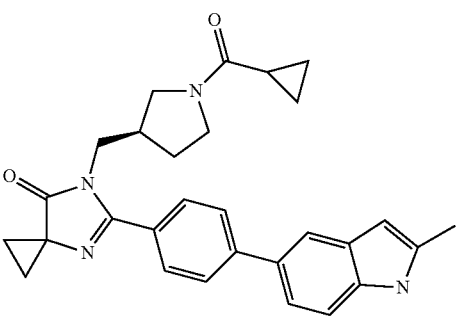 [SMILES: Cc1cc2cc(-c3ccc(C4=NC5(CC5)C(=O)N4C[C@@H]4CCN(C(=O)C5CC5)C4)cc3)ccc2[nH]1] | (R)-6-((1-(cyclopropanecarbonyl)pyrrolidin-3-yl)methyl)-5-(4-(2-methyl-1H-indol-5-yl)phenyl)-4,6-diazaspiro[2.4]hept-4-en-7-one<br>$^1$H NMR (300 MHz, DMSO-d$_6$) δ ppm 0.52-0.78 (m, 4 H), 1.60 (br. s., 4 H), 1.78 (br. s., 3 H), 2.29 (br. s., 1 H), 2.42 (s, 3 H), 2.92 (br. s., 0.5 H), 3.07-3.21 (m, 1 H), 3.27 (br. s., 1 H), 3.48 (br. s., 1.5 H), 3.78 (br. s., 2 H), 6.22 (br. s., 1 H), 7.39 (br. s., 2 H), 6.22 (br. s., 1 H), 7.39 (br. s., 2 H), 7.83 (s, 3 H), 7.79 (s, 2 H), 11.04 (br. s., 1 H). MS m/z 467 (M + H)+ |
| 215 | 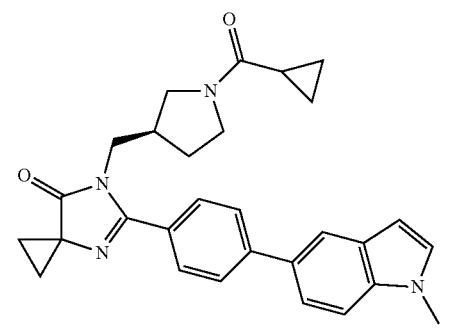 [SMILES: Cn1ccc2cc(-c3ccc(C4=NC5(CC5)C(=O)N4C[C@@H]4CCN(C(=O)C5CC5)C4)cc3)ccc21] | (R)-6-((1-(cyclopropanecarbonyl)pyrrolidin-3-yl)methyl)-5-(4-(1-methyl-1H-indol-5-yl)phenyl)-4,6-diazaspiro[2.4]hept-4-en-7-one<br>$^1$H NMR (300 MHz, DMSO-d$_6$) δ ppm 0.64 (d, J = 5.8 Hz, 4 H), 1.43 (d, J = 19.0 Hz, 1 H), 1.50-1.69 (m, 3 H), 1.79 (d, J = 3.8 Hz, 2 H), 1.88 (d, J = 6.3 Hz, 1 H), 2.29 (br. s., 1 H), 2.92 (d, J = 4.8 Hz, 0.5 H), 3.08-3.21 (m, 1 H), 3.21-3.31 (m, 1 H), 3.44-3.58 (m, 1.5 H), 3.78 (t, J = 6.7 Hz, 2 H), 3.84 (s, 3 H), 6.52 (d, J = 2.6 Hz, 1 H), 7.39 (d, J = 2.7 Hz, 1 H), 7.57 (s, 2 H), 7.72-7.82 (m, 2 H), 7.82-7.91 (m, 2 H), 7.95 (s, 1 H). MS m/z 467 (M + H)+ |
| 216 | 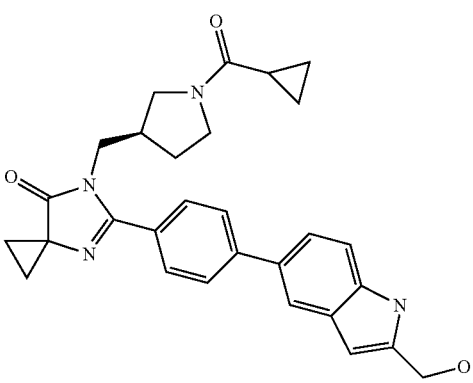 [SMILES: O=C(C1CC1)N1CC[C@@H](CN2C(=O)C3(CC3)N=C2c2ccc(-c3ccc4[nH]c(CO)cc4c3)cc2)C1] | (R)-6-((1-(cyclopropanecarbonyl)pyrrolidin-3-yl)methyl)-5-(4-(2-(hydroxymethyl)-1H-indol-5-yl)phenyl)-4,6-diazaspiro[2.4]hept-4-enn-7-one<br>$^1$H NMR (300 MHz, DMSO-d$_6$) δ ppm 0.67 (d, J = 5.8 Hz, 4 H), 1.46 (dd, J = 12.5, 7.3 Hz, 1 H), 1.57-1.72 (m, 3 H), 1.73-1.84 (m, 2 H), 1.84-1.98 (m, 1 H), 2.31 (t, J = 7.0 Hz, 0.5 H), 2.43 (d, J = 13.7 Hz, 0.5 H), 2.83-3.00 (m, 0.5 H), 3.09-3.23 (m, 1 H), 3.24-3.34 (m, 1 H), 3.40-3.59 (m, 1.5 H), 3.74-3.91 (m, 2 H), 4.67 (d, J = 5.5 Hz, 2 H), 5.32 (t, J = 5.6 Hz, 1 H), 6.40 (s, 1 H), 7.43-7.52 (m, 2 H), 7.74-7.84 (m, 2 H), 7.88 (d, J = 7.7 Hz, 3 H), 11.18 (s, 1 H). MS m/z 483 (M + H)+ |

-continued

| ID No. | Structure | Compound Name & Physical Data |
|---|---|---|
| 217 | 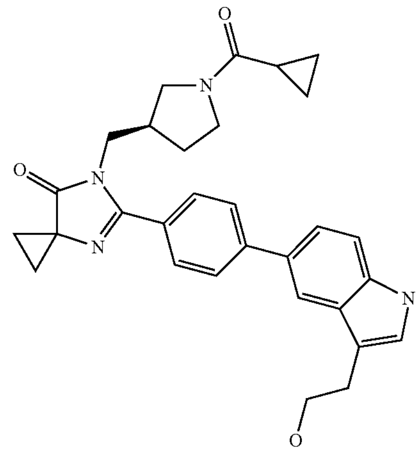 [SMILES: O=C(C1CC1)N1CC[C@@H](CN2C(=O)C3(CC3)N=C2c2ccc(-c3ccc4[nH]cc(CCO)c4c3)cc2)C1] | (R)-6-((1-(cyclopropanecarbonyl)pyrrolidin-3-yl)methyl)-5-(4-(3-(2-hydroxyethyl)-1H-indol-5-yl)phenyl)-4,6-diazaspiro[2.4]hept-4-en-7-one<br>¹H NMR (300 MHz, DMSO-d₆) δ ppm 0.51-0.75 (m, 4 H), 1.35-1.54 (m, 1 H), 1.54-1.68 (m, 3 H), 1.70-1.81 (m, 2 H), 1.81-1.96 (m, 1 H), 2.22-2.47 (m, 1 H), 2.85-3.01 (m, 2.5 H), 3.08-3.22 (m, 1 H), 3.22-3.32 (m, 1 H), 3.41-3.63 (m, 1.5 H), 3.65-3.74 (m, 2 H), 3.78 (t, J = 7.2 Hz, 2 H), 4.64 (t, J = 5.4 Hz, 1 H), 7.15-7.28 (m, 1 H), 7.39-7.53 (m, 2 H), 7.72-7.82 (m, 2 H), 7.82-7.97 (m, 3 H), 10.93 (s, 1 H). MS m/z 497 (M + H)+ |
| 218 | 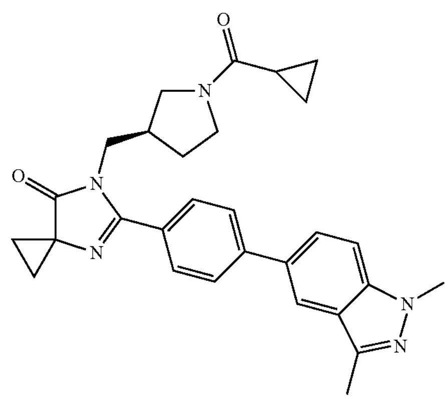 [SMILES: Cc1nn(C)c2ccc(-c3ccc(C4=NC5(CC5)C(=O)N4C[C@@H]4CCN(C(=O)C5CC5)C4)cc3)cc12] | (R)-6-((1-(cyclopropanecarbonyl)pyrrolidin-3-yl)methyl)-5-(4-(1,3-dimethyl-1H-indazol-5-yl)phenyl)-4,6-diazaspiro[2.4]hept-4-en-7-one<br>¹H NMR (300 MHz, CHLOROFORM-d) δ ppm 0.72 (dd, J = 7.7, 3.0 Hz, 2 H), 0.87-1.03 (m, 2 H), 1.46-1.58 (m, 1 H), 1.68-1.75 (m, 1 H), 1.75-1.83 (m, 2 H), 1.84-1.92 (m, 2 H), 2.02 (d, J = 6.0 Hz, 1 H), 2.37-2.52 (m, 1 H), 2.65 (s, 3 H), 3.07 (dd, J = 12.0, 7.1 Hz, 0.5 H), 3.23-3.40 (m, 1 H), 3.48-3.75 (m, 2.5 H), 3.75-3.93 (m, 2 H), 4.06 (s, 3 H), 7.44 (d, J = 8.7 Hz, 1 H), 7.64-7.74 (m, 3 H), 7.76-7.85 (m, 2 H), 7.90 (s, 1 H). MS m/z 482 (M + H)+ |
| 219 | 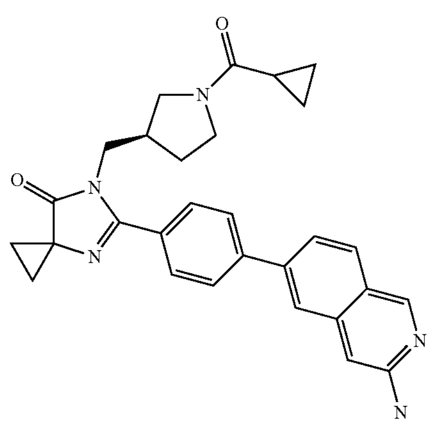 [SMILES: Nc1cc2cc(-c3ccc(C4=NC5(CC5)C(=O)N4C[C@@H]4CCN(C(=O)C5CC5)C4)cc3)ccc2cn1] | (R)-5-(4-(3-aminoisoquinolin-6-yl)phenyl)-6-((1-(cyclopropanecarbonyl)pyrrolidin-3-yl)methyl)-4,6-diazaspiro[2.4]hept-4-en-7-one<br>¹H NMR (300 MHz, CHLOROFORM-d) δ ppm 0.66-0.80 (m, 2 H), 0.88-1.05 (m, 2 H), 1.41-1.60 (m, 2 H), 1.60-1.85 (m, 2 H), 1.85-1.94 (m, 2 H), 1.94-2.10 (m, 1 H), 2.36-2.52 (m, 0.5 H), 2.52-2.68 (m, 0.5 H), 3.07 (dd, J = 12.0, 7.1 Hz, 0.5 H), 3.21-3.42 (m, 1 H), 3.51-3.73 (m, 2.5 H), 3.75-3.94 (m, 2 H), 4.55 (br. s., 2 H), 6.81 (s, 1 H), 7.53 (d, J = 8.5 Hz, 1 H), 7.67-7.81 (m, 3 H), 7.81-7.96 (m, 3 H), 8.92 (s, 1 H). MS m/z 480 (M + H)+ |

| ID No. | Structure | Compound Name & Physical Data |
|---|---|---|
| 220 | 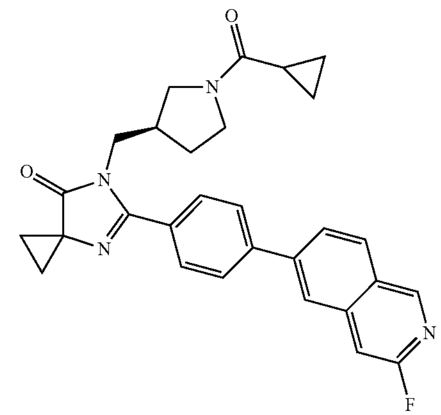 [SMILES: O=C(C1CC1)N1CC[C@@H](CN2C(=O)C3(CC3)N=C2c2ccc(-c3ccc4cnc(F)cc4c3)cc2)C1] | (R)-6-((1-(cyclopropanecarbonyl)pyrrolidin-3-yl)methyl)-5-(4-(3-fluoroisoquinolin-6-yl)phenyl)-4,6-diazaspiro[2.4]hept-4-en-7-one<br>$^1$H NMR (300 MHz, CHLOROFORM-d) δ ppm 0.65-0.79 (m, 2 H), 0.90-1.04 (m, 2 H), 1.52 (qd, J = 8.2, 4.2 Hz, 1 H), 1.77-1.85 (m, 3 H), 1.85-1.93 (m, 2 H), 1.93-2.10 (m, 1 H), 2.44 (dt, J = 14.3, 7.2 Hz, 1 H), 3.05 (dd, J = 12.0, 7.2 Hz, 0.5 H), 3.23-3.41 (m, 1 H), 3.43-3.62 (m, 2 H), 3.62-3.82 (m, 1.5 H), 3.82-3.90 (m, 1 H), 7.33 (s, 1 H), 7.73-7.81 (m, 2 H), 7.81-7.93 (m, 3 H), 8.05 (s, 1 H), 8.12 (d, J = 8.7 Hz, 1 H), 9.02 (s, 1 H). MS m/z 483 (M + H)+ |
| 221 | 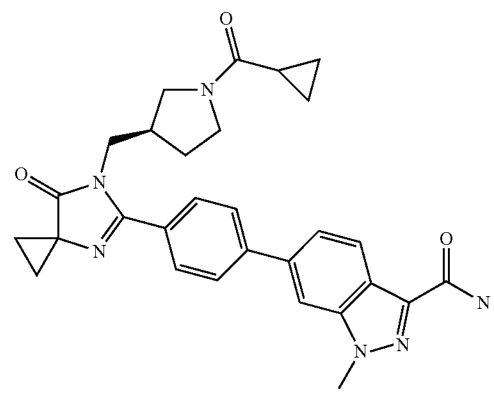 [SMILES: Cn1nc(C(N)=O)c2ccc(-c3ccc(C4=NC5(CC5)C(=O)N4C[C@@H]4CCN(C(=O)C5CC5)C4)cc3)cc21] | (R)-6-(4-(6-((1-(cyclopropanecarbonyl)pyrrolidin-3-yl)methyl)-7-oxo-4,6-diazaspiro[2.4]hept-4-en-5-yl)phenyl)-1-methyl-1H-indazole-3-carboxamide<br>$^1$H NMR (300 MHz, CHLOROFORM-d) δ ppm 0.65-0.81 (m, 2 H), 0.87-1.06 (m, 2 H), 1.46-1.58 (m, 1 H), 1.66 (d, J = 7.6 Hz, 1 H), 1.75-1.84 (m, 2 H), 1.84-1.93 (m, 2 H), 2.01 (d, J = 12.0 Hz, 1 H), 2.44 (br. s., 1 H), 3.07 (dd, J = 11.9, 7.1 Hz, 0.5 H), 3.22-3.41 (m, 1 H), 3.49-3.68 (m, 2.5 H), 3.75-3.95 (m, 2 H), 4.17 (s, 3 H), 5.55 (br. s., 1 H), 6.92 (br. s., 1 H), 7.54 (d, J = 8.8 Hz, 1 H), 7.66-7.80 (m, 3 H), 7.85 (dd, J = 8.0, 4.9 Hz, 2 H), 8.65 (s, 1 H). MS m/z 511 (M + H)+ |
| 222 | 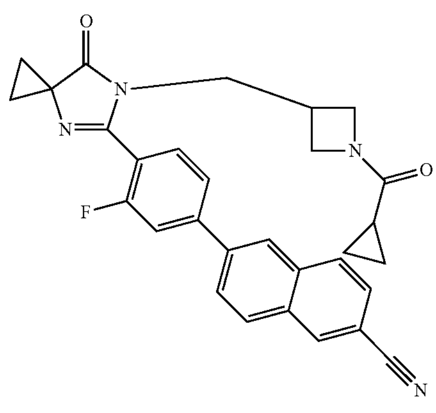 [SMILES: N#Cc1ccc2cc(-c3ccc(C4=NC5(CC5)C(=O)N4CC4CN(C(=O)C5CC5)C4)c(F)c3)ccc2c1] | 6-(4-(6-((1-(cyclopropanecarbonyl)azetidin-3-yl)methyl)-7-oxo-4,6-diazaspiro[2.4]hept-4-en-5-yl)-3-fluorophenyl)-2-naphthanitrile<br>$^1$H NMR (300 MHz, CHLOROFORM-d) δ ppm 0.66-0.76 (m, 2 H), 0.91 (t, J = 3.8 Hz, 2 H), 1.31 (dq, J = 8.3, 4.0 Hz, 1 H), 1.77-1.87 (m, 2 H), 1.88-1.97 (m, 2 H), 2.80-2.98 (m, 1 H), 3.56 (dd, J = 9.8, 5.6 Hz, 1 H), 3.75-3.88 (m, 1 H), 3.98 (q, J = 9.3 Hz, 3 H), 4.28 (t, J = 8.3 Hz, 1 H), 7.61 (d, J = 11.0 Hz, 1 H), 7.67-7.75 (m, 3 H), 7.85-7.93 (m, 1 H), 7.98-8.09 (m, 2 H), 8.15 (s, 1 H), 8.31 (s, 1 H). MS m/z 493 (M + H)+ |
| 223 | 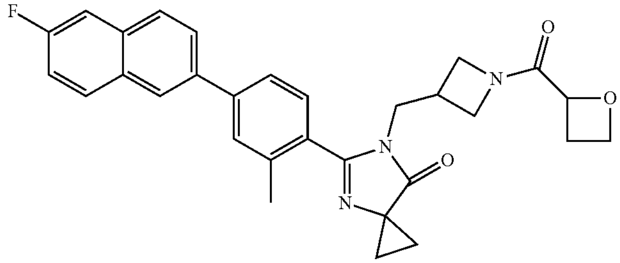 [SMILES: Cc1cc(-c2ccc3cc(F)ccc3c2)ccc1C1=NC2(CC2)C(=O)N1CC1CN(C(=O)C2CCO2)C1] | 5-(4-(6-fluoronaphthalen-2-yl)-2-methylphenyl)-6-((1-(oxetan-2-carbonyl)azetidin-3-yl)methyl)-4,6-diazaspiro[2.4]hept-4-en-7-one<br>$^1$H NMR (300 MHz, CHLOROFORM-d) δ ppm 1.70 (d, J = 4.9 Hz, 4 H), 1.79 (br. s., 2 H), 2.35 (s, 3 H), 2.58-2.72 (m, 1 H), 2.79 (d, J = 15.1 Hz, 1 H), 3.38-3.50 (m, 1 H), 3.50-3.81 (m, 3 H), 3.82-4.07 (m, 1.5 H), 4.09-4.32 (m, 1 H), 4.37-4.63 (m, 1 H), 4.95-5.12 (m, 0.5 H), 7.20-7.30 (m, 1 H), 7.36 (d, J = 7.6 Hz, 1 H), 7.39-7.48 (m, 1 H), 7.55-7.65 (m, 2 H), 7.67-7.77 (m, 1 H), 7.77-7.90 (m, 2 H), 8.00 (s, 1 H). MS m/z 498.2 (M + H)+ |

| ID No. | Structure | Compound Name & Physical Data |
|---|---|---|
| 224 | 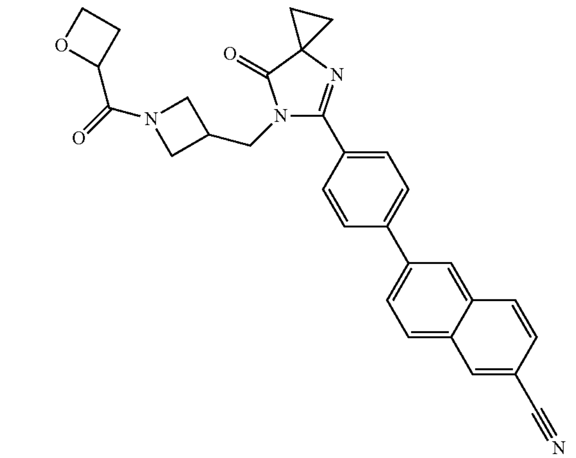 [SMILES: N#Cc1ccc2cc(-c3ccc(C4=NC5(CC5)C(=O)N4CC4CN(C(=O)C5CCO5)C4)cc3)ccc2c1] | 6-(3-methyl-4-(6-((1-(oxetane-2-carbonyl)azetidin-3-yl)methyl)-7-oxo-4,6-diazaspiro[2.4]hept-4-en-5-yl)phenyl)-2-naphthonitrile<br>¹H NMR (300 MHz, CHLOROFORM-d) δ ppm 1.80 (d, J = 6.3 Hz, 3 H), 1.85-1.93 (m, 2 H), 2.46 (s, 3 H), 2.68-2.81 (m, 1 H), 2.87 (d, J = 4.0 Hz, 1 H), 3.59-3.90 (m, 4 H), 3.91-4.16 (m, 2 H), 4.19-4.42 (m, 1 H), 4.47-4.71 (m, 1.5 H), 5.06-5.18 (m, 0.5 H), 7.48 (d, J = 7.7 Hz, 1 H), 7.65-7.75 (m, 3 H), 7.85-7.95 (m, 1 H), 8.02 (dd, J = 8.4, 3.4 Hz, 2 H), 8.14 (s, 1 H), 8.30 (s, 1 H). MS m/z 505 (M + H)+ |
| 225 | 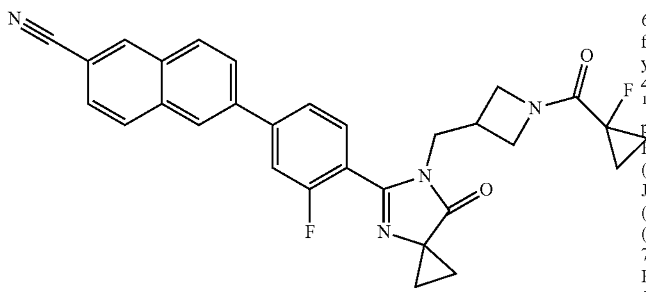 [SMILES: N#Cc1ccc2cc(-c3ccc(C4=NC5(CC5)C(=O)N4CC4CN(C(=O)C5(F)CC5)C4)c(F)c3)ccc2c1] | 6-(3-fluoro-4-(6-((1-(1-fluorocyclopropanecarbonyl)azetidin-3-yl)methyl)-7-oxo-4,6-diazaspiro[2.4]hept-4-en-5-yl)phenyl)-2-naphthonitrile<br>¹H NMR (300 MHz, CHLOROFORM-d) δ ppm 1.08-1.21 (m, 2 H), 1.30 (d, J = 8.9 Hz, 2 H), 1.78-1.88 (m, 2 H), 1.88-1.97 (m, 2 H), 2.89-3.01 (m, 1 H), 3.66 (d, J = 4.5 Hz, 1 H), 3.81-4.00 (m, 2 H), 4.09 (d, J = 9.3 Hz, 2 H), 4.45 (br. s., 1 H), 7.62 (d, J = 10.9 Hz, 1 H), 7.66-7.77 (m, 3 H), 7.85-7.94 (m, 1 H), 8.05 (t, J = 7.8 Hz, 2 H), 8.16 (s, 1 H), 8.32 (s, 1 H). MS m/z 511.2 (M + H)+ |
| 226 | 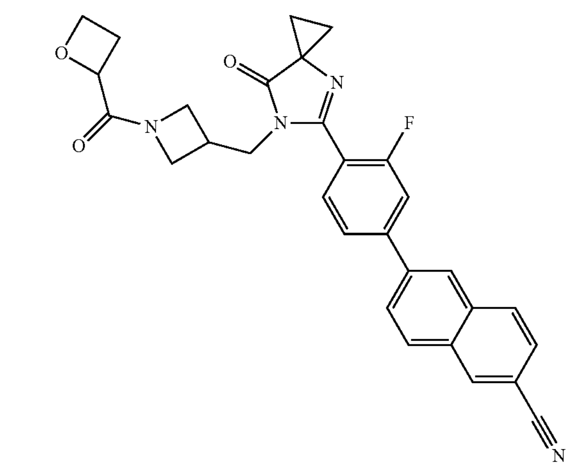 [SMILES: N#Cc1ccc2cc(-c3ccc(C4=NC5(CC5)C(=O)N4CC4CN(C(=O)C5CCO5)C4)c(F)c3)ccc2c1] | 6-(3-fluoro-4-(6-((1-(oxetane-2-carbonyl)azetidin-3-yl)methyl)-7-oxo-4,6-diazaspiro[2..4]hept-4-en-5-yl)phenyl)-2-naphthonitrile<br>¹H NMR (300 MHz, CHLOROFORM-d) δ ppm 1.73-1.85 (m, 2 H), 1.89 (br. s., 2 H), 2.67-3.00 (m, 3 H), 3.59-3.70 (m, 1 H), 3.73-3.96 (m, 2.5 H), 3.99-4.11 (m, 1.5 H), 4.25 (t, J = 8.9 Hz, 1 H), 4.45-4.69 (m, 2 H), 5.05-5.16 (m, 1 H), 7.54-7.63 (m, 1 H), 7.65-7.73 (m, 3 H), 7.83-7.91 (m, 1 H), 7.97-8.08 (m, 2 H), 8.13 (s, 1 H), 8.29 (s, 1 H). MS m/z 509.3 (M + H)+ |
| 227 | 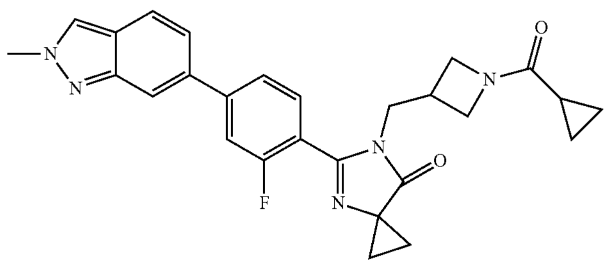 | 6-((1-(cyclopropanec arbonyl)azetidin-3-yl)methyl)-5-(2-fluoro-4-(2-methyl-2H-indazol-6-yl)phenyl)-4,6-diazaspiro[2.4]hept-4-en-7-one<br>¹H NMR (300 MHz, CHLOROFORM-d) δ ppm 0.61-0.74 (m, 2 H), 0.89 (quin, J = 3.6 Hz, 2 H), 1.21-1.34 (m, 1 H), 1.73-1.83 (m, 2 H), 1.83-1.94 (m, 2 H), 2.78-2.94 (m, 1 H), 3.58 (dd, J = 9.8, 5.7 Hz, 1 H), 3.83 (d, J = 6.3 Hz, 1 H), 3.86-4.05 (m, 3 H), 4.17-4.33 (m, 4 H), 7.31-7.38 (m, 1 H), 7.52 (d, J = 11.0 Hz, 1 H), 7.56-7.66 (m, 2 H), 7.76 (d, J = 8.7 Hz, 1 H), 7.93 (d, J = 4.8 Hz, 2 H). MS m/z 272.2 (M + H)+ |

| ID No. | Structure | Compound Name & Physical Data |
|---|---|---|
| 228 | 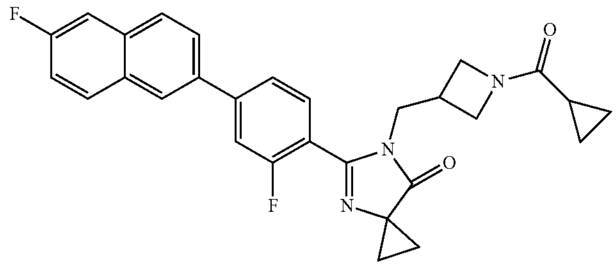 [SMILES: O=C(C1CC1)N1CC(CN2C(=O)C3(CC3)N=C2c2ccc(-c3ccc4cc(F)ccc4c3)cc2F)C1] | 6-((1-(cyclopropanecarbonyl)azetidin-3-yl)methyl)-5-(2-fluoro-4-(6-fluoroquinolin-2-yl)phenyl)-4,6-diazaspiro[2.4]hept-4-en-7-one<br>$^1$H NMR (300 MHz, CHLOROFORM-d) δ ppm 0.60-0.72 (m, 2 H), 0.86 (quin, J = 3.6 Hz, 2 H), 1.26 (td, J = 8.1, 3.9 Hz, 1 H), 1.73-1.84 (m, 2 H), 1.84-1.93 (m, 2 H), 2.73-2.91 (m, 1 H), 3.53 (dd, J = 9.9, 5.6 Hz, 1 H), 3.70-3.82 (m, 1 H), 3.85-4.01 (m, 3 H), 4.22 (t, J = 8.3 Hz, 1 H), 7.41-7.58 (m, 2 H), 7.67 (t, J = 7.6 Hz, 1 H), 7.91 (d, J = 8.7 Hz, 1 H), 8.02-8.20 (m, 3 H), 8.23 (d, J = 8.7 Hz, 1 H). MS m/z 487.2 (M + H)+ |
| 229 | 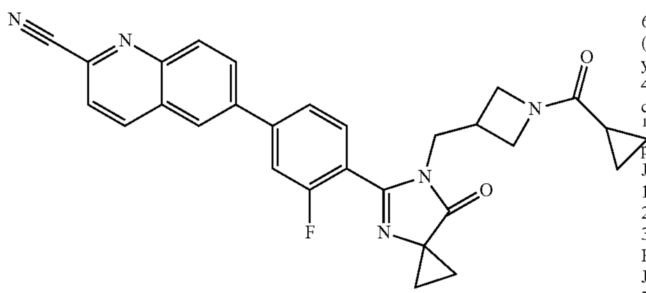 [SMILES: N#Cc1ccc2cc(-c3ccc(C4=NC5(CC5)C(=O)N4CC4CN(C(=O)C5CC5)C4)c(F)c3)ccc2n1] | 6-(4-(6-((1-(cyclopropanecarbonyl)azetidin-3-yl)methyl)-7-oxo-4,6-diazaspiro[2.4]hept-4-en-5-yl)-3-fluorophenyl)quinolin-2-carbonitrile<br>$^1$H NMR (300 MHz, CHLOROFORM-d) δ ppm 0.68 (dd, J = 6.8, 4.2 Hz, 2 H), 0.88 (t, J = 3.6 Hz, 2 H), 1.26-1.36 (m, 1 H), 1.74-1.85 (m, 2 H), 1.85-1.96 (m, 2 H), 2.76-2.99 (m, 1 H), 3.54 (d, J = 5.5 Hz, 1 H), 3.80 (d, J = 6.6 Hz, 1 H), 3.86-4.07 (m, 3 H), 4.26 (t, J = 8.3 Hz, 1 H), 7.60 (d, J = 10.9 Hz, 1 H), 7.64-7.73 (m, 2 H), 7.77 (d, J = 8.4 Hz, 1 H), 8.03-8.17 (m, 2 H), 8.30 (d, J = 8.7 Hz, 1 H), 8.39 (d, J = 8.5 Hz, 1 H). MS m/z 494 (M + H)+ |
| 230 | 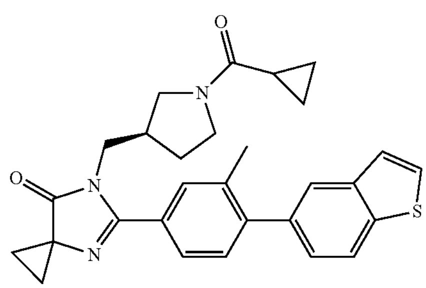 [SMILES: Cc1cc(C2=NC3(CC3)C(=O)N2C[C@@H]2CCN(C(=O)C3CC3)C2)ccc1-c1ccc2sccc2c1] | (R)-5-(4-(benzo[b]thiophen-5-yl)-3-methylphenyl)-6-((1-(cyclopropanecarbonyl)pyrrolidin-3-yl)methyl)-4,6-diazaspiro[2.4]hept-4-en-7-one<br>$^1$H NMR (300 MHz, CHLOROFORM-d) δ ppm 0.57-0.77 (m, 2 H), 0.79-1.00 (m, 2 H), 1.39-1.53 (m, 1 H), 1.65-1.75 (m, 2 H), 1.76-1.87 (m, 2 H), 1.89-2.04 (m, 1 H), 2.28 (s, 3 H), 2.44-2.60 (m, 1 H), 3.00 (dd, J = 11.8, 7.1 Hz, 0.5 H), 3.14-3.33 (m, 1 H), 3.36-3.61 (m, 3.5 H), 3.69-3.86 (m, 2 H), 7.17-7.40 (m, 4 H), 7.40-7.57 (m, 2 H), 7.70 (s, 1 H), 7.87 (d, J = 8.1 Hz, 1 H). MS m/z 484 (M + H)+ |
| 231 | 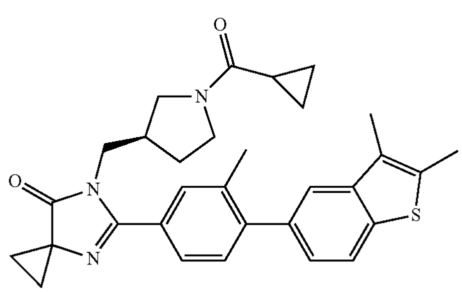 [SMILES: Cc1cc(C2=NC3(CC3)C(=O)N2C[C@@H]2CCN(C(=O)C3CC3)C2)ccc1-c1ccc2sc(C)c(C)c2c1] | (R)-6-((1-(cyclopropanecarbonyl)pyrrolidin-3-yl)methyl)-5-(4-(2,3-dimethylbenzo[b]thiophen-5-yl)-3-methylphenyl)-4,6-diazaspiro[2.4]hept-4-em-7-one<br>$^1$H NMR (300 MHz, DMSO-d$_6$) δ ppm 0.68 (br. s., 4 H), 1.47 (d, J = 7.4 Hz, 1 H), 1.61 (br. s., 2 H), 1.66 (br. s., 0.5 H), 1.79 (d, J = 3.8 Hz, 2 H), 1.89 (d, J = 5.5 Hz, 0.5 H), 2.32 (d, J = 8.5 Hz, 6 H), 2.45 (br s, 1 H), 2.50 (br. s., 3 H), 2.87-3.00 (m, 0.5 H), 3.10-3.23 (m, 1 H), 3.29 (br. s., 1 H), 3.44-3.58 (m, 2.5 H), 3.71-3.87 (m, 2 H), 7.31 (d, J = 8.1 Hz, 1 H), 7.44 (d, J = 7.8 Hz, 1 H), 7.62 (br. s., 3 H), 7.93 (d, J = 8.1 Hz, 1 H). MS m/z 512 (M + H)+ |

| ID No. | Structure | Compound Name & Physical Data |
|---|---|---|
| 232 | 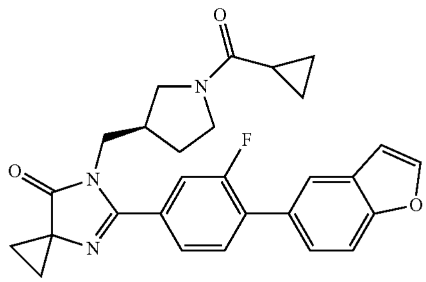 | (R)-5-(4-(benzofuran-5-yl)-3-fluorophenyl)-6-((1-(cyclopropanecarbonyl)pyrrolidin-3-yl)methyl)-4,6-diazaspiro[2.4]hept-4-en-7-one<br>$^1$H NMR (300 MHz, DMSO-$d_6$) δ ppm 0.67 (br. s., 4 H), 1.45 (br s., 0.5 H), 1.63 (br. s., 3.5 H), 1.76-1.85 (m, 2 H), 1.90 (br s., 1 H), 2.22-2.45 (m, 1 H), 2.88-2.95 (m, 0.5 H), 3.19 (d, J = 5.9 Hz, 1 H), 3.60 (br. s., 2.5 H), 3.78 (br. s., 2 H), 7.06 (br. s., 1 H), 7.56 (d, J = 8.4 Hz, 1 H), 7.61-7.81 (m, 4 H), 7.92 (br. s., 1 H), 8.08 (s, 1 H). MS m/z 472 (M + H)+ |
| 233 | 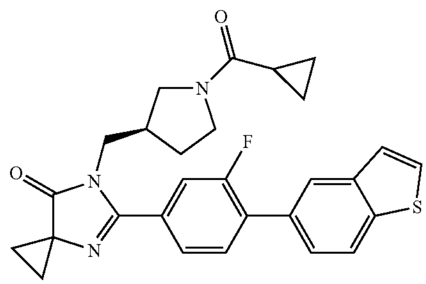 [SMILES: O=C(C1CC1)N1CC[C@@H](CN2C(=O)C3(CC3)N=C2c2ccc(-c3ccc4sccc4c3)c(F)c2)C1] | (R)-5-(4-(benzo[b]thiophen-5-yl)-3-fluorophenyl)-6-((1-(cyclopropanecarbonyl)pyrrolidin-3-yl)methyl)-4,6-diazaspiro[2.4]hept-4-en-7-one<br>$^1$H NMR (300 MHz, CHLOROFORM-d) δ ppm 0.65 (dd, J = 7.6, 3.1 Hz, 2 H), 0.83-0.95 (m, 2 H), 1.44 (td, J = 8.0, 4.3 Hz, 1 H), 1.63 (dd, J = 12.6, 7.8 Hz, 1 H), 1.69-1.76 (m, 2 H), 1.76-1.84 (m, 2 H), 1.84-2.01 (m, 1 H), 2.28-2.58 (m, 1 H), 3.01 (dd, J = 12.0, 7.1 Hz, 0.5 H), 3.15-3.34 (m, 1 H), 3.43-3.83 (m, 4.5 H), 7.34 (d, J = 5.4 Hz, 1 H), 7.36-7.53 (m, 4 H), 7.54-7.66 (m, 1 H), 7.91 (d, J = 8.4 Hz, 1 H), 7.97 (s, 1 H). MS m/z 488 (M + H)+ |
| 234 | 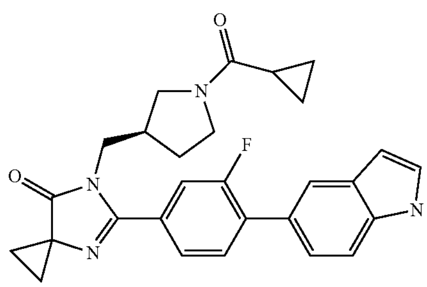 [SMILES: O=C(C1CC1)N1CC[C@@H](CN2C(=O)C3(CC3)N=C2c2ccc(-c3ccc4[nH]ccc4c3)c(F)c2)C1] | (R)-6-((1-(cyclopropanecarbonyl)pyrrolidin-3-yl)methyl)-5-(3-fluoro-4-(1H-indol-5-yl)phenyl)-4,6-diazaspiro[2.4]hept-4-en-7-one<br>$^1$H NMR (300 MHz, CHLOROFORM-d) δ ppm 0.65 (dd, J = 7.8, 3.0 Hz, 2 H), 0.83-0.97 (m, 2 H), 1.41-1.51 (m, 1 H), 1.55-1.68 (m, 1 H), 1.68-1.76 (m, 2 H), 1.76-1.84 (m, 2 H), 1.84-1.91 (m, 1 H), 2.29-2.58 (m, 1 H), 3.02 (dd, J = 12.0, 6.9 Hz, 0.5 H), 3.14-3.35 (m, 1 H), 3.43-3.67 (m, 2.5 H), 3.67-3.85 (m, 2 H), 5.54 (br. s., 1 H), 6.53 (br. s., 1 H), 7.28-7.45 (m, 4 H), 7.52-7.67 (m, 1 H), 7.79 (s, 1 H), 8.77 (br. s., 1 H). MS m/z 471 (M + H)+ |
| 235 | 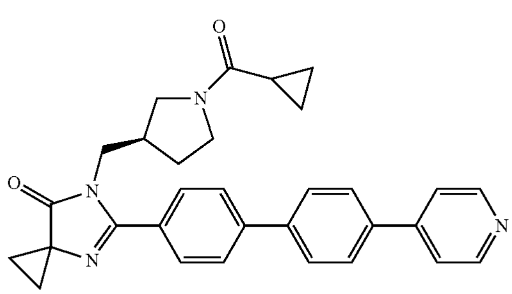 [SMILES: O=C(C1CC1)N1CC[C@@H](CN2C(=O)C3(CC3)N=C2c2ccc(-c3ccc(-c4ccncc4)cc3)cc2)C1] | (R)-6-((1-(cyclopropanecarbonyl)pyrrolidin-3-yl)methyl)-5-(4'-(pyridin-4-yl)-[1,1'-biphenyl]-4-yl)-4,6-diazaspiro[2.4]hept-4-en-7-one<br>$^1$H NMR (300 MHz, CHLOROFORM-d) δ ppm 0.68-0.81 (m, 2 H), 0.95 (dt, J = 7.1, 3.6 Hz, 2 H), 1.47-1.58 (m, 1 H), 1.77-1.93 (m, 4 H), 1.96-2.11 (m, 1 H), 2.37-2.52 (m, 1 H), 2.58 (d, J = 7.6 Hz, 1 H), 3.06 (dd, J = 12.0, 7.1 Hz, 0.5 H), 3.23-3.41 (m, 1 H), 3.49-3.74 (m, 2.5 H), 3.78-3.89 (m, 2 H), 7.58 (d, J = 5.9 Hz, 2 H), 7.67-7.76 (m, 2 H), 7.76-7.89 (m, 6 H), 8.71 (d, J = 5.5 Hz, 2 H). MS m/z 491 (M + H)+ |

| ID No. | Structure | Compound Name & Physical Data |
|---|---|---|
| 236 | 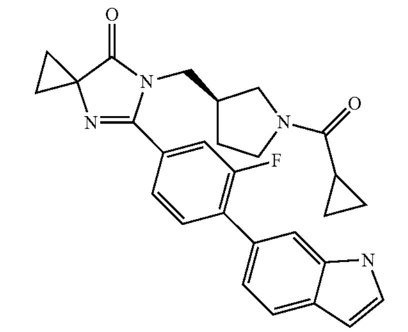 [SMILES: O=C(C1CC1)N1CC[C@@H](CN2C(=O)C3(CC3)N=C2c2ccc(-c3ccc4cc[nH]c4c3)c(F)c2)C1] | (R)-6-((1-(cyclopropanecarbonyl)pyrrolidin-3-yl)methyl)-5-(3-fluoro-4-(1H-indol-6-yl)phenyl)-4,6-diazaspiro[2.4]hept-4-en-7-one<br>$^1$H NMR (300 MHz, DMSO-$d_6$) δ ppm 0.57-0.74 (m, 4 H), 1.38-1.57 (m, 1 H), 1.57-1.68 (m, 3 H), 1.71-1.84 (m, 2 H), 1.84-1.97 (m, 1 H), 2.22-2.36 (m, 1 H), 2.92 (dd, J = 11.8, 6.8 Hz, 0.5 H), 3.11-3.24 (m, 1 H), 3.24-3.32 (m, 1 H), 3.46-3.66 (m, 1.5 H), 3.78 (t, J = 6.5 Hz, 2 H), 6.50 (br. s., 1 H), 7.26 (d, J = 8.1 Hz, 1 H), 7.46 (br. s., 1 H), 7.59-7.80 (m, 5 H), 11.28 (br. s., 1 H). MS m/z 471 (M + H)+ |
| 237 | 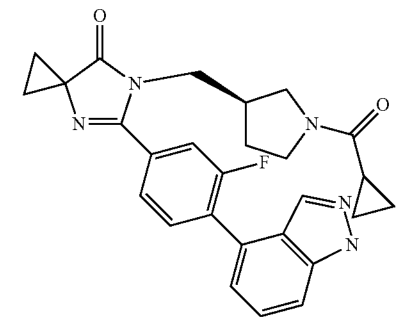 [SMILES: O=C(C1CC1)N1CC[C@@H](CN2C(=O)C3(CC3)N=C2c2ccc(-c3cccc4[nH]ncc34)c(F)c2)C1] | (R)-6-((1-(cyclopropanecarbonyl)pyrrolidin-3-yl)methyl)-5-(3-fluoro-4-(1H-indazol-4-yl)phenyl)-4,6-diazaspiro[2.4]hept-4-en-7-one<br>$^1$H NMR (300 MHz, DMSO-$d_6$) δ ppm 0.61-0.70 (m, 4 H), 1.41-1.60 (m, 1 H), 1.64 (br. s., 3 H), 1.80-1.85 (m, 2 H), 1.92 (d, J = 6.3 Hz, 1 H), 2.26-2.38 (m, 0.5 H), 2.38-2.48 (m, 0.5 H), 2.92 (dd, J = 11.8, 6.7 Hz, 0.5 H), 3.11-3.31 (m, 2 H), 3.46-3.66 (m, 1.5 H), 3.80 (t, J = 6.7 Hz, 2 H), 7.27 (d, J = 6.7 Hz, 1 H), 7.50 (t, J = 7.7 Hz, 1 H), 7.61-7.75 (m, 3 H), 7.75-7.85 (m, 2 H), 8.00 (br. s., 1 H), 13.29 (br. s., 1 H). MS m/z 472 (M + H)+ |
| 238 | 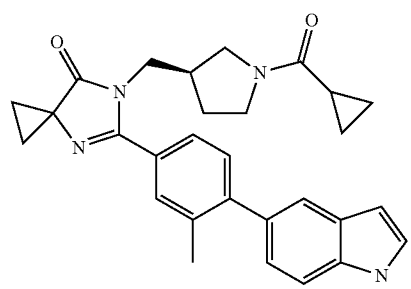 [SMILES: Cc1cc(C2=NC3(CC3)C(=O)N2C[C@@H]2CCN(C(=O)C3CC3)C2)ccc1-c1ccc2[nH]ccc2c1] | (R)-5-(4-(1H-indol-5-yl)-3-methylphenyl)-6-((1-(cyclopropanecarbonyl)pyrrolidin-3-yl)methyl)-4,6-diazaspiro[2.4]hept-4-en-7-one<br>$^1$H NMR (300 MHz, DMSO-$d_6$) δ ppm 0.68 (br. s., 4 H), 1.35-1.56 (m, 1 H), 1.56-1.69 (m, 3 H), 1.78 (d, J = 3.8 Hz, 2 H), 1.89 (dd, J = 12.4, 6.1 Hz, 1 H), 2.27-2.35 (m, 3 H), 2.43 (d, J = 13.6 Hz, 1 H), 2.94 (dd, J = 11.8, 6.7 Hz, 0.5 H), 3.10-3.23 (m, 1 H), 3.23-3.33 (m, 1 H), 3.45-3.63 (m, 1.5 H), 3.77 (t, J = 7.4 Hz, 2 H), 6.48 (br. s., 1 H), 7.11 (d, J = 8.2 Hz, 1 H), 7.34-7.44 (m, 2 H), 7.44-7.66 (m, 4 H), 11.20 (br. s., 1 H). MS m/z 467 (M + H)+ |
| 239 | 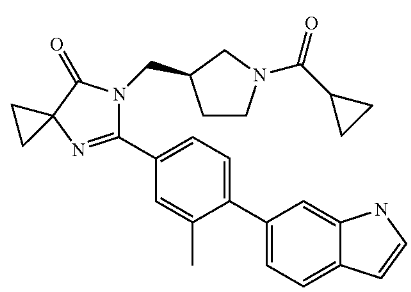 [SMILES: Cc1cc(C2=NC3(CC3)C(=O)N2C[C@@H]2CCN(C(=O)C3CC3)C2)ccc1-c1ccc2cc[nH]c2c1] | (R)-5-(4-(1H-indol-6-yl)-3-methylphenyl)-6-((1-(cyclopropanecarbonyl)pyrrolidin-3-yl)methyl)-4,6-diazaspiro[2.4]hept-4-en-7-one<br>$^1$H NMR (300 MHz, DMSO-$d_6$) δ ppm 0.61-0.74 (m, 4 H), 1.39-1.53 (m, 0.5 H), 1.54-1.68 (m, 3.5 H), 1.73-1.95 (m, 3 H), 2-27-2.48 (m, 1 H), 2.35 (s, 3 H), 2.88-3.00 (m, 0.5 H), 3.11-3.23 (m, 1 H), 3.25-3.42 (m, 1 H), 3.46-3.63 (m, 1.5 H), 3.77 (t, J = 7.3 Hz, 2 H), 6.49 (br s, 1 H), 7.02 (d, J = 8.0 Hz, 1 H), 7.35-7.45 (m, 3 H), 755-7.68 (m, 3 H), 11.19 (br s, 1H). MS m/z 467 (M + H)+ |
| 240 | 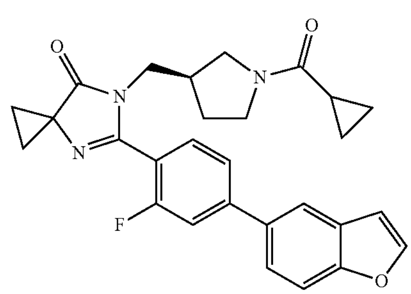 [SMILES: O=C(C1CC1)N1CC[C@@H](CN2C(=O)C3(CC3)N=C2c2ccc(-c3ccc4occc4c3)cc2F)C1] | (R)-5-(4-(benzofuran-5-yl)-2-fluorophenyl)-6-((1-(cyclopropanecarbonyl)pyrrolidin-3-yl)methyl)-4,6-diazaspiro[2.4]hept-4-en-7-one<br>$^1$H NMR (300 MHz, DMSO-$d_6$) δ ppm 0.58-0.71 (m, 4 H), 1.35-1.68 (m, 4 H), 1.72-1.92 (m, 3 H), 2.21-2.33 (m, 1 H), 2.87 (dd, J = 11.7, 7.0 Hz, 0.5 H), 3.08-3.31 (m, 2 H), 3.41-3.53 (m, 1.5 H), 3.53-3.63 (m, 2 H), 7.05 (d, J = 1.8 Hz, 1 H), 7.68-7.88 (m, 5 H), 8.04-8.14 (m, 2 H). MS m/z 472 (M + H)+ |

-continued

| ID No. | Structure | Compound Name & Physical Data |
|---|---|---|
| 241 | 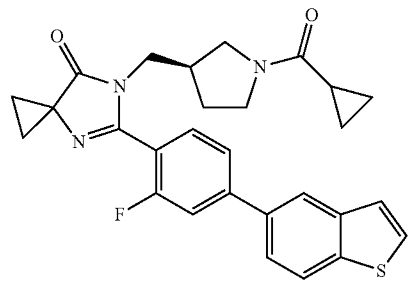 [SMILES: O=C(C1CC1)N1CC[C@@H](CN2C(=O)C3(CC3)N=C2c2ccc(-c3ccc4sccc4c3)cc2F)C1] | (R)-5-(4-(benzo[b]thiophen-5-yl)-2-fluorophenyl)-6-((1-(cyclopropanecarbonyl)pyrrolidin-3-yl)methyl)-4,6-diazaspiro[2.4]hept-4-en-7-one<br>$^1$H NMR (300 MHz, DMSO-d$_6$) δ ppm 0.58-0.72 (m, 4 H), 1.35-1.70 (m, 4 H), 1.70-1.95 (m, 3 H), 2.29 (d, J = 7.0 Hz, 0.5 H), 2.38 (br. s., 0.5 H), 2.87 (dd, J = 11.7, 6.9 Hz, 0.5 H), 3.07-3.32 (m, 2 H), 3.47 (t, J = 6.9 Hz, 1 H), 3.53-3.64 (m, 2.5 H), 7.55 (d, J = 5.4 Hz, 1 H), 7.73-7.93 (m, 5 H), 8.15 (d, J = 8.4 Hz, 1 H), 8.35 (s, 1 H). MS m/z 488 (M + H)+ |
| 242 | 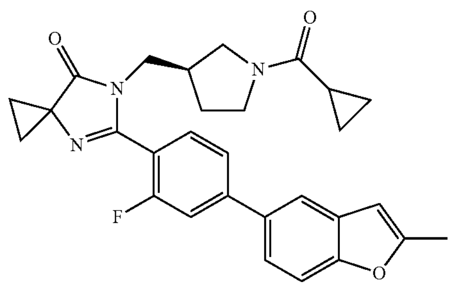 [SMILES: Cc1cc2cc(-c3ccc(C4=NC5(CC5)C(=O)N4C[C@@H]4CCN(C(=O)C5CC5)C4)c(F)c3)ccc2o1] | (R)-6-((1-(cyclopropanecarbonyl)pyrrolidin-3-yl)methyl)-5-(2-fluoro-4-(2-methylbenzofuran-5-yl)phenyl)-4,6-diazaspiro[2.4]hept-4-en-7-one<br>$^1$H NMR (300 MHz, DMSO-d$_6$) δ ppm 0.56-0.74 (m, 4 H), 1.31-1.68 (m, 4 H), 1.79-1.94 (m, 3 H), 2.19-2.34 (m, 1 H), 2.48 (s, 3 H), 2.86 (dd, J = 11.8, 7.1 Hz, 0.5 H), 3.07-3.32 (m, 2 H), 3.43-3.51 (m, 1 H), 3.51-3.63 (m, 2.5 H), 6.66 (s, 1 H), 7.56-7.68 (m, 5 H), 7.96 (s, 1 H). MS m/z 486 (M + H)+ |
| 243 | 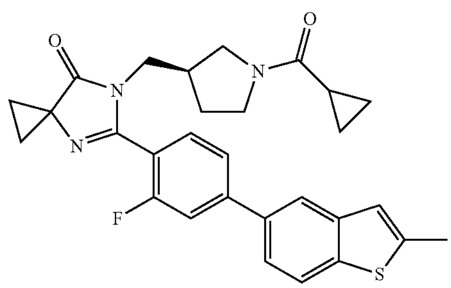 [SMILES: Cc1cc2cc(-c3ccc(C4=NC5(CC5)C(=O)N4C[C@@H]4CCN(C(=O)C5CC5)C4)c(F)c3)ccc2s1] | (R)-6-((1-(cyclopropanecarbonyl)pyrrolidin-3-yl)methyl)-5-(2-fluoro-4-(2-methylbenzo[b]thiophen-5-yl)phenyl)-4,6-diazaspiro[2.4]hept-4-en-7-one<br>$^1$H NMR (300 MHz, DMSO-d$_6$) δ ppm 0.55-0.72 (m, 4 H), 1.33-1.69 (m, 4 H), 1.69-1.94 (m, 3 H), 2.20-2.33 (m, 0.5 H), 2.33-2.47 (m, 0.5 H), 2.60 (s, 3 H), 2.86 (dd, J = 11.8, 6.9 Hz, 0.5 H), 3.06-3.32 (m, 2 H), 3.41-3.51 (m, 1 H), 3.51-3.64 (m, 2.5 H), 7.21 (s, 1 H), 7.65-7.90 (m, 4 H), 8.00 (d, J = 8.4 Hz, 1 H), 8.17 (s, 1 H). MS m/z 502 (M + H)+ |
| 244 | 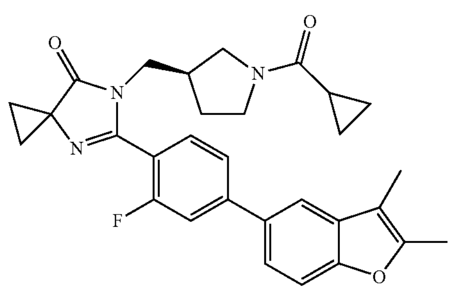 [SMILES: Cc1oc2ccc(-c3ccc(C4=NC5(CC5)C(=O)N4C[C@@H]4CCN(C(=O)C5CC5)C4)c(F)c3)cc2c1C] | (R)-6-((1-(cyclopropanecarbonyl)pyrrolidin-3-yl)methyl)-5-(4-(2,3-dimethylbenzofuran-5-yl)-2-fluorophenyl)-4,6-diazaspiro[2.4]hept-4-en-7-one<br>$^1$H NMR (300 MHz, DMSO-d$_6$) δ ppm 0.57-0.75 (m, 4 H), 1.32-1.52 (m, 1 H), 1.52-1.69 (m, 3 H), 1.69-1.95 (m, 3 H), 2.21 (s, 3 H), 2.24-2.38 (m, 1 H), 2.41 (s, 3 H), 2.86 (dd, J = 11.7, 7.0 Hz, 0.5 H), 3.05-3.32 (m, 2 H), 3.42-3.51 (m, 1 H), 3.51-3.64 (m, 2.5 H), 7.50-7.60 (m, 1 H), 7.62-7.90 (m, 4 H), 7.94 (s, 1 H). MS m/z 500 (M + H)+ |
| 245 | 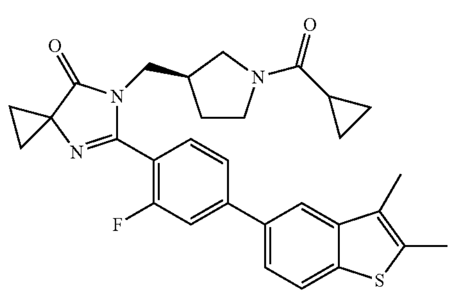 [SMILES: Cc1sc2ccc(-c3ccc(C4=NC5(CC5)C(=O)N4C[C@@H]4CCN(C(=O)C5CC5)C4)c(F)c3)cc2c1C] | (R)-6-((1-(cyclopropanecarbonyl)pyrrolidin-3-yl)methyl)-5-(4-(2,3-dimethylbenzo[b]thiophen-5-yl)-2-fluorophenyl)-4,6-diazaspiro}2.4[hept-4-en-7-one]<br>$^1$H NMR (300 MHz, DMSO-d$_6$) δ ppm 0.31-0.46 (m, 4 H), 1.07-1.43 (m, 4 H), 1.45-1.69 (m, 3 H), 1.94-2.09 (m, 1 H), 2.12 (s, 3 H), 2.25 (s, 3 H), 2.62 (dd, J = 11.8, 6.9 Hz, 0.5 H), 2.82-3.07 (m, 2 H), 3.12-3.27 (m, 1.5 H), 3.28-3.39 (m, 2 H), 7.42-7.76 (m, 5 H), 7.82 (s, 1 H). MS m/z 516 (M + H)+ |

| ID No. | Structure | Compound Name & Physical Data |
|---|---|---|
| 246 | 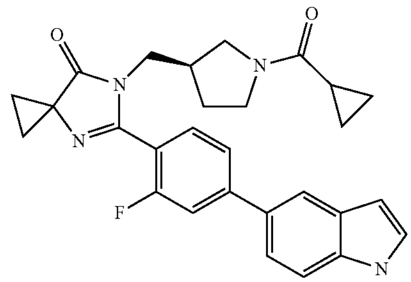 [SMILES: O=C(C1CC1)N1CC[C@@H](CN2C(=O)C3(CC3)N=C2c2ccc(-c3ccc4[nH]ccc4c3)cc2F)C1] | (R)-6-((1-(cyclopropanecarbonyl)pyrrolidin-3-yl)methyl)-5-(2-fluoro-4-(1H-indol-5-yl)phenyl)-4,6-diazaspiro[2.4]hept-4-en-7-one<br>$^1$H NMR (300 MHz, DMSO-d$_6$) δ ppm 0.56-0.73 (m, 4 H), 1.49-1.68 (m, 4 H), 1.68-1.95 (m, 3 H), 2.28 (br. s., 0.5 H), 2.37 (br. s., 0.5 H), 2.87 (dd, J = 11.8, 6.9 Hz, 0.5 H), 3.07-3.29 (m, 2 H), 3.43-3.52 (m, 1 H), 3.58 (br. s., 2.5 H), 6.53 (br. s., 1 H), 7.42 (t, J = 2.5 Hz, 1 H), 7.46-7.59 (m, 2 H), 7.61-7.83 (m, 3 H), 8.01 (s, 1 H), 11.27 (br. s., 1 H). MS m/z 471 (M + H)+ |
| 247 | 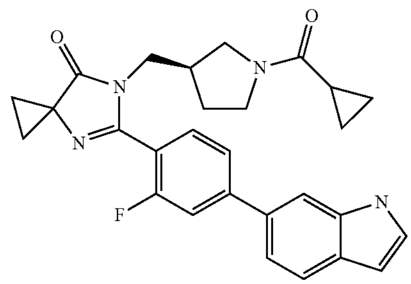 [SMILES: O=C(C1CC1)N1CC[C@@H](CN2C(=O)C3(CC3)N=C2c2ccc(-c3ccc4cc[nH]c4c3)cc2F)C1] | (R)-6-((1-(cyclopropanecarbonyl)pyrrolidin-3-yl)methyl)-5-(2-fluoro-4-(1H-indol-6-yl)phenyl)-4,6-diazaspiro[2.4]hept-4-en-7-one<br>$^1$H NMR (300 MHz, DMSO-d$_6$) δ ppm 0.57-0.71 (m, 4 H), 1.33-1.60 (m, 2 H), 1.60-1.68 (m, 2 H), 1.79-1.94 (m, 3 H), 2.22-2.35 (m, 0.5 H), 2.35-2.48 (m, 0.5 H), 2.88 (dd, J = 11.8, 6.9 Hz, 0.5 H), 3.07-3.32 (m, 2 H), 3.39-3.52 (m, 1.5 H), 3.58 (t, J = 8.3 Hz, 2 H), 6.50 (br. s., 1 H), 7.40-7.49 (m, 2 H), 7.63-7.84 (m, 5 H), 11.30 (br. s., 1 H). MS m/z 471 (M + H)+ |
| 248 | 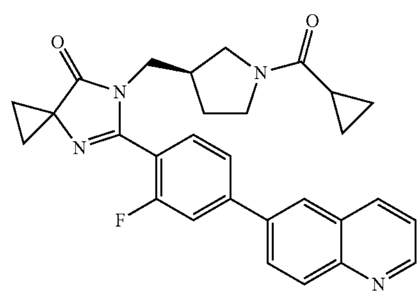 [SMILES: O=C(C1CC1)N1CC[C@@H](CN2C(=O)C3(CC3)N=C2c2ccc(-c3ccc4ncccc4c3)cc2F)C1] | (R)-6-((1-(cyclopropanecarbonyl)pyrrolidin-3-yl)methyl)-5-(2-fluoro-4-(quinolin-6-yl)phenyl)-4,6-diazaspiro[2.4]hept-4-en-7-one<br>$^1$H NMR (300 MHz, DMSO-d$_6$) δ ppm 0.54-0.72 (m, 4 H), 1.37-1.68 (m, 4 H), 1.71-1.93 (m, 3 H), 2.21-2.48 (m, 1 H), 2.82-2.92 (m, 0.5 H), 3.06-3.32 (m, 2 H), 3.43-3.53 (m, 1 H), 3.53-3.66 (m, 2.5 H), 7.61 (dd, J = 8.2, 4.1 Hz, 1 H), 7.82 (dt, J = 11.7, 7.7 Hz, 1 H), 7.88-8.04 (m, 2 H), 8.15 (d, J = 8.7 Hz, 1 H), 8.23 (d, J = 8.7 Hz, 1 H), 8.40-8.54 (m, 2 H), 8.87-9.06 (m, 1 H). MS m/z 483 (M + H)+ |
| 249 | 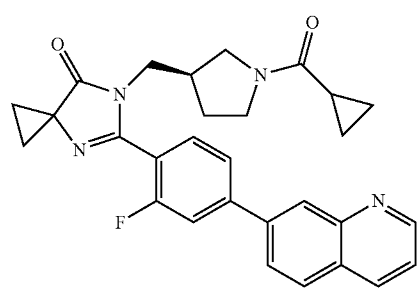 [SMILES: O=C(C1CC1)N1CC[C@@H](CN2C(=O)C3(CC3)N=C2c2ccc(-c3ccc4cccnc4c3)cc2F)C1] | (R)-6-((1-(cyclopropanecarbonyl)pyrrolidin-3-yl)methyl)-5-(2-fluoro-4-(quinolin-7-yl)phenyl)-4,6-diazaspiro[2.4]hept-4-en-7-one<br>$^1$H NMR (300 MHz, DMSO-d$_6$) δ ppm 0.56-0.70 (m, 4 H), 1.36-1.70 (m, 4 H), 1.70-1.96 (m, 3 H), 2.22-2.36 (m, 1 H), 2.88 (dd, J = 11.8, 6.9 Hz, 0.5 H), 3.06-3.32 (m, 2 H), 3.47 (t, J = 7.1 Hz, 1 H), 3.52-3.66 (m, 2.5 H), 7.59 (dd, J = 8.2, 4.3 Hz, 1 H), 7.81 (dt, J = 11.9, 7.7 Hz, 1 H), 7.89-8.18 (m, 4 H), 8.39-8.51 (m, 2 H), 8.89-9.06 (m, 1 H). MS m/z 483 (M + H)+ |

-continued

| ID No. | Structure | Compound Name & Physical Data |
|---|---|---|
| 250 | 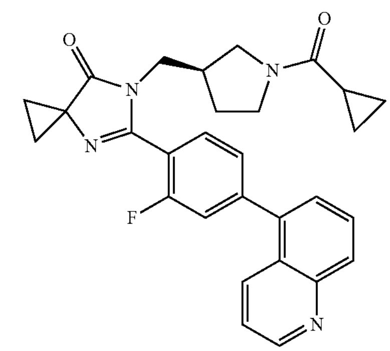 [SMILES: O=C(C1CC1)N1CC[C@@H](CN2C(=O)C3(CC3)N=C2c2ccc(-c3cccc4ncccc34)cc2F)C1] | (R)-6-((1-(cyclopropanecarbonyl)pyrrolidin-3-yl)methyl)-5-(2-fluoro-4-(quinolin-5-yl)phenyl)-4,6-diazaspiro[2.4]hept-4-en-7-one<br>$^1$H NMR (300 MHz, DMSO-d$_6$) δ ppm 0.67 (d, J = 6.0 Hz, 4 H), 1.45 (dd, J = 12.5, 7.3 Hz, 1 H), 1.57-1.71 (m, 3 H), 1.74-1.88 (m, 2 H), 1.88-2.01 (m, 1 H), 2.23-2.42 (m, 1 H), 2.88 (dd, J = 11.6, 6.9 Hz, 0.5 H), 3.10-3.31 (m, 2 H), 3.51 (t, J = 6.5 Hz, 1 H), 3.56-3.70 (m, 2.5 H), 7.46-7.73 (m, 4 H), 7.76-7.96 (m, 2 H), 8.14 (d, J = 8.4 Hz, 1 H), 8.27 (dd, J = 15.9, 8.6 Hz, 1 H), 8.98 (d, J = 3.4 Hz, 1 H). MS m/z 483 (M + H)+ |
| 251 | 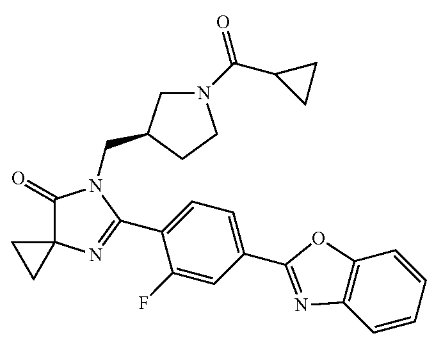 [SMILES: O=C(C1CC1)N1CC[C@@H](CN2C(=O)C3(CC3)N=C2c2ccc(-c3nc4ccccc4o3)cc2F)C1] | (R)-5-(4-(benzo[d]oxazol-2-yl)-2-fluorophenyl)-6-((1-(cyclopropanecarbonyl)pyrrolidin-3-yl)methyl)-4,6-diazaspiro[2.4]hept-4-en-7-one<br>$^1$H NMR (300 MHz, DMSO-d$_6$) δ ppm 0.51-0.75 (m, 4 H), 1.32-1.71 (m, 4 H), 1.71-1.94 (m, 3 H), 2.18-2.32 (m, 1 H), 2.85 (dd, J = 11.8, 6.9 Hz, 0.5 H), 3.05-3.30 (m, 2 H), 3.41-3..53 (m, 1 H), 3.53-3.66 (m, 2.5 H), 7.42-7.57 (m, 2 H), 7.97-8.00 (m, 3 H), 8.11-8.29 (m, 2 H). MS m/z 473 (M + H)+ |
| 252 | 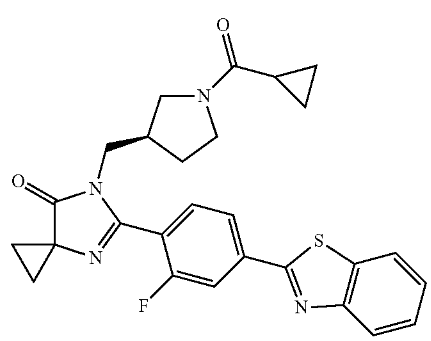 [SMILES: O=C(C1CC1)N1CC[C@@H](CN2C(=O)C3(CC3)N=C2c2ccc(-c3nc4ccccc4s3)cc2F)C1] | (R)-5-(4-(benzo[d]thiazol-2-yl)-2-fluorophenyl)-6-((1-(cyclopropanecarbonyl)pyrrolidin-3-yl)methyl)-4,6-diazaspiro[2.4]hept-4-en-7-one<br>$^1$H NMR (300 MHz, DMSO-d$_6$) δ ppm 0.55-0.73 (m, 4 H), 1.32-1.53 (m, 1 H), 1.58 (dd, J = 5.7, 2.3 Hz, 1 H), 1.63-1.70 (m, 2 H), 1.77 (br. s., 1 H), 1.81-1.95 (m, 2 H), 2.21-2.33 (m, 1 H), 2.86 (dd, J = 11.8, 6.9 Hz, 0.5 H), 3.06-3.31 (m, 2 H), 3.42-3.53 (m, 1 H), 3.53-3.66 (m, 2.5 H), 7.48-7.66 (m, 2 H), 7.88 (dt, J = 12.7, 7.7 Hz, 1 H), 8.06-8.18 (m, 3 H), 8.23 (d, J = 7.8 Hz, 1 H). MS m/z 489 (M + H)+ |
| 253 | 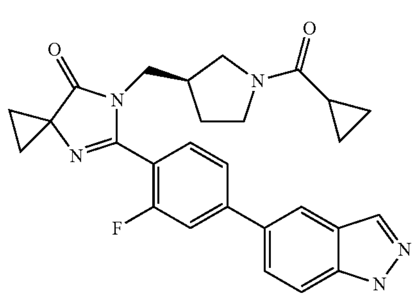 [SMILES: O=C(C1CC1)N1CC[C@@H](CN2C(=O)C3(CC3)N=C2c2ccc(-c3ccc4[nH]ncc4c3)cc2F)C1] | (R)-6-((1-(cyclopropanecarbonyl)pyrrolidin-3-yl)methyl)-5-(2-fluoro-4-(1H-indazol-5-yl)phenyl)-4,6-diazaspiro[2.4]hept-4-en-7-one<br>$^1$H NMR (300 MHz, DMSO-d$_6$) δ ppm 0.54-0.72 (m, 4 H), 1.35-1.69 (m, 4 H), 1.69-1.95 (m, 3 H), 2.17-2.33 (m, 0.5 H), 2.33-2.46 (m, 0.5 H), 2.87 (dd, J = 11.8, 6.9 Hz, 0.5 H), 3.05-3.31 (m, 2 H), 3.43-3.52 (m, 1 H), 3.52-3.67 (m, 2.5 H), 7.54-7.91 (m, 5 H), 8.23 (s, 1 H), 8.18 (s, 1 H), 13.23 (br. s., 1 H). MS m/z 472 (M + H)+ |

| ID No. | Structure | Compound Name & Physical Data |
|---|---|---|
| 254 | 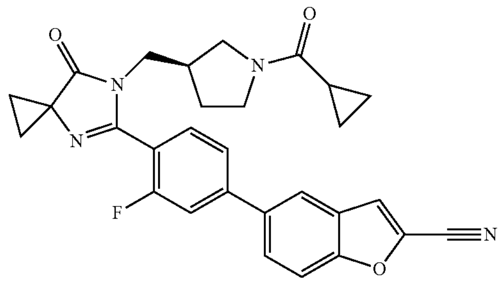 [SMILES: N#Cc1cc2cc(-c3ccc(C4=NC5(CC5)C(=O)N4C[C@@H]4CCN(C(=O)C5CC5)C4)c(F)c3)ccc2o1] | (R)-5-(4-(6-((1-(cyclopropanecarbonyl)pyrrolidin-3-yl)methyl)-7-oxo-4,6-diazaspiro[2.4]hept-4-en-5-yl)-3-fluorophenyl)benzofuran-2-carbonitrile<br>$^1$H NMR (300 MHz, DMSO-$d_6$) δ ppm 0.56-0.72 (m, 4 H), 1.47-1.69 (m, 4 H), 1.69-1.94 (m, 3 H), 2.20-2.33 (m, 0.5 H), 2.40 (d, J = 7.0 Hz, 0.5 H), 2.86 (dd, J = 11.8, 7.0 Hz, 0.5 H), 3.06-3.31 (m, 2 H), 3.43-3.52 (m, 1 H), 3.52-3.64 (m, 2.5 H), 7.73-7.82 (m, 2 H), 7.83-7.94 (m, 2 H), 8.05 (d, J = 9.1 Hz, 1 H), 8.20 (s, 1 H), 8.28 (s, 1 H). MS m/z 497 (M + H)+ |
| 255 | 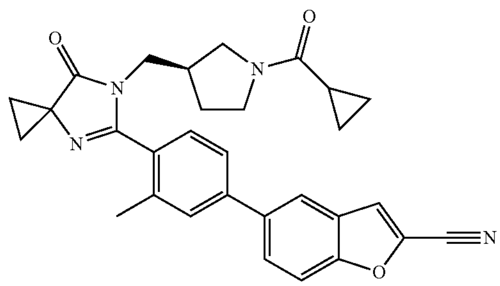 [SMILES: Cc1cc(-c2ccc3oc(C#N)cc3c2)ccc1C1=NC2(CC2)C(=O)N1C[C@@H]1CCN(C(=O)C2CC2)C1] | (R)-5-(4-(6-((1-(cyclopropanecarbonyl)pyrrolidin-3-yl)methyl)-7-oxo-4,6-diazaspiro[2.4]hept-4-en-5-yl)-3-methylphenyl)benzofuran-2-carbonitrile<br>$^1$H NMR (300 MHz, DMSO-$d_6$) δ ppm 0.42 (d, J = 5.2 Hz, 4 H), 1.07-1.28 (m, 1 H), 1.38 (br. s., 3 H), 1.45-1.71 (m, 3 H), 1.91-2.11 (m, 1 H), 2.15 (br. s., 3 H), 2.62 (dd, J = 11.3, 6.7 Hz, 0.5 H), 2.80-3.06 (m, 2 H), 3.16-3.36 (m, 3.5 H), 7.36 (dd, J = 13.0, 8.0 Hz, 1 H), 7.47 (br. s., 1 H), 7.554 (br. s., 1 H), 7.63 (d, J = 8.7 Hz, 1 H), 7.75 (d, J = 8.7 Hz, 1 H), 7.95 (d, J = 7.1 Hz, 2 H). MS m/z 493 (M + H)+ |
| 256 | 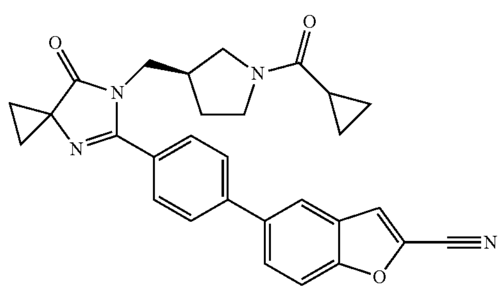 [SMILES: N#Cc1cc2cc(-c3ccc(C4=NC5(CC5)C(=O)N4C[C@@H]4CCN(C(=O)C5CC5)C4)cc3)ccc2o1] | (R)-5-(4-(6-((1-(cyclopropanecarbonyl)pyrrolidin-3-yl)methyl)-7-oxo-4,6-diazaspiro[2.4]hept-4-en-5-yl)phenyl)benzofuran-2-carbonitrile<br>$^1$H NMR (300 MHz, DMSO-$d_6$) δ ppm 0.58-0.71 (m, 4 H), 1.37-1.67 (m, 4 H), 1.69-1.94 (m, 3 H), 2.20-2.33 (m, 0.5 H), 2.38 (d, J = 6.9 Hz, 0.5 H), 2.90 (dd, J = 11.8, 6.9 Hz, 0.5 H), 3.07-3.31 (m, 2 H), 3.40-3.62 (m, 1.5 H), 3.77 (t, J = 6.3 Hz, 2 H), 7.79-7.95 (m, 5 H), 7.95-8.04 (m, 1 H), 8.18 (s, 1 H), 8.21 (s, 1 H). MS m/z 479 (M + H)+ |
| 257 | 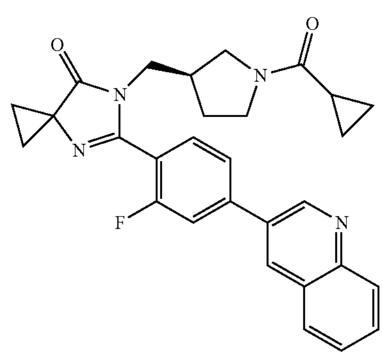 [SMILES: O=C(C1CC1)N1CC[C@@H](CN2C(=O)C3(CC3)N=C2c2ccc(-c3cnc4ccccc4c3)cc2F)C1] | (R)-6-((1-(cyclopropanecarbonyl)pyrrolidin-3-yl)methyl)-5-(2-fluoro-4-(quinolin-3-yl)phenyl)-4,6-diazaspiro[2.4]hept-4-en-7-one<br>$^1$H NMR (300 MHz, CHLOROFORM-d) δ ppm 0.62-0.83 (m, 2 H), 0.85-1.07 (m, 2 H), 1.39-1.60 (m, 1 H), 1.60-1.77 (m, 1 H), 1.80-2.08 (m, 5 H), 2.38-2.53 (m, 1 H), 2.92-3.10 (m, 0.5 H), 3.18-3.41 (m, 1 H), 3.50-3.83 (m, 4.5 H), 7.54-7.88 (m, 5 H), 7.93 (d, J = 7.8 Hz, 1 H), 8.18 (d, J = 8.5 Hz, 1 H), 8.33-8.50 (m, 1 H), 9.20 (d, J = 2.3 Hz, 1 H). MS m/z 483 (M + H)+ |

| ID No. | Structure | Compound Name & Physical Data |
|---|---|---|
| 258 | 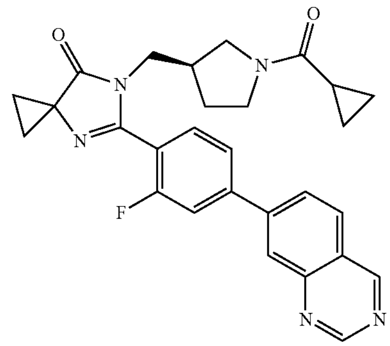 [SMILES: O=C(C1CC1)N1CC[C@@H](CN2C(=O)C3(CC3)N=C2c2ccc(-c3ccc4cncnc4c3)cc2F)C1] | (R)-6-((1-(cyclopropanecarbonyl)pyrrolidin-3-yl)methyl)-5-(2-fluoro-4-(quinazolin-7-yl)phenyl)-4,6-diazaspiro[2.4]hept-4-en-7-one<br>$^1$H NMR (300 MHz, CHLOROFORM-d) δ ppm 0.50-0.71 (m, 2 H), 0.72-0.95 (m, 2 H), 1.34-1.49 (m, 1 H), 1.51-1.68 (m, 1 H), 1.68-1.79 (m, 2 H), 1.79-1.88 (m, 2 H), 1.89-2.02 (m, 1 H), 2.29-2.44 (m, 0.5 H), 2.44-2.61 (m, 0.5 H), 2.90 (dd, J = 12.0, 7.3 Hz, 0.5 H), 3.10-3.31 (m, 1 H), 3.40-3.58 (m, 2.5 H), 3.59-3.76 (m, 2 H), 7.54 (dd, J = 10.9, 5.9 Hz, 1 H), 7.59-7.71 (m, 21 H), 7.87 (d, J = 8.4 Hz, 1 H), 8.01 (d, J = 8.4 Hz, 1 H), 8.22 (s, 1 H), 9.32 (s, 1 H), 9.40 (s, 1 H). MS m/z 484 (M + H)+ |
| 259 | 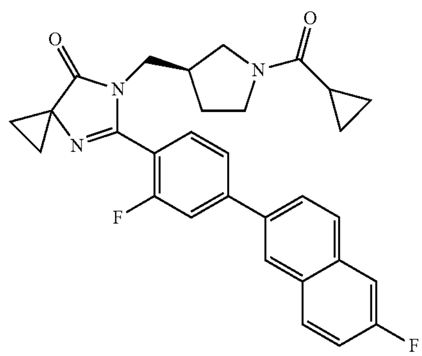 [SMILES: O=C(C1CC1)N1CC[C@@H](CN2C(=O)C3(CC3)N=C2c2ccc(-c3ccc4cc(F)ccc4c3)cc2F)C1] | (R)-6-((1-(cyclopropanecarbonyl)pyrrolidin-3-yl)methyl)-5-(2-fluoro-4-(6-fluoronaphthalen-2-yl)phenyl)-4,6-diazaspiro[2.4]hept-4-en-7-one<br>$^1$H NMR (300 MHz, CHLOROFORM-d) δ ppm 0.55-0.70 (m, 2 H), 0.75-0.94 (m, 2 H), 1.34-1.48 (m, 1.5 H), 1.52-1.63 (m, 0.5 H), 1.69-1.76 (m, 2 H), 1.78-1.87 (m, 2 H), 1.87-2.01 (m, 1 H), 2.36 (dt, J = 14.5, 7.3 Hz, 1 H), 2.90 (dd, J = 12.0, 7.3 Hz, 0.5 H), 3.09-3.30 (m, 1 H), 3.37-3.58 (m, 2.5 H), 3.58-3.72 (m, 2 H), 7.26 (td, J = 8.7, 2.0 Hz, 1 H), 7.38-7.53 (m, 2 H), 7.58 (d, J = 3.8 Hz, 2 H), 7.68 (d, J = 8.2 Hz, 1 H), 7.79-7.90 (m, 2 H), 8.01 (s, 1 H). MS m/z 500 (M + H)+ |
| 260 | 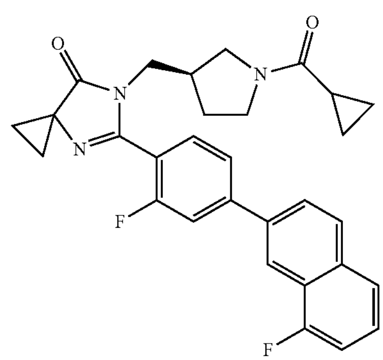 [SMILES: O=C(C1CC1)N1CC[C@@H](CN2C(=O)C3(CC3)N=C2c2ccc(-c3ccc4cccc(F)c4c3)cc2F)C1] | (R)-6-((1-(cyclopropanecarbonyl)pyrrolidin-3-yl)methyl)-5-(2-fluoro-4-(8-fluoronaphthalen-2-yl)phenyl)-4,6-diazaspiro[2.4]hept-4-en-7-one<br>$^1$H NMR (300 MHz, CHLOROFORM-d) δ ppm 0.40-0.56 (m, 2 H), 0.70 (br. s, 2 H), 1.18-1.33 (m, 1.5 H), 1.36-1.51 (m, 0.5 H), 1.55-1.63 (m, 2 H), 1.64-1.72 (m, 2 H), 1.73-1.87 (m, 1 H), 2.20-2.38 (m, 1 H), 2.77 (dd, J = 11.8, 7.3 Hz, 0.5 H), 2.93-3.17 (m, 1 H), 3.22-3.44 (m, 2.5 H), 3.44-3.62 (m, 2 H), 6.93-7.10 (m, 1 H), 7.17-7.31 (m, 1 H), 7.32-7.42 (m, 1 H), 7.46 (d, J = 6.7 Hz, 3 H), 7.57 (d, J = 8.7 Hz, 1 H), 7.76 (d, J = 8.5 Hz, 1 H), 8.13 (s, 1 H). MS m/z 500 (M + H)+ |
| 261 | 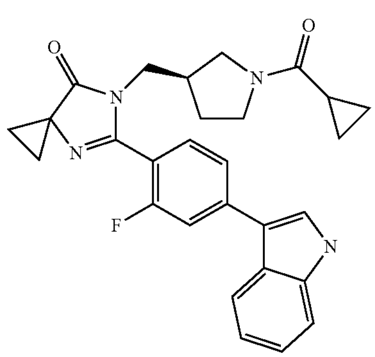 [SMILES: O=C(C1CC1)N1CC[C@@H](CN2C(=O)C3(CC3)N=C2c2ccc(-c3c[nH]c4ccccc34)cc2F)C1] | (R)-6-((1-(cyclopropanecarbonyl)pyrrolidin-3-yl)methyl)-5-(2-fluoro-4-(1H-indol-3-yl)phenyl)-4,6-diazaspiro[2.4]hept-4-en-7-one<br>$^1$H NMR (300 MHz, CHLOROFORM-d) δ ppm 0.54-0.71 (m, 2 H), 0.74-0.95 (m, 2 H), 1.32-1.49 (m, 1.5 H), 1.54-1.66 (m, 1 H), 1.68-1.76 (m, 2 H), 1.77-1.85 (m, 2 H), 1.86-2.01 (m, 0.5 H), 2.28-2.59 (m, 1 H), 2.94 (dd, J = 12.0, 7.1 Hz, 0.5 H), 3.09-3.31 (m, 1 H), 3.42-3.59 (m, 2.5 H), 3.59-3.72 (m, 2 H), 7.06-7.27 (m, 2 H), 7.40 (d, J = 2.9 Hz, 1 H), 7.37 (d, J = 2.2 Hz, 1 H), 7.42-7.58 (m, 3 H), 7.86 (d, J = 7.6 Hz, 1 H), 8.93 (d, J = 6.6 Hz, 1 H). MS m/z 471 (M + H)+ |

-continued

| ID No. | Structure | Compound Name & Physical Data |
|---|---|---|
| 262 | 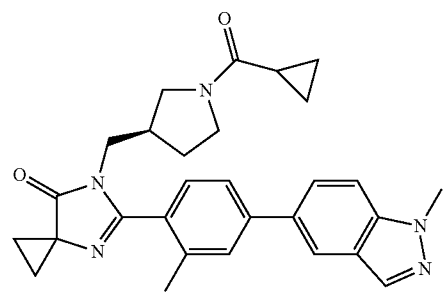 [SMILES: Cc1cc(-c2ccc3c(cnn3C)c2)ccc1C1=NC2(CC2)C(=O)N1C[C@@H]1CCN(C(=O)C2CC2)C1] | (R)-6-((1-(cyclopropanecarbonyl)pyrrolidin-3-yl)methyl)-5-(2-methyl-4-(1-methyl-1H-indazol-5-yl)phenyl)-4,6-diazaspiro[2.4]hept-4-en-7-one<br>$^1$H NMR (300 MHz, CHLOROFORM-d) δ ppm 0.71 (dd, J = 4.7, 3.0 Hz, 2 H), 0.90-1.01 (m, 2 H), 1.43-1.56 (m, 1.5 H), 1.59-1.74 (m, 0.5 H), 1.76-1.83 (m, 2 H), 1.84-1.89 (m, 2 H), 1.89-2.08 (m, 1 H), 2.43 (s, 3 H), 2.45-2.60 (m, 1 H), 3.00 (dd, J = 12.0, 6.9 Hz, 0.5 H), 3.15-3.39 (m, 1 H), 3.41-3.73 (m, 4.5 H), 4.14 (s, 3 H), 7.43 (d, J = 7.8 Hz, 1 H), 7.50 (d, J = 8.7 Hz, 1 H), 7.55-7.63 (m, 2 H), 7.65-7.73 (m, 1 H), 7.98 (s, 1 H), 8.06 (s, 1 H). MS m/z 482 (M + H)+ |
| 263 | 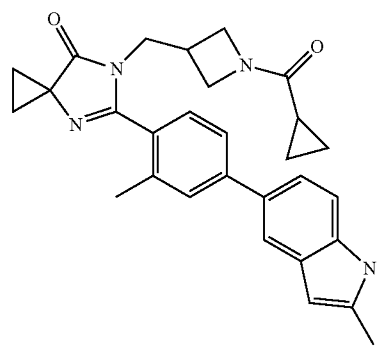 [SMILES: Cc1cc2cc(-c3ccc(C4=NC5(CC5)C(=O)N4CC4CN(C(=O)C5CC5)C4)c(C)c3)ccc2[nH]1] | 6-((1-(cyclopropanecarbonyl)azetidin-3-yl)methyl)-5-(2-methyl-4-(2-methyl-1H-indol-5-yl)phenyl)-4,6-diazaspiro[2.4]hept-4-en-7-one<br>$^1$H NMR (300 MHz, CHLOROFORM-d) δ ppm 0.36-0.52 (m, 2 H), 0.59-0.71 (m, 2 H), 0.98-1.11 (m, 2 H), 1.42-1.57 (m, 2 H), 1.57-1.76 (m, 3 H), 2.15 (s, 3 H), 2.22 (s, 3 H), 2.50 (dd, J = 7.6, 6.4 Hz, 1 H), 3.27-3.37 (m, 1 H), 3.38-3.51 (m, 1 H),. 3.51-3.66 (m, 2 H), 3.66-3.78 (m, 1 H), 3.96 (t, J = 8.2 Hz, 1 H), 6.03 (s, 1 H), 7.04-7.17 (m, 3 H), 7.26-7.42 (m, 2 H), 7.51 (s, 1 H), 8.19 (br. s., 1 H). MS m/z 467 (M + H)+ |
| 264 | 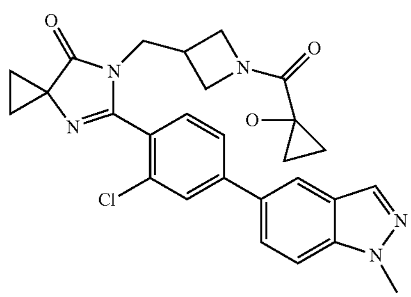 [SMILES: Cn1ncc2cc(-c3ccc(C4=NC5(CC5)C(=O)N4CC4CN(C(=O)C5(O)CC5)C4)c(Cl)c3)ccc21] | 5-(2-chloro-4-(1-methyl-1H-indazol-5-yl)phenyl)-6-((1-(1-hydroxycyclopropanecarbonyl)azetidin-3-yl)methyl)-4,6-diazaspiro[2.4]hept-4-en-7-one<br>$^1$H NMR (300 MHz, DMSO-d$_6$) δ ppm 0.42-0.52 (m, 2 H), 0.70 (d, J = 3.2 Hz, 2 H), 1.34-1.44 (m, 2 H), 1.51-1.63 (m, 2 H), 2.30-2.44 (m, 1 H), 3.19 (br. s., 1 H), 3.46 (t, J = 6.9 Hz, 2 H), 3.55 (br. s., 1 H), 3.79 (br. s., 1 H), 3.86 (s, 3 H), 4.14 (br. s., 1 H), 5.66 (br. s., 1 H), 7.47-7.58 (m, 2 H), 7.59-7.70 (m, 2 H), 7.80 (s, 1 H), 7.90 (s, 1 H), 7.99 (s, 1 H). MS m/z 504 (M + H)+ |
| 265 | 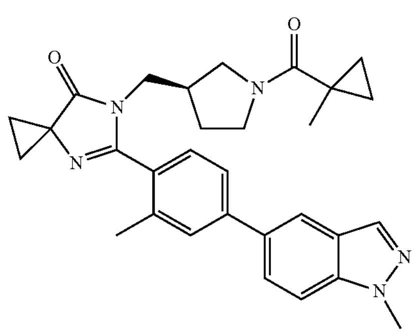 [SMILES: Cc1cc(-c2ccc3c(cnn3C)c2)ccc1C1=NC2(CC2)C(=O)N1C[C@@H]1CCN(C(=O)C2(C)CC2)C1] | (R)-5-(2-methyl-4-(1-methyl-1H-indazol-5-yl)phenyl)-6-((1-(1-methylcyclopropanecarbonyl)pyrrolidin-3-yl)methyl)-4,6-diazaspiro[2.4]hept-4-en-7-one<br>$^1$H NMR (300 MHz, DMSO-d$_6$) δ ppm 0.40 (br. s., 2 H), 0.57-0.83 (m, 2 H), 1.10 (br. s., 4 H), 1.43 (br. s., 1 H), 1.61 (br. s., 2 H), 1.79 (br. s., 3 H), 2.27 (br. s., 1 H), 2.39 (br. s., 3 H), 2.99 (br. s., 1 H), 3.18 (br. s., 2 H), 3.48 (br. s., 3 H), 4.10 (br. s., 3 H), 7.57 (br. s., 1 H), 7.79 (br. s., 4 H), 8.13 (br. s., 2 H). MS m/z 496 (M + H)+ |

-continued

| ID No. | Structure | Compound Name & Physical Data |
|---|---|---|
| 266 | 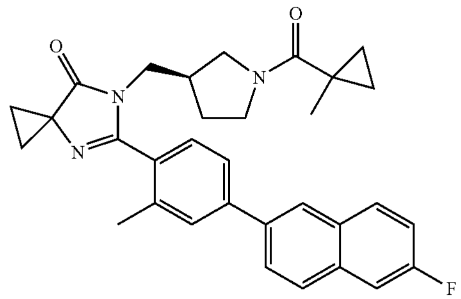 [SMILES: Cc1cc(-c2ccc3cc(F)ccc3c2)ccc1C1=NC2(CC2)C(=O)N1C[C@@H]1CCN(C(=O)C2(C)CC2)C1] | (R)-5-(4-(6-fluoronaaphthalen-2-yl)-2-methylphenyl)-6-((1-(1-methylcyclopropanecarbonyl)pyrrolidin-3-yl)methyl)-4,6-diazaspiro[2.4]hept-4-en-7-one<br>$^1$H NMR (300 MHz, DMSO-$d_6$) δ ppm 0.27 (br. s., 2 H), 0.59 (t, J = 10.7 Hz, 2 H), 0.97 (s, 3 H), 1.30 (br. s., 1 H), 1.43-1.53 (m, 2 H), 1.67 (d, J = 4.0 Hz, 3 H), 2.13 (br. s., 1 H), 2.28 (s, 3 H), 2.80 (d, J = 19.2 Hz, 1 H), 2.98-3.18 (m, 1.5 H), 3.24-3.30 (m, 1 H), 3.35 (br. s., 2.5 H), 7.31-7.41 (m, 1 H), 7.43-7.53 (m, 1 H), 7.60-7.72 (m, 2 H), 7.76 (s, 1 H), 7.85 (d, J = 8.7 Hz, 1 H), 7.92 (d, J = 8.7 Hz, 1 H), 8.00 (dd, J = 9.0, 5.8 Hz, 1 H), 8.26 (s, 1 H). MS m/z 510 (M + H)+ |
| 267 | 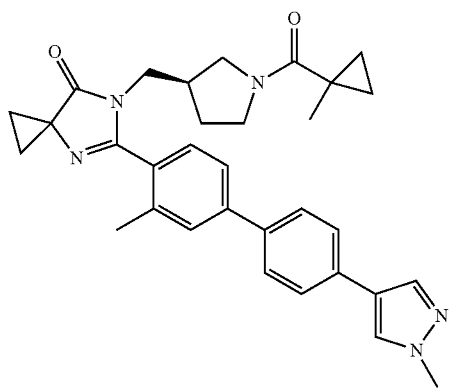 [SMILES: Cc1cc(-c2ccc(-c3cnn(C)c3)cc2)ccc1C1=NC2(CC2)C(=O)N1C[C@@H]1CCN(C(=O)C2(C)CC2)C1] | (R)-5-(3-methyl-4-(1-methyl-1H-pyrazol-4-yl)-[1,1-biphenyl]-4-yl)-6-((1-(1-methylcyclopropanecarbonyl)pyrrolidin-3-yl)methyl)-4,6-diazaspiro[2.4]hept-4-en-7-one<br>MS m/z 522 (M + H)+ |
| 268 | 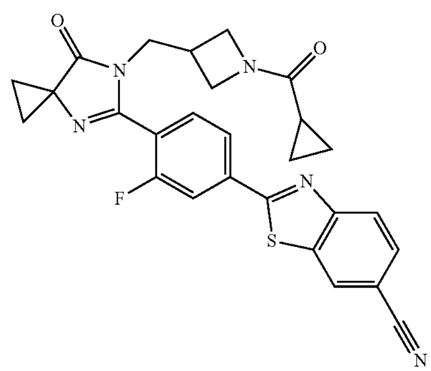 [SMILES: N#Cc1ccc2nc(-c3ccc(C4=NC5(CC5)C(=O)N4CC4CN(C(=O)C5CC5)C4)c(F)c3)sc2c1] | 2-(4-(6-((1-(cyclopropanecarbonyl)azetidin-3-yl)methyl)-7-oxo-4,6-diazaspiro[2.4]hept-4-en-5-yl)-3-fluorophenyl)benzo[d]thiazole-6-carbonitrile<br>$^1$H NMR (300 MHz, CHLOROFORM-d) δ ppm 0.62 (dd, J = 7.4, 3.2 Hz, 2 H), 0.77-0.88 (m, 2 H), 1.22 (td, J = 7.9, 1.4 Hz, 1 H), 1.70-1.80 (m, 2 H), 1.80-1.90 (m, 2 H), 2.69-2.85 (m, 1 H), 3.39-3.50 (m, 1 H), 3.63-3.76 (m, 1 H), 3.81-3.95 (m, 3 H), 4.19 (t, J = 8.2 Hz, 1 H), 7.65 (t, J = 7.5 Hz, 1 H), 7.73 (d, J = 8.4 Hz, 1 H), 7.91-8.04 (m, 2 H), 8.12 (d, J = 8.5 Hz, 1 H), 8.23 (s, 1 H). MS m/z 500 (M + H)+ |
| 269 | 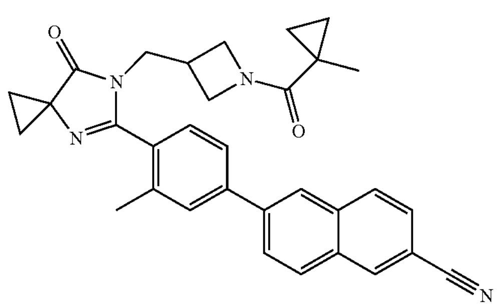 [SMILES: Cc1cc(-c2ccc3cc(C#N)ccc3c2)ccc1C1=NC2(CC2)C(=O)N1CC1CN(C(=O)C2(C)CC2)C1] | 6-(3-methyl-4-(6-((1-(1-methylcyclopropanecarbbonyl)azetidin-3-yl)methyl)-7-oxo-4,6-diazaspiro[2.4]hept-4-en-5-yl)phenyl)-2-naphthonitrile<br>$^1$H NMR (300 MHz, CHLOROFORM-d) δ ppm 0.44 (br. s., 2 H), 0.98 (br. s., 2 H), 1.20 (br. s., 3 H), 1.76 (br. s., 1 H), 1.82 (br. s., 2 H), 1.89 (br. s., 2 H), 2.47 (br. s., 3 H), 2.77 (br. s., 1 H), 3.49 (br. s., 1 H), 3.70-3.82 (m, 2 H), 4.14 (br. s., 2 H), 7.50 (d, J = 7.3 Hz, 1 H), 7.71 (d, J = 6.3 Hz, 3 H), 7.90 (d, J = 8.0 Hz, 1 H), 7.96-8.08 (m, 2 H), 8.13 (br. s., 1 H), 8.29 (br. s., 1 H). MS m/z 503 (M + H)+ |

| ID No. | Structure | Compound Name & Physical Data |
|---|---|---|
| 270 | 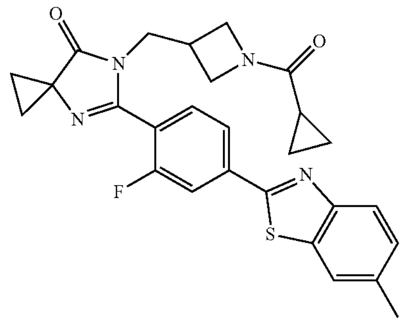 [SMILES: Cc1ccc2nc(-c3ccc(C4=NC5(CC5)C(=O)N4CC4CN(C(=O)C5CC5)C4)c(F)c3)sc2c1] | 6-((1-(cyclopropanecarbonyl)azetidin-3-yl)methyl)-5-(2-fluoro-4-(6-methylbenzo[d]thiazol-2-yl)phenyl)-4,6-diazaspiro[2.4]hept-4-en-7-one<br>¹H NMR (300 MHz, CHLOROFORM-d) δ ppm 0.46 (br. s., 2 H), 0.66 (br. s., 2 H), 1.06 (br. s., 1 H), 1.59 (br. s., 2 H), 1.67 (br. s., 2 H), 2.30 (br. s., 3 H), 2.59 (br. s., 1 H), 3.34 (br. s., 1 H), 3.46-3.62 (m, 1 H), 3.71 (br. s., 3 H), 4.01 (br. s., 1 H), 7.13 (d, J = 7.7 Hz, 1 H), 7.44 (br. s., 1 H), 7.52 (br. s., 1 H), 7.66-7.95 (m, 3 H). MS m/z 489 (M + H)+ |
| 271 | 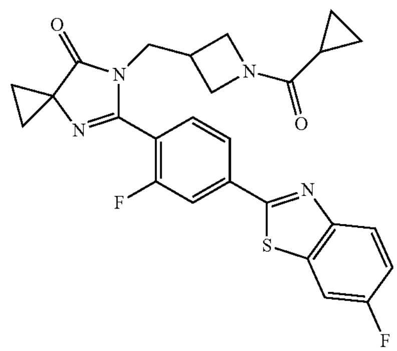 [SMILES: O=C(C1CC1)N1CC(CN2C(=O)C3(CC3)N=C2c2ccc(-c3nc4ccc(F)cc4s3)cc2F)C1] | 6-((1-(cyclopropanecarbonyl)azetidin-3-yl)methyl)-5-(2-fluoro-4-(6-fluorobenzo[d]thiazol-2-yl)phenyl)-4,6-diazaspiro[2.4]hept-4-en-7-one<br>¹H NMR (300 MHz, CHLOROFORM-d) δ ppm 0.71 (br. s., 2 H), 0.91 (br. s., 2 H), 1.31 (br. s., 1 H), 1.82 (br. s., 2 H), 1.92 (br. s., 2 H), 2.84 (br. s., 1 H), 3.57 (br. s., 1 H), 3.81 (d, J = 5.6 Hz, 1 H), 3.97 (d, J = 7.7 Hz, 3 H), 4.26 (br. s., 1 H), 7.29 (br. s., 1 H), 7.56-7.79 (m, 2 H), 7.86-8.20 (m, 3 H). MS m/z 493 (M + H)+ |
| 272 | 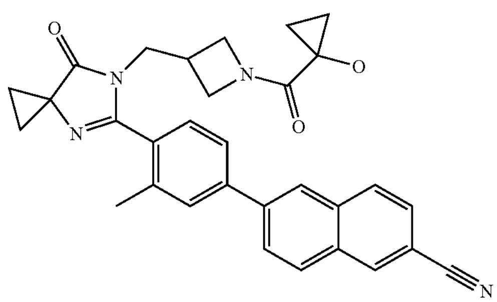 [SMILES: Cc1cc(-c2ccc3cc(C#N)ccc3c2)ccc1C1=NC2(CC2)C(=O)N1CC1CN(C(=O)C2(O)CC2)C1] | 6-(4-(6-((1-(1-hydroxycyclopropanecarbonyl)azetidin-3-yl)methyl)-7-oxo-4,6-diazaspiro[2.4]hept-4-en-5-yl)-3-methylphenyl)-2-naphthonitrile<br>¹H NMR (300 MHz, CHLOROFORM-d) δ ppm 0.81 (br. s., 2 H), 1.12 (br. s., 2 H), 1.71 (br. s., 2 H), 1.79 (br. s., 2 H), 2.54-2.75 (m, 1 H), 3.47 (br. s., 2 H), 3.68 (br. s., 2 H), 3.80-4.17 (m, 2 H), 4.35 (br. s., 1 H), 7.39 (d, J = 7.7 Hz, 1 H), 7.54-7.66 (m, 3 H), 7.81 (d, J = 8.5 Hz, 1 H), 7.92 (dd, J = 8.1, 3.0 Hz, 2 H), 8.04 (s, 1 H), 8.20 (s, 1 H). MS m/z 505 (M + H)+ |
| 273 | 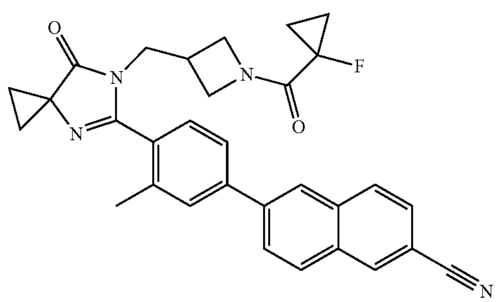 | 6-(4-(6-((1-(1-fluorocyclopropanecarbonyl)azetidin-3-yl)methyl)-7-oxo-4,6-diazaspiro[2.4]hept-4-en-5-yl)-3-methylphenyl)-2-naphthonitrile<br>¹H NMR (300 MHz, CHLOROFORM-d) δ ppm 0.97-1.15 (m, 2 H), 1.15-1.28 (m, 2 H), 1.68-1.76 (m, 2 H), 1.76-1.86 (m, 2 H), 2.67-2.85 (m, 1 H), 3.53 (dd, J = 9.9, 5.6 Hz, 1 H), 3.70 (t, J = 6.7 Hz, 2 H), 3.87-4.03 (m, 2 H), 4.32 (br. s., 1 H), 7.40 (d, J = 7.8 Hz, 1 H), 7.54-7.67 (m, 3 H), 7.81 (d, J = 8.5 Hz, 1 H), 7.93 (dd, J = 8.5, 3.9 Hz, 2 H), 8.05 (s, 1 H), 8.20 (s, 1 H). MS m/z 507 (M + H)+ |

| ID No. | Structure | Compound Name & Physical Data |
|---|---|---|
| 274 | 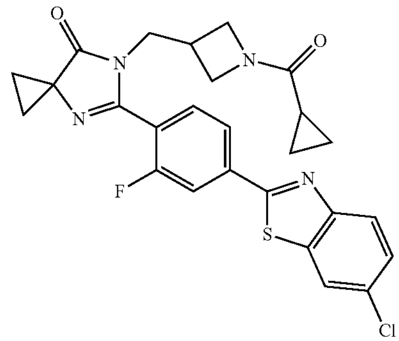 [SMILES: O=C(C1CC1)N1CC(CN2C(=O)C3(CC3)N=C2c2ccc(-c3nc4ccc(Cl)cc4s3)cc2F)C1] | 5-(4-(6-chlorobenzo[d]thiazol-2-yl)-2-fluorophenyl)-6-((1-(cyclopropanecarbonyl)azetidin-3-yl)methyl)-4,6-diazaspiro[2.4]hept-4-en-7-one<br>$^1$H NMR (300 MHz, CHLOROFORM-d) δ ppm 0.61 (dd, J = 7.2, 3.1 Hz, 2 H), 0.81 (br. s., 2 H), 1.21 (td, J = 7.8, 3.8 Hz, 1 H), 1.68-1.79 (m, 2 H), 1.79-1.89 (m, 2 H), 2.65-2.86 (m, 1 H), 3.39-3.55 (m, 1 H), 3.71 (d, J = 6.6 Hz, 1 H), 3.76-3.98 (m, 3 H), 4.17 (t, J = 8.3 Hz, 1 H), 7.37-7.49 (m, 1 H), 7.61 (t, J = 7.5 Hz, 1 H), 7.86 (s, 1 H), 7.88-8.04 (m, 3 H). MS m/z 509 (M + H)+ |
| 275 | 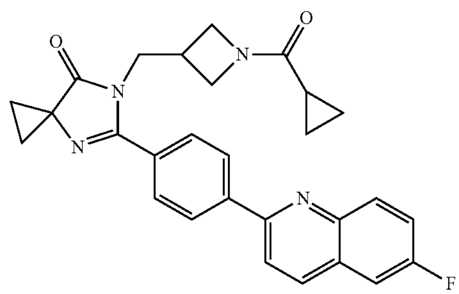 [SMILES: O=C(C1CC1)N1CC(CN2C(=O)C3(CC3)N=C2c2ccc(-c3ccc4cc(F)ccc4n3)cc2)C1] | 6-((1-(cyclopropanecarbonyl)azetidin-3-yl)methyl)-5-(4-(6-fluoroquinolin-2-yl)phenyl)-4,6-diazaspiro[2.4]hept-4-en-7-one<br>$^1$H NMR (300 MHz, CHLOROFORM-d) δ ppm 0.62-0.76 (m, 2 H), 0.85-0.98 (m, 2 H), 1.20-1.40 (m, 1 H), 1.79-1.86 (m, 2 H), 1.86-1.96 (m, 2 H), 2.74-2.93 (m, 1 H), 3.61 (dd, J = 9.6, 5.5 Hz, 1 H), 3.88-4.04 (m, 3 H), 4.04-4.15 (m, 1 H), 4.23 (t, J = 8.2 Hz, 1 H), 7.43-7.62 (m, 2 H), 7.76 (d, J = 8.2 Hz, 2 H), 7.97 (d, J = 8.5 Hz, 1 H), 8.14-8.30 (m, 2 H), 8.34 (d, J = 8.2 Hz, 2 H). MS m/z 469 (M + H)+ |
| 276 | 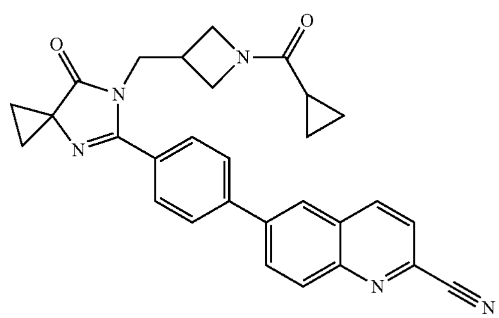 [SMILES: N#Cc1ccc2cc(-c3ccc(C4=NC5(CC5)C(=O)N4CC4CN(C(=O)C5CC5)C4)cc3)ccc2n1] | 6-(4-(6-((1-(cyclopropanecarbonyl)azetidin-3-yl)methyl)-7-oxo-4,6-diazaspiro[2.4]hept-4-en-5-yl)phenyl)quinolin-2-carbonitrile<br>$^1$H NMR (300 MHz, CHLOROFORM-d) δ ppm 0.62 (dd, J = 7.1, 4.0 Hz, 2 H), 0.82 (t, J = 3.6 Hz, 2 H), 1.14-1.30 (m, 1 H), 1.70-1.77 (m, 2 H), 1.77-1.87 (m, 2 H), 2.70-2.87 (m, 1 H), 3.51 (dd, J = 9.6, 5.5 Hz, 1 H), 3.81-3.96 (m, 3 H), 3.96-4.10 (m, 1 H), 4.18 (t, J = 8.2 Hz, 1 H), 7.62-7.74 (m, 3 H), 7.82 (d, J = 8.1 Hz, 2 H), 8.00-8.12 (m, 2 H), 8.15-8.26 (m, 1 H), 8.31 (d, J = 8.5 Hz, 1 H). MS m/z 476 (M + H)+ |
| 277 | 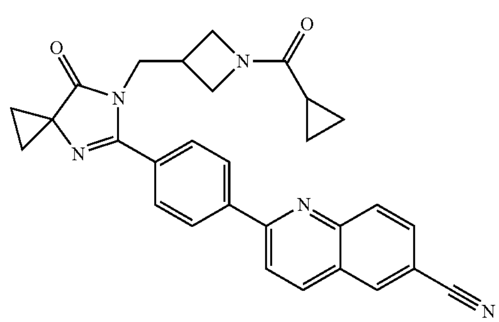 [SMILES: N#Cc1ccc2nc(-c3ccc(C4=NC5(CC5)C(=O)N4CC4CN(C(=O)C5CC5)C4)cc3)ccc2c1] | 2-(4-(6-((1-(cyclopropanecarbonyl)azetidin-3-yl)methyl)-7-oxo-4,6-diazaspiro[2.4]hept-4-en-5-yl)phenyl)quinoline-6-carbonitrile<br>$^1$H NMR (300 MHz, CHLOROFORM-d) δ ppm 0.51-0.71 (m, 2 H), 0.82 (br. s., 2 H), 1.14-1.27 (m, 1 H), 1.64 (br. s., 2 H), 1.73 (br. s., 2 H), 2.75 (br. s., 1 H), 3.51 (br. s., 1 H), 3.75-3.95 (m, 3 H), 3.95-4.08 (m, 1 H), 4.08-4.25 (m, 1 H), 7.71 (d, J = 7.8 Hz, 2 H), 7.83 (d, J = 8.5 Hz, 1 H), 7.99 (d, J = 8.5 Hz, 1 H), 8.09-8.24 (m, 2 H), 8.24-8.44 (m, 3 H). MS m/z 509 (M + H)+ |
| 278 | 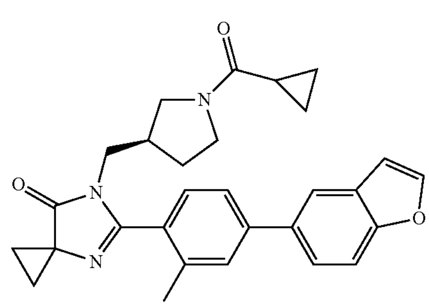 [SMILES: Cc1cc(-c2ccc3occc3c2)ccc1C1=NC2(CC2)C(=O)N1C[C@@H]1CCN(C(=O)C2CC2)C1] | (R)-5-(4-(benzofuran-5-yl)-2-methylphenyl)-6-((1-(cyclopropanecarbonyl)pyrrolidin-3-yl)methyl)-4,6-diazaspiro[2.4]hept-4-en-7-one<br>$^1$H NMR (300 MHz, DMSO-d$_6$) δ ppm 0.33-0.46 (m, 4 H), 1.10-1.28 (m, 1 H), 1.28-1.41 (m, 3 H), 1.44-1.69 (m, 3 H), 1.91-2.10 (m, 1 H), 2.14 (s, 3 H), 2.62 (dd, J = 11.7, 6.6 Hz, 0.5 H), 2.82-3.05 (m, 2 H), 3.15-3.37 (m, 3.5 H), 6.80 (s, 1 H), 7.32 (dd, J = 13.0, 7.9 Hz, 1 H), 7.40-7.50 (m, 3 H), 7.52 (br. s., 1 H), 7.79 (s, 1 H), 7.82 (d, J 1.9 Hz, 1 H). MS m/z 468 (M + H)+ |

| ID No. | Structure | Compound Name & Physical Data |
|---|---|---|
| 279 | 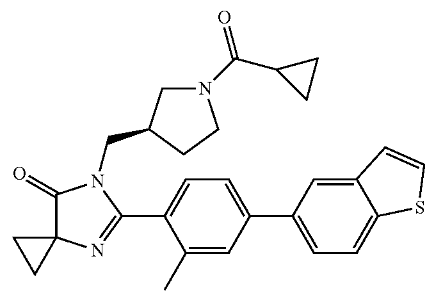 [SMILES: Cc1cc(-c2ccc3sccc3c2)ccc1C1=NC2(CC2)C(=O)N1C[C@@H]1CCN(C(=O)C2CC2)C1] | (R)-5-(4-(benzo[d]thiophen-5-yl)-2-methylphenyl)-6-((1-(cyclopropanecarbonyl)pyrrolidin-3-yl)methyl)-4,6-diazaspiro[2.4]hept-4-en-7-one<br>$^1$H NMR (300 MHz, DMSO-d$_6$) δ ppm 0.58-0.71 (m, 4 H), 1.39-1.65 (m, 4 H), 1.76-1.82 (m, 2 H), 1.82-1.94 (m, 1 H), 2.23 (d, J = 6.6 Hz, 1 H), 2.39 (s, 3 H), 2.81-2.92 (m, 0.5 H), 3.04-3.30 (m, 2 H), 3.47 (d, J = 7.1 Hz, 2.5 H), 3.55-3.66 (m, 1 H), 7.51-7.63 (m, 2 H), 7.69-7.79 (m, 2 H), 7.83 (t, J = 5.3 Hz, 2 H), 8.13 (d, J = 8.4 Hz, 1 H), 8.28 (s, 1 H). MS m/z 484 (M + H)+ |
| 280 | 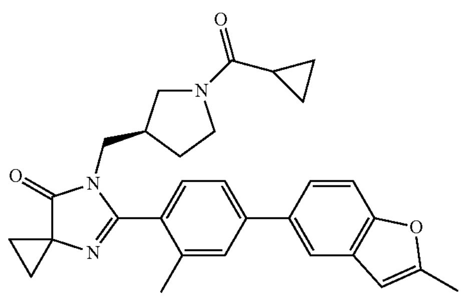 [SMILES: Cc1cc2cc(-c3ccc(C4=NC5(CC5)C(=O)N4C[C@@H]4CCN(C(=O)C5CC5)C4)c(C)c3)ccc2o1] | (R)-6-((1-(cyclopropanecarbonyl)pyrrolidin-3-yl)methyl)-5-(2-methyl-4-(2-methylbenzofuran-5-yl)phenyl)-4,6-diazaspiro[2.4]hept-4-en-7-one<br>$^1$H NMR (300 MHz, DMSO-d$_6$) δ ppm 0.54-0.73 (m, 4 H), 1.43-1.65 (m, 4 H), 1.65-1.93 (m, 3 H), 2.13-2.33 (m, 1 H), 2.37 (s, 3 H), 2.79-2.92 (m, 0.5 H), 3.04-3.29 (m, 2 H), 3.37-3.62 (m, 3.5 H), 6.65 (s, 1 H), 7.48-7.57 (m, 1 H), 7.57-7.61 (m, 2 H), 7.71-7.78 (m, 1 H), 7.89 (s, 1 H). MS m/z 482 (M + H)+ |
| 281 | 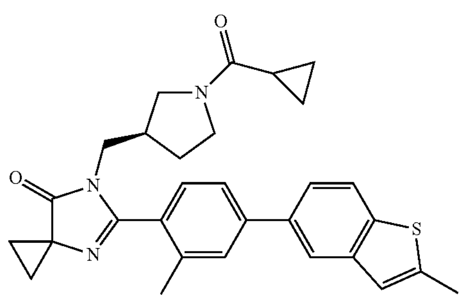 [SMILES: Cc1cc2cc(-c3ccc(C4=NC5(CC5)C(=O)N4C[C@@H]4CCN(C(=O)C5CC5)C4)c(C)c3)ccc2s1] | (R)-6-((1-(cyclopropanecarbonyl)pyrrolidin-3-yl)methyl)-5-(2-methyl-4-(2-methylbenzo[b]thiophen-5-yl)phenyl)-4,6-diazaspiro[2.4]hept-4-en-7-one<br>$^1$H NMR (300 MHz, DMSO-d$_6$) δ ppm 0.65 (d, J = 5.8 Hz, 4 H), 1.34-1.49 (m, 1 H), 1.49-1.66 (m, 3 H), 1.68-1.84 (m, 3 H), 2.24 (br. s., 1 H), 2.38 (s, 3 H), 2.60 (s, 3 H), 2.85 (d, J = 11.7 Hz, 0.5 H), 3.04-3.29 (m, 2 H), 3.36-3.53 (m, 2.5 H), 3.53-3.62 (m, 1 H), 7.22 (s, 1 H), 7.57 (dd, J = 13.4, 8.0 Hz, 1 H), 7.62-7.75 (m, 2 H), 7.78 (br. s., 1 H), 7.98 (d, J = 8.4 Hz, 1 H), 8.10 (s, 1 H). MS m/z 498 (M + H)+ |
| 282 | 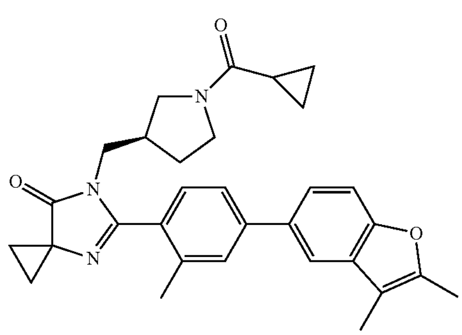 [SMILES: Cc1cc(-c2ccc3oc(C)c(C)c3c2)ccc1C1=NC2(CC2)C(=O)N1C[C@@H]1CCN(C(=O)C2CC2)C1] | (R)-6-((1-(cyclopropanecarbonyl)pyrrolidin-3-yl)methyl)-5-(4-(2,3-dimethylbenzofuran-5-yl)-2-methylphenyl)-4,6-diazaspiro[2.4]hept-4-en-7-one<br>$^1$H NMR (300 MHz, DMSO-d$_6$) δ ppm 0.46 (d, J = 5.5 Hz, 4 H), 1.14-1.35 (m, 1 H), 1.41 (br. s., 3 H), 1.49-1.64 (m, 3 H), 1.64-1.75 (m, 1 H), 2.02 (s, 3 H), 2.18 (s, 3 H), 2.22 (s, 3 H), 2.60-2.71 (m, 0.5 H), 2.86-3.00 (m, 1 H), 3.07 (br. s., 1 H), 3.15-3.42 (m, 3.5 H), 7.29-7.44 (m, 3 H), 7.48 (br. s., 1 H), 7.57 (br. s., 1 H), 7.65 (s, 1 H). MS m/z 496 (M + H)+ |

| ID No. | Structure | Compound Name & Physical Data |
|---|---|---|
| 283 | 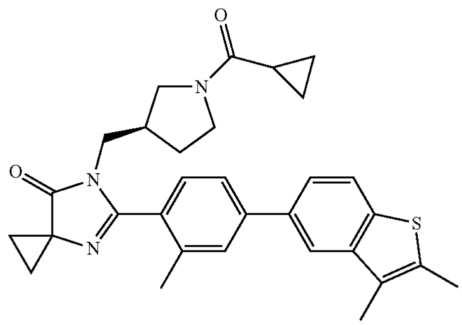 [SMILES: Cc1cc(-c2ccc3sc(C)c(C)c3c2)ccc1C1=NC2(CC2)C(=O)N1C[C@@H]1CCN(C(=O)C2CC2)C1] | (R)-6-((1-(cyclopropanecarbonyl)pyrrolidin-3-yl)methyl)-5-(4-(2,3-dimethylbenzo[b]thiophen-5-yl)-2-methylphenyl)-4,6-diazaspiro[2.4]hept-4-en-7-one<br>$^1$H NMR (300 MHz, DMSO-d$_6$) δ ppm 0.50-0.78 (m, 4 H), 1.32-1.48 (m, 1 H), 1.38-1.64 (m, 3 H), 1.69-1.83 (m, 2 H), 1.83-1.94 (m, 1 H), 2.14-2.34 (m, 1 H), 2.38 (d, J = 5.4 Hz, 6 H), 2.81-2.93 (m, 0.5 H), 3.06-3.23 (m, 1 H), 3.28 (d, J = 4.9 Hz, 1 H), 3.41-3.62 (m, 3.5 H), 7.57 (dd, J = 13.8, 7.9 Hz, 1 H), 7.64-7.71 (m, 1 H), 7.74 (br. s., 1 H), 7.81-7.87 (m, 1 H), 7.93-8.03 (m, 2 H). MS m/z 512 (M + H)+ |
| 284 | 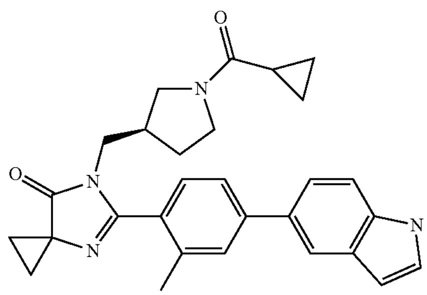 [SMILES: Cc1cc(-c2ccc3[nH]ccc3c2)ccc1C1=NC2(CC2)C(=O)N1C[C@@H]1CCN(C(=O)C2CC2)C1] | (R)-5-(4-(1H-indol-5-yl)-2-methylphenyl)-6-((1-(cyclopropanecarbonyl)pyrrolidin-3-yl)methyl)-4,6-diazaspiro[2.4]hept-4-en-7-one<br>$^1$H NMR (300 MHz, DMSO-d$_6$) δ ppm 0.57-0.71 (m, 4 H), 1.44 (d, J = 7.4 Hz, 1 H), 1.60 (br. s., 3 H), 1.78 (d, J = 3.8 Hz, 3 H), 1.87 (d, J = 6.0 Hz, 1 H), 2.25 (br. s., 1 H), 2.37 (s, 3 H), 2.88 (br. s., 0.5 H), 3.05-3.20 (m, 1 H), 3.26 (d, J = 7.0 Hz, 1 H), 3.43-3.53 (m, 2.5 H), 6.44-6.59 (m, 1 H), 7.40 (br. s., 1 H), 7.44-7.57 (m, 3 H), 7.64 (br. s., 1 H), 7.72 (br. s., 1 H), 7.93 (s, 1 H), 11.18 (br. s., 1 H). MS m/z 467 (M + H)+ |
| 286 | 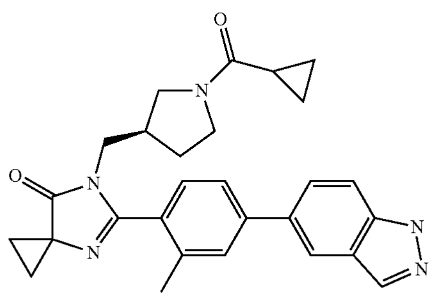 [SMILES: Cc1cc(-c2ccc3[nH]ncc3c2)ccc1C1=NC2(CC2)C(=O)N1C[C@@H]1CCN(C(=O)C2CC2)C1] | (R)-5-(4-(1H-indazol-5-yl)-2-methylphenyl)-6-((1-(cyclopropanecarbonyl)pyrrolidin-3-yl)methyl)-4,6-diazaspiro[2.4]hept-4-en-7-one<br>$^1$H NMR (300 MHz, DMSO-d$_6$) δ ppm 0.32-0.51 (m, 4 H), 1.15 (d, J = 12.4 Hz, 1 H), 1.38 (br. s., 3 H), 1.56 (d, J = 3.8 Hz, 2 H), 1.65 (br. s., 1 H), 2.02 (br. s., 1 H), 2.15 (s, 3 H), 2.64 (dd, J = 11.9, 6.7 Hz, 0.5 H), 2.87-3.10 (m, 3.5 H), 3.23 (br. s., 1 H), 3.25 (br. s., 1 H), 7.33 (dd, J = 13.1, 8.0 Hz, 1 H), 7.39-7.50 (m, 2 H), 7.53 (d, J = 8.8 Hz, 2 H), 7.92 (d, J = 4.0 Hz, 2 H), 12.3 (br. s., 1 H). MS m/z 468 (M + H)+ |
| 287 | 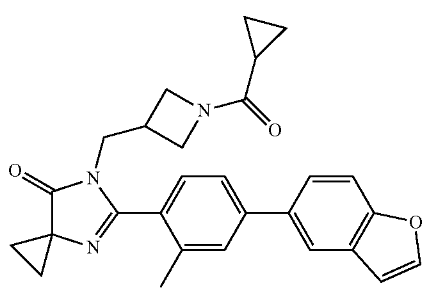 [SMILES: Cc1cc(-c2ccc3occc3c2)ccc1C1=NC2(CC2)C(=O)N1CC1CN(C(=O)C2CC2)C1] | 5-(4-(benzofuran-5-yl)-2-methylphenyl)-6-((1-(cyclopropanecarbonyl)azetidin-3-yl)methyl)-4,6-diazaspiro[2.4]hept-4-en-7-one<br>$^1$H NMR (300 MHz, DMSO-d$_6$) δ ppm 0.55-0.68 (m, 4 H), 1.37 (t, J = 6.1 Hz, 1 H), 1.55-1.65 (m, 2 H), 1.72-1.83 (m, 2 H), 2.36 (s, 3 H), 2.54-2.68 (m, 1 H), 3.36 (dd, J = 9.6, 5.4 Hz, 1 H), 3.64-3.81 (m, 4 H), 4.17 (t, J = 8.3 Hz, 1 H), 7.04 (d, J = 1.9 Hz, 1 H), 7.56 (d, J = 8.0 Hz, 1 H), 7.66-7.74 (m, 3 H), 7.77 (s, 1 H), 8.03 (s, 1 H), 8.06 (d, J = 2.1 Hz, 1 H). MS m/z 454 (M + H)+ |
| 288 | 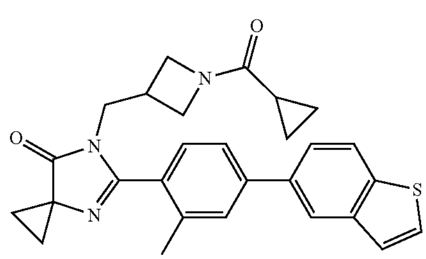 [SMILES: Cc1cc(-c2ccc3sccc3c2)ccc1C1=NC2(CC2)C(=O)N1CC1CN(C(=O)C2CC2)C1] | 5-(4-benzo[b]thiophen-5-yl)-2-methylphenyl)-6-((1-(cyclopropanecarbonyl)azetidin-3-yl)methyl)-4,6-diazaspiro[2.4]hept-4-en-7-one<br>$^1$H NMR (300 MHz, DMSO-d$_6$) δ ppm 0.53-0.70 (m, 4 H), 1.29-1.44 (m, 1 H), 1.53-1.66 (m, 2 H), 1.73-1.84 (m, 2 H), 2.37 (s, 3 H), 2.55-2.70 (m, 1 H), 3.33-3.44 (m, 1 H), 3.64-3.83 (m, 4 H), 4.17 (t, J = 8.4 Hz, 1 H), 7.50-7.63 (m, 2 H), 7.70-7.80 (m, 2 H), 7.80-7.88 (m, 2 H), 8.13 (d, J = 8.5 Hz, 1 H), 8.28 (s, 1 H). MS |

| ID No. | Structure | Compound Name & Physical Data |
|---|---|---|
| | | m/z 470 (M + H)+ |
| 289 | 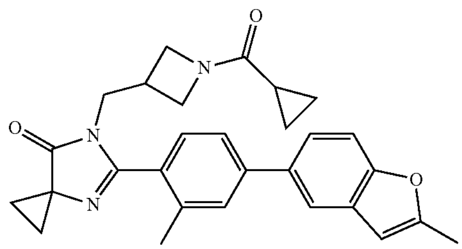 [SMILES: Cc1cc2cc(-c3ccc(C4=NC5(CC5)C(=O)N4CC4CN(C(=O)C5CC5)C4)c(C)c3)ccc2o1] | 6-((1-(cyclopropanecarbonyl)azetidin-3-yl)methyl)-5-(2-methyl-4-(2-methylbenzofuran-5-yl)phenyl)-4,6-diazspiro[2.4]hept-4-en-7-one<br>$^1$H NMR (300 MHz, DMSO-d$_6$) δ ppm 0.48-0.71 (m, 4 H), 1.26-1.46 (m, 1 H), 1.54-1.65 (m, 2 H), 1.78 (d, J = 3.7 Hz, 2 H), 2.36 (s, 3 H), 2.48 (s, 3 H), 2.54-2.68 (m, 1 H), 3.38 (br. s., 1 H), 3.61-3.83 (m, 4 H), 4.17 (t, J = 8.3 Hz, 1 H), 6.65 (s, 1 H), 7.51-7.63 (m, 3 H), 7.66 (s, 1 H), 7.75 (s, 1 H), 7.89 (s, 1 H). MS m/z 468 (M + H)+ |
| 290 | 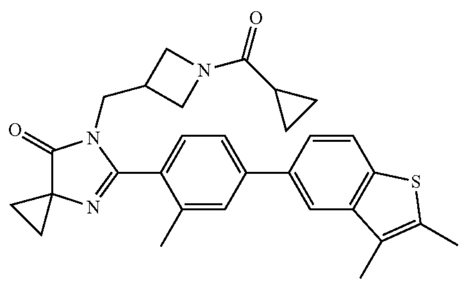 [SMILES: Cc1cc(-c2ccc3sc(C)c(C)c3c2)ccc1C1=NC2(CC2)C(=O)N1CC1CN(C(=O)C2CC2)C1] | 6-((1-(cyclopropanecarbonyl)azetidin-3-yl)methyl)-5-(4-(2,3-dimethylbenzo[b]thiophen-5-yl)-2-methylphenyl)-4,6-diazaspiro[2.4]hept-4-en-7-one<br>$^1$H NMR (300 MHz, DMSO-d$_6$) δ ppm 0.54-0.71 (m, 4 H), 1.37 (t, J = 6.0 Hz, 1 H), 1.55-1.65 (m, 2 H), 1.74-1.84 (m, 2 H), 2.37 (s, 6 H), 2.47 9s, 3 H), 2.56-2.69 (m, 1 H), 3.39 (d, J = 5.5 Hz, 1 H), 3.70 (d, J = 7.4 Hz, 3 H), 3.79 (br. s., 1 H), 4.17 (t, J = 8.2 Hz, 1 H), 7.58 (d, J = 8.0 Hz, 1 H), 7.68 (d, J = 8.4 Hz, 1 H), 7.77 (d, J = 8.1 Hz, 1 H), 7.84 (s, 1 H), 7.92-8.04 (m, 2 H). MS m/z 498 (M + H)+ |
| 291 | 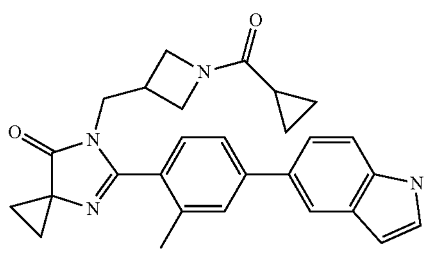 [SMILES: Cc1cc(-c2ccc3[nH]ccc3c2)ccc1C1=NC2(CC2)C(=O)N1CC1CN(C(=O)C2CC2)C1] | 5-(4-(1H-indol-5-yl)-2-methylphenyl)-6-((1-(cyclopropanecarbonyl)azetidin-3-yl)methyl)-4,6-diazaspiro[2.4]hept-4-en-7-one<br>$^1$H NMR (300 MHz, DMSO-d$_6$) δ ppm 0.53-0.71 (m, 4 H), 1.29-1.44 (m, 1 H), 1.51-1.64 (m, 2 H), 1.71-1.84 (m, 2 H), 2.35 (s, 3 H), 2.54-2.69 (m, 1 H), 3.35-3.44 (m, 1 H), 3.64-3.81 (m, 4 H), 4.17 (t, J = 8.4 Hz, 1 H), 6.52 (br. s., 1 H), 7.40 (t, J = 2.6 Hz, 1 H), 7.44-7.54 (s, 1 H), 7.93 (s, 1 H), 11.19 (br. s., 1 H). MS m/z 453 (M + H)+ |
| 292 | 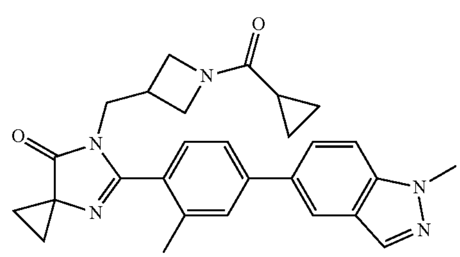 [SMILES: Cc1cc(-c2ccc3c(cnn3C)c2)ccc1C1=NC2(CC2)C(=O)N1CC1CN(C(=O)C2CC2)C1] | 6-((1-(cyclopropanecarbonyl)azetidin-3-yl)methyl)-5-(2-methyl-4-(1-methyl-1H-indazol-5-yl)phenyl)-4,6-diazaspiro[2.4]hept-4-en-7-one<br>$^1$H NMR (300 MHz, DMSO-d$_6$) δ ppm 0.51-0.71 (m, 4 H), 1.31-1.43 (m, 1 H), 1.54-1.65 (m, 2 H), 1.72-1.83 (m, 2 H), 2.36 (s, 3 H), 2.54-2.68 (m, 1 H), 3.36 (dd, J = 9.7, 5.6 Hz, 1 H), 3.65-3.82 (m, 4 H), 4.10 (s, 3 H), 4.12-4.22 (m, 1 H), 7.56 (d, J = 8.0 Hz, 1 H), 7.66-7.87 (m, 4 H), 8.13 (d, J = 3.6 Hz, 2 H). MS m/z 468 (M + H)+ |
| 293 | 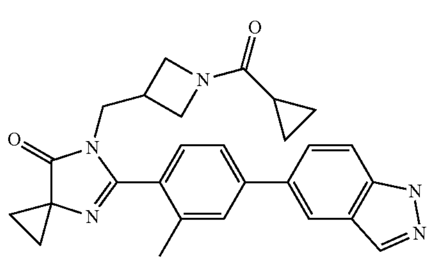 [SMILES: Cc1cc(-c2ccc3[nH]ncc3c2)ccc1C1=NC2(CC2)C(=O)N1CC1CN(C(=O)C2CC2)C1] | 5-(4-(1H-indazol-5-yl)-2-methylphenyl)-6-((1-(cyclopropanecarbonyl)azetidin-3-yl)methyl)-4,6-diazaspiro[2.4]hept-4-en-7-one<br>$^1$H NMR (300 MHz, DMSO-d$_6$) δ ppm 0.52-0.71 (m, 4 H), 1.30-1.44 (m, 1 H), 1.53-1.65 (m, 2 H), 1.72-1.84 (m, 2 H), 2.36 (s, 3 H), 2.54-2.68 (m, 1 H), 3.36 (dd, J = 9.4, 5.4 Hz, 1 H), 3.64-3.81 (m, 4 H), 4.17 (t, J = 8.4 Hz, 1 H), 7.55 (d, J = 8.0 Hz, 1 H), 7.62-7.81 (m, 4 H), 8.15 (d, J = 3.6 Hz, 2 H), 13.16 (br. s., 1 H). MS m/z 454 (M + H)+ |

-continued

| ID No. | Structure | Compound Name & Physical Data |
|---|---|---|
| 294 | 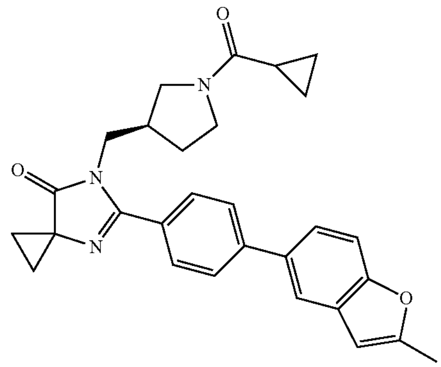 [SMILES: Cc1cc2cc(-c3ccc(C4=NC5(CC5)C(=O)N4C[C@@H]4CCN(C(=O)C5CC5)C4)cc3)ccc2o1] | (R)-6-((1-(cyclopropanecarbonyl)pyrrolidin-3-yl)methyl)-5-(4-(2-methylbenzofuran-5-yl)phenyl)-4,6-diazaspiro[2.4]hept-4-en-7-one<br>$^1$H NMR (300 MHz, DMSO-d$_6$) δ ppm 0.54-0.71 (m, 4 H), 1.35-1.50 (m, 1 H), 1.50-1.65 (m, 3 H), 1.69-1.85 (m, 3 H), 2.26 (d, J = 7.0 Hz, 0.5 H), 2.40 (d, J = 7.3 Hz, 0.5 H), 2.90 (dd, J = 11.8, 6.9 Hz, 05 H), 3.05-3.30 (m, 2 H), 3.43-3.60 (m, 1.5 H), 3.77 (t, J = 6.6 Hz, 2 H), 6.66 (s, 1 H), 7.60 (s, 2 H), 7.75-7.83 (m, 2 H), 7.83-7.95 (m, 3 H). MS m/z 468 (M + H)+ |
| 295 | 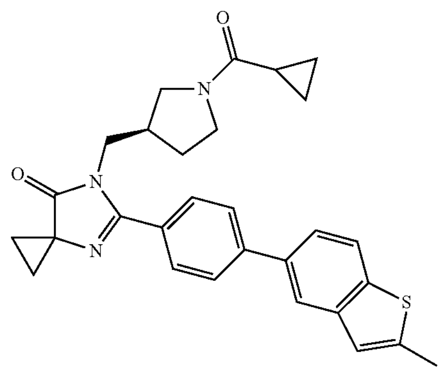 [SMILES: Cc1cc2cc(-c3ccc(C4=NC5(CC5)C(=O)N4C[C@@H]4CCN(C(=O)C5CC5)C4)cc3)ccc2s1] | (R)-6-((1-(cyclopropanecarbonyl)pyrrolidin-3-yl)methyl)-5-(4-(2-methylbenzo[b]thiophen-5-yl)phenyl)-4,6-diazaspiro[2.4]hept-4-en-7-one<br>$^1$H NMR (300 MHz, DMSO-d$_6$) δ ppm 0.64 (d, J = 6.6 Hz, 4 H), 1.38-1.69 (m, 4 H), 1.70-1.95 (m, 3 H), 2.28 (t, J = 7.0 Hz, 0.5 H), 2.41 (d, J = 6.7 Hz, 0.5 H), 2.61 (s, 3 H), 2.84-2.98 (m, 0.5 H), 3.07-3.21 (m, 1 H), 3.21-3.30 (m, 0.5 H), 3.40-3.67 (m, 2 H), 3.77 (t, J = 6.7 Hz, 2 H), 7.22 (s, 1 H), 7.67 (d, J = 8.4 Hz, 1 H), 7.78-7.86 (m, 2 H), 7.87-7.96 (m, 2 H), 7.99 (d, J = 8.4 Hz, 1 H), 8.12 (s, 1 H). MS m/z 484 (M + H)+ |
| 296 | 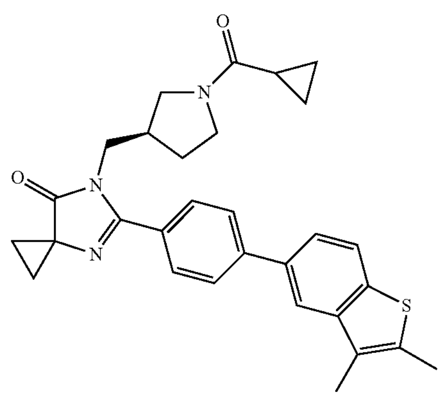 [SMILES: Cc1sc2ccc(-c3ccc(C4=NC5(CC5)C(=O)N4C[C@@H]4CCN(C(=O)C5CC5)C4)cc3)cc2c1C] | (R)-6-((1-(cyclopropanecarbonyl)pyrrolidin-3-yl)methyl)-5-(4-(2,3-dimethylbenzo[b]thiophen-5-yl)phenyl)-4,6-diazaspiro[2.4]hept-4-en-7-one<br>$^1$H NMR (300 MHz, DMSO-d$_6$) δ ppm 0.40 (d, J = 6.2 Hz, 4 H), 1.24-1.41 (m, 4 H), 1.46-1.71 (m, 3 H), 2.03 (d, J = 6.9 Hz, 1 H), 2.13 (s, 3 H), 2.28 (s, 3 H), 2.67 (br. s., 0.5 H), 2.83-2.99 (m, 2 H), 3.19-3.38 (m, 1.5 H), 3.53 (t, J = 6.8 Hz, 2 H), 7.44 (d, J = 8.2 Hz, 1 H), 7.53-7.63 (m, 2 H), 7.66-7.81 (m, 4 H). MS m/z 498 (M + H)+ |
| 297 | 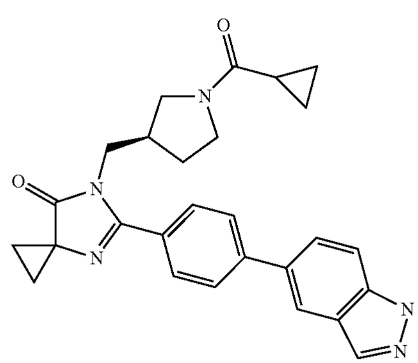 [SMILES: O=C(C1CC1)N1CC[C@@H](CN2C(=O)C3(CC3)N=C2c2ccc(-c3ccc4[nH]ncc4c3)cc2)C1] | (R)-5-(4-(1H-indazol-5-yl)phenyl)-6-((1-(cyclopropanecarbonyl)pyrrolidin-3-yl)methyl)-4,6-diazaspiro[2.4]hept-4-en-7-one<br>$^1$H NMR (300 MHz, DMSO-d$_6$) δ ppm 0.52-0.75 (m, 4 H), 1.36-1.50 (m, 1 H), 1.50-1.68 (m, 3 H), 1.69-1.96 (m, 3 H), 2.27 (t, J = 7.0 Hz, 1 H), 2.91 (dd, J = 11.8, 6.9 Hz, 0.5 H), 3.07-3.31 (m, 2 H), 3.44-3.64 (m, 1.5 H), 3.77 (t, J = 6.5 Hz, 2 H), 7.61-7.71 (m, 1 H), 7.73-7.85 (m, 3 H), 7.85-7.94 (m, 2 H), 8.16 (s, 2 H), 13.17 (br. s., 1 H). MS m/z 454 (M + H)+ |

-continued

| ID No. | Structure | Compound Name & Physical Data |
|---|---|---|
| 298 | 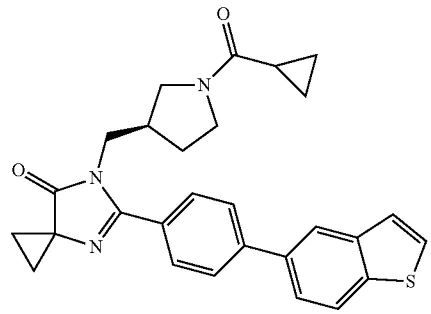 [SMILES: O=C(C1CC1)N1CC[C@@H](CN2C(=O)C3(CC3)N=C2c2ccc(-c3ccc4sccc4c3)cc2)C1] | (R)-5-(4-(benzo[b]thiophen-5-yl)phenyl)-6-((1-(cyclopropanecarbonyl)pyrrolidin-3-yl)methyl)-4,6-diazaspiro[2.4]hept-4-en-7-one<br>$^1$H NMR (300 MHz, DMSO-$d_6$) δ ppm 0.58-0.72 (m, 4 H), 1.38-1.69 (m, 4 H), 1.70-1.96 (m, 3 H), 2.29 (t, J = 6.9 Hz, 0.5 H), 2.37-2.49 (m, 0.5 H), 2.91 (dd, J = 11.9, 6.9 Hz, 0.5 H), 3.08-3.29 (m, 2 H), 3.39-3.63 (m, 1.5 H), 3.78 (t, J = 6.7 Hz, 2 H), 7.56 (d, J = 5.5 Hz, 1 H), 7.72-7.87 (m, 4 H), 7.90-7.98 (m, 2 H), 8.14 (d, J = 8.4 Hz, 1 H), 8.29 (s, 1 H). MS m/z 470 (M + H)+ |
| 299 | 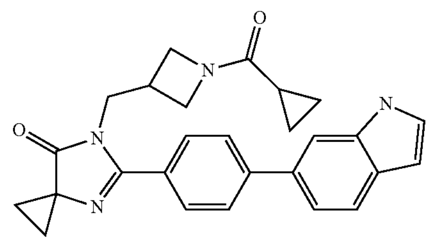 [SMILES: O=C(C1CC1)N1CC(CN2C(=O)C3(CC3)N=C2c2ccc(-c3ccc4cc[nH]c4c3)cc2)C1] | 5-(4-(1H-indol-6-yl)phenyl)-6-((1-(cyclopropanecarbonyl)azetidin-3-yl)methyl)-4,6-diazaspiro[2.4]hept-4-en-7-one<br>$^1$H NMR (300 MHz, DMSO-$d_6$) δ ppm 0.52-0.73 (m, 4 H), 1.28-1.47 (m, 1 H), 1.61 (br. s., 2 H), 1.78 (br. s., 2 H), 2.72 (br. s., 1 H), 3.44 (d, J = 9.1 Hz, 1 H), 3.69-3.89 (m, 2 H), 3.99 (d, J = 7.1 Hz, 2 H), 4.19 (t, J = 8.2 Hz, 1 H), 6.35-6.57 (m, 1 H), 7.43 (br. s., 2 H), 7.67 (d, J = 8.1 Hz, 1 H), 7.77 (d, J = 9.3 Hz, 3 H), 7.83-7.95 (m, 2 H), 11.21 (br. s., 1 H). MS m/z 439 (M + H)+ |
| 300 | 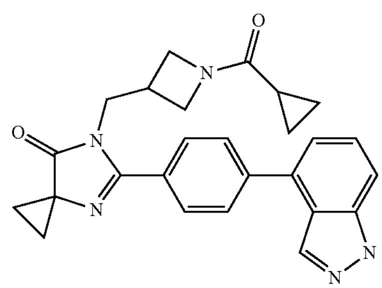 [SMILES: O=C(C1CC1)N1CC(CN2C(=O)C3(CC3)N=C2c2ccc(-c3cccc4[nH]ncc34)cc2)C1] | 5-(4-(1H-indazol-4-yl)phenyl)-6-((1-(cyclopropanecarbonyl)azetidin-3-yl)methyl)-4,6-diazaspiro[2.4]hept-4-en-7-one<br>$^1$H NMR (300 MHz, DMSO-$d_6$) δ ppm 0.62 (d, J = 5.1 Hz, 4 H), 1.30-1.45 (m, 1 H), 1.56-1.67 (m, 2 H), 1.75-1.87 (m, 2 H), 2.65-2.785 (m, 1 H), 3.46 (dd, J = 9.5, 5.5 Hz, 1 H), 3.73-3.86 (m, 2 H), 4.00 (d, J = 7.4 Hz, 2 H), 4.20 (t, J = 8.3 Hz, 1 H), 7.34 (d, J = 7.0 Hz, 1 H), 7.49 (t, J = 7.7 Hz, 1 H), 7.58-7.65 (m, 1 H), 7.85 (m, J = 8.2 Hz, 2 H), 7.93 (m, J = 8.2 Hz, 2 H), 8.24 (s, 1 H), 13.30 (s, 1 H). MS m/z 440 (M + H)+ |
| 301 | 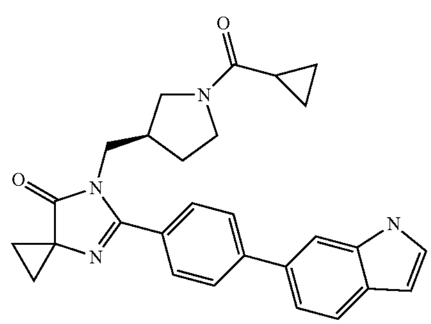 [SMILES: O=C(C1CC1)N1CC[C@@H](CN2C(=O)C3(CC3)N=C2c2ccc(-c3ccc4cc[nH]c4c3)cc2)C1] | (R)-5-(4-(1H-indol-6-yl)phenyl)-6-((1-(cyclopropanecarbonyl)pyrrolidin-3-yl)methyl)-4,6-diazaspiro[2.4]hept-4-en-7-one<br>$^1$H NMR (300 MHz, DMSO-$d_6$) δ ppm 0.65 (d, J = 5.9 Hz, 4 H), 1.34-1.51 (m, 1 H), 1.51-1.68 (m, 3 H), 1.69-1.95 (m, 3 H), 2.29 (d, J = 6.7 Hz, 1 H), 2.93 (m, 0.5 H), 3.07-3.25 (m, 1.5 H), 3.41-3.66 (m, 2 H), 3.78 (t, J = 6.8 Hz, 2 H), 6.48 (d, J = 2.7 Hz, 1 H), 7.34-7.48 (m, 2 H), 7.66 (d, J = 8.2 Hz, 1 H), 7.71-7.83 (m, 3 H), 7.83-7.93 (m, 2 H), 11.16 (br. s., 1 H). MS m/z 453 (M + H)+ |
| 302 | 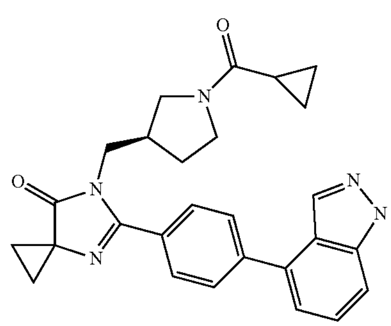 [SMILES: O=C(C1CC1)N1CC[C@@H](CN2C(=O)C3(CC3)N=C2c2ccc(-c3cccc4[nH]ncc34)cc2)C1] | (R)-5-(4-(1H-indol-4-yl)phenyl)-6-((1-(cyclopropanecarbonyl)pyrrolidin-3-yl)metyl)-4,6-diazaspiro[2.4]hept-4-en-7-one<br>$^1$H NMR (300 MHz, DMSO-$d_6$) δ ppm 0.56-0.76 (m, 4 H), 1.45 (dd, J = 12.4, 7.6 Hz, 1 H), 1.53-1.70 (m, 3 H), 1.71-1.97 (m, 3 H), 2.25-2.38 (m, 1 H), 2.93 (dd, J = 11.8, 6.7 Hz, 0.5 H), 3.06-3.28 (m, 1.5 H), 3.44-3.67 (m, 2 H), 3.79 (t, J = 7.1 Hz, 2 H), 7.34 (d, J = 7.0 Hz, 1 H), 7.49 (t, J = 7.7 Hz, 1 H), 7.62 (d, J = 8.2 Hz, 1 H), 7.81-7.98 (m, 4 H), 8.25 (d, J = 2.5 Hz, 1 H), 13.26 (br. s., 1 H). MS m/z 454 (M + H)+ |

| ID No. | Structure | Compound Name & Physical Data |
|---|---|---|
| 303 | 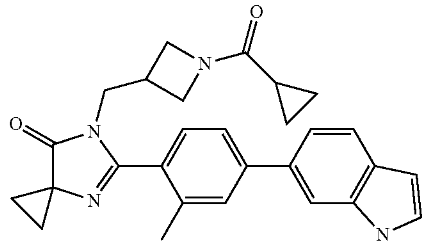 [SMILES: Cc1cc(-c2ccc3cc[nH]c3c2)ccc1C1=NC2(CC2)C(=O)N1CC1CN(C(=O)C2CC2)C1] | 5-(4-(1H-indol-6-yl)-2-methylphenyl)-6-((1-(cyclopropancarbonyl)azetidin-3-yl)methyl)-4,6-diazaspiro[2.4]hept-4-en-7-one<br>$^1$H NMR (300 MHz, DMSO-d$_6$) δ ppm 0.53-0.70 (m, 4 H), 1.37 (t, J = 6.2 Hz, 1 H), 1.53-1.64 (m, 2 H), 1.73-1.84 (m, 2 H), 2.54-2.73 (m, 1 H), 3.33-3.44 (m, 1 H), 3.64-3.82 (m, 4 H), 4.17 (t, J = 8.2 Hz, 1 H), 6.48 (br. s., 1 H), 7.35-7.45 (m, 2 H), 7.53 (d, J = 7.8 Hz, 1 H), 7.66 (dd, J = 8.0, 5.2 Hz, 2 H), 7.73 (s, 2 H), 11.20 (br. s., 1 H). MS m/z 453 (M + H)+ |
| 304 | 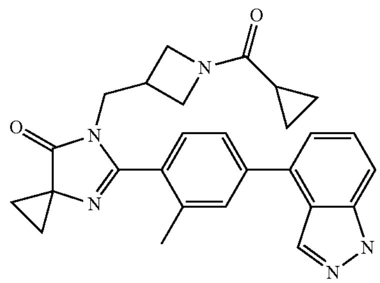 [SMILES: Cc1cc(-c2cccc3[nH]ncc23)ccc1C1=NC2(CC2)C(=O)N1CC1CN(C(=O)C2CC2)C1] | 5-(4-(1H-indazol-4-yl)-2-methylphenyl)-6-((1-(cyclopropanecarbonyl)azetidin-3-yl)methyl)-4,6-diazaspiro[2.4]hept-4-en-7-one<br>$^1$H NMR (300 MHz, DMSO-d$_6$) δ ppm 0.60 (d, J = 3.3 Hz, 4 H), 1.37 (quin, J = 6.3 Hz, 1 H), 1.56-1.67 (m, 2 H), 1.74-1.85 (m, 2 H), 2.39 (s, 3 H), 2.55-2.74 (m, 1 H), 3.38 (dd, J = 9.5, 5.5 Hz, 1 H), 3.64-3.85 (m, 4 H), 4.18 (t, J = 8.4 Hz, 1 H), 7.32 (d, J = 7.0 Hz, 1 H), 7.47 (t, J = 7.7 Hz, 1 H), 7.56-7.66 (m, 2 H), 7.68-7.76 (m, 1 H), 7.78 (s, 1 H), 8.25 (s, 1 H), 13.28 (br. s., 1 H). MS m/z 454 (M + H)+ |
| 305 | 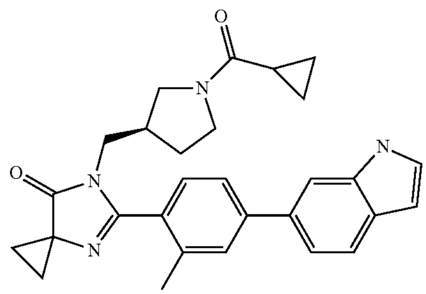 [SMILES: Cc1cc(-c2ccc3cc[nH]c3c2)ccc1C1=NC2(CC2)C(=O)N1C[C@@H]1CCN(C(=O)C2CC2)C1] | (R)-5-(4-(1H-indol-6-yl)-2-methylphenyl)-6-((1-(cyclopropanecarbonyl)pyrrolidin-3-yl)methyl)-4,6-diazaspiro[2.4]hept-4-en-7-one<br>$^1$H NMR (300 MHz, DMSO-d$_6$) δ ppm 0.51-0.74 (m, 4 H), 1.36-1.65 (m, 4 H), 1.69-1.94 (m, 3 H), 2.16-2.36 (m, 1 H), 2.38 (s, 3 H), 2.88 (dd, J = 11.9, 6.5 Hz, 0.5 H), 3.05-3.28 (m, 2 H), 3.41-3.64 (m, 3.5 H), 6.48 (d, J = 2.9 Hz, 1 H), 7.34-7.46 (m, 2 H), 7.53 (dd, J = 13.3, 8.0 Hz, 1 H), 7.65 (d, J = 8.2 Hz, 2 H), 7.73 (s, 2 H), 11.19 (br. s., 1 H). MS m/z 467 (M + H)+ |
| 306 | 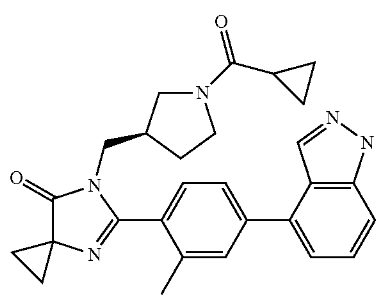 [SMILES: Cc1cc(-c2cccc3[nH]ncc23)ccc1C1=NC2(CC2)C(=O)N1C[C@@H]1CCN(C(=O)C2CC2)C1] | (R)-5-(4-(1H-indazol-4-yl)-2-methylphenyl)-6-((1-(cyclopropanecarbonyl)pyrrolidin-3-yl)methyl)-4,6-diazaspiro[2.4]hept-4-en-7-one<br>$^1$H NMR (300 MHz, DMSO-d$_6$) δ ppm 0.65 (d, J = 6.5 Hz, 4 H), 1.36-1.52 (m, 1 H), 1.52-1.66 (m, 3 H), 1.70-1.95 (m, 3 H), 2.27 (br. s., 1 H), 2.41 (s, 3 H), 2.88 (dd, J = 11.8, 6.4 Hz, 0.5 H), 3.07-3.21 (m, 2 H), 3.44-3.54 (m, 2.5 H), 3.56-3.65 (m, 1 H), 7.32 (d, J = 7.0 Hz, 1 H), 7.47 (t, J = 7.7 Hz, 1 H), 7.55-7.67 (m, 2 H), 7.67-7.74 (m, 1 H), 7.76 (br. s., 1 H), 8.25 (s, 1 H), 13.24 (br. s., 1 H). MS m/z 468 (M + H)+ |
| 307 | 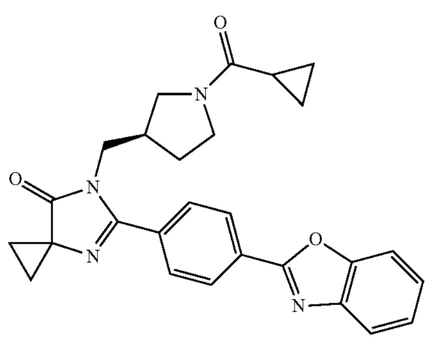 [SMILES: O=C(C1CC1)N1CC[C@@H](CN2C(=O)C3(CC3)N=C2c2ccc(-c3nc4ccccc4o3)cc2)C1] | (R)-5-(4-(benzo[d]oxazol-2-yl)phenyl)-6-((1-(cyclopropanecarbonyl)pyrrolidin-3-yl)methyl)-4,6-diazaspiro[2.4]hept-4-en-7-one<br>$^1$H NMR (300 MHz, DMSO-d$_6$) δ ppm 0.63 (d, J = 5.1 Hz, 4 H), 1.36-1.68 (m, 4 H), 1.69-1.94 (m, 3 H), 2.16-2.44 (m, 1 H), 2.88 (dd, J = 11.7, 6.9 Hz, 0.5 H), 3.07-3.31 (m, 2 H), 3.35-3.65 (m, 1.5 H), 3.77 (dd, J = 7.1, 3.6 Hz, 2 H), 7.39-7.56 (m, 2 H), 7.78-7.91 (m, 2 H), 7.97 (dd, J = 8.2, 4.3 Hz, 2 H), 8.36 (dd, J = 8.2, 1.8 Hz, 2 H). MS m/z 455 (M + H)+ |

-continued

| ID No. | Structure | Compound Name & Physical Data |
|---|---|---|
| 308 | 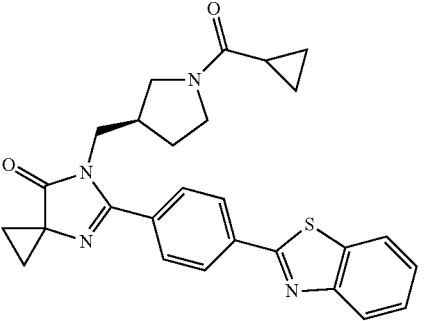 [SMILES: O=C(C1CC1)N1CC[C@@H](CN2C(=O)C3(CC3)N=C2c2ccc(-c3nc4ccccc4s3)cc2)C1] | (R)-5-(4-(benzo[d]thiazol-2-yl)phenyl)-6-((1-(cyclopropanecarbonyl)pyrrolidin-3-yl)methyl)-4,6-diazaspiro[2.4]hept-4-en-7-one<br>$^1$H NMR (300 MHz, DMSO-d$_6$) δ ppm 0.64 (d, J = 6.5 Hz, 4 H), 1.37-1.67 (m, 4 H), 1.69-1.96 (m, 3 H), 2.19-2.33 (m, 1 H), 2.90 (dd, J = 11.8, 6.9 Hz, 0.5 H),k 3.05-3.32 (m, 2 H), 3.36-3.64 (m, 1.5 H), 3.69-3.85 (m, 2 H),k 7.52 (t, J = 7.4 Hz, 1 H), 7.60 (t, J = 7.4 Hz, 1 H), 7.93 (dd, J = 8.2, 4.6 Hz, 2 H), 8.12 (d, J = 8.0 Hz, 1 H), 8.21 (d, J = 7.8 Hz, 1 H), 8.24-8.34 (m, 2 H). MS m/z 471 (M + H)+ |
| 309 | 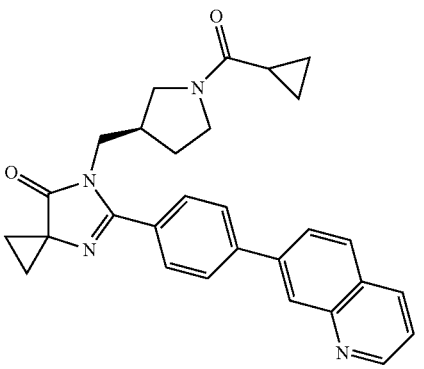 [SMILES: O=C(C1CC1)N1CC[C@@H](CN2C(=O)C3(CC3)N=C2c2ccc(-c3ccc4cccnc4c3)cc2)C1] | (R)-6-((1-(cyclopropanecarbonyl)pyrrolidin-3-yl)methyl)-5-(4-(quinolin-7-yl)phenyl)-4,6-diazaspiro[2.4]hept-4-en-7-one<br>$^1$H NMR (300 MHz, DMSO-d$_6$) δ ppm 0.64 (d, J = 6.3 Hz, 4 H), 1.38-1.68 (m, 4 H), 1.70-1.98 (m, 3 H),k 2.21-2.35 (m, 0.5 H), 2.35-2.48 (m, 0.5 H), 2.91 (dd, J = 11.8, 6.9 Hz, 0.5 H), 3.07-3.32 (m, 2 H), 3.44-3.64 (m, 1.5 H), 3.78 (t, J = 6.8 Hz, 2 H), 7.58 (dd, J = 8.2, 4.1 Hz, 1 H), 7.88 (dd, J = 8.2, 4.6 Hz, 2 H), 8.01-8.10 (m, 3 H), 8.10-8.18 (m, 1 H), 8.39 (s, 1 H), 8.44 (d, J = 8.0 Hz, 1 H), 8.98 (dd, J = 4.1, 1.4 Hz, 1 H). MS m/z 465 (M + H)+ |
| 310 | 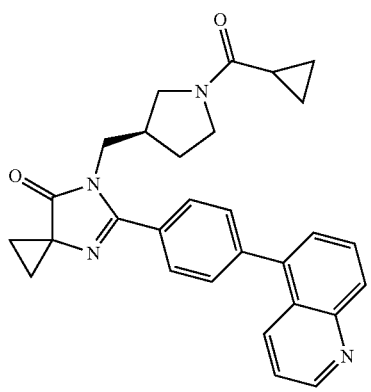 [SMILES: O=C(C1CC1)N1CC[C@@H](CN2C(=O)C3(CC3)N=C2c2ccc(-c3cccc4ncccc34)cc2)C1] | (R)-6-((1-(cyclopropanecarbonyl)pyrrolidin-3-yl)methyl)-5-(4-(quinolin-5-yl)phenyl)-4,6-diazaspiro[2.4]hept-4-en-7-one<br>$^1$H NMR (300 MHz, DMSO-d$_6$) δ ppm 0.56-0.75 (m, 4 H), 1.34-1.56 (m, 1 H), 1.56-1.68 (m, 3 H), 1.73-1.98 (m, 3 H), 2.33 (dt, J = 14.2, 7.2 Hz, 1 H), 2.91 (dd, J = 11.9, 6.8 Hz, 0.5 H), 3.09-3.32 (m, 2 H), 3.47-3.67 (m, 1.5 H), 3.73-3.86 (m, 2 H), 7.56 (dd, J = 8.5, 4.0 Hz, 1 H), 7.60-7.72 (m, 3 H), 7.88 (dt, J = 7.9, 3.9 Hz, 3 H), 8.12 (d, J = 8.4 Hz, 1 H), 8.23 (t, J = 9.2 Hz, 1 H), 8.98 (d, J = 2.9 Hz, 1 H). MS m/z 465 (M + H)+ |
| 311 | 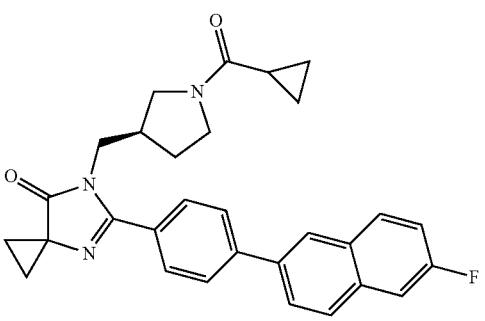 [SMILES: O=C(C1CC1)N1CC[C@@H](CN2C(=O)C3(CC3)N=C2c2ccc(-c3ccc4cc(F)ccc4c3)cc2)C1] | (R)-6-((1-(cyclopropanecarbonyl)pyrrolidin-3-yl)methyl)-5-(4-(6-fluoronaphthalen-2-yl)phenyl)-4,6-diazaspiro[2.4]hept-4-en-7-one<br>$^1$H NMR (300 MHz, DMSO-d$_6$) δ ppm 0.55-0.74 (m, 4 H), 1.35-1.66 (m, 4 H), 1.70-1.96 (m, 3 H), 2.21-2.45 (m, 1 H), 2.90 (dd, J = 11.8, 7.0 Hz, 0.5 H), 3.07-3.32 (m, 2 H), 3.42-3.64 (m, 1.5 H), 3.78 (t, J = 6.5 Hz, 2 H), 7.50 (td, J = 8.9, 2.5 Hz, 1 H), 7.78 (dd, J = 10.2, 2.3 Hz, 1 H), 7.86 (dd, J = 8.2, 4.1 Hz, 2 H), 7.95-8.09 (m, 4 H), 8.14 (dd, J = 9.1, 5.9 Hz, 1 H), 8.42 (s, 1 H). MS m/z 482 (M + H)+ |

| ID No. | Structure | Compound Name & Physical Data |
|---|---|---|
| 312 | 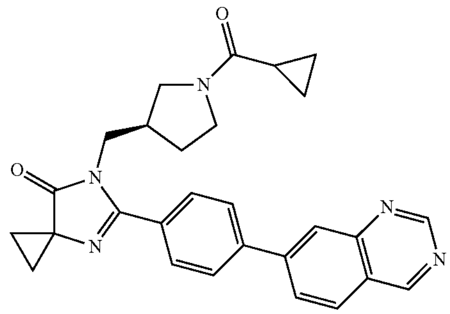 [SMILES: O=C(C1CC1)N1CC[C@@H](CN2C(=O)C3(CC3)N=C2c2ccc(-c3ccc4cncnc4c3)cc2)C1] | (R)-6-((1-(cyclopropanecarbonyl)pyrrolidin-3-yl)methyl)-5-(4-(quinazolin-7-yl)phenyl)-4,6-diazaspiro[2.4]hept-4-en-7-one<br>$^1$H NMR (300 MHz, CHLOROFORM-d) δ ppm 0.64-0.80 (m, 2 H), 0.86-1.07 (m, 2 H), 1.48-1.58 (m, 1 H), 1.69-1.85 (m, 3 H), 1.86-1.97 (m, 2.5 H), 1.97-2.11 (m, 0.5 H), 2.37-2.70 (m, 1 H), 3.07 (dd, J = 12.0, 7.1 Hz, 0.5 H), 3.24-3.42 (m, 1 H), 3.51-3.91 (m, 4.5 H), 7.74-7.84 (m, 2 H), 7.87-7.96 (m, 2 H), 7.99 (dd, J = 8.5, 1.4 Hz, 1 H), 8.09 (d, J = 8.4 Hz, 1 H), 8.33 (s, 1 H), 9.41 (s, 1 H), 9.48 (s, 1 H). MS m/z 466 (M + H)+ |
| 313 | 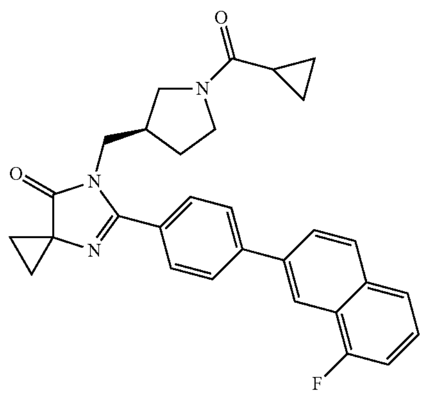 [SMILES: O=C(C1CC1)N1CC[C@@H](CN2C(=O)C3(CC3)N=C2c2ccc(-c3ccc4cccc(F)c4c3)cc2)C1] | (R)-6-((1-(cyclopropanecarbonyl)pyrrolidin-3-yl)methyl)-5-(4-(8-fluoronaphthalen-2-yl)phenyl)-4,6-diazaspiro[2.4]hept-4-en-7-one<br>$^1$H NMR (300 MHz, CHLOROFORM-d) δ ppm 0.56-0.67 (m, 2 H), 0.87 (dt, J = 7.4, 3.7 Hz, 2 H), 1.35-1.47 (m, 1 H), 1.55-1.75 (m, 3 H), 1.78-1.97 (m, 3 H), 2.28-2.56 (m, 1 H), 2.99 (dd, J = 12.0, 7.0 Hz, 0.5 H), 3.13-3.31 (m, 1 H), 3.42-3.82 (m, 4.5 H), 7.13 (dd, J = 10.2, 7.9 Hz, 1 H), 7.31-7.42 (m, 1 H), 7.55-7.70 (m, 3 H), 7.75 (dd, J = 8.6, 1.4 Hz, 1 H), 7.82 (dd, J = 8.2, 4.5 Hz, 2 H), 7.90 (d, J = 8.5 Hz, 1 H), 8.28 (s, 1 H). MS m/z 482 (M + H)+ |
| 314 | 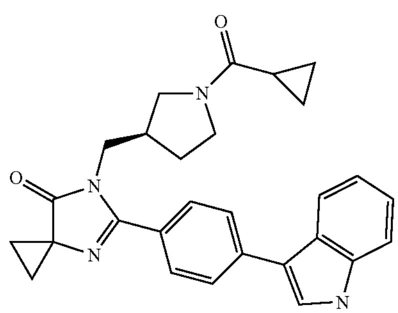 [SMILES: O=C(C1CC1)N1CC[C@@H](CN2C(=O)C3(CC3)N=C2c2ccc(-c3c[nH]c4ccccc34)cc2)C1] | (R)-5-(4-(1H-indol-3-yl)phenyl)-6-((1-(cyclopropanecarbonyl)pyrrolidin-3-yl)methyl)-4,6-diazaspiro[2.4]hept-4-en-7-one<br>$^1$H NMR (300 MHz, CHLOROFORM-d) δ ppm 0.63 (dd, J = 7.7, 3.0 Hz, 2 H), 0.77-0.95 (m, 2 H), 1.38-1.48 (m, 1 H), 1.60-1.73 (m, 3 H), 1.75-1.99 (m, 3 H), 2.29-2.59 (m, 1 H), 3.01 (dd, J = 12.0, 6.9 Hz, 0.5 H), 3.14-3.31 (m, 1 H), 3.43-3.65 (m, 2.5 H), 3.66-3.85 (m, 2 H), 7.12-7.27 (m, 2 H), 7.38 (dd, J = 7.3, 1.9 Hz, 2 H), 7.58 (dd, J = 8.1, 4.5 Hz, 2 H), 7.68-7.80 (m, 2 H), 7.88 (dd, J = 7.7 Hz, 1 H), 8.59 (br. s., 1 H). MS m/z 453 (M + H)+ |
| 315 | 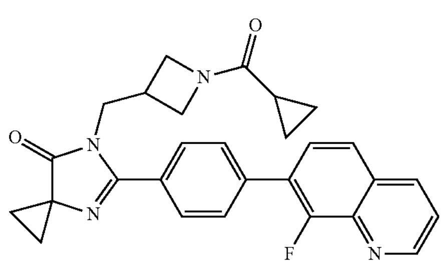 [SMILES: O=C(C1CC1)N1CC(CN2C(=O)C3(CC3)N=C2c2ccc(-c3ccc4cccnc4c3F)cc2)C1] | 6-((1-(cyclopropanecarbonyl)azetidin-3-yl)methyl)-5-(4-(8-fluoroquinolin-7-yl)phenyl)-4,6-diazaspiro[2.4]hept-4-en-7-one<br>$^1$H NMR (300 MHz, CHLOROFORM-d) δ ppm 0.72 (dd, J = 7.9, 3.1 Hz, 2 H), 0.92 (quin, J = 3.6 Hz, 2 H), 1.27-1.39 (m, 1 H), 1.75-1.86 (m, 2 H), 1.86-1.96 (m, 2 H), 2.81-2.98 (m, 1 H), 3.66 (dd, J = 9.9, 5.6 Hz, 1 H), 3.94-4.18 (m, 4 H), 4.27 (t, J = 8.2 Hz, 1 H), 7.55 (dd, J = 8.4, 4.3 Hz, 1 H), 7.63-7.72 (m, 1 H), 7.75 (d, J = 8.4 Hz, 3 H), 7.89 (d, J = 7.3 Hz, 2 H), 8.26 (d, J = 8.4 Hz, 1 H), 9.06 (dd, J = 4.1, 1.4 Hz, 1 H). MS m/z 469 (M + H)+ |

| ID No. | Structure | Compound Name & Physical Data |
|---|---|---|
| 316 | 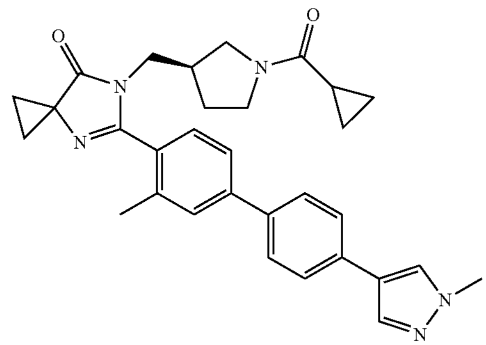 [SMILES: Cc1cc(-c2ccc(-c3cnn(C)c3)cc2)ccc1C1=NC2(CC2)C(=O)N1C[C@@H]1CCN(C(=O)C2CC2)C1] | (R)-6-((1-(cyclopropanecarbonyl)pyrrolidin-3-yl)methyl)-5-(3-methyl-4'-(1-methyl-1H-pyrazol-4-yl)-[1,1'-biphenyl]-4-yl)-4,6-diazaspiro[2.4]hept-4-en-7-one<br>$^1$H NMR (300 MHz, CHLOROFORM-d) δ ppm 0.67-0.82 (m, 2 H), 0.87-1.06 (m, 2 H), 1.44-1.57 (m, 1 H), 1.65 (dd, J = 12.6, 7.6 Hz, 0.5 H), 1.75-1.83 (m, 2.5 H), 1.84-1.91 (m, 2 H), 1.99 (dd, J = 12.4, 6.3 Hz, 1 H), 2.42 (s, 3 H), 2.53 (d, J = 8.2 Hz, 1 H), 2.99-3.04 (m, 0.5 H), 3.15-3.38 (m, 1 H), 3.46-3.69 (m, 4.5 H), 3.99 (s, 3 H), 7.38-7.45 (m, 1 H), 7.55-7.67 (m, 6 H), 7.69 (s, 1 H), 7.83 (s, 1 H). MS m/z 508 (M + H)+ |
| 317 | 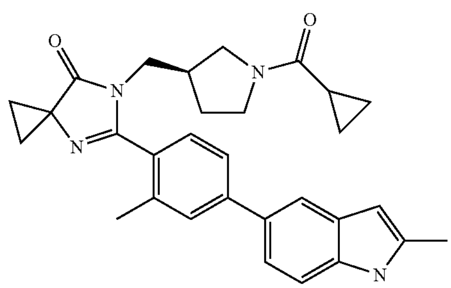 [SMILES: Cc1cc2cc(-c3ccc(C4=NC5(CC5)C(=O)N4C[C@@H]4CCN(C(=O)C5CC5)C4)c(C)c3)ccc2[nH]1] | (R)-6-((1-(cyclopropanecarbonyl)pyrrolidin-3-yl)methyl)-5-(2-methyl-4-(2-methyl-1H-indazol-5-yl)phenyl)-4,6-diazaspiro[2.4]hept-4-en-7-one<br>$^1$H NMR (300 MHz, CHLOROFORM-d) δ ppm 0.64-0.79 (m, 2 H), 0.89-1.04 (m, 2 H), 1.43-1.57 (m, 1 H), 1.66 (br. s., 1 H), 1.74-1.83 (m, 2.5 H), 1.83-1.91 (m, 2.5 H), 1.95-2.05 (m, 1 H), 2.41 (s, 3 H), 2.49 (s, 3 H), 3.04 (dd, J = 12.0, 6.5 Hz, 0.5 H), 3.14-3.20 (m, 0.5 H), 3.24-3.38 (m, 0.5 H), 3.48-3.71 (m, 4.5 H), 6.29 (s, 1 H), 7.34-7.45 (m, 3 H), 7.54-7.65 (m, 2 H), 7.78 (s, 1 H), 8.10 (br. s., 1 H). MS m/z 481 (M + H)+ |
| 318 | 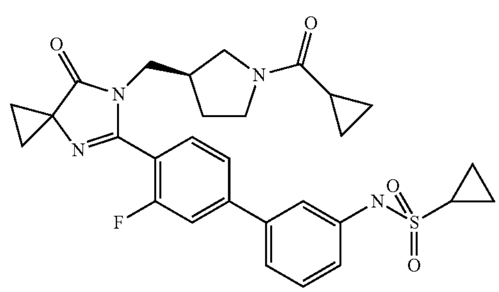 [SMILES: O=C(C1CC1)N1CC[C@@H](CN2C(=O)C3(CC3)N=C2c2ccc(-c3cccc(NS(=O)(=O)C4CC4)c3)cc2F)C1] | (R)-N-(4'-(6-((1-(cyclopropanecarbonyl)pyrrolidin-3-yl)methyl)-7-oxo-4,6-diazaspiro[2.4]hept-4-en-5-yl)-3-fluoro-[1,1'-biphenyl]-3-yl)cyclopropanesulfonamide<br>$^1$H NMR (300 MHz, CHLOROFORM-d) δ ppm 0.65-0.80 (m, 2 H), 0.88-0.98 (m, 2 H), 1.01 (d, J = 7.7 Hz, 2 H), 1.18-1.29 (m, 2 H), 1.42-1.58 (m, 1.5 H), 1.65-1.69 (m, 1 H), 1.77-1.87 (m, 2 H), 1.88-1.97 (m, 2 H), 1.97-2.11 (m, 0.5 H), 2.35-2.49 (m, 1 H), 2.49-2.65 (m, 1 H), 2.92-3.01 (m, 0.5 H), 3.19-3.39 (m, 1 H), 2.44-2.78 (m, 4.5 H), 6.99 (br. s., 1 H), 7.33 (d, J = 7.1 Hz, 1 H), 7.37-7.49 (m, 3 H), 7.49-7.59 (m, 2 H), 7.59-7.68 (m, 1 H). MS m/z 551 (M + H)+ |
| 319 | 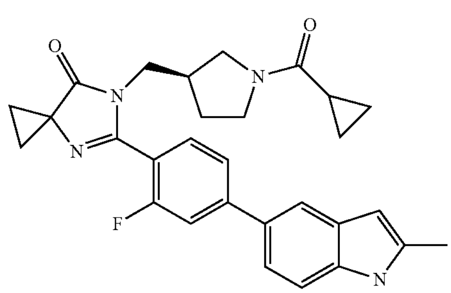 | (R)-6-((1-(cyclopropanecarbonyl)pyrrolidin-3-yl)methyl)-5-(2-fluoro-4-(2-methyl-1H-indol-5-yl)phenyl)-4,6-diazaspiro[2.4]hept-4-en-7-one<br>$^1$H NMR (300 MHz, CHLOROFORM-d) δ ppm 0.65-0.79 (m, 2 H), 0.86-1.03 (m, 2 H), 1.46-1.57 (m, 1 H), 1.57-1.74 (m, 1 H), 1.76-1.86 (m, 2 H), 1.86-1.92 (m, 2 H), 1.92-2.08 (m, 1 H), 2.50 (s, 3 H), 2.51-2.65 (m, 1 H), 3.03 (dd, J = 12.1, 7.0 Hz, 0.5 H), 3.16-3.37 (m, 1 H), 3.51-3.79 (m, 4.5 H), 6.31 (s, 1 H), 7.38 (s, 2 H), 7.50 (dd, J = 11.2, 6.3 Hz, 1 H), 7.54-7.64 (m, 2 H), 7.78 (s, 1 H), 8.15 (br. s., 1 H). MS m/z 485 (M + H)+ |

| ID No. | Structure | Compound Name & Physical Data |
|---|---|---|
| 320 | 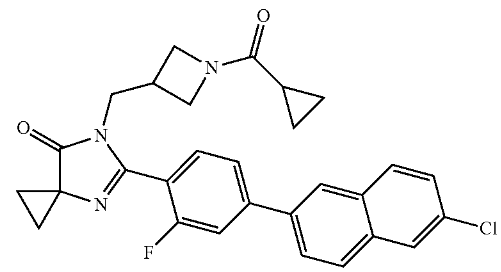 [SMILES: O=C(C1CC1)N1CC(CN2C(=O)C3(CC3)N=C2c2ccc(-c3ccc4cc(Cl)ccc4c3)cc2F)C1] | 5-(4-(6-chloronaphthalen-2-yl)-2-fluorophenyl)-6-((1-(cyclopropanecarbonyl)azetidin-3-yl)methyl)-4,6-diazaspiro[2.4]hept-4-en-7-one
¹H NMR (300 MHz, CHLOROFORM-d) δ ppm 0.64-0.76 (m, 2 H), 0.86-0.97 (m, 2 H), 1.26-1.37 (m, 1 H), 1.76-1.86 (m, 2 H), 1.86-1.97 (m, 2 H), 2.81-2.98 (m, 1 H), 3.58 (dd, J = 9.9, 5.6 Hz, 1 H), 3.75-3.87 (m, 1 H), 3.90-4.06 (m, 3 H), 4.27 (t, J = 8.3 Hz, 1 H), 7.52 (dd, J = 8.7, 2.0 Hz, 1 H), 7.56-7.63 (m, 1 H), 7.65-7.72 (m, 2 H), 7.78 (dd, J = 8.7, 1.8 Hz, 1 H), 7.84-7.94 (m, 3 H), 8.09 (s, 1 H). MS m/z 502 (M + H)+ |
| 321 | | 5-(4-(6-chloronaphthalen-2-yl)-2-methylphenyl)-6-((1-(1-methylcyclopropanecarbonyl)azetidin-3-yl)methyl)-4,6-diazaspiro[2.4]hept-4-en-7-one
¹H NMR (300 MHz, CHLOROFORM-d) δ ppm 0.39-0.48 (m, 2 H), 0.93-1.02 (m, 2 H), 1.19 (s, 3 H), 1.76-1.85 (m, 2 H), 1.85-1.94 (m, 2 H), 2.45 (s, 3 H), 2.68-2.86 (m, 1 H), 3.76 (d, J = 7.4 Hz, 4 H), 4.13 (br. s., 2 H), 7.41-7.53 (m, 2 H), 7.65-7.73 (m, 2 H), 7.76-7.83 (m, 1 H), 7.83-7.93 (m, 3 H), 8.07 (s, 1 H). MS m/z 512 (M + H)+ |
| 322 | | 6-((1-(cyclopropanecarbonyl)azetidin-3-yl)methyl)-5-(3-fluoro-4'-(1-methyl-1H-pyrazol-4-yl)-[1,1'-biphenyl]-4-yl)-4,6-diazaspiro[2.4]hept-4-en-7-one
¹H NMR (300 MHz, CHLOROFORM-d) δ ppm 0.63-0.75 (m, 2 H), 0.87-0.98 (m, 2 H), 1.25-1.37 (m, 1 H), 1.75-1.86 (m, 2 H), 1.86-1.95 (m, 2 H), 2.78-2.97 (m, 1 H), 3.58 (dd, J = 9.8, 5.6 Hz, 1 H), 3.72-3.86 (m, 1 H), 3.88-4.05 (m, 6 H), 4.26 (t, J = 8.3 Hz, 1 H), 7.49 (d, J = 11.7 Hz, 1 H), 7.54-7.68 (m, 6 H), 7.70 (s, 1 H), 7.84 (s, 1 H). MS m/z 498 (M + H)+ |
| 323 | | (R)-6-((1-(cyclopropanecarbonyl)pyrrolidin-3-yl)methyl)-5-(3-fluoro-4'-(1-methyl-1H-pyrazol-4-yl)-[1,1'-biphenyl]-4-yl)-4,6-diazaspiro[2.4]hept-4-en-7-one
¹H NMR (300 MHz, CHLOROFORM-d) δ ppm 0.65-0.78 (m, 2 H), 0.86-1.02 (m, 2 H), 1.40-1.65 (m, 2 H), 1.76-1.86 (m, 2 H), 1.86-1.93 (m, 2 H), 1.93-2.10 (m, 1 H), 2.37-2.65 (m, 1 H), 2.99 (dd, J = 12.0, 7.1 Hz, 0.5 H), 3.17-3.38 (m, 1 H), 3.47-3.65 (m, 2.5 H), 3.65-3.79 (m, 2 H), 3.95-4.06 (m, 3 H), 7.44-7.52 (m, 1 H), 7.53-7.68 (m, 6 H), 7.70 (s, 1 H), 7.84 (s, 1 H). MS m/z 512 (M + H)+ |

-continued

| ID No. | Structure | Compound Name & Physical Data |
|---|---|---|
| 324 | 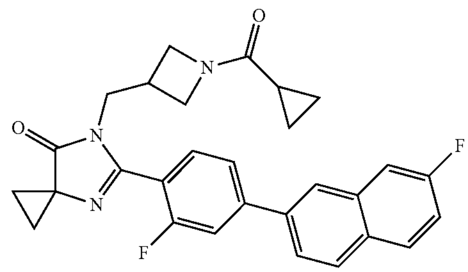 [SMILES: O=C(C1CC1)N1CC(CN2C(=O)C3(CC3)N=C2c2ccc(-c3ccc4ccc(F)cc4c3)cc2F)C1] | 6-((1-(cyclopropanecarbonyl)azetidin-3-yl)methyl)-5-(2-fluoro-4-(7-fluoronaphthalen-2-yl)phenyl)-4,6-diazaspiro[2.4]hept-4-en-7-one<br>$^1$H NMR (300 MHz, CHLOROFORM-d) δ ppm 0.65-0.74 (m, 2 H), 0.86-0.96 (m, 2 H), 1.26-1.37 (m, 1 H), 1.77-1.87 (m, 2 H), 1.92 (quin, J = 3.7 Hz, 2 H), 2.78-2.98 (m, 1 H), 3.60 (dd, J = 9.9, 5.6 Hz, 1 H), 3.76-3.89 (m, 1 H), 3.90-4.06 (m, 3 H), 4.27 (t, J = 8.3 Hz, 1 H), 7.24 (dd, J = 10.5, 7.8 Hz, 12 H), 7.49 (td, J = 7.9, 5.4 Hz, 1 H), 7.58-7.76 (m, 4 H), 7.81 (dd, J = 8.7, 1.6 Hz, 1 H), 8.01 (d, J = 8.7 Hz, 1 H), 8.37 (s, 1 H). MS m/z 486 (M + H)+ |
| 325 | 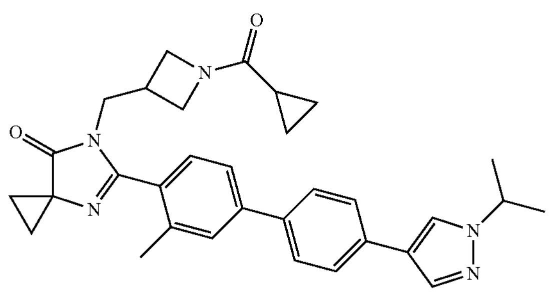 [SMILES: Cc1cc(-c2ccc(-c3cnn(C(C)C)c3)cc2)ccc1C1=NC2(CC2)C(=O)N1CC1CN(C(=O)C2CC2)C1] | 6-((1-(cyclopropanecarbonyl)azetidin-3-yl)methyl)-5-(4'-(1-isopropyl-1H-pyrazol-4-yl)-3-methyl-[1,1'-biphenyl]-4-yl)-4,6-diazaspiro[2.4]hept-4-en-7-one<br>$^1$H NMR (300 MHz, CHLOROFORM-d) δ ppm 0.47 (dd, J = 7.2, 3.6 Hz, 2 H), 0.62-0.74 (m, 2 H), 1.05 (td, J = 7.7, 3.4 Hz, 1 H), 1.31-1.42 (m, 6 H), 1.51-1.60 (m, 2 H), 1.61-1.70 (m, 2 H), 2.19 (s, 3 H), 2.44-2.62 (m, 1 H), 3.22-3.37 (m, 1 H), 3.41-3.52 (m, 1 H), 3.53-3.68 (m, 2 H), 3.73 (t, J = 9.1 Hz, 1 H), 3.99 (t, J = 8.2 Hz, 1 H), 4.34 (dt, J = 13.4, 6.7 Hz, 1 H), 7.18 (d, J = 7.8 Hz, 1 H), 7.29-7.47 (m, 6 H), 7.52 (s, 1 H), 7.62 (s, 1 H). MS m/z 522 (M + H)+ |
| 326 | 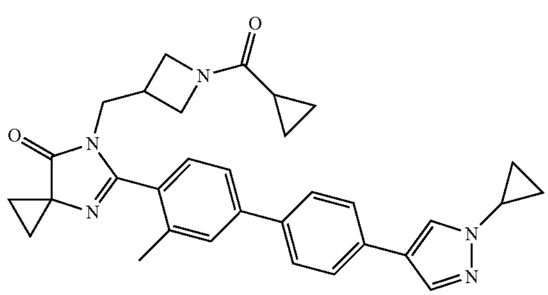 [SMILES: Cc1cc(-c2ccc(-c3cnn(C4CC4)c3)cc2)ccc1C1=NC2(CC2)C(=O)N1CC1CN(C(=O)C2CC2)C1] | 6-((1-(cyclopropanecarbonyl)azetidin-3-yl)methyl)-5-(4'-(1-cyclopropyl-1H-pyrazol-4-yl)-3-methyl-[1,1'-biphenyl]-4-yl)-4,6-diazaspiro[2.4]hept-4-en-7-one<br>$^1$H NMR (300 MHz, CHLOROFORM-d) δ ppm 0.70 (dd, J = 7.4, 3.8 Hz, 2 H), 0.86-0.95 (m, 2 H), 1.03-1.13 (m, 2 H), 1.13-1.27 (m, 2 H), 1.27-1.35 (m, 1 H), 1.75-1.83 (m, m2 H), 1.83-1.92 (m, 2 H), 2.42 (s, 3 H), 2.68-2.85 (m, 1 H), 3.54 (dd, J = 10.9, 6.3 Hz, 1 H), 3.62-3.75 (m, 2 H), 3.77-3.91 (m, 2 H), 3.96 (t, J = 9.1 Hz, 1 H), 4.22 (t, J = 8.3 Hz, 1 H), 7.41 (d, J = 8.0 Hz, 1 H), 7.54-7.68 (m, 6 H), 7.78 (s, 1 H), 7.82 (s, 1 H). MS m/z 520 (M + H)+ |
| 327 | 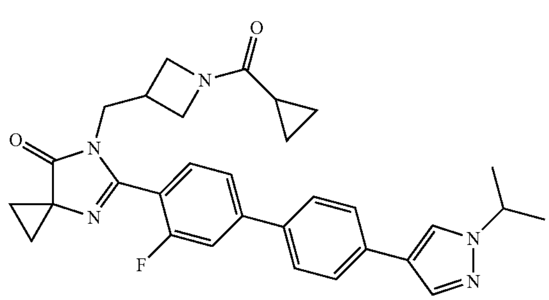 [SMILES: CC(C)n1cc(-c2ccc(-c3ccc(C4=NC5(CC5)C(=O)N4CC4CN(C(=O)C5CC5)C4)c(F)c3)cc2)cn1] | 6-((1-(cyclopropanecarbonyl)azetidin-3-yl)methyl)-5-(3-fluoro-4'-(1-isopropyl-1H-pyrazol-4-yl)-[1,1'-biphenyl]-4-yl)-4,6-diazaspiro[2.4]hept-4-en-7-one<br>$^1$H NMR (300 MHz, CHLOROFORM-d) δ ppm 0.70 (dd, J = 7.4, 3.7 Hz, 2 H), 0.87-0.97 (m, 2 H), 1.30 (td, J = 8.2, 3.9 Hz, 1 H), 1.60 (d, J = 6.7 Hz, 6 H), 1.76-1.86 (m, 2 H), 1.86-1.96 (m, 2 H), 2.77-2.97 (m, 1 H), 3.58 (dd, J = 9.7, 5.6 Hz, 1 H), 3.83 (d, J = 6.3 Hz, 1 H), 3.88-4.06 (m, 3 H), 4.26 (t, J = 8.3 Hz, 1 H), 4.58 (dt, J = 13.4, 6.7 Hz, 1 H), 7.49 (d, J = 11.7 Hz, 1 H), 7.54-7.70 (m, 6 H), 7.76 (s, 1 H), 7.86 (s, 1 H). MS m/z 526 (M + H)+ |

| ID No. | Structure | Compound Name & Physical Data |
|---|---|---|
| 328 | 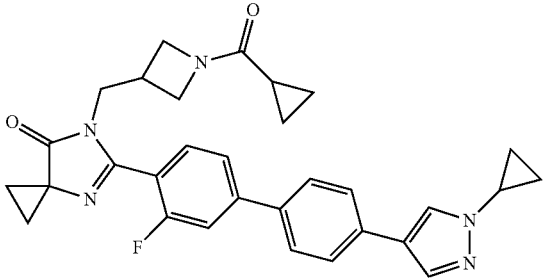 [SMILES: O=C(C1CC1)N1CC(CN2C(=O)C3(CC3)N=C2c2ccc(-c3ccc(-c4cnn(C5CC5)c4)cc3)cc2F)C1] | 6-((1-(cyclopropanecarbonyl)azetidin-3-yl)methyl)-5-(4'-(1-cyclopropyl-1H-pyrazol-4-yl)-3-fluoro-[1,1'-biphenyl]-4-yl)-4,6-diazaspiro[2.4]hept-4-en-7-one<br>$^1$H NMR (300 MHz, CHLOROFORM-d) δ ppm 0.65-0.75 (m, 2 H), 0.87-0.97 (m, 2 H), 1.04-1.14 (m, 2 H), 1.17-1.24 (m, 2 H), 1.30 (td, J = 8.2, 4.0 Hz, 1 H), 1.77-1.86 (m, 2 H), 1.86-1.95 (m, 2 H), 2.79-2.97 (m, 1 H), 3.58 (dd, J = 9.7, 5.7 Hz, 1 H), 3.68 (dt, J = 7.3, 3.5 Hz, 1 H), 3.83 (d, J = 6.3 Hz, 1 H), 3.88-4.06 (m, 3 H), 4.26 (t, J = 8.3 Hz, 1 H), 7.49 (d, J = 11.7 Hz, 1 H), 7.55-7.69 (m, 6 H), 7.79 (s, 1 H), 7.82 (s, 1 H). MS m/z 524 (M + H)+ |
| 329 | 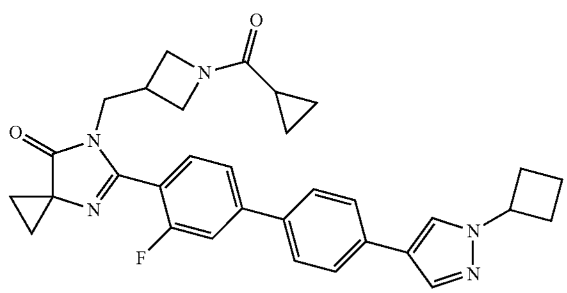 [SMILES: O=C(C1CC1)N1CC(CN2C(=O)C3(CC3)N=C2c2ccc(-c3ccc(-c4cnn(C5CCC5)c4)cc3)cc2F)C1] | 5-(4'-(1-cyclobutyl-1H-pyrazol-4-yl)-3-fluoro-[1,1'-biphenyl]-4-yl)-6-((1-(cyclopropanecarbonyl)azetidin-3-yl)methyl)-4,6-diazaspiro[2.4]hept-4-en-7-one<br>$^1$H NMR (300 MHz, CHLOROFORM-d) δ ppm 0.70 (dt, J = 7.2, 3.7 Hz, 2 H), 0.86-0.98 (m, 2 H), 1.30 (dq, J = 8.3, 4.0 Hz, 1 H), 1.77-1.85 (m, 2 H), 1.85-2.04 (m, 4 H), 2.47-2.72 (m, 4 H), 2.79-2.96 (m, 1 H), 3.58 (dd, J = 9.7, 5.7 Hz, 1 H), 3.74-3.86 (m, 1 H), 3.88-4.07 (m, 3 H), 4.26 (t, J = 8.2 Hz, 1 H), 4.84 (quin, J = 8.3 Hz, 1 H), 7.49 (d, J = 11.7 Hz, 1 H), 7.55-7.69 (m, 6 H), 7.78 (s, 1 H), 7.87 (s, 1 H). MS m/z 538 (M + H)+ |
| 330 | 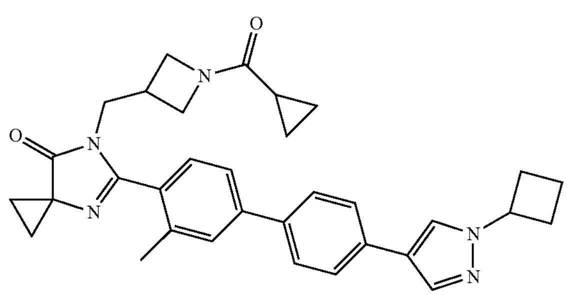 [SMILES: Cc1cc(-c2ccc(-c3cnn(C4CCC4)c3)cc2)ccc1C1=NC2(CC2)C(=O)N1CC1CN(C(=O)C2CC2)C1] | 5-(4'-(1-cyclobutyl-1H-pyrazol-4-yl)-3-methyl-[1,1'-biphenyl]-4-yl)-6-((1-(cyclopropanecarbonyl)azetidin-3-yl)methyl)4,6-diazaspiro[2.4]hept-4-en-7-one<br>$^1$H NMR (300 MHz, CHLOROFORM-d) δ ppm 0.70 (dd, J = 7.3, 3.7 Hz, 2 H), 0.91 (t, J = 3.5 Hz, 2 H), 1.26-1.34 (m, 1 H), 1.75-1.83 (m, 2 H), 1.83-2.01 (m, 4 H), 2.42 (s, 3 H), 2.48-2.68 (m, 4 H), 2.68-2.85 (m, 1 H), 3.52-3.60 (m, 1 H), 3.64-3.76 (m, 1 H), 3.77-3.92 (m, 2 H), 3.96 (t, J = 9.1 Hz, 1 H), 4.22 (t, J = 8.2 Hz, 1 H), 4.83 (t, J = 8.3 Hz, 1 H), 7.41 (d, J = 8.1 Hz, 1 H), 7.52-7.70 (m, 6 H), 7.77 (s, 1 H), 7.87 (s, 1 H). MS m/z 534 (M + H)+ |
| 331 | 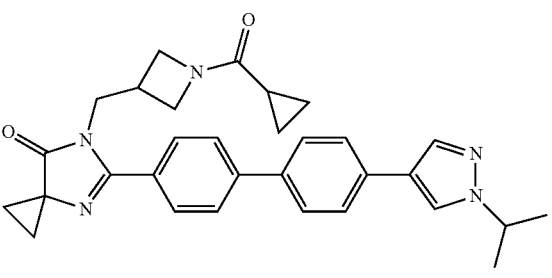 [SMILES: CC(C)n1cc(-c2ccc(-c3ccc(C4=NC5(CC5)C(=O)N4CC4CN(C(=O)C5CC5)C4)cc3)cc2)cn1] | 6-((1-(cyclopropanecarbonyl)azetidin-3-yl)methyl)-5-(4'-(1-isopropyl-1H-pyrazol-4-yl-[1,1'-biphenyl]-4-yl)-4,6-diazaspiro[2.4]hept-4-en-7-one<br>$^1$H NMR (300 MHz, CHLOROFORM-d) δ ppm 0.56-0.66 (m, 2 H), 0.79-0.87 (m, 2 H), 1.19-1.26 (m, 1 H), 1.49 (s, 3 H), 1.51 (s, 3 H), 1.66-1.75 (m, 2 H), 1.75-1.84 (m, 2 H), 2.70-2.83 (m, 1 H), 3.53 (dd, J = 9.9, 5.6 Hz, 1 H), 3.82-4.06 (m, 4 H), 4.15 (t, J = 8.3 Hz, 1 H), 4.48 (quin, J = 6.7 Hz, 1 H), 7.49-7.61 (m, 6 H), 7.64-7.73 (m, 3 H), 7.77 (s, 1 H). MS m/z 508 (M + H)+ |

| ID No. | Structure | Compound Name & Physical Data |
|---|---|---|
| 332 | 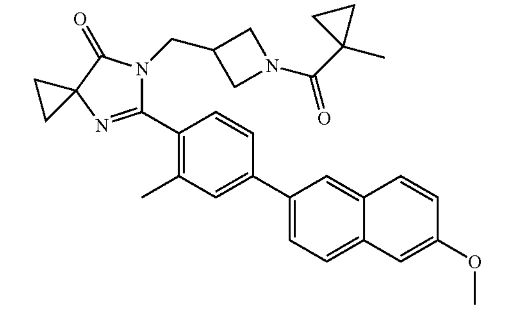 [SMILES: COc1ccc2cc(-c3ccc(C4=NC5(CC5)C(=O)N4CC4CN(C(=O)C5(C)CC5)C4)c(C)c3)ccc2c1] | 5-(4-(6-methoxynaphthalen-2-yl)-2-methylphenyl)-6-((1-(1-methylcyclopropanecarbonyl)azetidin-3-yl)methyl)-4,6-diazaspiro[2.4]hept-4-en-7-one<br>$^1$H NMR (300 MHz, CHLOROFORM-d) δ ppm 0.16-0.32 (m, 2 H), 0.74-0.83 (m, 2 H), 1.00 (s, 3 H), 1.55-1.65 (m, 2 H), 1.65-1.77 (m, 2 H), 2.25 (s, 3 H), 2.58 (d, J = 7.7 Hz, 1 H), 3.30-3.69 (m, 4 H), 3.79 (s, 3 H), 3.94 (br. s., 2 H), 6.97-7.07 (m, 2 H), 7.25 (d, J = 7.8 Hz, 1 H), 7.46-7.58 (m, 3 H), 7.66 (t, J = 8.0 Hz, 2 H), 7.84 (s, 1 H). MS m/z 508 (M + H)+ |
| 333 | 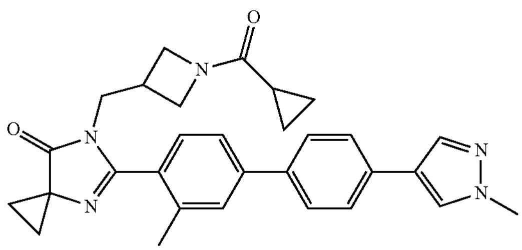 [SMILES: Cc1cc(-c2ccc(-c3cnn(C)c3)cc2)ccc1C1=NC2(CC2)C(=O)N1CC1CN(C(=O)C2CC2)C1] | 6-((1-(cyclopropanecarbonyl)azetidin-3-yl)methyl)-5-(3-methyl-4'-(1-methyl-1H-pyrazol-4-yl)-[1,1'-biphenyl]-4-yl)-4,6-diazaspiro[2.4]hept-4-en-7-one<br>$^1$H NMR (300 MHz, CHLOROFORM-d) δ ppm 0.54-0.67 (m, 2 H), 0.76-0.86 (m, 2 H), 1.20 (td, J = 8.0, 4.4 Hz, 1 H), 1.65-1.73 (m, 2 H), 1.75-1.82 (m, 2 H), 2.32 (s, 3 H), 2.60-2.75 (m, 1 H), 3.42-3.49 (m, 1 H), 3.54-3.66 (m, 1 H), 3.67-3.88 (m, 3 H), 3.89 (s, 3 H), 4.13 (t, J = 8.3 Hz, 1 H), 7.31 (d, J = 8.0 Hz, 1 H), 7.49 (d, J = 8.1 Hz, 4 H), 7.55 (d, J = 8.4 Hz, 2 H), 7.60 (s, 1 H), 7.74 (s, 1 H). MS m/z 494 (M + H)+ |
| 334 | 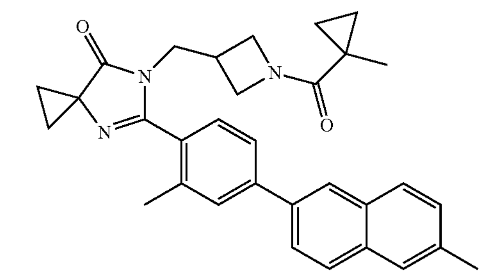 [SMILES: Cc1ccc2cc(-c3ccc(C4=NC5(CC5)C(=O)N4CC4CN(C(=O)C5(C)CC5)C4)c(C)c3)ccc2c1] | 5-(2-methyl-4-(6-methylnaphthalen-2-yl)phenyl)-6-((1-(1-methylcyclopropanecarbonyl)azetidin-3-yl)methyl)-4,6-diazaspiro[2.4]hept-4-en-7-one<br>$^1$H NMR (300 MHz, CHLOROFORM-d) δ ppm 0.22-0.32 (m, 2 H), 0.76-0.87 (m, 2 H), 1.02 (s, 3 H), 1.59-1.68 (m, 2 H), 1.68-1.77 (m, 2 H), 2.28 (s, 3 H), 2.40 (s, 3 H), 2.50-2.67 (m, 1 H), 3.60 (d, J = 7.4 Hz, 4 H), 3.97 (br. s., 2 H), 7.19-7.32 (m, 2 H), 7.48-7.60 (m, 4 H), 7.63-7.75 (m, 2 H), 7.89 (s, 1 H). MS m/z 492 (M + H)+ |
| 335 | 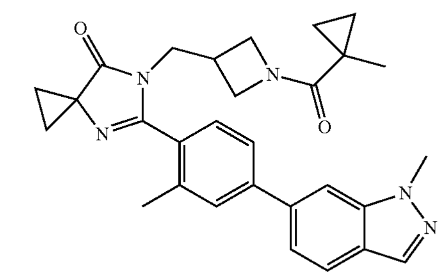 [SMILES: Cc1cc(-c2ccc3cnn(C)c3c2)ccc1C1=NC2(CC2)C(=O)N1CC1CN(C(=O)C2(C)CC2)C1] | 5-(2-methyl-4-(1-methyl-1H-indazol-6-yl)phenyl)-6-((1-(1-methylcyclopropanecarbonyl)azetidin-3-yl)methyl)-4,6-diazaspiro[2.4]hept-4-en-7-one<br>$^1$H NMR (300 MHz, CHLOROFORM-d) δ ppm 0.29-0.40 (m, 2 H), 0.83-0.93 (m, 2 H), 1.10 (s, 3 H), 1.65-1.74 (m, 2 H), 1.75-1.84 (m, 2 H), 2.35 (s, 3 H), 2.67 (br. s., 1 H), 3.54 (br. s., 1 H), 3.66 (t, J = 7.3 Hz, 4 H), 4.07 (s, 5 H), 7.34 (t, J = 7.8 Hz, 2 H), 7.48-7.60 (m, 3 H), 7.73 (d, J = 8.4 Hz, 1 H), 7.94 (s, 1 H). MS m/z 482 (M + H)+ |
| 336 | 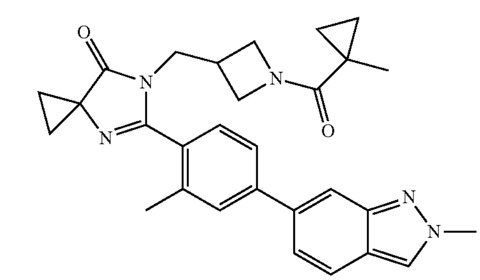 [SMILES: Cc1cc(-c2ccc3cn(C)nc3c2)ccc1C1=NC2(CC2)C(=O)N1CC1CN(C(=O)C2(C)CC2)C1] | 5-(2-methyl-4-(2-methyl-2H-indazol-6-yl)phenyl)-6-((1-(1-methylcyclopropanecarbonyl)azetidin-3-yl)methyl)-4,6-diazaspiro[2.4]hept-4-en-7-one<br>$^1$H NMR (300 MHz, CHLOROFORM-d) δ ppm 0.37-0.49 (m, 2 H), 0.92-1.02 (m, 2 H), 1.19 (s, 3 H), 1.75-1.83 (m, 2 H), 1.83-1.92 (m, 2 H), 2.43 (s, 3 H), 2.68-2.83 (m, 1 H), 3.76 (d, J = 7.6 Hz, 4 H), 4.13 (br. s., 2 H), 4.27 (s, 3 H), 7.33-7.47 (m, 2 H), 7.60-7.69 (m, 2 H), 7.76 (d, J = 8.8 Hz, 1 H), 7.94 (d, J = 6.9 Hz, 2 H). MS m/z 482 (M + H)+ |

-continued

| ID No. | Structure | Compound Name & Physical Data |
|---|---|---|
| 337 | 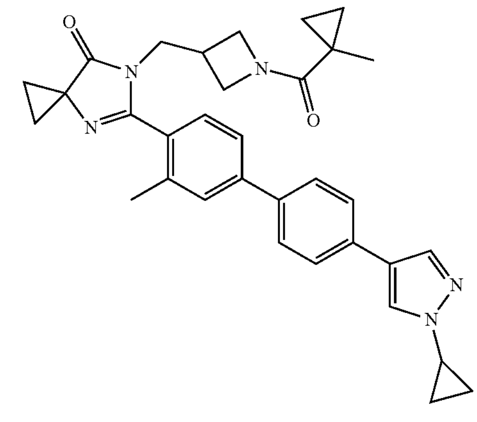 [SMILES: Cc1cc(-c2ccc(-c3cnn(C4CC4)c3)cc2)ccc1C1=NC2(CC2)C(=O)N1CC1CN(C(=O)C2(C)CC2)C1] | 5-(4'-(1-cyclopropyl-1H-pyrazol-4-yl)-3-methyl-[1,1'-biphenyl]-4-yl)-6-((1-(1-methylcyclopropanecarbonyl)azetidin-3-yl)methyl)-4,6-diazaspiro[2.4]hept-4-en-7-one<br>$^1$H NMR (300 MHz, CHLOROFORM-d) δ ppm 0.22-0.32 (m, 2 H), 0.77-0.85 (m, 2 H), 0.87-0.96 (m, 2 H), 0.99-1.10 (m, 5 H), 1.58-1.67 (m, 2 H), 1.68-1.75 (m, 2 H), 2.26 (s, 3 H), 2.49-2.68 (m, 1 H), 3.38-3.73 (m, 5 H), 3.96 (br. s., 2 H), 7.25 (d, J = 8.0 Hz, 1 H), 7.45 (q, J = 8.3 Hz, 6 H), 7.62 (s, 1 H), 7.66 (s, 1 H). MS m/z 534 (M + H)+ |
| 338 | 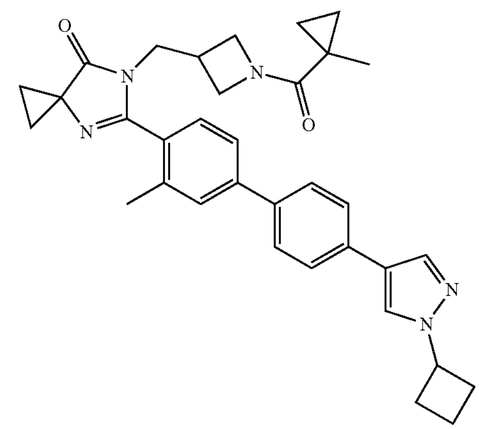 [SMILES: Cc1cc(-c2ccc(-c3cnn(C4CCC4)c3)cc2)ccc1C1=NC2(CC2)C(=O)N1CC1CN(C(=O)C2(C)CC2)C1] | 5-(4'-(1-cyclobutyl-1H-pyrazol-4-yl)-3-methyl-[1,1'-biphenyl]-4-yl)-6-((1-(1-methylcyclopropanecarbonyl)azetidin-3-yl)methyl)-4,6-diazaspiro[2.4]hept-4-en-7-one<br>$^1$H NMR (300 MHz, CHLOROFORM-d) δ ppm 0.29-0.38 (m, 2 H), 0.84-0.91 (m, 2 H), 1.09 (s, 3 H), 1.64-1.73 (m, 2 H), 1.78 (t, J = 3.4 Hz, 2 H), 1.79-1.90 (m, 2 H), 2.32 (s, 3 H), 2.38-2.58 (m, 4 H), 2.58-2.71 (m, 1 H), 3.53 (d, J = 6.7 Hz, 1 H), 3.65 (d, J = 7.4 Hz, 4 H), 4.02 (br. s., 2 H), 4.74 (quin, J = 8.4 Hz, 1 H), 7.31 (d, J = 8.0 Hz, 1 H), 7.44-7.59 (m, 6 H), 7.68 (s, 1 H), 7.77 (s, 1 H). MS m/z 548 (M + H)+ |
| 339 | 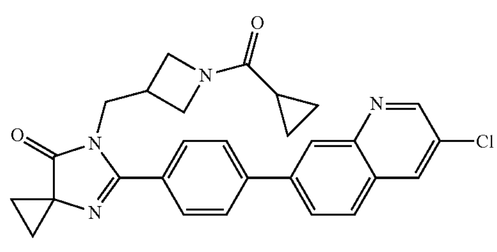 [SMILES: O=C(C1CC1)N1CC(CN2C(=O)C3(CC3)N=C2c2ccc(-c3ccc4cc(Cl)cnc4c3)cc2)C1] | 5-(4-(3-chloroquinolin-7-yl)phenyl)-6-((1-(cyclopropanecarbonyl)azetidin-3-yl)methyl)-4,6-diazaspiro[2.4]hept-4-en-7-one<br>$^1$H NMR (300 MHz, CHLOROFORM-d) δ ppm 0.62-0.75 (m, 2 H), 0.86-0.97 (m, 2 H), 1.30 (td, J = 8.2, 4.1 Hz, 1 H), 1.76-1.85 (m, 2 H), 1.86-1.95 (m, 2 H), 2.77-2.96 (m, 1 H), 3.63 (dd, J = 9.9, 5.5 Hz, 1 H), 3.90-4.06 (m, 3 H), 4.06-4.17 (m, 1 H), 4.26 (t, J = 8.3 Hz, 1 H), 7.75 (d, J = 8.2 Hz, 2 H), 7.86-7.97 (m, 4 H), 8.21 (d, J = 2.3 Hz, 1 H), 8.38 (s, 1 H), 8.89 (d, J = 2.5 Hz, 1 H). MS m/z 485 (M + H)+ |
| 340 | 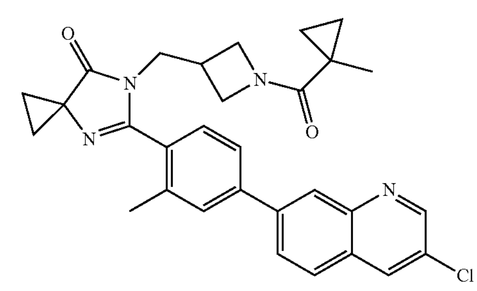 [SMILES: Cc1cc(-c2ccc3cc(Cl)cnc3c2)ccc1C1=NC2(CC2)C(=O)N1CC1CN(C(=O)C2(C)CC2)C1] | 5-(4-(3-chloroquinolin-7-yl)-2-methylphenyl)-6-((1-(1-methylcyclopropanecarbonyl)azetidin-3-yl)methyl)-4,6-diazaspiro[2.4]hept-4-en-7-one<br>$^1$H NMR (300 MHz, CHLOROFORM-d) δ ppm 0.29-0.39 (m, 2 H), 0.84-0.92 (m, 2 H), 1.10 (s, 3 H), 1.72 (t, J = 3.5 Hz, 2 H), 1.75-1.84 (m, 2 H), 2.36 (s, 3 H), 2.60-2.74 (m, 1 H), 3.67 (d, J = 7.4 Hz, 4 H), 4.06 (dt, J = 14.4, 7.3 Hz, 2 H), 7.40 (d, J = 7.7 Hz, 1 H), 7.58-7.68 (m, 2 H), 7.79 (s, 2 H), 8.11 (d, J = 2.1 Hz, 1 H), 8.27 (s, 1 H), 8.80 (d, J = 2.3 Hz, 1 H). MS m/z 513 (M + H)+ |

-continued

| ID No. | Structure | Compound Name & Physical Data |
|---|---|---|
| 341 | 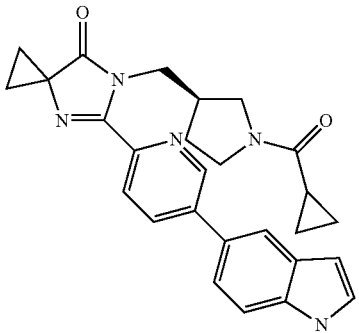 [SMILES: O=C(C1CC1)N1CC[C@@H](CN2C(=O)C3(CC3)N=C2c2ccc(-c3ccc4[nH]ccc4c3)cn2)C1] | (R)-5-(5-(1H-indol-5-yl)pyridin-2-yl)-6-((1-(cyclopropanecarbonyl)pyrrolidin-3-yl)methyl)-4,6-diazaspiro[2.4]hept-4-en-7-one<br>$^1$H NMR (300 MHz, CHLOROFORM-d) δ ppm 0.18-0.34 (m, 2 H), 0.44 (d, J = 4.3 Hz, 2 H), 1.03-1.30 (m, 2 H), 1.30-1.37 (m, 2 H), 1.39-1.48 (m, 2 H), 1.61 (m, J = 19.0, 12.5, 6.4, 6.4 Hz, 1 H), 2.22-2.39 (m, 0.5 H), 2.39-2.52 (m, 0.5 H), 2.72-2.83 (m, 0.5 H), 2.89-3.02 (m, 1 H), 3.11-3.25 (m, 1.5 H), 3.26-3.43 (m, 1 H), 3.73-4.04 (m, 2 H), 6.13 (br. s., 1 H), 6.80-6.92 (m, 1 H), 7.03 (d, J = 8.7 Hz, 1 H), 7.13 (d, J = 8.4 Hz, 1 H), 7.50 (s, 1 H), 7.62-7.72 (m, 1 H), 7.72-7.81 (m, 1 H), 8.53 (s, 1 H), 10.35 (br. s., 1 H). MS m/z 454 (M + H)+ |
| 342 | 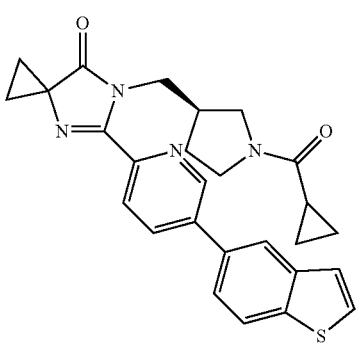 [SMILES: O=C(C1CC1)N1CC[C@@H](CN2C(=O)C3(CC3)N=C2c2ccc(-c3ccc4sccc4c3)cn2)C1] | (R)-5-(5-(benzo[b]thiophen-5-yl)pyridin-2-yl)-6-((1-(cyclopropanecarbonyl)pyrrolidin-3-yl)methyl)-4,6-diazaspiro[2.4]hept-4-en-7-one<br>$^1$H NMR (300 MHz, CHLOROFORM-d) δ ppm 0.56-0.69 (m, 2 H), 0.82-0.96 (m, 2 H), 1.55-1.73 (m, 2 H), 1.73-1.79 (m, 2 H), 1.80-1.86 (m, 2 H), 1.87-2.08 (m, 1 H), 2.67 (dt, J = 15.1, 7.4 Hz, 0.5 H), 2.74-2.89 (m, 0.5 H), 3.07-3.23 (m, 0.5 H), 3.27-3.38 (m, 1 H), 3.48-3.76 (m, 2.5 H), 4.12 (dd, J = 13.5, 8.4 Hz, 1 H), 4.21-4.42 (m, 2 H), 7.37 (d, J = 5.4 Hz, 1 H), 7.48 (d, J = 5.5 Hz, 1 H), 7.55 (d, J = 8.5 Hz, 1 H), 7.95 (d, J = 8.4 Hz, 1 H), 7.99-8.08 (m, 2 H), 8.11-8.21 (m, 1 H), 8.89 (br. s., 1 H). MS m/z 471 (M + H)+ |
| 343 | 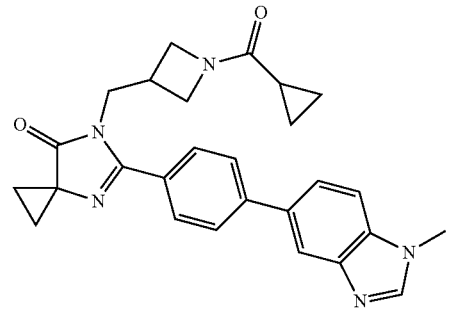 [SMILES: Cn1cnc2cc(-c3ccc(C4=NC5(CC5)C(=O)N4CC4CN(C(=O)C5CC5)C4)cc3)ccc21] | 6-((1-(cyclopropanecarbonyl)azetidin-3-yl)mehtyl)-5-(4-(1-methyl-1H-benzo[d]imidazol-5-yl)phenyl)-4,6-diazaspiro[2.4]hept-4-en-7-one<br>$^1$H NMR (300 MHz, CHLOROFORM-d) δ ppm 0.56-0.65 (m, 2 H), 0.76-0.87 (m, 2 H), 1.19-1.26 (m, 1 H), 1.68-1.74 (m, 2 H), 1.75-1.84 (m, 2 H), 2.69-2.86 (m, 1 H), 3.55 (dd, J = 9.8, 5.6 Hz, 1 H), 3.83 (s, 3 H), 3.85-4.07 (m, 4 H), 4.16 (t, J = 8.3 Hz, 1 H), 7.35-7.47 (m, 1 H), 7.49-7.63 (m, 3 H), 7.74 (d, J = 8.2 Hz, 2 H), 7.86 (s, 1 H), 7.99 (s, 1 H). MS m/z 454 (M + H)+ |
| 344 | 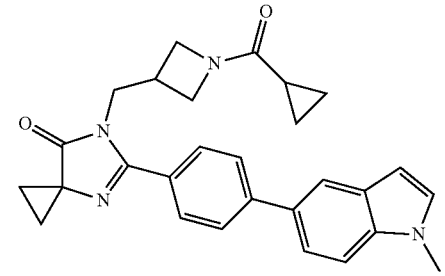 [SMILES: Cn1ccc2cc(-c3ccc(C4=NC5(CC5)C(=O)N4CC4CN(C(=O)C5CC5)C4)cc3)ccc21] | 6-((1-(cyclopropanecarbonyl)azetidin-3-yl)methyl)-5-(4-(1-methyl-1H-indol-5-yl)phenyl)-4,6-diazaspiro[2.4]hept-4-en-7-one<br>$^1$H NMR (300 MHz, CHLOROFORM-d) δ ppm 0.53-0.67 (m, 2 H), 0.76-0.88 (m, 2 H), 1.19-1.26 (m, 1 H), 1.64-1.74 (m, 2 H), 1.74-1.84 (m, 2 H), 2.66-2.86 (m, 1 H), 3.55 (dd, J = 9.8, 5.5 Hz, 1 H), 3.77 (s, 3 H), 3.81-4.07 (m, 4 H), 4.14 (t, J = 8.3 Hz, 1 H), 6.49 (d, J = 2.9 Hz, 1 H), 7.04 (d, J = 3.0 Hz, 1 H), 7.34 (d, J = 8.5 Hz, 1 H), 7.39-7.49 (m, 1 H), 7.56 (m, J = 8.2 Hz, 2 H), 7.73 (m, J = 8.1 Hz, 2 H), 7.82 (s, 1 H). MS m/z 453 (M + H)+ |

| ID No. | Structure | Compound Name & Physical Data |
|---|---|---|
| 345 | 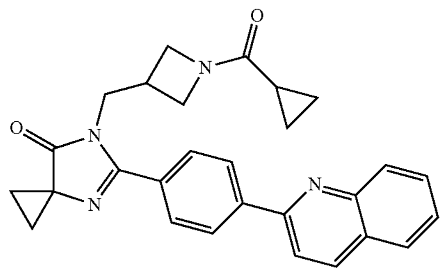 [SMILES: O=C(C1CC1)N1CC(CN2C(=O)C3(CC3)N=C2c2ccc(-c3ccc4ccccc4n3)cc2)C1] | 6-((1-(cyclopropanecarbonyl)azetidin-3-yl)methyl)-5-(4-(quinolin-2-yl)phenyl)-4,6-diazaspiro[2.4]hept-4-en-7-one<br>$^1$H NMR (300 MHz, CHLOROFORM-d) δ ppm 0.70 (dd, J = 7.6, 3.2 Hz, 2 H), 0.91 (br. s., 2 H), 1.30 (td, J = 8.0, 3.9 Hz, 1 H), 1.75-1.86 (m, 2 H), 1.86-1.97 (m, 2 H), 2.72-2.93 (m, 1 H), 3.62 (dd, J = 9.5, 5.6 Hz, 1 H), 3.88-4.17 (m, 4 H), 4.24 (t, J = 8.1 Hz, 1 H), 7.49-7.66 (m, 1 H), 7.70-7.84 (m, 3 H), 7.89 (d, J = 8.0 Hz, 1 H), 7.96 (d, J = 8.5 Hz, 1 H), 8.21 (d, J = 8.4 Hz, 1 H), 8.27-8.46 (m, 3 H). MS m/z 451 (M + H)+ |
| 346 | 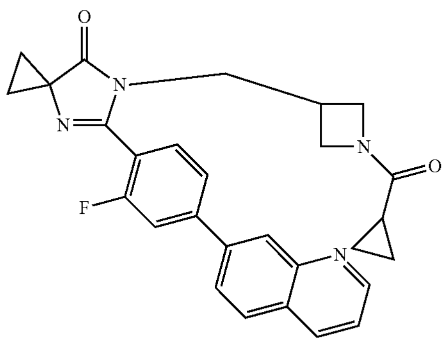 [SMILES: O=C(C1CC1)N1CC(CN2C(=O)C3(CC3)N=C2c2ccc(-c3ccc4cccnc4c3)cc2F)C1] | 6-((1-(cyclopropanecarbonyl)azetidin-3-yl)methyl)-5-(2-fluoro-4-(quinolin-7-yl)phenyl)-4,6-diazaqspiro[2.4]hept-4-en-7-one<br>$^1$H NMR (300 MHz, CHLOROFORM-d) δ ppm 0.42-0.54 (m, 2 H), 0.69 (dt, J = 7.2, 3.4 Hz, 2 H), 1.05-1.12 (m, 1 H), 1.54-1.65 (m, 2 H), 1.65-1.75 (m, 2 H), 2.61-2.76 (m, 1 H), 3.38 (dd, J = 9.9, 5.6 Hz, 1 H), 3.55-3.68 (m, 1 H), 3.68-3.85 (m, 3 H), 4.06 (t, J = 8.3 Hz, 1 H), 7.27 (dd, J = 8./2, 4.3 Hz, 1 H), 7.38-7.56 (m, 3 H), 7.57-7.67 (m, 1 H), 7.76 (d, J = 8.5 Hz, 1 H), 8.02 (d, J = 8.1 Hz, 1 H), 8.17 (s, 1 H), 8.69-8.86 (m, 1 H). MS m/z 469 (M + H)+ |
| 347 | 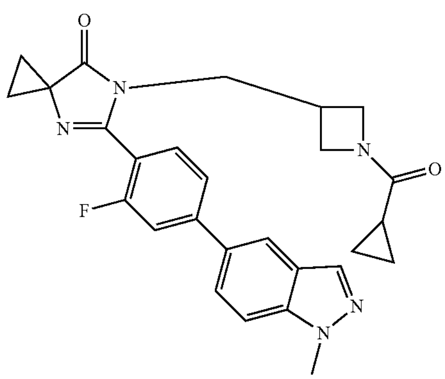 [SMILES: Cn1ncc2cc(-c3ccc(C4=NC5(CC5)C(=O)N4CC4CN(C(=O)C5CC5)C4)c(F)c3)ccc21] | 6-((1-(cyclopropanecarbonyl)azetidin-3-yl)methyl)-5-(2-fluoro-4-(1-methyl-1H-indazol-5-yl)phenyl)-4,6-diazaspiro[2.4]hept-4-en-7-one<br>$^1$H NMR (300 MHz, CHLOROFORM-d) δ ppm 0.61 (br. s., 2 H), 0.82 (br. s., 2 H), 1.16-1.27 (m, 1 H), 1.73 (br. s., 2 H), 1.81 (br. s., 2 H), 2.79 (br. s., 1 H), 3.43-3.56 (m, 1 H), 3.76 (br. s., 1 H), 3.80-3.97 (m, 3 H), 4.06 (s, 3 H), 4.18 (t, J = 8.1 Hz, 1 H), 7.35-7.48 (m, 2 H), 7.48-7.65 (m, 3 H), 7.90 (br. s., 1 H), 7.99 (s, 1 H). MS m/z 472 (M + H)+ |
| 348 | 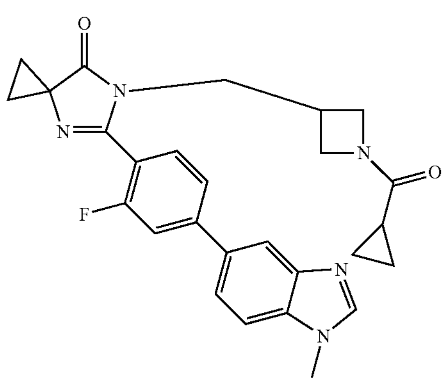 [SMILES: Cn1cnc2cc(-c3ccc(C4=NC5(CC5)C(=O)N4CC4CN(C(=O)C5CC5)C4)c(F)c3)ccc21] | 6-((1-(cyclopropanecarbonyl)azetidin-3-yl)methyl)-5-(2-fluoro-4-(1-methyl-1H-benzo[d]imidazol-5-yl)phenyl)-4,6-diazaspiro[2.4]hept-4-en-7-one<br>$^1$H NMR (300 MHz, CHLOROFORM-d) δ ppm 0.61 (dd, J = 7.3, 3.7 Hz, 2 H), 0.78-0.87 (m, 2 H), 1.21 (td, J = 8.0, 4.0 Hz, 1 H), 1.69-1.77 (m, 2 H), 1.77-1.88 (m, 2 H), 2.72-2.87 (m, 1 H), 3.51 (dd, J = 9.8, 5.6 Hz, 1 H), 3.68-3.80 (m, 1 H), 3.84 (s, 3 H), 3.85-3.97 (m, 3 H), 4.18 (t, J = 8.4 Hz, 1 H), 7.39-7.49 (m, 2 H), 7.49-7.58 (m, 3 H), 7.88 (s, 1 H), 7.908 (s, 1 H). MS m/z 472 (M + H)+ |

| ID No. | Structure | Compound Name & Physical Data |
|---|---|---|
| 349 | 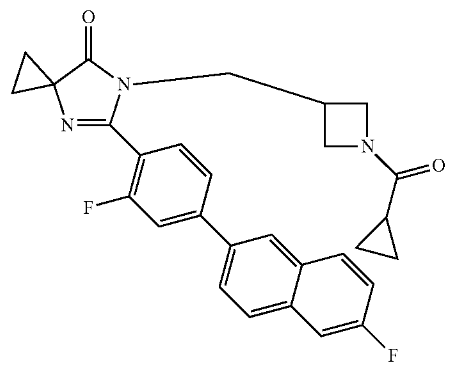 [SMILES: O=C(C1CC1)N1CC(CN2C(=O)C3(CC3)N=C2c2ccc(-c3ccc4cc(F)ccc4c3)cc2F)C1] | 6-((1-(cyclopropanecarbonyl)azetidin-3-yl)methyl)-5-(2-fluoro-4-(6-fluoronaphthalen-2-yl)phenyl)-4,6-diazaspiro[2.4]hept-4-en-7-one<br>$^1$H NMR (300 MHz, CHLOROFORM-d) δ ppm 0.56-0.66 (m, 2 H), 0.77-0.87 (m, 2 H), 1.19-1.27 (m, 1 H), 1.69-1.77 (m, 2 H), 1.79-1.87 (m, 2 H), 2.74-2.88 (m, 1 H), 3.49 (dd, J = 9.9, 5.6 Hz, 1 H), 3.68-3.79 (m, 1 H), 3.82-3.97 (m, 3 H), 4.19 (t, J = 8.4 Hz, 1 H), 7.27 (td, J = 8.7, 2.4 Hz, 1 H), 7.40-7.53 (m, 2 H), 7.53-7.64 (m, 2 H), 7.71 (s, 1 H), 7.79-7.91 (m, 2 H), 8.02 (s, 1 H). MS m/z 486 (M + H)+ |
| 350 | 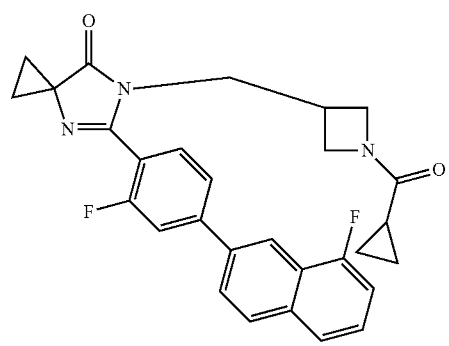 [SMILES: O=C(C1CC1)N1CC(CN2C(=O)C3(CC3)N=C2c2ccc(-c3ccc4cccc(F)c4c3)cc2F)C1] | 6-((1-(cyclopropanecarbonyl)azetidin-3-yl)methyl)-5-(2-fluoro-4-(8-fluoronaphthalen-2-yl)phenyl)-4,6-diazaspiro[2.4]hept-4-en-7-one<br>$^1$H NMR (300 MHz, CHLOROFORM-d) δ ppm 0.61 (dd, J = 7.1, 4.0 Hz, 2 H), 0.77-0.88 (m, 2 H), 1.19-1.26 (m, 1 H), 1.68-1.78 (m, 2 H), 1.78-1.89 (m, 2 H), 2.71-2.89 (m, 1 H), 3.51 (dd, J = 9.8, 5.6 Hz, 1 H), 3.67-3.80 (m, 1 H), 3.80-3.98 (m, 3 H), 4.19 (t, J = 8.3 Hz, 1 H), 7.08-7.17 (m, 1 H), 7.40 (td, J = 7.9, 5.6 Hz, 1 H), 7.50-7.67 (m, 4 H), 7.68-7.76 (m, 1 H), 7.92 (d, J = 8.4 Hz, 1 H), 8.28 (s, 1 H). MS m/z 486 (M + H)+ |
| 351 | 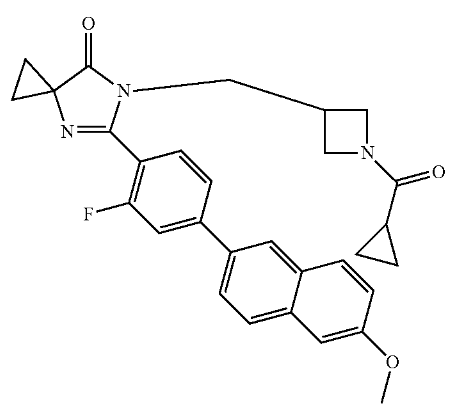 [SMILES: COc1ccc2cc(-c3ccc(C4=NC5(CC5)C(=O)N4CC4CN(C(=O)C5CC5)C4)c(F)c3)ccc2c1] | 6-((1-(cyclopropanecarbonyl)azetidin-3-yl)methyl)-5-(2-fluoro-4-(6-methoxynaphthalen-2-yl)phenyl)-4,6-diazaspiro[2.4]hept-4-en-7-one<br>$^1$H NMR (300 MHz, CHLOROFORM-d) δ ppm 0.56-0.65 (m, 2 H), 0.78-0.86 (m, 2 H), 1.20-1.27 (m, 1 H), 1.68-1.76 (m, 2 H), 1.82 (quin, J = 3.7 Hz, 2 H), 2.71-2.87 (m, 1 H), 3.50 (dd, J = 9.9, 5.6 Hz, 1 H), 3.68-3.79 (m, 1 H), 3.80-3.97 (m, 6 H), 4.18 (t, J = 8.3 Hz, 1 H), 7.08-7.17 (m, 2 H), 7.46-7.66 (m, 4 H), 7.77 (t, J = 9.1 Hz, 2 H), 7.95 (s, 1 H). MS m/z 498 (M + H)+ |
| 352 | 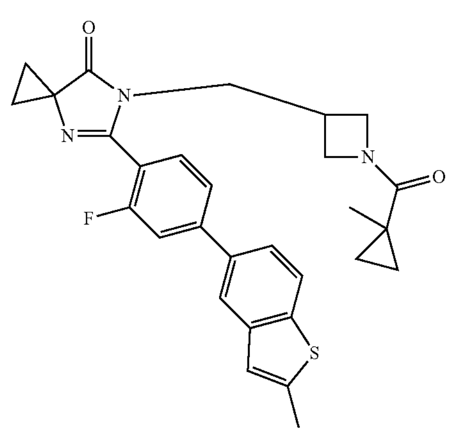 [SMILES: Cc1cc2cc(-c3ccc(C4=NC5(CC5)C(=O)N4CC4CN(C(=O)C5(C)CC5)C4)c(F)c3)ccc2s1] | 5-(2-fluoro-4-(2-methylbenzo[b]thiophen-5-yl)phenyl)-6-((1-(1-methylcyclopropanecarbonyl)azetidin-3-yl)methyl)-4,6-diazaspiro[2.4]hept-4-en-7-one $^1$H NMR (300 MHz, CHLOROFORM-d) δ ppm 0.44 (br. s., 2 H), 0.99 (br. s., 2 H), 1.20 (s, 3 H), 1.82 (br. s., 2 H), 1.90 (br. s., 2 H), 2.65 (s, 3 H), 2.85 (br. s., 1 H), 3.86 (br. s., 4 H), 4.17 (br. s., 2 H), 7.07 (s, 1 H), 7.46-7.58 (m, 2 H), 7.58-7.68 (m, 2 H), 7.83-7.96 (m, 2 H). MS m/z 502 (M + H)+ |

| ID No. | Structure | Compound Name & Physical Data |
|---|---|---|
| 353 | 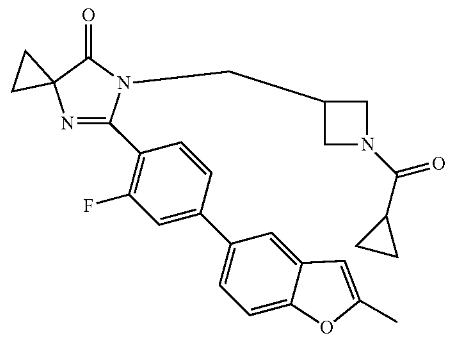 [SMILES: Cc1cc2cc(-c3ccc(C4=NC5(CC5)C(=O)N4CC4CN(C(=O)C5CC5)C4)c(F)c3)ccc2o1] | 6-((1-(cyclopropanecarbonyl)azetidin-3-yl)methyl)-5-(2-fluoro-4-(2-methylbenzofuran-5-yl)phenyl)-4,6-diazaspiro[2.4]hept-4-en-7-one<br>$^1$H NMR (300 MHz, DMSO-$d_6$) δ ppm 0.52-0.73 (m, 4 H), 1.32-1.45 (m, 1 H), 1.57-1.69 (m, 2 H), 1.77-1.89 (m, 2 H), 2.59-2.77 (m, 1 H), 3.41 (dd, J = 9.8, 5.8 Hz, 1 H), 3.69-3.90 (m, 4 H), 4.18 (t, J = 8.4 Hz, 1 H), 6.66 (s, 1 H), 7.57-7.86 (m, 5 H), 7.97 (s, 1 H). MS m/z 472 (M + H)+ |
| 354 | 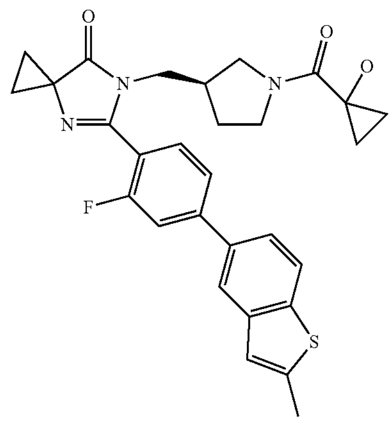 [SMILES: Cc1cc2cc(-c3ccc(C4=NC5(CC5)C(=O)N4C[C@@H]4CCN(C(=O)C5(O)CC5)C4)c(F)c3)ccc2s1] | (R)-5-(2-fluoro-4-(2-methylbenzo[b]thiophen-5-yl)phenyl)-6-((1-(1-hydroxycyclopropanecarbonyl)pyrrolidin-3-yl)methyl)-4,6-diazaspiro[2.4]hept-4-en-7-one<br>$^1$H NMR (300 MHz, CHLOROFORM-d) δ ppm 0.59-0.95 (m, 4 H), 1.47 (br. s., 2 H), 1.67-1.75 (m, 2 H), 1.77-1.90 (m, 3 H), 2.29-2.43 (m, 1 H), 2.55 (s, 3 H), 2.97 (br. s., 1 H), 3.41 (br. s., 2 H), 3.57 (br. s., 2.5 H), 3.71 (br. s., 0.5 H), 6.97 (s, 1 H), 7.36-7.47 (m, 2 H), 7.48-7.58 (m, 2 H), 7.77 (d, J = 8.4 Hz, 1 H), 7.79-7.87 (m, 1 H). MS m/z 518 (M + H)+ |
| 355 | 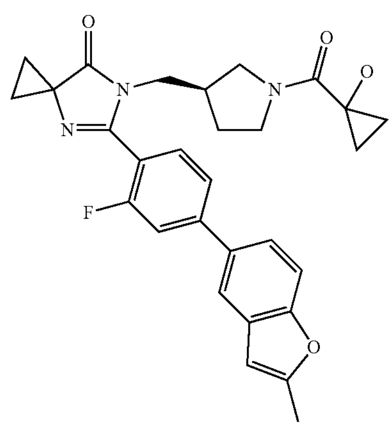 [SMILES: Cc1cc2cc(-c3ccc(C4=NC5(CC5)C(=O)N4C[C@@H]4CCN(C(=O)C5(O)CC5)C4)c(F)c3)ccc2o1] | (R)-5-(2-fluoro-4-(2-methylbenzofuran-5-yl)phenyl)-6-((1-(1-hydroxycyclopropanecarbonyl)pyrrolidin-3-yl)methyl)-4,6-diazaspiro[2.4]hept-4-en-7-one<br>$^1$H NMR (300 MHz, CHLOROFORM-d) δ ppm 0.79 (br. s., 2 H), 0.91-1.05 (m, 1 H), 1.11 (br. s., 1 H), 1.36 (br. s., 2 H), 1.66-1.74 (m, 2 H), 1.76-1.90 (m, 3 H), 2.27-2.39 (m, 1 H), 2.95 (br. s., 0.5 H), 3.17-3.50 (m, 2 H), 3.57 (br. s., 2.5 H), 3.71 (br. s., 1 H), 6.36 (s, 1 H), 7.33-7.44 (m, 3 H), 7.44-7.56 (m, 2 H), 7.63 (s, 1 H). MS m/z 502 (M + H)+ |
| 356 | 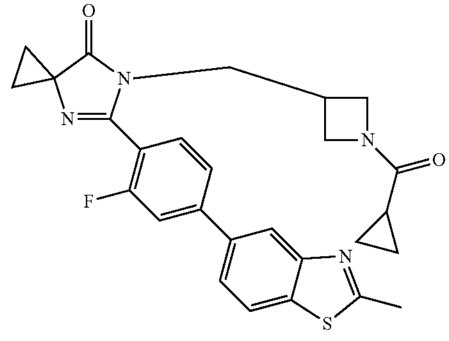 [SMILES: Cc1nc2cc(-c3ccc(C4=NC5(CC5)C(=O)N4CC4CN(C(=O)C5CC5)C4)c(F)c3)ccc2s1] | 6-((1-(cyclopropanecarbonyl)azetidin-3-yl)methyl)-5-(2-fluoro-4-(2-methylbenzo[d]thiazol-5-yl)phenyl)-4,6-diazaspiro[2.4]hept-4-en-7-one<br>$^1$H NMR (300 MHz, CHLOROFORM-d) δ ppm 0.64-0.75 (m, 2 H), 0.87-0.96 (m, 2 H), 1.26-1.37 (m, 1 H), 1.76-1.86 (m, 2 H), 1.86-1.96 (m, 2 H), 2.83-2.96 (m, 4 H), 3.60 (dd, J = 9.8, 5.7 Hz, 1 H), 3.85 (d, J = 6.3 Hz, 1 H), 3.91-4.06 (m, 3 H), 4.27 (t, J = 8.3 Hz, 1 H), 7.28 (s, 2 H), 7.54 (d, J = 11.5 Hz, 1 H), 7.60-7.70 (m, 3 H), 7.96 (d, J = 8.2 Hz, 1 H), 8.21 (d, J = 1.4 Hz, 1 H). MS m/z 489 (M + H)+ |

| ID No. | Structure | Compound Name & Physical Data |
|---|---|---|
| 357 | 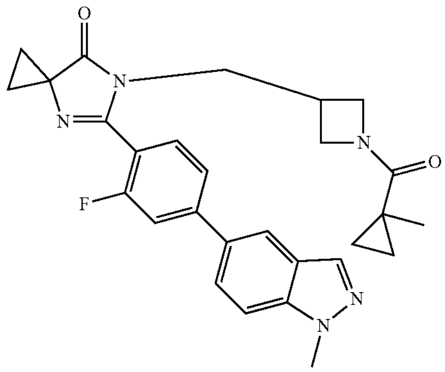 [SMILES: Cn1ncc2cc(-c3ccc(C4=NC5(CC5)C(=O)N4CC4CN(C(=O)C5(C)CC5)C4)c(F)c3)ccc21] | 5-(2-fluoro-4-(1-methyl-1H-indaozl-5-yl)phenyl)-6-((1-(1-methylcyclopropanecarbonyl)azetidin-3-yl)methyl)-4,6-diazaspiro[2.4]hept-4-en-7-one<br>¹H NMR (300 MHz, CHLOROFORM-d) δ ppm 0.24-0.34 (m, 2 H), 0.78-0.89 (m, 2 H), 1.05 (s, 3 H), 1.61-1.70 (m, 2 H), 1.70-1.81 (m, 2 H), 2.61-2.78 (m, 1 H), 3.70 (br. s., 4 H), 4.00 (br. s., 5 H), 7.31-7.42 (m, 2 H), 7.42-7.57 (m, 3 H), 7.84 (s, 1 H), 7.93 (s, 1 H). MS m/z 486 (M + H)+ |
| 358 | 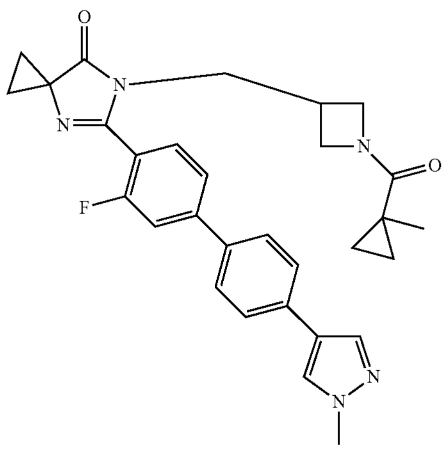 [SMILES: Cn1cc(-c2ccc(-c3ccc(C4=NC5(CC5)C(=O)N4CC4CN(C(=O)C5(C)CC5)C4)c(F)c3)cc2)cn1] | 5-(3-fluoro-4'-(1-methyl-1H-pyrazol-4-yl)-[1,1'-biphenyl]-4-yl)-6-((1-(1-methylcyclopropanecarbonyl)azetidin-3-yl)methyl)-4,6-diazaspiro[2.4]hept-4-en-7-one<br>¹H NMR (300 MHz, CHLOROFORM-d) δ ppm 0.40-0.49 (m, 2 H), 0.93-1.03 (m, 2 H), 1.20 (s, 3 H), 1.76-1.85 (m, 2 H), 1.86-1.96 (m, 2 H), 2.78-2.92 (m, 1 H), 3.81-3.94 (m, 3 H), 4.00 (br. s., 4 H), 4.16 (br. s., 2 H), 7.49 (d, J = 11.5 Hz, 1 H), 7.55-7.67 (m, 6 H), 7.71 (s, 1 H), 7.84 (s, 1 H). MS m/z 512 (M + H)+ |
| 359 | 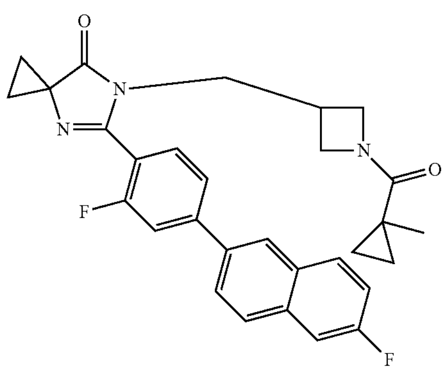 [SMILES: CC1(C(=O)N2CC(CN3C(=O)C4(CC4)N=C3c3ccc(-c4ccc5cc(F)ccc5c4)cc3F)C2)CC1] | 5-(2-fluoro-4-(6-fluoronaphthalen-2-yl)phenyl)-6-((1-(1-methylcyclopropanecarbonyl)azetidin-3-yl)methyl)-4,6-diazaspiro[2.4]hept-4-en-7-one<br>¹H NMR (300 MHz, CHLOROFORM-d) δ ppm 0.24-0.34 (m, 2 H), 0.80-0.88 (m, 2 H), 1.06 (s, 3 H), 1.62-1.72 (m, 2 H), 1.72-1.82 (m, 2 H), 2.62-2.80 (m, 1 H), 3.52 (br. s., 1 H), 3.57-3.82 (m, 3 H), 4.00 (br. s., 2 H), 7.16-7.26 (m, 1 H), 7.34-7.48 (m, 2 H), 7.48-7.57 (m, 2 H), 7.64 (s, 1 H), 7.73-7.85 (m, 2 H), 7.95 (s, 1 H). MS m/z 500 (M + H)+ |
| 361 | 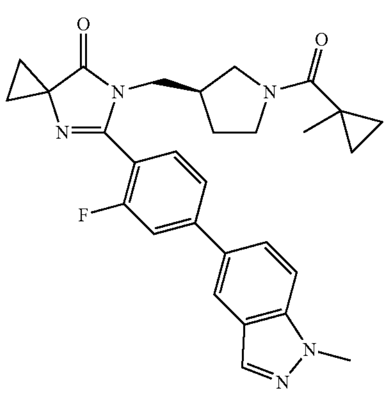 [SMILES: Cn1ncc2cc(-c3ccc(C4=NC5(CC5)C(=O)N4C[C@@H]4CCN(C(=O)C5(C)CC5)C4)c(F)c3)ccc21] | (R)-5-(2-fluoro-4-(1-methyl-1H-indazol-5-yl)phenyl)-6-((1-(1-methylcyclopropanecarbonyl)pyrrolidin-3-yl)methyl)-4,6-diazaspiro[2.4]hept-4-en-7-one<br>¹H NMR (300 MHz, CHLOROFORM-d) δ ppm 0.44-0.58 (m, 2 H), 0.80-0.99 (m, 2 H), 1.52-1.73 (m, 2 H), 1.78-1.87 (m, 2 H), 1.87-2.03 (m, 3 H), 2.50 (dt, J = 14.6, 7.3 Hz, 1 H), 2.96-3.12 (m, 1.5 H), 3.66-3.80 (m, 3.5 H), 4.15 (s, 3 H), 7.45-7.56 (m, 2 H), 7.58-7.72 (m, 3 H), 7.99 (s, 1 H), 8.09 (s, 1 H). MS m/z 500 (M + H)+ |

| ID No. | Structure | Compound Name & Physical Data |
|---|---|---|
| 362 | 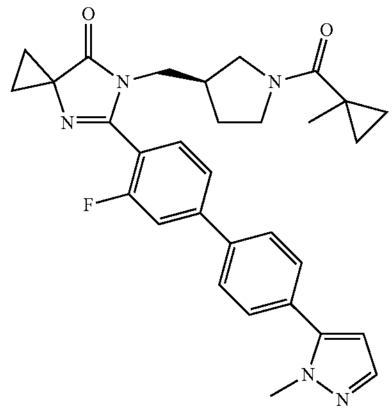 | (R)-5-(3-fluoro-4'-(1-methyl-1H-indaozl-5-yl)-[1,1'-biphenyl]-4-yl)-6-((1-(1-methylcyclopropanecarbonyl)pyrrolidin-3-yl)methyl)-4,6-diazaspiro[2.4]hept-4-en-7-one<br>¹H NMR (300 MHz, CHLOROFORM-d) δ ppm 0.52 (s, 2 H), 0.76-1.02 (m, 2 H), 1.23-1.28 (m, 3 H), 1.48-1.70 (m, 2 H), 1.75-1.87 (m, 2 H), 1.88-2.05 (m, 3 H), 2.40-2.59 (m, 1 H), 3.06 (br. s., 1 H), 3.27-3.48 (m, 1 H), 3.69 (br. s., 3 H), 3.97 (s, 3 H), 6.40 (d, J = 1.8 Hz, 1 H), 7.51 (d, J = 11.3 Hz, 1 H), 7.55-7.71 (m, 5 H), 7.74 (d, J = 8.2 Hz, 2 H). MS m/z 526 (M + H)+ |
| 363 | 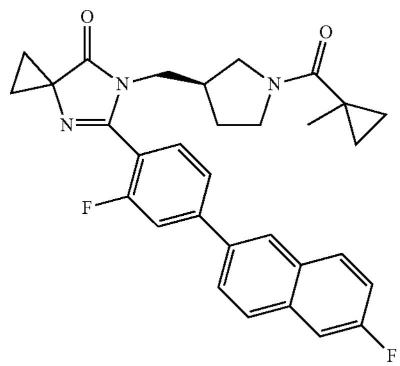 [SMILES: CC1(C(=O)N2CC[C@@H](CN3C(=O)C4(CC4)N=C3c3ccc(-c4ccc5cc(F)ccc5c4)cc3F)C2)CC1] | (R)-5-(2-fluoro-4-(6-fluoronaphthalen-2-yl)phenyl)-6-((1-(1-methylcyclopropancecarbonyl)pyrrolidin-3-yl)methyl)-4,6-diazaspiro[2.4]hept-4-en-7-one<br>¹H NMR (300 MHz, CHLOROFORM-d) δ ppm 0.35-0.46 (m, 2 H), 0.68-0.92 (m, 2 H), 1.09-1.16 (m, 3 H), 1.51 (br. s., 1 H), 1.65-1.78 (m, 2 H), 1.78-1.89 (m, 3 H), 2.40 (dt, J = 14.5, 7.3 Hz, 1 H), 2.98 (br. s., 1 H), 3.20-3.52 (m, 2.5 H), 3.60 (br. s., 2.5 H), 7.20-7.30 (m, 1 H), 7.38-7.53 (m, 2 H), 7.54-7.62 (m, 2 H), 7.68 (d, J = 7.8 Hz, 1 H), 7.78-7.89 (m, 2 H), 8.00 (s, 1 H). MS m/z 514 (M + H)+ |
| 364 | 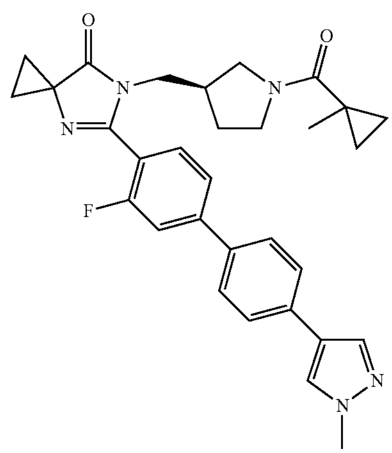 | (R)-5-(3-fluoro-4'-(1-methyl-1H-pyrazol-4-yl)-[1,1'-biphenyl]-4-yl)-6-((1-(1-methylcyclopropanecarbonyl)pyrrolidin-3-yl)methyl)-4,6-diazaspiro[2.4]hept-4-en-7-one<br>¹H NMR (300 MHz, CHLOROFORM-d) δ ppm 0.34-0.48 (m, 2 H), 0.70-0.90 (m, 2 H), 1.14 (s, 3 H), 1.51 (br. s., 1 H), 1.68-1.76 (m, 2 H), 1.77-1.90 (m, 3 H), 2.39 (dt, J = 14.3, 7.2 Hz, 1 H), 2.98 (br. s., 1 H), 3.40 (br. s., 2.5 H), 3.52-3.68 (m, 2.5 H), 3.90 (s, 3 H), 7.39 (d, J = 11.3 Hz, 1 H), 7.45-7.59 (m, 6 H), 7.61 (s, 1 H), 7.75 (s, 1 H). MS m/z 526 (M + H)+ |
| 365 | 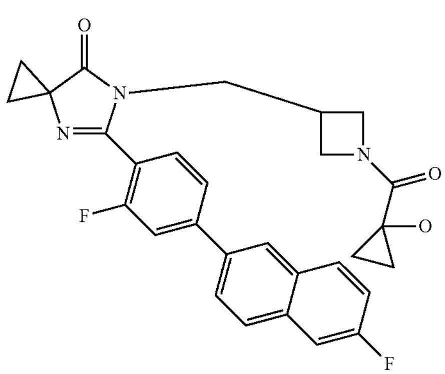 [SMILES: O=C(N1CC(CN2C(=O)C3(CC3)N=C2c2ccc(-c3ccc4cc(F)ccc4c3)cc2F)C1)C1(O)CC1] | 5-(2-fluoro-4-(6-fluoronaphthalen-2-yl)phenyl)-6-((1-(1-hydroxycyclopropanecarbonyl)azetidin-3-yl)methyl)-4,6-diazaspiro[2.4]hept-4-en-7-one<br>¹H NMR (300 MHz, CHLOROFORM-d) δ ppm 0.83 (d, J = 2.7 Hz, 2 H), 1.19 (br. s., 2 H), 1.67-1.77 (m, 2 H), 1.77-1.86 (m, 2 H), 2.68-2.84 (m, 1 H), 3.49-3.66 (m, 1 H), 3.80 (br. s., 2 H), 4.00 (br. s., 2 H), 4.36 (br. s., 1 H), 7.27 (td, J = 8.8, 2.3 Hz, 1 H), 7.39-7.53 (m, 2 H), 7.54-7.62 (m, 2 H), 7.70 (s, 1 H), 7.78-7.90 (m, 2 H), 8.01 (s, 1 H). MS m/z 502 (M + H)+ |

-continued

| ID No. | Structure | Compound Name & Physical Data |
|---|---|---|
| 366 | 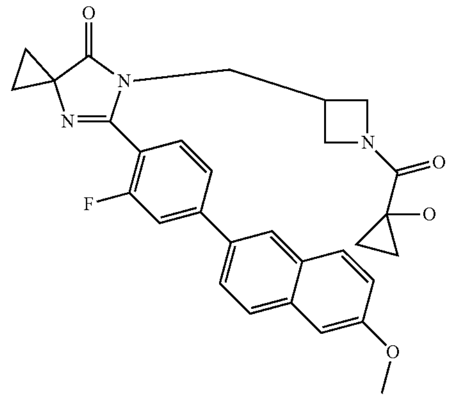 [SMILES: COc1ccc2cc(-c3ccc(C4=NC5(CC5)C(=O)N4CC4CN(C(=O)C5(O)CC5)C4)c(F)c3)ccc2c1] | 5-(2-fluoro-4-(6-methoxynaphthalen-2-yl)phenyl)-6-((1-(1-hydroxycyclopropanecarbonyl)azetidin-3-yl)methyl)-4,6-diazaspiro[2.4]hept-4-en-7-one<br>$^1$H NMR (300 MHz, CHLOROFORM-d) δ ppm 0.63-0.91 (m, 2 H), 1.65 (br. s., 1 H), 1.72 (br. s., 1 H), 1.81 (br. s., 2 H), 1.96 (br. s., 2 H), 2.73 (br. s., 1 H), 3.27-3.65 (m, 3 H), 3.70-4.09 (m, 6 H), 4.19-4.58 (m, 1 H), 7.03-7.28 (m, 2 H), 7.39-7.61 (m, 3 H), 7.64 (br. s., 1 H), 7.77 (br. s., 2 H), 7.95 (br. s., 1 H). MS m/z 514 (M + H)+ |
| 368 | 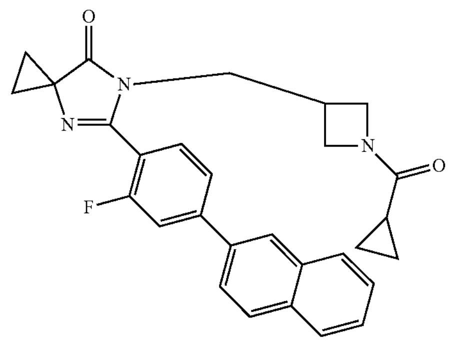 [SMILES: O=C(C1CC1)N1CC(CN2C(=O)C3(CC3)N=C2c2ccc(-c3ccc4ccccc4c3)cc2F)C1] | 6-((1-(1-cyclopropanecarbonyl)azetidin-3-yl)methyl)-5-(2-fluoro-4-(naphthalen-2-yl)phenyl)-4,6-diazaspiro[2.4]hept-4-en-7-one<br>$^1$H NMR (300 MHz, CHLOROFORM-d) δ ppm 0.72 (br. s., 2 H), 0.92 (br. s., 2 H), 1.32 (br. s., 1 H), 1.84 (br. s., 2 H), 1.92 (br. s., 2 H), 2.90 (br. s., 1 H), 3.61 (br. s., 1 H), 3.86 (br. s., 1 H), 3.98 (br. s., 3 H), 4.28 (br. s., 1 H), 7.59 (br. s., 5 H), 7.95 (br. s., 4 H), 8.13 (br. s., 1 H). MS m/z 468 (M + H)+ |
| 369 | 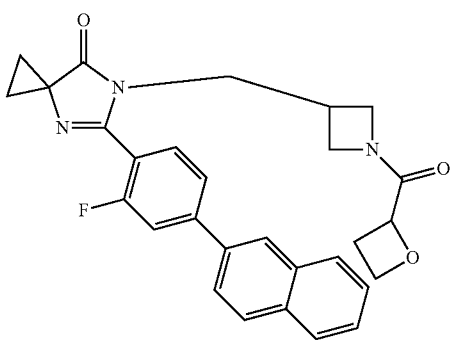 [SMILES: O=C(C1CCO1)N1CC(CN2C(=O)C3(CC3)N=C2c2ccc(-c3ccc4ccccc4c3)cc2F)C1] | 5-(2-fluoro-4-(6-fluoronaphthalen-2-yl)phenyl)-6-((1-(oxetan-2-carbonyl)azetidin-3-yl)methyl)-4,6-diazaspiro[2.4]hept-4-en-7-one<br>$^1$H NMR (300 MHz, CHLOROFORM-d) δ ppm 1.75-1.86 (m, 2 H), 1.86-1.97 (m, 2 H), 2.69-3.03 (m, 3 H), 3.62-3.74 (m, 1 H), 3.79-3.96 (m, 2 H), 4.02-4.16 (m, 2 H), 4.21-4.32 (m, 1 H), 4.47-4.70 (m, 2 H), 5.06-5.20 (m, 1 H), 7.36 (td, J = 8.7, 2.5 Hz, 1 H), 7.49-7.63 (m, 2 H), 7.64-7.72 (m, 2 H), 7.78 (d, J = 7.8 Hz, 1 H), 7.88-7.99 (m, 2 H), 8.11 (s, 1 H). MS m/z 502 (M + H)+ |
| 370 | 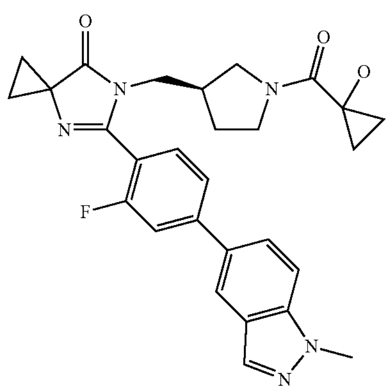 [SMILES: Cn1ncc2cc(-c3ccc(C4=NC5(CC5)C(=O)N4C[C@@H]4CCN(C(=O)C5(O)CC5)C4)c(F)c3)ccc21] | (R)-5-(2-fluoro-4-(1-methyl-1H-indazol-5-yl)phenyl)-6-((1-(1-hydroxycyclopropanecarbonyl)pyrrolidin-3-yl)methyl)-4,6-diazaspiro[2.4]hept-4-en-7-one<br>$^1$H NMR (300 MHz, CHLOROFORM-d) δ ppm 0.72-0.85 (m, 2 H), 0.88-1.01 (m, 1 H), 1.05 (br. s., 1 H), 1.46 (br. s., 1.5 H), 1.64-1.76 (m, 2.5 H), 1.76-1.92 (m, 3 H), 2.28-2.46 (m, 1 H), 2.96 (br. s., 0.5 H), 3.27 (br. s., 1 H), 3.57 (br. s., 3 H), 3.71 (br. s., 1.5 H), 4.05 (s, 3 H), 7.33-7.46 (m, 2 H), 7.47-7.63 (m, 3 H), 7.90 (s, 1 H), 7.98 (s, 1 H). MS m/z 502 (M + H)+ |

| ID No. | Structure | Compound Name & Physical Data |
|---|---|---|
| 371 | 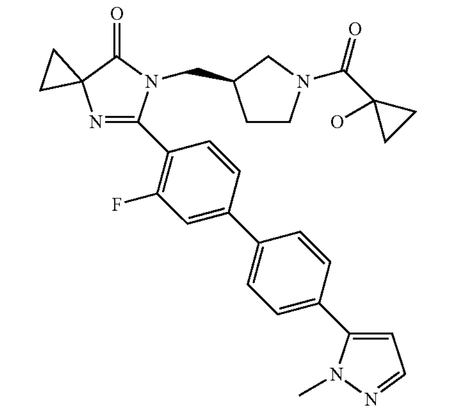 [SMILES: Cn1nccc1-c1ccc(-c2ccc(C3=NC4(CC4)C(=O)N3C[C@@H]3CCN(C(=O)C4(O)CC4)C3)c(F)c2)cc1] | (R)-5-(3-fluoro-4'-(1-methyl-1H-pyrazol-5-yl)-[1,1'-biphenyl]-4-yl)-6-((1-(1-hydroxycyclopropanecarbonyl)pyrrolidin-3-yl)methyl)-4,6-diazaspiro[2.4]hept-4-en-7-one<br>$^1$H NMR (300 MHz, CHLOROFORM-d) δ ppm 0.72-.087 (m, 2 H), 0.91-1.14 (m, 2 H), 1.43 (br. s., 1 H), 1.67-1.77 (m, 2 H), 1.78-1.89 (m, 3 H), 2.27-2.44 (m, 1 H), 2.95 (br. s., 0.5 H), 3.29 (br. s., 2 H), 3.50-3.67 (m, 2.5 H), 3.78 (br. s., 1 H), 3.87 (s, 4 H), 6.30 (d, J = 1.6 Hz, 1 H), 7.42 (d, J = 11.1 Hz, 1 H), 7.45-7.61 (m, 5 H), 7.64 (d, J = 8.2 Hz, 2 H). MS m/z 528 (M + H)+ |
| 372 | 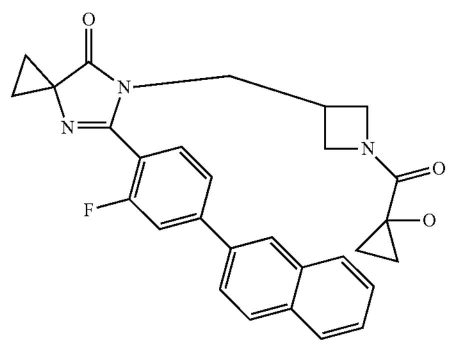 [SMILES: O=C(N1CC(CN2C(=O)C3(CC3)N=C2c2ccc(-c3ccc4ccccc4c3)cc2F)C1)C1(O)CC1] | 5-(2-fluoro-4-(naphthalen-2-yl)phenyl)-6-((1-(1-hydroxycyclopropanecarbbonyl)azetidin-3-yl)methyl)-4,6-diazaspiro[2.4]hept-4-en-7-one<br>$^1$H NMR (300 MHz, CHLOROFORM-d) δ ppm 0.82 (br. s., 2 H), 1.13 (br. s., 2 H), 1.72 (br. s., 2 H), 1.81 (br. s., 2 H), 2.61-2.84 (m, 1 H), 3.07 (br. s., 1 H), 3.57 (br. s., 1 H), 3.80 (br. s., 2 H), 3.97 (br. s., 2 H), 4.38 (br. s., 1 H), 7.41-7.72 (m, 6 H), 7.76-7.96 (m, 3 H), 8.02 (s, 1 H). MS m/z 484 (M + H)+ |
| 373 | 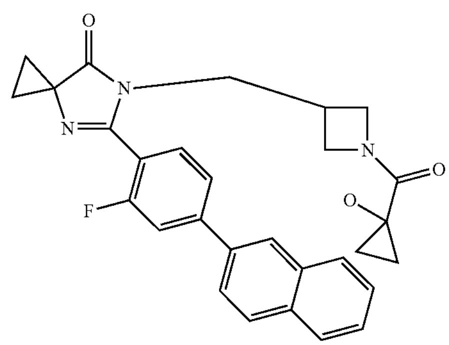 [SMILES: O=C(N1CC(CN2C(=O)C3(CC3)N=C2c2ccc(-c3ccc4ccccc4c3)cc2F)C1)C1(O)CC1] | 6-(3-fluoro-4-(6-((1-(1-hydroxycyclopropanecarbonyl)azetidin-3-yl)methyl)-7-oxo-4,6-diazaspiro[2.4]hept-4-en-5-yl)phenyl)-2-naphthonitrile<br>$^1$H NMR (300 MHz, CHLOROFORM-d) δ ppm 0.85 (br. s., 2 H), 1.17-1.28 (m, 2 H), 1.69-1.78 (m, 2 H), 1.78-1.88 (m, 2 H), 2.77 (br. s., 1 H), 3.57 (br. s., 1 H), 3.71-3.88 (m, 2 H), 4.00 (br. s., 2 H), 4.35 (br. s., 1 H), 7.52 (d, J = 10.7 Hz, 1 H), 7.56-7.66 (m, 3 H), 7.76-7.84 (m, 1 H), 7.90-8.01 (m, 2 H), 8.06 (s, 1 H), 8.22 (s, 1 H). MS m/z 509 (M + H)+ |
| 374 | 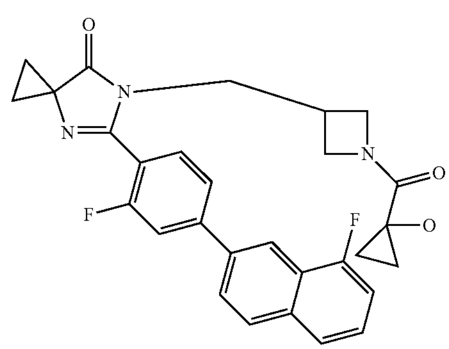 [SMILES: O=C(N1CC(CN2C(=O)C3(CC3)N=C2c2ccc(-c3ccc4cccc(F)c4c3)cc2F)C1)C1(O)CC1] | 5-(2-fluoro-4-(8-fluoronaphthalen-2-yl)phenyl)-6-((1-(1-hydroxycyclopropanecarbonyl)azetidin-3-yl)methyl)-4,6-diazaspiro[2.4]hept-4-en-7-one<br>$^1$H NMR (300 MHz, CHLOROFORM-d) δ ppm 0.83 (d, J = 3.0 Hz, 2 H), 1.14-1.21 (m , 2 H), 1.67-1.77 (m, 2 H), 1.77-1.89 (m, 2 H), 2.64-2.68 (m, 2 H), 3.57 (br. s., 1 H), 3.80 (br. s., 2 H), 4.00 (br. s., 2 H), 4.38 (br. s., 1 H), 7.15 (dd, J = 10.4, 7.9 Hz, 1 H), 7.40 (td, J = 7.9, 5.4 Hz, 1 H), 7.48-7.67 (m, 4 H), 77.2 (dd, J = 8.6, 1.7 Hz, 1 H), 7.90 (s, 1 H), 8.28 (s, 1 H). MS m/z 502 (M + H)+ |

| ID No. | Structure | Compound Name & Physical Data |
|---|---|---|
| 375 | 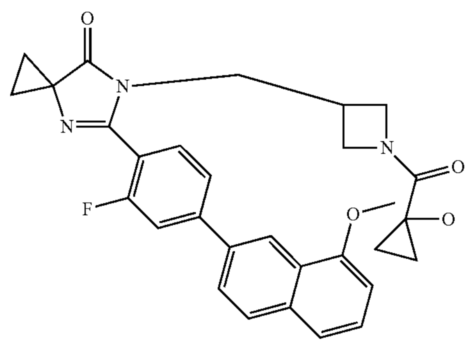 [SMILES: COc1cccc2ccc(-c3ccc(C4=NC5(CC5)C(=O)N4CC4CN(C(=O)C5(O)CC5)C4)c(F)c3)cc12] | 5-(2-fluoro-4-(8-methoxynaphthalen-2-yl)phenyl)-6-((1-(1-hydroxycyclopropanecarbonyl)azetidin-3-yl)methyl)-4,6-diazaspiro[2.4]hept-4-en-7-one<br>$^1$H NMR (300 MHz, CHLOROFORM-d) δ ppm 0.82 (br. s., 2 H), 1.14 (br. s., 2 H), 1.72 (br. s., 2 H), 1.81 (br. s., 2 H), 2.73 (br. s., 1 H), 2.90 (br. s., 1 H), 3.57 (br. s., 1 H), 3.67-3.85 (m, 2 H), 3.85-4.11 (m, 5 H), 4.35 (br. s., 1 H), 6.80 (br. s., 1 H), 7.39 (br. s., 2 H), 7.46-7.59 (m, 2 H), 7.59-7.72 (m, 2 H), 7.84 (d, J = 8.4 Hz, 1 H), 8.46 (br. s., 1 H). MS m/z 514 (M + H)+ |
| 377 | 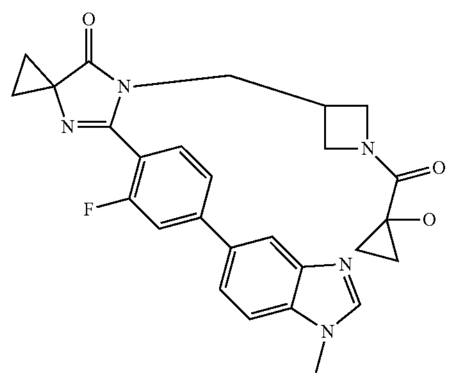 [SMILES: Cn1cnc2cc(-c3ccc(C4=NC5(CC5)C(=O)N4CC4CN(C(=O)C5(O)CC5)C4)c(F)c3)ccc21] | 5-(2-fluoro-4-(1-methyl-1H-benzo[d]imidazol-5-yl)phenyl)-6-((1-(1-hydroxycyclopropanecarbonyl)azetidin-3-yl)methyl)-4,6-diazaspiro[2.4]hept-4-en-7-one<br>$^1$H NMR (300 MHz, DMSO-d$_6$) δ ppm 0.39-0.51 (m, 2 H), 0.64-0.75 (m, 2 H), 1.38 (d, J = 3.7 Hz, 2 H), 1.57 (d, J = 3.6 Hz, 2 H), 2.34-2.51 (m, 1 H), 3.18 (br. s., 1 H), 3.53 (br. s., 3 H), 3.65 (s, 3 H), 3.79 (br. s., 1 H), 4.04-4.21 (m, 1 H), 7.40-7.66 (m, 6 H), 7.87 (s, 1 H), 8.03 (s, 1 H). MS m/z 488 (M + H)+ |
| 378 | 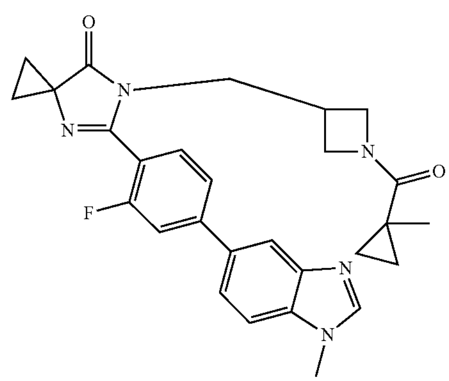 [SMILES: Cn1cnc2cc(-c3ccc(C4=NC5(CC5)C(=O)N4CC4CN(C(=O)C5(C)CC5)C4)c(F)c3)ccc21] | 5-(2-fluoro-4-(1-methyl-1H-benzo[d]imidazol-5-yl)phenyl)-6-((1-(1-methylcyclopropanecarbonyl)azetidin-3-yl)methyl)-4,6-diazaspiro[2.4]hept-4-en-7-one<br>$^1$H NMR (300 MHz, CHLOROFORM-d) δ ppm 0.29-0.39 (m, 2 H), 0.89 (br. s., 2 H), 1.67-1.76 (m, 2 H), 1.77-1.85 (m, 2 H), 2.65-2.83 (m, 1 H), 3.50-3.82 (m, 4 H), 3.83 (s, 3 H), 4.06 (br. s., 2 H), 7.37-7.48 (m, 2 H), 7.48-7.59 (m, 3 H), 7.87 (s, 1 H), 7.97 (s, 1 H). MS m/z 486 (M + H)+ |
| 379 | 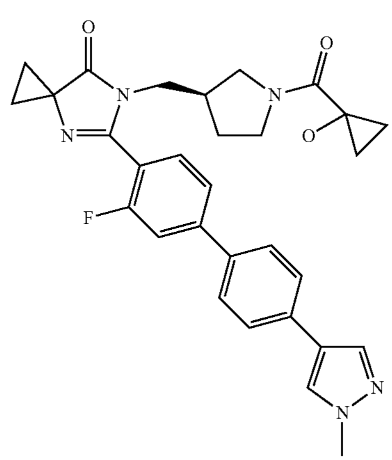 [SMILES: Cn1cc(-c2ccc(-c3ccc(C4=NC5(CC5)C(=O)N4C[C@@H]4CCN(C(=O)C5(O)CC5)C4)c(F)c3)cc2)cn1] | (R)-5-(3-fluoro-4'-(1-methyl-1H-pyrazol-4-yl)-[1,1'-biphenyl]-4-yl)-6-((1-(1-hydroxycyclopropanecarbonyl)pyrrolidin-3-yl)methyl)-4,6-diazaspiro[2.4]hept-4-en-7-one<br>$^1$H NMR (300 MHz, CHLOROFORM-d) δ ppm 0.69-0.85 (m, 2 H), 0.88-0.99 (m, 1 H), 1.03 (br. s., 1 H), 1.28-1.55 (m, 1 H), 1.66-1.76 (m, 2 H), 1.76-1.89 (m, 3 H), 2.34 (dt, J = 14.2, 7.1 Hz, 0.5 H), 3.29 (br. s., 2 H), 3.49-3.66 (m, 2.5 H), 3.75 (br. s., 1 H), 3.89 (s, 3 H), 3.96-4.17 (m, 1 H), 7.38 (d, J = 11.3 Hz, 1 H), 7.43-7.58 (m, 6 H), 7.60 (s, 1 H), 7.74 (s, 1 H). MS m/z 528 (M + H)+ |

-continued

| ID No. | Structure | Compound Name & Physical Data |
|---|---|---|
| 380 | 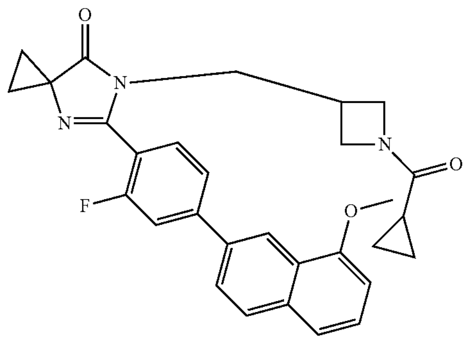 [SMILES: COc1cccc2ccc(-c3ccc(C4=NC5(CC5)C(=O)N4CC4CN(C(=O)C5CC5)C4)c(F)c3)cc12] | 6-((1-(cyclopropanecarbonyl)azetidin-3-yl)methyl)-5-(2-fluoro-4-(8-methoxynaphthalen-2-yl)phenyl)-4,6-diazaspiro[2.4]hept-4-en-7-one<br>$^1$H NMR (300 MHz, CHLOROFORM-d) δ ppm 0.62-0.77 (m, 2 H), 0.91 (br. s., 2 H), 1.30 (dd, J = 7.8, 3.6 Hz, 1 H), 1.82 (br. s., 2 H), 1.91 (br. s., 2 H), 2.78-2.99 (m, 1 H), 3.60 (dd, J = 9.1, 5.6 Hz, 1 H), 3.77-3.88 (m, 1 H), 3.88-4.03 (m, 3 H), 4.07 (s, 3 H), 4.26 (t, J = 8.2 Hz, 1 H), 6.90 (d, J = 4.3 Hz, 1 H), 7.41-7.53 (m, 2 H), 7.57-7.69 (m, 2 H), 7.69-7.81 (m, 2 H), 7.93 (d, J = 8.5 Hz, 1 H), 8.55 (s, 1 H). MS m/z 498 (M + H)+ |
| 381 | 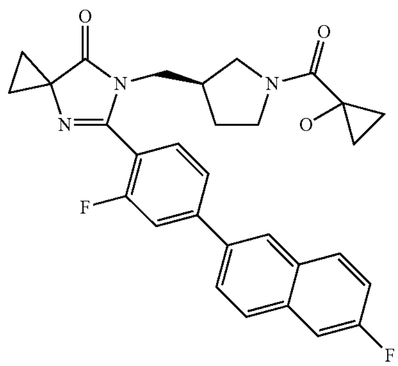 [SMILES: O=C(N1CC[C@@H](CN2C(=O)C3(CC3)N=C2c2ccc(-c3ccc4cc(F)ccc4c3)cc2F)C1)C1(O)CC1] | (R)-5-(2-fluoro-4-(6-fluoronaphthalen-2-yl)phenyl)-6-((1-(1-hydroxycyclopropanecarbonyl)pyrrolidin-3-yl)methyl)-4,6-diazaspiro[2.4]hept-4-en-7-one<br>$^1$H NMR (300 MHz, CHLOROFORM-d) δ ppm 0.00 (br. s., 2 H), 0.11-0.31 (m, 2 H), 0.62-0.76 (m, 1 H), 0.86-0.98 *nm m2 H), 0.98-1.11 (m, 3 H), 1.59 (br. s., 1 H), 2.22 (br. s., 1 H), 2.48-2.65 (m, 2 H), 2.86 (d, J = 7.3 Hz, 3 H), 2.98-3.20 (m, 1 H), 5.03 (br. s., 1 H), 6.57 (td, J = 8.7, 2.3 Hz, 1 H), 6.77 (dd, J = 9.8, 2.2 Hz, 1 H), 6.84-7.00 (m, 3 H), 7.02-7.11 (m, 1 H), 7.12-7.28 (m, 2 H), 7.43 (s, 1 H). MS m/z 516 (M + H)+ |
| 382 | 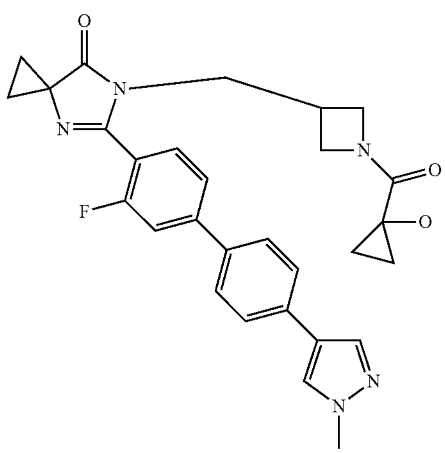 [SMILES: Cn1cc(-c2ccc(-c3ccc(C4=NC5(CC5)C(=O)N4CC4CN(C(=O)C5(O)CC5)C4)c(F)c3)cc2)cn1] | 5-(3-fluoro-4'-(1-methyl-1H-pyrazol-4-yl)-[1,1'-biphenyl]-4-yl)-6-((1-(1-hydroxycyclopropanecarbonyl)azetidin-3-yl)methyl)-4,6-diazaspiro[2.4]hept-4-en-7-one<br>$^1$H NMR (300 MHz, CHLOROFORM-d) δ ppm 0.76-0.89 (m, 2 H), 1.14-1.23 (m, 2 H), 1.66-1.76 (m, 2 H), 1.76-1.87 (m, 2 H), 2.65-2.77 (m, 1 H), 2.81 (br. s., 1 H), 3.58 (br. s., 1 H), 3.78 (br. s., 2 H), 3.90 (s, 3 H), 4.01 (br. s., 2 H), 4.36 (br. s., 1 H), 7.39 (d, J = 11.5 Hz, 1 H), 7.45-7.58 (m, 6 H), 7.61 (s, 1 H), 7.75 (s, 1 H). MS m/z 514 (M + H)+ |
| 383 | 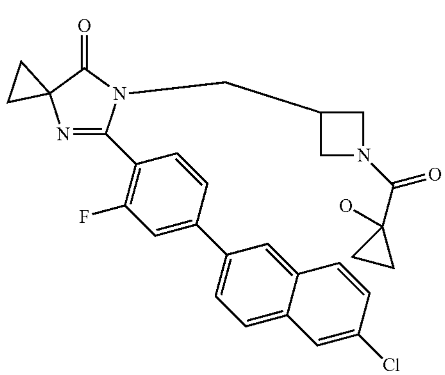 [SMILES: O=C(N1CC(CN2C(=O)C3(CC3)N=C2c2ccc(-c3ccc4cc(Cl)ccc4c3)cc2F)C1)C1(O)CC1] | 5-(4-(6-chloronaphthalen-2-yl)-2-fluorophenyl)-6-((1-(1-hydroxycyclopropanecarbonyl)azetidin-3-yl)methyl)-4,6-diazaspiro[2.4]hept-4-en-7-one<br>$^1$H NMR (300 MHz, CHLOROFORM-d) δ ppm 0.76-0.88 (m, 2 H), 1.16 (br. s., 2 H), 1.68-1.77 (m, 2 H), 1.78-1.88 (m, 2 H), 2.65-2.87 (m, 2 H), 3.57 (br. s., 1 H), 3.80 (br. s., 2 H), 3.98 (br. s., 2 H), 4.36 (br. s., 1 H), 7.37-7.53 (m, 2 H), 7.53-7.63 (m, 2 H), 7.63-7.75 (m, 1 H), 7.75-7.88 (m, 3 H), 7.99 (s, 1 H). MS m/z 518 (M + H)+ |

-continued

| ID No. | Structure | Compound Name & Physical Data |
|---|---|---|
| 384 | 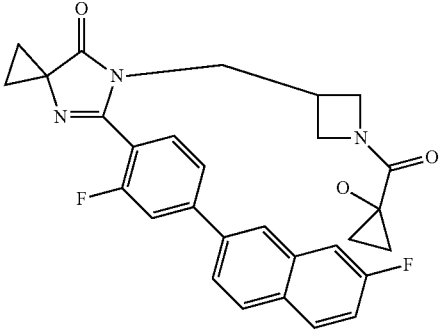 [SMILES: O=C(N1CC(CN2C(=O)C3(CC3)N=C2c2ccc(-c3ccc4ccc(F)cc4c3)cc2F)C1)C1(O)CC1] | 5-(2-fluoro-4-(7-fluoronaphthalen-2-yl)phenyl)-6-((1-(1-hydroxycyclopropanecarbonyl)azetidin-3-yl)methyl)-4,6-diazaspiro[2.4]hept-4-en-7-one<br>$^1$H NMR (300 MHz, CHLOROFORM-d) δ ppm 0.82 (br s, 2 H), 1.13 (br s, 2 H), 1.72 (br s, 2 H), 1.81 (br s, 2 H), 2.65-2.82 (m, 1 H), 2.95 (br s, 2 H), 3.36-4.58 (m, 6 H), 7.24 (t, J = 8.2 Hz, 1 H), 7.44-7.62 (m, 5 H), 7.80 (t, J = 6.9 Hz, 1 H), 7.88 (d, J = 8.3 Hz, 1 H), 7.94 (s, 1 H) MS m/z 502 (M + H)+ |
| 385 | 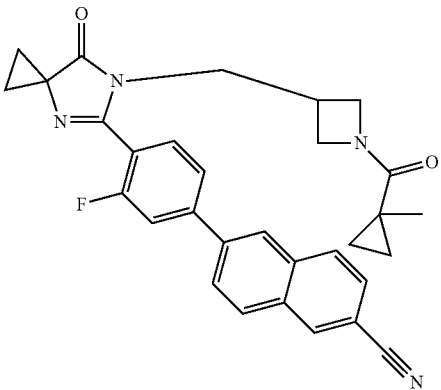 [SMILES: CC1(C(=O)N2CC(CN3C(=O)C4(CC4)N=C3c3ccc(-c4ccc5cc(C#N)ccc5c4)cc3F)C2)CC1] | 6-(3-fluoro-4-(6-((1-(1-methylcyclopropanecarbonyl)azetidin-3-yl)methyl)-7-oxo-4,6-diazaspiro[2.4]hept-4-en-5-yl)phenyl)-2-naphthonitrile<br>$^1$H NMR (300 MHz, CHLOROFORM-d) δ ppm 0.45 (br. s., 2 H), 0.99 (br. s., 2 H), 1.21 (br. s., 3 H), 2.87 (br. s., 1 H), 3.50 (d, J = 6.2 Hz, 1 H), 3.61-4.00 (m, 3 H), 4.17 (br. s., 2 H), 7.62 (d, J = 10.7 Hz, 1 H), 7.71 (br. s., 3 H), 7.88 (d, J = 8.0 Hz, 1 H), 7.96-8.11 (m, 2 H), 8.15 (br. s., 1 H), 8.31 (br. s., 1 H). MS m/z 507 (M + H)+ |
| 387 | 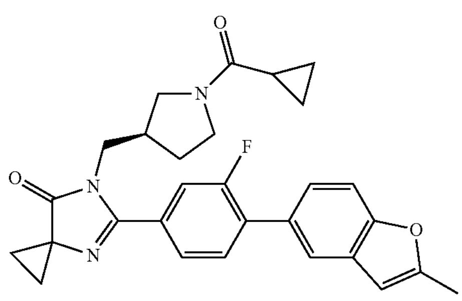 [SMILES: Cc1cc2cc(-c3ccc(C4=NC5(CC5)C(=O)N4C[C@@H]4CCN(C(=O)C5CC5)C4)cc3F)ccc2o1] | 6-{[(3R)-1-(Cyclopropylcarbonyl)pyrrolidin-3-yl]methyl}-5-[3-fluoro-4-(2-methyl-1-benzofuran-5-yl)phenyl]-4,6-diazaspiro[2.4]hept-4-en-7-one<br>MS m/z 486 (M + H)+ |
| 388 | 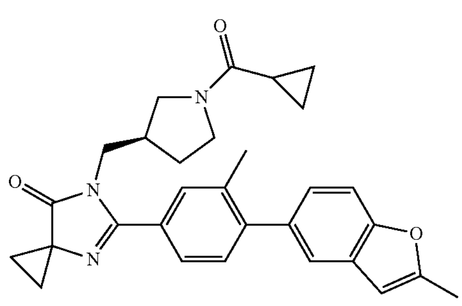 [SMILES: Cc1cc2cc(-c3ccc(C4=NC5(CC5)C(=O)N4C[C@@H]4CCN(C(=O)C5CC5)C4)cc3C)ccc2o1] | 6-{[(3R)-1-(Cyclopropylcarbonyl)pyrrolidin-3-yl]methyl}-5-[3-methyl-4-(2-methyl-1-benzofuran-5-yl)phenyl]-4,6-diazaspiro[2.4]hept-4-en-7-one<br>MS m/z 482 (M + H)+ |

| ID No. | Structure | Compound Name & Physical Data |
|---|---|---|
| 389 | 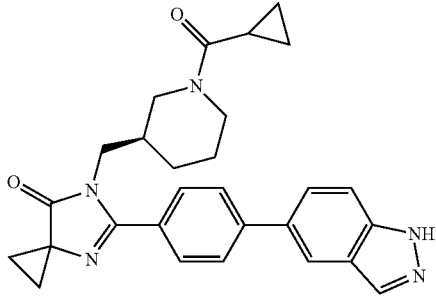 [SMILES: O=C(C1CC1)N1CCC[C@@H](CN2C(=O)C3(CC3)N=C2c2ccc(-c3ccc4[nH]ncc4c3)cc2)C1] | 6-{[(3R)-1-(Cyclopropylcarbonyl)piperidin-3-yl]methyl}-5-[4-(1H-indazol-5-yl)phenyl]-4,6-diazaspiro[2.4]hept-4-en-7-one<br>MS m/z 468 (M + H)+ |
| 390 | 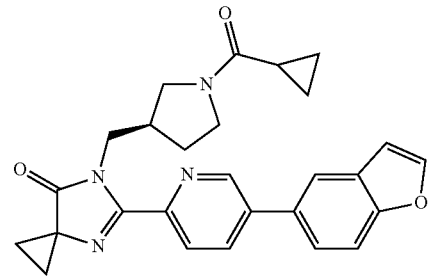 [SMILES: O=C(C1CC1)N1CC[C@@H](CN2C(=O)C3(CC3)N=C2c2ccc(-c3ccc4occc4c3)cn2)C1] | 5-[5-(1-Benzofuran-5-yl)pyridin-2-yl]-6-{[(3R)-1-(cyclopropylcarbonyl)pyrrolidin-3-yl]methyl}-4,6-diazaspiro[2.4]hept-4-en-7-one<br>MS m/z (M + H)+ |
| 391 | 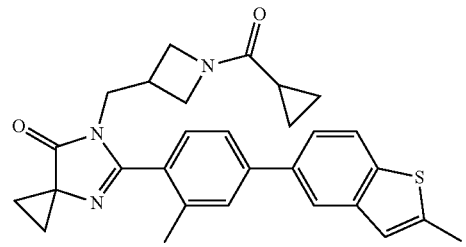 | 6-{[1-(Cyclopropylcarbonyl)azetidin-3-yl]methyl}-5-[2-methyl-4-(2-methyl-1-benzothiophen-5-yl)phenyl]-4,6-diazaspiro[2.4]hept-4-en-7-one<br>MS m/z 484 (M + H)+ |
| 392 | 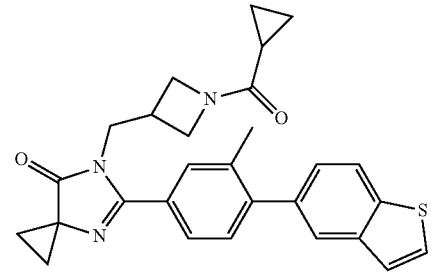 [SMILES: Cc1cc(C2=NC3(CC3)C(=O)N2CC2CN(C(=O)C3CC3)C2)ccc1-c1ccc2sccc2c1] | 5-[4-(1-Benzothiophen-5-yl)-3-methylphenyl]-6-{[1-(cyclopropylcarbonyl)azetidin-3-yl]methyl}-4,6-diazaspiro[2.4]hept-4-en-7-one<br>MS m/z 470 (M + H)+ |
| 393 | 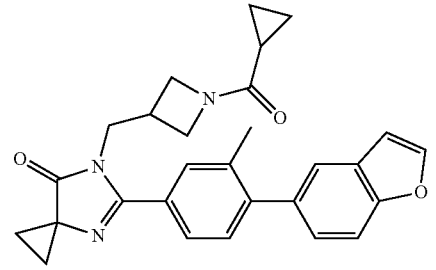 [SMILES: Cc1cc(C2=NC3(CC3)C(=O)N2CC2CN(C(=O)C3CC3)C2)ccc1-c1ccc2occc2c1] | 5-[4-(1-Benzofuran-5-yl)-3-methylphenyl]-6-{[1-(cyclopropylcarbonyl)azetidin-3-yl]methyl}-4,6-diazaspiro[2.4]hept-4-en-7-one<br>MS m/z 454 (M + H)+ |

| ID No. | Structure | Compound Name & Physical Data |
|---|---|---|
| 394 | 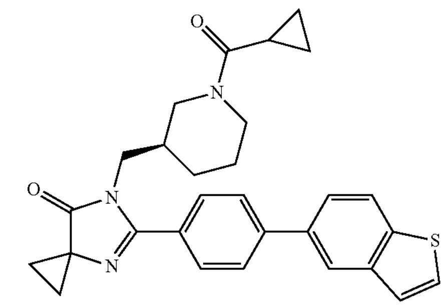 [SMILES: O=C(C1CC1)N1CCC[C@@H](CN2C(=O)C3(CC3)N=C2c2ccc(-c3ccc4sccc4c3)cc2)C1] | 5-[4-(1-Benzothiophen-5-yl)phenyl]-6-{[(3R)-1-(cyclopropylcarbonyl)piperidin-3-yl]methyl}-4,6-diazaspiro[2.4]hept-4-en-7-one<br>MS m/z 484 (M + H)+ |
| 395 | 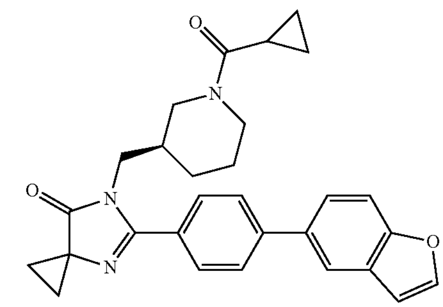 [SMILES: O=C(C1CC1)N1CCC[C@@H](CN2C(=O)C3(CC3)N=C2c2ccc(-c3ccc4occc4c3)cc2)C1] | 5-[4-(1-Benzofuran-5-yl)phenyl]-6-{[(3R)-1-(cyclopropylcarbonyl)piperidin-3-yl]methyl}-4,6-diazaspiro[2.4]hept-4-en-7-one<br>MS m/z 468 (M + H)+ |
| 396 | 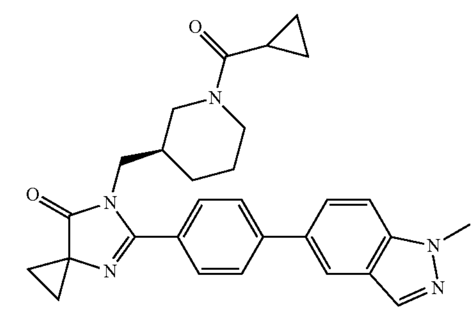 [SMILES: Cn1ncc2cc(-c3ccc(C4=NC5(CC5)C(=O)N4C[C@@H]4CCCN(C(=O)C5CC5)C4)cc3)ccc21] | 6-{[(3R)-1-(Cyclopropylcarbonyl)piperidin-3-yl]methyl}-5-[4-(1-methyl-1H-indazol-5-yl)phenyl]-4,6-diazaspiro[2.4]hept-4-en-7-one<br>MS m/z 482 (M + H)+ |
| 397 | 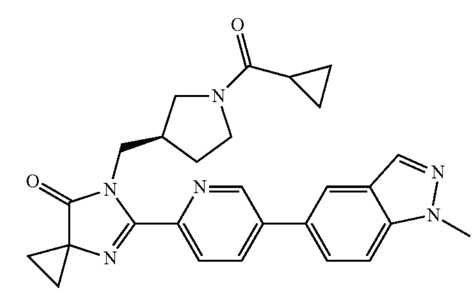 | 6-{[(3R)-1-(Cyclopropylcarbonyl)pyrrolidin-3-yl]methyl}-5-[5-(1-methyl-1H-indazol-5-yl)pyridin-2-yl]-4,6-diazaspiro[2.4]hept-4-en-7-one<br>MS m/z (M + H)+ |
| 398 | 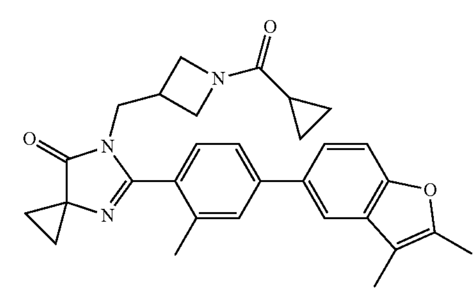 | 6-{[1-(Cyclopropylcarbonyl)azetidin-3-yl]methyl}-5-[4-(2,3-dimethyl-1-benzofuran-5-yl)-2-methylphenyl]-4,6-diazaspiro[2.4]hept-4-en-7-one<br>MS m/z 482 (M + H)+ |

-continued

| ID No. | Structure | Compound Name & Physical Data |
|---|---|---|
| 399 | 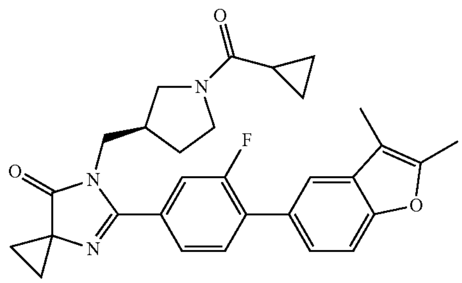 | 6-{[(3R)-1-(Cyclopropylcarbonyl)pyrrolidin-3-yl]methyl}-5-[4-(2,3-dimethyl-1-benzofuran-5-yl)-3-fluorophenyl]-4,6-diazaspiro[2.4]hept-4-en-7-one<br>MS m/z 500 (M + H)+ |
| 400 | 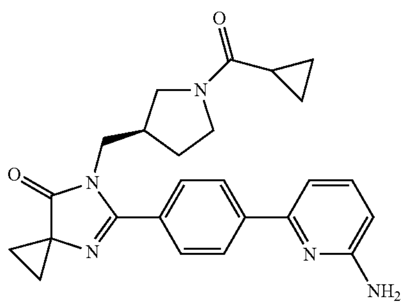 [SMILES: Nc1cccc(-c2ccc(C3=NC4(CC4)C(=O)N3C[C@@H]3CCN(C(=O)C4CC4)C3)cc2)n1] | 5-[4-(6-Aminopyridin-2-yl)phenyl]-6-{[(3R)-1-(cyclopropylcarbonyl)pyrrolidin-3-yl]methyl}-4,6-diazaspiro[2.4]hept-4-en-7-one<br>MS m/z 430 (M + H)+ |
| 401 | 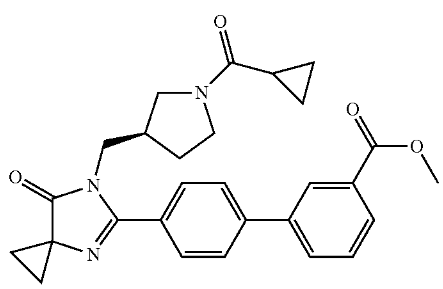 [SMILES: COC(=O)c1cccc(-c2ccc(C3=NC4(CC4)C(=O)N3C[C@@H]3CCN(C(=O)C4CC4)C3)cc2)c1] | Methyl 4'-(6-{[(3R)-1-(cyclopropylcarbonyl)pyrrolidin-3-yl]methyl}-7-oxo-4,6-diazaspiro[2.4]hept-4-en-5-yl)biphenyl-3-carboxylate<br>MS m/z 472 (M + H)+ |
| 402 | 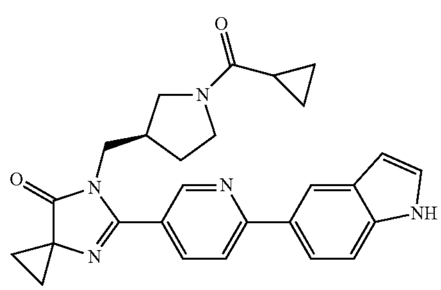 [SMILES: O=C(C1CC1)N1CC[C@@H](CN2C(=O)C3(CC3)N=C2c2ccc(-c3ccc4[nH]ccc4c3)nc2)C1] | 6-{[(3R)-1-(Cyclopropylcarbonyl)pyrrolidin-3-yl]methyl}-5-[6-(1H-indol-5-yl)pyridin-3-yl]-4,6-diazaspiro[2.4]hept-4-en-7-one<br>MS m/z 454 (M + H)+ |
| 404 | 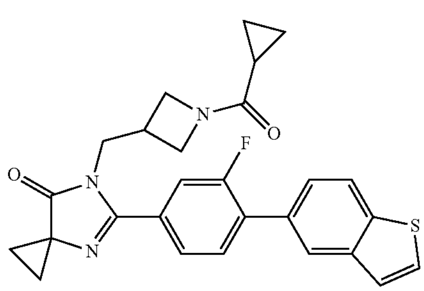 [SMILES: O=C(C1CC1)N1CC(CN2C(=O)C3(CC3)N=C2c2ccc(-c3ccc4sccc4c3)c(F)c2)C1] | 5-[4-(1-Benzothiophen-5-yl)-3-fluorophenyl]-6-{[1-(cyclopropylcarbonyl)azetidin-3-yl]methyl}-4,6-diazaspiro[2.4]hept-4-en-7-one<br>MS m/z 474 (M + H)+ |

-continued

| ID No. | Structure | Compound Name & Physical Data |
|---|---|---|
| 405 | 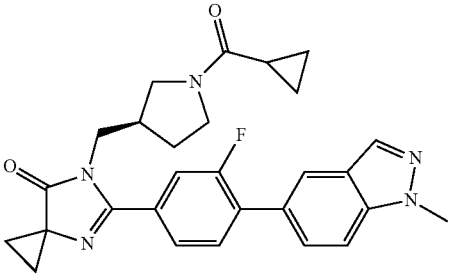 [SMILES: Cn1ncc2cc(-c3ccc(C4=NC5(CC5)C(=O)N4C[C@@H]4CCN(C(=O)C5CC5)C4)cc3F)ccc21] | 6-{[(3R)-1-(Cyclopropylcarbonyl)pyrrolidin-3-yl]methyl}-5-[3-fluoro-4-(1-methyl-1H-indazol-5-yl)phenyl]-4,6-diazaspiro[2.4]hept-4-en-7-one<br>MS m/z 486 (M + H)+ |
| 406 | 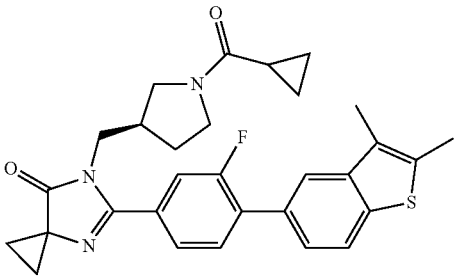 | 6-{[(3R)-1-(Cyclopropylcarbonyl)pyrrolidin-3-yl]methyl}-5-[4-(2,3-dimethyl-1-benzothiophen-5-yl)-3-fluorophenyl]-4,6-diazaspiro[2.4]hept-4-en-7-one<br>MS m/z 516 (M + H)+ |
| 407 | 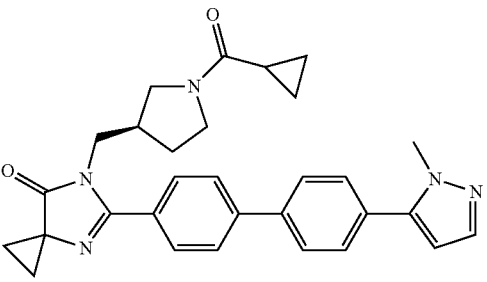 [SMILES: Cn1nccc1-c1ccc(-c2ccc(C3=NC4(CC4)C(=O)N3C[C@@H]3CCN(C(=O)C4CC4)C3)cc2)cc1] | 6-{[(3R)-1-(Cyclopropylcarbonyl)pyrrolidin-3-yl]methyl}-5-[4'-(1-methyl-1H-pyrazol-5-yl)biphenyl-4-yl]-4,6-diazaspiro[2.4]hept-4-en-7-one<br>MS m/z 494 (M + H)+ |
| 408 | 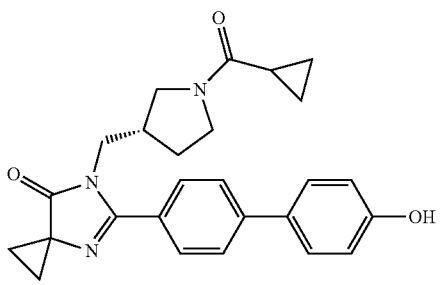 [SMILES: O=C(C1CC1)N1CC[C@H](CN2C(=O)C3(CC3)N=C2c2ccc(-c3ccc(O)cc3)cc2)C1] | 6-{[(3S)-1-(Cyclopropylcarbonyl)pyrrolidin-3-yl]methyl}-5-(4'-hydroxybiphenyl-4-yl)-4,6-diazaspiro[2.4]hept-4-en-7-one<br>MS m/z 430 (M + H)+ |
| 409 | 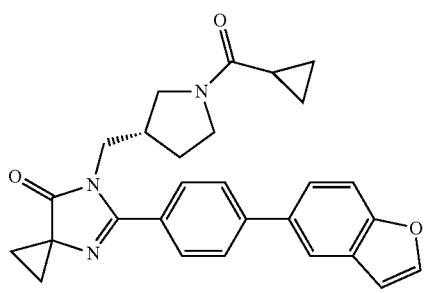 [SMILES: O=C(C1CC1)N1CC[C@H](CN2C(=O)C3(CC3)N=C2c2ccc(-c3ccc4occc4c3)cc2)C1] | 5-[4-(1-Benzofuran-5-yl)phenyl]-6-{[(3S)-1-(cyclopropylcarbonyl)pyrrolidin-3-yl]methyl}-4,6-diazaspiro[2.4]hept-4-en-7-one<br>MS m/z 454 (M + H)+ |

| ID No. | Structure | Compound Name & Physical Data |
|---|---|---|
| 410 | 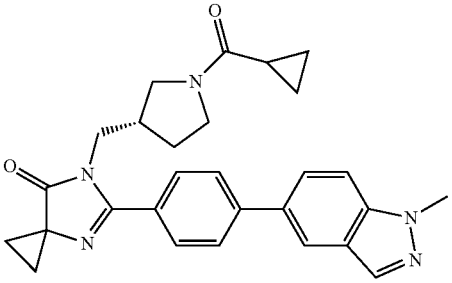 [SMILES: Cn1ncc2cc(-c3ccc(C4=NC5(CC5)C(=O)N4C[C@H]4CCN(C(=O)C5CC5)C4)cc3)ccc21] | 6-{[(3S)-1-(Cyclopropylcarbonyl)pyrrolidin-3-yl]methyl}-5-[4-(1-methyl-1H-indazol-5-yl)phenyl]-4,6-diazaspiro[2.4]hept-4-en-7-one<br>MS m/z 468 (M + H)+ |
| 411 | 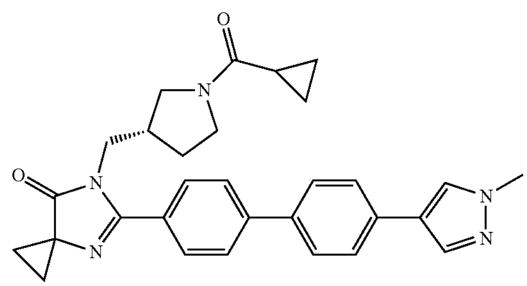 [SMILES: Cn1cc(-c2ccc(-c3ccc(C4=NC5(CC5)C(=O)N4C[C@H]4CCN(C(=O)C5CC5)C4)cc3)cc2)cn1] | 6-{[(3S)-1-(Cyclopropylcarbonyl)pyrrolidin-3-yl]methyl}-5-[4'-(1-methyl-1H-pyrazol-4-yl)biphenyl-4-yl]-4,6-diazaspiro[2.4]hept-4-en-7-one<br>MS m/z 494 (M + H)+ |
| 412 | 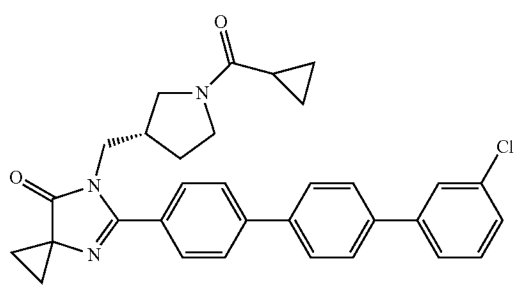 [SMILES: O=C(C1CC1)N1CC[C@H](CN2C(=O)C3(CC3)N=C2c2ccc(-c3ccc(-c4cccc(Cl)c4)cc3)cc2)C1] | 5-(3''-Chloro-1,1':4',1''-terphenyl-4-yl)-6-{[(3S)-1-(cyclopropylcarbonyl)pyrrolidin-3-yl]methyl}-4,6-diazaspiro[2.4]hept-4-en-7-one<br>MS m/z 524 (M + H)+ |
| 413 | 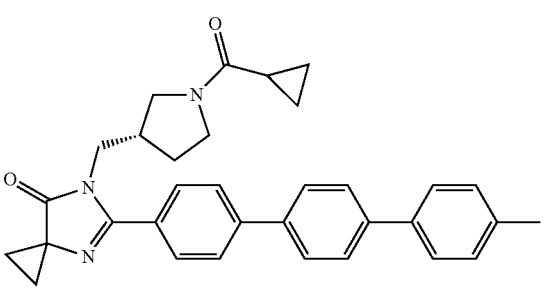 [SMILES: Cc1ccc(-c2ccc(-c3ccc(C4=NC5(CC5)C(=O)N4C[C@H]4CCN(C(=O)C5CC5)C4)cc3)cc2)cc1] | 6-{[(3S)-1-(Cyclopropylcarbonyl)pyrrolidin-3-yl]methyl}-5-(4''-methyl-1,1':4',1''-terphenyl-4-yl)-4,6-diazaspiro[2.4]hept-4-en-7-one<br>MS m/z 504 (M + H)+ |
| 414 | 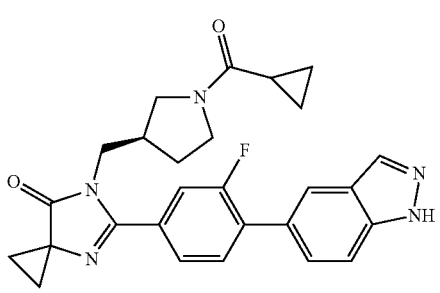 [SMILES: O=C(C1CC1)N1CC[C@@H](CN2C(=O)C3(CC3)N=C2c2ccc(-c3ccc4[nH]ncc4c3)c(F)c2)C1] | 6-{[(3R)-1-(Cyclopropylcarbonyl)pyrrolidin-3-yl]methyl}-5-[3-fluoro-4-(1H-indazol-5-yl)phenyl]-4,6-diazaspiro[2.4]hept-4-en-7-one<br>MS m/z 472 (M + H)+ |

-continued

| ID No. | Structure | Compound Name & Physical Data |
|---|---|---|
| 415 | 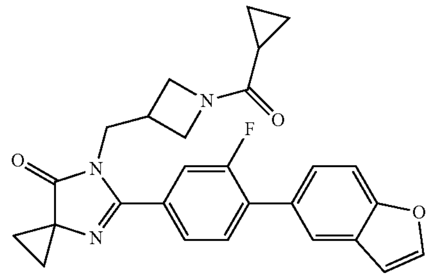 [SMILES: O=C(C1CC1)N1CC(CN2C(=O)C3(CC3)N=C2c2ccc(-c3ccc4occc4c3)c(F)c2)C1] | 5-[4-(1-Benzofuran-5-yl)-3-fluorophenyl]-6-{[(1-(cyclopropylcarbonyl)azetidin-3-yl]methyl}-4,6-diazaspiro[2.4]hept-4-en-7-one<br>MS m/z 458 (M + H)+ |
| 416 | 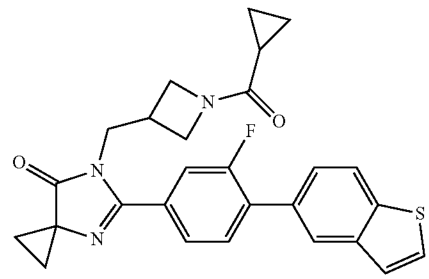 [SMILES: O=C(C1CC1)N1CC(CN2C(=O)C3(CC3)N=C2c2ccc(-c3ccc4sccc4c3)c(F)c2)C1] | 6-{[1-(Cyclopropylcarbonyl)azetidin-3-yl]methyl}-5-[3-fluoro-4-(2-methyl-1-benzofuran-5-yl)phenyl]-4,6-diazaspiro[2.4]hept-4-en-7-one<br>MS m/z 472 (M + H)+ |
| 417 | 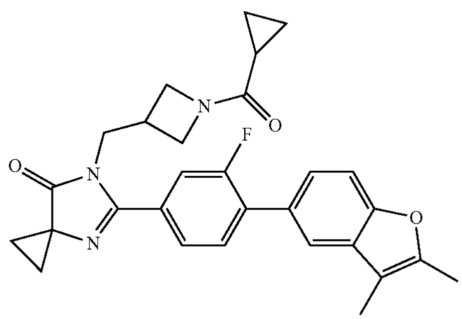 | 6-{[1-(Cyclopropylcarbonyl)azetidin-3-yl]methyl}-5-[4-(2,3-dimethyl-1-benzofuran-5-yl)-3-fluorophenyl]-4,6-diazaspiro[2.4]hept-4-en-7-one<br>MS m/z 486 (M + H)+ |
| 418 | 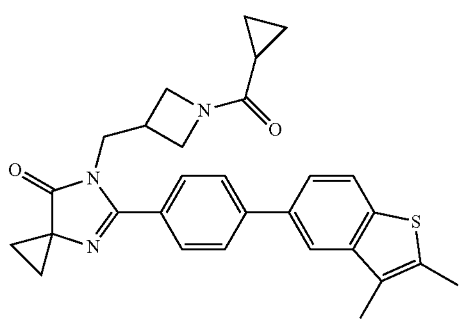 [SMILES: Cc1sc2ccc(-c3ccc(C4=NC5(CC5)C(=O)N4CC4CN(C(=O)C5CC5)C4)cc3)cc2c1C] | 6-{[1-(Cyclopropylcarbonyl)azetidin-3-yl]methyl}-5-[4-(2,3-dimethyl-1-benzothiophen-5-yl)phenyl]-4,6-diazaspiro[2.4]hept-4-en-7-one<br>MS m/z 484 (M + H)+ |
| 419 | 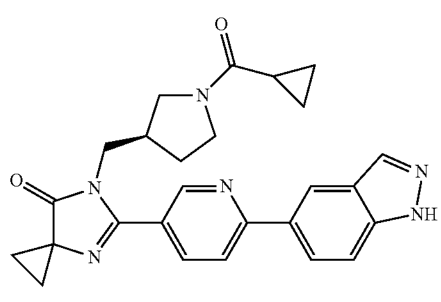 [SMILES: O=C(C1CC1)N1CC[C@@H](CN2C(=O)C3(CC3)N=C2c2ccc(-c3ccc4[nH]ncc4c3)nc2)C1] | 6-{[(3R)-1-(Cyclopropylcarbonyl)pyrrolidin-3-yl]methyl}-5-[5-(1H-indazol-5-yl)pyridin-2-yl]-4,6-diazaspiro[2.4]hept-4-en-7-one<br>MS m/z 455 (M + H)+ |

| ID No. | Structure | Compound Name & Physical Data |
|---|---|---|
| 420 | 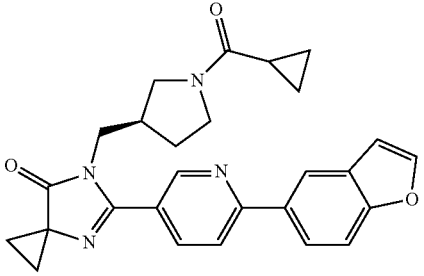 [SMILES: O=C(C1CC1)N1CC[C@@H](CN2C(=O)C3(CC3)N=C2c2ccc(-c3ccc4occc4c3)nc2)C1] | 5-[6-(1-Benzofuran-5-yl)pyridin-3-yl]-6-{[(3R)-1-(cyclopropylcarbonyl)pyrrolidin-3-yl]methyl}-4,6-diazaspiro[2.4]hept-4-en-7-one<br>MS m/z 455 (M + H)+ |
| 421 | 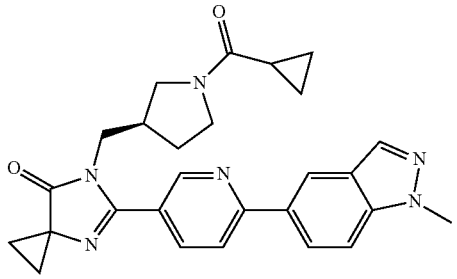 [SMILES: Cn1ncc2cc(-c3ccc(C4=NC5(CC5)C(=O)N4C[C@@H]4CCN(C(=O)C5CC5)C4)cn3)ccc21] | 6-{[(3R)-1-(Cyclopropylcarbonyl)pyrrolidin-3-yl]methyl}-5-[6-(1-methyl-1H-indazol-5-yl)pyridin-3-yl]-4,6-diazaspiro[2.4]hept-4-en-7-one<br>MS m/z 469 (M + H)+ |
| 422 | 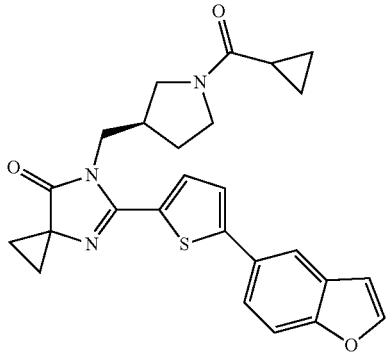 [SMILES: O=C(C1CC1)N1CC[C@@H](CN2C(=O)C3(CC3)N=C2c2ccc(-c3ccc4occc4c3)s2)C1] | 5-[5-(1-Benzofuran-5-yl)thiophen-2-yl]-6-{[(3R)-1-(cyclopropylcarbonyl)pyrrolidin-3-yl]methyl}-4,6-diazaspiro[2.4]hept-4-en-7-one<br>MS m/z 460 (M + H)+ |
| 423 | 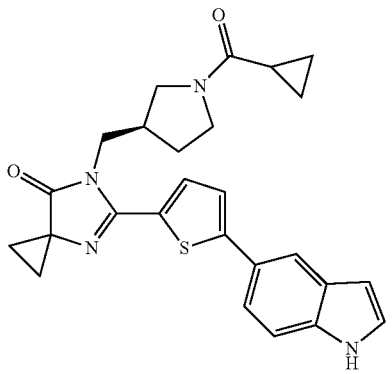 [SMILES: O=C(C1CC1)N1CC[C@@H](CN2C(=O)C3(CC3)N=C2c2ccc(-c3ccc4[nH]ccc4c3)s2)C1] | 6-{[(3R)-1-(Cyclopropylcarbonyl)pyrrolidin-3-yl]methyl}-5-[5-(1H-indol-5-yl)thiophen-2-yl]-4,6-diazaspiro[2.4]hept-4-en-7-one<br>MS m/z 459 (M + H)+ |

| ID No. | Structure | Compound Name & Physical Data |
|---|---|---|
| 424 | 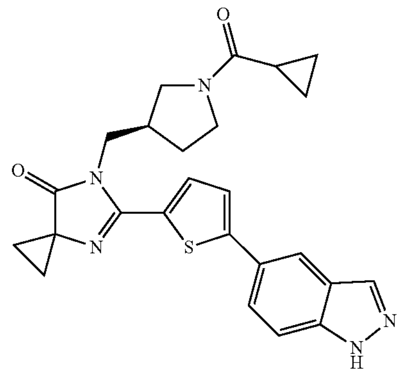 [SMILES: O=C(C1CC1)N1CC[C@@H](CN2C(=O)C3(CC3)N=C2c2ccc(-c3ccc4[nH]ncc4c3)s2)C1] | 6-{[(3R)-1-(Cyclopropylcarbonyl)pyrrolidin-3-yl]methyl}-5-[5-(1H-indazol-5-yl)thiophen-2-yl]-4,6-diazaspiro[2.4]hept-4-en-7-one<br>MS m/z 460 (M + H)+ |
| 425 | 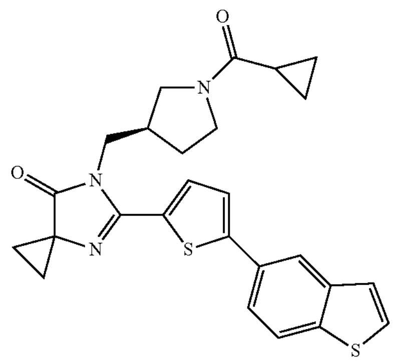 [SMILES: O=C(C1CC1)N1CC[C@@H](CN2C(=O)C3(CC3)N=C2c2ccc(-c3ccc4sccc4c3)s2)C1] | 5-[5-(1-Benzothiophen-5-yl)thiophen-2-yl]-6-{[(3R)-1-(cyclopropylcarbonyl)pyrrolidin-3-yl]methyl}-4,6-diazaspiro[2.4]hept-4-en-7-one<br>MS m/z 476 (M + H)+ |
| 426 | 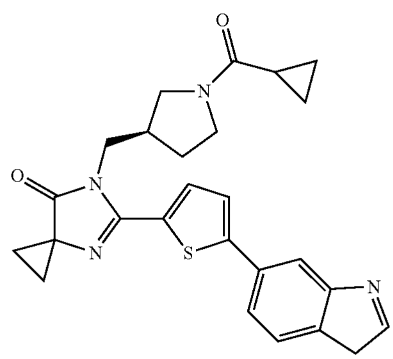 [SMILES: O=C(C1CC1)N1CC[C@@H](CN2C(=O)C3(CC3)N=C2c2ccc(-c3ccc4c(c3)N=CC4)s2)C1] | 6-{[(3R)-1-(Cyclopropylcarbonyl)pyrrolidin-3-yl]methyl}-5-[5-(3H-indol-6-yl)thiophen-2-yl]-4,6-diazaspiro[2.4]hept-4-en-7-one<br>MS m/z 459 (M + H)+ |
| 427 | 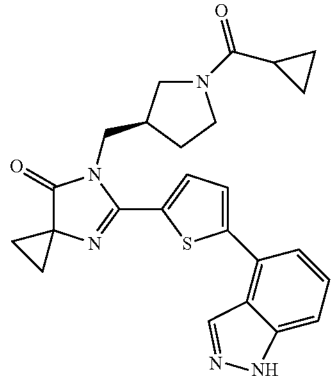 [SMILES: O=C(C1CC1)N1CC[C@@H](CN2C(=O)C3(CC3)N=C2c2ccc(-c3cccc4[nH]ncc34)s2)C1] | 6-{[(3R)-1-(Cyclopropylcarbonyl)pyrrolidin-3-yl]methyl}-5-[5-(1H-indazol-4-yl)thiophen-2-yl]-4,6-diazaspiro[2.4]hept-4-en-7-one<br>MS m/z 460 (M + H)+ |

-continued

| ID No. | Structure | Compound Name & Physical Data |
|---|---|---|
| 428 | 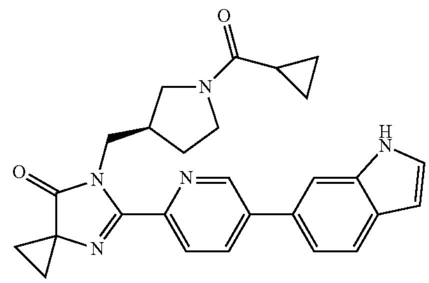 [SMILES: O=C(C1CC1)N1CC[C@@H](CN2C(=O)C3(CC3)N=C2c2ccc(-c3ccc4cc[nH]c4c3)cn2)C1] | 6-{[(3R)-1-(Cyclopropylcarbonyl)pyrrolidin-3-yl]methyl}-5-[5-(1H-indol-6-yl)pyridin-2-yl]-4,6-diazaspiro[2.4]hept-4-en-7-one<br>MS m/z 454 (M + H)+ |
| 429 | 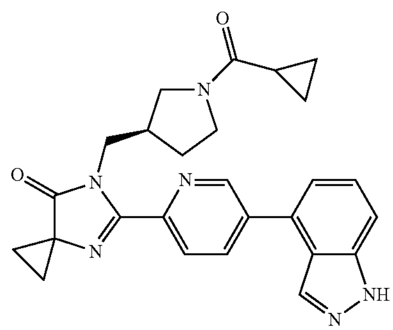 [SMILES: O=C(C1CC1)N1CC[C@@H](CN2C(=O)C3(CC3)N=C2c2ccc(-c3cccc4[nH]ncc34)cn2)C1] | 6-{[(3R)-1-(Cyclopropylcarbonyl)pyrrolidin-3-yl]methyl}-5-[5-(1H-indazol-4-yl)pyridin-2-yl]-4,6-diazaspiro[2.4]hept-4-en-7-one<br>MS m/z 455 (M + H)+ |
| 430 | 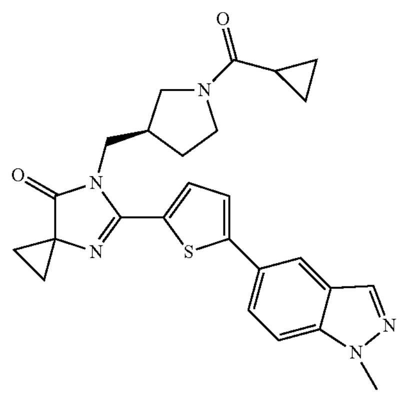 [SMILES: Cn1ncc2cc(-c3ccc(C4=NC5(CC5)C(=O)N4C[C@@H]4CCN(C(=O)C5CC5)C4)s3)ccc21] | 6-{[(3R)-1-(Cyclopropylcarbonyl)pyrrolidin-3-yl]methyl}-5-[5-(1-methyl-1H-indazol-5-yl)thiophen-2-yl]-4,6-diazaspiro[2.4]hept-4-en-7-one<br>MS m/z 474 (M + H)+ |
| 431 | 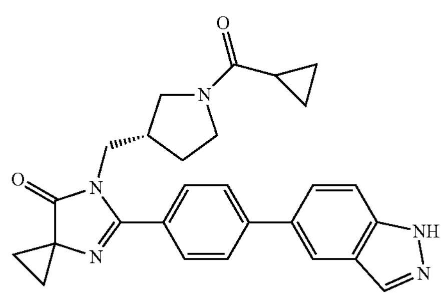 [SMILES: O=C(C1CC1)N1CC[C@H](CN2C(=O)C3(CC3)N=C2c2ccc(-c3ccc4[nH]ncc4c3)cc2)C1] | 6-{[(3S)-1-(Cyclopropylcarbonyl)pyrrolidin-3-yl]methyl}-5-[4-(1H-indazol-5-yl)phenyl]-4,6-diazaspiro[2.4]hept-4-en-7-one<br>MS m/z 454 (M + H)+ |
| 432 | 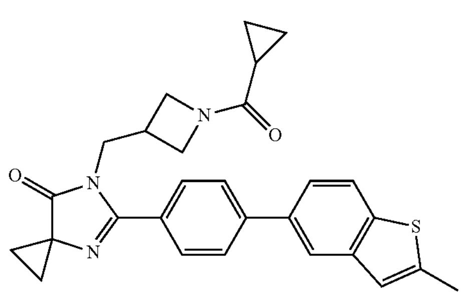 [SMILES: Cc1cc2cc(-c3ccc(C4=NC5(CC5)C(=O)N4CC4CN(C(=O)C5CC5)C4)cc3)ccc2s1] | 6-{[1-(Cyclopropylcarbonyl)azetidin-3-yl]methyl}-5-[4-(2-methyl-1-benzothiophen-5-yl)phenyl]-4,6-diazaspiro[2.4]hept-4-en-7-one<br>MS m/z 470 (M + H)+ |

-continued

| ID No. | Structure | Compound Name & Physical Data |
|---|---|---|
| 433 | 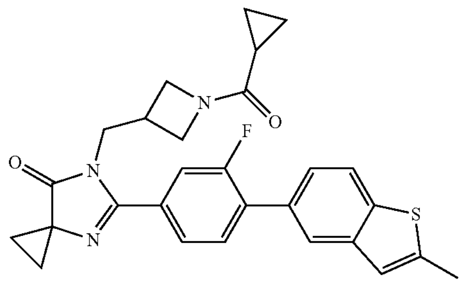 [SMILES: Cc1cc2cc(-c3ccc(C4=NC5(CC5)C(=O)N4CC4CN(C(=O)C5CC5)C4)cc3F)ccc2s1] | 6-{[1-(Cyclopropylcarbonyl)azetidin-3-yl]methyl}-5-[3-fluoro-4-(2-methyl-1-benzothiophen-5-yl)phenyl]-4,6-diazaspiro[2.4]hept-4-en-7-one<br>MS m/z 488 (M + H)+ |
| 434 | 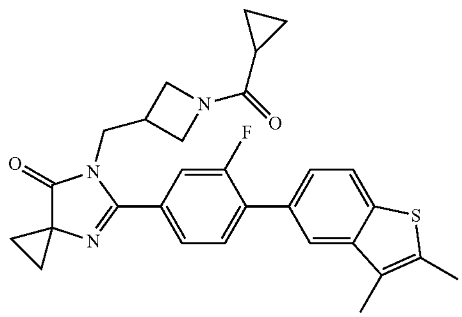 | 6-{[1-(Cyclopropylcarbonyl)azetidin-3-yl]methyl}-5-[4-(2,3-dimethyl-1-benzothiophen-5-yl)-3-fluorophenyl]-4,6-diazaspiro[2.4]hept-4-en-7-one<br>MS m/z 502 (M + H)+ |
| 435 | 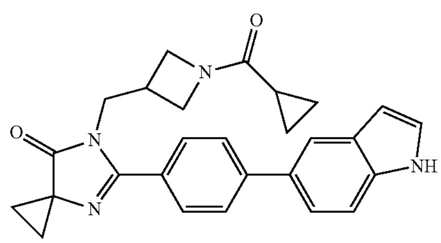 [SMILES: O=C(C1CC1)N1CC(CN2C(=O)C3(CC3)N=C2c2ccc(-c3ccc4[nH]ccc4c3)cc2)C1] | 6-{[1-(Cyclopropylcarbonyl)azetidin-3-yl]methyl}-5-[4-(1H-indol-5-yl)-3-methylphenyl]-4,6-diazaspiro[2.4]hept-4-en-7-one<br>MS m/z 453 (M + H)+ |
| 436 | 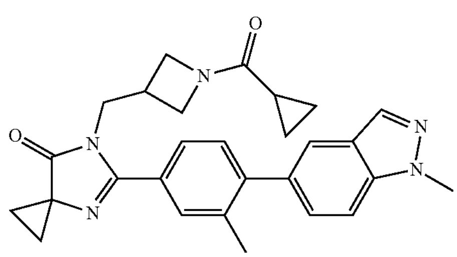 [SMILES: Cc1cc(C2=NC3(CC3)C(=O)N2CC2CN(C(=O)C3CC3)C2)ccc1-c1ccc2c(cnn2C)c1] | 6-{[1-(Cyclopropylcarbonyl)azetidin-3-yl]methyl}-5-[3-methyl-4-(1-methyl-1H-indazol-5-yl)phenyl]-4,6-diazaspiro[2.4]hept-4-en-7-one<br>MS m/z 468 (M + H)+ |
| 437 | 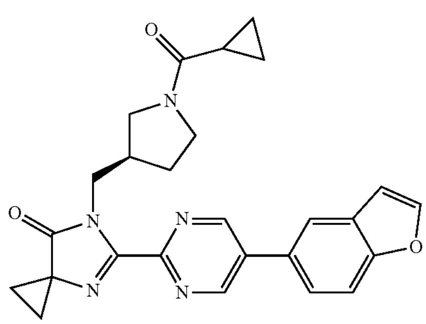 [SMILES: O=C(C1CC1)N1CC[C@@H](CN2C(=O)C3(CC3)N=C2c2ncc(-c3ccc4occc4c3)cn2)C1] | 5-[5-(1-Benzofuran-5-yl)pyrimidin-2-yl]-6-{[(3R)-1-(cyclopropylcarbonyl)pyrrolidin-3-yl]methyl}-4,6-diazaspiro[2.4]hept-4-en-7-one<br>MS m/z 456 (M + H)+ |

| ID No. | Structure | Compound Name & Physical Data |
|---|---|---|
| 438 | 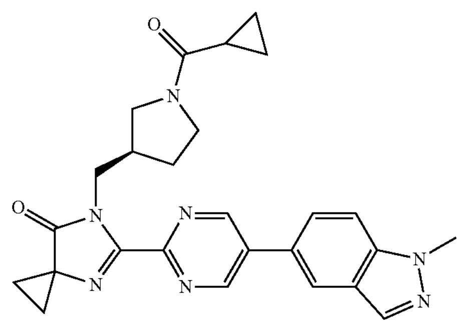 [SMILES: Cn1ncc2cc(-c3cnc(C4=NC5(CC5)C(=O)N4C[C@@H]4CCN(C(=O)C5CC5)C4)nc3)ccc21] | 6-{[(3R)-1-(Cyclopropylcarbonyl)pyrrolidin-3-yl]methyl}-5-[5-(1-methyl-1H-indazol-5-yl)pyrimidin-2-yl]-4,6-diazaspiro[2.4]hept-4-en-7-one<br>MS m/z 470 (M + H)+ |
| 439 | 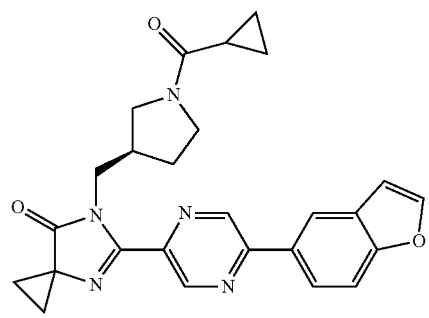 [SMILES: O=C(C1CC1)N1CC[C@@H](CN2C(=O)C3(CC3)N=C2c2cnc(-c3ccc4occc4c3)cn2)C1] | 5-[5-(1-Benzofuran-5-yl)pyrazin-2-yl]-6-{[(3R)-1-(cyclopropylcarbonyl)pyrrolidin-3-yl]methyl}-4,6-diazaspiro[2.4]hept-4-en-7-one<br>MS m/z 456 (M + H)+ |
| 440 | 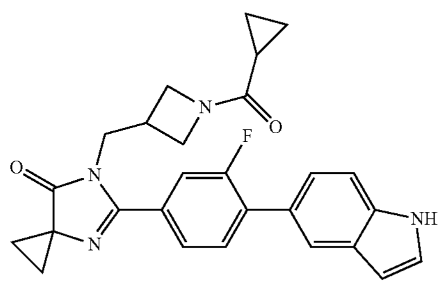 [SMILES: O=C(C1CC1)N1CC(CN2C(=O)C3(CC3)N=C2c2ccc(-c3ccc4[nH]ccc4c3)c(F)c2)C1] | 6-{[1-(Cyclopropylcarbonyl)azetidin-3-yl]methyl}-5-[3-fluoro-4-(1H-indol-5-yl)phenyl]-4,6-diazaspiro[2.4]hept-4-en-7-one<br>MS m/z 457 (M + H)+ |
| 441 | 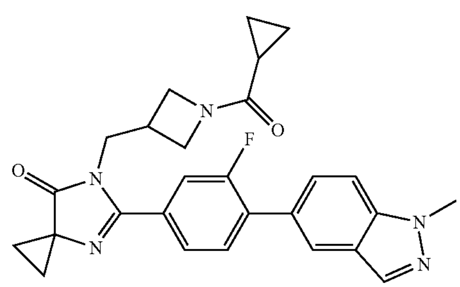 [SMILES: Cn1ncc2cc(-c3ccc(C4=NC5(CC5)C(=O)N4CC4CN(C(=O)C5CC5)C4)cc3F)ccc21] | 6-{[1-(Cyclopropylcarbonyl)azetidin-3-yl]methyl}-5-[3-fluoro-4-(1-methyl-1H-indazol-5-yl)phenyl]-4,6-diazaspiro[2.4]hept-4-en-7-one<br>MS m/z 472 (M + H)+ |
| 442 | 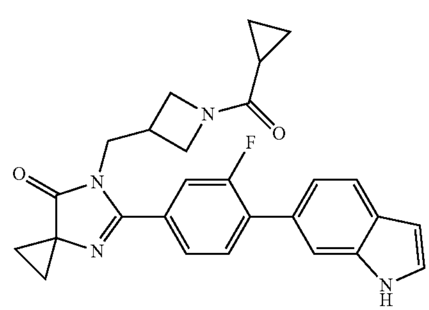 [SMILES: O=C(C1CC1)N1CC(CN2C(=O)C3(CC3)N=C2c2ccc(-c3ccc4cc[nH]c4c3)c(F)c2)C1] | 6-{[1-(Cyclopropylcarbonyl)azetidin-3-yl]methyl}-5-[3-fluoro-4-(1H-indol-6-yl)phenyl]-4,6-diazaspiro[2.4]hept-4-en-7-one<br>MS m/z 457 (M + H)+ |

-continued

| ID No. | Structure | Compound Name & Physical Data |
|---|---|---|
| 443 | 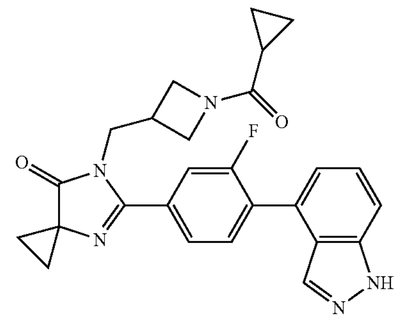 [SMILES: O=C(C1CC1)N1CC(CN2C(=O)C3(CC3)N=C2c2ccc(-c3cccc4[nH]ncc34)c(F)c2)C1] | 6-{[1-(Cyclopropylcarbonyl)azetidin-3-yl]methyl}-5-[3-fluoro-4-(1H-indazol-4-yl)phenyl]-4,6-diazaspiro[2.4]hept-4-en-7-one<br>MS m/z 458 (M + H)+ |
| 444 | 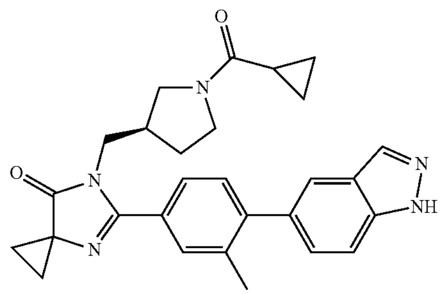 [SMILES: Cc1cc(C2=NC3(CC3)C(=O)N2C[C@@H]2CCN(C(=O)C3CC3)C2)ccc1-c1ccc2[nH]ncc2c1] | 6-{[(3R)-1-(Cyclopropylcarbonyl)pyrrolidin-3-yl]methyl}-5-[4-(1H-indazol-5-yl)-3-methylphenyl]-4,6-diazaspiro[2.4]hept-4-en-7-one<br>MS m/z 468 (M + H)+ |
| 445 | 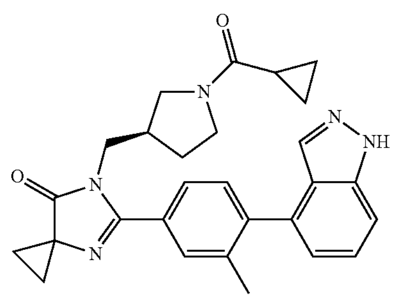 [SMILES: Cc1cc(C2=NC3(CC3)C(=O)N2C[C@@H]2CCN(C(=O)C3CC3)C2)ccc1-c1cccc2[nH]ncc12] | 6-{[(3R)-1-(Cyclopropylcarbonyl)pyrrolidin-3-yl]methyl}-5-[4-(1H-indazol-4-yl)-3-methylphenyl]-4,6-diazaspiro[2.4]hept-4-en-7-one<br>MS m/z 468 (M + H)+ |
| 446 | 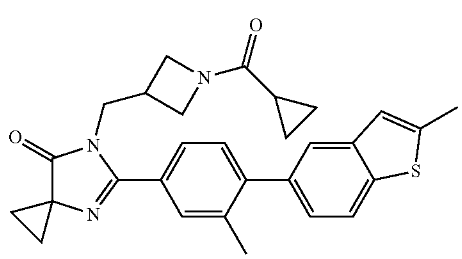 [SMILES: Cc1cc2cc(-c3ccc(C4=NC5(CC5)C(=O)N4CC4CN(C(=O)C5CC5)C4)cc3C)ccc2s1] | 6-{[1-(Cyclopropylcarbonyl)azetidin-3-yl]methyl}-5-[3-methyl-4-(2-methyl-1-benzothiophen-5-yl)phenyl]-4,6-diazaspiro[2.4]hept-4-en-7-one<br>MS m/z 484 (M + H)+ |
| 447 | 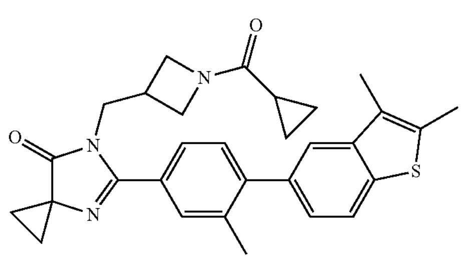 [SMILES: Cc1cc(C2=NC3(CC3)C(=O)N2CC2CN(C(=O)C3CC3)C2)ccc1-c1ccc2sc(C)c(C)c2c1] | 6-{[1-(Cyclopropylcarbonyl)azetidin-3-yl]methyl}-5-[4-(2,3-dimethyl-1-benzothiophen-5-yl)-3-methylphenyl]-4,6-diazaspiro[2.4]hept-4-en-7-one<br>MS m/z 498 (M + H)+ |

-continued

| ID No. | Structure | Compound Name & Physical Data |
|---|---|---|
| 448 | 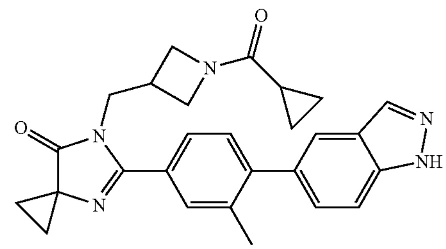 [SMILES: Cc1cc(C2=NC3(CC3)C(=O)N2CC2CN(C(=O)C3CC3)C2)ccc1-c1ccc2[nH]ncc2c1] | 6-{[1-(Cyclopropylcarbonyl)azetidin-3-yl]methyl}-5-[4-(1H-indazol-5-yl)-3-methylphenyl]-4,6-diazaspiro[2.4]hept-4-en-7-one<br>MS m/z 454 (M + H)+ |
| 449 | 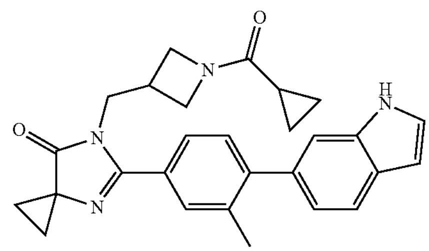 [SMILES: Cc1cc(C2=NC3(CC3)C(=O)N2CC2CN(C(=O)C3CC3)C2)ccc1-c1ccc2cc[nH]c2c1] | 6-{[1-(Cyclopropylcarbonyl)azetidin-3-yl]methyl}-5-[4-(1H-indazol-6-yl)-3-methylphenyl]-4,6-diazaspiro[2.4]hept-4-en-7-one<br>MS m/z 453 (M + H)+ |
| 450 | 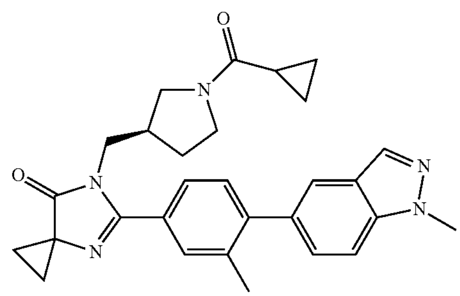 [SMILES: Cc1cc(C2=NC3(CC3)C(=O)N2C[C@@H]2CCN(C(=O)C3CC3)C2)ccc1-c1ccc2c(cnn2C)c1] | 6-{[(3R)-1-(Cyclopropylcarbonyl)pyrrolidin-3-yl]methyl}-5-[3-methyl-4-(1-methyl-1H-indazol-5-yl)phenyl]-4,6-diazaspiro[2.4]hept-4-en-7-one<br>MS m/z 482 (M + H)+ |
| 451 | 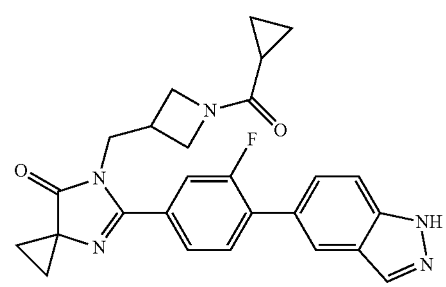 [SMILES: O=C(C1CC1)N1CC(CN2C(=O)C3(CC3)N=C2c2ccc(-c3ccc4[nH]ncc4c3)c(F)c2)C1] | 6-{[1-(Cyclopropylcarbonyl)azetidin-3-yl]methyl}-5-[3-fluoro-4-(1H-indazol-5-yl)phenyl]-4,6-diazaspiro[2.4]hept-4-en-7-one<br>MS m/z 458 (M + H)+ |
| 452 | 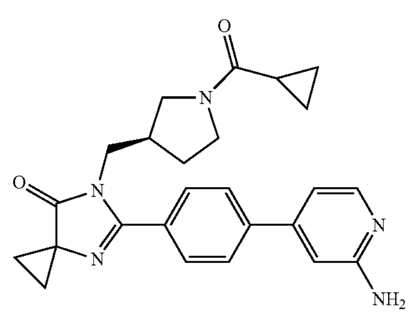 [SMILES: Nc1cc(-c2ccc(C3=NC4(CC4)C(=O)N3C[C@@H]3CCN(C(=O)C4CC4)C3)cc2)ccn1] | 5-[4-(2-Aminppyridin-4-yl)phenyl]-6-{[(3R)-1-(cyclopropylcarbonyl)pyrrolidin-3-yl]methyl}-4,6-diazaspiro[2.4]hept-4-en-7-one<br>MS m/z 430 (M + H)+ |

| ID No. | Structure | Compound Name & Physical Data |
|---|---|---|
| 453 | 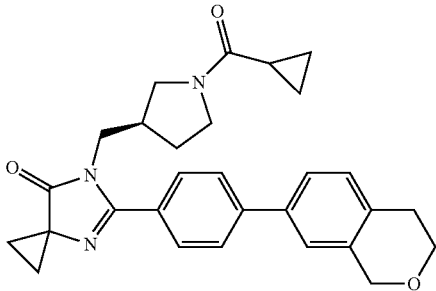 [SMILES: O=C(C1CC1)N1CC[C@@H](CN2C(=O)C3(CC3)N=C2c2ccc(-c3ccc4c(c3)COCC4)cc2)C1] | 6-{[(3R)-1-(Cyclopropylcarbonyl)pyrrolidin-3-yl]methyl}-5-[4-(3,4-dihydro-1H-2-benzopyran-7-yl)phenyl]-4,6-diazaspiro[2.4]hept-4-en-7-one<br>MS m/z 470 (M + H)+ |
| 454 | 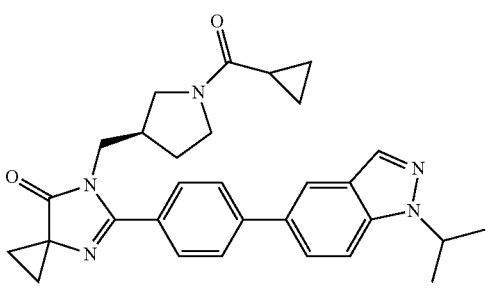 [SMILES: CC(C)n1ncc2cc(-c3ccc(C4=NC5(CC5)C(=O)N4C[C@@H]4CCN(C(=O)C5CC5)C4)cc3)ccc21] | 6-{[(3R)-1-(Cyclopropylcarbonyl)pyrrolidin-3-yl]methyl}-5-{4-[1-(1-methylethyl)-1H-indazol-5-yl]phenyl}-4,6-diazaspiro[2.4]hept-4-en-7-one<br>MS m/z 496 (M + H)+ |
| 455 | 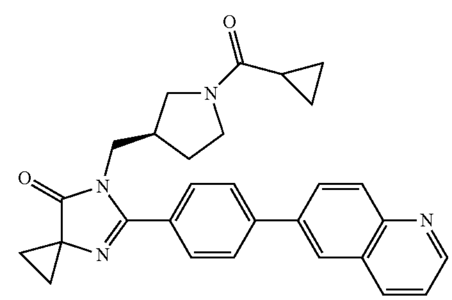 [SMILES: O=C(C1CC1)N1CC[C@@H](CN2C(=O)C3(CC3)N=C2c2ccc(-c3ccc4ncccc4c3)cc2)C1] | 6-{[(3R)-1-(Cyclopropylcarbonyl)pyrrolidin-3-yl]methyl}-5-(4-quinolin-6-ylphenyl)-4,6-diazaspiro[2.4]hept-4-en-7-one<br>MS m/z 465 (M + H)+ |
| 456 | 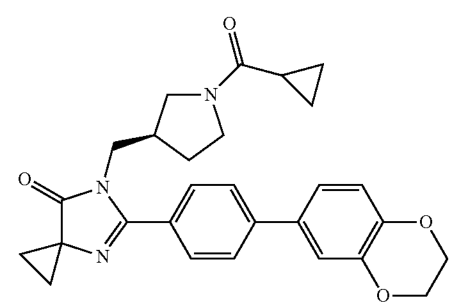 [SMILES: O=C(C1CC1)N1CC[C@@H](CN2C(=O)C3(CC3)N=C2c2ccc(-c3ccc4c(c3)OCCO4)cc2)C1] | 6-{[(3R)-1-(Cycloprop-ylcarbonyl)pyrrolidin-3-yl]methyl}-5-[4-(2,3-dihydro-1,4-benzodioxin-6-yl)phenyl]-4,6-diazaspiro[2.4]hept-4-en-7-one<br>MS m/z 472 (M + H)+ |
| 457 | 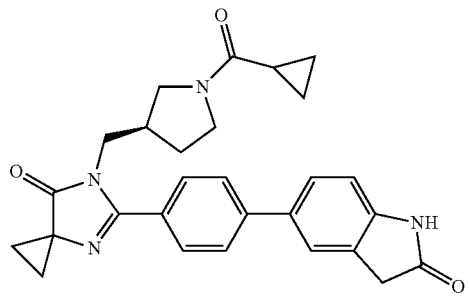 [SMILES: O=C1Cc2cc(-c3ccc(C4=NC5(CC5)C(=O)N4C[C@@H]4CCN(C(=O)C5CC5)C4)cc3)ccc2N1] | 5-[4-(6-{[(3R)-1-(Cyclopropylcarbonyl)pyrrolidin-3-yl]methyl}-7-oxo-4,6-diazaspiro[2.4]hept-4-en-5-yl)phenyl]-1,3-dihydro-2H-indol-2-one<br>MS m/z 469 (M + H)+ |

-continued

| ID No. | Structure | Compound Name & Physical Data |
|---|---|---|
| 458 | 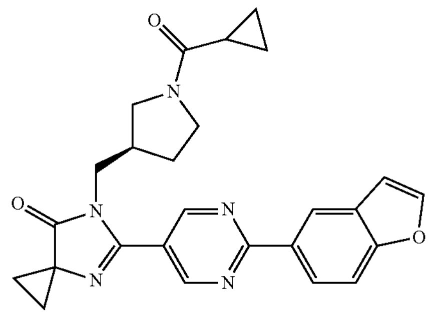 [SMILES: O=C(C1CC1)N1CC[C@@H](CN2C(=O)C3(CC3)N=C2c2cnc(-c3ccc4occc4c3)nc2)C1] | 5-[2-(1-Benzofuran-5-yl)pyrimidin-5-yl]-6-{[(3R)-1-(cyclopropylcarbonyl)pyrrolidin-3-yl]methyl}0-4,6-diazaspiro[2.4]hept-4-en-7-one<br>MS m/z 456 (M + H)+ |
| 459 | 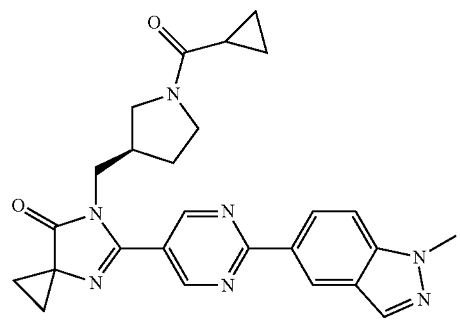 [SMILES: Cn1ncc2cc(-c3ncc(C4=NC5(CC5)C(=O)N4C[C@@H]4CCN(C(=O)C5CC5)C4)cn3)ccc21] | 6-{[(3R)-1-(Cyclopropylcarbonyl)pyrrolidin-3-yl]methyl}-5-[2-(1-methyl-1H-indazol-5-yl)pyrimidin-5-yl]-4,6-diazaspiro[2.4]hept-4-en-7-one<br>MS m/z 470 (M + H)+ |
| 460 | 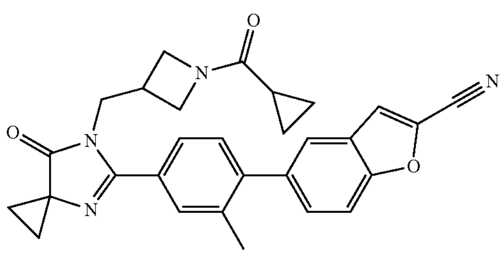 [SMILES: Cc1cc(C2=NC3(CC3)C(=O)N2CC2CN(C(=O)C3CC3)C2)ccc1-c1ccc2oc(C#N)cc2c1] | 5-[4-(6-{[1-(Cyclopropylcarbonyl)azetidin-3-yl]methyl}-7-oxo-4,6-diazaspiro[2.4]hept-4-en-5-yl)-2-methylphenyl]-1-benzofuran-2-carbonitrile<br>MS m/z 479 (M + H)+ |
| 461 | 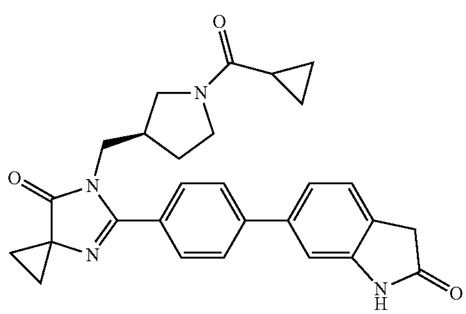 [SMILES: O=C1Cc2ccc(-c3ccc(C4=NC5(CC5)C(=O)N4C[C@@H]4CCN(C(=O)C5CC5)C4)cc3)cc2N1] | 6-[4-(6-{[(3R)-1-(Cyclopropylcvarbonyl)pyrrolidin-3-yl]methyl}-7-oxo-4,6-diazaspiro[2.4]hept-4-en-5-yl)phenyl]-1,3-dihydro-2H-indol-2-one<br>MS m/z 469 (M + H)+ |
| 462 | 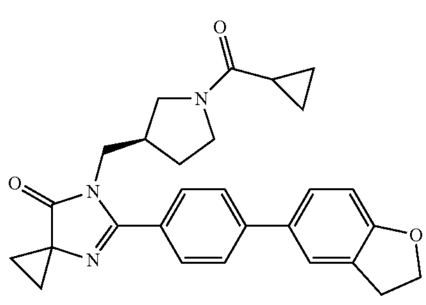 [SMILES: O=C(C1CC1)N1CC[C@@H](CN2C(=O)C3(CC3)N=C2c2ccc(-c3ccc4c(c3)CCO4)cc2)C1] | 6-{[(3R)-1-(Cyclopropylcarbonyl)pyrrolidin-3-yl]methyl}-5-[4-(2,3-dihydro-1-benzofuran-5-yl)phenyl]-4,6-diazaspiro[2.4]hept-4-en-7-one<br>MS m/z 456 (M + H)+ |

-continued

| ID No. | Structure | Compound Name & Physical Data |
|---|---|---|
| 463 | 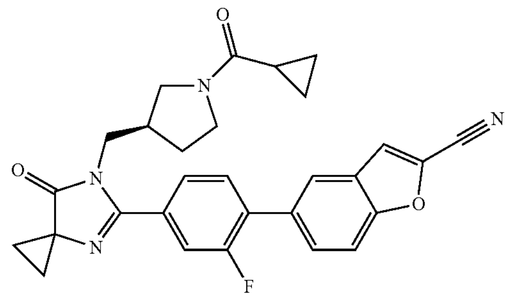 [SMILES: N#Cc1cc2cc(-c3ccc(C4=NC5(CC5)C(=O)N4C[C@@H]4CCN(C(=O)C5CC5)C4)cc3F)ccc2o1] | 5-[4-(6-{[(3R)-1-(Cyclopropylcarbonyl)pyrrolidin-3-yl]methyl}-7-oxo-4,6-diazaspiro[2.4]hept-4-en-5-yl)-2-fluorophenyl]-1-benzofuran-2-carbonitrile<br>MS m/z 497 (M + H)+ |
| 464 | 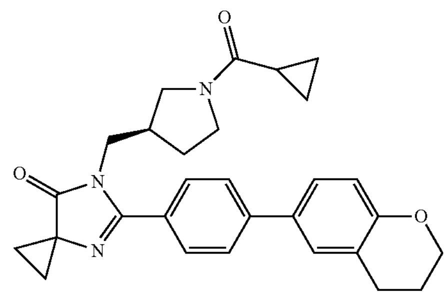 [SMILES: O=C(C1CC1)N1CC[C@@H](CN2C(=O)C3(CC3)N=C2c2ccc(-c3ccc4c(c3)CCCO4)cc2)C1] | 6-{[(3R)-1-(Cyclopropylcarbonyl)pyrrolidin-3-yl]methyl}-5-[4-(3,4-dihydro-2H-chromen-6-yl)phenyl]-4,6-diazaspiro[2.4]hept-4-en-7-one<br>MS m/z 470 (M + H)+ |
| 465 | 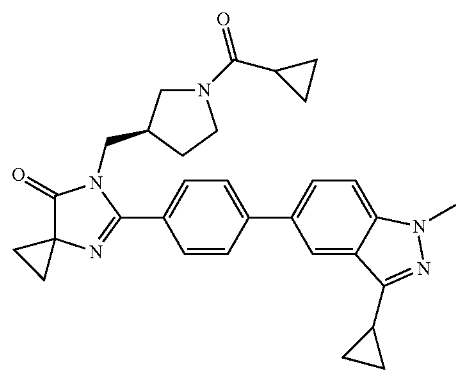 [SMILES: Cn1nc(C2CC2)c2cc(-c3ccc(C4=NC5(CC5)C(=O)N4C[C@@H]4CCN(C(=O)C5CC5)C4)cc3)ccc21] | 6-{[(3R)-1-(Cyclopropylcarbonyl)pyrrolidin-3-yl]methyl}-5-[4-(3-cyclopropyl-1-methyl-1H-indazol-5-yl)phenyl]-4,6-diazaspiro[2.4]hept-4-en-7-one<br>MS m/z 508 (M + H)+ |
| 466 | 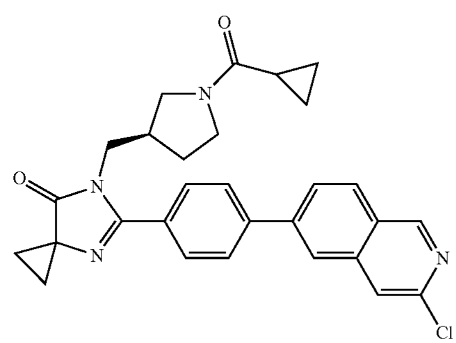 [SMILES: O=C(C1CC1)N1CC[C@@H](CN2C(=O)C3(CC3)N=C2c2ccc(-c3ccc4cnc(Cl)cc4c3)cc2)C1] | 5-[4-(3-Chloroisoquinolin-6-yl)phenyl]-6-{[(3R)-1-(cyclopropylcarbonyl)pyrrolidin-3-yl]methyl}-4,6-diazaspiro[2.4]hept-4-en-7-one<br>MS m/z 499 (M + H)+ |
| 467 | 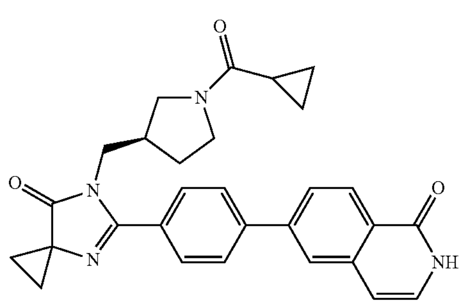 [SMILES: O=C(C1CC1)N1CC[C@@H](CN2C(=O)C3(CC3)N=C2c2ccc(-c3ccc4c(=O)[nH]ccc4c3)cc2)C1] | 6-[4-(6-{[(3R)-1-(Cyclopropylcarbonyl)pyrrolidin-3-yl]methyl}-7-oxo-4,6-diazaspiro[2.4]hept-4-en-5-yl)phenyl]isoquinolin-1(2H)-one<br>MS m/z 481 (M + H)+ |

-continued

| ID No. | Structure | Compound Name & Physical Data |
|---|---|---|
| 468 | 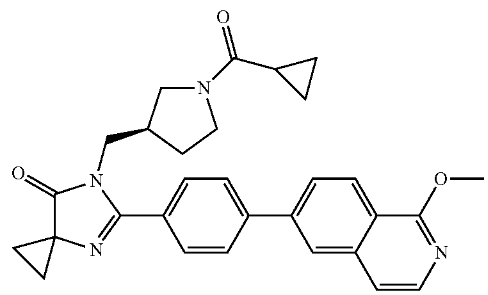 [SMILES: COc1nccc2cc(-c3ccc(C4=NC5(CC5)C(=O)N4C[C@@H]4CCN(C(=O)C5CC5)C4)cc3)ccc12] | 6-{[(3R)-1-(Cyclopropylcarbonyl)pyrrolidin-3-yl]methyl}-5-[4-(1-methoxyisoquinolin-6-yl)phenyl]-4,6-diazaspiro[2.4]hept-4-en-7-one<br>MS m/z 495 (M + H)+ |
| 469 | 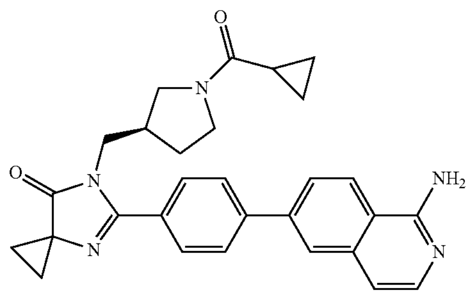 [SMILES: Nc1nccc2cc(-c3ccc(C4=NC5(CC5)C(=O)N4C[C@@H]4CCN(C(=O)C5CC5)C4)cc3)ccc12] | 5-[4-(1-Aminoisoquinolin-6-yl)phenyl]-6-{[(3R)-1-(cyclopropylcarbonyl)pyrrolidin-3-yl]methyl}-4,6-diazaspiro[2.4]hept-4-en-7-one<br>MS m/z 480 (M + H)+ |
| 470 | 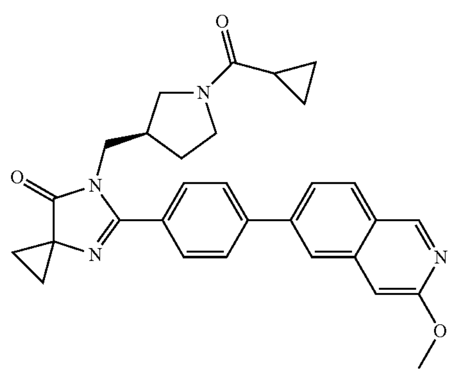 [SMILES: COc1cc2cc(-c3ccc(C4=NC5(CC5)C(=O)N4C[C@@H]4CCN(C(=O)C5CC5)C4)cc3)ccc2cn1] | 6-{[(3R)-1-(Cyclopropylcarbonyl)pyrrolidin-3-yl]methyl}-5-[4-(3-methoxyisoquinolin-6-yl)phenyl]-4,6-diazaspiro[2.4]hept-4-en-7-one<br>MS m/z 495 (M + H)+ |
| 71 | 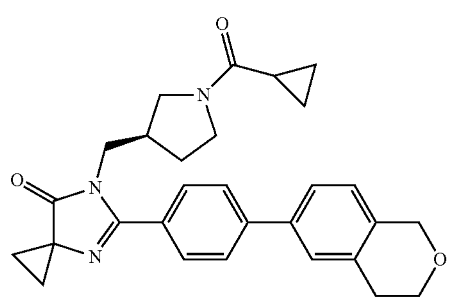 [SMILES: O=C(C1CC1)N1CC[C@@H](CN2C(=O)C3(CC3)N=C2c2ccc(-c3ccc4c(c3)CCOC4)cc2)C1] | 6-{[(3R)-1-(Cyclopropylcarbonyl)pyrrolidin-3-yl]methyl}-5-[4-(3,4-dihydro-1H-2-benzopyran-6-yl)phenyl]-4,6-diazaspiro[2.4]hept-4-en-7-one<br>MS m/z 470 (M + H)+ |
| 471 | 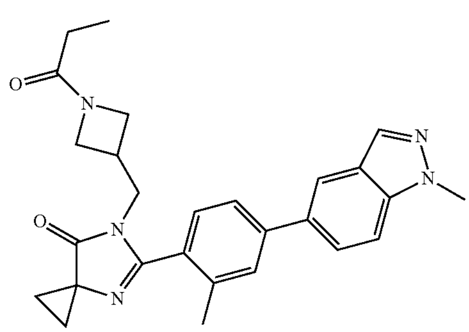 [SMILES: CCC(=O)N1CC(CN2C(=O)C3(CC3)N=C2c2ccc(-c3ccc4c(cnn4C)c3)cc2C)C1] | 5-[2-Methyl-4-(1-methyl-1H-indazol-5-yl)phenyl]-6-[(1-propanoylazetidin-3-yl)methyl]-4,6-diazaspiro[2.4]hept-4-en-7-one<br>MS m/z 456.3 (M + H)+ |

| ID No. | Structure | Compound Name & Physical Data |
|---|---|---|
| 473 | 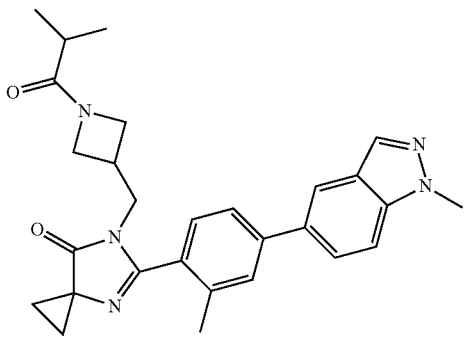 [SMILES: Cc1cc(-c2ccc3c(cnn3C)c2)ccc1C1=NC2(CC2)C(=O)N1CC1CN(C(=O)C(C)C)C1] | 5-[2-Methyl-4-(1-methyl-1H-indazol-5-yl)phenyl]-6-{[1-(2-methylpropanoyl)azetidin-3-yl]methyl}-4,6-diazaspiro[2.4]hept-4-en-7-one<br>MS m/z 470.3 (M + H)+ |
| 474 | 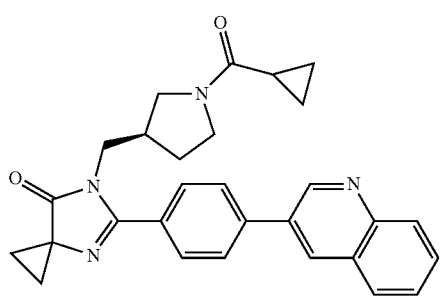 [SMILES: O=C(C1CC1)N1CC[C@@H](CN2C(=O)C3(CC3)N=C2c2ccc(-c3cnc4ccccc4c3)cc2)C1] | 6-{[(3R)-1-(Cyclopropylcarbonyl)pyrrolidin-3-yl]methyl}-5-(4-quinolin-3-ylphenyl)-4,6-diazaspiro[2.4]hept-4-en-7-one<br>MS m/z 465 (M + H)+ |
| 475 | 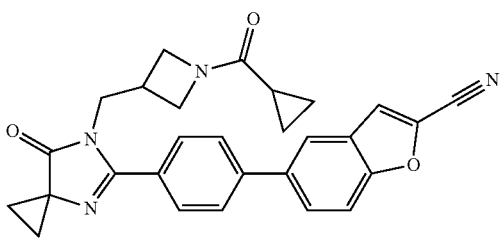 [SMILES: N#Cc1cc2cc(-c3ccc(C4=NC5(CC5)C(=O)N4CC4CN(C(=O)C5CC5)C4)cc3)ccc2o1] | 5-[4-(6-{[1-(Cyclopropylcarbonyl)azetidin-3-yl]methyl}-7-oxo-4,6-diazaspiro[2.4]hept-4-en-5-yl)phenyl]-1-benzofuran-2-carbonitrile<br>MS m/z 465 (M + H)+ |
| 476 | 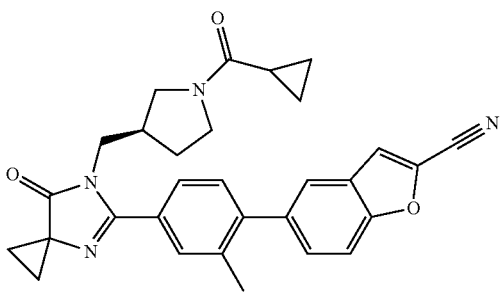 [SMILES: Cc1cc(C2=NC3(CC3)C(=O)N2C[C@@H]2CCN(C(=O)C3CC3)C2)ccc1-c1ccc2oc(C#N)cc2c1] | 5-[4-(6-{[(3R)-1-(Cyclopropylcarbonyl)pyrrolidin-3-yl]methyl}-7-oxo-4,6-diazaspiro[2.4]hept-4-en-5-yl)-2-methylphenyl]-1-benzofuran-2-carbonitrile<br>MS m/z 493 (M + H)+ |
| 477 | 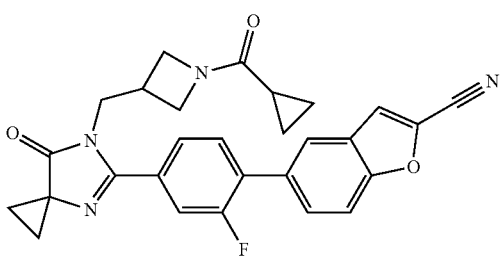 [SMILES: N#Cc1cc2cc(-c3ccc(C4=NC5(CC5)C(=O)N4CC4CN(C(=O)C5CC5)C4)cc3F)ccc2o1] | 5-[4-(6-{[1-(Cyclopropylcarbonyl)azetidin-3-yl]methyl}-7-oxo-4,6-diazaspiro[2.4]hept-4-en-5-yl)-2-fluorophenyl]-1-benzofu8ran-2-carbonitrile<br>MS m/z 483 (M + H)+ |

-continued

| ID No. | Structure | Compound Name & Physical Data |
|---|---|---|
| 478 | 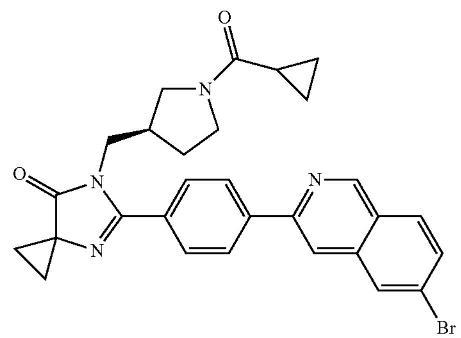 [SMILES: O=C(C1CC1)N1CC[C@@H](CN2C(=O)C3(CC3)N=C2c2ccc(-c3cc4cc(Br)ccc4cn3)cc2)C1] | 5-[4-(6-Bromoisoquinolin-3-yl)phenyl]-6-{[(3R)-1-(cyclopropylcarbonyl)pyrrolidin-3-yl]methyl}-4,6-diazaspiro[2.4]hept-4-en-7-one<br>MS m/z 543 (M + H)+ |
| 479 | 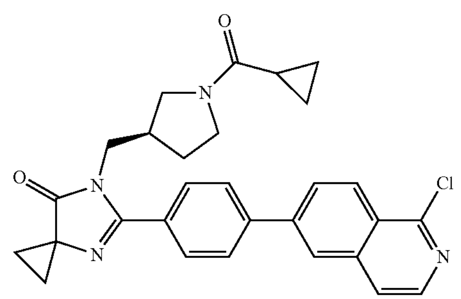 [SMILES: O=C(C1CC1)N1CC[C@@H](CN2C(=O)C3(CC3)N=C2c2ccc(-c3ccc4c(Cl)nccc4c3)cc2)C1] | 5-[4-(1-Chloroisoquinolin-6-yl)phenyl]-6-{[(3R)-1-(cyclopropylcarbonyl)pyrrolidin-3-yl]methyl}-4,6-diazaspiro[2.4]hept-4-en-7-one<br>MS m/z 499 (M + H)+ |
| 480 | 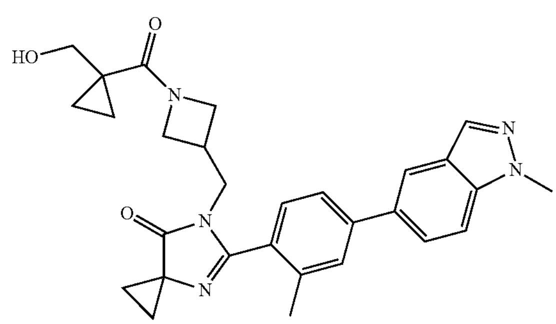 [SMILES: Cc1cc(-c2ccc3c(cnn3C)c2)ccc1C1=NC2(CC2)C(=O)N1CC1CN(C(=O)C2(CO)CC2)C1] | 6-[(1-{[1-(Hydroxymethyl)cyclopropyl]carbonyl}azetidin-3-yl)methyl]-5-[2-methyl-4-(1-methyl-1H-indazol-5-yl)phenyl]-4,6-diazaspiro[2.4]hept-4-en-7-one<br>MS m/z 498.3 (M + H)+ |
| 481 | 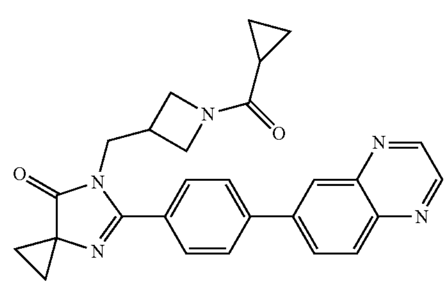 [SMILES: O=C(C1CC1)N1CC(CN2C(=O)C3(CC3)N=C2c2ccc(-c3ccc4nccnc4c3)cc2)C1] | 6-{[1-(Cyclopropylcarbonyl)azetidin-3-yl]methyl}-5-(4-quinoxalin-6-ylphenyl)-4,6-diazaspiro[2.4]hept-4-en-7-one<br>MS m/z 452 (M + H)+ |
| 482 | 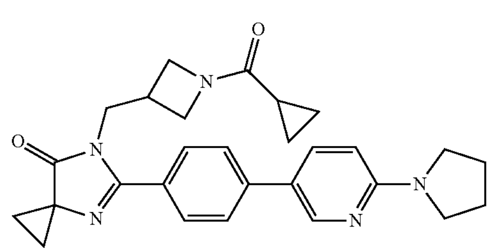 [SMILES: O=C(C1CC1)N1CC(CN2C(=O)C3(CC3)N=C2c2ccc(-c3ccc(N4CCCC4)nc3)cc2)C1] | 6-{[1-(Cyclopropylcarbonyl)azetidin-3-yl]methyl}-5-[4-(6-pyrrolidin-1-ylpyridin-3-yl)phenyl]-4,6-diazaspiro[2.4]hept-4-en-7-one<br>MS m/z 470 (M + H)+ |

| ID No. | Structure | Compound Name & Physical Data |
|---|---|---|
| 483 | 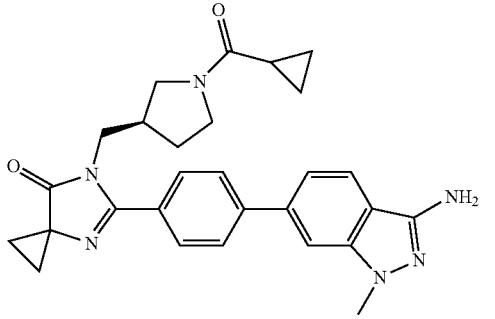 [SMILES: Cn1nc(N)c2ccc(-c3ccc(C4=NC5(CC5)C(=O)N4C[C@@H]4CCN(C(=O)C5CC5)C4)cc3)cc21] | 5-[4-(3-Amino-1-methyl-1H-indazol-6-yl)phenyl]-6-{[(3R)-1-(cyclopropylcarbonyl)pyrrolidin-3-yl]methyl}-4,6-diazaspiro[2.4]hept-4-en-7-one<br>MS m/z 483 (M + H)+ |
| 484 | 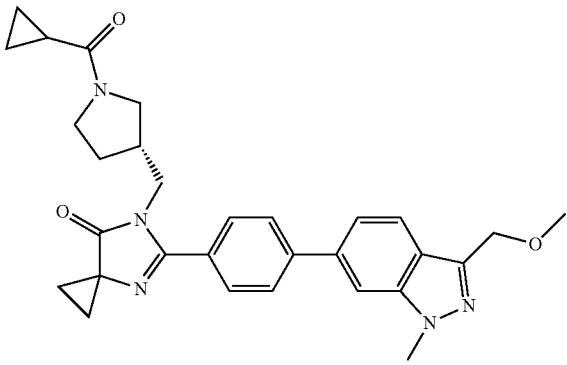 [SMILES: COCc1nn(C)c2cc(-c3ccc(C4=NC5(CC5)C(=O)N4C[C@@H]4CCN(C(=O)C5CC5)C4)cc3)ccc12] | 6-{[(3R)-1-(Cyclopropylcarbonyl)pyrrolidin-3-yl]methyl}-5-{4-[3-(methoxymethyl)-1-methyl-1H-indazol-6-yl]phenyl}-4,6-diazaspiro[2.4]hept-4-en-7-one<br>MS m/z 512 (M + H)+ |
| 485 | 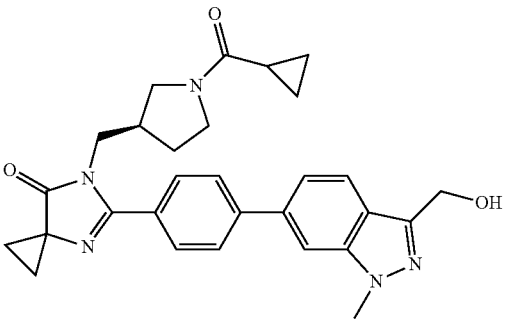 [SMILES: Cn1nc(CO)c2ccc(-c3ccc(C4=NC5(CC5)C(=O)N4C[C@@H]4CCN(C(=O)C5CC5)C4)cc3)cc21] | 6-{[(3R)-1-(Cyclopropylcarbonyl)pyrrolidin-3-yl]methyl}-5-{4-[3-(hydroxymethyl)-1-methyl-1H-indazol-6-yl]phenyl}-4,6-diazaspiro[2.4]hept-4-en-7-one<br>MS m/z 498 (M + H)+ |
| 486 | 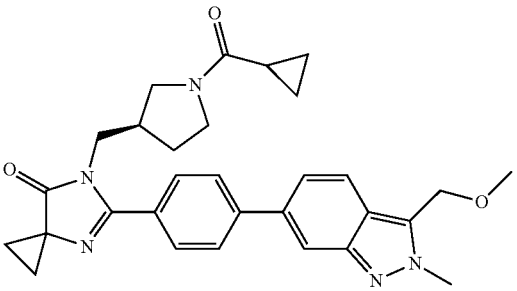 [SMILES: COCc1c2ccc(-c3ccc(C4=NC5(CC5)C(=O)N4C[C@@H]4CCN(C(=O)C5CC5)C4)cc3)cc2nn1C] | 6-{[(3R)-1-(Cyclopropylcarbonyl)pyrrolidin-3-yl]methyl}-5-{4-[3-(methoxymethyl)-2-methyl-2H-indazol-6-yl]phenyl}-4,6-diazaspiro[2.4]hept-4-en-7-one<br>MS m/z 512 (M + H)+ |

| ID No. | Structure | Compound Name & Physical Data |
|---|---|---|
| 487 | 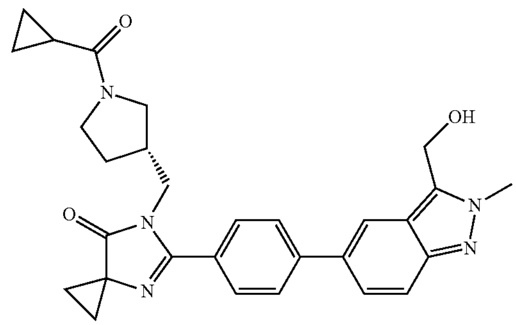 [SMILES: Cn1nc2ccc(-c3ccc(C4=NC5(CC5)C(=O)N4C[C@@H]4CCN(C(=O)C5CC5)C4)cc3)cc2c1CO] | 6-{[(3R)-1-(Cyclopropylcarbonyl)pyrrolidin-3-yl]methyl}-5-{4-[3-(hydroxymethyl)-2-methyl-2H-indazol-5-yl]phenyl}-4,6-diazaspiro[2.4]hept-4-en-7-one<br>MS m/z 498 (M + H)+ |
| 488 | 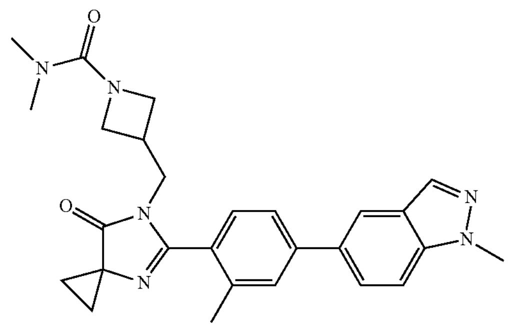 | N,N-Dimethyl-3-({5-[2-methyl-4-(1-methyl-1H-indazol-5-yl)phenyl]-7-oxo-4,6-diazaspiro[2.4]hept-4-en-6-yl}methyl)azetidine-1-carboxamide[]<br>MS m/z 471.3 (M + H)+ |
| 489 | 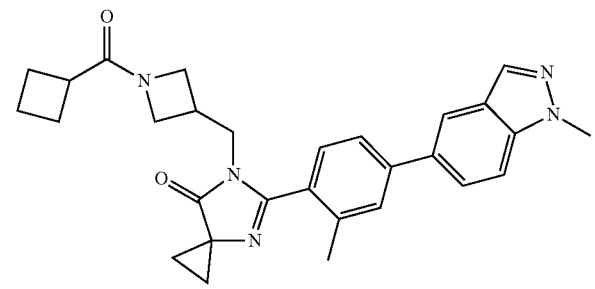 [SMILES: Cc1cc(-c2ccc3c(cnn3C)c2)ccc1C1=NC2(CC2)C(=O)N1CC1CN(C(=O)C2CCC2)C1] | 6-{[1-(Cyclopropylcarbonyl)azetidin-3-yl]methyl}-5-[2-methyl-4-(1-methyl-1H-indazol-5-yl)phenyl]-4,6-diazaspiro[2.4]hept-4-en-7-one<br>MS m/z 482.3 (M + H)+ |

| ID No. | Structure | Compound Name & Physical Data |
|---|---|---|
| 490 | 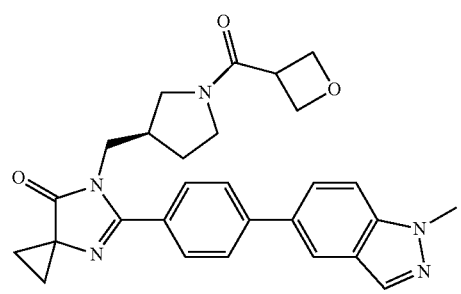 [SMILES: Cn1ncc2cc(-c3ccc(C4=NC5(CC5)C(=O)N4C[C@@H]4CCN(C(=O)C5COC5)C4)cc3)ccc21] | 5-[4-(1-Methyl-1H-indazol-5-yl)phenyl]-6-{[(3R)-1-(oxetan-3-ylcarbonyl)pyrrolidin-3-yl]methyl}-4,6-diazaspiro[2.4]hept-4-en-7-one<br>MS m/z 484.1 (M + H)+ |

-continued

| ID No. | Structure | Compound Name & Physical Data |
|---|---|---|
| 491 | 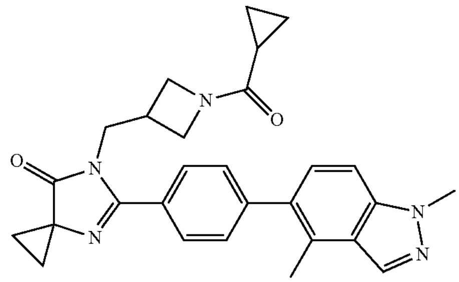 [SMILES: Cc1c(-c2ccc(C3=NC4(CC4)C(=O)N3CC3CN(C(=O)C4CC4)C3)cc2)ccc2c1cnn2C] | 6-{[1-(Cyclopropylcarbonyl)azetidin-3-yl]methyl}-5-[4-(1,4-dimethyl-1H-indazol-5-yl)phenyl]-4,6-diazaspiro[2.4]hept-4-en-7-one<br>MS m/z 468 (M + H)+ |
| 492 | 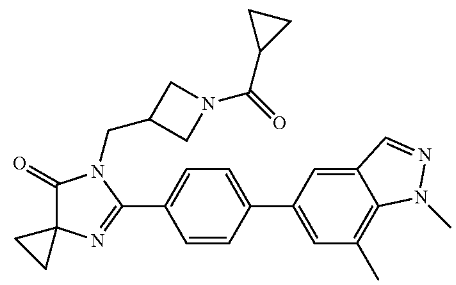 [SMILES: Cc1cc(-c2ccc(C3=NC4(CC4)C(=O)N3CC3CN(C(=O)C4CC4)C3)cc2)cc2cnn(C)c12] | 6-{[1-(Cyclopropylcarbonyl)azetidin-3-yl]methyl}-5-[4-(1,7-dimethyl-1H-indazol-5-yl)phenyl]-4,6-dazaspiro[2.4]hept-7-one<br>MS m/z 468 (M + H)+ |
| 493 | 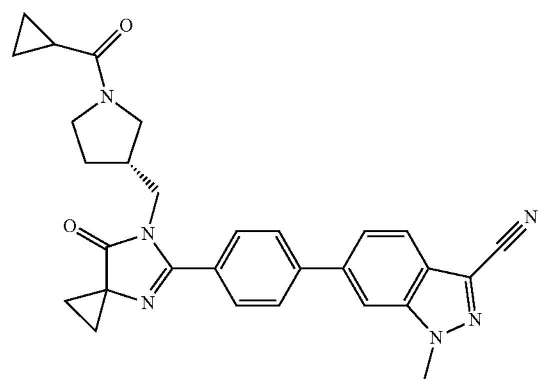 [SMILES: Cn1nc(C#N)c2ccc(-c3ccc(C4=NC5(CC5)C(=O)N4C[C@@H]4CCN(C(=O)C5CC5)C4)cc3)cc21] | 6-[4-(6-{[(3R)-1-(Cyclopropylcarbonyl)pyrrolidin-3-yl]methyl}-7-oxo-4,6-diazaspiro[2.4]hept-4-en-5-yl)phenyl]-1-methyl-1H-indazole-3-carbonitrile<br>MS m/z 493 (M + H)+ |
| 494 | 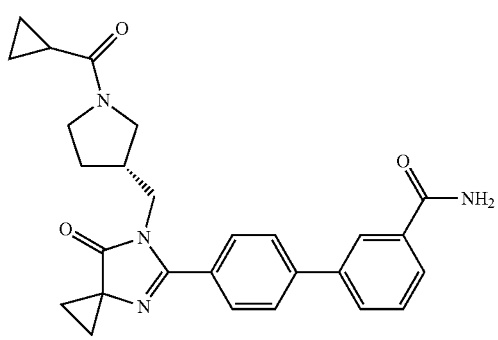 [SMILES: NC(=O)c1cccc(-c2ccc(C3=NC4(CC4)C(=O)N3C[C@@H]3CCN(C(=O)C4CC4)C3)cc2)c1] | 4'-(6-{[(3R)-1-(Cyclopropylcarbonyl)pyrrolidin-3-yl]methyl}-7-oxo-4,6-diazaspiro[2.4]hept-4-en-5-yl)biphenyl-3-carboxamide<br>MS m/z 457 (M + H)+ |
| 495 | 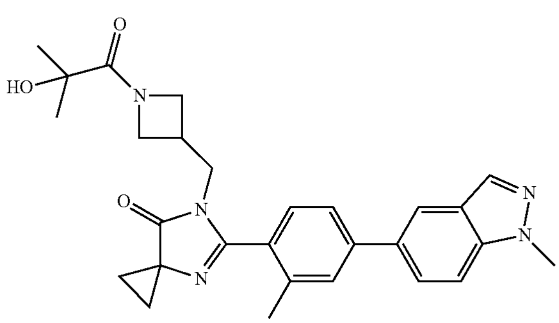 [SMILES: Cc1cc(-c2ccc3c(cnn3C)c2)ccc1C1=NC2(CC2)C(=O)N1CC1CN(C(=O)C(C)(C)O)C1] | 6-{[1-(2-Hydroxy-2-methylpropanoyl)azetidin-3-yl]methyl}-5-[2-methyl-4-(1-methyl-1H-indazol-5-yl)phenyl]-4,6-diazaspiro[2.4]hept-4-en-7-one<br>MS m/z 486.3 (M + H)+ |

| ID No. | Structure | Compound Name & Physical Data |
|---|---|---|
| 496 | 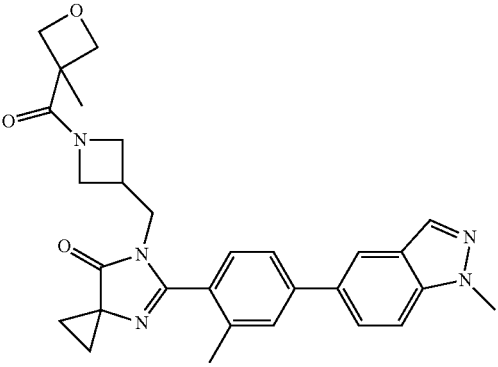 [SMILES: Cc1cc(-c2ccc3c(cnn3C)c2)ccc1C1=NC2(CC2)C(=O)N1CC1CN(C(=O)C2(C)COC2)C1] | 5-[2-Methyl-4-(1-methyl-1H-indazol-5-yl)phenyl]-6-({1-[(3-methyloxetan-3-yl)carbonyl]azetidin-3-yl}methyl)-4,6-diazaspiro[2.4]hept-4-en-7-one<br>MS m/z 498.2 (M + H)+ |
| 497 | 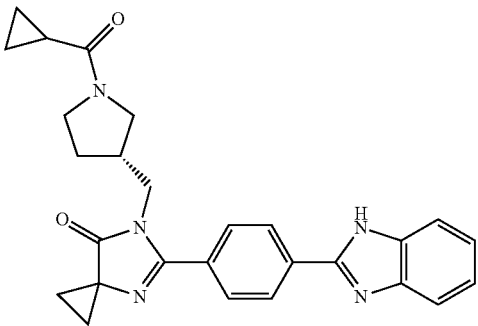 [SMILES: O=C(C1CC1)N1CC[C@@H](CN2C(=O)C3(CC3)N=C2c2ccc(-c3nc4ccccc4[nH]3)cc2)C1] | 5-[4-(1H-Benzimidazol-2-yl)phenyl]-6-{[(3R)-1-(cyclopropylcarbonyl)pyrrolidin-3-yl]methyl}-4,6-diazaspiro[2.4]hept-4-en-7-one<br>MS m/z 454 (M + H)+ |
| 498 | 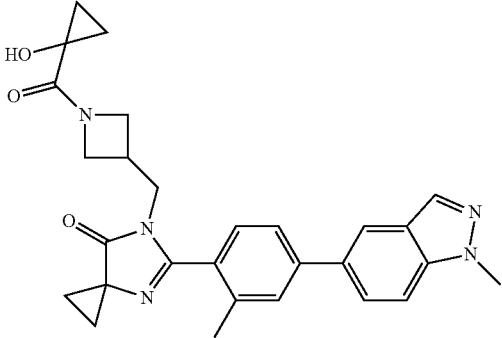 [SMILES: Cc1cc(-c2ccc3c(cnn3C)c2)ccc1C1=NC2(CC2)C(=O)N1CC1CN(C(=O)C2(O)CC2)C1] | 6-({1-[(1-Hydroxycyclopropyl)carbonyl]-azetidin-3-yl}methyl)-5-[2-methyl-4-(1-methyl-1H-indazol-5-yl)phenyl]-4,6-diazaspiro[2.4]hept-4-en-7-one<br>MS m/z 484.3 (M + H)+ |
| 499 | 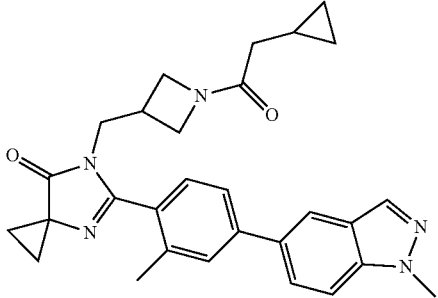 [SMILES: Cc1cc(-c2ccc3c(cnn3C)c2)ccc1C1=NC2(CC2)C(=O)N1CC1CN(C(=O)CC2CC2)C1] | 6-{[1-(Cyclopropylacetyl)azetidin-3-yl]methyl}-5-[2-methyl-4-(1-methyl-1H-indazol-5-yl)phenyl]-4,6-diazaspiro[2.4]hept-4-en-7-one<br>MS m/z 482.3 (M + H)+ |

| ID No. | Structure | Compound Name & Physical Data |
|---|---|---|
| 500 | 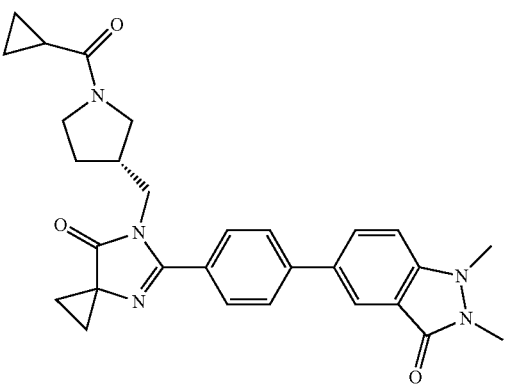 [SMILES: Cn1c(=O)c2cc(-c3ccc(C4=NC5(CC5)C(=O)N4C[C@@H]4CCN(C(=O)C5CC5)C4)cc3)ccc2n1C] | 5-[4-(6-{[(3R)-1-(Cyclopropylcarbonyl)pyrrolidin-3-yl]methyl}-7-oxo-4,6-diazaspiro[2.4]hept-4-rn-5-yl)phenyl]-1,2-dimethyl-1,2-dihydro-3H-indazol-3-one<br>MS m/z 498 (M + H)+ |
| 501 | 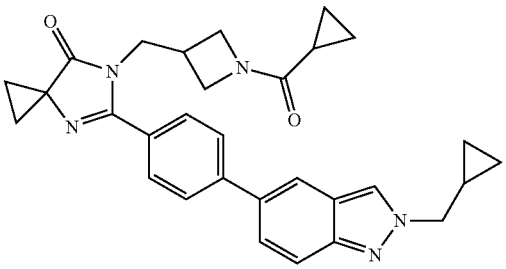 [SMILES: O=C(C1CC1)N1CC(CN2C(=O)C3(CC3)N=C2c2ccc(-c3ccc4nn(CC5CC5)cc4c3)cc2)C1] | 6-{[1-(Cyclopropylcarbonyl)azetidin-3-yl]methyl}-5-{4-[2-(cyclopropylmethyl)-2H-indazol-5-yl]phenyl}-4,6-diazaspiro[2.4]hept-4-en-7-one<br>MS m/z 494 (M + H)+ |
| 502 | 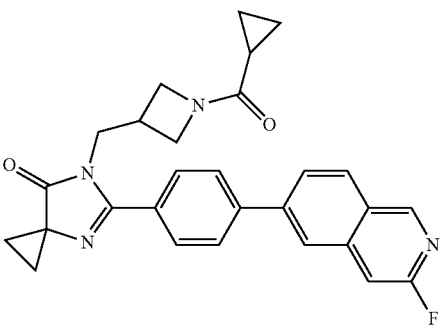 [SMILES: O=C(C1CC1)N1CC(CN2C(=O)C3(CC3)N=C2c2ccc(-c3ccc4cnc(F)cc4c3)cc2)C1] | 6-{[1-(Cyclopropylcarbonyl)azetidin-3-yl]methyl}-5-[4-(3-fluoroisoquinolin-6-yl)phenyl]-4,6-diazaspiro[2.4]hept-4-en-7-one<br>MS m/z 469 (M + H)+ |
| 503 | 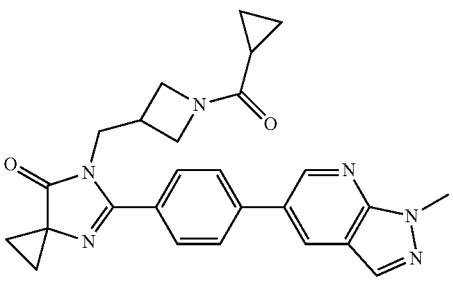 [SMILES: Cn1ncc2cc(-c3ccc(C4=NC5(CC5)C(=O)N4CC4CN(C(=O)C5CC5)C4)cc3)cnc21] | 6-{[1-(Cyclopropylcarbonyl)azetidin-3-yl]methyl}-5-[4-(1-methyl-1H-pyrazolo[3,4-b]pyridin-5-yl)phenyl]-4,6-diazaspiro[2.4]hept-4-en-7-one<br>MS m/z 455 (M + H)+ |
| 504 | 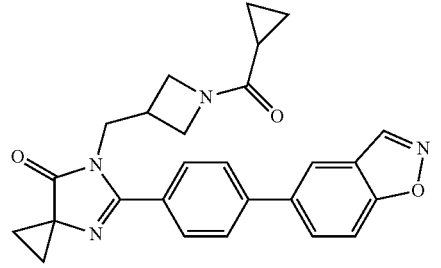 [SMILES: O=C(C1CC1)N1CC(CN2C(=O)C3(CC3)N=C2c2ccc(-c3ccc4oncc4c3)cc2)C1] | 5-[4-(1,2-Benzisoxazol-5-yl)phenyl]-6-{[1-(cyclopropylcarbonyl)azetidin-3-yl]methyl}-4,6-diazaspiro[2.4]hept-4-en-7-one<br>MS m/z 441 (M + H)+ |

| ID No. | Structure | Compound Name & Physical Data |
|---|---|---|
| 505 | 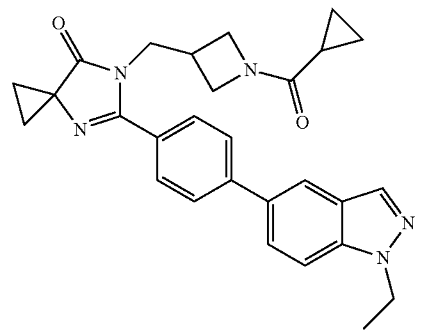 [SMILES: CCn1ncc2cc(-c3ccc(C4=NC5(CC5)C(=O)N4CC4CN(C(=O)C5CC5)C4)cc3)ccc21] | 6-{[1-(Cyclopropylcarbonyl)azetidin-3-yl]methyl}-5-[4-(1-ethyl-1H-indazol-5-yl)phenyl]-4,6-diazaspiro[2.4]hept-4-en-7-one<br>MS m/z 468 (M + H)+ |
| 506 | 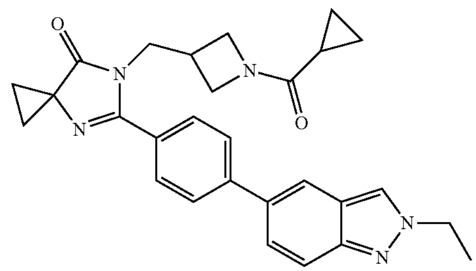 [SMILES: CCn1cc2cc(-c3ccc(C4=NC5(CC5)C(=O)N4CC4CN(C(=O)C5CC5)C4)cc3)ccc2n1] | 6-{[1-(Cyclopropylcarbonyl)azetidin-3-yl]methyl}-5-[4-(2-ethyl-2H-indazol-5-yl)phenyl]-4,6-diazaspiro[2.4]hept-4-en-7-one<br>MS m/z 468 (M + H)+ |
| 507 | 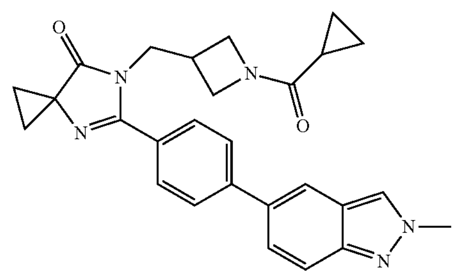 [SMILES: Cn1cc2cc(-c3ccc(C4=NC5(CC5)C(=O)N4CC4CN(C(=O)C5CC5)C4)cc3)ccc2n1] | 6-{[1-(Cyclopropylcarbonyl)azetidin-3-yl]methyl}-5-[4-(2-methyl-2H-indazol-5-yl)phenyl]-4,6-diazaspiro[2.4]hept-4-en-7-one<br>MS m/z 454 (M + H)+ |
| 508 | 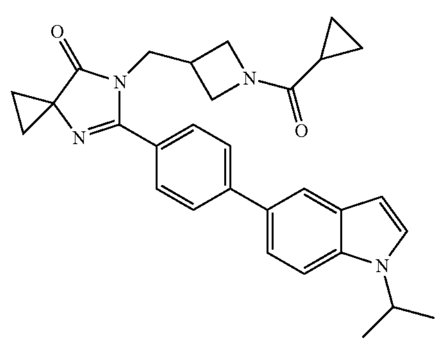 [SMILES: CC(C)n1ccc2cc(-c3ccc(C4=NC5(CC5)C(=O)N4CC4CN(C(=O)C5CC5)C4)cc3)ccc21] | 6-{[1-(Cyclopropylcarbonyl)azetidin-3-yl]methyl}-5-{4-[1-(1-methylethyl)-1H-indol-5-yl]phenyl}-4,6-diazaspiro[2.4]hept-4-en-7-one<br>MS m/z 481 (M + H)+ |
| 509 | 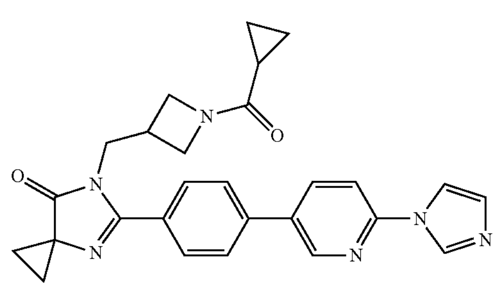 [SMILES: O=C(C1CC1)N1CC(CN2C(=O)C3(CC3)N=C2c2ccc(-c3ccc(-n4ccnc4)nc3)cc2)C1] | 6-{[1-(Cyclopropylcarbonyl)azetidin-3-yl]methyl}-5-{4-[6-(1H-imidazol-1-yl)pyridin-3-yl]phenyl}-4,6-diazaspiro[2.4]hept-4-en-7-one<br>MS m/z 467 (M + H)+ |

| ID No. | Structure | Compound Name & Physical Data |
|---|---|---|
| 510 | 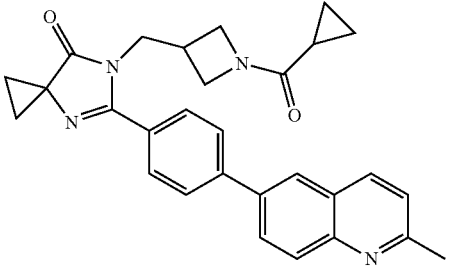 [SMILES: Cc1ccc2cc(-c3ccc(C4=NC5(CC5)C(=O)N4CC4CN(C(=O)C5CC5)C4)cc3)ccc2n1] | 6-{[1-(Cyclopropylcarbonyl)azetidin-3-yl]methyl}-5-[4-(2-methylquinolin-6-yl)phenyl]-4,6-diazaspiro[2.4]hept-4-en-7-one<br>MS m/z 465 (M + H)+ |
| 511 | 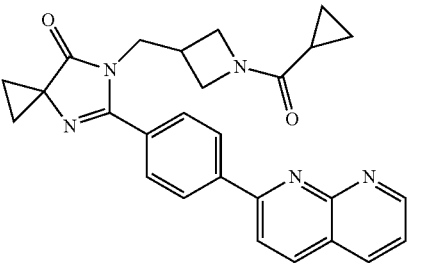 [SMILES: O=C(C1CC1)N1CC(CN2C(=O)C3(CC3)N=C2c2ccc(-c3ccc4cccnc4n3)cc2)C1] | 6-{[1-(Cyclopropylcarbonyl)azetidin-3-yl]methyl}-5-[4-(1,8-naphthyridin-2-yl)phenyl]-4,6-diazaspiro[2.4]hept-4-en-7-one<br>MS m/z 452 (M + H)+ |
| 512 | 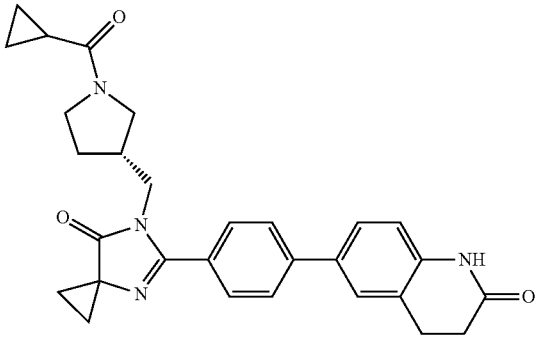 [SMILES: O=C1CCc2cc(-c3ccc(C4=NC5(CC5)C(=O)N4C[C@@H]4CCN(C(=O)C5CC5)C4)cc3)ccc2N1] | 6-[4-(6-{[(3R)-1-(Cyclopropylcarbonyl)pyrrolidin-3-yl]methyl}-7-oxo-4,6-diazaspiro[2.4]hept-4-en-5-yl)phenyl]-3,4-dihydroquinolin-2(1H)-one<br>MS m/z 483 (M + H)+ |
| 513 | 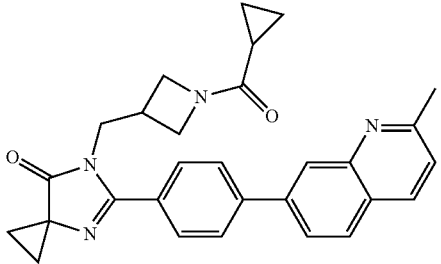 | 6-{[1-(Cyclopropylcarbonyl)azetidin-3-yl]methyl}-5-[4-(2-methylquinolin-7-yl)phenyl]-4,6-diazaspiro[2.4]hept-4-en-7-one<br>MS m/z 465 (M + H)+ |
| 514 | 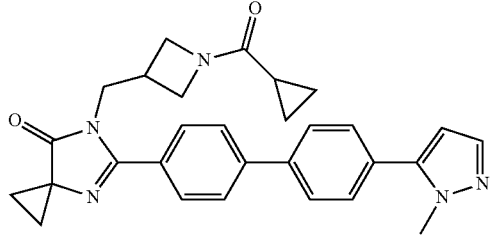 [SMILES: Cn1nccc1-c1ccc(-c2ccc(C3=NC4(CC4)C(=O)N3CC3CN(C(=O)C4CC4)C3)cc2)cc1] | 6-{[1-(Cyclopropylcarbonyl)azetidin-3-yl]methyl}-5-[4'-(1-methyl-1H-pyrazol-5-yl)biphenyl-4-yl]-4,6-diazaspiro[2.4]hept-4-en-7-one<br>MS m/z 480 (M + H)+ |

| ID No. | Structure | Compound Name & Physical Data |
|---|---|---|
| 515 | 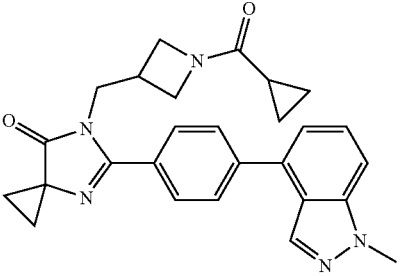 [SMILES: Cn1ncc2c(-c3ccc(C4=NC5(CC5)C(=O)N4CC4CN(C(=O)C5CC5)C4)cc3)cccc21] | 6-{[1-(Cyclopropylcarbonyl)azetidin-3-yl]methyl}-5-[4-(1-methyl-1H-indazol-4-yl)phenyl]-4,6-diazaspiro[2.4]hept-4-en-7-one<br>MS m/z 454 (M + H)+ |
| 516 | 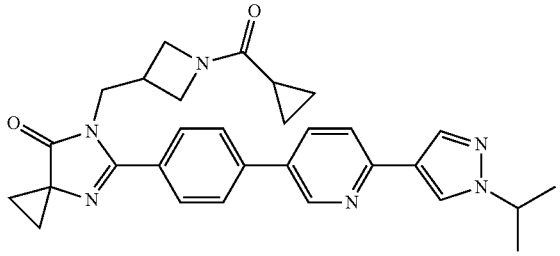 [SMILES: CC(C)n1cc(-c2ccc(-c3ccc(C4=NC5(CC5)C(=O)N4CC4CN(C(=O)C5CC5)C4)cc3)cn2)cn1] | 6-{[1-(Cyclopropylcarbonyl)azetidin-3-yl]methyl}-5-(4-{6-[1-(1-methylethyl)-1H-pyrazol-4-yl]pyridin-3-yl}phenyl)-4,6-diazaspiro[2.4]hept-4-en-7-one<br>MS m/z 509 (M + H)+ |
| 517 | 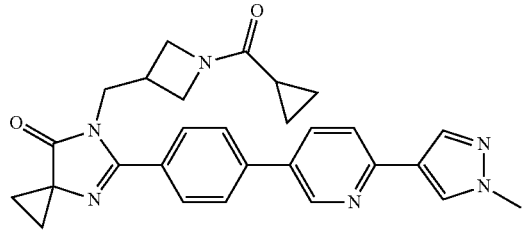 [SMILES: Cn1cc(-c2ccc(-c3ccc(C4=NC5(CC5)C(=O)N4CC4CN(C(=O)C5CC5)C4)cc3)cn2)cn1] | 6-{[1-(Cyclopropylcarbonyl)azetidin-3-yl]methyl}-5-{4-[6-(1-methyl-1H-pyrazol-4-yl)pyridin-3-yl]phenyl}-4,6-diazaspiro[2.4]hept-4-en-7-one<br>MS m/z 481 (M + H)+ |
| 518 | 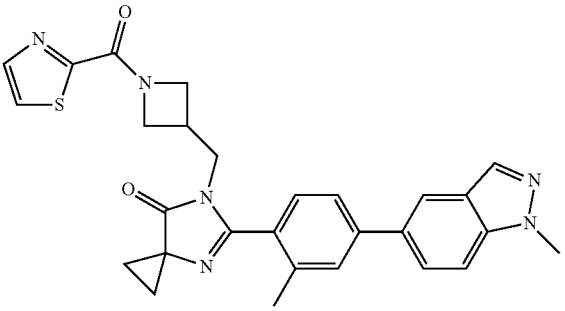 [SMILES: Cc1cc(-c2ccc3c(cnn3C)c2)ccc1C1=NC2(CC2)C(=O)N1CC1CN(C(=O)c2nccs2)C1] | 5-[2-Methyl-4-(1-methyl-1H-indazol-5-yl)phenyl]-6-{[1-(1,3-thiazol-2-ylcarbonyl)azetidin-3-yl]methyl}-4,6-diazaspiro[2.4]hept-4-en-7-one<br>MS m/z 511.2 (M + H)+ |
| 519 | 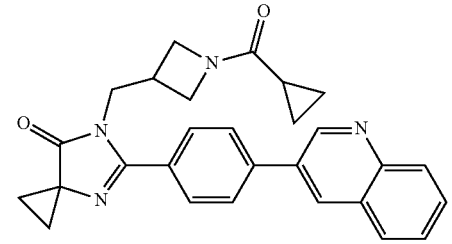 [SMILES: O=C(C1CC1)N1CC(CN2C(=O)C3(CC3)N=C2c2ccc(-c3cnc4ccccc4c3)cc2)C1] | 6-{[1-(Cyclopropylcarbonyl)azetidin-3-yl]methyl}-5-(4-quinolin-3-ylphenyl)-4,6-diazaspiro[2.4]hept-4-en-7-one<br>MS m/z 451 (M + H)+ |

-continued

| ID No. | Structure | Compound Name & Physical Data |
|---|---|---|
| 520 | 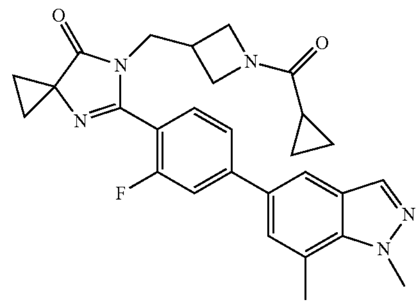 [SMILES: Cc1cc(-c2ccc(C3=NC4(CC4)C(=O)N3CC3CN(C(=O)C4CC4)C3)c(F)c2)cc2cnn(C)c12] | 6-{[1-(Cyclopropylcarbonyl)azetidin-3-yl]methyl}-5-[4-(1,7-dimethyl-1H-indazol-5-yl)-2-fluorophenyl]-4,6-diazaspiro[2.4]hept-4-en-7-one<br>MS m/z 486 (M + H)+ |
| 521 | 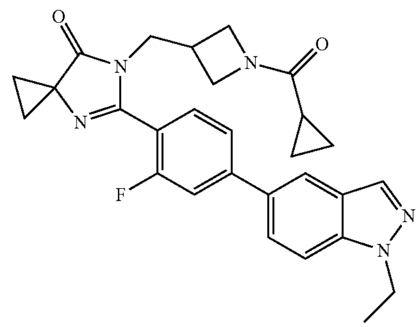 [SMILES: CCn1ncc2cc(-c3ccc(C4=NC5(CC5)C(=O)N4CC4CN(C(=O)C5CC5)C4)c(F)c3)ccc21] | 6-{[1-(Cyclopropylcarbonyl)azetidin-3-yl]methyl}-5-[4-(1-ethyl-1H-indazol-5-yl)-2-fluorophenyl]-4,6-diazaspiro[2.4]hept-4-en-7-one<br>MS m/z 486 (M + H)+ |
| 522 | 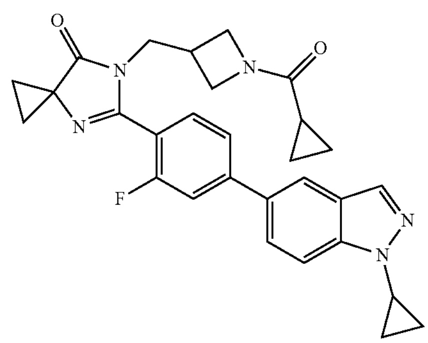 [SMILES: O=C(C1CC1)N1CC(CN2C(=O)C3(CC3)N=C2c2ccc(-c3ccc4c(cnn4C4CC4)c3)cc2F)C1] | 6-{[1-(Cyclopropylcarbonyl)azetidin-3-yl]methyl}-5-[4-(1-cyclopropyl-1-indazol-5-yl)-2-fluorophenyl]-4,6-diazaspiro[2.4]hept-4-en-7-one<br>MS m/z 498 (M + H)+ |
| 423 | 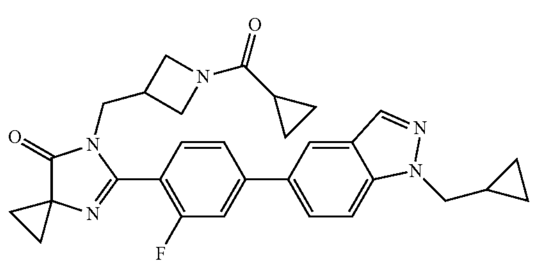 [SMILES: O=C(C1CC1)N1CC(CN2C(=O)C3(CC3)N=C2c2ccc(-c3ccc4c(cnn4CC4CC4)c3)cc2F)C1] | 6-{[1-(Cyclopropylcarbonyl)azetidin-3-yl]methyl}-5-{4-[1-(cyclopropylmethyl)-1H-indazol-5-yl]-2-fluorophenyl}-4,6-diazaspiro[2.4]hept-4-en-7-one<br>MS m/z 512 (M + H)+ |
| 524 | 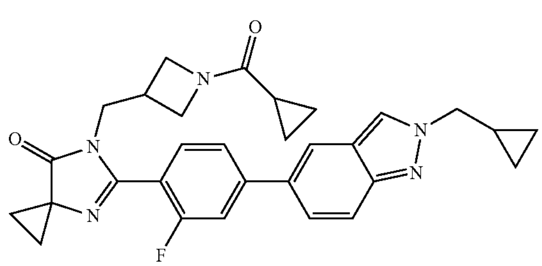 [SMILES: O=C(C1CC1)N1CC(CN2C(=O)C3(CC3)N=C2c2ccc(-c3ccc4nn(CC5CC5)cc4c3)cc2F)C1] | 6-{[1-(Cyclopropylcarbonyl)azetidin-3-yl]methyl}-5-{4-[2-(cyclopropylmethyl)-2H-indazol-5-yl]-2-fluorophenyl}-4,6-diazaspiro[2.4]hept-4-en-7-one<br>MS m/z 512 (M + H)+ |

| ID No. | Structure | Compound Name & Physical Data |
|---|---|---|
| 525 | 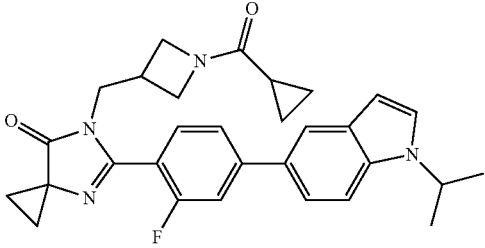 [SMILES: CC(C)n1ccc2cc(-c3ccc(C4=NC5(CC5)C(=O)N4CC4CN(C(=O)C5CC5)C4)c(F)c3)ccc21] | 6-{[1-(Cyclopropylcarbonyl)azetidin-3-yl]methyl}-5-{2-fluoro-4-[1-(1-methylethyl)-1H-indol-5-yl]phenyl}-4,6-diazaspiro[2.4]hept-4-en-7-one<br>MS m/z 499 (M + H)+ |
| 526 | 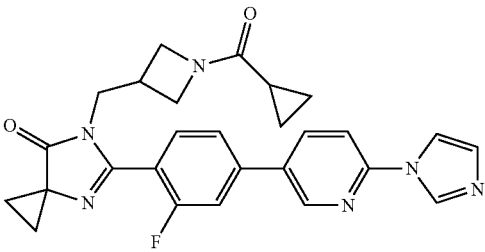 [SMILES: O=C(C1CC1)N1CC(CN2C(=O)C3(CC3)N=C2c2ccc(-c3ccc(-n4ccnc4)nc3)cc2F)C1] | 6-{[1-(Cyclopropylcarbonyl)azetidin-3-yl]methyl}-5-{2-fluoro-4-[6-(1H-imidazol-1-yl)pyridin-3-yl]phenyl}-4,6-diazaspiro[2.4]hept-4-en-7-one<br>MS m/z 485 (M + H)+ |
| 527 | 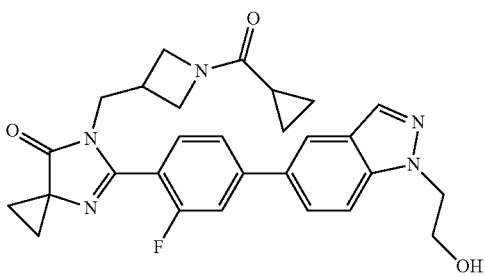 [SMILES: O=C(C1CC1)N1CC(CN2C(=O)C3(CC3)N=C2c2ccc(-c3ccc4c(cnn4CCO)c3)cc2F)C1] | 6-{[1-(Cyclopropylcarbonyl)azetidin-3-yl]methyl}-5-{2-fluoro-4-[1-(2-hydroxyethyl)-1H-indazol-5-yl]phenyl}-4,6-diazaspiro[2.4]hept-4-en-7-one<br>MS m/z 502 (M + H)+ |
| 528 | 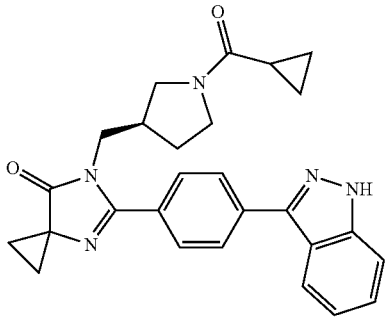 [SMILES: O=C(C1CC1)N1CC[C@@H](CN2C(=O)C3(CC3)N=C2c2ccc(-c3n[nH]c4ccccc34)cc2)C1] | 6-{[(3R)-1-(Cyclopropylcarbonyl)pyrrolidin-3-yl]methyl}-5-[4-(1H-indazol-3-yl)phenyl]-4,6-diazaspiro[2.4]hept-4-en-7-one<br>MS m/z 454 (M + H)+ |
| 529 | 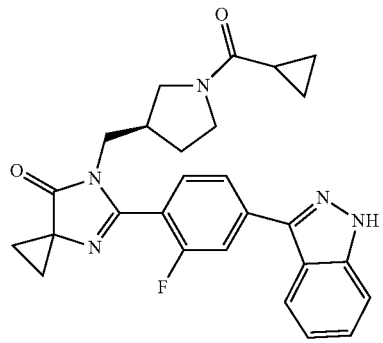 [SMILES: O=C(C1CC1)N1CC[C@@H](CN2C(=O)C3(CC3)N=C2c2ccc(-c3n[nH]c4ccccc34)cc2F)C1] | 6-{[(3R)-1-(Cyclopropylcarbonyl)pyrrolidin-3-yl]methyl}-5-[2-fluoro-4-(1H-indazol-3-yl)phenyl]-4,6-diazaspiro[2.4]hept-4-en-7-one<br>MS m/z 472 (M + H)+ |

-continued

| ID No. | Structure | Compound Name & Physical Data |
|---|---|---|
| 530 | 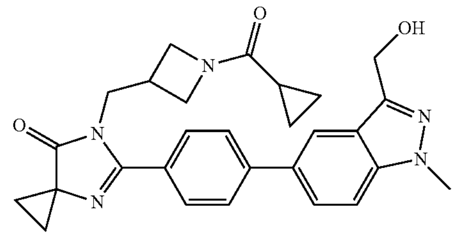 [SMILES: Cn1nc(CO)c2cc(-c3ccc(C4=NC5(CC5)C(=O)N4CC4CN(C(=O)C5CC5)C4)cc3)ccc21] | 6-{[1-(Cyclopropylcarbonyl)azetidin-3-yl]methyl}-5-{4-[3-(hydroxymethyl)-1-methyl-1H-indazol-5-yl]phenyl}-4,6-diazaspiro[2.4]hept-4-en-7-one<br>MS m/z 484 (M + H)+ |
| 531 | 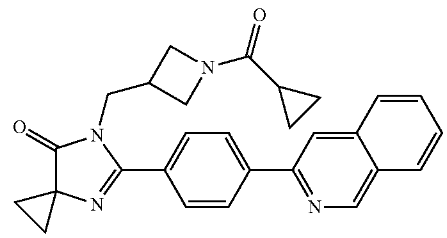 [SMILES: O=C(C1CC1)N1CC(CN2C(=O)C3(CC3)N=C2c2ccc(-c3cc4ccccc4cn3)cc2)C1] | 6-{[1-(Cyclopropylcarbonyl)azetidin-3-yl]methyl}-5-(4-isoquinolin-3-ylphenyl)-4,6-diazaspiro[2.4]hept-4-en-7-one<br>MS m/z 451 (M + H)+ |
| 532 | 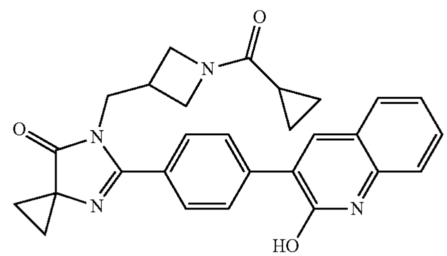 [SMILES: O=C(C1CC1)N1CC(CN2C(=O)C3(CC3)N=C2c2ccc(-c3cc4ccccc4nc3O)cc2)C1] | 6-{[1-(Cyclopropylcarbonyl)azetidin-3-yl]methyl}-5-[4-(2-hydroxyquinolin-3-yl)phenyl]-4,6-diazaspiro[2.4]hept-4-en-7-one<br>MS m/z 467 (M + H)+ |
| 533 | 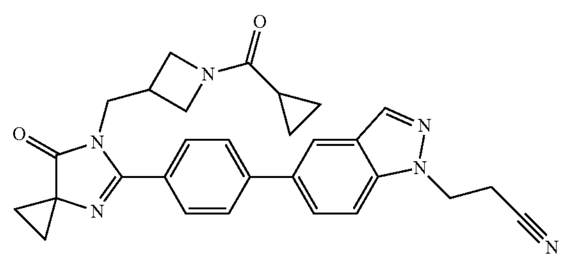 [SMILES: N#CCCn1ncc2cc(-c3ccc(C4=NC5(CC5)C(=O)N4CC4CN(C(=O)C5CC5)C4)cc3)ccc21] | 3-{5-[4-(6-{[1-(Cyclopropylcarbonyl)azetidin-3-yl]methyl}-7-oxo-4,6-diazaspiro[2.4]hept-4-en-5-yl)phenyl]-1H-indazol-1-yl}propanenitrile<br>MS m/z 493 (M + H)+ |
| 534 | 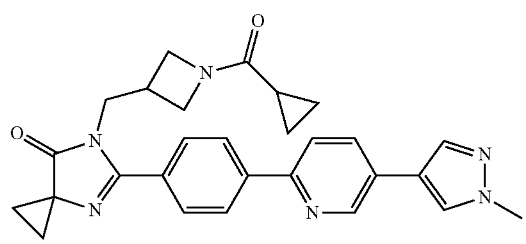 [SMILES: Cn1cc(-c2ccc(-c3ccc(C4=NC5(CC5)C(=O)N4CC4CN(C(=O)C5CC5)C4)cc3)nc2)cn1] | 6-{[1-(Cycloprropylcarbonyl)azetidin-3-yl]methyl}-5-{4-[5-(1-methyl-1H-pyrazol-4-yl)pyridin-2-yl]phenyl}-4,6-diazaspiro[2.4]hept-4-en-7-one<br>MS m/z 481 (M + H)+ |
| 535 | 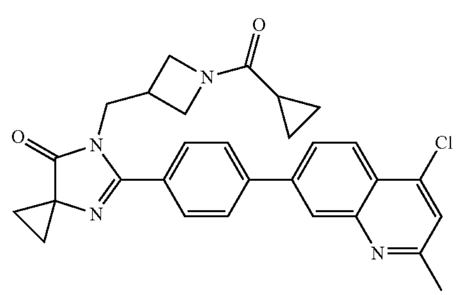 [SMILES: Cc1cc(Cl)c2ccc(-c3ccc(C4=NC5(CC5)C(=O)N4CC4CN(C(=O)C5CC5)C4)cc3)cc2n1] | 5-[4-(4-Chloro-2-methylquinolin-7-yl)phenyl]-6-{[1-(cyclopropylcarbonyl)azetidin-3-yl]methyl}-4,6-diazaspiro[2.4]hept-4-en-7-one<br>MS m/z 499 (M + H)+ |

| ID No. | Structure | Compound Name & Physical Data |
|---|---|---|
| 536 | 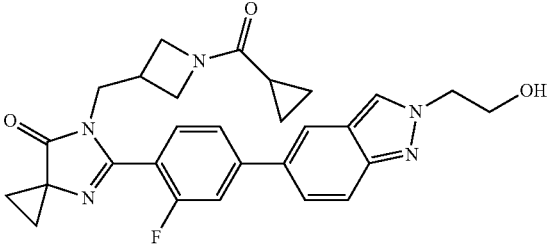 [SMILES: O=C(C1CC1)N1CC(CN2C(=O)C3(CC3)N=C2c2ccc(-c3ccc4nn(CCO)cc4c3)cc2F)C1] | 6-{[1-(Cyclopropylcarbonyl)azetidin-3-yl]methyl}-5-{2-fluoro-4-[2-(2-hydroxyethyl)-2H-indazol-5-yl]phenyl}-4,6-diazaspiro[2.4]hept-4-en-7-one<br>MS m/z 502 (M + H)+ |
| 537 | 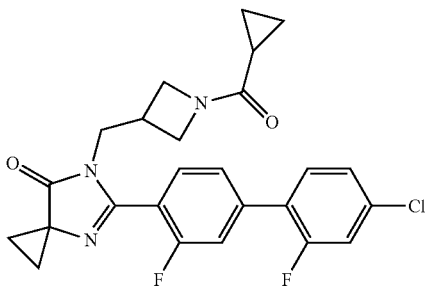 [SMILES: O=C(C1CC1)N1CC(CN2C(=O)C3(CC3)N=C2c2ccc(-c3ccc(Cl)cc3F)cc2F)C1] | 5-(4'-Chloro-2',3-difluorobiphenyl-4-yl)-6-{[1-(cyclopropylcarbonyl)azetidin-3-yl]methyl}-4,6-diazaspiro[2.4]hept-4-en-7-one<br>MS m/z 470 (M + H)+ |
| 538 | 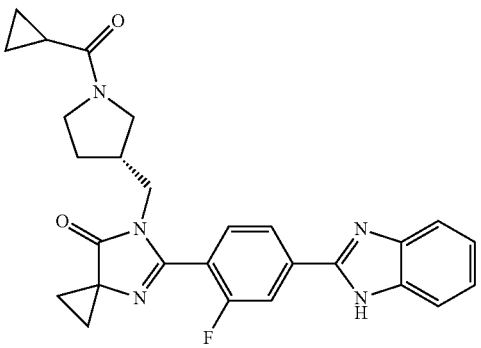 [SMILES: O=C(C1CC1)N1CC[C@@H](CN2C(=O)C3(CC3)N=C2c2ccc(-c3nc4ccccc4[nH]3)cc2F)C1] | 5-[4-(1H-Benzimidazol-2-yl)-2-fluorophenyl]-6-{[(3R)-1-(cyclopropylcarbonyl)pyrrolidin-3-yl]methyl}-4,6-diazaspiro[2.4]hept-4-en-7-one<br>MS m/z 472 (M + H)+ |
| 539 | 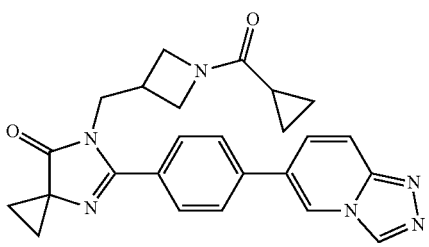 [SMILES: O=C(C1CC1)N1CC(CN2C(=O)C3(CC3)N=C2c2ccc(-c3ccc4nncn4c3)cc2)C1] | 6-{[1-(Cyclopropylcarbonyl)azetidin-3-yl]methyl}-5-(4-[1,2,4]triazolo[4,3-a]pyridin-6-ylphenyl)-4,6-diazaspiro[2.4]hept-4-en-7-one<br>MS m/z 441 (M + H)+ |
| 540 | 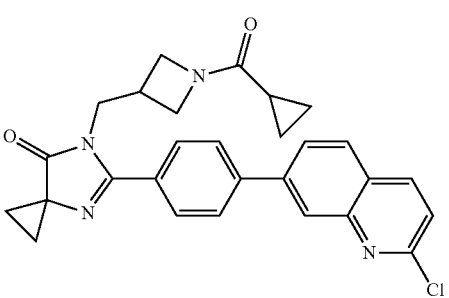 [SMILES: O=C(C1CC1)N1CC(CN2C(=O)C3(CC3)N=C2c2ccc(-c3ccc4ccc(Cl)nc4c3)cc2)C1] | 5-[4-(2-Chloroquinolin-7-yl)phenyl]-6-{[1-(cyclopropylcarbonyl)azetidin-3-yl]methyl}-4,6-diazaspiro[2.4]hept-4-en-7-one<br>MS m/z 485 (M + H)+ |

-continued

| ID No. | Structure | Compound Name & Physical Data |
|---|---|---|
| 541 | 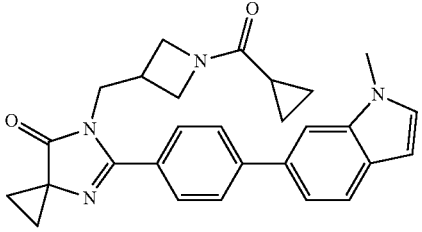 [SMILES: Cn1ccc2ccc(-c3ccc(C4=NC5(CC5)C(=O)N4CC4CN(C(=O)C5CC5)C4)cc3)cc21] | 6-{[1-(Cyclopropylcarbonyl)azetidin-3-yl]methyl}-5-[4-(1-methyl-1H-indol-6-yl)phenyl]-4,6-diazaspiro[2.4]hept-4-en-7-one<br>MS m/z 453 (M + H)+ |
| 542 | 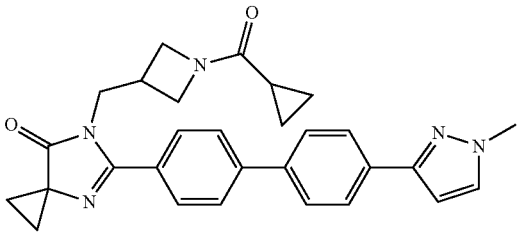 [SMILES: Cn1ccc(-c2ccc(-c3ccc(C4=NC5(CC5)C(=O)N4CC4CN(C(=O)C5CC5)C4)cc3)cc2)n1] | 6-{[1-(Cyclopropylcarbonyl)azetidin-3-yl]methyl}-5-[4'-(1-methyl-1H-pyrazol-3-yl)biphenyl-4-yl]-4,6-diazaspiro[2.4]hept-4-en-7-one<br>MS m/z 480 (M + H)+ |
| 543 | 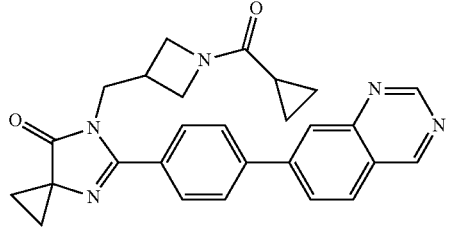 [SMILES: O=C(C1CC1)N1CC(CN2C(=O)C3(CC3)N=C2c2ccc(-c3ccc4cncnc4c3)cc2)C1] | 6-{[1-(Cyclopropylcarbonyl)azetidin-3-yl]methyl}-5-(4-quinazolin-7-ylphenyl)-4,6-diazaspiro[2.4]hept-4-en-7-one<br>MS m/z 452 (M + H)+ |
| 544 | 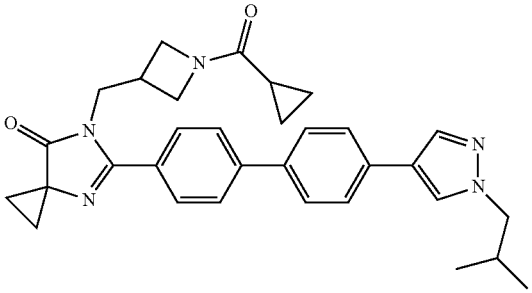 [SMILES: CC(C)Cn1cc(-c2ccc(-c3ccc(C4=NC5(CC5)C(=O)N4CC4CN(C(=O)C5CC5)C4)cc3)cc2)cn1] | 6-{[1-(Cyclopropylcarbonyl)azetidin-3-yl]methyl}-5-{4'-[1-(2-methylpropyl)-1H-pyrazol-4-yl]biphenyl-4-yl}-4,6-diazaspiro[2.4]hept-4-en-7-one<br>MS m/z 522 (M + H)+ |
| 545 | 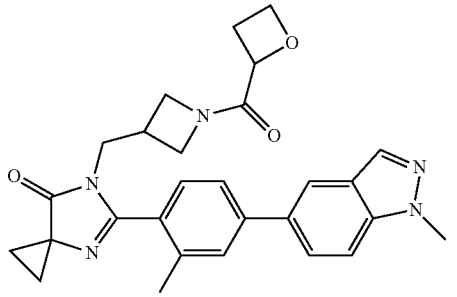 [SMILES: Cc1cc(-c2ccc3c(cnn3C)c2)ccc1C1=NC2(CC2)C(=O)N1CC1CN(C(=O)C2CCO2)C1] | 5-[2-Methyl-4-(1-methyl-1H-indazol-5-yl)phenyl]-6-{[1-(oxetan-2-ylcarbonyl)azetidin-3-yl]methyl}-4,6-diazaspiro[2.4]hept-4-en-7-one<br>MS m/z 484.2 (M + H)+ |

| ID No. | Structure | Compound Name & Physical Data |
|---|---|---|
| 546 | 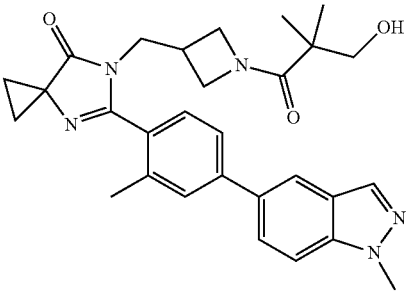 [SMILES: Cc1cc(-c2ccc3c(cnn3C)c2)ccc1C1=NC2(CC2)C(=O)N1CC1CN(C(=O)C(C)(C)CO)C1] | 6-{[1-(3-Hydroxy-2,2-dimethylpropanoyl)azetidin-3-yl]methyl}-5-[2-methyl-4-(1-methyl-1H-indazol-5-yl)phenyl]-4,6-diazaspiro[2.4]hept-4-en-7-one<br>MS m/z 500.3 (M + H)+ |
| 547 | 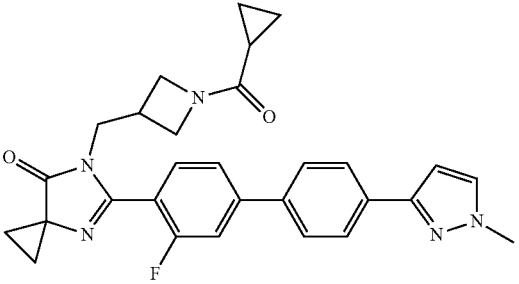 [SMILES: Cn1ccc(-c2ccc(-c3ccc(C4=NC5(CC5)C(=O)N4CC4CN(C(=O)C5CC5)C4)c(F)c3)cc2)n1] | 6-{[1-(Cyclopropylcarbonyl)azetidin-3-yl]methyl}-5-[3-fluoro-4'-(1-methyl-1H-pyrazol-3-yl)biphenyl-4-yl]-4,6-diazaspiro[2.4]hept-4-en-7-one<br>MS m/z 498 (M + H)+ |
| 548 | 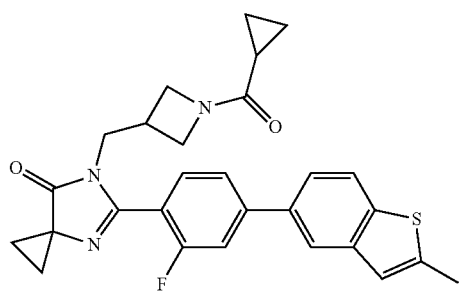 [SMILES: Cc1cc2cc(-c3ccc(C4=NC5(CC5)C(=O)N4CC4CN(C(=O)C5CC5)C4)c(F)c3)ccc2s1] | 6-{[1-(Cyclopropylcarbonyl)azetidin-3-yl]methyl}-5-[2-fluoro-4-(2-methyl-1-benzothiophen-5-yl)phenyl]-4,6-diazaspiro[2.4]hept-4-en-7-one<br>MS m/z 488 (M + H)+ |
| 549 | 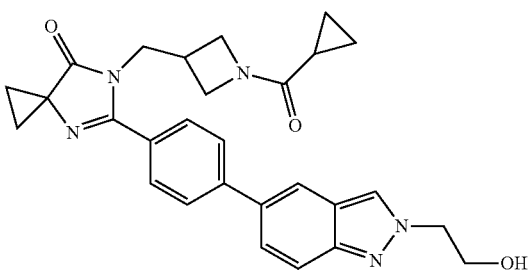 [SMILES: O=C(C1CC1)N1CC(CN2C(=O)C3(CC3)N=C2c2ccc(-c3ccc4nn(CCO)cc4c3)cc2)C1] | 6-{[1-(Cyclopropylcarbonyl)azetidin-3-yl]methyl}-5-{4-[2-(2-hydroxyethyl)-2H-indazol-5-yl]phenyl}-4,6-diazaspiro[2.4]hept-4-en-7-one<br>MS m/z 484 (M + H)+ |
| 550 | 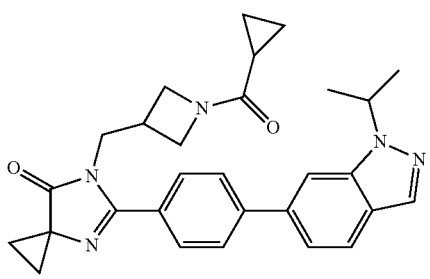 [SMILES: CC(C)n1ncc2ccc(-c3ccc(C4=NC5(CC5)C(=O)N4CC4CN(C(=O)C5CC5)C4)cc3)cc21] | 6-{[1-(Cyclopropylcarbonyl)azetidin-3-yl]methyl}-5-{4-[1-(1-methylethyl)-1H-indazol-6-yl]phenyl}-4,6-diazaspiro[2.4]hept-4-en-7-one<br>MS m/z 482 (M + H)+ |

| ID No. | Structure | Compound Name & Physical Data |
|---|---|---|
| 551 | 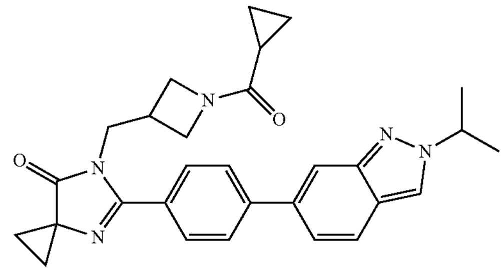 [SMILES: CC(C)n1cc2ccc(-c3ccc(C4=NC5(CC5)C(=O)N4CC4CN(C(=O)C5CC5)C4)cc3)cc2n1] | 6-{[1-(Cyclopropylcarbonyl)azetidin-3-yl]methyl}-5-{4-[1-(1-methylethyl)-1H-indazol-6-yl]phenyl}-4,6-diazaspiro[2.4]hept-4-en-7-one<br>MS m/z 482 (M + H)+ |
| 552 | 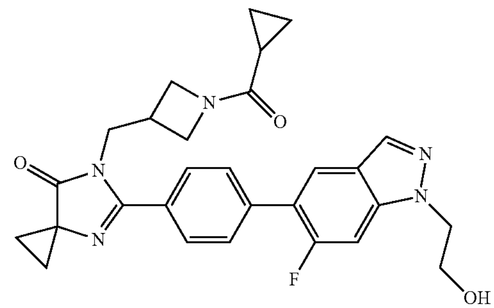 [SMILES: O=C(C1CC1)N1CC(CN2C(=O)C3(CC3)N=C2c2ccc(-c3cc4cnn(CCO)c4cc3F)cc2)C1] | 6-{[1-(Cyclopropylcarbonyl)azetidin-3-yl]methyl}-5-{4-[6-fluoro-1-(2-hydroxyethyl)-1H-indazol-5-yl]phenyl}-4,6-diazaspiro[2.4]hep-t-4-en-7-one<br>MS m/z 502 (M + H)+ |
| 553 | 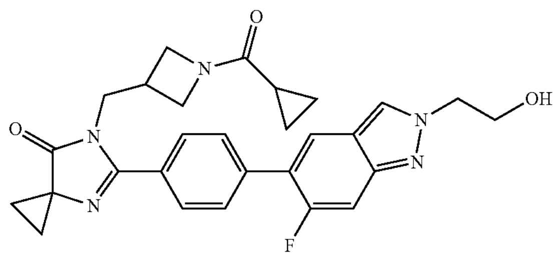 [SMILES: O=C(C1CC1)N1CC(CN2C(=O)C3(CC3)N=C2c2ccc(-c3cc4cn(CCO)nc4cc3F)cc2)C1] | 6-{[1-(Cyclopropylcarbonyl)azetidin-3-yl]methyl}-5-{4-[6-fluoro-2-(2-hydroxyethyl)-2H-indazol-5-yl]phenyl}-4,6-diazaspiro[2.4]hept-4-en-7-one<br>MS m/z 502 (M + H)+ |
| 554 | 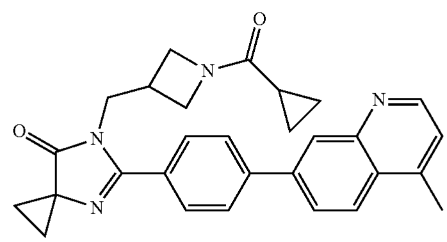 [SMILES: Cc1ccnc2cc(-c3ccc(C4=NC5(CC5)C(=O)N4CC4CN(C(=O)C5CC5)C4)cc3)ccc12] | 6-{[1-(Cyclopropylcarbonyl)azetidin-3-yl]methyl}-5-[4-(4-methylquinolin-7-yl)phenyl]-4,6-diazaspiro[2.4]hept-4-en-7-one<br>MS m/z 465 (M + H)+ |
| 555 | 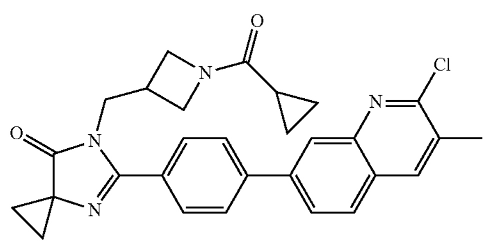 [SMILES: Cc1cc2ccc(-c3ccc(C4=NC5(CC5)C(=O)N4CC4CN(C(=O)C5CC5)C4)cc3)cc2nc1Cl] | 5-[4-(2-Chloro-3-methylquinolin-7-yl)phenyl]-6-{[1-(cyclopropylcarbonyl)azetidin-3-yl]methyl}-4,6-diazaspiro[2.4]hept-4-en-7-one<br>MS m/z 499 (M + H)+ |
| 556 | 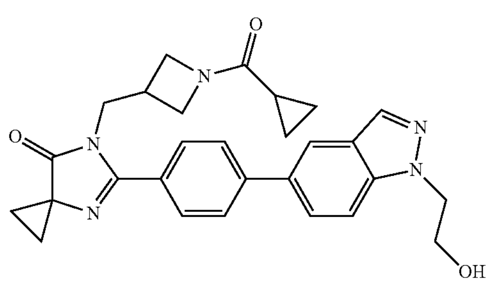 [SMILES: O=C(C1CC1)N1CC(CN2C(=O)C3(CC3)N=C2c2ccc(-c3ccc4c(cnn4CCO)c3)cc2)C1] | 6-{[1-(Cyclopropylcarbonyl)azetidin-3-yl]methyl}-5-{4-[1-(2-hydroxyethyl)-1H-indazol-5-yl]phenyl}-4,6-diazaspiro[2.4]hept-4-en-7-one<br>MS m/z 484 (M + H)+ |

| ID No. | Structure | Compound Name & Physical Data |
|---|---|---|
| 557 | 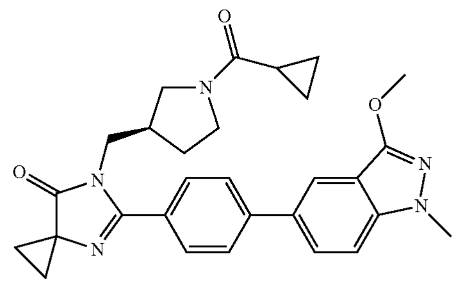 [SMILES: COc1nn(C)c2ccc(-c3ccc(C4=NC5(CC5)C(=O)N4C[C@@H]4CCN(C(=O)C5CC5)C4)cc3)cc12] | 6-{[(3R)-1-(Cyclopropylcarbonyl)pyrrolidin-3-yl]methyl}-5-[4-(3-methoxy-1-methyl-1H-indazol-5-yl)phenyl]-4,6-diazaspiro[2.4]hept-4-en-7-one<br>MS m/z 498 (M + H)+ |
| 558 | 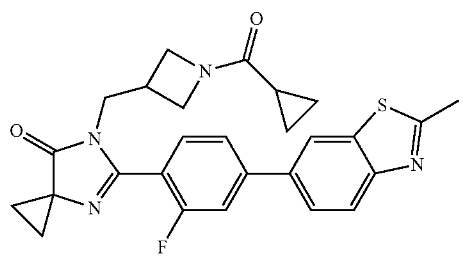 [SMILES: Cc1nc2ccc(-c3ccc(C4=NC5(CC5)C(=O)N4CC4CN(C(=O)C5CC5)C4)c(F)c3)cc2s1] | 6-{[1-(Cyclopropylcarbonyl)azetidin-3-yl]methyl}-5-[2-fluoro-4-(2-methyl-1,3-benzothiazol-6-yl)phenyl]-4,6-diazaspiro[2.4]hept-4-en-7-one<br>MS m/z 489 (M + H)+ |
| 559 | 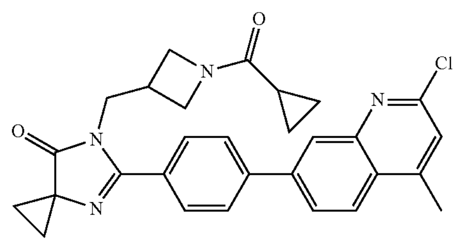 [SMILES: Cc1cc(Cl)nc2cc(-c3ccc(C4=NC5(CC5)C(=O)N4CC4CN(C(=O)C5CC5)C4)cc3)ccc12] | 5-[4-(2-Chloro-4-methylquinolin-7-yl)phenyl]-6-{[1-(cyclopropylcarbonyl)azetidin-3-yl]methyl}-4,6-diazaspiro[2.4]hept-4-en-7-one<br>MS m/z 499 (M + H)+ |
| 560 | 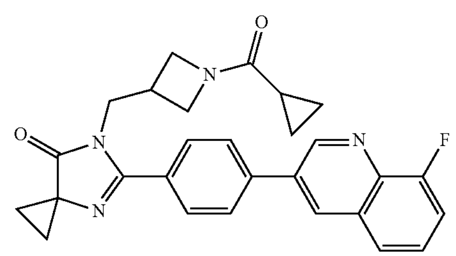 [SMILES: O=C(C1CC1)N1CC(CN2C(=O)C3(CC3)N=C2c2ccc(-c3cnc4c(F)cccc4c3)cc2)C1] | 6-{[1-(Cyclopropylcarbonyl)azetidin-3-yl]methyl}-5-[4-(8-fluoroquinolin-3-yl)phenyl]-4,6-diazaspiro[2.4]hept-4-en-7-one<br>MS m/z 469 (M + H)+ |
| 561 | 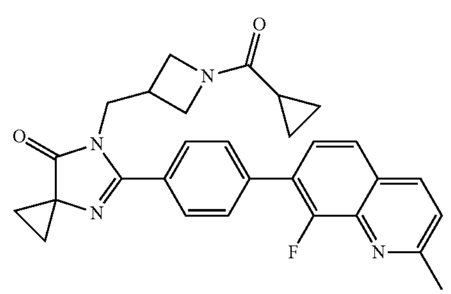 [SMILES: Cc1ccc2ccc(-c3ccc(C4=NC5(CC5)C(=O)N4CC4CN(C(=O)C5CC5)C4)cc3)c(F)c2n1] | 6-{[1-(Cyclopropylcarbonyl)azetidin-3-yl]methyl}-5-[4-(8-fluoro-2-methylquinolin-7-yl)phenyl]-4,6-diazaspiro[2.4]hept-4-en-7-one<br>MS m/z 483 (M + H)+ |
| 562 | 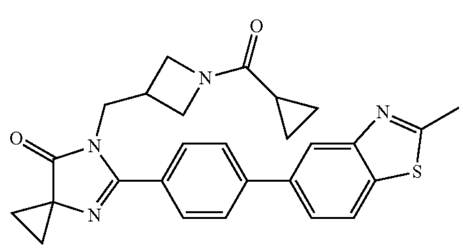 [SMILES: Cc1nc2cc(-c3ccc(C4=NC5(CC5)C(=O)N4CC4CN(C(=O)C5CC5)C4)cc3)ccc2s1] | 6-{[1-(Cyclopropylcarbonyl)azetidin-3-yl]methyl}-5-[4-(2-methyl-1,3-benzothiazol-5-yl)phenyl]-4,6-diazaspiro[2.4]hept-4-en-7-one<br>MS m/z 471 (M + H)+ |

-continued

| ID No. | Structure | Compound Name & Physical Data |
|---|---|---|
| 563 | 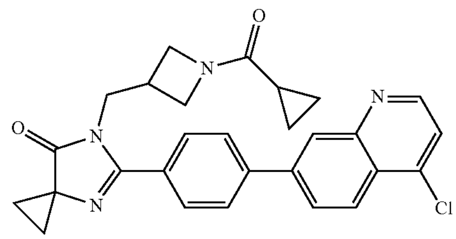 [SMILES: O=C(C1CC1)N1CC(CN2C(=O)C3(CC3)N=C2c2ccc(-c3ccc4c(Cl)ccnc4c3)cc2)C1] | 5-[4-(4-Chloroquinolin-7-yl)phenyl]-6-{[1-(cyclopropylcarbonyl)azetidin-3-yl]methyl}-4,6-diazaspiro[2.4]hept-4-en-7-one<br>MS m/z 485 (M + H)+ |
| 564 | 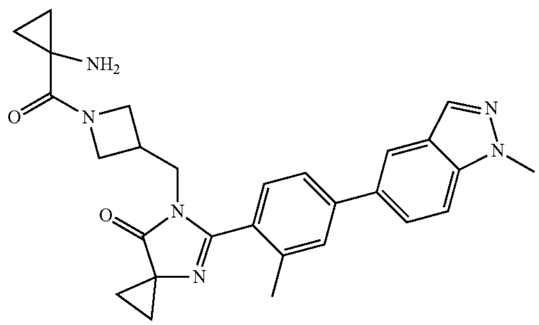 [SMILES: Cc1cc(-c2ccc3c(cnn3C)c2)ccc1C1=NC2(CC2)C(=O)N1CC1CN(C(=O)C2(N)CC2)C1] | 6-({1-[(1-Aminocyclopropyl)carbonyl]azetidin-3-yl}methyl)-5-[2-methyl-4-(1-methyl-1H-indazol-5-yl)phenyl]-4,6-diazaspiro[2.4]hept-4-en-7-one<br>MS m/z 483.3 (M + H)+ |
| 566 | 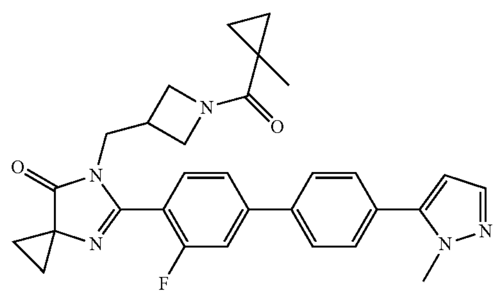 [SMILES: Cn1nccc1-c1ccc(-c2ccc(C3=NC4(CC4)C(=O)N3CC3CN(C(=O)C4(C)CC4)C3)c(F)c2)cc1] | 5-[3-Fluoro-4'-(1-methyl-1H-pyrazol-5-yl)biphenyl-4-yl]-6-({1-[(1-methylcyclopropyl)carbonyl]azetidin-3-yl}methyl)-4,6-diazaspiro[2.4]hept-4-en-7-one<br>MS m/z 512 (M + H)+ |
| 568 | 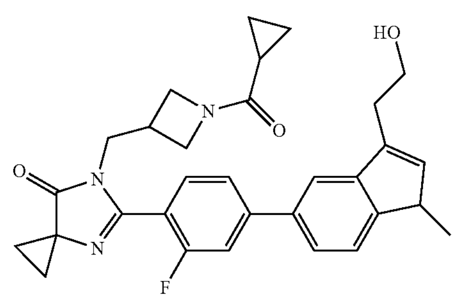 [SMILES: CC1C=C(CCO)c2cc(-c3ccc(C4=NC5(CC5)C(=O)N4CC4CN(C(=O)C5CC5)C4)c(F)c3)ccc21] | 6-{[1-(Cyclopropylcarbonyl)azetidin-3-yl]methyl}-5-{2-fluoro-4-[3-(2-hydroxyethyl)-1-methyl-1H-indol-5-yl]phenyl}-4,6-diazaspiro[2.4]hept-4-en-7-one<br>MS m/z 515 (M + H)+ |
| 569 | 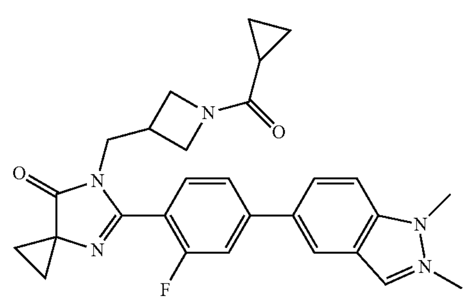 | 6-{[1-(Cyclopropylcarbonyl)azetidin-3-yl]methyl}-5-[4-(1,2-dimethyl-1H-indol-5-yl)-2-fluorophenyl]-4,6-diazaspiro[2.4]hept-4-en-7-one<br>MS m/z 485 (M + H)+ |

| ID No. | Structure | Compound Name & Physical Data |
|---|---|---|
| 570 | 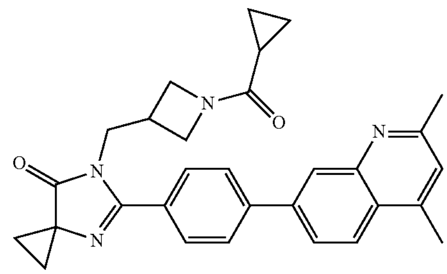 | 6-{[1-(Cyclopropylcarbonyl)azetidin-3-yl]methyl}-5-[4-(2,4-dimetrhylquinolin-7-yl)phenyl]-4,6-diazaspiro[2.4]hept-4-en-7-one<br>MS m/z 479 (M + H)+ |
| 571 | 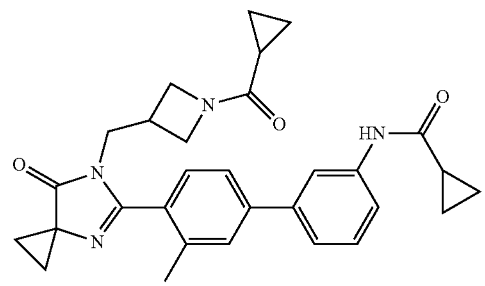 [SMILES: Cc1cc(-c2cccc(NC(=O)C3CC3)c2)ccc1C1=NC2(CC2)C(=O)N1CC1CN(C(=O)C2CC2)C1] | N-[4'-(6-{[1-(Cyclopropylcarbonyl)azetidin-3-yl}methyl]-7-oxo-4,6-diazaspiro[2.4]hept-4-en-5-yl)-3'-methylbiphenyl-3-yl]cyclopropanecarboxamide<br>MS m/z 497 (M + H)+ |
| 572 | 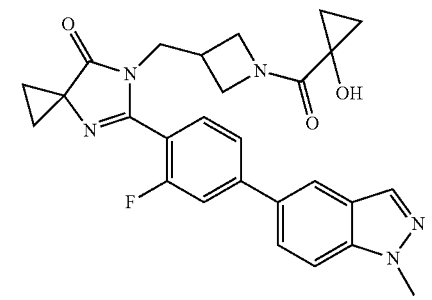 [SMILES: Cn1ncc2cc(-c3ccc(C4=NC5(CC5)C(=O)N4CC4CN(C(=O)C5(O)CC5)C4)c(F)c3)ccc21] | 5-[2-Fluoro-4-(1-methyl-1H-indazol-5-yl)phenyl]-6-({1-[(1-hydroxycyclopropyl)carbonyl]azetidin-3-yl}methyl)-4,6-diazaspiro[2.4]hept-4-en-7-one<br>MS m/z 488 (M + H)+ |
| 573 | 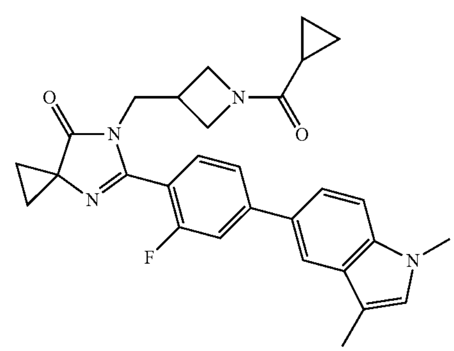 [SMILES: Cc1cn(C)c2ccc(-c3ccc(C4=NC5(CC5)C(=O)N4CC4CN(C(=O)C5CC5)C4)c(F)c3)cc12] | 6-{[1-(Cyclopropylcarbonyl)azetidin-3-yl]methyl}-5-[4-(1,3-dimethyl-1H-indol-5-yl)-2-fluorophenyl]-4,6-diazaspiro[2.4]hept-4-en-7-one<br>MS m/z 485 (M + H)+ |
| 574 | 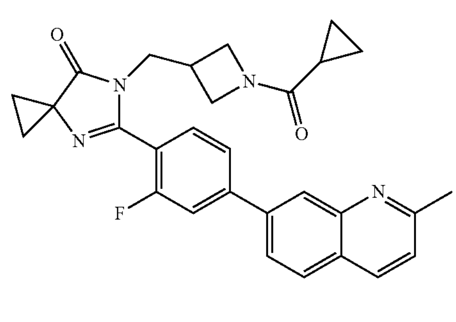 [SMILES: Cc1ccc2ccc(-c3ccc(C4=NC5(CC5)C(=O)N4CC4CN(C(=O)C5CC5)C4)c(F)c3)cc2n1] | 6-{[1-(Cyclopropylcarbonyl)azetidin-3-yl]methyl}-5-[2-fluoro-4-(2-methylquinolin-7-yl)phenyl]-4,6-diazaspiro[2.4]hept-4-en-7-one<br>MS m/z 483 (M + H)+ |

-continued

| ID No. | Structure | Compound Name & Physical Data |
|---|---|---|
| 575 | 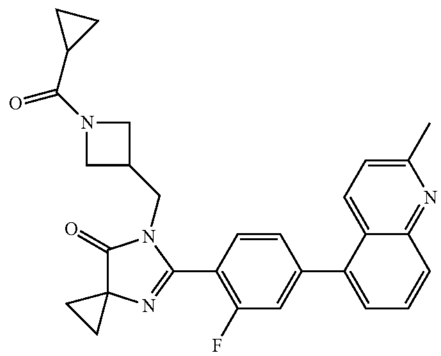 [SMILES: Cc1ccc2c(-c3ccc(C4=NC5(CC5)C(=O)N4CC4CN(C(=O)C5CC5)C4)c(F)c3)cccc2n1] | 6-{[1-(Cyclopropylcarbonyl)azetidin-3-yl]methyl}-5-[2-fluoro-4-(2-methylquinolin-5-yl)phenyl]-4,6-diazaspiro[2.4]hept-4-en-7-one<br>MS m/z 483 (M + H)+ |
| 576 | 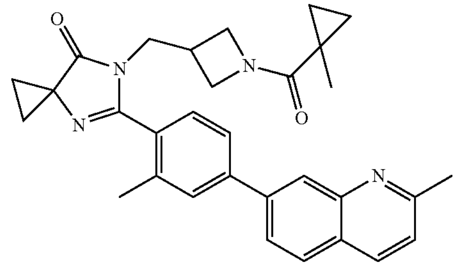 [SMILES: Cc1ccc2ccc(-c3ccc(C4=NC5(CC5)C(=O)N4CC4CN(C(=O)C5(C)CC5)C4)c(C)c3)cc2n1] | 6-({1-[(1-Methylcyclopropyl)carbonyl]azetidin-3-yl}methyl)-5-[2-methyl-4-(2-methylquinolin-7-yl)phenyl]-4,6-diazaspiro[2.4]hept-4-en-7-one<br>MS m/z 493 (M + H)+ |
| 577 | 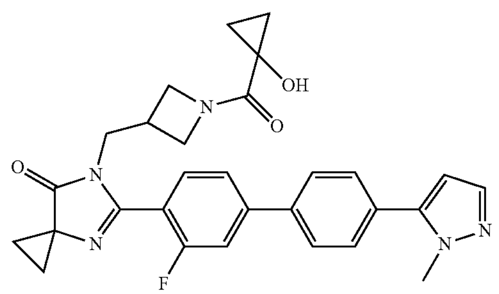 [SMILES: Cn1nccc1-c1ccc(-c2ccc(C3=NC4(CC4)C(=O)N3CC3CN(C(=O)C4(O)CC4)C3)c(F)c2)cc1] | 5-[3-Fluoro-4'-(1-methyl-1H-pyrazol-5-yl)biphenyl-4-yl]-6-({1-[(1-hydroxycyclopropyl)carbonyl]azetidin-3-yl}methyl)-4,6-diazaspiro[2.4]hept-4-en-7-one<br>MS m/z 514 (M + H)+ |
| 578 | 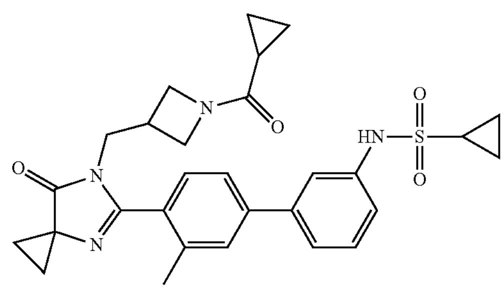 [SMILES: Cc1cc(-c2cccc(NS(=O)(=O)C3CC3)c2)ccc1C1=NC2(CC2)C(=O)N1CC1CN(C(=O)C2CC2)C1] | N-[4'-(6-{[1-(Cyclopropylcarbonyl)azetidin-3-yl]methyl}-7-oxo-4,6-diazaspiro[2.4]hept-4-en-5-yl)-3'-methylbiphenyl-3-yl]cyclopropanesulfonamide<br>MS m/z 533 (M + H)+ |
| 579 | 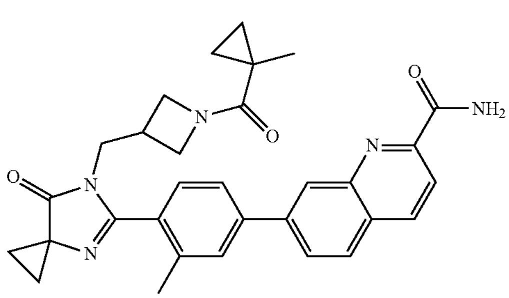 [SMILES: Cc1cc(-c2ccc3ccc(C(N)=O)nc3c2)ccc1C1=NC2(CC2)C(=O)N1CC1CN(C(=O)C2(C)CC2)C1] | 7-{3-Methyl-4-[6-({1-[(1-methylcyclopropyl)carbonyl]azetidin-3-yl}methyl)-7-oxo-4,6-diazaspiro[2.4]hept-4-en-5-yl]phenyl}quinoline-2-carboxamide<br>MS m/z 522 (M + H)+ |

| ID No. | Structure | Compound Name & Physical Data |
|---|---|---|
| 580 | 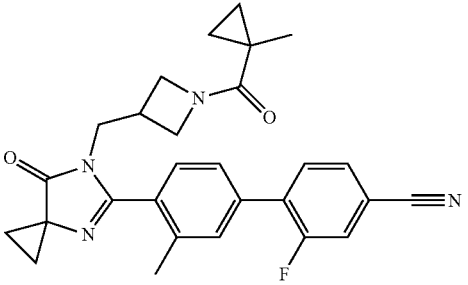 [SMILES: Cc1cc(-c2ccc(C#N)cc2F)ccc1C1=NC2(CC2)C(=O)N1CC1CN(C(=O)C2(C)CC2)C1] | 2-Fluoro-3'-methyl-4'-[6-(]1-{(1-methylcyclopropyl)carbonyl]azetidin-3-yl}methyl)-7-oxo-4,6-diazaspiro[2.4]hept-4-en-5-yl]biphenyl-4-carbonitrile<br>MS m/z 471 (M + H)+ |
| 581 | 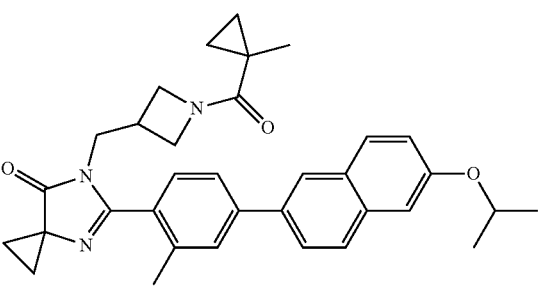 [SMILES: Cc1cc(-c2ccc3cc(OC(C)C)ccc3c2)ccc1C1=NC2(CC2)C(=O)N1CC1CN(C(=O)C2(C)CC2)C1] | 6-({1-[(1-Methylcyclopropyl)carbonyl]azetidin-3-yl}methyl)-5-{2-methyl-4-[6-(1-methylethoxy)naphthalen-2-yl]phenyl}-4,6-diazaspiro[2.4]hept-4-en-7-one<br>MS m/z 536 (M + H)+ |
| 582 | 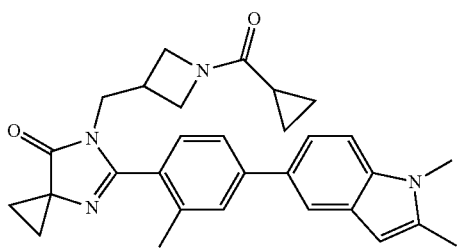 [SMILES: Cc1cc(-c2ccc3c(c2)cc(C)n3C)ccc1C1=NC2(CC2)C(=O)N1CC1CN(C(=O)C2CC2)C1] | 6-{[1-(Cyclopropylcarbonyl)azetidin-3-yl]methyl}-5-[4-(1,2-dimethyl-1H-indol-5-yl)-2-methylphenyl]-4,6-diazaspiro[2.4]hept-4-en-7-one<br>MS m/z 481 (M + H)+ |
| 583 | 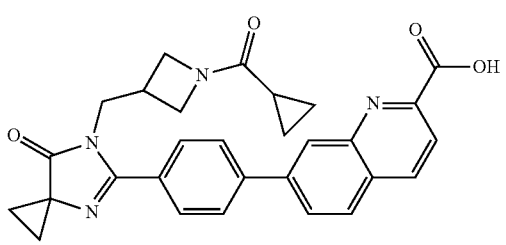 [SMILES: O=C(O)c1ccc2ccc(-c3ccc(C4=NC5(CC5)C(=O)N4CC4CN(C(=O)C5CC5)C4)cc3)cc2n1] | 7-[4-(6-{[1-(Cyclopropylcarbonyl)azetidin-3-yl]methyl}-7-oxo-4,6-diazaspiro[2.4]hept-4-en-5-yl)phenyl]quinoline-2-carboxylic acid<br>MS m/z 495 (M + H)+ |
| 584 | 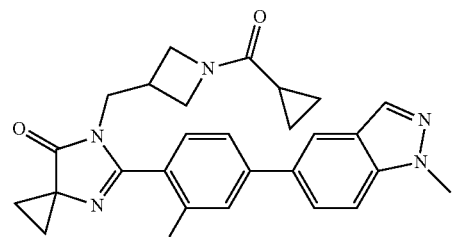 | 5-[2-Chloro-4-(1-methyl-1H-indazol-5-yl)phenyl]-6-{[1-(cyclopropylcarbonyl)azetidin-3-yl]methyl}-4,6-diazaspiro[2.4]hept-4-en-7-one<br>MS m/z 488 (M + H)+ |

-continued

| ID No. | Structure | Compound Name & Physical Data |
|---|---|---|
| 585 | 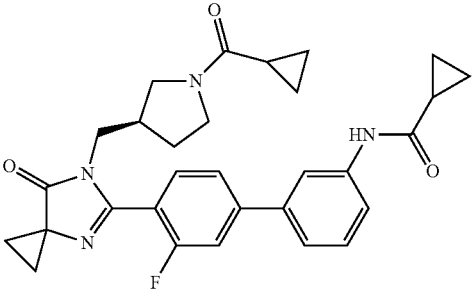 [SMILES: O=C(Nc1cccc(-c2ccc(C3=NC4(CC4)C(=O)N3C[C@@H]3CCN(C(=O)C4CC4)C3)c(F)c2)c1)C1CC1] | N-[4'-(6-{[(3R)-1-(Cyclopropylcarbonyl)pyrrolidin-3-yl]methyl}-7-oxo-4,6-diazaspiro[2.4]hept-4-en-5-yl)-3'-fluorobiphenyl-3-yl]cyclopropanecarboxamide<br>MS m/z 515 (M + H)+ |
| 586 | 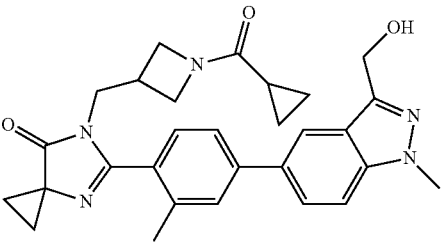 [SMILES: Cc1cc(-c2ccc3c(c2)c(CO)nn3C)ccc1C1=NC2(CC2)C(=O)N1CC1CN(C(=O)C2CC2)C1] | 6-{[1-(Cyclopropylcarbonyl)azetidin-3-yl]methyl}-5-{4-[3-(hydroxymethyl)-1-methyl-1H-indazol-5-yl]-2-methylphenyl}-4,6-diazaspiro[2.4]hept-4-en-7-one<br>MS m/z 498 (M + H)+ |
| 587 | 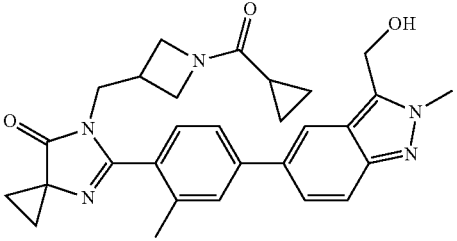 [SMILES: Cc1cc(-c2ccc3nn(C)c(CO)c3c2)ccc1C1=NC2(CC2)C(=O)N1CC1CN(C(=O)C2CC2)C1] | 6-{[1-(Cyclopropylcarbonyl)azetidin-3-yl]methyl}-5-{4-[3-(hydroxymethyl)-2-methyl-2H-indazol-5-yl]-2-methylphenyl}-4,6-diazaspiro[2.4]hept-4-en-7-one<br>MS m/z 498 (M + H)+ |
| 588 | 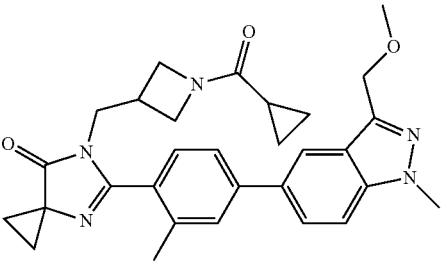 [SMILES: COCc1nn(C)c2ccc(-c3ccc(C4=NC5(CC5)C(=O)N4CC4CN(C(=O)C5CC5)C4)c(C)c3)cc12] | 6-{[1-(Cyclopropylcarbonyl)azetidin-3-yl]methyl}-5-{4-[3-(methoxymethyl)-1-methyl-1H-indazol-5-yl]-2-methylphenyl}-4,6-diazaspiro[2.4]hept-4-en-7-one<br>MS m/z 512 (M + H)+ |
| 589 | 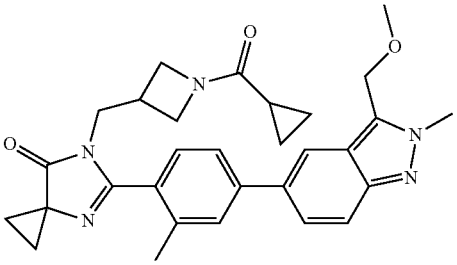 [SMILES: COCc1c2cc(-c3ccc(C4=NC5(CC5)C(=O)N4CC4CN(C(=O)C5CC5)C4)c(C)c3)ccc2nn1C] | 6-{[1-(Cyclopropylcarbonyl)azetidin-3-yl]methyl}-5-{4-[3-(methoxymethyl)-2-methyl-2H-indazol-5-yl]-2-methylphenyl}-4,6-diazaspiro[2.4]hept-4-en-7-one<br>MS m/z 512 (M + H)+ |

-continued

| ID No. | Structure | Compound Name & Physical Data |
|---|---|---|
| 590 | 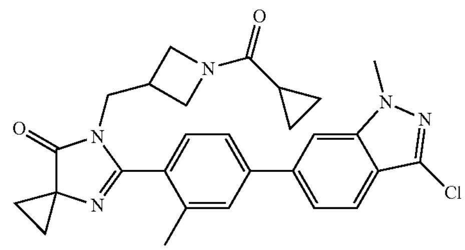 [SMILES: Cc1cc(-c2ccc3c(Cl)nn(C)c3c2)ccc1C1=NC2(CC2)C(=O)N1CC1CN(C(=O)C2CC2)C1] | 5-[4-(3-Chloro-1-methyl-1H-indazol-6-yl)-2-methylphenyl]-6-{[1-(cyclopropylcarbonyl)azetidin-3-yl]methyl}-4,6-diazaspiro[2.4]hept-4-en-7-one<br>MS m/z 502 (M + H)+ |
| 591 | 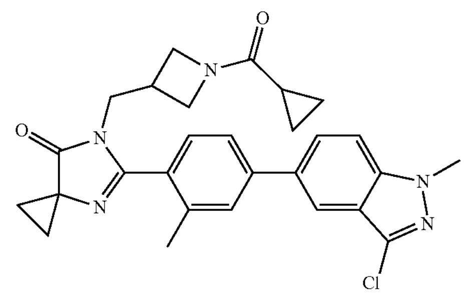 [SMILES: Cc1cc(-c2ccc3c(c2)c(Cl)nn3C)ccc1C1=NC2(CC2)C(=O)N1CC1CN(C(=O)C2CC2)C1] | 5-[4-(3-Chloro-1-methyl-1H-indazol-5-yl)-2-methylphenyl]-6-{[1-(cyclopropylcarbonyl)azetidin-3-yl]methyl}-4,6-diazaspiro[2.4]hept-4-en-7-one<br>MS m/z 502 (M + H)+ |
| 592 | 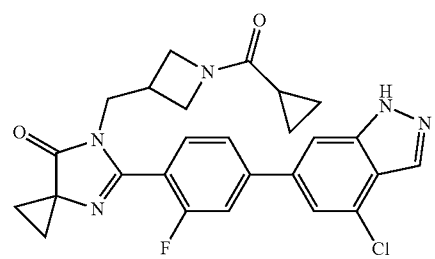 [SMILES: O=C(C1CC1)N1CC(CN2C(=O)C3(CC3)N=C2c2ccc(-c3cc(Cl)c4cn[nH]c4c3)cc2F)C1] | 5-[4-(4-Chloro-1H-indazol-6-yl)-2-fluorophenyl]-6-{[1-(cyclopropylcarbonyl)azetidin-3-yl]methyl}-4,6-diazaspiro[2.4]hept-4-en-7-one<br>MS m/z 492 (M + H)+ |
| 593 | 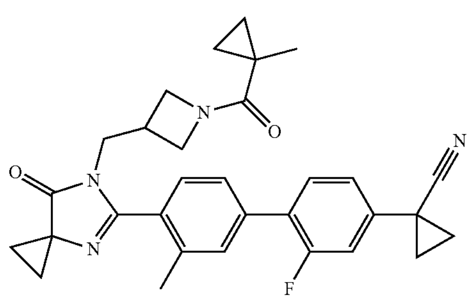 [SMILES: Cc1cc(-c2ccc(C3(C#N)CC3)cc2F)ccc1C1=NC2(CC2)C(=O)N1CC1CN(C(=O)C2(C)CC2)C1] | 1-{2-Fluoro-3-methyl-4-[6-({1-[(1-methylcyclopropyl)carbonyl]azetidin-3-yl}methyl)-7-oxo-4,6-diazaspiro[2.4]hept-4-en-5-yl]biphenyl-4-yl}cyclopropanecarbonitrile<br>MS m/z 511 (M + H)+ |
| 594 | 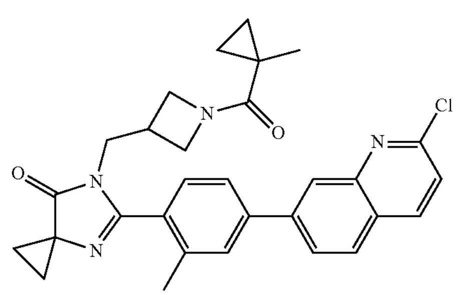 [SMILES: Cc1cc(-c2ccc3ccc(Cl)nc3c2)ccc1C1=NC2(CC2)C(=O)N1CC1CN(C(=O)C2(C)CC2)C1] | 5-[4-(2-Chloroquinolin-7-yl)-2-methylphenyl]-6-({1-[(1-methylcyclopropyl)carbonyl]azetidin-3-yl}methyl)-4,6-diazaspiro[2.4]hept-4-en-7-one<br>MS m/z 513 (M + H)+ |

| ID No. | Structure | Compound Name & Physical Data |
|---|---|---|
| 595 | 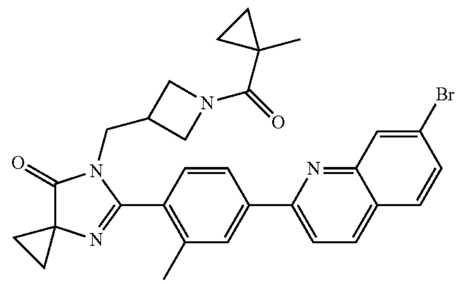 [SMILES: Cc1cc(-c2ccc3ccc(Br)cc3n2)ccc1C1=NC2(CC2)C(=O)N1CC1CN(C(=O)C2(C)CC2)C1] | 5-[4-(7-Bromoquinolin-2-yl)-2-methylphenyl]-6-({1-[(1-methylcyclopropyl)carbonyl]azetidin-3-yl}methyl)-4,6-diazaspiro[2.4]hept-4-en-7-one<br>MS m/z 557 (M + H)+ |
| 596 | 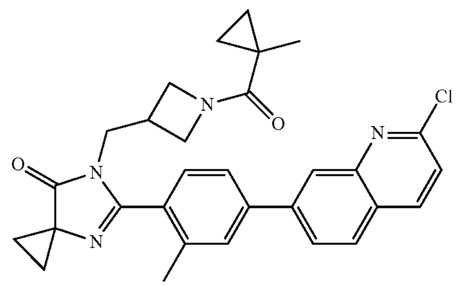 | 5-[4-(2-CHloro-3-methylquinolin-7-yl)-2-methylphenyl]-6-({1-[(1-methylcyclopropyl)carbonyl]azetidin-3-yl}methyl)-4,6-diazaspiro[2.4]hept-4-en-7-one<br>MS m/z 527 (M + H)+ |
| 597 | 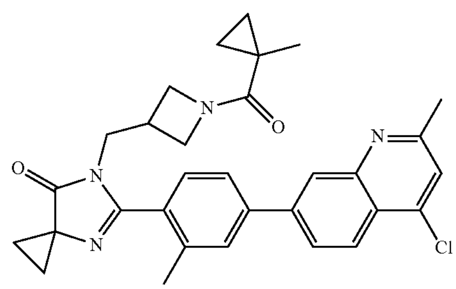 [SMILES: Cc1cc(Cl)c2ccc(-c3ccc(C4=NC5(CC5)C(=O)N4CC4CN(C(=O)C5(C)CC5)C4)c(C)c3)cc2n1] | 5-[4-(4-Chloro-2-methylquinolin-7-yl)-2-methylphenyl]-6-({1-[(1-methylcyclopropyl)carbonyl]azetidin-3-yl}methyl)-4,6-diazaspiro[2.4]hept-4-en-7-one<br>MS m/z 527 (M + H)+ |
| 598 | 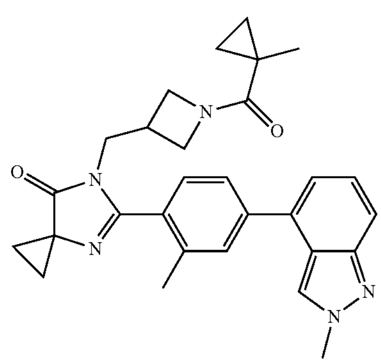 [SMILES: Cc1cc(-c2cccc3nn(C)cc23)ccc1C1=NC2(CC2)C(=O)N1CC1CN(C(=O)C2(C)CC2)C1] | 6-({1-[(1-Methylcyclopropyl)carbonyl]azetidin-3-yl}methyl)-5-[2-methyl-4-(2-methyl-2H-indazol-4-yl)phenyl]-4,6-diazaspiro[2.4]hept-4-en-7-one<br>MS m/z 482 (M + H)+ |
| 599 | 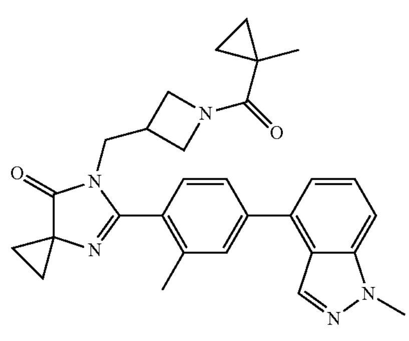 [SMILES: Cc1cc(-c2cccc3c2cnn3C)ccc1C1=NC2(CC2)C(=O)N1CC1CN(C(=O)C2(C)CC2)C1] | 6-({1-[(1-Methylcyclopropyl)carbonyl]azetidin-3-yl}methyl)-5-[2-methyl-4-(1-methyl-1H-indazol-4-yl)phenyl]-4,6-diazaspiro[2.4]hept-4-en-7-one<br>MS m/z 482 (M + H)+ |

| ID No. | Structure | Compound Name & Physical Data |
|---|---|---|
| 600 | 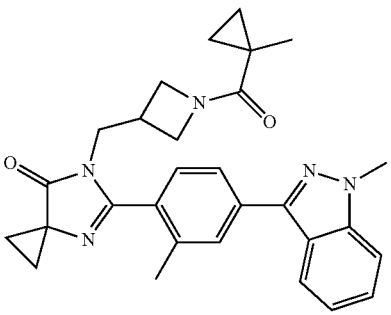 [SMILES: Cc1cc(-c2nn(C)c3ccccc23)ccc1C1=NC2(CC2)C(=O)N1CC1CN(C(=O)C2(C)CC2)C1] | 6-({1-[(1-Methylcyclopropyl)carbonyl]azetidin-3-yl}methyl)-5-[2-methyl-4-(1-methyl-1H-indazol-3-yl)phenyl]-4,6-diazaspiro[2.4]hept-4-en-7-one<br>MS m/z 482 (M + H)+ |
| 601 | 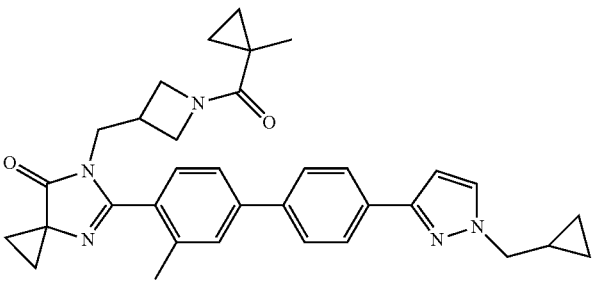 [SMILES: Cc1cc(-c2ccc(-c3ccn(CC4CC4)n3)cc2)ccc1C1=NC2(CC2)C(=O)N1CC1CN(C(=O)C2(C)CC2)C1] | 5-{4'-[1-(Cyclopropylmethyl)-1H-pyrazol-3-yl]-3-methylbiphenyl-4-yl}-6-({1-[(1-methylcyclopropyl)carbonyl]azetidin-3-yl}methyl)-4,6-diazaspiro[2.4]hept-4-en-7-one<br>MS m/z 548 (M + H)+ |
| 602 | 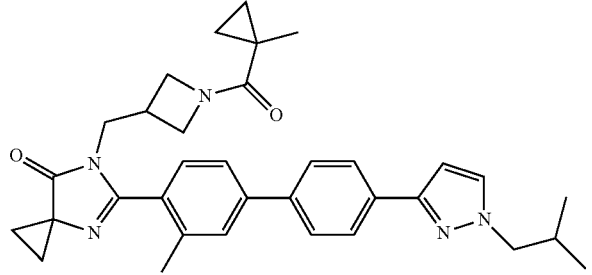 [SMILES: Cc1cc(-c2ccc(-c3ccn(CC(C)C)n3)cc2)ccc1C1=NC2(CC2)C(=O)N1CC1CN(C(=O)C2(C)CC2)C1] | 6-({1-[(1-Methylcyclopropyl)carbonyl]azetidin-3-yl}methyl)-5-{3-methyl-4'-[1-(2-methylpropyl)-1H-pyrazol-3-yl]biphenyl-4-yl}-4,6-diazaspiro[2.4]hept-4-en-7-one<br>MS m/z 550 (M + H)+ |
| 603 | 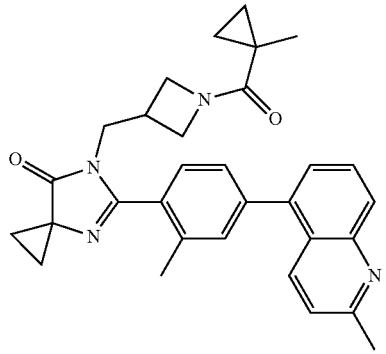 [SMILES: Cc1ccc2c(-c3ccc(C4=NC5(CC5)C(=O)N4CC4CN(C(=O)C5(C)CC5)C4)c(C)c3)cccc2n1] | 6-({1-[(1-Methylcyclopropyl)carbonyl]azetidin-3-yl}methyl)-5-[2-methyl-4-(2-methylquinolin-5-yl)phenyl]-4,6-diazaspiro[2.4]hept-4-en-7-one<br>MS m/z 493 (M + H)+ |
| 604 | 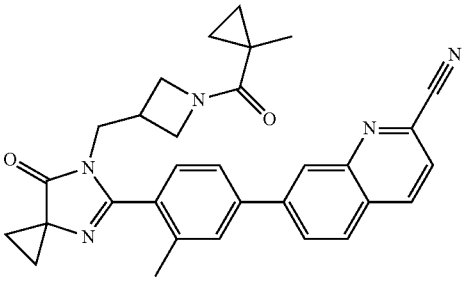 [SMILES: Cc1cc(-c2ccc3ccc(C#N)nc3c2)ccc1C1=NC2(CC2)C(=O)N1CC1CN(C(=O)C2(C)CC2)C1] | 7-{3-Methyl-4-[6-({1-[(1-methylcyclopropyl)carbonyl]azetidin-3-yl}methyl)-7-oxo-4,6-diazaspiro[2.4]hept-4-en-5-yl]phenyl}quinoine-2-carbonitrile<br>MS m/z 504 (M + H)+ |

-continued

| ID No. | Structure | Compound Name & Physical Data |
|---|---|---|
| 605 | 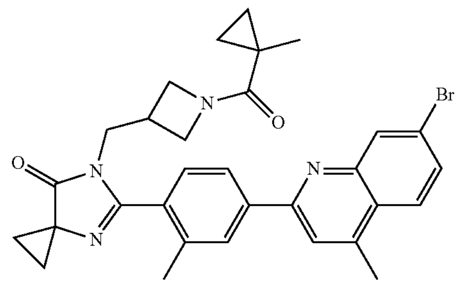 [SMILES: Cc1cc(-c2cc(C)c3ccc(Br)cc3n2)ccc1C1=NC2(CC2)C(=O)N1CC1CN(C(=O)C2(C)CC2)C1] | 5-[4-(7-Bromo-4-methylquinolin-2-yl)-2-methylphenyl]-6-({1-[(1-methylcyclopropyl)carbonyl]azetidin-3-yl}methyl)-4,6-diazaspiro[2.4]hept-4-en-7-one<br>MS m/z 571 (M + H)+ |
| 606 | 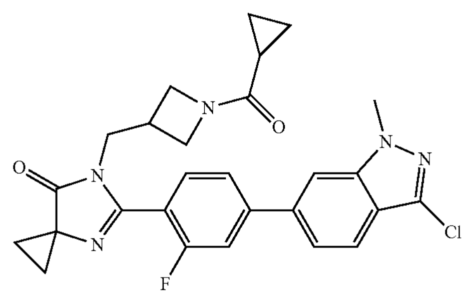 [SMILES: Cn1nc(Cl)c2ccc(-c3ccc(C4=NC5(CC5)C(=O)N4CC4CN(C(=O)C5CC5)C4)c(F)c3)cc21] | 5-[4-(3-Chloro-1-methyl-1H-indazol-6-yl)-2-fluorophenyl]-6-{[1-(cyclopropylcarbonyl)azetidin-3-yl]methyl}-4,6-diazaspiro[2.4]hept-4-en-7-one<br>MS m/z 506 (M + H)+ |
| 607 | 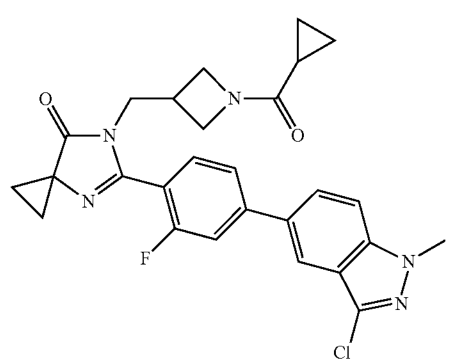 [SMILES: Cn1nc(Cl)c2cc(-c3ccc(C4=NC5(CC5)C(=O)N4CC4CN(C(=O)C5CC5)C4)c(F)c3)ccc21] | 5-[4-(3-Chloro-1-methyl-1H-indazol-5-yl)-2-fluorophenyl]-6-{[1-(cyclopropylcarbonyl)azetidin-3-yl]methyl}-4,6-diazaspiro[2.4]hept-4-en-7-one<br>MS m/z 506 (M + H)+ |
| 608 | 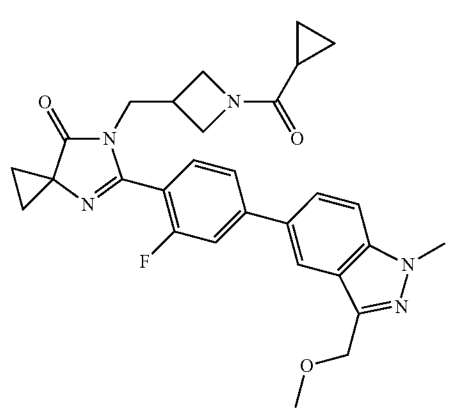 [SMILES: COCc1nn(C)c2ccc(-c3ccc(C4=NC5(CC5)C(=O)N4CC4CN(C(=O)C5CC5)C4)c(F)c3)cc12] | 6-{[1-(Cyclopropylcarbonyl)azetidin-3-yl]methyl}-5-{2-fluoro-4-[3-(methoxymethyl)-1-methyl-01H-indazol-5-yl]phenyl}-4,6-diazaspiro[2.4]hept-4-en-7-one<br>MS m/z 516 (M + H)+ |

| ID No. | Structure | Compound Name & Physical Data |
|---|---|---|
| 609 | 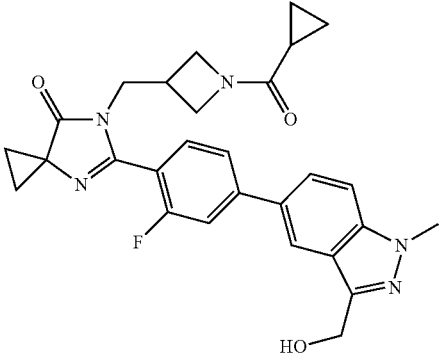 [SMILES: Cn1nc(CO)c2cc(-c3ccc(C4=NC5(CC5)C(=O)N4CC4CN(C(=O)C5CC5)C4)c(F)c3)ccc21] | 6-{[1-(Cyclopropylcarbonyl)azetidin-3-yl]methyl}-5-{2-fluoro-4-[3-(hydroxymethyl)-1-methyl-1H-indazol-5-yl]phenyl}-4,6-diazaspiro[2.4]hept-4-en-7-one<br>MS m/z 502 (M + H)+ |
| 610 | 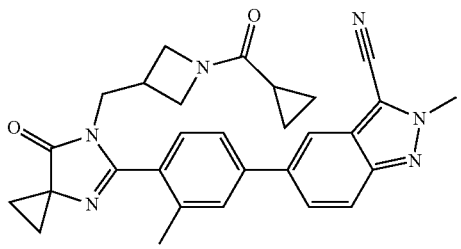 [SMILES: Cc1cc(-c2ccc3nn(C)c(C#N)c3c2)ccc1C1=NC2(CC2)C(=O)N1CC1CN(C(=O)C2CC2)C1] | 5-[4-(6-{1-(Cyclopropylcarbonyl)azetidin-3-yl]methyl}-7-oxo-4,6-diazaspiro[2.4]hept-4-en-5-yl)-3-methylphenyl]-2-methyl-2H-indazole-3-carbonitrile<br>MS m/z 493 (M + H)+ |
| 611 | 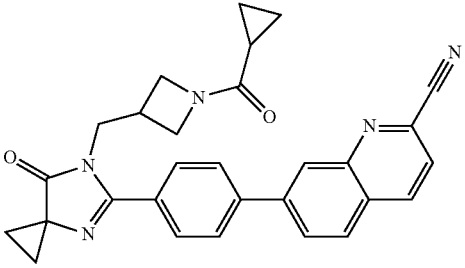 [SMILES: N#Cc1ccc2ccc(-c3ccc(C4=NC5(CC5)C(=O)N4CC4CN(C(=O)C5CC5)C4)cc3)cc2n1] | 7-[4-(6-{[1-(Cyclopropylcarbonyl)azetidin-3-yl]methyl}-7-oxo-4,6-diazaspiro[2.4]hept-4-en-5-yl)phenyl]quinolin-2-carbonitrile<br>MS m/z 476 (M + H)+ |
| 612 | 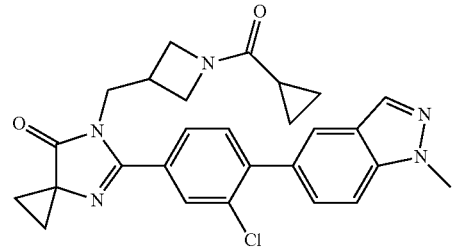 [SMILES: Cn1ncc2cc(-c3ccc(C4=NC5(CC5)C(=O)N4CC4CN(C(=O)C5CC5)C4)cc3Cl)ccc21] | 5-[3-Chloro-4-(1-methyl-1H-indazol-5-yl)phenyl]-6-{[1-(cyclopropylcarbonyl)azetidin-3-yl]methyk}-4,6-diazaspiro[2.4]hept-4-en-7-one<br>MS m/z 488 (M + H)+ |
| 613 | 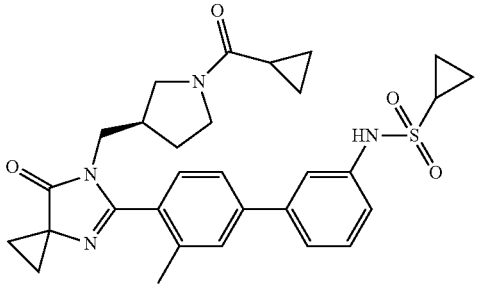 [SMILES: Cc1cc(-c2cccc(NS(=O)(=O)C3CC3)c2)ccc1C1=NC2(CC2)C(=O)N1C[C@@H]1CCN(C(=O)C2CC2)C1] | N-[4'-(6-{[(3R)-1-(Cyclopropylcarbonyl)pyrrolidin-3-yl]methyl}-7-oxo-4,6-diazaspiro[2.4]hept-4-en-5-yl)-3'-methylbiphenyl-3-yl]cyclopropanesulfonamide<br>MS m/z 547 (M + H)+ |

-continued

| ID No. | Structure | Compound Name & Physical Data |
|---|---|---|
| 614 | 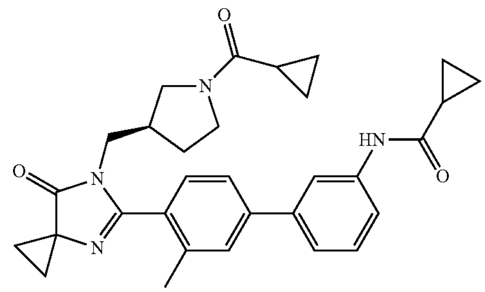 [SMILES: Cc1cc(-c2cccc(NC(=O)C3CC3)c2)ccc1C1=NC2(CC2)C(=O)N1C[C@@H]1CCN(C(=O)C2CC2)C1] | N-[4'-(6-{[(3R)-1-(Cyclopropylcarbonyl)pyrrolidin-3-yl]methyl}-7-oxo-4,6-diazaspiro[2.4]hept-4-en-5-yl)-3'-methylbiphenyl-3-yl]cyclopropanecarboxamide<br>MS m/z 511 (M + H)+ |
| 615 | 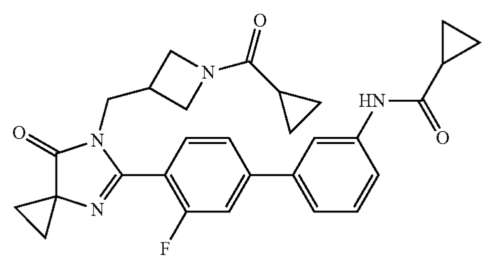 [SMILES: O=C(Nc1cccc(-c2ccc(C3=NC4(CC4)C(=O)N3CC3CN(C(=O)C4CC4)C3)c(F)c2)c1)C1CC1] | N-[4'-(6-{[1-(Cyclopropylcarbonyl)azetidin-3-yl]methyl}-7-oxo-4,6-diazaspiro[2.4]hept-4-en-5-yl)-3'-fluorobiphenyl-3-yl]cyclopropanecarboxamide<br>MS m/z 501 (M + H)+ |
| 616 | 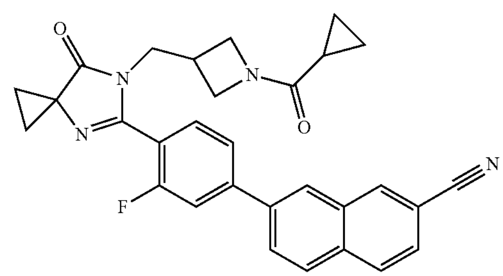 [SMILES: N#Cc1ccc2ccc(-c3ccc(C4=NC5(CC5)C(=O)N4CC4CN(C(=O)C5CC5)C4)c(F)c3)cc2c1] | 7-[4-(6-{[1-(Cyclopropylcarbonyl)azetidin-3-yl]methyl}-7-oxo-4,6-diazaspiro[2.4]hept-4-en-5-yl)-3-fluorophenyl]naphthalene-2-carbonitrile<br>MS m/z 493 (M + H)+ |
| 617 | 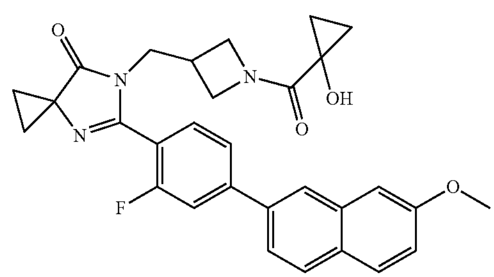 [SMILES: COc1ccc2ccc(-c3ccc(C4=NC5(CC5)C(=O)N4CC4CN(C(=O)C5(O)CC5)C4)c(F)c3)cc2c1] | 5-[2-Fluoro-4-(7-methoxynaphthalen-2-yl)phenyl]-6-({1-[(1-hydroxycyclopropyl)carbonyl]azetidin-3-yl}methyl)-4,6-diazaspiro[2.4]hept-4-en-7-one<br>MS m/z 514 (M + H)+ |
| 618 | 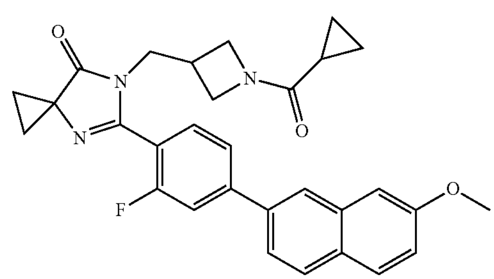 [SMILES: COc1ccc2ccc(-c3ccc(C4=NC5(CC5)C(=O)N4CC4CN(C(=O)C5CC5)C4)c(F)c3)cc2c1] | 6-{[1-(Cyclopropylcarbonyl)azetidin-3-yl]methyl}-5-[2-fluoro-4-(7-methoxynaphthalen-2-yl)phenyl]-4,6-diazaspiro[2.4]hept-4-en-7-one<br>MS m/z 498 (M + H)+ |

-continued

| ID No. | Structure | Compound Name & Physical Data |
|---|---|---|
| 619 | 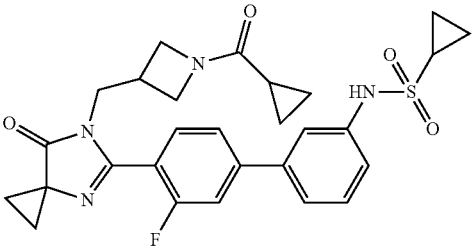 [SMILES: O=C(C1CC1)N1CC(CN2C(=O)C3(CC3)N=C2c2ccc(-c3cccc(NS(=O)(=O)C4CC4)c3)cc2F)C1] | N-[4'-(6-{[1-(Cyclopropylcarbonyl)azetidin-3-yl]methyl}-7-oxo-4,6-diazaspiro[2.4]hept-4-en-5-yl)-3'-fluorobiphenyl-3-yl]cyclopropanesulfonamide<br>MS m/z 537 (M + H)+ |
| 620 | 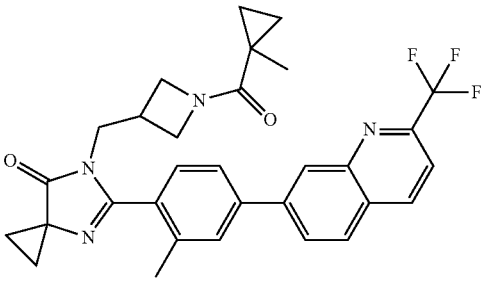 [SMILES: Cc1cc(-c2ccc3ccc(C(F)(F)F)nc3c2)ccc1C1=NC2(CC2)C(=O)N1CC1CN(C(=O)C2(C)CC2)C1] | 6-({1-[(1-Methylcyclopropyl)carbonyl]azetidin-3-yl}methyl)-5-{2-methyl-4-[2-(trifluoromethyl)quinolin-7-yl]phenyl}-4,6-diazaspiro[2.4]hept-4-en-7-one<br>MS m/z 547 (M + H)+ |
| 621 | 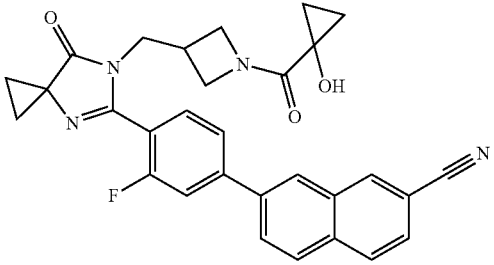 [SMILES: N#Cc1ccc2ccc(-c3ccc(C4=NC5(CC5)C(=O)N4CC4CN(C(=O)C5(O)CC5)C4)c(F)c3)cc2c1] | 7-{3-Fluoro-4-[6-({1-[(1-hydroxycyclopropyl)carbonyl]azetidin-3-yl}methyl)-7-oxo-4,6-diazaspiro[2.4]hept-4-en-5-yl]phenyl}naphthalene-2-carbonitrile<br>MS m/z 509 (M + H)+ |
| 622 | 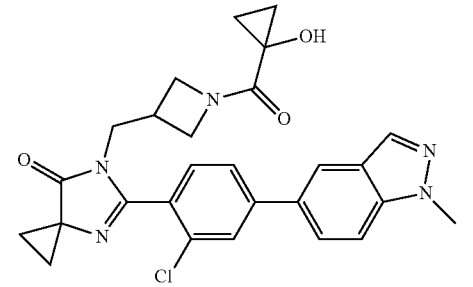 [SMILES: Cn1ncc2cc(-c3ccc(C4=NC5(CC5)C(=O)N4CC4CN(C(=O)C5(O)CC5)C4)c(Cl)c3)ccc21] | 5-[3-Chloro-4-(1-methyl-1H-indazol-5-yl)phenyl]-6-({1-[(1-hydroxycyclopropyl)carbonyl]azetidin-3-yl}methyl)-4,6-diazaspiro[2.4]hept-4-en-7-one<br>MS m/z 504 (M + H)+ |
| 623 | 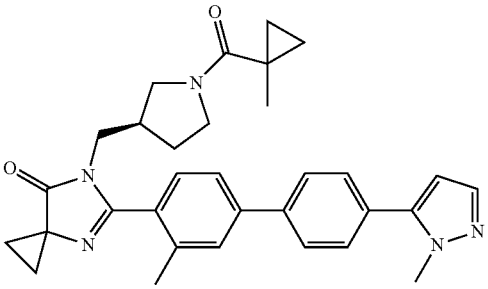 [SMILES: Cc1cc(-c2ccc(-c3ccnn3C)cc2)ccc1C1=NC2(CC2)C(=O)N1C[C@@H]1CCN(C(=O)C2(C)CC2)C1] | 6-({(3R)-1-[(1-Methylcyclopropyl)carbonyl]pyrrolidin-3-yl}methyl)-5-[3-methyl-4'-(1-methyl-1H-pyrazol-5-yl)biphenyl-4-yl]-4,6-diazaspiro[2.4]hept-4-en-7-one<br>MS m/z 522 (M + H)+ |

| ID No. | Structure | Compound Name & Physical Data |
|---|---|---|
| 624 | 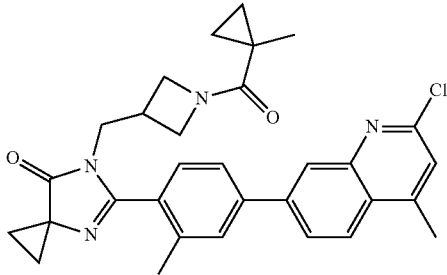 [SMILES: Cc1cc(-c2ccc3c(C)cc(Cl)nc3c2)ccc1C1=NC2(CC2)C(=O)N1CC1CN(C(=O)C2(C)CC2)C1] | 5-[4-(2-Chloro-4-methylquinolin-7-yl)-2-methylphenyl]-6-({1-[(1-methylcyclopropyl)carbonyl]azetidin-3-yl}methyl)-4,6-diazaspiro[2.4]hept-4-en-7-one<br>MS m/z 527 (M + H)+ |
| 627 | 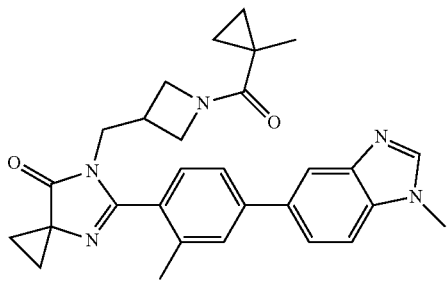 [SMILES: Cc1cc(-c2ccc3c(c2)ncn3C)ccc1C1=NC2(CC2)C(=O)N1CC1CN(C(=O)C2(C)CC2)C1] | 6-({1-[(1-Methylcyclopropyl)carbonyl]azetidin-3-yl}methyl)-5-[2-methyl-4-(1-methyl-1H-benzimidazol-5-yl)phenyl]-4,6-diazaspiro[2.4]hept-4-en-7-one<br>MS m/z 482 (M + H)+ |
| 628 | 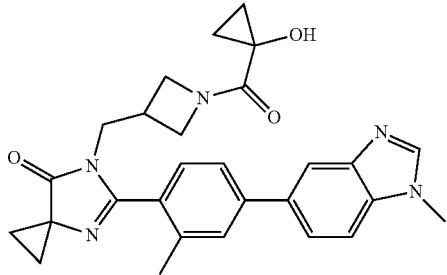 [SMILES: Cc1cc(-c2ccc3c(c2)ncn3C)ccc1C1=NC2(CC2)C(=O)N1CC1CN(C(=O)C2(O)CC2)C1] | 6-({1-[(1-Hydroxycyclopropyl)carbonyl]azetidin-3-yl}methyl)-5-[2-methyl-4-(1-methyl-1H-benzimidazol-5-yl)phenyl]-4,6-diazaspiro[2.4]hept-4-en-7-one<br>MS m/z 484 (M + H)+ |
| 629 | 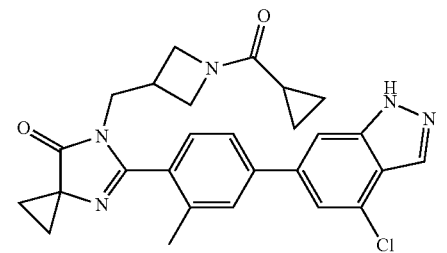 [SMILES: Cc1cc(-c2cc(Cl)c3cn[nH]c3c2)ccc1C1=NC2(CC2)C(=O)N1CC1CN(C(=O)C2CC2)C1] | 5-[4-(4-Chloro-1H-indazol-6-yl)-2-methylphenyl]-6-{[1-(cyclopropylcarbonyl)azetidin-3-yl]methyl}-4,6-diazaspiro[2.4]hept-4-en-7-one<br>MS m/z 488 (M + H)+ |
| 630 | 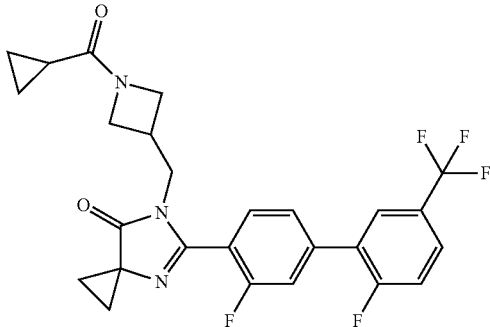 [SMILES: O=C(C1CC1)N1CC(CN2C(=O)C3(CC3)N=C2c2ccc(-c3cc(C(F)(F)F)ccc3F)cc2F)C1] | 6-{[1-(Cyclopropylcarbonyl)azetidin-3-yl]methyl}-5-[2',3-difluoro-5'-(trifluoromethyl)biphenyl-4-yl]-4,6-diazaspiro[2.4]hept-4-en-7-one<br>MS m/z 504 (M + H)+ |

| ID No. | Structure | Compound Name & Physical Data |
|---|---|---|
| 631 | 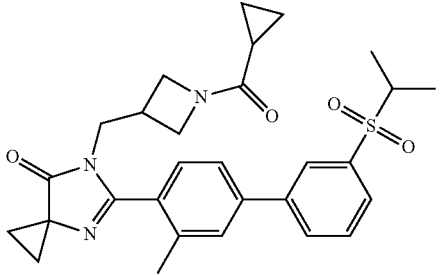 | 6-{[1-(Cyclopropylcarbonyl)azetidin-3-yl]methyl}-5-{3-fluoro-3'-[(1-methylethyl)sulfonyl]biphenyl-4-yl}-4,6-diazaspiro[2.4]hept-4-en-7-one<br>MS m/z 524 (M + H)+ |
| 632 | 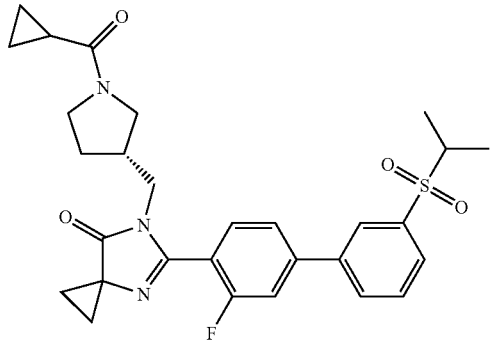 [SMILES: CC(C)S(=O)(=O)c1cccc(-c2ccc(C3=NC4(CC4)C(=O)N3C[C@@H]3CCN(C(=O)C4CC4)C3)c(F)c2)c1] | 6-{[(3R)-1-(Cyclopropylcarbonyl)pyrrolidin-3-yl]methyl}-5-{3-fluoro-3'-[(1-methylethyl)sulfonyl]biphenyl-4-yl}-4,6-diazaspiro[2.4]hept-4-en-7-one<br>MS m/z 538 (M + H)+ |
| 633 | 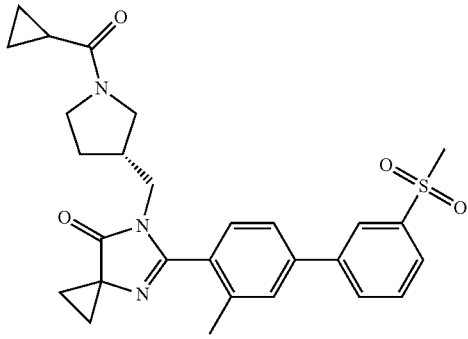 [SMILES: Cc1cc(-c2cccc(S(C)(=O)=O)c2)ccc1C1=NC2(CC2)C(=O)N1C[C@@H]1CCN(C(=O)C2CC2)C1] | 6-{[(3R)-1-(Cyclopropylcarbonyl)pyrrolidin-3-yl]methyl}-5-[3-methyl-3'-(methylsulfonyl)biphenyl-4-yl]-4,6-diazaspiro[2.4]hept-4-en-7-one<br>MS m/z 506 (M + H)+ |
| 634 | 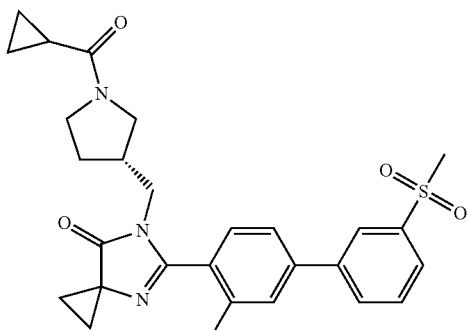 | 6-{[(3R)-1-(Cyclopropylcarbonyl)pyrrolidin-3-yl]methyl}-5-[3-fluoro-3'-(methylsulfonyl)biphenyl-4-yl]-4,6-diazaspiro[2.4]hept-4-en-7-one<br>MS m/z (M + H)+ |

-continued

| ID No. | Structure | Compound Name & Physical Data |
|---|---|---|
| 635 | 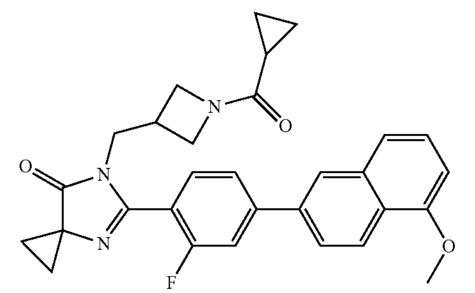 [SMILES: COc1cccc2cc(-c3ccc(C4=NC5(CC5)C(=O)N4CC4CN(C(=O)C5CC5)C4)c(F)c3)ccc12] | 6-{[1-(Cyclopropylcarbonyl)azetidin-3-yl]methyl}-5-[2-fluoro-4-(5-methoxynaphthalen-2-yl)phenyl]-4,6-diazaspiro[2.4]hept-4-en-7-one<br>MS m/z 498 (M + H)+ |
| 636 | 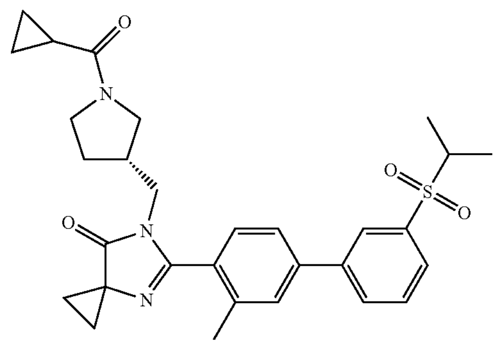 [SMILES: Cc1cc(-c2cccc(S(=O)(=O)C(C)C)c2)ccc1C1=NC2(CC2)C(=O)N1C[C@@H]1CCN(C(=O)C2CC2)C1] | 6-{[(3R)-1-(Cyclopropylcarbonyl)pyrrolidin-3-yl]methyl}-5-{3-methyl-3'-[(1-methylethyl)sulfonyl]biphenyl-4-yl}-4,6-diazaspiro[2.4]hept-4-en-7-one<br>MS m/z 534 (M + H)+ |
| 637 | 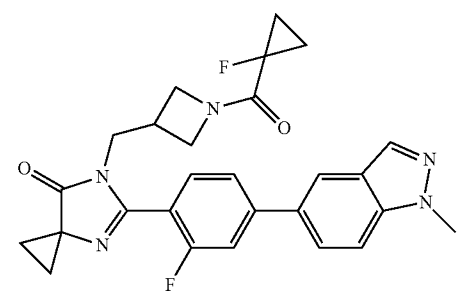 [SMILES: Cn1ncc2cc(-c3ccc(C4=NC5(CC5)C(=O)N4CC4CN(C(=O)C5(F)CC5)C4)c(F)c3)ccc21] | 6-({1-[(1-Fluorocyclopropyl)carbonyl]azetidin-3-yl}methyl)-5-[2-fluoro-4-(1-methyl-1H-indazol-5-yl)phenyl]-4,6-diazaspiro[2.4]hept-4-en-7-one<br>MS m/z 490,2 (M + H)+ |
| 638 | 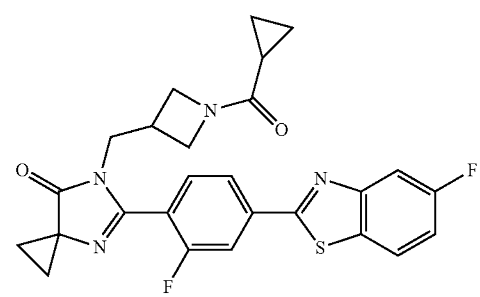 [SMILES: O=C(C1CC1)N1CC(CN2C(=O)C3(CC3)N=C2c2ccc(-c3nc4cc(F)ccc4s3)cc2F)C1] | 6-{[1-(Cyclopropylcarbonyl)azetidin-3-yl]methyl}-5-[2-fluoro-4-(5-fluoro-1,3-benzothiazol-2-yl)phenyl]-4,6-diazaspiro[2.4]hept-4-en-7-one<br>MS m/z 493 (M + H)+ |
| 639 | 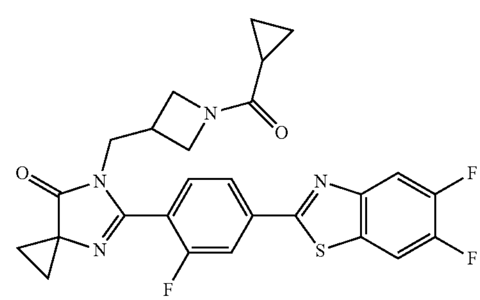 [SMILES: O=C(C1CC1)N1CC(CN2C(=O)C3(CC3)N=C2c2ccc(-c3nc4cc(F)c(F)cc4s3)cc2F)C1] | 6-{[1-(Cyclopropylcarbonyl)azetidin-3-yl]methyl}-5-[4-(5,6-difluoro-1,3-benzothiazol-2-yl)-2-fluorophenyl]-4,6-diazaspiro[2.4]hept-4-en-7-one<br>MS m/z 511 (M + H)+ |

-continued

| ID No. | Structure | Compound Name & Physical Data |
|---|---|---|
| 640 | 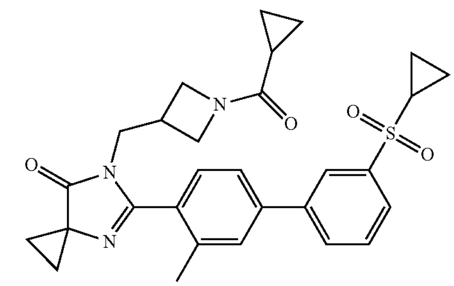 [SMILES: Cc1cc(-c2cccc(S(=O)(=O)C3CC3)c2)ccc1C1=NC2(CC2)C(=O)N1CC1CN(C(=O)C2CC2)C1] | 6-{[1-(Cyclopropylcarbonyl)azetidin-3-yl]methyl}-5-[3'-(cyclopropylsulfonyl)-3-methylbiphenyl-4-yl]-4,6-diazaspiro[2.4]hept-4-en-7-one<br>MS m/z 518 (M + H)+ |
| 641 | 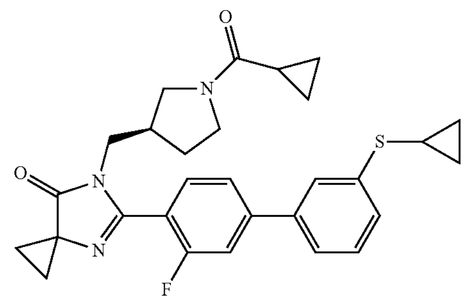 [SMILES: O=C(C1CC1)N1CC[C@@H](CN2C(=O)C3(CC3)N=C2c2ccc(-c3cccc(SC4CC4)c3)cc2F)C1] | 6-{[(3R)-1-(Cyclopropylcarbonyl)pyrrolidin-3-yl]methyl}-5-[3'-(cyclopropylsulfanyl)-3-fluorobiphenyl-4-yl]-4,6-diazaspiro[2.4]hept-4-en-7-one<br>MS m/z 504 (M + H)+ |
| 642 | 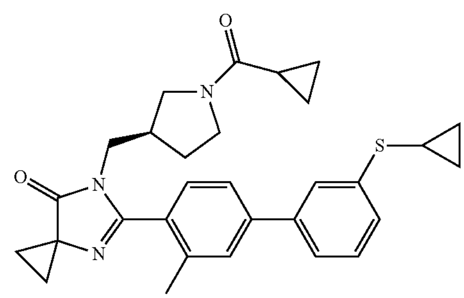 [SMILES: Cc1cc(-c2cccc(SC3CC3)c2)ccc1C1=NC2(CC2)C(=O)N1C[C@@H]1CCN(C(=O)C2CC2)C1] | 6-{[(3R)-1-(Cyclopropylcarbonyl)pyrrolidin-3-yl]methyl}-5-[3'-(cyclopropylsulfanyl)-3-methylbiphenyl-4-yl]-4,6-diazaspiro[2.4]hept-4-en-7-one<br>MS m/z 500 (M + H)+ |
| 643 | 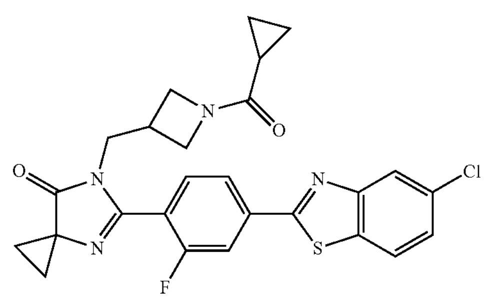 [SMILES: O=C(C1CC1)N1CC(CN2C(=O)C3(CC3)N=C2c2ccc(-c3nc4cc(Cl)ccc4s3)cc2F)C1] | 5-[4-(5-Chloro-1,3-benzothiazol-2-yl)-2-fluorophenyl]-6-{[1-(cyclopropylcarbonyl)azetidin-3-yl]methyl}-4,6-diazaspiro[2.4]hept-4-en-7-one<br>MS m/z 509 (M + H)+ |
| 644 | 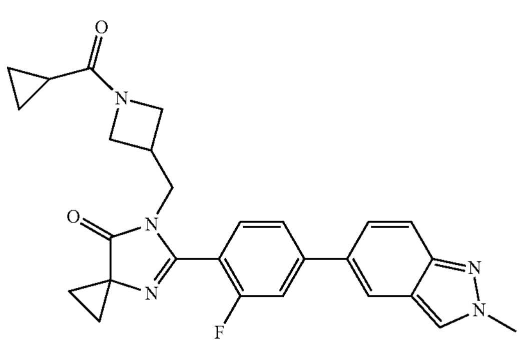 [SMILES: Cn1cc2cc(-c3ccc(C4=NC5(CC5)C(=O)N4CC4CN(C(=O)C5CC5)C4)c(F)c3)ccc2n1] | 6-{[1-(Cyclopropylcarbonyl)azetidin-3-yl]methyl}-5-[2-fluoro-4-(2-methyl-2H-indazol-5-yl)phenyl]-4,6-diazaspiro[2.4]hept-4-en-7-one<br>MS m/z 472.2 (M + H)+ |

-continued

| ID No. | Structure | Compound Name & Physical Data |
|---|---|---|
| 645 | 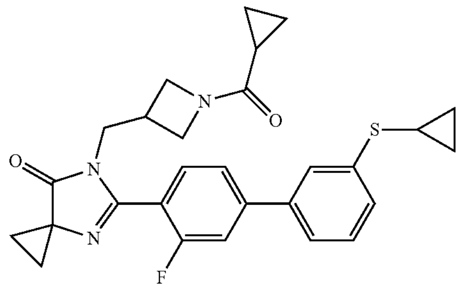 [SMILES: O=C(C1CC1)N1CC(CN2C(=O)C3(CC3)N=C2c2ccc(-c3cccc(SC4CC4)c3)cc2F)C1] | 6-{[1-(Cyclopropylcarbonyl)azetidin-3-yl]methyl}-5-[3'-(cyclopropylsulfanyl)-3-fluorobiphenyl-4-yl]-4,6-diazaspiro[2.4]hept-4-en-7-one<br>MS m/z 490 (M + H)+ |
| 646 | 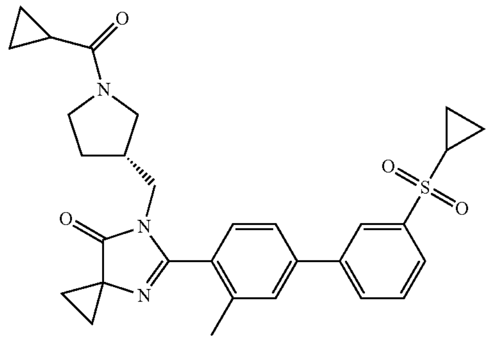 [SMILES: Cc1cc(-c2cccc(S(=O)(=O)C3CC3)c2)ccc1C1=NC2(CC2)C(=O)N1C[C@@H]1CCN(C(=O)C2CC2)C1] | 6-{[(3R)-1-(Cyclopropylcarbonyl)pyrrolidin-3-yl]methyl}-5-[3'-(cyclopropylsulfonyl)-3-methylbiphenyl-4-yl]-4,6-diazaspiro[2.4]hept-4-en-7-one<br>MS m/z 532 (M + H)+ |
| 647 | 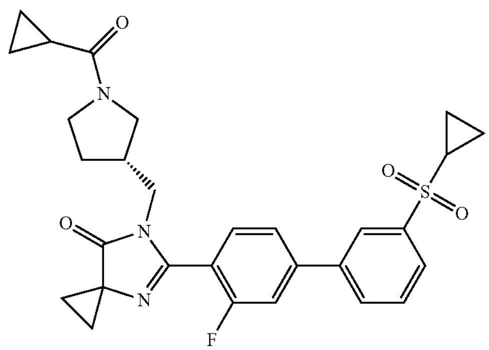 [SMILES: O=C(C1CC1)N1CC[C@@H](CN2C(=O)C3(CC3)N=C2c2ccc(-c3cccc(S(=O)(=O)C4CC4)c3)cc2F)C1] | 6-{[(3R)-1-(Cyclopropylcarbonyl)pyrrolidin-3-yl]methyl}-5-[3'-(cyclopropylsulfonyl)-3-fluorobiphenyl-4-yl]-4,6-diazaspiro[2.4]hept-4-en-7-one<br>MS m/z 536 (M + H)+ |
| 648 | 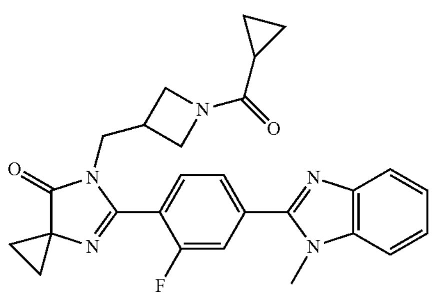 [SMILES: Cn1c(-c2ccc(C3=NC4(CC4)C(=O)N3CC3CN(C(=O)C4CC4)C3)c(F)c2)nc2ccccc21] | 6-{[1-(Cyclopropylcarbonyl)azetidin-3-yl]methyl}-5-[2-fluoro-4-(1-methyl-1H-benzimidazol-2-yl)phenyl]-4,6-diazaspiro[2.4]hept-4-en-7-one<br>MS m/z 472 (M + H)+ |
| 649 | 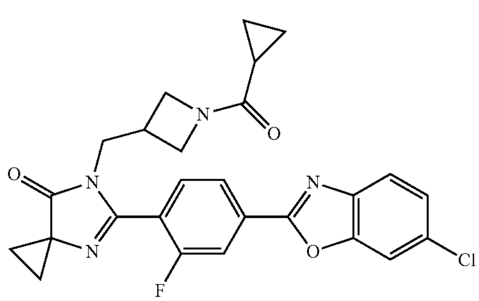 [SMILES: O=C(C1CC1)N1CC(CN2C(=O)C3(CC3)N=C2c2ccc(-c3nc4ccc(Cl)cc4o3)cc2F)C1] | 5-[4-(6-Chloro-1,3-benzoxazol-2-yl)-2-fluorophenyl]-6-{[1-(cyclopropylcarbonyl)azetidin-3-yl]methyl}-4,6-diazaspiro[2.4]hept-4-en-7-one<br>MS m/z 493 (M + H)+ |

| ID No. | Structure | Compound Name & Physical Data |
|---|---|---|
| 650 | 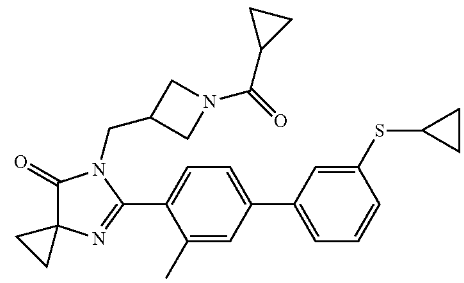 [SMILES: Cc1cc(-c2cccc(SC3CC3)c2)ccc1C1=NC2(CC2)C(=O)N1CC1CN(C(=O)C2CC2)C1] | 6-{[1-(Cyclopropylcarbonyl)azetidin-3-yl]methyl}-5-[3'-(cyclopropylsulfanyl)-3-methylbiphenyl-4-yl]-4,6-diazaspiro[2.4]hept-4-en-7-one<br>MS m/z 486 (M + H)+ |
| 651 | 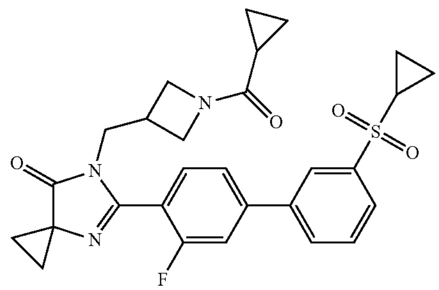 [SMILES: O=C(C1CC1)N1CC(CN2C(=O)C3(CC3)N=C2c2ccc(-c3cccc(S(=O)(=O)C4CC4)c3)cc2F)C1] | 6-{[1-(Cyclopropylcarbonyl)azetidin-3-yl]methyl}-5-[3'-(cyclopropylsulfonyl)-3-fluorobiphenyl-4-yl]-4,6-diazaspiro[2.4]hept-4-en-7-one<br>MS m/z 522 (M + H)+ |
| 652 | 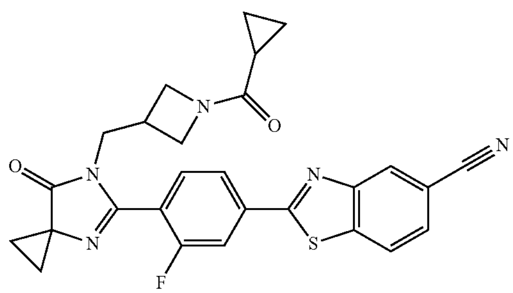 [SMILES: N#Cc1ccc2sc(-c3ccc(C4=NC5(CC5)C(=O)N4CC4CN(C(=O)C5CC5)C4)c(F)c3)nc2c1] | 2-[4-(6-{[1-(Cyclopropylcarbonyl)azetidin-3-yl]methyl}-7-oxo-4,6-diazaspiro[2.4]hept-4-en-5-yl)-3-fluorophenyl]-1,3-benzothiazole-5-carbonitrile<br>MS m/z 500 (M + H)+ |
| 653 | 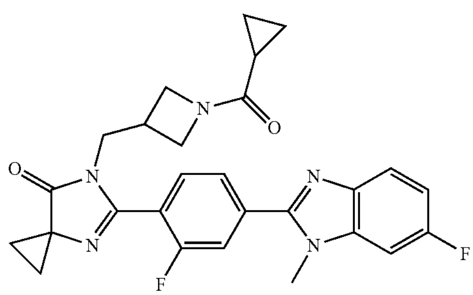 [SMILES: Cn1c(-c2ccc(C3=NC4(CC4)C(=O)N3CC3CN(C(=O)C4CC4)C3)c(F)c2)nc2ccc(F)cc21] | 6-{[1-(Cyclopropylcarbonyl)azetidin-3-yl]methyl}-5-[2-fluoro-4-(6-fluoro-1-methyl-1H-benzimidazol-2-yl)phenyl]-4,6-diazaspiro[2.4]hept-4-en-7-one<br>MS m/z 490 (M + H)+ |
| 654 | 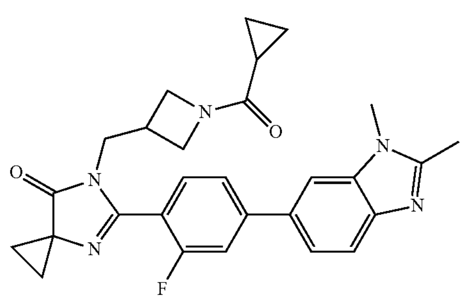 [SMILES: Cc1nc2ccc(-c3ccc(C4=NC5(CC5)C(=O)N4CC4CN(C(=O)C5CC5)C4)c(F)c3)cc2n1C] | 6-{[1-(Cyclopropylcarbonyl)azetidin-3-yl]methyl}-5-[4-(1,2-dimethyl-1H-benzimidazol-6-yl)-2-fluorophenyl]-4,6-diazaspiro[2.4]hept-4-en-7-one<br>MS m/z 486 (M + H)+ |

| ID No. | Structure | Compound Name & Physical Data |
|---|---|---|
| 655 | 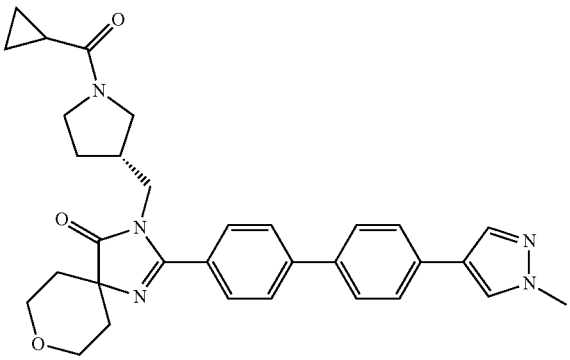 [SMILES: Cn1cc(-c2ccc(-c3ccc(C4=NC5(CCOCC5)C(=O)N4C[C@@H]4CCN(C(=O)C5CC5)C4)cc3)cc2)cn1] | 3-{[(3R)-1-(cyclopropylcarbonyl)pyrrolidin-3-yl]methyl}-2-[4'-(1-methyl-1H-pyrazol-4-yl)biphenyl-4-yl]-8-oxa-1,3-diazaspiro[4.5]dec-1-en-4-one<br>$^1$H NMR (600 MHz, CHLOROFORM-d) δ ppm 0.67-0.74 (m, 2 H), 0.90-0.97 (m, 2 H), 1.41-1.56 (m, 4 H), 1.56-1.75 (m, 2 H), 1.77-1.86 (m, 0.5 H), 1.88-1.99 (m, 0.5 H), 2.07-2.18 (m, 2 H), 2.30-2.39 (m, 0.5 H), 2.41-2.52 (m, 0.5 H), 3.00 (dd, J = 12.1, 7.2 Hz, 0.5 H), 3.20 (dd, J = 9.8, 7.9 Hz, 0.5 H), 3.29 (dt, J = 12.1, 7.7 Hz, 0.5 H), 3.46-3.55 (m, 1.5 H), 3.56-3.68 (m, 1.5 H), 3.69-3.79 (m, 1.5 H), 3.96-3.99 (m, 3 H), 3.99-4.08 (m, 4 H), 7.57-7.61 (m, 2 H), 7.61-7.79 (m, 5 H), 7.73-7.79 (m, 2 H), 7.82 (s, 1 H)<br>MS m/z 538.3 (M + H)+ |
| 656 | 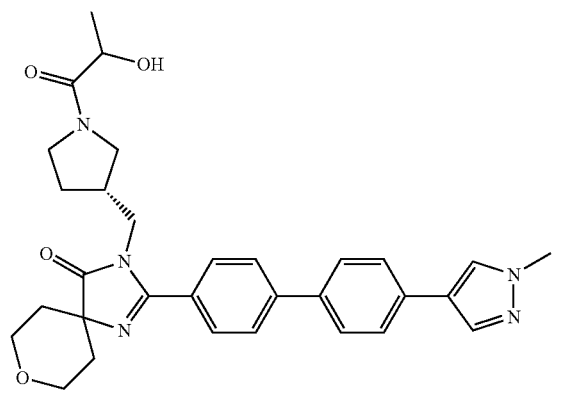 [SMILES: CC(O)C(=O)N1CC[C@@H](CN2C(=O)C3(CCOCC3)N=C2c2ccc(-c3ccc(-c4cnn(C)c4)cc3)cc2)C1] | 3-{[(3R)-1-(2-Hydroxypropanoyl)pyrrolidin-3-yl]methyl}-2-[4'-(1-methyl-1H-pyrazol-4-yl)biphenyl-4-yl]-8-oxa-1,3-diazaspiro[4.5]dec-1-en-4-one<br>MS m/z 542.2 (M + H)+ |
| 657 | 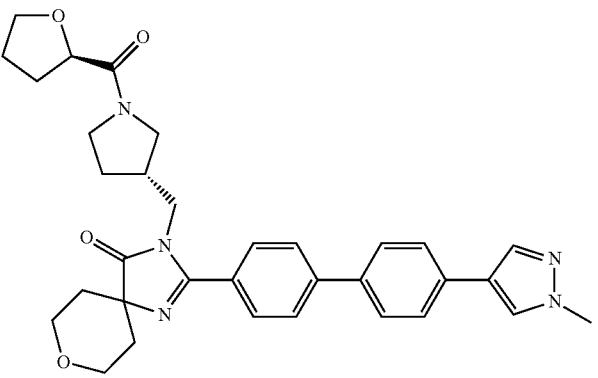 [SMILES: Cn1cc(-c2ccc(-c3ccc(C4=NC5(CCOCC5)C(=O)N4C[C@@H]4CCN(C(=O)[C@H]5CCCO5)C4)cc3)cc2)cn1] | 2-[4'-(1-Methyl-1H-pyrazol-4-yl)biphenyl-4-yl]-3-({(3R)-1-[(2R)-tetrahydro-furan-2-ylcarbonyl]pyrrolidin-3-yl}methyl)-8-oxa-1,3-diazaspiro[4.5]dec-1-en-4-one<br>$^1$H NMR (600 MHz, CHLOROFORM-d) δ ppm 1.41-1.61 (m, 4 H), 1.77-1.93 (m, 2 H), 1.93-2.05 (m, 2 H), 2.05-2.20 (m, 3 H), 2.32-2.44 (m, 1 H), 3.02 (dd, J = 12.3, 7.4 Hz, 0.5 H), 3.08 (dd, J = 10.6, 7.2 Hz, 0.5 H), 3.28-3.39 (m, 1 H), 3.45-3.55 (m, 1 H), 3.58-3.68 (m, 1.5 H), 3.68-3.75 (m, 1.5 H), 3.77-3.84 (m, 1 H), 3.90 (quin, J = 7.3 Hz, 1 H), 3.99 (s, 3 H), 4.00-4.08 (m, 4 H), 4.33 (t, J = 6.6 Hz, 0.5 H), 4.40 (dd, J = 7.4, 5.9 Hz, 0.5 H), 7.56-7.61 (m, 2 H), 7.61-7.70 (m, 5 H), 7.76 (dd, J = 8.3, 5.3 Hz, 2 H), 7.82 (s, 1 H)<br>MS m/z 568.2 (M + H)+ |
| 658 | 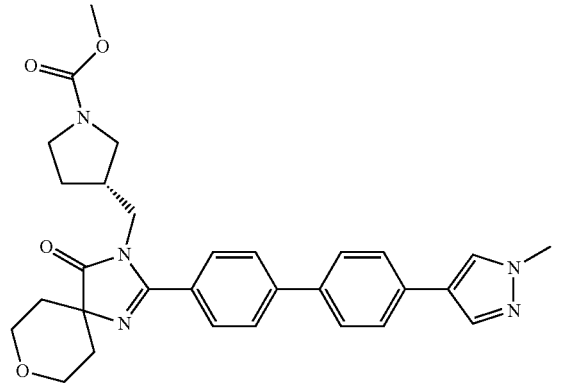 [SMILES: COC(=O)N1CC[C@@H](CN2C(=O)C3(CCOCC3)N=C2c2ccc(-c3ccc(-c4cnn(C)c4)cc3)cc2)C1] | Methyl (3S)-3-({2-[4'-(1-methyl-1H-pyrazol-4-yl)biphenyl-4-yl]-4-oxo-8-oxa-1,3-diazaspiro[4.5]dec-1-en-3-yl}methyl)pyrrolidin-1-carboxlate<br>MS m/z 528.2 (M + H)+ |

| ID No. | Structure | Compound Name & Physical Data |
|---|---|---|
| 659 | 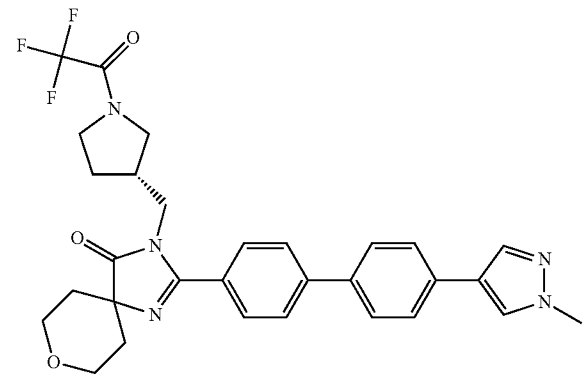 [SMILES: Cn1cc(-c2ccc(-c3ccc(C4=NC5(CCOCC5)C(=O)N4C[C@@H]4CCN(C(=O)C(F)(F)F)C4)cc3)cc2)cn1] | 2-[4'-(1-Methyl-1H-pyrazol-4-yl)biphenyl-4-yl]-3-{[(3R)-1-(trifluoroacetyl)pyrrolidin-3-yl]methyl}-8-oxa-1,3-diazaspiro[4.5]dec-1-en-4-one<br>MS m/z 566.2 (M + H)+ |
| 660 | 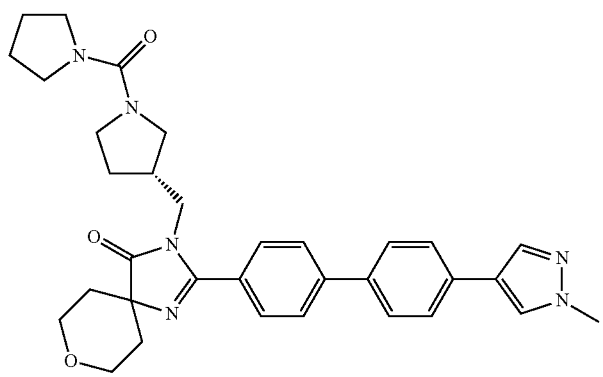 [SMILES: Cn1cc(-c2ccc(-c3ccc(C4=NC5(CCOCC5)C(=O)N4C[C@@H]4CCN(C(=O)N5CCCC5)C4)cc3)cc2)cn1] | 2-[4'-(1-Methyl-1H-pyrazol-4-yl)biphenyl-4-yl]-3-{[(3S)-1-(pyrrolidin-1-ylcarbonyl)pyrrolidin-3-yl]methyl}-8-oxa-1,3-diazaspiro[4.5]dec-1-en-4-one<br>$^1$H NMR (400 MHz, CHLOROFORM-d) δ ppm 1.38-1.58 (m, 4 H), 1.68-1.84 (m, 5 H), 2.06-2.18 (m, 2 H), 2.25-2.38 (m, 1 H), 2.98 (dd, J = 10.5, 7.3 Hz, 1 H), 3.20-3.29 (m, 6 H), 3.32 (dd, J = 10.5, 7.0 Hz, 1 H), 3.67 (dd, J = 14.4, 7.2 Hz, 1 H), 3.73 (dd, J = 14.3, 7.8 Hz, 1 H), 3.98 (s, 3 H), 4.00-4.08 (m, 3 H), 7.59 (m, J = 8.3 Hz, 2 H), 7.62-7.70 (m, 5 H), 7.76 (d, J = 8.3 Hz, 2 H), 7.83 (s, 1 H)<br>MS m/z 567.3 (M + H)+ |
| 661 | 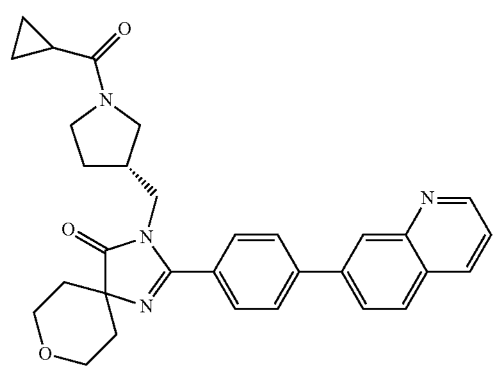 [SMILES: O=C(C1CC1)N1CC[C@@H](CN2C(=O)C3(CCOCC3)N=C2c2ccc(-c3ccc4cccnc4c3)cc2)C1] | 3-{[(3R)-1-(Cyclopropylcarbonyl)pyrrolidin-3-yl]methyl}-2-(4-quinolin-7-ylphenyl)-8-oxa-1,3-diazaspiro[4.5]dec-1-en-4-one<br>$^1$H NMR (600 MHz, CHLOROFORM-d) δ ppm 0.66-0.75 (m, 2 H), 0.88-0.99 (m, 2 H), 1.41-1.58 (m, 3 H), 1.58-1.65 (m, 1 H), 1.77-1.88 (m, 0.5 H), 1.91-1.99 (m, 0.5 H), 2.09-2.20 (m, 2 H), 2.37 (dt, J = 14.3, 7.4 Hz, 0.5 H), 2.48 (dt, J = 15.3, 7.5 Hz, 0.5 H), 3.02 (dd, J = 10.0, 7.7 Hz, 0.5 H), 3.30 (dt, J = 12.3, 7.8 Hz, 0.5 H), 3.45-3.57 (m, 1.5 H), 3.58-3.70 (m, 1.5 H), 3.72-3.82 (m, 1.5 H), 3.98-4.09 (m, 4 H), 7.43-7.48 (m, 1 H), 7.70-7.77 (m, 2 H), 7.85 (dd, J = 8.3, 1.5 Hz, 1 H), 7.88-7.99 (m, 3 H), 8.22 (dd, J = 8.3 Hz, 1 H), 8.38 (s, 1 H), 8.95-9.01 (m, 1 H)<br>MS m/z 509.2 (M + H)+ |
| 662 | 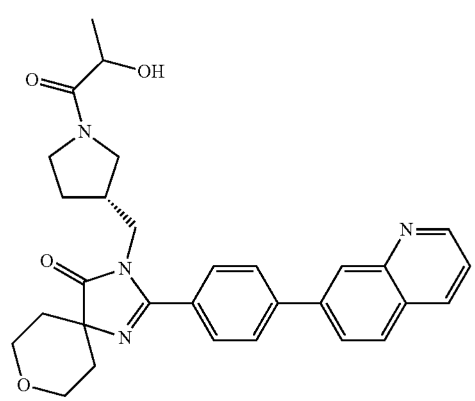 [SMILES: CC(O)C(=O)N1CC[C@@H](CN2C(=O)C3(CCOCC3)N=C2c2ccc(-c3ccc4cccnc4c3)cc2)C1] | 3-{[(3R)-1-(2-Hydroxypropanoyl)pyrrolidin-3-yl]methyl}-2-(4-quinolin-7-ylphenyl)-8-oxa-1,3-diazaspiro[4.5]dec-1-en-4-one<br>$^1$H NMR (400 MHz, CHLOROFORM-d) δ ppm 1.17 (dd, J = 12.8, 6.5 Hz, 3 H), 1.34-1.52 (m, 3 H), 1.52-1.70 (m, 2 H), 1.70-1.95 (m, 1 H), 2.01-2.14 (m, 2 H), 2.25-2.52 (m, 1 H), 2.94-3.08 (m, 1 H), 3.19-3.36 (m, 2 H), 3.40-3.69 (m, 3 H), 3.88-4.03 (m, 3 H), 4.03-4.19 (m, 1 H), 7.39 (dd, J = 8.2, 4.1 Hz, 1 H), 7.62-7.69 (m, 2 H), 7.74-7.80 (m, 1 H), 7.82-7.87 (m, 2 H), 7.89 (m, J = 8.5 Hz, 1 H), 8.16 (d, J = 7.8 Hz, 1 H), 8.30 (br. s., 1 H), 8.91 (dd, J = 4.1, 1.6 Hz, 1 H)<br>MS m/z 513.2 (M + H)+ |

-continued

| ID No. | Structure | Compound Name & Physical Data |
|---|---|---|
| 663 | 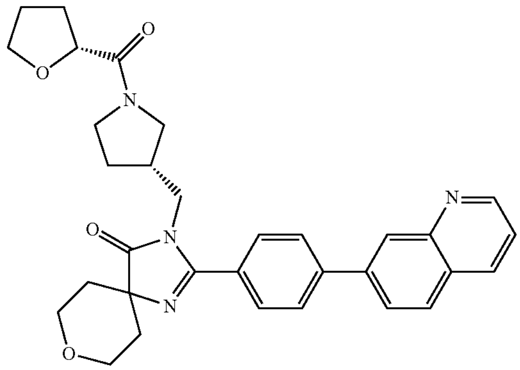 | 2-(4-Quinolin-7-ylphenyl)-3-({(3R)-1-[(2R)-tetrahydro-furan-2-ylcarbonyl]pyrrolidin-3-yl}methyl)-8-oxa-1,3-diazaspiro[4.5]dec-1-en-4-one<br>¹H NMR (600 MHz, CHLOROFORM-d) δ ppm 1.43-1.63 (m, 4 H), 1.79-2.04 (m, 4 H), 2.05-2.20 (m, 3 H), 2.39 (dq, J = 18.4, 7.3 Hz, 1 H), 3.04 (dd, J = 12.3, 7.4 Hz, 0.5 H), 3.10 (dd, J = 10.8, 7.4 Hz, 0.5 H), 3.30-3.40 (m, 1 H), 3.45-3.57 (m, 1 H), 3.60-3.71 (m, 1.5 H), 3.71-3.77 (m, 1.5 H), 3.77-3.84 (m, 1 H), 3.85-3.95 (m, 1 H), 3.98-4.09 (m, 4 H), 4.35 (t, J = 6.6 Hz, 0.5 H), 4.37-4.43 (m, 0.5 H), 7.43-7.48 (m, 1 H), 7.68-7.78 (m, 2 H), 7.83-7.88 (m, 1 H), 7.89-7.99 (m, 3 H), 8.22 (d, J = 8.3 Hz, 1 H), 8.38 (s, 1 H), 8.95-9.01 (m, 1 H)<br>MS m/z 539.2 (M + H)+ |
| 664 | 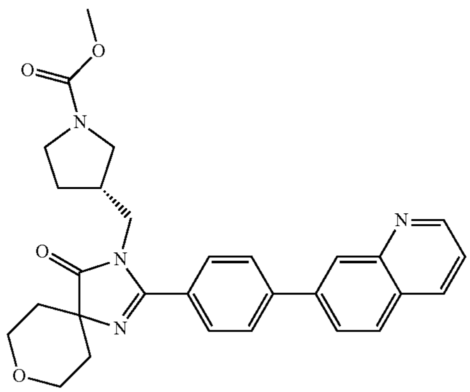 [SMILES: COC(=O)N1CC[C@@H](CN2C(=O)C3(CCOCC3)N=C2c2ccc(-c3ccc4cccnc4c3)cc2)C1] | Methyl (3S)-3-{[4-oxo-2-(4-quinolin-7-ylphenyl)-8-oxa-1,3-diazaspiro[4.5]dec-1-en-3-yl]methyl}pyrrolidine-1-carboxylate<br>MS m/z 499.3 (M + H)+ |
| 665 | 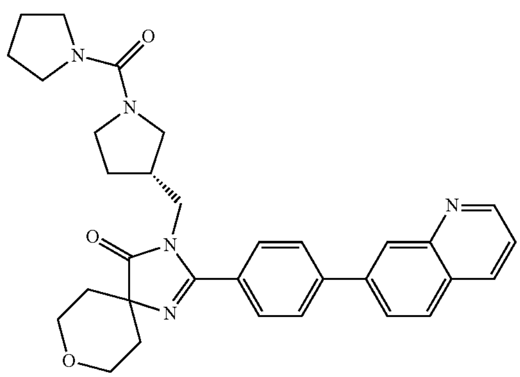 [SMILES: O=C(N1CCCC1)N1CC[C@@H](CN2C(=O)C3(CCOCC3)N=C2c2ccc(-c3ccc4cccnc4c3)cc2)C1] | 3-{[(3S)-1-(Pyrrolidin-1-ylcarbonyl)pyrrolidin-3-yl]methyl}-2-(4-quinolin-7-ylphenyl)-8-oxa-1,3-diazaspiro[4.5]dec-1-en-4-one<br>¹H NMR (600 MHz, CHLOROFORM-d) δ ppm 1.38-1.50 (m, 1 H), 1.50-1.58 (m, 2 H), 1.70-1.85 (m, 5 H), 2.09-2.19 (m, 2 H), 2.28-2.42 (m, 1 H), 3.00 (dd, J = 10.6, 7.2 Hz, 1 H), 3.18-3.30 (m, 6 H), 3.33 (dd, J = 10.4, 7.0 Hz, 1 H), 3.69 (m, J = 14.4, 7.2 Hz, 1 H), 3.75 (dd, J = 14.7, 7.9 Hz, 1 H), 3.97-4.10 (m, 4 H), 7.46 (dd, J = 8.3, 4.2 Hz, 1 H), 7.73 (d, 2 H), 7.85 (dd, J = 8.7, 1.9 Hz, 1 H), 7.89-7.93 (m, 2 H), 7.95 (d, J = 8.3 Hz, 1 H), 8.22 (d, J = 7.6 Hz, 1 H), 8.36-8.40 (m, 1 H), 8.98 (dd, J = 4.2, 1.5 Hz, 1 H)<br>MS m/z 538.2 (M + H)+ |
| 666 | 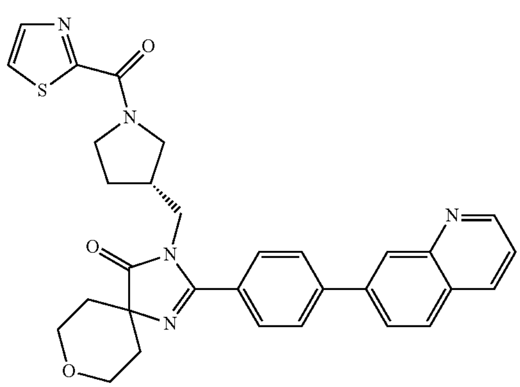 [SMILES: O=C(c1nccs1)N1CC[C@@H](CN2C(=O)C3(CCOCC3)N=C2c2ccc(-c3ccc4cccnc4c3)cc2)C1] | 2-(4-Quinolin-7-ylphenyl)-3-{[(3R)-1-(1,3-thiazol-2-ylcarbonyl)pyrrolidin-3-yl]methyl}-8-oxa-1,3-diazaspiro[4.5]dec-1-en-4-one<br>MS m/z 552.1 (M + H)+ |

| ID No. | Structure | Compound Name & Physical Data |
|---|---|---|
| 667 | 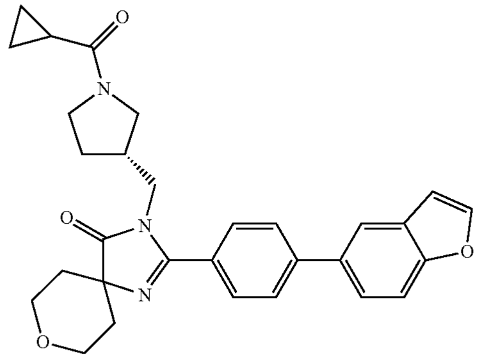 [SMILES: O=C(C1CC1)N1CC[C@@H](CN2C(=O)C3(CCOCC3)N=C2c2ccc(-c3ccc4occc4c3)cc2)C1] | 2-[4-(1-Benzofuran-5-yl)phenyl]-3-{[(3R)-1-(cyclopropylcarbonyl)pyrrolidin-3-yl]methyl}-8-oxa-1,3-diazaspiro[4.5]dec-1-en-4-one<br>$^1$H NMR (600 MHz, CHLOROFORM-d) δ ppm −0.06-0.02 (m, 3 H), 0.68-0.73 (m, 2 H), 0.86-1.00 (m, 2 H), 1.41-1.57 (m, 3 H), 1.78-1.86 (m, 0.5 H), 1.88-2.00 (m, 0.5 H), 2.07-2.20 (m, 2 H), 2.35 (m, 0.5 H), 2.47 (dt, J = 15.2, 7.3 Hz, 0.5 H), 3.01 (dd, J = 11.9, 7.0 Hz, 0.5 H), 3.21 (dd, J = 10.0, 7.7 Hz, 0.5 H), 3.29 (dt, J = 12.3, 7.8 Hz, 0.5 H), 3.44-3.56 (m, 1.5 H), 3.56-3.69 (m, 1.5 H), 3.71-3.79 (m, 1.5 H), 3.98-4.10 (m, 4 H), 6.85 (d, J = 1.5 Hz, 1 H), 7.55 (dd, J = 8.3, 1.9 Hz, 1 H), 7.61 (dd, J = 8.7, 2.3 Hz, 1 H), 7.64-7.71 (m, 3 H), 7.74-7.80 (m, 2 H), 7.84 (d, J = 1.9 Hz, 1 H)<br>MS m/z 498.2 (M + H)+ |
| 668 | 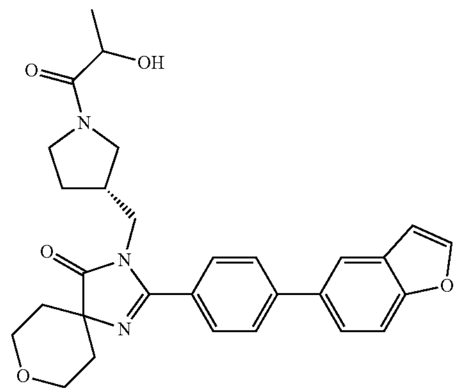 [SMILES: CC(O)C(=O)N1CC[C@@H](CN2C(=O)C3(CCOCC3)N=C2c2ccc(-c3ccc4occc4c3)cc2)C1] | 2-[4-(1-Benzofuran-5-yl)phenyl]-3-{[(3R)-1-(2-hydroxypropanoyl)pyrrolidin-3-yl]methyl}-8-oxa-1,3-diazaspiro[4.5]dec-1-en-4-one<br>$^1$H NMR (400 MHz, CHLOROFORM-d) δ ppm 1.13-1.35 (m, 3 H), 1.42-1.72 (m, 3 H), 1.76-2.04 (m, 1 H), 2.04-2.22 (m, 2 H), 2.29-2.43 (m, 1 H), 2.43-2.65 (m, 1 H), 3.09 (d, J = 16.1 Hz, 1 H), 3.23-3.44 (m, 2 H), 3.52-3.64 (m, 1 H), 3.64-3.80 (m, 2 H), 3.96-4.11 (m, 3 H), 4.11-4.29 (m, 1 H), 6.86 (s, 1 H), 7.49-7.74 (m, 5 H), 7.75-7.91 (m, 3 H)<br>MS m/z 502.3 (M + H)+ |
| 669 | 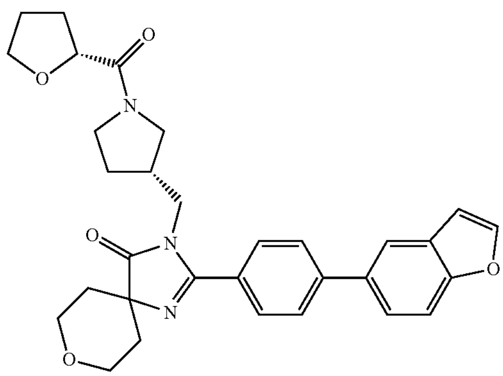 [SMILES: O=C([C@H]1CCCO1)N1CC[C@@H](CN2C(=O)C3(CCOCC3)N=C2c2ccc(-c3ccc4occc4c3)cc2)C1] | 2-[4-(1-Benzofuran-5-yl)phenyl]-3-({(3R)-1-[(2R)-tetrahydro-furan-2-ylcarbonyl]pyrrolidin-3-yl}methyl)-8-oxa-1,3-diazaspiro[4.5]dec-1-en-4-one<br>$^1$H NMR (600 MHz, CHLOROFORM-d) δ ppm 1.39-1.60 (m, 4 H), 1.76-1.93 (m, 2 H), 1.93-2.05 (m, 2 H), 2.05-2.18 (m, 3 H), 2.38 (dq, J = 15.5, 7.7 Hz, 1 H), 3.02 (dd, J = 12.3, 7.4 Hz, 0.5 H), 3.08 (dd, J = 10.6, 7.2 Hz, 0.5 H), 3.31-3.41 (m, 1 H), 3.42-3.57 (m, 1 H), 3.58-3.76 (m, 3 H), 3.76-3.85 (m, 1 H), 3.85-3.95 (m, 1 H), 3.98-4.11 (m, 4 H), 4.34 (dd, J = 7.2, 5.7 Hz, 0.5 H), 4.40 (dd, J = 7.6, 6.0 Hz, 0.5 H), 6.85 (s, 1 H), 7.56 (d, J = 8.7 Hz, 1 H), 7.61 (dd, J = 8.5, 3.6 Hz, 1 H), 7.63-7.72 (m, 2 H), 7.74-7.80 (m, 2 H), 7.84 (s, 1 H)<br>MS m/z 528.2 (M + H)+ |
| 670 | 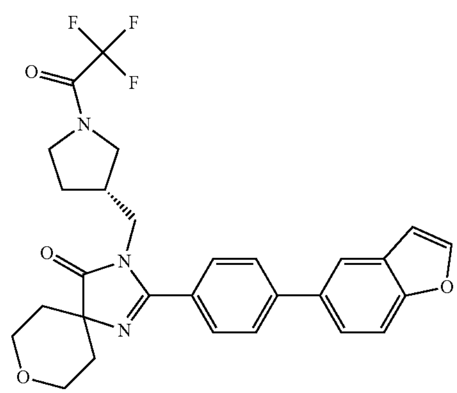 [SMILES: O=C(N1CC[C@@H](CN2C(=O)C3(CCOCC3)N=C2c2ccc(-c3ccc4occc4c3)cc2)C1)C(F)(F)F] | 2-[4-(1-Benzofuran-5-yl)phenyl]-3-{[(3R)-1-(trifluoroacetyl)pyrrolidin-3-yl]methyl}-8-oxa-1,3-diazaspiro[4.5]dec-1-en-4-one<br>MS m/z 526.1 (M + H)+ |

| ID No. | Structure | Compound Name & Physical Data |
|---|---|---|
| 671 | 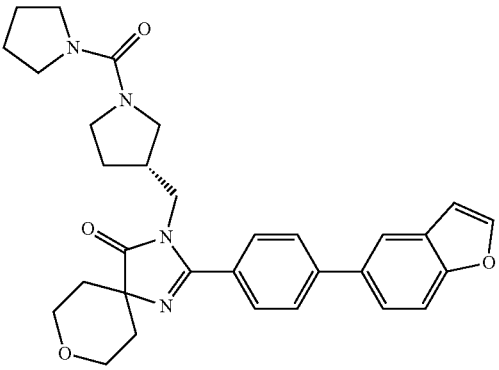 [SMILES: O=C(N1CCCC1)N1CC[C@@H](CN2C(=O)C3(CCOCC3)N=C2c2ccc(-c3ccc4occc4c3)cc2)C1] | 2-[4-(1-Benzofuran-5-yl)phenyl]-3-{[(3S)-1-(pyrrolidin-1-ylcarbonyl)pyrrolidin-3-yl]methyl}-8-oxa-1,3-diazaspiro[4.5]dec-1-en-4-one<br>MS m/z 527.2 (M + H)+ |
| 672 | 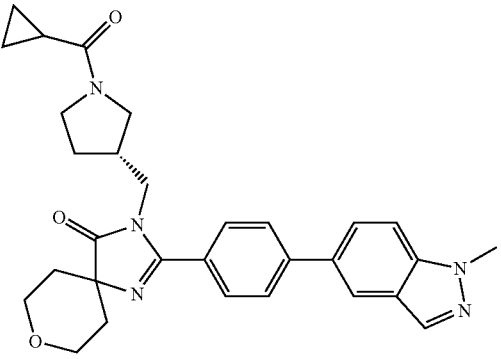 [SMILES: Cn1ncc2cc(-c3ccc(C4=NC5(CCOCC5)C(=O)N4C[C@@H]4CCN(C(=O)C5CC5)C4)cc3)ccc21] | 3-{[(3R)-1-(Cyclopropylcarbonyl)pyrrolidin-3-yl]methyl}-2-[4-(1-methyl-1H-indazol-5-yl)phenyl]-8-oxa-1,3-diazaspiro[4.5]dec-1-en-4-one<br>MS m/z 512.2 (M + H)+ |
| 673 | 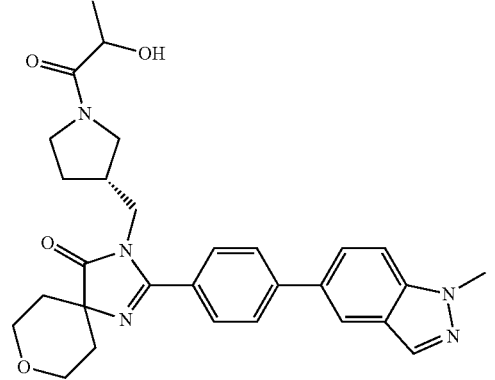 [SMILES: CC(O)C(=O)N1CC[C@@H](CN2C(=O)C3(CCOCC3)N=C2c2ccc(-c3ccc4c(cnn4C)c3)cc2)C1] | 3-{[(3R)-1-(2-Hycdroxypropanoyl)pyrrolidin-3-yl]methyl}-2-[4-(1-methyl-1H-indazol-5-yl)phenyl]-8-oxa-1,3-diazaspiro[4.5]dec-1-en-4-one<br>MS m/z 516.3 (M + H)+ |
| 674 | 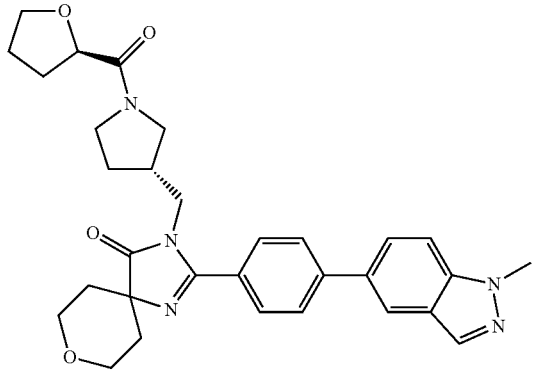 [SMILES: Cn1ncc2cc(-c3ccc(C4=NC5(CCOCC5)C(=O)N4C[C@@H]4CCN(C(=O)[C@H]5CCCO5)C4)cc3)ccc21] | 2-[4-(1-Methyl-1H-indazol-5-yl)phenyl]-3-({(3R)-1-[(2R)-tetrahydro-furan-2-ylcarbonyl]pyrrolidin-3-yl}methyl)-8-oxa-1,3-diazaspiro[4.5]dec-1-en-4-one<br>MS m/z 542.2 (M + H)+ |

| ID No. | Structure | Compound Name & Physical Data |
|---|---|---|
| 675 | 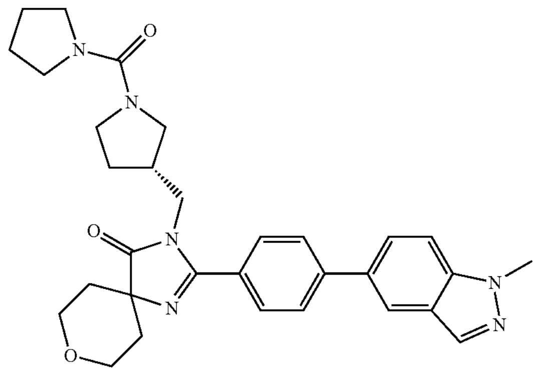 [SMILES: Cn1ncc2cc(-c3ccc(C4=NC5(CCOCC5)C(=O)N4C[C@@H]4CCN(C(=O)N5CCCC5)C4)cc3)ccc21] | 2-[4-(1-Methyl-1H-indazol-5-yl)phenyl]-3-{[(3S)-1-(pyrrolidin-1-ylcarbonyl)pyrrolidin-1-ylcarbonyl)pyrrolidin-3-yl]methyl}-8-oxa-1,3-diazaspiro[4.5]dec-1-en-4-one<br>MS m/z 541.2 (M + H)+ |
| 676 | 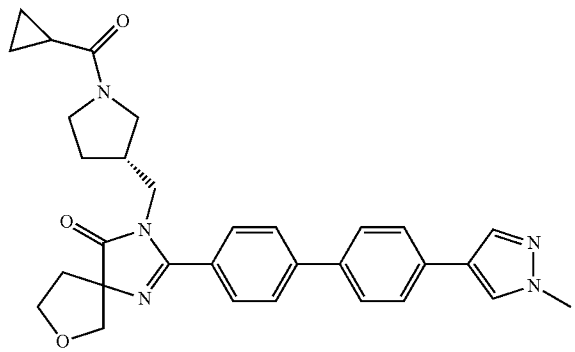 [SMILES: Cn1cc(-c2ccc(-c3ccc(C4=NC5(CCOC5)C(=O)N4C[C@@H]4CCN(C(=O)C5CC5)C4)cc3)cc2)cn1] | 3-{[(3R)-1-(Cyclopropylcarbonyl)pyrrolidin-3-yl]methyl}-2-[4'-(1-methyl-1H-pyrazol-4-yl)biphenyl-4-yl]-7-oxa-1,3-diazaspiro[4.4]non-1-en-4-one<br>¹H NMR (600 MHz, CHLOROFORM-d) δ ppm 0.68-0.74 (m, 2 H), 0.86-0.99 (m, 2 H), 1.38-1.54 (m, 2 H), 1.79-1.88 (m, 0.5 H), 1.89-2.00 (m, 0.5 H), 2.21-2.29 (m, 1 H), 2.3-2.53 (m, 2 H), 3.03 (ddd, J = 11.9, 7.0, 4.9 Hz, 0.5 H), 3.19-3.26 (m, 0.5 H), 3.30 (dt, J = 12.1, 7.9 Hz, 0.5 H), 3.46-3.57 (m, 1.5 H), 3.57-3.66 (m, 1 H), 3.66-3.72 (m, 0.5 H), 3.72-3.82 (m, 1.5 H), 3.97 (s, 3 H), 3.99-4.07 (m, 2 H), 4.16-4.29 (m, 2 H), 7.54-7.61 (m, 2 H), 7.64 (d, J = 8.3 Hz, 2 H), 7.66-7.70 (m, 3 H), 77.3-7.79 (m, 2 H), 7.82 (s, 1 H)<br>MS m/z 524.3 (M + H)+ |
| 677 | 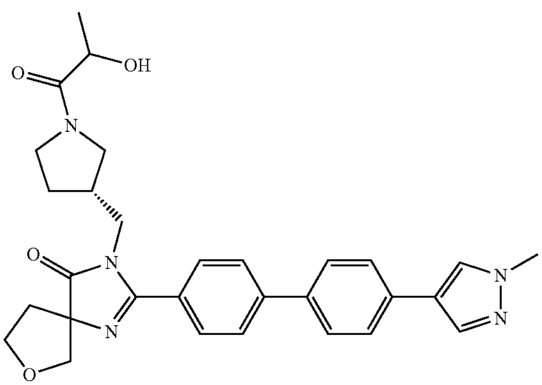 [SMILES: CC(O)C(=O)N1CC[C@@H](CN2C(=O)C3(CCOC3)N=C2c2ccc(-c3ccc(-c4cnn(C)c4)cc3)cc2)C1] | 3-{[(3R)-1-(2-Hydroxypropanoyl)pyrrolidin-3-yl]methyl}-2-[4'-(1-methyl-1H-pyrazol-4-yl)biphenyl-4-yl]-7-oxa-1,3-diazaspiro[4.4]non-1-en-4-one<br>¹H NMR (400 MHz, CHLOROFORM-d) δ ppm 1.19-1.32 (m, 3 H), 1.41-1.71 (m, 1 H), 1.91-2.01 (m, 1 H), 2.19-2.57 (m, 3 H), 3.01-3.18 (m, 1 H), 3.26-3.43 (m, 2 H), 3.60 (dd, J = 12.2, 6.9 Hz, 1 H), 3.67-3.79 (m, 2 H), 3.98 (s, 3 H), 4.00-4.07 (m, 2 H), 4.09-4.31 (m, 3 H), 7.55-7.62 (m, 2 H), 7.62-7.71 (m, 5 H), 7.73-7.80 (m, 2 H), 7.83 (s, 1 H)<br>MS m/z 528.3 (M + H)+ |
| 678 | 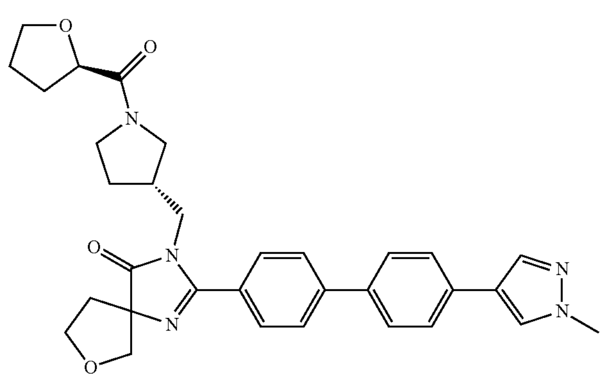 [SMILES: Cn1cc(-c2ccc(-c3ccc(C4=NC5(CCOC5)C(=O)N4C[C@@H]4CCN(C(=O)[C@H]5CCCO5)C4)cc3)cc2)cn1] | 2-[4'-(1-Methyl-1H-pyrazol-4-yl)biphenyl-4-yl]-3-({(3R)-1-[(2R)-tetrahydro-furan-2-ylcarbonyl]pyrrolidin-3-yl}methyl)-7-oxa-1,3-diazaspiro[4.4]non-1-en-4-one<br>MS m/z 554.3 (M + H)+ |

| ID No. | Structure | Compound Name & Physical Data |
|---|---|---|
| 679 | 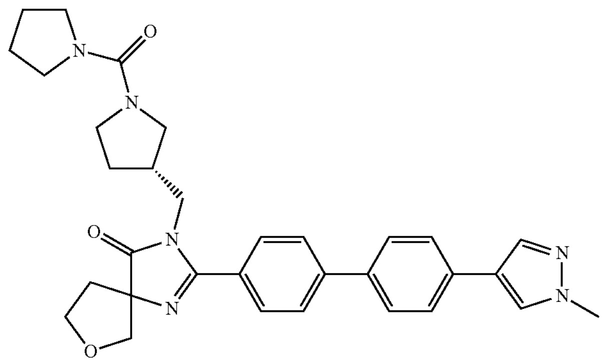 [SMILES: Cn1cc(-c2ccc(-c3ccc(C4=NC5(CCOC5)C(=O)N4C[C@@H]4CCN(C(=O)N5CCCC5)C4)cc3)cc2)cn1] | 2-[4'-(1-Methyl-1H-pyrazol-4-yl)biphenyl-4-yl]-3-{[(3S)-1-(pyrrolidin-1-ylcarbonyl)pyrrolidin-3-yl]methyl}-7-oxa-1,3-diazaspiro[4.4]non-1-en-4-one<br>MS m/z 553.2 (M + H)+ |
| 680 | 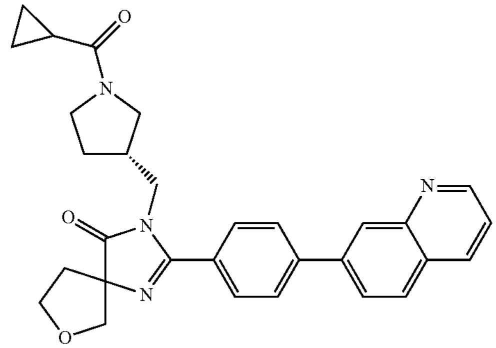 [SMILES: O=C(C1CC1)N1CC[C@@H](CN2C(=O)C3(CCOC3)N=C2c2ccc(-c3ccc4cccnc4c3)cc2)C1] | 3-{[(3R)-1-(Cyclopropylcarbonyl)pyrrolidin-3-yl]methyl}-2-(4-quinolin-7-ylphenyl)-7-oxa-1,3-diazaspiro[4.4]non-1-en-4-one<br>¹H NMR (600 MHz, CHLOROFORM-d) δ ppm 0.65-0.76 (m, 2 H), 0.88-1.01 (m, 2 H), 1.41-1.56 (m, 1.5 H), 1.59-1.65 (m, 0.5 H), 1.81-1.90 (m, 0.5 H), 1.91-2.02 (m, 0.5 H), 2.22-2.32 (m, 1 H), 2.31-2.55 (m, 2 H), 3.04 (ddd, J = 11.9, 7.0, 4.9 Hz, 0.5 H), 3.21-3.28 (m, 0.5 H), 3.31 (dt, J = 12.1, 7.9 Hz, 0.5 H), 3.48-3.58 (m, 1.5 H), 3.58-3.85 (m, 3 H), 3.99-4.07 (m, 2 H), 4.15-4.29 (m, 2 H), 7.42-7.48 (m, 1 H), 7.71-7.78 (m, 2 H), 7.85 (dd, J = 8.5, 1.7 Hz, 1 H), 7.88-7.97 (m, 3 H), 8.22 (d, J = 8.3 Hz, 1 H), 8.38 (s, 1 H)<br>MS m/z 495.2 (M + H)+ |
| 681 | 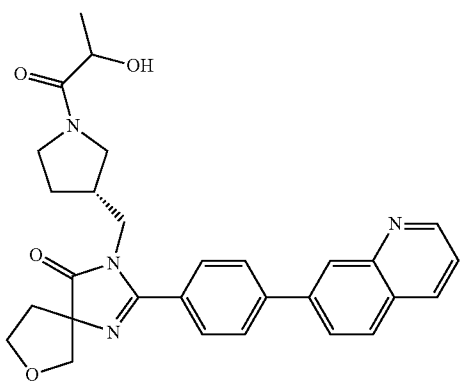 [SMILES: CC(O)C(=O)N1CC[C@@H](CN2C(=O)C3(CCOC3)N=C2c2ccc(-c3ccc4cccnc4c3)cc2)C1] | 3-{[(3R)-1-(2-Hydroxypropanoyl)pyrrolidin-3-yl]methyl}-2-(4-quinolin-7-ylphenyl)-7-oxa-1,3-diazaspiro[4.4]non-1-en-4-one<br>¹H NMR (600 MHz, CHLOROFORM-d) δ ppm 1.20-1.31 (m, 3 H), 1.44-1.71 (m, 2 H), 1.83-1.93 (m, 1 H), 1.97 (dt, J = 13.4, 6.5 Hz, 1 H), 2.21-2.31 (m, 1 H), 2.33-2.59 (m, 2 H), 3.03-3.17 (m, 1 H), 3.27-3.43 (m, 2 H), 3.57-3.66 (m, 1 H), 3.68-3.80 (m, 2 H), 3.99-4.08 (m, 2 H), 4.10-4.29 (m, 3 H), 7.46 (dd, J = 8.1, 4.3 Hz, 1 H), 7.75 (dd, J = 8.5, 2.8 Hz, 2 H), 7.81-7.89 (m, 1 H), 7.90-7.94 (m, 2 H), 7.96 (d, J = 8.7 Hz, 1 H), 8.23 (d, J =8.3 Hz, 1 H), 8.36-8.41 (m, 1 H), 8.98 (dd, J = 4.2, 1.9 Hz, 1 H)<br>MS m/z 499.2 (M + H)+ |
| 682 | 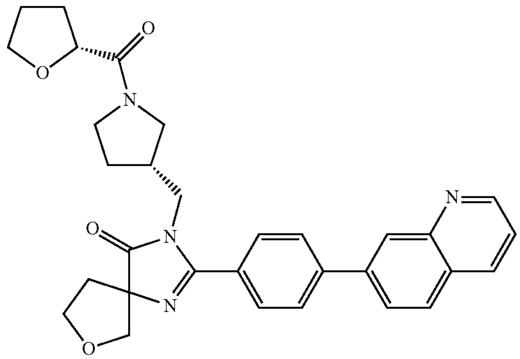 [SMILES: O=C([C@H]1CCCO1)N1CC[C@@H](CN2C(=O)C3(CCOC3)N=C2c2ccc(-c3ccc4cccnc4c3)cc2)C1] | 2-(4-Quinolin-7-ylphenyl)-3-({(3R)-1-[(2R)-tetrahydro-furan-2-ylcarbonyl]pyrrolidin-3-yl}methyl)-7-oxa-1,3-diazaspiro[4.4]non-1-en-4-one<br>¹H NMR (600 MHz, CHLOROFORM-d) δ ppm 1.38-2.22 (m, 6 H), 2.22-2.31 (m, 1 H), 2.31-2.50 (m, 2 H), 3.00-3.09 (m, 0.5 H), 3.13 (ddd, J = 10.4, 7.6, 2.5 Hz, 0.5 H), 3.30-3.43 (m, 1 H), 3.46-3.59 (m, 1 H), 3.58-3.85 (m, 4 H), 3.85-3.96 (m, 1 H), 3.97-4.09 (m, 2 H), 4.16-4.29 (m, 2 H), 4.36 (t, J = 6.0 Hz, 0.5 H), 4.38-4.44 (m, 0.5 H), 7.44-7.51 (m, 1 H), 7.70-7.79 (m, 2 H), 7.84-7.89 (m, 1 H), 7.89-7.95 (m, 2 H), 7.96 (dd, J = 8.5, 2.8 Hz, 1 H), 8.25 (d, J = 7.9 Hz, 1 H), 8.41 (s, 1 H), 8.93-9.01 (m, 1 H)<br>MS m/z 525.3 (M + H)+ |

-continued

| ID No. | Structure | Compound Name & Physical Data |
|---|---|---|
| 683 | 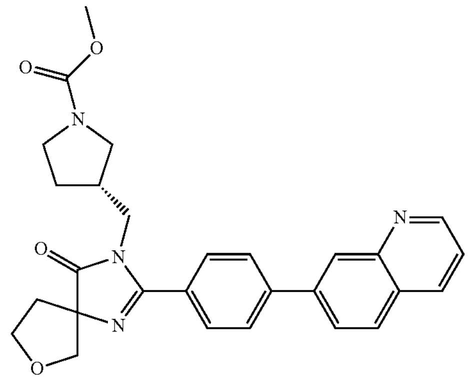 | Methyl (3S)-{[4-oxo-2-(4-quinolin-7-ylphenyl)-7-oxa-1,3-diazaspiro[4.4]non-1-en-3-yl]methyl}pyrrolidin-1-carboxylate<br>MS m/z 458.2 (M + H)+ |
| 684 | 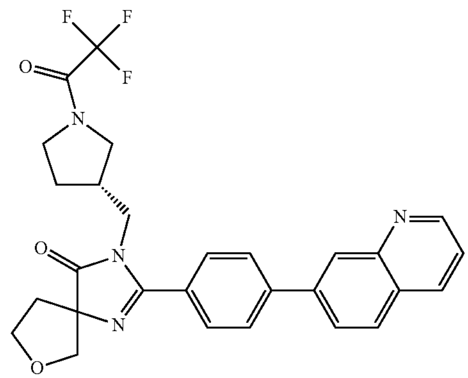 [SMILES: O=C(N1CC[C@@H](CN2C(=O)C3(CCOC3)N=C2c2ccc(-c3ccc4cccnc4c3)cc2)C1)C(F)(F)F] | 2-(4-Quinolin-7-ylphenyl)-3-{[(3R)-1-(trifluoroacetyl)pyrrolidin-3-yl]methyl}-7-oxa-1,3-diazaspiro[4.4]non-1-en-4-one<br>MS m/z 523.1 (M + H)+ |
| 685 | 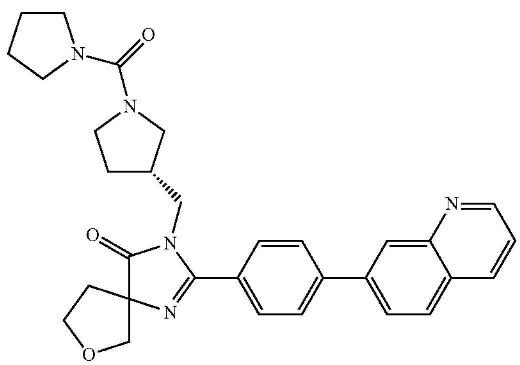 | 3-{[(3S)-1-(Pyrrolidin-1-ylcarbonyl)pyrrolidin-3-yl]methyl}-2-(4-quinolin-7-ylphenyl)-7-oxa-1,3-diazaspiro[4.4]non-1-en-4-one<br>MS m/z 524.2 (M + H)+ |
| 686 | 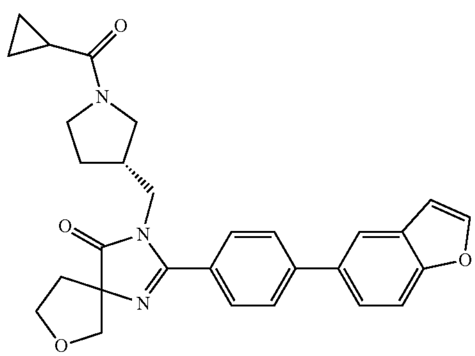 [SMILES: O=C(C1CC1)N1CC[C@@H](CN2C(=O)C3(CCOC3)N=C2c2ccc(-c3ccc4occc4c3)cc2)C1] | 2-[4-(1-Benzofuran-5-yl)phenyl]-3-{[(3R)-1-(cyclopropylcarbonyl)pyrrolidin-3-yl]methyl}-7-oxa-1,3-diazaspiro[4.4]non-1-en-4-one<br>$^1$H NMR (600 MHz, CHLOROFORM-d) δ ppm 0.64-0.77 (m, 2 H), 0.85-1.01 (m, 2 H), 1.40-1.55 (m, 1.5 H), 1.84 (td, J = 11.7, 6.8 Hz, 0.5 H), 1.89-2.02 (m, 0.5 H), 2.21-2.30 (m, 1 H), 2.30-2.57 (m, 2 H), 3.03 (ddd, J = 10.1, 7.6, 6.0 Hz, 0.5 H), 3.31 (dt, J = 12.1, 7.9 Hz, 0.5 H), 3.47-3.57 (m, 1.5 H), 3.57-3.66 (m, 1 H), 3.66-3.73 (m, 0.5 H), 3.73-3.85 (m, 1.5 H), 3.97-4.08 (m, 2 H), 4.14-4.30 (m, 2 H), 6.85 (d, J = 1.5 Hz, 1 H), 7.53-7.58 (m, 1 H), 7.58-7.63 (m, 1 H), 7.64-7.72 (m, 3 H), 7.73-7.80 (m, 2 H), 7.84 (d, J = 1.9 Hz, 1 H)<br>MS m/z 484.2 (M + H)+ |

| ID No. | Structure | Compound Name & Physical Data |
|---|---|---|
| 687 | 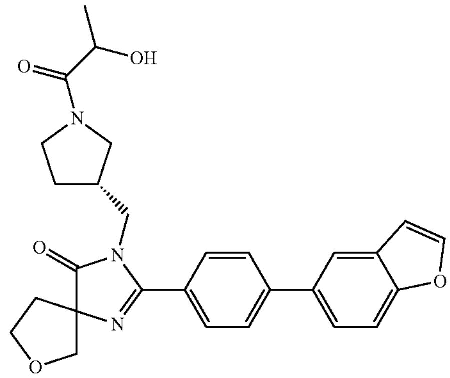 [SMILES: CC(O)C(=O)N1CC[C@@H](CN2C(=O)C3(CCOC3)N=C2c2ccc(-c3ccc4occc4c3)cc2)C1] | 2-[4-(1-Benzofuran-5-yl)phenyl]-3-{[(3R)-1-(2-hydroxypropanoyl)pyrrolidin-3-yl]methyl}-7-oxa-1,3-diazaspiro[4.4]non-1-en-4-one<br>$^1$H NMR (400 MHz, CHLOROFORM-d) δ ppm 1.18-1.36 (m, 3 H), 1.38-1.59 (m, 1 H), 1.59-1.76 (m, 1 H), 1.81-2.07 (m, 1 H), 2.22-2.49 (m, 2 H), 2.97-3.26 (m, 3 H), 3.29-3.46 (m, 2 H), 3.62 (dd, J = 12.3, 6.5 Hz, 1 H), 3.69-3.81 (m, 2H), 4.10-4.10 (m, 2 H), 4.18-4.30 (m, 2 H), 6.86 (d, J = 1.5 Hz, 1 H), 7.52-7.59 (m, 1 H), 7.62 (m, J = 8.5 Hz, 1 H), 7.66-7.73 (m, 3 H), 7.76-7.83 (m, 2 H), 7.83-7.88 (m, 1 H)<br>MS m/z 488.1 (M + H)+ |
| 688 | 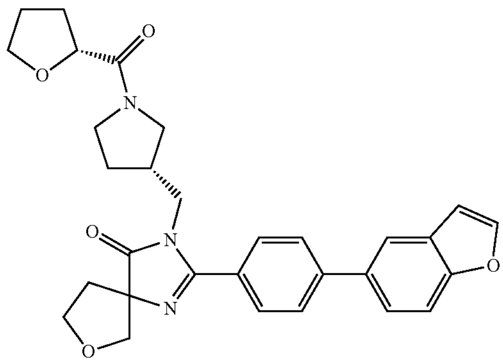 | 2-[4-(1-Benzofuran-5-yl)phenyl]-3-({(3R)-1-[(2R)-tetrahydro-furan-2-ylcarbonyl]pyrrolidin-3-yl}methyl)-7-oxa-1,3-diazaspiro[4.4]non-1-en-4-one<br>$^1$H NMR (600 MHz, CHLOROFORM-d) δ ppm 1.38-1.61 (m, 2 H), 1.78-2.07 (m, 4 H), 2.06-2.21 (m, 1 H), 2.21-2.30 (m, 1 H), 2.30-2.49 (m, 2 H), 3.05 (ddd, J = 12.2, 7.5, 3.0 Hz, 0.5 H), 3.08-3.15 (m, 0.5 H), 3.29-3.42 (m, 1 H), 3.46-3.58 (m, 1 H), 3.58-3.78 (m, 3 H), 3.78-3.85 (m, 1 H), 3.85-3.95 (m, 1 H), 3.96-4.07 (m, 2 H), 4.13-4.28 (m, 2 H), 4.31-4.38 (m, 0.5 H), 4.38-4.44 (m, 0.5 H), 6.85 (s, 1 H), 7.53-7.58 (m, 1 H), 7.58-7.64 (m, 1 H), 7.64-7.73 (m, 3 H), 7.77 (dd, J = 8.3, 5.3 Hz, 2 H), 7.85 (s, 1 H)<br>MS m/z 514.2 (M + H)+ |
| 689 | 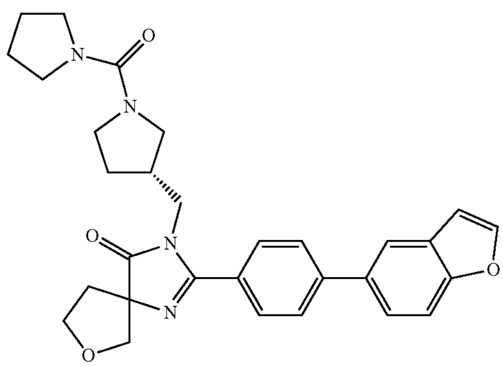 [SMILES: O=C(N1CCCC1)N1CC[C@@H](CN2C(=O)C3(CCOC3)N=C2c2ccc(-c3ccc4occc4c3)cc2)C1] | 2-[4-(1-Benzofuran-5-yl)phenyl]-3-{[(3S)-1-(pyrrolidin-1-ylcarbonyl)pyrrolidin-3-yl]methyl}-7-oxa-1,3-diazaspiro[4.4]non-1-en-4-one<br>MS m/z 513.2 (M + H)+ |
| 690 | 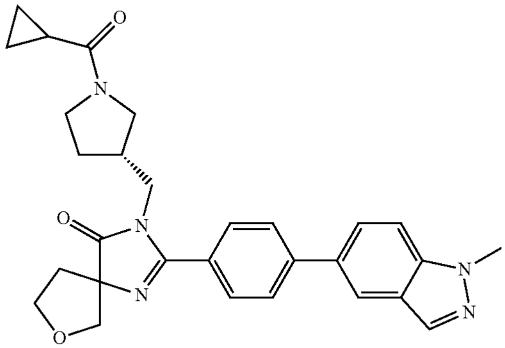 [SMILES: Cn1ncc2cc(-c3ccc(C4=NC5(CCOC5)C(=O)N4C[C@@H]4CCN(C(=O)C5CC5)C4)cc3)ccc21] | 3-{[(3R)-1-(Cyclopropylcarbonyl)pyrrolidin-3-yl]methyl}-2-[4-(1-methyl-1H-indazol-5-yl)phenyl]-7-oxa-1,3-diazaspiro[4.4]non-1-en-4-one<br>MS m/z 498.2 (M + H)+ |

| ID No. | Structure | Compound Name & Physical Data |
|---|---|---|
| 691 | 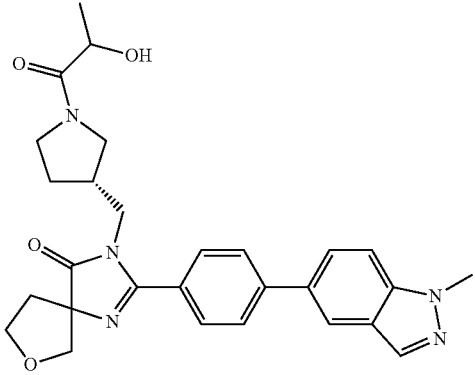 [SMILES: CC(O)C(=O)N1CC[C@@H](CN2C(=O)C3(CCOC3)N=C2c2ccc(-c3ccc4c(cnn4C)c3)cc2)C1] | 3-{[(3R)-1-(2-Hydroxypropanoyl)pyrrolidin-3-yl]methyl}-2-[4-(1-methyl-1H-indazol-5-yl)phenyl]-7-oxa-1,3-diazaspiro[4.4]non-1-en-4-one<br>MS m/z 502.3 (M + H)+ |
| 692 | 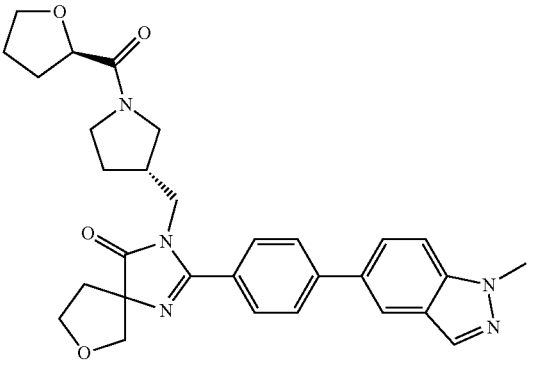 [SMILES: Cn1ncc2cc(-c3ccc(C4=NC5(CCOC5)C(=O)N4C[C@@H]4CCN(C(=O)[C@H]5CCCO5)C4)cc3)ccc21] | 2-[4-(1-Methyl-1H-indazol-5-yl)phenyl]-3-({(3R)-1-[(2R)-tetrahydro-furan-2-ylcarbonyl]pyrrolidin-3-yl}metrhyl)-7-oxa-1,3-diazaspiro[4.4]non-1-en-4-one<br>MS m/z 528.2 (M + H)+ |
| 693 | 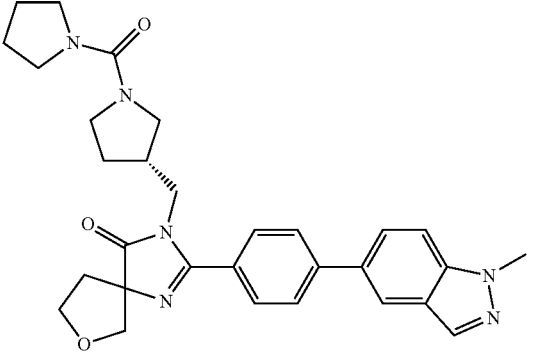 [SMILES: Cn1ncc2cc(-c3ccc(C4=NC5(CCOC5)C(=O)N4C[C@@H]4CCN(C(=O)N5CCCC5)C4)cc3)ccc21] | 2-[4-(1-Methyl-1H-indazol-5-yl)phenyl]-3-{[(3S)-1-(pyrrolidin-1-ylcarbonyl)pyrrolidin-3-yl]methyl}-7-oxa-1,3-diazaspiro[4.4]non-1-en-4-one<br>MS m/z 527.2 (M + H)+ |
| 694 | 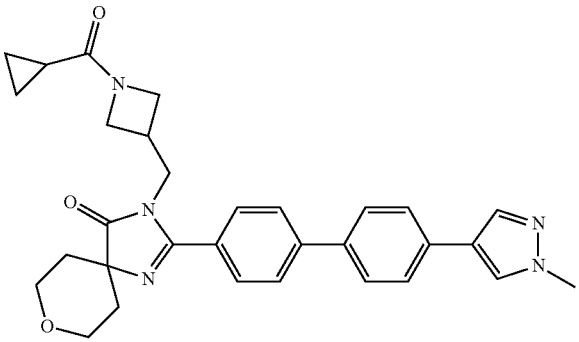 [SMILES: Cn1cc(-c2ccc(-c3ccc(C4=NC5(CCOCC5)C(=O)N4CC4CN(C(=O)C5CC5)C4)cc3)cc2)cn1] | 3-{[1-(Cyclopropylcarbonyl)azetidin-3-yl]methyl}-2-[4-(1-methyl-1H-pyrazol-4-yl)biphenyl-4-yl]-8-oxa-1,3-diazaspiro[4.5]dec-1-en-4-one<br>MS m/z 524.3 (M + H)+ |

-continued

| ID No. | Structure | Compound Name & Physical Data |
|---|---|---|
| 695 | 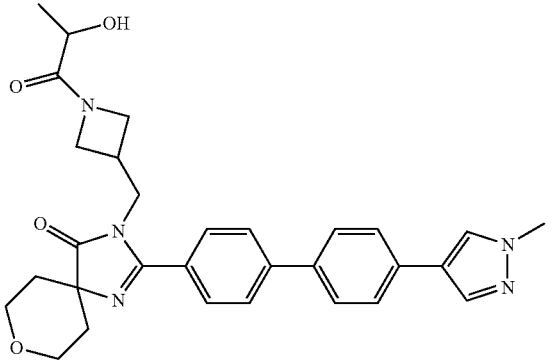 | 3-{[1-(2-Hydroxypropanoyl)azetidin-3-yl]methyl}-2-[4'-(1-methyl-1H-pyrazol-4-yl)biphenyl-4-yl]-8-oxa-1,3-diazaspiro[4.5]dec-1-en-4-one<br>MS m/z 524.3 (M + H)+ |
| 696 | 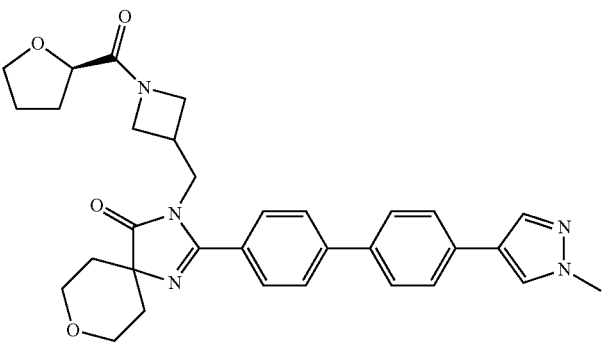 [SMILES: Cn1cc(-c2ccc(-c3ccc(C4=NC5(CCOCC5)C(=O)N4CC4CN(C(=O)[C@H]5CCCO5)C4)cc3)cc2)cn1] | 2-[4'-(1-Mehtyl-1H-pyrazol-4-yl)biphenyl-4-yl]-3-({1-[(2R)-tetrahydro-furan-2-ylcarbonyl]azetidin-3-yl}methyl)-8-oxa-1,3-diazaspiro[4.5]dec-1-en-4-one<br>MS m/z 554.2 (M + H)+ |
| 697 | 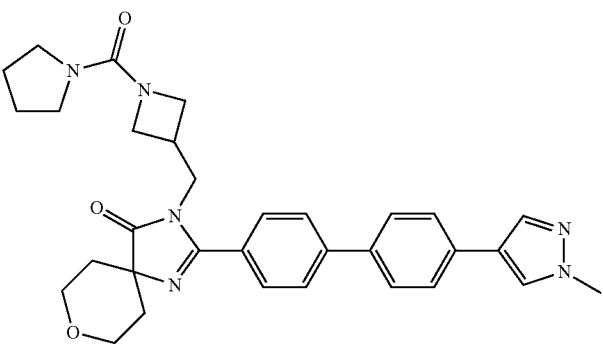 [SMILES: Cn1cc(-c2ccc(-c3ccc(C4=NC5(CCOCC5)C(=O)N4CC4CN(C(=O)N5CCCC5)C4)cc3)cc2)cn1] | 2-[4'-(1-Methyl-1H-pyrazol-4-yl)biphenyl-4-yl]-3-{[1-(pyrrolidin-1-ylcarbonyl)azetidin-3-yl]methyl}-8-oxa-1,3-diazaspiro[4.5]dec-1-en-4-one<br>MS m/z 553.3 (M + H)+ |
| 698 | 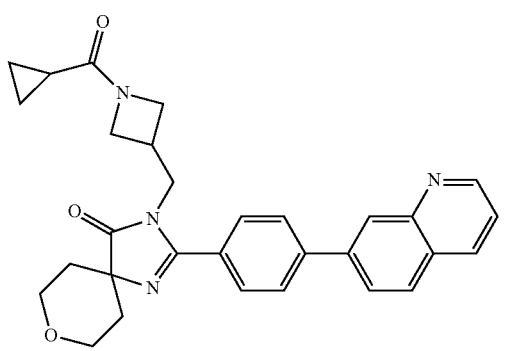 [SMILES: O=C(C1CC1)N1CC(CN2C(=O)C3(CCOCC3)N=C2c2ccc(-c3ccc4cccnc4c3)cc2)C1] | 3-{[1-(Cyclopropylcarbonyl)azetidin-3-yl]methyl}-2-(4-quinolin-7-ylphenyl)-8-oxa-1,3-diazaspiro[4.5]dec-1-en-4-one<br>$^1$H NMR (600 MHz, CHLOROFORM-d) δ ppm 0.63-0.73 (m, 2 H), 0.84-0.94 (m, 2 H), 1.24-1.32 (m, 1 H), 1.48-1.55 (m, 2 H), 2.07-2.18 (m, 2 H), 2.72-2.82 (m, 1 H), 3.58 (dd, J = 9.8, 5.7 Hz, 1 H), 3.87-4.07 (m, 8 H), 4.20 (t, J = 8.3 Hz, 1 H), 7.46 (dd, J = 8.3, 4.2 Hz, 1 H), 7.72 (d, J = 8.3 Hz, 2 H), 7.85 (dd, J = 8.3, 1.9 Hz, 1 H), 7.93 (d, J = 8.7 Hz, 2 H), 7.96 (d, J = 8.3 Hz, 1 H), 8.22 (d, J = 8.3 Hz, 1 H), 8.36-8.40 (m, 1 H), 8.98 (dd, J = 4.2, 1.9 Hz, 1 H)<br>MS m/z 495.2 (M + H)+ |

| ID No. | Structure | Compound Name & Physical Data |
|---|---|---|
| 699 | 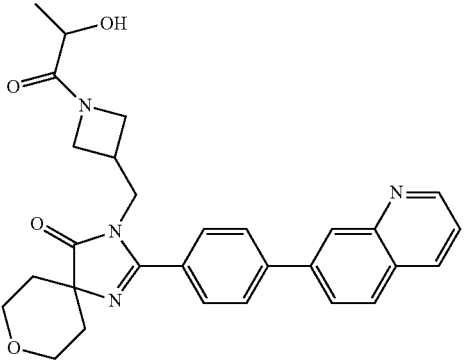 [SMILES: CC(O)C(=O)N1CC(CN2C(=O)C3(CCOCC3)N=C2c2ccc(-c3ccc4cccnc4c3)cc2)C1] | 3-{[1-(2-Hydroxypropanoyl)azetidin-3-yl]methyl}-2-(4-quinolin-7-ylphenyl)-8-oxa-1,3-diazaspiro[4.5]dec-1-en-4-one<br>MS m/z 499.2 (M + H)+ |
| 700 | 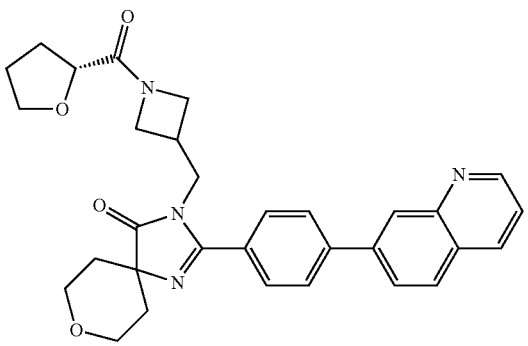 [SMILES: O=C([C@H]1CCCO1)N1CC(CN2C(=O)C3(CCOCC3)N=C2c2ccc(-c3ccc4cccnc4c3)cc2)C1] | 2-(4-Quinolin-7-ylphenyl)-3-({1-[(2R)-tetrahydro-furan-2-ylcarbonyl]azetidin-3-yl}methyl)-8-oxa-1,3-diazaspiro[4.5]dec-1-en-4-one<br>$^1$H NMR (600 MHz, CHLOROFORM-d) δ ppm 1.51 (d, J = 13.2 Hz, 2 H), 1.77-1.91 (m, 2 H), 1.98-2.18 (m, 4 H), 2.71-2.80 (m, 1 H), 3.57-3.64 (m, 1 H), 3.72-3.85 (m, 2 H), 3.86-4.06 (m, 8 H), 4.18-4.37 (m, 2 H), 7.46 (dd, J = 8.3, 4.2 Hz, 1 H), 7.72 (dd, J = 8.3, 4.5 Hz, 2 H), 7.85 (d, J = 8.3 Hz, 1 H), 7.92 (d, 2 H), 7.96 (d, J = 8.3 Hz, 1 H), 8.22 (d, J = 8.3 Hz, 1 H), 8.38 (s, 1 H), 8.98 (dd, J = 4.2, 1.5 Hz, 1 H)<br>MS m/z 525.2 (M + H)+ |
| 701 | 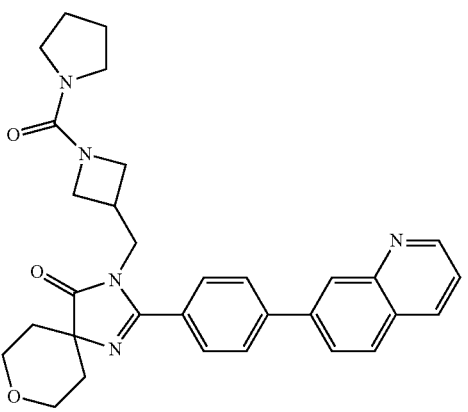 [SMILES: O=C(N1CCCC1)N1CC(CN2C(=O)C3(CCOCC3)N=C2c2ccc(-c3ccc4cccnc4c3)cc2)C1] | 3-{[1-(Pyrrolidin-1-ylcarbonyl)azetidin-3-yl]methyl}-2-(4-quinolin-7-ylphenyl)-8-oxa-1,3-diazaspiro[4.5]dec-1-en-4-one<br>MS m/z 524.2 (M + H)+ |
| 702 | 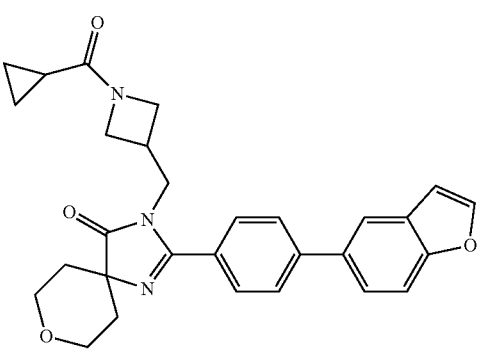 [SMILES: O=C(C1CC1)N1CC(CN2C(=O)C3(CCOCC3)N=C2c2ccc(-c3ccc4occc4c3)cc2)C1] | 2-[4-(1-Benzofuran-5-yl)phenyl]-3-{[1-(cyclopropylcarbonyl)azetidin-3-yl]methyl}-8-oxa-1,3-diazaspiro[4.5]dec-1-en-4-one<br>MS m/z 484.2 (M + H)+ |

-continued

| ID No. | Structure | Compound Name & Physical Data |
|---|---|---|
| 703 | 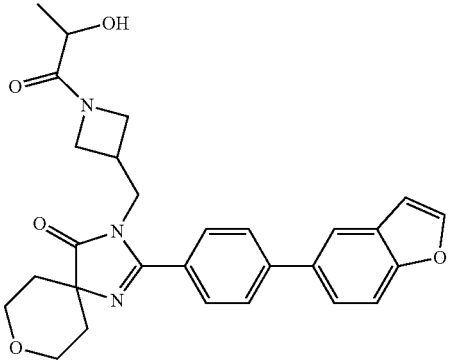 [SMILES: CC(O)C(=O)N1CC(CN2C(=O)C3(CCOCC3)N=C2c2ccc(-c3ccc4occc4c3)cc2)C1] | 2-[4-(1-Benzofuran-5-yl)phenyl]-3-{[1-(2-hydroxypropanoyl)azetidin-3-yl]methyl}-8-oxa-1,3-diazaspiro[4.5]dec-1-en-4-one<br>MS m/z 488.2 (M + H)+ |
| 704 | 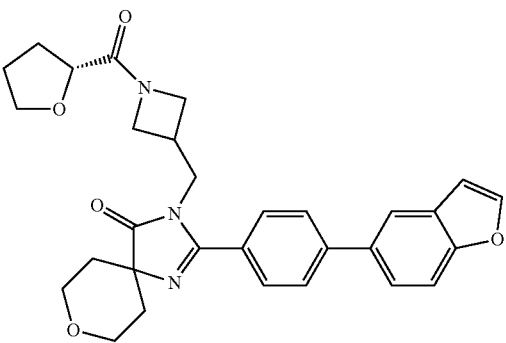 [SMILES: O=C([C@H]1CCCO1)N1CC(CN2C(=O)C3(CCOCC3)N=C2c2ccc(-c3ccc4occc4c3)cc2)C1] | 2-[4-(1-Benzofuran-5-yl)phenyl]-3-({1-[(2R)-tetrahydro-furan-2-ylcarbonyl]azetidin-3-yl}methyl)-8-oxa-1,3-diazaspiro[4.5]dec-1-en-4-one<br>MS m/z 514.2 (M + H)+ |
| 705 | 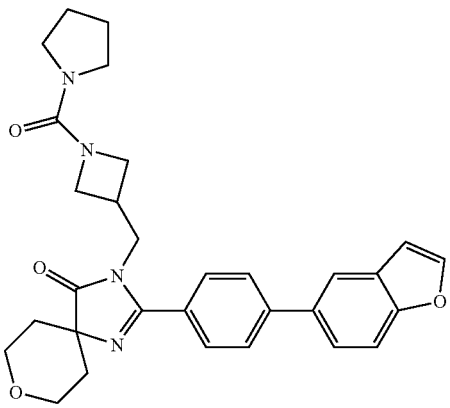 [SMILES: O=C(N1CCCC1)N1CC(CN2C(=O)C3(CCOCC3)N=C2c2ccc(-c3ccc4occc4c3)cc2)C1] | 2-[4-(1-Benzofuran-5-yl)phenyl]-3-{[1-(pyrrolidin-1-ylcarbonyl)azetidin-3-yl]methyl}-8-oxa-1,3-diazaspiro[4.5]dec-1-en-4-one<br>MS m/z 513.2 (M + H)+ |
| 706 | 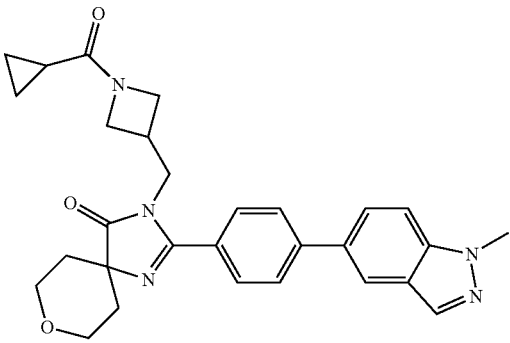 [SMILES: Cn1ncc2cc(-c3ccc(C4=NC5(CCOCC5)C(=O)N4CC4CN(C(=O)C5CC5)C4)cc3)ccc21] | 3-{[1-(Cyclopropylcarbonyl)azetidin-3-yl]methyl}-2-[4-(1-methyl-1H-indazol-5-yl)phenyl]-8-oxa-1,3-diazaspiro[4.5]dec-1-en-4-one<br>$^1$H NMR (400 MHz, CHLOROFORM-d) δ ppm 0.70 (dd, J = 7.9, 3.1 Hz, 2 H), 0.85-0.94 (m, 2 H), 1.22-1.33 (m, 1 H), 1.51 (d, J = 13.6 Hz, 2 H), 2.12 (ddd, J = 13.7, 9.0, 5.4 Hz, 2 H), 2.70-2.83 (m, 1 H), 3.57 (dd, J = 9.7, 5.6 Hz, 1 H), 3.85-3.93 (m,m 2 H), 3.93-4.00 (m, 2 H), 4.00-4.07 (m, 4 H), 4.14 (s, 3 H), 4.20 (t, J = 8.8 Hz, 1H), 7.52 (d, J = 8.8 Hz, 1 H), 7.63-7.71 (m, 3 H), 7.80 (d, J = 8.3 Hz, 2 H), 7.95-8.00 (m, 1 H), 8.07 (d, J = 1.0 Hz, 1 H)<br>MS m/z 498.2 (M + H)+ |

| ID No. | Structure | Compound Name & Physical Data |
|---|---|---|
| 707 | 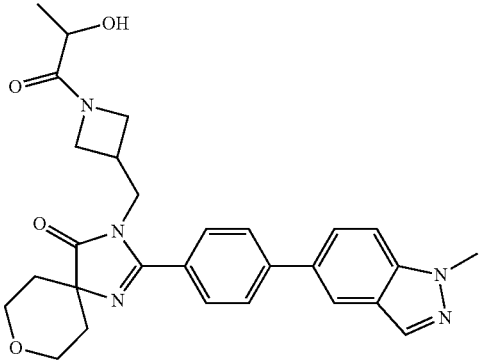 [SMILES: CC(O)C(=O)N1CC(CN2C(=O)C3(CCOCC3)N=C2c2ccc(-c3ccc4c(cnn4C)c3)cc2)C1] | 3-{[1-(2-Hydroxypropanoyl)azetidin-3-yl]methyl}-2-[4-(1-methyl-1H-indazol-5-yl)phenyl]-8-oxa-1,3-diazaspiro[4.5]dec-1-en-4-one<br>MS m/z 502.2 (M + H)+ |
| 708 | 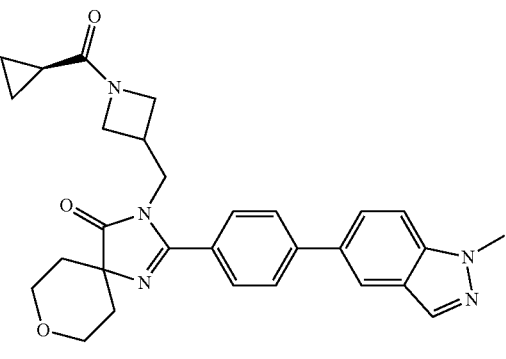 | 2-[4-(1-Methyl-1H-indazol-5-yl)phenyl]-3-({1-[(2R)-tetrahydro-furan-2-ylcarbonyl]azetidin-3-yl}methyl)-8-oxa-1,3-diazaspiro[4.5]dec-1-en-4-one<br>MS m/z 528.2 (M + H)+ |
| 709 | 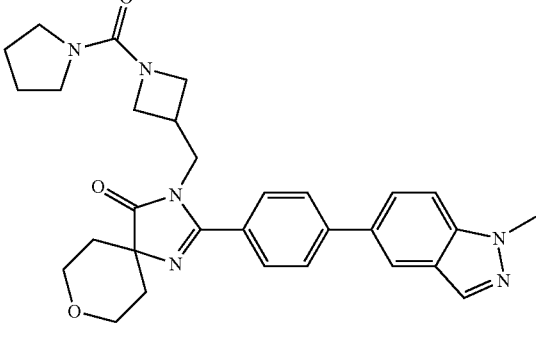 | 2-[4-(1-Methyl-1H-indazol-5-yl)phenyl]-3-{[1-(pyrrolidin-1-ylcarbonyl)azetidin-3-yl]methyl}-8-oxa-1,3-diazaspiro[4.5]dec-1-en-4-one<br>$^1$H NMR (400 MHz, CHLOROFORM-d) δ ppm 1.46-1.55 (m, 2 H), 1.76 (dt, J = 6.5, 3.5 Hz, 4 H), 2.12 (ddd, J = 13.7, 8.8, 5.5 Hz, 2 H), 2.59-2.72 (m, 1 H), 3.17-3.25 (m, 4 H), 3.54 (dd, J = 8.2, 5.6 Hz, 2 H), 3.85-3.94 (m, 4 H), 4.00-4.07 (m, 4 H), 4.14 (s, 3 H), 7.51 (d, J = 8.8 Hz, 1 H), 7.63-7.71 (m, 3 H), 7.79 (d, J = 8.3 Hz, 2 H), 7.97 (s, 1 H), 8.07 (s, 1 H)<br>MS m/z 527.3 (M + H)+ |
| 710 | 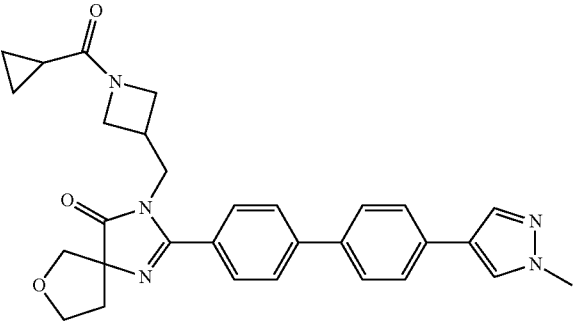 [SMILES: Cn1cc(-c2ccc(-c3ccc(C4=NC5(CCOC5)C(=O)N4CC4CN(C(=O)C5CC5)C4)cc3)cc2)cn1] | 3-{[1-(Cyclopropylcarbonyl)azetidin-3-yl]methyl}-2-[4'-(1-methyl-1H-pyrazol-4-yl)biphenyl-4-yl]-7-oxa-1,3-diazaspiro[4.4]non-1-en-4-one<br>MS m/z 510.3 (M + H)+ |

| ID No. | Structure | Compound Name & Physical Data |
|---|---|---|
| 711 | 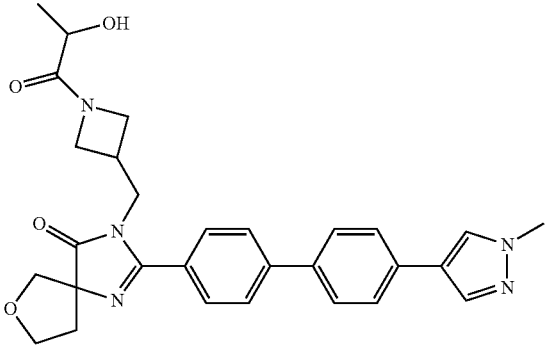 [SMILES: CC(O)C(=O)N1CC(CN2C(=O)C3(CCOC3)N=C2c2ccc(-c3ccc(-c4cnn(C)c4)cc3)cc2)C1] | 3-{[1-(2-Hydroxypropanoyl)azetidin-3-yl]methyl}-2-[4'-(1-methyl-1H-pyrazol-4-yl)biphenyl-4-yl]-7-oxa-1,3-diazaspiro[4.4]non-1-en-4-one<br>MS m/z 514.2 (M + H)+ |
| 712 | 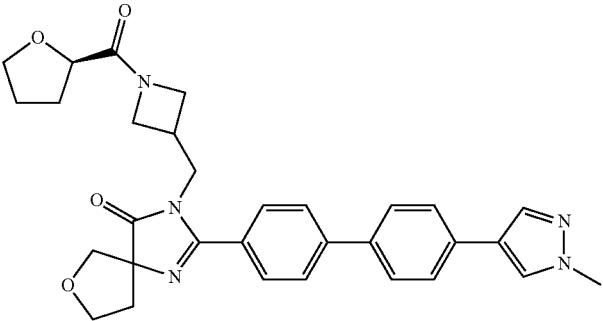 [SMILES: Cn1cc(-c2ccc(-c3ccc(C4=NC5(CCOC5)C(=O)N4CC4CN(C(=O)[C@H]5CCCO5)C4)cc3)cc2)cn1] | 2-[4'-(1-Methyl-1H-pyrazol-4-yl)biphenyl-4-yl]-3-({1-[(2R)-tetrahydro-furan-2-ylcarbonyl]azetidin-3-yl}methyl)-7-oxa-1,3-diazaspiro[4.4]non-1-en-4-one<br>MS m/z 540.2 (M + H)+ |
| 713 | 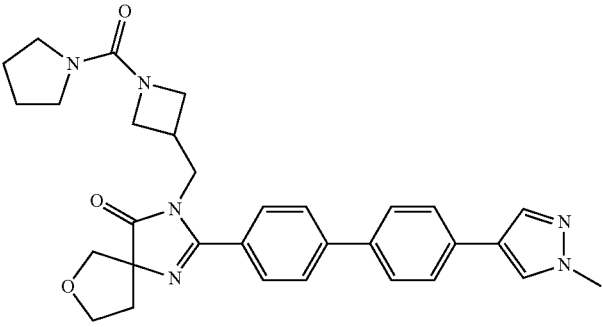 [SMILES: Cn1cc(-c2ccc(-c3ccc(C4=NC5(CCOC5)C(=O)N4CC4CN(C(=O)N5CCCC5)C4)cc3)cc2)cn1] | 2-[4'-(1-Methyl-1H-pyrazol-4-yl)biphenyl-4-yl]-3-{[1-(pyrrolidin-1-ylcarbonyl)azetidin-3-yl]methyl}-7-oxa-1,3-diazaspiro[4.4]non-1-en-4-one<br>MS m/z 539.2 (M + H)+ |
| 714 | 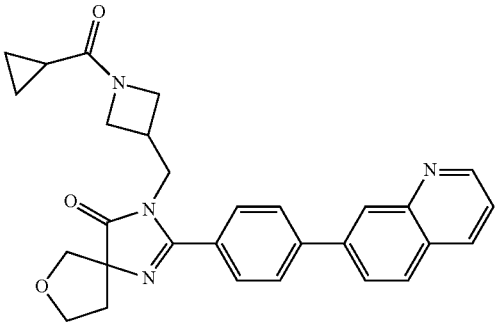 [SMILES: O=C(C1CC1)N1CC(CN2C(=O)C3(CCOC3)N=C2c2ccc(-c3ccc4cccnc4c3)cc2)C1] | 3-{[1-(Cycloprppylcarbonyl)azetidin-3-yl]methyl}-2-(4-quinolin-7-ylphenyl)-7-oxa-1,3-diazaspiro[4.4]non-1-en-4-one<br>MS m/z 481.2 (M + H)+ |

-continued

| ID No. | Structure | Compound Name & Physical Data |
|---|---|---|
| 715 | 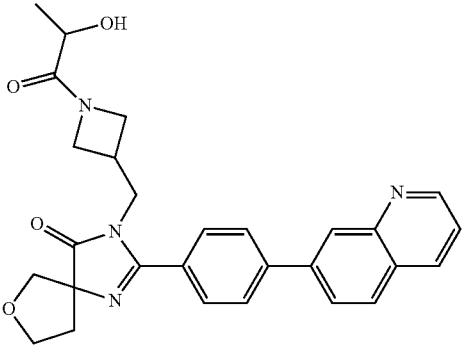 [SMILES: CC(O)C(=O)N1CC(CN2C(=O)C3(CCOC3)N=C2c2ccc(-c3ccc4cccnc4c3)cc2)C1] | 3-{[1-(2-Hydroxypropanoyl)azetidin-3-yl]methyl}-2-(4-quinolin-7-ylphenyl)-7-oxa-1,3-diazaspiro[4.4]non-1-en-4-one<br>$^1$H NMR (400 MHz, CHLOROFORM-d) δ ppm 1.16-1.30 (m, 3 H), 2.26 (dt, J = 12.4, 6.0 Hz, 1 H), 2.37-2.50 (m, 1 H), 2.78-2.96 (m, 1 H), 3.61-3.70 (m, 0.5 H), 3.73 (dd, J = 10.5, 5.5 Hz, 0.5 H), 3.78-3.86 (m, 0.5 H), 3.86-4.06 (m, 6 H), 4.06-4.18 (m, 2.5 H), 4.18-4.29 (m, 2.5 H), 7.48 (dd, J = 8.3, 4.3 Hz, 1 H), 7.69-7.78 (m, 2 H), 7.82-7.90 (m, 1 H), 7.90-8.01 (m, 3 H), 8.24 (d, J = 8.3 Hz, 1 H), 8.40 (br. s., 1 H), 8.99 (dd, J = 4.3, 1.5 Hz, 1 H)<br>MS m/z 485.2 (M + H)+ |
| 716 | 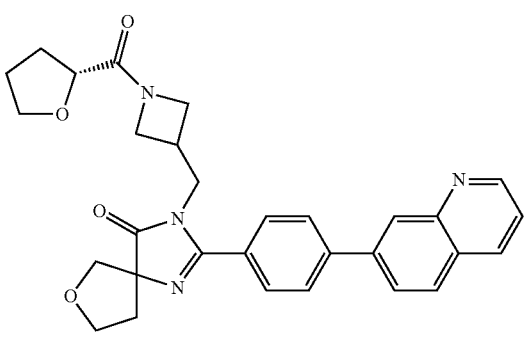 [SMILES: O=C([C@H]1CCCO1)N1CC(CN2C(=O)C3(CCOC3)N=C2c2ccc(-c3ccc4cccnc4c3)cc2)C1] | 2-(4-Quinolin-7-ylphenyl)-3-({1-[(2R)-tetrahydro-furan-2-ylcarbonyl]azetidin-3-yl}methyl)-7-oxa-1,3-diazaspiro[4.4]non-1-en-4-one<br>MS m/z 511.3 (M + H)+ |
| 717 | 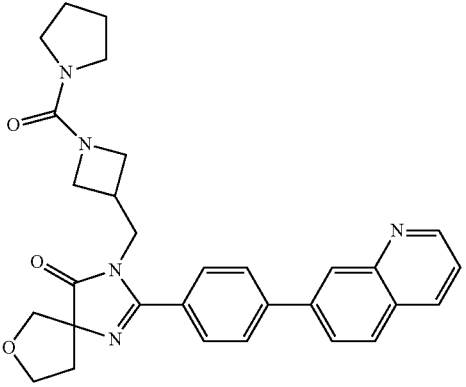 [SMILES: O=C(N1CCCC1)N1CC(CN2C(=O)C3(CCOC3)N=C2c2ccc(-c3ccc4cccnc4c3)cc2)C1] | 3-{[1-(Pyrrolidin-1-ylcarbonyl)azetidin-3-yl]methyl}-2-(4-quinolin-7-ylphenyl)-7-oxa-1,3-diazaspiro[4.4]non-1-en-4-one<br>MS m/z 510.2 (M + H)+ |
| 718 | 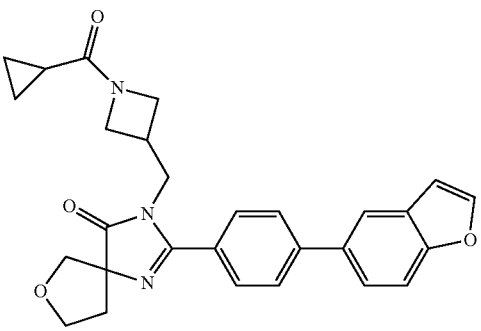 [SMILES: O=C(C1CC1)N1CC(CN2C(=O)C3(CCOC3)N=C2c2ccc(-c3ccc4occc4c3)cc2)C1] | 2-[4-(1-Benzofuran-5-yl)phenyl]-3-{[1-(cyclopropylcarbonyl)azetidin-3-yl]methyl}-7-oxa-1,3-diazaspiro[4.4]non-1-en-4-one<br>MS m/z 470.2 (M + H)+ |

| ID No. | Structure | Compound Name & Physical Data |
|---|---|---|
| 719 | 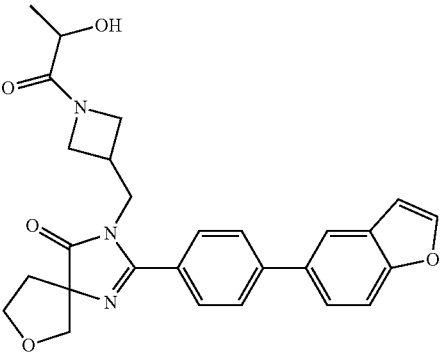 [SMILES: CC(O)C(=O)N1CC(CN2C(=O)C3(CCOC3)N=C2c2ccc(-c3ccc4occc4c3)cc2)C1] | 2-[4-(1-Benzofuran-5-yl)phenyl]-3-{[1-(2-hydroxypropanoyl)azetidin-3-yl]methyl}-7-oxa-1,3-diazaspiro[4.4]non-1-en-4-one<br>MS m/z 474.1 (M + H)+ |
| 720 | 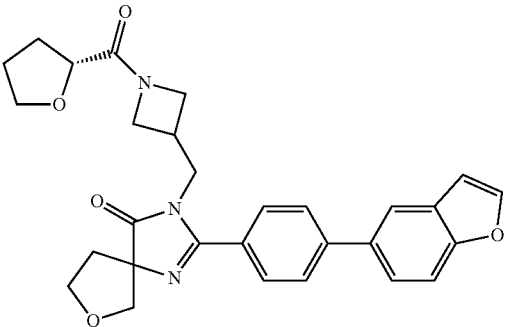 [SMILES: O=C([C@H]1CCCO1)N1CC(CN2C(=O)C3(CCOC3)N=C2c2ccc(-c3ccc4occc4c3)cc2)C1] | 2-[4-(1-Benzofuran-5-yl)phenyl]-3-({1-[(2R)-tetrahydro-furan-2-ylcarbonyl]azetidin-3-yl}methyl)-7-oxa-1,3-diazaspiro[4.4]non-1-en-4-one<br>MS m/z 500.2 (M + H)+ |
| 721 | 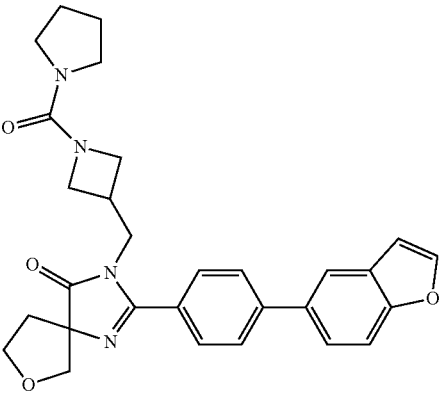 [SMILES: O=C(N1CCCC1)N1CC(CN2C(=O)C3(CCOC3)N=C2c2ccc(-c3ccc4occc4c3)cc2)C1] | 2-[4-(1-Benzofuran-5-yl)phenyl]-3-{[1-(pyrrolidin-1-ylcarbonyl)azetidin-3-yl]methyl}-7-oxa-1,3-diazaspiro[4.4]non-1-en-4-one<br>MS m/z 499.3 (M + H)+ |
| 722 | 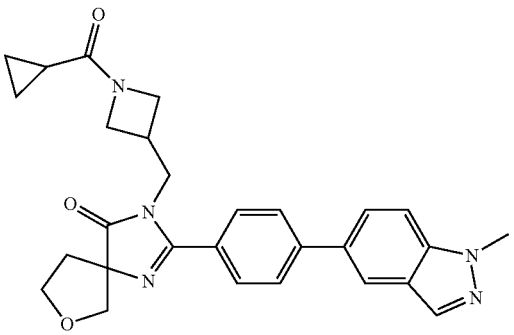 [SMILES: Cn1ncc2cc(-c3ccc(C4=NC5(CCOC5)C(=O)N4CC4CN(C(=O)C5CC5)C4)cc3)ccc21] | 3-{[1-(Cyclopropylcarbonyl)azetidin-3-yl]methyl}-2-[4-(1-methyl-1H-indazol-5-yl)phenyl]-7-oxa-1,3-diazaspiro[4.4]non-1-en-4-one<br>MS m/z 484.3 (M + H)+ |

| ID No. | Structure | Compound Name & Physical Data |
| --- | --- | --- |
| 723 | 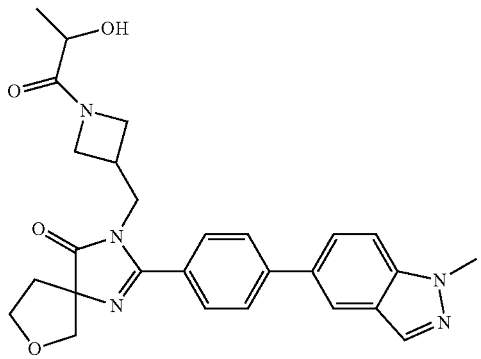 [SMILES: CC(O)C(=O)N1CC(CN2C(=O)C3(CCOC3)N=C2c2ccc(-c3ccc4c(cnn4C)c3)cc2)C1] | 3-{[1-(2-Hydroxypropanoyl)azetidin-3-yl]methyl}-2-[4-(1-methyl-1H-indazol-5-yl)phenyl]-7-oxa-1,3-diazaspiro[4.4]non-1-en-4-one<br>MS m/z 488.2 (M + H)+ |
| 724 | 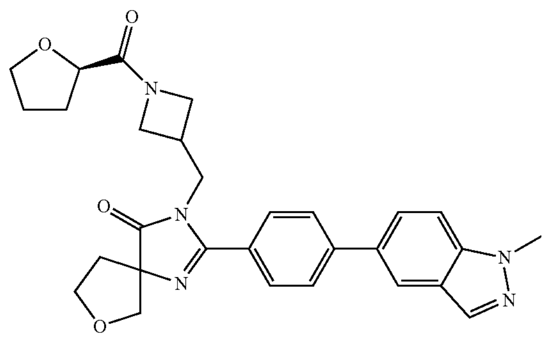 [SMILES: Cn1ncc2cc(-c3ccc(C4=NC5(CCOC5)C(=O)N4CC4CN(C(=O)[C@H]5CCCO5)C4)cc3)ccc21] | 2-[4-(1-Methyl-1H-indazol-5-yl)phenyl]-3-({1-[(2R)-tetrahydro-furan-2-ylcarbonyl]azetidin-3-yl}methyl)-7-oxa-1,3-diazaspiro[4.4]non-1-en-4-one<br>MS m/z 514.2 (M + H)+ |
| 725 | 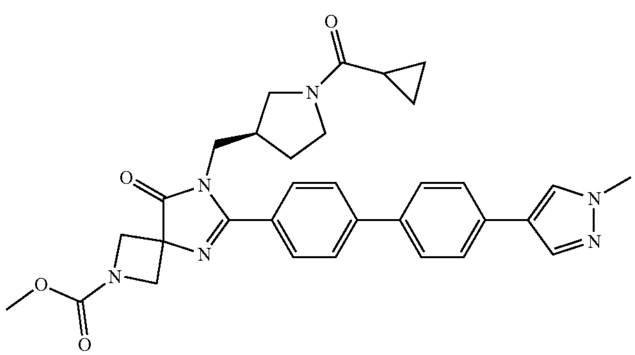 | Methyl 7-{[(3R)-1-(cyclopropylcarbonyl)pyrrolidin-3-yl]methyl}-6-[4'-(1-methyl-1H-pyrazol-4-yl)biphenyl-4-yl]-8-oxo-2,5,7-triazaspiro[3.4]oct-5-ene-2-carboxylate<br>$^1$H NMR (600 MHz, CHLOROFORM-d) δ ppm 0.65-0.76 (m, 2 H), 0.85-1.00 (m, 2 H), 1.39-1.55 (m, 1.5 H), 1.79-1.90 (m, 0.5 H), 1.96 (td, J = 12.3, 6.8 Hz, 0.5 H), 2.37 (br. s., 0.5 H), 2.44-2.55 (m, 0.5 H), 3.02 (dd, J = 12.1, 7.2 Hz, 0.5 H), 3.21-3.27 (m, 0.5 H), 3.31 (dt, J = 12.1, 7.9 Hz, 0.5 H), 3.46-3.58 (m, 1.5 H), 3.58-3.82 (m, 6 H), 3.97 (s, 3 H), 4.28-4.33 (m, 2 H), 4.33-4.38 (m, 2 H), 7.56-7.61 (m, 2 H), 7.62-7.66 (m, 2 H), 7.66-7.71 (m, 3 H), 7.74-7.80 (m, 2 H), 7.82 (s, 1 H)<br>MS m/z 567.3 (M + H)+ |
| 726 | 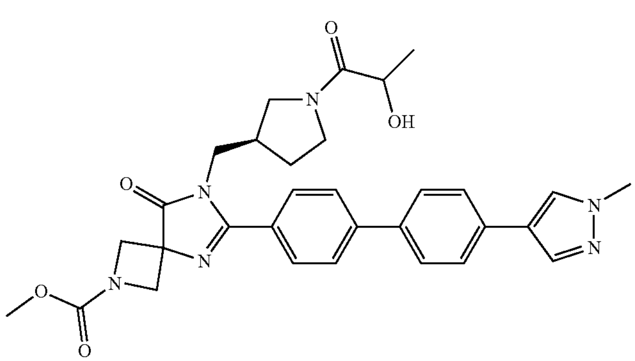 | Methyl 7-{[(3R)-1-(2-hydroxypropanoyl)pyrrolidin-3-yl]methyl}-6-[4'-(1-methyl-1H-pyrazol-4-yl)biphenyl-4-yl]-8-oxo-2,5,7-triazaspiro[3.4]oct-5-ene-2-carboxylate<br>$^1$H NMR (400 MHz, CHLOROFORM-d) δ ppm 1.26 (t, J = 6.9 Hz, 3 H), 1.39-1.65 (m, 1 H), 1.59-1.73 (m, 1.5 H), 1.83-2.04 (m, 1.5 H), 2.32-2.47 (m, 0.5 H), 2.48-2.60 (m, 0.5 H), 3.00-3.18 (m, 1 H), 3.28-=3.44 (m, 2 H), 3.54-3.66 (m, 1 H), 3.68-3.79 (m, 5 H), 3.98 (s, 3 H), 4.08-4.24 (m, 1 H), 4.29-4.40 (m, 4 H), 7.57-7.62 (m, 2 H), 7.62-7.72 (m, 5 H), 7.75-7.81 (m, 2 H), 7.83 (s, 1 H)<br>MS m/z 571.3 (M + H)+ |

| ID No. | Structure | Compound Name & Physical Data |
|---|---|---|
| 727 | 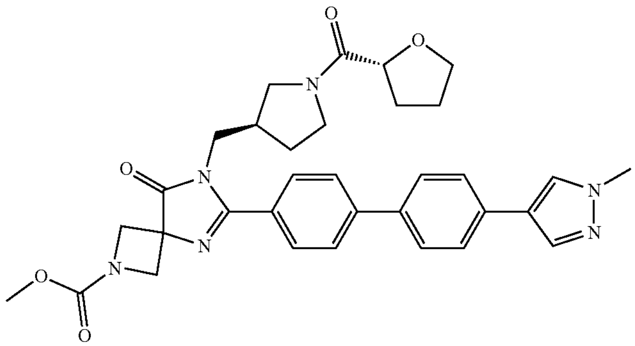 | Methyl 6-[4'-(1-methyl-1H-pyrazol-4-yl)biphenyl-4-yl]-8-oxo-7-({(3R)-1-[(2R)-tetrahydro-furan-2-ylcarbonyl]pyrrolidin-3-yl}methyl)-2,5,7-triazaspiro[3.4]ect-5-ene-2-carboxylate<br>$^1$H NMR (600 MHz, CHLOROFORM-d) δ ppm 1.38-1.61 (m, 1.5 H), 1.78-2.24 (m, 5.5 H), 2.42 (m, 1 H), 3.04 (dd, J = 12.1, 7.2 Hz, 0.5 H), 3.13 (dd, J = 10.6, 7.2 Hz, 0.5 H), 3.37 (dq, J = 11.3, 7.8 Hz, 1 H), 3.46-3.58 (m, 1 H), 3.59-3.77 (m, 6 H), 3.78-3.84 (m, 1 H), 3.84-3.94 (m, 1 H), 3.98 (s, 3 H), 4.27-4.38 (m, 4.5 H), 4.38-4.43 (m, 0.5 H), 7.56-7.62 (m, 2 H), 7.62-7.72 (m, 5 H), 7.75-7.80 (m, 2 H), 7.80-7.84 (m, 1 H)<br>MS m/z 597.4 (M + H)+ |
| 728 | 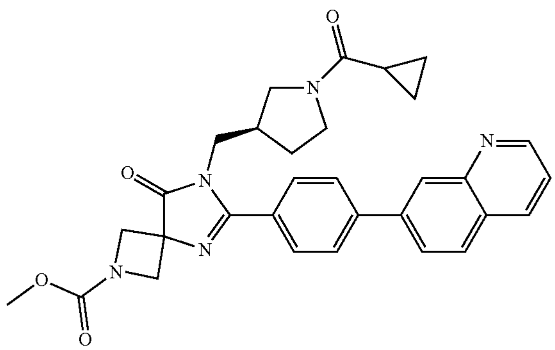 [SMILES: COC(=O)N1CC2(C1)N=C(c1ccc(-c3ccc4cccnc4c3)cc1)N(C[C@@H]1CCN(C(=O)C3CC3)C1)C2=O] | Methyl 7-{[(3R)-1-(cyclopropylcarbonyl)pyrrolidin-3-yl]methyl}-8-oxo-6-(4-quinolin-7-ylphenyl)-2,5,7-triazaspiro[3.4]ect-5-ene-2-carboxylate<br>$^1$H NMR (600 MHz, CHLOROFORM-d) δ ppm 0.60-0.77 (m, 2 H), 0.84-1.01 (m, 2 H), 1.36-1.56 (m, 2 H), 1.79-1.92 (m, 0.5 H), 1.92-2.03 (m, 0.5 H), 2.30-2.46 (m, 0.5 H), 2.51 (m, 0.5 H), 3.04 (dd, J = 12.1, 7.2 Hz, 0.5 H), 3.22-3.29 (m, 1 H), 3.29-3.36 (m, 0.5 H), 3.48-3.59 (m, 1.5 H), 3.59-3.85 (m, 6 H), 4.25-4.42 (m, 4 H), 7.41-7.50 (m, 1 H), 7.76 (t, J = 8.3 Hz, 2 H), 7.85 (dd, J = 8.7, 1.9 Hz, 1 H), 7.88-8.00 (m, 3 H), 8.21 (d, J = 7.9 Hz, 1 H), 8.37 (s, 1 H), 8.90-9.01 (m, 1 H)<br>MS m/z 538.2 (M + H)+ |
| 729 | 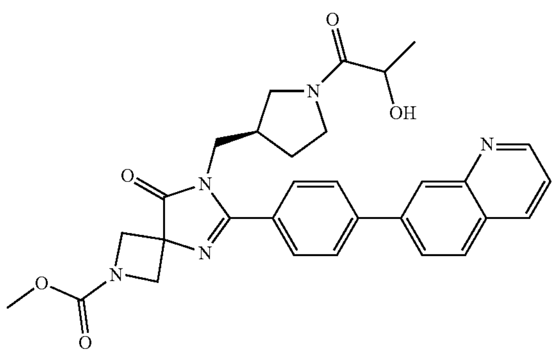 [SMILES: COC(=O)N1CC2(C1)N=C(c1ccc(-c3ccc4cccnc4c3)cc1)N(C[C@@H]1CCN(C(=O)C(C)O)C1)C2=O] | Methyl 7-{[(3R)-1-(2-hydroxypropanoyl)pyrrolidin-3-yl]methyl}-8-oxo-6-(4-quinolin-7-ylphenyl)-2,5,7-triazaspiro[3.4]oct-5-ene-2-carboxylate<br>$^1$H NMR (600 MHz, CHLOROFORM-d) δ ppm 1.17-1.31 (m, 3 H), 1.45-1.57 (m, 1 H), 1.90 (m, 0.5 H), 1.98 (m, 0.5 H), 2.31-2.48 (m, 0.5 H), 2.49-2.61 (m, 0.5 H), 3.07 (dd, J = 12.3, 6.2 Hz, 0.5 H), 3.11-3.19 (m, 0.5 H), 3.27-3.44 (m, 2 H), 3.57-3.65 (m, 1 H), 3.67-3.79 (m, 2 H), 3.74 (s, 3 H), 4.14 (q, J = 6.3 Hz, 0.5 H), 4.20 (q, J = 6.5 Hz, 0.5 H), 4.28-4.41 (m, 4 H), 7.46 (dd, J = 12.5, 4.3 Hz, 1 H), 7.75 (dd, J = 8.3, 3.4 Hz, 2 H), 7.80-7.89 (m, 1 H), 7.87-7.99 (m, 3 H), 8.23 (d, J = 8.3 Hz, 1 H), 8.39 (d, J = 4.9 Hz, 1 H), 8.92-9.04 (m, 1 H)<br>MS m/z 542.3 (M + H)+ |
| 730 | 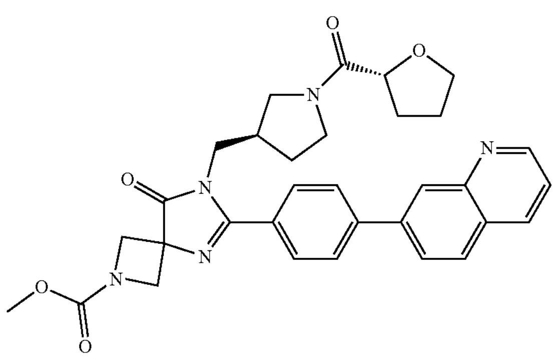 | Methyl 8-oxo-6-(4-quinolin-7-ylphenyl)-7-({(3R)-1-[(2R)-tetrahydro-furan-2-ylcarbonyl]pyrrolidin-3-yl}methyl)-2,5,7-triazaspiro[3.4]oct-5-ene-2-carboxylate<br>$^1$H NMR (600 MHz, CHLOROFORM-d) δ ppm 1.41-1.56 (m, 1 H), 1.78-1.90 (m, 1.5 H), 1.90-2.07 (m, 2.5 H), 2.07-2.15 (m, 0.5 H), 2.15-2.23 (m, 0.5 H), 2.44 (m, 1 H), 3.06 (dd, J = 12.1, 7.2 Hz, 0.5 H), 3.15 (dd, J = 10.6, 7.2 Hz, 0.5 H), 3.29-3.44 (m, 1 H), 3.47-3.59 (m, 1 H), 3.60-3.86 (m, 4 H), 3.73 (s, 3 H), 3.85-3.95 (m, 1 H), 4.28-4.39 (m, 4 H), 4.38-4.44 (m, 1 H), 7.42-7.51 (m, 1 H), 7.76 (dd, J = 12.5, 8.3 Hz, 2 H), 7.86 (d, J = 8.3 Hz, 1 H), 7.89-8.01 (m, 3 H), 8.22 (d, J = 8.3 Hz, 1 H), 8.36 (s, 1 H), 8.93-9.04 (m, 1 H)<br>MS m/z 568.3 (M + H)+ |

| ID No. | Structure | Compound Name & Physical Data |
|---|---|---|
| 731 | 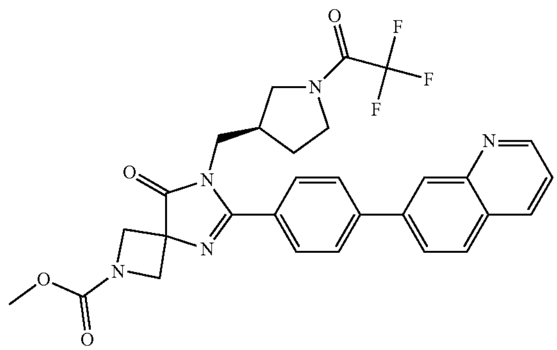 [SMILES: COC(=O)N1CC2(C1)N=C(c1ccc(-c3ccc4cccnc4c3)cc1)N(C[C@@H]1CCN(C(=O)C(F)(F)F)C1)C2=O] | Methyl 8-oxo-6-(4-quinolin-7-ylphenyl)-7-{[(3R)-1-(trifluoroacetyl)pyrrolidin-3-yl]methyl}-2,5,7-triazaspiro[3.4]oct-5-ene-2-carboxylate<br>MS m/z 566.1 (M + H)+ |
| 732 | 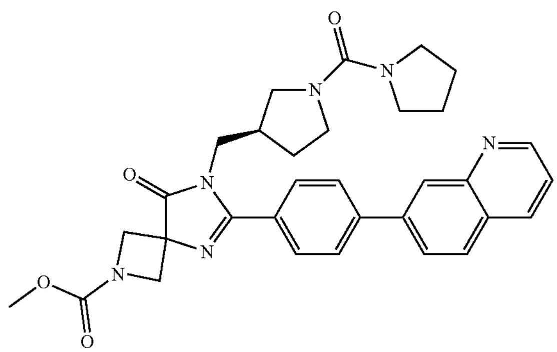 [SMILES: COC(=O)N1CC2(C1)N=C(c1ccc(-c3ccc4cccnc4c3)cc1)N(C[C@@H]1CCN(C(=O)N3CCCC3)C1)C2=O] | Methyl 8-oxo-7-{[(3S)-1-(pyrrolidin-1-ylcarbonyl)pyrrolidin-3-yl]methyl}-6-(4-quinolin-7-ylphenyl)-2,5,7-triazaspiro[3.4]oct-5-ene-2-carboxylate<br>MS m/z 567.2 (M + H)+ |
| 733 | 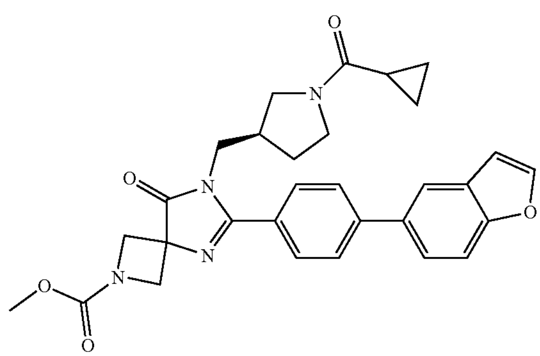 [SMILES: COC(=O)N1CC2(C1)N=C(c1ccc(-c3ccc4occc4c3)cc1)N(C[C@@H]1CCN(C(=O)C3CC3)C1)C2=O] | Methyl 6-[4-(1-benzofuran-5-yl)phenyl]-7-{[(3R)-1-(cycloprropylcarbonyl)pyrrolidin-3-yl]methyl}-8-oxo-2,5,7-triazaspiro[3.4]oct-5-ene-2-carboxylate<br>$^1$H NMR (600 MHz, CHLOROFORM-d) δ ppm 0.72 (m, 2 H), 0.86-1.01 (m, 2 H), 1.39-1.55 (m, 1.5 H), 1.64 (m, 1 H), 1.81-1.91 (m, 0.5 H), 1.92-2.04 (m, 0.5 H), 2.38 (br. s., 0.5 H), 2.44-2.56 (m, 0.5 H), 3.02 (dd, J = 11.9, 7.0 Hz, 0.5 H), 3.25 (dd, J = 10.0, 7.7 Hz, 0.5 H), 3.32 (dt, J = 12.1, 7.9 Hz, 0.5 H), 3.48-3.57 (m, 1.5 H), 3.58-3.72 (m, 1.5 H), 3.75 (s, 3 H), 3.74-3.81 (m, 1 H), 4.26-4.39 (m, 4 H), 6.85 (d, J = 2.3 Hz, 1 H), 7.56 (dd, J = 8.3, 1.9 Hz, 1 H), 7.57-7.64 (m, 1 H), 7.65-7.73 (m, 3 H), 7.74-7.82 (m, 2 H), 7.85 (d, J = 1.5 Hz, 1 H)<br>MS m/z 527.3 (M + H)+ |
| 734 | 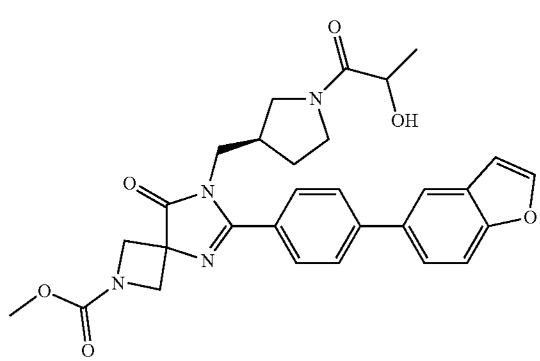 [SMILES: COC(=O)N1CC2(C1)N=C(c1ccc(-c3ccc4occc4c3)cc1)N(C[C@@H]1CCN(C(=O)C(C)O)C1)C2=O] | Methyl 6-[4-(1-benzofuran-5-yl)phenyl]-7-{[(3R)-1-(2-hydroxypropanoyl)pyrrolidin-3-yl]methyl}-8-oxo-2,5,7-triazaspiro[3.4]oct-5-ene-2-carboxylate<br>MS m/z 531.2 (M + H)+ |

| ID No. | Structure | Compound Name & Physical Data |
|---|---|---|
| 735 | 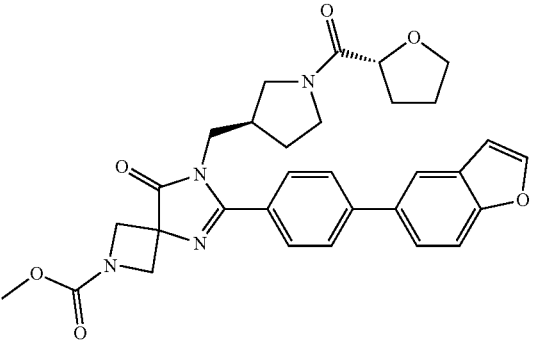 | Methyl 6-[4-(1-benzofuran-5-yl)phenyl]-8-oxo-7-({(3R)-1-[(2T)-tetrahydro-furan-2-ylcarbonyl]pyrrolidin-3-yl}methyl)-2,5,7-triazaspiro[3.4]oct-5-ene-2-carboxylate<br>$^1$H NMR (600 MHz, CHLOROFORM-d) δ ppm 1.42-1.55 (m, 0.5 H), 1.78-2.07 (m, 4 H), 2.06-2.23 (m, 1 H), 2.31-2.50 (m, 1 H), 3.04 (dd, J = 12.5, 7.2 Hz, 0.5 H), 3.13 (dd, J = 10.6, 7.2 Hz, 0.5 H), 3.30-3.41 (m, 1 H), 3.47-3.58 (m, 1 H), 3.60-3.69 (m, 1 H), 3.68-3.77 (m, 4.5 H), 3.81 (q, J = 6.7 Hz, 1 H), 3.84-3.94 (m, 1 H), 4.27-4.38 (m, 4 H), 4.38-4.43 (m, 0.5 H), 6.82-6.87 (m, 1 H), 7.54-7.59 (m, 1 H), 7.61 (dd, J = 8.7, 3.8 Hz, 1 H), 7.63-7.73 (m, 3 H), 7.78 (dd, J = 8.3, 6.0 Hz, 2 H), 7.85 (s, 1 H)<br>MS m/z 557.2 (M + H)+ |
| 736 | 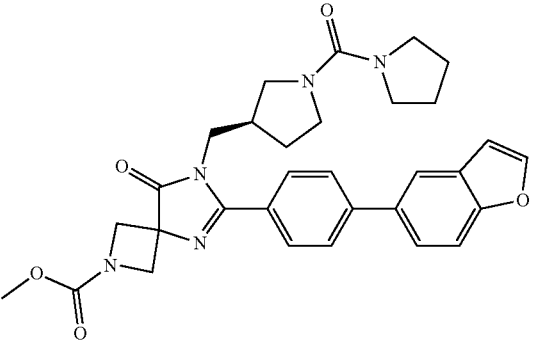 [SMILES: COC(=O)N1CC2(C1)N=C(c1ccc(-c3ccc4occc4c3)cc1)N(C[C@@H]1CCN(C(=O)N3CCCC3)C1)C2=O] | Methyl 6-[4-(1-benzofuran-5-yl)phenyl]-8-oxo-7-{[(3S)-1-(pyrrolidin-1-ylcarbonyl)pyrrolidin-3-yl]methyl}-2,5,7-triazaspiro[3.4]oct-5-ene-3-carboxylate<br>MS m/z 556.2 (M + H)+ |
| 737 | 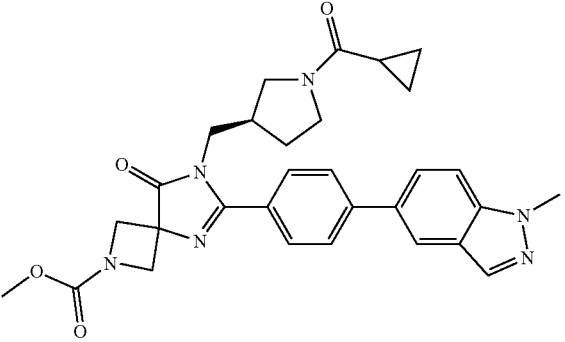 | Methyl 7-{[(3R)-1-(cyclopropylcarbonyl)pyrrolidin-3-yl]methyl}-6-[4-(1-methyl-1H-indazol-5-yl)phenyl]-8-oxo-2,5,7-triazaspiro[3.4]oct-5-ene-2-carboxylate<br>$^1$H NMR (600 MHz, CHLOROFORM-d) δ ppm 0.63-0.77 (m, 2 H), 0.87-1.01 (m, 2 H), 1.41-1.55 (m, 1.5 H), 1.80-1.91 (m, 0.5 H), 1.92-2.02 (m, 0.5 H), 2.38 (br. s., 0.5 H), 2.43-2.57 (m, 0.5 H), 3.02 (dd, J = 12.1, 7.2 Hz, 0.5 H), 3.49-3.57 (m, 1.5 H), 3.60-3.80 (m, 6 H), 4.13 (s, 3 H), 4.29-4.34 (m, 2 H), 4.34-4.38 (m, 2 H), 7.51 (d, J = 8.7 Hz, 1 H), 7.66-7.73 (m, 3 H), 7.77-7.83 (m, 2 H), 7.98 (s, 1 H), 8.06 (s, 1 H)<br>MS m/z 541.3 (M + H)+ |
| 738 | 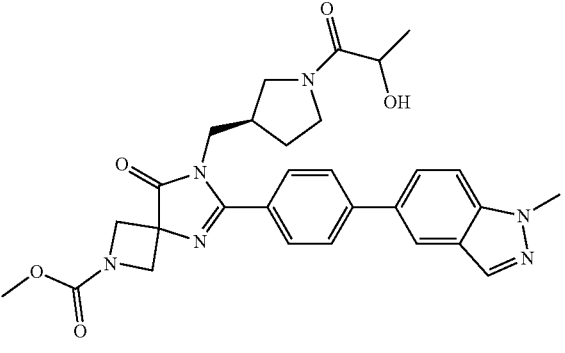 | Methyl 7-{[(3R)-1-(2-hydroxypropanoyl)pyrrolidin-3-yl]methyl}-6-[4-(1-methyl-1H-indazol-5-yl)phenyl]-8-oxo-2,5,7-triazaspiro[3.4]oct-5-ene-2-carboxylate<br>MS m/z 545.2 (M + H)+ |

-continued

| ID No. | Structure | Compound Name & Physical Data |
|---|---|---|
| 739 | 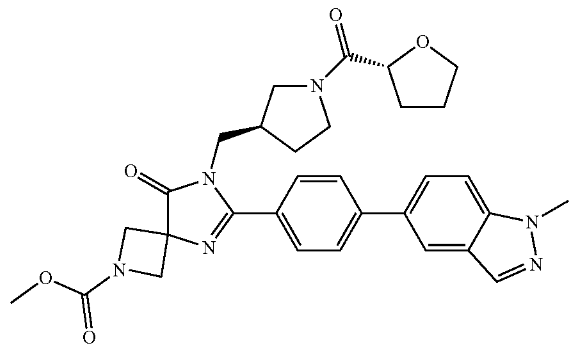 | Methyl 6-[4-(1-methyl-1H-indazol-5-yl)phenyl]-8-oxo-7-({(3R)-1-[(2R)-tetrahydro-furan-2-ylcarbonyl]pyrrolidin-3-yl}methyl)-2,5,7-triazaspiro[3.4]oct-5-ene-2-carboxylate<br>¹H NMR (600 MHz, CHLOROFORM-d) δ ppm 1.44-1.54 (m, 1 H), 1.79-2.22 (m, 5.5 H), 2.32-2.52 (m, 1 H), 3.04 (dd, J = 12.3, 7.4 Hz, 0.5 H), 3.14 (dd, J = 10.6, 7.2 Hz, 0.5 H), 3.31-3.41 (m, 1 H), 3.48-3.58 (m, 1 H), 3.59-3.78 (m, 6.5 H), 3.78-3.84 (m, 1 H), 3.84-3.95 (m, 1 H), 4.10-4.15 (m, 3 H), 4.29-4.38 (m, 4.5 H), 4.38-4.44 (m, 0.5 H), 7.51 (dd, J = 8.7, 3.4 Hz, 1 H), 7.66-7.73 (m, 3 H), 7.77-7.83 (m, 2 H), 7.98 (s, 1 H), 8.05-8.08 (m, 1 H)<br>MS m/z 571.2 (M + H)+ |
| 740 | 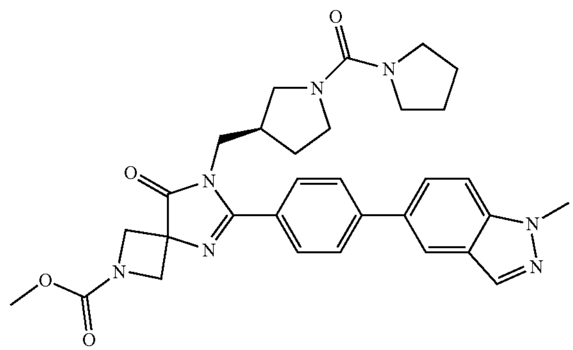 | Methyl 6-[4-(1-methyl-1H-indazol-5-yl)phenyl]-8-oxo-7-{[(3S)-1-(pyrrolidin-1-ylcarbonyl)pyrrolidin-3-yl]methyl}-2,5,7-triazaspiro[3.4]oct-5-ene-2-carboxylate<br>MS m/z 570.2 (M + H)+ |
| 741 | 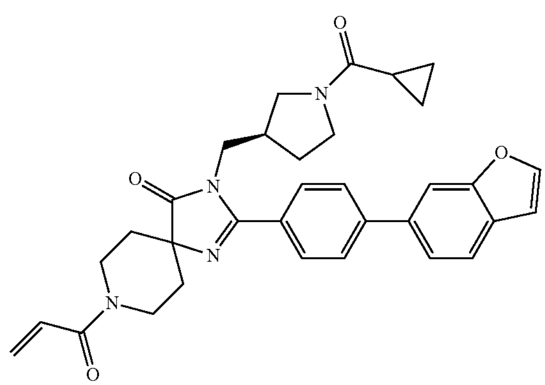 [SMILES: C=CC(=O)N1CCC2(CC1)N=C(c1ccc(-c3ccc4ccoc4c3)cc1)N(C[C@@H]1CCN(C(=O)C3CC3)C1)C2=O] | 8-Acryloyl-2-[4-(1-benzofuran-6-yl)phenyl]-3-{[(3R)-1-(cyclopropylcarbonyl)pyrrolidin-3-yl]methyl}-1,3,8-triazaspiro[4.5]dec-1-en-4-one<br>¹H NMR (400 MHz, CDCl3) d 0.71-0.72 (m, 2 H), 0.88-0.98 (m, 3 H), 1.44-1.65 (m, 5 H), 2.30-2.48 (m, 2 H), 3.01-3.31 (m, 2 H), 3.50-3.79 (m, 6 H), 4.00-4.07 (m, 1 H), 4.50-4.59 (m, 1 H), 5.72 (d, J = 10.6 Hz, 1 H), 6.34 (m, 1 H), 6.63 (dd, J = 10.6, 16.7 Hz, 1 H), 6.85 (d, J = 1.5 Hz, 1 H), 7.54-7.70 (m, 5 H), 7.76-7.80 (m, 2 H), 7.84 (s, 1 H)<br>MS m/z 551.2 (M + H)+ |
| 742 | 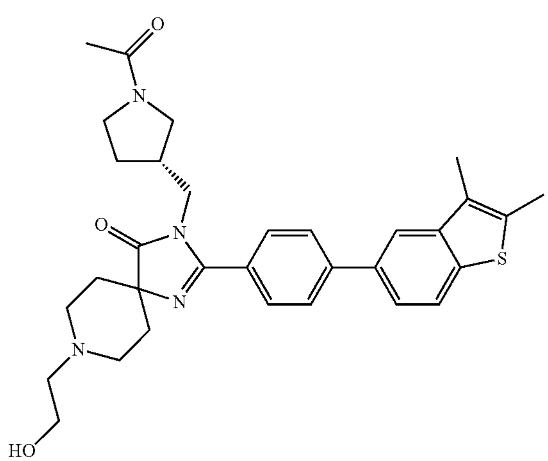 | 3-{[(3R)-1-(Cyclopropylcarbonyl)pyrrolidin-3-yl]methyl}-2-[4-(2,3-dimethyl-1-benzothiophen-5-yl)phenyl]-8-(2-hydroxyethyl)-1,3,8-triazaspiro[4.5]dec-1-en-4-one<br>¹H NMR (400 MHz, CDCl3) d 0.61-0.87 (m, 5 H), 1.40-1.57 (m, 4 H), 1.75-2.10 (m, 4 H), 2.30 (s, 3 H), 2.45 (s, 3 H), 2.61 (t, J = 5.0 Hz, 1 H), 2.68-2.75 (m, 1 H), 2.85-2.97 (m, 3 H), 3.10-3.25 (m, 1 H), 3.39-3.70 (m, 8 H), 7.45 (dd, J = 1.4, 8.2 Hz, 1 H), 7.59 (dd, J = 2.7, 8.2 Hz, 2 H), 7.72-7.77 (m, 4 H)<br>MS m/z 585 (M + H)+ |

-continued

| ID No. | Structure | Compound Name & Physical Data |
|---|---|---|
| 743 | 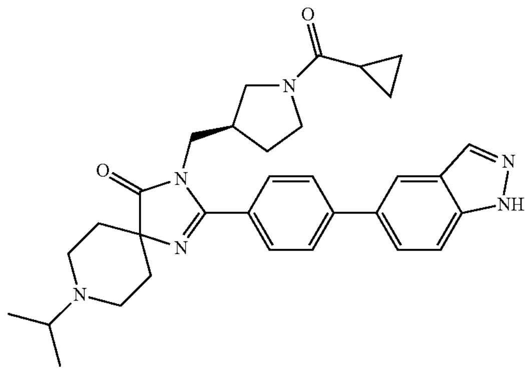 [SMILES: CC(C)N1CCC2(CC1)N=C(c1ccc(-c3ccc4[nH]ncc4c3)cc1)N(C[C@@H]1CCN(C(=O)C3CC3)C1)C2=O] | 3-{[(3R)-1-(Cyclopropylcarbonyl)pyrrolidin-3-yl]methyl}-2-[4-(1H-indazol-5-yl)phenyl]-8-(1-methylethyl)-1,3,8-triazaspiro[4.5]dec-1-en-4-one<br>¹H NMR (400 MHz, CDCl3) d 0.61-0.87 (m, 5 H), 1.40-1.57 (m, 4 H), 1.75-2.10 (m, 4 H), 2.30 (s, 3 H), 2.45 (s, 3 H), 2.61 (t, J = 5.0 Hz, 1 H), 2.68-2.75 (m, 1 H), 2.85-2.97 (m, 3 H), 3.10-3.25 (m, 1 H), 3.39-3.70 (m, 8 H), 7.45 (dd, J = 1.4, 8.2 Hz, 1 H), 7.59 (dd, J = 2.7, 8.2 Hz, 2 H), 7.72-7.77 (m, 4 H)<br>MS m/z 539 (M + H)+ |
| 744 | 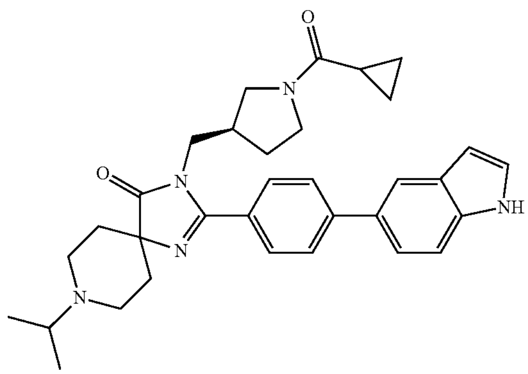 [SMILES: CC(C)N1CCC2(CC1)N=C(c1ccc(-c3ccc4[nH]ccc4c3)cc1)N(C[C@@H]1CCN(C(=O)C3CC3)C1)C2=O] | 3-{[(3R)-1-(Cyclopropylcarbonyl)pyrrolidin-3-yl]methyl}-2-[4-(1H-indol-5-yl)phenyl]-8-(1-methylethyl)-1,3,8-triazaspiro[4.5]dec-1-en-4-one<br>¹H NMR (400 MHz, CDCl3) d 0.6-1.0 (m, 5 H), 1.05-1.20 (m, 6 H), 1.25-3.60 (m, 18 H), 6.58 (s, 1 HG), 7.47 (s, 1 H), 7.51-7.60 (m, 2 H), 7.78-7.82 (m, 2 H), 7.91 (d, J = 7.0 Hz, 2 H), 7.99 (s, 1 H), 11.28 (s, 1 H)<br>MS m/z 538 (M + H)+ |
| 745 | 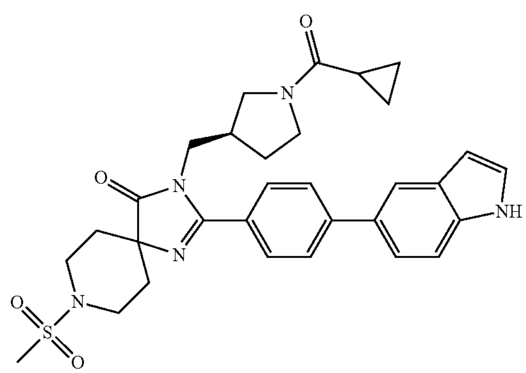 [SMILES: CS(=O)(=O)N1CCC2(CC1)N=C(c1ccc(-c3ccc4[nH]ccc4c3)cc1)N(C[C@@H]1CCN(C(=O)C3CC3)C1)C2=O] | 3-{[(3R)-1-(Cyclopropylcarbonyl)pyrrolidin-3-yl]methyl}-2-[4-(1H-indol-5-yl)phenyl]-8-(methylsulfonyl)-1,3,8-triazaspiro[4.5]dec-1-en-4-one<br>¹H NMR (300 MHz, DMSO-d₆) δ ppm 0.55-0.65 (m, 4 H), 1.35-2.40 (m, 7 H), 2.85-3.71 (m, 10 H), 2.96 (s, 3 H), 6.53 (s, 1 H), 7.41 (t, J = 2.6 Hz, 1 H), 7.48-7.54 (m, 2 H), 7.75-7.79 (m, 2 H), 7.86-7.88 (m, 2 H), 7.94 (s, 1 H), 11.21 (s, 1 H)<br>MS m/z 574 (M + H)+ |
| 746 | 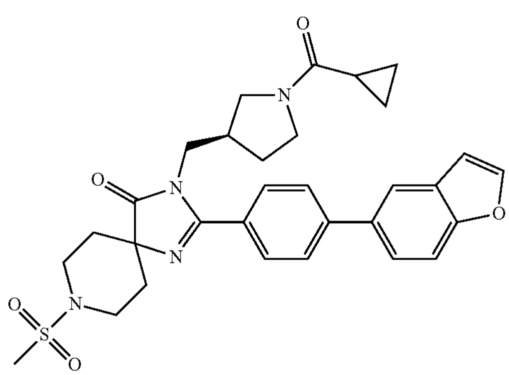 [SMILES: CS(=O)(=O)N1CCC2(CC1)N=C(c1ccc(-c3ccc4occc4c3)cc1)N(C[C@@H]1CCN(C(=O)C3CC3)C1)C2=O] | 2-[4-(1-Benzofuran-5-yl)phenyl]-3-{[(3R)-1-(cyclopropylcarbonyl)pyrrolidin-3-yl]methyl}-8-(methylsulfonyl)-1,3,8-triazaspiro[4.5]dec-1-en-4-one<br>¹H NMR (300 MHz, DMSO-d₆) δ ppm 0.53-0.65 (m, 4 H), 1.20-2.35 (m, 7 H), 2.79-3.65 (m, 10 H), 2.92 (s, 3 H), 7.01 (d, J = 1.9 Hz, 1 H), 7.64-7.71 (m, 2 H), 7.75-7.78 (m, 2 H), 7.84-7.88 (m, 2 H), 8.00-8.03 (m, 2 H)<br>MS m/z 575 (M + H)+ |

-continued

| ID No. | Structure | Compound Name & Physical Data |
|---|---|---|
| 747 | 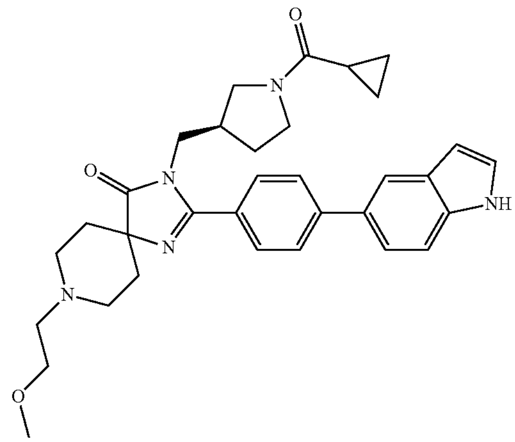 [SMILES: COCCN1CCC2(CC1)N=C(c1ccc(-c3ccc4[nH]ccc4c3)cc1)N(C[C@@H]1CCN(C(=O)C3CC3)C1)C2=O] | 3-{[(3R)-1-(Cyclopropylcarbonyl)pyrrolidin-3-yl]methyl}-2-[4-(1H-indol-5-yl)phenyl]-8-(2-methoxyethyl)-1,3,8-triazaspiro[4.5]dec-1-en-4-one<br>$^1$H NMR (300 MHz, DMSO-d$_6$) δ ppm 0.62-0.67 (m, 4 H), 1.32-1.95 (m, 7 H), 2.15-2.38 (m, 1 H), 2.52-2.60 (m, 3 H), 2.83-2.89 (m, 3 H), 3.07-3.15 (m, 2 H), 3.32 (s, 3 H), 3.45-3.70 (m, 6 H), 6.53 (s, 1 H), 7.41 (t, J = 2.6 Hz, 1 H), 7.46-7.54 (m, 2 H), 7.73-7.77 (m, 2 H), 7.84-7.87 (m, 2 H), 7.94 (s, 1 H), 11.22 (s, 1 H)<br>MS m/z 554 (M + H)+ |
| 748 | 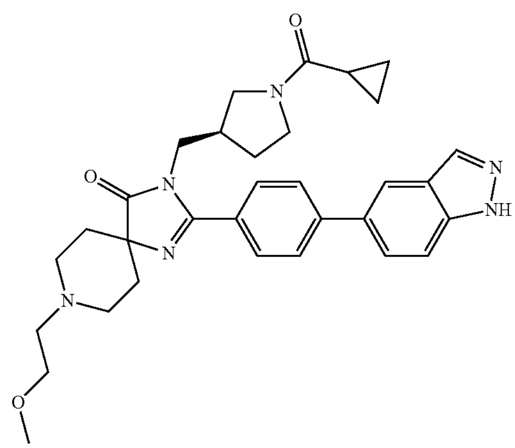 [SMILES: COCCN1CCC2(CC1)N=C(c1ccc(-c3ccc4[nH]ncc4c3)cc1)N(C[C@@H]1CCN(C(=O)C3CC3)C1)C2=O] | 3-{[(3R)-1-(Cyclopropylcarbonyl)pyrrolidin-3-yl]methyl}-2-[4-(1H-indazxol-5-yl)phenyl]-8-(2-methoxyethyl)-1,3,8-trisazaspiro[4.5]dec-1-en-4-one<br>$^1$H NMR (300 MHz, DMSO-d$_6$) δ ppm 0.60-0.67 (m, 4 H), 1.35-1.95 (m, 7 H), 2.15-2.35 (m, 1 H), 2.50-2.60 (m, 3 H), 2.80-2.90 (m, 3 H), 3.05-3.15 (m, 2 H), 3.26 (s, 3 H), 3.45-3.69 (m, 6 H), 7.66-7.69 (m, 1 H), 7.75-7.80 (m, 3 H), 7.88-7.91 (m, 2 H), 8.16 (d, J = 5.2 Hz, 2 H), 13.18 (s, 1 H)<br>MS m/z 555 (M + H)+ |
| 749 | 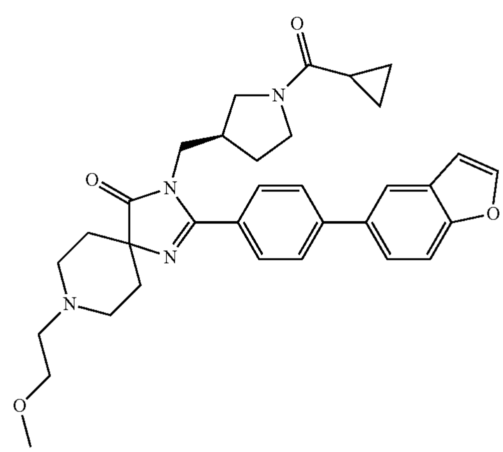 [SMILES: COCCN1CCC2(CC1)N=C(c1ccc(-c3ccc4occc4c3)cc1)N(C[C@@H]1CCN(C(=O)C3CC3)C1)C2=O] | 2-[4-(1-Benzofurann-5-yl)phenyl]-3-{[(3R)-1-(cyclopropylcarbonyl)pyrrolidin-3-yl]methyl}-8-(2-methoxyethyl)-1,3,8-triazaspiro[4.5]dec-1-en-4-one<br>$^1$H NMR (300 MHz, DMSO-d$_6$) δ ppm 0.65-0.70 (m, 4 H), 1.42-2.0 (m, 7 H), 2.20-2.45 (m, 1 H), 2.55-2.65 (m, 3 H), 2.85-2.92 (m, 3 H), 3.10-3.35 (m, 2 H), 3.31 (s, 3 H), 3.48-3.65 (m, 4 H), 3.69-3.74 (m, 2 H), 7.10 (d, J = 1.7 Hz, 1 H), 7.75-7.86 (m, 4 H), 7.92-7.95 (m, 2 H), 8.09-8.13 (m, 2 H)<br>MS m/z 555 (M + H)+ |

| ID No. | Structure | Compound Name & Physical Data |
|---|---|---|
| 750 | 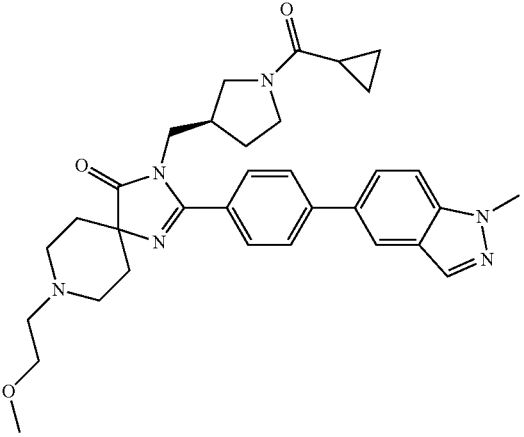 [SMILES: COCCN1CCC2(CC1)N=C(c1ccc(-c3ccc4c(cnn4C)c3)cc1)N(C[C@@H]1CCN(C(=O)C3CC3)C1)C2=O] | 3-{[(3R)-1-(Cyclopropylcarbonyl)pyrrolidin-3-yl]methyl}-8-(2-methoxyethyl)-2-[4-(1-methyl-1H-indazol-5-yl)phenyl]-1,3,8-triazaspiro[4.5]dec-1-en-4-one<br>$^1$H NMR (300 MHz, DMSO-d$_6$) δ ppm 0.54-0.70 (m, 4 H), 1.26-1.99 (m, 7 H), 2.11-2.38 (m, 1 H), 2.56 (t, J = 5.9 Hz, 3 H), 2.75-2.91 (m, 2.5 H), 3.02-3.17 (m, 1 H), 3.17-3.24 (m, 0.5 H), 3.25 (s, 3 H), 3.35-3.59 (m, 4 H), 3.65 (t, J = 7.2 Hz, 2 H), 4.09 (s, 3 H), 7.72-7.85 (m, 4 H), 7.85-7.94 (m, 2 H), 8.13 (s, 2 H)<br>MS m/z 569 (M + H)+ |
| 751 | 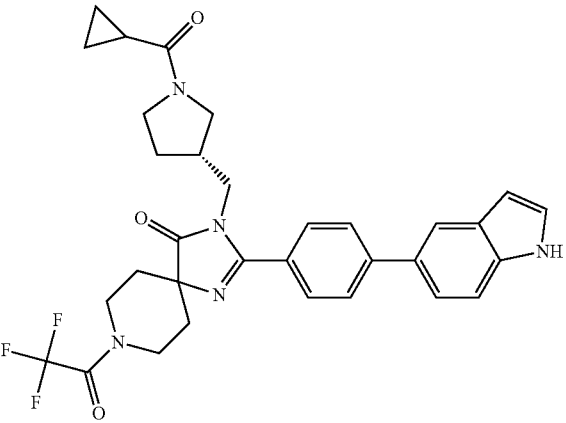 [SMILES: O=C(C1CC1)N1CC[C@@H](CN2C(=O)C3(CCN(C(=O)C(F)(F)F)CC3)N=C2c2ccc(-c3ccc4[nH]ccc4c3)cc2)C1] | 3-{[(3R)-1-(Cyclopropylcarbonyl)pyrrolidin-3-yl]methyl}-2-[4-(1H-indol-5-yl)phenyl]-8-(trifluoroacetyl)-1,3,8-triazaspiro[4.5]dec-1-en-4-one<br>$^1$H NMR (300 MHz, DMSO-d$_6$) δ ppm 0.52-0.71 (m, 4 H), 1.26-1.97 (m, 7 H), 2.12-2.42 (m, 1 H), 2.87 (dd, J = 11.3, 6.6 Hz, 0.5 H), 3.03-3.18 (m, 1 H), 3.19-3.29 (m, 1 H), 3.38-3.56 (m, 2.5 H), 3.63-3.81 (m, 3 H), 3.95 (d, J = 13.9 Hz, 1 H), 4.29 (d, J = 13.2, Hz, 1 H), 6.52 (br. s., 1 H), 7.40 (t, J = 2.5 Hz, 1 H), 7.44-7.56 (m, 2 H), 77.2-7.83 (m, 2 H), 7.83-7.91 (m, 2 H), 7.94 (s, 1 H), 11.21 (br. s., 1 H)<br>MS m/z 592 (M + H)+ |
| 752 | 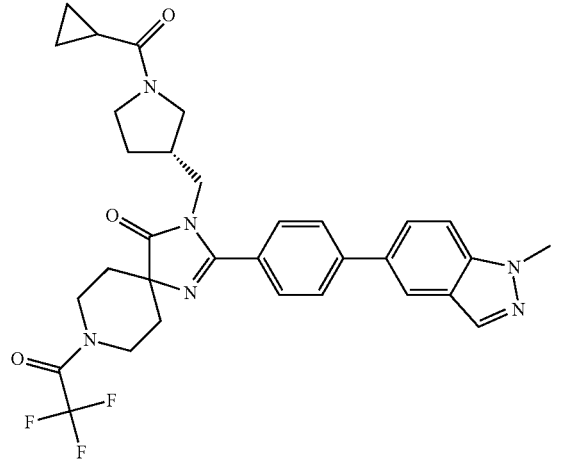 [SMILES: Cn1ncc2cc(-c3ccc(C4=NC5(CCN(C(=O)C(F)(F)F)CC5)C(=O)N4C[C@@H]4CCN(C(=O)C5CC5)C4)cc3)ccc21] | 3-{[(3R)-1-(Cyclopropylcarbonyl)pyrrolidin-3-yl]methyl}-2-[4-(1-methyl-1H-indazol-5-yl)phenyl]-8-(trifluoroacetyl)-1,3,8-triazaspiro[4.5]dec-1-en-4-one<br>$^1$H NMR (300 MHz, DMSO-d$_6$) δ ppm 0.63 (d, J = 5.4 Hz, 4 H), 1.29-1.98 (m, 7 H), 2.12-2.40 (m, 1 H), 2.86 (dd, J = 11.5, 6.7 Hz, 0.5 H), 3.01-3.18 (m, 1 H), 3.19-3.29 (m, 1 H), 3.38-3.52 (m, 2.5 H), 3.63-3.80 (m, 3 H), 3.95 (d, J = 13.9 Hz, 1 H), 4.09 (s, 3 H), 4.29 (d, J = 13.7 Hz, 1 H), 7.73-7.87 (m, 4 H), 7.92 (dd, J = 8.2, 2.1 Hz, 2 H), 8.14 (d, J = 4.1 Hz, 2 H)<br>MS m/z 607 (M + H)+ |

| ID No. | Structure | Compound Name & Physical Data |
|---|---|---|
| 753 | 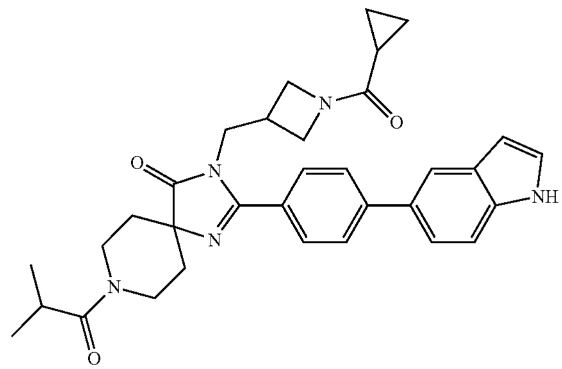 [SMILES: CC(C)C(=O)N1CCC2(CC1)N=C(c1ccc(-c3ccc4[nH]ccc4c3)cc1)N(CC1CN(C(=O)C3CC3)C1)C2=O] | 3-{[1-(Cyclopropylcarbonyl)azetidin-3-yl]methyl}-2-[4-(1H-indol-5-yl)phenyl]-8-(2-methylpropanoyl)-1,3,8-triazaspiro[4.5]dec-1-en-4-one<br>$^1$H NMR (300 MHz, CHLOROFORM-d) δ ppm 0.62-0.76 (m, 2 H), 0.91 (br. s., 2 H), 1.18 (t, J = 7.8 Hz, 6 H), 1.22-1.36 (m, 1 H), 1.49-1.67 (m, 2 H), 1.86-2.10 (m, 2 H), 2.76 (br. s., 1 H), 2.80-2.97 (m, 1 H), 3.37-3.52 (m, 1 H), 3.59 (dd, J = 9.6, 5.6 Hz, 1 H), 3.73 (t, J = 11.3 Hz, 1 H), 3.80-4.07 (m, 5 H), 4.19 (t, J = 8.1 Hz, 1 H), 4.51 (d, J = 13.2 Hz, 1 H), 6.56-6.70 (m, 1 H), 7.27-7.35 (m, 1 H), 7.42-7.56 (m, 2 H), 7.63 (d, J = 8.2 Hz, 2 H), 7.81 (d, J = 8.2 Hz, 2 H), 7.91 (s, 1 H), 8.55 (br. s., 1 H)<br>MS m/z 552 (M + H)+ |
| 754 | 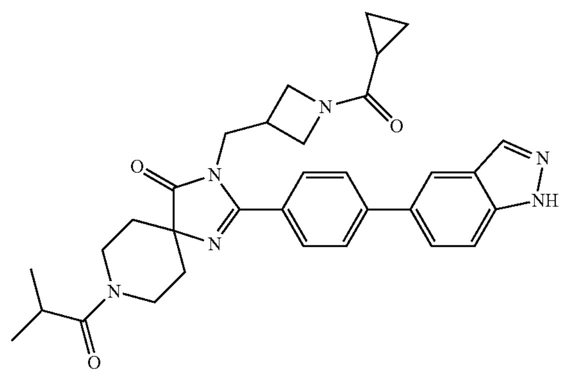 [SMILES: CC(C)C(=O)N1CCC2(CC1)N=C(c1ccc(-c3ccc4[nH]ncc4c3)cc1)N(CC1CN(C(=O)C3CC3)C1)C2=O] | 3-{[1-(Cyclopropylcarbonyl)azetidin-3-yl]methyl}-2-[4-(1H-indazol-5-yl)phenyl]-8-(2-methylpropanoyl)-1,3,8-triazaspiro[4.5]dec-1-en-4-one<br>$^1$H NMR (300 MHz, CHLOROFORM-d) δ ppm 0.62-0.77 (m, 2 H), 0.86-0.99 (m, 2 H), 1.18 (t, J = 7.8 Hz, 6 H), 1.23-1.31 (m, 1 H), 1.50-1.80 (m, 4 H), 1.88-2.09 (m, 2 H), 2.80 (br. s., 1 H), 2.82-2.95 (m, 1 H), 3.35-3.51 (m, 1 H), 3.57 (dd, J = 9.5, 5.6 Hz, 1 H), 3.63-3.82 (m, 1 H), 3.82-4.07 (m, 4 H), 4.21 (t, J = 8.2 Hz, 1 H), 4.51 (d, J = 13.3 Hz, 1 H), 7.52-7.62 (m, 1 H), 7.66 (d, J = 7.8 Hz, 3 H), 7.79 (d, J = 8.0 Hz, 2 H), 8.00 (s, 1 H), 8.17 (br. s., 1 H)<br>MS m/z 553 (M + H)+ |
| 755 | 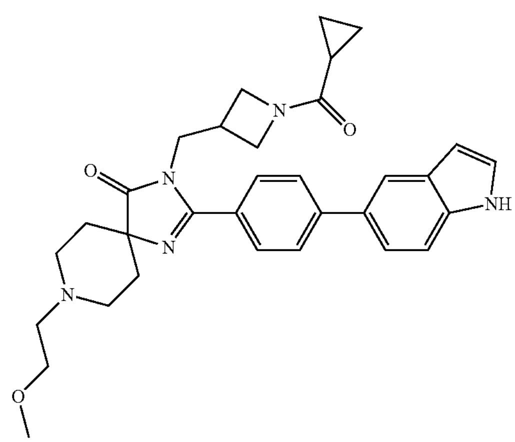 [SMILES: COCCN1CCC2(CC1)N=C(c1ccc(-c3ccc4[nH]ccc4c3)cc1)N(CC1CN(C(=O)C3CC3)C1)C2=O] | 3-{[1-(Cyclopropylcarbonyl)azetidin-3-yl]methyl}-2-[4-(1H-indol-5-yl)phenyl]-8-triazaspiro[4.5]dec-1-en-4-one<br>$^1$H NMR (300 MHz, CHLOROFORM-d) δ ppm 0.58-0.77 (m, 2 H), 0.79-0.98 (m, 2 H), 1.22-1.35 (m, 1 H), 1.59 (d, J = 12.8 Hz, 2 H), 2.05-2.27 (m, 3 H), 2.60-2.84 (m, 5 H), 2.96 (d, J = 11.3 Hz, 2 H), 3.39 (s, 3 H), 3.58 (t, J = 5.4 Hz, 2 H), 3.76-4.03 (m, 4 H), 4.17 (t, J = 8.0 Hz, 1 H), 6.64 (br. s., 1 H), 7.28-7.36 (m, 1 H), 7.41-7.55 (m, 2 H), 7.61 (d, J = 8.1 Hz, 2 H), 7.79 (d, J = 8.1 Hz, 2 H), 7.90 (s, 1 H), 8.44 (br. s., 1 H)<br>MS m/z 540 (M + H)+ |

| ID No. | Structure | Compound Name & Physical Data |
|---|---|---|
| 756 | 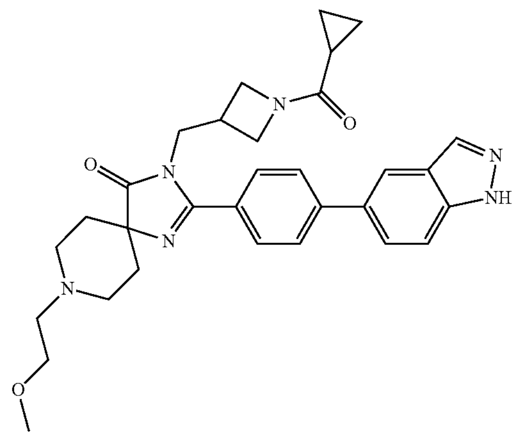 [SMILES: COCCN1CCC2(CC1)N=C(c1ccc(-c3ccc4[nH]ncc4c3)cc1)N(CC1CN(C(=O)C3CC3)C1)C2=O] | 3-{[1-(Cyclopropylcarbonyl)azetidin-3-yl]methyl}-2-[2-(1H-indazol-5-yl)phenyl]-8-(2-methoxyethyl)-1,3,8-triazaspiro[4.5]dec-1-en-4-one<br>¹H NMR (300 MHz, CHLOROFORM-d) δ ppm 0.61-0.75 (m, 2 H), 0.85-0.94 (m, 2 H), 1.25-1.33 (m, 1 H), 1.59 (d, J = 13.2 Hz, 2 H), 2.07-2.25 (m, 2 H), 2.62-2.84 (m, 5 H), 2.91-3.03 (m, 2 H), 3.39 (s, 3 H), 3.55-3.62 (m, 2 H), 3.78-4.05 (m, 4 H), 4.19 (t, J = 8.2 Hz, 1 H), 7.58 (m, J = 8.8 Hz, 1 H), 7.61-7.68 (m, 3 H), 7.71-7.86 (m, 2 H), 7.99 (s, 1 H), 8.16 (s, 1 H), 10.56 (br. s., 1 H)<br>MS m/z 541 (M + H)+ |
| 757 | 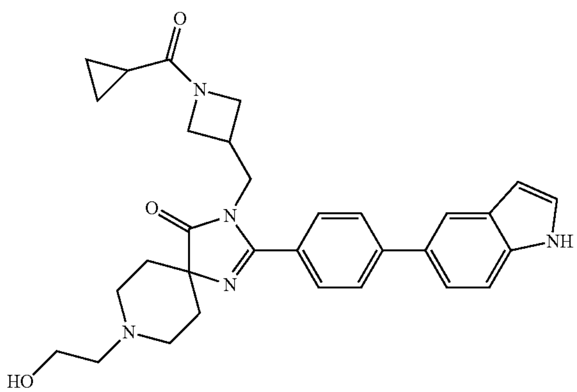 [SMILES: O=C(C1CC1)N1CC(CN2C(=O)C3(CCN(CCO)CC3)N=C2c2ccc(-c3ccc4[nH]ccc4c3)cc2)C1] | 3-{[1-(Cyclopropylcarbonyl)azetidin-3-yl]methyl}-8-(2-hydroxyethyl)-2-[4-(1H-indol-5-yl)phenyl]-1,3,8-triazaspiro[4.5]dec-1-en-4-one<br>¹H NMR (300 MHz, CHLOROFORM-d) δ ppm 0.69 (dd, J = 7.5, 3.0 Hz, 2 H), 0.84-0.95 (m, 2 H), 1.60 (d, J = 12.8 Hz, 2 H), 1.98-2.23 (m, 3 H), 2.68 (t, J = 5.1 Hz, 2 H), 2.72-2.86 (m, 3 H), 2.94 (d, J = 11.5 Hz, 2 H), 3.54-3.62 (m, 1 H), 3.62-3.73 (m, 2 H), 3.77-4.04 (m, 4 H), 4.18 (t, J = 8.1 Hz, 1 H), 6.65 (br. s., 1 H), 7.29 (br. s., 1 H), 7.41-7.58 (m, 2 H), 7.62 (d, J = 8.0 Hz, 1 H), 7.80 (d, J = 8.1 Hz, 2 H), 7.91 (s, 1 H), 8.34 (br. s., 1 H)<br>MS m/z 526 (M + H)+ |
| 758 | 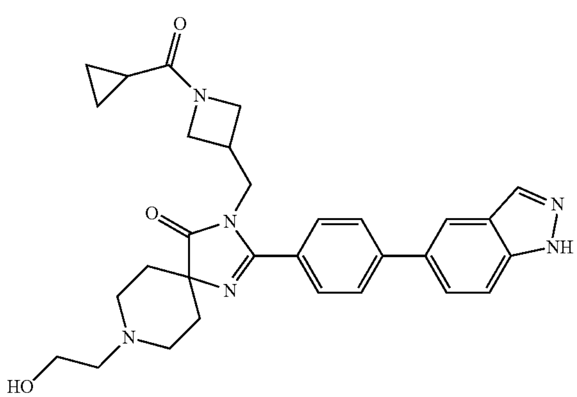 [SMILES: O=C(C1CC1)N1CC(CN2C(=O)C3(CCN(CCO)CC3)N=C2c2ccc(-c3ccc4[nH]ncc4c3)cc2)C1] | 3-{[1-(Cyclopropylcarbonyl)azetidin-3-yl]methyl}-8-(2-hydroxyethyl)-2-[4-(1H-indazol-5-yl)phenyl]-1,3,8-triazaspiro[4.5]dec-1-en-4-one<br>¹H NMR (300 MHz, CHLOROFORM-d) δ ppm 0.63-0.77 (m, 2 H), 0.87-0.96 (m, 2 H), 1.25-1.32 (m, 2 H), 1.61 (d, J 13.2 Hz, 2 H), 2.04-2.16 (m, 2 H), 2.69 (t, J = 5.2 Hz, 2 H), 2.73-2.86 (m, 3 H), 2.88-3.00 (m, 2 H), 3.54-3.62 (m, 1 H), 3.67 (t, J = 5.2 Hz, 2 H), 3.78-4.04 (m, 4 H), 4.20 (t, J = 8.1 Hz, 1 H), 7.59 (m, J = 8.7 Hz, ,1 H), 7.63-7.71 (m, 3 H), 7.78 (d, J = 8.1 Hz, 2 H), 8.00 (s, 1 H), 8.16 (s, 1 H)<br>MS m/z 527 (M + H)+ |
| 759 | 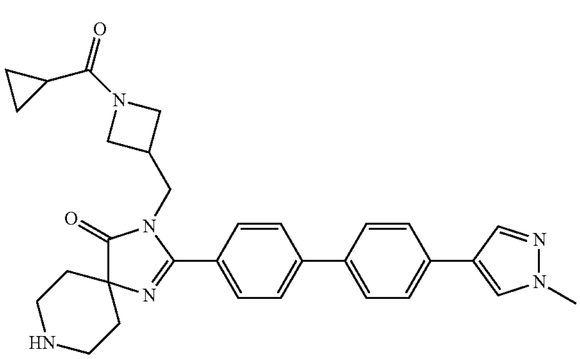 [SMILES: Cn1cc(-c2ccc(-c3ccc(C4=NC5(CCNCC5)C(=O)N4CC4CN(C(=O)C5CC5)C4)cc3)cc2)cn1] | 3-{[1-(Cyclopropylcarbonyl)azetidin-3-yl]methyl}-2-[4'-(1-methyl-1H-pyrazol-4-yl)biphenyl-4-yl]-1,3,8-triazaspiro[4.5]dec-1-en-4-one<br>¹H NMR (300 MHz, CHLOROFORM-d) δ ppm 0.63-0.75 (m, 2 H), 0.85-0.95 (m, 2 H), 1.19-1.34 (m, 1 H), 1.54 (d, J = 13.3 Hz, 2 H), 1.87-2.03 (m, 2 H), 2.60-2.83 (m, 1 H), 3.09-3.29 (m, 4 H), 3.56 (dd, J = 9.7, 5.7 Hz, 1 H), 3.80-3.97 (m, 4 H), 3.98 (s, 3 H), 4.18 (t, J = 8.4 Hz, 1 H), 7.56-7.70 (m, 7 H), 7.77 (d, J = 8.2 Hz, 2 H), 7.83 (s, 1 H)<br>MS m/z 523 (M + H)+ |

| ID No. | Structure | Compound Name & Physical Data |
|---|---|---|
| 760 | 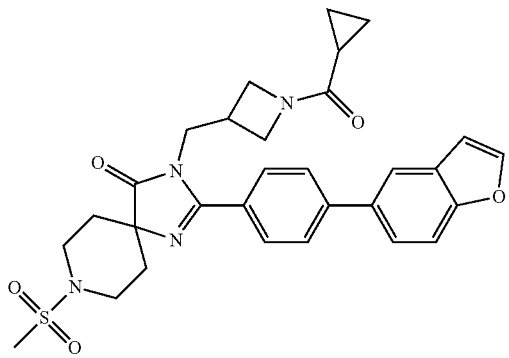 [SMILES: CS(=O)(=O)N1CCC2(CC1)N=C(c1ccc(-c3ccc4occc4c3)cc1)N(CC1CN(C(=O)C3CC3)C1)C2=O] | 2-[4-(1-Benzofuran-5-yl)phenyl]-3-{[1-(cyclopropylcarbonyl)azetidin-3-yl]methyl}-8-(methylsulfonyl)-1,3,8-triazaspiro[4.5]dec-1-en-4-one<br>$^1$H NMR (300 MHz, CHLOROFORM-d) δ ppm 0.59-0.78 (m, 2 H), 0.90 (br. s., 2 H), 1.72 (br. s., 1 H), 2.16 (t, J = 10.0 Hz, 2 H), 2.66-2.81 (m, 1 H), 2.85 (s, 3 H), 3.31-3.43 (m, 2 H), 3.54-3.64 (m, 1 H), 3.67-4.07 (m, 7 H), 4.20 (t, J = 7.6 Hz, 1 H), 6.86 (br. s., 1 H), 7.52-7.73 (m, 5 H), 7.75-7.92 (m, 3 H)<br>MS m/z 561 (M + H)+ |
| 761 | 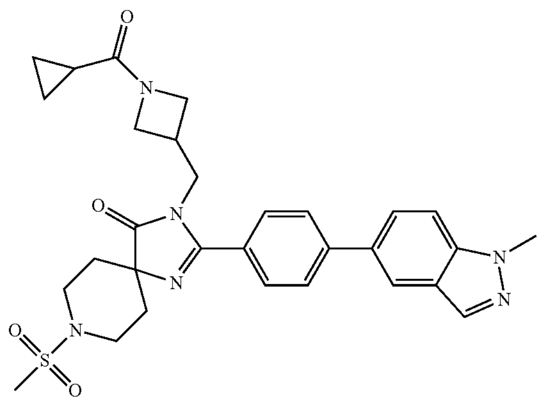 | 3-{[1-(Cyclopropylcarbonyl)azetidin-3-yl]methyl}-2-[4-(1-methyl-1H-indazol-5-yl)phenyl]-8-(methylsulfonyl)-1,3,8-triazaspiro[4.5]dec-1-en-4-one<br>$^1$H NMR (300 MHz, CHLOROFORM-d) δ ppm 0.61-0.77 (m, 2 H), 0.90 (br. s., 2 H), 1.14-1.36 (m, 2 H), 2.06-2.25 (m, 2 H), 2.67-2.80 (m, 1 H), 2.85 (s, 3 H), 3.29-3.63 (m, 3 H), 3.80 (d, J = 11.7 Hz, 2 H), 3.86-4.05 (m, 4 H), 4.13 (s, 3 H), 4.16-4.26 (m, 1 H), 7.51 (d, J = 8.7 Hz, 1 H), 7.66 (t, J = 8.7 Hz, 3 H), 7.81 (d, J = 8.0 Hz, 2 H), 7.97 (s, 1 H), 8.07 (s, 1 H)<br>MS m/z 575 (M + H)+ |
| 762 | 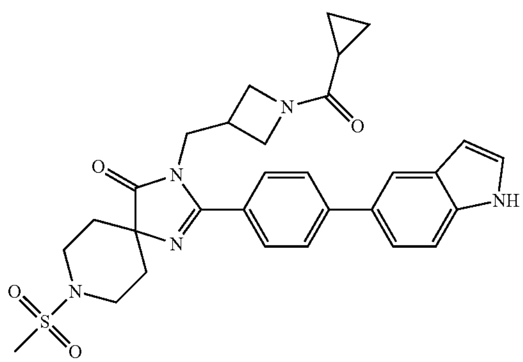 [SMILES: CS(=O)(=O)N1CCC2(CC1)N=C(c1ccc(-c3ccc4[nH]ccc4c3)cc1)N(CC1CN(C(=O)C3CC3)C1)C2=O] | 3-{[1-(Cyclopropylcarbonyl)azetidin-3-yl]methyl}-2-[4-(1H-indol-5-yl)phenyl]-8-(methylsulfonyl)-1,3,8-triazaspiro[4.5]dec-1-en-4-one<br>$^1$H NMR (300 MHz, DMSO-d$_6$) δ ppm 0.47-0.73 (m, 4 H), 1.30-1.45 (m, 1 H), 1.62 (d, J = 12.8 Hz, 2 H), 1.91 (t, J = 10.3 Hz, 2 H), 2.56-2.71 (m, 1 H), 2.95 (s, 3 H), 3.21 (t, J = 10.3 Hz, 2 H), 3.61 (d, J = 11.5 Hz, 2 H), 3.67-3.82 (m, 2 H), 3.88 (d, J = 7.3 Hz, 2 H), 4.15 (t, J = 8.3 Hz, 1 H), 6.52 (br. s., 1 H), 7.41 (br. s., 1 H), 7.44-7.58 (m, 2 H), 7.74 (d, J = 8.1 Hz, 2 H), 7.87 (d, J = 8.0 Hz, 2 H), 7.94 (s, 1 H)<br>MS m/z 560 (M + H)+ |
| 763 | 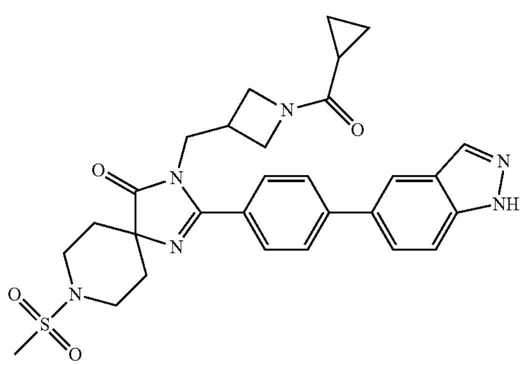 [SMILES: CS(=O)(=O)N1CCC2(CC1)N=C(c1ccc(-c3ccc4[nH]ncc4c3)cc1)N(CC1CN(C(=O)C3CC3)C1)C2=O] | 3-{[1-(Cyclopropylcarbonyl)azetidin-3-yl]methyl}-2-[4-(1H-indazol-5-yl)phenyl]-8-(methylsulfonyl)-1,3,8-triazaspiro[4.5]dec-1-en-4-one<br>$^1$H NMR (300 MHz, DMSO-d$_6$) δ ppm 0.51-0.70 (m, 4 H), 1.29-1.45 (m, 1 H), 1.64 (d, J = 13.2 Hz, 2 H), 1.92 (t, J = 10.4 Hz, 2 H), 2.57-2.70 (m, 1 H), 2.95 (s, 3 H), 3.19-3.27 (m, 2 H), 3.54-3.68 (m, 2 H), 3.68-3.82 (m, 2.5 H), 2.88 (d, J = 7.1 Hz, 2.5 H), 4.15 (t, J = 8.0 Hz, 1 H), 7.63-7.70 (m, 1 H), 7.71-7.83 (m, 3 H), 7.91 (d, J = 8.2 Hz, 2 H), 8.16 (br. s., 2 H), 13.18 (br. s., 1 H)<br>MS m/z 561 (M + H)+ |

-continued

| ID No. | Structure | Compound Name & Physical Data |
|---|---|---|
| 764 | 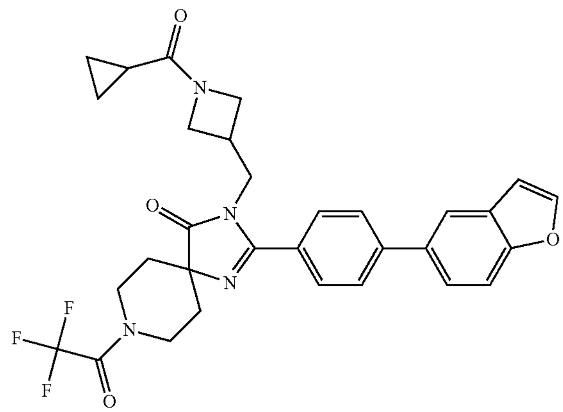 [SMILES: O=C(C1CC1)N1CC(CN2C(=O)C3(CCN(C(=O)C(F)(F)F)CC3)N=C2c2ccc(-c3ccc4occc4c3)cc2)C1] | 2-[4-(1-Benzofuran-5-yl)phenyl]-3-{[1-(cycloprropylcarbonyl)azetidin-3-yl]methyl}-8-(trifluoroacetyl)-1,3,8-triazaspiro[4.5]dec-1-en-4-one<br>$^1$H NMR (300 MHz, CHLOROFORM-d) δ ppm 0.58-0.77 (m, 2 H), 0.91 (br. s., 2 H), 1.26 (br. s., 3 H), 1.96-2.16 (m, 2 H), 2.64-2.88 (m, 1 H), 3.53-3.70 (m, 2 H), 3.71-4.12 (m, 6 H), 4.20 (t, J = 7.7 Hz, 1 H), 4.46 (d, J = 13.3 Hz, 1 H), 6.86 (s, 1 H), 7.52-7.73 (m, 5 H), 7.76-7.92 (m, 3 H)<br>MS m/z 579 (M + H)+ |
| 765 | 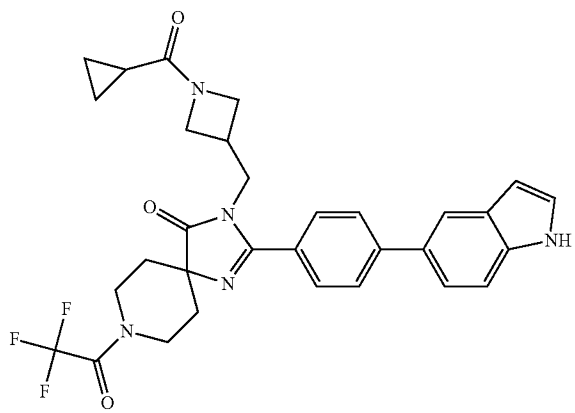 [SMILES: O=C(C1CC1)N1CC(CN2C(=O)C3(CCN(C(=O)C(F)(F)F)CC3)N=C2c2ccc(-c3ccc4[nH]ccc4c3)cc2)C1] | 3-{[1-(Cyclopropylcarbonyl)azetidin-3-yl]methyl}-2-[4-(1H-indol-5-yl)phenyl]-8-(trifluoroacetyl)-1,3,8-triazaspiro[4.5]dec-1-en-4-one<br>$^1$H NMR (300 MHz, CHLOROFORM-d) δ ppm 0.62-0.77 (m, 2 H), 0.87-0.97 (m, 2 H), 1.24-1.34 (m, 2 H), 1.97-2.15 (m, 3 H), 2.67-2.86 (m, 1 H), 3.54-3.68 (m, 2 H), 3.74-4.12 (m, 6 H), 4.20 (t, J = 8.0 Hz, 1 H), 4.46 (d, J = 13.3 Hz, 1 H), 6.65 (br. s., 1 H), 7.30 (t, J = 2.7 Hz, 1 H), 7.43-7.55 (m, 2 H), 7.64 (d, J = 8.2 Hz, 2 H), 7.83 (d, J = 8.1 Hz, 2 H), 7.92 (s, 1 H), 8.40 (br. s., 1 H)<br>MS m/z 578 (M + H)+ |
| 766 | 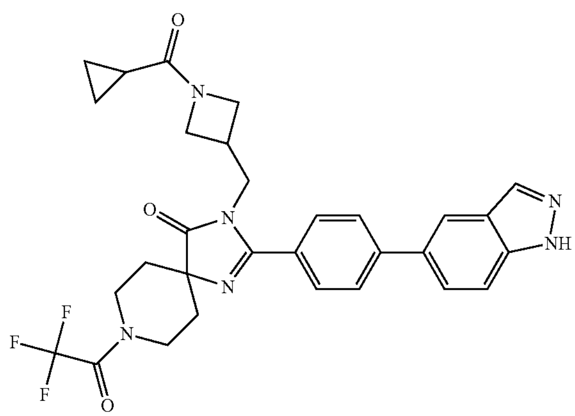 [SMILES: O=C(C1CC1)N1CC(CN2C(=O)C3(CCN(C(=O)C(F)(F)F)CC3)N=C2c2ccc(-c3ccc4[nH]ncc4c3)cc2)C1] | 3-{[1-(Cyclopropylcarbonyl)azetidin-3-yl]methyl}-2-[4-(1H-indazol-5-yl)phenyl]-8-(trifluoroacetyl)-1,3,8-triazaspiro[4.5]dec-1-en-4-one<br>$^1$H NMR (300 MHz, CHLOROFORM-d) δ ppm 0.57-0.69 (m, 2 H), 0.78-0.88 (m, 2 H), 1.59 (d, J = 13.5 Hz, 3 H), 1.90-2.08 (m, 2 H), 2.71 (br. s., 1 H), 3.46-3.60 (m, 2 H), 3.67-4.05 (m, 6 H), 4.14 (t, J = 7.8 Hz, 1 H), 4.38 (d, J = 13.5 Hz, 1 H), 7.189 (s, 2 H), 7.46-7.67 (m, 4 H), 7.73 (d, J = 8.0 Hz, 2 H), 7.93 (s, 1 H)<br>MS m/z 579 (M + H)+ |
| 767 | 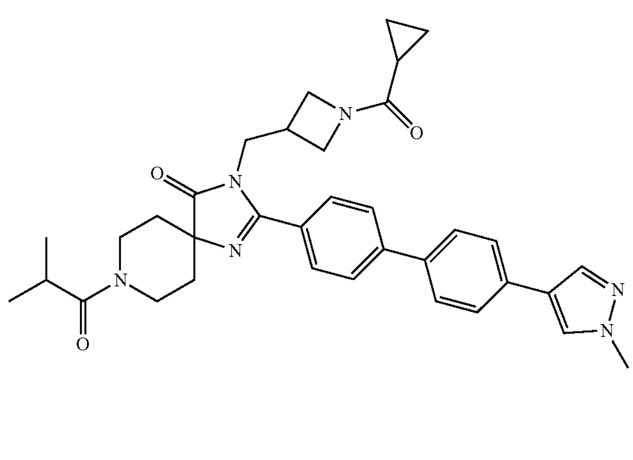 [SMILES: CC(C)C(=O)N1CCC2(CC1)N=C(c1ccc(-c3ccc(-c4cnn(C)c4)cc3)cc1)N(CC1CN(C(=O)C3CC3)C1)C2=O] | 3-{[1-(Cycloprropylcarbonyl)azetidin-3-yl]methyl}-8-(2-methylpropanoyl)-2-[4'-(1-methyl-1H-pyrazol-4-yl)biphenyl-4-yl]-1,3,8-triazaspiro[4.5]dec-1-en-4-one<br>$^1$H NMR (300 MHz, DMSO-d$_6$) δ ppm 0.56-0.70 (m, 4 H), 1.03 (br. s., 6 H), 1.23 (s, 1 H), 1.30-1.42 (m, 1 H), 1.45-1.59 (m, 2 H), 1.62-1.85 (m, 2 H), 2.61 (m, J = 5.5 Hz, 1 H), 2.86-3.02 (m, 1 H), 3.09-3.26 (m, 2 H), 3.46-3.62 (m, 1 H), 3.65-3.81 (m, 2 H), 3.86 (br. s., 1 H), 3.88 (s, 3 H), 3.97 (d, J = 12.1 Hz, 1 H), 4.10-4.19 (m, 1 H), 4.23-4.37 (m, 1 H), 7.66-7.73 (m, 2 H), 7.77 (d, J = 9.9 Hz, 4 H), 7.90 (d, J = 8.2 Hz, 2 H), 7.94 (s, 1 H), 8.22 (s, 1 H)<br>MS m/z 593 (M + H)+ |

| ID No. | Structure | Compound Name & Physical Data |
|---|---|---|
| 768 | 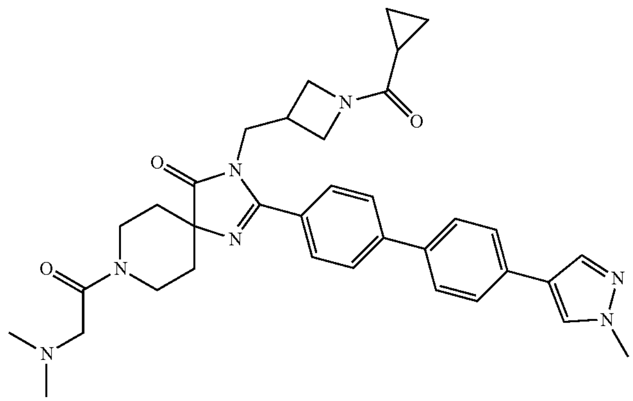 | 3-{[1-(Cyclopropylcarbonyl)azetidin-3-yl]methyl}-8-(N,N-dimethylglycyl)-2-[4'-(1-methyl-1H-pyrazol-4-yl)biphenyl-4-yl]-1,3,8-triazaspiro[4.5]dec-1-en-4-one<br>$^1$H NMR (300 MHz, CHLOROFORM-d) δ ppm 0.51-0.71 (m, 2 H), 0.82 (br. s., 2 H), 1.06-1.31 (m, 3 H), 1.40-1.68 (m, 2 H), 1.77-2.05 (m, 3 H), 2.46 (br. s., 6 H), 2.67 (br. s., 1 H), 3.24-3.55 (m, 4 H), 3.55-3.72 (m, 1 H), 3.72-3.87 (m, 3 H), 3.90 (br. s., 3 H), 4.02-4.20 (m, 1 H), 4.25-4.51 (m, 1 H), 7.19 (s, 1 H), 7.45-7.65 (m, 5 H), 7.65-7.84 (m, 3 H)<br>MS m/z 608 (M + H)+ |
| 769 | 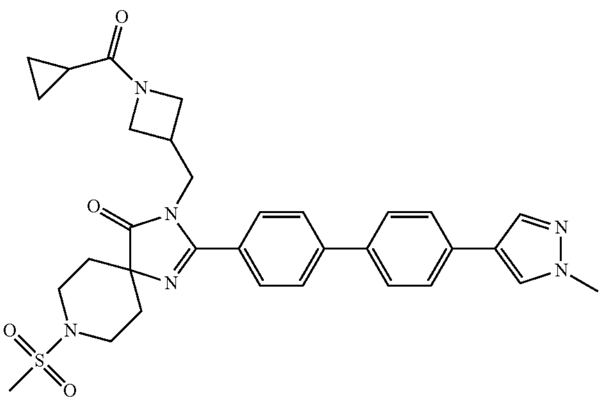 | 3-{[1-(Cyclopropylcarbonyl)azetidin-3-yl]methyl}-2-[4'-(1-methyl-1H-pyrazol-4-yl)biphenyl-4-yl]-8-(methylsulfonyl)-1,3,8-triazaspiro[4.5]dec-1-en-4-one<br>$^1$H NMR (300 MHz, DMSO-d$_6$) δ ppm 0.56-0.88 (m, 4 H), 1.09 (t, J = 6.8 Hz, 1 H), 1.18-1.30 (m, 1 H), 1.30-1.48 (m, 1 H), 1.63 (d, J = 12.5 Hz, 2 H), 1.91 (t, J = 10.2 Hz, 2 H), 2.55-2.74 (m, 1 H), 2.95 (s, 2 H), 3.08-3.28 (m, 3 H), 3.35-3.44 (m, 3 H), 3.50-3.66 (m, 2 H), 3.67-3.84 (m, 2 H), 3.83-3.86 (m, 2 H), 3.88 (s, 3 H), 4.15 (t, J = 8.2 Hz, 1 H), 7.66-7.73 (m, 2 H), 7.77 (d, J = 7.6 Hz, 4 H), 7.83-7.99 (m, 3 H), 8.22 (s, 1 H)<br>MS m/z 601 (M + H)+ |
| 770 | 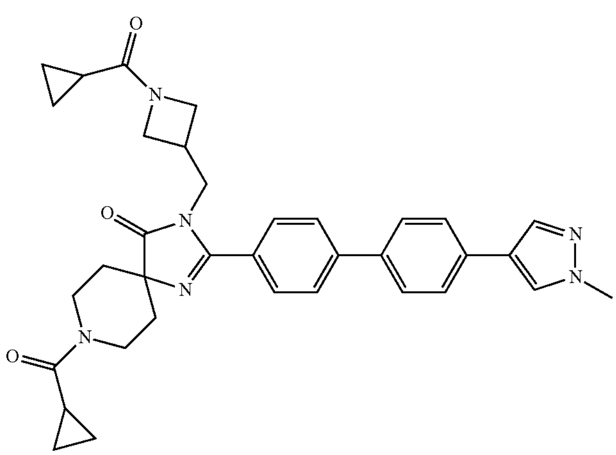 [SMILES: Cn1cc(-c2ccc(-c3ccc(C4=NC5(CCN(C(=O)C6CC6)CC5)C(=O)N4CC4CN(C(=O)C5CC5)C4)cc3)cc2)cn1] | 8-(Cyclopropylcarbonyl)-3-{[1-(cyclopropylcarbonyl)azetidin-3-yl]methyl}-2-[4'-(1-methyl-1H-pyrazol-4-yl)biphenyl-4-yl]-1,3,8-triazaspiro[4.5]dec-1-en-4-one<br>$^1$H NMR (300 MHz, DMSO-d$_6$) δ ppm 0.53-0.67 (m, 4 H), 0.67-0.83 (m, 4 H), 1.23 (br. s., 1 H), 1.29-1.43 (m, 1 H), 1.43-1.63 (m, 2 H), 1.63-1.76 (m, 1 H), 1.76-1.92 (m, 1 H), 1.92-2.15 (m, 1 H), 2.54-2.69 (m, 1 H), 3.12-3.27 (m, 2 H), 3.52-3.79 (m, 3 H), 3.79-3.86 (m, 1 H), 3.88 (s, 3 H), 4.14 (t, J = 7.0 Hz, 1 H), 4.20-4.37 (m, 2 H), 7.70 (m, J = 8.0 Hz, 2 H), 7.76 (d, J = 10.0 Hz, 4 H), 7.85-7.96 (m, 3 H), 8.22 (s, 1 H)<br>MS m/z 591 (M + H)+ |

| ID No. | Structure | Compound Name & Physical Data |
|---|---|---|
| 771 | 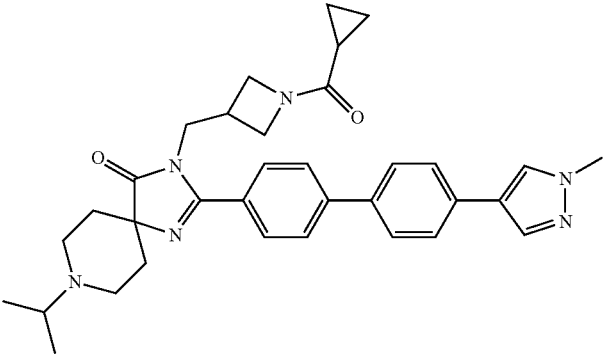 [SMILES: CC(C)N1CCC2(CC1)N=C(c1ccc(-c3ccc(-c4cnn(C)c4)cc3)cc1)N(CC1CN(C(=O)C3CC3)C1)C2=O] | 3-{[1-(Cyclopropylcarbonyl)azetidin-3-yl]methyl}-8-(1-methylethyl)-2-[4'-(1-methyl-1H-pyrazol-4-yl)biphenyl-4-yl]-1,3,8-triazaspiro[4.5]dec-1-en-4-one<br>$^1$H NMR (300 MHz, CHLOROFORM-d) δ ppm 0.56-0.68 (m, 2 H), 0.75-0.89 (m, 2 H), 1.01-1.28 (m, 6 H), 1.49-1.88 (m, 5 H), 2.03-2.29 (m, 2 H), 2.67 (dt, J = 13.4, 6.6 Hz, 1 H), 2.83-3.20 (m, 4 H), 3.47 (dd, J = 9.1, 5.8 Hz, 1 H), 3.71-3.88 (m, 3 H), 3.90 (s, 3 H), 4.11 (t, J = 7.9 Hz, 1 H), 7.19 (s, 1 H), 7.48-7.63 (m, 6 H), 7.69 (d, J = 8.1 Hz, 2 H), 7.74 (s, 1 H)<br>MS m/z 565 (M + H)+ |
| 772 | 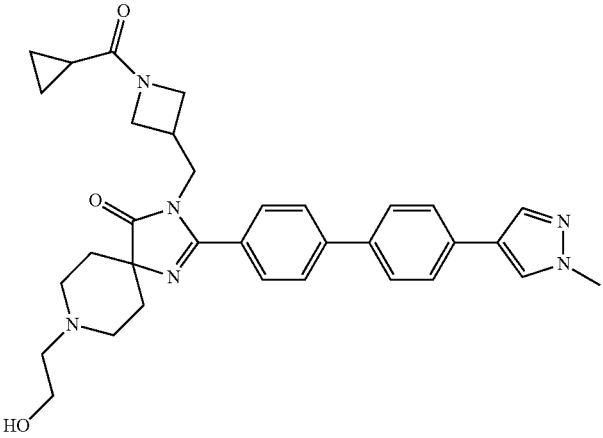 [SMILES: Cn1cc(-c2ccc(-c3ccc(C4=NC5(CCN(CCO)CC5)C(=O)N4CC4CN(C(=O)C5CC5)C4)cc3)cc2)cn1] | 3-{[1-(Cyclopropylcarbonyl)azetidin-3-yl]methyl}-8-(2-hydroxyethyl)-2-[4'-(1-methyl-1H-pyrazol-4-yl)biphenyl-4-yl]-1,3,8-triazaspiro[4.5]dec-1-en-4-one<br>$^1$H NMR (300 MHz, CHLOROFORM-d) δ ppm 0.54-0.68 (m, 2 H), 0.75-0.88 (m, 2 H), 1.56 (d, J = 13.3 Hz, 2 H), 1.76-2.15 (m, 6 H), 2.59-2.71 (m, 2 H), 2.78 (t, J = 10.6 Hz, 2 H), 2.86-3.02 (m, 2 H), 3.63 (t, J = 4.7 Hz, 2 H), 3.71-3.88 (m, 3 H), 3.90 (s, 3 H), 4.11 (t, J = 8.1 Hz, 1 H), 7.19 (s, 1 H), 7.47-7.63 (m, 6 H), 7.69 (d, J = 8.1 Hz, 2 H), 7.74 (s, 1 H)<br>MS m/z 567 (M + H)+ |
| 829 | 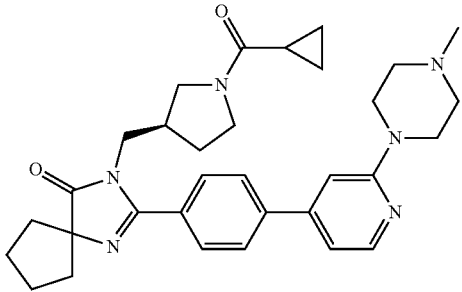 [SMILES: CN1CCN(c2cc(-c3ccc(C4=NC5(CCCC5)C(=O)N4C[C@@H]4CCN(C(=O)C5CC5)C4)cc3)ccn2)CC1] | (R)-3-((1-(cyclopropanecarbonyl)pyrrolidin-3-yl)methyl)-2-(4-(2-(4-methylpiperazin-1-yl)pyridin-4-yl)phenyl)-1,3-diazaspiro[4.4]non-1-en-4-one<br>MS m/z 541.3 (M + H)+ |
| 828 | 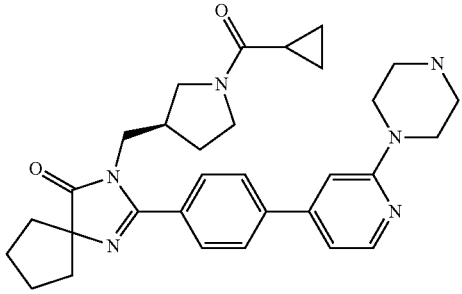 [SMILES: O=C(C1CC1)N1CC[C@@H](CN2C(=O)C3(CCCC3)N=C2c2ccc(-c3ccnc(N4CCNCC4)c3)cc2)C1] | (R)-3-((1-(cyclopropanecarbonyl)pyrrolidin-3-yl)methyl)-2-(4-(2-(piperazin-1-yl)pyridin-4-yl)phenyl)-1,3-diazaspiro[4.4]non-1-en-4-one<br>MS m/z 527.2 (M + H)+ |

-continued

| ID No. | Structure | Compound Name & Physical Data |
|---|---|---|
| 822 | 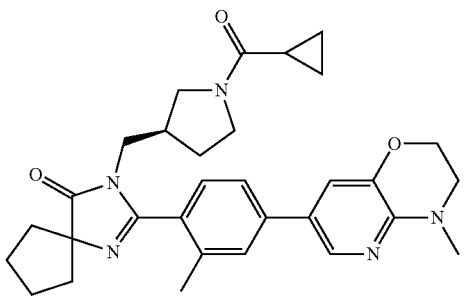 [SMILES: Cc1cc(-c2cnc3c(c2)OCCN3C)ccc1C1=NC2(CCCC2)C(=O)N1C[C@@H]1CCN(C(=O)C2CC2)C1] | (R)-3-((1-(cyclopropanecarbonyl)pyrrolidin-3-yl)methyl)-2-(2-methyl-4-(4-methyl-3,4-dihydro-2H-pyrido[3,2-b][1,4]oxazin-7-yl)phenyl)-1,3-diazaspiro[4.4]non-1-en-4-one<br>MS m/z 528.3 (M + H)+ |
| 845 | 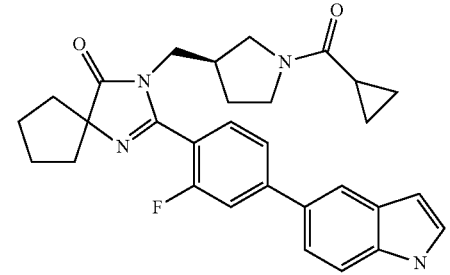 [SMILES: O=C(C1CC1)N1CC[C@@H](CN2C(=O)C3(CCCC3)N=C2c2ccc(-c3ccc4[nH]ccc4c3)cc2F)C1] | (R)-3-((1-(cyclopropanecarbonyl)pyrrolidin-3-yl)methyl)-2-(2-fluoro-4-(1H-dinol-5-yl)phenyl)-1,3-diazaspiro[4.4]non-1-en-4-one<br>$^1$H NMR (400 MHz, CHLOROFORM-d) δ ppm 0.66-0.79 (m, 2 H), 0.89-1.01 (m, 2 H), 1.45-1.55 (m, 1.5 H), 1.58-1.68 (m, 1.5 H), 1.80-1.91 (m, 0.5 H), 1.94-2.03 (m, 4 H), 2.06-2.17 (m, 4 H), 2.35-2.46 (m, 0.5 H), 2.46-2.58 (m, 0.5 H), 3.01 (dd, J = 12.1, 7.1 Hz, 0.5 H), 3.16-3.24 (m, 0.5 H), 3.31 (dt, J = 11.6, 8.1 Hz, 0.5 H), 3.49-3.58 (m, 2 H), 3.62-3.70 (m, 2 H), 6.66 (br. s., 1 H), 7.31 (d, J = 3.0 Hz, 1 H), 7.42-7.54 (m, 3 H), 7.60 (d, J = 5.1 Hz, 2 H), 7.91 (s, 1 H), 8.46 (br. s., 1 H). MS m/z 499.2 (M + H)+ |
| 805 | 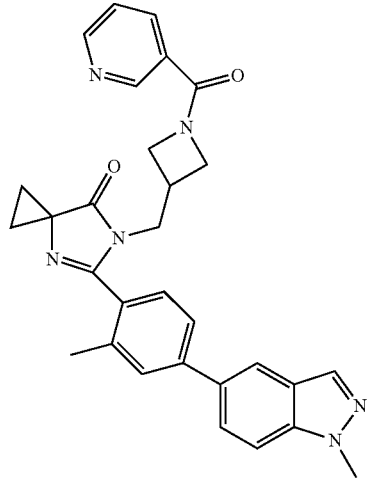 [SMILES: Cc1cc(-c2ccc3c(cnn3C)c2)ccc1C1=NC2(CC2)C(=O)N1CC1CN(C(=O)c2cccnc2)C1] | 5-(2-methyl-4-(1-methyl-1H-indazol-5-yl)phenyl)-6-((1-nicotinoylazetidin-3-yl)methyl)-4,6-diazaspiro[2.4]hept-4-en-7-one<br>MS m/z 505.2 (M + H)+ |

| ID No. | Structure | Compound Name & Physical Data |
|---|---|---|
| 796 | 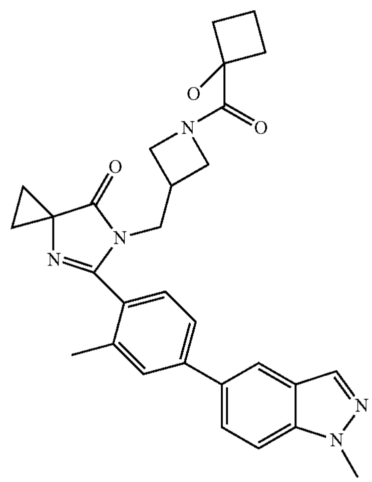 [SMILES: Cc1cc(-c2ccc3c(cnn3C)c2)ccc1C1=NC2(CC2)C(=O)N1CC1CN(C(=O)C2(O)CCC2)C1] | 6-((1-(1-hydroxycyclobutanecarbonyl)azetidin-3-yl)methyl)-5-(2-methyl-4-(1-methyl-1H-indazol-5-yl)phenyl)-4,6-diazaspiro[2.4]hept-4-en-7-one<br>MS m/z 498.3 (M + H)+ |
| 851 | 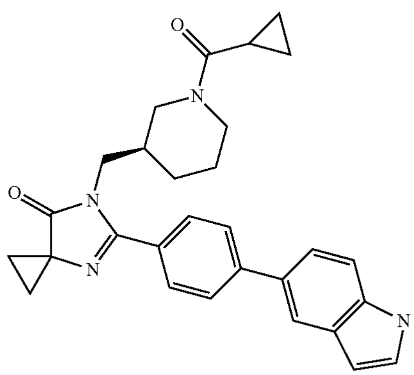 [SMILES: O=C(C1CC1)N1CCC[C@@H](CN2C(=O)C3(CC3)N=C2c2ccc(-c3ccc4[nH]ccc4c3)cc2)C1] | (R)-5-(4-(1H-indol-5-yl)phenyl)-6-((1-(cyclopropanecarbonyl)piperidin-3-yl)methyl)-4,6-diazaspiro[2.4]hept-4-en-7-one<br>MS m/z 467 (M + H)+ |
| 823 | 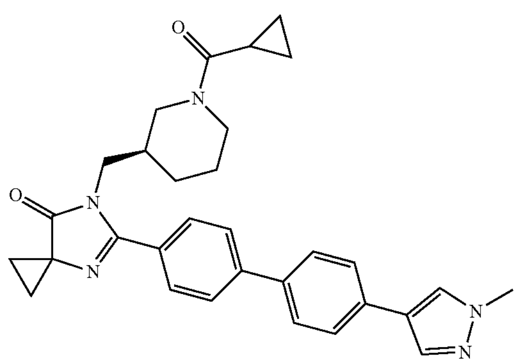 [SMILES: Cn1cc(-c2ccc(-c3ccc(C4=NC5(CC5)C(=O)N4C[C@@H]4CCCN(C(=O)C5CC5)C4)cc3)cc2)cn1] | (R)-6-((1-(cyclopropanecarbonyl)piperidin-3-yl)methyl)-5-(4'-(1-methyl-1H-pyrazol-4-yl)-[1,1'-biphenyl]-4-yl)-4,6-diazaspiro[2.4]hept-4-en-7-one<br>MS m/z 508 (M + H)+ |
| 820 | 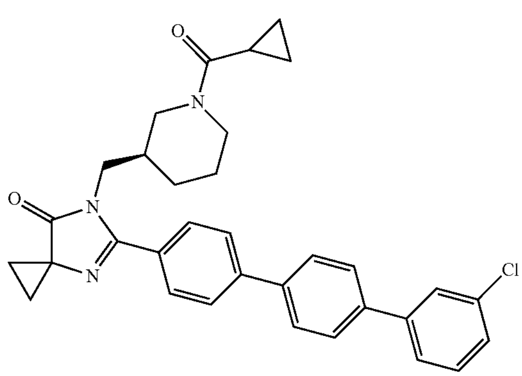 [SMILES: O=C(C1CC1)N1CCC[C@@H](CN2C(=O)C3(CC3)N=C2c2ccc(-c3ccc(-c4cccc(Cl)c4)cc3)cc2)C1] | (R)-5-(3''-chloro-[1,1':4',1''-terphenyl]-4-yl)-6-((1-(cyclopropanecarbonyl)piperidin-3-yl)methyl)-4,6-diazaspiro[2.4]hept-4-en-7-one<br>MS m/z 538 (M + H)+ |

-continued

| ID No. | Structure | Compound Name & Physical Data |
|---|---|---|
| 821 | 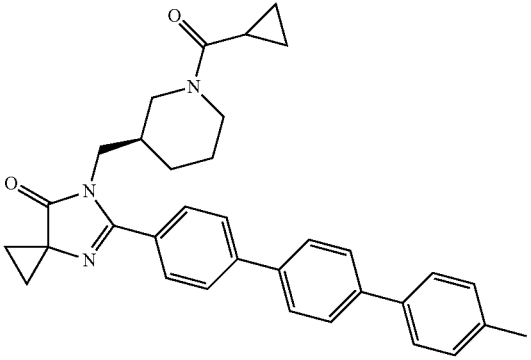 [SMILES: Cc1ccc(-c2ccc(-c3ccc(C4=NC5(CC5)C(=O)N4C[C@@H]4CCCN(C(=O)C5CC5)C4)cc3)cc2)cc1] | (R)-6-((1-(cyclopropanecarbonyl)piperidin-3-yl)methyl)-5-(4''-methyl-[1,1':4',1''-terphenyl]-4-yl)-4,6-diazaspiro[2.4]hept-4-en-7-one<br>MS m/z 518 (M + H)+ |
| 848 | 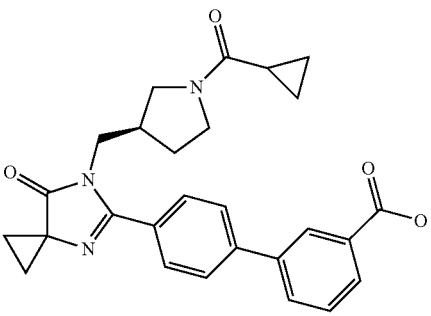 [SMILES: O=C(O)c1cccc(-c2ccc(C3=NC4(CC4)C(=O)N3C[C@@H]3CCN(C(=O)C4CC4)C3)cc2)c1] | (R)-4'-(6-((1-(cyclopropanecarbonyl)pyrrolidin-3-yl)methyl)-7-oxo-4,6-diazaspiro[2.4]hept-4-en-5-yl)-[1,1'-biphenyl]-3-carboxylic acid<br>MS m/z 458 (M + H)+ |
| 819 | 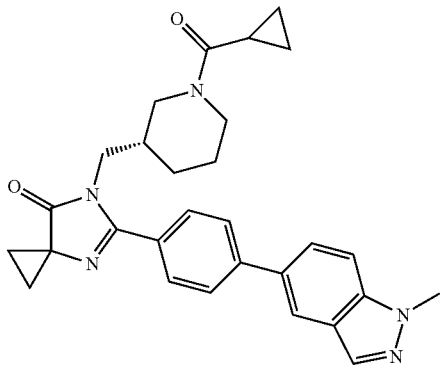 [SMILES: Cn1ncc2cc(-c3ccc(C4=NC5(CC5)C(=O)N4C[C@H]4CCCN(C(=O)C5CC5)C4)cc3)ccc21] | (S)-6-((1-(cyclopropanecarbonyl)piperidin-3-yl)methyl)-5-(4-(1-methyl-1H-indazol-5-yl)phenyl)-4,6-diazaspiro[2.4]hept-4-en-7-one<br>MS m/z 482 (M + H)+ |
| 818 | 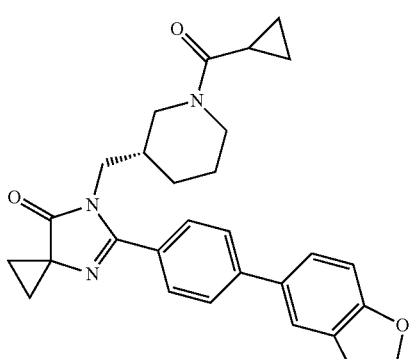 | (S)-5-(4-(benzofuran-5-yl)phenyl)-6-((1-(cyclopropanecarbonyl)piperidin-3-yl)methyl)-4,6-diazaspiro[2.4]hept-4-en-7-one<br>MS m/z 468 (M + H)+ |

| ID No. | Structure | Compound Name & Physical Data |
|---|---|---|
| 817 | 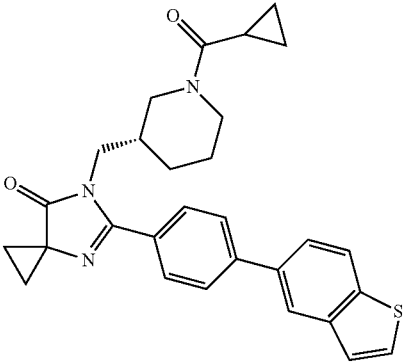 [SMILES: O=C(C1CC1)N1CCC[C@H](CN2C(=O)C3(CC3)N=C2c2ccc(-c3ccc4sccc4c3)cc2)C1] | (S)-5-(4-(benzo[b]thiophen-5-yl)phenyl)-6-((1-(cyclopropanecarbonyl)piperidin-3-yl)methyl)-4,6-diazaspiro[2.4]hept-4-en-7-one<br>MS m/z 484 (M + H)+ |
| 843 | 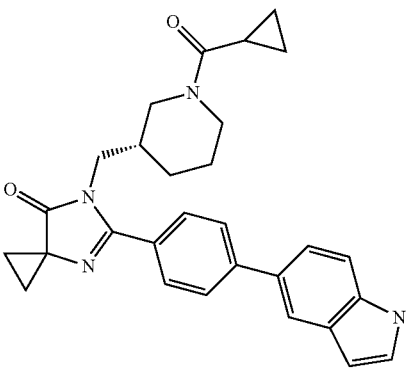 [SMILES: O=C(C1CC1)N1CCC[C@H](CN2C(=O)C3(CC3)N=C2c2ccc(-c3ccc4[nH]ccc4c3)cc2)C1] | (S)-5-(4-(1H-indol-5-yl)phenyl)-6-((1-(cyclopropanecarbonyl)piperidin-3-yl)methyl)-4,6-diazaspiro[2.4]hept-4-en-7-one<br>MS m/z 467 (M + H)+ |
| 816 | 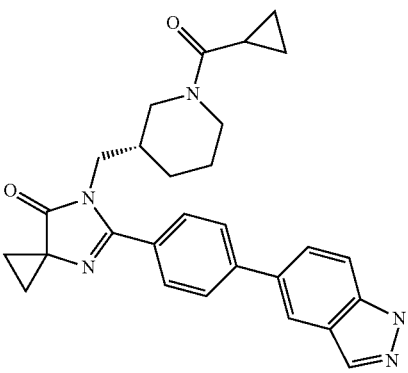 [SMILES: O=C(C1CC1)N1CCC[C@H](CN2C(=O)C3(CC3)N=C2c2ccc(-c3ccc4[nH]ncc4c3)cc2)C1] | (S)-5-(4-(1H-indazol-5-yl)phenyl)-6-((1-(cyclopropanecarbonyl)piperidin-3-yl)methyl)-4,6-diazaspiro[2.4]hept-4-en-7-one<br>MS m/z 468 (M + H)+ |
| 815 | 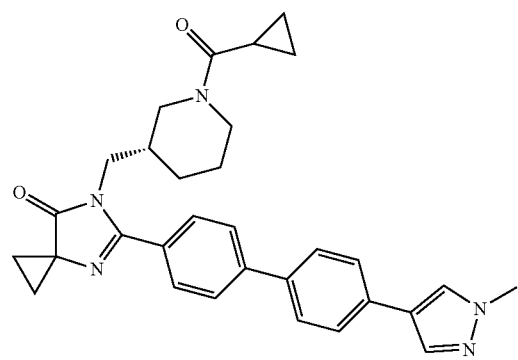 [SMILES: Cn1cc(-c2ccc(-c3ccc(C4=NC5(CC5)C(=O)N4C[C@H]4CCCN(C(=O)C5CC5)C4)cc3)cc2)cn1] | (S)-6-((1-(cyclopropanecarbonyl)piperidin-3-yl)methyl)-5-(4'-(1-methyl-1H-pyrazol-4-yl)-[1,1'-biphenyl]-4-yl)-4,6-diazaspiro[2.4]hept-4-en-7-one<br>MS m/z 508 (M + H)+ |

| ID No. | Structure | Compound Name & Physical Data |
|---|---|---|
| 813 | 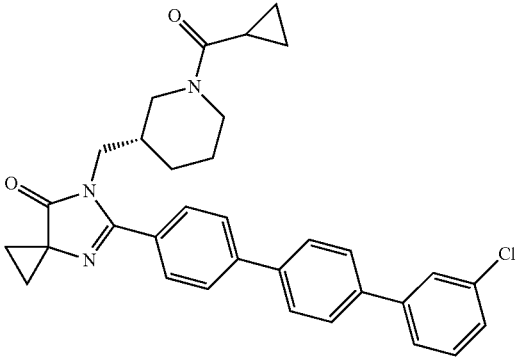 [SMILES: O=C(C1CC1)N1CCC[C@H](CN2C(=O)C3(CC3)N=C2c2ccc(-c3ccc(-c4cccc(Cl)c4)cc3)cc2)C1] | (S)-5-(3"-chloro-[1,1':4',1"-tertphenyl]-4-yl)-6-((1-(cyclopropanecarbonyl)piperidin-3-yl)methyl)-4,6-diazaspiro[2.4]hept-4-en-7-one<br>MS m/z 538 (M + H)+ |
| 812 | 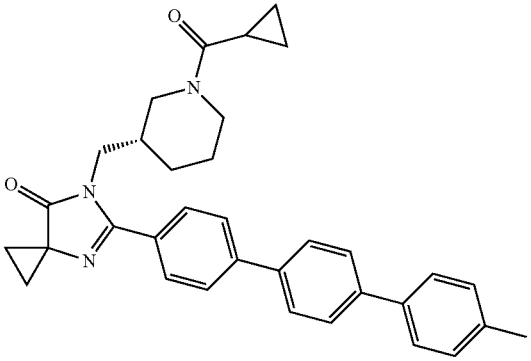 [SMILES: Cc1ccc(-c2ccc(-c3ccc(C4=NC5(CC5)C(=O)N4C[C@H]4CCCN(C(=O)C5CC5)C4)cc3)cc2)cc1] | (S)-6-((1-(cyclopropanecarbonyl)piperidin-3-yl)methyl)-5-(4"-methyl[1,1':4',1"-terphenyl]-4-yl)-4,6-diazaspiro[2.4]hept-4-en-7-one<br>MS m/z 518 (M + H)+ |
| 811 | 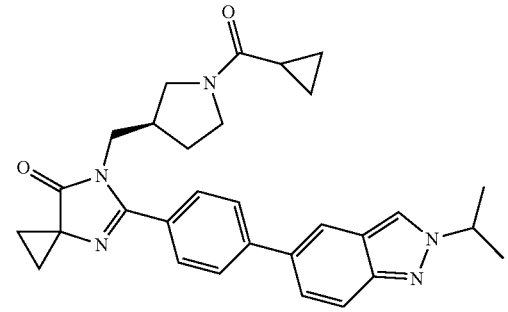 [SMILES: CC(C)n1cc2cc(-c3ccc(C4=NC5(CC5)C(=O)N4C[C@@H]4CCN(C(=O)C5CC5)C4)cc3)ccc2n1] | (R)-6-((1-(cyclopropanecarbonyl)pyrrolidin-3-yl)methyl)-5-(4-(2-isopropyl-2H-indazol-5-yl)phenyl)-4,6-diazaspiro[2.4]hept-4-en-7-one<br>MS m/z 496 (M + H)+ |
| 809 | 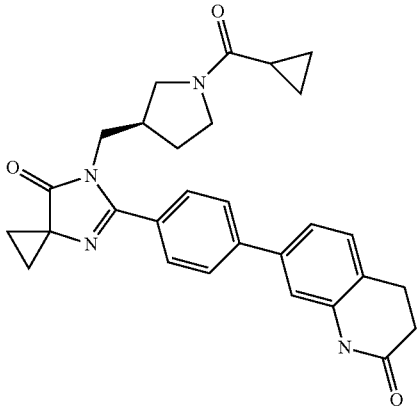 [SMILES: O=C1CCc2ccc(-c3ccc(C4=NC5(CC5)C(=O)N4C[C@@H]4CCN(C(=O)C5CC5)C4)cc3)cc2N1] | (R)-7-(4-(6-((1-(cyclopropanecarbonyl)pyrrolidin-3-yl)methyl)-7-oxo-4,6-diazaspiro[2.4]hept-4-en-5-yl)phenyl)-3,4-dihydroquinolin-2(1H)-one<br>MS m/z 483 (M + H)+ |

-continued

| ID No. | Structure | Compound Name & Physical Data |
|---|---|---|
| 802 | 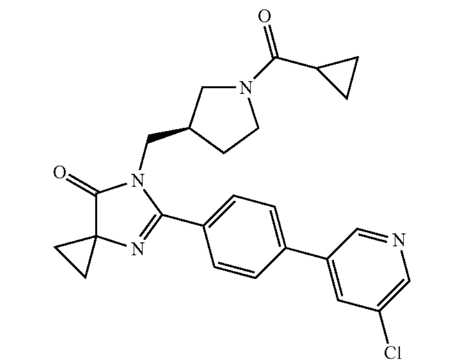 [SMILES: O=C(C1CC1)N1CC[C@@H](CN2C(=O)C3(CC3)N=C2c2ccc(-c3cncc(Cl)c3)cc2)C1] | (R)-5-(4-(5-chlorppyridin-3-yl)phenyl)-6-((1-(cyclopropanecarbonyl)pyrrolidin-3-yl)methyl)-4,6-diazaspiro[2.4]hept-4-en-7-one<br>MS m/z 449 (M + H)+ |
| 849 | 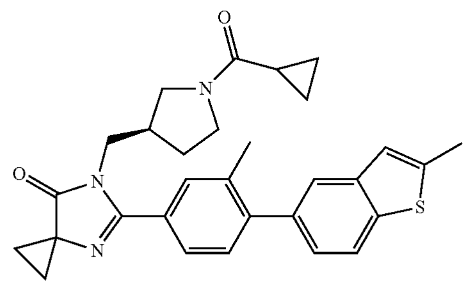 [SMILES: Cc1cc2cc(-c3ccc(C4=NC5(CC5)C(=O)N4C[C@@H]4CCN(C(=O)C5CC5)C4)cc3C)ccc2s1] | (R)-6-((1-(cyclopropanecarbonyl)pyrrolidin-3-yl)methyl)-5-(3-methyl-4-(2-methylbenzo[b]thiophen-5-yl)phenyl)-4,6-diazaspiro[2.4]hept-4-en-7-one<br>MS m/z 498 (M + H)+ |
| 850 | 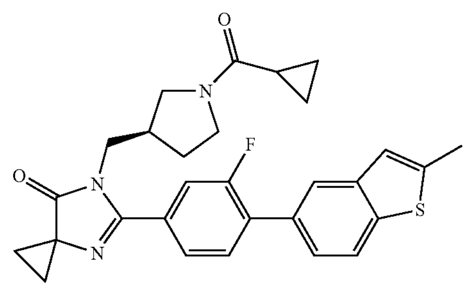 [SMILES: Cc1cc2cc(-c3ccc(C4=NC5(CC5)C(=O)N4C[C@@H]4CCN(C(=O)C5CC5)C4)cc3F)ccc2s1] | (R)-6-((1-(cyclopropanecarbonyl)pyrrolidin-3-yl)methyl)-5-(3-fluoro-4-(2-methylbenzo[b]thiophen-5-yl)phenyl)-4,6-diazaspiro[2.4]hept-4-en-7-one<br>MS m/z 502 (M + H)+ |
| 814 | 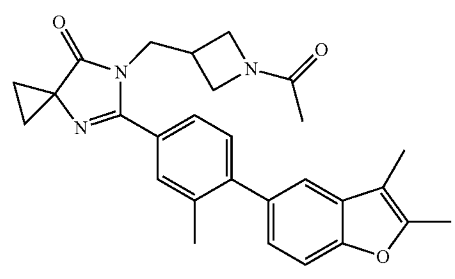 | 6-((1-(cyclopropanecarbonyl)azetidin-3-yl)methyl)-5-(4-(2,3-dimethylbenzofuran-5-yl)-3-methylphenyl)-4,6-diazaspiro[2.4]hept-4-en-7-one<br>MS m/z 482 (M + H)+ |
| 827 | 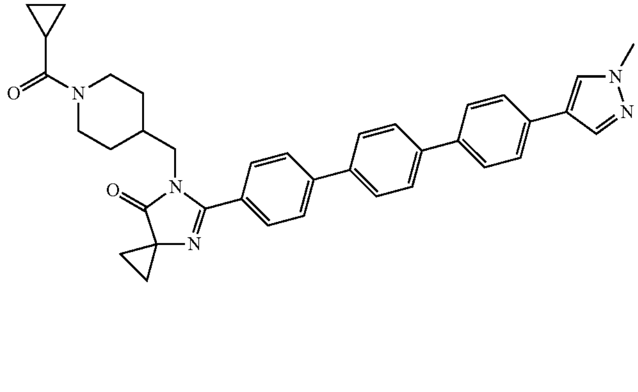 [SMILES: Cn1cc(-c2ccc(-c3ccc(-c4ccc(C5=NC6(CC6)C(=O)N5CC5CCN(C(=O)C6CC6)CC5)cc4)cc3)cc2)cn1] | 6-((1-cyclopropanecarbonyl)piperidin-4-yl)methyl)-5-(4''-methyl-(1-methyl-1H-pyrazol-4-yl)-[1,1':4',1''-terphenyl]-4-yl)-4,6-diazaspiro[2.4]hept-4-en-7-one<br>MS m/z 584 (M + H)+ |

| ID No. | Structure | Compound Name & Physical Data |
| --- | --- | --- |
| 836 | 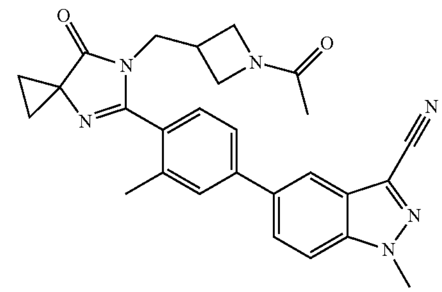 | 5-(4-(6-((1-(cyclopropanecarbonyl)azetidin-3-yl)methyl)-7-oxo-4,6-diazaspiro[2.4]hept-4-en-5-yl)-3-methylphenyl)-1-methyl-1H-indazole-3-carbonitrile<br>MS m/z 493 (M + H)+ |
| 847 | 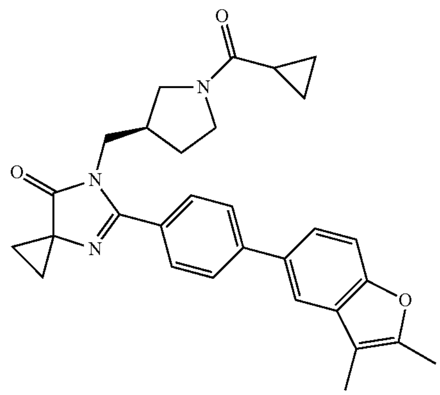 [SMILES: Cc1oc2ccc(-c3ccc(C4=NC5(CC5)C(=O)N4C[C@@H]4CCN(C(=O)C5CC5)C4)cc3)cc2c1C] | (R)-6-((1-(cyclopropanecarbonyl)pyrrolidin-3-yl)methyl)-5-(4-(2,3-dimethylbenzofuran-5-yl)phenyl)-4,6-diazaspiro[2.4]hept-4-en-7-one<br>MS m/z 482 (M + H)+ |
| 846 | 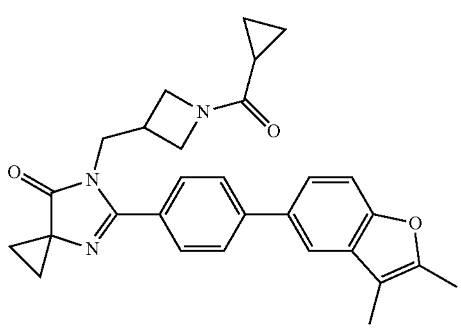 [SMILES: Cc1oc2ccc(-c3ccc(C4=NC5(CC5)C(=O)N4CC4CN(C(=O)C5CC5)C4)cc3)cc2c1C] | 6-((1-cyclopropanecarbonyl)azetidin-3-yl)methyl)-5-(4-(2,3-dimethylbenzofuran-5-yl)phenyl)-4,6-diazaspiro[2.4]hept-4-en-7-one<br>MS m/z 468 (M + H)+ |
| 806 | 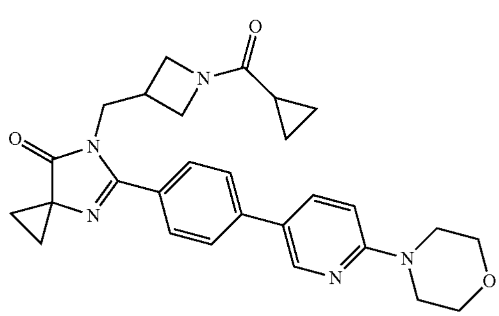 [SMILES: O=C(C1CC1)N1CC(CN2C(=O)C3(CC3)N=C2c2ccc(-c3ccc(N4CCOCC4)nc3)cc2)C1] | 6-((1-(cyclopropanecarbonyl)azetidin-3-yl)methyl)-5-(4-(6-morpholinopyridin-3-yl)phenyl)-4,6-diazaspiro[2.4]hept-4-en-7-one<br>MS m/z 486 (M + H)+ |

| ID No. | Structure | Compound Name & Physical Data |
|---|---|---|
| 807 | 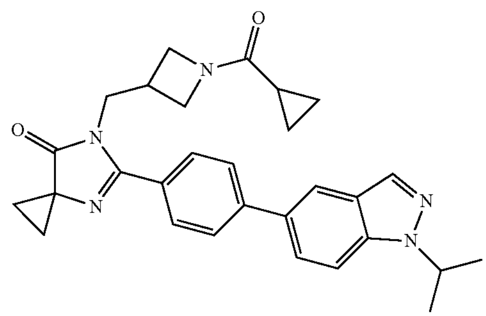 [SMILES: CC(C)n1ncc2cc(-c3ccc(C4=NC5(CC5)C(=O)N4CC4CN(C(=O)C5CC5)C4)cc3)ccc21] | 6-((1-(cyclopropanecarbonyl)azetidin-3-yl)methyl)-5-(4-(1-isopropyl-1H-indazol-5-yl)phenyl)-4,6-diazaspiro[2.4]hept-4-en-7-one<br>MS m/z 482 (M + H)+ |
| 808 | 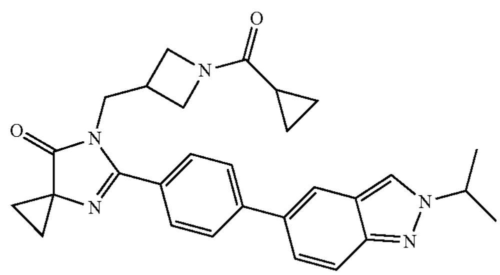 [SMILES: CC(C)n1cc2cc(-c3ccc(C4=NC5(CC5)C(=O)N4CC4CN(C(=O)C5CC5)C4)cc3)ccc2n1] | 6-((1-(cyclopropanecarbonyl)azetidin-3-yl)methyl)-5-(4-(2-isopropyl-2H-indazol-5-yl)phenyl)-4,6-diazaspiro[2.4]hept-4-en-7-one<br>MS m/z 482 (M + H)+ |
| 803 | 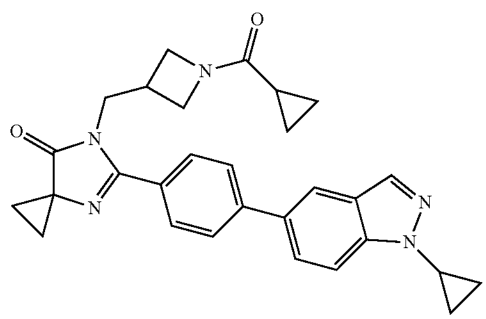 [SMILES: O=C(C1CC1)N1CC(CN2C(=O)C3(CC3)N=C2c2ccc(-c3ccc4c(cnn4C4CC4)c3)cc2)C1] | 6-((1-(cyclopropanecarbonyl)azetidin-3-yl)methyl)-5-(4-(1-cyclopropyl-1H-indazol-5-yl)phenyl)-4,6-diazaspiro[2.4]hept-4-en-7-one<br>MS m/z 480 (M + H)+ |
| 804 | 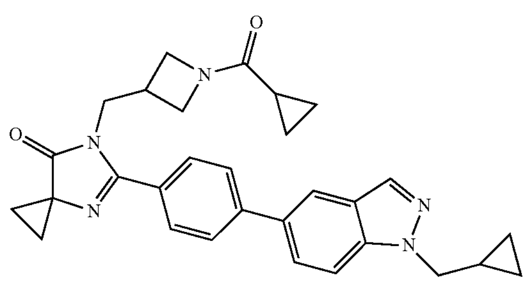 [SMILES: O=C(C1CC1)N1CC(CN2C(=O)C3(CC3)N=C2c2ccc(-c3ccc4c(cnn4CC4CC4)c3)cc2)C1] | 6-((1-(cyclopropanecarbonyl)azetidin-3-yl)methyl)-5-(4-(1-(cyclopropylmethyl)-1H-indazol-5-yl)phenyl)-4,6-diazaspiro[2.4]hept-4-en-7-one<br>MS m/z 494 (M + H)+ |
| 801 | 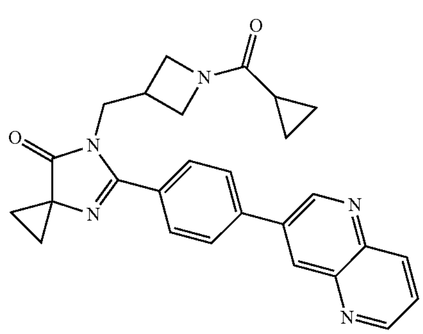 [SMILES: O=C(C1CC1)N1CC(CN2C(=O)C3(CC3)N=C2c2ccc(-c3cnc4cccnc4c3)cc2)C1] | 5-(4-(1,5-naphthyridin-3-yl)phenyl)-6-((1-(cyclopropanecarbonyl)azetidin-3-yl)methyl),4-6diazaspiro[2.4]hept-4-en-7-one<br>MS m/z 452 (M + H)+ |

-continued

| ID No. | Structure | Compound Name & Physical Data |
|---|---|---|
| 800 | 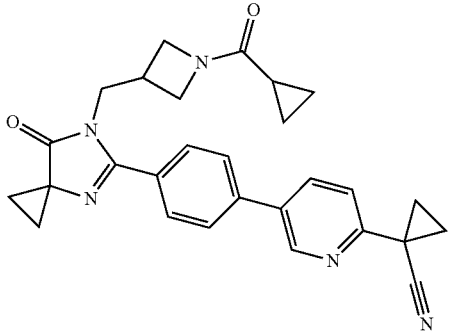 [SMILES: N#CC1(c2ccc(-c3ccc(C4=NC5(CC5)C(=O)N4CC4CN(C(=O)C5CC5)C4)cc3)cn2)CC1] | 1-(5-(4-(6-((1-(cyclopropanecarbonyl)azetidin-3-yl)methyl)-7-oxo-4,6-diazaspiro[2.4]hept-4-en-5-yl)phenyl)pyridin-2-yl)cyclopropanecarbonitrile<br>MS m/z 466 (M + H)+ |
| 797 | 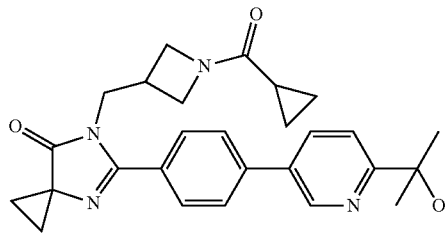 [SMILES: CC(C)(O)c1ccc(-c2ccc(C3=NC4(CC4)C(=O)N3CC3CN(C(=O)C4CC4)C3)cc2)cn1] | 6-((1-(cyclopropanecarbonyl)azetidin-3-yl)methyl)-5-(4-(6-(2-hydroxypropan-2-yl)pyridin-3-yl)phenyl)-4,6-diazaspiro[2.4]hept-4-en-7-one<br>MS m/z 459 (M + H)+ |
| 794 | 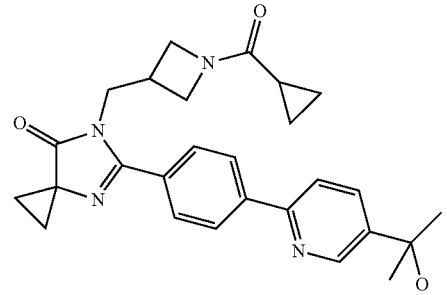 [SMILES: CC(C)(O)c1ccc(-c2ccc(C3=NC4(CC4)C(=O)N3CC3CN(C(=O)C4CC4)C3)cc2)nc1] | 6-((1-(cyclopropanecarbonyl)azetidin-3-yl)methyl)-5-(4-(5-(2-hydroxypropan-2-yl)pyridin-2-yl)phenyl)-4,6-diazaspiro[2.4]hept-4-en-7-one<br>MS m/z 459 (M + H)+ |
| 798 | 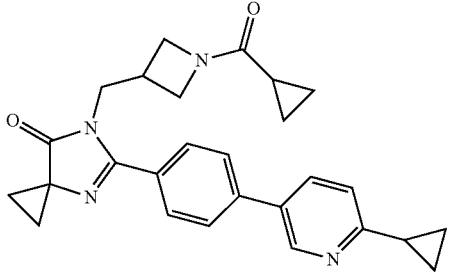 [SMILES: O=C(C1CC1)N1CC(CN2C(=O)C3(CC3)N=C2c2ccc(-c3ccc(C4CC4)nc3)cc2)C1] | 6-((1-(cyclopropanecarbonyl)azetidin-3-yl)methyl)-5-(4-(6-cyclopropylpyridin-3-yl)phenyl)-4,6-diazaspiro[2.4]hept-4-en-7-one<br>MS m/z 441 (M + H)+ |
| 842 | 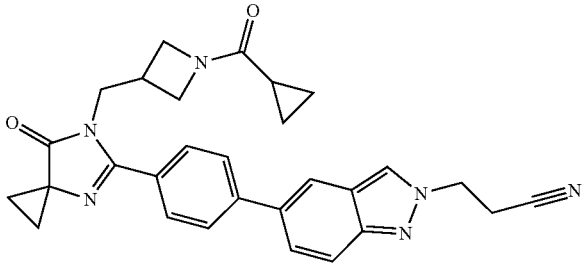 [SMILES: N#CCCn1cc2cc(-c3ccc(C4=NC5(CC5)C(=O)N4CC4CN(C(=O)C5CC5)C4)cc3)ccc2n1] | 3-(5-(4-(6-((1-(cyclopropanecarbonyl)azetidin-3-yl)methyl)-7-oxo-4,6-diazaspiro[2.4]hept-4-en-5-yl)phenyl)-2H-indazol-2-yl)propanenitrile<br>MS m/z 493 (M + H)+ |

| ID No. | Structure | Compound Name & Physical Data |
|---|---|---|
| 792 | 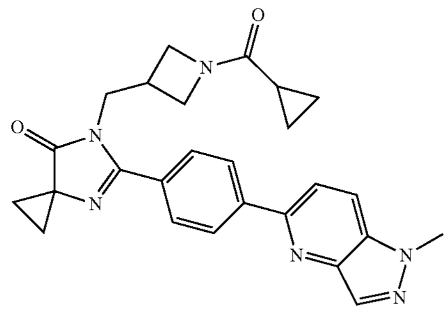 [SMILES: Cn1ncc2nc(-c3ccc(C4=NC5(CC5)C(=O)N4CC4CN(C(=O)C5CC5)C4)cc3)ccc21] | 6-((1-(cyclopropanecarbonyl)azetidin-3-yl)methyl)-5-(4-(1-methyl-1H-pyrazolo[4,3-b]pyridin-5-yl)phenyl)-4,6-diazaspiro[2.4]hept-4-en-7-one<br>MS m/z 455 (M + H)+ |
| 795 | 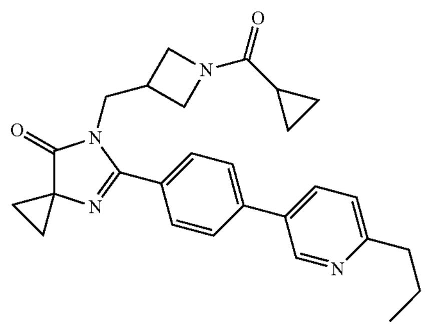 [SMILES: CCCc1ccc(-c2ccc(C3=NC4(CC4)C(=O)N3CC3CN(C(=O)C4CC4)C3)cc2)cn1] | 6-((1-(cyclopropanecarbonyl)azetidin-3-yl)methyl)-5-(4-(6-propylpyridin-3-yl)phenyl)-4,6-diazaspiro[2.4]hept-4-en-7-one<br>MS m/z 443 (M + H)+ |
| 838 | 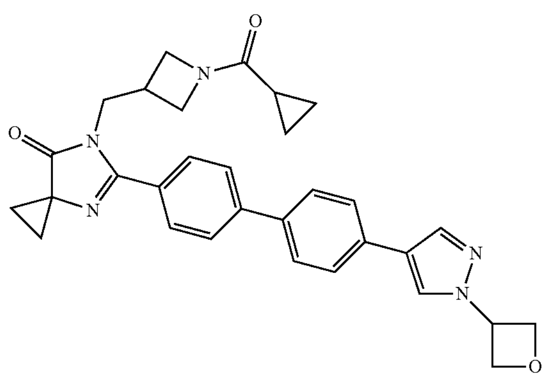 [SMILES: O=C(C1CC1)N1CC(CN2C(=O)C3(CC3)N=C2c2ccc(-c3ccc(-c4cnn(C5COC5)c4)cc3)cc2)C1] | 6-((1-(cyclopropanecarbonyl)azetidin-3-yl)methyl)-5-(4'-(1-(oxetan-3-yl)-1H-pyrazol-4-yl)-[1,1'-biphenyl]-4-yl)-4,6-diazaspiro[2.4]hept-4-en-7-one<br>MS m/z 522 (M + H)+ |
| 789 | 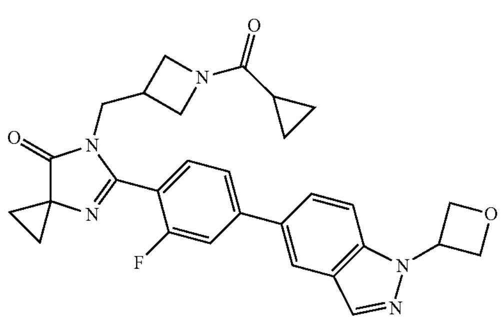 [SMILES: O=C(C1CC1)N1CC(CN2C(=O)C3(CC3)N=C2c2ccc(-c3ccc4c(cnn4C4COC4)c3)cc2F)C1] | 6-((1-(cyclopropanecarbonyl)azetidin-3-yl)methyl)-5-(2-fluoro-4-(1-(oxetan-3-yl)-1H-indazol-5-yl)phenyl)-4,6-diazaspiro[2.4]hept-4-en-7-one<br>MS m/z 514 (M + H)+ |

-continued

| ID No. | Structure | Compound Name & Physical Data |
|---|---|---|
| 788 | 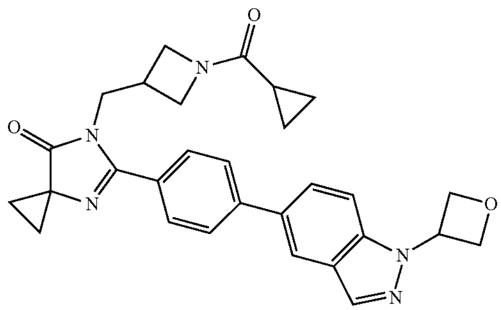 [SMILES: O=C(C1CC1)N1CC(CN2C(=O)C3(CC3)N=C2c2ccc(-c3ccc4c(cnn4C4COC4)c3)cc2)C1] | 6-((1-(cyclopropanecarbonyl)azetidin-3-yl)methyl)-5-(4-(1-(oxetan-3-yl)-1H-indazol-5-yl)phenyl)-4,6-diazaspiro[2.4]hept-4-en-7-one<br>MS m/z 496 (M + H)+ |
| 777 | 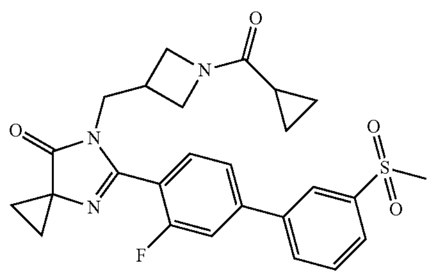 | 6-((1-(cyclopropanecarbonyl)azetidin-3-yl)methyl)-5-(3-fluoro-3'-(methylsulfonyl)-[1,1'-biphenyl]-4-yl)-4,6-diazaspiro[2.4]hept-4-en-7-one<br>MS m/z 496 (M + H)+ |
| 775 | 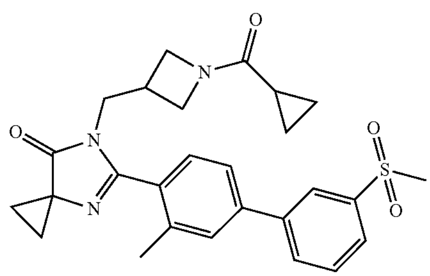 [SMILES: Cc1cc(-c2cccc(S(C)(=O)=O)c2)ccc1C1=NC2(CC2)C(=O)N1CC1CN(C(=O)C2CC2)C1] | 6-((1-(cyclopropanecarbonyl)azetidin-3-yl)methyl)-5-(3-methyl-3'-(methylsulfonyl)-[1,1'-biphenyl]-4-yl)-4,6-diazaspiro[2.4]hept-4-en-7-one<br>MS m/z 492 (M + H)+ |
| 776 | 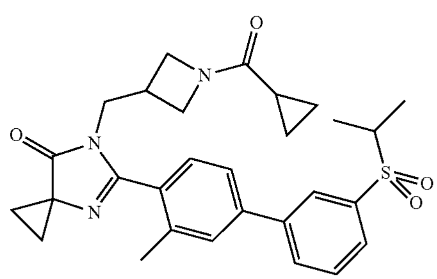 [SMILES: Cc1cc(-c2cccc(S(=O)(=O)C(C)C)c2)ccc1C1=NC2(CC2)C(=O)N1CC1CN(C(=O)C2CC2)C1] | 6-((1-(cyclopropanecarbonyl)azetidin-3-yl)methyl)-5-(3'-(isopropylsulfonyl)-3-methyl-[1,1'-biphenyl]-4-yl)-4,6-diazaspiro[2.4]hept-4-en-7-one<br>MS m/z 520 (M + H)+ |
| 841 | 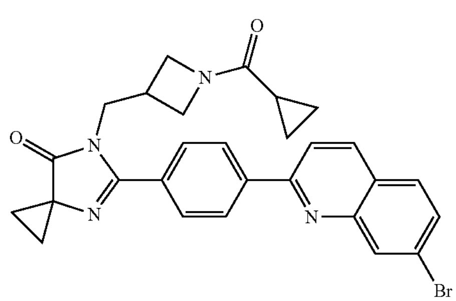 [SMILES: O=C(C1CC1)N1CC(CN2C(=O)C3(CC3)N=C2c2ccc(-c3ccc4ccc(Br)cc4n3)cc2)C1] | 5-(4-(7-bromoquinolin-2-yl)phenyl)-6-((1-(cyclopropanecarbonyl)azetidin-3-yl)methyl)-4,6-diazaspiro[2.4]hept-4-en-7-one<br>MS m/z 529 (M + H)+ |

-continued

| ID No. | Structure | Compound Name & Physical Data |
|---|---|---|
| 839 | 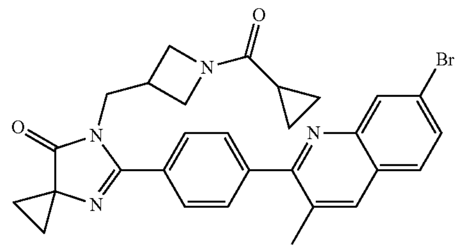 [SMILES: Cc1cc2ccc(Br)cc2nc1-c1ccc(C2=NC3(CC3)C(=O)N2CC2CN(C(=O)C3CC3)C2)cc1] | 5-(4-(7-bromo-3-methylquinolin-2-yl)phenyl)-6-((1-(cyclopropanecarbonyl)azetidin-3-yl)methyl)-4,6-diazaspiro[2.4]hept-4-en-7-one<br>MS m/z 543 (M + H)+ |
| 840 | 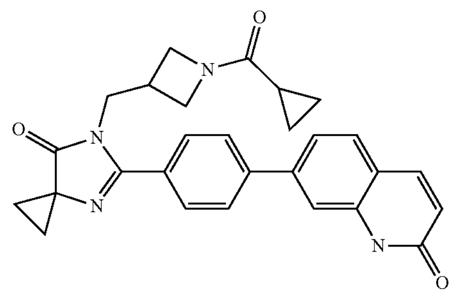 [SMILES: O=C(C1CC1)N1CC(CN2C(=O)C3(CC3)N=C2c2ccc(-c3ccc4ccc(=O)[nH]c4c3)cc2)C1] | 7-(4-(6-((1-(cyclopropanecarbonyl)azetidin-3-yl)methyl)-7-oxo-4,6-diazaspiro[2.4]hept-4-en-5-yl)quinolin-2(1H)-one<br>MS m/z 467 (M + H)+ |
| 793 | 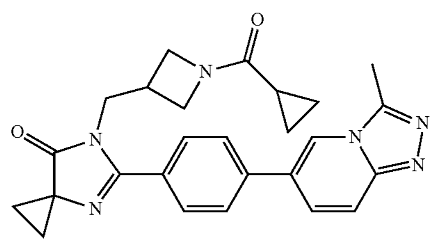 [SMILES: Cc1nnc2ccc(-c3ccc(C4=NC5(CC5)C(=O)N4CC4CN(C(=O)C5CC5)C4)cc3)cn12] | 6-((1-(cyclopropanecarbonyl)azetidin-3-yl)methyl)-5-(4-(3-methyl-[1,2,4]triazolo[4,3-a]pyridin-6-yl)phenyl)-4,6-diazaspiro[2.4]hept-4-en-7-one<br>MS m/z 455 (M + H)+ |
| 791 | 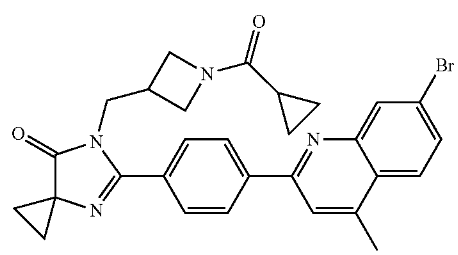 [SMILES: Cc1cc(-c2ccc(C3=NC4(CC4)C(=O)N3CC3CN(C(=O)C4CC4)C3)cc2)nc2cc(Br)ccc12] | 5-(4-(7-bromo-4-methylquinolin-2-yl)phenyl)-6-((1-(cyclopropanecarbonyl)azetidin-3-yl)methyl)4,6-diazaspiro[2.4]hept-4-en-7-one<br>MS m/z 543 (M + H)+ |
| 790 | 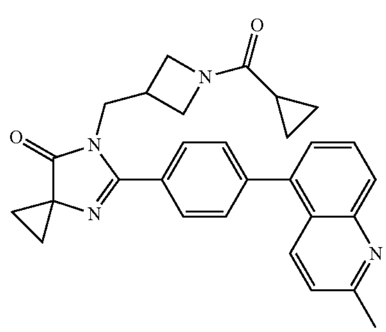 [SMILES: Cc1ccc2c(-c3ccc(C4=NC5(CC5)C(=O)N4CC4CN(C(=O)C5CC5)C4)cc3)cccc2n1] | 6-((1-(cyclopropanecarbonyl)azetidin-3-yl)methyl)-5-(4-(2-methy7lquinolin-5-yl)phenyl)-4,6-diazaspiro[2.4]jept-4-en-7-one<br>MS m/z 465 (M + H)+ |

| ID No. | Structure | Compound Name & Physical Data |
|---|---|---|
| 787 | 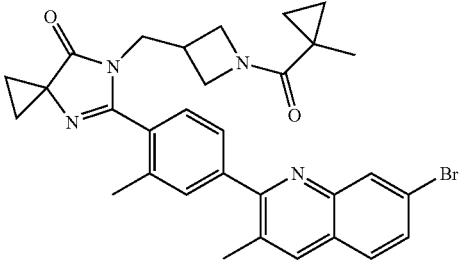 [SMILES: Cc1cc(-c2nc3cc(Br)ccc3cc2C)ccc1C1=NC2(CC2)C(=O)N1CC1CN(C(=O)C2(C)CC2)C1] | 5-(4-(7-bromo-3-methylquinolin-2-yl)-2-methylphenyl)-6-((1-(1-methylcyclopropanecarbonyl)azetidin-3-yl)methyl)-4,6-diazaspiro[2.4]hept-4-en-7-one<br>MS m/z 571 (M + H)+ |
| 786 | 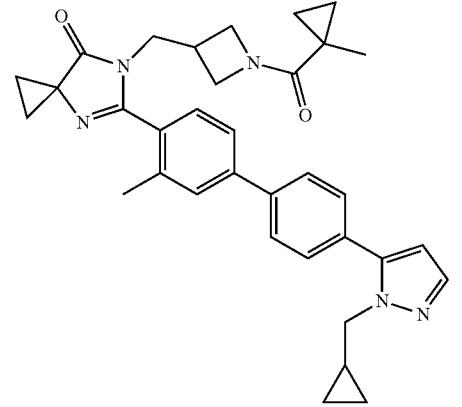 [SMILES: Cc1cc(-c2ccc(-c3ccnn3CC3CC3)cc2)ccc1C1=NC2(CC2)C(=O)N1CC1CN(C(=O)C2(C)CC2)C1] | 5-(4'-(1-(cyclopropylmethyl)-1H-pyrazol-5-yl)-3-methyl-[1,1'-biphenyl]-4-yl)-6-((1-(1-methylcyclopeopanecarbonyl)azetidin-3-yl)methyl)-4,6-diazaspiro[2.4]hept-4-en-7-one<br>MS m/z 548 (M + H)+ |
| 785 | 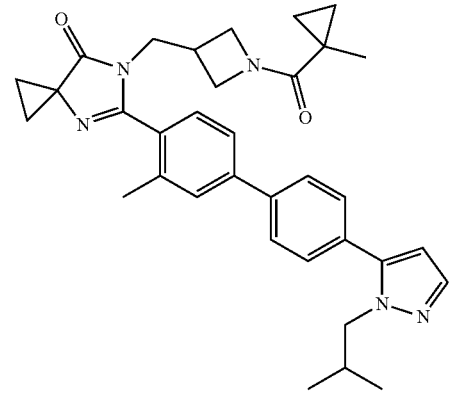 [SMILES: Cc1cc(-c2ccc(-c3ccnn3CC(C)C)cc2)ccc1C1=NC2(CC2)C(=O)N1CC1CN(C(=O)C2(C)CC2)C1] | 5-(4'-(1-isobutyl-1H-p[yrazol-5-yl)-3-methyl-[1,1'-biphenyl]-4-yl)-6-((1-(1-methylcyclopropanecarbonyl)azetidin-3-yl)methyl)-4,6-diazaspiro[2.4]hept-4-en-7-one<br>MS m/z 550 (M + H)+ |
| 784 | 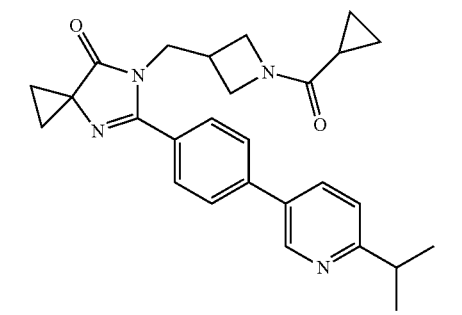 [SMILES: CC(C)c1ccc(-c2ccc(C3=NC4(CC4)C(=O)N3CC3CN(C(=O)C4CC4)C3)cc2)cn1] | 6-((1-(cyclopropanecarbonyl)azetidin-3-yl)methyl)-5-(4-(6-isopropylpyridin-3-yl)phenyl)-4,6-diazaspiro[2.4]hept-4-en-7-one<br>MS m/z 443 (M + H)+ |

-continued

| ID No. | Structure | Compound Name & Physical Data |
|---|---|---|
| 844 | 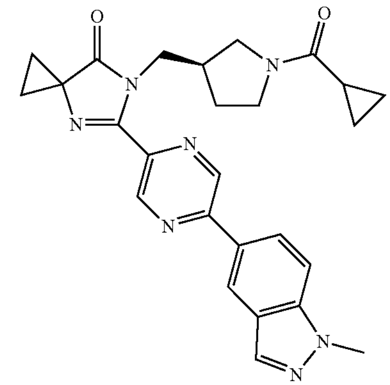 | (R)-6-((1-(cyclopropanecarbonyl)pyrrolidin-3-yl)methyl)-5-(5-(1-methyl-1H-indazol-5-yl)pyrazin)-4,6-diazaspiro[2.4]hept-4-en-7-one<br>MS m/z 443 (M + H)+ |
| 799 | 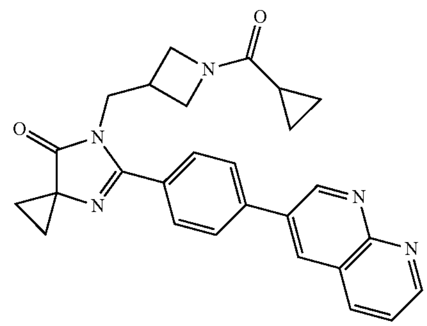 [SMILES: O=C(C1CC1)N1CC(CN2C(=O)C3(CC3)N=C2c2ccc(-c3cnc4ncccc4c3)cc2)C1] | 5-(4-(1,8-baphthyridin-3-yl)phenyl)-6-((1-(cyclopropanecarbonyl)azetidin-3-yl)methyl)-4,6-diazaspiro[2.4]hept-4-en-7-one<br>MS m/z 452 (M + H)+ |
| 837 | 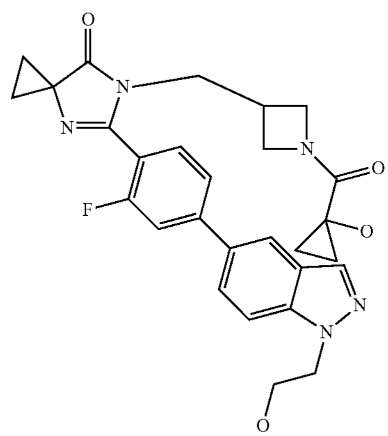 [SMILES: O=C(N1CC(CN2C(=O)C3(CC3)N=C2c2ccc(-c3ccc4c(cnn4CCO)c3)cc2F)C1)C1(O)CC1] | 5-(2-fluoro-4-(1-(2-hydroxyethyl)-1H-indazol-5-yl)phenyl)-6-((1-(1-hydroxycyclopropanecarbonyl)azetidin-3-yl)methyl)-4,6-diazaspiro[2.4]hept-4-en-7-one<br>MS m/z 518 (M + H)+ |
| 834 | 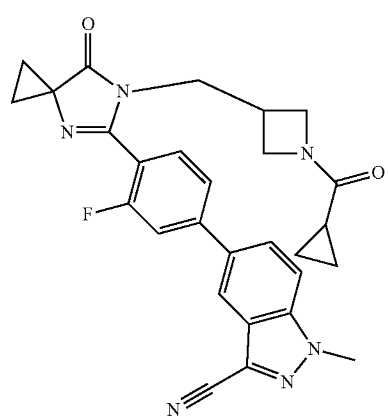 [SMILES: Cn1nc(C#N)c2cc(-c3ccc(C4=NC5(CC5)C(=O)N4CC4CN(C(=O)C5CC5)C4)c(F)c3)ccc21] | 5-(4-(6-((1-(cyclopropanecarbonyl)azetidin-3-yl)methyl)-7-oxo-4,6-diazaspiro[2.4]hept-4-en-5-yl)-3-fluorophenyl)-1-methyl-1H-indazole-3-carbonitrile<br>MS m/z 497 (M + H)+ |

-continued

| ID No. | Structure | Compound Name & Physical Data |
|---|---|---|
| 783 | 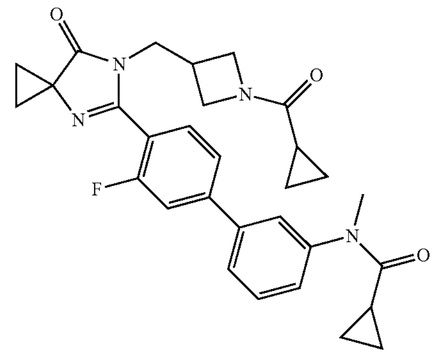 [SMILES: CN(C(=O)C1CC1)c1cccc(-c2ccc(C3=NC4(CC4)C(=O)N3CC3CN(C(=O)C4CC4)C3)c(F)c2)c1] | N-(4'-(6-((1-(cyclopropanecarbonyl)azetidin-3-yl)methyl)-7-oxo-4,6-diazaspiro[2.4]hept-4-en-5-yl)-3'-fluoro-[1,1'-biphenyl]-3-yl)-N-methylcyclopropanecarboxamide<br>MS m/z 515 (M + H)+ |
| 778 | 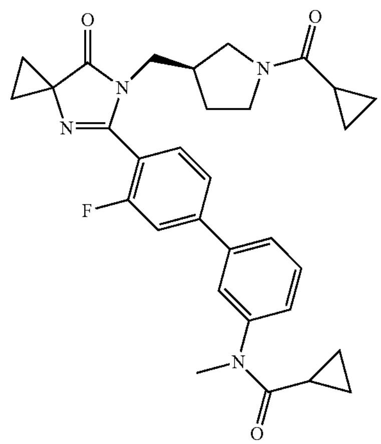 [SMILES: CN(C(=O)C1CC1)c1cccc(-c2ccc(C3=NC4(CC4)C(=O)N3C[C@@H]3CCN(C(=O)C4CC4)C3)c(F)c2)c1] | (R)-N-(4'-(6-((1-(cyclopropanecarbonyl)pyrrolidin-3-yl)methyl)-7-oxo-4,6-diazaspiro[2.4]hept-4-en-5-yl)-3'-fluoro-[1,1'-biphenyl]-3-yl)-N-methylcyclopropanecarboxamide<br>MS m/z 529 (M + H)+ |
| 782 | 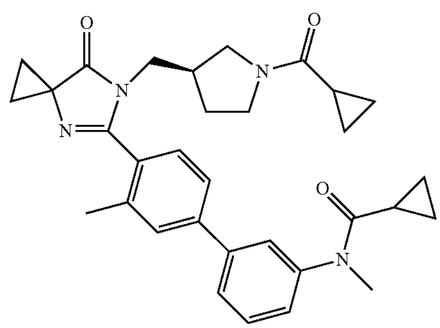 [SMILES: Cc1cc(-c2cccc(N(C)C(=O)C3CC3)c2)ccc1C1=NC2(CC2)C(=O)N1C[C@@H]1CCN(C(=O)C2CC2)C1] | (R)-N-(4'-(6-((1-(cyclopropanecarbonyl)pyrrolidin-3-yl)methyl)-7-oxo-4,6-diazaspiro[2.4]hept-4-en-5-yl)-3'-methyl-[1,1'-biphenyl]-3-yl)-N-methylcyclopropanecarboxamide<br>MS m/z 525 (M + H)+ |
| 779 | 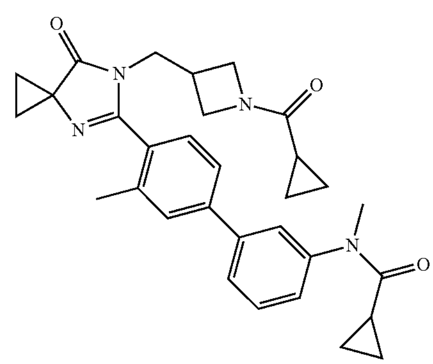 [SMILES: Cc1cc(-c2cccc(N(C)C(=O)C3CC3)c2)ccc1C1=NC2(CC2)C(=O)N1CC1CN(C(=O)C2CC2)C1] | N-(4'-(6-((1-(cyclopropanecarbonyl)azetidin-3-yl)methyl)-7-oxo-4,6-diazaspiro[2.4]hept-4-en-5-yl)-3'-methyl-[1,1'-biphenyl]-3-yl)-N-methylcyclopropanecarboxamide<br>MS m/z 511 (M + H)+ |

-continued

| ID No. | Structure | Compound Name & Physical Data |
|---|---|---|
| 780 | 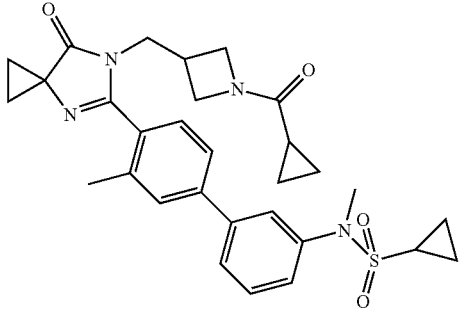 [SMILES: Cc1cc(-c2cccc(N(C)S(=O)(=O)C3CC3)c2)ccc1C1=NC2(CC2)C(=O)N1CC1CN(C(=O)C2CC2)C1] | N-(4'-(6-((1-(cyclopropanecarbonyl)azetidin-3-yl)methyl)-7-oxo-4,6-diazaspiro[2.4]hept-4-en-5-yl)-3'-methyl-[1,1'-biphenyl]-3-yl)-N-methylcyclopropanecarboxamide<br>MS m/z 547 (M + H)+ |
| 781 | 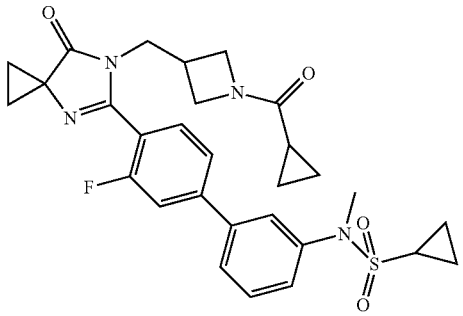 [SMILES: CN(c1cccc(-c2ccc(C3=NC4(CC4)C(=O)N3CC3CN(C(=O)C4CC4)C3)c(F)c2)c1)S(=O)(=O)C1CC1] | N-(4'-(6-((1-(cyclopropanecarbonyl)azetidin-3-yl)methyl)-7-oxo-4,6-diazaspiro[2.4]hept-4-en-5-yl)-3'-fluoro-[1,1'-biphenyl]-3-yl)-N-methylcyclopropanecarboxamide<br>MS m/z 551 (M + H)+ |
| 855 | 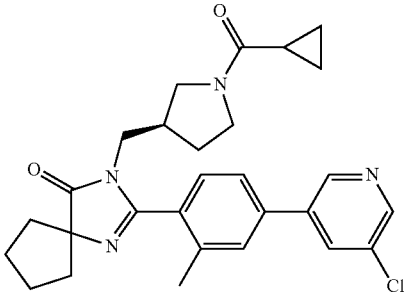 [SMILES: Cc1cc(-c2cncc(Cl)c2)ccc1C1=NC2(CCCC2)C(=O)N1C[C@@H]1CCN(C(=O)C2CC2)C1] | (R)-2-(4-(5-chloropyridin-3-yl)-2-methylphenyl)-3-((1-(cyclopropanecarbonyl)pyrrolidin-3-yl)methyl)-1,3-diazaspiro[4.4]non-1-rn-4-one<br>MS m/z 491.2 (M + H)+ |
| 867 | 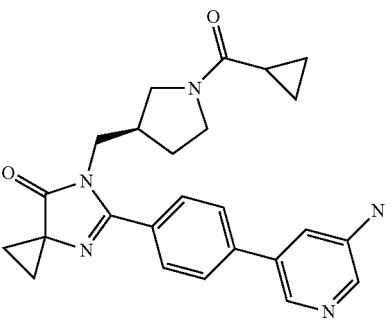 [SMILES: Nc1cncc(-c2ccc(C3=NC4(CC4)C(=O)N3C[C@@H]3CCN(C(=O)C4CC4)C3)cc2)c1] | (R)-5-(4-(5-aminopyridi9n-3-yl)phenyl)-6-((1-(cyclopropanecarbonyl)pyrrolidin-3-yl)methyl)-4,6-diazaspiro[2.4]hept-4-en-7-one<br>MS m/z 430 (M + H)+ |
| 859 | 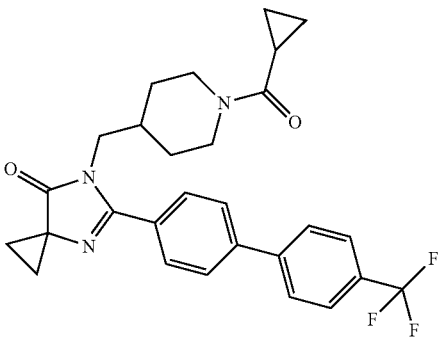 [SMILES: O=C(C1CC1)N1CCC(CN2C(=O)C3(CC3)N=C2c2ccc(-c3ccc(C(F)(F)F)cc3)cc2)CC1] | 6-((1-(cyclopropanecarbonyl)piperidin-4-yl)methyl)-5-(4'-(trifluoromethyl)-[1,1'-biphenyl]-4-yl)-4,6-diazaspiro[2.4]hept-4-en-7-one<br>MS m/z 496 (M + H)+ |

| ID No. | Structure | Compound Name & Physical Data |
|---|---|---|
| 868 | 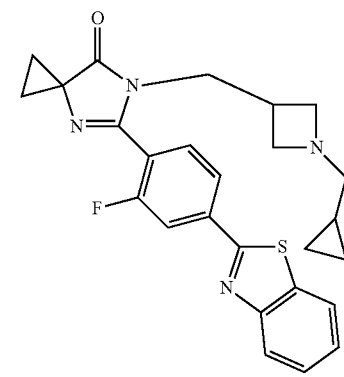 | 5-(4-benzo[d]thiazol-2-yl)-2-fluorophenyl)-6-((1-(cyclopropanecarbonyl)azetidin-3-yl)methyl)-4,6-diazaspiro[2.4]hept-4-en-7-one<br>$^1$H NMR (300 MHz, CHLOROFORM-d) δ ppm 0.62 (dd, J = 7.4, 3.3 Hz, 2 H), 0.76-0.89 (m, 2 H), 1.21 (td, J = 7.9, 4.1 Hz, 1 H), 1.69-1.79 (m, 2 H), 1.79-1.91 (m, 2 H), 2.66-2.85 (m, 1 H), 3.48 (dd, J = 9.7, 5.7 Hz, 1 H), 3.63-3.77 (m, 1 H), 3.78-3.98 (m, 3 H), 4.17 (t, J = 8.3 Hz, 1 H), 7.39 (t, J = 7.5 Hz, 1 H), 7.49 (t, J = 7.5 Hz, 1 H), 7.61 (t, J = 7.5 Hz, 1 H), 7.89 (d, J = 7.8 Hz, 1 H), 7.92-8.01 (m, 2 H), 8.05 (d, J = 8.1 Hz, 1 H). MS m/z 541.3 (M + H)+ |
| 869 | 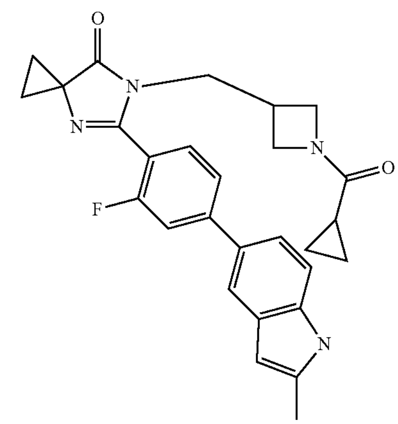 | 6-((1-(cyclopropanecarbonyl)azetidin-3-yl)methyl)-5-(2-fluoro-4-(2-methyl-1H-indol-5-yl)phenyl)-4,6-diazaspiro[2.4]hept-4-en-7-one<br>$^1$H NMR (300 MHz, CHLOROFORM-d) δ ppm 0.51-0.66 (m, 2 H), 0.77-0.87 (m, 2 H), 1.18-1.27 (m, 1 H), 1.66-1.76 (m, 2 H), 1.76-1.86 (m, 2 H), 2.42 (s, 3 H), 2.69-2.88 (m, 1 H), 3.47-3.58 (m, 1 H), 3.68-3.80 (m, 1 H), 3.80-3.91 (m, 2 H), 3.94 (s, 1 H), 4.16 (t, J = 8.3 Hz, 1 H), 6.23 (s, 1 H), 7.30 (s, 2 H), 7.37-7.56 (m, 3 H), 7.70 (s, 1 H), 7.97 (br. s., 1 H). MS m/z 541.3 (M + H)+ |
| 870 | 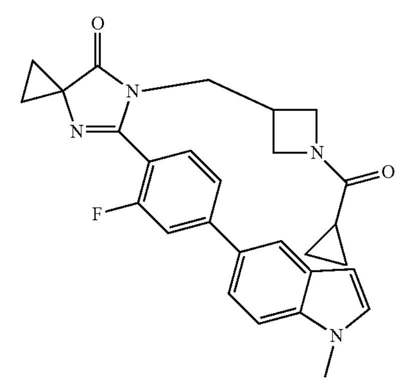 | 6-((1-(cyclopropanecarbonyl)azetidin-3-yl)methyl)-5-(2-fluoro-4-(1-methyl-1H-indol-5-yl)phenyl)-4,6-diazaspiro[2.4]hept-4-en-7-one<br>$^1$H NMR (300 MHz, CHLOROFORM-d) δ ppm 0.60 (br. s., 2 H), 0.81 (br. s., 2 H), 1.21 (br. s., 1 H), 1.72 (br. s., 2 H), 1.80 (br. s., 2 H), 2.67-2.90 (m, 1 H), 3.43-3.59 (m, 1 H), 3.71 (br. s., 1 H), 3.77 (s, 3 H), 3.83 (d, J = 8.2 Hz, 3 H), 4.16 (br. s., 1 H), 6.49 (br. s., 1 H), 6.98-7.12 (m, 1 H), 7.28-7.61 (m, 5 H), 7.81 (br. s., 1 H). MS m/z 527.2 (M + H)+ |
| 871 | 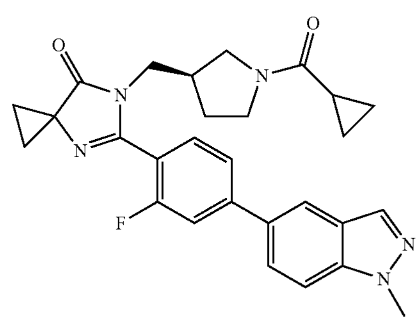 | (R)-6-((1-(cyclopropanecarbonyl)pyrrolidin-3-yl)methyl)-5-(2-fluoro-4-(1-methyl-1H-indazol-5-yl)phenyl)-4,6-diazaspiro[2.4]hept-4-en-7-one<br>$^1$H NMR (300 MHz, CHLOROFORM-d) δ ppm 0.64-0.76 (m, 2 H), 0.85-0.99 (m, 2 H), 1.42-1.55 (m, 1.5 H), 1.59-1.73 (m, 0.5 H), 1.76-1.84 (m, 2 H), 1.86-1.92 (m, 2 H), 1.94-2.06 (m, 1 H), 2.35-2.51 (m, 1 H), 2.99 (dd, J = 12.0, 7.3 Hz, 0.5 H), 3.16-3.38 (m, 1 H), 3.44-3.68 (m, 3 H), 3.68-3.76 (m, 1.5 H), 4.13 (s, 3 H), 7.43-7.55 (m, 2 H), 7.55-7.70 (m, 3 H), 7.98 (s, 1 H), 8.07 (s, 1 H). MS m/z 509.9 (M + H)+ |

| ID No. | Structure | Compound Name & Physical Data |
|---|---|---|
| 872 | 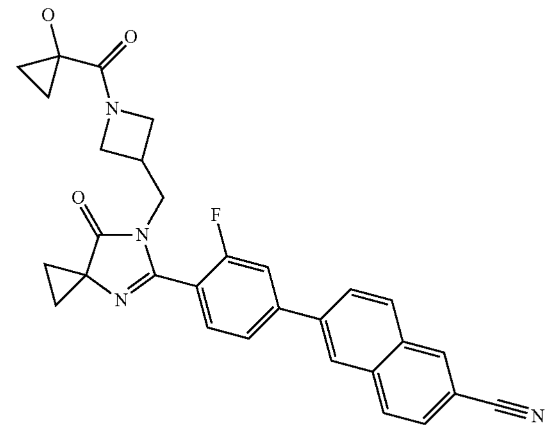 [SMILES: N#Cc1ccc2cc(-c3ccc(C4=NC5(CC5)C(=O)N4CC4CN(C(=O)C5(O)CC5)C4)c(F)c3)ccc2c1] | 6-(3-fluoro-4-(6-((1-(1-hydroxycyclopropanecarbonyl)azetidin-3-yl)methyl)-7-oxo-4,6-diazaspiro[2.4]hept-4-en-5-yl)phenyl)-2-naphthonitrile<br>¹H NMR (300 MHz, CHLOROFORM-d) δ ppm 0.85 (br. s., 2 H), 1.15 (d, J = 7.0 Hz, 2 H), 1.67-1.78 (m, 2 H), 1.78-1.89 (m, 2 H), 2.37 (br. s., 1 H), 2.77 (br. s., 1 H), 3.57 (br. s., 1 H), 3.71-3.88 (m, 2 H), 4.00 (br. s., 2 H), 4.35 (br. s., 1 H), 7.52 (d, J = 10.7 Hz, 1 H), 7.56-7.66 (m, 3 H), 7.76-7.84 (m, 1 H), 7.90-8.00 (m, 2 H), 8.06 (s, 1 H), 8.22 (s, 1 H). MS m/z 509 (M + H)+ |
| 873 | 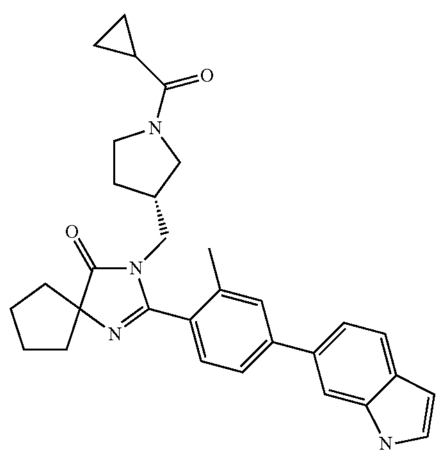 | (R)-2-(4-(1H-indol-6-yl)-2-methylphenyl)-3-((1-(cyclopropanecarbonyl)pyrrolidin-3-yl)methyl)-1,3-diazaspiro[4.4]non-1-en-4-one<br>¹H NMR (400 MHz, CHLOROFORM-d) δ ppm 0.65-0.79 (m, 2 H), 0.87-1.02 (m, 2 H), 1.44-1.55 (m, 1.5 H), 1.60-1.68 (m, 1.5 H), 1.68 (br. s., 0.5 H), 1.93-2.05 (m, 4 H), 2.06-2.20 (m, 4 H), 2.42 (s, 3 H), 2.44-2.52 (m, 0.5 H), 3.01 (dd, J = 11.9, 6.8 Hz, 0.5 H), 3.13-3.23 (m, 0.5 H), 3.27-3.44 (m, 1 H), 3.46-3.70 (m, 4 H), 6.60 (br. s., 1 H), 7.29 (d, J = 4.0 Hz, 1 H), 7.34-7.44 (m, 2 H), 7.53-7.64 (m, 3 H), 77.3 (dd, J = 8.3, 3.3 Hz, 1 H), 8.64 (s, 0.5 H), 8.62 (s, 0.5 H). MS m/z 595.3 (M + H)+ |
| 874 | 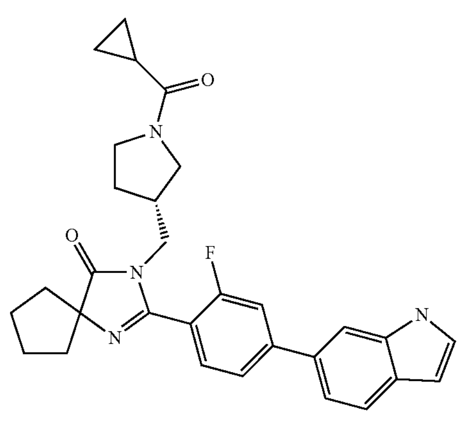 [SMILES: O=C(C1CC1)N1CC[C@@H](CN2C(=O)C3(CCCC3)N=C2c2ccc(-c3ccc4cc[nH]c4c3)cc2F)C1] | (R)-3-((1-(cyclopropanecarbonyl)pyrrolidin-3-yl)methyl)-2-(2-fluoro-4-(1H-indol-6-yl)phenyl)-1,3-diazaspiro[4.4]non-1-en-4-one<br>¹H NMR (400 MHz, CHLOROFORM-d) δ ppm 0.63-0.77 (m, 2 H), 0.83-0.96 (m, 2 H), 1.35-1.49 (m, 1.5 H), 1.56 (dd, J = 12.6, 7.6 Hz, 0.5 H), 1.78-1.89 (m, 0.5 H), 1.89-2.08 (m, 5 H), 2.14 (br. s., 4 H), 2.30-2.45 (m, 0.5 H), 2.45-2.59 (m, 0.5 H), 2.97 (dd, J = 12.4, 7.3 Hz, 0.5 H), 3.17 (t, J = 8.8 Hz, 0.5 H), 3.28 (d, J = 11.6 Hz, 0.5 H), 3.42-3.54 (m, 1.5 H), 3.60-3.74 (m, 2.5 H), 6.53 (br. s., 1 H), 7.25 (br. s., 1 H), 7.29 (d, J = 8.6 Hz, 1 H), 7.48 (s, 0.5 H), 7.45 (s, 0.5 H), 7.58 (br. s., 2 H), 7.63-7.72 (m, 2 H), 8.41 (br. s., 1 H)<br>MS m/z 499.2 (M + H)+ |

| ID No. | Structure | Compound Name & Physical Data |
|---|---|---|
| 875 | 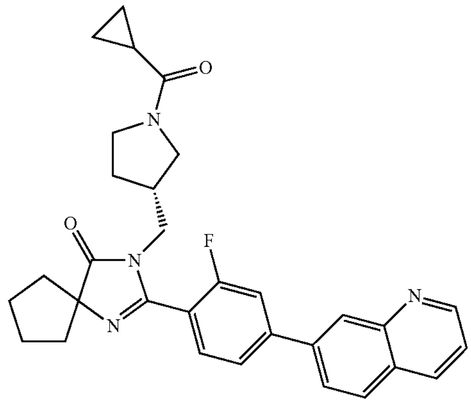 [SMILES: O=C(C1CC1)N1CC[C@@H](CN2C(=O)C3(CCCC3)N=C2c2ccc(-c3ccc4cccnc4c3)cc2F)C1] | (R)-3-((1-(cyclopropanecarbonyl)pyrrolidin-3-yl)methyl)-2-(2-fluoro-4-(quinolin-7-yl)phenyl)-1,3-diazaspiro[4.4]non-1-en-4-one<br>$^1$H NMR (400 MHz, CHLOROFORM-d) δ ppm 0.65-0.78 (m, 2 H), 0.87-1.02 (m, 2 H), 1.44-1.56 (m, 1.5 H), 1.58-1.71 (m, 0.5 H), 1.80-1.91 (m, 1 H), 1.95-2.13 (m, 8 H), 2.41 (dt, J = 14.4, 7.5 Hz, 0.5 H), 2.47-2.59 (m, 0.5 H), 3.00 (dd, J = 11.9, 7.3 Hz, 0.5 H), 3.19-3.27 (m, 0.5 H), 3.32 (dt, J = 12.0, 7.9 Hz, 0.5 H), 3.48-3.59 (m, 2 H), 3.60-3.72 (m, 2.5 H), 7.49 (dd, J = 8.1, 4.0 Hz, 1 H), 7.57-7.65 (m, 1 H), 7.65-7.76 (m, 2 H), 7.81-7.87 (m, 1 H), 7.98 (d, J = 8.6 Hz, 1 H), 8.25 (d, J = 8.1 Hz, 1 H), 8.39 (s, 1 H), 8.94-9.10 (m, 1 H). MS m/z 511.2 (M + H)+ |
| 876 | 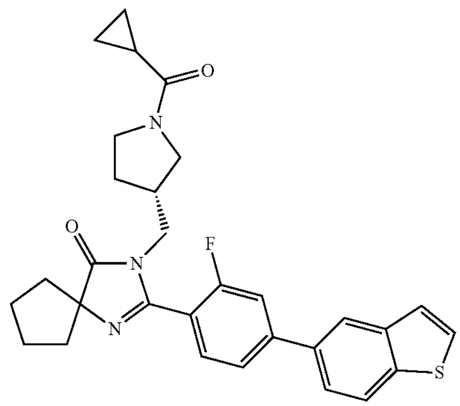 [SMILES: O=C(C1CC1)N1CC[C@@H](CN2C(=O)C3(CCCC3)N=C2c2ccc(-c3ccc4sccc4c3)cc2F)C1] | (R)-2-(4-(benzo[b]thiophen-5-yl)-2-fluorophenyl)-3-((1-(cyclopropanecarbonyl)pyrrolidin-3-yl)methyl)-1,3-diazaspiro{4.4[non-1-en-4-one<br>$^1$H NMR (400 MHz, CHLOROFORM-d) δ ppm 0.64-0.77 (m, 2 H), 0.91 (br. s., 2 H), 1.39-1.48 (m, 1.5 H), 1.56 (dd, J = 12.9, 7.8 Hz, 0.5 H), 1.78-1.88 (m, 0.5 H), 1.90-2.06 (m, 4.5 H), 2.13 (br. s., 4 H), 2.31-2.41 (m, 0.5 H), 2.42-2.57 (m, 0.5 H), 2.97 (dd, J = 12.1, 7.6 Hz, 0.5 H), 3.13-3.21 (m, 0.5 H), 3.22-3.33 (m, 0.5 H), 3.44-3.54 (m, 1.5 H), 3.55-3.72 (m, 3 H), 7.35 (d, J = 5.1 Hz, 1 H), 7.45-7.54 (m, 3 H), 7.61 (d, J = 7.1 Hz, 1 H), 7.68-7.77 (m, 1 H), 7.92 (d, J = 8.6 Hz, 1 H), 8.00 (s, 1 H). MS m/z 516.2 (M + H)+ |
| 877 | 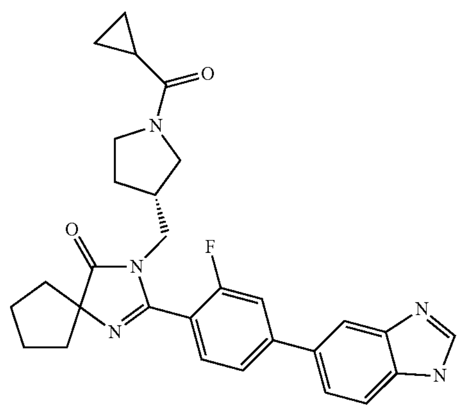 [SMILES: O=C(C1CC1)N1CC[C@@H](CN2C(=O)C3(CCCC3)N=C2c2ccc(-c3ccc4[nH]cnc4c3)cc2F)C1] | (R)-2-(4-(1H-benzo[d]imidazol-5-yl)-21-fluorophenyl)-3-((1-(cyclopropanecarbonyl)pyrrolidin-3-yl)methyl)-1,3-diazaspiro[4.4]non-1-en-4-one<br>$^1$H NMR (400 MHz, CHLOROFORM-d) δ ppm 0.60-0.72 (m, 2 H), 0.78-0.93 (m, 2 H), 1.31-1.49 (m, 1.5 H), 1.57 (dd, J = 12.6, 8.1 Hz, 0.5 H), 1.76 (dd, J = 10.9, 5.3 Hz, 0.5 H), 1.82-2.07 (m, 8.5 H), 2.23-2.38 (m, 0.5 H), 2.38-2.51 (m, 0.5 H), 2.89 (dd, J = 11.9, 7.3 Hz, 0.5 H), 3.10-3.27 (m, 1 H), 3.37=3.49 (m, 2 H), 3.50-3.63 (m, 2.5 H), 7.30-7.53 (m, 4 H), 7.58-7.70 (m, 2 H), 8.06 (s, 1 H). MS m/z 500.2 (M + H)+ |
| 878 | 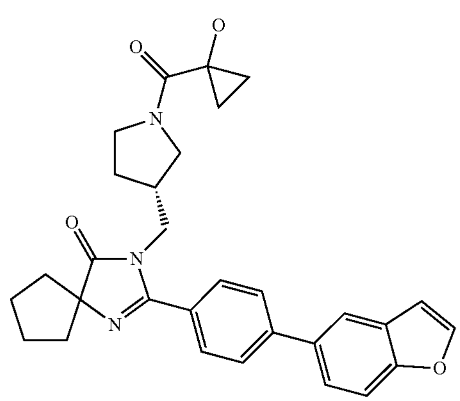 [SMILES: O=C(N1CC[C@@H](CN2C(=O)C3(CCCC3)N=C2c2ccc(-c3ccc4occc4c3)cc2)C1)C1(O)CC1] | (R)-2-(4-(benzofuran-5-yl)phenyl)-3-((1-(1-hydroxycyclopropanecarbonyl)pyrrolidin-3-yl)methyl)-1,3-diazaspiro[4.4]non-1-en-4-one<br>$^1$H NMR (400 MHz, CHLOROFORM-d) δ ppm 0.90-1.01 (m, 2 H), 1.17 (br. s., 2 H), 1.51 (br. s., 0.5 H), 1.65 (br. s., 0.5 H), 1.90-2.11 (m, 5 H), 2.14-2.33 (m, 4 H), 2.49 (br. s., 1 H), 3.09 (br. s., 0.5 H), 3.44 (br. ., 0.5 H), 3.50 (s, 1.5 H), 3.72 (br. s., 0.5 H), 3.92 (d, J = 7.3 Hz, 3 H), 6.85 (d, J = 1.5 Hz, 1 H), 7.57 (d, J = 2.0 Hz, 1 H), 7.58-7.64 (m, 1 H), 7.70 (d, J = 2.2 Hz, 1 H), 7.79-7.89 (m, 5 H). MS m/z 498.2 (M + H)+ |

| ID No. | Structure | Compound Name & Physical Data |
|---|---|---|
| 879 | 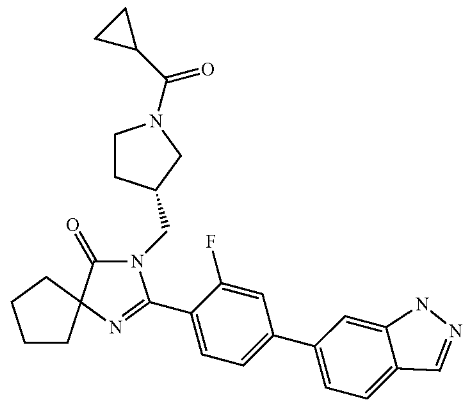 [SMILES: O=C(C1CC1)N1CC[C@@H](CN2C(=O)C3(CCCC3)N=C2c2ccc(-c3ccc4cn[nH]c4c3)cc2F)C1] | (R)-3-((1-(cyclopropanecarbonyl)pyrrolidin-3-yl)methyl)-2-(2-fluoro-4-(1H-indazol-6-yl)phenyl)-1,3-diazaspiro[4.4]non-1-en-4-one<br>$^1$H NMR (400 MHz, CHLOROFORM-d) δ ppm 0.69 (d, J = 7.6 Hz, 2 H), 0.82-0.96 (m, 2 H), 1.43 (dd, J = 7.8, 4.8 Hz, 1.5 H), 1.57 (br. s., 0.5 H), 1.81 (br. s., 0.5 H), 1.90-2.10 (m, 4.5 H), 2.14 (br. s., 4 H), 2.36 (br. s.,k 0.5 H), 2.52 (br. s., 0.5 H), 2.86-2.97 (m, 0.5 H), 3.18 (t, J = 8.6 Hz, 0.5 H), 3.23-3.34 (m, 0.5 H), 3.39-3.56 (m, 2 H), 3.58 (br. s., 1 H), 3.64 (br. s., 1.5 H), 7.28 (d, J = 8.1 Hz, 1 H), 7.36-7.49 (m, 2 H), 7.61-7.75 (m,l 2 H), 7.79 (d, J = 8.1 Hz, 1 H), 8.11 (s, 1 H). MS m/z 500.1 (M + H)+ |
| 880 | 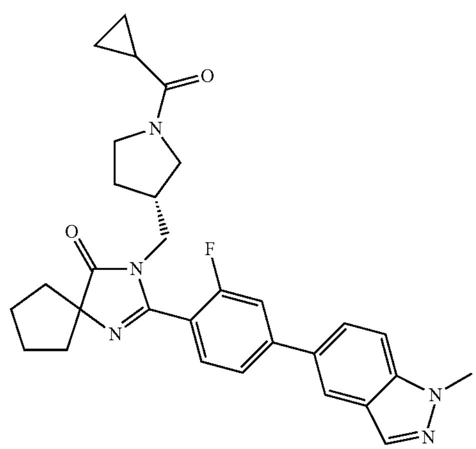 [SMILES: Cn1ncc2cc(-c3ccc(C4=NC5(CCCC5)C(=O)N4C[C@@H]4CCN(C(=O)C5CC5)C4)c(F)c3)ccc21] | (R)-3-((1-(cyclopropanecarbonyl)pyrrolidin-3-yl)methyl)-2-(2-fluoro-4-(1-methyl-1H-indazol-5-yl)phenyl)-1,3-diazaspiro[4.4]non-1-en-4-one<br>$^1$H NMR (400 MHz, CHLOROFORM-d) δ ppm 0.65-0.76 (m, 2 H), 0.84-0.97 (m, 2 H), 1.35-1.49 (m, 1.5 H), 1.50-1.63 (m, 0.5 H), 1.84 (br. s., 0.5 H), 1.91-2.05 (m, 5 H), 2.12 (br. s., 3.5 H), 2.31-2.41 (m, 0.5 H), 2.50 (d, J = 7.6 Hz, 0.5 H), 2.96 (dd, J = 12.1, 7.1 Hz, 0.5 H), 3.13-3.34 (m, 0.5 H), 3.43-3.54 (m, 2 ), 3.55-3.70 (m, 3 H), 4.07 (s, 3 H), 7.43-7.51 (m, 2 H), 7.59 (t, J = 9.9 Hz, 2 H), 7.65-7.74 (m, 1 H), 7.93 (s, 1 H), 8.04 (s, 1 H). MS m/z 514.21 (M + H)+ |
| 881 | 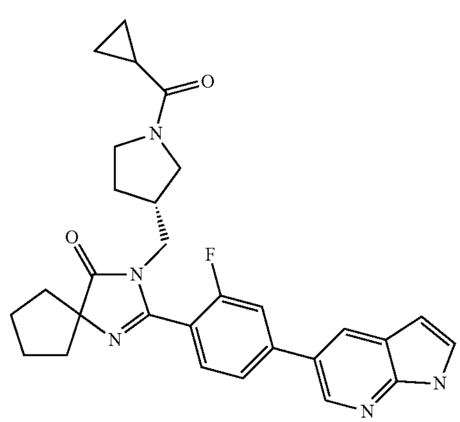 [SMILES: O=C(C1CC1)N1CC[C@@H](CN2C(=O)C3(CCCC3)N=C2c2ccc(-c3cnc4[nH]ccc4c3)cc2F)C1] | (R)-3-((1-(cyclopropanecarbonyl)pyrrolidin-3-yl)methyl)-2-(2-fluoro-4-(1H-pyrrolo[2,3-b]pyridin-5-yl)phenyl)-1,3-diazaspiro[4.4]non-1-en-4-one<br>$^1$H NMR (400 MHz, CHLOROFORM-d) δ ppm 0.55-0.69 (m, 2 H), 0.79-0.94 (m, 2 H), 1.31-1.48 (m, 1.5 H), 1.55 (dd, J = 12.6, 8.1 Hz, 0.5 H), 1.70-1.80 (m, 0.5 H), 1.81-2.06 (m, 8.5 H), 2.25-2.36 (m, 0.5 H), 2.37-2.49 (m, 0.5 H), 2.88 (dd, J = 11.9, 7.3 Hz, 0.5 H), 3.07-3.17 (m, 0.5 H), 3.22 (dt, J = 11.5, 8.1 Hz, 0.5 H), 3.36-3.49 (m, 2 H), 3.50-3.64 (m, 2.5 H), 6.55 (d, J = 3.5 Hz, 1 H), 7.33-7.44 (m, 2 H), 7.46-7.59 (m, 2 H), 8.12 (s, 1 H), 8.49 (br. s., 1 H), 9.63 (s, 0.5 H), 9.59 (s, 0.5 H). MS m/z 500.3 (M + H)+ |

| ID No. | Structure | Compound Name & Physical Data |
|---|---|---|
| 882 | 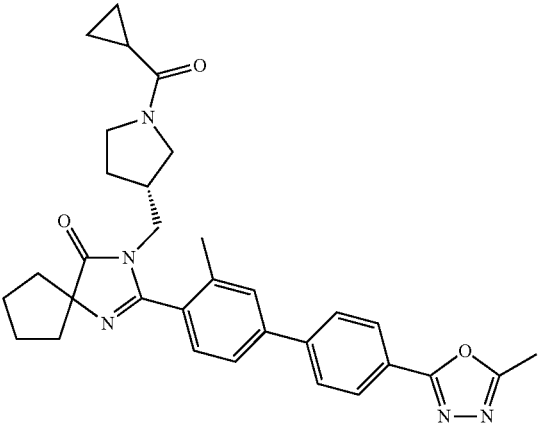 [SMILES: Cc1nnc(-c2ccc(-c3ccc(C4=NC5(CCCC5)C(=O)N4C[C@@H]4CCN(C(=O)C5CC5)C4)c(C)c3)cc2)o1] | (R)-3-((1-(cyclopropanecarbonyl)pyrrolidin-3-yl)methyl)-2-(3-methyl-4'-(5-methyl-1,3,4-oxadiazol-2-yl)-[1,1'-biphenyl]-4-yl)-1,3-diazaspiro[4.4]non-1-en-4-one<br>MS m/z 538.2 (M + H)+ |
| 883 | 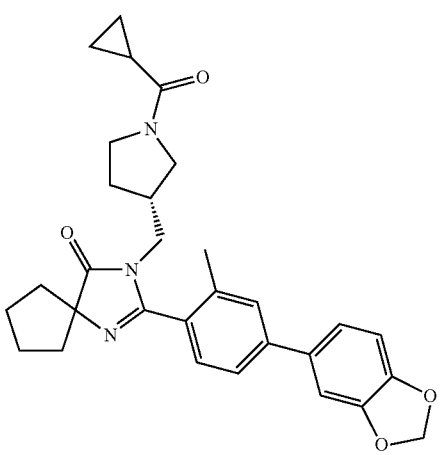 [SMILES: Cc1cc(-c2ccc3c(c2)OCO3)ccc1C1=NC2(CCCC2)C(=O)N1C[C@@H]1CCN(C(=O)C2CC2)C1] | (R)-2-(4-(benzo[d][1,3]dioxol-5-yl)-2-methylphenyl)-3-((1-(cyclopropanecarbonyl)pyrrolidin-3-yl)methyl)-1,3-diazaspiro[4.4]non-1-en-4-one<br>MS m/z 500.3 (M + H)+ |
| 884 | 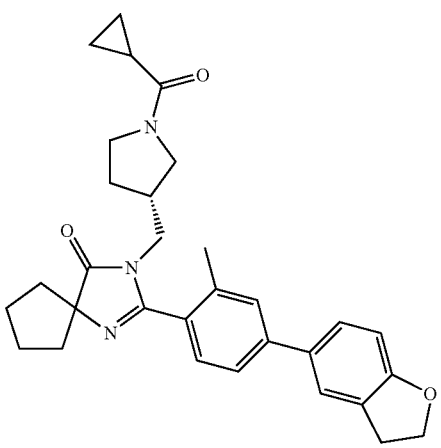 [SMILES: Cc1cc(-c2ccc3c(c2)CCO3)ccc1C1=NC2(CCCC2)C(=O)N1C[C@@H]1CCN(C(=O)C2CC2)C1] | (R)-3-((1-(cyclopropanecarbonyl)pyrrolidin-3-yl)methyl)-2-(4-(2,3-dihydrobenzofuran-5-yl)-2-methylphenyl)-1,3-diazaspiro[4.4]non-1-en-4-one<br>MS m/z 498.2 (M + H)+ |

-continued

| ID No. | Structure | Compound Name & Physical Data |
|---|---|---|
| 885 | 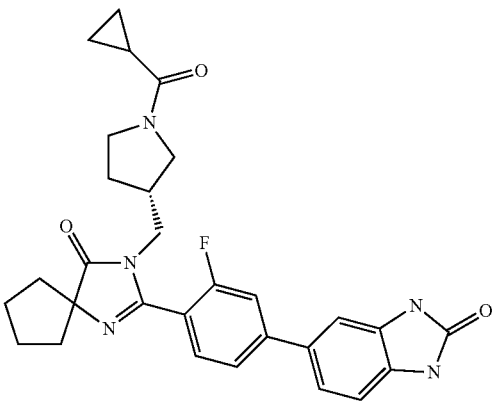 [SMILES: O=C(C1CC1)N1CC[C@@H](CN2C(=O)C3(CCCC3)N=C2c2ccc(-c3ccc4[nH]c(=O)[nH]c4c3)cc2F)C1] | (R)-5-(4-(3-((1-(cyclopropanecarbonyl)pyrrolidin-3-yl)methuyl)-4-oxo-1,3-diazaspiro[4.4]non-1-en-2-yl)-3-fluorophenyl)-1H-benzo[d]imidazol-2(3H)-one<br>MS m/z 516.2 (M + H)+ |
| 886 | 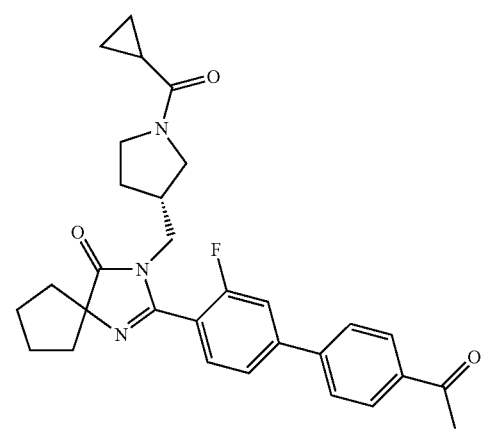 [SMILES: CC(=O)c1ccc(-c2ccc(C3=NC4(CCCC4)C(=O)N3C[C@@H]3CCN(C(=O)C4CC4)C3)c(F)c2)cc1] | (R)-2-(4'-acetyl-3-fluoro-[1,1'-biphenyl]-4-yl)-3-((1-(cyclopropanecarbonyl)pyrrolidin-3-yl)methyl)-1,3-diazaspiro[4.4]non-1-en-4-one<br>MS m/z 502.2 (M + H)+ |
| 887 | 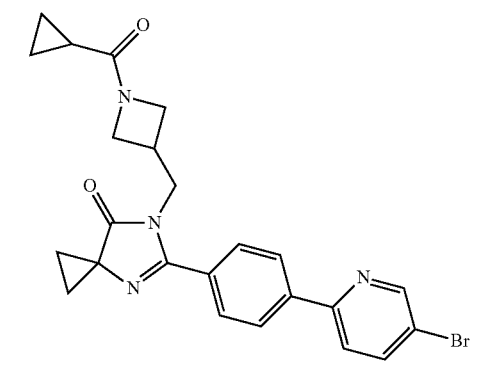 [SMILES: O=C(C1CC1)N1CC(CN2C(=O)C3(CC3)N=C2c2ccc(-c3ccc(Br)cn3)cc2)C1] | 5-(4-(5-bromopyridin-2-yl)phenyl)-6-((1-(cyclopropanecarbonyl)azetidin-3-yl)methyl)-4,6-diazaspiro[2.4]hept-4-en-7-one<br>MS m/z 479 (M + H)+ |
| 888 | 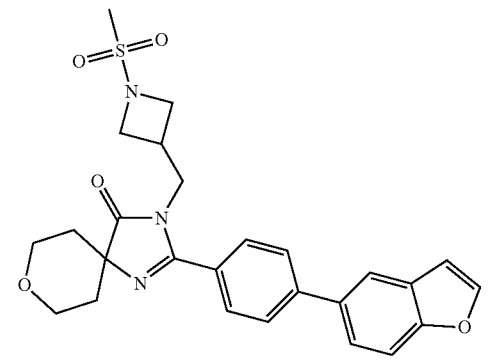 [SMILES: CS(=O)(=O)N1CC(CN2C(=O)C3(CCOCC3)N=C2c2ccc(-c3ccc4occc4c3)cc2)C1] | 2-(4-(benzofuran-5-yl)phenyl)-3-((1-(methylsulfonyl)azetidin-3-yl)methyl)-8-oxa-1,3-diazaspiro[4.5]dec-1-en-4-one<br>MS m/z 494.1 (M + H)+ |

| ID No. | Structure | Compound Name & Physical Data |
|---|---|---|
| 889 | 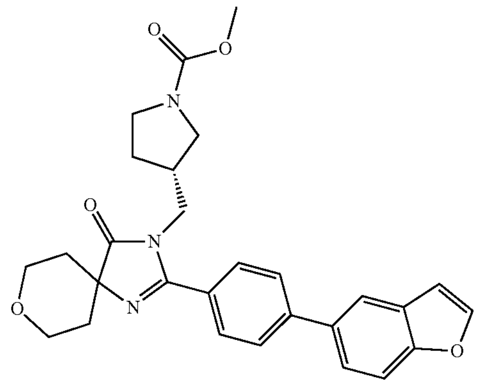 [SMILES: COC(=O)N1CC[C@@H](CN2C(=O)C3(CCOCC3)N=C2c2ccc(-c3ccc4occc4c3)cc2)C1] | (S)-methyl 3-((2-(4-(benzofuran-5-yl)phenyl)-4-oxo-8-oxa-1,3-diazaspiro[4.5]dec-1-en-3-yl)methyl)pyrrolidin-1-carboxylate<br>MS m/z 488.1 (M + H)+ |
| 890 | 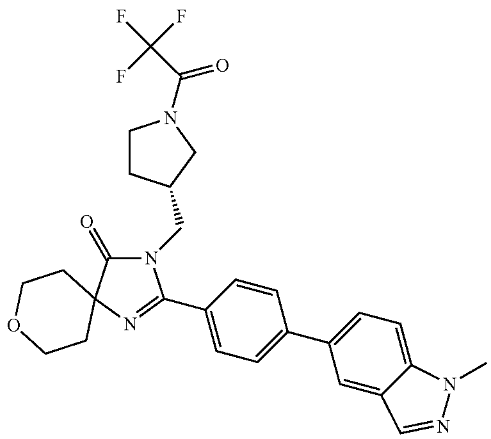 [SMILES: Cn1ncc2cc(-c3ccc(C4=NC5(CCOCC5)C(=O)N4C[C@@H]4CCN(C(=O)C(F)(F)F)C4)cc3)ccc21] | (R)-2-(4-(1-methyl-1H-indazol-5-yl)phenyl)-3-((1-(2,2,2-trifluoroacetyl)pyrrolidin-3-yl)methyl)-8-oxa-1,3-diazaspiro[4.5]dec-1-en-4-one<br>MS m/z 540.2 (M + H)+ |
| 891 | 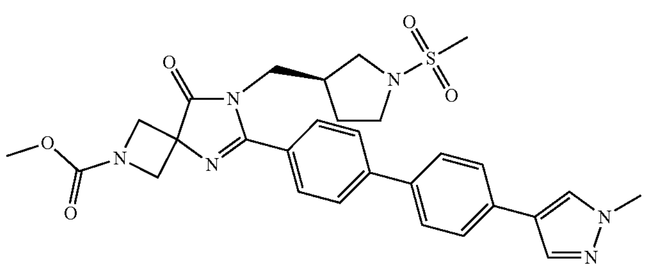 | (S)-methyl 6-(4'-(1-methyl-1H-pyrazol-4-yl)-[1,1'-biphenyl]-4-yl)-7-((1-(methylsulfonyl)pyrrolidin-3-yl)methyl)-8-oxo-2,5,7-triazaspiro3.4[ovt-5-ene-2-carboxylate<br>MS m/z 577.3 (M + H)+ |
| 892 | 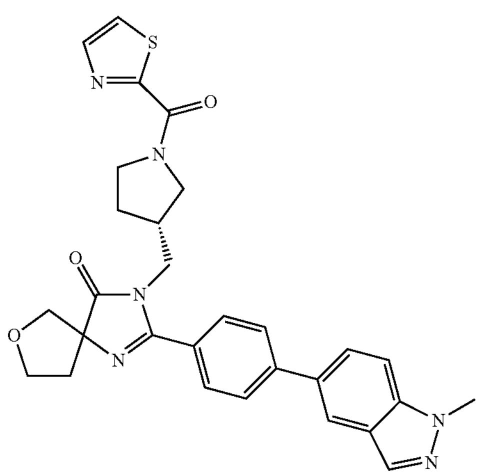 [SMILES: Cn1ncc2cc(-c3ccc(C4=NC5(CCOC5)C(=O)N4C[C@@H]4CCN(C(=O)c5nccs5)C4)cc3)ccc21] | 2-(4-(1-methyl-1H-indazol-5-yl)phenyl)-3-(((R)-1-(thiazole-2-carbonyl)pyrrolidin-3-yl)methyl)-7-oxa-1,3-diazxaspiro[4.4]non-1-en-4-one<br>MS m/z 541.1 (M + H)+ |

-continued

| ID No. | Structure | Compound Name & Physical Data |
|---|---|---|
| 893 | 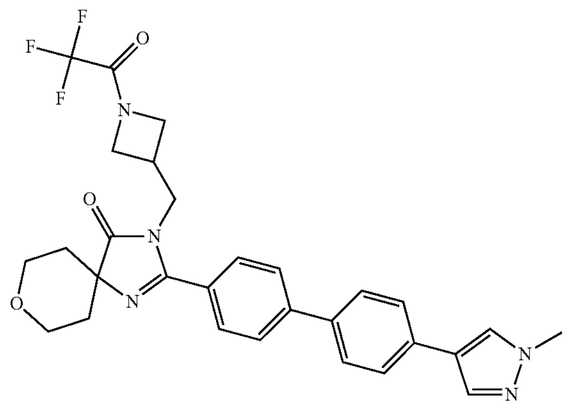 [SMILES: Cn1cc(-c2ccc(-c3ccc(C4=NC5(CCOCC5)C(=O)N4CC4CN(C(=O)C(F)(F)F)C4)cc3)cc2)cn1] | 2-(4'-(1-methyl-1H-pyrazol-4-yl)-[1,1'-biphenyl]-4-yl)-3-((1-(2,2,2-trifluoroacetyl)azetidin-3-yl)methyl)-8-oxa-1,3-diazaspiro[4.5]dec-1-en-4-one<br>MS m/z 552.3 (M + H)+ |
| 894 | 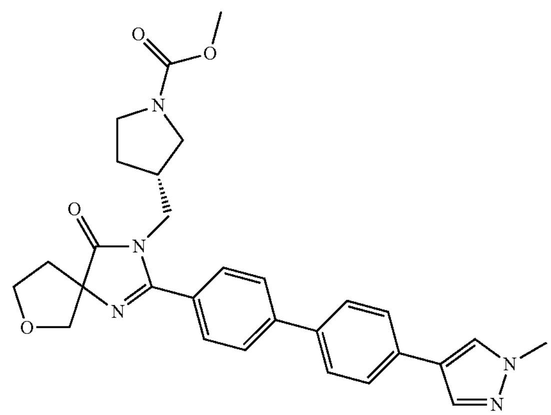 [SMILES: COC(=O)N1CC[C@@H](CN2C(=O)C3(CCOC3)N=C2c2ccc(-c3ccc(-c4cnn(C)c4)cc3)cc2)C1] | (3S)-methyl 3-((2-(4'-(1-methyl-1H-pyrazol-4-yl)-[1,1'-biphenyl]-4-yl)-4-oxo-7-oxa-1,3-diazaspiro[4.4]non-1-en-3-yl)methyl)pyrrolidin-1-carboxylate<br>MS m/z 514.2 (M + H)+ |
| 895 | 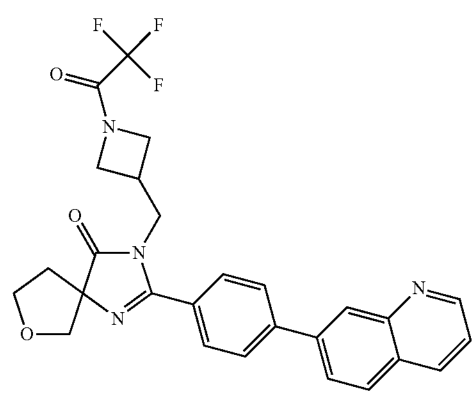 [SMILES: O=C(N1CC(CN2C(=O)C3(CCOC3)N=C2c2ccc(-c3ccc4cccnc4c3)cc2)C1)C(F)(F)F] | 2-(4-(quinolin-7-yl)phenyl)-3-((1-(2,2,2-trifluoroacetyl)azetidin-3-yl)methyl)-7-oxa-1,3-diazaspiro[4.4]non-1-en-4-one<br>MS m/z 509.1 (M + H)+ |
| 896 | 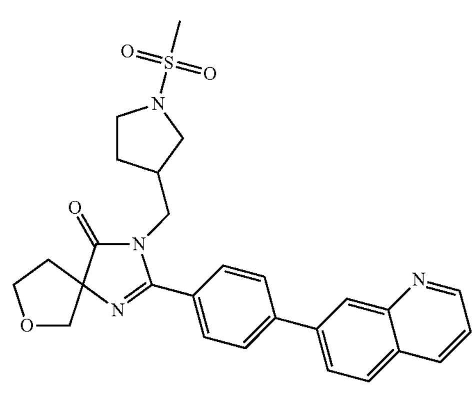 [SMILES: CS(=O)(=O)N1CCC(CN2C(=O)C3(CCOC3)N=C2c2ccc(-c3ccc4cccnc4c3)cc2)C1] | 3-((1-(methylsulfonyl)pyrrolidin-3-yl)methyl)-2-(4-(quinolin-7-yl)phenyl)-7-oxa-1,3-diazaspiro[4.4]non-1-en-4-one<br>MS m/z 505.2 (M + H)+ |

| ID No. | Structure | Compound Name & Physical Data |
|---|---|---|
| 897 | 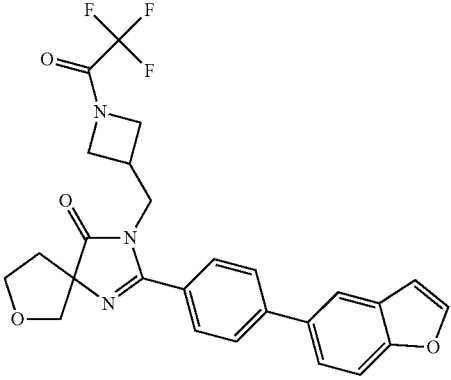 [SMILES: O=C(N1CC(CN2C(=O)C3(CCOC3)N=C2c2ccc(-c3ccc4occc4c3)cc2)C1)C(F)(F)F] | 2-(4-(benzofuran-5-yl)phenyl)-3-((1-(2,2,2-trifluoroacetyl)azetidin-3-yl)methyl)-7-oxa-1,3-diazaspiro[4.4]non-1-en-4-one<br>MS m/z 498.2 (M + H)+ |
| 898 | 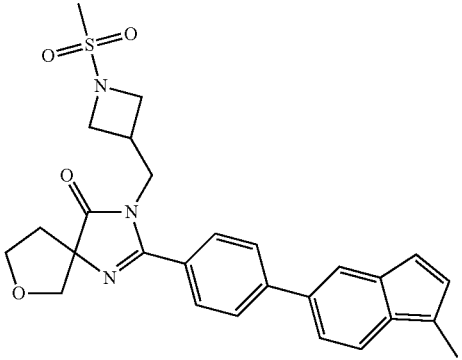 | 2-(4-(benzofuran-5-yl)phenyl)-3-((1-(methylsulfonyl)azetidin-3-yl)methyl)-7-oxa-1,3-diazaspiro[4.4]non-1-en-4-one<br>MS m/z 480.2 (M + H)+ |
| 899 | 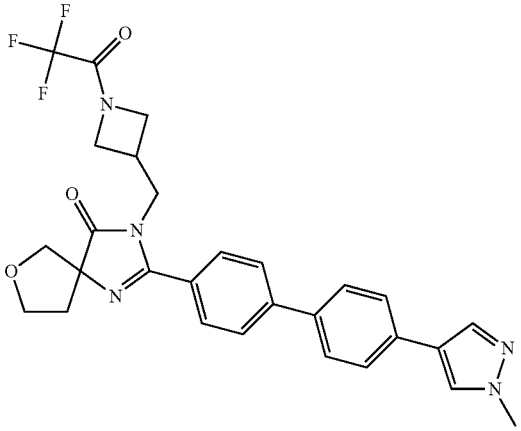 [SMILES: Cn1cc(-c2ccc(-c3ccc(C4=NC5(CCOC5)C(=O)N4CC4CN(C(=O)C(F)(F)F)C4)cc3)cc2)cn1] | 2-(4'-(1-methyl-1H-pyrazol-4-yl)-[1,1'-biphenyl]-4-yl)-3-((1-(2,2,2-trifluoroacetyl)azetidin-3-yl)methyl)-7-oxa-1,3-diazaspiro[4.4]non-1-en-4-one<br>MS m/z 538.2 (M + H)+ |
| 900 | 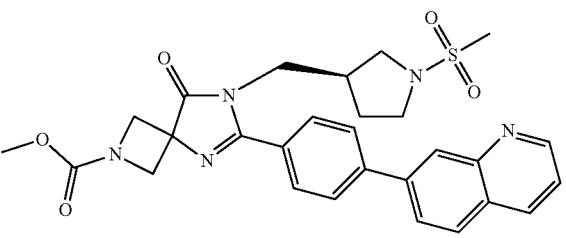 [SMILES: COC(=O)N1CC2(C1)N=C(c1ccc(-c3ccc4cccnc4c3)cc1)N(C[C@@H]1CCN(S(C)(=O)=O)C1)C2=O] | (S)-methyl 7-((1-(methylsulfonyl)pyrrolidin-3-yl)methyl)-8-oxo-6-(4-(quinolin-7-yl)phenyl)-2,5,7-triazaspiro[3.4]oct-5-ene-2-carboxylate<br>MS m/z 548.2 (M + H)+ |

-continued

| ID No. | Structure | Compound Name & Physical Data |
|---|---|---|
| 901 | 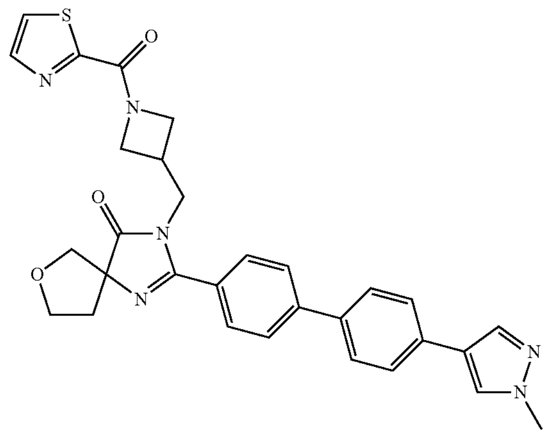 [SMILES: Cn1cc(-c2ccc(-c3ccc(C4=NC5(CCOC5)C(=O)N4CC4CN(C(=O)c5nccs5)C4)cc3)cc2)cn1] | 2-(4'-(1-methyl-1H-pyrazol-4-yl)-[1,1'-biphenyl]-4-yl)-3-((1-(thiazol-2-carbonyl)azetidin-3-yl)methyl)-7-oxa-1,3-diazaspiro[4.4]non-1-en-4-one<br>MS m/z 553.2 (M + H)+ |
| 902 | 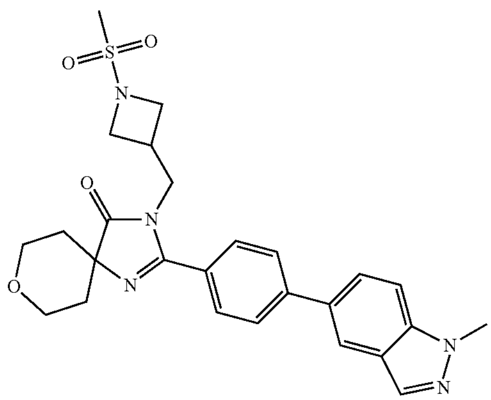 [SMILES: Cn1ncc2cc(-c3ccc(C4=NC5(CCOCC5)C(=O)N4CC4CN(S(C)(=O)=O)C4)cc3)ccc21] | 2-(4-(1-methyl-1H-indazol-5-yl)phenyl)-3-((1-(methylsulfonyl)azetidin-3-yl)methyl)-8-oxa-1,3-diazaspiro[4.5]dec-1-en-4-one<br>MS m/z 508.1 (M + H)+ |
| 903 | 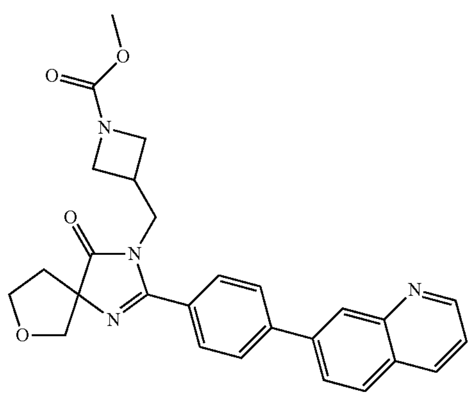 [SMILES: COC(=O)N1CC(CN2C(=O)C3(CCOC3)N=C2c2ccc(-c3ccc4cccnc4c3)cc2)C1] | methyl 3-((4-oxo-2-(4-(quinolin-7-yl)phenyl)-7-oxa-1,3-diazaspiro[4.4]non-1-en-3-yl)methyl)azetidine-1-carboxylate<br>MS m/z 471.2 (M + H)+ |
| 904 | 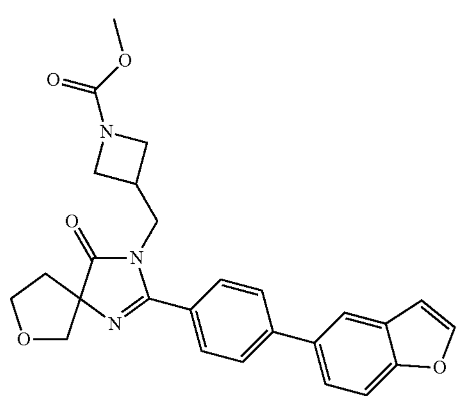 [SMILES: COC(=O)N1CC(CN2C(=O)C3(CCOC3)N=C2c2ccc(-c3ccc4occc4c3)cc2)C1] | methyl 3-((2-(4-(benzofuran-5-yl)phenyl)-4-oxo-7-oxa-1,3-diazaspiro[4.4]non-1-en-3-yl)methyl)azetidin-1-carboxylate<br>MS m/z 460.2 (M + H)+ |

| ID No. | Structure | Compound Name & Physical Data |
|---|---|---|
| 905 | 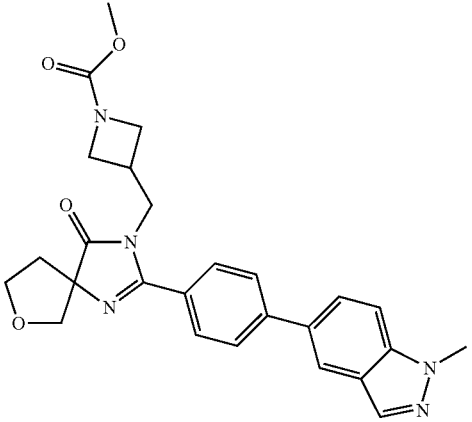 [SMILES: COC(=O)N1CC(CN2C(=O)C3(CCOC3)N=C2c2ccc(-c3ccc4c(cnn4C)c3)cc2)C1] | methyl 3-((2-(4-(1-methyl-1H-indazol-5-yl)phenyl)-4-oxo-7-oxa-1,3-diazaspiro[4.4]non-1-en-3-yl)methyl)azetidine-1-carboxylate<br>MS m/z 474.3 (M + H)+ |
| 906 | 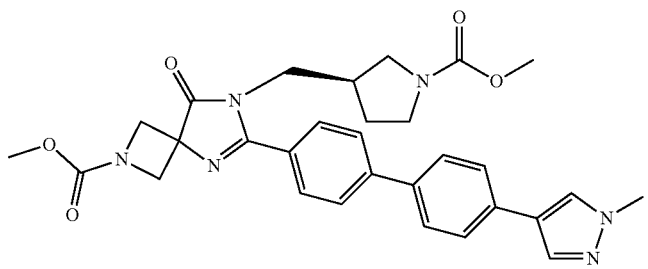 | (S)-methyl 7-((1-(methoxycarbonyl)pyrrolidin-3-yl)methyl)-6-(4'-(1-methyl-1H-pyrazol-4-yl)-[1,1'-biphenyl]-4-yl)-8-oxo-2,5,7-triazaspiro[3.4]oct-5-ene-2-carboxylate<br>MS m/z 557.2 (M + H)+ |
| 907 | 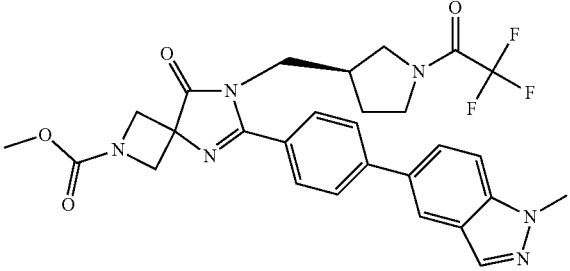 | (R)-methyl 6-(4-(1-methyl-1H-indazol-5-yl)phenyl)-8-oxo-7-((1-(2,2,2-trifluoroacetyl)pyrrolidin-3-yl)methyl)-2,5,7-triazaspiro[3.4]oct-5-ene-2-carboxylate<br>MS m/z 569.1 (M + H)+ |
| 908 | 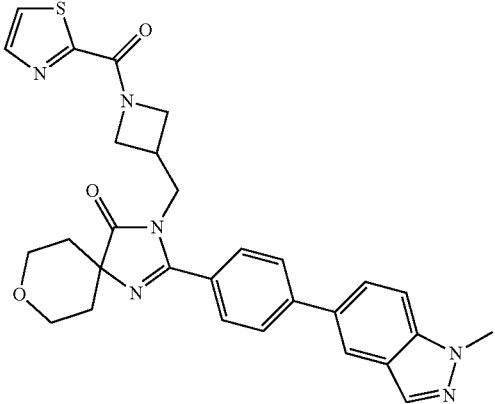 [SMILES: Cn1ncc2cc(-c3ccc(C4=NC5(CCOCC5)C(=O)N4CC4CN(C(=O)c5nccs5)C4)cc3)ccc21] | 2-(4-(1-methyl-1H-indazol-5-yl)phenyl)-3-((1-(thiazole-2-carbonyl)azetidin-3-yl)methyl)-8-oxa-1,3-diazaspiro[4.5]dec-1-en-4-one<br>MS m/z 541.1 (M + H)+ |

-continued

| ID No. | Structure | Compound Name & Physical Data |
|---|---|---|
| 909 | 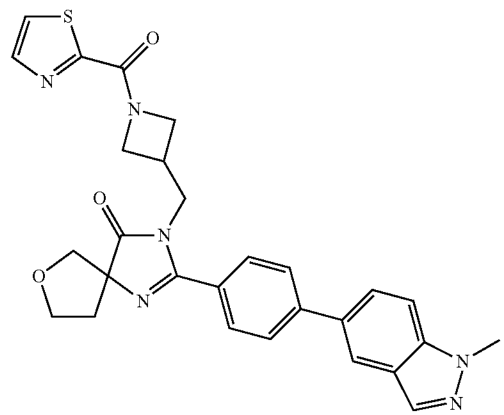 [SMILES: Cn1ncc2cc(-c3ccc(C4=NC5(CCOC5)C(=O)N4CC4CN(C(=O)c5nccs5)C4)cc3)ccc21] | 2-(4-(1-methyl-1H-indazol-5-yl)phenyl)-3-((1-(thiazole-2-carbonyl)azetidin-3-yl)methyl)-7-oxa-1,3-diazaspiro[4.4]non-1-en-4-one<br>MS m/z 527.1 (M + H)+ |
| 910 | 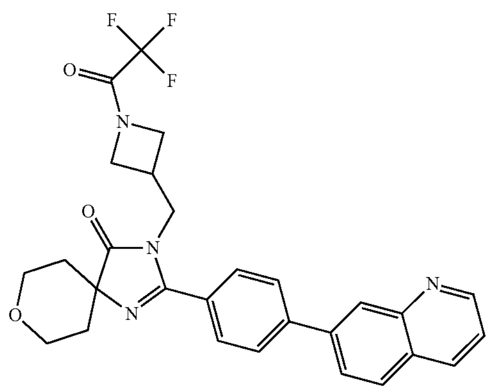 [SMILES: O=C(N1CC(CN2C(=O)C3(CCOCC3)N=C2c2ccc(-c3ccc4cccnc4c3)cc2)C1)C(F)(F)F] | 2-(4-(quinolin-7-yl)phenyl)-3-((1-(2,2,2-trifluoroacetyl)azetidin-3-yl)methyl)-8-oxa-1,3-diazaspiro[4.5]dec-1-en-4-one<br>MS m/z 523.2 (M + H)+ |
| 911 | 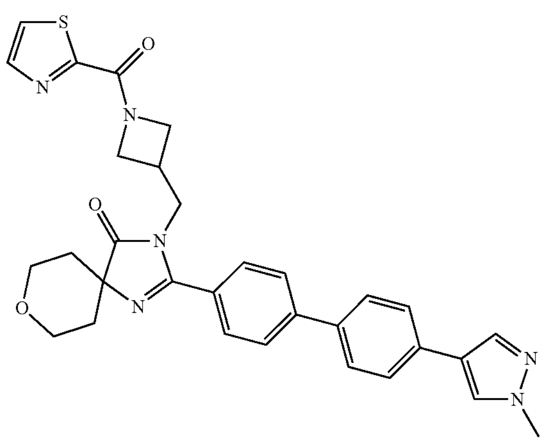 [SMILES: Cn1cc(-c2ccc(-c3ccc(C4=NC5(CCOCC5)C(=O)N4CC4CN(C(=O)c5nccs5)C4)cc3)cc2)cn1] | 2-(4'-(1-methyl-1H-pyrazol-4-yl)-[1,1'-biphenyl]-4-yl)-3-((1-(thiazole-2-carbonyl)azetidin-3-yl)methyl)-8-oxa-1,3-diazaspiro[4.5]dec-1-en-4-one<br>MS m/z 567.2 (M + H)+ |
| 912 | 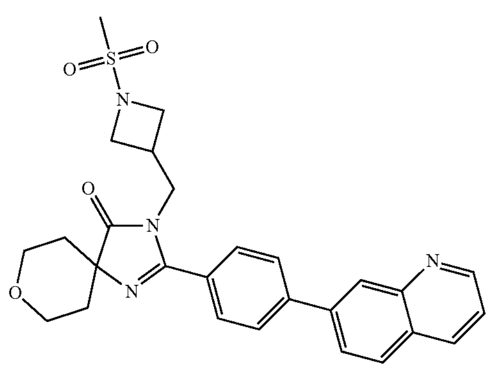 [SMILES: CS(=O)(=O)N1CC(CN2C(=O)C3(CCOCC3)N=C2c2ccc(-c3ccc4cccnc4c3)cc2)C1] | 3-((1-(methylsulfonyl)azetidin-3-yl)methyl)-2-(4-(quinolin-7-yl)phenyl)-8-oxa-1,3-diazaspiro[4.5]dec-1-en-4-one<br>MS m/z 505.2 (M + H)+ |

| ID No. | Structure | Compound Name & Physical Data |
|---|---|---|
| 913 | 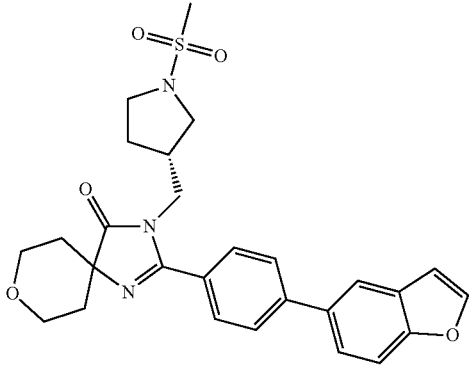 [SMILES: CS(=O)(=O)N1CC[C@@H](CN2C(=O)C3(CCOCC3)N=C2c2ccc(-c3ccc4occc4c3)cc2)C1] | (S)-2-(4-(benzofuran-5-yl)phenyl)-3-((1-(methylsulfonyl)pyrrolidin-3-yl)methyl)-8-oxa-1,3-diazaspiro[4.5]dec-1-en-4-one<br>MS m/z 508.1 (M + H)+ |
| 914 | 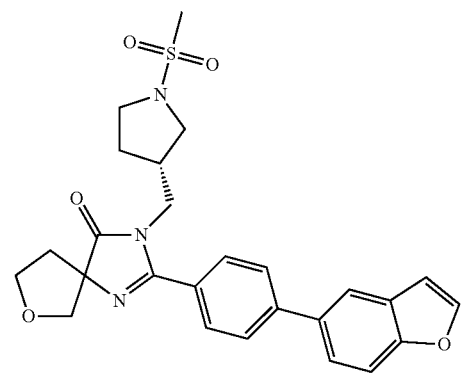 [SMILES: CS(=O)(=O)N1CC[C@@H](CN2C(=O)C3(CCOC3)N=C2c2ccc(-c3ccc4occc4c3)cc2)C1] | 2-(4-(benzofuran-5-yl)phenyl)-3-(((S)-1-(methylsulfonyl)pyrrolidin-3-yl)methyl)-7-oxa-1,3-diazaspiro[4.4]non-1-en-4-one<br>MS m/z 494.1 (M + H)+ |
| 915 | 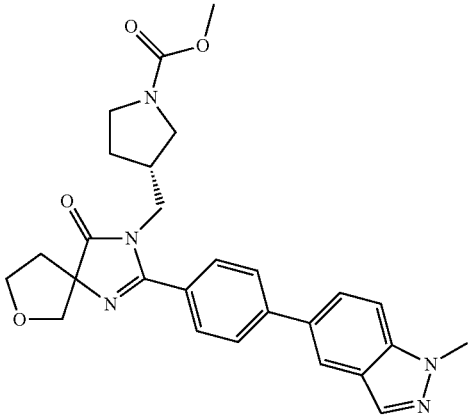 [SMILES: COC(=O)N1CC[C@@H](CN2C(=O)C3(CCOC3)N=C2c2ccc(-c3ccc4c(cnn4C)c3)cc2)C1] | (3S)-methyl 3-((2-(4-(1-methyl-1H-indazol-5-yl)phenyl)-4-oxo-7-oxa-1,3-diazaspiro[4.4]non-1-en-3-yl)methyl)pyrrolidin-1-carboxylate<br>MS m/z 488.2 (M + H)+ |
| 916 | 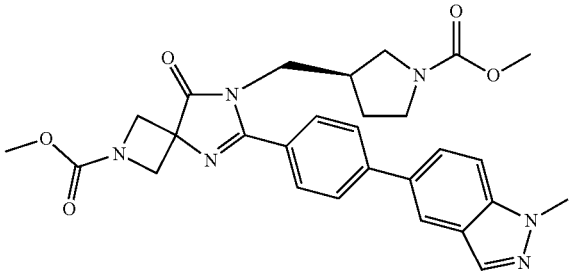 | (S)-methyl 7-((1-(methoxycarbonyl)pyrrolidin-3-yl)methyl)-6-(4-(1-methyl-1H-indazol-5-yl)phenyl)-8-oxo-5,7-triazaspiro[3.4]oct-5-ene-2-carboxylate<br>MS m/z 531.2 (M + H)+ |

-continued

| ID No. | Structure | Compound Name & Physical Data |
|---|---|---|
| 917 | 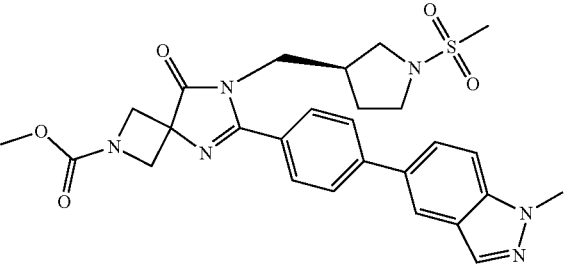 | (S)-methyl 6-(4-(1-methyl-1H-indazol-5-yl)phenyl)-7-((1-(methylsulfonyl)pyrrolidin-3-yl)methyl)-8-oxo-2,5,7-triazaspiro[3.4]oct-5-ene-2-carboxylate<br>MS m/z 551.3 (M + H)+ |
| 918 | 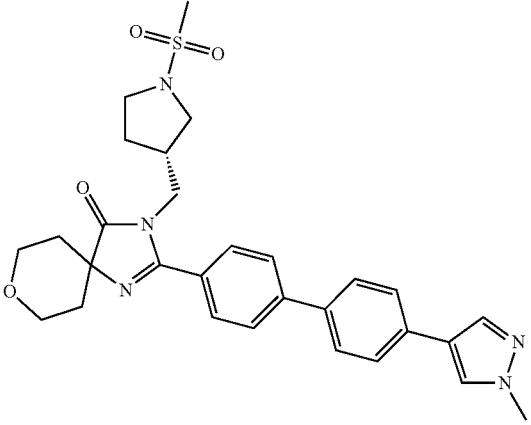 [SMILES: Cn1cc(-c2ccc(-c3ccc(C4=NC5(CCOCC5)C(=O)N4C[C@@H]4CCN(S(C)(=O)=O)C4)cc3)cc2)cn1] | (S)-2-(4'-(1-metrhyl-1H-pyrazol-4-yl)-[1,1'-biphenyl]-4-yl)-3-((1-(methylsulfonyl)pyrrolidin-3-yl)methyl)-8-oxa-1,3-diazaspiro[4.5]dec-1-en-4-one<br>MS m/z 548.3 (M + H)+ |
| 919 | 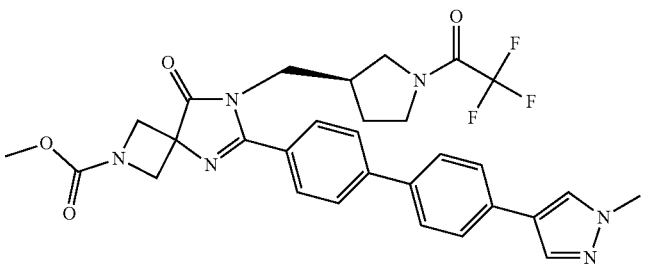 | (R)-methyl 6-(4'-(1-methyl-1H-pyrazol-4-yl)-[1,1'-biphenyl]-4-yl)-8-oxo-7-((1-(2,2,2-trifluoroacetyl)pyrrolidin-3-yl)methyl)-2,5,7-triazaspiro[3.4]oct-5-ene-2-carboxylate<br>MS m/z 595.1 (M + H)+ |
| 920 | 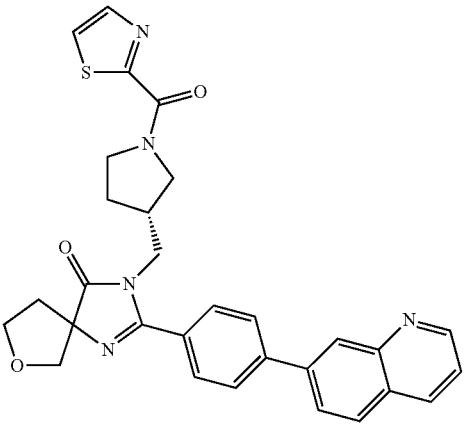 [SMILES: O=C(c1nccs1)N1CC[C@@H](CN2C(=O)C3(CCOC3)N=C2c2ccc(-c3ccc4cccnc4c3)cc2)C1] | 2-(4-(quinolin-7-yl)phenyl)-3-(((R)-1-(thiazole-2-carbonyl)pyrrolidin-3-yl)methyl)-7-oxa-1,3-diazaspiro[4.4]non-1-en-4-one<br>MS m/z 538.1 (M + H)+ |

| ID No. | Structure | Compound Name & Physical Data |
|---|---|---|
| 921 | 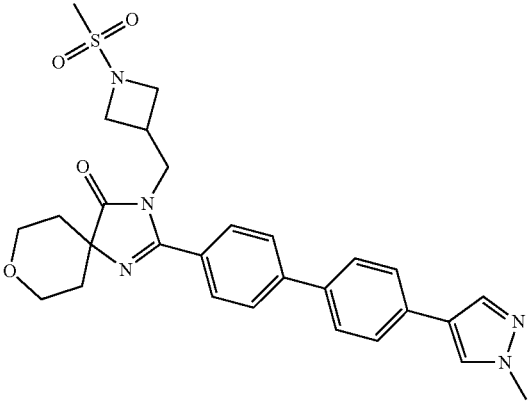 [SMILES: Cn1cc(-c2ccc(-c3ccc(C4=NC5(CCOCC5)C(=O)N4CC4CN(S(C)(=O)=O)C4)cc3)cc2)cn1] | 2-(4'-(1-methyl-1H-pyrazol-4-yl)-[1,1'-biphenyl]-4-yl)-3-((1-(methylsulfonyl)azetidin-3-yl)methyl)-8-oxa-1,3-diazaspiro[4.5]dec-1-en-4-one<br>MS m/z 534.2 (M + H)+ |
| 922 | 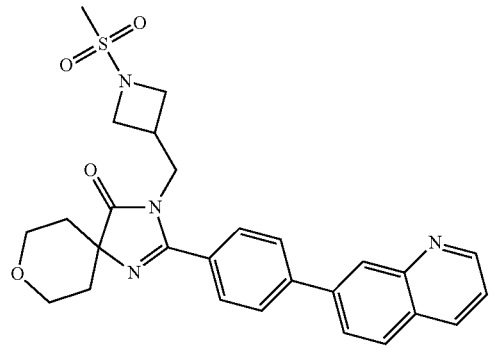 | methyl 3-((4-oxo-2-(4-(quinolin-7-yl)phenyl)-8-oxa-1,3-diazaspiro[4.5]dec-1-en-3-yl)methyl)azetidine-1-carboxylate<br>MS m/z 485.2 (M + H)+ |
| 923 | 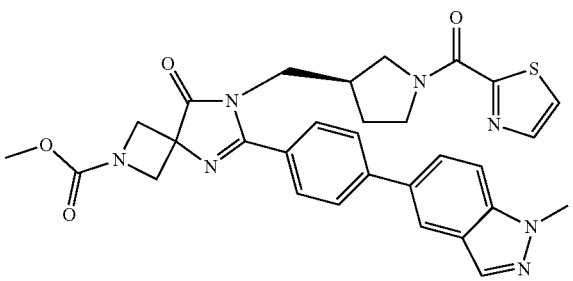 | (R)-methyl 6-(4-(1-methyl-1H-indazol-5-yl)phenyl)-8-oxo-7-((1-(thiazole-2-carbonyl)pyrrolidin-3-yl)methyl)-2,5,7-triazaspiro[3.4]oct-5-ene-2-carboxylate<br>MS m/z 584.2 (M + H)+ |
| 924 | 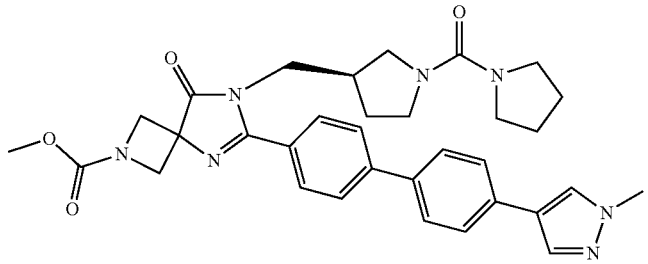 | (S)-methyl 6-(4'-(1-methyl-1H-pyrazol-4-yl)-[1,1'-biphenyl]-4-yl)-8-oxo-7-((1-(pyrrolidine-1-carbonyl)pyrrolidin-3-yl)metrhyl)-2,5,7-triazaspiro[3.4]oct-5-ene-2-carboxylate<br>MS m/z 596.3 (M + H)+ |

| ID No. | Structure | Compound Name & Physical Data |
|---|---|---|
| 925 | 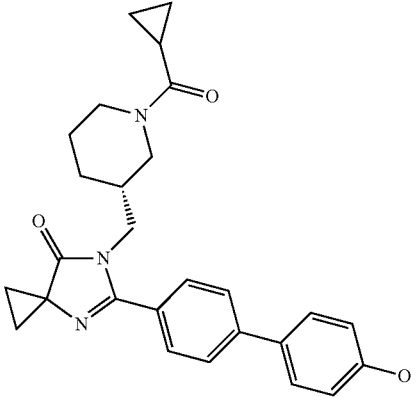 [SMILES: O=C(C1CC1)N1CCC[C@@H](CN2C(=O)C3(CC3)N=C2c2ccc(-c3ccc(O)cc3)cc2)C1] | (R)-6-((1-(cyclopropanecarbonyl)piperidin-3-yl)methyl)-5-(4'-hydroxy-[1,1'-biphenyl]-4-yl)-4,6-diazaspiro[2.4]hept-4-en-7-one<br>MS m/z 444 (M + H)+ |
| 926 | 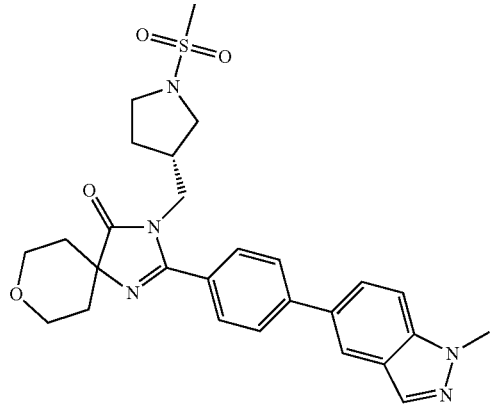 [SMILES: Cn1ncc2cc(-c3ccc(C4=NC5(CCOCC5)C(=O)N4C[C@@H]4CCN(S(C)(=O)=O)C4)cc3)ccc21] | (S)-2-(4-(1-methyl-1H-indazol-5-yl)phenyl)-3-((1-(methylsulfonyl)pyrrolidin-3-yl)methyl)-8-oxa-1,3-diazaspiro[4.5]dec-1-en-4-one<br>MS m/z 522.1 (M + H)+ |
| 927 | 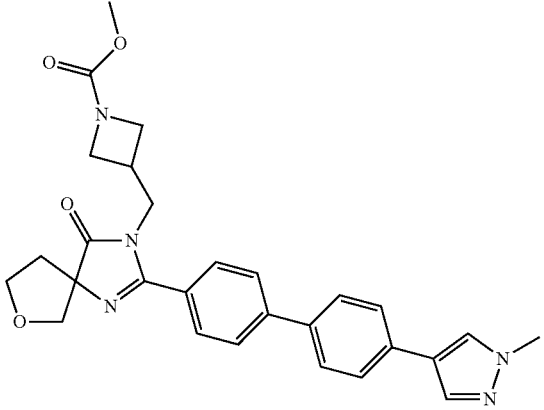 [SMILES: COC(=O)N1CC(CN2C(=O)C3(CCOC3)N=C2c2ccc(-c3ccc(-c4cnn(C)c4)cc3)cc2)C1] | methyl 3-((2-(4'-(1-methyl-1H-pyrazol-4-yl)-[1,1'-biphenyl]-4-yl)-4-oxo-7-oxa-1,3-diazaspiro[4.4]non-1-en-3-yl)methyl)azetidine-1-carboxylate<br>MS m/z 500.2 (M + H)+ |

| ID No. | Structure | Compound Name & Physical Data |
|---|---|---|
| 928 | 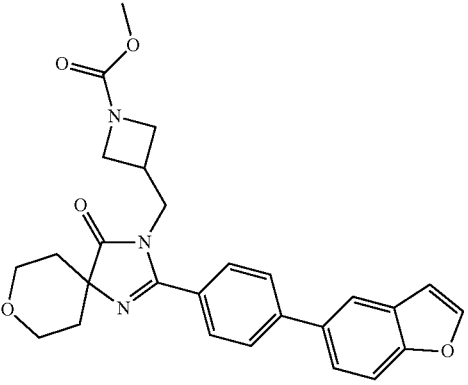 [SMILES: COC(=O)N1CC(CN2C(=O)C3(CCOCC3)N=C2c2ccc(-c3ccc4occc4c3)cc2)C1] | methyl 3-((2-(4-(benzofuran-5-yl)phenyl)-4-oxo-8-oxa-1,3-diazaspiro[4.5]dec-1-en-3-yl)azetidine-1-carboxylate<br>MS m/z 474.2 (M + H)+ |
| 929 | 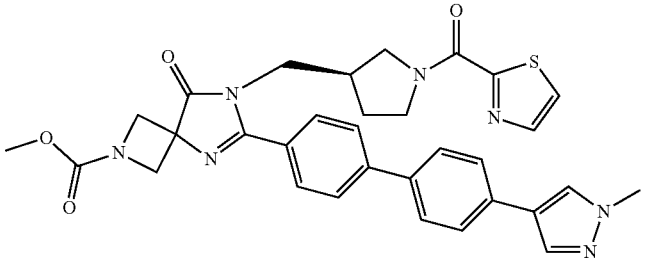 | (R)-methyl 6-(4'-(1-methyl-1H-pyrazol-4-yl)-[1,1'-biphenyl]-4-yl)-8-oxo-7-((1-(thiazole-2-carbonyl)pyrrolidin-3-yl)methyl)-2,5,7-triazaspiro[3.4]oct-5-ene-2-carboxylate<br>MS m/z 610.1 (M + H)+ |
| 930 | 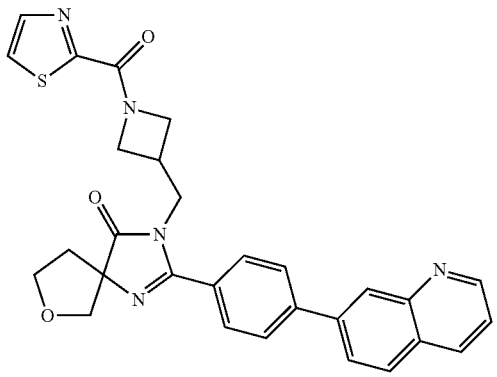 [SMILES: O=C(c1nccs1)N1CC(CN2C(=O)C3(CCOC3)N=C2c2ccc(-c3ccc4cccnc4c3)cc2)C1] | 2-(4-(quinolin-7-yl)phenyl)-3-((1-(thiazole-2-carbonyl)azetidin-3-yl)methyl)-7-oxa-1,3-diazaspiro[4.4]non-1-en-4-one<br>MS m/z 524.1 (M + H)+ |
| 931 | 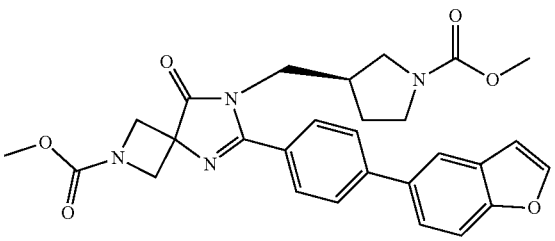 [SMILES: COC(=O)N1CC[C@@H](CN2C(=O)C3(CN(C(=O)OC)C3)N=C2c2ccc(-c3ccc4occc4c3)cc2)C1] | (S)-methyl 6-(4-(benzofuran-5-yl)phenyl)-7-((1-(methoxycarbonyl)pyrrolidin-3-yl)methyl)-8-oxo-2,5,7-triazaspiro[3.4]oct-5-ene-2-carboxylate<br>MS m/z 517.1 (M + H)+ |

| ID No. | Structure | Compound Name & Physical Data |
|---|---|---|
| 932 | 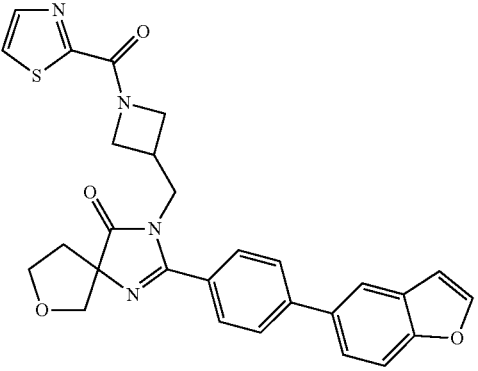 [SMILES: O=C(c1nccs1)N1CC(CN2C(=O)C3(CCOC3)N=C2c2ccc(-c3ccc4occc4c3)cc2)C1] | 2-(4-(benzofuran-5-yl)phenyl)-3-((1-(thiazole-2-carbonyl)azetidin-3-yl)methyl)-7-oxa-1,3-diazaspiro[4.4]non-1-en-4-one<br>MS m/z 513.1 (M + H)+ |
| 933 | 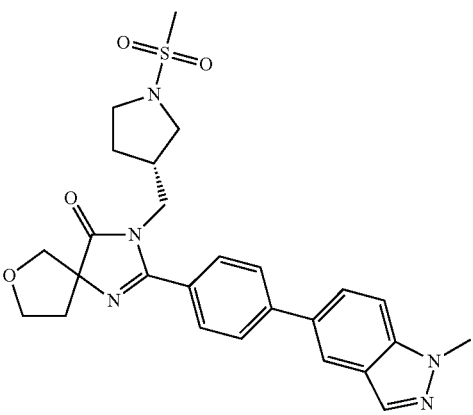 [SMILES: Cn1ncc2cc(-c3ccc(C4=NC5(CCOC5)C(=O)N4C[C@@H]4CCN(S(C)(=O)=O)C4)cc3)ccc21] | 2-(4-(1-methyl-1H-indazol-5-yl)phenyl)-3-(((S)-1-(methylsulfonyl)pyrrolidin-3-yl)methyl)-7-oxa-1,3-diazaspiro[4.4]non-1-en-4-one<br>MS m/z 508.1 (M + H)+ |
| 934 | 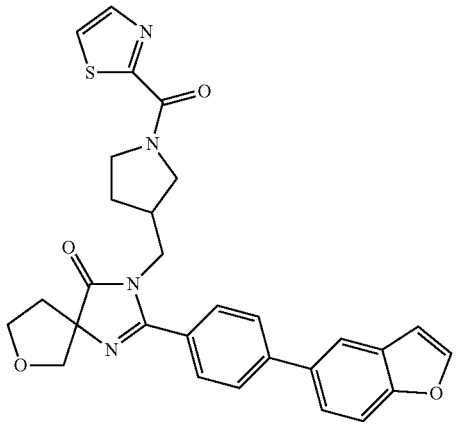 [SMILES: O=C(c1nccs1)N1CCC(CN2C(=O)C3(CCOC3)N=C2c2ccc(-c3ccc4occc4c3)cc2)C1] | 2-(4-(benzofuran-5-yl)phenyl)-3-((1-(thiazole-2-carbonyl)pyrrolidin-3-yl)methyl)-7-oxa-1,3-diazaspiro[4.4]non-1-en-4-one<br>MS m/z 527.1 (M + H)+ |

| ID No. | Structure | Compound Name & Physical Data |
|---|---|---|
| 935 | 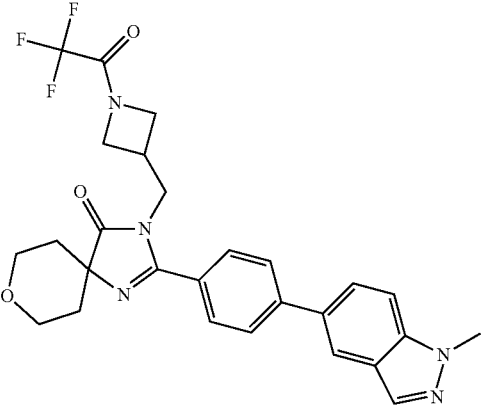 [SMILES: Cn1ncc2cc(-c3ccc(C4=NC5(CCOCC5)C(=O)N4CC4CN(C(=O)C(F)(F)F)C4)cc3)ccc21] | 2-(4-(1-methyl-1H-indazol-5-yl)phenyl)-3-((1-(2,2,2-trifluoroacetyl)azetidin-3-yl)methyl)-8-oxa-1,3-diazaspiro[4.5]dec-1-en-4-one<br>MS m/z 526.2 (M + H)+ |
| 936 | 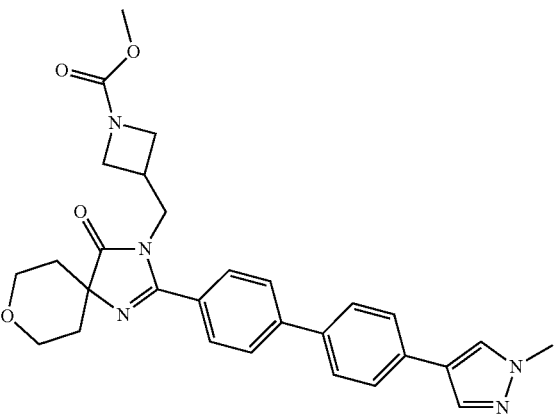 [SMILES: COC(=O)N1CC(CN2C(=O)C3(CCOCC3)N=C2c2ccc(-c3ccc(-c4cnn(C)c4)cc3)cc2)C1] | methyl 3-((2-(4'-(1-methyl-1H-pyrazol-4-yl)-[1,1'-biphenyl]-4-yl)-4-oxo-8-oxa-1,3-diazaspiro[4.5]dec-1-en-3-yl)methyl)azetidine-1-carboxylate<br>MS m/z 514.2 (M + H)+ |
| 937 | 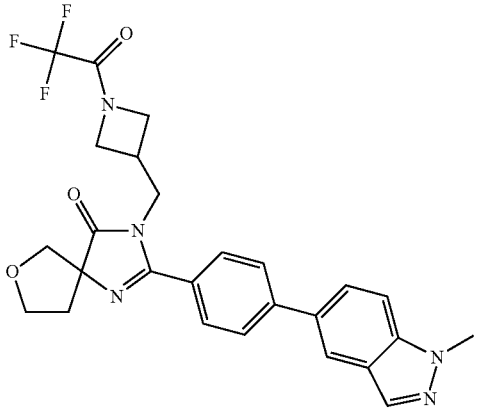 [SMILES: Cn1ncc2cc(-c3ccc(C4=NC5(CCOC5)C(=O)N4CC4CN(C(=O)C(F)(F)F)C4)cc3)ccc21] | 2-(4-(1-methyl-1H-indazol-5-yl)phenyl)-3-((1-(2,2,2-trifluoroacetyl)azetidin-3-yl)methyl)-7-oxa-1,3-diazaspiro[4.4]non-1-en-4-one<br>MS m/z 512.3 (M + H)+ |

| ID No. | Structure | Compound Name & Physical Data |
|---|---|---|
| 938 | 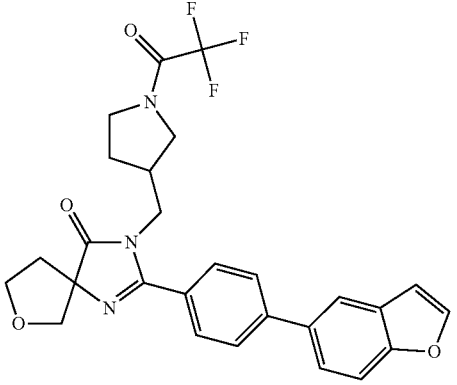 [SMILES: O=C(N1CCC(CN2C(=O)C3(CCOC3)N=C2c2ccc(-c3ccc4occc4c3)cc2)C1)C(F)(F)F] | 2-(4-(benzofuran-5-yl)phenyl)-3-((1-(2,2,2-trifluoroacetyl)pyrrolidin-3-yl)methyl)-7-oxa-1,3-diazaspiro[4.4]non-1-en-4-one<br>MS m/z 512.2 (M + H)+ |
| 939 | 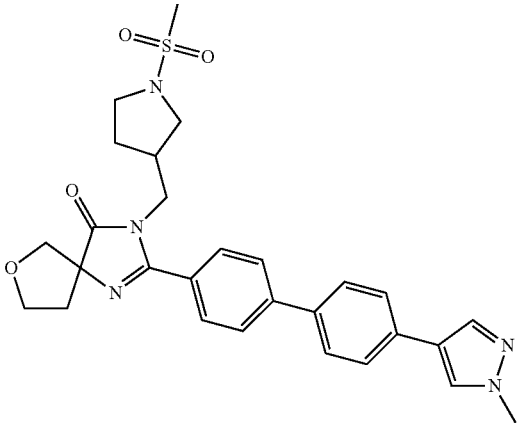 [SMILES: Cn1cc(-c2ccc(-c3ccc(C4=NC5(CCOC5)C(=O)N4CC4CCN(S(C)(=O)=O)C4)cc3)cc2)cn1] | 2-(4'-(1-methyl-1H-pyrazol-4-yl)-[1,1'-biphenyl]-4-yl)-3-((1-(methylsulfonyl)pyrrolidin-3-yl)methyl)-7-oxa-1,3-diazaspiro[4.4]non-1-en-4-one<br>MS m/z 534.2 (M + H)+ |
| 940 | 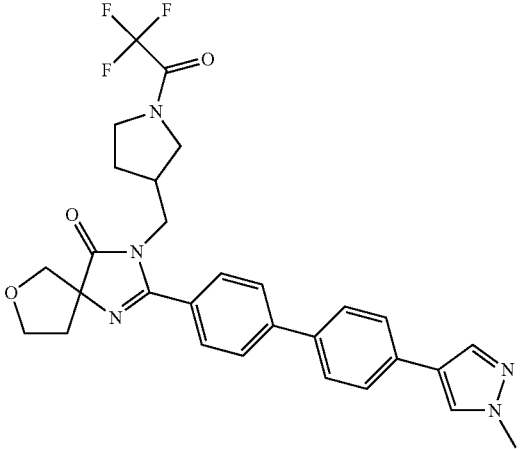 [SMILES: Cn1cc(-c2ccc(-c3ccc(C4=NC5(CCOC5)C(=O)N4CC4CCN(C(=O)C(F)(F)F)C4)cc3)cc2)cn1] | 2-(4'-(1-methyl-1H-pyrazol-4-yl)-[1,1'-biphenyl]-4-yl)-3-((1-(2,2,2-trifluoroacetyl)pyrrolidin-3-yl)methyl)-7-oxa-1,3-diazaspiro[4.4]non-1-en-4-one<br>MS m/z 552.2 (M + H)+ |

| ID No. | Structure | Compound Name & Physical Data |
|---|---|---|
| 941 | 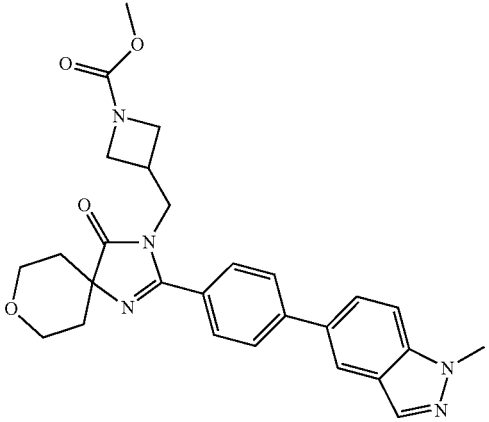 [SMILES: COC(=O)N1CC(CN2C(=O)C3(CCOCC3)N=C2c2ccc(-c3ccc4c(cnn4C)c3)cc2)C1] | methyl 3-((2-(4-(1-methyl-1H-indazol-5-yl)phenyl)-4-oxo-8-oxa-1,3-diazaspiro[4.5]dec-1-en-3-yl)methyl)azetidine-1-carboxylate<br>MS m/z 488.2 (M + H)+ |
| 942 | 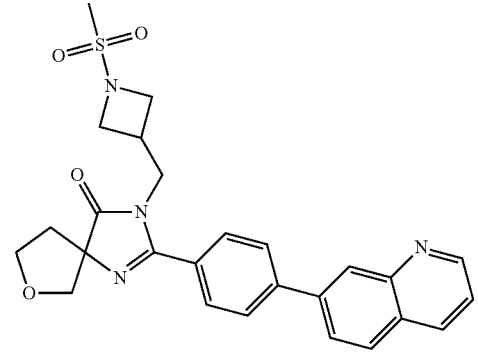 [SMILES: CS(=O)(=O)N1CC(CN2C(=O)C3(CCOC3)N=C2c2ccc(-c3ccc4cccnc4c3)cc2)C1] | 3-((1-(methylsulfonyl)azetidin-3-yl)methyl)-2-(4-(quinolin7-yl)phenyl)-7-oxa-1,3-diazaspiro[4.4]non-1-en-4-one<br>MS m/z 491.2 (M + H)+ |
| 943 | 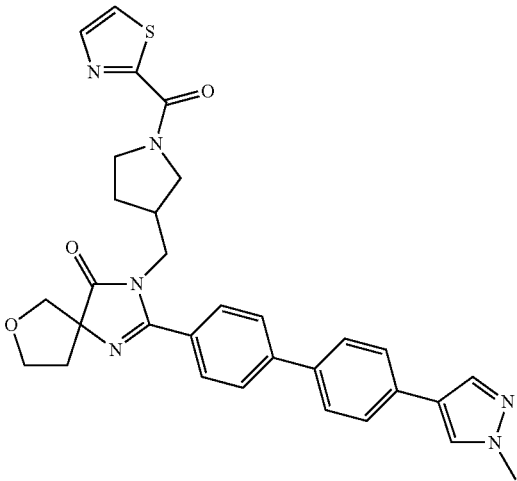 [SMILES: Cn1cc(-c2ccc(-c3ccc(C4=NC5(CCOC5)C(=O)N4CC4CCN(C(=O)c5nccs5)C4)cc3)cc2)cn1] | 2-(4'-(1-methyl-1H-pyrazol-4-yl)-[1,1'-biphenyl]-4-yl)-3-((1-(thiazole-2-carbonyl)pyrrolidin-3-yl)methyl)-7-oxa-1,3-diazaspiro[4.4]non-1-en-4-one<br>MS m/z 567.2 (M + H)+ |

| ID No. | Structure | Compound Name & Physical Data |
|---|---|---|
| 944 | 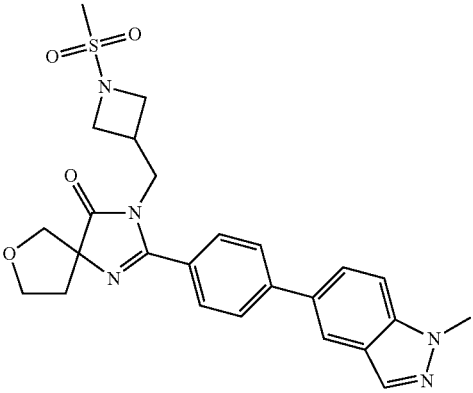 [SMILES: Cn1ncc2cc(-c3ccc(C4=NC5(CCOC5)C(=O)N4CC4CN(S(C)(=O)=O)C4)cc3)ccc21] | 2-(4-(1-methyl-1H-indazol-5-yl)phenyl)-3-((1-(methylsulfonyl)azetidin-3-yl)methyl)-7-oxa-1,3-diazaspiro[4.4]non-1-en-4-one<br>MS m/z 494.2 (M + H)+ |
| 945 | 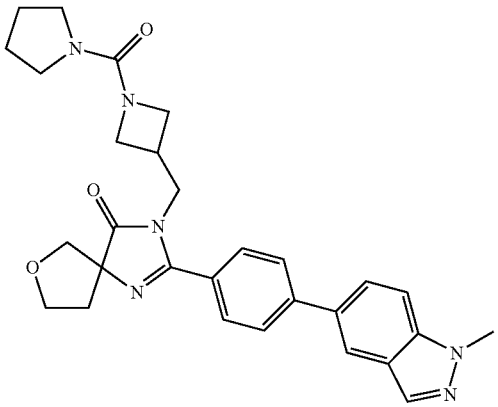 [SMILES: Cn1ncc2cc(-c3ccc(C4=NC5(CCOC5)C(=O)N4CC4CN(C(=O)N5CCCC5)C4)cc3)ccc21] | 2-(4-(1-methyl-1H-indazol-5-yl)phenyl)-3-((1-(pyrrolidine-1-carbonyl)azetidin-3-yl)methyl)-7-oxa-1,3-diazaspiro[4.4]non-1-en-4-one<br>MS m/z 513.3 (M + H)+ |
| 946 | 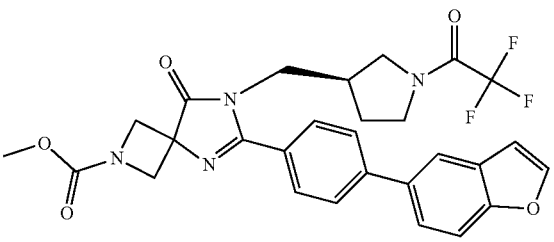 [SMILES: COC(=O)N1CC2(C1)N=C(c1ccc(-c3ccc4occc4c3)cc1)N(C[C@@H]1CCN(C(=O)C(F)(F)F)C1)C2=O] | (R)-methyl 6-(4-(benzofuran-5-yl)phenyl)-8-oxo-7-((1-(2,2,2-trifluoroacetyl)pyrrolidin-3-yl)methyl)-2,5,7-triazaspiro[3.4]oct-5-ene-2-carboxylate<br>MS m/z 555.1 (M + H)+ |
| 947 | 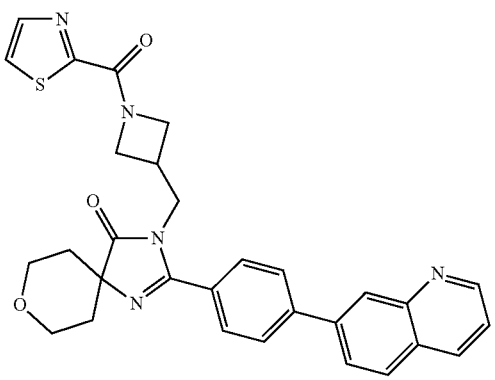 [SMILES: O=C(c1nccs1)N1CC(CN2C(=O)C3(CCOCC3)N=C2c2ccc(-c3ccc4cccnc4c3)cc2)C1] | 2-(4-(quinolin-7-yl)phenyl)-3-((1-(thiazole-2-carbonyl)azetidin-3-yl)methyl)-8-oxa-1,3-diazaspiro[4.5]dec-1-ene-4-one<br>MS m/z 538.1 (M + H)+ |

| ID No. | Structure | Compound Name & Physical Data |
|---|---|---|
| 948 | 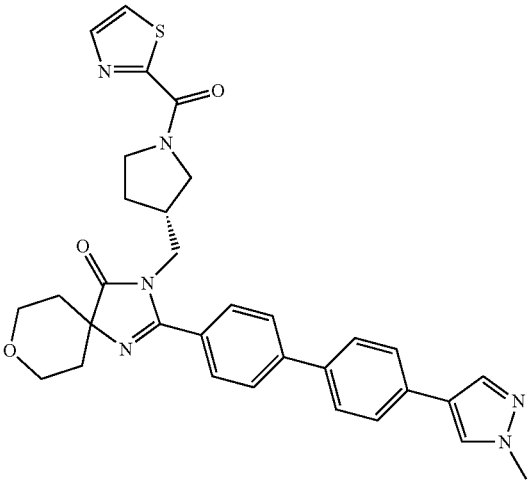 [SMILES: Cn1cc(-c2ccc(-c3ccc(C4=NC5(CCOCC5)C(=O)N4C[C@@H]4CCN(C(=O)c5nccs5)C4)cc3)cc2)cn1] | (R)-2-(4'-(1-methyl-1H-pyrazol-4-yl)-[1,1'-biphenyl]-4-yl)-3-((1-(thiazole-2-carbonyl)pyrrolidin-3-yl)methyl)-8-oxa-1,3-diazaspiro[4.5]dec-1-en-4-one<br>MS m/z 581.2 (M + H)+ |
| 949 | 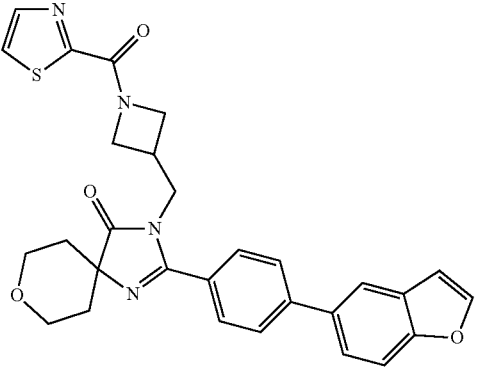 [SMILES: O=C(c1nccs1)N1CC(CN2C(=O)C3(CCOCC3)N=C2c2ccc(-c3ccc4occc4c3)cc2)C1] | 2-(4-(benzofuran-5-yl)phenyl)-3-((1-(thiazole-2-carbonyl)azetidin-3-yl)methyl)-8-oxa-1,3-diazaspiro[4.5]dec-1-en-4-one<br>MS m/z 527.2 (M + H)+ |
| 950 | 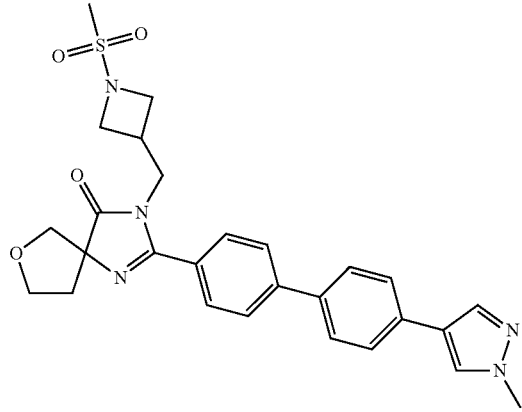 [SMILES: Cn1cc(-c2ccc(-c3ccc(C4=NC5(CCOC5)C(=O)N4CC4CN(S(C)(=O)=O)C4)cc3)cc2)cn1] | 2-(4'-(1-methyl-1H-pyrazol-4-yl)-[1,1'-biphenyl]-4-yl)-3-((1-(methylsulfonyl)azetidin-3-yl)methyl)-7-oxa-1,3-diazaspiro[4.4]non-1-en-4-one<br>MS m/z 520.2 (M + H)+ |
| 951 | 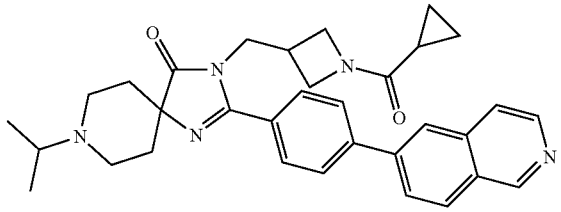 [SMILES: CC(C)N1CCC2(CC1)N=C(c1ccc(-c3ccc4cnccc4c3)cc1)N(CC1CN(C(=O)C3CC3)C1)C2=O] | 3-((1-(cyclopropanecarbonyl)azetidin-3-yl)methyl)-8-isopropyl-2-(4-(isoquinolin-6-yl)phenyl)-1,3,8-triazaspiro[4.5]dec-1-en-4-one<br>MS m/z 536 (M + H)+ |

| ID No. | Structure | Compound Name & Physical Data |
|---|---|---|
| 952 | 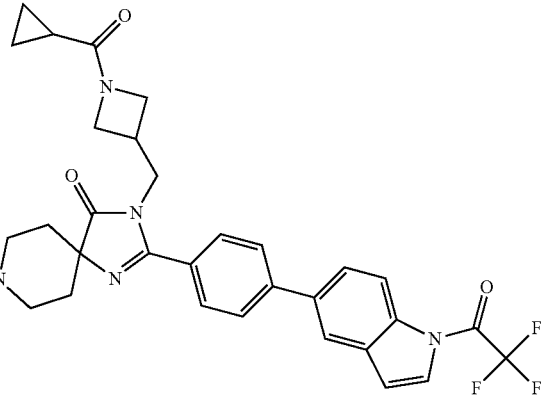 | 3-((1-(cyclopropanecarbonyl)azetidin-3-yl)methyl)-8-(2,2,2-trifluoroacetyl)-2-(4-(1-(2,2,2-trifluoroacetyl)-1H-indol-5-yl)phenyl)-1,3,8-triazaspiro[4.5]dec-1-en-4-one<br>MS m/z 578 (M + H)+ |
| 953 | 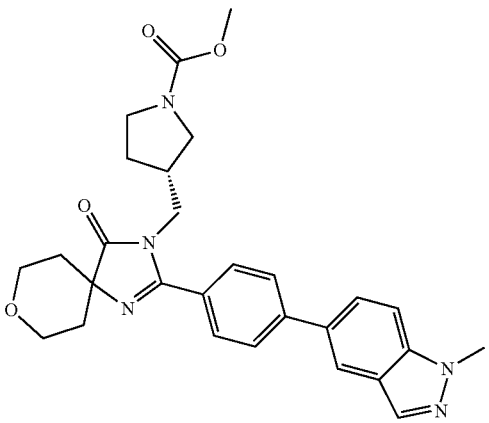 [SMILES: COC(=O)N1CC[C@@H](CN2C(=O)C3(CCOCC3)N=C2c2ccc(-c3ccc4c(cnn4C)c3)cc2)C1] | (S)-methyl 3-((2-(4-(1-methyl-1H-indazol-5-yl)phenyl)-4-oxo-8-oxa-1,3-diazaspiro[4.5]dec-1-en-3-yl)methyl)pyrrolidine-1-carboxylate<br>MS m/z 502.2 (M + H)+ |
| 954 | 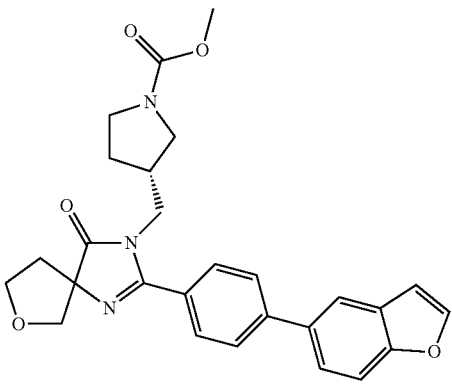 [SMILES: COC(=O)N1CC[C@@H](CN2C(=O)C3(CCOC3)N=C2c2ccc(-c3ccc4occc4c3)cc2)C1] | (3S)-methyl 3-((2-(4-(benzofuran-5-yl)phenyl)-4-oxo-7-oxa-1,3-diazaspiro[4.4]non-1-en-3-yl)methyl)pyrrolidine-1-carboxylate<br>MS m/z 47 4.2 (M + H)+ |

| ID No. | Structure | Compound Name & Physical Data |
|---|---|---|
| 955 | 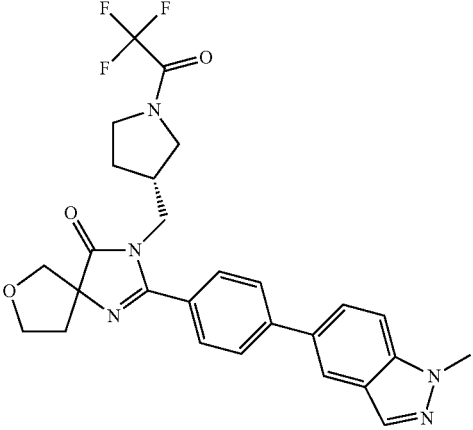 [SMILES: Cn1ncc2cc(-c3ccc(C4=NC5(CCOC5)C(=O)N4C[C@@H]4CCN(C(=O)C(F)(F)F)C4)cc3)ccc21] | 2-(4-(1-methyl-1H-indazol-5-yl)phenyl)-3-(((R)-1-(2,2,2-trifluoroacetyl)pyrrolidin-3-yl)methyl)-7-oxa-1,3-diazaspiro[4.4]non-1-en-4-one<br>MS m/z 526.1 (M + H)+ |
| 956 | 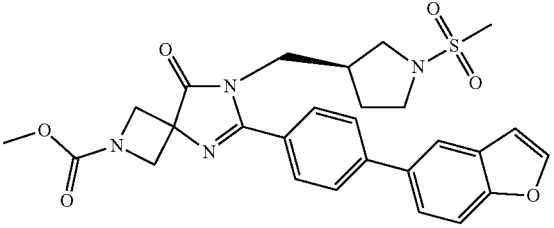 [SMILES: COC(=O)N1CC2(C1)N=C(c1ccc(-c3ccc4occc4c3)cc1)N(C[C@@H]1CCN(S(C)(=O)=O)C1)C2=O] | (S)-methyl 6-(4-(benzofuran-5-yl)phenyl)-7-((1-(methylsulfonyl)pyrrolidin-3-yl)methyl)-8-oxo-2,5,7-triazaspiro[3.4]oct-5-ene-2-carboxylate<br>MS m/z 537.1 (M + H)+ |
| 957 | 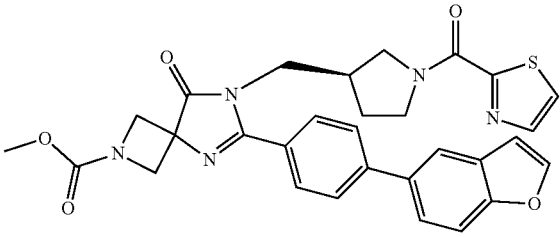 [SMILES: COC(=O)N1CC2(C1)N=C(c1ccc(-c3ccc4occc4c3)cc1)N(C[C@@H]1CCN(C(=O)c3nccs3)C1)C2=O] | (R)-methyl 6-(4-(benzofuran-5-yl)phenyl)-8-oxo-7-((1-(thiazole-2-carbonyl)pyrrolidin-3-yl)methyl)-2,5,7-triazaspiro[3.4]oct-5-ene-2-carboxylate<br>MS m/z 570.2 (M + H)+ |
| 958 | 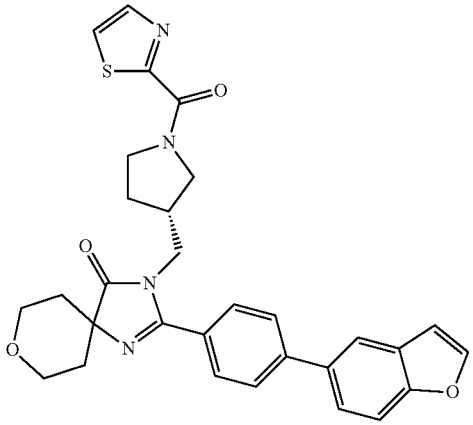 [SMILES: O=C(c1nccs1)N1CC[C@@H](CN2C(=O)C3(CCOCC3)N=C2c2ccc(-c3ccc4occc4c3)cc2)C1] | (R)-2-(4-(benzofuran-5-yl)phenyl)-3-((1-(thiazole-2-carbonyl)pyrrolidin-3-yl)methyl)-8-oxa-1,3-diazaspiro[4.5]dec-1-en-4-one<br>MS m/z 541.1 (M + H)+ |

| ID No. | Structure | Compound Name & Physical Data |
|---|---|---|
| 959 | 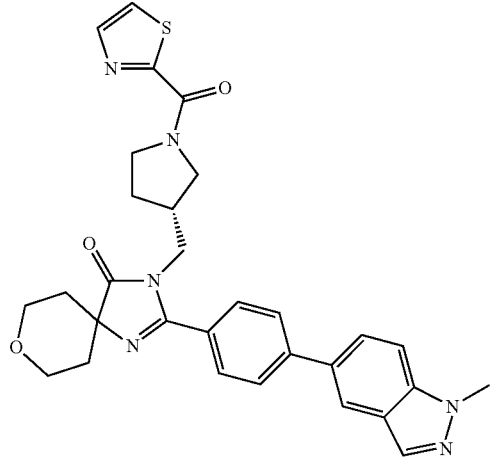 [SMILES: Cn1ncc2cc(-c3ccc(C4=NC5(CCOCC5)C(=O)N4C[C@@H]4CCN(C(=O)c5nccs5)C4)cc3)ccc21] | (R)-2-(4-(1-methyl-1H-indazol-5-yl)phenyl)-3-((1-(thiazole-2-carbonyl)pyrrolidin-3-yl)methyl)-8-oxa-1,3-diazaspiro[4.5]dec-1-en-4-one<br>MS m/z 555.1 (M + H)+ |
| 960 | 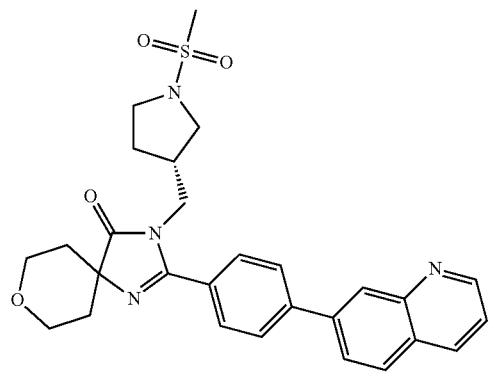 [SMILES: CS(=O)(=O)N1CC[C@@H](CN2C(=O)C3(CCOCC3)N=C2c2ccc(-c3ccc4cccnc4c3)cc2)C1] | (S)-3-((1-(methylsulfonyl)pyrrolidin-3-yl)methyl)-2-(4-quinolin-7-yl)phenyl)-8-oxa-1,3-diazaspiro[4.5]dec-1-en-4-one<br>MS m/z 519.2 (M + H)+ |
| 961 | 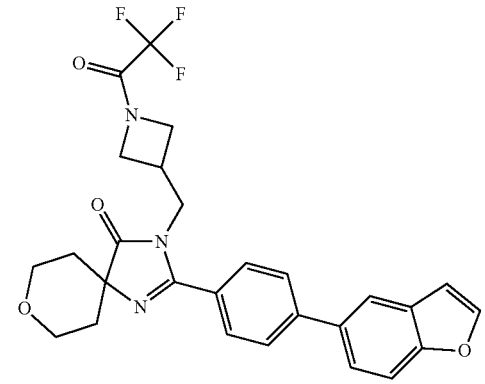 [SMILES: O=C(N1CC(CN2C(=O)C3(CCOCC3)N=C2c2ccc(-c3ccc4occc4c3)cc2)C1)C(F)(F)F] | 2-(4-(benzofuran-5-yl)phenyl)-3-((1-(2,2,2-trifluoroacetyl)azetidin-3-yl)methyl)-8-oxa-1,3-diazaspiro[4.5]dec-1-en-4-one<br>MS m/z 512.2 (M + H)+ |
| 962 | 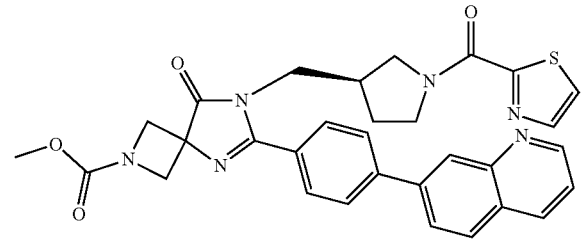 [SMILES: COC(=O)N1CC2(C1)N=C(c1ccc(-c3ccc4cccnc4c3)cc1)N(C[C@@H]1CCN(C(=O)c3nccs3)C1)C2=O] | (R)-methyl 8-oxo-6-(4-(quinolin-7-yl)phenyl)-7-((1-(thiazole-2-carbonyl)pyrrolidin-3-yl)methyl)-2,5,7-triazaspiro[3.4]oct-5-ene-2-carboxylate<br>MS m/z 581.1 (M + H)+ |

| ID No. | Structure | Compound Name & Physical Data |
|---|---|---|
| 963 | 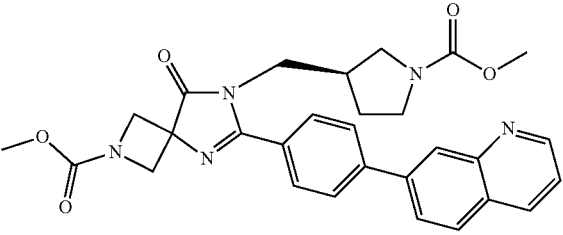 [SMILES: COC(=O)N1CC[C@@H](CN2C(=O)C3(CN(C(=O)OC)C3)N=C2c2ccc(-c3ccc4cccnc4c3)cc2)C1] | (S)-methyl 7-((1-(methoxycarbonyl)pyrrolidin-3-yl)methyl)-8-oxo-6-(4-(quinolin-7-yl)phenyl)-2,5,7-triazaspiro[3.4]oct-5-ene-2-carboxylate<br>MS m/z 528.3 (M + H)+ |
| 964 | 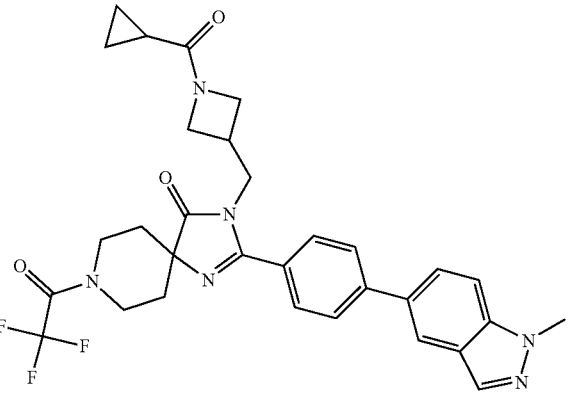 [SMILES: Cn1ncc2cc(-c3ccc(C4=NC5(CCN(C(=O)C(F)(F)F)CC5)C(=O)N4CC4CN(C(=O)C5CC5)C4)cc3)ccc21] | 3-((1-(cyclopropanecarbonyl)azetidin-3-yl)methyl)-2-(4-(1-methyl-1H-indazol-5-yl)phenyl)-8-(2,2,2,-trifluoroacetyl)-1,3,8-triazaspiro[4.5]dec-1-en-4-one<br>MS m/z 593 (M + H)+ |
| 965 | 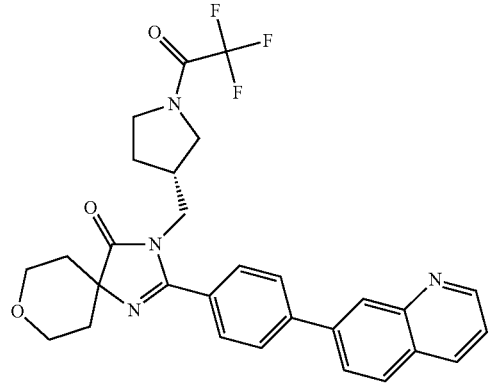 [SMILES: O=C(N1CC[C@@H](CN2C(=O)C3(CCOCC3)N=C2c2ccc(-c3ccc4cccnc4c3)cc2)C1)C(F)(F)F] | (R)-2-(4-(quinolin-7-yl)phenyl)-3-((1-(2,2,2-trifluoroacetyl)pyrrolidin-3-yl)methyl)-8-oxa-1,3-diazaspiro[4.5]dec-1-en-4-one<br>MS m/z 537.2 (M + H)+ |
| 966 | 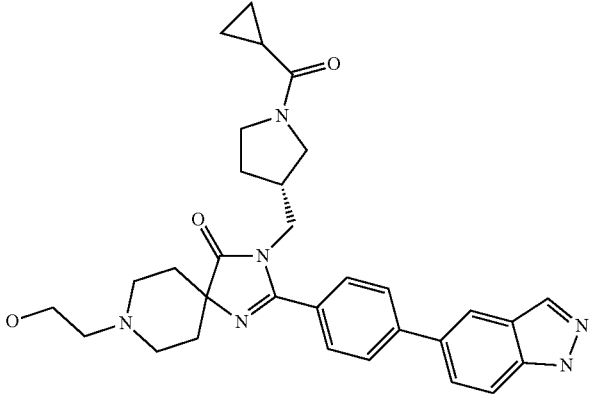 [SMILES: O=C(C1CC1)N1CC[C@@H](CN2C(=O)C3(CCN(CCO)CC3)N=C2c2ccc(-c3ccc4[nH]ncc4c3)cc2)C1] | (R)-2-(4-(1H-indazol-5-yl)phenyl)-3-((1-(cyclopropanecarbonyl)pyrrolidin-3-yl)methyl)-8-(2-hydroxyethyl)-1,3,8-triazaspiro[4.5]dec-1-en-4-one<br>MS m/z 541 (M + H)+ |

| ID No. | Structure | Compound Name & Physical Data |
|---|---|---|
| 967 | 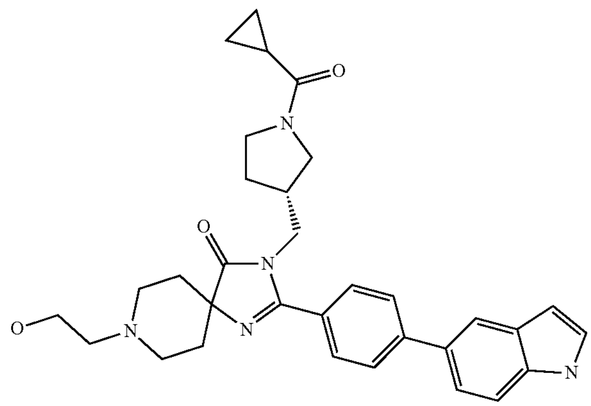 [SMILES: O=C(C1CC1)N1CC[C@@H](CN2C(=O)C3(CCN(CCO)CC3)N=C2c2ccc(-c3ccc4[nH]ccc4c3)cc2)C1] | (R)-2-(4-(1H-indol-5-yl)phenyl)-3-((1-(cyclopropanecarbonyl)pyrrolidin-3-yl)methyl)-8-(2-hydroxyethyl)-1,3,8-triazaspiro[4.5]dec-1-en-4-one<br>MS m/z 540 (M + H)+ |
| 968 | 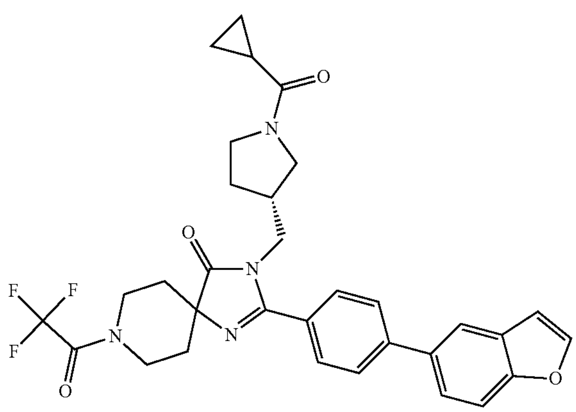 [SMILES: O=C(C1CC1)N1CC[C@@H](CN2C(=O)C3(CCN(C(=O)C(F)(F)F)CC3)N=C2c2ccc(-c3ccc4occc4c3)cc2)C1] | (R)-2-(4-(benzofuran-5-yl)phenyl)-3-((1-(cyclopropanecarbonyl)pyrrolidin-3-yl)methyl)-8-(2,2,2-trifluoroacetyl)-1,3,8-triazaspiro[4.5]dec-1-en-4-one<br>MS m/z 593 (M + H)+ |
| 969 | 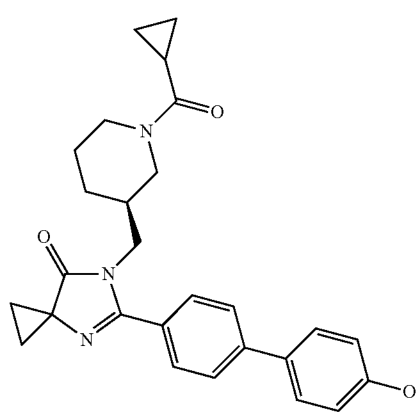 [SMILES: O=C(C1CC1)N1CCC[C@H](CN2C(=O)C3(CC3)N=C2c2ccc(-c3ccc(O)cc3)cc2)C1] | (S)-6-((1-(cyclopropanecarbonyl)piperidin-3-yl)methyl)-5-(4'-hydroxy-[1,1'-biphenyl]-4-yl)-4,6-diazaspiro[2.4]hept-4-en-7-one<br>MS m/z 444 (M + H)+ |

-continued

| ID No. | Structure | Compound Name & Physical Data |
|---|---|---|
| 970 | 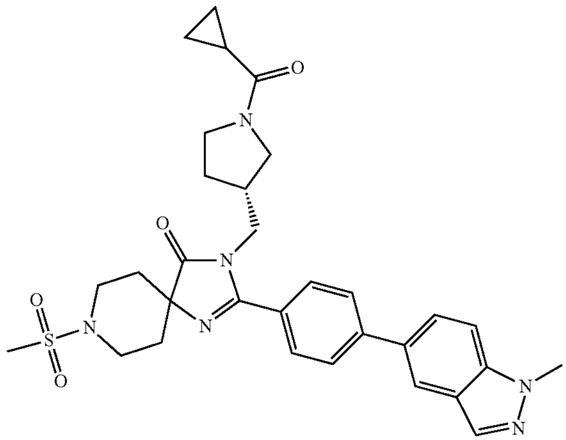 | (R)-3-((1-(cyclopropanecarbonyl)pyrrolidin-3-yl)methyl)-2-(4-(1-methyl-1H-indazol-5-yl)phenyl)-8-(methylsulfonyl)-1,3,8-triazaspiro[4.5]dec-1-en-4-one<br>MS m/z 589 (M + H)+ |

BIOLOGICAL EXAMPLES

Biological Example 1

Fatty Acid Synthase (FASN) Inhibition Scintillation Proximity Assay

In this assay, inhibition of FASN activity is measured using $^3$H-acetyl-CoA and malonyl-CoA as substrates. $^3$H-Acetyl CoA is converted to $^3$H-palmitate through a series of reactions by the FASN protein, which contains 7 functional domains and carries out 7 enzymatic reactions to ultimately produce $^3$H-palmitate. The assay principle is based upon the fact that $^3$H-acetyl-CoA is hydrophilic and the end product, $^3$H-palmitate is hydrophobic. The hydrophobic $^3$H-palmitate binds to scintillation proximity assay (SPA) imaging beads (resulting in light emission from the imaging beads) whereas the hydrophilic $^3$H-acetyl-CoA does not bind to the imaging beads (and therefore does not result in light emission from the imaging beads).

10 μL assay buffer (100 mM $KH_2PO_4$ pH 7.5, 1 mM DTT) (20 μL in blanks) was added to a 384-well white optiplate plate (Perkin Elmer). 0.9 μL test compound (at concentrations of 30 μM, 10 μM, 3 μM, 1 μM, 0.30 μM, 0.10 μM, 0.03 μM and 0.01 μM)/DMSO and 10 μL hFASN enzyme (full length, 300 ng, purified in house) or 10 μL assay buffer was added to the wells. Then 10 μL 450 μM NADPH (Sigma N7505), 18.75 μM [$^3$H]-acetyl-CoA (Perkin Elmer NET-290L), 150 μM malonyl-CoA (Sigma M4263) were added, mixed and incubated at room temperature for 60 minutes. The reaction was stopped by adding 20 μL Streptavidin coupled imaging beads (25 mg/ml). After incubation for 30 minutes at room temperature in the dark, the 384 well plate was centrifuged at 1500 rpm for 3 minutes and was measured after at least 24 hrs by the LEADseeker™, measuring emission using a 610±20 nm pass filter. (Bays, N. W., et al., "A simplified scintillation proximity assay for fatty acid synthase activity: development and comparison with other FAS activity assays", *J. Biomol. Screen.*, 2009, pp 636-642, Vol. 14(6).)

Raw data generated by the instrument were normalized to % Controlmin values, which were calculated as:

% Controlmin=$100*(x-mLC)/(mHC-mLC)$ where mLC and mHC were the means of the low control wells and high control wells on the plate, after manual exclusion of outliers. A plot of Controlmin versus test compound concentration was fitted to a 4-parameter logistic curve using a non-linear least squares regression method. From the plot, an $IC_{50}$ (concentration at such 50% inhibition is achieved) was calculated. $pIC_{50}$ values were calculated as $-\log(IC_{50})$, when $IC_{50}$ is expressed in molar units.

Representative compounds of formula (I) the present invention were tested according to the procedure as described in Biological Example 1 above, with results as listed in Table 6, below. Wherein the results listed below, the $pIC_{50}$ value is preceded with a "~", the "~" indicates that the standard error of the $pIC_{50}$ value, as estimated by the non-linear regression algorithm, is larger than 0.5. This corresponds to a factor of uncertainly on the $IC_{50}$ that is larger than square root of 10 (>3.162).

TABLE 6

FASN pIC50

| ID No. | Human FASN pIC$_{50}$ | Human FASN % inhibition @ 10 μM |
|---|---|---|
| 1 | 6.24 | 93 |
| 2 | 7.34 | 108.6 |
| 3 | <5 | 44.3 |
| 4 | 7.47 | 102.6 |
| 5 | 5.67 | 74.6 |
| 6 | 5.14 | 61.6 |
| 7 | <5 | 33.7 |
| 8 | <5 | 5.1 |
| 9 | <5 | 11.4 |
| 10 | 6.69 | 89.7 |
| 11 | 6.03 | 82.2 |
| 12 | 7.59 | 99.4 |
| 13 | <5 | 29.7 |
| 14 | 6.83 | 98.2 |
| 15 | 7.36 | 113 |
| 16 | 5.86 | 72.5 |
| 17 | 6.64 | 97 |
| 18 | <5 | 42.7 |
| 19 | 5.86 | 78 |
| 20 | 6.8 | 101 |
| 22 | 5.97 | 85 |
| 24 | 5.73 | 76.4 |
| 25 | ~5.31 | 64.4 |
| 27 | 7.15 | 100.1 |

TABLE 6-continued

FASN pIC50

| ID No. | Human FASN pIC$_{50}$ | Human FASN % inhibition @ 10 μM |
|---|---|---|
| 28 | 7.53 | 109.6 |
| 29 | 6.03 | 81.7 |
| 30 | 7.24 | 107.5 |
| 31 | 7.66 | 106.7 |
| 32 | <5 | 6.8 |
| 33 | 7.59 | 109.4 |
| 34 | 6.93 | 101.7 |
| 35 | 7.08 | 106.8 |
| 36 | 6.26 | 96.2 |
| 37 | <5 | 28.6 |
| 38 | 6.57 | 94.9 |
| 39 | 7.19 | 103 |
| 40 | 7.73 | 105.6 |
| 41 | 6.34 | 92.6 |
| 42 | <5 | 23.5 |
| 43 | ~5 | 45.4 |
| 44 | <5 | −0.97 |
| 47 | 7.69 | 102.6 |
| 48 | 7.01 | 107.6 |
| 49 | 7.22 | 101.4 |
| 50 | 5.46 | 64.8 |
| 51 | 7.1 | 101.9 |
| 52 | 6.12 | 89.9 |
| 53 | 5.71 | 78.6 |
| 54 | 5.33 | 64.7 |
| 55 | <5 | 32.7 |
| 56 | 6.39 | 89.2 |
| 57 | 6.12 | 88.1 |
| 58 | 7.6 | 107.7 |
| 59 | 7.38 | 98.7 |
| 60 | 7.03 | 99.4 |
| 61 | 5.4 | 63.2 |
| 62 | <5 | 29.3 |
| 63 | 7.13 | 115 |
| 64 | 6.15 | 92.9 |
| 65 | 7.55 | 101.1 |
| 66 | 7.13 | 106.5 |
| 67 | 6.55 | 100.1 |
| 68 | 7.2 | 107 |
| 69 | 6.65 | 100.1 |
| 70 | 6.27 | 92.5 |
| 71 | 7.38 | 102 |
| 72 | 7.32 | 106.3 |
| 73 | 7.48 | 111.1 |
| 74 | 7.65 | 113.7 |
| 75 | 6.29 | 92.7 |
| 76 | 6.89 | 99.2 |
| 77 | 6.76 | 102.6 |
| 78 | 7.23 | 111.3 |
| 79 | 7.21 | 107.5 |
| 80 | 6.36 | 92.1 |
| 81 | 7.04 | 109.4 |
| 82 | 6.67 | 105.2 |
| 83 | 5.32 | 65.6 |
| 84 | 6.0 | 89.2 |
| 85 | 6.45 | 97.9 |
| 90 | 6.51 | 101 |
| 91 | <5 | 21.3 |
| 92 | 7.29 | 111.3 |
| 93 | 7.12 | 115.8 |
| 94 | 6.84 | 110.8 |
| 95 | <5 | 24.4 |
| 96 | 5.3 | 71.2 |
| 97 | 5.25 | 58.7 |
| 98 | <5 | 35.1 |
| 99 | 5.33 | 61.4 |
| 100 | 7.13 | 110.2 |
| 101 | 7.09 | 112.1 |
| 102 | 6.68 | 106.6 |
| 103 | 7.17 | 108.6 |
| 104 | 5.49 | 71.7 |
| 105 | 7.0 | 104.1 |
| 106 | 6.95 | 109.9 |
| 107 | <5 | 10.6 |
| 108 | 5.82 | 83.8 |
| 109 | 5.29 | 62.1 |
| 110 | <5 | 32.6 |
| 111 | 5.36 | 62.2 |
| 112 | 7.3 | 104.2 |
| 113 | 6.93 | 109.4 |
| 114 | 7.12 | 106.9 |
| 115 | 7.52 | 113 |
| 116 | 7.55 | 121.2 |
| 117 | 6.69 | 107.7 |
| 118 | 6.45 | 101.1 |
| 119 | 6.76 | 107.4 |
| 120 | 7.41 | 115.9 |
| 121 | 7.04 | 115.1 |
| 122 | 6.91 | 112.3 |
| 123 | 5.9 | 81.5 |
| 124 | 6.94 | 113.2 |
| 125 | 5.4 | 64.6 |
| 126 | 6.19 | 96.3 |
| 127 | 6.31 | 106.7 |
| 129 | 5.93 | 90.7 |
| 130 | 5.42 | 74 |
| 131 | 5.05 | 52.1 |
| 132 | 5.77 | 83.7 |
| 133 | 6.35 | 99.1 |
| 134 | 6.25 | 91.7 |
| 135 | 5.61 | 78.9 |
| 136 | 5.53 | 77.7 |
| 137 | 6.75 | 111.6 |
| 138 | 6.41 | 101.5 |
| 139 | 6.76 | 111.5 |
| 140 | 6.65 | 113.9 |
| 141 | 6.6 | 110.3 |
| 142 | 7.16 | 119.3 |
| 143 | 7.44 | 118.6 |
| 144 | 7.2 | 116.6 |
| 145 | 6.4 | 105.5 |
| 146 | <5 | 38 |
| 147 | 7.15 | 89.5 |
| 148 | 6.52 | 104.6 |
| 150 | 6.98 | 112.9 |
| 151 | 6.89 | 111.8 |
| 152 | 6.91 | 123 |
| 153 | 6.98 | 115.6 |
| 154 | 6.57 | 109.4 |
| 155 | 6.11 | 96.5 |
| 156 | 6.72 | 107.8 |
| 157 | 7.17 | 112.2 |
| 158 | <5 | 33 |
| 159 | 7.1 | 116 |
| 160 | <5 | 29.3 |
| 161 | <5 | 16 |
| 162 | 5.96 | 90.9 |
| 163 | 6.64 | 110.5 |
| 164 | 7.4 | 115.2 |
| 165 | 6.64 | 108.3 |
| 166 | 5.47 | 71.6 |
| 167 | 6.28 | 96.4 |
| 168 | 6.84 | 108 |
| 169 | <5 | 45.7 |
| 170 | 5.1 | 55.6 |
| 171 | 6.67 | 106.6 |
| 172 | 6.6 | 107.9 |
| 173 | 6.42 | 97 |
| 174 | 6.61 | 109.4 |
| 178 | 6.99 | 108 |
| 179 | 5.2 | 59.5 |
| 180 | 6.86 | 100.8 |
| 181 | 6.91 | 109.4 |
| 182 | 6.86 | 103.9 |
| 183 | 6.86 | 108.8 |
| 184 | 6.36 | 106.6 |
| 186 | 5.81 | 80.4 |
| 187 | 6.22 | 96.5 |
| 188 | ~5 | 50.4 |
| 189 | <5 | 16.7 |

TABLE 6-continued

FASN pIC50

| ID No. | Human FASN pIC$_{50}$ | Human FASN % inhibition @ 10 μM |
|---|---|---|
| 190 | 6.53 | 105.2 |
| 191 | 7.1 | 108.3 |
| 192 | 6.23 | 94.3 |
| 200 | 7.46 | 102 |
| 201 | 7.36 | 100 |
| 202 | 7.08 | 101 |
| 203 | 7.24 | 99 |
| 204 | 7.24 | 103 |
| 205 | 7.01 | 94 |
| 206 | 7.43 | 101 |
| 207 | 7.08 | 101 |
| 208 | 7.19 | 99 |
| 209 | 7.05 | 108 |
| 210 | 7.05 | 103 |
| 211 | 7.07 | 107 |
| 212 | 7.55 | 101 |
| 213 | 7.33 | 95 |
| 214 | 7.65 | 99 |
| 215 | 7.63 | 102 |
| 216 | 7.54 | 102 |
| 217 | 7.54 | 103 |
| 218 | 7.14 | 95 |
| 219 | 7.12 | 103 |
| 220 | 7.04 | 99 |
| 221 | 7.01 | 92 |
| 222 | 7.56 | 103 |
| 223 | 7.27 | 104 |
| 224 | 7.6 | 103 |
| 225 | 7.42 | 95 |
| 226 | 7.63 | 98 |
| 227 | 7.37 | 99 |
| 228 | 7.35 | 103 |
| 230 | 7.39 | 107 |
| 231 | 7 | 108 |
| 232 | 7.08 | 105 |
| 233 | 7.3 | 110 |
| 234 | 7.68 | 108 |
| 235 | 7.63 | 111 |
| 236 | 7.46 | 98 |
| 237 | 7.1 | 100 |
| 238 | 7.36 | 98 |
| 239 | 7.23 | 96 |
| 240 | 7.91 | 101 |
| 241 | 7.66 | 100 |
| 242 | 7.72 | 103 |
| 243 | 7.65 | 104 |
| 244 | 7.25 | 101 |
| 245 | 7.49 | 98 |
| 246 | 7.77 | 101 |
| 247 | 7.79 | 103 |
| 248 | 7.16 | 99 |
| 249 | 7.77 | 102 |
| 250 | 7.31 | 100 |
| 251 | 7.49 | 101 |
| 252 | 7.57 | 100 |
| 253 | 7.45 | 97 |
| 254 | 7.53 | 100 |
| 255 | 7.2 | 99 |
| 256 | 7.27 | 95 |
| 257 | 7.31 | 99 |
| 258 | 7.14 | 94 |
| 259 | 7.6 | 95 |
| 260 | 7.79 | 101 |
| 261 | 7.26 | 98 |
| 262 | ~7.29 | 94 |
| 263 | 7.29 | 105 |
| 264 | 7.43 | 108 |
| 265 | 7.34 | 103 |
| 266 | 7.47 | 102 |
| 267 | 7.58 | 97 |
| 268 | 7.26 | 104 |
| 269 | 7.65 | 102 |
| 270 | 7.45 | 102 |
| 271 | 7.25 | 104 |
| 272 | 7.73 | 105 |
| 273 | 7.37 | 102 |
| 274 | 7.3 | 101 |
| 278 | 7.59 | 113 |
| 279 | 7.55 | 107 |
| 280 | 7.52 | 109 |
| 281 | 7.35 | 114 |
| 282 | 7.06 | 106 |
| 283 | 7.38 | 112 |
| 284 | 7.59 | 106 |
| 286 | 7.36 | 103 |
| 287 | 7.36 | 110 |
| 288 | 7.57 | 107 |
| 289 | 7.01 | 102 |
| 290 | 7.1 | 110 |
| 291 | 7.56 | 108 |
| 292 | 7.06 | 100 |
| 293 | 7.42 | 105 |
| 294 | 7.37 | 100 |
| 295 | 7.27 | 100 |
| 296 | 7.41 | 106 |
| 297 | 7.5 | 111 |
| 298 | 7.66 | 100 |
| 299 | 7.64 | 101 |
| 300 | 7.24 | 102 |
| 301 | 7.7 | 99 |
| 302 | 7.48 | 101 |
| 303 | 7.51 | 102 |
| 304 | 7.01 | 99 |
| 305 | 7.6 | 103 |
| 306 | 7.3 | 98 |
| 307 | 7.17 | 100 |
| 308 | 7.32 | 102 |
| 309 | 7.7 | 101 |
| 310 | 7.4 | 102 |
| 311 | 7.6 | 101 |
| 312 | 7.12 | 101 |
| 313 | 7.41 | 99 |
| 314 | 7.39 | 103 |
| 315 | 7.18 | 98 |
| 316 | 7.38 | 108 |
| 317 | 7.24 | 103 |
| 318 | 7.18 | 100 |
| 319 | 7.54 | 105 |
| 320 | 7.59 | 102 |
| 321 | 7.52 | 99 |
| 322 | 7.42 | 102 |
| 323 | 7.6 | 101 |
| 324 | 7.49 | 105 |
| 325 | 7.1 | 100 |
| 326 | 7.4 | 103 |
| 327 | 7.49 | 104 |
| 328 | 7.5 | 98 |
| 331 | 7.18 | 100 |
| 332 | 7.73 | 100 |
| 333 | 7.26 | 98 |
| 334 | 7.66 | 97 |
| 335 | 7.19 | 105 |
| 336 | 7.3 | 103 |
| 337 | 7.44 | 105 |
| 338 | 7.36 | 106 |
| 339 | 7.51 | 95 |
| 340 | 7.54 | 101 |
| 341 | 7.19 | 102 |
| 342 | 7.16 | 106 |
| 343 | 7.29 | 98 |
| 344 | 7.59 | 99 |
| 345 | 7.05 | 99 |
| 346 | 7.31 | 97 |
| 347 | 7.31 | 98 |
| 348 | 7.2 | 96 |
| 349 | 7.78 | 102 |
| 350 | 7.82 | 99 |
| 351 | 7.13 | 95 |
| 352 | 7.13 | 94 |
| 353 | 7.26 | 101 |

TABLE 6-continued

FASN pIC50

| ID No. | Human FASN pIC$_{50}$ | Human FASN % inhibition @ 10 μM |
|---|---|---|
| 354 | 7.3 | 100 |
| 355 | 7.52 | 96 |
| 356 | 6.99 | 99 |
| 357 | 7.4 | 97 |
| 358 | 7.51 | 100 |
| 359 | 7.4 | 95 |
| 361 | 7.4 | 103 |
| 362 | 7.11 | 96 |
| 363 | 7.4 | 94 |
| 364 | 7.24 | 89 |
| 365 | 7.63 | 97 |
| 366 | 7.21 | 89 |
| 368 | 7.55 | 90 |
| 369 | 7.58 | 102 |
| 370 | 7.54 | 100 |
| 371 | 7.25 | 101 |
| 372 | 7.79 | 101 |
| 374 | 7.59 | 99 |
| 375 | 7.36 | 103 |
| 377 | 7.45 | 100 |
| 378 | 7.41 | 100 |
| 379 | 7.7 | 102 |
| 380 | 7.18 | 100 |
| 381 | 7.64 | 98 |
| 382 | 7.6 | 99 |
| 383 | 7.62 | 102 |
| 384 | 7.2 | 100 |
| 385 | 7.64 | 103 |
| 387 | 6.66 | 103 |
| 388 | 6.45 | 99 |
| 389 | 5.14 | 56 |
| 390 | 6.49 | 99 |
| 391 | 6.89 | 104 |
| 392 | 6.61 | 91 |
| 393 | ~5.54 | 62 |
| 394 | 5.97 | 84 |
| 395 | 5.2 | 54 |
| 396 | ~5.07 | 52 |
| 397 | 6.1 | 90 |
| 398 | 6.58 | 102 |
| 399 | 6.44 | 99 |
| 400 | 6.71 | 101 |
| 401 | 5.43 | 70 |
| 402 | 6.86 | 102 |
| 404 | 6.75 | 97 |
| 405 | 6.89 | 102 |
| 406 | 6.9 | 99 |
| 407 | 5.63 | 69 |
| 408 | 5.29 | 63 |
| 409 | 6.76 | 100 |
| 410 | 6.6 | 96 |
| 411 | 6.8 | 100 |
| 412 | 6.49 | 96 |
| 413 | 6.52 | 91 |
| 414 | 6.87 | 101 |
| 415 | 5.9 | 80 |
| 416 | ~5.75 | 76 |
| 417 | 5.28 | 62 |
| 418 | 6.82 | 103 |
| 419 | 6.29 | 96 |
| 420 | 6.31 | 92 |
| 421 | 6.34 | 94 |
| 422 | 5.48 | 70 |
| 423 | 6.5 | 90 |
| 424 | 5.4 | 68 |
| 425 | 6.56 | 93 |
| 426 | 6.46 | 94 |
| 427 | 6.38 | 91 |
| 428 | 6.86 | 101 |
| 429 | 6.62 | 96 |
| 430 | 5.05 | 52 |
| 431 | 6.5 | 97 |
| 432 | 6.85 | 98 |
| 433 | 5.74 | 72 |
| 434 | 5.69 | 73 |
| 435 | 6.58 | 91 |
| 436 | ~5 | 43 |
| 437 | 5.56 | 72 |
| 438 | 5.48 | 65 |
| 439 | 5.02 | 48 |
| 440 | 6.71 | 97 |
| 441 | 5.4 | 63 |
| 442 | 6.7 | 94 |
| 443 | 6.04 | 88 |
| 444 | 6.6 | 95 |
| 445 | 6.74 | 100 |
| 446 | 5.3 | 60 |
| 447 | 5.92 | 79 |
| 448 | 5.07 | 50 |
| 449 | 6.26 | 89 |
| 450 | 6.53 | 98 |
| 451 | 5.9 | 82 |
| 452 | 6.64 | 97 |
| 453 | 6.61 | 94 |
| 454 | ~5.22 | 53 |
| 455 | 6.79 | 99 |
| 456 | 5.16 | 65 |
| 457 | 6.34 | 91 |
| 458 | 5.09 | 48 |
| 459 | 5.06 | 43 |
| 460 | 5.51 | 63 |
| 461 | 6.85 | 95 |
| 462 | 6.8 | 98 |
| 463 | 6.65 | 93 |
| 464 | 5.39 | 66 |
| 465 | 6.82 | 99 |
| 466 | 6.32 | 87 |
| 467 | 6.48 | 93 |
| 468 | 6.37 | 90 |
| 469 | 6.93 | 97 |
| 470 | 6.74 | 98 |
| 471 | 6.74 | 99 |
| 472 | 6.89 | 97 |
| 473 | 6.57 | 95 |
| 474 | 6.91 | 99 |
| 475 | 6.78 | 93 |
| 476 | 6.58 | 90 |
| 477 | 5.51 | 67 |
| 478 | 5.86 | 92 |
| 479 | 6.79 | 95 |
| 480 | 6.81 | 97 |
| 481 | 5.66 | 68 |
| 482 | 5.88 | 76 |
| 483 | 6.97 | 95 |
| 484 | 6.82 | 99 |
| 485 | 6.79 | 96 |
| 486 | 5.82 | 81 |
| 487 | 5.93 | 81 |
| 488 | 6.67 | 88 |
| 489 | 6.93 | 97 |
| 490 | 6.48 | 81 |
| 491 | 6.94 | 100 |
| 492 | 6.0 | 77 |
| 493 | 6.78 | 98 |
| 494 | 6.66 | 95 |
| 495 | 6.59 | 95 |
| 496 | 6.52 | 94 |
| 497 | 6.23 | 87 |
| 498 | 6.94 | 99 |
| 499 | 6.61 | 96 |
| 500 | ~5.56 | 74 |
| 501 | 5.08 | 52 |
| 502 | 6.45 | 94 |
| 503 | 5.24 | 58 |
| 504 | 5.07 | 42 |
| 505 | 5.93 | 80 |
| 506 | 5.47 | 61 |
| 507 | 6.38 | 89 |
| 508 | 5.54 | 74 |
| 509 | 5.7 | 69 |

TABLE 6-continued

FASN pIC50

| ID No. | Human FASN pIC$_{50}$ | Human FASN % inhibition @ 10 μM |
|---|---|---|
| 510 | 6.02 | 80 |
| 511 | 6.45 | 94 |
| 512 | 6.17 | 87 |
| 513 | 5.91 | 85 |
| 514 | 5.13 | 56 |
| 515 | 6.74 | 96 |
| 516 | 5.93 | 83 |
| 517 | 6.19 | 88 |
| 518 | ~5.33 | 62 |
| 519 | 6.8 | 96 |
| 520 | 6.37 | 97 |
| 521 | 6.29 | 94 |
| 522 | 5.78 | 79 |
| 523 | 6.29 | 92 |
| 524 | 5.68 | 73 |
| 525 | 5.98 | 84 |
| 526 | 6.04 | 93 |
| 527 | 5.8 | 83 |
| 528 | 6.44 | 105 |
| 529 | 6.99 | 96 |
| 530 | 6.58 | 97 |
| 531 | 6.77 | 96 |
| 532 | 5.27 | 58 |
| 533 | 5.12 | 54 |
| 534 | 6.79 | 95 |
| 535 | 5.0 | 53 |
| 536 | 5.91 | 88 |
| 537 | 6.76 | 99 |
| 538 | 6.77 | 99 |
| 539 | ~5.2 | 54 |
| 540 | 5.3 | 64 |
| 541 | 6.96 | 100 |
| 542 | 6.16 | 89 |
| 543 | 6.84 | 97 |
| 544 | 6.69 | 98 |
| 545 | 6.96 | 101 |
| 546 | 6.69 | 100 |
| 547 | 6.75 | 98 |
| 548 | 6.79 | 88 |
| 549 | 5.75 | 83 |
| 550 | 5.74 | 80 |
| 551 | ~5.12 | 57 |
| 552 | 5.31 | 66 |
| 553 | 5.87 | 85 |
| 554 | 6.89 | 97 |
| 555 | 5.73 | 75 |
| 556 | 5.28 | 61 |
| 557 | 6.43 | 97 |
| 558 | 6.73 | 96 |
| 559 | 5.22 | 59 |
| 560 | 5.43 | 68 |
| 561 | ~5.14 | 56 |
| 562 | 6.61 | 97 |
| 563 | 6.2 | 88 |
| 564 | 6.58 | 97 |
| 566 | 6.42 | 93 |
| 568 | 6.89 | 89 |
| 569 | 6.68 | 86 |
| 570 | 5.38 | 65 |
| 571 | 5.86 | 79 |
| 572 | 6.87 | 87 |
| 573 | 6.78 | 88 |
| 574 | 6.09 | 82 |
| 575 | 5.09 | 52 |
| 576 | 6.42 | 99 |
| 577 | 5.63 | 67 |
| 578 | 6.19 | 92 |
| 579 | 5.96 | 83 |
| 580 | 6.91 | 108 |
| 581 | 6.5 | 93 |
| 582 | 6.49 | 103 |
| 583 | 5.4 | 74 |
| 584 | 6.87 | 91 |
| 585 | 6.95 | 99 |
| 586 | 6.28 | 93 |
| 587 | 5.48 | 70 |
| 588 | 6.22 | 93 |
| 589 | 5.02 | 52 |
| 590 | 5.76 | 80 |
| 591 | 6.71 | 93 |
| 592 | 5.53 | 70 |
| 593 | 5.15 | 56 |
| 594 | 6.61 | 102 |
| 595 | 5.87 | 83 |
| 596 | 6.73 | 102 |
| 597 | ~5.37 | 65 |
| 598 | 6.68 | 103 |
| 599 | 6.95 | 102 |
| 600 | 6.38 | 98 |
| 601 | 6.73 | 100 |
| 602 | 6.49 | 94 |
| 603 | 5.94 | 87 |
| 604 | 5.95 | 84 |
| 605 | 5.18 | 62 |
| 606 | 6.68 | 97 |
| 607 | 6.8 | 102 |
| 608 | 6.83 | 98 |
| 609 | 6.73 | 99 |
| 610 | 5.98 | 87 |
| 611 | ~5 | 46 |
| 612 | 5.69 | 74 |
| 613 | 6.94 | 102 |
| 614 | 6.82 | 102 |
| 615 | 6.49 | 98 |
| 616 | 6.29 | 94 |
| 617 | 6.78 | 100 |
| 618 | 6.64 | 98 |
| 619 | 6.73 | 101 |
| 620 | 5.4 | 71 |
| 621 | 6.21 | 92 |
| 622 | 5.8 | 82 |
| 623 | 6.84 | 101 |
| 624 | 5.65 | 76 |
| 627 | 6.97 | 105 |
| 628 | 6.93 | 100 |
| 629 | 5.13 | 55 |
| 630 | 5.5 | 67 |
| 631 | 5.07 | 47 |
| 632 | 5.56 | 70 |
| 633 | 5.08 | 56 |
| 634 | 5.52 | 68 |
| 635 | 6.66 | 97 |
| 636 | 5.17 | 59 |
| 637 | 6.92 | 99 |
| 638 | 6.72 | 100 |
| 639 | 6.55 | 97 |
| 640 | 5.27 | 64 |
| 641 | 6.94 | 102 |
| 642 | 6.66 | 99 |
| 643 | 6.42 | 96 |
| 644 | 6.75 | 97 |
| 645 | 6.56 | 100 |
| 646 | 5.93 | 88 |
| 647 | 6.2 | 91 |
| 648 | 5.59 | 74 |
| 649 | 6.8 | 97 |
| 650 | 5.87 | 84 |
| 651 | 5.51 | 77 |
| 652 | 6.73 | 97 |
| 653 | 5.52 | 71 |
| 654 | 5.94 | 83 |
| 655 | 6.75 | 99 |
| 656 | 5.7 | 74 |
| 657 | 6.51 | 97 |
| 658 | 5.06 | 52 |
| 659 | ~5.08 | 38 |
| 660 | 5.65 | 76 |
| 661 | 7.23 | 95 |
| 662 | 6.52 | 98 |
| 663 | 7.19 | 100 |

TABLE 6-continued

| | FASN pIC50 | |
|---|---|---|
| ID No. | Human FASN pIC$_{50}$ | Human FASN % inhibition @ 10 μM |
| 664 | 5.43 | 87 |
| 665 | 6.49 | 94 |
| 666 | ~5.3 | 62 |
| 667 | 6.81 | 97 |
| 668 | 5.93 | 86 |
| 669 | 6.77 | 96 |
| 670 | ~5.12 | 56 |
| 671 | 5.78 | 76 |
| 672 | 6.34 | 92 |
| 673 | 5.26 | 61 |
| 674 | 6.34 | 94 |
| 675 | 5.55 | 66 |
| 676 | 6.57 | 98 |
| 677 | ~5.15 | 63 |
| 678 | 6.43 | 95 |
| 679 | ~5.21 | 57 |
| 680 | 7.1 | 98 |
| 681 | 6.53 | 91 |
| 682 | 6.94 | 96 |
| 683 | 5.38 | 63 |
| 684 | 5.37 | 61 |
| 685 | 6.07 | 84 |
| 686 | 6.74 | 98 |
| 687 | 5.54 | 73 |
| 688 | 6.67 | 99 |
| 689 | 5.39 | 61 |
| 690 | 6.26 | 86 |
| 691 | ~5.13 | 63 |
| 692 | 6.1 | 99 |
| 693 | 5.01 | 48 |
| 694 | 5.61 | 69 |
| 695 | 5.23 | 43 |
| 696 | 5.77 | 72 |
| 697 | 5.23 | 58 |
| 698 | 6.6 | 92 |
| 699 | ~6.14 | 89 |
| 700 | 6.62 | 94 |
| 701 | 6.32 | 95 |
| 702 | ~5.58 | 75 |
| 703 | 5.35 | 61 |
| 704 | 6.06 | 86 |
| 705 | 5.57 | 71 |
| 706 | ~5.63 | 65 |
| 707 | 5.19 | 55 |
| 708 | 5.73 | 76 |
| 709 | 5.39 | 64 |
| 710 | 5.55 | 66 |
| 711 | 5.22 | 60 |
| 712 | 5.61 | 69 |
| 713 | ~5.17 | 59 |
| 714 | 6.44 | 89 |
| 715 | 6.14 | 86 |
| 716 | 6.4 | 88 |
| 717 | 6.17 | 87 |
| 718 | ~5.62 | 72 |
| 719 | 5.41 | 67 |
| 720 | 6.11 | 87 |
| 721 | 5.24 | 63 |
| 722 | 5.18 | 56 |
| 723 | 5.1 | 55 |
| 724 | 5.38 | 47 |
| 725 | 6.61 | 93 |
| 726 | 5.71 | 73 |
| 727 | 6.69 | 98 |
| 728 | 7.19 | 100 |
| 729 | 6.51 | 95 |
| 730 | 7.0 | 102 |
| 731 | 5.42 | 63 |
| 732 | ~5.92 | 88 |
| 733 | 6.7 | 96 |
| 734 | 5.77 | 84 |
| 735 | 6.87 | 97 |
| 736 | 5.38 | 51 |
| 737 | 6.52 | 97 |
| 738 | 5.72 | 80 |
| 739 | 6.63 | 92 |
| 740 | 5.05 | 46 |
| 741 | 6.8 | 102 |
| 742 | 6.72 | 99 |
| 743 | 6.15 | 90 |
| 744 | 6.94 | 98 |
| 745 | 7.15 | 104 |
| 746 | 6.56 | 94 |
| 747 | 7.07 | 96 |
| 748 | 6.45 | 99 |
| 749 | 6.86 | 97 |
| 750 | 6.51 | 94 |
| 751 | 6.87 | 98 |
| 752 | 6.11 | 91 |
| 753 | 6.87 | 107 |
| 754 | 5.53 | 67 |
| 755 | 6.64 | 107 |
| 756 | 5.8 | 82 |
| 757 | 6.8 | 104 |
| 758 | 5.47 | 71 |
| 759 | 5.04 | 38 |
| 760 | 5.32 | 62 |
| 761 | ~5.12 | 45 |
| 762 | 6.5 | 95 |
| 763 | ~5.27 | 63 |
| 764 | ~5.36 | 63 |
| 765 | 6.44 | 96 |
| 766 | ~5.35 | 67 |
| 767 | 5.72 | 76 |
| 768 | 5.84 | 79 |
| 769 | 5.3 | 60 |
| 770 | 5.66 | 77 |
| 771 | 5.12 | 44 |
| 772 | 5.4 | 64 |
| 775 | <5 | 34 |
| 776 | <5 | 25 |
| 777 | <5 | 34 |
| 784 | <5 | 14 |
| 785 | <5 | 24 |
| 786 | <5 | 31 |
| 787 | <5 | 38 |
| 788 | <5 | 14 |
| 789 | <5 | 26 |
| 790 | <5 | 47 |
| 791 | <5 | −2 |
| 792 | <5 | 38 |
| 793 | <5 | 13 |
| 794 | <5 | −15 |
| 795 | <5 | 34 |
| 796 | <5 | 19 |
| 797 | <5 | 1 |
| 798 | <5 | 30 |
| 799 | <5 | 39 |
| 800 | <5 | 16 |
| 801 | <5 | 6 |
| 802 | <5 | 24 |
| 803 | <5 | 48 |
| 804 | <5 | 41 |
| 805 | <5 | 14 |
| 806 | <5 | −6 |
| 807 | <5 | 7 |
| 808 | <5 | 31 |
| 809 | <5 | 29 |
| 811 | <5 | 35 |
| 812 | <5 | 5 |
| 813 | <5 | 2 |
| 814 | <5 | 39 |
| 815 | <5 | 1 |
| 816 | <5 | 4 |
| 817 | <5 | 1 |
| 818 | <5 | 2 |
| 819 | <5 | 10 |
| 820 | <5 | 33 |
| 821 | <5 | 7 |
| 822 | <5 | 25 |

TABLE 6-continued

| ID No. | Human FASN pIC$_{50}$ | Human FASN % inhibition @ 10 μM |
|---|---|---|
| 823 | <5 | 31 |
| 828 | <5 | 4 |
| 829 | <5 | 7 |
| 845 | 7.7 | 106 |
| 855 | <5 | 52 |
| 859 | <5 | 11 |
| 867 | <5 | 44 |
| 868 | 7.32 | |
| 869 | 7.33 | |
| 870 | 7.57 | |
| 871 | 7.65 | |
| 872 | 7.63 | 99 |
| 873 | 7.61 | 109 |
| 874 | 7.6 | 108 |
| 875 | 7.6 | 104 |
| 876 | 7.51 | 105 |
| 877 | 7.47 | 103 |
| 878 | 7.44 | 113 |
| 879 | 7.38 | 104 |
| 880 | 7.1 | 101 |
| 881 | 6.97 | 101 |
| 882 | 6.87 | 107 |
| 883 | 6.57 | 100 |
| 884 | 6.54 | 100 |
| 885 | 6.51 | 98 |
| 886 | 5.72 | 79 |
| 887 | 5.39 | 73 |
| 888 | <5 | 1 |
| 889 | <5 | 44 |
| 890 | <5 | 37 |
| 891 | <5 | 8 |
| 892 | <5 | −29 |
| 893 | <5 | −12 |
| 894 | <5 | 20 |
| 895 | <5 | 6 |
| 896 | <5 | 10 |
| 897 | <5 | 15 |
| 898 | <5 | 6 |
| 899 | <5 | −10 |
| 900 | <5 | 9 |
| 901 | <5 | 2 |
| 902 | <5 | 6 |
| 903 | <5 | 15 |
| 904 | <5 | −24 |
| 905 | <5 | −7 |
| 906 | <5 | 14 |
| 907 | <5 | 21 |
| 908 | <5 | 2 |
| 909 | <5 | 6 |
| 910 | <5 | 12 |
| 911 | <5 | 7 |
| 912 | <5 | 1 |
| 913 | <5 | 0.4 |
| 914 | <5 | 1 |
| 915 | <5 | 11 |
| 916 | <5 | 20 |
| 917 | <5 | 2 |
| 918 | <5 | 2 |
| 919 | <5 | 12 |
| 920 | <5 | 35 |
| 921 | <5 | −7 |
| 922 | <5 | 38 |
| 923 | <5 | 27 |
| 924 | <5 | 41 |
| 925 | <5 | 5 |
| 926 | <5 | −8 |
| 927 | <5 | −2 |
| 928 | <5 | 10 |
| 929 | <5 | 6 |
| 930 | <5 | −14 |
| 931 | <5 | 31 |
| 932 | <5 | 2 |
| 933 | <5 | 5 |
| 934 | <5 | 27 |
| 935 | <5 | −2 |
| 936 | <5 | 7 |
| 937 | <5 | −9 |
| 938 | <5 | 43 |
| 939 | <5 | 2 |
| 940 | <5 | 33 |
| 941 | <5 | 5 |
| 942 | <5 | 11 |
| 943 | <5 | 9 |
| 944 | <5 | 5 |
| 945 | <5 | 38 |
| 946 | <5 | 37 |
| 947 | <5 | −14 |
| 948 | <5 | 25 |
| 949 | <5 | −4 |
| 950 | <5 | −1.27 |
| 951 | <5 | 41 |
| 952 | <5 | 45 |
| 953 | <5 | 35 |
| 954 | <5 | 27 |
| 955 | <5 | 34 |
| 956 | <5 | 8 |
| 957 | <5 | 13 |
| 958 | <5 | −6 |
| 959 | <5 | −7 |
| 960 | <5 | −2 |
| 961 | <5 | 7 |
| 962 | <5 | 43 |
| 963 | ~4.99 | 62 |
| 964 | ~4.96 | 41 |

Biological Example 2

Fatty Acid Synthase Keto-reductase Domain (FASN KR) Inhibition

10 μL assay buffer (100 mM KH$_2$PO$_4$ pH 7.5) was added to a 384-well clear plate (costar 3702). 0.3 μL compound (at concentrations of 30 μM, 10 μM, 3 μM, 1 μM, 0.30 μM, 0.10 μM, 0.03 μM and 0.01 μM) DMSO, 10 μL hFASN enzyme (full length, 300 ng, purified in house) and 360 μM NADPH (except in blank) were then added. Then, 10 μL 180 mM ethyl acetoacetate (Aldrich 688983) was added, mixed and immediately thereafter, the absorbance at 340 nm (T1) by Multiscan (Labsystems) was measured. After 20 minutes incubation at room temperature the plate was measured again (T2).

Enzymatic activity of FASN KR was measured as the oxidation of NADPH to NADP$^+$ (a decrease in NADPH signal was observed at OD 340 nm,). The decrease in absorbance was calculated as (Absorbance before incubation T1)−(Absorbance following incubation T2).

Raw data generated by the instrument were normalized to % Controlmin values, which were calculated as:

% Controlmin=100*(x−mLC)/(mHC−mLC)

where mLC and mHC were the means of the low control wells and high control wells on the plate, after manual exclusion of outliers. A plot of Controlmin versus test compound concentration was fitted to a 4-parameter logistic curve using a non-linear least squares regression method. From the plot, an IC$_{50}$ (concentration at such 50% inhibition is achieved) was calculated. pIC$_{50}$ values were calculated as −log(IC$_{50}$), when IC$_{50}$ is expressed in molar units.

Representative compounds of the present invention were tested according to the procedure as described in Biological Example 2 above, with results as listed in Table 7 below.

TABLE 7

| ID No. | FASN Keto-reductase Domain pIC$_{50}$ |
|---|---|
| 1 | 6.12 |
| 2 | 7.05 |
| 4 | 7.34 |
| 10 | 6.3 |
| 11 | 5.69 |
| 12 | 7.31 |
| 14 | 6.52 |
| 15 | 7.15 |
| 17 | 6.46 |
| 19 | 5.5 |
| 20 | 6.17 |
| 27 | 6.92 |
| 28 | 7.17 |
| 29 | 5.63 |
| 30 | 6.55 |
| 31 | 7.45 |
| 33 | 7.25 |
| 34 | 6.45 |
| 35 | 6.56 |
| 36 | 5.85 |
| 38 | 6.19 |
| 39 | 6.67 |
| 40 | 7.37 |
| 41 | 6.07 |
| 47 | 7.56 |
| 48 | 6.55 |
| 49 | 6.81 |
| 51 | 6.79 |
| 52 | 5.75 |
| 56 | 5.86 |
| 57 | 5.77 |
| 58 | 7.28 |
| 59 | 6.88 |
| 60 | 6.54 |
| 63 | 7.07 |
| 65 | 7.27 |
| 66 | 6.55 |
| 67 | 5.81 |
| 68 | 6.79 |
| 69 | 6.07 |
| 70 | 5.87 |
| 71 | 7.18 |
| 72 | 6.76 |
| 73 | 7.19 |
| 74 | 7.22 |
| 75 | 5.67 |
| 76 | 6.1 |
| 77 | 6.06 |
| 78 | 6.65 |
| 79 | 6.49 |
| 80 | 5.83 |
| 81 | 6.73 |
| 82 | 5.92 |
| 85 | 5.69 |
| 90 | 5.87 |
| 92 | 7.11 |
| 93 | 6.58 |
| 94 | 6.05 |
| 100 | 6.68 |
| 101 | 6.42 |
| 102 | 5.97 |
| 103 | 6.5 |
| 105 | 6.3 |
| 106 | 6.22 |
| 112 | 6.69 |
| 113 | 5.97 |
| 114 | 6.63 |
| 115 | 6.91 |
| 200 | 7.46 |
| 201 | 7.47 |
| 202 | 7.13 |
| 203 | 7.33 |
| 204 | 6.93 |
| 205 | 6.94 |
| 206 | 7.12 |
| 207 | 6.95 |
| 208 | 6.98 |
| 209 | 6.59 |
| 210 | 6.77 |
| 211 | 6.7 |
| 212 | 7.43 |
| 213 | 7.12 |
| 214 | 7.09 |
| 215 | 7.61 |
| 216 | 7.31 |
| 217 | 7.31 |
| 218 | 6.99 |
| 219 | 6.58 |
| 220 | 6.58 |
| 221 | 6.63 |
| 222 | ~7.29 |
| 224 | 7.11 |
| 225 | 7.13 |
| 226 | 7.62 |
| 227 | 6.82 |
| 228 | 6.95 |
| 230 | 6.98 |
| 231 | 6.55 |
| 232 | 6.49 |
| 233 | 7.03 |
| 234 | 7.29 |
| 235 | 7.34 |
| 236 | 7.02 |
| 237 | 6.92 |
| 238 | 6.98 |
| 239 | 6.89 |
| 240 | 7.58 |
| 241 | 7.54 |
| 242 | 7.45 |
| 243 | 7.38 |
| 244 | 7.25 |
| 245 | 7.43 |
| 246 | 7.42 |
| 247 | 7.75 |
| 248 | 6.83 |
| 249 | 7.71 |
| 250 | 7.16 |
| 251 | 7.37 |
| 252 | 7.64 |
| 253 | 7.56 |
| 254 | 7.3 |
| 255 | 7.08 |
| 256 | 7.02 |
| 257 | 6.7 |
| 258 | 7.08 |
| 259 | 7.53 |
| 260 | 7.43 |
| 261 | 7.05 |
| 262 | 7.14 |
| 263 | 6.6 |
| 264 | 6.8 |
| 265 | ~7.27 |
| 266 | 7.33 |
| 267 | 7.29 |
| 268 | 7.16 |
| 269 | 7.18 |
| 270 | 6.78 |
| 271 | 6.78 |
| 272 | ~7.41 |
| 273 | 6.84 |
| 274 | 7.0 |
| 278 | 7.16 |
| 279 | 7.35 |
| 280 | 6.9 |
| 281 | 6.96 |
| 282 | 6.65 |
| 283 | 7.03 |
| 284 | 7.51 |
| 286 | 7.22 |
| 287 | 6.78 |

TABLE 7-continued

FASN Keto-reductase domain pIC$_{50}$

| ID No. | FASN Keto-reductase Domain pIC$_{50}$ |
|---|---|
| 288 | 7.27 |
| 289 | 6.49 |
| 290 | 6.48 |
| 291 | 7.42 |
| 292 | 6.61 |
| 293 | 6.76 |
| 294 | 6.95 |
| 295 | 6.98 |
| 296 | 7.09 |
| 297 | 7.21 |
| 298 | 7.57 |
| 299 | 7.23 |
| 300 | 6.9 |
| 301 | 7.56 |
| 302 | 7.22 |
| 303 | 7.16 |
| 304 | 6.65 |
| 305 | 7.51 |
| 306 | 6.98 |
| 307 | 6.84 |
| 308 | 6.89 |
| 309 | 7.61 |
| 310 | 7.22 |
| 311 | 7.35 |
| 312 | 7.12 |
| 313 | 7.28 |
| 314 | 7.09 |
| 315 | 6.6 |
| 316 | 7.12 |
| 317 | 7.23 |
| 318 | 6.91 |
| 319 | 7.27 |
| 320 | ~7.57 |
| 321 | 7.32 |
| 322 | 7.1 |
| 323 | 7.35 |
| 324 | 7.17 |
| 325 | 6.31 |
| 326 | 6.39 |
| 327 | 6.8 |
| 328 | 7.1 |
| 331 | 6.61 |
| 332 | 7.22 |
| 333 | 6.75 |
| 334 | 7.36 |
| 335 | 6.78 |
| 336 | 7.16 |
| 337 | 7.1 |
| 338 | 6.83 |
| 339 | 7.32 |
| 340 | 7.42 |
| 341 | 6.68 |
| 342 | 6.71 |
| 343 | 6.93 |
| 344 | 7.34 |
| 345 | 6.64 |
| 346 | 7.27 |
| 347 | 6.92 |
| 348 | 7.06 |
| 349 | 7.23 |
| 350 | 7.26 |
| 351 | 7.21 |
| 352 | 7.03 |
| 353 | 6.97 |
| 354 | 6.95 |
| 355 | 7.37 |
| 356 | 6.32 |
| 357 | 7.2 |
| 358 | 7.29 |
| 359 | 7.38 |
| 361 | 7.34 |
| 362 | 6.9 |
| 365 | 7.27 |
| 368 | 7.23 |
| 369 | 7.43 |
| 370 | 7.39 |
| 371 | 6.89 |
| 372 | 7.31 |
| 374 | 7.45 |
| 375 | 7.05 |
| 377 | ~7.44 |
| 378 | 7.34 |
| 379 | 7.56 |
| 380 | 7.02 |
| 381 | 7.45 |
| 382 | 7.18 |
| 383 | 7.21 |
| 384 | ~6.07 |
| 385 | 7.36 |
| 387 | 6.12 |
| 388 | 5.96 |
| 390 | 6.17 |
| 391 | 6.41 |
| 392 | 6.06 |
| 397 | ~5.41 |
| 398 | 6.02 |
| 399 | 5.88 |
| 400 | 6.32 |
| 402 | 6.52 |
| 404 | 6.31 |
| 405 | 6.4 |
| 406 | 6.44 |
| 409 | 6.46 |
| 410 | 6.4 |
| 411 | 6.37 |
| 412 | 6.37 |
| 413 | 6.05 |
| 414 | 6.53 |
| 418 | 6.52 |
| 419 | 5.96 |
| 420 | 6.01 |
| 421 | 5.75 |
| 423 | 6.26 |
| 425 | 6.19 |
| 426 | 6.15 |
| 427 | 5.95 |
| 428 | 6.23 |
| 429 | 6.29 |
| 431 | 6.33 |
| 432 | 6.35 |
| 435 | 5.91 |
| 440 | 6.67 |
| 442 | 6.47 |
| 443 | 5.98 |
| 444 | 6.25 |
| 445 | 6.68 |
| 449 | 6.02 |
| 450 | 6.19 |
| 452 | 6.28 |
| 453 | 5.95 |
| 455 | 6.45 |
| 457 | 5.84 |
| 461 | 5.93 |
| 462 | 6.04 |
| 463 | 6.01 |
| 465 | 6.7 |
| 466 | 5.87 |
| 467 | 6.01 |
| 468 | 5.8 |
| 469 | 6.47 |
| 470 | 6.94 |
| 471 | 6.48 |
| 472 | 6.41 |
| 473 | 6.28 |
| 474 | 6.74 |
| 475 | 6.43 |
| 476 | 6.21 |
| 479 | 6.35 |
| 480 | 6.28 |
| 483 | 6.76 |

TABLE 7-continued

FASN Keto-reductase domain pIC$_{50}$

| ID No. | FASN Keto-reductase Domain pIC$_{50}$ |
|---|---|
| 484 | 6.59 |
| 485 | 6.52 |
| 486 | 5.58 |
| 488 | 6.3 |
| 489 | 6.57 |
| 490 | 6.44 |
| 491 | 6.49 |
| 493 | 6.37 |
| 494 | 6.18 |
| 495 | 6.14 |
| 496 | 6.24 |
| 497 | 5.56 |
| 498 | 6.54 |
| 499 | 6.32 |
| 502 | 5.67 |
| 507 | 5.44 |
| 510 | 5.27 |
| 511 | 5.5 |
| 512 | 5.51 |
| 515 | 6.36 |
| 517 | 5.82 |
| 519 | 6.41 |
| 520 | 6.2 |
| 521 | 6.17 |
| 523 | 5.83 |
| 526 | 5.66 |
| 528 | 6.21 |
| 529 | 6.81 |
| 530 | 5.53 |
| 531 | 6.27 |
| 534 | 5.86 |
| 536 | 5.45 |
| 537 | 6.37 |
| 538 | 6.48 |
| 541 | 6.47 |
| 542 | 5.79 |
| 543 | 6.32 |
| 544 | 6.14 |
| 545 | 6.59 |
| 546 | 6.22 |
| 547 | 6.17 |
| 548 | 6.78 |
| 554 | 6.57 |
| 557 | 6.37 |
| 558 | 6.15 |
| 562 | 5.86 |
| 566 | 6.11 |
| 576 | 6.17 |
| 578 | 5.81 |
| 579 | 5.34 |
| 580 | 6.22 |
| 581 | 6.2 |
| 582 | 5.92 |
| 584 | 6.77 |
| 585 | 6.79 |
| 586 | 5.78 |
| 588 | 5.93 |
| 591 | 5.98 |
| 594 | 5.97 |
| 596 | 6.23 |
| 598 | 6.51 |
| 599 | 6.56 |
| 600 | 5.92 |
| 601 | 6.3 |
| 602 | 5.81 |
| 604 | 5.06 |
| 606 | 5.84 |
| 607 | 6.27 |
| 608 | 5.99 |
| 609 | 6.17 |
| 613 | 6.64 |
| 614 | 6.51 |
| 615 | 5.98 |
| 616 | 5.81 |
| 617 | 6.2 |
| 618 | 5.95 |
| 619 | 6.42 |
| 621 | 6.29 |
| 622 | 5.6 |
| 623 | 6.63 |
| 627 | 6.9 |
| 628 | 6.32 |
| 635 | 5.87 |
| 637 | 6.06 |
| 638 | 6.0 |
| 639 | 5.84 |
| 641 | 6.45 |
| 642 | 6.11 |
| 644 | 5.84 |
| 645 | 6.17 |
| 647 | 5.86 |
| 649 | 6.43 |
| 652 | 6.46 |
| 655 | 6.39 |
| 657 | 6.18 |
| 661 | 6.88 |
| 662 | 6.21 |
| 663 | 6.56 |
| 665 | 6.2 |
| 667 | 6.47 |
| 669 | 6.27 |
| 672 | 6.26 |
| 674 | 5.5 |
| 676 | 6.22 |
| 678 | 6.08 |
| 680 | 6.65 |
| 681 | 5.86 |
| 682 | 6.74 |
| 685 | 5.79 |
| 686 | 6.17 |
| 688 | 6.28 |
| 690 | 5.99 |
| 692 | 5.49 |
| 698 | 6.34 |
| 699 | 5.27 |
| 700 | 6.08 |
| 701 | 5.41 |
| 704 | 5.18 |
| 714 | 5.82 |
| 715 | 5.26 |
| 716 | 5.98 |
| 717 | 5.7 |
| 720 | 5.19 |
| 725 | 6.19 |
| 727 | 5.96 |
| 728 | 6.5 |
| 729 | 6.09 |
| 730 | 6.45 |
| 733 | 6.27 |
| 735 | 6.07 |
| 737 | 5.65 |
| 739 | 6.29 |
| 741 | 6.27 |
| 742 | 6.45 |
| 743 | 5.8 |
| 744 | 6.6 |
| 745 | 6.8 |
| 746 | 5.97 |
| 747 | 6.89 |
| 748 | 6.28 |
| 749 | 6.22 |
| 750 | 5.94 |
| 751 | 6.78 |
| 752 | 5.98 |
| 753 | 6.19 |
| 755 | 6.2 |
| 757 | 6.0 |
| 762 | 6.12 |
| 765 | 6.08 |
| 845 | 7.6 |

TABLE 7-continued

FASN Keto-reductase domain pIC$_{50}$

| ID No. | FASN Keto-reductase Domain pIC$_{50}$ |
|---|---|
| 872 | 7.37 |
| 873 | 7.39 |
| 874 | 7.39 |
| 875 | 7.54 |
| 876 | 7.44 |
| 877 | 7.13 |
| 878 | 7.22 |
| 879 | 7.26 |
| 880 | 6.95 |
| 881 | 6.5 |
| 882 | 6.53 |
| 883 | 5.98 |
| 884 | 6.13 |
| 885 | 6.31 |

Biological Example 3

A2780 Ovarian Cell Proliferation Assay in Lipid Reduced Medium, with and without Palmitate The biological assays described below correspond to comparative assays for ovarian cell proliferation. The assay procedure described below which includes addition of added palmitate correspond to the control relative to the assay procedure which does not include addition of the palmitate. Compounds active in the absence of palmitate would not be expected to be active in the control.

With Palmitate:

2500 cells were seeded in a 96-well clear well plate in 200 µL RPMI1640 with 10% Fetal Calf Serum (Hyclone), and incubated at 37° C., 5% CO$_2$. Blanks were wells without cells. The next day the culture medium was aspirated and replaced by 160 µL culture medium with 10% Lipid-Reduced Serum (LRS, Hyclone). 20 µL test compound (at concentrations of 30 µM, 10 µM, 3 µM, 1 µM, 0.30 µM, 0.10 µM, 0.03 µM and 0.01 µM)/DMSO dilution followed by 20 µL palmitate-BSA solution were added to a final concentrations of 0.2% DMSO, 25 µM palmitate (Sigma, P0500, 10 mM stock solution in ethanol) 0.2% fatty-acid-free BSA, 0.25% ethanol. After 96 h incubation, an MTT assay was performed. The absorbance was measured at 544 nm on a SPECTRAMAX brand microplate reader (Molecular Devices).

A best fit curve was fitted by a minimum sum of squares method, plotting Controlmin versus test compound concentration. From the plot, an IC$_{50}$ (concentration at such 50% inhibition is achieved) was calculated. pIC$_{50}$ values, presented in the Table below, were calculated as −log(IC$_{50}$).

Without Palmitate:

2500 cells were seeded in a 96-well clear well plate in 200 µL RPMI1640 with 10% Fetal Calf Serum (Hyclone), and incubated at 37° C., 5% CO$_2$. Blanks were wells without cells. The next day the culture medium was aspirated and replaced by 160 µL culture medium with 10% Lipid-Reduced Serum (LRS, Hyclone). 20 µL test compound (at concentrations of 30 µM, 10 µM, 3 µM, 1 µM, 0.30 µM, 0.10 µM, 0.03 µM and 0.01 µM)/DMSO dilution followed by 20 µL ethanol-BSA solution were added to a final concentrations of 0.2% DMSO, 0.2% fatty-acid-free BSA, 0.25% ethanol. After 96 h incubation an MTT assay was performed. The absorbance was measured at 544 nm on a SPECTRAMAX brand microplate reader (Molecular Devices).

Raw data generated by the instrument were normalized to % Controlmin values, which were calculated as:

% Controlmin=100*(x−mLC)/(mHC−mLC)

where mLC and mHC were the means of the low control wells and high control wells on the plate, after manual exclusion of outliers. A plot of Controlmin versus test compound concentration was fitted to a 4-parameter logistic curve using a non-linear least squares regression method. From the plot, an IC$_{50}$ (concentration at such 50% inhibition is achieved) was calculated. pIC$_{50}$ values were calculated as −log(IC$_{50}$), when IC$_{50}$ is expressed in molar units.

Representative compounds of the present invention were tested according to the procedure as described in Biological Example 3 above, with results as listed in Table 8, below. Where a compound was tested more than once, the IC$_{50}$ value listed below represents the mean of the three measurements. Wherein the results listed below, the pIC$_{50}$ value is preceded with a "~", the "~" the "~" indicates that the standard error of the pIC$_{50}$ value, as estimated by the non-linear regression algorithm, is larger than 0.5. This corresponds to a factor of uncertainly on the IC$_{50}$ that is larger than square root of 10 (>3.162).

TABLE 8 pIC50 Ovarian Cell, Reduced Lipid Medium With and Without Palmitate

| ID No. | pIC$_{50}$ A2780 Ovarian Cell, With Palmitate | pIC$_{50}$ A2780 Ovarian Cell, Without Palmitate |
|---|---|---|
| 1 | <5 | 5.95 |
| 2 | <5 | 6.01 |
| 4 | 5.29 | 7.23 |
| 10 | <5 | 6.06 |
| 11 | <5 | ~5.52 |
| 12 | 5.42 | ~7.44 |
| 14 | <5 | 5.91 |
| 15 | <5 | ~7.2 |
| 17 | <5 | 6.4 |
| 19 | <5.21 | 5.33 |
| 20 | 5.09 | 6.19 |
| 27 | <5 | 6.6 |
| 28 | <5 | 6.88 |
| 29 | <5 | 5.47 |
| 30 | <5 | 6.42 |
| 31 | <5 | 7.54 |
| 33 | <5 | 6.6 |
| 34 | <5 | 6.11 |
| 35 | <5 | 6.32 |
| 36 | <5 | 5.46 |
| 38 | <5 | 5.92 |
| 39 | <5 | 6.48 |
| 40 | <5 | 7.14 |
| 41 | <5 | 5.92 |
| 47 | <5 | 8.11 |
| 48 | <5 | 6.74 |
| 49 | <5 | 6.48 |
| 51 | <5 | 6.91 |
| 52 | <5 | 5.73 |
| 56 | 5.22 | 5.8 |
| 57 | <5 | 5.6 |
| 58 | <5 | 6.47 |
| 59 | <5 | 7.02 |
| 60 | <5 | 6.58 |
| 63 | <5 | 7.12 |
| 64 | <5 | 6.2 |
| 65 | <5 | ~7.88 |
| 66 | <5 | 5.96 |
| 67 | <5 | 5.79 |
| 68 | <5 | 6.47 |
| 69 | <5 | 5.94 |
| 70 | <5 | ~5.62 |
| 71 | <5 | 7.44 |
| 72 | <5 | 5.86 |

TABLE 8-continued pIC50 Ovarian Cell, Reduced Lipid Medium With and Without Palmitate

| ID No. | pIC$_{50}$ A2780 Ovarian Cell, With Palmitate | pIC$_{50}$ A2780 Ovarian Cell, Without Palmitate |
|---|---|---|
| 73 | <5 | ~7.54 |
| 74 | <5 | 8.06 |
| 75 | <5 | 5.23 |
| 76 | <5 | 6.29 |
| 77 | <5 | 6.18 |
| 78 | <5 | 6.83 |
| 79 | <5 | 6.84 |
| 80 | <5 | 5.64 |
| 81 | <5.21 | 6.99 |
| 82 | <5 | 5.43 |
| 85 | <5 | ~5.54 |
| 90 | <5 | 5.2 |
| 92 | <5 | 7.34 |
| 93 | <5 | ~5.68 |
| 94 | <5 | ~5.67 |
| 100 | <5 | 6.11 |
| 101 | <5 | 5.77 |
| 102 | <5 | 5.64 |
| 103 | <5 | 6.07 |
| 105 | <5 | 6.02 |
| 106 | <5 | 6.13 |
| 112 | <5 | 5.99 |
| 113 | <5 | ~5.75 |
| 114 | <5 | ~6.08 |
| 115 | <5 | ~7.21 |
| 116 | ~5.52 | 7.45 |
| 117 | 5.04 | ~5.62 |
| 118 | <5 | 5.78 |
| 119 | 4.96 | ~5.65 |
| 120 | 5.3 | ~6.12 |
| 121 | <5 | 5.66 |
| 122 | ~5 | 6.63 |
| 124 | <5 | ~6.54 |
| 126 | <5 | <5 |
| 127 | 5.12 | 6.03 |
| 133 | <5 | ~5.5 |
| 134 | <5 | 5.35 |
| 137 | ~5.22 | ~6.07 |
| 200 | <5 | ~8.41 |
| 201 | ~5.46 | ~8.36 |
| 202 | <5 | 7.23 |
| 203 | <5 | ~8.34 |
| 204 | <5 | ~7.39 |
| 205 | <5 | 7.44 |
| 206 | <5 | ~7.98 |
| 207 | <5 | 7.22 |
| 208 | 5.22 | ~7.14 |
| 209 | <5 | 5.73 |
| 210 | <5 | 7.28 |
| 211 | <5 | ~6.15 |
| 212 | <5 | 8.14 |
| 213 | <5 | 6.94 |
| 214 | <5 | ~7.19 |
| 215 | <5 | 7.69 |
| 216 | <5 | 7.2 |
| 217 | <5 | 7.52 |
| 218 | <5 | 7.07 |
| 219 | 5.93 | 7.17 |
| 220 | <5 | 6.47 |
| 221 | 5.16 | 7.33 |
| 222 | ~5.61 | 8.21 |
| 223 | 5.48 | ~7.7 |
| 224 | ~5 | 8.11 |
| 225 | 5.28 | 7.6 |
| 226 | <5 | 8.63 |
| 227 | <5 | 7.88 |
| 228 | <5 | 7.74 |
| 230 | <5 | 6.26 |
| 231 | <5.21 | 5.6 |
| 232 | <5.21 | 5.62 |
| 233 | <5 | 6.04 |
| 234 | <5 | ~7.54 |
| 235 | <5 | 8.0 |
| 236 | <5 | ~7.05 |
| 237 | <5 | 7.45 |
| 238 | <5 | 7.37 |
| 239 | <5 | 7.22 |
| 240 | <5.21 | 6.7 |
| 241 | <5 | ~7.12 |
| 242 | <5 | ~6.14 |
| 243 | <5.21 | 6.19 |
| 244 | <5 | ~5.65 |
| 245 | <5 | 5.81 |
| 246 | <5 | ~8.3 |
| 247 | <5 | 8.3 |
| 248 | <5 | 6.29 |
| 249 | <5 | ~8.26 |
| 250 | <5 | 6.52 |
| 251 | <5 | 7.14 |
| 252 | <5 | ~7.11 |
| 253 | <5 | 7.92 |
| 254 | <5 | 6.36 |
| 255 | <5 | ~6.01 |
| 256 | <5 | 6.08 |
| 258 | <5 | ~7.95 |
| 259 | <5 | 6.98 |
| 260 | <5 | ~7.15 |
| 261 | <5 | 8.18 |
| 262 | 5.22 | 7.11 |
| 263 | <5 | 6.92 |
| 264 | <5 | 7.13 |
| 265 | <5 | ~8.54 |
| 266 | 5.87 | ~8.66 |
| 267 | <5 | 8.77 |
| 268 | <5 | ~7.35 |
| 269 | 5.37 | ~8.43 |
| 270 | ~5.26 | ~7.56 |
| 271 | <5 | ~7.13 |
| 272 | <5 | ~8.14 |
| 273 | 5.1 | ~7.68 |
| 274 | 5.14 | ~7.62 |
| 278 | <5 | ~6.16 |
| 279 | <5 | 6.39 |
| 280 | <5 | ~5.71 |
| 281 | <5.21 | ~6.09 |
| 282 | <5 | ~5.68 |
| 283 | <5 | ~5.73 |
| 284 | <5 | ~7.63 |
| 286 | <5 | ~7.67 |
| 287 | <5 | ~6.55 |
| 288 | <5 | ~6.97 |
| 289 | <5 | 5.95 |
| 290 | <5 | ~5.71 |
| 291 | <5 | 7.34 |
| 292 | <5 | 6.9 |
| 293 | <5 | 7.06 |
| 294 | <5 | ~5.73 |
| 295 | <5 | 6.2 |
| 296 | <5 | ~5.68 |
| 297 | <5 | 7.6 |
| 298 | <5 | 7.23 |
| 299 | <5 | 7.51 |
| 300 | <5 | 7.13 |
| 301 | <5 | 7.83 |
| 302 | <5 | 7.88 |
| 303 | <5.21 | 7.54 |
| 304 | <5 | 7.07 |
| 305 | <5 | 7.39 |
| 306 | <5 | 7.75 |
| 307 | <5 | 7.04 |
| 308 | <5 | 6.84 |
| 309 | <5 | 8.21 |
| 310 | <5.21 | 6.23 |
| 311 | <5 | ~6.64 |
| 313 | 5.06 | 7.27 |
| 316 | <5 | ~7.8 |
| 317 | <5 | 7.61 |
| 318 | <5 | ~7.15 |

TABLE 8-continued pIC50 Ovarian Cell, Reduced Lipid Medium With and Without Palmitate

| ID No. | $pIC_{50}$ A2780 Ovarian Cell, With Palmitate | $pIC_{50}$ A2780 Ovarian Cell, Without Palmitate |
|---|---|---|
| 319 | <5 | ~7.87 |
| 320 | 5.19 | 7.6 |
| 321 | 5.36 | 7.75 |
| 322 | <5 | 7.83 |
| 323 | <5 | ~8.54 |
| 324 | <5 | 7.71 |
| 325 | <5 | ~7.31 |
| 326 | 5.04 | ~7.92 |
| 327 | 5.09 | 7.98 |
| 328 | 5 | 8.29 |
| 329 | 5.51 | 7.85 |
| 330 | ~5.21 | 7.49 |
| 331 | 5.25 | 7.16 |
| 332 | 5.38 | 7.91 |
| 333 | <5 | ~7.48 |
| 334 | 5.16 | 7.62 |
| 335 | <5 | 6.86 |
| 336 | <5 | 7.7 |
| 337 | 5.16 | 7.42 |
| 338 | ~5.37 | 7.66 |
| 339 | ~5.55 | 7.54 |
| 340 | 5.22 | 7.81 |
| 341 | <5.21 | 6.88 |
| 342 | <5 | 5.73 |
| 346 | <5 | ~7.77 |
| 347 | <5 | ~7.3 |
| 348 | <5 | 7.54 |
| 349 | <5 | ~7.51 |
| 350 | <5 | ~7.55 |
| 351 | 5.07 | 7.55 |
| 352 | 5.52 | ~6.91 |
| 353 | 5.22 | 6.61 |
| 354 | <5 | 7.51 |
| 355 | <5 | 7.52 |
| 356 | <5 | ~6.79 |
| 357 | <5 | 7.65 |
| 358 | <5 | 8.5 |
| 359 | <5.21 | 8.09 |
| 361 | <5 | ~8.44 |
| 362 | <5 | ~7.37 |
| 363 | ~5.82 | ~8.19 |
| 364 | 6.64 | ~8.53 |
| 365 | ~5 | 8.19 |
| 366 | 6.25 | ~8.25 |
| 368 | 5.35 | 7.67 |
| 369 | 5.68 | 8.37 |
| 370 | <5 | ~8.62 |
| 371 | 5.09 | 7.14 |
| 372 | <5 | 8.3 |
| 374 | <5 | 8.0 |
| 375 | <5 | 7.14 |
| 377 | <5 | 7.64 |
| 378 | <5 | ~8.29 |
| 379 | <5 | ~8.97 |
| 380 | <5 | 6.88 |
| 381 | <5 | ~8.6 |
| 382 | <5 | ~8.17 |
| 383 | ~5.33 | 7.98 |
| 384 | 5.28 | 7.14 |
| 385 | ~5.59 | ~8.44 |
| 387 | <5 | ~5.49 |
| 388 | <5 | ~5.61 |
| 390 | <5 | ~5.58 |
| 391 | <5 | 5.93 |
| 392 | <5 | 5.6 |
| 397 | <5 | 5.81 |
| 398 | <5 | ~5.64 |
| 399 | <5.21 | <5.21 |
| 400 | <5.21 | 6.64 |
| 402 | <5 | 6.76 |
| 404 | <5 | 5.96 |
| 405 | <5 | 6.32 |
| 406 | <5 | 5.22 |
| 409 | <5 | 5.68 |
| 410 | <5 | 6.27 |
| 411 | <5 | 6.9 |
| 412 | <5 | 5.79 |
| 413 | 5.14 | ~6.17 |
| 414 | <5 | ~6.7 |
| 418 | <5 | ~5.67 |
| 419 | <5 | 6.19 |
| 420 | <5 | ~5.68 |
| 421 | <5 | 5.94 |
| 423 | <5 | 5.89 |
| 425 | <5 | ~5.16 |
| 426 | <5 | 5.63 |
| 427 | <5 | 6.08 |
| 428 | <5 | ~5.96 |
| 429 | <5 | 6.38 |
| 431 | <5 | 6.69 |
| 432 | <5.21 | 5.82 |
| 435 | <5 | ~6.03 |
| 440 | <5 | 7.02 |
| 442 | <5 | 6.59 |
| 443 | <5 | 6.1 |
| 444 | <5 | ~6.68 |
| 445 | <5 | 7.17 |
| 449 | <5 | ~5.02 |
| 450 | <5 | ~6.21 |
| 452 | <5 | 6.2 |
| 453 | <5 | 5.67 |
| 455 | <5 | ~6.05 |
| 457 | <5.21 | 5.9 |
| 461 | <5 | ~6.37 |
| 462 | <5 | 5.73 |
| 463 | <5 | ~5.42 |
| 465 | <5 | 6.74 |
| 466 | <5 | ~5.57 |
| 467 | <5 | 6.12 |
| 468 | <5 | 6.18 |
| 469 | <5 | 7.13 |
| 470 | <5 | ~6.03 |
| 471 | <5 | 6.38 |
| 472 | <5 | 6.63 |
| 473 | <5 | ~6.56 |
| 474 | <5 | 6.7 |
| 475 | <5 | 6.09 |
| 476 | <5 | ~5.69 |
| 479 | <5 | 6.16 |
| 480 | <5 | ~6.59 |
| 483 | <5 | 7.32 |
| 484 | <5 | 7.02 |
| 485 | <5 | ~6.91 |
| 486 | <5 | ~5.66 |
| 488 | <5 | 6.52 |
| 489 | <5 | 6.83 |
| 490 | <5 | 7.03 |
| 491 | <5 | 7.14 |
| 493 | <5 | ~6.68 |
| 494 | <5 | 6.16 |
| 495 | <5 | 6.56 |
| 496 | <5 | 6.68 |
| 512 | <5 | 6.0 |
| 518 | ~5.39 | ~5.4 |
| 520 | <5 | 6.41 |
| 521 | <5 | ~6.47 |
| 522 | <5 | 5.54 |
| 523 | <5 | 6.17 |
| 524 | <5 | 5.31 |
| 525 | <5 | 5.31 |
| 526 | <5 | ~5.99 |
| 527 | <5 | ~5.71 |
| 528 | <5 | ~6.4 |
| 529 | <5 | ~7.08 |
| 530 | <5 | 6.11 |
| 531 | <5 | 6.83 |
| 532 | <5 | <5 |
| 533 | <5 | <5 |

TABLE 8-continued pIC50 Ovarian Cell, Reduced Lipid Medium With and Without Palmitate

| ID No. | pIC$_{50}$ A2780 Ovarian Cell, With Palmitate | pIC$_{50}$ A2780 Ovarian Cell, Without Palmitate |
|---|---|---|
| 534 | <5 | 6.11 |
| 535 | 5.11 | 5.18 |
| 536 | <5 | 6.02 |
| 537 | <5 | 6.58 |
| 538 | ~5 | 6.88 |
| 539 | <5 | <5 |
| 540 | 5.03 | 5.35 |
| 541 | <5 | 6.55 |
| 542 | <5 | 6.08 |
| 543 | <5 | 6.85 |
| 544 | 5.79 | 7.28 |
| 545 | <5 | 7.04 |
| 546 | <5 | ~6.71 |
| 547 | 5.23 | ~6.76 |
| 548 | 5.21 | ~6.53 |
| 549 | <5 | 5.42 |
| 550 | ~5 | 5.46 |
| 551 | <5 | ~5 |
| 552 | <5 | 5.77 |
| 553 | <5 | 5.56 |
| 554 | 5.11 | ~6.84 |
| 555 | <5 | ~5.29 |
| 556 | <5 | 5.23 |
| 557 | 5.32 | 6.7 |
| 558 | 5.2 | ~6.25 |
| 559 | <5 | 5.03 |
| 560 | <5 | ~5.12 |
| 561 | <5 | <5 |
| 562 | <5 | 6.02 |
| 563 | <5 | 5.5 |
| 564 | <5 | 6.28 |
| 566 | <5 | 6.53 |
| 568 | 5.62 | 7.33 |
| 569 | 5.66 | 6.69 |
| 570 | <5 | ~5.28 |
| 571 | <5 | 6.01 |
| 572 | <5 | 7.28 |
| 573 | 5.86 | 7.27 |
| 574 | 5.24 | 6.06 |
| 575 | <5 | ~5.1 |
| 576 | <5 | 6.54 |
| 577 | <5 | 5.61 |
| 578 | <5 | 6.48 |
| 579 | <5 | 5.96 |
| 580 | <5 | 7.25 |
| 581 | 5.37 | ~6.7 |
| 582 | <5 | ~6.2 |
| 583 | <5 | 5.59 |
| 584 | 5.18 | 7.2 |
| 585 | <5 | 7.08 |
| 586 | <5 | ~6.07 |
| 587 | <5 | ~5.07 |
| 588 | <5 | ~6.17 |
| 589 | <5 | 5.25 |
| 590 | <5 | 5.48 |
| 591 | <5 | ~6.46 |
| 592 | <5 | 5.28 |
| 593 | 5.02 | 5.17 |
| 594 | <5 | 6.21 |
| 595 | 5.18 | 5.49 |
| 596 | 5.2 | 6.34 |
| 597 | 5.36 | 5.44 |
| 598 | <5 | 6.7 |
| 599 | 5.26 | 6.84 |
| 600 | <5 | ~6.22 |
| 601 | 5.41 | 6.66 |
| 602 | 5.21 | 6.42 |
| 603 | <5 | ~5.48 |
| 604 | ~5 | 5.63 |
| 605 | 5.2 | 5.32 |
| 606 | <5 | 5.91 |
| 607 | <5 | 6.19 |
| 608 | <5 | 6.43 |
| 609 | <5 | ~6.58 |
| 610 | 5.34 | 5.54 |
| 611 | <5 | <5 |
| 612 | <5 | 5.42 |
| 613 | <5 | 6.97 |
| 614 | <5 | 6.77 |
| 615 | <5 | 6.3 |
| 616 | <5 | 5.74 |
| 617 | <5 | 6.61 |
| 618 | <5 | 6.1 |
| 619 | <5 | ~6.65 |
| 620 | <5 | ~5.32 |
| 621 | 5.21 | 6.15 |
| 622 | <5 | 5.66 |
| 623 | 5.29 | ~7.49 |
| 624 | 5.18 | 5.84 |
| 627 | <5 | 7.92 |
| 628 | <5 | 7.18 |
| 629 | <5 | 5.11 |
| 630 | <5 | 5.39 |
| 631 | <5 | 5.23 |
| 632 | <5 | ~5.62 |
| 633 | <5 | 5.28 |
| 634 | <5 | 5.7 |
| 635 | <5 | 6.89 |
| 636 | <5 | ~5.23 |
| 637 | <5 | 7.07 |
| 638 | <5 | ~6.71 |
| 639 | <5 | ~6.44 |
| 640 | <5 | 5.08 |
| 641 | <5 | ~5.65 |
| 642 | <5 | ~5.42 |
| 643 | ~5 | ~6.17 |
| 644 | <5 | 6.79 |
| 645 | <5 | ~5.69 |
| 646 | <5 | 5.61 |
| 647 | <5 | 5.71 |
| 648 | <5 | 5.6 |
| 649 | 5.13 | 6.7 |
| 650 | <5 | 5.31 |
| 651 | <5 | 5.56 |
| 652 | <5.21 | 6.76 |
| 653 | <5 | 5.38 |
| 654 | <5 | 5.66 |
| 661 | <5 | 7.37 |
| 662 | <5 | 6.34 |
| 664 | <5 | ~5.54 |
| 665 | <5 | 6.26 |
| 667 | <5 | ~6 |
| 672 | <5 | ~6.39 |
| 678 | <5 | 6.17 |
| 681 | <5 | 6.1 |
| 682 | <5 | 6.93 |
| 683 | <5 | <5 |
| 685 | <5 | 5.91 |
| 690 | <5 | 6.15 |
| 698 | <5 | 6.42 |
| 700 | <5 | 6.33 |
| 701 | <5 | 6.05 |
| 714 | <5 | 6.03 |
| 716 | <5 | 6.29 |
| 717 | <5 | 5.79 |
| 729 | <5 | 5.89 |
| 741 | <5 | ~5.6 |
| 742 | ~5.22 | ~5.6 |
| 743 | <5 | 5.68 |
| 744 | <5 | ~6.67 |
| 745 | <5 | 7.02 |
| 746 | <5 | ~5.73 |
| 747 | <5 | ~7.13 |
| 748 | <5 | ~6.65 |
| 749 | <5 | 5.81 |
| 750 | <5 | 6.17 |
| 751 | <5 | 7.05 |
| 752 | <5 | 5.79 |

TABLE 8-continued pIC50 Ovarian Cell, Reduced Lipid Medium With and Without Palmitate

| ID No. | pIC$_{50}$ A2780 Ovarian Cell, With Palmitate | pIC$_{50}$ A2780 Ovarian Cell, Without Palmitate |
|---|---|---|
| 753 | <5 | ~6.61 |
| 755 | <5.21 | ~6.5 |
| 757 | <5 | 6.15 |
| 762 | <5 | ~6.01 |
| 765 | <5 | 5.66 |
| 775 | <5 | <5 |
| 776 | <5 | <5 |
| 777 | <5 | 5.02 |
| 784 | <5 | 5.23 |
| 785 | ~5.21 | 5.41 |
| 786 | 5.23 | 5.17 |
| 787 | <5 | 5.03 |
| 788 | <5 | <5 |
| 789 | <5 | <5 |
| 790 | <5 | <5 |
| 791 | <5.21 | <5.21 |
| 792 | <5 | <5 |
| 793 | <5 | <5 |
| 794 | <5 | <5 |
| 795 | <5 | <5 |
| 836 | <5.52 | 6.43 |
| 837 | <5.52 | 5.91 |
| 840 | <5.52 | <5.52 |
| 842 | <5.52 | <5.52 |
| 844 | <5.52 | <5.52 |
| 845 | <5 | 7.96 |
| 872 | ~5.1 | 8.57 |
| 873 | <5 | 7.2 |
| 874 | <5 | 7.68 |
| 875 | <5 | 7.87 |
| 876 | <5 | 6.64 |
| 877 | <5 | 7.67 |
| 878 | <5 | ~7.03 |
| 879 | <5 | 7.6 |
| 880 | <5 | 7.18 |
| 881 | <5 | 6.62 |
| 882 | <5 | ~7.05 |
| 883 | <5 | ~5.61 |
| 884 | <5 | ~5.67 |
| 885 | <5 | ~5.65 |
| 891 | <5 | <5 |
| 896 | <5 | <5 |
| 897 | <5 | <5 |
| 898 | <5 | <5 |
| 899 | <5 | <5 |
| 900 | <5 | <5 |
| 918 | <5 | <5 |
| 922 | <5 | <5 |
| 923 | <5 | <5 |
| 937 | <5 | <5 |
| 938 | <5 | 5.1 |
| 939 | <5 | <5 |
| 940 | <5 | <5 |
| 943 | <5 | <5 |
| 957 | <5 | <5 |
| 963 | <5 | <5 |

Biological Example 4

Example 4a

In Vitro LNCaP Vancouver Prostate Cell Proliferation Assay in Lipid Reduced Medium LNCaP-Vancouver prostate cells were obtained from the Vancouver Prostate Cancer Centre. Cells were maintained in RPMI-1640, 10% Fetal Calf Serum (FCS, Hyclone), 2 mM glutamine and 50 µg/ml Gentamicin.

For the proliferation experiment 1500 LNCaP-Vancouver cells per well were seeded in a 384-well black with clear bottom plate (costar 3712BC) in 40 µl RPMI-1640, 10% Lipid reduced serum (LRS, Hyclone), 50 µg/ml Gentamicin and 2 mM Glutamine and incubated at 37° C., 5% CO$_2$. The next day 10 µl of test compound/DMSO diluted in medium was added (3E-5M, 1E-5M, 3E-6M, 1E-6M, 3E-7M, 1E-7M, 3E-8M, 1E-8M final concentration). Compounds were tested in duplicate. After 96 h incubation at 37° C., 5% CO$_2$ 25 µl ATP-glow mix was added. The plate was incubated for 30 min at 37° C. and luminescence was measured with the Envision.

Example 4b

In Vitro PC-3M-Luc-C6 Prostate Cell Proliferation Assay in Lipid Reduced Medium

PC-3M-Luc-C6 prostate cells were obtained from Xenogen Corporation. Cells were maintained in MEM supplemented with 10% Fetal Calf Serum (FCS, Hyclone), 2 mM glutamine, 1 mM sodium pyruvate, 1% BME vitamins (available from for example, Sigma Aldrich), 0.1 mM non Essential Amino Acid and 50 µg/ml Gentamicin. The cells were passaged twice a week.

1000 PC-3M-Luc-C6 prostate cells (Xenogen) were seeded in a 384-well black with clear bottom plate (costar 3712BC) in 40 µl MEM, 10% LRS (Hyclone), 50 µg/ml Gentamicin, 2 mM Glutamine, 1 mM Sodium pyruvaat, 1% BME vitamins and 0.1 mM non Essential Amino Acid and incubated at 37° C., 5% CO$_2$. The next day 10 µl test compound/DMSO diluted in medium was added (3E-5M, 1E-5M, 3E-6M, 1E-6M, 3E-7M, 1E-7M, 3E-8M, 1E-8M final concentration). Compounds were tested in duplicate. After 96 h incubation at 37° C., 5% CO$_2$ 25 µl ATP-glow mix was added. The plate was incubated for 30 min at 37° C. and luminescence was measured with the Envision.

Analysis: Determination of pIC50 Values pIC$_{50}$ values were calculated as follows. Raw data generated by the instruments were normalized to % Controlmin, values, which were calculated as:

$$\% \ Control_{min} = 100*(x - mLC)/(mHC - mLC),$$

where mLC and mHC are the means of the low control wells and high control wells on the plate, after manual exclusion of outliers. The relation between the % Control$_{min}$ values and concentration was fitted to a 4-parameter logistic curve using a non-linear least squares regression method to determine the pIC$_{50}$ value. Outlying data points were excluded manually to get a correct fit. The pIC$_{50}$ corresponds to −log 10(IC$_{50}$), if the IC$_{50}$ is expressed in molar units (http://www.ncbi.nlm.nih.gov/books/NBK91994). The IC$_{50}$ parameter was always determined by non-linear regression, but one or more of the other parameters may have been held fixed on a relevant input value, such as 0 for the bottom values.

For dose response curves with FASN inhibitors in LNCaP-Vancouver or PC-3M-Luc-C6 cells the curves bottom out around 30 to 40% of the control value. A standard fit PL2, forcing the lower bound to this level was used. For those test compounds which did not exhibit FASN related toxicities (but other non-target related cellular toxicity), the % control value may go to 0, and curve fit was calculated using 0% as lower bound.

Representative compounds of the present invention were tested according to the procedure as described in Biological Example 4a and 4b above, with results as listed in Table 9, below. Where a compound was tested more than once, the pIC$_{50}$ value listed below represents the mean of the measurements. Wherein the results listed below, the pIC$_{50}$ value is preceded with a "~", the "~" the "~" indicates that the standard error of the pIC$_{50}$ value, as estimated by the non-linear regression algorithm, is larger than 0.5. This corresponds to a factor of uncertainty on the pIC$_{50}$ that is larger than square root of 10 (>3.162).

TABLE 9 pIC50 Prostate Cell Proliferation, Reduced Lipid Medium

| ID No. | pIC$_{50}$ LNCaP_Vancouver prostate cell | pIC$_{50}$ PC-3M-Luc-C6 prostate cell |
| --- | --- | --- |
| 2 | ~5.71 | ~6.18 |
| 39 | 5.98 | 6.82 |
| 49 | 6.04 | 6.66 |
| 59 | 6.58 | 7.0 |
| 65 | 7.18 | ~7.61 |
| 200 | ~7.47 | 8.19 |
| 201 | 7.68 | ~8.18 |
| 202 | 6.26 | ~7.02 |
| 203 | 7.67 | 8.25 |
| 204 | 6.39 | 7.29 |
| 205 | 6.99 | 7.27 |
| 206 | 7.0 | 7.72 |
| 207 | 6.29 | ~7.17 |
| 208 | 6.93 | 7.36 |
| 209 | 5.38 | ~6.11 |
| 212 | 6.96 | 7.74 |
| 213 | 6.45 | ~6.95 |
| 214 | 6.44 | 7.18 |
| 215 | 7.15 | 7.8 |
| 216 | 6.79 | ~7.27 |
| 217 | 6.75 | 7.3 |
| 218 | 6.38 | 7.14 |
| 219 | 6.52 | 6.9 |
| 220 | 5.97 | ~6.54 |
| 221 | ~6.42 | 6.88 |
| 222 | 7.33 | 8.03 |
| 223 | 6.62 | 7.22 |
| 224 | 7.25 | 7.9 |
| 225 | 6.8 | 7.57 |
| 226 | 7.66 | ~8.23 |
| 227 | 6.45 | 7.26 |
| 228 | 6.12 | 7.01 |
| 230 | 5.91 | 6.42 |
| 231 | 5.66 | ~5.79 |
| 232 | 5.74 | 5.97 |
| 233 | 5.77 | 6.24 |
| 234 | 6.61 | 7.63 |
| 236 | 6.19 | 7.29 |
| 237 | 6.2 | ~7.13 |
| 238 | 6.61 | 7.15 |
| 239 | 6.09 | 6.87 |
| 240 | 6.27 | ~6.78 |
| 241 | 6.78 | ~7.25 |
| 242 | ~5.8 | ~6.19 |
| 243 | 6.08 | ~6.62 |
| 244 | 5.74 | ~5.85 |
| 245 | ~5.77 | ~6.19 |
| 246 | 7.81 | 8.32 |
| 247 | 7.63 | 8.14 |
| 248 | 6.32 | 6.58 |
| 249 | 7.78 | 8.38 |
| 250 | 6.16 | 6.63 |
| 251 | 6.86 | ~7.38 |
| 252 | 6.6 | 7.25 |
| 253 | 7.19 | 7.85 |
| 254 | 5.86 | 6.65 |
| 255 | 5.95 | ~6.28 |
| 256 | 5.62 | ~6.38 |
| 257 | 6.58 | 7.15 |
| 258 | 7.5 | 7.84 |
| 259 | 6.35 | 7.17 |
| 260 | 7.07 | 7.43 |
| 261 | ~6.99 | 7.67 |
| 262 | 6.53 | ~6.93 |
| 263 | | 6.95 |
| 264 | 6.3 | 7.35 |
| 265 | 7.86 | ~8.15 |
| 266 | 7.82 | 8.33 |
| 267 | 7.91 | ~8.51 |
| 268 | 6.54 | 7.23 |
| 269 | 7.55 | ~8.08 |
| 270 | 6.71 | 7.46 |
| 271 | 6.38 | 7.01 |
| 272 | 7.31 | 7.97 |
| 273 | 6.45 | 7.17 |
| 274 | 6.47 | 7.33 |
| 282 | ~5.67 | ~5.77 |
| 284 | 7.42 | 7.74 |
| 286 | 6.91 | 7.6 |
| 288 | 6.27 | 7.11 |
| 290 | ~5.67 | ~5.93 |
| 291 | 6.53 | ~7.37 |
| 292 | 6.16 | 6.75 |
| 293 | ~6.29 | ~6.85 |
| 294 | 5.69 | ~6.06 |
| 295 | 5.89 | ~6.24 |
| 296 | 5.44 | ~5.91 |
| 297 | 6.19 | ~7.52 |
| 298 | 6.21 | 7.18 |
| 299 | 6.63 | 7.41 |
| 300 | 5.72 | 6.91 |
| 301 | 6.56 | 7.92 |
| 302 | 6.36 | 7.78 |
| 303 | ~6.04 | 7.4 |
| 304 | 5.9 | 7.14 |
| 305 | 6.58 | 7.54 |
| 306 | 6.29 | 7.77 |
| 307 | 6.18 | 6.99 |
| 308 | 6.32 | 7.0 |
| 309 | 7.5 | 8.13 |
| 310 | 6.09 | ~6.49 |
| 311 | 6.52 | 6.97 |
| 312 | 6.91 | ~7.28 |
| 313 | 6.81 | ~7.28 |
| 314 | 6.51 | 7.24 |
| 315 | 6.2 | 6.91 |
| 316 | 6.99 | 7.71 |
| 317 | 6.59 | 7.29 |
| 318 | 5.84 | 7.28 |
| 319 | 6.95 | 7.73 |
| 320 | 6.6 | 7.3 |
| 321 | 6.74 | 7.3 |
| 322 | 6.82 | ~7.46 |
| 323 | 7.48 | 8.08 |
| 324 | 6.8 | ~7.52 |
| 325 | 6.44 | 7.08 |
| 326 | 6.77 | 7.31 |
| 327 | 6.86 | 7.46 |
| 328 | 7.27 | 7.79 |
| 331 | 6.21 | 6.83 |
| 332 | 6.97 | 7.91 |
| 333 | 6.27 | ~6.47 |
| 334 | 6.79 | 7.43 |
| 335 | 6.22 | ~6.94 |
| 336 | 6.98 | |
| 337 | 7.1 | 7.69 |
| 338 | 6.9 | 7.72 |
| 339 | 6.49 | 7.5 |
| 340 | 7.03 | 7.74 |
| 341 | 6.28 | 6.9 |
| 342 | 5.79 | ~6.05 |
| 343 | 6.62 | 7.09 |
| 344 | 6.85 | ~7.49 |
| 345 | 5.92 | 6.25 |
| 346 | 7.36 | 7.65 |
| 347 | 6.15 | ~7.05 |
| 348 | 6.55 | 7.39 |
| 349 | 6.86 | 7.47 |
| 350 | 7.09 | 7.65 |
| 351 | 7.24 | 7.86 |
| 352 | 6.25 | 6.79 |

TABLE 9-continued pIC50 Prostate Cell Proliferation, Reduced Lipid Medium

| ID No. | pIC$_{50}$ LNCaP_Vancouver prostate cell | pIC$_{50}$ PC-3M-Luc-C6 prostate cell |
|---|---|---|
| 353 | 5.94 | 6.36 |
| 354 | 6.61 | 7.45 |
| 355 | 6.24 | 7.23 |
| 356 | 5.83 | ~6.49 |
| 357 | 6.43 | 7.6 |
| 358 | 7.11 | 7.83 |
| 359 | ~7.1 | 8.08 |
| 361 | ~7.89 | 8.49 |
| 362 | ~6.53 | ~7.25 |
| 365 | 7.25 | 8.12 |
| 368 | 6.67 | 7.54 |
| 369 | 7.34 | 8.0 |
| 370 | 7.69 | ~8.41 |
| 371 | 6.31 | 7.26 |
| 372 | 7.12 | 7.88 |
| 374 | 7.06 | 7.69 |
| 375 | 6.34 | 7.11 |
| 377 | 7.09 | 7.55 |
| 378 | 7.13 | 7.98 |
| 379 | 8.3 | ~8.61 |
| 380 | 5.94 | 6.51 |
| 381 | 7.98 | 8.72 |
| 382 | 7.26 | 7.57 |
| 383 | 7.3 | ~7.74 |
| 384 | 6.08 | 6.78 |
| 385 | 7.73 | ~8.32 |
| 390 | 5.56 | 5.83 |
| 391 | 5.77 | 6.14 |
| 392 | ~5.77 | 5.79 |
| 397 | 5.52 | 5.97 |
| 398 | 5.63 | 5.76 |
| 399 | <5.52 | <5.52 |
| 400 | 5.92 | 6.67 |
| 402 | 5.76 | 6.76 |
| 405 | 5.64 | 6.34 |
| 406 | 5.15 | 5.73 |
| 409 | 5.66 | 5.93 |
| 410 | 6.01 | 6.35 |
| 411 | 6.28 | 6.79 |
| 412 | 6.34 | 6.24 |
| 413 | 6.35 | 6.32 |
| 414 | 5.94 | 6.75 |
| 418 | ~5.6 | 5.8 |
| 419 | 5.39 | 6.11 |
| 420 | 5.19 | 5.78 |
| 421 | 5.89 | 5.98 |
| 423 | 5.59 | 5.87 |
| 425 | 5.5 | 5.66 |
| 426 | 5.63 | 5.76 |
| 427 | 5.58 | 6.07 |
| 428 | 5.55 | 6.1 |
| 429 | 5.88 | 6.41 |
| 432 | 5.69 | 6.06 |
| 435 | 5.46 | 5.91 |
| 440 | 5.94 | 6.63 |
| 442 | 5.71 | 6.29 |
| 443 | 5.64 | 6.07 |
| 444 | 5.74 | 6.38 |
| 445 | 5.93 | 6.63 |
| 449 | <5 | 5.62 |
| 450 | 5.63 | 6.1 |
| 452 | 5.69 | 6.26 |
| 453 | 5.53 | 5.79 |
| 455 | 5.67 | ~6.16 |
| 457 | <5.52 | 5.66 |
| 461 | ~5.6 | ~6.22 |
| 462 | 5.63 | 5.93 |
| 463 | 5.14 | 5.72 |
| 465 | 6.28 | 6.73 |
| 466 | 5.42 | 5.73 |
| 467 | 5.54 | 6.11 |
| 468 | 5.69 | 6.26 |
| 469 | 6.54 | 7.23 |
| 470 | 5.83 | ~6.2 |
| 471 | 5.89 | 6.54 |
| 472 | 5.75 | 6.88 |
| 473 | 5.66 | 6.56 |
| 474 | 6.0 | 6.15 |
| 475 | 5.48 | 6.18 |
| 476 | 5.43 | ~5.67 |
| 479 | 6.03 | 6.52 |
| 480 | 5.94 | 6.74 |
| 483 | 6.42 | ~7.04 |
| 484 | 6.26 | 6.82 |
| 485 | 6.2 | 6.67 |
| 486 | 5.35 | ~5.55 |
| 488 | 5.81 | 6.24 |
| 489 | 6.15 | ~6.6 |
| 490 | 5.98 | ~6.69 |
| 491 | 6.0 | ~6.75 |
| 493 | 5.9 | 6.8 |
| 494 | 5.33 | 6.05 |
| 495 | ~5.49 | ~6.23 |
| 496 | 5.76 | ~6.45 |
| 497 | 5.27 | 6.32 |
| 498 | 5.61 | 6.63 |
| 499 | 5.37 | 6.34 |
| 502 | 5.38 | 5.93 |
| 507 | 5.22 | ~5.93 |
| 510 | 5.32 | ~5.42 |
| 511 | 5.33 | ~6.05 |
| 512 | 5.4 | 5.88 |
| 515 | 5.67 | 6.25 |
| 517 | ~5.28 | 5.9 |
| 519 | 5.57 | 6.26 |
| 520 | 5.59 | 6.3 |
| 521 | 5.72 | 6.22 |
| 523 | 5.49 | 5.93 |
| 526 | 5.23 | 5.83 |
| 528 | 5.63 | 6.3 |
| 529 | 6.14 | ~7.08 |
| 530 | 5.29 | 5.91 |
| 531 | 5.87 | 6.52 |
| 534 | ~5.25 | 6.0 |
| 536 | ~5.12 | ~5.51 |
| 537 | 5.88 | 6.21 |
| 538 | 5.71 | ~6.69 |
| 541 | ~5.99 | 6.51 |
| 542 | 5.52 | 5.35 |
| 543 | 5.7 | 6.59 |
| 544 | 6.11 | 6.85 |
| 545 | 6.57 | 6.9 |
| 546 | 5.82 | ~6.51 |
| 547 | 6.0 | 6.27 |
| 548 | 5.96 | 6.41 |
| 554 | 6.19 | ~6.76 |
| 557 | 5.86 | 6.37 |
| 558 | 5.6 | 6.14 |
| 562 | 5.51 | 5.79 |
| 566 | 5.81 | 6.24 |
| 576 | 5.67 | 6.17 |
| 578 | 5.3 | 6.06 |
| 579 | 5.34 | 5.7 |
| 580 | 6.12 | 6.73 |
| 581 |  | ~6.53 |
| 582 | 5.49 | 6.1 |
| 584 | 6.19 | 7.08 |
| 585 |  | 7.0 |
| 586 |  | 5.99 |
| 588 |  | ~6.02 |
| 591 |  | 6.43 |
| 594 | 5.72 | ~6.23 |
| 596 | 5.73 | ~6.12 |
| 598 | 5.63 | ~6.45 |
| 599 | 6.04 | 6.98 |
| 600 | 5.65 | 6.3 |
| 601 | 5.99 | 6.5 |
| 602 | 5.83 | 6.16 |
| 604 | <5 | 5.38 |
| 606 | 5.62 | 5.95 |

TABLE 9-continued pIC50 Prostate Cell Proliferation, Reduced Lipid Medium

| ID No. | pIC$_{50}$ LNCaP_Vancouver prostate cell | pIC$_{50}$ PC-3M-Luc-C6 prostate cell |
|---|---|---|
| 607 | 5.96 | 6.75 |
| 608 | 5.73 | ~6.58 |
| 609 | 5.32 | 6.18 |
| 613 | 6.07 | 7.01 |
| 614 | 5.87 | 6.42 |
| 615 | 5.49 | ~5.63 |
| 616 | 5.5 | <5 |
| 617 | 5.59 | 6.19 |
| 618 | 5.46 | ~5.59 |
| 619 | 5.49 | 6.2 |
| 621 | 5.67 | 6.36 |
| 622 | <5 | 5.66 |
| 623 | 6.25 | 6.91 |
| 627 | ~6.89 | 7.32 |
| 628 | 6.14 | 6.79 |
| 635 | 5.99 | 6.45 |
| 637 | 5.74 | ~6.63 |
| 638 | 5.77 | 6.32 |
| 639 | 5.63 | 6.1 |
| 641 | 5.34 | ~6.25 |
| 642 | 5.21 | ~5.67 |
| 643 | 5.52 | 6.01 |
| 644 | 5.55 | 6.4 |
| 645 | 5.46 | 5.76 |
| 647 | 5.29 | 5.76 |
| 649 | 5.76 | 6.36 |
| 652 | 5.92 | 6.41 |
| 655 | ~5.6 | ~6.63 |
| 657 | 5.42 | 6.23 |
| 661 | 6.72 | ~7.1 |
| 662 | 5.54 | 6.15 |
| 663 | 6.26 | 6.93 |
| 665 | 5.91 | 6.1 |
| 667 | 5.75 | ~5.81 |
| 669 | 5.55 | ~6.09 |
| 672 | 5.58 | ~6.26 |
| 674 | ~5.31 | ~6.09 |
| 676 | 5.75 | 6.3 |
| 678 | 5.48 | 6.05 |
| 680 | 6.47 | 6.97 |
| 681 | 5.31 | 5.86 |
| 682 | 6.0 | 6.66 |
| 685 | 5.52 | 5.93 |
| 686 | 5.42 | 5.96 |
| 688 | 5.53 | 6.08 |
| 690 | 5.63 | 5.88 |
| 692 | 5.34 | 5.8 |
| 698 | 5.58 | 6.24 |
| 699 | <5 | 5.29 |
| 700 | 5.47 | 6.0 |
| 701 | 5.34 | 5.9 |
| 704 | 5.16 | ~5.24 |
| 714 | 5.28 | 6.1 |
| 715 | <5 | 5.3 |
| 716 | 5.26 | 5.97 |
| 717 | 5.3 | 5.77 |
| 720 | 5.04 | 5.33 |
| 725 | 5.78 | 6.31 |
| 727 | 5.62 | 6.24 |
| 728 | 6.28 | 6.82 |
| 729 | 5.06 | 5.84 |
| 730 | ~6.39 | 7.01 |
| 733 | 5.48 | 5.89 |
| 735 | 5.42 | ~6.04 |
| 737 | ~5.43 | 6.15 |
| 739 | 5.42 | ~6.06 |
| 741 | 5.56 | ~5.79 |
| 742 | ~5.35 | ~5.76 |
| 744 | 6.07 | 6.74 |
| 745 | 6.07 | 6.74 |
| 746 | ~5.41 | ~5.78 |
| 747 | 6.2 | 7.24 |
| 748 | 5.52 | 6.24 |
| 749 | 5.64 | 6.12 |
| 750 | 5.5 | 6.23 |
| 751 | 6.14 | 6.69 |
| 752 | 5.4 | 5.72 |
| 762 | 5.41 | 6.09 |
| 765 | 5.05 | 5.68 |
| 872 | 7.62 | 8.32 |
| 873 | 6.58 | 7.46 |
| 875 | 7.06 | 7.98 |
| 876 | 6.21 | 6.92 |
| 877 | ~6.39 | 7.34 |
| 879 | 6.42 | 7.51 |
| 880 | 6.19 | 6.93 |
| 881 | 5.88 | 6.73 |
| 884 | 5.52 | ~5.74 |
| 885 | <5 | ~5.58 |

Biological Example 5

$^{14}$C-acetate Incorporation in HEPG2 Liver Cells

HepG2 liver cells are obtained from the American Type Culture Collection. Cells are seeded in a 24-well plate at 7·10$^5$ cells/well in 400 µL MEM with 10% FCS (Hyclone). 100 µL of test compound dilution (25 µM to 5 µM final) is added and plates are incubated for 4 hours at 37° C. in 5% CO$_2$. 50 µL of $^{14}$C-acetic acid (Acetic acid, sodium salt (1,2-14C): Amersham CFA13; 50-62 mCi/mMol, 200 µCi/ml (7.4 mBq/ml)) diluted 1/50 in medium is added and plates are incubated for another 2 h at 37° C. in 5% CO$_2$. Medium is aspirated, and lipids are extracted from the cells by 3 rounds of chloroform: methanol: MgSO$_4$ mixture and centrifugation steps (2 min at 10000 rpm). Each time the upper layer is removed. Finally the remaining organic layer is evaporated under nitrogen gas, the pellet are dissolved in 500 µL heptanes and in 3 ml of scintillation fluid added to scintillation tubes. Incorporated $^{14}$C-labelled is counted in a Pachard, Tri-Carb Liquid scintillation counter, (2 minutes)

Biological Example 6

Analysis of Intact Phospholipid Species by Electrospray Ionization Tandem Mass Spectrometry PC-3 prostate and A2780 ovarian cells are obtained from the American Type Culture Collection. Cells are cultured in HamF12 or RPMI 1640 respectively, supplemented with 10% FCS (Invitrogen). Palmitic acid (Sigma) is complexed to fatty acid-free bovine serum albumin (Invitrogen). Cells are cultured for 72 hours in the presence or absence of test compound (10 µM to 0.1 µM). Xenografts are collected after 21 days treatment with or without compound (100-10 mg/kg).

Tissue or cells are homogenized in 1 N HCl/CH$_3$OH (1:8, v/v). CHCl$_3$, 200 µg/mL of the antioxidant 2,6-di-tert-butyl-4-methylphenol (Sigma; ref. 29), and lipid standards are added. The organic fractions are evaporated and reconstituted in CH$_3$OH/CHCl$_3$/NH$_4$OH (90:10:1.25, v/v/v). Phospholipids are analyzed by electrospray ionization tandem mass spectrometry (ESI-MS/MS) on a hybrid quadrupole linear ion trap mass spectrometer (4000 QTRAP system, Applied Biosystems) equipped with a robotic nanoflow/ion source (Advion Biosciences). The collision energy is varied as follows: prec 184, 50 eV; nI 141, 35 eV; nI 87, −40 eV;

prec 241, −55 eV. The system is operated in the multiple reaction monitoring (MRM) mode for quantification of individual species. Typically, a 3-minute period of signal averaging is used for each spectrum. Data are corrected for $^{13}C$ isotope effects if the contribution is >10%. Corrected data were presented as heat maps using the HeatMap Builder software (Clifton Watt, Stanford University).

Biological Example 7

In Vivo Xenograft Assay

Animals:

Male NMRI-nude mice (obtained from Janvier) are used for the study. Mice with an initial weight of approximately 20 to 25 g are obtained. The animals are habituated for one week prior to any experimental protocols/procedures being performed.

All animals are maintained under SPF "full barrier" conditions with free access to food and water. Mice are group housed under a 12-h light:dark cycle (lights on at 06:00 h) at a temperature of 19 to 22° C. and 35 to 40% humidity in Techniplast type-3 IVC cages. Mice are fed a standard Laboratory chow. All experiments are carried out in accordance with the European Communities Council Directives (86/609/EEC) and are approved by the local ethical committee.

Prostate Tumor Cells:

The human PC-3 prostate tumor cells are cultured at 37° C. in a humidified atmosphere (5% $CO_2$, 95% air), in F12-Ham medium supplemented with 2 mM Sodium Pyruvate, 50 μg/ml Gentamycin, 1.5 g/l Sodium Bicarbonate, 0.1 mM Non Essential Amino Acids and 10% fetal bovine calf serum. Cells are maintained as cell monolayer cultures, passaged twice weekly at $3 \times 10^6$ cells per T175 flask, according to the following procedure. Cells are washed with PBS (w/o $Mg^{2+}$, $Ca^{2+}$), before addition of trypsin-EDTA to the culture flasks. After detachment of cells, the trypsin-EDTA is inactivated by addition of complete medium. The cell suspension is then transferred to 50 ml Falcon tube and centrifuged for 3 min at 1200 rpm. Medium is aspirated, with the cells being re-suspended in an appropriate volume of complete medium. The cells are counted in a haemocytometer and their viability is assessed by 0.25% trypan blue exclusion. An appropriate volume of cell suspension is then added to either a new T175 culture flask(s) or roller bottle containing fresh medium. For large scale-up growth of PC3 prostate tumor cells, an appropriate number of roller bottles are seeded with $1.2 \times 10^7$ cells 1 week prior to inoculation of the mice. The medium is changed twice during this period, with the last change being the day prior to cell injection. Cells are collected as described above, with the exception that after centrifugation, the cells are re-suspended in cold (4° C.) serum free medium at $5 \times 10^7$ cells/ml.

Experimental Design:

Human PC-3 prostate tumor cells are injected directly into the inguinal region of the male NMRI Nude mice ($1 \times 10^7$ cells/200 μl/animal) on day 0. Approximately 35 days after inoculation, when tumor volumes reach an approximate average of 200 mm³, mice are randomized into test groups according to tumor volume, and treated for 21 days with either control (no test compound) or test compound at one of three dosage levels: 10 mg/kg, 30 mg/kg or 100 mg/kg.

Data Analysis:

For each individual animal, body weight and tumor size [using the commonly accepted formula: Tumor Volume (mm³)=(a×b₂/2); where 'a' represents the length, and 'b' the width of the tumor as determined by caliper measurements], are monitored twice weekly throughout the study. A sustained body weight loss greater than 15% of the initial body weight is considered as clinical toxicity, with the animal removed from the study and sacrificed. Clinical signs of toxicity include, but are not limited to, persistent anorexia or dehydration, posture, moribund, lethargy, hypothermia and/or laboured respiration (according to the UKCCCR guidelines for welfare of animals in experimental neoplasia A time-course of tumor growth is expressed as median values, or normalized to initial tumor volume on the day treatment started and expressed as mean±SEM (8 to 10 animals per group). For pre-established tumors, relative tumor volumes is calculated for each mouse (treated tumor volume/tumor volume on day 0) and expressed as mean±SEM for each treatment group. Twenty-four hours after the last treatment, animals are sacrificed, tumors excised and weighed. The anti-tumor effect of test compound versus control is determined and represented by a bar chart of median values±25/75 and 10/90 percentiles. Statistical significance is indicated by one-sided p-values from Wilcoxon-Mann-Whitney analysis (Wilcoxon rank sum test), with p<0.05 considered statistically significant. Treatment/control (T/C) ratios are calculated based on final relative tumor volumes, using the NCI criteria—"The effective criteria for T/C ratios is 42%".

Formulation Example 1

Solid, Oral Dosage Form

As a specific embodiment of an oral composition, 100 mg of the Compound #65, prepared as in Example 3, above is formulated with sufficient finely divided lactose to provide a total amount of 580 to 590 mg to fill a size O hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:

1. A compound of formula (I)

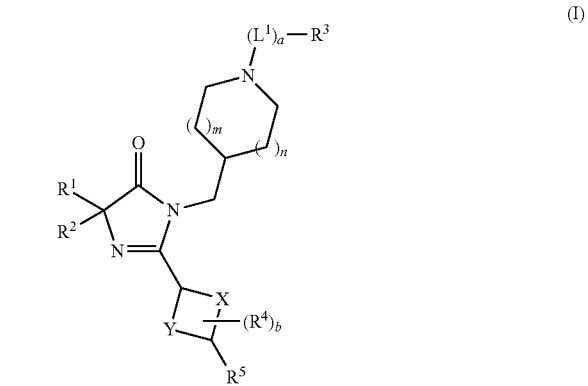

wherein
R¹ and R² are taken together to form an optionally substituted ring structure selected from the group consisting of $C_{3-6}$cycloalkyl and 4 to 6-membered, saturated heterocyclyl; wherein the 4 to 6-membered saturated heterocyclyl contains $NR^{10}$; provided that the $NR^{10}$ is not present at the 2-position relative to the carbon atom of the imidazolidin-5-one;

wherein $R^{10}$ is selected from the group consisting of hydrogen, $C_{1-4}$alkyl, $C_{2-4}$alkenyl, —$CH_2$-(hydroxy substituted $C_{1-2}$alkyl), —$CH_2$-(phenyl), —($C_2$alkyl)-O—($C_{1-2}$alkyl), —C(O)—($C_{1-4}$alkyl), —C(O)-(fluorinated $C_{1-2}$alkyl), —C(O)-(cyclopropyl), —C(O)O—($C_{1-4}$alkyl), —C(O)—$NR^AR^B$, and —$SO_2$—($C_{1-2}$alkyl), wherein $R^A$ and $R^B$ are each independently selected from the group consisting of hydrogen and methyl;

m is an integer from 0 to 1; and n is an integer from 0 to 2 provide that when n is 2, then m is 0;

such that

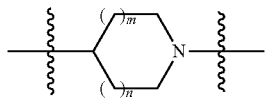

is selected from the group consisting of azetidin-3-yl, pyrrolidin-3-yl, pyrrolidin-3R-yl, pyrrolidin-3S-yl, piperidin-3-yl, piperidin-3R-yl, piperidin-3S-yl, and piperidin-4-yl;

a is 1;

$L^1$ is selected from the group consisting of C(O)—, —C(O)O—, and $SO_2$—;

$R^3$ is selected from the group consisting of $C_{1-4}$alkyl, hydroxy substituted $C_{1-4}$alkyl, fluorinated $C_{1-2}$alkyl, $C_{2-4}$alkenyl, $C_{3-5}$cycloalkyl, 4 to 5-membered, saturated heterocyclyl, 5 to 6-membered heteroaryl, and $NR^VR^W$; wherein the $C_{3-5}$cycloalkyl, 4 to 5-membered, saturated heterocyclyl or 5 to 6-membered heteroaryl are each optionally substituted with a substituent selected from the group consisting of halogen, hydroxy, $C_{1-2}$ alkyl, ($C_{1-2}$ alkyl)-OH, fluorinated $C_{1-2}$alkyl, cyano, and $NH_2$; and wherein $R^V$ and $R^W$ are each independently selected from the group consisting of hydrogen and methyl;

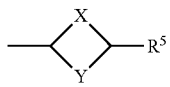

is selected from the group consisting of

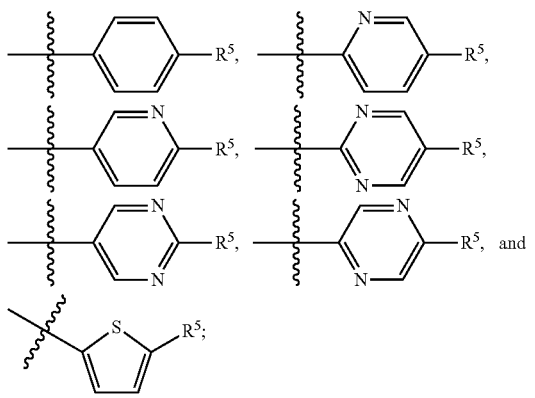

b is an integer from 0 to 1;

$R^4$ is selected from the group consisting of halogen, $C_{1-2}$alkyl, and $C_{1-2}$alkoxy;

$R^5$ is selected from the group consisting of

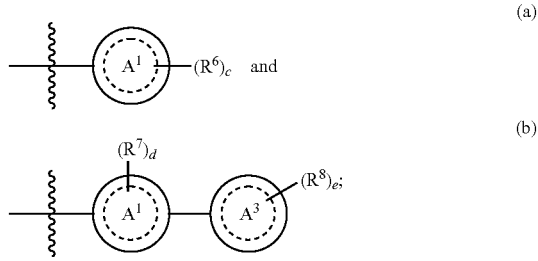

wherein

selected from the group consisting of phenyl, naphthyl, 5 to 6-membered heteroaryl, 9 to 10-membered heteroaryl, and partially unsaturated 9 to 10-membered heterocyclyl;

c is an integer from 0 to 2;

each $R^6$ is independently selected from the group consisting of hydroxy, oxo, halogen, cyano, $C_{1-4}$ alkyl, fluorinated $C_{1-2}$alkyl, hydroxy substituted $C_{1-4}$ alkyl, cyano-substituted $C_{1-2}$alkyl, —($C_{1-2}$alkyl)-O—($C_{1-2}$alkyl), $C_{1-4}$alkoxy, fluorinated $C_{1-2}$alkoxy, —$SO_2$—($C_{1-4}$alkyl), —$CO^2H$, —C(O)O—($C_{1-2}$alkyl), —C(O)—($C_{1-2}$alkyl), —C(O)-(fluorinated $C_{1-2}$alkyl), —C(O)—$NR^MR^N$, —$NR^MR^N$, —$NR^M$—C(O)H, —$NR^M$—$SO_2$—($C_{1-2}$alkyl), $C_{3-5}$cycloalkyl, 1-cyanocyclopropyl, —($C_{1-2}$alkyl)-($C_{3-5}$cycloalkyl), —S—($C_{3-5}$cycloalkyl), —$SO_2$—($C_{3-5}$cycloalkyl), —NH—C(O)—($C_3$-5cycloalkyl)-NH—$SO_2$—($C_{3-5}$cycloalkyl), and oxetan-3-yl; and wherein $R^M$ and $R^N$ are each independently selected from the group consisting of hydrogen and $C_{1-2}$alkyl;

wherein

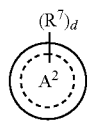

is selected from the group consisting of phenyl and 6-membered, nitrogen containing heteroaryl;

wherein

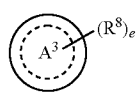

is selected from the group consisting of phenyl, 5 to 6-membered, saturated, nitrogen containing heterocylyl and 5 to 6-membered, nitrogen containing heteroaryl;

e is an integer from 0 to 1;

R⁸ is selected from the group consisting of halogen, $C_{1-4}$alkyl, $C_{3-5}$cycloalkyl, —($C_{1-2}$alkyl)-($C_{3-5}$cycloalkyl), and oxetanyl;

provided that the

is bound at the 3- or 4-position of the

relative to the point of attachment of the

to the

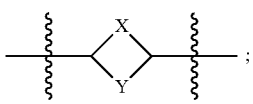;

provided that when R¹ and R² are taken together with the carbon atom to which they are bound to form 1-(methoxycarbonyl)-azetidin-3-yl, m is 1 and n is 0 or m is 0 and n is 1;

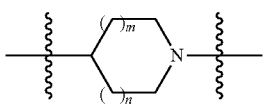

is pyrrolidin-3R-yl; -(L¹)ₐ-R³ is selected from the group consisting of —C(O)—CF₃, —C(O)-cyclopropyl, —C(O)-(thiazol-2-yl), —C(O)OCH₃, and —SO₂—CH₃,

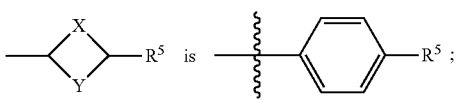;

and b=0; then R⁵ is other than quinolin-7-yl, benzofuran-5-yl, 1-methyl-pyrazol-4-yl, 4-(1-methyl-pyrazol-4-yl)-phenyl, 1,2,3,4,4a,8a-hexahydro-2-methyl-carbonyl-isoquinolin-6-yl), or 1,2,3,4-trihydro-2-methylcarbonyhisoquinolin-2-yl;

provided further that when R¹ and R² are taken together with the carbon atom to which they are bound to form cyclopentyl; m is 1 and n is 0 or m is 0 and n is 1;

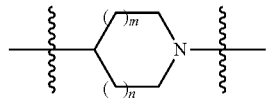

is pyrrolidin-3R-yl; -(L¹)ₐ-R³ is —C(O)-cyclopropyl;

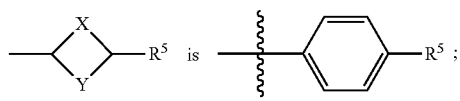;

b=0 or (R⁴)ᵦ is 2-methyl; then R⁵ is other than 1-methyl-pyrazol-4-yl, 4-methyl-3,4-dihydro-pyrido[2,3-b]oxazon-7-yl, 2-(piperazin-1-yl)-pyridin-4-yl, or 2-(4-methyl-piperazin-1-yl)-pyridin-4-yl;

provided further that when R¹ and R² are taken together with the carbon atom to which they are bound to form cyclopentyl; m is 1 and n is 0 or m is 0 and m is 1;

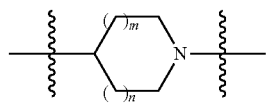

is pyrrolidin-3R-yl; -(L¹)ₐ-R³ is —SO₂-pyrrolidin-1-yl;

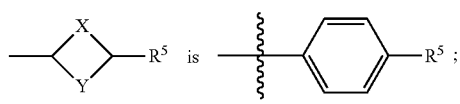;

b=0 or (R⁴)ᵦ is 2-methyl; then R⁵ is other than benzofuran-5-yl;

provided further that when R¹ and R² are taken together with the carbon atom to which they are bound to form cyclopropyl; m is 0, n is 0,

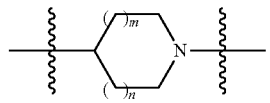

is azetidin-3-yl; -(L¹)ₐ-R³ is selected from the group consisting of —C(O)-cyclopropyl, —C(O)-(1-methyl-cyclopropyl), and —C(O)-(1-hydroxy-cyclopropyl);

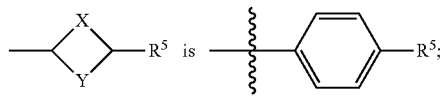;

b=0 or (R⁴)ᵦ is selected from the group consisting of 2-fluoro and 2-methyl; then R⁵ is other than 1-isopropylsulfonyl-phenyl, 1-methyl-indazol-5-yl, 1-isopropyl-indazol-5-yl, 1-oxetan-3-yl, indazol-5-yl, 1-methyl-pyrazol-4-yl, 4-methyl-7-bromo-quinolin-2-yl, 5-(2-hydroxy-2-methyl-propyl)-pyridin-2-yl, 6-isopropyl-pyridin-3-yl, 6-(1-cyanomethyl)-pyridin-3-yl, 6-(2-hydroxy-2-methyl-propyl)- pyridin-3-yl, 1,5-naphthyridin-3-yl, 3-methyl-[1,2,4]triazolo[4,3-a]pyridin-6-yl, 4-(1-isobutyl-pyrazol-5-yl)-phenyl, or 6-(morpholin-4-yl)-pyridin-3-yl;
provided further that when R¹ and R² are taken together with the carbon atom to which they are bound to form cyclopropyl; m is 0, n is 0,

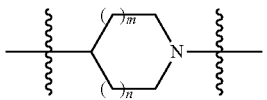

is azetidin-3-yl; -(L¹)ₐ-R³ is —C(O)-(1-hydroxy-cyclopropyl);

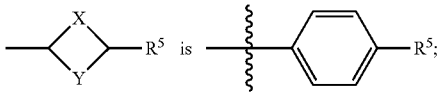

and (R⁴)ᵦ is 2-methyl; then R⁵ is other 1-methyl-indazol-5-yl;
provided further that when R¹ and R² are taken together with the carbon atom to which they are bound to form cyclopropyl; m is 0, n is 0,

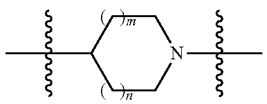

is azetidin-3-yl; -(L¹)ₐ-R³ is —C(O)-pyridin-3-yl;

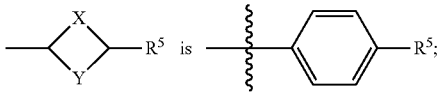

(R⁴)ᵦ is 2-methyl; then R⁵ is other than 1-methyl-indazol-5-yl;
provided further that when R¹and R² are taken together with the carbon atom to which they are bound to form cyclopropyl; m is 0, n is 2,

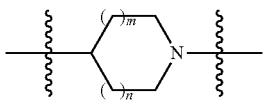

is piperidin-3R-yl or piperidin-3S-yl; -(L¹)ₐ-R³ is —C(O)-cyclopropyl;

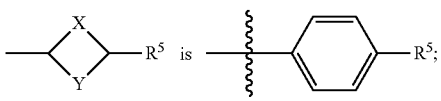

and b=0; then R⁵ is other than indazol-5-yl, benzofuran-5-yl, benzothien-5-yl, 1-methyl-indazol-5-yl, 4-(4-methylphenyl)phenyl, or 4-(3-chlorophenyl)-phenyl;

provided further that when R¹ and R² are taken together with the carbon atom to which they are bound to form cyclopropyl; m is 1, n is 1,

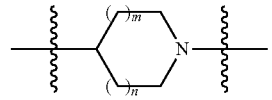

is piperidin-4-yl; -(L¹)ₐ-R³ is —C(O)-cyclopropyl;

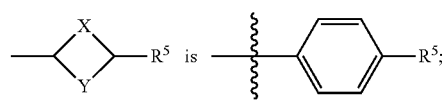

and b=0; then R⁵ is other than 4-trifluoromethyl-phenyl, 1-methyl-pyrazol-4-yl, benzoxazol-5-yl, pyridin-4-yl, or 4-(1-methyl-pyrazol-4-yl)-phenyl;
provided further that when R¹and R² are taken together with the carbon atom to which they are bound to form cyclopropyl; m is 0 and n is 1 or m is 1 and n is 0;

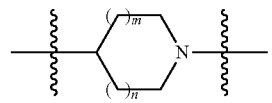

is pyrrolidin-3R-yl; -(L¹)ₐ-R³ is —C(O)-cyclopropyl;

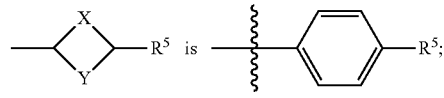

and b=0; then R⁵ is other than 5-chloro-pyridin-3-yl, 2-oxo-3,4-dihydro-quinolin-7-yl, or 6-(4-methyl-piperazin-1-yl)-pyridin-3-yl;
provided further that when R¹and R² are taken together with the carbon atom to which they are bound to form tetrahydrofuran-3,3-diyl or tetrahydropyran-4,4-diyl; m is an integer from 0 to 1 and n is 0 or m is 0 and n is an integer from 0 to 1;

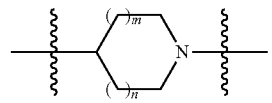

is selected from the group consisting of azetidin-3-yl, pyrrolidin-3R-yl and pyrrolidin-3-yl; -(L¹)ₐ-R³ is selected from the group consisting of —C(O)-thiazol-2-yl, —C(O)—CF₃, —C(O)OCH₃ and —SO₂—CH₃;

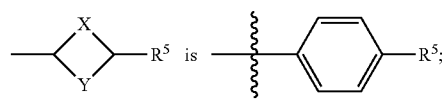

and b=0; then $R^5$ is other than quinolin-7-yl, 1-methyl-indazol-5-yl, benzofuran-5-yl, or 4-(1-methyl-pyrazol-4-yl)-phenyl; and
a stereoisomer, a tautomer and a pharmaceutically acceptable salt thereof.

2. A compound as in claim 1, wherein
$R^1$ and $R^2$ are taken together to form a ring structure selected from the group consisting of cyclopropyl, cyclopentyl, piperidin-4,4-diyl, 1-(methyl)-piperidin-4,4-diyl, 1-(isopropyl)-piperidin-4,4-diyl, 1-(ethenyl)-piperidin-4,4-diyl, 1-(2-hydroxy-ethyl)-piperidin-4,4-diyl, 1-(methoxy-carbonyl)-piperidin-4,4-diyl, 1-(benzyl)-piperidin-4,4-diyl, 1-(methyl-carbonyl)-piperidin-4,4-diyl, 1-(isopropyl-carbonyl)-piperidin-4,4-diyl, 1-(trifluoromethyl-carbonyl)-piperidin-4,4-diyl, 1-(cyclopropyl-carbonyl)-piperidin-4,4-diyl, 1-(dimethylamino-carbonyl)-piperidin-4,4-diyl, 1-(methylsulfonyl)-piperidin-4,4-diyl, 1-(2-methoxy-ethyl)-piperidin-4,4-diyl, 1-(benzyl)-piperidin-4,4-diyl, tetrahydro-pyran-4,4-diyl, tetrahydro-furan-3,3-diyl, and 1-(methoxycarbonyl)-azetidin-3,3-diyl;
m is an integer from 0 to 1; and n is an integer from 0 to 2; provided that when n is 2 then m is 1;

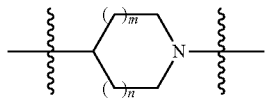

is selected from the group consisting of azetidin-3-yl, pyrrolidin-3-yl, pyrrolidin-3R-yl, pyrrolidin-3S-yl, piperidin-3R-yl, piperidin-3S-yl, and piperidin-4-yl;
a is 1;
$L^1$ is selected from the group consisting of —C(O)—, —C(O)O— and —SO$_2$—;
$R^3$ is selected from the group consisting of methyl, ethyl, isopropyl, 1-hydroxyethyl, trifluoromethyl, 2,2,2-trifluoroethyl, 2-hydroxy-propan-2-yl, 3-hydroxy-2-methyl-propan-2-yl, ethenyl, cyclopropyl, 1-fluoro-cyclopropyl, 1-hydroxy-cyclopropyl, 1-hydroxymethyl-cyclopropyl, 1-methyl-cyclopropyl, 1-cyano-cyclopropyl, 1-amino-cyclopropyl, cyclobutyl, 1-methyl-cyclobutyl, amino, dimethylamino, pyrrolidin-1-yl, 1-methyl-pyrazol-3-yl, thiazol-2-yl, tetrahydro-furan-2-yl, tetrahydro-furan-2R-yl, oxetan-2-yl, oxetan-3-yl, 3-methyl-oxetan-3-yl, and pyridin-3-yl;

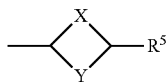

is selected from the group consisting of

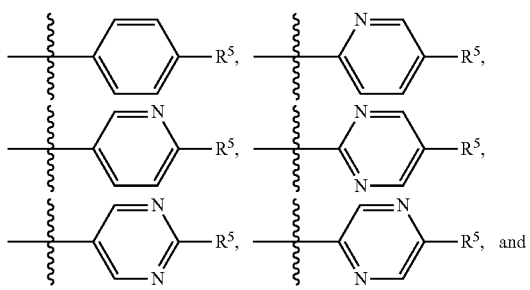

-continued

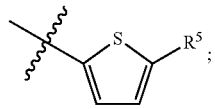

b is an integer from 0 to 1;
$R^4$ is selected from the group consisting of 2-fluoro, 3-fluoro, 2-chloro, 3-chloro, 2-methyl, 3-methyl, and 2-methoxy;
$R^5$ is selected from the group consisting of

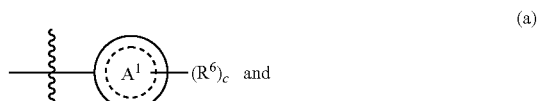
(a)

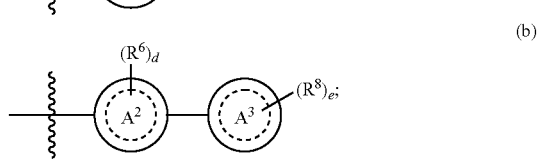
(b)

wherein

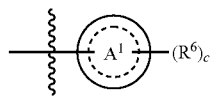

is selected from the group consisting of 3-cyano-phenyl, 4-cyano-phenyl, 3-hydroxy-phenyl, 4-hydroxy-phenyl, 3-fluoro-phenyl, 4-fluoro-phenyl, 3-chloro-phenyl, 4-chloro-phenyl, 2-fluoro-4-chloro-phenyl, 3-chloro-4-fluoro-phenyl, 2-fluoro-4-cyano-phenyl, 2-fluoro-4-(1-cyano-cuclopropyl)-phenyl, 2-fluoro-5-trifluoromethyl-phenyl, 2,4-dichloro-phenyl, 3-methyl-phenyl, 4-methyl-phenyl, 3-trifluoromethyl-phenyl, 4-trifluoromethyl-phenyl, 2-methoxy-phenyl, 3-methoxy-phenyl, 4-methoxy-phenyl, 3-trifluoromethoxy-phenyl, 4-trifluoromethoxy-phenyl, 4-(methylcarbonyl)-phenyl, 3-dimethylamino-phenyl, 4-dimethylamino-phenyl, 3-methylsulfonyl-amino-phenyl, 3-amino-4-hydroxy-phenyl, 3-formamido-4-hydroxy-phenyl 3-(cyclopropylthio)-phenyl, 3-(cyclopropylsulfonyl)-phenyl, 3-(cyclopropylcarbonyl-amino)-phenyl, 3-(cyclopropylsulfonyl-amino)-phenyl, 3-(methylsulfonyl)-phenyl, 3-(isopropylsulfonyl)-phenyl, 3-(aminocarbonyl)-phenyl, 3-carboxy-phenyl, 3-(methoxycarbonyl)-phenyl, naphth-2-yl, 6-fluoro-naphth-2-yl, 7-fluoro-naphth-2-yl, 8-fluoro-naphth-2-yl, 6-chloro-naphth-2-yl, 6-methyl-naphth-2-yl, 6-methoxy-naphth-2-yl, 8-methoxy-naphth-2-yl, 6-isopropyloxy-naphth-2-yl, 2-cyano-naphth-7-yl, 6-cyano-naphth-2-yl, 7-cyano-naphth-2-yl, 5-methoxy-naphth-2-yl, 7-methoxy-naphth-2-yl, 1,5-naphthyridin-3-yl, 1,8-naphthyridin-2-yl, 1,8-naphthyridin-3-yl, chroman-6-yl, isochroman-6-yl, isochroman-7-yl, pyridin-2-yl, pyridin-3-yl, pyridin-4-yl, 6-isopropyl-pyridin-3-yl, 6-n-propyl-pyridin-3-yl, 5-bromo-pyridin-2-yl, 5-chloro-pyridin-3-yl, 5-(2-hydroxy-2-methyl-propyl)-pyridin-2-yl, 5-(2-hydroxy-2-methyl-propyl)-pyridin-3-yl, 6-cycloprpoyl-pyridin-3-yl, 6-(1-cyano-cyclopropyl)-pyridin-3-yl, 2-amino-pyrid-4-yl, 5-amino-pyridin-3-yl, 6-amino-pyridin-2-yl, 1-methyl-pyrazol-4-yl, 1-methyl-pyrazol-5-yl, indol-3-yl, indol-4-yl, indol-5-yl, indol-6-yl, 1-methyl-indol-5-yl, 1-methyl-indol-6-yl, 2-methyl-indol-5-yl, 2-hydroxymethyl-indol-5-yl, 3-(2-hydroxyethyl)-indol-5-yl, 3-cyanomethyl-indol-5-yl, 1,2-dimethyl-indol-5-yl, 1,3-dimethyl-indol-5-yl, 2,3-dimethyl-indol-5-yl, 1-methyl-3-(2-hydroxyethyl)-indol-5-yl, 1-(trifluoromethyl-carbonyl)-indol-5-yl, 2-oxo-indolin-5-yl, quinolin-2-yl, quinolin-3-yl, quinolin-5-yl, quinolin-6-yl, quinolin-7-yl, 2-chloro-quinolin-7-yl, 3-chloro-quinolin-7-yl, 4-chloro-quinolin-7-yl, 6-fluoro-quinolin-2-yl, 8-fluoro-quinolin-2-yl, 7-bromo-quinolin-2-yl, 2-hydroxy-quinolin-3-yl, 2-cyano-quinolin-6-yl, 2-cyano-quinolin-7-yl, 6-cyano-quinolin-2-yl, 2-methyl-quinolin-5-yl, 2-methyl-quinolin-6-yl, 2-methyl-quinolin-7-yl, 4-methyl-quinolin-7-yl, 2,4-dimethyl-quinolin-7-yl, 2-chloro-3-methyl-quinolin-7-yl, 2-chloro-4-methyl-quinolin-7-yl, 2-methyl-8-fluoro-quinolin-2-yl, 2-methyl-quinolin-7-yl, 2-methyl-7-bromo-quinolin-7-yl, 3-methyl-7-bromo-quinolin-7-yl, 2-methyl-4-chloro-quinolin-7-yl, 4-methyl-7-bromo-quinolin-2-yl, 2-trifluoromethyl-quinolin-7-yl, 2-oxo-quinolin-7-yl, 2-carboxy-quinolin-7-yl, 2-aminocarbonyl-quinolin-7-yl, isoquinolin-3-yl, isoquinolin-5-yl, isoquinolin-6-yl, isoquinolin-7-yl, 1-chloro-isoquinolin-6-yl, 3-chloro-isoquinolin-6-yl, 3-fluoro-isoquinolin-6-yl, 6-bromo-isoquinolin-3-yl, 1-methoxy-isoquinolin-6-yl, 3-methoxy-isoquinolin-6-yl, 1-amino-isoquinolin-6-yl, 3-amino-isoquinolin-6-yl, 1-oxo-isoquinolin-6-yl, quinazlin-7-yl, quinoxalin-6-yl, indazol-3-yl, indazol-4-yl, indazol-5-yl, indazol-6-yl, 4-chloro-indazol-5-yl, 1-methyl-indazol-3-yl, 1-methyl-indazol-4-yl, 1-methyl-indazol-5-yl, 1-methyl-indazol-6-yl, 2-methyl-indazol-4-yl, 2-methyl-indazol-5-yl, 2-methyl-indazol-6-yl, 1,3-dimethyl-indazol-5-yl, 1,4-dimethyl-indazol-5-yl, 1,7-dimethyl-indazol-5-yl, 1,8-dimethyl-indazol-5-yl, 1-ethyl-indazol-5-yl, 2-ethyl-indazol-5-yl, 1-isopropyl-indazol-5-yl, 2-isopropyl-indazol-5-yl, 1-(2-hydroxyethyl)-indazol-5-yl, 2-(2-hydroxyethyl)-indazol-5-yl, 1-(2-hydroxyethyl)-6-fluoro-indazol-5-yl, 2-(2-hydroxyethyl)-6-fluoro-indazol-5-yl, 1-methyl-3-chloro-indazol-5-yl, 1-methyl-3-chloro-indazol-6-yl, 1-methyl-3-amino-indazol-6-yl, 1-methyl-3-aminocarbonyl-indazol-6-yl, 1-methyl-3-cyano-indazol-5-yl, 1-methyl-3-cyano-indazol-6-yl, 1-methyl-3-methoxy-indazol-5-yl, 1-methyl-3-methoxymethyl-indazol-5-yl, 1-methyl-3-methoxymethyl-indazol-6-yl, 1-methyl-7-methoxymethyl-indazol-4-yl, 1-methyl-3-hydroxymethyl-indazol-5-yl, 1-methyl-3-hydroxymethyl-indazol-6-yl, 1-methyl-7-hydroxymethyl-indazol-4-yl, 1-methyl-3-cyclopropyl-indazol-5-yl, 2-methyl-3-cyano-indazol-5-yl, 2-methyl-3-hydroxymethyl-indazol-5-yl, 2-methyl-3-methoxymethyl-indazol-5-yl, 1-(2-hydroxyethyl)-indazol-5-yl, 2-(2-hydroxyethyl)-indazol-5-yl), 1-(2-cyanoethyl)-indazol-5-yl, 2-(2-cyanoethyl)-indazol-5-yl, 1-oxetan-3-yl-indazol-5-yl, 1-cyclopropyl-indazol-5-yl, 1-cyclopropylmethyl-indazol-5-yl, 2-cyclopropylmethyl-indazol-5-yl, benzofuran-5-yl, benzofuran-6-yl, 2-methyl-benzofuran-5-yl, 2,3-dimethyl-benzofuran-5-yl, 2-cyano-benzofuran-5-yl, benzimidazol-2-yl, benzimidazol-5-yl, 1-methyl-benzimidazol-2-yl, 1,2-dimethyl-benzimidazol-6-yl, 1-methyl-6-fluoro-benzimidazol-2-yl, 2-oxo-benzimidazol-5-yl, benzoxazol-2-yl, benzoxazol-5-yl, 6-chloro-benzoxazol-2-yl, benzisoxazol-5-yl, benzthiazol-2-yl, benzthiazol-5-yl, 5-fluoro-benzothiazol-2-yl, 6-fluoro-benzothiazol-2-yl, 5-chloro-benzothiazol-2-yl, 6-chloro-benzothiazol-2-yl, 5,6-difluoro-benzothiazol-2-yl, 2-methyl-benzothiazol-5-yl, 2-methyl-benzothiazol-6-yl, 6-methyl-benzothiazol-2-yl, 2-methyl-benzothiazol-5-yl, 5-cyano-benzothiazol-2-yl, 6-cyano-benzothiazol-2-yl, benzothien-5-yl, 2-methyl-benzothien-5-yl, 2,3-dimethyl-benzothioen-5-yl, 2,3-dihydro-benzofuran-5-yl, 2-oxo-3,4-dihydro-quinolin-7-yl, 1,2,3,4-tetrahydro-2-methylcarbonyl-isoquinolin-6-yl, 1,2,3,4,4a,8a-hexahydro-2-methyl-carbonyl-isoquinolin-6-yl, 2,3-dihydro-benzo[1,4]dioxin-6-yl, 2,3-dihydrobenzofuran-5-yl, 1,2-dimethyl-1,2-dihydro-3-oxo-indazol-5-yl, 2-oxo-3,4-dihydro-quinolin-6-yl, benzo[1,3]dioxol-5-yl, pyrrolo[2,3-b]pyridin-5-yl, 1-methyl-pyrazolo[4,3-b]pyridin-5-yl, [1,2,4]triazo[4,3-a]pyridin-6-yl, 3-methyl-[1,2,4]triazo[4,3-a]pyridin-6-yl, and 4-methyl-3,4-dihydro-pyrido[3,2-b][1,4]oxazin-7-yl;

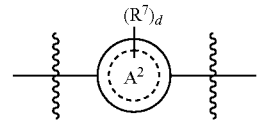

is selected from the group consisting of phenyl, pyridin-3-yl, and pyridin-4-yl;
and

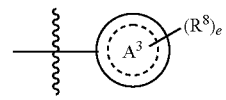

is selected from the group consisting of 4-bromo-phenyl, 3-chloro-phenyl, 4-methyl-phenyl, pyridin-3-yl, pyridin-4-yl, 1-methyl-pyrazol-3-yl, 1-methyl-pyrazol-4-yl, 1-methyl-pyrazol-5-yl, 1-isopropyl-pyrazol-4-yl, 1-isobutyl-pyrazol-5-yl, 1-(2-methylpropyl)-pyrazol-3-yl, 1-cyclopropyl-pyrazol-4-yl, 1-cyclobutyl-pyrazol-4-yl, 1-cyclopropylmethyl-pyrazol-3-yl, 1-cyclopropylmethyl-pyrazol-5-yl, 1,2,3,4-tetrazol-5-yl, pyrazol-3-yl, pyrrolidin-1-yl, morpholin-4-yl, 4-methyl-piperazin-1-yl, imidazol-1-yl, piperazin-1-yl, 4-methyl-piperazin-1-yl, and 1-(oxetan-3-yl)-pyrazol-4-yl;

provided that when

is phenyl or pyridin-3-yl, then

is bound to

at the 4-position, relative to the point of attachment of the

to the

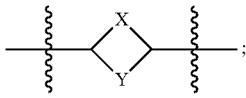

provided further that when

is pyridin-4-yl, then

is bound to

at the 3-position, relative to the point of attachment of the

to the

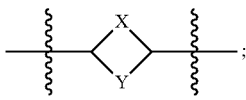

provided that when $R^1$ and $R^2$ are taken together with the carbon atom to which they are bound to form 1-(methoxycarbonyl)-azetidin-3-yl, m is 1 and n is 0 or m is 0 and n is 1;

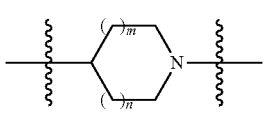

is pyrrolidin-3R-yl; -(L$^1$)$_a$-R$^3$ is selected from the group consisting of —C(O)—CF$_3$, —C(O)-cyclopropyl, —C(O)-(thiazol-2-yl), —C(O)OCH$_3$, and —SO$_2$—CH$_3$,

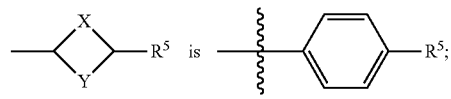

and b=0; then $R^5$ is other than quinolin-7-yl, benzofuran-5-yl, 1-methyl-indazol-5-yl, 1-methyl-pyrazol-4-yl, 4-(1-methyl-pyrazol-4-yl)-phenyl, 1,2,3,4,4a, 8a-hexahydro-2-methyl-carbonyl-isoquinolin-6-yl, or 1,2,3,4-trihydro-2-methylcarbonyl-isoquinolin-2-yl;

provided further that when $R^1$ and $R^2$ are taken together with the carbon atom to which they are bound to form cyclopentyl; m is 1 and n is 0 or m is 0 and m is 1;

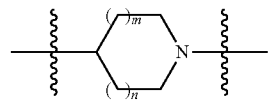

is pyrrolidin-3R-yl; -(L')$_a$-R$^3$ is —C(O)-cyclopropyl;

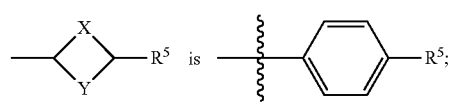

b=0 or (R$^4$)$_b$ is 2-methyl; then $R^5$ is other than 1-methyl-pyrazol-4-yl, 4-methyl-3,4-dihydro-pyrido[2,3-b]oxazon-7-yl, 2-(piperazin-1-yl)-pyridin-4-yl, or 2-(4-methyl-piperazin-1-yl)-pyridin-4-yl;

provided further that when $R^1$ and $R^2$ are taken together with the carbon atom to which they are bound to form cyclopentyl; m is 1 and n is 0 or m is 0 and m is 1;

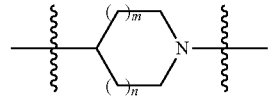

is pyrrolidin-3R-yl; -(L$^1$)$_a$-R$^3$ is —SO$_2$-pyrrolidin-1-yl;

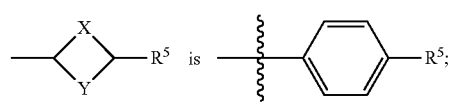

b=0 or (R$^4$)$_b$ is 2-methyl; then $R^5$ is other than benzofuran-5-yl;

provided further that when $R^1$ and $R^2$ are taken together with the carbon atom to which they are bound to form cyclopropyl; m is 0, n is 0,

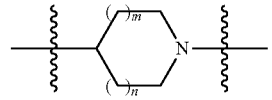

is azetidin-3-yl; -(L$^1$)$_a$-R$^3$ is selected from the group consisting of —C(O)-cyclopropyl, —C(O)-(1-methyl-cyclopropyl), and —C(O)-(1-hydroxy-cyclopropyl);

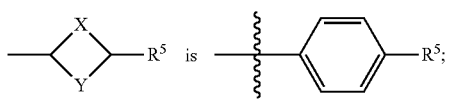 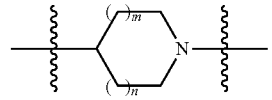

b=0 or (R⁴)$_b$ is selected from the group consisting of 2-fluoro and 2-methyl; then R⁵ is other than 1-isopropylsulfonyl-phenyl, 1-methyl-indazol-5-yl, 1-isopropyl-indazol-5-yl, 1-oxetan-3-yl, indazol-5-yl, 1-methyl-pyrazol-4-yl, 4-methyl-7-bromo-quinolin-2-yl, 5-(2-hydroxy-2-methyl-propyl)-pyridin-2-yl, 6-isopropyl-pyridin-3-yl, 6-(1-cyanomethyl)-pyridin-3-yl, 6-(2-hydroxy-2-methyl-propyl)-pyridin-3-yl, 1,5-naphthyridin-3-yl, 3-methyl-[1,2,4]triazolo[4,3-a]pyridin-6-yl, 4-(1-isobutyl-pyrazol-5-yl)-phenyl, or 6-(morpholin-4-yl)-pyridin-3-yl;

provided further that when R¹ and R² are taken together with the carbon atom to which they are bound to form cyclopropyl; m is 0, n is 0, is piperidin-3R-yl or piperidin-3S-yl; -(L¹)$_a$-R³ is —C(O)-cyclopropyl;

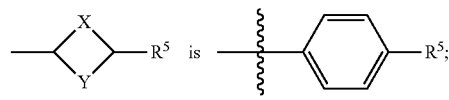

and b=0; then R⁵ is other than indazol-5-yl, benzofuran-5-yl, benzothien-5-yl, 1-methyl-indazol-5-yl, 4-(4-methylphenyl)phenyl, or 4-(3-chlorophenyl)-phenyl;

provided further that when R¹ and R² are taken together with the carbon atom to which they are bound to form cyclopropyl; m is 1, n is 1,

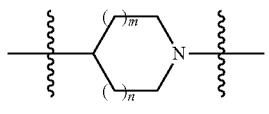

is azetidin-3-yl;
(L¹)$_a$-R³ is —C(O)-(1-hydroxy-cyclopropyl);

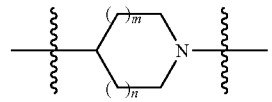

is piperidin-4-yl; -(L¹)$_a$-R³ is —C(O)-cyclopropyl;

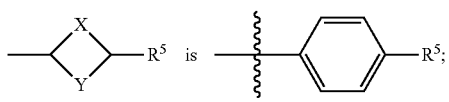

and (R⁴)$_b$ is 2-methyl; then R⁵ is other 1-methyl-indazol-5-yl;

provided further that when R¹ and R² are taken together with the carbon atom to which they are bound to form cyclopropyl; m is 0, n is 0,

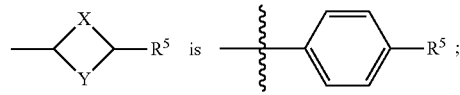

and b=0; then R⁵ is other than 4-trifluoromethyl-phenyl, 1-methyl-pyrazol-4-yl, benzoxazol-5-yl, pyridin-4-yl or 4-(1-methyl-pyrazol-4-yl)-phenyl;

provided further that when R¹ and R² are taken together with the carbon atom to which they are bound to form cyclopropyl; m is 0 and n is 1 or m is 1 and n is 0;

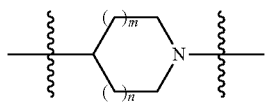

is azetidin-3-yl; -(L¹)$_a$-R³ is —C(O)-pyridin-3-yl;

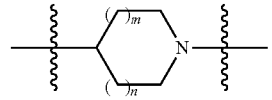

is pyrrolidin-3R-yl; -(L¹)$_a$-R³ is —C(O)-cyclopropyl;

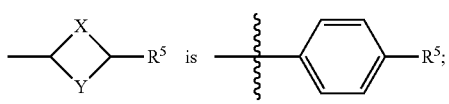

(R⁴)$_b$ is 2-methyl; then R⁵ is other than 1-methyl-indazol-5-yl;

provided further that when R¹ and R² are taken together with the carbon atom to which they are bound to form cyclopropyl; m is 0, n is 2,

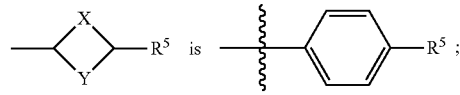

and b=0; then R⁵ is other than 5-chloro-pyridin-3-yl, 2-oxo-3,4-dihydro-quinolin-7-yl, or 6-(4-methyl-piperazin-1-yl)-pyridin-3-yl;

provided further that when R¹ and R² are taken together with the carbon atom to which they are bound to form tetrahydrofuran-3,3-diyl or tetrahydropyran-4,4-diyl; m is an integer from 0 to 1 and n is 0 or m is 0 and n is an integer from 0 to 1;

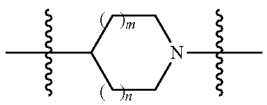

is selected from the group consisting of azetidin-3-yl, pyrrolidin-3R-yl and pyrrolidin-3-yl; -(L¹)ₐ-R³ is selected from the group consisting of —C(O)-thiazol-2-yl, —C(O)—CF₃, —C(O)OCH₃, and —SO₂—CH₃;

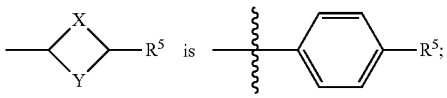

and b=0; then R⁵ is other than quinolin-7-yl, 1-methyl-indazol-5-yl, benzofuran-5-yl, or 4-(1-methyl-pyrazol-4-yl)-phenyl; and a stereoisomer, a tautomer and a pharmaceutically acceptable salt thereof.

3. A compound as in claim 2, wherein

R¹ and R² are taken together to form a ring structure selected from the group consisting of cyclopropyl, cyclopentyl, piperidin-4,4-diyl, 1-(methyl)-piperidin-4,4-diyl, 1-(isopropyl)-piperidin-4,4-diyl, 1-(2-hydroxyethyl)-piperidin-4,4-diyl, 1-(ethenylcarbonyl)-piperidin-4,4-diyl, 1-(trifluoromethyl-carbonyl)piperidin-4,4-diyl, 1-(methoxy-carbonyl)-piperidin-4,4-diyl, 1-(2-methoxyethyl)-piperidin-4,4-diyl, 1-(benzyl)-piperidin-4,4-diyl, 1-(methyl-carbonyl)-piperidin-4,4-diyl, 1-(isopropyl-carbonyl)-piperidin-4,4-diyl, 1-(cyclopropyl-carbonyl)-piperidin-4,4-diyl, 1-(methylsulfonyl)-piperidin-4,4-diyl, 1-(dimethylamino-carbonyl)-piperidin-4,4-diyl, 1-(methoxycarbonyl)-azetidin-3,3-diyl, tetrahyrdofuran-3,3-diyl, and tetrahydropyran-4,4-diyl;

m is an integer from 0 to 1; and n is an integer from 0 to 1;

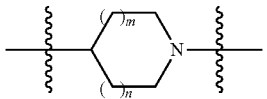

is selected from the group consisting of azetidin-3-yl, pyrrolidin-3R-yl, pyrrolidin-3S-yl, and piperidin-4-yl;

a is 1;

L¹ is —C(O)—;

R³ is selected from the group consisting of ethyl, 1-hydroxy-ethyl, isopropyl, 2-hydroxy-propan-2-yl, 3-hydroxy-2-methyl-propan-2-yl, 2,2,2-trifluoroethyl, ethenyl, cyclopropyl, 1-fluoro-cyclopropyl, 1-methyl-cyclopropyl, 1-hydroxy-cyclopropyl, 1-hydroxymethyl-cyclopropyl, 1-amino-cyclopropyl, cyclobutyl, 1-methyl-cyclobutyl, pyrrolidin-1-yl, 1-methyl-pyrazol-3-yl, oxetan-2-yl, oxetan-3yl, 3-methyl-oxetan-3-yl, tetrahydro-furan-2yl, tetrahydro-furan-2R-yl, tetrahydro-furan-2S-yl, and dimethylamino;

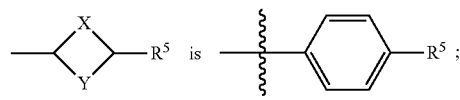

b is an integer from 0 to 1;
R⁴ is selected from the group consisting of 2-fluoro, 2-chloro, 2-methyl, 2-methoxy, 3-fluoro, and 3-methyl;
R⁵ is

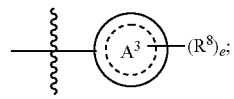

wherein

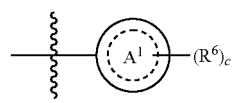

is selected from the group consisting of 4-cyano-phenyl, 3-hydroxy-phenyl, 4-hydroxy-phenyl, 3-fluoro-phenyl, 4-fluoro-phenyl, 3-chloro-phenyl, 4-chloro-phenyl, 2,4-dichloro-phenyl, 2-fluoro-4-chloro-phenyl, 3-chloro-4-fluoro-phenyl, 3-methyl-phenyl, 4-methyl-phenyl, 3-trifluoromethyl-phenyl, 3-methoxy-phenyl, 4-methoxy-phenyl, 3-aminocarbonyl-phenyl, 3-dimethylamino-phenyl, 4-dimethylamino-phenyl, 3-methylsulfonyl-amino-phenyl, 3-(cyclopropyl-sulfonylamino)-phenyl, 3-(cyclopropyl-carbonylamino)-phenyl, 3-(cyclopropyl-thio)-phenyl, 3-(cyclopropyl-sulfonyl)-phenyl, naphtha-2-yl, 6-fluoro-naphth-2-yl, 8-fluoro-naphth-2-yl, 6-chloro-naphth-2-yl, 7-fluoro-naphth-2-yl, 8-fluoro-naphth-2-yl, 6-methyl-naphth-2-yl, 5-methoxy-naphth-2-yl, 6-methoxy-naphth-2-yl, 8-methoxy-naphth-2-yl, 6-isopropoxy-naphth-2-yl, 6-cyano-naphth-2-yl, 7-methoxy-naphth-2-yl, 7-cyano-naphth-2-yl, 6-amino-pyridin-2-yl, isochroman-6-yl, isochroman-7-yl, 2-oxo-indolin-5-yl, indol-3-yl, indol-4-yl, indol-5-yl, indol-6-yl, 1-methyl-indol-5-yl, 1-methyl-indol-6-yl, 2-methyl-indol-5-yl, 1,2-dimethyl-indol-5-yl, 1,3-dimethyl-indol-5-yl, 2,3-dimethyl-indol-5-yl, 2-hydroxymethyl-indol-5-yl, 3-(2-hydroxyethyl-indol-5-yl), 3-cyanomethyl-indol-5-yl, 1-methyl-3-(2-hydroxyethyl)-indol-5-yl, quinolin-2-yl, quinolin-3-yl, quinolin-5-yl, quinolin-6-yl, quinolin-7-yl, 2-chloro-quinolin-7-yl, 4-chloro-quinolin-7-yl, 6-fluoro-quinolin-2-yl, 8-fluoro-quinolin-2-yl, 3-chloro-quinolin-7-yl, 2-methyl-quinolin-6-yl, 2-methyl-quinolin-6-yl, 4-methyl-quinolin-7-yl, 2-cyano-quinolin-6-yl, 2-chloro-3-methyl-quinolin-7-yl, isoquinolin-3-yl, isoquinolin-5-yl, isoquinolin-6-yl, isoquinolin-7-yl, 3-fluoro-isoquinolin-6-yl, 1-chloro-isoquinolin-6-yl, 3-chloro-isoquinolin-6-yl, 1-methoxy-isoquinolin-6-yl, 3-methoxy-isoquinolin-6-yl, 1-amino-isoquinolin-6-yl, 3-amino-isoquinolin-6-yl, 1-oxo-isoquinolin-6-yl, quinazolin-7-yl, indazol-3-yl, indazol-4-yl, indazol-5-yl, indazol-6-yl, 1-methyl-indazol-5-yl, 1-methyl-indazol-6-yl, 1-methyl-indazol-3-yl, 1-methyl-indazol-4-yl, 1-methyl-indazol-5-yl, 1-methyl-indazol-6-yl, 2-methyl-indazol-4-yl, 2-methyl-indazol-5-yl, 2-methyl-indazol-6-yl, 1,3-dimethyl-indazol-5-yl, 1,4-dimethyl-indazol-5-yl, 1,8-dimethyl-indazol-5-yl, 1-ethyl-indazol-5-yl, 1-methyl-3-chloro-indazol-5-yl, 1-methyl-3-chloro-indazol-6-yl, 1-methyl-3-aminocarbonyl-indazol-6-yl, 1-methyl-3-cyanoindazol-6-yl, 1-methyl-3-amino-indazol-6-yl, 1-methyl-3-methoxy-indazol-5-yl, 1-methyl-3-methoxymethyl-indazol-5-yl, 1-methyl-3-methoxymethyl-indazol-6-yl, 1-methyl-3-hydroxymethyl-indazol-5-yl, 1-methyl-3-hydroxymethyl-indazol-6-yl, 1-methyl-3-cyclopropyl-indazol-5-yl, 1-(cyclopropylmethyl)-indazol-5-yl, benzofuran-5-yl, benzofuran-6-yl, 2-methyl-benzofuran-5-yl, 2-cyano-benzofuran-5-yl, 2,3-dimethyl-benzofuran-5-yl, benzoxazol-2-yl, benzoxazol-5-yl, 6-chloro-benzoxazol-2-yl, benzimidazol-2-yl, benzimidazol-5-yl, 1-methyl-benzimidazol-5-yl, 2-oxo-benzimidazol-5-yl, benzothiazol-2-yl, benzthiazol-5-yl,5-chloro-benzothiazol-2-yl, 5-fluoro-benzothiazol-2-yl, 6-fluoro-benzothiazol-2-yl, 6-chloro-benzothiazol-2-yl, 5,6-difluoro-benzothiazol-2-yl, 2-methyl-benzothiazol-5-yl, 2-methyl-benzothiazol-6-yl, 5-cyano-benzothiazol-2-yl, 6-cyano-benzthiazol-2-yl, benzothien-5-yl, 2-methyl-benzothien-5-yl, 2,3-dimethyl-benzothioen-5-yl, 2,3-dihydrobenzofuran-5-yl, 2-oxo-3,4-dihydro-quinolin-6-yl, benzo[1,3]dioxol-5-yl, 1,8-naphthyridin-2-yl, and pyrrolo[2,3-b]pyridin-5-yl;

provided that when $R^1$ and $R^2$ are taken together with the carbon atom to which they are bound to form 1-(methoxycarbonyl)-azetidin-3-yl; m is 1 and n is 0 or m is 0 and m is 1;

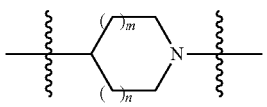

is pyrrolidin-3R-yl; -(L$^1$)$_a$-R$^3$ is —C(O)-cyclopropyl;

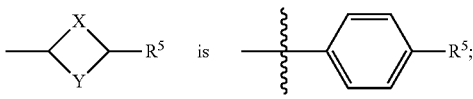

and b=0; then R$^5$ is other than quinolin-7-yl, benzofuran-5-yl or 1-methyl-indazol-5-yl;
provided further that when $R^1$ and $R^2$ are taken together with the carbon atom to which they are bound to form cyclopropyl; m is 0, n is 0,

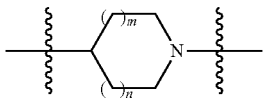

is azetidin-3-yl; -(L')$_a$-R$^3$ is selected from the group consisting of —C(O)-cyclopropyl, —C(O)-(1-methyl-cyclopropyl) and —C(O)-(1-hydroxy-cyclopropyl);

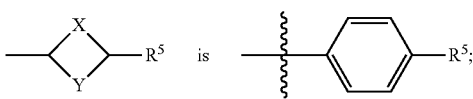

b=0 or (R$^4$)$_b$ is selected from the group consisting of 2-fluoro and 2-methyl; then R$^5$ is other than 1-methyl-indazol-5-yl, and indazol-5-yl;
provided further that when $R^1$ and $R^2$ are taken together with the carbon atom to which they are bound to form cyclopropyl; m is 0, n is 0,

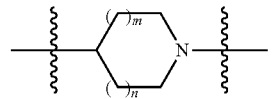

is azetidin-3-yl; -(L$^1$)$_a$-R$^3$ is —C(O)-(1-hydroxy-cyclopropyl);

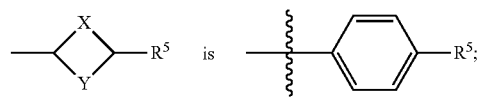

and (R$^4$)$_b$ is 2-methyl; then R$^5$ is other 1-methyl-indazol-5-yl;
provided further that when $R^1$ and $R^2$ are taken together with the carbon atom to which they are bound to form cyclopropyl; m is 0, n is 0,

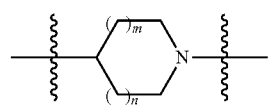

is azetidin-3-yl; -(L$^1$), —R$^3$ is —C(O)-pyridin-3-yl;

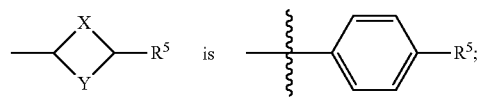

(R$^4$)$_b$ is 2-methyl; then R$^5$ is other than 1-methyl-indazol-5-yl;
provided further that when $R^1$ and $R^2$ are taken together with the carbon atom to which they are bound to form cyclopropyl; m is 1, n is 1,

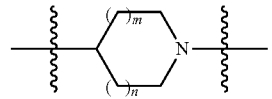

is piperidin-4-yl; -(L$^1$)$_a$-R$^3$ is —C(O)-cyclopropyl;

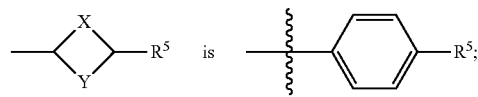

and b=0; then R$^5$ is other than benzoxazol-5-yl;
provided further that when $R^1$ and $R^2$ are taken together with the carbon atom to which they are bound to form cyclopropyl; m is 0 and n is 1 or m is 1 and n is 0;

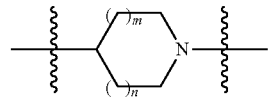

is pyrrolidin-3R-yl; -(L$^1$)$_a$-R$^3$ is —C(O)-cyclopropyl;

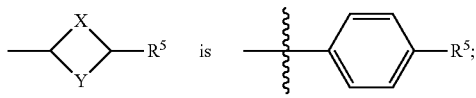

and b=0; then R$^5$ is other than 2-oxo-3,4-dihydro-quinolin-7-yl; and a stereoisomer, a tautomer and a pharmaceutically acceptable salt thereof.

4. A compound as in claim 2, wherein

R$^1$ and R$^2$ are taken together to form a ring structure selected from the group consisting of cyclopropyl, cyclopentyl, piperidin-4,4-diyl, 1-(methyl)-piperidin-4,4-diyl, 1-(isopropyl)-piperidin-4,4-diyl, 1-(2-hydroxyethyl)-piperidin-4,4-diyl, 1-(methoxy-carbonyl)-piperidin-4,4-diyl, 1-(benzyl)-piperidin-4,4-diyl, 1-(methyl-carbonyl)-piperidin-4,4-diyl, 1-(isopropyl-carbonyl)-piperidin-4,4-diyl, 1-(cyclopropyl-carbonyl)-piperidin-4,4-diyl, 1-(dimethylamino-carbonyl)-piperidin-4,4-diyl, 1-(trifluoromethyl-carbonyl)-piperidin-4,4-diyl, 1-(methyl-sulfonyl)-piperidin-4,4-diyl, 1-(2-methoxyethyl)-piperidin-4,4-diyl, 1-(methoxycarbonyl)azetidin-3,3-diyl, tetrahydro-furan-3,3-diyl, and tetrahydro-pyran-4,4-diyl;

m is an integer from 0 to 1; and n is an integer from 0 to 1;

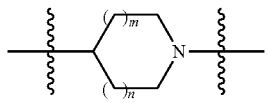

is selected from the group consisting of azetidin-3-yl, pyrrolidin-3R-yl and piperidin-4-yl;

a is 1;

L$^1$ is —C(O)—;

R$^3$ is selected from the group consisting of ethyl, cyclopropyl, 1-hydroxy-cyclopropyl, 1-fluoro-cyclopropyl, 1-methyl-cyclopropyl, 1-hydroxymethyl-cyclopropyl, cyclobutyl, tetrahydro-furan-2-yl, tetrahydro-furan-2R-yl, tetrahydro-furan-2S-yl, and oxetan-2-yl;

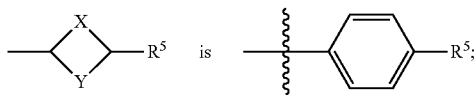

b is an integer from 0 to 1;

R$^4$ is selected from the group consisting of 2-fluoro, 2-chloro, 2-methyl, 2-methoxy, 3-fluoro, and 3-methyl;

R$^5$ is

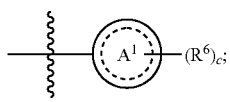

wherein

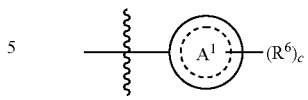

is selected from the group consisting of 4-cyano-phenyl, 3-hydroxy-phenyl, 4-fluoro-phenyl, 3-chloro-phenyl, 4-chloro-phenyl, 2-fluoro-4-chloro-phenyl, 3-chloro-4-fluoro-phenyl, 2-fluoro-4-cyano-phenyl, 2,4-dichloro-phenyl, 3-methyl-phenyl, 4-methyl-phenyl, 3-methoxy-phenyl, 4-methoxy-phenyl, 4-dimethylamino-phenyl, 3-(cyclopropyl-sulfonylamino)-phenyl, 3-(cyclopropyl-carbonylamino)-phenyl, 3-(cyclopropyl-thio)-phenyl, naphth-2-yl, 6-fluoro-naphth-2-yl, 7-fluoro-naphth-2-yl, 8-fluoro-naphth-2-yl, 6-chloro-naphth-2-yl, 6-methyl-naphth-2-yl, 6-methoxy-naphth-2-yl, 8-methoxy-naphth-2-yl, 6-cyano-naphth-2-yl, indol-3-yl, indol-4-yl, indol-5-yl, indol-6-yl, 1-methyl-indol-5-yl, 1-methyl-indol-6-yl, 2-methyl-indol-5-yl, 2,3-dimethyl-indol-5-yl, 2-(hydroxymethyl)-indol-5-yl, 3-(2-hydroxyethyl)-indol-5-yl, 3-(cyanomethyl)-indol-5-yl, 1-methyl-3-(2-hydroxyethyl)-indol-5-yl, 2-oxo-indolin-5-yl, quinolin-2-yl, quinolin-3-yl, quinolin-5-yl, quinolin-6-yl, quinolin-7-yl, 3-chloro-quinolin-7-yl, 6-fluoro-quinolin-2-yl, 8-fluoro-quinolin-2-yl, 8-fluoro-quinolin-7-yl, 4-methyl-quinolin-7-yl, 2-cyano-quinolin-6-yl, isoquinolin-5-yl, isoquinolin-6-yl, isoquinolin-7-yl, 6-fluoro-isoquinolin-6-yl, 1-amino-isoquinolin-6-yl, 3-amino-isoquinolin-6-yl, quinazolin-7-yl, indazol-3-yl, indazol-4-yl, indazol-5-yl, indazol-6-yl, 1-methyl-indazol-4-yl, 1-methyl-indazol-5-yl, 1-methyl-indazol-6-yl, 2-methyl-indazol-6-yl, 1,3-dimethyl-indazol-5-yl, 1,4-dimethyl-indazol-5-yl, 1-methyl-3-amino-indazol-6-yl, 1-methyl-3-aminocarbonyl-indazol-6-yl, 1-methyl-3-methoxymethyl-indazol-5-yl, 1-methyl-3-methoxymethyl-indazol-6-yl, 1-methyl-3-cyclopropyl-indazol-5-yl, benzofuran-5-yl, 2-methyl-benzofuran-5-yl, 2-cyano-benzofuran-5-yl, 2,3-dimethyl-benzofuran-5-yl, benzothiazol-2-yl, benzothiazol-5-yl, 6-fluoro-benzothiazol-2-yl, 6-chloro-benzothiazol-2-yl, 2-methyl-benzothiazol-5-yl, 6-methyl-benzothiazol-2-yl, 6-cyano-benzothiazol-2-yl, benzoxazol-2-yl, benzimidazol-5-yl, 1-methyl-benzimidazol-5-yl, benzothien-5-yl, 2-methyl-benzothien-5-yl, 2,3-dimethyl-benzothien-5-yl, and pyrrolo[2,3-b]pyridin-5-yl;

provided that when R$^1$ and R$^2$ are taken together with the carbon atom to which they are bound to form 1-(methoxycarbonyl)-azetidin-3-yl; m is 1 and n is 0 or m is 0 and m is 1;

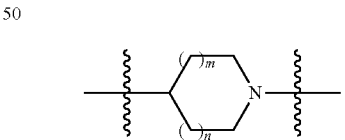

is pyrrolidin-3R-yl; -(L$^1$)$_a$-R$^3$ is —C(O)-cyclopropyl;

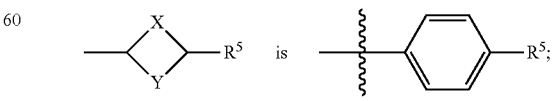

and b=0; then R$^5$ is other than a compound selected from the group consisting of quinolin-7-yl, benzofuran-5-yl and 1-methyl-indazol-5-yl;

provided further that when R¹ and R² are taken together with the carbon atom to which they are bound to form cyclopropyl; m is 0, n is 0,

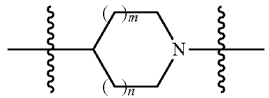

is azetidin-3-yl; -(L¹)$_a$-R³ is selected from the group consisting of —C(O)-cyclopropyl, —C(O)-(1-methyl-cyclopropyl), and —C(O)-(1-hydroxy-cyclopropyl);

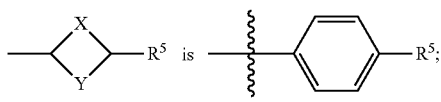

b=0 or (R⁴)$_b$ is selected from the group consisting of 2-fluoro and 2-methyl; then R⁵ is other than 1-methyl-indazol-5-yl or indazol-5-yl;

provided further that when R¹ and R² are taken together with the carbon atom to which they are bound to form cyclopropyl; m is 0, n is 0,

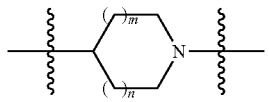

is azetidin-3-yl; -(L¹)$_a$-R³ is —C(O)-(1-hydroxy-cyclopropyl);

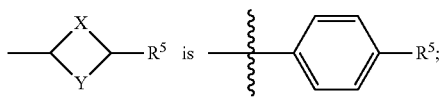

and (R⁴)$_b$ is 2-methyl; then R⁵ is other 1-methyl-indazol-5-yl; and
a stereoisomer, a tautomer and a pharmaceutically acceptable salt thereof.

5. A compound as in claim 2, wherein
R¹ and R² are taken together to form a ring structure selected from the group consisting of cyclopropyl, cyclopentyl, 1-(methoxy-carbonyl)-piperidin-4,4-diyl, 1-(isopropyl-carbonyl)-piperidin-4,4-diyl, and 1-(dimethylamino-carbonyl)-piperidin-4,4-diyl;
m is an integer from 0 to 1; and n is 0;

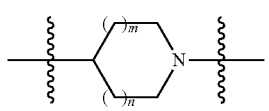

is selected from the group consisting of azetidin-3-yl and pyrrolidin-3R-yl;
a is 1;
L¹ is —C(O)—;

R³ is selected from the group consisting of cyclopropyl, 1-fluoro-cyclopropyl, 1-hydroxy-cyclopropyl, 1-methyl-cyclopropyl, tetrahydrfuran-2S-yl, and oxetan-2-yl;

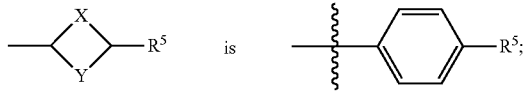 is 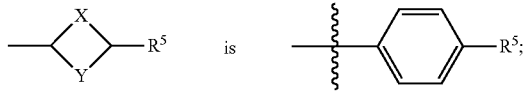

b is an integer from 0 to 1;
R⁴ is selected from the group consisting of 2-fluoro, 2-chloro, and 2-methyl;
R⁵ is

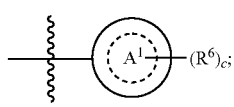

wherein

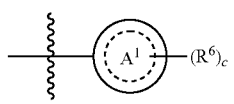

is selected from the group consisting of 3-hydroxy-phenyl, naphth-2-yl, 6-fluoro-naphth-2-yl, 7-fluoro-naphth-2-yl, 8-fluoro-naphth-2-yl, 6-chloro-naphth-2-yl, 6-methyl-naphth-2-yl, 6-methoxy-naphth-2-yl, 8-methoxy-naphth-2-yl, 6-cyano-naphth-2-yl, indol-3-yl, indol-5-yl, indol-6-yl, 1-methyl-indol-5-yl, 2-methyl-indol-5-yl, 2,3-dimethyl-indol-5-yl, 3-cyanomethyl-indol-5-yl, 2-hydroxymethyl-indol-5-yl, 3-(2-hydroxyethyl)-indol-5-yl, quinolin-3-yl, quinolin-5-yl, quinolin-7-yl, 3-chloro-quinolin-7-yl, 6-fluoro-quinolin-2-yl, 8-fluoro-quinolin-2-yl, 2-cyano-quinolin-6-yl, isoquinolin-6-yl, indazol-4-yl, indazol-5-yl, indazol-6-yl, 1-methyl-indazol-5-yl, 2-methyl-indazol-6-yl, benzofuran-5-yl, 2-methyl-benzofuran-5-yl, 2-cyano-benzofuran-5-yl, benzothiazol-2-yl, benzthiazol-5-yl, 6-chloro-benzothiazol-2-yl, 6-methyl-benzothiazol-2-yl, 6-cyano-benzothiazol-2-yl, benzoxazol-2-yl, benzimidazol-5-yl, 1-methyl-benzimidazol-5-yl, benzothien-5-yl, 2-methyl-benzothien-5-yl, and 2,3-dimethyl-benzothien-5-yl;

provided that when R¹ and R² are taken together with the carbon atom to which they are bound to form cyclopropyl; m is 0, n is 0,

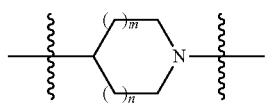

is azetidin-3-yl; -(L¹)$_a$-R³ is selected from the group consisting of —C(O)-cyclopropyl, —C(O)-(1-methyl-cyclopropyl), and —C(O)-(1-hydroxy-cyclopropyl);

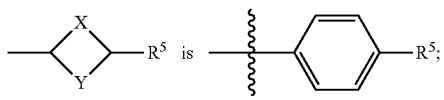 is 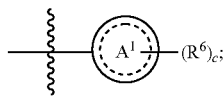

b=0 or $(R^4)_b$ is selected from the group consisting of 2-fluoro and 2-methyl; then $R^5$ is other than 1-methyl-indazol-5-yl or indazol-5-yl;

provided further that when $R^1$ and $R^2$ are taken together with the carbon atom to which they are bound to form cyclopropyl; m is 0, n is 0,

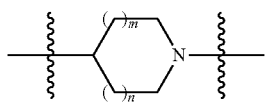

is azetidin-3-yl; $-(L^1)_a-R^3$ is —C(O)-(1-hydroxy-cyclopropyl);

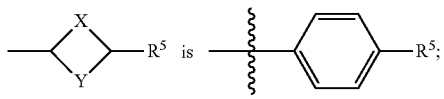 is 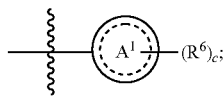

and $(R^4)_b$ is 2-methyl; then $R^5$ is other 1-methyl-indazol-5-yl; and a stereoisomer, a tautomer and a pharmaceutically acceptable salt thereof.

6. A compound as in claim 2, wherein $R^1$ and $R^2$ are taken together to form a ring structure selected from the group consisting of cyclopropyl and cyclopentyl;

m is an integer from 0 to 1; and n is 0;

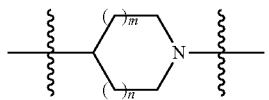

is selected from the group consisting of azetidin-3-yl and pyrrolidin-3R-yl;

a is 1;

$L^1$ is —C(O)—;

$R^3$ is selected from the group consisting of cyclopropyl, 1-hydroxy-cyclopropyl, 1-methyl-cyclopropyl, and oxetan-2-yl;

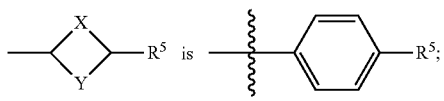 is 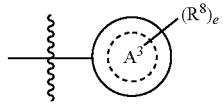

b is an integer from 0 to 1;

$R^4$ is selected from the group consisting of 2-fluoro and 2-methyl;

$R^5$ is selected from the group consisting of

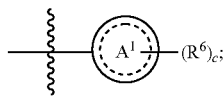

and

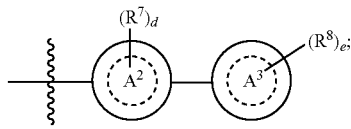

wherein

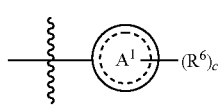

is selected from the group consisting of naphtha-2-yl, 6-chloro-naphth-2-yl, 6-fluoro-naphth-2-yl, 6-methyl-naphth-2-yl, 6-methoxy-naphth-2-yl, 6-cyano-naphth-2-yl, indol-5-yl, indol-6-yl, 1-methyl-indol-5-yl, 2-methyl-indol-5-yl, 2-hydroxymethyl-indol-5-yl, 3-(2-hydroxyethyl)-indol-5-yl, 3-cyanomethyl-indol-5-yl, indazol-5-yl, indazol-6-yl, 1-methyl-indazol-5-yl, quinolin-7-yl, 3-chloro-quinolin-7-yl, 6-fluoro-quinolin-2-yl, 8-fluoro-quinolin-2-yl, isoquinolin-6-yl, benzofuran-5-yl, 2-methyl-benzofuran-5-yl, 2-cyano-benzofuran-5-yl, benzothien-5-yl, 2-methyl-benzothien-5-yl, 2,3-dimethyl-benzothien-5-yl, benzoxazol-2-yl, benzothiazol-2-yl, and 1-methyl-benzimidazol-5-yl;

wherein

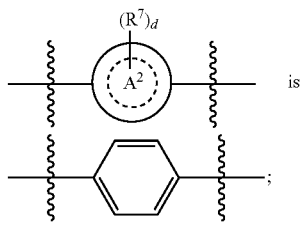 is and wherein

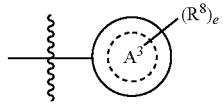

is selected from the group consisting of pyridin-4-yl and 1-methyl-pyrazol-4-yl;

provided that when $R^1$ and $R^2$ are taken together with the carbon atom to which they are bound to form cyclopropyl; m is 0, n is 0,

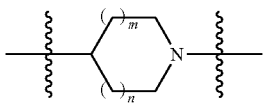

is azetidin-3-yl; -(L$^1$)$_a$-R$^3$ is —C(O)-(1-hydroxy-cyclopropyl);

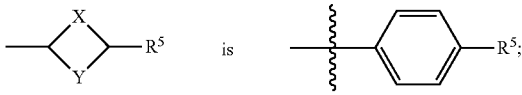

and (R$^4$)$_b$ is 2-methyl; then R$^5$ is other 1-methyl-indazol-5-yl; and a stereoisomer, a tautomer and a pharmaceutically acceptable salt thereof.

7. A compound as in claim 2, wherein

R$^1$ and R$^2$ are taken together to form a ring structure selected from the group consisting of cyclopropyl, cyclopentyl, and tetrahydropyran-4,4-diyl;

m is an integer from 0 to 1; and n is 0;

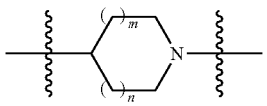

is selected from the group consisting of azetidin-3-yl and pyrrolidin-3R-yl;

a is 1;

L$^1$ is —C(O)—;

R$^3$ is selected from the group consisting of cyclopropyl, 1-fluoro-cyclopropyl, 1-hydroxy-cyclopropyl, 1-methyl-cyclopropyl, tetrahydrofuran-2-yl, tetrahydrofuran-2S-yl, and oxetan-2-yl;

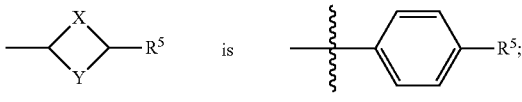

b is an integer from 0 to 1;

R$^4$ is selected from the group consisting of 2-fluoro and 2-methyl;

R$^5$ is selected from the group consisting of

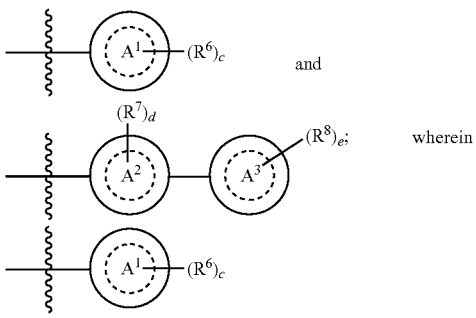

wherein is selected from the group consisting of naphth-2-yl, 6-chloro-naphth-2-yl, 6-fluoro-naphth-2-yl, 7-fluoro-naphth-2-yl, 8-fluoro-naphth-2-yl, 6-methyl-naphth-2-yl, 6-methoxy-naphth-2-yl, 6-cyano-naphth-2-yl, indol-3-yl, indol-5-yl, indol-6-yl, 1-methyl-indol-5-yl, 2-methyl-indol-6-yl, 3-(2-hydroxyethyl)-indol-5-yl, 3-cyanomethyl-indol-5-yl, 1,3-dimethyl-indol-5-yl, 1-methyl-3-(2-hydroxyethyl)-indol-5-yl, quinolin-7-yl, 3-chloro-quinolin-7-yl, 6-fluoro-quinolin-6-yl, isoquinolin-6-yl, quinazolin-7-yl, indazol-4-yl, indazol-5-yl, indazol-6-yl, 1-methyl-indazol-5-yl, 2-methyl-indazol-6-yl, 1-methyl-3-amino-indazol-6-yl, 1-methyl-3-aminocarbonyl-indazol-6-yl, benzofuran-5-yl, 2-methyl-benzofuran-5-yl, 2-methyl-benzothien-5-yl, benzothiazol-5-yl, 6-chloro-benzothiazol-2-yl, 6-methyl-benzothiazol-2-yl, 6-cyano-benzothiazol-2-yl, benzimidazol-5-yl, and 1-methyl-benzimidazol-5-yl;

wherein

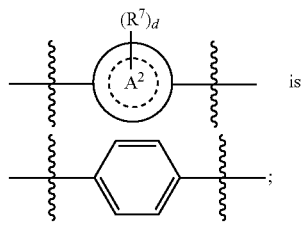

is and wherein

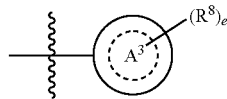

is selected from the group consisting of 1-methyl-pyrazol-4-yl, 1-isopropyl-pyrazol-4-yl, 1-cyclopropyl-pyrazol-4-yl, 1-cyclobutyl-pyrazol-4-yl, 1-methyl-pyrazol-5-yl, and pyridin-4-yl;

provided that when R$^1$ and R$^2$ are taken together with the carbon atom to which they are bound to form cyclopropyl; m is 0, n is 0,

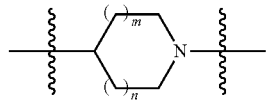

is azetidin-3-yl; -(L$^1$)$_a$-R$^3$ is selected from the group consisting of —C(O)-cyclopropyl, —C(O)-(1-methyl-cyclopropyl), and —C(O)-(1-hydroxy-cyclopropyl);

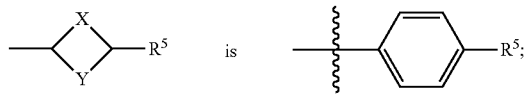

b=0 or (R$^4$)$_b$ is selected from the group consisting of 2-fluoro and 2-methyl; then R$^5$ is other than 1-methyl-indazol-5-yl, indazol-5-yl, or 4-(1-isobutyl-pyrazol-5-yl)-phenyl;

provided that when R¹ and R² are taken together with the carbon atom to which they are bound to form cyclopropyl; m is 0, n is 0,

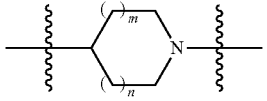

is azetidin-3-yl; -(L¹), —R³ is —C(O)-(1-hydroxy-cyclopropyl);

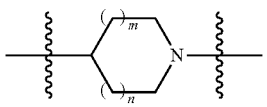   is   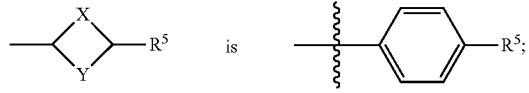

and (R⁴)$_b$ is 2-methyl; then R⁵ is other 1-methyl-indazol-5-yl; and a stereoisomer, a tautomer and a pharmaceutically acceptable salt thereof.

8. A compound as in claim 2, wherein

R¹ and R² are taken together to form cyclopropyl;
m is an integer from 0 to 1; and n is 0;

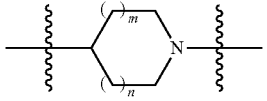

is selected from the group consisting of azetidin-3-yl and pyrrolidin-3R-yl;

a is 1;

L¹ is —C(O)—;

R³ is cyclopropyl;

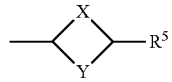

is selected from the group consisting of

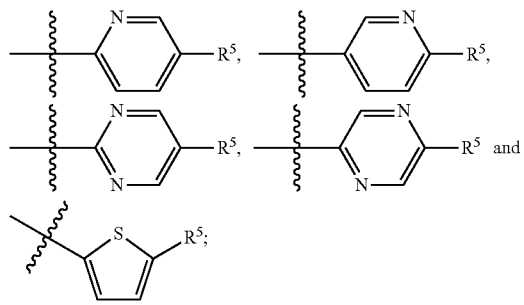

b is 0;

R⁵ is

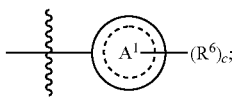

wherein

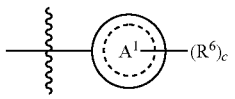

is selected from the group consisting of indol-5-yl, indol-6-yl, indazol-4-yl, indazol-5-yl, 1-methyl-indazol-5-yl, benzthiazol-5-yl, benzofuran-5-yl, benzothien-5-yl, and 6-cyano-naphth-2-yl; and a stereoisomer, a tautomer and a pharmaceutically acceptable salt thereof.

9. A compound as in claim 2, wherein

R¹ and R² are taken together to form a ring structure selected from the group consisting of cyclopropyl, cyclopentyl, tetrahydro-furan-3,3-diyl, tetrahydro-pyran-4,4-diyl, 1-(methoxycarbonyl)-azetidin-3,3-diyl, piperidin-4,4-diyl, 1-(isopropylcarbonyl)-piperidin-4,4-diyl, 1-(2-hydroxy ethyl)-piperidin-4,4-diyl, 1-(dimethylamino-methylcarbonyl)-piperidin-4,4-diyl, 1-(methylsulfonyl)piperidin-4,4-diyl, and 1-(cyclopropylcarbonyl)-piperidin-4,4-diyl;

m is an integer from 0 to 2; and n is an integer from 0 to 1; provided that when m is 2, then n is 0;

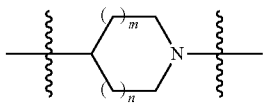

is selected from the group consisting of azetidin-3-yl, pyrrolidin-3R-yl, pyrrolidin-3R-yl, piperidin-3R-yl, and piperidin-4-yl;

a is 1;

L¹ is selected from the group consisting of —C(O)—, —C(O)O— and —SO₂—;

R³ is selected from the group consisting of methyl, 1-hydroxyethyl, trifluoromethyl, cyclopropyl, 1-methyl-cyclopropyl, 1-hydroxy-cyclopropyl, tetrahydro-furan-2R-yl, pyrrolidin-1-yl, and thiazol-2-yl;

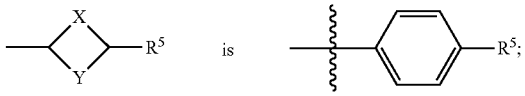

b is an integer from 0 to 1;

R⁴ is selected from the group consisting of 2-fluoro and 2-methyl;

$R^5$ is

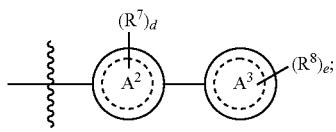

wherein

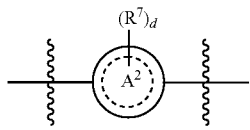

is selected from the group consisting of phenyl, pyridin-3-yl, pyridin-4-yl, and pyrazol-4-yl;

and wherein

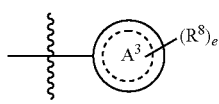

is selected from the group consisting of 4-bromo-phenyl, 3-chloro-phenyl, 4-methyl-phenyl, pyridin-3-yl, pyridin-4-yl, 1-methyl-pyrazol-3-yl, 1-(cyclopropylmethyl)-pyrazol-3-yl, 1-(2-methylpropyl)-pyrazol-3-yl, 1-methyl-pyrazol-4-yl, 1-isopropyl-pyrazol-4-yl, 1-cyclopropyl-pyrazol-4-yl, 1-cyclobutyl-pyrazol-4-yl, 1-methyl-pyrazol-5-yl, 1-isobutyl-pyrazol-5-yl, 1-(cyclopropylmethyl)-pyrazol-5-yl, tetrazol-5-yl, 5-methyl-oxazdiazol-2-yl, piperazin-1-yl, 4-methyl-piperazin-1-yl, pyrrolidin-1-yl, morpholin-14-yl, imidazol-1-yl, and oxetan-3-yl;

provided that when

is phenyl or pyridin-3-yl, then

is bound to

at the 4-position, relative to the binding position of the

to the

provided further that when

is pyridin-4-yl or pyrazol-4-yl, then

is bound to

at the 3-position, relative to the binding position of the

to the

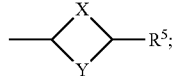

provided that when $R^1$ and $R^2$ are taken together with the carbon atom to which they are bound to form 1-(methoxycarbonyl)-azetidin-3-yl; m is 1 and n is 0 or m is 0 and m is 1;

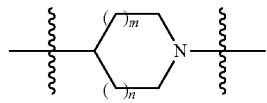

is pyrrolidin-3R-yl; $-(L^1)_a-R^3$ is selected from the group consisting of —C(O)—CF$_3$, —C(O)-cyclopropyl, —C(O)-(thiazol-2-yl), —C(O)OCH$_3$, and —SO$_2$—CH$_3$;

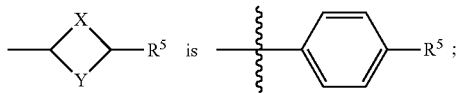 is 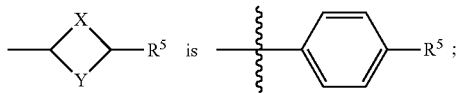

and b=0; then R⁵ is other than 4-(1-methyl-pyrazol-4-yl)-phenyl;

provided further that when R¹ and R² are taken together with the carbon atom to which they are bound to form cyclopentyl; m is 1 and n is 0 or m is 0 and m is 1;

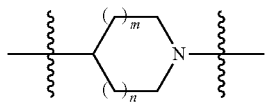

is pyrrolidin-3R-yl; -(L¹)$_a$-R³ is —C(O)-cyclopropyl;

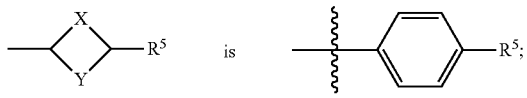

b=0 or (R⁴)$_b$ is 2-methyl; then R⁵ is other than 2-(piper-azin-1-yl)-pyridin-4-yl, or 2-(4-methyl-piperazin-1-yl)-pyridin-4-yl;

provided further that when R¹ and R² are taken together with the carbon atom to which they are bound to form cyclopropyl; m is 0, n is 0, and

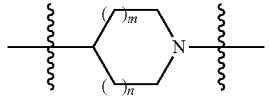

is azetidin-3-yl; -(L¹)$_a$-R³ is selected from the group consisting of —C(O)-cyclopropyl, —C(O)-(1-methyl-cyclopropyl) and —C(O)-(1-hydroxy-cyclopropyl);

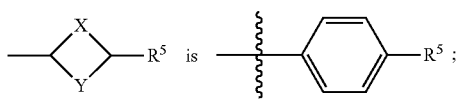

b=0 or (R⁴)$_b$ is selected from the group consisting of 2-fluoro and 2-methyl; then R⁵ is other than 4-(1-isobutyl-pyrazol-5-yl)-phenyl;

provided further that when R¹ and R² are taken together with the carbon atom to which they are bound to form cyclopropyl; m is 0, n is 2,

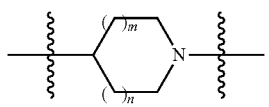

is piperidin-3R-yl; -(L¹)$_a$-R³ is —C(O)-cyclopropyl;

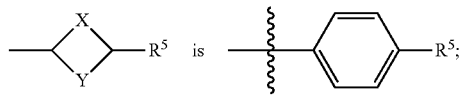 is 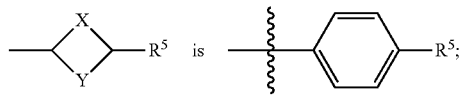

and b=0; then R⁵ is other than 4-(4-methylphenyl)phenyl or 4-(3-chlorophenyl)-phenyl;

provided further that when R¹ and R² are taken together with the carbon atom to which they are bound to form cyclopropyl; m is 1, n is 1, and

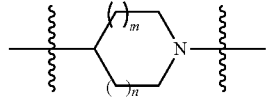

is piperidin-4-yl; -(L¹)$_a$-R³ is —C(O)-cyclopropyl;

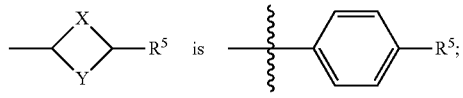

and b=0; then R⁵ is other than 4-(1-methyl-pyrazol-4-yl)-phenyl;

provided further that when R¹ and R² are taken together with the carbon atom to which they are bound to form cyclopropyl; m is 0 and n is 1 or m is 1 and n is 0;

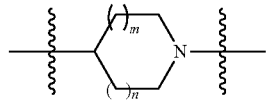

is pyrrolidin-3R-yl; -(L¹)$_a$-R³ is —C(O)-cyclopropyl;

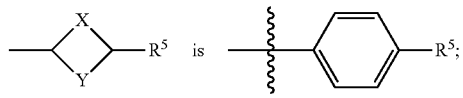

and b=0; then R⁵ is other than 6-(4-methyl-piperazin-1-yl)-pyridin-3-yl;

provided further that when R¹ and R² are taken together with the carbon atom to which they are bound to form tetrahydrofuran-3,3-diyl or tetrahydropyran-4,4-diyl; m is an integer from 0 to 1 and n is 0 or m is 0 and n is an integer from 0 to 1;

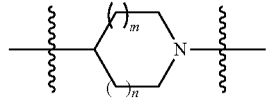

is selected from the group consisting of azetidin-3-yl, pyrrolidin-3R-yl, and pyrrolidin-3-yl; -(L¹)$_a$-R³ is selected from the group consisting of —C(O)—CF₃, —C(O)OCH₃ and —SO₂—CH₃;

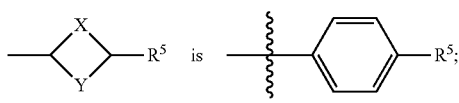 is 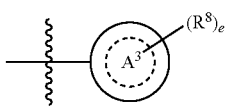

and b=0; then R⁵ is other than 4-(1-methyl-pyrazol-4-yl)-phenyl; and a stereoisomer, a tautomer and a pharmaceutically acceptable salt thereof.

10. A compound as in claim 8, wherein

R¹ and R² are taken together to form a ring structure selected from the group consisting of cyclopropyl and cyclopentyl;

m is an integer from 0 to 1; and n is 0;

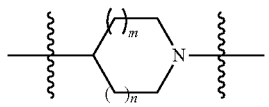

is selected from the group consisting of azetidin-3-yl and pyrrolidin-3R-yl;

a is 1;

L¹ is —C(O)—;

R³ is selected from the group consisting of cyclopropyl, 1-hydroxy-cyclopropyl, and 1-methyl-cyclopropyl;

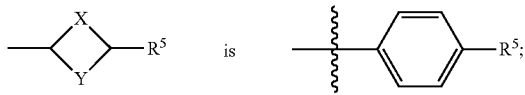

b is an integer from 0 to 1;

R⁴ is selected from the group consisting of 2-fluoro and 2-methyl;

R⁵ is

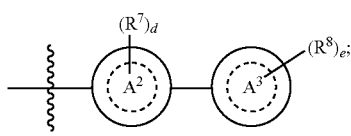

wherein

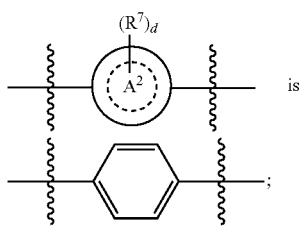

and wherein

is selected from the group consisting of pyridin-3-yl, pyridin-4-yl, 1-methyl-pyrazol-4-yl, 1-isopropyl-pyrazol-4-yl, 1-cyclopropyl-pyrazol-4-yl, 1-cyclobutyl-pyrazol-4-yl, 1-methyl-pyrazol-5-yl, and 5-methyl-oxadiazol-2-yl;

wherein

is bound to the

phenyl at the 4-position, relative to the point of attachment of the

phenyl to the

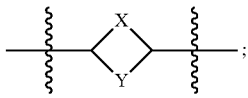

and a stereoisomer, a tautomer and a pharmaceutically acceptable salt thereof.

11. A compound as in claim 1, selected from the group consisting of

5-[4-(1-Benzofuran-5-yl)phenyl]-6-{[1-(cyclopropylcarbonyl)azetidin-3-yl]methyl}-4,6-diazaspiro[2.4]hept-4-en-7-one;

6-{[1-(Cyclopropylcarbonyl)azetidin-3-yl]methyl}-5-[4'-(1-methyl-1H-pyrazol-4-yl)biphenyl-4-yl]-4,6-diazaspiro[2.4]hept-4-en-7-one;

(R)-6-((1-(Cyclopropanecarbonyl)pyrrolidin-3-yl)methyl)-5-methyl-1H-pyrazol-4-yl)-[1,1'-biphenyl]-4-yl)-4,6-diazaspiro[2.4]hept-4-en-7-one;

(R)-6-((1-(cyclopropanecarbonyl)pyrrolidin-3-yl)methyl)-5-(4-(2-methyl-1H-indol-5-yl)phenyl)-4,6-diazaspiro[2.4]hept-4-en-7-one;

6-(4-(6-((1-(cyclopropanecarbonyl)azetidin-3-yl)methyl)-7-oxo-4,6-diazaspiro[2.4]hept-4-en-5-yl)-3-fluorophenyl)-2-naphthonitrile;

(R)-6-((1-(cyclopropanecarbonyl)pyrrolidin-3-yl)methyl)-5-(2-methyl-4-(1-methyl-1H-indazol-5-yl)phenyl)-4,6-diazaspiro[2.4]hept-4-en-7-one;

6-((1-(cyclopropanecarbonyl)azetidin-3-yl)methyl)-5-(2-methyl-4-(1-methyl-1H-indazol-5-yl)phenyl)-4,6-diazaspiro[2.4]hept-4-en-7-one;

6-((1-(cyclopropanecarbonyl)azetidin-3-yl)methyl)-5-(2-fluoro-4-(1-methyl-1H-indazol-5-yl)phenyl)-4,6-diazaspiro[2.4]hept-4-en-7-one;

5-(4-(benzo[d]thiazol-2-yl)-2-fluorophenyl)-6-((1-(cyclpropanecarbonyl)azetidin-3-yl)methyl)-4,6-diazaspiro[2.4]hept-4-en-7-one;

6-((1-(cyclopropanecarbonyl)azetidin-3-yl)methyl)-5-(2-fluoro-4-(2-methyl-1H-indol-5-yl)phenyl)-4,6-diazaspiro[2.4]hept-4-en-7-one;

6-((1-(cyclopropanecarbonyl)azetidin-3-yl)methyl)-5-(2-fluoro-4-(1-methyl-1H-indol-5-yl)phenyl)-4,6-diazaspiro[2.4]hept-4-en-7-one;

(R)-6-((1-(cyclopropanecarbonyl)pyrrolidin-3-yl)methyl)-5-(2-fluoro-4-(1-methyl-1H-indazol-5-yl)phenyl)-4,6-diazaspiro[2.4]hept-4-en-7-one; and stereoisomers, tautomers and pharmaceutically acceptable salts thereof.

12. A compound as in claim 1, selected from the group consisting of

6-{[1-(Cyclopropylcarbonyl)azetidin-3-yl]methyl}-5-[4'-(1-methyl-1H-pyrazol-4-yl)biphenyl-4-yl]-4,6-diazaspiro[2.4]hept-4-en-7-one;

(R)-6-((1-(Cyclopropanecarbonyl)pyrrolidin-3-yl)methyl)-5-methyl-1H-pyrazol-4-yl)-[1,1'-biphenyl]-4-yl)-4,6-diazaspiro[2.4]hept-4-en-7-one;

(R)-6-((1-(cyclopropanecarbonyl)pyrrolidin-3-ylmethyl)-5-(2-fluoro-4-(1-methyl-1H-indazol-5-yl)phenyl)-4,6-diazaspiro[2.4]hept-4-en-7-one; and stereoisomers, tautomers and pharmaceutically acceptable salts thereof.

13. A pharmaceutical composition comprising a pharmaceutically acceptable carrier and a compound of claim 1.

14. A pharmaceutical composition made by mixing a compound of claim 1 and a pharmaceutically acceptable carrier.

15. A pharmaceutical composition comprising a compound as in claim 1 and a pharmaceutically acceptable excipient.

16. A method of treating a disorder comprising administering to a subject in need thereof a therapeutically effective amount of a compound as in claim 1;

wherein the disorder is selected from the group consisting of
(a) cancer selected from the group consisting of breast, prostate, head, neck, skin, lung, ovary, endometrium, thyroid, colon, rectum, esophagus, stomach, kidney, liver, bladder, pancreas, brain, spinal cord, blood, and bone;
(b) obesity,
(c) Type II diabetes mellitus, and
(d) Syndrome X.

* * * * *